United States Patent
Falb et al.

(10) Patent No.: US 11,879,123 B2
(45) Date of Patent: Jan. 23, 2024

(54) BACTERIA FOR THE TREATMENT OF DISORDERS

(71) Applicant: Synlogic Operating Company, Inc., Cambridge, MA (US)

(72) Inventors: Dean Falb, Sherborn, MA (US); Adam B. Fisher, Cambridge, MA (US); Vincent M. Isabella, Medford, MA (US); Jonathan W. Kotula, Berkeley, CA (US); David Lubkowicz, Somerville, MA (US); Paul F. Miller, Salem, CT (US); Yves Millet, Newton, MA (US); Sarah Elizabeth Rowe, Durham, NC (US)

(73) Assignee: Synlogic Operating Company, Inc., Cambridge, MA (US)

( * ) Notice: Subject to any disclaimer, the term of this patent is extended or adjusted under 35 U.S.C. 154(b) by 592 days.

(21) Appl. No.: 16/621,792

(22) PCT Filed: Jun. 21, 2018

(86) PCT No.: PCT/US2018/038840
§ 371 (c)(1),
(2) Date: Dec. 12, 2019

(87) PCT Pub. No.: WO2018/237198
PCT Pub. Date: Dec. 27, 2018

(65) Prior Publication Data
US 2020/0172857 A1   Jun. 4, 2020

Related U.S. Application Data

(60) Provisional application No. 62/624,299, filed on Jan. 31, 2018, provisional application No. 62/614,213, filed on Jan. 5, 2018, provisional application No. 62/552,829, filed on Aug. 31, 2017, provisional application No. 62/552,785, filed on Aug. 31, 2017, provisional application No. 62/523,225, filed on Jun. 21, 2017, provisional application No. 62/523,202, filed on Jun. 21, 2017.

(51) Int. Cl.
| | | |
|---|---|---|
| A61K 9/00 | (2006.01) |
| C07K 14/245 | (2006.01) |
| A61K 35/74 | (2015.01) |
| C12Q 1/527 | (2006.01) |
| C12N 15/63 | (2006.01) |
| C12N 1/20 | (2006.01) |
| A61K 35/741 | (2015.01) |

(52) U.S. Cl.
CPC ............. *C12N 1/20* (2013.01); *A61K 9/0053* (2013.01); *A61K 35/74* (2013.01); *A61K 35/741* (2013.01); *C07K 14/245* (2013.01); *C12N 15/63* (2013.01); *C12N 2510/00* (2013.01); *C12N 2795/00021* (2013.01); *C12N 2800/202* (2013.01); *C12Q 1/527* (2013.01)

(58) Field of Classification Search
CPC ...... C12N 1/20; C12N 15/63; C12N 2510/00; C12N 2795/00021; C12N 2800/202; A61K 9/0053; A61K 35/74; A61K 35/741; C07K 14/245; C12Q 1/527
See application file for complete search history.

(56) References Cited

U.S. PATENT DOCUMENTS

| | | |
|---|---|---|
| 5,589,168 A | 12/1996 | Allen et al. |
| 5,989,463 A | 11/1999 | Tracy et al. |
| 6,203,797 B1 | 3/2001 | Perry |
| 6,835,376 B1 | 12/2004 | Neeser et al. |
| 7,731,976 B2 | 6/2010 | Cobb et al. |
| 9,889,164 B2 | 2/2018 | Falb et al. |
| 2014/0079701 A1 | 3/2014 | Miller et al. |
| 2015/0238545 A1 | 8/2015 | Borody |
| 2015/0359894 A1 | 12/2015 | Weinrich et al. |
| 2017/0136073 A1 | 5/2017 | Falb et al. |
| 2017/0232043 A1 | 8/2017 | Falb et al. |

FOREIGN PATENT DOCUMENTS

| | | |
|---|---|---|
| CN | 1154845 A | 7/1997 |
| CN | 101068919 A | 11/2007 |
| CN | 101586111 A | 11/2009 |
| EP | 1666588 A1 | 6/2006 |
| EP | 2344626 B1 | 7/2011 |
| WO | WO 2008/073148 A2 | 6/2008 |
| WO | WO 2009/004595 A2 | 1/2009 |
| WO | 2011/080505 A2 | 7/2011 |
| WO | WO2011106874 A1 | 9/2011 |
| WO | WO 2012/078311 A1 | 6/2012 |
| WO | WO 2013/134174 A2 | 9/2013 |
| WO | WO 2013/192543 A2 | 12/2013 |

(Continued)

OTHER PUBLICATIONS

Sun, et al. "Genomic peculiarity of coding sequences and metabolic potential of probiotic *Escherichia coli* strain Nissle 1917 inferred from raw genome data", Journal of Biotechnology, 2005, vol. 117, pp. 147-161. (Year: 2005).*

Bobay et al. "Pervasive domestication of defective prophages by bacteria", PNAS, 2014, vol. 111, No. 33, pp. 12127-12132. (Year: 2014).*

(Continued)

*Primary Examiner* — Louise W Humphrey
*Assistant Examiner* — Deepa Mishra
(74) *Attorney, Agent, or Firm* — McCarter & English, LLP; Marcie B. Clarke

(57) ABSTRACT

Modified probiotics, pharmaceutical compositions thereof, and methods of modulating and treating disorders are disclosed.

24 Claims, 58 Drawing Sheets

Specification includes a Sequence Listing.

(56) References Cited

FOREIGN PATENT DOCUMENTS

| WO | WO 2014/018832 A1 | 1/2014 | |
|---|---|---|---|
| WO | WO 2014/066945 A1 | 5/2014 | |
| WO | WO 2014/138324 A1 | 9/2014 | |
| WO | WO 2016/183531 A1 | 11/2016 | |
| WO | WO 2016/183532 A1 | 11/2016 | |
| WO | WO-2016183531 A1 * | 11/2016 | ............ A61K 35/74 |
| WO | WO 2016/210373 A2 | 12/2016 | |

OTHER PUBLICATIONS

GenBank reference corresponding to accession No. CP007799.1 for *Escherichia coli* Nissle 1917, complete genome, that was deposited in the GenBank on Jun. 25, 2015. (Year: 2015).*

Adams et al. (Jul. 1, 19905) "Nucleotide sequence and genetic characterization reveal six essential genes for the LIV-I and LS transport systems of *Escherichia coli*" *J Biol Chem.* 265(20):11436-43.

Al Hafid et al. (Jun. 2002) "Phenylketonuria: a Review of Current and Future Treatments" *Transl Pediatr.* 3:49-62.

Al Hafid et al. (Oct. 2015) "Phenylketonuria: a review of current and future treatments" *Transl Pediatr.* 4(4):304-317.

Albiniak et al. (2013) "High-level secretion of a recombinant protein to the culture medium with a Bacillus subtilis twin-arginine translocation system in *Escherichia coli*" *FEBS J.* 280:3810-3821.

Altenhoefer et al. (Apr. 9, 2004) "The probiotic *Escherichia coli* strain Nissle 1917 interferes with invasion of human intestinal epithelial cells by different enteroinvasive bacterial pathogens" *FEMS Immunol Med Microbiol.* 40(3):223-229.

Andersen et al. (Apr. 1995) "Uracil uptake in *Escherichia coli* K-12: isolation of uraA mutants and cloning of the gene" *J Bacteriol.* 177(8):2008-2013.

Anderson et al. (Apr. 1977) "*Escherichia coli* transport mutants lacking binding protein and other components of the branched-chain amino acid transport systems" *J Bacteriol.* 130(1):384-92.

Anderson et al. (Oct. 1978) "Genetic separation of high- and low-affinity transport systems for branched-chain amino acids in *Escherichia coli* K-12" *J Bacteriol.* 136(1):168-74.

Arai et al. (Aug. 2, 19958) "Expression of the nir and nor genes for denitrification of Pseudomonas aeruginosa requires a novel CRP/FNR-related transcriptional regulator, DNR, in addition to ANR" *FEBS Lett.* 371(1):73-76.

Argos (1989) "A possible homology between immunodeficiency virus p24 core protein and picornaviral VP2 coat protein: prediction of HIV p24 antigenic sites" *EMBO J.* 8(3):779-785.

Arrach et al. (Jun. 15, 2008) "*Salmonella* promoters preferentially activated inside tumors" *Cancer Res.* 68(12):4827-32.

Arthur et al. (Oct. 5, 2012) "Intestinal inflammation targets cancer-inducing activity of the microbiota" *Science* 338(6103): 120-123. NIH Public Access Author Manuscript; available in PMC May 6, 2013 (11 pages).

Ashida et al. (2012) "Bacteria and host interactions in the gut epithelial barrier" *Nature Chem Biol.* 8: 36-45.

Baek et al. (Apr. 2011) "Expression and characterization of a second L-amino acid deaminase isolated from *Proteus mirabilis* in *Escherichia coli*" *J Basic Microbiol.* 51:129-135.

Barel et al. (Feb. 6, 2015) "The complex amino acid diet of Francisella in infected macrophages" *Front Cell Infect Microbiol.* 5:9. 5 pages.

Bearden et al. (Apr. 1999) "The Yfe system of Yersinia pestis transports iron and manganese and is required for full virulence of plague" *Mol Microbiol.* 32(2):403-14.

Becker et al. (Aug. 1996) "$O_2$ as the regulatory signal for FNR-dependent gene regulation in *Escherichia coli*" *J Bacteriol.* 178(15):4515-21.

Becker et al. (Oct. 1997) "Regulatory $O_2$ tensions for the synthesis of fermentation products in *Escherichia coli* and relation to aerobic respiration" Arch Microbiol. 168(4):290-6.

Bifulco et al. (2013) "A thermostable L-aspartate oxidase: a new tool for biotechnological applications" *Appl Microbiol Biotechnol.* 97:7285-7295.

Bikandi et al. (Mar. 22, 2004) "In Silico Analysis of Complete Bacterial Genomes: PCR, AFLP-PCR and Endonuclease Restriction" Bioinformatics 20 (5), 798-9 2004.

Blau et al. (2015) "Alternative therapies to address the unmet medical needs of patients with phenylketonuria" *Expert Opin Pharmacother.* 16(6): 791-800.

Boysen et al. (Apr. 2010) "Translational Regulation of Gene Expression by an Anaerobically Induced Small Non-coding RNA in *Escherichia coli*" *J Biol Chem.* 285(14):10690-10702.

Braat et al.(2006) "A Phase I Trial With Transgenic Bacteria Expressing Interleukin-10 in Crohn's Disease" *Clinical Gastroenterology and Hepatology* 4:754-759.

Bucarey et al. (Oct. 2005) "The *Salmonella enterica* serovar Typhi tsx gene, encoding a nucleoside-specific porin, is essential for prototrophic growth in the absence of nucleosides" *Infect Immun.* 73(10):6210-9.

Cabrita et al. (2002) "Molecular biology and regulation of nucleoside and nucleobase transporter proteins in eukaryotes and prokaryotes" *Biochem Cell Biol.* 80(5):623-38.

Caldara et al. (Oct. 19, 2007) "ArgR-dependent repression of arginine and histidine transport genes in *Escherichia coli*" K-12. *J Mol Biol.* 373(2):251-67.

Callura et al. (Sep. 7, 2010) "Tracking, tuning, and terminating microbial physiology using synthetic riboregulators" *Proc Natl Acad Sci USA*, 107(36):15898-15903.

Castiglione et al. (Sep. 2009) "The transcription factor DNR from *Pseudomonas aeruginosa* specifically requires nitric oxide and haem for the activation of a target promoter in *Escherichia coli*" *Microbiology*, 155(Pt 9):2838-2844.

Celis (Jun. 1977) "Properties of an *Escherichia coli* K-12 mutant defective in the transport of arginine and ornithine" *J Bacteriol.* 130(3):1234-43.

Cellier et al. (Jun. 1996) "Resistance to intracellular infections: comparative genomic analysis of Nramp" *Trends Genet.* 12(6):201-4.

Chang (2007) "Use of Enzyme Artificial Cells for Genetic Enzyme Defects" In *Artificial Cells: Biotechnology, Nanomedicine, Regenerative Medicine, Blood Substitutes, Bioencapsulation, and Cell/Stem Cell Therapy. Regenerative Medicine, Artificial Cells and Nanomedicine*—vol. 1. Singapore: World Scientific Publishing pp. 147-159.

Charbonneau et al. (Apr. 8, 2020) "Developing a new class of engineered live bacterial therapeutics to treat human diseases" *Nat Commun* 11, 1738 (2020). https://doi.org/10.1038/s41467-020-15508-1.

Chen et al. (Mar. 2006) "High-level Expression of Phenylalanine Ammonia-lyase in *Lactococcus lactis* via Synthesized Sequence Based on Bias Codons" *Chin J Biotech.* 22(2):187-190.

Christodoulou et al. (Nov. 2012) "Enzyme substitution therapy for phenylketonuria delivered orally using a genetically modified probiotic: Proof of principle" 62nd Annual Meeting of the American Society of Human Genetics, Nov. 6-10, 2012, San Francisco, CA; Program No. 166, Nov. 8, 2012.

Chye et al. (Jan. 1987) Transcription control of the aroP gene in *Escherichia coli* K-12: analysis of operator mutants. *J Bacteriol.* 169(1):386-93.

Clarkson et al. (1971) "Diaminopimelic Acid and Lysine Auxotrophs of *Pseudomonas aeruginosa* 8602" *J Gen Microbiol.* 66:161-169.

Coban et al. (2014) "Screening of phenylpyruvic acid producers and optimization of culture conditions in bench scale bioreactors" Bioprocess Biosyst Eng. 37:2343-2352.

Collinson et al. (2015) "Channel crossing: how are proteins shipped across the bacterial plasma membrane?" *Philos Trans R Soc B* 370:20150025 [online]. Retrieve from: http://rstb.royalsocietypublishing.org/, on Jun. 16, 2016 (13 pages).

Costa et al. (May 2015) "Secretion systems in Gram-negative bacteria: structural and mechanistic insights" *Nat Rev Microbiol.* 13(6):343-359.

(56) References Cited

OTHER PUBLICATIONS

Cuevas-Ramos et al. (Jun. 22, 2010) "*Escherichia coli* induces DNA damage in vivo and triggers genomic instability in mammalian cells" *Proc Natl Acad Sci USA*, 107(25):11537-11542.
Danino et al. (May 2015) "Programmable probiotics for detection of cancer in urine" *Sci Transl Med*. 7(289): 289ra84 [online]. Retrieved from: www.sciencetranslational medicine.org, on Jul. 30, 2015 (11 pages).
Den Hengst et al. (May 2006) "Identification and functional characterization of the Lactococcus lactis CodY-regulated branched-chain amino acid permease BcaP (CtrA)" *J Bacteriol*. 188(9):3280-9.
Deutscher (Apr. 2008) "The mechanisms of carbon catabolite repression in bacteria" *Curr Opin Microbiol*. 11(2):87-93.
Dinleyici et al. (Nov. 2014) "*Saccharomyces boulardii* CNCM I-745 in different clinical conditions" *Expert Opin Biol Ther.* 14(11):1593-1609.
Dobbelaere et al. (2003) "Evaluation of nutritional status and pathophysiology of growth retardation in patients with phenylketonuria" *J Inherit Metab Dis*, 26(1):1-11.
Drouault et al. (Jun. 2002)Oral Treatment with *Lactococcus Lactis* Expressing *Syaphylococcus hyicus* Lipase Enhances lipid Digestion in Pigs with Induced Pancreatic Insufficienty *Applied and Envoronmental Microbiology*, pp. 3166-3168.
Duan et al. (2008) "Secretion of Insulinotropic Proteins by Commensal Bacteria: Rewiring the Gut To Treat Diabetes" *Appl. Environ. Microbial*. pp. 7437-7438.
Duarte et al. (Feb. 2010) "PerR vs OhrR: selective peroxide sensing in *Bacillus subtilis*" *Mol Biosyst*. 6(2):316-23.
Dubbs et al. (Oct. 2012) "Peroxide-sensing transcriptional regulators in bacteria" *J Bacteriol*. 194(20):5495-503.
Duerre et al. (Feb. 1975) "L-Amino Acid Oxidases of Proteus rettgeri" *J Bacteriol*. 121(2):656-663.
Dunn et al. (Jul. 1, 2010) "The alternative oxidase (AOX) gene in Vibrio fischeri is controlled by NsrR and upregulated in response to nitric oxide" *Mol Microbiol*. 77(1):44-55.
Durand et al. (Mar. 2010) "Reprogramming of Anaerobic Metabolism by the FnrS Small RNA" *Mol Microbiol*. 75(5):1215-1231. NIH Public Access Author Manuscript; available in PMC Sep. 17, 2010 (28 pages).
Durrer et al. (May 2017) "Genetically engineered probiotic for the treatment of phenylketonuria (PKU); assessment of a novel treatment in vitro and in the PAHenu2 mouse model of PKU" *Plos One*, 12(5): e0176286.
Eiglmeier et al. (Jul. 1989) "Molecular genetic analysis of FNR-dependent promoters" *Mol Microbiol*. 3(7):869-878.
Elkins et al. (Dec. 2001) "Genes encoding bile salt hydrolases and conjugated bile salt transporters in Lactobacillus johnsonii 100-100 and other *Lactobacillus* species" *Microbiology* 147(Pt 12):3403-12.
Estrem et al. (Aug. 1998) "Identification of an UP element consensus sequence for bacterial promoters" *Proc Natl Acad Sci USA*, 95(17):9761-9766.
Folling (1994) "The Discovery of Phenylketonuria" *Act Paediatr Suppl* 407:4-10.
Forbes (Nov. 2010) "Engineering the perfect (bacterial) cancer therapy" *Nat Rev Cancer* 10(11 ):785-94.
Galimand et al. (Mar. 1991) "Positive FNR-like control of anaerobic arginine degradation and nitrate respiration in *Pseudomonas aeruginosa*" *J Bacteriol*. 173(5):1598-1606.
Gardner et al. (2000) "Construction of a genetic toggle switch in *Escherichia coli*" *Nature*, 403:339-342.
Genbank Database Accession No. AAA86752 (Feb. 3, 1996) "amino acid deaminase [Proteus mirabilis HI4320" [online]. National Center for Biotechnology Information (NCBI), U.S. National Library of Medicine; http://www.ncbi.nlm.nih.gov/protein/AAA86752 (1 page).
Genbank Database Accession No. AAH26251.1 (Jul. 15, 2006) "Phenylalanine hydroxylase [*Homo sapiens*]" [online]. National Center for Biotechnology Information (NCBI), U.S. National Library of Medicine; http://www.ncbi.nlm.nih.gov/protein/AAH26251 (2 pages).

Genbank Database Accession No. ABA23593.1 (Jan. 28, 2014) "histidine ammonia-lyase [Anabaena variabilis ATCC 29413]" [online]. National Center for Biotechnology Information (NCBI), U.S. National Library of Medicine; http://www.ncbi.nlm.nih.gov/protein/ABA23593 (2 pages).
Genbank Database Accession No. ACD36582.1 (Aug. 15, 2011) "L-amino acid deaminase [Proteus mirabilis]" [online]. National Center for Biotechnology Information (NCBI), U.S. National Library of Medicine; http://www.ncbi.nlm.nih.gov/protein/ACD36582 (1 page).
Genbank Database Accession No. BAA90864.1 (Feb. 18, 2000) "L-amino acid deaminase [Proteus vulgaris]" [online]. National Center for Biotechnology Information (NCBI), U.S. National Library of Medicine; http://www.ncbi.nlm.nih.gov/protein/BAA90864 (1 page).
Genbank Database Accession No. CAE15566.1 (Feb. 27, 2015) "Histidine ammonia-lyase (histidase) [*Photorhabdus luminescens* subsp. *laumondii* TT01]" [online]. National Center for Biotechnology Information (NCBI), U.S. National Library of Medicine; http://www.ncbi.nlm.nih.gov/protein/CAE15566 (2 pages).
Genbank Database Accession No. EDV65095.1 (Jun. 20, 2008) "arromatic amino acid transport protein AroP [*Escherichia coli* F11]" [online]. National Center for Biotechnology Information (NCBI), U.S. National Library of Medicine; http://www.ncbi.nlm.nih.gov/protein/EDV65095 (2 pages).
Genbank Database Accession No. EU669819.1 (Aug. 15, 2011) "Proteus mirabilis L-amino acid deaminase gene, complete cds" [online]. National Center for Biotechnology Information (NCBI), U.S. National Library of Medicine; http://www.ncbi.nlm.nih.gov/nuccore/EU669819 (2 pages).
Genbank Database Accession No. U35383.1 (Feb. 3, 1996) "Proteus mirabilis amino acid deaminase (aad) gene, complete cds" [online]. National Center for Biotechnology Information (NCBI), U.S. National Library of Medicine; http://www.ncbi.nlm.nih.gov/nuccore/U35383 (2 pages).
Gerdes et al. (Oct. 2006) "Essential genes on metabolic maps" *Curr Opin Biotechnol*. 17(5):448-456.
Gilbert et al. (Jan. 1985) "Molecular cloning of the phenylalanine ammonia lyase gene from Rhodosporidium toruloides in *Escherichia coli* K-12" *J Bacteriol*. 161(1):314-320.
Görke et al. (Aug. 2008) "Carbon catabolite repression in bacteria: many ways to make the most out of nutrients" *Nat Rev Microbiol*, 6(8):613-624.
Gouzy et al. (Feb. 2, 20140) "*Mycobacterium tuberculosis* exploits asparagine to assimilate nitrogen and resist acid stress during infection" *PLOS Pathog*. 10{2}:e1003928. 14 pages.
Grothe et al. (Apr. 1986) "Proline transport and osmotic stress response in *Escherichia coli* K-12" *J Bacteriol*. 166(1):253-9.
Guardiola et al. (Feb. 1974) "Mutations affecting the different transport systems for isoleucine, leucine, and valine in *Escherichia coli* K-12" *J Bacteriol*. 117(2):393-405.
Guardiola et al., (Dec. 1971) "*Escherichia coli* K-12 mutants altered in the transport of branched-chain amino acids" *J Bacteriol*. 108{3}:1034-44.
Guarner et al. (Feb. 8, 2003) "Gut flora in health and disease" *Lancet* 361 (9356):512-9.
Haney et al. (Jan. 1992) "Lrp, a leucine-responsive protein, regulates branched-chain amino acid transport genes in *Escherichia coli*" *J Bacteriol*. 174(1):108-15.
Hasegawa et al. (Sep. 15, 1998) "Activation of a consensus FNR-dependent promoter by DNR of *Pseudomonas aeruginosa* in response to nitrite" *FEMS Microbiol Lett*. 166(2):213-217.
He et al. (Apr. 13, 1999) "Noninvasive measurement of anatomic structure and intraluminal oxygenation in the gastrointestinal tract of living mice with spatial and spectral EPR imaging" *Proc Natl Acad Sci USA*, 96(8):4586-4591.
Heatwole et al. (Jun. 1991) The tryptophan-specific permease gene, mtr, is differentially regulated by the tryptophan and tyrosine repressors in *Escherichia coli* K-12 *J Bacteriol*. 173(11):3601-4.
Higgins (1992) "ABC transporters: from microorganisms to man" *Annu Rev Cell Biol*. 8:67-113.
Ho et al. (2014) "Phenylkentonuria: translating research into novel therapies" *Transl Pediatr.* 3:49-62.

(56) References Cited

OTHER PUBLICATIONS

Hoeks et al. (Jan. 2009) "Adult issues in phenylketonuria" *Neth J Med.* 67(1):2-7.
Hoeren et al. (Nov. 15, 1993) "Sequence and expression of the gene encoding the respiratory nitrous-oxide reductase from *Paracoccus denitrificans*" *Eur J Biochem.* 218(1):49-57.
Horsburgh et al. (Jun. 2002) "MntR modulates expression of the PerR regulon and superoxide resistance in *Staphylococcus aureus* through control of manganese uptake" *Mol Microbiol.* 44(5):1269-86.
Horsburgh et al. (May 2004) "PheP, a putative amino acid permease of *Staphylococcus aureus*, contributes to survival in vivo and during starvation" *Infect Immun.* 72(5):3073-6.
Hosseini et al. (May 2011) "Propionate as a health-promoting microbial metabolite in the human gut" *Nutr Rev.* 69(5):245-258.
Hou et al. (Oct. 2015) "Production of phenylpyruvic acid from L-phenylalanine using an L-amino acid deaminase from *Proteus mirabilis*: comparison of enzymatic and whole-cell biotransformation approaches" *Appl Microbiol Biotechnol.* 99(20):8391-8402.
Hu et al. (Nov. 15, 1998) "Membrane topology of the *Escherichia coli* gamma-aminobutyrate transporter: implications on the topography and mechanism of prokaryotic and eukaryotic transporters from the APC superfamily" *Biochem J.* 336 (Pt 1):69-76.
Huibregtse et al.(2012) "Genetically Modified *Lactococcus lactis* for Delivery of Human Interleukin-10 to Dendritic Cells" *Gastroenterology Research and Practice*, vol. 2012, Article ID 639291 (7 pages).
International Patent Application No. PCT/US2016/032562, filed May 13, 2016, by Synlogic, Inc.: International Search Report and Written Opinion; dated Aug. 22, 2016.
International Patent Application No. PCT/US2016/062369, filed Nov. 16, 2016, by Synlogic, Inc.: International Search Report and Written Opinion; dated Mar. 10, 2017.
International Patent Application No. PCT/US2016/032565, filed May 13, 2016, by Synlogic, Inc.: International Search Report and Written Opinion; dated Aug. 5, 2016.
International Patent Application No. PCT/US2018/038840, filed Jun. 21, 2018, by Synlogic Operating Company, Inc. International Search Report and Written Opinion; dated Nov. 21, 2018.
Isabella et al. (Jan. 2009) "Functional analysis of NsrR, a nitric oxide-sensing Rrf2 repressor in Neisseria gonorrhoeae" *Mol Microbiol.* 71(1):227-39.
Isabella et al. (Jan. 20, 2011) "Deep sequencing-based analysis of the anaerobic stimulon in *Neisseria gonorrhoeae*" *BMC Genomics*, 12:51 (24 pages).
Isabella et al. (Oct. 2011) "Identification of a conserved protein involved in anaerobic unsaturated fatty acid synthesis in Neiserria gonorrhoeae: implications for facultative and obligate anaerobes that lack FabA" *Mol Microbiol.* 82(2):489-501.
Ivanovska et al. (2014) "Pediatric Drug Formulations: A Review of Challenges and Progress" *Pediatrics*, 134:361-372.
Jack et al. (Aug. 2000) "The amino acid/polyamine/organocation (APC) superfamily of transporters specific for amino acids, polyamines and organocations" *Microbiology* 146 (Pt 8):1797-814.
Jennings et al. (Jan. 1995) "Cloning and molecular analysis of the *Salmonella enterica* ansP gene, encoding an L-asparagine permease" *Microbiology* 141 (Pt 1): 141-6.
Jensen et al. (2015) "Manganese Transport, Trafficking and Function in Invertebrates" Issues in Toxicology No. 22, Manganese in Health and Disease. Lucio G. Costa (Ed.). The Royal Society of Chemistry. Chapter 1, pp. 1-33(2015).
Jia, X. et al. (2000) "A new strategeutics of gene therapy for hyperphenylalaninemia rats" *National Medical Journal of China*, 2000 Issue 06, English Abstract. [online]. Retrieved from: http://en.cnki.com.cn/Article_en/CJFDTOTAL-ZHYX200006029.htm, on Jan. 30, 2017 (3 pages).
Jia, X. et al. (2000) "A new strategeutics of gene therapy for hyperphenylalaninemia rats" *National Medical Journal of China*, 2000 Issue 06. English translation, Phoenix Translations, Elgin, TX: Nov. 2015 (15 pages).

Jolkver et al. (Feb. 2009) "Identification and characterization of a bacterial transport system for the uptake of pyruvate,propionate, and acetate in Corynebacterium glutamicum" *J Bacteriol.* 191(3):940-8.
Kadaba et al. (Jul. 11, 2008) "The high-affinity *E. coli* methionine ABC transporter: structure and allosteric regulation" *Science.* 321(5886):250-3.
Kadner et al. (Aug. 1974) "Methionine transport in *Escherichia coli* physiological and genetic evidence for two uptake systems" *J Bacteriol.* 119(2):401-9.
Kang et al. (2010) "Converting an injectable protein therapeutic into an oral form: Phenylalanine ammonia lyase for phenylketonuria" *Mol Genet Metabol.* 99:4-9.
Kehres et al. (Jun. 2002) "SilABCD Is the Alkaline Mn2+ Transporter of *Salmonella enterica* Serovar Typhimurium" *Journal of Bacteriology* 184(12):3159-3166.
Kobe et al. (Jun. 1997) "Regulation and crystallization of phosphorylated and dephosphorylated forms of truncated dimeric phenylalanine hydroxylase" *Protein Sci.* 6(6):1352-1357.
Koo et al. (Jun. 2, 2003) "A reducing system of the superoxide sensor SoxR in *Escherichia coli*" *EMBO J* 22(11):2614-22.
Kwok et al. (Jan. 29, 1985) "Nucleotide sequence of a full-length complementary DNA clone and amino acid sequence of human phenylalanine hydroxylase" *Biochemistry*, 24(3): 556-561.
Landick et al., (Jul. 15, 1985) "The complete nucleotide sequences of the *Escherichia coli* LIV-BP and LS-BP genes. Implications for the mechanism of high-affinity branched-chain amino acid transport" *J Biol Chem.* 260(14):8257-61.
Lee et al. (2011) "Cumulative No. of Cell Divisions as a Meaningful Timescale for Adaptive Laboratory Evolution of *Escherichia coli*" *PLoS One*, 6:e26172, http://dx.doi.org/10.1371/journal.pone.0026172 (8 pages).
Lee et al. (May 17, 2012) "Systems metabolic engineering of microorganisms for natural and non-natural chemicals" *Nat Chem Biol.* 8(6):536-46.
Leonard, "Disorders of the urea cycle and related enzymes" in *Inborn Metabolic Diseases*, 4th ed. Heidelberg: Springer Medizin Verlag, 2006; pp. 263-272.
Levanon et al. (2005) "Effect of oxygen on the *Escherichia coli* ArcA and FNR regulation systems and metabolic responses" *Biotech. Bioeng.* pp. 556-564.
Li et al. (Apr. 13, 2001) "Monomeric state and ligand binding of recombinant GABA transporter from *Escherichia coli*" *FEBS Lett.* 494(3):165-9.
Liu et al. (2002) "Study on a Novel Strategy to Treatment of Phenylketonuria" *Art Cells, Blood Subs, and Immob Biotech.* 30(4):243-257.
Longo et al. (Jul. 5, 2014) "Phase 1 Trial of Subcutaneous rAvPAL-PEG in Subjects with Phenylketonuria" *Lancet*, 384(9937):37-44. HHS Public Access Author Manuscript; available in PMC Jul. 5, 2015 (18 pages).
Lopez et al. (Dec. 2015) "Synthetic Auxotrophs with Ligand-Dependent Essential Genes for a BL21(DE3) Biosafety Strain" *ACS Synthetic Biology*, 4(12): 1279-1286.
Ma et al. (2014) Oral Administration of Recombinant Lastococcus Lactis Expressing HSP65 and Tandemly Repeated P277 Reduces the Incidence of Type 1 Diabetes in Non-Obese Diabetic Mice PLoS One 9:105701.
MacDonald et al. (2007) "A modern view of phenylalanine ammonia lyase" *Biochem Cell Biol.* 85(3):273-282.
MacLeod et al. (Jun. 2010) "Nutritional Management of Phenylketonuria" *Ann Nestle Eng.* 68(2):58-69.
Marbach et al. (2012) "lac operon Indcution in *Escherichia coli*: Systematic Comparison of IPTG and TMG induction and influence of Transacetylase LacA" *Journal of Biotechnology*, 157:82-88.
Matano et al. (Jun. 2014) "Engineering of Corynebacterium glutamicum for growth and L-lysine and lycopene production from N-acetyl-glucosamine" *Appl Microbiol Biotechnol.* 98(12):5633-43.
McAllister et al. (Aug. 2004) "Molecular analysis of the psa permease complex of *Streptococcus pneumoniae*" *Mol Microbiol.* 53(3): 889-901.
McEwen et al. (Mar. 2013) "Engineering Synechococcus elongatus PCC 7942 for continuous growth under diurnal conditions" *Appl Environ Microbiol.* 79(5):1668-75.

(56) References Cited

OTHER PUBLICATIONS

Meadow et al. (1959) "Biosynthesis of diaminopimelic acid and lysine in *Escherichia coli*" *Biochem J.* 72(3):396-400.
Mengesha, A. et al. (2006) "Development of a flexible and potent hypoxia-inducible promoter for tumor-targeted gene expression in attenuated *Salmonella*" *Cancer Biology & Therapy*, 5:9, 1120-1128.
Menzel et al. (Sep. 2, 19815) "Purification of the putA gene product. A bifunctional membrane-bound protein from *Salmonella typhimurium* responsible for the two-step oxidation of proline to glutamate" *J Biol Chem.* 256(18):9755-61.
Merlin et al. (Oct. 2002) "The *Escherichia coli* metD locus encodes an ABC transporter which includes Abe (MetN), YaeE (MetI), and YaeC (MetQ)" *J Bacteriol.* 184(19):5513-7.
Mironov et al. (Jul. 15, 1999) "Computer analysis of transcription regulatory patterns in completely sequenced bacterial genomes" *Nucleic Acids Res.* 27(14):2981-9.
Moffitt et al. (Jan. 3, 20070) "Discovery of two cyanobacterial phenylalanine ammonia lyases: kinetic and structural characterization" *Biochemistry*, 46(4):1004-1012.
Moore et al. (Nov. 3, 2006) "Regulation of FNR dimerization by subunit charge repulsion" *J Biol Chem.* 281(44):33268-33275.
Nazos et al. (Sep. 1985) "Identification of livG, a membrane-associated component of the branched-chain amino acid transport in *Escherichia coli*" *J Bacteriol.* 163(3):1196-202.
Nazos et al. (May 1986) Cloning and characterization of livH, the structural gene encoding a component of the leucine transport system in *Escherichia coli. J Bacteriol.* 166(2):565-73.
Nji et al. (Oct. 2014) Cloning, expression, purification, crystallization and preliminary X-ray diffraction of a lysine-specific permease from Pseudomonas aeruginosa *Acta Crystallogr F Struct Biol Commun.* 70(Pt 10):1362-7.
Norholm et al. (Aug. 2001) "Specificity and topology of the *Escherichia coli* xanthosine permease, a representative of the NHS subfamily of the major facilitator superfamily" *J Bacteriol.* 183(16):4900-4.
Nougayrede et al. (Aug. 11, 2006) "*Escherichia coli* induces DNA double-strand breaks in eukaryotic cells" *Science*, 313(5788):848-851.
Ogawa et al. (Dec. 1997) "Isolation and characterization of an *Escherichia coli* mutant lacking the major serine transporter, and cloning of a serine transporter gene" *J Biochem.* 122(6):1241-5.
Ogawa et al. (Dec. 1998) "Cloning and expression of the gene for the Na+-coupled serine transporter from *Escherichia coli* and characteristics of the transporter" *J Bacteriol.* 180(24):6749-52.
Oh et al. (Oct. 21, 1994) "Structural basis for multiple ligand specificity of the periplasmic lysine-, arginine-, ornithine-binding protein" *J Biol Chem.* 269(42):26323-30.
Ohnishi et al. (Aug. 1988) "Cloning and nucleotide sequence of the brnQ gene, the structural gene for a membrane-associated component of the LIV-II transport system for branched-chain amino acids in *Salmonella typhimurium*" *Jpn J Genet.* 63(4 ):343-57.
Olier et al. (Nov.-Dec. 2012) "Genotoxicity of *Escherichia coli* Nissle 1917 strain cannot be dissociated from its probiotic activity" *Gut Microbes*, 3(6):501-509.
Ortuno-Olea et al. (Aug. 15, 2000) "The L-asparagine operon of Rhizobium elli contains a gene encoding an atypical asparaginase" *FEMS Microbiol Lett.* 189(2):177-82.
Ostrovsky De Spicer et al. (May 1, 1993) "PulA protein, a membrane-associated flavin dehydrogenase, acts as a redox-:lependent transcriptional regulator" *Proc Natl Acad Sci U S A.* 90(9):4295-8.
Oxender et al. (Mar. 1980) "Structural and functional analysis of cloned DNA containing genes responsible for branched-chain amino acid transport in *Escherichia coli*" *Proc Natl Acad Sci US A.* 77(3):1412-6.
Pascalle et al. (1996) "Controlled Gene Expression Systems for Lactococcus lactis with the Food-Grade Inducer Nisin" Applied and Environmental Microbiology p. 3662-3667.
Pelmont et al. (1972) "L-aminoacide oxydases des enveloppes de *Proteus mirabilis*: propriétés générales (L-amino acid oxidases of *Proteus mirabilis*: general properties)" *Biochimie* 54(10):1359-1374 (French; English summary on p. 1359).
Pi et al. (Jun. 1991) "Cloning and sequencing of the pheP gene, which encodes the phenylalanine-specific transport system of *Escherichia coli*" *J Bacteriol.* 173(12):3622-3629.
Pi et al. (May 1996) "Topology of the phenylalanine-specific permease of *Escherichia coli*" *J Bacteriol.* 178(9):2650-2655.
Pi et al. (Nov. 1998) "Functional consequences of changing proline residues in the phenylalanine-specific permease of *Escherichia coli*" *J Bacteriol.* 180(21):5515-5519.
Porcheron et al. (Dec. 5, 2013) "Iron, copper, zinc, and manganese transport and regulation in pathogenic Enterobacteria: correlations between strains, site of infection and the relative importance of the different metal transport systems for virulence" *Front Cell Infect Microbiol.* 3:90.
Pugsley (Mar. 1993) "The complete general secretory pathway in gram-negative bacteria" *Microbiol Rev.* 57(1):50-108.
Purcell et al. (2013) "Towards a whole-cell modeling approach for synthetic biology" *Chaos*, 23(2):025112 (8 pages).
Quay et al. (Mar. 1977) "Role of transport systems in amino acid metabolism: leucine toxicity and the branched-chain amino acid transport systems" *J Bacteriol.* 129(3):1257-65.
Que et al. (Mar. 2000)"Manganese homeostasis in Bacillus subtilis is regulated by MntR, a bifunctional regulator related to the diphtheria toxin repressor family of proteins" *Mol Microbiol.* 35(6):1454-68.
Rahmanian et al. (Dec. 1973) "Multiplicity of leucine transport systems in *Escherichia coli* K-12" *J Bacteriol.* 116(3):1258-66.
Ray et al. (Nov. 15, 1997) "The effects of mutation of the anr gene on the aerobic respiratory chain of *Pseudomonas aeruginosa*" *FEMS Microbiol Lett.* 156(2):227-232.
Rees et al. (Mar. 2009) "ABC transporters: The power to change" *Nat Rev Mol Cell Biol.* 10(3):218-227.
Reeves et al. (Apr. 2015) "Engineering *E. coli* into a protein delivery system for mammalian cells" *ACS Synth Biol.* Just Accepted Manuscript, DOI: 10.1021/acssynbio.5b00002 [online]. Retrieved from: http://pubs.acs.org, on Apr. 20, 2015 (26 pages). Final publication in vol. 5, pp. 644-654.
Refseq Database Accession No. NP_415108.1 (Dec. 16, 2014) "phenylalanine transporter [*Escherichia coli* str. K-12 substr. MG1655]" [online]. National Center for Biotechnology Information (NCBI), U.S. National Library of Medicine; http://www.ncbi.nlm.nih.gov/protein/NP_415108 (3 pages).
Refseq Database Accession No. WP_011146484.1 (May 24, 2013) "histidine ammonia-lyase [Photorhabdus luminescens]" [online]. National Center for Biotechnology Information (NCBI), U.S. National Library of Medicine; http://www.ncbi.nlm.nih.gov/protein/WP_011146484 (1 page).
Reister et al. (Oct. 10, 2014) "Complete genome sequence of the Gram-negative probiotic *Escherichia coli* strain Nissle 1917" *J Biotechnol.* 187:106-107.
Rembacken et al. (Aug. 21, 1999) "Non-pathogenic *Escherichia coli* versus mesalazine for the treatment of ulcerative colitis: a randomised trial" *Lancet*, 354(9179):635-639.
Rigel et al. (2008) "A new twist on an old pathway—accessory secretion systems" *Mol Microbiol.* 69(2):291-302.
Rodionov et al. (Dec. 1, 2003) "Regulation of lysine biosynthesis and transport genes in bacteria: yet another RNA riboswitch?" *Nucleic Acids Res.* 31(23):6748-57.
Rosen (Jun. 10, 1971) "Basic amino acid transport in *Escherichia coli*" *J Biol Chem.* 246(11 ):3653-62.
Ryan et al. (May 2007) "The uncoupled chloride conductance of a bacterial glutamate transporter homolog" *Nat Struct Mol Biol.* 14(5):365-71.
Ryan et al. (Mar. 2009) "Bacterial delivery of a novel cytolysin to hypoxic areas of solid tumors" *Gene Ther.* 16(3):329-39.
Saier Jr. (2006) "Protein Secretion and Membrane Insertion Systems in Gram-Negative Bacteria" *J Membrane Biol.* 214:75-90.
Saier Jr., M.H. (2006) "Protein Secretion Systems in Gram-Negative Bacteria. Gram-negative bacteria possess many protein secretion-membrane insertion systems that apparently evolved independently" *Microbe*, 1(9):414-419.

(56) References Cited

OTHER PUBLICATIONS

Salmon et al. (Aug. 8, 2003) "Global gene expression profiling in *Escherichia coli* K12. The effects of oxygen availability and FNR" *J Biol Chem.* 278(32):29837-29855.
Sarkissian et al. (Mar. 1999) "A different approach to treatment of phenylketonuria: Phenylalanine degradation with recombinant phenylalanine ammonia lyase" *Proc Natl Acad Sci USA*, 96(5):2339-2344.
Sarkissian et al. (Jun. 2007) "Quantitation of phenylalanine and its trans-cinnamic, benzoic and hippuric acid metabolites in biological fluids in a single GC-MS analysis" *J Mass Spectrom.* 42(6):811-817.
Sarkissian et al. (Nov. 2011) "Evaluation of orally administered PEGylated phenylalanine ammonia lyase in mice for the treatment of Phenylketonuria" *Mol Genet Metab.* 104(3): 249-254. NIH Public Access Author Manuscript; available in PMC Nov. 1, 2012 (15 pages).
Sat et al. (Mar. 2003) "The *Escherichia coli* mazEF suicide module mediates thymineless death" *J Bacteriol.* 185(6):1803-1807.
Sawers (Jun. 1991) "Identification and molecular characterization of a transcriptional regulator from Pseudomonas aeruginosa PAO1 exhibiting structural and functional similarity to the FNR protein of *Escherichia coli*" *Mol Microbiol*, 5(6):1469-1481.
Schultz (Jul. 2008) "Clinical use of *E. coli* Nissle 1917 in inflammatory bowel disease" *Inflamm Bowel Dis*, 14(7):1012-1018.
Seep-Feldhaus et al. (Dec. 1991) "Molecular analysis of the Corynebacterium glutamicum lysI gene involved in lysine uptake" Mol Microbiol. 5(12):2995-3005.
Shao et al. (Jun. 1, 19945) "Sequencing and characterization of the sdaC gene and identification of the sdaCB operon in *Escherichia coli* K12" *Eur J Biochem.* 222(3):901-7.
Sheehan et al. (Mar. 2006) "Heterologous expression of BetL, a belaine uptake system, enhances the stress tolerance of laclobacillus salivarius UCC118" *Appl Environ Microbiol.* 72(3):2170-7.
Silhavy et al. (2010) "The bacterial cell envelope" *Cold Spring Harb Perspect Biol.* 2, a000414 (17 pages).
Sleator et al. (2009) "Rational Design of Improved Pharmabiotics" *Journal of Biomedicine and Biotechnology*, vol. 9 (7pages).
Slotboom et al. (Jun. 1999) "Structural features of the glutamate transporter family" *Microbiol Mol Biol Rev.* 63(2):293-307.
Sonnenborn et al. (2009) "The non-pathogenic *Escherichia coli* strain Nissle 1917—features of a versatile probiotic" *Microbial Ecology in Health and Disease*, 21:122-158.
Stanley et al. (Oct. 2003) "Acute infection and macrophage subversion by *Mycobacterium tuberculosis* require a specialized secretion system" *PNAS*, 100(22):13001-13006.
Steele (Jun. 1986) "Blood-brain barrier transport of the alpha-keto acid analogs of amino acids" *Fed Proc.* 45(7):2060-2064.
Steffes et al. (May 1992) "The lysP gene encodes the lysine-specific permease" *J Bacteriol.* 174(10):3242-9.
Steidler et al.(Jul. 1, 2003) "Biological containment of genetically modified Lactococcus lactis for intestinal delivery of human interleukin 10" *Nature Biotechnology*, 21(7)785-789.
Strauch et al.(Feb. 1985) "Oxygen Regulation in *Salmonella typhimurium*" *J. Bacteriol.* 161(2):673-680.
Sun et al. (2005) "Genomic peculiarity of coding sequences and metabolic potential of probiotic *Escherichia coli* strain Nissle 1917 inferred from raw genome data" *J. Biotechnol.* 117(2):147-61.
Takahashi et al. (Sep. 2015) "Multiple Functions of Glutamate Uptake via Meningococcal GltT-GltM L-Glutamate ABC Transporter in Neisseria meningitidis Internalization into Human Brain Microvascular Endothelial Cells" Infect Immun. 83(9):3555-67.
Tolner et al. (Oct. 1992) "Characterization and functional expression in *Escherichia coli* of the sodium/proton/glutamate symport proteins of Bacillus stearothermophilus and Bacillus caldotenax" *Mol Microbiol.* 6(19):2845-56.
Trip et al. (Jan. 2013;) "Cloning, expression, and functional characterization of secondary amino acid transporters of Lactococcus lactis" *J Bacteriol.* 195(2):340-50.
Trotschel et al. (Jun. 2005) "Characterization of methionine export in Corynebacterium glutamicum" *J Bacteriol.* 187 (11):3786-94.

Trunk et al. (Jun. 2010) "Anaerobic adaptation in *Pseudomonas aeruginosa*: definition of the Anr and Dnr regulons" *Environ Microbiol.* 12(6):1719-1733.
U.S. Appl. No. 62/183,935, filed Jun. 24, 2015, by Kotula et al.
U.S. Appl. No. 62/184,811, filed Jun. 25, 2015, by Falb et al.
U.S. Appl. No. 62/263,329, filed Dec. 4, 2015, by Kotula et al.
Ukena et al. (Dec. 12, 2007) "Probiotic *Escherichia coli* Nissle 1917 inhibits leaky gut by enhancing mucosal integrity" *PLoS One*, 2(12):e1308. [online] DOI: 10.1371/journal.pone.0001308 (11 pages).
Unden et al.(2002) "Control of FNR Function of *Escherichia coli* by $O_2$ and Reducing Conditions" *J. Mol. Microbiol. Biotechnol.* 4(3):263-268.
Unden et al. (Jul. 4, 1997) "Alternative respiratory pathways of *Escherichia coli*: energetics and transcriptional regulation in response to electron acceptors" *Biochim Biophys Acta*, 1320(3):217-234.
Uniprotkb/Swiss-Prot Database Accession No. Q3M5Z3.1 (Nov. 11, 2015) "RecName: Full=Phenylalanine ammonia-lyase" National Center for Biotechnology Information (NCBI), U.S. National Library of Medicine, http://www.ncbi.nlm.nih.gov/protein/Q3M5Z3 (7 pages).
Vaziri et al. (Mar. 2013) Use of molecular modelling to probe the mechanism of the nucleoside transporter NupG*Mol Membr Biol.* 30(2):114-28.
Vockley et al. (Feb. 2014) "Phenylalanine hydroxylase deficiency: diagnosis and management guideline" *Genet Med.* 16(2):188-200.
Wanner et al. (Jan. 1995) "The phenylalanine ammonia-lyase gene family in *Arabidopsis thaliana*" *Plant Mol Biol.* 27(2):327-338.
Weisser et al. (Jun. 1995) "Functional expression of the glucose transporter of Zymomonas mobilis leads to restoration of glucose and fructose uptake in *Escherichia coli* mutants and provides evidence for its facilitator action" *J Bacteriol.* 177(11):3351-4.
Widhalm et al. "Identification of a Plastidial Phenylalanine Exporter the Influences Flux Distribution Through the Phenylalanine Biosynthetic Network" *Nature Comomunications* pp. 1-11.
Williams et al. (Aug. 2005) "The gene stlA encodes a phenylalanine ammonia-lyase that is involved in the production of a stilbene antibiotic in *Photorhabdus luminescens* TT01" *Microbiology*, 151 (Pt 8):2543-2550.
Willis et al. (Sep. 1975) "L-asparagine uptake in *Escherichia coli*" *J Bacteriol.* 123(3):937-45.
Winteler et al. (Mar. 1996) "The homologous regulators ANR of *Pseudomonas aeruginosa* and FNR of *Escherichia coli* have overlapping but distinct specificities for anaerobically inducible promoters" *Microbiology*, 142(Pt 3):685-693.
Wissenbach et al. (Jun. 1993) "Physical map location of the new artPIQMJ genes of *Escherichia coli*, encoding a periplasmic arginine transport system" J Bacteriol. 175(11):3687-8.
Wissenbach et al. (Aug. 1995) "A third periplasmic transport system for L-arginine in *Escherichia coli*: molecular characterization of the artPIQMJ genes, arginine binding and transport" *Mol Microbiol.* 17(4):675-86.
Wolken et al. (Mar. 2006) "The mechanism of the tyrosine transporter TyrP supports a proton motive tyrosine decarboxylation pathway in Lactobacillus brevis" *J Bacteriol.* 188(6):2198-206.
Wood (Jun. 25, 1975) "Leucine transport in *Escherichia coli*. The resolution of multiple transport systems and their coupling to metabolic energy" *J Biol Chem.* 250(12):4477-85.
Wright et al. (Mar. 20, 2015) "GeneGuard: A modular plasmid system designed for biosafety" *ACS Synth Biol.* 4(3):307-316.
Wu et al. (Oct. 7, 2015) "Direct regulation of the natural competence regulator gene tfoX by cyclic Amp (Camp) and cAMP receptor protein in *Vibrios*" *Sci Rep.* 5:14921 (15 pages).
Xiang et al. (Jun. 2005) "Biochemical characterization of a prokaryotic phenylalanine ammonia lyase" *J Bacteriol.* 187(12):4286-4289.
Xingyuan et al. (1999) "A New Strategeutics of Gene Therapy for Hyperphenylalaninemia Rats" Beijing Red-Cross Chaoyang Hospital, Capital University of Medical Sciences Beijing, 100020: China.
Yamato et al. (Apr. 1979) "Genetic and biochemical studies of transport systems for branched-chain amino acids in *Escherichia coli*" *J Bacteriol.* 138(1):24-32.

(56) References Cited

OTHER PUBLICATIONS

Yamato et al. (Oct. 1980) "Genetic and biochemical studies of transport systems for branched-chain amino acids in *Escherichia coli* K-12: isolation and properties of mutants defective in leucine-repressible transport activities" *J Bacteriol.* 144(1):36-44.

Yanofsky et al. (Oct. 1991) "Physiological studies of tryptophan transport and tryptophanase operon induction in *Escherichia coli*" *J Bacteriol.* . . 173(19):6009-17.

Zaprasis et al. (Jan. 2015) "Uptake of amino acids and their metabolic conversion into the compatible solute proline confers osmoprotection to Bacillus subtilis" *Appl Environ Microbiol.* 81(1):250-9.

Zhang et al. (2009) "DEG 5.0, a database of essential genes in both prokaryotes and eukaryotes" *Nucl Acids Res.* 37(suppl. 1): D455-D458.

Zhou et al. (Apr. 1999) "Salmonella typhimurium encodes a putative iron transport system within the centisome 63 pathogenicity island" *Infect Immun.* 67(4):1974-81.

Archer et al. (2012) "Engineered *E. coli* That Detect and Respond to Gut Inflammation through Nitric Oxide Sensing" ACS Synth. Biol. 1(10): 451-457.

Bobay et al., "Pervasive Domestication of Defective Prophages by Bacteria", Proc. Natl. Acad. Sci. USA, 2004, vol. 111, No. 33, pp. 12127-12132.

Brophy et al. (2014) "Principles of Genetic Circuit Design" Nat. Methods 11(5): 508-520.

Cosgriff et al. (2000) A Study of AroP-PheP Chimeric Proteins and Identification of a Residue Involved in Tryptophan Transport J. Bacteriol. 182(8): 2207-2217.

Ou et al., Genetic Engineering of Probiotic Escherichia Coli Nissle 1917 For Clinical Application, Appl Microbiol Biotochnol, 2016, vol. 100, pp. 8693-8699.

Roquet et al. (2014 ) "Digital and analog gene circuits for biotechnology" Biotechnol. J 9(5): 597-608, DOI: 10.1002 / biot. 201300258.

Siuti et al. (2014) "Engineering genetic circuits that compute and remember" Nat Protoc 9, 1292-1300, DOI: 10.1038 / nprot.2014. 089.

Van Der Meer et al. (2010) "Where microbiology meets microengineering: design and applications of reporter bacteria" Nat Rev Microbiol, 8(7): 511-522, DOI: 10.1038 / nrmicro2392.

Zhang et al., Construction of Prophage CP-933Y Deletion Mutant Strain of Enter-hemorrhagic *E.coli* O157:H7. Lett. Biotech. Nov. 2016;27(6):804-7.

* cited by examiner

TOTAL : 5 PROPHAGE REGIONS HAVE BEEN IDENTIFIED, OF WHICH 3 REGIONS ARE INTACT, 1 REGIONS ARE INCOMPLETE, 1 REGIONS ARE QUESTIONABLE.

| REGION | REGION_LENGTH | COMPLETENESS | SCORE | #CDS | REGION_POSITION | POSSIBLE_PHAGE | GC_PERCENTAGE | DETAIL |
|---|---|---|---|---|---|---|---|---|
| 1 | 18.8Kb | INTACT | 110 | 32 | 241563-260441 | PHAGE_Stx2_c_1717_NC_011357,...... | 50.41% | DETAIL |
| 2 | 52.4Kb | INTACT | 150 | 69 | 1325883-1378287 | PHAGE_Entero_lambda_NC_001416,...... | 49.66% | DETAIL |
| 3 | 59Kb | INTACT | 150 | 58 | 2023188-2082243 | PHAGE_Entero_c_1_NC_019706,...... | 51.33% | DETAIL |
| 4 | 13Kb | INCOMPLETE | 10 | 28 | 3405101-3418180 | PHAGE_Cronob_vB_CsaM_GAP32_NC_019401,...... | 54.22% | DETAIL |
| 5 | 22.4Kb | QUESTIONABLE | 80 | 20 | 5321242-5343732 | PHAGE_Shigel_SfIV_NC_022749,...... | 42.56% | DETAIL |

PROPHAGE REGION: 3
NUMBER OF CDS: 60
LOCATION: FROM 2023188 TO 2082256 (59069 bps)
PREDICTED STATUS: INTACT PROPHAGE
GC CONTENT: 51.33%

PHAGE 3 DIAGRAM

SCORE 150

IDENTIFIED CDS TYPES:
- 1 LYSIS
- 2 TERMINASE
- 3 PORTAL
- 4 PROTEASE
- 5 COAT
- 6 TAIL SHAFT
- 7 ATTACHMENT SITE
- 8 INTERGRASE
- 9 OTHER PHAGE-LIKE PROTEIN
- 10 HYPOTHETICAL PROTEIN
- 11 OTHER
- 12 TRANSPOSASE
- 13 TAIL FIBER
- 14 PLATE
- 15 tRNA

FIG. 4

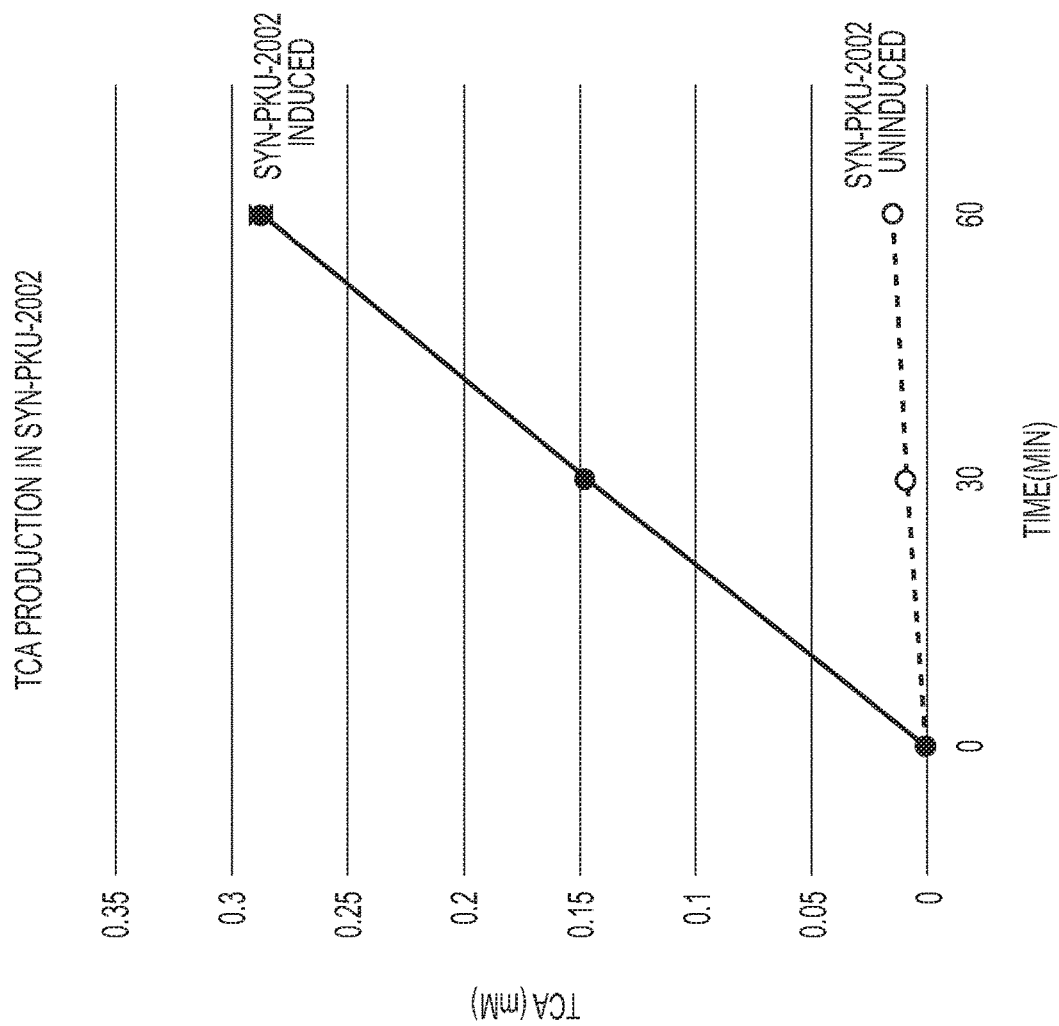

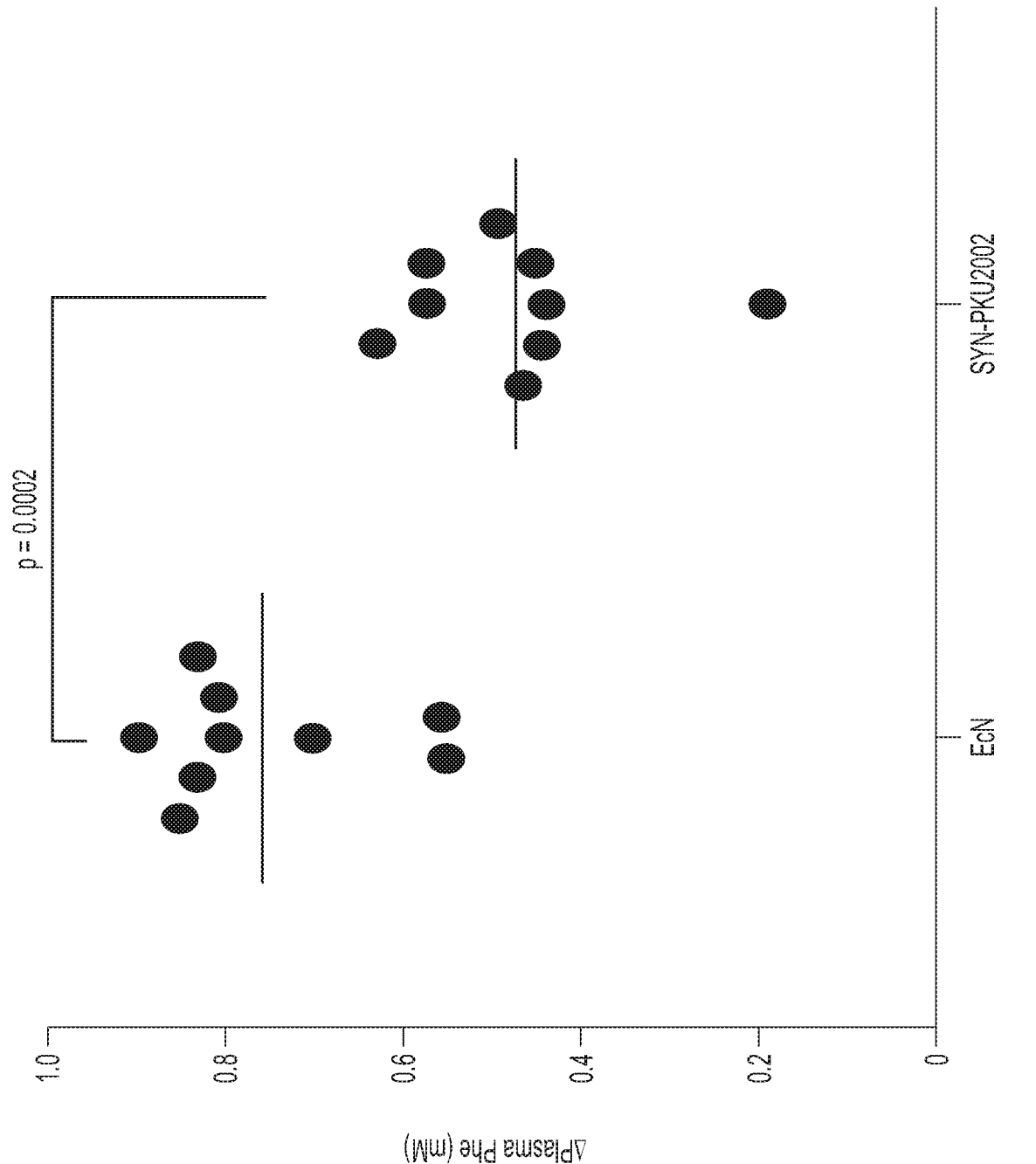

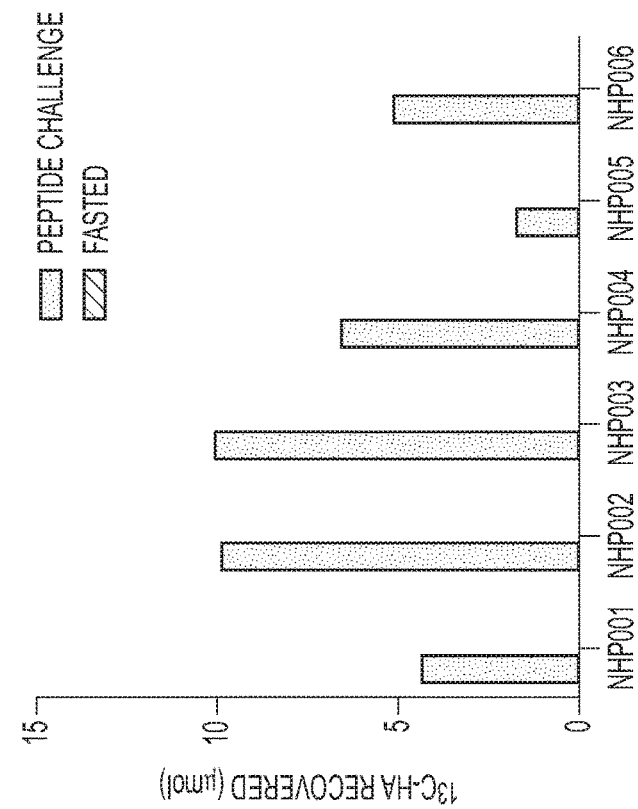
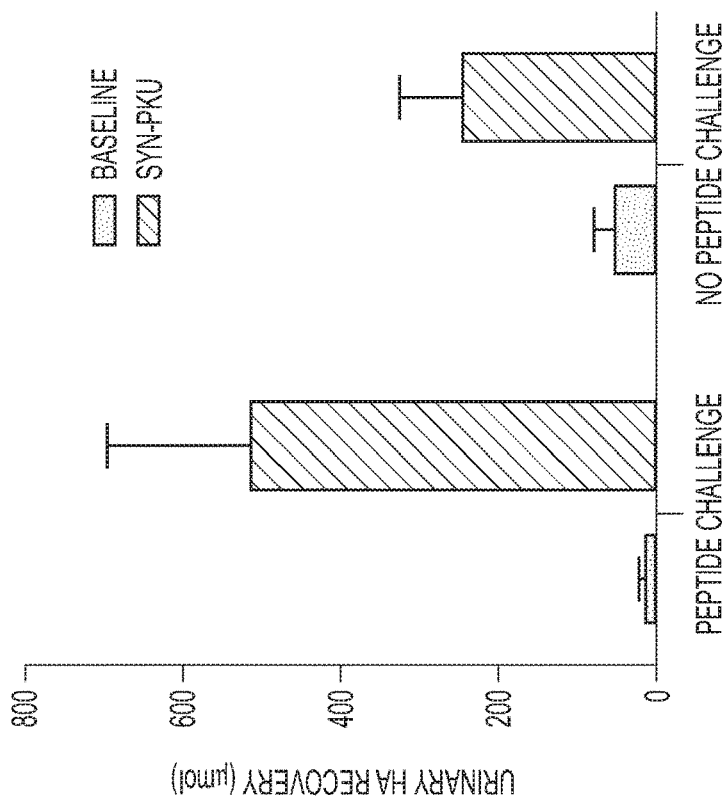
FIG. 22B
FIG. 22A

```
                        SEQUENCE LISTING

<160> NUMBER OF SEQ ID NOS: 304

<210> SEQ ID NO 1
<211> LENGTH: 567
<212> TYPE: PRT
<213> ORGANISM: Anabaena variabilis

<400> SEQUENCE: 1

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
```

-continued

```
        145                 150                 155                 160
Glu Phe Gly Ser Ile Gly Ala Ser Gly Asp Leu Val Pro Leu Ser Tyr
                165                 170                 175
Ile Thr Gly Ser Leu Ile Gly Leu Asp Pro Ser Phe Lys Val Asp Phe
                180                 185                 190
Asn Gly Lys Glu Met Asp Ala Pro Thr Ala Leu Arg Gln Leu Asn Leu
                195                 200                 205
Ser Pro Leu Thr Leu Leu Pro Lys Glu Gly Leu Ala Met Met Asn Gly
        210                 215                 220
Thr Ser Val Met Thr Gly Ile Ala Ala Asn Cys Val Tyr Asp Thr Gln
225                 230                 235                 240
Ile Leu Thr Ala Ile Ala Met Gly Val His Ala Leu Asp Ile Gln Ala
                245                 250                 255
Leu Asn Gly Thr Asn Gln Ser Phe His Pro Phe Ile His Asn Ser Lys
                260                 265                 270
Pro His Pro Gly Gln Leu Trp Ala Ala Asp Gln Met Ile Ser Leu Leu
        275                 280                 285
Ala Asn Ser Gln Leu Val Arg Asp Glu Leu Asp Gly Lys His Asp Tyr
        290                 295                 300
Arg Asp His Glu Leu Ile Gln Asp Arg Tyr Ser Leu Arg Cys Leu Pro
305                 310                 315                 320
Gln Tyr Leu Gly Pro Ile Val Asp Gly Ile Ser Gln Ile Ala Lys Gln
                325                 330                 335
Ile Glu Ile Glu Ile Asn Ser Val Thr Asp Asn Pro Leu Ile Asp Val
                340                 345                 350
Asp Asn Gln Ala Ser Tyr His Gly Gly Asn Phe Leu Gly Gln Tyr Val
        355                 360                 365
Gly Met Gly Met Asp His Leu Arg Tyr Tyr Ile Gly Leu Leu Ala Lys
        370                 375                 380
His Leu Asp Val Gln Ile Ala Leu Leu Ala Ser Pro Glu Phe Ser Asn
385                 390                 395                 400
Gly Leu Pro Pro Ser Leu Leu Gly Asn Arg Glu Arg Lys Val Asn Met
                405                 410                 415
Gly Leu Lys Gly Leu Gln Ile Cys Gly Asn Ser Ile Met Pro Leu Leu
                420                 425                 430
Thr Phe Tyr Gly Asn Ser Ile Ala Asp Arg Phe Pro Thr His Ala Glu
                435                 440                 445
Gln Phe Asn Gln Asn Ile Asn Ser Gln Gly Tyr Thr Ser Ala Thr Leu
        450                 455                 460
Ala Arg Arg Ser Val Asp Ile Phe Gln Asn Tyr Val Ala Ile Ala Leu
465                 470                 475                 480
Met Phe Gly Val Gln Ala Val Asp Leu Arg Thr Tyr Lys Lys Thr Gly
                485                 490                 495
His Tyr Asp Ala Arg Ala Cys Leu Ser Pro Ala Thr Glu Arg Leu Tyr
                500                 505                 510
Ser Ala Val Arg His Val Val Gly Gln Lys Pro Thr Ser Asp Arg Pro
        515                 520                 525
Tyr Ile Trp Asn Asp Asn Glu Gln Gly Leu Asp Glu His Ile Ala Arg
        530                 535                 540
Ile Ser Ala Asp Ile Ala Ala Gly Gly Val Ile Val Gln Ala Val Gln
545                 550                 555                 560
Asp Ile Leu Pro Cys Leu His
                565
```

<210> SEQ ID NO 2
<211> LENGTH: 567
<212> TYPE: PRT
<213> ORGANISM: Anabaena variabilis

<400> SEQUENCE: 2

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys

-continued

```
            370                 375                 380
His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
        450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
            515                 520                 525

Tyr Ile Trp Asn Asp Asn Glu Gln Gly Leu Asp Glu His Ile Ala Arg
        530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 3
<211> LENGTH: 532
<212> TYPE: PRT
<213> ORGANISM: Photorhabdus luminescens

<400> SEQUENCE: 3

Met Lys Ala Lys Asp Val Gln Pro Thr Ile Ile Asn Lys Asn Gly
1               5                   10                  15

Leu Ile Ser Leu Glu Asp Ile Tyr Asp Ile Ala Ile Lys Gln Lys Lys
            20                  25                  30

Val Glu Ile Ser Thr Glu Ile Thr Glu Leu Leu Thr His Gly Arg Glu
        35                  40                  45

Lys Leu Glu Glu Lys Leu Asn Ser Gly Glu Val Ile Tyr Gly Ile Asn
    50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Ser Ala Gly Thr Gly
                85                  90                  95

Asp Tyr Met Ser Lys Pro Cys Ile Lys Ala Ser Gln Phe Thr Met Leu
            100                 105                 110

Leu Ser Val Cys Lys Gly Trp Ser Ala Thr Arg Pro Ile Val Ala Gln
        115                 120                 125

Ala Ile Val Asp His Ile Asn His Asp Ile Val Pro Leu Val Pro Arg
    130                 135                 140

Tyr Gly Ser Val Gly Ala Ser Gly Asp Leu Ile Pro Leu Ser Tyr Ile
145                 150                 155                 160

Ala Arg Ala Leu Cys Gly Ile Gly Lys Val Tyr Tyr Met Gly Ala Glu
                165                 170                 175
```

Ile Asp Ala Ala Glu Ala Ile Lys Arg Ala Gly Leu Thr Pro Leu Ser
            180                 185                 190

Leu Lys Ala Lys Glu Gly Leu Ala Leu Ile Asn Gly Thr Arg Val Met
195                 200                 205

Ser Gly Ile Ser Ala Ile Thr Val Ile Lys Leu Glu Lys Leu Phe Lys
            210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
            245                 250                 255

Gln Asn Ala Val Ala Ser Ala Leu Arg Asn Leu Leu Ala Gly Ser Thr
            260                 265                 270

Gln Val Asn Leu Leu Ser Gly Val Lys Glu Gln Ala Asn Lys Ala Cys
275                 280                 285

Arg His Gln Glu Ile Thr Gln Leu Asn Asp Thr Leu Gln Glu Val Tyr
            290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
            325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
            355                 360                 365

Ile Ala Leu Ile Ala Asn His Leu His Ala Ile Val Ala Leu Met Met
370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
            405                 410                 415

Val Ala Ala Ile Arg His Asp Cys Ala Ala Ser Gly Ile His Thr Leu
            420                 425                 430

Ala Thr Glu Gln Tyr Asn Gln Asp Ile Val Ser Leu Gly Leu His Ala
            435                 440                 445

Ala Gln Asp Val Leu Glu Met Glu Gln Lys Leu Arg Asn Ile Val Ser
450                 455                 460

Met Thr Ile Leu Val Val Cys Gln Ala Ile His Leu Arg Gly Asn Ile
465                 470                 475                 480

Ser Glu Ile Ala Pro Glu Thr Ala Lys Phe Tyr His Ala Val Arg Glu
            485                 490                 495

Ile Ser Ser Pro Leu Ile Thr Asp Arg Ala Leu Asp Glu Asp Ile Ile
                500                 505                 510

Arg Ile Ala Asp Ala Ile Ile Asn Asp Gln Leu Pro Leu Pro Glu Ile
            515                 520                 525

Met Leu Glu Glu
        530

<210> SEQ ID NO 4
<211> LENGTH: 514
<212> TYPE: PRT
<213> ORGANISM: Photorhabdus luminescens

<400> SEQUENCE: 4

Met Lys Gln Leu Thr Ile Tyr Pro Gly Lys Leu Thr Leu Asp Glu Leu
1               5                   10                  15

```
Arg Gln Val Tyr Leu Gln Pro Val Lys Ile Thr Leu Asp Ser Gln Ile
             20                  25                  30
Phe Pro Ala Ile Glu Arg Ser Val Glu Cys Val Asn Ala Ile Leu Ala
         35                  40                  45
Glu Asn Arg Thr Ala Tyr Gly Ile Asn Thr Gly Phe Gly Leu Leu Ala
     50                  55                  60
Ser Thr Arg Ile Glu Glu Asp Asn Leu Glu Lys Leu Gln Arg Ser Leu
 65                  70                  75                  80
Val Val Ser His Ala Ala Gly Val Gly Lys Ala Leu Asp Asp Asn Met
                 85                  90                  95
Thr Arg Leu Ile Met Val Leu Lys Ile Asn Ser Leu Ser Arg Gly Tyr
            100                 105                 110
Ser Gly Ile Arg Leu Ala Val Ile Gln Ala Leu Ile Ala Leu Val Asn
        115                 120                 125
Ala Glu Ile Tyr Pro His Ile Pro Cys Lys Gly Ser Val Gly Ala Ser
    130                 135                 140
Gly Asp Leu Ala Pro Leu Ala His Met Ser Leu Leu Leu Leu Gly Glu
145                 150                 155                 160
Gly Gln Ala Arg Tyr Gln Gly Glu Trp Leu Pro Ala Lys Glu Ala Leu
                165                 170                 175
Ala Lys Ala Asn Leu Gln Pro Ile Thr Leu Ala Ala Lys Glu Gly Leu
            180                 185                 190
Ala Leu Leu Asn Gly Thr Gln Val Ser Thr Ala Phe Ala Leu Arg Gly
        195                 200                 205
Leu Phe Glu Ala Glu Asp Leu Leu Ala Ala Ala Ile Val Cys Gly Ser
    210                 215                 220
Leu Ser Val Glu Ala Ala Leu Gly Ser Arg Lys Pro Phe Asp Ala Arg
225                 230                 235                 240
Val His Val Val Arg Gly Gln Gln Gly Gln Ile Asp Val Ala Ala Leu
                245                 250                 255
Tyr Arg His Val Leu Glu Glu Ser Ser Glu Leu Ser Asp Ser His Ile
            260                 265                 270
Asn Cys Pro Lys Val Gln Asp Pro Tyr Ser Leu Arg Cys Gln Pro Gln
        275                 280                 285
Val Met Gly Ala Cys Leu Thr Gln Leu Arg His Ala Ala Asp Val Ile
    290                 295                 300
Leu Thr Glu Ala Asn Ala Val Ser Asp Asn Pro Leu Val Phe Ala Glu
305                 310                 315                 320
Gln Gly Glu Val Ile Ser Gly Gly Asn Phe His Ala Glu Pro Val Ala
                325                 330                 335
Met Ala Ser Asp Asn Leu Ala Leu Val Leu Ala Glu Ile Gly Ala Leu
            340                 345                 350
Ser Glu Arg Arg Ile Ala Leu Leu Met Asp Ser His Met Ser Gln Leu
        355                 360                 365
Pro Pro Phe Leu Val Glu Asn Gly Gly Val Asn Ser Gly Phe Met Ile
    370                 375                 380
Ala Gln Val Thr Ala Ala Ala Leu Ala Ser Glu Asn Lys Ala Leu Ala
385                 390                 395                 400
His Pro Ala Ser Val Asp Ser Leu Pro Thr Ser Ala Asn Gln Glu Asp
                405                 410                 415
His Val Ser Met Ala Pro Ala Ala Gly Arg Arg Leu Trp Glu Met Ala
            420                 425                 430
```

Glu Asn Thr Arg Gly Ile Leu Ala Ile Glu Trp Leu Ser Ala Cys Gln
            435                 440                 445

Gly Ile Asp Phe Arg Asn Gly Leu Lys Ser Ser Pro Ile Leu Glu Glu
450                 455                 460

Ala Arg Val Ile Leu Arg Ala Lys Val Asp Tyr Tyr Asp Gln Asp Arg
465                 470                 475                 480

Phe Phe Ala Pro Asp Ile Asp Ala Ala Val Lys Leu Leu Ala Glu Gln
            485                 490                 495

His Leu Ser Ser Leu Leu Pro Ser Gly Gln Ile Leu Gln Arg Lys Asn
            500                 505                 510

Asn Arg

<210> SEQ ID NO 5
<211> LENGTH: 471
<212> TYPE: PRT
<213> ORGANISM: Proteus mirabilis

<400> SEQUENCE: 5

Met Ala Ile Ser Arg Arg Lys Phe Ile Leu Gly Gly Thr Val Val Ala
1               5                   10                  15

Val Ala Ala Gly Ala Gly Val Leu Thr Pro Met Leu Thr Arg Glu Gly
            20                  25                  30

Arg Phe Val Pro Gly Thr Pro Arg His Gly Phe Val Glu Gly Thr Gly
        35                  40                  45

Gly Pro Leu Pro Lys Gln Asp Asp Val Val Ile Gly Ala Gly Ile
    50                  55                  60

Leu Gly Ile Met Thr Ala Ile Asn Leu Ala Glu Arg Gly Leu Ser Val
65                  70                  75                  80

Thr Ile Val Glu Lys Gly Asn Ile Ala Gly Glu Gln Ser Ser Arg Phe
                85                  90                  95

Tyr Gly Gln Ala Ile Ser Tyr Lys Met Pro Asp Glu Thr Phe Leu Leu
            100                 105                 110

His His Leu Gly Lys His Arg Trp Arg Glu Met Asn Ala Lys Val Gly
        115                 120                 125

Ile Asp Thr Thr Tyr Arg Thr Gln Gly Arg Val Glu Val Pro Leu Asp
    130                 135                 140

Glu Glu Asp Leu Glu Asn Val Arg Lys Trp Ile Asp Ala Lys Ser Lys
145                 150                 155                 160

Asp Val Gly Ser Asp Ile Pro Phe Arg Thr Lys Met Ile Glu Gly Ala
                165                 170                 175

Glu Leu Lys Gln Arg Leu Arg Gly Ala Thr Thr Asp Trp Lys Ile Ala
            180                 185                 190

Gly Phe Glu Glu Asp Ser Gly Ser Phe Asp Pro Glu Val Ala Thr Phe
        195                 200                 205

Val Met Ala Glu Tyr Ala Lys Lys Met Gly Ile Lys Ile Phe Thr Asn
    210                 215                 220

Cys Ala Ala Arg Gly Leu Glu Thr Gln Ala Gly Val Ile Ser Asp Val
225                 230                 235                 240

Val Thr Glu Lys Gly Pro Ile Lys Thr Ser Arg Val Val Ala Gly
                245                 250                 255

Gly Val Gly Ser Arg Leu Phe Met Gln Asn Leu Asn Val Asp Val Pro
            260                 265                 270

Thr Leu Pro Ala Tyr Gln Ser Gln Gln Leu Ile Ser Ala Ala Pro Asn
        275                 280                 285

```
Ala Pro Gly Gly Asn Val Ala Leu Pro Gly Gly Ile Phe Phe Arg Asp
    290                 295                 300

Gln Ala Asp Gly Thr Tyr Ala Thr Ser Pro Arg Val Ile Val Ala Pro
305                 310                 315                 320

Val Val Lys Glu Ser Phe Thr Tyr Gly Tyr Lys Tyr Leu Pro Leu Leu
                325                 330                 335

Ala Leu Pro Asp Phe Pro Val His Ile Ser Leu Asn Glu Gln Leu Ile
            340                 345                 350

Asn Ser Phe Met Gln Ser Thr His Trp Asp Leu Asn Glu Glu Ser Pro
        355                 360                 365

Phe Glu Lys Tyr Arg Asp Met Thr Ala Leu Pro Asp Leu Pro Glu Leu
    370                 375                 380

Asn Ala Ser Leu Glu Lys Leu Lys Lys Glu Phe Pro Ala Phe Lys Glu
385                 390                 395                 400

Ser Thr Leu Ile Asp Gln Trp Ser Gly Ala Met Ala Ile Ala Pro Asp
                405                 410                 415

Glu Asn Pro Ile Ile Ser Asp Val Lys Glu Tyr Pro Gly Leu Val Ile
            420                 425                 430

Asn Thr Ala Thr Gly Trp Gly Met Thr Glu Ser Pro Val Ser Ala Glu
        435                 440                 445

Ile Thr Ala Asp Leu Leu Gly Lys Lys Pro Val Leu Asp Ala Lys
    450                 455                 460

Pro Phe Ser Leu Tyr Arg Phe
465                 470

<210> SEQ ID NO 6
<211> LENGTH: 473
<212> TYPE: PRT
<213> ORGANISM: Proteus mirabilis

<400> SEQUENCE: 6

Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
                20                  25                  30

Lys Phe Val Glu Ala Lys Ser Arg Ala Ser Phe Val Glu Gly Thr Gln
            35                  40                  45

Gly Ala Leu Pro Lys Glu Ala Asp Val Val Ile Gly Ala Gly Ile
        50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95

Tyr Ser Gln Ile Ile Ser Tyr Gln Thr Ser Pro Glu Ile Phe Pro Leu
            100                 105                 110

His His Tyr Gly Lys Ile Leu Trp Arg Gly Met Asn Glu Lys Ile Gly
        115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190
```

```
Ala Phe Glu Glu Asp Ser Gly Ser Val Asp Pro Glu Thr Gly Thr Pro
            195                 200                 205

Ala Leu Ala Arg Tyr Ala Lys Gln Ile Gly Val Lys Ile Tyr Thr Asn
        210                 215                 220

Cys Ala Val Arg Gly Ile Glu Thr Ala Gly Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470

<210> SEQ ID NO 7
<211> LENGTH: 471
<212> TYPE: PRT
<213> ORGANISM: Proteus vulgaris

<400> SEQUENCE: 7

Met Ala Ile Ser Arg Arg Lys Phe Ile Ile Gly Gly Thr Val Val Ala
1               5                   10                  15

Val Ala Ala Gly Ala Gly Ile Leu Thr Pro Met Leu Thr Arg Glu Gly
            20                  25                  30

Arg Phe Val Pro Gly Thr Pro Arg His Gly Phe Val Glu Gly Thr Glu
        35                  40                  45

Gly Ala Leu Pro Lys Gln Ala Asp Val Val Val Gly Ala Gly Ile
    50                  55                  60

Leu Gly Ile Met Thr Ala Ile Asn Leu Val Glu Arg Gly Leu Ser Val
65                  70                  75                  80

Val Ile Val Glu Lys Gly Asn Ile Ala Gly Glu Gln Ser Ser Arg Phe
```

```
                        85                  90                  95
Tyr Gly Gln Ala Ile Ser Tyr Lys Met Pro Asp Glu Thr Phe Leu Leu
                100                 105                 110

His His Leu Gly Lys His Arg Trp Arg Glu Met Asn Ala Lys Val Gly
                115                 120                 125

Ile Asp Thr Thr Tyr Arg Thr Gln Gly Arg Val Glu Val Pro Leu Asp
                130                 135                 140

Glu Glu Asp Leu Val Asn Val Arg Lys Trp Ile Asp Glu Arg Ser Lys
145                 150                 155                 160

Asn Val Gly Ser Asp Ile Pro Phe Lys Thr Arg Ile Ile Glu Gly Ala
                165                 170                 175

Glu Leu Asn Gln Arg Leu Arg Gly Ala Thr Thr Asp Trp Lys Ile Ala
                180                 185                 190

Gly Phe Glu Glu Asp Ser Gly Ser Phe Asp Pro Glu Val Ala Thr Phe
                195                 200                 205

Val Met Ala Glu Tyr Ala Lys Lys Met Gly Val Arg Ile Tyr Thr Gln
                210                 215                 220

Cys Ala Ala Arg Gly Leu Glu Thr Gln Ala Gly Val Ile Ser Asp Val
225                 230                 235                 240

Val Thr Glu Lys Gly Ala Ile Lys Thr Ser Gln Val Val Ala Gly
                245                 250                 255

Gly Val Trp Ser Arg Leu Phe Met Gln Asn Leu Asn Val Asp Val Pro
                260                 265                 270

Thr Leu Pro Ala Tyr Gln Ser Gln Leu Ile Ser Gly Ser Pro Thr
                275                 280                 285

Ala Pro Gly Gly Asn Val Ala Leu Pro Gly Gly Ile Phe Phe Arg Glu
                290                 295                 300

Gln Ala Asp Gly Thr Tyr Ala Thr Ser Pro Arg Val Ile Val Ala Pro
305                 310                 315                 320

Val Val Lys Glu Ser Phe Thr Tyr Gly Tyr Lys Tyr Leu Pro Leu Leu
                325                 330                 335

Ala Leu Pro Asp Phe Pro Val His Ile Ser Leu Asn Glu Gln Leu Ile
                340                 345                 350

Asn Ser Phe Met Gln Ser Thr His Trp Asn Leu Asp Glu Val Ser Pro
                355                 360                 365

Phe Glu Gln Phe Arg Asn Met Thr Ala Leu Pro Asp Leu Pro Glu Leu
                370                 375                 380

Asn Ala Ser Leu Glu Lys Leu Lys Ala Glu Phe Pro Ala Phe Lys Glu
385                 390                 395                 400

Ser Lys Leu Ile Asp Gln Trp Ser Gly Ala Met Ala Ile Ala Pro Asp
                405                 410                 415

Glu Asn Pro Ile Ile Ser Glu Val Lys Glu Tyr Pro Gly Leu Val Ile
                420                 425                 430

Asn Thr Ala Thr Gly Trp Gly Met Thr Glu Ser Pro Val Ser Ala Glu
                435                 440                 445

Leu Thr Ala Asp Leu Leu Gly Lys Lys Pro Val Leu Asp Pro Lys
450                 455                 460

Pro Phe Ser Leu Tyr Arg Phe
465                 470

<210> SEQ ID NO 8
<211> LENGTH: 452
<212> TYPE: PRT
<213> ORGANISM: Homo sapiens
```

```
<400> SEQUENCE: 8

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
        130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Gly Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
```

|       |     |     |     |     |     | 405 |     |     |     |     | 410 |     |     |     |     | 415 |     |
|-------|-----|-----|-----|-----|-----|-----|-----|-----|-----|-----|-----|-----|-----|-----|-----|-----|-----|
| Tyr   | Thr | Gln | Arg | Ile | Glu | Val | Leu | Asp | Asn | Thr | Gln | Gln | Leu | Lys | Ile |     |     |
|       |     |     | 420 |     |     |     |     | 425 |     |     |     |     | 430 |     |     |     |     |
| Leu   | Ala | Asp | Ser | Ile | Asn | Ser | Glu | Ile | Gly | Ile | Leu | Cys | Ser | Ala | Leu |     |     |
|       |     |     | 435 |     |     |     |     | 440 |     |     |     |     | 445 |     |     |     |     |
| Gln   | Lys | Ile | Lys |     |     |     |     |     |     |     |     |     |     |     |     |     |     |
|       |     |     | 450 |     |     |     |     |     |     |     |     |     |     |     |     |     |     |

<210> SEQ ID NO 9
<211> LENGTH: 433
<212> TYPE: DNA
<213> ORGANISM: Escherichia coli

<400> SEQUENCE: 9

| cggcccgatc gttgaacata gcggtccgca ggcggcactg cttacagcaa acggtctgta | 60  |
| cgctgtcgtc tttgtgatgt gcttcctgtt aggtttcgtc agccgtcacc gtcagcataa | 120 |
| cacccctgacc tctcattaat tgctcatgcc ggacggcact atcgtcgtcc ggccttttcc | 180 |
| tctcttcccc cgctacgtgc atctatttct ataaacccgc tcattttgtc tattttttgc | 240 |
| acaaacatga atatcagac aattccgtga cttaagaaaa tttatacaaa tcagcaatat | 300 |
| acccattaag gagtatataa aggtgaattt gatttacatc aataagcggg gttgctgaat | 360 |
| cgttaaggta ggcggtaata gaaaagaaat cgaggcaaaa atgtttgttt aactttaaga | 420 |
| aggagatata cat | 433 |

<210> SEQ ID NO 10
<211> LENGTH: 290
<212> TYPE: DNA
<213> ORGANISM: Escherichia coli

<400> SEQUENCE: 10

| gtcagcataa cacccctgacc tctcattaat tgctcatgcc ggacggcact atcgtcgtcc | 60  |
| ggccttttcc tctcttcccc cgctacgtgc atctatttct ataaacccgc tcattttgtc | 120 |
| tattttttgc acaaacatga atatcagac aattccgtga cttaagaaaa tttatacaaa | 180 |
| tcagcaatat acccattaag gagtatataa aggtgaattt gatttacatc aataagcggg | 240 |
| gttgctgaat cgttaaggta ggcggtaata gaaaagaaat cgaggcaaaa | 290 |

<210> SEQ ID NO 11
<211> LENGTH: 173
<212> TYPE: DNA
<213> ORGANISM: Escherichia coli

<400> SEQUENCE: 11

| atttcctctc atcccatccg gggtgagagt cttttccccc gacttatggc tcatgcatgc | 60  |
| atcaaaaaag atgtgagctt gatcaaaaac aaaaaatatt tcactcgaca ggagtattta | 120 |
| tattgcgccc gttacgtggg cttcgactgt aaatcagaaa ggagaaaaca cct | 173 |

<210> SEQ ID NO 12
<211> LENGTH: 305
<212> TYPE: DNA
<213> ORGANISM: Escherichia coli

<400> SEQUENCE: 12

| gtcagcataa cacccctgacc tctcattaat tgttcatgcc gggcggcact atcgtcgtcc | 60  |
| ggccttttcc tctcttactc tgctacgtac atctatttct ataaatccgt tcaatttgtc | 120 |

-continued

```
tgttttttgc acaaacatga atatcagac aattccgtga cttaagaaaa tttatacaaa      180
tcagcaatat accccttaag gagtatataa aggtgaattt gatttacatc aataagcggg      240
gttgctgaat cgttaaggat ccctctagaa ataattttgt ttaactttaa gaaggagata      300
tacat                                                                 305

<210> SEQ ID NO 13
<211> LENGTH: 180
<212> TYPE: DNA
<213> ORGANISM: Escherichia coli

<400> SEQUENCE: 13
catttcctct catcccatcc ggggtgagag tcttttcccc cgacttatgg ctcatgcatg       60
catcaaaaaa gatgtgagct tgatcaaaaa caaaaaatat ttcactcgac aggagtattt      120
atattgcgcc cggatccctc tagaaataat tttgtttaac tttaagaagg agatatacat      180

<210> SEQ ID NO 14
<211> LENGTH: 199
<212> TYPE: DNA
<213> ORGANISM: Escherichia coli

<400> SEQUENCE: 14
agttgttctt attggtggtg ttgctttatg gttgcatcgt agtaaatggt tgtaacaaaa       60
gcaatttttc cggctgtctg tatacaaaaa cgccgtaaag tttgagcgaa gtcaataaac      120
tctctaccca ttcagggcaa tatctctctt ggatccctct agaaataatt tgtttaact      180 ttaagaagga gatatacat                                                  199

<210> SEQ ID NO 15
<211> LENGTH: 207
<212> TYPE: DNA
<213> ORGANISM: Escherichia coli

<400> SEQUENCE: 15
agttgttctt attggtggtg ttgctttatg gttgcatcgt agtaaatggt tgtaacaaaa       60
gcaatttttc cggctgtctg tatacaaaaa cgccgcaaag tttgagcgaa gtcaataaac      120
tctctaccca ttcagggcaa tatctctctt ggatccaaag tgaactctag aaataatttt     180
gtttaacttt aagaaggaga tatacat                                         207

<210> SEQ ID NO 16
<211> LENGTH: 390
<212> TYPE: DNA
<213> ORGANISM: Escherichia coli

<400> SEQUENCE: 16
tcgtctttgt gatgtgcttc ctgttaggtt tcgtcagccg tcaccgtcag cataacaccc       60
tgacctctca ttaattgctc atgccggacg gcactatcgt cgtccggcct tttcctctct      120
tcccccgcta cgtgcatcta tttctataaa cccgctcatt ttgtctattt tttgcacaaa      180
catgaaatat cagacaattc cgtgacttaa gaaaatttat acaaatcagc aatatacccca     240 ttaaggagta tataaaggtg aatttgattt acatcaataa gcggggttgc tgaatcgtta      300
aggtagaaat gtgatctagt tcacatttgc ggtaatagaa agaaatcga ggcaaaaatg       360 tttgtttaac tttaagaagg agatatacat                                      390

<210> SEQ ID NO 17
<211> LENGTH: 200
```

```
<212> TYPE: DNA
<213> ORGANISM: Escherichia coli

<400> SEQUENCE: 17
agttgttctt attggtggtg ttgctttatg gttgcatcgt agtaaatggt tgtaacaaaa    60 gcaattttc  cggctgtctg tatacaaaaa cgccgcaaag tttgagcgaa gtcaataaac   120
tctctaccca ttcagggcaa tatctctcaa atgtgatcta gttcacattt tttgtttaac   180
tttaagaagg agatatacat                                               200

<210> SEQ ID NO 18
<211> LENGTH: 355
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
tgtggctttt atgaaaatca cacagtgatc acaaatttta aacagagcac aaaatgctgc    60
ctcgaaatga gggcgggaaa ataaggttat cagccttgtt ttctccctca ttacttgaag   120
gatatgaagc taaaacccctt ttttataaag catttgtccg aattcggaca taatcaaaaa   180
agcttaatta agatcaattt gatctacatc tctttaacca acaatatgta agatctcaac   240
tatcgcatcc gtggattaat tcaattataa cttctctcta acgctgtgta tcgtaacggt   300
aacactgtag aggggagcac attgatgcga attcattaaa gaggagaaag gtacc        355

<210> SEQ ID NO 19
<211> LENGTH: 228
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
ttccgaaaat tcctggcgag cagataaata agaattgttc ttatcaatat atctaactca    60
ttgaatcttt attagttttg tttttcacgc ttgttaccac tattagtgtg ataggaacag   120
ccagaatagc ggaacacata gccggtgcta tacttaatct cgttaattac tgggacataa   180
catcaagagg atatgaaatt cgaattcatt aaagaggaga aggtacc                 228

<210> SEQ ID NO 20
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
gcttagatca ggtgattgcc ctttgtttat gagggtgttg taatccatgt cgttgttgca    60
tttgtaaggg caacacctca gcctgcaggc aggcactgaa gataccaaag ggtagttcag   120
attacacggt cacctggaaa gggggccatt ttacttttta tcgccgctgg cggtgcaaag   180
ttcacaaagt tgtcttacga aggttgtaag gtaaaactta tcgatttgat aatggaaacg   240
cattagccga atcggcaaaa attggttacc ttacatctca tcgaaaacac ggaggaagta   300
```

```
tagatgcgaa ttcattaaag aggagaaagg tacc                                   334
```

<210> SEQ ID NO 21
<211> LENGTH: 134
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

```
ctcgagttca ttatccatcc tccatcgcca cgatagttca tggcgatagg tagaatagca        60
atgaacgatt atccctatca agcattctga ctgataattg ctcacacgaa ttcattaaag       120
aggagaaagg tacc                                                         134
```

<210> SEQ ID NO 22
<211> LENGTH: 4428
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
ctcttgatcg ttatcaattc ccacgctgtt tcagagcgtt accttgccct taaacattag        60
caatgtcgat ttatcagagg gccgacaggc tcccacagga gaaaaccgat gaaaacacta       120
tcacaggccc aatctaaaac ttcttcacag caattcagct ttaccgggaa ctcgtctgcg       180
aatgtaatta tcggcaatca aaagctgacc attaatgatg tagctcgcgt tgcccggaat       240
ggcactttgg tgtcactgac gaacaatacc gacattctgc aaggtattca agctagctgc       300
gattatatca ataacgccgt tgaatctggc gagccaatct acggggtaac aagcggtttt       360
ggtgggatgc gaacgttgc cattagccgt gaacaggcga gcgaacttca gaccaacctc       420
gtttggttcc taaagacagg agctggtaat aagttacctc tggctgacgt aagagccgcg       480
atgctgcttc gcgctaatag tcacatgcgc ggcgccagtg gtatccgtct tgagcttatc       540
aagaggatgg aaatcttcct caacgcgggt gtcacaccat atgtttatga gtttggtagt       600
atcggagcca gtggtgatct tgttcccctg agttatatta cgggttcatt gattggttta       660
gacccgtcct ttaaagtgga ttttaacggg aaagaaatgg acgccccgac cgctttacga       720
cagcttaatc tgagcccact tactttgctc cctaaagaag gtcttgccat gatgaatggc       780
acctctgtga tgactggaat tgccgcgaat tgtgtgtatg acacgcagat cctaacggcc       840
attgccatgg tgttcacgc gttggacatt caagccctga atggtacaaa ccagtcgttt       900
catccgttta tccataattc aaaacccat ccgggacagc tttgggctgc tgatcagatg       960
atctcactcc tggccaatag tcaactggtt cgggacgagc tcgacggcaa acatgattat      1020
cgcgatcatg agctcatcca ggaccggtat tcacttcgtt gtctcccaca ataccctgggg      1080 cctatcgttg atggtatatc tcaaattgcg aagcaaattg aaattgagat caatagcgta      1140
accgacaacc cgcttatcga tgttgataat caggcctctt atcacggtgg caattttctg      1200
ggccagtatg ttggtatggg gatggatcac ctgcggtact atattgggct tctggctaaa      1260
catcttgatg tgcagattgc cttattagct tcaccagaat tttcaaatgg actgccgcca      1320
tcattgctcg gtaacagaga aaggaaagta aatatgggcc ttaagggcct tcagatatgt      1380
ggtaactcaa tcatgcccct cctgaccttt tatgggaact caattgctga tcgttttccg      1440
```

```
acacatgctg aacagtttaa ccaaaacatt aactcacagg gctatacatc cgcgacgtta    1500
gcgcgtcggt ccgtggatat cttccagaat tatgttgcta tcgctctgat gttcggcgta    1560
caggccgttg atttgcgcac ttataaaaaa accggtcact acgatgctcg ggcttgcctg    1620
tcgcctgcca ccgagcggct ttatagcgcc gtacgtcatg ttgtgggtca gaaaccgacg    1680
tcggaccgcc cctatatttg aatgataat gaacaagggc tggatgaaca catcgcccgg    1740
atatctgccg atattgccgc cggaggtgtc atcgtccagg cggtacaaga catacttcct    1800
tgcctgcatt aagcttggcg taatcatggt catagctgtt tcctgtgtga aattgttatc    1860
cgctcacaat tccacacaac atacgagccg gaagcataaa gtgtaaagcc tggggtgcct    1920
aatgagtgag ctaactcaca ttaattgcgt tgcgctcact gcccgctttc cagtcgggaa    1980
acctgtcgtg ccagctgcat taatgaatcg gccaacgcgc ggggagaggc ggtttgcgta    2040
ttgggcgctc ttccgcttcc tcgctcactg actcgctgcg ctcggtcgtt cggctgcggc    2100
gagcggtatc agctcactca aaggcggtaa tacggttatc cacagaatca ggggataacg    2160
caggaaagaa catgtgagca aaaggccagc aaaaggccag gaaccgtaaa aaggccgcgt    2220
tgctggcgtt tttccatagg ctccgccccc ctgacgagca tcacaaaaat cgacgctcaa    2280
gtcagaggtg gcgaaacccg acaggactat aaagatacca ggcgtttccc cctggaagct    2340
ccctcgtgcg ctctcctgtt ccgaccctgc cgcttaccgg atacctgtcc gcctttctcc    2400
cttcgggaag cgtggcgctt tctcatagct cacgctgtag gtatctcagt tcggtgtagg    2460
tcgttcgctc caagctgggc tgtgtgcacg aaccccccgt tcagcccgac cgctgcgcct    2520
tatccggtaa ctatcgtctt gagtccaacc cggtaagaca cgacttatcg ccactggcag    2580
cagccactgg taacaggatt agcagagcga ggtatgtagg cggtgctaca gagttcttga    2640
agtggtggcc taactacggc tacactagaa gaacagtatt tggtatctgc gctctgctga    2700
agccagttac cttcggaaaa agagttggta gctcttgatc cggcaaacaa accaccgctg    2760
gtagcggtgg tttttttgtt tgcaagcagc agattacgcg cagaaaaaaa ggatctcaag    2820
aagatccttt gatcttttct acggggtctg acgctcagtg gaacgaaaac tcacgttaag    2880
ggattttggt catgagatta tcaaaaagga tcttcaccta gatccttta aattaaaaat    2940 gaagttttaa atcaatctaa agtatatatg agtaaacttg gtctgacagt taccaatgct    3000
taatcagtga ggcacctatc tcagcgatct gtctatttcg ttcatccata gttgcctgac    3060
tccccgtcgt gtagataact acgatacggg agggcttacc atctggcccc agtgctgcaa    3120
tgataccgcg agacccacgc tcaccggctc cagatttatc agcaataaac cagccagccg    3180
gaagggccga gcgcagaagt ggtcctgcaa ctttatccgc ctccatccag tctattaatt    3240
gttgccggga agctagagta agtagttcgc cagttaatag tttgcgcaac gttgttgcca    3300
ttgctacagg catcgtggtg tcacgctcgt cgtttggtat ggcttcattc agctccggtt    3360
cccaacgatc aaggcgagtt acatgatccc ccatgttgtg caaaaaagcg gttagctcct    3420
tcggtcctcc gatcgttgtc agaagtaagt tggccgcagt gttatcactc atggttatgg    3480
cagcactgca taattctctt actgtcatgc catccgtaag atgcttttct gtgactggtg    3540
agtactcaac caagtcattc tgagaatagt gtatgcggcg accgagttgc tcttgcccgg    3600
cgtcaatacg ggataatacc gcgccacata gcagaacttt aaaagtgctc atcattggaa    3660
aacgttcttc ggggcgaaaa ctctcaagga tcttaccgct gttgagatcc agttcgatgt    3720
aacccactcg tgcacccaac tgatcttcag catctttta c tttcaccagc gtttctgggt    3780
```

```
gagcaaaaac aggaaggcaa aatgccgcaa aaaagggaat aagggcgaca cggaaatgtt    3840
gaatactcat actcttcctt tttcaatatt attgaagcat ttatcagggt tattgtctca    3900
tgagcggata catatttgaa tgtatttaga aaaataaaca aatagggtt ccgcgcacat     3960 ttccccgaaa agtgccacct gacgtctaag aaaccattat tatcatgaca ttaacctata    4020
aaaataggcg tatcacgagg cccttccgtc tcgcgcgttt cggtgatgac ggtgaaaacc    4080
tctgacacat gcagctcccg gagacggtca cagcttgtct gtaagcggat gccgggagca    4140
gacaagcccg tcagggcgcg tcagcgggtg ttggcgggtg tcggggctgg cttaactatg    4200
cggcatcaga gcagattgta ctgagagtgc accatatgcg gtgtgaaata ccgcacagat    4260
gcgtaaggag aaaataccgc atcaggcgcc attcgccatt caggctgcgc aactgttggg    4320
aagggcgatc ggtgcgggcc tcttcgctat tacgccagct ggcgaaaggg ggatgtgctg    4380
caaggcgatt aagttgggta acgccagggt tttcccagtc acgacgtt                4428

<210> SEQ ID NO 23
<211> LENGTH: 305
<212> TYPE: DNA
<213> ORGANISM: Escherichia coli

<400> SEQUENCE: 23
cagacattgc cgtcactgcg tctttactg gctcttctcg ctaacccaac cggtaacccc       60
gcttattaaa agcattctgt aacaaagcgg gaccaaagcc atgacaaaaa cgcgtaacaa     120
aagtgtctat aatcacggca gaaaagtcca cattgattat ttgcacggcg tcacactttg    180
ctatgccata gcatttttat ccataagatt agcggatcca gcctgacgct ttttttcgca    240
actctctact gtttctccat acctctagaa ataattttgt ttaactttaa gaaggagata    300
tacat                                                                305

<210> SEQ ID NO 24
<211> LENGTH: 897
<212> TYPE: DNA
<213> ORGANISM: Escherichia coli

<400> SEQUENCE: 24
ttattcacaa cctgccctaa actcgctcgg actcgccccg gtgcattttt taaatactcg     60
cgagaaatag agttgatcgt caaaaccgac attgcgaccg acggtggcga taggcatccg    120
ggtggtgctc aaaagcagct tcgcctgact gatgcgctgg tcctcgcgcc agcttaatac    180
gctaatccct aactgctggc ggaacaaatg cgacagacgc gacggcgaca ggcagacatg    240
ctgtgcgacg ctggcgatat caaaattact gtctgccagg tgatcgctga tgtactgaca    300
agcctcgcgt acccgattat ccatcggtgg atggagcgac tcgttaatcg cttccatgcg    360
ccgcagtaac aattgctcaa gcagatttat cgccagcaat tccgaatagc gcccttcccc    420
ttgtccggca ttaatgattt gcccaaacag gtcgctgaaa tgcggctggt gcgcttcatc    480
cgggcgaaag aaaccggtat tggcaaatat cgacggccag ttaagccatt catgccagta    540
ggcgcgcgga cgaaagtaaa cccactggtg ataccattcg tgagcctccg gatgacgacc    600
gtagtgatga atctctccag gcgggaacag caaaatatca cccggtcggc agacaaattc    660
tcgtccctga ttttcacca ccccctgacc gcgaatggtg agattgagaa tataaccttt    720
cattcccagc ggtcggtcga taaaaaaatc gagataaccg ttggcctcaa tcggcgttaa    780
acccgccacc agatgggcgt taaacagta tcccggcagc aggggatcat tttgcgcttc    840
agccatactt ttcatactcc cgccattcag agaagaaacc aattgtccat attgcat       897
```

<210> SEQ ID NO 25
<211> LENGTH: 298
<212> TYPE: PRT
<213> ORGANISM: Escherichia coli

<400> SEQUENCE: 25

Met Gln Tyr Gly Gln Leu Val Ser Ser Leu Asn Gly Gly Ser Met Lys
1               5                   10                  15

Ser Met Ala Glu Ala Gln Asn Asp Pro Leu Leu Pro Gly Tyr Ser Phe
            20                  25                  30

Asn Ala His Leu Val Ala Gly Leu Thr Pro Ile Glu Ala Asn Gly Tyr
        35                  40                  45

Leu Asp Phe Phe Ile Asp Arg Pro Leu Gly Met Lys Gly Tyr Ile Leu
    50                  55                  60

Asn Leu Thr Ile Arg Gly Gln Gly Val Val Lys Asn Gln Gly Arg Glu
65                  70                  75                  80

Phe Val Cys Arg Pro Gly Asp Ile Leu Leu Phe Pro Pro Gly Glu Ile
                85                  90                  95

His His Tyr Gly Arg His Pro Glu Ala His Glu Trp Tyr His Gln Trp
            100                 105                 110

Val Tyr Phe Arg Pro Arg Ala Tyr Trp His Glu Trp Leu Asn Trp Pro
        115                 120                 125

Ser Ile Phe Ala Asn Thr Gly Phe Phe Arg Pro Asp Glu Ala His Gln
    130                 135                 140

Pro His Phe Ser Asp Leu Phe Gly Gln Ile Ile Asn Ala Gly Gln Gly
145                 150                 155                 160

Glu Gly Arg Tyr Ser Glu Leu Leu Ala Ile Asn Leu Leu Glu Gln Leu
                165                 170                 175

Leu Leu Arg Arg Met Glu Ala Ile Asn Glu Ser Leu His Pro Pro Met
            180                 185                 190

Asp Asn Arg Val Arg Glu Ala Cys Gln Tyr Ile Ser Asp His Leu Ala
        195                 200                 205

Asp Ser Asn Phe Asp Ile Ala Ser Val Ala Gln His Val Cys Leu Ser
    210                 215                 220

Pro Ser Arg Leu Ser His Leu Phe Arg Gln Gln Leu Gly Ile Ser Val
225                 230                 235                 240

Leu Ser Trp Arg Glu Asp Gln Arg Ile Ser Gln Ala Lys Leu Leu Leu
                245                 250                 255

Ser Thr Thr Arg Met Pro Ile Ala Thr Val Gly Arg Asn Val Gly Phe
            260                 265                 270

Asp Asp Gln Leu Tyr Phe Ser Arg Val Phe Lys Lys Cys Thr Gly Ala
        275                 280                 285

Ser Pro Ser Glu Phe Arg Ala Gly Cys Glu
    290                 295

<210> SEQ ID NO 26
<211> LENGTH: 280
<212> TYPE: DNA
<213> ORGANISM: Escherichia coli

<400> SEQUENCE: 26
cggtgagcat cacatcacca caattcagca aattgtgaac atcatcacgt tcatctttcc      60
ctggttgcca atggcccatt ttcctgtcag taacgagaag gtcgcgaatc aggcgctttt    120
tagactggtc gtaatgaaat tcagctgtca ccggatgtgc tttccggtct gatgagtccg    180

```
tgaggacgaa acagcctcta caaataattt tgtttaaaac acacccact aagataactc    240 tagaaataat tttgtttaac tttaagaagg agatatacat                          280
```

<210> SEQ ID NO 27
<211> LENGTH: 326
<212> TYPE: DNA
<213> ORGANISM: Escherichia coli

<400> SEQUENCE: 27

```
attcaccacc ctgaattgac tctcttccgg gcgctatcat gccataccgc gaaaggtttt    60
gcgccattcg atggcgcgcc gcttcgtcag gccacatagc tttcttgttc tgatcggaac   120
gatcgttggc tgtgttgaca attaatcatc ggctcgtata atgtgtggaa ttgtgagcgc   180
tcacaattag ctgtcaccgg atgtgctttc cggtctgatg agtccgtgag gacgaaacag   240
cctctacaaa taattttgtt taaaacaaca cccactaaga taactctaga aataattttg   300
tttaacttta agaaggagat atacat                                        326
```

<210> SEQ ID NO 28
<211> LENGTH: 1083
<212> TYPE: DNA
<213> ORGANISM: Escherichia coli

<400> SEQUENCE: 28

```
tcactgcccg ctttccagtc gggaaacctg tcgtgccagc tgcattaatg aatcggccaa    60
cgcgcgggga gaggcggttt gcgtattggg cgccagggtg ttttttcttt tcaccagtga   120
gactggcaac agctgattgc ccttcaccgc ctggccctga gagagttgca gcaagcggtc   180
cacgctggtt tgccccagca ggcgaaaatc ctgtttgatg gtggttaacg gcgggatata   240
acatgagcta tcttcggtat cgtcgtatcc cactaccgag atatccgcac caacgcgcag   300
cccggactcg gtaatggcgc gcattgcgcc cagcgccatc tgatcgttgg caaccagcat   360
cgcagtggga acgatgccct cattcagcat ttgcatggtt tgttgaaaac cggacatggc   420
actccagtcg ccttcccgtt ccgctatcgg ctgaatttga ttgcgagtga gatatttatg   480
ccagccagcc agacgcagac gcgccgagac agaacttaat gggcccgcta acagcgcgat   540
ttgctggtga cccaatgcga ccagatgctc cacgcccagt cgcgtaccgt cctcatggga   600
gaaaataata ctgttgatgg gtgtctggtc agagacatca agaaataacg ccggaacatt   660
agtgcaggca gcttccacag caatggcatc ctggtcatcc agcggatagt taatgatcag   720
cccactgacg cgttgcgcga aagattgtg caccgccgct ttacaggctt cgacgccgct   780
tcgttctacc atcgacacca ccacgctggc acccagttga tcggcgcgag atttaatcgc   840
cgcgacaatt tgcgacggcg cgtgcagggc cagactggag gtggcaacgc caatcagcaa   900
cgactgtttg cccgccagtt gttgtgccac gcggttggga atgtaattca gctccgccat   960
cgccgcttcc acttttttccc gcgttttcgc agaaacgtgg ctggcctggt tcaccacgcg  1020
ggaaacggtc tgataagaga caccggcata ctctgcgaca tcgtataacg ttactggttt  1080
cat                                                                 1083
```

<210> SEQ ID NO 29
<211> LENGTH: 360
<212> TYPE: PRT
<213> ORGANISM: Escherichia coli

<400> SEQUENCE: 29

```
Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
        50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
            115                 120                 125

Asp Asp Gln Asp Ala Ile Ala Val Glu Ala Ala Cys Thr Asn Val Pro
        130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
            195                 200                 205

Gln Ile Gln Pro Ile Ala Glu Arg Glu Gly Asp Trp Ser Ala Met Ser
        210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
            275                 280                 285

Ile Lys Gln Asp Phe Arg Leu Leu Gly Gln Thr Ser Val Asp Arg Leu
        290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
            355                 360

<210> SEQ ID NO 30
<211> LENGTH: 222
<212> TYPE: DNA
<213> ORGANISM: Escherichia coli

<400> SEQUENCE: 30
acgttaaatc tatcaccgca agggataaat atctaacacc gtgcgtgttg actatttac        60
```

```
ctctggcggt gataatggtt gcatagctgt caccggatgt gctttccggt ctgatgagtc    120
cgtgaggacg aaacagcctc tacaaataat tttgtttaaa acaacaccca ctaagataac    180
tctagaaata attttgttta actttaagaa ggagatatac at                       222
```

```
<210> SEQ ID NO 31
<211> LENGTH: 714
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
```

```
tcagccaaac gtctcttcag gccactgact agcgataact ttccccacaa cggaacaact    60
ctcattgcat gggatcattg ggtactgtgg gtttagtggt tgtaaaaaca cctgaccgct    120
atccctgatc agtttcttga aggtaaactc atcaccccca gtctggcta tgcagaaatc    180 acctggctca acagcctgct cagggtcaac gagaattaac attccgtcag gaaagcttgg    240
cttggagcct gttggtgcgg tcatggaatt accttcaacc tcaagccaga atgcagaatc    300
actggctttt ttggttgtgc ttacccatct ctccgcatca cctttggtaa aggttctaag    360
cttaggtgag aacatccctg cctgaacatg agaaaaaaca gggtactcat actcacttct    420
aagtgacggc tgcatactaa ccgcttcata catctcgtag atttctctgg cgattgaagg    480
gctaaattct tcaacgctaa ctttgagaat ttttgtaagc aatgcggcgt tataagcatt    540
taatgcattg atgccattaa ataaagcacc aacgcctgac tgccccatcc ccatcttgtc    600
tgcgacagat tcctgggata agccaagttc attttctttt ttttcataaa ttgctttaag    660
gcgacgtgcg tcctcaagct gctcttgtgt taatggtttc tttttttgtgc tcat          714
```

```
<210> SEQ ID NO 32
<211> LENGTH: 43
<212> TYPE: DNA
<213> ORGANISM: Escherichia coli

<400> SEQUENCE: 32
```

```
ctctagaaat aattttgttt aactttaaga aggagatata cat                      43
```

```
<210> SEQ ID NO 33
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33
```

```
Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Thr Lys Ile Leu Lys Val Ser Val Glu Glu Phe Ser Pro Ser
65                  70                  75                  80
```

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Lys Leu Arg Thr Phe Thr Lys Gly Asp Ala Glu
            115                 120                 125

Arg Trp Val Ser Thr Thr Lys Lys Ala Ser Asp Ser Ala Phe Trp Leu
        130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235

<210> SEQ ID NO 34
<211> LENGTH: 748
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
ttaagaccca ctttcacatt taagttgttt ttctaatccg catatgatca attcaaggcc     60
gaataagaag gctggctctg caccttggtg atcaaataat tcgatagctt gtcgtaataa    120
tggcggcata ctatcagtag taggtgtttc cctttcttct ttagcgactt gatgctcttg    180
atcttccaat acgcaaccta agtaaaatg ccccacagcg ctgagtgcat ataatgcatt     240
ctctagtgaa aaaccttgtt ggcataaaaa ggctaattga ttttcgagag tttcatactg    300
tttttctgta ggccgtgtac ctaaatgtac ttttgctcca tcgcgatgac ttagtaaagc    360
acatctaaaa cttttagcgt tattacgtaa aaaatcttgc cagctttccc cttctaaagg    420
gcaaaagtga gtatggtgcc tatctaacat tcaatggct aaggcgtcga gcaaagcccg     480
cttatttttt acatgccaat acaatgtagg ctgctctaca cctagcttct gggcgagttt    540
acgggttgtt aaaccttcga ttccgacctc attaagcagc tctaatgcgc tgttaatcac    600
tttactttta tctaatctag acatcattaa ttcctaattt ttgttgacac tctatcattg    660
atagagttat ttaccactc cctatcagtg atagagaaaa gtgaactcta gaaataattt     720
tgtttaactt taagaaggag atatacat                                       748

<210> SEQ ID NO 35
<211> LENGTH: 225
<212> TYPE: DNA
<213> ORGANISM: Escherichia coli

<400> SEQUENCE: 35
tcacctttcc cggattaaac gcttttttgc ccggtggcat ggtgctaccg gcgatcacaa     60
acggttaatt atgacacaaa ttgacctgaa tgaatataca gtattggaat gcattacccg    120

-continued

```
gagtgttgtg taacaatgtc tggccaggtt tgtttcccgg aaccgaggtc acaacatagt    180
aaaagcgcta ttggtaatgg tacaatcgcg cgtttacact tattc                   225
```

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64
<211> LENGTH: 1955
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64

```
ttattcacaa cctgccctaa actcgctcgg actcgccccg gtgcattttt taaatactcg      60
cgagaaatag agttgatcgt caaaaccgac attgcgaccg acggtggcga taggcatccg     120
ggtggtgctc aaaagcagct tcgcctgact gatgcgctgg tcctcgcgcc agcttaatac     180
gctaatccct aactgctggc ggaacaaatg cgacagacgc gacggcgaca ggcagacatg     240
ctgtgcgacg ctggcgatat caaaattact gtctgccagg tgatcgctga tgtactgaca     300
agcctcgcgt acccgattat ccatcggtgg atggagcgac tcgttaatcg cttccatgcg     360
ccgcagtaac aattgctcaa gcagatttat cgccagcaat tccgaatagc gcccttcccc     420
ttgtccggca ttaatgattt gcccaaacag gtcgctgaaa tgcggctggt gcgcttcatc     480
cgggcgaaag aaaccggtat tggcaaatat cgacggccag ttaagccatt catgccagta     540
ggcgcgcgga cgaaagtaaa cccactggtg ataccattcg tgagcctccg gatgacgacc     600
gtagtgatga atctctccag gcgggaacag caaaatatca cccggtcggc agacaaattc     660
tcgtccctga tttttcacca cccccctgacc gcgaatggtg agattgagaa tataaccttt     720
```

| | |
|---|---|
| cattcccagc ggtcggtcga taaaaaaatc gagataaccg ttggcctcaa tcggcgttaa | 780 |
| acccgccacc agatgggcgt taaacgagta tcccggcagc aggggatcat tttgcgcttc | 840 |
| agccatactt ttcatactcc cgccattcag agaagaaacc aattgtccat attgcatcag | 900 |
| acattgccgt cactgcgtct tttactggct cttctcgcta acccaaccgg taaccccgct | 960 |
| tattaaaagc attctgtaac aaagcgggac caaagccatg acaaaaacgc gtaacaaaag | 1020 |
| tgtctataat cacggcagaa aagtccacat tgattatttg cacggcgtca cactttgcta | 1080 |
| tgccatagca ttttatcca taagattagc ggatccagcc tgacgctttt tttcgcaact | 1140 |
| ctctactgtt tctccatacc tctagaaata attttgttta actttaagaa ggagatatac | 1200 |
| atatgatccc ggaaaagcga attatacggc gcattcagtc tggcggttgt gctatccatt | 1260 |
| gccaggattg ctatatcagc cagctttgca tcccgttcac actcaacgaa catgagcttg | 1320 |
| atcagcttga taatatcatt gagcggaaga agcctattca gaaaggccag acgctgttta | 1380 |
| aggctggaga tgaacttaaa tcgctttatg ccatccgctc cggtacgatt aaaagttata | 1440 |
| ccatcactga gcaaggcgac gagcaaatca ctggtttcca tttagcaggc gatctggtgg | 1500 |
| gatttgatgc catcggcagc ggtcatcacc cgagtttcgc gcaggcgctg aaacctcga | 1560 |
| tggtatgtga atcccgttc gaaacgctgg acgatttgtc tggtaaaatg ccgaatctgc | 1620 |
| gtcagcagat gatgcgtctg atgagcggtg aaatcaaagg cgatcaggac atgatcctgc | 1680 |
| tgttgtcgaa gaaaaatgcc gaggaacgtc tggctgcatt catctacaac ctgtcccgtc | 1740 |
| gttttgccca acgcggcttc tcccctcgtg aattccgcct gacgatgact cgtggtgata | 1800 |
| tcggtaacta tctgggcctg acggttgaaa ccatcagccg tctgctgggt cgcttccaga | 1860 |
| aaagcggtat gctggcagtc aaaggtaaat acatcactat cgaaaataac gatgcgctgg | 1920 |
| cccagcttgc tggtcatacg cgtaacgttg cctga | 1955 |

<210> SEQ ID NO 65
<211> LENGTH: 753
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65

| | |
|---|---|
| atgatcccgg aaaagcgaat tatacggcgc attcagtctg gcggttgtgc tatccattgc | 60 |
| caggattgct atatcagcca gctttgcatc ccgttcacac tcaacgaaca tgagcttgat | 120 |
| cagcttgata atatcattga gcggaagaag cctattcaga aaggccagac gctgtttaag | 180 |
| gctggagatg aacttaaatc gctttatgcc atccgctccg gtacgattaa agttatacc | 240 |
| atcactgagc aaggcgacga gcaaatcact ggtttccatt tagcaggcga tctggtggga | 300 |
| tttgatgcca tcggcagcgg tcatcacccg agtttcgcgc aggcgctgga aacctcgatg | 360 |
| gtatgtgaaa tcccgttcga aacgctggac gatttgtctg gtaaaatgcc gaatctgcgt | 420 |
| cagcagatga tgcgtctgat gagcggtgaa atcaaaggcg atcaggacat gatcctgctg | 480 |
| ttgtcgaaga aaaatgccga ggaacgtctg gctgcattca tctacaacct gtcccgtcgt | 540 |
| tttgcccaac gcggcttctc ccctcgtgaa ttccgcctga cgatgactcg tggtgatatc | 600 |
| ggtaactatc tgggcctgac ggttgaaacc atcagccgtc tgctgggtcg cttccagaaa | 660 |
| agcggtatgc tggcagtcaa aggtaaatac atcactatcg aaaataacga tgcgctggcc | 720 |
| cagcttgctg gtcatacgcg taacgttgcc tga | 753 |

<210> SEQ ID NO 66
<211> LENGTH: 897
<212> TYPE: DNA
<213> ORGANISM: Escherichia coli

<400> SEQUENCE: 66
ttattcacaa cctgccctaa actcgctcgg actcgccccg gtgcattttt taaatactcg      60
cgagaaatag agttgatcgt caaaaccgac attgcgaccg acggtggcga taggcatccg     120
ggtggtgctc aaaagcagct tcgcctgact gatgcgctgg tcctcgcgcc agcttaatac     180
gctaatccct aactgctggc ggaacaaatg cgacagacgc gacggcgaca ggcagacatg     240
ctgtgcgacg ctggcgatat caaaattact gtctgccagg tgatcgctga tgtactgaca     300
agcctcgcgt acccgattat ccatcggtgg atggagcgac tcgttaatcg cttccatgcg     360
ccgcagtaac aattgctcaa gcagatttat cgccagcaat tccgaatagc gcccttcccc     420
ttgtccggca ttaatgattt gcccaaacag gtcgctgaaa tgcggctggt gcgcttcatc     480
cgggcgaaag aaaccggtat tggcaaatat cgacggccag ttaagccatt catgccagta     540
ggcgcgcgga cgaaagtaaa cccactggtg ataccattcg tgagcctccg gatgacgacc     600
gtagtgatga atctctccag gcgggaacag caaaatatca cccggtcggc agacaaattc     660
tcgtccctga ttttcacca ccccctgacc gcgaatggtg agattgagaa tataaccttt     720
cattcccagc ggtcggtcga taaaaaaatc gagataaccg ttggcctcaa tcggcgttaa     780
acccgccacc agatgggcgt taaacgagta tcccggcagc aggggatcat tttgcgcttc     840
agccatactt ttcatactcc cgccattcag agaagaaacc aattgtccat attgcat       897

<210> SEQ ID NO 67
<211> LENGTH: 305
<212> TYPE: DNA
<213> ORGANISM: Escherichia coli

<400> SEQUENCE: 67
cagacattgc cgtcactgcg tcttttactg gctcttctcg ctaacccaac cggtaacccc      60
gcttattaaa agcattctgt aacaaagcgg gaccaaagcc atgacaaaaa cgcgtaacaa     120
aagtgtctat aatcacggca gaaaagtcca cattgattat ttgcacggcg tcacactttg     180
ctatgccata gcatttttat ccataagatt agcggatcca gcctgacgct ttttttcgca     240
actctctact gtttctccat acctctagaa ataattttgt ttaactttaa gaaggagata     300
tacat                                                                 305

<210> SEQ ID NO 68
<211> LENGTH: 43
<212> TYPE: DNA
<213> ORGANISM: Escherichia coli

<400> SEQUENCE: 68
ctctagaaat aattttgttt aactttaaga aggagatata cat                        43

<210> SEQ ID NO 69
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

```
Met Ile Pro Glu Lys Arg Ile Arg Arg Ile Gln Ser Gly Gly Cys
1               5                   10                  15

Ala Ile His Cys Gln Asp Cys Tyr Ile Ser Gln Leu Cys Ile Pro Phe
            20                  25                  30

Thr Leu Asn Glu His Glu Leu Asp Gln Leu Asp Asn Ile Ile Glu Arg
        35                  40                  45

Lys Lys Pro Ile Gln Lys Gly Gln Thr Leu Phe Lys Ala Gly Asp Glu
    50                  55                  60

Leu Lys Ser Leu Tyr Ala Ile Arg Ser Gly Thr Ile Lys Ser Tyr Thr
65                  70                  75                  80

Ile Thr Glu Gln Gly Asp Glu Gln Ile Thr Gly Phe His Leu Ala Gly
                85                  90                  95

Asp Leu Val Gly Phe Asp Ala Ile Gly Ser Gly His His Pro Ser Phe
            100                 105                 110

Ala Gln Ala Leu Glu Thr Ser Met Val Cys Glu Ile Pro Phe Glu Thr
        115                 120                 125

Leu Asp Asp Leu Ser Gly Lys Met Pro Asn Leu Arg Gln Gln Met Met
    130                 135                 140

Arg Leu Met Ser Gly Glu Ile Lys Gly Asp Gln Asp Met Ile Leu Leu
145                 150                 155                 160

Leu Ser Lys Lys Asn Ala Glu Glu Arg Leu Ala Ala Phe Ile Tyr Asn
                165                 170                 175

Leu Ser Arg Arg Phe Ala Gln Arg Gly Phe Ser Pro Arg Glu Phe Arg
            180                 185                 190

Leu Thr Met Thr Arg Gly Asp Ile Gly Asn Tyr Leu Gly Leu Thr Val
        195                 200                 205

Glu Thr Ile Ser Arg Leu Leu Gly Arg Phe Gln Lys Ser Gly Met Leu
    210                 215                 220

Ala Val Lys Gly Lys Tyr Ile Thr Ile Glu Asn Asn Asp Ala Leu Ala
225                 230                 235                 240

Gln Leu Ala Gly His Thr Arg Asn Val Ala
                245                 250
```

<210> SEQ ID NO 70
<211> LENGTH: 298
<212> TYPE: PRT
<213> ORGANISM: Escherichia coli

<400> SEQUENCE: 70

```
Met Gln Tyr Gly Gln Leu Val Ser Ser Leu Asn Gly Gly Ser Met Lys
1               5                   10                  15

Ser Met Ala Glu Ala Gln Asn Asp Pro Leu Leu Pro Gly Tyr Ser Phe
            20                  25                  30

Asn Ala His Leu Val Ala Gly Leu Thr Pro Ile Glu Ala Asn Gly Tyr
        35                  40                  45

Leu Asp Phe Phe Ile Asp Arg Pro Leu Gly Met Lys Gly Tyr Ile Leu
    50                  55                  60

Asn Leu Thr Ile Arg Gly Gln Gly Val Val Lys Asn Gln Gly Arg Glu
65                  70                  75                  80

Phe Val Cys Arg Pro Gly Asp Ile Leu Leu Phe Pro Pro Gly Glu Ile
                85                  90                  95

His His Tyr Gly Arg His Pro Glu Ala His Glu Trp Tyr His Gln Trp
            100                 105                 110
```

```
Val Tyr Phe Arg Pro Arg Ala Tyr Trp His Glu Trp Leu Asn Trp Pro
            115                 120                 125

Ser Ile Phe Ala Asn Thr Gly Phe Phe Arg Pro Asp Glu Ala His Gln
        130                 135                 140

Pro His Phe Ser Asp Leu Phe Gly Gln Ile Ile Asn Ala Gly Gln Gly
145                 150                 155                 160

Glu Gly Arg Tyr Ser Glu Leu Leu Ala Ile Asn Leu Leu Glu Gln Leu
                165                 170                 175

Leu Leu Arg Arg Met Glu Ala Ile Glu Ser Leu His Pro Pro Met
            180                 185                 190

Asp Asn Arg Val Arg Glu Ala Cys Gln Tyr Ile Ser Asp His Leu Ala
        195                 200                 205

Asp Ser Asn Phe Asp Ile Ala Ser Val Ala Gln His Val Cys Leu Ser
210                 215                 220

Pro Ser Arg Leu Ser His Leu Phe Arg Gln Gln Leu Gly Ile Ser Val
225                 230                 235                 240

Leu Ser Trp Arg Glu Asp Gln Arg Ile Ser Gln Ala Lys Leu Leu Leu
                245                 250                 255

Ser Thr Thr Arg Met Pro Ile Ala Thr Val Gly Arg Asn Val Gly Phe
            260                 265                 270

Asp Asp Gln Leu Tyr Phe Ser Arg Val Phe Lys Lys Cys Thr Gly Ala
        275                 280                 285

Ser Pro Ser Glu Phe Arg Ala Gly Cys Glu
    290                 295
```

```
<210> SEQ ID NO 71
<211> LENGTH: 753
<212> TYPE: DNA
<213> ORGANISM: Escherichia coli

<400> SEQUENCE: 71
atgatcccgg aaaagcgaat tatacggcgc attcagtctg gcggttgtgc tatccattgc      60
caggattgca cgatcagcca gctttgcatc ccgttcacac tcaacgaaca tgagcttgat     120
cagcttgata atatcattga gcggaagaag cctattcaga aaggccagac gctgtttaag     180
gctggagatg aacttaaatc gctttatgcc atccgctccg gtacgattaa agtttatacc     240
atcactgagc aaggcgacga gcaaatcact ggtttccatt tagcaggcga tctggtggga     300
tttgatgcca tcggcagcgg tcatcacccg agtttcgcgc aggcgctgga aacctcgatg     360
gtatgtgaaa tcccgttcga aacgctggac gatttgtctg gtaaaatgcc gaatctgcgt     420
cagcagatga tgcgtctgat gagcggtgaa atcaaaggcg atcaggacat gatcctgctg     480
ttgtcgaaga aaaatgccga ggaacgtctg gctgcattca tctacaacct gtcccgtcgt     540
tttgcccaac gcggcttctc ccctcgtgaa ttccgcctga cgatgactcg tggtgatatc     600
ggtaactatc tgggcctgac ggttgaaacc atcagccgtc tgctgggtcg cttccagaaa     660
agcggtatgc tggcagtcaa aggtaaatac atcactatcg aaaataacga tgcgctggcc     720
cagcttgctg gtcatacgcg taacgttgcc tga                                  753
```

```
<210> SEQ ID NO 72
<211> LENGTH: 250
<212> TYPE: PRT
<213> ORGANISM: Escherichia coli

<400> SEQUENCE: 72

Met Ile Pro Glu Lys Arg Ile Ile Arg Arg Ile Gln Ser Gly Gly Cys
```

```
1               5                    10                   15
Ala Ile His Cys Gln Asp Cys Ser Ile Ser Gln Leu Cys Ile Pro Phe
             20                  25                  30

Thr Leu Asn Glu His Glu Leu Asp Gln Leu Asp Asn Ile Ile Glu Arg
             35                  40                  45

Lys Lys Pro Ile Gln Lys Gly Gln Thr Leu Phe Lys Ala Gly Asp Glu
50                       55                  60

Leu Lys Ser Leu Tyr Ala Ile Arg Ser Gly Thr Ile Lys Ser Tyr Thr
65                   70                  75                  80

Ile Thr Glu Gln Gly Asp Glu Gln Ile Thr Gly Phe His Leu Ala Gly
                 85                  90                  95

Asp Leu Val Gly Phe Asp Ala Ile Gly Ser Gly His His Pro Ser Phe
                100                 105                 110

Ala Gln Ala Leu Glu Thr Ser Met Val Cys Glu Ile Pro Phe Glu Thr
             115                 120                 125

Leu Asp Asp Leu Ser Gly Lys Met Pro Asn Leu Arg Gln Gln Met Met
130                      135                 140

Arg Leu Met Ser Gly Glu Ile Lys Gly Asp Gln Asp Met Ile Leu Leu
145                      150                 155                 160

Leu Ser Lys Lys Asn Ala Glu Glu Arg Leu Ala Ala Phe Ile Tyr Asn
                 165                 170                 175

Leu Ser Arg Arg Phe Ala Gln Arg Gly Phe Ser Pro Arg Glu Phe Arg
                 180                 185                 190

Leu Thr Met Thr Arg Gly Asp Ile Gly Asn Tyr Leu Gly Leu Thr Val
             195                 200                 205

Glu Thr Ile Ser Arg Leu Leu Gly Arg Phe Gln Lys Ser Gly Met Leu
210                      215                 220

Ala Val Lys Gly Lys Tyr Ile Thr Ile Glu Asn Asn Asp Ala Leu Ala
225                      230                 235                 240

Gln Leu Ala Gly His Thr Arg Asn Val Ala
                 245                 250

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77
```

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 2555
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
actcttcctt tttcaatatt attgaagcat ttatcagggt tattgtctca tgagcggata      60
catatttgaa tgtatttaga aaataaaca ataggggaa ttaaaaaaa gcccgctcat       120
taggcgggct actacctagg ccgcggccgc gcgaattcga gctcggtacc cggggatcct     180
ctagagtcga cctgcaggca tgcaagcttg cggccgcgtc gtgactggga aaccctggc      240
gactagtctt ggactcctgt tgatagatcc agtaatgacc tcagaactcc atctggattt     300
gttcagaacg ctcggttgcc gccgggcgtt ttttattggt gagaatccag ggtccccaa      360
taattacgat ttaaatcaca gcaaacacca cgtcggccct atcagctgcg tgctttctat     420
gagtcgttgc tgcataactt gacaattaac atccggctcg tagggtttgt ggagggccca    480
agttcactta aaaaggagat caacaatgaa agcaattttc gtactgaaac atcttaatca    540
tgctggggag ggtttctaat gttcacggga agtattgtcg cgattgttac tccgatggat    600
gaaaaggta atgtctgtcg ggctagcttg aaaaaactga ttgattatca tgtcgccagc    660
ggtacttcgg cgatcgtttc tgttggcacc actggcgagt ccgctacctt aaatcatgac    720
gaacatgctg atgtggtgat gatgacgctg gatctggctg atgggcgcat tccggtaatt    780
gccgggaccg gcgctaacgc tactgcggaa gccattagcc tgacgcagcg cttcaatgac    840
agtggtatcg tcggctgcct gacggtaacc ccttactaca atcgtccgtc gcaagaaggt    900
ttgtatcagc atttcaaagc catcgctgag catactgacc tgccgcaaat tctgtataat    960
gtgccgtccc gtactggctg cgatctgctc ccggaaacgg tgggccgtct ggcgaaagta   1020
aaaaatatta tcggaatcaa agaggcaaca gggaacttaa cgcgtgtaaa ccagatcaaa   1080
gagctggttt cagatgattt tgttctgctg agcggcgatg atgcgagcgc gctggacttc   1140
atgcaattgg gcggtcatgg ggttatttcc gttacggcta acgtcgcagc gcgtgatatg   1200
gcccagatgt gcaaactggc agcagaaggg catttgccg aggcacgcgt tattaatcag   1260
cgtctgatgc cattacacaa caactatttt gtcgaaccca tccaatccc ggtgaaatgg   1320
```

```
gcatgtaagg aactgggtct tgtggcgacc gatacgctgc gcctgccaat gacaccaatc    1380
accgacagtg gccgtgagac ggtcagagcg gcgcttaaac atgccggttt gctgtaagac    1440
ttttgtcagg ttcctactgt gacgactacc accgatagac tggagtgttg ctgcgaaaaa    1500
accccgccga agcgggtttt tttgcgagaa gtcaccacga ttgtgcttta cacggagtag    1560
tcggcagttc cttaagtcag aatagtggac aggcggccaa gaacttcgtt catgatagtc    1620
tccggaaccc gttcgagtcg ttttccgccc cgtgctttca tatcaattgt ccggggttga    1680
tcgcaacgta caacacctgt ggtacgtatg ccaacaccat ccaacgacac cgcaaagccg    1740
gcagtgcggg caaaattgcc tccgctggtt acgggcacaa caacaggcag gcgggtcacg    1800
cgattaaagg ccgccggtgt gacaatcagc accggccgcg ttccctgctg ctcatgacct    1860
gcggtaggat caagcgagac aagccagatt tcccctcttt ccatctagta taactattgt    1920
ttctctagta acatttattg tacaacacga gcccatttt gtcaaataaa ttttaaatta     1980
tatcaacgtt aataagacgt tgtcaataaa attattttga caaaattggc cggccggcgc    2040
gccgatctga agatcagcag ttcaacctgt tgatagtacg tactaagctc tcatgtttca    2100
cgtactaagc tctcatgttt aacgtactaa gctctcatgt ttaacgaact aaaccctcat    2160
ggctaacgta ctaagctctc atggctaacg tactaagctc tcatgtttca cgtactaagc    2220
tctcatgttt gaacaataaa attaatataa atcagcaact aaatagcct ctaaggtttt     2280 aagtttata agaaaaaaa gaatatataa ggcttttaaa gcctttaagg tttaacggtt      2340
gtggacaaca agccagggat gtaacgcact gagaagccct tagagcctct caaagcaatt    2400
ttgagtgaca caggaacact taacggctga catggggcgc gcccagctgt ctagggcggc    2460
ggatttgtcc tactcaggag agcgttcacc gacaaacaac agataaaacg aaaggcccag    2520
tctttcgact gagcctttcg ttttatttga tgcct                              2555

<210> SEQ ID NO 82
<211> LENGTH: 2472
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
actcttcctt tttcaatatt attgaagcat ttatcagggt tattgtctca tgagcggata      60
catatttgaa tgtatttaga aaataaaca aataggggaa ttaaaaaaaa gcccgctcat     120
taggcgggct actacctagg ccgcggccgc gcgaattcga gctcggtacc cggggatcct    180
ctagagtcga cctgcaggca tgcaagcttg cggccgcgtc gtgactggga aaaccctggc    240
gactagtctt ggactcctgt tgatagatcc agtaatgacc tcagaactcc atctggattt    300
gttcagaacg ctcggttgcc gccggcgtt ttttattggt gagaatccag ggtccccaa      360 taattacgat ttaaatcaca gcaaacacca cgtcggccct atcagctgcg tgctttctat    420
gagtcgttgc tgcataactt gacaattaat catccggctc gtagggtttg tggagggccc    480
aagttcactt aaaaaggaga tcaacaatga agcaattttt cgtactgaaa catcttaatc    540
atgctgggga gggttctaa tgaaacagta tttagaactg atgcaaaaag tgctcgacga     600
aggcacacag aaaaacgacc gtaccggaac cggaacgctt ccatttttg gtcatcagat     660 gcgttttaac ctgcaagatg gattcccgct ggtgacaact aaacgttgcc acctgcgttc    720
```

```
catcatccat gaactgctgt ggtttcttca gggcgacact aacattgctt atctacacga      780
aaacaatgtc accatctggg acgaatgggc cgatgaaaac ggcgacctcg ggccagtgta      840
tggtaaacag tggcgtgcct ggccaacgcc agatggtcgt catattgacc agatcactac      900
ggtactgaac cagctgaaaa acgacccgga ttcgcgccgc attattgttt cagcgtggaa      960
cgtaggcgaa ctggataaaa tggcgctggc accgtgccat gcattcttcc agttctatgt     1020
ggcagacggc aaactctctt gccagcttta tcagcgctcc tgtgacgtct tcctcggcct     1080
gccgttcaac attgccagct acgcgttatt ggtgcatatg atggcgcagc agtgcgatct     1140
ggaagtgggt gattttgtct ggaccggtgg cgacacgcat ctgtacagca accatatgga     1200
tcaaactcat ctgcaattaa gccgcgaacc gcgtccgctg ccgaagttga ttatcaaacg     1260
taaacccgaa tccatcttcg actaccgttt cgaagacttt gagattgaag gctacgatcc     1320
gcatccgggc attaaagcgc cggtggctat ctaagacttt tgtcaggttc ctactgtgac     1380
gactaccacc gatagactgg agtgttgctg cgaaaaaacc ccgccgaagc ggggttttt      1440
gcgagaagtc accacgattg tgctttacac ggagtagtcg gcagttcctt aagtcagaat     1500
agtggacagg cggccaagaa cttcgttcat gatagtctcc ggaacccgtt cgagtcgttt     1560
tccgcccgt gctttcatat caattgtccg gggttgatcg caacgtacaa cacctgtggt     1620
acgtatgcca acaccatcca acgacaccgc aaagccggca gtgcgggcaa aattgcctcc     1680
gctggttacg ggcacaacaa caggcaggcg ggtcacgcga ttaaaggccg ccggtgtgac     1740
aatcagcacc ggccgcgttc cctgctgctc atgacctgcg gtaggatcaa gcgagacaag     1800
ccagatttcc cctctttcca tctagtataa ctattgtttc tctagtaaca tttattgtac     1860
aacacgagcc cattttttgtc aaataaattt taaattatat caacgttaat aagacgttgt     1920
caataaaatt attttgacaa aattggccgg ccggcgcgcc gatctgaaga tcagcagttc     1980
aacctgttga tagtacgtac taagctctca tgtttcacgt actaagctct catgtttaac     2040
gtactaagct ctcatgttta acgaactaaa ccctcatggc taacgtacta agctctcatg     2100
gctaacgtac taagctctca tgtttcacgt actaagctct catgtttgaa caataaaatt     2160
aatataaatc agcaacttaa atagcctcta aggttttaag ttttataaga aaaaaagaa     2220
tatataaggc ttttaaagcc tttaaggttt aacggttgtg gacaacaagc cagggatgta     2280
acgcactgag aagcccttag agcctctcaa agcaattttg agtgacacag gaacacttaa     2340
cggctgacat ggggcgcgcc cagctgtcta gggcggcgga tttgtcctac tcaggagagc     2400
gttcaccgac aaacaacaga taaaacgaaa ggcccagtct ttcgactgag cctttcgttt     2460
tatttgatgc ct                                                        2472

<210> SEQ ID NO 83
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
ttaagtcaga atagtggaca ggcggccaag aacttcgttc atgatagtct ccggaacccg      60
ttcgagtcgt tttccgcccc gtgctttcat atcaattgtc cggggttgat cgcaacgtac     120
aacacctgtg gtacgtatgc caacaccatc caacgacacc gcaaagccgg cagtgcgggc     180
aaaattgcct ccgctggtta cgggcacaac aacaggcagg cgggtcacgc gattaaaggc     240
```

```
cgccggtgtg acaatcagca ccggccgcgt tccctgctgc tcatgacctg cggtaggatc    300
aagcgagaca agccagattt ccccctcttc cat                                 333
```

<210> SEQ ID NO 84
<211> LENGTH: 879
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84

```
atgttcacgg gaagtattgt cgcgattgtt actccgatgg atgaaaaagg taatgtctgt    60
cgggctagct tgaaaaaact gattgattat catgtcgcca gcggtacttc ggcgatcgtt   120
tctgttggca ccactggcga gtccgctacc ttaaatcatg acgaacatgc tgatgtggtg   180
atgatgacgc tggatctggc tgatgggcgc attccggtaa ttgccgggac cggcgctaac   240
gctactgcgg aagccattag cctgacgcag cgcttcaatg acagtggtat cgtcggctgc   300
ctgacggtaa ccccttacta caatcgtccg tcgcaagaag gtttgtatca gcatttcaaa   360
gccatcgctg agcatactga cctgccgcaa attctgtata atgtgccgtc ccgtactggc   420
tgcgatctgc tcccggaaac ggtgggccgt ctggcgaaag taaaaaatat tatcggaatc   480
aaagaggcaa cagggaactt aacgcgtgta accagatca aagagctggt ttcagatgat   540
tttgttctgc tgagcggcga tgatgcgagc gcgctggact tcatgcaatt gggcggtcat   600
ggggttattt ccgttacggc taacgtcgca gcgcgtgata tggcccagat gtgcaaactg   660
gcagcagaag gcatttttgc cgaggcacgc gttattaatc agcgtctgat gccattacac   720
aacaaactat ttgtcgaacc caatccaatc ccggtgaaat gggcatgtaa ggaactgggt   780
cttgtggcga ccgatacgct gcgcctgcca atgacaccaa tcaccgacag tggccgtgag   840
acggtcagag cggcgcttaa acatgccggt ttgctgtaa                          879
```

<210> SEQ ID NO 85
<211> LENGTH: 795
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

```
atgaaacagt atttagaact gatgcaaaaa gtgctcgacg aaggcacaca gaaaaacgac    60
cgtaccggaa ccggaacgct ttccattttt ggtcatcaga tgcgttttaa cctgcaagat   120
ggattcccgc tggtgacaac taaacgttgc cacctgcgtt ccatcatcca tgaactgctg   180
tggtttcttc agggcgacac taacattgct tatctcacg aaaacaatgt caccatctgg   240
gacgaatggg ccgatgaaaa cggcgacctc gggccagtgt atggtaaaca gtggcgtgcc   300
tggccaacgc cagatggtcg tcatattgac cagatcacta cggtactgaa ccagctgaaa   360
aacgacccgg attcgcgccg cattattgtt tcagcgtgga acgtaggcga actggataaa   420
atggcgctgg caccgtgcca tgcattcttc cagttctatg tggcagacgg caaactctct   480
tgccagcttt atcagcgctc ctgtgacgtc ttcctcggcc tgccgttcaa cattgccagc   540
tacgcgttat tggtgcatat gatggcgcag cagtgcgatc tggaagtggg tgattttgtc   600
```

```
tggaccggtg gcgacacgca tctgtacagc aaccatatgg atcaaactca tctgcaatta    660
agccgcgaac cgcgtccgct gccgaagttg attatcaaac gtaaacccga atccatcttc    720
gactaccgtt tcgaagactt tgagattgaa ggctacgatc cgcatccggg cattaaagcg    780
ccggtggcta tctaa                                                     795
```

<210> SEQ ID NO 86
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 86

```
Met Glu Arg Gly Glu Ile Trp Leu Val Ser Leu Asp Pro Thr Ala Gly
1               5                   10                  15

His Glu Gln Gln Gly Thr Arg Pro Val Leu Ile Val Thr Pro Ala Ala
            20                  25                  30

Phe Asn Arg Val Thr Arg Leu Pro Val Val Pro Val Thr Ser Gly
        35                  40                  45

Gly Asn Phe Ala Arg Thr Ala Gly Phe Ala Val Ser Leu Asp Gly Val
    50                  55                  60

Gly Ile Arg Thr Thr Gly Val Val Arg Cys Asp Gln Pro Arg Thr Ile
65                  70                  75                  80

Asp Met Lys Ala Arg Gly Gly Lys Arg Leu Glu Arg Val Pro Glu Thr
                85                  90                  95

Ile Met Asn Glu Val Leu Gly Arg Leu Ser Thr Ile Leu Thr
            100                 105                 110
```

<210> SEQ ID NO 87
<211> LENGTH: 292
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

```
Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
            20                  25                  30

Ala Ser Gly Thr Ser Ala Ile Val Ser Val Gly Thr Thr Gly Glu Ser
        35                  40                  45

Ala Thr Leu Asn His Asp Glu His Ala Asp Val Val Met Met Thr Leu
    50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140
```

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290

<210> SEQ ID NO 88
<211> LENGTH: 264
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Met Lys Gln Tyr Leu Glu Leu Met Gln Lys Val Leu Asp Glu Gly Thr
1               5                   10                  15

Gln Lys Asn Asp Arg Thr Gly Thr Gly Thr Leu Ser Ile Phe Gly His
                20                  25                  30

Gln Met Arg Phe Asn Leu Gln Asp Gly Phe Pro Leu Val Thr Thr Lys
            35                  40                  45

Arg Cys His Leu Arg Ser Ile Ile His Glu Leu Leu Trp Phe Leu Gln
        50                  55                  60

Gly Asp Thr Asn Ile Ala Tyr Leu His Glu Asn Asn Val Thr Ile Trp
65                  70                  75                  80

Asp Glu Trp Ala Asp Glu Asn Gly Asp Leu Gly Pro Val Tyr Gly Lys
                85                  90                  95

Gln Trp Arg Ala Trp Pro Thr Pro Asp Gly Arg His Ile Asp Gln Ile
            100                 105                 110

Thr Thr Val Leu Asn Gln Leu Lys Asn Asp Pro Asp Ser Arg Arg Ile
        115                 120                 125

Ile Val Ser Ala Trp Asn Val Gly Glu Leu Asp Lys Met Ala Leu Ala
130                 135                 140

Pro Cys His Ala Phe Phe Gln Phe Tyr Val Ala Asp Gly Lys Leu Ser
145                 150                 155                 160

Cys Gln Leu Tyr Gln Arg Ser Cys Asp Val Phe Leu Gly Leu Pro Phe
                165                 170                 175

Asn Ile Ala Ser Tyr Ala Leu Leu Val His Met Met Ala Gln Gln Cys
            180                 185                 190

```
Asp Leu Glu Val Gly Asp Phe Val Trp Thr Gly Gly Asp Thr His Leu
            195                 200                 205

Tyr Ser Asn His Met Asp Gln Thr His Leu Gln Leu Ser Arg Glu Pro
210                 215                 220

Arg Pro Leu Pro Lys Leu Ile Ile Lys Arg Lys Pro Glu Ser Ile Phe
225                 230                 235                 240

Asp Tyr Arg Phe Glu Asp Phe Glu Ile Glu Gly Tyr Asp Pro His Pro
                245                 250                 255

Gly Ile Lys Ala Pro Val Ala Ile
            260

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000
```

-continued

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
agtgcctgta ccagacgttc                                              20

<210> SEQ ID NO 119
<211> LENGTH: 20
<212> TYPE: DNA
<213> ORGANISM: Artificial Sequence

```
-continued

<220> FEATURE:
<221> NAME/KEY: source
<223> OTHER INFORMATION: /note="Description of Artificial Sequence:
      Synthetic primer"

<400> SEQUENCE: 119
agaaatgaca accagagagc                                                      20

<210> SEQ ID NO 120
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
ttgagtttaa tatggcagaa c                                                    21

<210> SEQ ID NO 121
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
aaatgatcat cgcgtcatc                                                       19

<210> SEQ ID NO 122
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
gcatcaatca gtgattggc                                                       19

<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
acgtctgaat atacgggctg                                                      20

<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
tccagcttga ctcgtttcag                                                      20
```

<210> SEQ ID NO 125
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 125
agcaccttac ccgaagagt                                                19

<210> SEQ ID NO 126
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 126
tggaggcttt aagaaatacc tcgatgtgaa caaccgcctg ccacgaatct tcgtcaagcg     60
attacacgtc ttgagcgat                                                 79

<210> SEQ ID NO 127
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 127
gataatggtg agattatccc cggttatacc ggacttatcg cctattcaga atcactggat     60
ctgacatggg aattagcca                                                 79

<210> SEQ ID NO 128
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 128
tggaggcttt aagaaatacc                                                20

<210> SEQ ID NO 129
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 129
gctggcgatt caggttcatc                                                20

<210> SEQ ID NO 130
<211> LENGTH: 9687
<212> TYPE: DNA
<213> ORGANISM: Escherichia coli

<400> SEQUENCE: 130

```
aatcgccggt gtactccgcg tcagaaaggt atacagccac ggcagggaga tcctgctctt      60
caagaaaaac agggcgcccg tcaaaccagg tgaccgtgtc ggtgatctcg gctttcagtt     120
tggccagaat ggctgcacga attgcgctgt gtctgttcat cgcttcaggt ggatcctcag     180
ttggtttttc agggctgcgg aaagttcttt gggcatatcg ctttcaataa ggcgctttga     240
aatagcggtg aaggccacgg tgagcggtgt ctcaagagga actttgacca catcaatcgg     300
ataacgggcc tgacctacgc gccgcatgac ctgccagcgc ccgttcgcaa gctgttggat     360
aaaagcgtta cgaaaggtat agggcccgat tttaaggacg ctgcccgctc cgtttctggc     420
cccttttta cgcgagagcc tgacgcgcgc cgtgccgagc tttatcgcag gaagattacc     480
gcggttgatt tttatcgacg cgaccgggcg atcgtgacgg gccttgcgca gacgggaacg     540
ctggcggacc agacgaaccg gaagcccctt tttccggtta tcatcaactg ttgcttcttt     600
cgctacagct ttgctccct ggcttatcgt tcttctggcc accctgttaa gtgcttttgc      660
ggttgcctca ggaacgatta accggctgag gctgttcagg ttctgaatag cccttttccag    720
tcctttcaca gacatagcgc ctcctcattc gagatggatg cggggttttc cgttgaacat     780
gtcatagcgg gtaacgatca ggttcttacc gtcgtagtcg acgctgtcgt ttcggcgtgg     840
ctggtaaagc tcagagaaaa ccaccagcga agtacctgtt cccgacaatg gccccatttc     900
ctcgagttgc tcggcgggaa caacgtcata gctgctgcca ttgatgatcg ctgtctttcc     960
catctttttt atagtggccg cgtccatgcg cgccgccatc cggtcaaagg agttaggcat    1020
tgatcttaac ttcaacaacg gtggtgtttg ccctgcatc ttcccaggcg atgcccgcgg     1080
caacggcgtc cgtttcttcg atcgtgattt tgccgtcctt cagatacacc tgcgccccgg    1140
cagtaaccgc atctgcggat acttttggca ggaggaaaac accctcagta aaaccgtccc    1200
cggtatcgcc agccgggata tcggtaattg ccaccgcgat aagttttcca acaacaaccg    1260
ggtcgccgct gtgaacatcg gttgcaccac tgtttaccag agggatcgtt ttcccgtcct    1320
gcgcatagtt cttagccata acttctccat tcagcccctt tcgaggctgg tttcaggtat    1380
aaaaaaagcc cttacgggcg tctgtttgtc aggactgttt tttactgacc agaggatttg    1440
gtcatgccgc gatagtccag cggcgccacg ccagcatcaa tacgcacttt cgtggcgata    1500
ccatcagtgg tgaagccttc ctgctgatcg atgtatggcg tgtcgacgcc gttgagataa    1560
gcgacctcaa tggtgtcggt gcccttcgcg gcagccagat accaggcttt cgcatcagct    1620
tcatccagac gtggttcggc aatgacttct gcaaagttct ggatagggtt aacgatcccg    1680
gcattgatgt ctgcaccttt aacactggcc gacttgatgg tctgatttgc cagagttttcc   1740
agggcgacgg gcaccagcat gtaggccgga cggatattca gggttcgctc ccctccttc    1800
tgcagacgca tcagcttgcg cgattcgtcc aggctggcca cagaaattgc acccgagctc   1860
aggttcttgt gatcggcatg gaacagcgcc tttccgtctg agagtttcgg gttttttggtc   1920
agaatggcgt aaaccagatc gccaatcgtt gctttcgccg cgcgccccat cttcatcggt    1980
acgtcggtaa gctggttcag atcgtcgttg atgatcgcct ggcgagttac tgagaagatt    2040
tcaccatacg tggcaagcgc gatggtttcg cctttgtcac tggtagtgat gtacttgtac    2100
tcagccccctt cgcgaacctg tcgcagagaa gggaacccac ccataccgac acgatgcgcc   2160
gttttgaagt ccgacagctg gccttttttg gtccactgct cgaaggtttc ctgcgcctcg    2220
tcccagccct gaatcagcgc tttgttcgca acatcaagca gaatgttgcc aaagtcagag    2280
```

```
gtgctgtggg tcagcgccag gccaaccatc tgcatcgggt tgtagctggc cacgccgata    2340 ccttttctg  tcagggccat acgcgcatac tcgcgcagcg tcataccgtt ataaacgtta    2400
tcccgctcct gaccttcgaa cccggcacgc gccatcagtg cctggcgaat accatccgcg    2460
acgaagttac cgttgcccgc atgaatatgc ggctgagtgg tttttattgga cggcgtggcc    2520 gttttaccga gttctgccag cagcaaatct ttcgccttat cgacggagca atcagggtcg    2580
gccacacact gattctgcag ttccatgtgc ttattaccga acatggcaaa gagatcgccg    2640
atagcgttaa cacgggtttt ctgctcagcc aacacctgcg cgcggatcgc attttcatcc    2700
ggtgccgggt ctgttttgc  ctgcggtgcc tgaggctggg taataaccgg gtcacgctgg    2760
gtagtgttgc gcggcggggt gatcatgttg cgaatgcttt ttggcatttt ttcaaattcc    2820
tcaatacgtt ttgaatgaat acaggccata gcctgaaggg atggtgtcac ctggtcggca    2880
aaacccagtt caaggcactc gctgccgttc atccaggttt cgtcctccag cattaccgca    2940
atttcttcgg tggattttcc ggttttctgt gcataagccg ggataagaac ggattcaacc    3000
ttgtcgagaa gatccgcata gtcgcgcata tcgctcgcgt caccaccagc aaaccccag    3060 ggcttatgga tcatcatcat cgtgttttca ggcatgatga ccggattgcc taccatcgca    3120
atcaccgagg ccatggaggc cgccagaccg tcgatatgta cggtaatcgc cgcgccgtgg    3180
tgcttcagcg cgttataaat agcaattccg tcgaagacat caccaccggg cgagttgata    3240
taaaggttga tgtgggtgac gtccccaagt gcccggagat cattgacgaa ctgtttcgcc    3300
gttacgcccc agtacccgat ttcgtcataa ataaaaatgt cggcctcact gttattgctg    3360
gcctgcatgc ggaaccacga attacttttt gcgctggctt tcggacggtg gcgcgcccgg    3420
ttctttggct tcggcactgg tgcctccttt atcattggcg gggtcggtgt caaacaccag    3480
gccctgttca cggttctcgt caacctcagc tttacggcgt gacttaacat catccgggtt    3540
gcgaccgctg gcacgtatcc agtcggattc agtagcagca ccgccgcgga tctgcgtttt    3600
ccaggcattc gcttctttaa cgggatcaat ccacggcata acgggccccg aataaaccgc    3660
gttataaagc gagtccatat caatgcctct cggcagcttg atttctccgg cagcaatagc    3720
catcttgagc caggctcgt  acatgggccg ggtcactgaa ccgatgaacc agtcctgaag    3780
aatcagatag ccgtcggttg actcgacaag ctcctgccgc tgggcactgt acgttccgtt    3840
gtagtttctg gatgtgctgg aaaagctgag gcgactgccg gcggacacgg cacgcagctg    3900
tccgttacga aaagattcga ggttagggtt cgggcgatcg gatttaatca tcccgatttc    3960
ttccccggcc tgcagttcgt catagagcat accgggctga atcatcagct cgcggtcatc    4020
gctgcttgaa tcagaatcga agctctgtcc gtcgcctttt ttgatataca tgccgagtgc    4080
cgcagcaatt ctggcagcag taagctccga gtcctcgtat tctttcagcg cgctcagacg    4140
catcagaaca ccagacaaaa gagacgttcc gcgggtctgg tgcaggcgtc gggtgaattt    4200
gagatgcagc atgttctctg catctatctc tttggtatca aactgacgcc cggatactgg    4260
caggctttta tagacctgat atttttcgg  gcgtccccag ttatcgacaa aaacgccctg    4320
attgagctgg gtggcagcat cgctgttcat cggcacaaag tccggctcca gcgcttccag    4380
ccagaacggc acgccagcaa ccggctgaag accatttccg gtaccgcgaa ccagctgagc    4440
aaatacctca ccgtcccgga gccacgttcg cagcatcagc cgctccagca ttgggcgggt    4500
aaactgggtt gtgacatctg gccttacgga ccattcgccc cactttcggc ggatatcagt    4560
ggccagcttt ttagcgatct tcccgttact cagcatcgga tgcggttcaa ctatgatgcc    4620
cttcgcaccc accacccttt cttccagctt gtcgaaaacg ccgatcacca gatcgtggtt    4680
```

-continued

```
gttatccagc cagcgcgcct gctgcctcag cgaaaccgcc cccatctggc tgagctgatc    4740
ggctgaacga ttttccttct gggctttgtg ggtacgcgtt tgctttaccg cctcatacgc    4800
tttaataact gcgcgggcac gcaggcgtga ggctttccag cctggtgaaa acaggccaat    4860
cgcatcatct aaaaaactca tccaaacctc gccagcctgt agccgggtcg cccacggcgt    4920
ttgttattga gcgttgccag tcgtcgctcc cattcctgac ggccttttct gatttccgac    4980
aggttttcga gcgtcatctg ctgcccgttg aaagtgattg atttcccctc cagaacagac    5040
agctcggctg cagcatagcg gtcgatcatg ttttgaatat ctgctggatt cacacccaac    5100
ctcctgacga agaccacgga ttagcctgct cggttacggg cttctcacgt tttggttttg    5160
gtttagattt cggcgcaggc ggcggggatg gcatttcgcc agcttccgtc tgcgtgtcct    5220
cgatccacgt ttcccgccgt gcccactcag gagctgacgg ccatttgatt ttttcgtaac    5280
cactaaggat ggcgagcgcg tcggcataaa cgagcaggtc aaatgcttcg tttgcgcccc    5340
ggccgggctt actccatttc ccttcattcg agcgttcctc atacgtcagt tcgtcataga    5400
accagctgcc cagccaggcg gggaaatgca catagccagg gccgggtgaa tcacgccaca    5460
gcgcattatt caccccggtct ttaagggcat cggtctggag aagataaaga ggcacatcac    5520
cagtcgcctg tgcgcggcgc gttgatctgc ccgtgttgtc gggaaacgtt cgctggataa    5580
gtttgctgcg cctgacgctg tcccctttga agagatagat acgcttaccc agcccctcac    5640
ggcgacatct gcgccagaac ttgtaggcat tatccgtcac gccatcttcg cccctgagt    5700
ccacggccat cgacatcagc cgcatgccct ttgatgggtc agctgcgagc ggccacgttt    5760
tatcaaagac gtcagtgagt aaaagatccc agtcctccgg atagctcgcc ggatccacct    5820
gaatgctttc accgttgccg tcgcagcgca gcgaatgccg gatgttgtaa cggtcaacta    5880
tccagcgctc acccatactt ccataacccg taatctgcac aacaaagcgc cggttgcgcc    5940
cggcctgcac gtccacggtc gcagtgagaa actgcacgcc gttcggtacc gaacgttttg    6000
ggacgtcttc ggcacgctgc tcgagcaatt cacttttacg ctgctccatg ctggctcgcg    6060
gcaaataggg cctgccgaaa tcggtgttga tcaccgtctt cagggtttct tcgctgcgcg    6120
tggattcata ttcctgctcg gcggtcagaa acttataaat aagctgcgcc caggtctggt    6180
aagcagctgc cggaccttcc atccagaagg aggcaatacg ggaacgacgg ccatcaccgc    6240
taaccaggcc tttcctgtcg atggtttgcc cgtcccggag ccagacacat tcatgttaa     6300
gcgcacgctt catgtccggt gtgatcctgc ctttacaggc agggcactga agaaacgccg    6360
cttcgctggc aagcacagga tcgctgctgt cgcggtatcc ggtcatattg tccatttccg    6420
gctggaaata ttcgccgcaa tgcgggcatg ccagtaaag acgacggcgg tcaccacggt    6480
tatagagcga taaaattccg gtggtcgag gggcttcatg gggcgtggag cgccgccatt    6540
ttgtgtctct gatatccctc ccgggcgagc tctcaaccag cgtcatcccg gaggacatga    6600
atgtcgtggt tcgtttcgat gccagtgaaa aagcatcccc ctccccgtcg atatcttccg    6660
gaaagcggtc ataatccgtc agcgccacac ttttatagtc cgaggacgac atgatattga    6720
cggatggcca gcccagcttc agatagttac cggcgcggaa tgtacggtcg tagacgttgt    6780
tatcgttacg tcttgggctt agccgggttt aacttcagg gctacagcga aaagtacggt    6840
ccaggcgttt tttggaatgc tcgcgcgctt tttcctcaga tacctgaatt acaagcatat    6900
ctgccggatc gcagacaatg ttataaacga tccagccgtc aatcagcccg atggttttac    6960
ccgttcgcgc tgggcccaca aacacaaccg catcgtattc acgcgatgcc agacagttca    7020
```

```
tcggctcaat cacatagggt gccagatccg gatcccacgg aactgagttt cccgccccca   7080
ttggcacgcg catataagta ctgaccgcat cggccaccgg catacgacgc ggggctcgta   7140
aaataccgga aacatcgcgg cggatgtccc tggcggatgc ccgctttgcc atcagtcctc   7200
ctcaggctgc tcctcctctt ttccagcgtc ctgcaccttc tccgccatct ggtcgcgcag   7260
atcatcgata acgctttgca cacgaactac cgcagcaggc gttaaagcac agtcgcgctc   7320
gagcacatcc gggagggttt caagtaccat gacgacggct ttcgccatca atgagaattc   7380
tcgcgccact tcatctgcgg gtattaactg ccccgtatcc tgttcgaact tcagcctctc   7440
gttctctgct ttccagtggg acagcctgtc agaaggggc atatcgtcga tgttggccga    7500
aacggtaggg atcatcagtt cggtcagaat gtcggtcacc agatagagct ttaacttgct   7560
attgctgcct ggagcaggtt caacattttt cagtctcgcg gcaaccgtct gacggtgtac   7620
gccggttatc cctgccagct ggttgatatt gagttttaaa gtggcaattt cctggtccat   7680
gatggtgaac acttttttgaa cgattcgaca tgttgcgaaa atggcctcta attaaatcaa   7740
agacctgcgc acatgatgat gatgaccctg gatccgaaaa actagccgtt tcccgcgagc   7800
acgccgcccc gtggcagggt ccccctccgg gagtaccttt tgataataat tatcaattgc   7860
acactatcga cggcactgct gccagataac accaccgggg aaacattcca tcatgatggc   7920
cgtgcggaca taggaagcca gttcatccat cgctttcttg tctgctgcca tttgctttgt   7980
gacatccagc gccgcacatt cagcagcgtt tttcagcgcg ttttcgatca acgtttcaat   8040
gttggtatca acaccaggtt taactttgaa cttatcggca ctgacggtta ccttgttctg   8100
cgctggctca tcacgctgga taccaaggct gatgttgtag atattggtca ccggctgagg   8160
tgtttcgatt gccgctgcgt ggatagcacc atttgcgata gcggcgtcct tgatgaatga   8220
cactccattg cgaataagtt cgaaggagac ggtgtcacga atgcgctggt ccagctcgtc   8280
gattgccttt tgtgcagcag aggtatcaat ctcaacgcca agcgtcatcg aagcgcaata   8340
ttgctgctca ccaaaacgcg tattgaccag gtgttcaacg gcaaatttct gcccttctga   8400
tgtcagaaag gtaaagtgat tttctttctg gtattcagtt gctgtgtgtc tggtttcagc   8460
aaaaccaagc tcgcgcaatt cggctgtgcc agatttagaa ggcagatcac cagacagcaa   8520
cgcgccacgg aaaaacagcg cataaagcac ttcattagca gcgccagata gcgtaatgat   8580
tttgttactc atgaatatt tccttttagg cgtgagcctg tcgcacggca atgccgcccg    8640
agaggtaaac gcaacctaac ggcatcaccc aggctcacta ctgaaagact ctctttgatg   8700
tgcgcgtgcg atgcgcgtag aagactgatt tatcaacctg tctttatatc aggattcatt   8760
acctgactat ttgtgggtaa agttcgtagt gcgctgatcg tgcaaaatga ttttagttgg   8820
gaacagttcg caactctgtc ccataaaaat cagcatattc ccatctatcc catatccagc   8880
gcattgacca tcgggatact gaagggagat tccatcatct cttagaaaga tcaccatctc   8940
ttttgtttca atttgcatat agctacctgg aggatttatg aatgcaagga ttttcatgga   9000
ctattaccat gagattgatt ttccatcttt attcgcgaga gcagtggaaa gcgatgacga   9060
tgtgggtact acattgcgca ttcacctact ttgtgagcgc atggtcgaag catggatatg   9120
cgcatgctgt gactgccaag atctctttgg aagagataaa aacaaacttt taatcgaatg   9180
taatactaaa atatccatgg cgggaaacct gggaatcccc ccggaactta tgaaatcact   9240
taaaaccatc aactcaatgc gtaatgacct tgcacacaat ccatcaatac aaagcattgc   9300
tgattcaagg atccagagcc tgaaggatac tctgactgaa tactttaaac agcatccaac   9360
ggaacccagc atggaagaat caaaactggg tattttttaac gccgagaatc aattaaccga   9420
```

-continued

```
agaagtttcc ttagatagtg acagttcaaa aaacagactt aagttaatct tgctgttcag    9480
caagttaatg caggcgttaa tgcaattagt tgcagctaat cataatgggc gctgggataa    9540
ccaatttagc caattcgttt accatgtgac catgaacgca acaaagagat aaatccaagc    9600
ccgttttgta cgggctgttg cattatcaca ggcactcagt gaatgcctgc tgtaatgccg    9660
ctagtcgtcg agttgcaaca caccgtg                                       9687
```

<210> SEQ ID NO 131

<400> SEQUENCE: 131

000

<210> SEQ ID NO 132
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 132

```
gcatcaatca gtgattggc                                                  19
```

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 133

```
acgtctgaat atacgggctg                                                 20
```

<210> SEQ ID NO 134
<211> LENGTH: 59056
<212> TYPE: DNA
<213> ORGANISM: Escherichia coli

<400> SEQUENCE: 134

```
aggcctctcc tcgcgagagg catttttat ttgatgggat aaagatcttt gcgcttatac     60
ggttggattt cgcccggttt gcgagttttc agcaatttta atatccaggt gtattgttct    120
ggtcgcggac caacaaaaat ctcgacttct tcattcatcc gccgcgcaat cgtatgatca    180
tccgcctcta acagatcatc catcggtggg cgcacctgaa tcgtcagacg atgcgtcttg    240
ccatcataaa tcggaaatag cggtacaacg cgcgcacggc acactttcat caaacgacca    300
atcgcgggca acgtcgcttt ataggtggca aagaaatcaa caaattcgct gtgttctggg    360
ccatgatcct gatcgggtaa ataatatccc cagtaaccct gacgtaccga ctggatgaat    420
ggtttaatac catcatttct cgcatgcaga cgaccaccaa agcgacggcg caccgtgttc    480
cagacataat caaaaaccgg gttgccctga ttatggaaca tcgctgccat tttctgccct    540
tgcgaggcca tcagcatggc aggaatatcg acggcccaac cgtgcggcac cagaaaaatc    600
actttctcgt tattacgtcg tatctcttcg atgatctcca gccctttgcca gtcaacgcgc    660 ggctgaattt tctccggccc gcgtattgcc aactcagcca tcattaccat cgcttgcggc    720
gcggtggcaa acatctcatc tacaatcgct tcgcgttcag cttcactacg ttctggaaag    780
```

```
cagagcgaca gattgattaa cgcacgacgg cgtgagcttt ttcccagtcg tccggcaaaa    840
cgtcccagcc gtgccagaat gggatcacgg aactttggcg gcgttaaagc gatacccgcc    900
atcgctgcta cgcccagcca tgctccccag tagcgcgggt ggcgaaagga tttatcaaac    960
tcaggaatgt attcgctatt atttttttc gtttccatgc ttttccagtt tcggataagg   1020
caaaaatcaa tctggtgata gtgtagcggc gcaacttgcc ccgcaccaaa taaaaaagcc   1080
ggtactgact gcgtaccggc tgcgaatgga tgttaattaa tcaaaccgta gctgcggcac   1140
aatctctttg gcctgtgcca ggaattcgcg acgatcggag ccggtcagcc cttcggtacg   1200
cggcagtttt gccgtcagcg ggtttacggc ctgctggttt atccatactt catagtgcag   1260
atgcggcccg gttgaacgtc cggtattacc ggaaagcgcg atacggtcgc cacgtttcac   1320
cttctgtccc ggtttcacca ggatcttgcg caagtgcata taacgcgtgg tgtagctgcg   1380
accatgacga atagccacat aataacctgc tgcgccacta cgtttggcaa ccaccacttc   1440
accgtcaccc actgaaagca ctggcgtacc ttgtggcatg gcaaaatcaa cacctctgtg   1500
tggcgcaacg cgaccggtca ccggattagt acgacgcggg ttaaagttag atgagatacg   1560
gaactgtttc gccgtcggga atcgcaagaa tcctttcgcc agaccagtac cgttacgatc   1620
gtagaatttg ccatcttcag cgcggattgc gtaataatct ttaccttctg aacgcaaacg   1680
tacgcccagc agctggcttt gctcacgttt accatcaagc atttctcgtg acattaacac   1740
cgcaaattca tcgcctttt tcagtttgcg gaaatccatt tgccactgca tggctttaat   1800
cactgcgctc acttcggcgc tggttaaacc ggcgtttctg cgctggcaa caaagcttcc   1860
cccgacggta cctttcagca gattgttgac ccactctcct tgctgcattt cgctggtcat   1920
tttaaaaccg ttagcggcag tacggtcata ggttcgggtt tcacgacgag acacttccca   1980
ggtgaggcgc tgcagttcgc cgtccgcggt taatgtccag gagagttgtt gaccgatttt   2040
caggttacgc aattctttgt cggcagcagc cagttgggtg atatcaccca tatcaatacc   2100
atactgattg agaatgctgc ttagcgtatc gccagtggaa acaacatatt catgcacgcc   2160
cgcttcaccg gcgattttgt catccagttc gtcctgggga atggcttcat cttcttgtgc   2220
agcttgatca atcggctcac tggcttcagg taagagcgaa cgaatttcgt tctgttccag   2280
ctcaatggtt ttgacaattg gcgtggcatc gcggtgataa acatagggcc gccagacagc   2340
gacggccaga gtaagaacgg tgagcgaccc caacataacg cggtgtggtc gcggtaaatt   2400
attaaacgcc agggcgacag agcgggctat ctgttgcacg taatcacttc ctcattaatc   2460
tcctttcagg cagctcgcat actggttggc taattgattc aggaattctg aatagcttgt   2520
tttacccagt ttgatattcg tccccagggg atccaacgtt cccatacgaa cggatgtccc   2580
tcgtgcgacg ctctcaacga ccgctggcct gaactgtggc tcagcaaaaa cgcaggttgc   2640
tttttgctca accaactgtg ttcttatttc atgtaaacgc tgcgcgccag gttgaatctc   2700
agggttaacg gtaaaatgac caagcggtgt cagtccgaac tgtttttcga atagccgta   2760
agcatcgtga aaaacgaaat aacctttccc cttgagcggc gcgagctcgt taccaacctg   2820
cttttcggtt gaggctaatt gtgcctcaaa atccttcagg ttggcgtcaa gtttggctcg   2880
actttgcggc ataagttcca ctaatttccc atggattgca accgctgtag cccgcgctat   2940
ctctggggaa agccaaagat gcatgttgaa atcgccgtga tggtgatctt cgtcactttt   3000
ttccgcgtgg tcgtgatcat catcatcgcc gtgaatactt ttcatcagca gcggtttcac   3060
attctctagc tgcgcaatcg ttacctgttt cgcttcaggt aatttactta ccggttttg   3120
```

-continued

```
catgaacgct tccatctccg ggccaaccca aacgactaag tccgcgttct gtaagcgttt    3180
tacatctgat ggacgcagtg aataatcatg ttctgaagcc ccgtcaggta gtaaaacctc    3240
cgtttctgtt accccatcag caatggcaga agcgatgaac ccaacgggtt taagcgaagc    3300
gacaacggca gcatctgcgg cctgtgttgc accgccccag agagcggcgg ataatgctgc    3360
gaaaagaagc gttttttat gtaacataat gcgaccaatc atcgtaatga atatgagaag    3420
tgtgatatta taacatttca tgactactgc aagactaaaa ttaacatgac aagtctggtt    3480
tccctggaaa atgtctcggt ttcttttggc caacgccgcg tcctctctga tgtgtcgctg    3540
gaacttaaac ctggaaaaat tttgacttta cttgggccaa acggcgcagg taagtcgaca    3600
ctggtacggg tagtgctcgg gctggtaaca cccgatgaag gggttatcaa gcgcaacgga    3660
aaactgcgca tcggctatgt accgcagaag ctgtatctcg acaccacgtt gccactgacc    3720
gtaaaccgtt ttttacgctt acgccctggc acacataaag aagatatttt gcctgcactg    3780
aaacgtgtcc aggccgggca tctgattaac gcaccgatgc aaaagctctc gggtggcgaa    3840
acgcagcgtg tactgttagc gcgagcattg ttaaatcgac cgcaattatt agtgctggat    3900
gaacccactc agggcgtgga tgtgaatggt caggtggcgt tatatgacct tattgaccaa    3960
ctgcgtcgcg aactggattg tggcgttta atggtatctc acgatctgca tctggtaatg    4020
gcaaaaaccg atgaagtgct ttgcctgaat caccacattt gttgttccgg cacaccggaa    4080
gttgtttccc tgcatccgga gtttatttct atgtttggtc ctcgtggtgc tgaacaactg    4140
ggtatctatc gccatcatca taatcatcgt cacgatttac agggacgaat tgttttgcgt    4200
cggggaaatg atcgctcatg attgaattat tatttcccgg ttggttagcc gggatcatgc    4260
tcgcctgtgc cgcgggtccg ctgggttcgt ttgtagtctg gcgtcgtatg tcttatttcg    4320
gtgatacgct ggctcatgcc tcattacttg gcgtcgcgtt tggtttgttg ctggacgtga    4380
atccattcta tgcggtgatt gccgttacgc tgctgctggc gggcggtctg gtatggctgg    4440
agaagcgtcc acagctggcg atcgacacgt tattagggat tatggcgcac agtgccctgt    4500
cgctgggcct ggtggtcgtt agtctgatgt ctaatattcg tgttgatttg atggcttacc    4560
tgttcggtga tttactggca gtgacgccag aagatctcat ctctattgcg attggcgtgg    4620
tcatcgtggt ggctatttg ttctggcaat ggcgcaattt gctgtcgatg acgattagcc    4680
cggatctggc gtttgttgat ggtgtgaaat tacagcgcgt gaaattgttg ttgatgctgg    4740
tgacggcatt gacgattggt gtagcgatga aattcgtcgg cgcgttgatt attacttcac    4800
tgctgattat tcctgctgct actgcacgtc gctttgcccg cacgccggaa cagatggctg    4860
gtgtcgctgt tttggtgggg atggtggcag tgactggcgg tttaaccttt tccgcatttt    4920
acgatacacc tgcaggcccg tcggtggtgc tatgcgcggc actgttattt attatcagta    4980
tgatgaaaaa gcaggccagc taatctgtcg ctgaacacat ttgtcggatg cggcgcgagc    5040
gccttatccc acctgcggtt cgctatctct ggtaggcctg ataagacgcg aacagcgtcg    5100
catcaggcac actgccagtg tcggatgcgg ctcgagcgac caatccgact tacggcattt    5160
ctggcggcgt gatgccgaag tggttccacg cccgcactgt cgccatacgc ccgcgcggtg    5220
tacgctgcaa aaagccttgc tgaatcaaat aaggttccag tacatcctca atggtttcac    5280
gttcttcgcc aatggctgcc gccaggttat ccagacctac cggcccacca agaacttat     5340 cgattaccgc cagcaacaat ttgcggtcca tataatcgaa accttcagca tcgacattca    5400
acatatccag cgcctgagca gcgatatctg ccgagatggt gccatcgtgc ttcacttcag    5460
cgaaatcacg cactcgacgc agcagacggt tggcaatacg tggcgtaccg cgcgcacgac    5520
```

```
gagcaacttc cagcgcgccg tcatcactca tctcaagccc cataaagcgt gcgctgcgac   5580
tgacgatata ttgcagatcc ggcacctgat aaaactccag acgttgcaca ataccaaaac   5640
gatcgcgcaa cggtgatgtc agcgaacctg cgcgcgtggt tgcaccaatc agggtaaacg   5700
gcggcaaatc aattttaatg gagcgtgccg ccggaccttc accaatcatg atatccagtt   5760
ggtaatcttc cattgccgga tacaacacct cttccaccac tggtgaaaga cggtggatct   5820
catcaataaa cagtacatcg tgtggttcaa ggttagtgag cattgctgcc agatcgcccg   5880
ccttttccag caccggacca gaagtcgtgc gtaaattaac gcccatttca ttggcgacaa   5940
tattggcaag cgtagtttta cccaaccccg gaggaccaaa aatcaataga tgatcgaggg   6000
catcgccgcg cagtttcgct gctttgatga aaatctccat ctgcgaacga acctgcggct   6060
gaccaacata ctcttccagt aatttagggc gaatggcgcg atctgccaca tcttccggca   6120
aagtggtacc ggcagaaatc agacggtctg cttcaatcat cctttacctc ataacgcggc   6180
gcgtagggct tcgcgaatta atgtttcact gctggcgtca gggcgagcga ttttgctcac   6240
catgcggctt gcttcttgtg gtttatagcc cagtgccacc agcgcagcaa ccgcttcctg   6300
ttcagcatcg tcggtcgccg ggctggcagg agacgtgagt accaggtcgg cggctggcgt   6360
aaagagatcg ccatgcaaac ctttaaatcg gtctttcatt tcgacaatca agcgttcggc   6420 ggttttttg ccaatacccg gcagtttcac cagtgccccc acttcttcac gctcaacggc   6480
attaacgaac tgctgcgctg acattccgga gaggatcgcc agcgccaact tcgggccgac   6540
gccgttggtt ttgatcaact ctttgaacaa cgtgcgctct tgtttattgt taaaaccgta   6600
cagcagttgc gcgtcttcac gcaccacaaa gtgggtgaaa acgatcgctt cctgacccgc   6660
ttcagggagt tcataaaaac aggtcatcgg catatgcact tcatagccta cgccgcccac   6720
ttcaattaac accagcgggg gttgtttttc aatgatgatg cctctgagtc tgcctatcac   6780
atgacgctcc tgcgtaatga atcaaagata atgctgtatg ataaaaaaat gctggataga   6840
tatccagcga aggatgaaga aaacttgcga ggtgtctcga tgatctgaaa aatggcgcag   6900
tataatttat tctacagatt atattggaag caaatattta aatattacat attcagcgaa   6960
gaaatgtgta ataaaaatac acattgcgac ccctgaaaaa aataaatttt ttatgctatt   7020
acgtatattc atatctattt caatggaatg acaacgtgaa tattaattat cctgctgaat   7080
atgaaattgg tgatatcgtc tttacatgta taagtgctgc cttatttggt caaatatcag   7140
ctgcatcaaa ttgctggagt aatcacgtcg ggatcattat cggtcataac ggtgaagact   7200
ttctggttgc agaaagccgt gttcccctct caaccatcac tacgctatcc cgttttatta   7260
aacgctctgc taatcaacgc tatgctataa agcgattaga cgccggacta acagaacaac   7320
aaaatcaacg aattgttgaa caggttcctt cccggctacg caaaatttac cacaccggtt   7380
ttaaatacga atcttcgcgc cagttctgtt caaaatttgt ttttgatatt tataaagagg   7440
cgctatgtat tccggtgggt gaaatagaga cgtttggaga attgttaaat agcaatccaa   7500
atgcaaaact cactttctgg aaattctggt tcttaggttc tattccgtgg gagcgtaaaa   7560
ccgtcacgcc agccagtttg tggcatcatc cgggtttggt gttgattcac gcggtgggag   7620
ttgaaacgcc tcagcctgaa ctgaccgagg cggtataact aacgcagtc gccctctcgc   7680 caggttcagt cgcgattcgc tcatttgcat cgcattctga ctaacgtggc agtgggtgat   7740
ggcaatcgcc agcgcatcgg cggcatccgc ctgtggatta gcgggcagtt tcagcaaggt   7800
gcggaccata tgctgcacct ggctttttc ggcactacca ataccaccca ctgtttgctt   7860
```

```
tacctgacgt gccgcatatt caaataccgg caattcctga ttcaccgccg ccacaatcgc    7920
cacgccgcgc gcctgcccca gtttcagggc tgagtcagcg ttcttcgcca taaagacctg    7980
ttcaatggcg aaataatcag gctggaattg ggtgatgatt tccgtcacgc ccgcatagat    8040
gagcttcaga cgagacggta aatcatccac tttggtgcgt atgcatccgc tacccaggta    8100
ggacagttgc ctgcctacct ggcggatgac gccatagccg gtcacgcgcg aacccgggtc    8160
aatgccgaga taatagcca tcacgcgtct ccgttttgct gtttagcagg cctcatcaga    8220
gagtcgctgc aacctcatca gagatttcac cgttatggta aacttcctgc acgtcgtcgc    8280
aatcttccag catatcgatc agacgcatca gtttcggtgc ggtttctgca tccatatcag    8340
ctttggtgga cgggatcatg gaaacttccg cgctgtctgc tttcagacct gccgcttcca    8400
gagcgtcgcg tactttgccc atttcttccc atgcagtgta gacatcaatc gcgccgtcat    8460
cataggtcac aacgtcttca gcaccggctt ccagggctgc ttccatgatg gtgtcttcat    8520
cgcctttctc gaaggagatc acgcctttt tgctgaacaa ataagctacg gaaccatcag    8580
taccgaggtt accgccacat tgctgaatg catgacgcac ttcagcaacg gtacggttgc    8640
ggttgtcaga cagacattca atcatgattg ccgtgccgcc aggaccgtaa ccttcgtaga    8700
tgatggtttc catgtttgca tcatcatcac cgcccacacc tcgtgcaatt gcgcggttca    8760
gagtgtcacg ggtcatgttg ttagacagtg ctttatcaat tgctgcacgc aaacgcgggt    8820
tagcgtccgg atcaccaccg cccagcttag ccgcggttac cagctcacga atgattttag    8880
tgaagatttt accgcgctta gcatcctgcg cagctttacg atgtctggtg ttggcccatt    8940
tactatgacc tgccataaaa atatctccag atagccctgc ctgttcaggc agcgttaatt    9000
acaaactgtt caatcgcctg ccggttgctc caggacttag tgagcgccgc cgcagcagac    9060
gcatcaagcc acttgtaagc cagatgttca gtgaaaacga tctggcgctc gtgcggaagc    9120
gcaagacaga accatgattc cgtattacgc gtcacgcccg gcgcatagcg atgacgtaaa    9180
tgtgaaaaaa tttcaaactc taccgtgcgc tgacagtcaa ttaaggtcag ttgttcagcg    9240
acaacatcaa tggtgacctc ttcctttact tcgcgcatgg cagcttgcgg cgcggtttca    9300
ccctcttcca cgctgccggt taccgactgc cagaaatcgg gatcgtcacg ccgctgcaac    9360
atcagcaccc gtttcgtatc ttgtgcgtag atgaccacta agatcgaaac gggacgctta    9420
taagccatat cagttattct cagccttctt cacaacctga atgctcagct cagccagtgc    9480
agtcgggtta gcaaagctcg gcgcttcagt catcaaacac gctgccgccg tggttttcgg    9540
gaaggcgata acgtcacgga tattgtcggt gccggtcagc agcatcgtca gacggtcaag    9600
accgaatgcc aaacctgcgt gcggcggagt accgtatttc agggcgtcga gcaggaagcc    9660
gaatttctcg cgctgttcct cttcgttgat acccagaata ccaaacaccg tctgctgcat    9720
atcaccatta tggatacgca cagaaccacc gcccacttcg taaccattga tgaccatatc    9780
gtaagcgtta gccaccgcat tttccggtgc agctttcagt tctgctgccg tcatgtcttt    9840
cggtgaggtg aacggatggt gcattgctgt caggccgcct tcaccgtcgt cttcaaacat    9900
cgggaagtcg ataacccaca gcggtgccca tttgctttcg tcggtcagac caaggtcttt    9960
acccactttc aggcgcagtg cgcccatcgc gtcggcaaca attttcttgt tgtcggcacc   10020
gaagaaaatc atatcgccat cttgcgcgcc agtacgctcc aggatggctt cgatgatttc   10080
tgcattaagg aacttcgcta ccgggctatt gataccttcc agacctttcg cgcgttcgtt   10140
aactttgatg taagccagac ctttcgcgcc gtagatttta cgaagttac cgtattcgtc   10200
gatctgctta cgggtcaacg atgcgccgcc cggaacacgc agagcggcaa cacggccttt   10260
```

```
cggatcgttc gccggacctg caaatactgc aaactcaaca gatttcagca gatcggcaac    10320
gtcggtcagt tccatcgggt tacgcagatc cggtttatca gaaccataac ggcgttctgc    10380
ttctgcaaag gtcattaccg ggaaatcgcc cagatccacg cccttcactt ccagccacag    10440
atgacgcacc agcgcttcca tcacttcacg cacttgcggc gcggtcatga aagaagtttc    10500
cacatcgatc tgagtaaatt caggctgacg gtcagcacgc aggtcttcgt cacggaagca    10560
tttaacgatc tgatagtagc ggtcaaagcc ggacatcatc agtagctgtt tgaacaactg    10620
cggggattgc ggcagcgcgt agaatttacc tttgtgcaca cgagaaggca ccaggtagtc    10680
acgcgcgcct tcaggcgtgg ctttggtcag catcggagtt tcgatgtcga ggaagccgtg    10740
gtcatccata aaacggcgca ccaggctggt gattttagcg cgggttttca ggcgctgagc    10800
catttccggg cgacgcaggt cgaggtagcg gtatttcaga cgcgcttctt cggtgttgac    10860
gtggttagag tcaagcggca gaacatctgc acggttgatg atagtcagcg aggacgccag    10920
tacttcgatt tcgccagtcg ccatatcgcg gttaatattt ttttcgtcac gcgcacgtac    10980
ggtgcccgtg acctgaatgc agaactcatt acgcagttca gaggccagct ttaacgcgtc    11040
cgcacgatcc ggatcgaaaa ataccgcac gataccttcg cggtcgcgca tatcgatgaa    11100
gatcaggcta ccaagatcac gacgacggtt gacccaacca cacagagtca cctgctgccc    11160
cacgtgggac aaacggagct gtccacaata ttctgtacgc atgagatatc ccttaactta    11220
gctgccggcg gatgccccct gctgcgcagg tgaccaagtc gcagcgttag ctgtatgtca    11280
caactgaatg aaaaaaggcg gctattatac tggaaattct gccgcaccgt aagagcctgg    11340
cccgcgctgg aacgcctcgt taccacttta tatcgggcct gaaatcagac tctacgccag    11400
tttgctataa aggtgttgcc cgaactcata aaaattaaca aaatttgtcg ttccgccatc    11460
ggctaatcgc attaaggtga gaggcacgat tttgttttgt caggagtcat catgcttgaa    11520
cttaatgcta aaaccaccgc gctggtggtg attgatttac aagaaggcat cttgcctttt    11580
gccggaggtc cacatactgc cgatgagtg gttaatcgcg ccgggaagct ggcggcgaaa    11640
tttcgcgcca gcggtcagcc cgtgtttctg gtgcgcgttg gctggtctgc cgattacgcc    11700
gaagcattaa aacagccggt tgatgccccc tcccccgcaa aagtgttgcc cgaaaactgg    11760
tggcaacatc ctgctgcatt aggtgcaacc gacagcgata tcgaaatcat caaacgtcaa    11820
tggggtgcgt tttacggtac ggatctggag ttgcaattac gccgcgggg tatcgataca    11880 atagtgttat gtgggatctc gaccaatatc ggtgttgaat ccaccgcccg caatgcctgg    11940
gaactcggtt ttaatctggt gattgccgaa gatgcctgta gcgccgctag cgccgagcag    12000
cacaataaca gcattaatca tatctacccg cgcatcgccc gtgtgcgtag cgttgaagag    12060
atcctcaacg cgttatgatt tacatcggtt tgccacaatg gtcgcatcct aaatgggtgc    12120
ggttggggat caccagcctt gaagagtatg cccgccactt taactgcgtg acgcgggcat    12180
tttaaaaatc actaaagaac gcccaagagc atgtgttttc tttagtttat tcaatgcatt    12240
aaaaaatagt ttcgcatgaa attcggtaaa cttcatgtgt gcaataatgt cccattcatg    12300
ccccaaaatg ccccaaagca gacattttg ccccaagtat gccccacaag tcacgtcttc    12360
aagtcgtcta tatccatagc acaccgagtt acattcttgc atccggggtg tcgacaatac    12420
ctactttatt gagtgtgcga gaattaccag gaacctttcc acaatgtagt agtctaatag    12480
tcgaatccat ctaacattaa gaagcgttat gatcactagc ctctcattga tatcttctgt    12540
aatagtcact ctatgtatca tggtgttcgc tacagtaaag gtagggattg gtttgtctaa    12600
```

```
caatccagac agaaatgata attaacctca accacgtaac cacacttcat acttcatact    12660
tcacttaaca gtgaagtgct cacatcaccg ggcagtcatc aaactccgca ttcctggcat    12720
cattaatgat gtacgtgatc actccaaata tagcgggtgc agaactgtaa ccatcatcat    12780
ctgctggcag cgcttccctt ctcccgttat ccagattaac caggtgcggc tgaggatgag    12840
tccgatatcg cttgatcctg aattccccgt cgattgcaca tatcagcagt gaaccatcgc    12900
aggcagtaag tgacgcatcc acaacaagca acgctccctg gattatccct tccctgaaat    12960
gtgaacgcga tgcccgcatg aaataagtcg ctgcgggctg actgattagc tgctgatcga    13020
gggagattcg tgtttcaaca taatctgccg caggtgaagg aaatcccatg tttacgccct    13080
ctcttgaata ccggataaaa acacagtata aatactgtat atccatccag caaagaggca    13140
atgagcaatg ttcgtggaac tcgtttatga caaaaggaat tttgatggtc tgcccggtgc    13200
aaaagatatc attctgggcg agttaactaa gagagttcac cggatcttcc ccgatgctga    13260
tgttcgggtt aaaccgatga tgacactgcc ggcgatcaac actgacgcca gcaagcatga    13320
gaaggaacag ataagccgta ctgttcagga aatgtttgaa gaggctgaat tctggttagt    13380
gagtgagtaa agattttcaa tgcccgccac agttacgtat tgattatgct gtggaggata    13440
ttcattttcg taaacgttgg tttggggaaa gcggcaaaac ggaatgtggg aacagggaaa    13500
aatcagatac cagatatgtc tgcatttcca tctggcaata actggtttca gttaccaagt    13560
ggacatatcg ttcagatatt ttccatgaac gttcttggtg cagatgctaa tggcacgtca    13620
gctaattacc ccattgcttt tccaacaacg atgattgctg tcagtgctct atggtctgat    13680
gggactgtag caaatgcacc gacatacaag atgatgggga acacgactaa cagaacaact    13740
ttgacgataa aagtatcagc cagctcaggt acttacggga caatgattat tgcggtggga    13800 cgataaatatg aataaataca gttactctcc ttcagaaaat gccttttatg ctgttgcgtt    13860
aaaaaatacc tatgaattga gtggcacatg gccagctgat gcattagata ttcctgatga    13920
catttctgta aaatatatgg cggaaccgcc acaagggaaa atccgagttg caggggaaaa    13980
tggttttccc acatgggctg aaataccctcc accatcacat gaggaactta ttgaacaggc    14040
cgaatcagag aggcaattat tgattaacca ggccaacgaa tacatgaaca gtaaacaatg    14100
gcccggtaaa gccgctattg gtcgtctgaa aggcgaggaa ctggcacaat ataattcgtg    14160
gctggattat ctggacgcac tggaactggt cgatacttcc ggtacgcccg atattgaatg    14220
gcctacgcct ccggcagttc aggccagatg acatccggcg cggtgctggt atctgttgca    14280
gtcaccgcgt caatgtaatc cagcacggcg ttaagtcggg ttgtttctgc ctgagtcagt    14340
ttccgtccgg cctgtaattt cagctgaatc agactaatgg aagccattgc tgcatcaatc    14400
agtgattggc gctgtgcttc tgccgcttct actgaggcac cgtgttgtgc ctcagtatct    14460
gtcacccatt tctcaccatc ccatttatca tatggcgtta acggtgaaag cgtgacataa    14520 ccgttttttga tggcaccgat ataatccact gtaacagctg cgccatttttc gattgagtaa    14580 acagtctcat tgcgatggtc ttcctcatgg ctccatccct tacctgtaaa tactgccact    14640
cttcccggaa tgttttcgtc cgggtcaata ccagtggaac aggcgggcat acttacgcca    14700
gtattaatat attcatcaga ccagcccgta tattcagacg ttactgcatc ataataaaaa    14760
caacgcatat cacccggcac tgcagccagc ccattttcat caaaaacagg tttcattatt    14820
tagccctcac cagaaagtta aatgcaatat ttcgcggtct gacagcaaca aaattcacac    14880
catcacccac agagttactg ttgaaattaa atcgtgaaaa tcctggctga tttccggcga    14940
tgccatcatg aaagttaatt gcgtgtccag cacctccgcc tatattcccg gcaaactgag    15000
```

```
aaaagtttgt agcttcctgc cagcttaata attcgcgacc accatctgca cctcgcccgt   15060
catcccagac acgaatgaaa tcaccgcggg cttcaggtaa taccagcgaa ggaaacactt   15120
tcgccagcac aggataatca gtggcagaga atttcgcgcc gttgaacttc aaaaacacca   15180
tactggacca gctgtcgatt acagtatttg gcattgcagc ggacggccag aagaacggaa   15240
cgccaatagc tggagaacct tctcccaaac caaggtttgt gcgagcgtct gcggcattcg   15300
ttgcgccggt tccgccgtct gcgacagtaa ccgcaccgtt gctccctttc tgcgcaagtt   15360
taccgatgcc tgggatggtt acggcggtgc cgttgatggt aactgtgatg ctttggtttg   15420
ctgaggtggt ggcgaacgtc tcccacgcgc aatattctc gtcgtactct ttgatgagct   15480
gtgacatggc ctgcgccagg ccgtcgactg agatattgtc cgacacaagg attccatact   15540
tctggccgct cagcgccggg gaaactgctg gcgtaaccgt cattgacgtg gcgctgttca   15600
cggatgaaat ctgaaacagc tgcaccgggt tagacatcac gataatcgtc tggccagcgc   15660
ggacctggct ggcgggagct gtccagtttg tgccggagcc ggttgcggta tttccgttaa   15720
tagagatagt tccggtgcta taaatcataa caactcctaa atttagacaa catgaagccc   15780
ggagaggtat ataaccctca ccagaaataa tttctgaatt ggtttttaat acatgttggg   15840
caacgccagt gttggcatag ctatagttgt atcaaatgcc attgaccacc cacccaaata   15900
ataattgccg actactttat tcctttctgc tctgacattc ccacctgtca ttacaattcc   15960
tttataccta atatttccgt aaccaccaac gtgtcgacag ttagccccgg tataaacaat   16020
ctggcaaaat tcatcaccaa tattcaggtt cgcattggcg atatttattg tcccatcaaa   16080
aatgaatggc ttcgtgcaag taagaagacg tttgcgttga cgattggttt attcaatcca   16140
tcaactaaaa tatcatgtaa acgaattgcc ataacatttc ccactttatt ttacttactc   16200
aacacaacaa gtatattaaa attgaacctt gtcaacaaca caaggagtc ccaatgaaac   16260 tcgctctaat tatgctgcca ttatgtctgt ccctcactgc atgtggtaat ggtttaaata   16320
ccggtaaacc aaattccggt gtcattccaa aacctttgga tcgagatggt aacggttctt   16380
taatttatga taccgaaaac cttccaatga cggggcagtg gtgtcacgag attgatcacg   16440
aataccgacg aatcggtagc ccttctaact gtgttataga ctactaaata ttaacccctc   16500
aaaagagggg ttaatatttt aacctgtgaa tgaaccagat ccgtgtgata ctatgatagt   16560
aggcgaagaa attgacgcac ccctgttatt ttgagcggac actttaatac gcactgttac   16620
gtttggacct gttacaaccg cagaatgcat gataagtctc tccatgtctt gcacggatga   16680
accactctca ttgccgttaa tgtcgattgt tcctgcacca ttacctttaa cgtttgctat   16740
aacacagacg tgtcttgcgt gcccagaact ggatgaatca ttataagtca ttacctttc   16800 taaatatccg tcactagacc gactcacatt cgtccctgtg tgcatatttg caatgtcccc   16860
gataaaactt tgggcttcca cagtcccttt gaatttaccg cttgttgctt ggatctcacc   16920
agtaaagcta ccgccactag catatactac acctctgacg gtcacattgt tgaattcagc   16980
atctccagct ttattcaact tccaaccagc agaaccagct gcatagttgt tggactggat   17040
atagttaccg attttgcgt tctcaatggt gccgtcctgg atgaagctgg cccggatgaa   17100
tgtctgcccg ttctgatca cgaacggcaa agctacgcta tttccggctg ccgtggtgac   17160
ggcgaagcgg tcagccagga agataacctg cgactgcatg ccggatggcg tattctccac   17220
gccgataccc atcccgcgg cgtaatactg cccgttgctg gagacaccaa ccttgatgtt   17280
gtacatcgcg ctgagttcgc cattaacgtt ggctatagcc tgagcgttag tggtgatggc   17340
```

```
ggaggtatgc cgttcacgg tcgccgtgat gccgtttatc tgcgtggcgg tggcctgctg   17400
atagtcggag agcgtctgat tcaggctgtt gatggatgcc ttgttgccgt tgacgtccgt   17460
ctgcaggctc agcaatgaac gtgctgtggc ttccttctca ctgacgatca cctcgtcgag   17520
acggtccaga ttcgcgctgt tgccggcgac cgatgcagaa agggttttac gcgtggccac   17580
ctgagcgagg ttggcctgga ttatcgcaat tgcagagttc ttcaccccgc cgtcatgcc   17640
gtccatagaa acgctgatgt tgtcgattcg ctggcccagg gcggtatcag ccgtcgcaac   17700
ggtctgctca agctgactga gtgaagacga aacattcccg accgtgctgg aaagctcatt   17760
aacgctggtc tgaaccttcc cgacgtcctg gcattttttg cgatatcttt cgcttgctg   17820
ctccagttcg tcgttggcct gtttgatatc gttagccatg ccagcaattt tttcgttgct   17880
gtccaccgcg ttctcgatca ggtctttgaa cgtttccgac tctttcatat cctccagaat   17940
gtcattagtt atttcgctga catctatcga ggacgtgccc atgatccagt cggtccagtc   18000
cccggcgtta ccgatacggt caatcaggcg cgcgcggtac cactggcgaa cgccggcagg   18060
catgggccca tgctgataat ctgcagccgg gtacggcacc aggaccagca gttcaggatt   18120
ggcgtagtcg gcagttgtgg cgcgctgaat ctctgtatag gccgtgtcgc ctgagccatc   18180
cggaaatttc caggtcaggt cgatatgcca gaccacatct tcggtcgcca ggaagttgag   18240
cggagtaccc ggttttcccg ttttaccgga gagataagtt gtttcaccgt atccccatgg   18300
tgacgacgta tcctgcgcat tcagcgcccg tacgcgcacg tcatagctgc ccgaataaat   18360
gccctgaacc gagaaaccct gcgcgctggt aaccggaacg tttatccagt ccccgttgtc   18420
cttacgccac tggcaacat accggattgc gccctctacc ttatcccatg acacgtccag   18480
gcttgctaca gtcagcccct gagacacatg atcgctctca gtcaccacga tattcttcgg   18540
agcagacagg acgcttatcg gcgtgacggt gatcggggga gactcgaccc gaacgccgtc   18600
atcgatgtaa cgatatttgt ttggatcgtg ctgaacggcc gtaatagtga aaccgcctgt   18660
actgtcgtcg ttagccgcga ttgaggtgac cctgaagtac tgtattgcga ggttatcact   18720
gtctatcgcc caaacagcgc ccgccacagg aacctgactg aatgccgtag ccaccgtcac   18780
cgttttttta tcggcgctca ccgcgctgat tgtccgcgtc tgggcttttc cgtcgggaag   18840
gttaaccacc agccggtctt tcgccgcgta gtctatttct cgatcgaggg taatttggcg   18900
gccgttggcc gcgcttatac ggccccccgtt tccttacca gagcggaaag gatcggcgac   18960
accgataatt tcagcgggca aagggatata accgtccagc cccacgccaa acgatacggt   19020
cccgtctttg gcattggaga gcaatacccca gcgaccgcgt cggtgcgctt cactttgcga   19080
ggtgcagccg attgcggtca gggacgtctg ccggacgtcg taacgttcta caagcgccga   19140
atcgtaaacc ccctcaacgg tatcgctgta atggttctgc ggatcggacc aggacaccag   19200
gcaggagctg tagcgattct tgtatgagcc gcccgcataa gtaaacagcc catcgataac   19260
gtttgagacg ttataaaccc agtcaacatc gtcctgcggg acgtctgcct ggacataaat   19320
ctgatcgttt ccccagaacg ttattccacg aaataccgcg gcgagatcgt taagtacctg   19380
ccaggcgtcc tcctggctct gaatgaaaac gttgcaggtg aaacgcggtt cggtgccacc   19440
ggccccgtcg gaaccatttt cgtcacagta ctgggcgatt gaatacagcg cccacttatc   19500
caccatggac gcatccacgc gcgtgcccat gccgtaaatt tcatccagaa ccagatcgta   19560
aaagatccag gcagggttat tggaccatgc cattttgaac ccgccggacc atgaaccaga   19620
ataggttcgg gttttcggat cgtaattatc cggaacctta atcagcttgc cttttatctt   19680
acaggtcact ttcggcgcgc tgccgttgaa ttggctgctg tccacttcga catacaggag   19740
```

```
cgctgttaaa ggataacgaa gcttgctgtc gatgacttcc gcatacgaaa acaccttgaa    19800
ggcgttaacc agtttcgaat ttgatccgct ggcatcagcc gtaatacgcc tgaccctgac    19860
agaccagccg gacgtggatt ttggcagatc gatacggtgg tcacgctgat attccgtcgt    19920
ggtctttccg tcaaacttgc cgtttacaac cgttttccag gcgccgccgt ccgttgataa    19980
atcgatcgca tactcggtga ccgtgcccac catatcgcca ttatctttat agagatactg    20040
gaccggaagg ctgagcttga tacgatggc atccagggaa aggtttgtaa actggcgcgt     20100
ccagggcgcg gtggtggtga cagttgtgcc cacggccagc tcgttgtcga cctggggcat    20160
cccggcaata taggtctggt cctgtgtgcc cttgcggaac tcccatttca cgccgctgaa    20220
gttgtattcc ccgctgtcgt ttgccagcgg cgtatcgttg agaaaatgt tctgagcggt     20280 caggtcgccc tgtatttccc cctcagaaac ggcaatgagc attttttaatt ttgcgaccga   20340 cagcagatcg tcaggctgct caaccggagt atgtgaactg ccacctcccc ctttggcacc    20400
ctgcaggatg gttcttgtt taagaagctg cattttttca cccataaaaa aggtgccga     20460 agcacctta agttagtggc cgctggccta ctgctgatcg ctcgagtaca taccggcgct    20520
gactatcgct cccctgcct cagtcagacc gtaggccagg gggacaggat gccccatagc     20580
gacggtattg accggcgccc cgaaggcgta gttaggcgtg ttgtccgtgc tggaggattt    20640
acccgcgccg aaggatggct ggggcgtgag catctggaca acgcccccca gcatcatcga    20700
cactccgacc cctgtcagaa ttgacgtggc gctgatagct gttgcactca tcgccgcgcc    20760
ccaggctgcc atgctcgcac cagcggtaaa gaatgcagcg accagcgcaa cagccccgac    20820
aactatctgc aggacgcccg aacttttggc cccctcataa acgggcacga tccggtacac    20880
gcttccaccg cgggtcatat caaactcttc cagcccgata ttgttgccac cgttaaaaaa    20940
ggcgaaacgg atcccccttca tatgagcttc agacatatat ttttttgaatc cgggaacctg   21000 tgaacacatg gccctgagca tctcgcgcag gtcggcaaca tcaaactgaa cgcgtttacc    21060 gaatttttt gccatttac cttcgagaat aagcgtctta accatgcatt ctgtccttat      21120
gcctgaccac ccggaccgtt ctgtcgcgat aatatttttcc ataaggcgtt cgcgaagaaa    21180
ggtgcccgaa aagatgatgg agaatgatgt tatcacccac atataccgcg gcgtgattag    21240
tcaccgatgc ctgcacactc atcatgatga tatctccggg ctgcattgca ccggcggcaa    21300
tctcaacgaa tccctcacgc tcccagttgt cgtcgtagag acgctccttg ccgctctccc    21360
accattcgta aggtactgaa taattgccga gaacaatgcc gtattcgcgc agataaaatt    21420 cacgggataag cgaccagcag tcggcgtaac ccagcaccca ctgccgcccg gcataatccc   21480
ggtcttcacg cggggaaatc gtacaaaaat ccccgtccgg ccaggacatg atcccccact    21540
caatccccga ccagtcgcac tggatccggt ccagctctga gggcaccagc cgaaccacat    21600
ccggatggga atgaatgagc atgatgatct caccgcgcgc gcgggcagcg agctggtctt    21660
ccggggagag cgtgaatgtc tcctcgggtt tatcggcaat gttgcggcag ggaataaaga    21720
tttgttgctg gcctgactga acaatcaggc cgcaggcttc tttgggggtat tcagcagcga   21780 cgtgctgacg gatagcatcc agcaattttt cacgcatttt tatttcccct gcaggtttgc    21840
agccggaaaa ccgccgaacg gcagcggcgc atccgggccg tgacgatcct gacaatcctg    21900
ccggcggccg ccacaaacat ctttcgacgg gtcatcggtc ggtgtaccgt ctttggtaaa    21960
gtatttcgtg ccgttgtaat cgcatccggt cccgcttcgg taccagcccc gcatacacca    22020
ggtgcagaca ggcgtaatct gccgtgtcgg cagctgcagg ctctgaatat cgaaaggaga    22080
```

-continued

```
acacagctcg aaatcaacct gtacccgcgt ctctgcggtt ttagcattga cgtaaaagag    22140
ctgtaagcgc tcatcggccg ggctggcacc cggattaccg tttttccagt tggcggcatc    22200
gagatacttc gaaagcgtgg tatggatttt gaccttagcc ctgaccatat cgtcatattc    22260
aagacacagc gcggtgacat agtttccgac gttcccgacg gacagcgtgg gcgttggctg    22320
ggaacctgta ctcgataact ccatcccctt aagttcgtag ggatggggat cgtactggtt    22380
tccctgccag ataatggcgg gcagattttc tgcggcgaag gctgcccacc cctcttcctg    22440
aatattgtgc gcatgaaaac gcagcacctg atccataccg aattcagtgc cgtcgatctc    22500
aatcagctga ataacgctgc cgggctcaag ctgttgtatg tctgccgtaa aactcatact    22560
ccccccataa aaaaagccg cccggaggca gctttcagtg ttttttcgaga aaatcagggc    22620 gcgaacgcct gttcaaaagt gaaggccaca gtggcttttt tcccggtagg gaaagaaacg    22680
ctgaacgaat cggccttcat tctgaacagc tttttttcac cccatggagt ggtccaccag    22740
aacgatttag taacgtgaga catcaggaaa gcgcgcagcg cagccgcctc ctgtctggtg    22800
cccgtccagt ccaggttcca cgtttcctgt ttgtcgttga tccccatccc cgctatctgt    22860
ttgtagccat ccccgaactg ggcctgcagc gttcgggctg tttcagtgcc ctgcgctgtt    22920
tttcgcgtgc gccaggtaaa cgtgtccgtc actgtgtcct cctcgaataa agcacgccgc    22980
ccgcggacat ttcttttttc agtcgctcgg tgattgtctg ctgaacaatc gcctgcagct    23040
gtttcgccgt ccccgtggcg ttcgcctgat ttatgcttcc gtcactcccc tgctggctga    23100
tgctgactgg ggcataaaca ctgatcccgc ccatgccagc accggctgcg ttcccgccgc    23160
cgaccagacc acccgaggca tacccgcgca tcaggcgata gagattagcc acgccgatgc    23220
ggctggttga ttcttttggtg aagacgaatt ccccgcggtg aacgataccg gctggctcgt    23280
acttgccgcc gtgcccggta aaaccgccca cgtcaaaacc ctgtggccgg tatgacggga    23340
ccgcgaatga ctgaccggca gaggaggttt tcgccccgcc gctaacccag cccattgcac    23400
tctggatggt gtaagccacc agcagctggt tgataacgga cacaatcatt ttaaggatcg    23460
agctggtgaa ttccctgaag ctcgccttcc cggttgtcgt caggctggta agctggcccg    23520
ccaacccgct gaacgtagcc tgagaaatct gctgaacgga gctgaaaacg tttgtcgctg    23580
aatcctgata ttcggcccaa ccctgtttcg caccggccag ccagtttgca cgcagggcat    23640
cttcagcttc gaacgtcgcc ctttgctctt ccagaaacctt tgctgcgcc tgagggttgt    23700 acgaatagct ttcgctgaga cgctgcagcg tagtttgtcg cccggcttcc cgggtggata    23760
acccctcaga ctgagcctgc aggcccgccc tggcggcttt tgctgctgc tcaaacttca    23820 cggcctgatc ggccagctgg ttgagctttt gctggctggc aaccttatcg cccaggtcgg    23880
ccagctgccg cttgtactcg agcgtttctt ctttgtgcgc cagcagggat ttttcctgcg    23940
ccgtaagctg acgacgccca gcggcctcct gcagaacggt gaactgattt tcagtttgcc    24000
agagatcctg acgctgttta cttatgacgt cgttcacgct ggtatgctgc tcaagcgttt    24060
taagctgggc ctgaagggtg agaagttcgg cctgcgcctt ttcctcggct tgtcccgg    24120 cgggcgttga gtagcttttg cctttcggtg ttttggatc cttccactgc ttttcaatcc    24180
cggcgcgggc cgcggcaatg tccttttcag tccacagcgt ggcgacaccg tctttcgcat    24240
cctggcggtt tttctcaata agctgactga gcttttctc tgctgaagcc cgcttttctg    24300
ccgccgtcgc gccggactcc accagctggt taaactgctg ctggctgcgg attgcctgag    24360
cctgctggtc cgttcgcatt ttttcccgcg cggctgccag cccttcctgg gcgtattgct    24420
gatcggcaag atcgtaagcc tgctttttca gctccacctg ctggcgcgcg tttctcagcc    24480
```

```
tttccgcatc cgctttctgc agaacgttgt taccggcata atccgggtcg accttaagat  24540
tgctggacag cgcgcggtac tctttctctg ctgcctgcca ctcagcaaaa gagtcctggc  24600
gcttcatcgc ggtgtcagga ttacgcccga cgcccagcat cgcatccac gcaccggagg  24660
cggcattctt cacccagttc caggcttttt cgagggatcc gagattatcc tcgaccgcac  24720
cggcgcgctg aatgaccgcg tcggaatatg cccgcatggc cagctcggca gccttctgag  24780
aatcccccag cgcctgagca gaagctatct gttcatactg ggtggctgtc agaaaatgaa  24840
gggaatcgtt gagcgtcgcg accgcgttaa ccggatcatc cttcaggcgt ttaaactgat  24900
ttatggtttc gtcaacggcc tgcccggtag cctgctgcag cctggcggca acattgctga  24960
ccatgctgac gtcattaccg ctgaacgcgc cgctgccaac gacctgcgcc agcacgcctg  25020
cagcggcatc ctgagtgatg ccattacctg ccagcgagcg cgccagcgcc tgcagctgcc  25080
ctgacgtttt ccccgcgtag ttcccggtca ggatcagctg cctgttaaat tcctcagact  25140
ctttgctgcc gtcgtaccag gccttaccca acccgaatac cgccgcggca atccctccga  25200
ccatgctggc gatcccaaga ccgcgcagtg acagaagctg gtctatccac cctgcccggt  25260
tagccagcgt gatcccggag ccgcgcagcg cgccgaagtt accgcgcatg acctcgccga  25320
tcagtattcc cagttcctgc cgggcggcgg cactttgcag ccccagaccg tgcgtggcga  25380
cttttggcagc ttcgagcttg cggatataga cttcagccgc atcgtggca ccgacctgcg  25440
ccgccttcat gcgcagtagc tcggtaccgg agagcttttg ctctgcaacc tgttgcttca  25500
gctggctgag gaatcgcgtg cgcgctgcgg ccgattttc ctccacgatc tgcagttctt  25560
tttgacgggc cgtggtgcgg gaaataaggg cgagataatc ctgctgggtt atgttgccct  25620
gtgccctcgc tgcgcgaaag cgcgcctgca cgttcgcaag cgactgtgtt tcaccattga  25680
gctggcgtac gccgtcgatc tggcggaaaa atgatgccgc aagttcatcc tgtcgacggg  25740
caagcgcagc ggcctgcccg tcattctcac gcatgcgctg attaagctcg gtcacgcggc  25800
ggtgagtttc atcaacggac tttgaaacgt tctgccagtc tttggtaagc ccttccgttg  25860
cggccgactg gcgggatttc atatctgcgg cagccgccgc gccagcgtca cccacggttt  25920
taaacgcagc cgcctgccgc tctgaagcgc gctgcattcg cgtctggact ttttcagagt  25980
cctcagccat cccggttagc tggccctta tgcgggcaac ctgctcacta aacgtggcgc  26040
tgtcgacgtc aaggttgatg accagatcgc taatctgctg ggccatatcg gatacctcct  26100
gttatcccct cagctgcggc catcagcgca tcatcatccg gctcgtcatc gctgatgacg  26160
ataccggaag gagaaagcag gctgaaatgt gcggggtaa gttccgggtc gcggaagaaa  26220
agagtggaga tggaataaag cagctctgag aaatgcgcat cgagctgagc gtcctgaaaa  26280
taatgctccc ggtagaactg gtgccagtcg cccagctcag tggaagtcat tccagccagc  26340
atggcgcgcc agtcgggtcg cccgaactcg cgcgccagat tcaggacaaa cttcagctcg  26400
ctggcaaggg cttttccgcc gcaacggggt ctgcgctttc ggcctccgct ggggcatccg  26460
gatcggcagc tttgtcatcc tcaaccggaa cgagcatgcc ggagagcagc tttatttcca  26520
tttctgcttt accgatcgcc tccggcggcc agccgctaag cacctgctgg taaagcgtct  26580
ccacatccgt gccagccgga tcgttatgcc acaaagacat cgcaatcaaa cgcgcaccgc  26640
agcgaatatt tgagccaatc agcctggccg tcatttcctg atcgctgatg ccgtcgctgt  26700
cagcgctgac ggccttttcc tctgcggcca taaacgtgat gtactcaata cgctgaagcg  26760
ccgacagctc gaagatggtc agtgattctt tttgccaggt gaacttctct tttttcagaa  26820
```

```
acatgcgtcc ttccttacgc tgcagttacg gtaactttgc agaccgcaac gaaattaccg   26880
tcgctggtca taacaataac gtcagcggtg cctgccgcca cgccggtgac ggtgatcgca   26940
ttaccgctaa cggtgaccgt tgcttttgcc ccgtctgagg ttgccacacg gaacgaggta   27000
tctgaggcac tggctgggtt aaccgtcaca ttgagcgttg tggttgcgcc gacggccacg   27060
cttgccgtgg ctttatcgag cgtaacgcct gtcacgggga tattcggggt cccgctttct   27120
tctgccagtt ccggcttgcc ggtattggta attttcgctg tacgggttat gacctctttt   27180
gccggaatgg ctttacccag gctgctgcac cagccgcgga aaacgtcgac ggtaccgttc   27240
gggtatttga ttttgtaata gcgtactgag ccatcaataa accatgcgac aaggtctttt   27300
tgcccttctt cgcccggctt ccaggcgagg gtgaacgagg tatcgccagc agattttgcc   27360
ccctgggccg tcgcgttcca gtcggcatcc tcgtcgtcga ggtaagtgtc gtcatacgat   27420
tcggcggtca tttcgcccgg cgtcagctct ttaattttcg ccaggcggtt ccagtcgata   27480
tccgagagtg ggttagcgaa agcgttgccc gttccggtgt aaagccagag ggtggtaccg   27540
gcacctttca caggggccag cgggtttgga gtaggcataa gtacctctta aattgaatag   27600
gtgattaagt acgtgaaatc gactgaaccc caggtggcca tttcatcatc ccgctgatag   27660
tcataaccct gcggggtgaa cgtctcgacc agttcggtca gacctgggat gaaggccatt   27720
gccggataca ctttctcttc catccaggaa tcaagcgcgc tgtcggggct ggaggcttta   27780
agaaatacct cgatgtgaac aaccgcctgc cacgaatctt cgtcaagcga atcgccggtg   27840
tactccgcgt cagaaaggta tacagccacg gcagggagat cctgctcttc aagaaaaaca   27900
gggcgcccgt caaaccaggt gaccgtgtcg gtgatctcgg ctttcagttt ggccagaatg   27960
gctgcacgaa ttgcgctgtg tctgttcatc gcttcaggtg gatcctcagt tggtttttca   28020
gggctgcgga aagttctttg gcatatcgc tttcaataag gcgctttgaa atagcggtga   28080
aggccacggt gagcggtgtc tcaagaggaa ctttgaccac atcaatcgga taacgggcct   28140
gacctacgcg ccgcatgacc tgccagcgcc cgttcgcaag ctgttggata aaagcgttac   28200
gaaaggtata gggcccgatt ttaaggacgc tgcccgctcc gtttctggcc ccttttttac   28260
gcgagagcct gacgcgcgcc gtgccgagct ttatcgcagg aagattaccg cggttgattt   28320
ttatcgacgc gaccgggcga tcgtgacggg ccttgcgcag acgggaacgc tggcggacca   28380
gacgaaccgg aagcccctttt ttccggttat catcaactgt tgcttctttc gctacagctt   28440
tgctcccctg gcttatcgtt cttctggcca ccctgttaag tgcttttgcg gttgcctcag   28500
gaacgattaa ccggctgagg ctgttcaggt tctgaatagc cctttccagt cctttcacag   28560
acatagcgcc tcctcattcg agatggatgc ggggttttcc gttgaacatg tcatagcggg   28620
taacgatcag gttcttaccg tcgtagtcga cgctgtcgtt tcggcgtggc tggtaaagct   28680
cagagaaaac caccagcgaa gtacctgttc ccgacaatgg ccccatttcc tcgagttgct   28740
cggcgggaac aacgtcatag ctgctgccat tgatgatcgc tgtctttccc atctttttta   28800
tagtggccgc gtccatgcgc gccgccatcc ggtcaaagga gttaggcatt gatcttaact   28860
tcaacaacgg tggtgtttgc ccctgcatct tcccaggcga tgcccgcggc aacggcgtcc   28920
gtttcttcga tcgtgatttt gccgtccttc agatacacct cgcccccggc agtaaccgca   28980
tctgcggata cttttggcag gaggaaaaca ccctcagtaa aaccgtcccc ggtatcgcca   29040
gccgggatat cggtaattgc caccgcgata agttttccaa caacaaccgg tcgccgctg   29100 tgaacatcgg ttgcaccact gtttaccaga gggatcgttt tcccgtcctg cgcatagttc   29160
ttagccataa cttctccatt cagcccctttt cgaggctggt ttcaggtata aaaaaagccc   29220
```

```
ttacgggcgt ctgtttgtca ggactgtttt ttactgacca gaggatttgg tcatgccgcg    29280
atagtccagc ggcgccacgc cagcatcaat acgcactttc gtggcgatac catcagtggt    29340
gaagccttcc tgctgatcga tgtatggcgt gtcgacgccg ttgagataag cgacctcaat    29400
ggtgtcggtg cccttcgcgg cagccagata ccaggctttc gcatcagctt catccagacg    29460
tggttcggca atgacttctg caaagttctg gatagggtta acgatcccgg cattgatgtc    29520
tgcaccttta acactggccg acttgatggt ctgatttgcc agagtttcca gggcgacggg    29580
caccagcatg taggccggac ggatattcag ggttcgctcc ccctccttct gcagacgcat    29640
cagcttgcgc gattcgtcca ggctggccac agaaattgca cccgagctca ggttcttgtg    29700
atcggcatgg aacagcgcct ttccgtctga gagtttcggg ttttggtca gaatggcgta    29760 aaccagatcg ccaatcgttg ctttcgccgc gcgcccatc ttcatcggta cgtcggtaag    29820
ctggttcaga tcgtcgttga tgatcgcctg gcgagttact gagaagattt caccatacgt    29880
ggcaagcgcg atggtttcgc ctttgtcact ggtagtgatg tacttgtact cagcccttc    29940 gcgaacctgt cgcagagaag ggaacccacc cataccgaca cgatgcgccg ttttgaagtc    30000
cgacagctgg cctttttttgg tccactgctc gaaggtttcc tgcgcctcgt cccagccctg    30060
aatcagcgct tgttcgcaa catcaagcag aatgttgcca aagtcagagg tgctgtgggt    30120
cagcgccagg ccaaccatct gcatcgggtt gtagctggcc acgccgatac ctttttctgt    30180
cagggccata cgcgcatact cgcgcagcgt cataccgtta taaacgttat cccgctcctg    30240
accttcgaac ccggcacgcg ccatcagtgc ctggcgaata ccatccgcga cgaagttacc    30300
gttgcccgca tgaatatgcg gctgagtggt tttattggac ggcgtggccg ttttaccgag    30360
ttctgccagc agcaaatctt tcgccttatc gacggagcaa tcagggtcgg ccacacactg    30420
attctgcagt tccatgtgct tattaccgaa catggcaaag agatcgccga tagcgttaac    30480
acgggttttc tgctcagcca acacctgcgc gcggatcgca ttttcatccg gtgccgggtc    30540
tgtttttgcc tgcggtgcct gaggctgggt aataaccggg tcacgctggg tagtgttgcg    30600
cggcggggtg atcatgttgc gaatgctttt tggcattttt tcaaattcct caatacgttt    30660
tgaatgaata caggccatag cctgaaggga tggtgtcacc tggtcggcaa acccagttc    30720 aaggcactcg ctgccgttca tccaggtttc gtcctccagc attaccgcaa tttcttcggt    30780
ggattttccg gttttctgtg cataagccgg gataagaacg gattcaacct tgtcgagaag    30840
atccgcatag tcgcgcatat cgctcgcgtc accaccagca aaccccagg gcttatggat    30900 catcatcatc gtgtttttcag gcatgatgac cggattgcct accatcgcaa tcaccgaggc    30960
catggaggcc gccagaccgt cgatatgtac ggtaatcgcc gcgccgtggt gcttcagcgc    31020
gttataaata gcaattccgt cgaagacatc accaccgggc gagttgatat aaaggttgat    31080
gtgggtgacg tccccaagtg cccggagatc attgacgaac tgtttcgccg ttacgcccca    31140
gtacccgatt tcgtcataaa taaaaatgtc ggcctcactg ttattgctgg cctgcatgcg    31200
gaaccacgaa ttacttttttg cgctggcttt cggacggtgg cgcgcccggt tctttggctt    31260
cggcactggt gcctccttta tcattggcgg ggtcggtgtc aaacaccagg ccctgttcac    31320
ggttctcgtc aacctcagct ttacggcgtg acttaacatc atccggggttg cgaccgctgg    31380 cacgtatcca gtcggattca gtagcagcac cgccgcggat ctgcgttttc caggcattcg    31440
cttctttaac gggatcaatc cacggcataa cgggccccga ataaccgcg ttataaagcg    31500 agtccatatc aatgcctctc ggcagcttga tttctccggc agcaatagcc atcttgagcc    31560
```

```
aggctcggta catgggccgg gtcactgaac cgatgaacca gtcctgaaga atcagatagc    31620
cgtcggttga ctcgacaagc tcctgccgct gggcactgta cgttccgttg tagtttctgg    31680
atgtgctgga aaagctgagg cgactgccgg cggacacggc acgcagctgt ccgttacgaa    31740
aagattcgag gttagggttc gggcgatcgg atttaatcat cccgatttct tccccggcct    31800
gcagttcgtc atagagcata ccgggctgaa tcatcagctc gcggtcatcg ctgcttgaat    31860
cagaatcgaa gctctgtccg tcgccttttt tgatatacat gccgagtgcc gcagcaattc    31920
tggcagcagt aagctccgag tcctcgtatt ctttcagcgc gctcagacgc atcagaacac    31980
cagacaaaag agacgttccg cgggtctggt gcaggcgtcg ggtgaatttg agatgcagca    32040
tgttctctgc atctatctct ttggtatcaa actgacgccc ggatactggc aggcttttat    32100
agacctgata ttttttcggg cgtccccagt tatcgacaaa aacgccctga ttgagctggg    32160
tggcagcatc gctgttcatc ggcacaaagt ccggctccag cgcttccagc cagaacggca    32220
cgccagcaac cggctgaaga ccatttccgg taccgcgaac cagctgagca aatacctcac    32280
cgtcccggag ccacgttcgc agcatcagcc gctccagcat gggcgggta aactgggttg    32340 tgacatctgg ccttacggac cattcgcccc actttcggcg gatatcagtg gccagctttt    32400
tagcgatctt cccgttactc agcatcggat gcggttcaac tatgatgccc ttcgcaccca    32460
ccaccctttc ttccagcttg tcgaaaacgc cgatcaccag atcgtggttg ttatccagcc    32520
agcgcgcctg ctgcctcagc gaaaccgccc ccatctggct gagctgatcg gctgaacgat    32580
tttccttctg ggctttgtgg gtacgcgttt gctttaccgc ctcatacgct ttaataactg    32640
cgcgggcacg caggcgtgag gctttccagc ctggtgaaaa caggccaatc gcatcatcta    32700
aaaaactcat ccaaacctcg ccagcctgta gccgggtcgc ccacggcgtt tgttattgag    32760
cgttgccagt cgtcgctccc attcctgacg gccttttctg atttccgaca ggttttcgag    32820
cgtcatctgc tgcccgttga aagtgattga tttcccctcc agaacagaca gctcggctgc    32880
agcatagcgg tcgatcatgt tttgaatatc tgctggattc acacccaacc tcctgacgaa    32940
gaccacggat tagcctgctc ggttacgggc ttctcacgtt ttggttttgg tttagatttc    33000
ggcgcaggcg gcggggatgg catttcgcca gcttccgtct gcgtgtcctc gatccacgtt    33060
tcccgccgtg cccactcagg agctgacggc catttgattt tttcgtaacc actaaggatg    33120
gcgagcgcgt cggcataaac gagcaggtca aatgcttcgt ttgcgccccg gccgggctta    33180
ctccatttcc cttcattcga gcgttcctca tacgtcagtt cgtcatagaa ccagctgccc    33240
agccaggcgg ggaaatgcac atagccaggg ccgggtgaat cacgccacag cgcattattc    33300
acccggtctt taagggcatc ggtctggaga agataaagag gcacatcacc agtcgcctgt    33360
gcgcggcgcg ttgatctgcc cgtgttgtcg ggaaacgttc gctggataag tttgctgcgc    33420
ctgacgctgt cccctttgaa gagatagata cgcttaccca gccccctcacg gcgacatctg    33480 cgccagaact tgtaggcatt atccgtcacg ccatcttcgc ccctgagtc cacggccatc    33540 gacatcagcc gcatgccctt tgatgggtca gctgcgagcg ccacgttttt atcaaagacg    33600
tcagtgagta aaagatccca gtcctccgga tagctcgccg gatccacctg aatgctttca    33660
ccgttgccgt cgcagcgcag cgaatgccgg atgttgtaac ggtcaactat ccagcgctca    33720
cccatacttc cataacccgt aatctgcaca acaaagcgcc ggttgcgccc ggcctgcacg    33780
tccacggtcg cagtgagaaa ctgcacgccg ttcggtaccg aacgttttgg gacgtcttcg    33840
gcacgctgct cgagcaattc acttttacgc tgctccatgc tggctcgcgg caaataggc    33900 ctgccgaaat cggtgttgat caccgtcttc agggtttctt cgctgcgcgt ggattcatat    33960
```

```
tcctgctcgg cggtcagaaa cttataaata agctgcgccc aggtctggta agcagctgcc   34020
ggaccttcca tccagaagga ggcaatacgg gaacgacggc catcaccgct aaccaggcct   34080
ttcctgtcga tggtttgccc gtcccggagc cagacacatt tcatgttaag cgcacgcttc   34140
atgtccggtg tgatcctgcc tttacaggca gggcactgaa gaaacgccgc ttcgctggca   34200
agcacaggat cgctgctgtc gcggtatccg gtcatattgt ccatttccgg ctggaaatat   34260
tcgccgcaat gcgggcatgg ccagtaaaga cgacggcggt caccacggtt atagagcgat   34320
aaaattccgg tggtcggagg ggcttcatgg ggcgtggagc gccgccattt tgtgtctctg   34380
atatccctcc cgggcgagct ctcaaccagc gtcatcccgg aggacatgaa tgtcgtggtt   34440
cgtttcgatg ccagtgaaaa agcatccccc tccccgtcga tatcttccgg aaagcggtca   34500
taatccgtca gcgccacact tttatagtcc gaggacgaca tgatattgac ggatggccag   34560
cccagcttca gatagttacc ggcgcggaat gtacggtcgt agacgttgtt atcgttacgt   34620
cttgggctta gccgggtttt aacttcaggg ctacagcgaa aagtacggtc caggcgtttt   34680
ttggaatgct cgcgcgcttt ttcctcagat acctgaatta caagcatatc tgccggatcg   34740
cagacaatgt tataaacgat ccagccgtca atcagcccga tggttttacc cgttcgcgct   34800
gggcccacaa acacaaccgc atcgtattca cgcgatgcca gacagttcat cggctcaatc   34860
acatagggtg ccagatccgg atcccacgga actgagtttc ccgcccccat ggcacgcgc   34920
atataagtac tgaccgcatc ggccaccggc atacgacgcg gggctcgtaa aataccggaa   34980
acatcgcggc ggatgtccct ggcggatgcc cgctttgcca tcagtcctcc tcaggctgct   35040
cctcctcttt tccagcgtcc tgcaccttct ccgccatctg gtcgcgcaga tcatcgataa   35100
cgctttgcac acgaactacc gcagcaggcg ttaaagcaca gtcgcgctcg agcacatccg   35160
ggagggtttc aagtaccatg acgacggctt tcgccatcaa tgagaattct cgcgccactt   35220
catctgcggg tattaactgc cccgtatcct gttcgaactt cagcctctcg ttctctgctt   35280
tccagtggga cagcctgtca aagggggca tatcgtcgat gttggccgaa acggtaggga   35340
tcatcagttc ggtcagaatg tcggtcacca gatagagctt taacttgcta ttgctgcctg   35400
gagcaggttc aacatttttc agtctcgcgg caaccgtctg acggtgtacg ccggttatcc   35460
ctgccagctg gttgatattg agttttaaag tggcaatttc ctggtccatg atggtgaaca   35520
cttttttgaac gattcgacat gttgcgaaaa tggcctctaa ttaaatcaaa gacctgcgca   35580
catgatgatg atgaccctgg atccgaaaaa ctagccgttt cccgcgagca cgccgccccg   35640
tggcagggtc cccctccggg agtacctttt gataataatt atcaattgca cactatcgac   35700
ggcactgctg ccagataaca ccaccgggga acattccat catgatggcc gtgcggacat   35760
aggaagccag ttcatccatc gctttcttgt ctgctgccat ttgctttgtg acatccagcg   35820
ccgcacattc agcagcgttt ttcagcgcgt tttcgatcaa cgtttcaatg ttggtatcaa   35880
caccaggttt aactttgaac ttatcggcac tgacggttac cttgttctgc gctggctcat   35940
cacgctggat accaaggctg atgttgtaga tattggtcac cggctgaggt gtttcgattg   36000
ccgctgcgtg gatagcacca tttgcgatag cggcgtcctt gatgaatgac actccattgc   36060
gaataagttc gaaggagacg gtgtcacgaa tgcgctggtc cagctcgtcg attgcctttt   36120
gtgcagcaga ggtatcaatc tcaacgccaa gcgtcatcga agcgcaatat tgctgctcac   36180
caaaacgcgt attgaccagg tgttcaacgg caaatttctg cccttctgat gtcagaaagg   36240
taaagtgatt ttctttctgg tattcagttg ctgtgtgtct ggtttcagca aaaccaagct   36300
```

```
cgcgcaattc ggctgtgcca gattagaag gcagatcacc agacagcaac gcgccacgga      36360
aaaacagcgc ataaagcact tcattagcag cgccagatag cgtaatgatt ttgttactca      36420
tggaatattt cctttaggc gtgagcctgt cgcacggcaa tgccgcccga gaggtaaacg       36480
caacctaacg gcatcaccca ggctcactac tgaaagactc tctttgatgt gcgcgtgcga      36540
tgcgcgtaga agactgattt atcaacctgt ctttatatca ggattcatta cctgactatt      36600
tgtgggtaaa gttcgtagtg cgctgatcgt gcaaaatgat tttagttggg aacagttcgc      36660
aactctgtcc cataaaaatc agcatattcc catctatccc atatccagcg cattgaccat      36720
cgggatactg aagggagatt ccatcatctc ttagaaagat caccatctct tttgtttcaa      36780
tttgcatata gctacctgga ggatttatga atgcaaggat tttcatggac tattaccatg      36840
agattgattt tccatcttta ttcgcgagag cagtggaaag cgatgacgat gtgggtacta      36900
cattgcgcat tcacctactt tgtgagcgca tggtcgaagc atggatatgc gcatgctgtg      36960
actgccaaga tctctttgga agagataaaa acaaactttt aatcgaatgt aatactaaaa      37020
tatccatggc gggaaacctg gaatccccc cggaacttat gaaatcactt aaaaccatca      37080
actcaatgcg taatgacctt gcacacaatc catcaataca aagcattgct gattcaagga      37140
tccagagcct gaaggatact ctgactgaat actttaaaca gcatccaacg gaacccagca      37200
tggaagaatc aaaactgggt attttaacg ccgagaatca attaaccgaa gaagtttcct       37260
tagatagtga cagttcaaaa aacagactta agttaatctt gctgttcagc aagttaatgc      37320
aggcgttaat gcaattagtt gcagctaatc ataatgggcg ctgggataac caatttagcc      37380
aattcgttta ccatgtgacc atgaacgcaa caaagagata aatccaagcc cgttttgtac      37440
gggctgttgc attatcacag gcactcagtg aatgcctgct gtaatgccgc tagtcgtcga      37500
gttgcaacac accgtgatcc agtgattctg aataggcgat aagtccggta taaccgggga     37560
taatctcacc attatcagct tcaaattcag gaattgtgcc ggtggtgatg gtgtattgag      37620
gctggccatc ttccttcgcg aaggctgcca ggtcttcaat ctgcttagct gtaagaacta      37680
ctgtcatgct cattcctcag ttgtaaaaaa gccccgcgag tgcgaggcga tttgattgaa      37740
ttctcggctc ttatctcagc gcagcccctt actgcgtgcc ggttgctcgg tgatgagcat      37800
cagcgatgag acattaaagc cgaccgaagg ccagcggcgt tcctcatgtt gccgacagag      37860
ccatatcgac aagaggacga aaactagcag catgaatcgc ctattggtta ttcgacagtc      37920
gcactgattc gtaaatccgc tcacacgtca ttcctgcccg gtagctttcg tcagatcgtc      37980
cagcataata tcgagctgct tctgcaaggc ttccgagcat gtcggcaagc attgctgcgt      38040
tggctccggc tgttttgctt ctgacggaag tggcgagatc tgcggtgtgc tttgcggcgt      38100
ccatgtgggt agcgagtttt gttgcttcgg cgcgcagctg cttaacagtg gtagccaggc      38160
cagcagaagt aacggcagcg ctcgctgctt gagcttgagc atctttaacg gcctcatccc      38220
gggcgattgt tcgcccttgt tcaatcatac gagctgcggt ctgtgcattc gcttcctgtg      38280
aagattccgc gctatcccgg tcagcccact ttattttcca gctgcggttc gtccactcac      38340
tgccagcgag aaacgaacct accaacgcaa caatcacaat gatgcagatg cacccggct      38400 tcactggtct atccccagc acgtcagtgc gctttcctgg tcccgccgtt ctacctgccc      38460
ataacatcca tccttctggc ccttggtcag gcggcaatcg cggccaccgt ctttaatcca      38520
ccagcggata gcttcacagg ctccttcgt atcgccagca ttaattcgct tatagaacgt      38580
agacgggaaa cattttccgg ggccgatgtt atatgggcag aaagaagcga tacccgcttt      38640
ctgtggttcg gtcagtggta ctttgatatt tcggtcaacc cacgccagcg ccttgtcgcg      38700
```

```
ttcaatggcg tttacctggg cgcatttctc agctgacagc ttcatgccct gtactactgg   38760
cttgccatca accattgttg caccacggca aatggtccag agtccgccgc cgtcgcgata   38820
tgctgtcaag ctgttaccct ctttctcatc cagaaactga tcgagaatca cgggtgcgga   38880
agccccggca agaatcaaac caacgaccgc tgcgctcaat ttattcttca gctttagaga   38940
catagccatt gcgccgatcc tcccgttctt ccagcggaa ataccagttc actgcacagg    39000
tgattaccgt gcatgcgata ccgacaataa ttgcccagtc gctcaggctt aaccctgcaa   39060
ttctgtcggc caacatccag gacacctctt ttgctgtttt agctgtttcg gcatatgcct   39120
tcgctgatac accgcagccg gcaagcgtgg ttcctgatcc atatgaaagt ctgctgtaaa   39180
tggtgctcat tctggtcata gcctcacctc cgatagttcg gatggcgctg tgtgtgattg   39240 aagggggatca ggcaaccggg ctcttatgtt caagtaaaaa ttaaggatga ttcccggtgc   39300
ctgaagatgg tgatcaccac agcaacgggg gagcgtggtg atcgttatga ttttttcagt   39360
ttttccacct cttcggtggt ctgtataaac ctgtctgcct ccagttctac gccgatcgcc   39420
cgacggccaa gttctattgc agctttcaca gttgaaccag agcccataaa gaaatcggca   39480
acgatatccc ccggtctgct gctggcgcta atgatctgtt tcagcatgtc ggcaggtttt   39540
tcgcatggat gtttgcctgg ataaaactga acaggcttat gtgtccatac gtcggtataa   39600
ggaacaagag cggaaacaga gaagcagcgc cgaaggattt tgtattcctc cagcaattct   39660
gaatacttgc ggtttaatga ctggtaggta gccaccagct ggtggtgagg atgttcaagc   39720
ttttgctgaa tatgtttatc gatggcgatc cgcgtgaaca gttcctgcaa ttttcgatag   39780
tccacttcat tcggtagttg ccattggctt gcaccaaacc agtgtgacgc catgtttttc   39840
tttccggttg cctcagctat ttctttcgag ctgacaccca gtgattcacg ggcattacgg   39900
aagtaatcaa tcagcggcgt cataatgtgc tgctttagct ctgtgctttt cctttcgtaa   39960
acatcctctt tacctgtata cggtccaaga tagtgctcag caaacaaaat ccgttccgta   40020
gatggaaagt acgcacgcag gctttcttta ttacatccat tccagcggcc cgatggtttt   40080
gcccaaatga tgtgattcaa aacgttgaat cgggcgcgca tcataatctc tatatctgag   40140
gccagtcggt gaccgcaaaa caggtagatg ctgccagcag gtttaagaac gcgagcatac   40200
tcagccaggc agctatcaag ccagcgtaag tagtcctcgt cccccttcca ttggttgtcc   40260
cagccgttgg gcttcacttt gaagtacgga ggatccgtaa ctataagatc aatagagtta   40320
tccgggaggg tggcgacgta atgcagacta tcagcgttga ttaactcaac actgtttatt   40380
tttacagtat ttttcataga tcagtaagcg taactctgat aggctcacgt tgcttttgcg   40440
ctaaagcagt gggccttggt tagcttgtga cctgaaagca tgagctgatg gctggccggg   40500
tgcgctaaca cccaccagcc gcccatttcc acagcagaaa accccattca ctggaggcgt   40560
ttataacatc cgaactggta atcagataac cccgccatca ccagctgcgt aagtatgagc   40620
tggcaacgtt cgtggctgag gtgggtattc tgtgcaatct ccccagccgt tgctggttta   40680
tcgcttaatt cattgaaaac agcctttgcc gtttctgtca tatcttcctg atttagcatg   40740
tcttttacct aaaattagtt gcgtgacata cagataactc tggttggtga taccagcaag   40800
agaagaattt gattctgcaa ccaacaaggc ctttaggcat caggcaggaa tgagatgcaa   40860
taaaaaaacc acccgaaggt ggtcttatat gaatctttaa cgcggactta gcaaatattc   40920
cacatcatcg tactaccgtt atggttttcg ataatttttg cggctgggct agtaccaaaa   40980
gagtgcatat agcaatgatg aatagtaagg accagatcct gcaacgtttg gtcactctct   41040
```

-continued

```
agctccatga tatttaaacc aatattttga gctttgtcca aatgaatatg tctggcatgt    41100
gcatacgttg cttggtggtt gtttaactca tcacatatac gcttagcctt agcttcagcg    41160
tcagcctgac ctgcgaacat accagtacaa agccatttct ggacaatttc gttcgcccag    41220
agaattgctt tttcacactc gccaatcaac gttggattta gttttttggaa cgtaaattgc   41280 caccattgca gtgcagcagg gttggcaaaa atttccgctt ttgctctctc atactcctca    41340
ataattgcat gagatgataa cccattaaac tgtggatcaa ttggcccaa gttcgactgt     41400 ttacctaaaa cgatctgctc agcacaacaa gcaagcattg tgccacaact cattgaaatc    41460
ataggtacaa tcgctcggat attggttccg aactttgaac gaagataatg accaattgat    41520
tctagagctg cgatatcgcc tccaggagta tggagtaaga tatccaatcc cagactcgta   41580
tctaacccat tgatagcaga cataagacca tttttatcat catctgacat ctggatcaga    41640
tgttgaaacc caggcccccc tttttgaagg aagcctgagt aataagaaat tacatttcgg    41700
ccagtatgtt tcgataaatc acgtaagtac ttgtggcgaa cctcatccgc tggtgtacgt    41760
tgagcgatag tacccatctc acccaatacg tctatccaat ttggcatgtt atcaatttat    41820
cagtatgagt acagttggtg agattgctga ccgttctgct cagtagtatt tggtgttact    41880
gtgctgtatg aatagagcac accacttctc acattcagat cgtttttgctg agcgagaaca   41940 cgcatagcaa aatgctgtac ggattcgcct ttttgaaact cttggggttg tatgcccatt    42000
ttttcgtaaa attcagcagc gctcatgata tgtccctcgt ttttttctac atctatgcaa    42060
ttccaggagc catcaacaca agatgtagta gttagcagtc gtcaaataca cgaaaagcct    42120
caagatgagg cttaaaaaga ttctttttga taaagattta gccaaactat agcggtcaaa    42180
atgcagattt gacaagtata aaaagcactt aaagcctata ataggcagt ttttgagaat      42240 taaagcatct ttaatgaggt tgaacaaaat gcagtcttga cgctgaacag gactttactg    42300
gaacgtagag ctaaatggtt cgatttcatg aaccagttac aaaaaaaccc gctcatcggc    42360
gggtttataa aactttggca acatatcaaa tatgcttcaa atatggctta ttttgttgca    42420
ttttgcaagc gtgtttgaag gagatggtga aatttacttc acatttctgc cactttgagg    42480
gcttcttctt cctcatagta ttcaagagcc atggccaacg cagattcatc aagctgggta    42540
aaagcggcct ttaacccagc ccagtgccct gaatagacac gcaaccatgt cgaacggtca    42600
acgctaacca tgcgggccaa cgctgcacca gcatagtctt tataggtttc attatttctg    42660
gttgcggcaa tttcctgccc tgccagccat accaggccta tcagtttctt tactacgcgc    42720
tcctgaaggg agttatcacc caggcatttc tgataagttt tccagacgta ttcacacatc    42780
atcacctggt gcttatagct aaggtcaaaa ccgtagcagt accgcaacca ggcctgctgg    42840
tatccactaa gcgcggacac tgccctacgc cacggcgcgg actcaaattc cgcatctttt    42900
atcggcggca ttggcctgcg gcggctgcgt gtttccagca catacagtgg cgcggaaagt    42960
gagttaacaa agcgtggccc cttctctcct tcgagttcga cgagatgaat tccacgcgca    43020
ggggtggcat ttttgtctgc tggtgggtgt tcactgaaag cctcaagctg ccctttttgtt   43080 cccccagaca ggtcaggtag cgcgcggcgc aattctattc ttacaaaatt caggtcttgt    43140
tgattcatgc ttcttttgcgc tccatacact taagctttcg caattacgcc gatcgccagc    43200
gcccgatcca taaaacgcag tagcagctca agctgcgtac catgcttctg ctcgaatgcc    43260
ggtacatcgg cgtgtaactc gtcgtggcac tctctgcaca gagggatcac gaagagatca    43320
tgggcttttg ttgctgtccc ccccataccg tgccctacga tatggtgcgg atcatctgct    43380
ggccgtcggc aacactcaca gggttgtgtt ttaacccagc gggtgtacgt ctcatttatc    43440
```

```
cagcggcgtc gctttggcct gagcatgaaa gattctggag actccggatc aacagagagc  43500
gtgaggatct tcttcgcctt ctcctgcacg aggctggttg cagaagcgga aggcacaatg  43560
tcgctttccc tcatgaccga gcggatctta tcatccggaa ggcgtagccc cttgtgcgca  43620
acgctttccg gaataacatc agccaggtcg tttctgacca tccaccagca cagttccgga  43680
agcgtcagga tatgcgactc gggaaaacca gaatcacgcc gaatgacttc cagaatccag  43740
gataccaggt ttcctgccgc tatacctgca agctgttcgg tatgctgccc cgacaaagtg  43800
tgatcgcaat gccagcacag gcgaatactt cctggtgggt gccgcattgt tgtgaagttc  43860
ttgtcgtgcc acgatgaatg tggccactgg cattcaaacc gattactcaa ccattgctca  43920
agggaaggaa gcccaccagc acgctgaata acccgatcat tctcgaagac ctgccgcatt  43980
accggatcat cagccagcgg ctgaatggcg gcgggaacag ctcctgtact gaatgacgcc  44040
atttcttctg gttcaggctc aagcagaacg cgaccgcgca taaagaggtg catcagttcc  44100
gcgccgggac gaaacaacac aatccccata cgatgggcga tctcgggggt aagcagagct  44160
ctcacgcgac ctgccccctg gcaatgtgtt ctgcccacag tccaccaatc cagcgcacgc  44220
cttccgccgt gaaacgtgcc tggctgaatg catgatttga ggttacggat gtgccggttt  44280
tcacttcaaa acggcccgca tcaatatgct gatgccgtgg ggtcatcgtt ccgccaagac  44340
gatacatgat gtcgttctca aggaggaata accgcagatc gggctctttg gccttaagca  44400
gttttgccac ctggcggaat gacattgacc cactggctgt acagtaccga tcaacaaacg  44460
ctaccttcgg cgccgcggca gccagttcgt tagtcaactg ctgttttttgt tctgcaaggt  44520
cagctgcaag acgtagggct tcagagaatg attgaggaat cgtctgctgc tgtgcctgct  44580
caagctcctg ccagcgatca accagacgcg cggtaaactc cggcgacagc tgcgcgacaa  44640
cgatataact gtcccgcttc cctatcagat aaaccgatac cgactgattg aggtgatttt  44700
taacttcccc cattgggggg agttcaataa caccgcgctc tgccaggcgt tcaatggacc  44760
gtttaacatg gtcatgtctt gattccacca gctcagcaat atcgctgctg acatggtta   44820
acgctgttgt tgctaactgg ctcatacttt tctccatatc aggcggctgc acccgccggt  44880
tcatatctgc tgattgttat ctctacccga cctttcggca caacgggtcc ccattccacc  44940
agcatgcgct taatctggct gtcgtcttcc cagacacccg catgcgtcag cgcgtcaaac  45000
agggctttgt tgtaattatc gatatcccgg cggcgcgcat ccggcgggta cagagtgatt  45060
tctaccgctg ccagttcagt cgatggcttc gggagacgtc gtaattgctc aatgatcgcc  45120
acgcaggcag cgctctggta tttacggcca gcggcgctaa tgaggtgacg accggccagc  45180
ggccccttgt tagggcgcg ccagtaagtg ttcacgctcg gaggaaaagg caggatcagt   45240
ttcacgcggc ctctcccccgc atattgcgaa caagttcaga agcagcagta atgatttcgc  45300
tggtggcagt ccgctccagc cagagttgat tgatattggc tttcagcttg tgttgcagtg  45360
actcatccag catgtcagca ccatccacct ggtcgaatac aattctaacc tccagcggcc  45420
agatacggga ctcgggaagc ggatccgata ctggtttagc tttctcacga atgtgcatgc  45480
ggatctggcg aatattggac caactggaaa catccaggct tcccatggct gcaatgaagt  45540
cagtgctgtt catgccatat tcaccggatg cttcaagggc aacagtgcga atacgttccg  45600
acatatccag gcgcacagca gcgtcatcga attcaatcga caacagccac tcatccacac  45660
cgaacaaaat actctcacga ataagcagct tcgctttgtc gatcgttaaa ggtgatacct  45720
gagtgaattc cggtgcttcg acagaatccg ccgcccaggt atgcccaaac ttcgattcac  45780
```

```
tgaatgtgta ttcttcttta tcgccaaacg cagctctaac gcatgcccac gcctcgacac    45840
cgctgatagc aaaaatatct ttctgggtga gtggcaactc tgcttctggc ttatcagctg    45900
caggaggtgt ggcagttaca ggttgagact tgctggcagc aaattgtgcc aaagccataa    45960
acgcccgccc ttttgcctcc agttctgtgc ggttgatata gctgaaccgc tcgccacgcc    46020
atgacttatc gaatacagct atggcaccgg caaaaaacgc gctggtgggt ttctgttttt    46080
cgtcagcagg tacaaaccac acaggcagat cgaacccaat gcgcccgcga atgaatacaa    46140
tgtgatcggc atcttccggc caccacgttt cactcggcgc ggcttttatc aggaatacat    46200
agcgaccgcc cttctcgcgc tgggctgctg cgtagttcat gatgtgcgtc atgccggtga    46260
tcgcctgctt ctcgtggtac tgcgaacggc tatacggtgg gttgccatag ccagcgccac    46320
ccagttcagc cagacgttca gaccagtcct gcgtcagcgc gttatcttcg gcggtgtacc    46380
atgccgggca tttcgcgttg tcgtcgtcag caaacaaatc cagaactaat ggaccaaata    46440
gcgcgttgat cccccaaaaa agcagatccg gtgtccgcca ctgatcgcca acctcttcca    46500
attcgtgagc tggtttgcta cgcagtgccg ccagcgcctg gcaatattta ttggtcatca    46560
tgaacggaac cccgaatttt ctggcagtga gtaatcaaca ctctggaagt ttgcgcggct    46620
ggctgagtta gtctcccatt tgccgttaac gcgttcaggc cggccagcac tggaccattt    46680
ggtcgcgctt tgcaggtaac cagggaagtt ttttggaatg aacagagttg ccgggcggag    46740
gtattgcgcc tgctcgctat cacgccaatc ggcattttg taatccacta ccaagcacag    46800
gtcatcaaca gtgaattgtt cccgaagacg ggcgcgaata ttctccagcg acgtgctgca    46860
tacctggtag cgtgagccag tagtctgatt caggtaagac aaaacctgtc tggcctgatc    46920
agtaatcaca acctcagggt cgggttgcgc cgcaaccgga caagagggtt ttgaagttac    46980
ttgtggttct tgttttgatt ttactgacgg atccccacca gattctgacg ggtcaaaacc    47040
gccttttttg ctggatttcg acgcctcaaa ttttgacggg tcggattttg atgcatcaga    47100
ttttgatggg tcagattttg atgcgtcaga ttctgacagg tgagaaaaag cagcctctcg    47160
caacttaacg acgttaagct gatatacgtt cgatgcgtta cggttcccat tacggcgctg    47220
cttacgggaa agccagccat ccttctcaag ctgagcaagg gccgtcctta ccgtactttc    47280
tccagcaccg atttgacgtg cgatcgtgcc aatagacggc cagctaacac cctcatcact    47340
actgaagtcg gccagacgcg ccatgatggc aacgctggat aacttcatgc ctgacgaagc    47400
gcatgcatcc catacgtaac cggttaattt agtgctcatg gtcgtccttt aattctgtaa    47460
atttacgctg gaattgttca gagggctga agcactcatg atcgtaccct tcgcgaaggt    47520
atataacgcg ctgtgtatct ggctcccagc ggacaactct gacgggaact ccgtagtgat    47580
ctctgaaccg ccggttaact tcagccattc ctcgcgcccc ttctcgttca tctgaacaaa    47640
tgcttctacc atcaagtctg ctggctggta gttgcctcca tcagccgcgt tatttatgat    47700
ttccacatag ccgaactggg catctttacc caccagcggc aaacatctga attgcttagc    47760
tggtctgaat cggtttacac tgttcatgcg ttagttctc cactgatacg acacgccaag    47820
gcgcccggag ctgcacactc gcgggcgtca ccttttctgc ctgttgaaac gaatacgtca    47880
atcgcctgat ctgaaacacc aaccccataa agcgccataa atcccaggaa cccgtgaatc    47940
tggtggcgga gcttcttact gaataattct gaaagcattt tgcgctctga tgaatcaatt    48000
accccatcag ccgctgctgc catcttggca ttagccagct caccagatgc tgctgccgct    48060
ttcatctcaa tgctgtacag ctcaacgtta tccaggctct cagcagttgg aacatccacc    48120
agccatttcc ctttccggtt cgcctggtac tcggccaagt aacaagaacc agacaggtcc    48180
```

```
tccatccgtt ccagttctgc caaggtaaag aaccgactgc cacacttctg gtacaggtgg   48240
ttgtggaact ggtcgatagt catccctaaa tcggaagcca tacctaagcg accatgcttg   48300
tgtgccttac acatcaggcg gattgctgta tttatgctgt ctaccatgtt gatttccctc   48360
tggtagttaa taatcaactt aaagttgact attgttgtta gcggaaggta tgccgtcatt   48420
tttgttcgga taaatatcag gtcgtaattg atggggagtt actacccatc cgccccattg   48480
gcagagttga ataactcttt cagaaggtac tcggttcttt gcaatccagt tcgcaacaga   48540
ttgaactgat tggaattcaa accgccttga tacctctgaa atcgacccga tcgccttcac   48600
agctttagct gttacattct tgtgttgaga tgacatgtgt tctcctatga ctaagcctgc   48660
atcaatacta cttatagtag caattattag caacttaaaa tagaaatgac aactatgcct   48720
tgtgcgctta atcttctact tatggtggaa aatgctaaat acaaagactt tgccgaaagg   48780
ctaaacaggt ctctccaaga gcaatctatt ggagttaaag aattgtcaga gttcagtggt   48840
gtctcgtatg agatggcgcg cgctacact cttggtactg caaagccgag agatgagaag    48900
atgattcgaa ttgcagaaag acttgccgtc tcaccggctt atcttgatta tggtgtgcct   48960
gttaatggtg cgacgcgcc agccaaaggc acggtcagaa tagagcaatt ggatgttcat    49020
gcttcagccg gttccggata tataaaccaa ccattcccta caatagtgag ctcaatagag   49080
attccagaag agaggatctt cgagttgttt ggtcgtagaa gccttgatgg catcgtcatg   49140
ataaatgttg atggcgatag catgatgccc acgctttgcc caaggacct gcttttcata    49200
gacagcaagg ttgaacaatt cagcggcgac ggcgtttatg tgttcaattt tgaagacagt   49260
acgttcgtta aacgtttgca gaaggtaaaa gggcgccgac tggcagttct ttcagacaat   49320
gaacattacc cgcccttctt catagaggag catgaaatga atgaactata catattcggc   49380
aagctaatca gatgcttacc tctaaaaatg atagagtttg gctaataatt aattcatcaa   49440
gaaaccggcg aaagccggtt ttttttacgc ctccaattcc tcacctcata acactacact   49500
actaaaaatt tcattttcta cttttgttg ttgcaattat ctacttaaag tagctatagt    49560
cattgcatcg aaagcgaaca ggcaggacgc ccacgaagta gccgccggtg gcatatgaat   49620
aaccggatga ttcgctgaca gaaaacttag gttgggggta gaggtttaca tgaatcattt   49680
attcacatgc tcattttgcg gagcaaccga actgggagcg ataaagatcg tcgcaaaagg   49740
tggtaaggac gaacctgcca tctgttcgga atgcgtagtc acatgtgtag aaaaaatgat   49800
cctgactaaa aaatcagagg ctgaaaaacc aacctctgat aacgaaataa tatcagtcga   49860
taaaaaacta tttaaagagc ttcttcagct tgtcctcaac cttcctgatt tcggaagtaa   49920
gctggctgct gttgacattg atagtagctc cacatcgaca agtgaaactt tgttcgact    49980
tgagccaagc gattttcttc ttcgtcttag tgccgcactt agggcatgcg ggtaacgtaa   50040
tttcctggtt atcaaaagcg cccataaaca tccctcttgg ttgtgtgaga acaccaagat   50100
accaccgcgc ctgatgtggt taaaagcagg ctaaagcaat aacaagtaac tccctgttct   50160
ggcggcccgg tgttttcccg tgtatttccg gtaaccgcca gccttttca gggcacaaca    50220
gaaaagggca tcaccgggcg acgggctcat aacccaatcc acccgggcaa aagaaagcg    50280
gtctctgcaa gccgccgacc aatgcaggtg cccttctctg ttgtgtatgg agaaactaac   50340
tttttagcgt ctgtgcagat gcgctgagga accgagaatg aataatccgt ttttcaaaaa   50400
tatgttggtg tatcgcatta gtcgcgattt caccatcaac caggaagagc tggaacagca   50460
gcttgaacta tttcgcttca ctccatgcgg tagccaggat atggcaaaaa ccggttgggt   50520
```

| | | | | | |
|---|---|---|---|---|---|
| atcaccactt | ggtcagctgt | cagatcgctt | gcatcacact | gtcaataatc | aagtgttgtt | 50580 |
| ggttattcgc | cgggaagaaa | aaatactgcc | atctcctgtc | attactgaag | aactgcgcaa | 50640 |
| gcgtgtgtcg | cgtctagaat | ccgatcaggg | gcgtcgcctc | aaaaaaactg | agaaagattc | 50700 |
| gctgcgtgat | gaagtgttgc | actccctgct | tcctcgggcg | ttctccaaaa | actcgactgt | 50760 |
| tggtttgtgg | atcaacgtca | ccgacggtct | gatcatggtt | gatgcagcca | gcgctaaacg | 50820 |
| tgccgaagac | tcactggccc | tgcttcgtaa | aactctcggt | tctctcccgg | tggtaccgct | 50880 |
| gactatggaa | acgccgatcg | aactaactat | gaccgactgg | gttcgttccg | gtagtgcgcc | 50940 |
| tgctggcttt | ggcctgggtg | atgaagccga | actgaaagct | attcttgaag | atggcggtat | 51000 |
| tggacgcttt | aaaaaacaga | ctctggtcag | tgacgaaatt | catgtgcatc | tggaagctgg | 51060 |
| caaagtagtt | acaaagctgt | ctatcgactg | caacagcgc | attcagttcg | ttctttgcga | 51120 |
| tgacggcagc | atcaaacgcc | ttaagttctc | taatgagatt | acagaacaaa | acgacgatat | 51180 |
| cgaccgtgag | gatgcggctc | agcggttcga | cgctgactt | gttctgatga | ccggcgagct | 51240 |
| tatctctctc | attaacggat | taacaacctc | tctcggcggc | gaagccaagc | gataaacacc | 51300 |
| aggcaacaat | tacccccata | agcatggggtt | gggttgctgc | acgctaaatt | cagcaattca | 51360 |
| ttaatttaat | ggcgcggtgc | agcgcgcaa | tatggagaaa | accatgagct | acattcagac | 51420 |
| attatccggc | aaacatttta | attacctcga | tatccaacag | gacgatatcg | tgatcgagga | 51480 |
| tattgctacc | gcgttgtctc | atatctgccg | cttttgcaggg | catcttcctg | agttttacag | 51540 |
| tgtcggccag | catagcgttt | taaccagcca | cctcgttccg | caggagtttg | cattagaagc | 51600 |
| actgcttcat | gatgctgctg | aagcctacct | gcaggacatc | ccctcccccac | ttaagcgcct | 51660 |
| gcttccggat | taccaggcaa | tcgaagctcg | tgtggacgca | gccattcggc | agaagttcgg | 51720 |
| tctaccaact | gagcaacacc | caaccgtgaa | atatgccgac | ctggtgatgc | tcgccagcga | 51780 |
| acgccgcgat | tttgagattg | acgaaggttc | catttggcca | tgcctcgagg | gagttgtccc | 51840 |
| aacggattta | ttcattatca | acccagttcg | tcctggccag | tcatacgcca | tgttcatcaa | 51900 |
| tcgctttaac | gagttgatgg | agcagcgcca | atgcgccgca | tgaaggtaaa | agaactcgta | 51960 |
| gcggaggcgt | ttgcctccgt | tgctgaattg | ccaccaaagc | atgcgccgct | tatgcgcgaa | 52020 |
| gtcgccacca | gactggacgc | tacgttcgca | gcattaaaag | agtctctggt | gcaactggaa | 52080 |
| caggaacgta | aagataaaac | gccatgaccg | tatttgaata | tctccaggct | catccgaata | 52140 |
| ccaccagcgg | tgaaatcgcc | aaaggtatga | acaaaaagac | cccagcggtc | gccggagcat | 52200 |
| tatctcagct | ctatggcacc | ggtcggatcg | tgaagtctgg | tgttcgcaag | ggtattccaa | 52260 |
| cataccgcat | taacgatatg | ccgtttggtt | gcagtaacag | cctaaccatg | atgtttaacc | 52320 |
| agctcttgag | cagagccaga | caaggagcag | cccaatgaca | gcactcaaca | acaggcgct | 52380 |
| gcgtgaagaa | ttccagttca | tgcaggacaa | ctatagcgac | ccggcagacc | acgatcggca | 52440 |
| ggtgatttac | atcgaggcgg | aggcgctgct | ggatgagttg | gaagccaaag | actcaacgat | 52500 |
| agcagcacaa | caacatgaga | tccgtatgtt | gctgaatgcg | cttgaggaaa | aaccatgccc | 52560 |
| gaaatgcaac | gacacaggaa | tgactgatag | tggcggcacg | cagccatggg | gcgagccgat | 52620 |
| tgagattgaa | tgcgactgcc | gacagcagga | tgccaacacc | gcagaacttg | tagccgctgg | 52680 |
| cattggcgtg | aagggggagt | gagatggata | aattaatcaa | acctaccgcc | aaaggtaaat | 52740 |
| atgacggttc | atgtgattat | ctttgctcgg | aagatgcgcg | attcatcgtt | atgcgcggcg | 52800 |
| attatacgga | agcggaaata | attcaggctt | ctgtgtctca | agatgtaatc | gactcggatg | 52860 |
| gtgcggctga | ttttgcaagt | agcgcccgct | attatcagtg | ctggtacaaa | gttagcccaa | 52920 |

```
taggtggtca ggatggctat tcaggctggc atcatcctcg tgattcgccg tgtcgcggtg   52980
catatttcgc atcagttttg caatgggatt aaggaggact aacccatgac aactaacaac   53040
cacccggcgc acggtcctgt atcactcgat cgcctgcacc agatacgcga acacctgctg   53100
catgataccc aatactcaaa cggcgggaac agagcctaca ttctcgctga tgtattgaag   53160
gtgattgatg gggctattgc ccgcgagctg gtacgccgtg agcatgcagc gtggtcacag   53220
gctactttcg gcgatgtcgg tccagttggt ccgctgaagc acctttccaa agaagcgctc   53280
gaggctgctg ctgaaccagg cgaccttagc gaatgggctg acatgcaatt cctgttatgg   53340
gatgcgcaac gtcgtgccgg tatcagtgat gagcagatta cccaggcaat gataaaaaag   53400
ctggctataa ataaggttcg ccaatggcct gagccgaaag acggggaacc tcgattgcat   53460
atcaaagaac agtcagagca ggagaaaaaa taagaatgtt tagcctgatt cggcgcggtc   53520
aaatctacac ggacagtagc aactggcccg taattatcca tagctgtagt gatcactcgg   53580
tccgaattaa acgcaatgat ggcgagctga gaacgattag catcaaacgc tttaacgaag   53640
attttgaacg agtggagcat gatgagtatc gcaaaatatg tgccgaaata gagcaggaaa   53700
caaacctgaa aaacctacgt gcgatgcgtc gcggcaagat tactgaatag ccaaacagga   53760
gaatatttaa cgtgaacaac ttaatgatcg accttgagtc catgggcaaa aaaccgaatg   53820
cccctattgt ctccattggt gccgtattct tcgatccgca aagcggtgaa ctgggtcagg   53880
agttttacac cgctgttaat cttgaaagcg ctatggagca gggagcggtg ccggatggtg   53940
acactattct gtggtggtta agacaaagct cagaagcacg atcagcaatc tgtgttgatg   54000
atgcgatgcc gatatcatct gccctatctg aactgagcca tttcattaat cggcattctg   54060 ataacccctaa atatttaaaa gtttgggca atggagctac tttcgacaac gttatattgc   54120
gcggcgcata tgagcgtgcc ggccaggttt gcccgtggca attttggaat gatcacgacg   54180
tcagaaccat cgtcacatta ggcagatctg taggtttcga tcctaagcgt gatatgccat   54240
ttgatggggt tgcacataac gcactggctg atgcccgcca ccaggcgaaa tatgtttcag   54300
cgatttggca gaaactaatc ccaaccacca gcaacagcta aagttttccc cgggtgcagc   54360
cgggataatg gagaaataac tatgagcaat attttccagt tagctcccaa cgattgggtt   54420
tgtgaaagcg ttttgatcgc ggttactggg ctcaaacccg gaaccatcct ccgtgccaga   54480
aaagaatgct ggatgattgg gagggagtat atccacgtat cgcctgacgg aaatcctaaa   54540
ccttccagtg agtgcatgta aacagaaag gctgtagatg cctgggtcgc ttcaatgaaa   54600
agcaagcaac cagggtgatt tgatgccatg aaaaaggtaa gctcgtatcg ctcttgggcg   54660
tctggaggta acaccaatgg ataaagtcac atatccaaca ggcgtcgaaa accacggtgg   54720
cacattacgc atctggttta attttaaagg taagcgtgtc agggaaagtc tcggtgtccc   54780
tgacaccgct aagaacagga agatagccgg ggaactgcgg acatcagtat gttttgccat   54840
ccgcacagga acctttgatt atgcaaccca gtttcctgac tcccctaacc tcaaggcttt   54900
tggtgtaagt aaaaaagaca ttacagtgaa agaacttgaa gaaaaatggc tggatctgaa   54960
acggatggaa atctgcgcga acgcatttaa tcgctatgaa tctgtcgcaa ggaatatggt   55020
gccgaggatc ggaggtaatc gcctggtgtc agcagtaacc aaagaggaat tgctgtatct   55080
gaggaaatat ttgctaactg gttatcagaa tccgacgaaa aacaaagccc cggcaaaagg   55140
gcgaagcgtt gttactgtga actattacat gacgacaatg gccggaatgt ttcagtttgc   55200
tgcggatcac ggttacttag aggtgaaccc attcgaggga attaagcctc tgaaaaaagc   55260
```

```
cagggcagaa ccagatcctc tgtctcgtga tgaatttatt cgcctgatag atgcatgccg   55320
gcatcagcag acgaaaaacc tgtggtcatt agcagtgtac acaggaatgc gtcacgggga   55380
actggtctcc ctggcctggg aagatatcga cctgaaggct ggaacaatta ccgtcagacg   55440
taattatacg aaacttggtg agttcactct accgaaaacc gaggcaagca cagatcgagt   55500
ggtgcatctt atccagcccg caatcagtat cctgaaaaat caggctgaaa tgacaaggct   55560
gggcaggcaa tatcacattg aagtgcagtt acgtgagtac ggccgttcgg tgaaccatga   55620
gtgtacattc gtctttaatc cgcatgtggt cagacgcagt aagcaggtcg gatttatcta   55680
ccgggtcgat tcagtaggcg actcatggga agcggcactt aagcgtgcgg ggatcagaca   55740
cagaaaggcg taccagtcac gacacaccta tgcgtgctgg tcattatcag ctggtgcaaa   55800
ccctagtttt attgccagtc agatggggca tgcgagcgcg cagatggtgt tcaatgttta   55860
cggtgcatgg atggctgaca gcagcgcaga gcagatcgca atgctgaatc agaagctggc   55920
agattttgcc ccattgatgc cccatagcca cgagaacagt acgggaggat tattaaaatc   55980
agtaagttaa cccctaacgc ccgtcatgtt aactgtgtgg agggtaacac cacgctttat   56040
gccctgccga aacccgaggt tgtcctgcgc tggcgtgagc agaccacaga tgacttccgc   56100
ttctgtttta agtttccggc gaccatttcg catcaggcag cattacggca ttgcgatgat   56160
ttagtgactg aattttttgac ccgcatgtca ccgttggctc cgcgcattgg acaatactgg   56220
ctgcaactgc ctgccacatt cggcccacgg gagctgcctg cgctttggca ttttctcgat   56280
tctcttcccg gtgaatttaa ttatggggtg gaagtccgcc atccacagtt tttcgccaaa   56340
ggggaagagg aacaaacgct taatcgcggt ttacatcagc gcggcgttaa tcgggtgatt   56400
ttagacagcc gcccggttca tgcagcacgt ccatacagtg aagctattcg cgacgctcaa   56460
cgaaaaaaac ctaaagttcc ggtacatgct gtactgacgg cgaaaaatcc actgatccgt   56520
tttatcggta gtgatgatat gacgcaaaac cgggaattat ttcaggtctg gttacaaaaa   56580
ttagcgcagt ggcatcagac cactacgcct tatcttttttt tacatacgcc agatattgcc   56640
caggccccgg aactggtaca taccctgtgg gaagacttac gtaaaacgct tccagagatc   56700
ggagcagttc cggctattcc acagcaatct tctcttttct gaatttgcca cctatcatag   56760
acaggtgcca tcggccattt taaagggagt ttgtatggta agcgcgctgt atgccgtttt   56820
aagtgcgttg ttattaatga agttctcttt tgatgtcgtt cgcctgcgaa tgcagtaccg   56880
cgttgcctat ggcgacggcg gttttagcga actgcaaagc gctattcgca ttcatggtaa   56940
cgcggtggaa tatattccta tcgcgattgt gttgatgctg tttatggaaa tgaatggcgc   57000
agaaacctgg atggtgcata tttgcggcat cgttttgctt gctggtcgtc tgatgcatta   57060
ttacggtttt catcaccgtc tgttccgctg gcgacgttct ggcatgagcg ccacctggtg   57120
tgcgctgttg ctgatggtgc tggcgaatct ttggtatatg ccctgggagt tggttttctc   57180
cctgcgttag cgcacaatac gccactttct ttttcccgga ttttacgtt atgtctcacc   57240 gcgacacgct attttctgcc cctatcgcca gactgggcga ctggaccttt gatgaacggg   57300
tagctgaagt cttcccggat atgatccagc gttccgttcc cggctattcc aatattattt   57360
ccatgattgg tatgttagcc gagcgcttcg ttcaacctgg tacgcaggtt tacgatctgg   57420
gttgttctct gggcgcggcg acgctctcgg tgcgtcgcaa cattcatcat gataattgca   57480
aaattattgc catcgacaac tccccggcga tgattgaacg ctgccgtcgt catattgacg   57540
cctataaagc ccctacgcca gtagacgtta ttgaaggtga tattcgcgat atcgccattg   57600
aaaacgcatc gatggtggtg ctgaatttta ccctgcaatt cctggaacct tccgagcgcc   57660
```

```
aggcgttact ggataaaatt tatcaagggc tgaacccggg cggtgcgctg gtgctttcgg   57720
aaaaattcag tttcgaagat gccaaagttg gtgaactgct gttcaacatg caccacgact   57780
ttaaacgtgc caacggttac agcgaactgg agatcagcca gaaacgcagc atgctggaaa   57840
acgtgatgct gaccgattcc gtggaaaccc ataaagcacg cctgcataaa gccggttttg   57900
agcatagcga gctgtggttc cagtgcttta actttggttc actggtggca ttaaaagcag   57960
aggacgctgc atgatcgact ttggtaactt ttattctctg attgccaaaa atcatctttc   58020
acactggctc gaaacgctgc cgcgcagat tgctaactgg cagcgcgagc agcagcacgg   58080
gctgtttaag cagtggtcca acgcggtgga atttctgcct gaaattaaac cgtatcgtct   58140
ggatttattg catagcgtaa ccgccgaaag cgaagagcca ctgagcgccg gcaaattaa   58200 gcgcattgaa acgctgatgc gcaacctgat gccgtggcgc aaagggccgt tctcactgta   58260
tggcgtcaac atcgataccg aatggcgttc cgactggaaa tgggatcgcg ttatgcccca   58320
tctttctgat ttaaccgggc gcaccattct tgatgtcggc tgtggcagcg gttatcacat   58380
gtggcgcatg attggcgcag gggcgcatct ggcggtgggt atcgatccca cgcagctatt   58440
cctctgccag tttgaagcag tgcgtaaact gctgggtaac gatcagcgcg cacatttgtt   58500
accgttaggt attgaacaac ttccggcact gaaagccttt gataccgtct tttcgatggg   58560
cgtgctttat catcgtcgtt caccgctgga gcatctctgg cagttaaaag accaactggt   58620
gaatgaaggc gaactggtgc tggaaacgct ggttattgat ggcgacgaaa acacggtgct   58680
ggtgccgggc gatcgttacg ctcaaatgcg taatgtctat ttcattcctt ccgcgctggc   58740
gctgaaaaac tggctgaaga agtgtggttt tgttgatatt cgcattgcag atgtgagcgt   58800
taccaccaca gaaagagcag cgacgcaccga atggatggtc accgagtctc tggccgattt   58860
tctcgacccg catgatccgg gtaaaacggt ggaaggttat cctgcgccta aacgcgcggt   58920
gctgattgcg cgcaagccgt aaaggtctgg taatactgcc ggatgcggcg tgaacgcctt   58980
atccggccta caaagtcttg ctaattcaat atattgcagg ggctatgtag gcctgataag   59040
catagcgcat caggca                                                  59056
```

<210> SEQ ID NO 135
<211> LENGTH: 972
<212> TYPE: DNA
<213> ORGANISM: Escherichia coli

<400> SEQUENCE: 135

```
ttatttgatg ggataaagat ctttgcgctt atacggttgg atttcgcccg gtttgcgagt     60
tttcagcaat tttaatatcc aggtgtattg ttctggtcgc ggaccaacaa aaatctcgac    120
ttcttcattc atccgccgcg caatcgtatg atcatccgcc tctaacagat catccatcgg    180
tgggcgcacc tgaatcgtca gacgatgcgt cttgccatca taaatcggaa atagcggtac    240
aacgcgcgca cggcacactt tcatcaaacg accaatcgcg ggcaacgtcg ctttataggt    300
ggcaaagaaa tcaacaaatt cgctgtgttc tgggccatga tcctgatcgg gtaaataata    360
tccccagtaa ccctgacgta ccgactggat gaatggttta ataccatcat ttctcgcatg    420
cagacgacca ccaaagcgac ggcgcaccgt gttccagaca taatcaaaaa ccgggttgcc    480
ctgattatgg aacatcgctg ccattttctg cccttgcgag gccatcagca tggcaggaat    540
atcgacggcc caaccgtgcg gcaccagaaa aatcactttc tcgttattac gtcgtatctc    600
ttcgatgatc tccagcccct tgccagtcaac gcgcggctga attttctccg gcccgcgtat    660
```

| | |
|---|---|
| tgccaactca gccatcatta ccatcgcttg cggcgcggtg gcaaacatct catctacaat | 720 |
| cgcttcgcgt tcagcttcac tacgttctgg aaagcagagc gacagattga ttaacgcacg | 780 |
| acggcgtgag cttttttccca gtcgtccggc aaaacgtccc agccgtgcca gaatgggatc | 840 |
| acggaacttt ggcggcgtta aagcgatacc cgccatcgct gctacgccca gccatgctcc | 900 |
| ccagtagcgc gggtggcgaa aggatttatc aaactcagga atgtattcgc tattattttt | 960 |
| tttcgtttcc at | 972 |

<210> SEQ ID NO 136
<211> LENGTH: 1323
<212> TYPE: DNA
<213> ORGANISM: Escherichia coli

<400> SEQUENCE: 136

| | |
|---|---|
| ttaatcaaac cgtagctgcg gcacaatctc tttggcctgt gccaggaatt cgcgacgatc | 60 |
| ggagccggtc agcccttcgg tacgcggcag ttttgccgtc agcgggttta cggcctgctg | 120 |
| gtttatccat acttcatagt gcagatgcgg cccggttgaa cgtccggtat taccggaaag | 180 |
| cgcgatacgg tcgccacgtt tcaccttctg tcccggtttc accaggatct gcgcaagtg | 240 |
| catataacgc gtggtgtagc tgcgaccatg acgaatagcc acataataac ctgctgcgcc | 300 |
| actacgtttg gcaaccacca cttcaccgtc acccactgaa agcactggcg taccttgtgg | 360 |
| catggcaaaa tcaacacctc tgtgtggcgc aacgcgaccg gtcaccggat tagtacgacg | 420 |
| cgggttaaag ttagatgaga tacggaactg tttcgccgtc gggaatcgca agaatccttt | 480 |
| cgccagacca gtaccgttac gatcgtagaa tttgccatct tcagcgcgga ttgcgtaata | 540 |
| atctttacct tctgaacgca aacgtacgcc cagcagctgg ctttgctcac gtttaccatc | 600 |
| aagcatttct cgtgacatta acaccgcaaa ttcatcgcct ttttttcagtt tgcggaaatc | 660 |
| catttgccac tgcatggctt taatcactgc gctcacttcg gcgctggtta accggcgtt | 720 |
| tctggcgctg gcaacaaagc ttcccccgac ggtacctttc agcagattgt tgacccactc | 780 |
| tccttgctgc atttcgctgg tcattttaaa accgttagcg gcagtacggt cataggttcg | 840 |
| ggtttcacga cgagacactt cccaggtgag gcgctgcagt tcgccgtccg cggttaatgt | 900 |
| ccaggagagt tgttgaccga ttttcaggtt acgcaattct ttgtcggcag cagccagttg | 960 |
| ggtgatatca cccatatcaa taccatactg attgagaatg ctgcttagcg tatcgccagt | 1020 |
| ggaaacaaca tattcatgca cgcccgcttc accggcgatt ttgtcatcca gttcgtcctg | 1080 |
| gggaatggct tcatcttctt gtgcagcttg atcaatcggc tcactggctt caggtaagag | 1140 |
| cgaacgaatt tcgttctgtt ccagctcaat ggttttgaca attggcgtgg catcgcggtg | 1200 |
| ataaacatag gccgccaga cagcgacggc cagagtaaga acggtgagcg accccaacat | 1260 |
| aacgcggtgt ggtcgcggta aattattaaa cgccagggcg acagagcggg ctatctgttg | 1320 |
| cac | 1323 |

<210> SEQ ID NO 137
<211> LENGTH: 933
<212> TYPE: DNA
<213> ORGANISM: Escherichia coli

<400> SEQUENCE: 137

| | |
|---|---|
| ttaatctcct ttcaggcagc tcgcatactg gttggctaat tgattcagga attctgaata | 60 |
| gcttgtttta cccagtttga tattcgtccc caggggatcc aacgttccca tacgaacgga | 120 |
| tgtccctcgt gcgacgctct caacgaccgc tggcctgaac tgtggctcag caaaaacgca | 180 |

```
ggttgctttt tgctcaacca actgtgttct tatttcatgt aaacgctgcg cgccaggttg    240
aatctcaggg ttaacggtaa aatgaccaag cggtgtcagt ccgaactgtt tttcgaaata    300
gccgtaagca tcgtgaaaaa cgaaataacc tttcccttg agcggcgcga gctcgttacc     360
aacctgcttt tcggttgagg ctaattgtgc ctcaaaatcc ttcaggttgg cgtcaagttt    420
ggctcgactt tgcggcataa gttccactaa ttttccatgg attgcaaccg ctgtagcccg    480
cgctatctct ggggaaagcc aaagatgcat gttgaaatcg ccgtgatggt gatcttcgtc    540
acttttttcc gcgtggtcgt gatcatcatc atcgccgtga atactttca tcagcagcgg     600 tttcacattc tctagctgcg caatcgttac ctgtttcgct tcaggtaatt tacttaccgg    660 ttttgcatg aacgcttcca tctccgggcc aacccaaacg actaagtccg cgttctgtaa     720 gcgtttaca tctgatggac gcagtgaata atcatgttct gaagcccgt caggtagtaa      780 aacctccgtt tctgttaccc catcagcaat ggcagaagcg atgaacccaa cgggtttaag    840
cgaagcgaca acggcagcat ctgcggcctg tgttgcaccg ccccagagag cggcggataa    900
tgctgcgaaa agaagcgttt ttttatgtaa cat                                 933

<210> SEQ ID NO 138
<211> LENGTH: 756
<212> TYPE: DNA
<213> ORGANISM: Escherichia coli

<400> SEQUENCE: 138
atgacaagtc tggtttccct ggaaaatgtc tcggtttctt ttggccaacg ccgcgtcctc     60
tctgatgtgt cgctggaact aaacctgga aaaattttga ctttacttgg gccaaacggc    120
gcaggtaagt cgacactggt acgggtagtg ctcgggctgg taacaccga tgaaggggtt     180 atcaagcgca acggaaaact gcgcatcggc tatgtaccgc agaagctgta tctcgacacc    240
acgttgccac tgaccgtaaa ccgttttta cgcttacgcc ctggcacaca taaagaagat    300
attttgcctg cactgaaacg tgtccaggcc gggcatctga ttaacgcacc gatgcaaaag    360
ctctcgggtg gcgaaacgca gcgtgtactg ttagcgcgag cattgttaaa tcgaccgcaa    420
ttattagtgc tggatgaacc cactcaggc gtggatgtga atggtcaggt ggcgttatat     480
gaccttattg accaactgcg tcgcgaactg gattgtggcg ttttaatggt atctcacgat    540
ctgcatctgg taatggcaaa aaccgatgaa gtgctttgcc tgaatcacca catttgttgt    600
tccggcacac cggaagttgt ttccctgcat ccggagttta tttctatgtt tggtcctcgt    660
ggtgctgaac aactgggtat ctatcgccat catcataatc atcgtcacga tttacaggga    720
cgaattgttt tgcgtcgggg aaatgatcgc tcatga                              756

<210> SEQ ID NO 139
<211> LENGTH: 786
<212> TYPE: DNA
<213> ORGANISM: Escherichia coli

<400> SEQUENCE: 139
atgattgaat tattatttcc cggttggtta gccgggatca tgctcgcctg tgccgcgggt     60
ccgctgggtt cgtttgtagt ctggcgtcgt atgtcttatt tcggtgatac gctggctcat    120
gcctcattac ttggcgtcgc gtttggtttg ttgctggacg tgaatccatt ctatgcggtg    180
attgccgtta cgctgctgct ggcggcggt ctggtatggc tggagaagcg tccacagctg     240
gcgatcgaca cgttattagg gattatggcg cacagtgccc tgtcgctggg cctggtggtc    300
```

| | |
|---|---|
| gttagtctga tgtctaatat tcgtgttgat ttgatggctt acctgttcgg tgatttactg | 360 |
| gcagtgacgc cagaagatct catctctatt gcgattggcg tggtcatcgt ggtggctatt | 420 |
| ttgttctggc aatggcgcaa tttgctgtcg atgacgatta gcccggatct ggcgtttgtt | 480 |
| gatggtgtga aattacagcg cgtgaaattg ttgttgatgc tggtgacggc attgacgatt | 540 |
| ggtgtagcga tgaaattcgt cggcgcgttg attattactt cactgctgat tattcctgct | 600 |
| gctactgcac gtcgctttgc ccgcacgccg aacagatgg ctggtgtcgc tgttttggtg | 660 |
| gggatggtgg cagtgactgg cggtttaacc ttttccgcat tttacgatac acctgcaggc | 720 |
| ccgtcggtgg tgctatgcgc ggcactgtta tttattatca gtatgatgaa aaagcaggcc | 780 |
| agctaa | 786 |

<210> SEQ ID NO 140
<211> LENGTH: 1011
<212> TYPE: DNA
<213> ORGANISM: Escherichia coli

<400> SEQUENCE: 140

| | |
|---|---|
| ttacggcatt tctggcggcg tgatgccgaa gtggttccac gcccgcactg tcgccatacg | 60 |
| cccgcgcggt gtacgctgca aaagccttg ctgaatcaaa taaggttcca gtacatcctc | 120 |
| aatggtttca cgttcttcgc caatggctgc cgccaggtta ccagaccta ccggcccacc | 180 |
| aaagaactta tcgattaccg ccagcaacaa tttgcggtcc atataatcga aaccttcagc | 240 |
| atcgacattc aacatatcca gcgcctgagc agcgatatct gccgagatgg tgccatcgtg | 300 |
| cttcacttca gcgaaatcac gcactcgacg cagcagacgg ttggcaatac gtggcgtacc | 360 |
| gcgcgcacga cgagcaactt ccagcgcgcc gtcatcactc atctcaagcc ccataaagcg | 420 |
| tgcgctgcga ctgacgatat attgcagatc cggcacctga taaaactcca gacgttgcac | 480 |
| aataccaaaa cgatcgcgca acggtgatgt cagcgaacct gcgcgcgtgg ttgcaccaat | 540 |
| cagggtaaac ggcggcaaat caatttttaat ggagcgtgcc gccggacctt caccaatcat | 600 |
| gatatccagt tggtaatctt ccattgccgg atacaacacc tcttccacca ctggtgaaag | 660 |
| acggtggatc tcatcaataa acagtacatc gtgtggttca aggttagtga gcattgctgc | 720 |
| cagatcgccc gccttttcca gcaccggacc agaagtcgtg cgtaaattaa cgcccatttc | 780 |
| attggcgaca atattggcaa gcgtagtttt acccaacccc ggaggaccaa aaatcaatag | 840 |
| atgatcgagg gcatcgccgc gcagtttcgc tgctttgatg aaaatctcca tctgcgaacg | 900 |
| aacctgcggc tgaccaacat actcttccag taatttaggg cgaatggcgc gatctgccac | 960 |
| atcttccggc aaagtggtac cggcagaaat cagacggtct gcttcaatca t | 1011 |

<210> SEQ ID NO 141
<211> LENGTH: 612
<212> TYPE: DNA
<213> ORGANISM: Escherichia coli

<400> SEQUENCE: 141

| | |
|---|---|
| tcataacgcg gcgcgtaggg cttcgcgaat taatgtttca ctgctggcgt cagggcgagc | 60 |
| gattttgctc accatgcggc ttgcttcttg tggtttatag cccagtgcca ccagcgcagc | 120 |
| aaccgcttcc tgttcagcat cgtcggtcgc cgggctggca ggagacgtga gtaccaggtc | 180 |
| ggcggctggc gtaaagagat cgccatgcaa acctttaaat cggtctttca tttcgacaat | 240 |
| caagcgttcg gcggtttttt tgccaatacc cggcagtttc accagtgccc ccacttcttc | 300 |
| acgctcaacg gcattaacga actgctgcgc tgacattccg gagaggatcg ccagcgccaa | 360 |

| | |
|---|---|
| cttcgggccg acgccgttgg tttttgatcaa ctctttgaac aacgtgcgct cttgtttatt | 420 |
| gttaaaaccg tacagcagtt gcgcgtcttc acgcaccaca aagtgggtga aaacgatcgc | 480 |
| ttcctgaccc gcttcaggga gttcataaaa acaggtcatc ggcatatgca cttcatagcc | 540 |
| tacgccgccc acttcaatta acaccagcgg gggttgtttt tcaatgatga tgcctctgag | 600 |
| tctgcctatc ac | 612 |

<210> SEQ ID NO 142
<211> LENGTH: 603
<212> TYPE: DNA
<213> ORGANISM: Escherichia coli

<400> SEQUENCE: 142

| | |
|---|---|
| gtgaatatta attatcctgc tgaatatgaa attggtgata tcgtctttac atgtataagt | 60 |
| gctgccttat ttggtcaaat atcagctgca tcaaattgct ggagtaatca cgtcgggatc | 120 |
| attatcggtc ataacggtga agactttctg gttgcagaaa gccgtgttcc cctctcaacc | 180 |
| atcactacgc tatcccgttt tattaaacgc tctgctaatc aacgctatgc tataaagcga | 240 |
| ttagacgccg gactaacaga acaacaaaat caacgaattg ttgaacaggt tccttcccgg | 300 |
| ctacgcaaaa tttaccacac cggttttaaa tacgaatctt cgcgccagtt ctgttcaaaa | 360 |
| tttgttttg atatttataa agaggcgcta tgtattccgg tgggtgaaat agagacgttt | 420 |
| ggagaattgt taaatagcaa tccaaatgca aaactcactt tctggaaatt ctggttctta | 480 |
| ggttctattc cgtgggagcg taaaaccgtc acgccagcca gtttgtggca tcatccgggt | 540 |
| ttggtgttga ttcacgcggt gggagttgaa acgcctcagc ctgaactgac cgaggcggta | 600 |
| taa | 603 |

<210> SEQ ID NO 143
<211> LENGTH: 522
<212> TYPE: DNA
<213> ORGANISM: Escherichia coli

<400> SEQUENCE: 143

| | |
|---|---|
| ttaacgcagt cgccctctcg ccaggttcag tcgcgattcg ctcatttgca tcgcattctg | 60 |
| actaacgtgg cagtgggtga tggcaatcgc cagcgcatcg gcggcatccg cctgtggatt | 120 |
| agcgggcagt tcagcaaggt gcggaccat atgctgcacc tggctttttt cggcactacc | 180 |
| aataccacc actgtttgct ttacctgacg tgccgcatat tcaaataccg gcaattcctg | 240 |
| attcaccgcc gccacaatcg ccacgccgcg cgcctgcccc agtttcaggg ctgagtcagc | 300 |
| gttcttcgcc ataaagacct gttcaatggc gaaataatca ggctggaatt gggtgatgat | 360 |
| ttccgtcacg cccgcataga tgagcttcag acgagacggt aaatcatcca ctttggtgcg | 420 |
| tatgcatccg ctacccaggt aggacagttg cctgcctacc tggcggatga cgccatagcc | 480 |
| ggtcacgcgc gaacccgggt caatgccgag aataatagcc at | 522 |

<210> SEQ ID NO 144
<211> LENGTH: 741
<212> TYPE: DNA
<213> ORGANISM: Escherichia coli

<400> SEQUENCE: 144

| | |
|---|---|
| tcagagagtc gctgcaacct catcagagat ttcaccgtta tggtaaactt cctgcacgtc | 60 |
| gtcgcaatct tccagcatat cgatcagacg catcagtttc ggtgcggttt ctgcatccat | 120 |

```
atcagctttg gtggacggga tcatggaaac ttccgcgctg tctgctttca gacctgccgc    180
ttccagagcg tcgcgtactt tgcccatttc ttcccatgca gtgtagacat caatcgcgcc    240
gtcatcatag gtcacaacgt cttcagcacc ggcttccagg gctgcttcca tgatggtgtc    300
ttcatcgcct ttctcgaagg agatcacgcc tttttgctg aacaaataag ctacggaacc     360
atcagtaccg aggttaccgc cacatttgct gaatgcatga cgcacttcag caacggtacg    420
gttgcggttg tcagacagac attcaatcat gattgccgtg ccgccaggac cgtaaccttc    480
gtagatgatg gtttccatgt ttgcatcatc atcaccgccc acacctcgtg caattgcgcg    540
gttcagagtg tcacgggtca tgttgttaga cagtgcttta tcaattgctg cacgcaaacg    600 cggggttagcg tccggatcac caccgcccag cttagccgcg gttaccagct cacgaatgat   660
tttagtgaag attttaccgc gcttagcatc ctgcgcagct ttacgatgtc tggtgttggc    720
ccatttacta tgacctgcca t                                              741

<210> SEQ ID NO 145
<211> LENGTH: 444
<212> TYPE: DNA
<213> ORGANISM: Escherichia coli

<400> SEQUENCE: 145
tcaggcagcg ttaattacaa actgttcaat cgcctgccgg ttgctccagg acttagtgag     60
cgccgccgca gcagacgcat caagccactt gtaagccaga tgttcagtga aaacgatctg    120
gcgctcgtgc ggaagcgcaa gacagaacca tgattccgta ttacgcgtca cgcccggcgc    180
atagcgatga cgtaaatgtg aaaaaatttc aaactctacc gtgcgctgac agtcaattaa    240
ggtcagttgt tcagcgacaa catcaatggt gaccctcttcc tttacttcgc gcatggcagc    300
ttgcggcgcg gtttcacccct cttccacgct gccggttacc gactgccaga atcgggatc    360 gtcacgccgc tgcaacatca gcacccgttt cgtatcttgt gcgtagatga ccactaagat    420
cgaaacggga cgcttataag ccat                                           444

<210> SEQ ID NO 146
<211> LENGTH: 1773
<212> TYPE: DNA
<213> ORGANISM: Escherichia coli

<400> SEQUENCE: 146
tcagttattc tcagccttct tcacaacctg aatgctcagc tcagccagtg cagtcgggtt     60
agcaaagctc ggcgcttcag tcatcaaaca cgctgccgcc gtggttttcg ggaaggcgat    120
aacgtcacgg atattgtcgg tgccggtcag cagcatcgtc agacggtcaa gaccgaatgc    180
caaacctgcg tgcggcggag taccgtattt cagggcgtcg agcaggaagc cgaatttctc    240
gcgctgttcc tcttcgttga tacccagaat accaaacacc gtctgctgca tatcaccatt    300
atggatacgc acagaaccac cgcccacttc gtaaccattg atgaccatat cgtaagcgtt    360
agccaccgca ttttccggtg cagctttcag ttctgctgcc gtcatgtctt tcggtgaggt    420
gaacggatgg tgcattgctg tcaggccgcc ttcaccgtcg tcttcaaaca tcgggaagtc    480
gataacccac agcggtgccc atttgctttc gtcggtcaga ccaaggtctt tacccacttt    540
caggcgcagt gcgcccatcg cgtcggcaac aatttcttg ttgtcggcac cgaagaaaat    600
catatcgcca tcttgcgcgc cagtacgctc caggatggct tcgatgattt ctgcattaag    660
gaacttcgct accgggctat tgatacccttc cagacctttc gcgcgttcgt taactttgat    720
gtaagccaga ccttcgcgc cgtagatttt aacgaagtta ccgtattcgt cgatctgctt    780
```

```
acgggtcaac gatgcgccgc ccggaacacg cagagcggca acacggcctt tcggatcgtt    840
cgccggacct gcaaatactg caaactcaac agatttcagc agatcggcaa cgtcggtcag    900
ttccatcggg ttacgcagat ccggtttatc agaaccataa cggcgttctg cttctgcaaa    960
ggtcattacc gggaaatcgc ccagatccac gcccttcact tccagccaca gatgacgcac   1020
cagcgcttcc atcacttcac gcacttgcgg cgcggtcatg aaagaagttt ccacatcgat   1080
ctgagtaaat tcaggctgac ggtcagcacg caggtcttcg tcacgaagc atttaacgat    1140 ctgatagtag cggtcaaagc cggacatcat cagtagctgt ttgaacaact gcggggattg   1200
cggcagcgcg tagaatttac ctttgtgcac acgagaaggc accaggtagt cacgcgcgcc   1260
ttcaggcgtg gctttggtca gcatcggagt ttcgatgtcg aggaagccgt ggtcatccat   1320
aaaacggcgc accaggctgg tgattttagc gcgggttttc aggcgctgag ccatttccgg   1380
gcgacgcagg tcgaggtagc ggtatttcag acgcgcttct tcggtgttga cgtggttaga   1440
gtcaagcgga agaacatctg cacggttgat gatagtcagc gaggacgcca gtacttcgat   1500
ttcgccagtc gccatatcgc ggttaatatt tttttcgtca cgcgcacgta cggtgcccgt   1560
gacctgaatg cagaactcat tacgcagttc agaggccagt tttaacgcgt ccgcacgatc   1620
cggatcgaaa ataccgtgca cgataccttc gcggtcgcgc atatcgatga agatcaggct   1680
accaagatca cgacgacggt tgacccaacc acacagagtc acctgctgcc ccacgtggga   1740
caaacggagc tgtccacaat attctgtacg cat                                1773

<210> SEQ ID NO 147
<211> LENGTH: 567
<212> TYPE: DNA
<213> ORGANISM: Escherichia coli

<400> SEQUENCE: 147
atgcttgaac ttaatgctaa aaccaccgcg ctggtggtga ttgatttaca agaaggcatc     60
ttgccttttg ccggaggtcc acatactgcc gatgaggtgg ttaatcgcgc cgggaagctg    120
gcggcgaaat ttcgcgccag cggtcagccc gtgtttctgg tgcgcgttgg ctggtctgcc    180
gattacgccg aagcattaaa acagccggtt gatgcccct cccccgcaaa agtgttgccc     240
gaaaactggt ggcaacatcc tgctgcatta ggtgcaaccg acagcgatat cgaaatcatc    300
aaacgtcaat ggggtgcgtt ttacggtacg gatctggagt tgcaattacg ccgcggggt    360 atcgatacaa tagtgttatg tgggatctcg accaatatcg gtgttgaatc caccgcccgc    420
aatgcctggg aactcggttt taatctggtg attgccgaag atgcctgtag cgccgctagc    480
gccgagcagc acaataacag cattaatcat atctacccgc gcatcgcccg tgtgcgtagc    540
gttgaagaga tcctcaacgc gttatga                                        567

<210> SEQ ID NO 148
<211> LENGTH: 390
<212> TYPE: DNA
<213> ORGANISM: Escherichia coli

<400> SEQUENCE: 148
tcacatcacc gggcagtcat caaactccgc attcctggca tcattaatga tgtacgtgat     60
cactccaaat atagcgggtg cagaactgta accatcatca tctgctggca gcgcttccct    120
tctcccgtta tccagattaa ccaggtgcgc ctgaggatga gtccgatatc gcttgatcct    180
gaattccccg tcgattgcac atatcagcag tgaaccatcg caggcagtaa gtgacgcatc    240
```

```
cacaacaagc aacgctccct ggattatccc ttccctgaaa tgtgaacgcg atgcccgcat    300
gaaataagtc gctgcgggct gactgattag ctgctgatcg agggagattc gtgtttcaac    360
ataatctgcc gcaggtgaag gaaatcccat                                     390

<210> SEQ ID NO 149
<211> LENGTH: 243
<212> TYPE: DNA
<213> ORGANISM: Escherichia coli

<400> SEQUENCE: 149
atgttcgtgg aactcgttta tgacaaaagg aattttgatg gtctgcccgg tgcaaaagat     60
atcattctgg gcgagttaac taagagagtt caccggatct tccccgatgc tgatgttcgg    120
gttaaaccga tgatgacact gccggcgatc aacactgacg ccagcaagca tgagaaggaa    180
cagataagcc gtactgttca ggaaatgttt gaagaggctg aattctggtt agtgagtgag    240
taa                                                                  243

<210> SEQ ID NO 150
<211> LENGTH: 381
<212> TYPE: DNA
<213> ORGANISM: Escherichia coli

<400> SEQUENCE: 150
atgctgtgga ggatattcat tttcgtaaac gttggtttgg gagaagcggc aaaacggaat     60
gtgggaacag gggaaaatca gataccagat atgtctgcat ttccatctgg caataactgg    120
tttcagttac caagtggaca tatcgttcag atattttcca tgaacgttct tggtgcagat    180
gctaatggca cgtcagctaa ttaccccatt gcttttccaa caacgatgat tgctgtcagt    240
gctctatggt ctgatgggac tgtagcaaat gcaccgacat acaagatgat ggggaacacg    300
actaacagaa caactttgac gataaaagta tcagccagct caggtactta cgggacaatg    360
attattgcgg tgggacgata a                                              381

<210> SEQ ID NO 151
<211> LENGTH: 444
<212> TYPE: DNA
<213> ORGANISM: Escherichia coli

<400> SEQUENCE: 151
atgaataaat acagttactc tccttcagaa atgcctttt atgctgttgc gttaaaaaat      60
acctatgaat tgagtggcac atggccagct gatgcattag atattcctga tgacatttct    120
gtaaaatata tggcggaacc gccacaaggg aaaatccgag ttgcagggga aatggttttt    180
cccacatggg ctgaaatacc tccaccatca catgaggaac ttattgaaca ggccgaatca    240
gagaggcaat tattgattaa ccaggccaac gaatacatga acagtaaaca atggcccggt    300
aaagccgcta ttggtcgtct gaaaggcgag gaactggcac aatataattc gtggctggat    360
tatctggacg cactgaact ggtcgatact tccggtacgc ccgatattga atggcctacg     420
cctccggcag ttcaggccag atga                                           444

<210> SEQ ID NO 152
<211> LENGTH: 594
<212> TYPE: DNA
<213> ORGANISM: Escherichia coli

<400> SEQUENCE: 152
ctacgcctcc ggcagttcag gccagatgac atccggcgcg gtgctggtat ctgttgcagt     60
```

```
caccgcgtca atgtaatcca gcacggcgtt aagtcgggtt gtttctgcct gagtcagttt    120
ccgtccggcc tgtaatttca gctgaatcag actaatggaa gccattgctg catcaatcag    180
tgattggcgc tgtgcttctg ccgcttctac tgaggcaccg tgttgtgcct cagtatctgt    240
cacccatttc tcaccatccc atttatcata tggcgttaac ggtgaaagcg tgacataacc    300 gttttgatg gcaccgatat aatccactgt aacagctgcg ccattttcga ttgagtaaac     360
agtctcattg cgatggtctt cctcatggct ccatcccta cctgtaaata ctgccactct     420
tcccggaatg ttttcgtccg ggtcaatacc agtggaacag gcgggcatac ttacgccagt    480
attaatatat tcatcagacc agcccgtata ttcagacgtt actgcatcat aataaaaaca    540
acgcatatca cccggcactg cagccagccc attttcatca aaaacaggtt tcat          594
```

<210> SEQ ID NO 153
<211> LENGTH: 933
<212> TYPE: DNA
<213> ORGANISM: Escherichia coli

<400> SEQUENCE: 153

```
ttatttagcc ctcaccagaa agttaaatgc aatatttcgc ggtctgacag caacaaaatt     60
cacaccatca cccacagagt tactgttgaa attaaatcgt gaaaatcctg ctgatttcc     120 ggcgatgcca tcatgaaagt taattgcgtg tccagcacct ccgcctatat tcccggcaaa    180
ctgagaaaag tttgtagctt cctgccagct taataattcg gaccaccat ctgcacctcg     240 cccgtcatcc cagacacgaa tgaaatcacc gcgggcttca ggtaatacca gcgaaggaaa    300
cactttcgcc agcacaggat aatcagtggc agagaatttc gcgccgttga acttcaaaaa    360
caccatactg gaccagctgt cgattacagt atttggcatt gcagcggacg gccagaagaa    420
cggaacgcca atagctggag aaccttctcc caaaccaagg tttgtgcgag cgtctgcggc    480
attcgttgcg ccggttccgc cgtctgcgac agtaaccgca ccgttgctcc ctttctgcgc    540
aagtttaccg atgcctggga tggttacggc ggtgccgttg atggtaactg tgatgctttg    600
gtttgctgag gtggtggcga acgtctccca cgcgccaata ttctcgtcgt actctttgat    660
gagctgtgac atggcctgcg ccaggccgtc gactgagata ttgtccgaca caaggattcc    720
atacttctgg ccgctcagcg ccggggaaac tgctggcgta accgtcattg acgtggcgct    780
gttcacggat gaaatctgaa acagctgcac cgggttagac atcacgataa tcgtctggcc    840
agcgcggacc tggctggcgg gagctgtcca gtttgtgccg gagccggttg cggtatttcc    900
gttaatagag atagttccgg tgctataaat cat                                 933
```

<210> SEQ ID NO 154
<211> LENGTH: 3927
<212> TYPE: DNA
<213> ORGANISM: Escherichia coli

<400> SEQUENCE: 154

```
ttaacctgtg aatgaaccag atccgtgtga tactatgata gtaggcgaag aaattgacgc     60
acccctgtta ttttgagcgg acactttaat acgcactgtt acgtttggac ctgttacaac    120
cgcagaatgc atgataagtc tctccatgtc ttgcacggat gaaccactct cattgccgtt    180
aatgtcgatt gttcctgcac cattacccttt aacgtttgct ataacacaga cgtgtcttgc    240
gtgcccagaa ctgatgaat cattataagt cattaccttt tctaaatatc cgtcactaga    300
ccgactcaca ttcgtccctg tgtgcatatt tgcaatgtcc ccgataaaac tttgggcttc    360
```

-continued

```
cacagtccct ttgaatttac cgcttgttgc ttggatctca ccagtaaagc taccgccact    420
agcatatact acacctctga cggtcacatt gttgaattca gcatctccag ctttattcaa    480
cttccaacca gcagaaccag ctgcatagtt gttggactgg atatagttac cgattttgc     540 gttctcaatg gtgccgtcct ggatgaagct ggcccggatg aatgtctgcc cgttctggat    600
cacgaacggc aaagctacgc tatttccggc tgccgtggtg acggcgaagc ggtcagccag    660
gaagataacc tgcgactgca tgccggatgg cgtattctcc acgccgatac catccccgc     720 ggcgtaatac tgcccgttgc tggagacacc aaccttgatg ttgtacatcg cgctgagttc    780
gccattaacg ttggctatag cctgagcgtt agtggtgatg gcggaggtat gcccgttcac    840
ggtcgccgtg atgccgttta tctgcgtggc ggtggcctgc tgatagtcgg agagcgtctg    900
attcaggctg ttgatggatg ccttgttgcc gttgacgtcc gtctgcaggc tcagcaatga    960
acgtgctgtg gcttccttct cactgacgat cacctcgtcg agacggtcca gattcgcgct   1020
gttgccggcg accgatgcag aaagggtttt acgcgtggcc acctgagcga ggttggcctg   1080
gattatcgca attgcagagt tcttcacccc gcccgtcatg ccgtccatag aaacgctgat   1140
gttgtcgatt cgctggccca gggcggtatc agccgtcgca acggtctgct caagctgact   1200
gagtgaagac gaaacattcc cgaccgtgct ggaaagctca ttaacgctgg tctgaacctt   1260
cccgacgtcc tgggcatttt tggcgatatc tttcgcttgc tgctccagtt cgtcgttggc   1320
ctgtttgata tcgttagcca tgccagcaat ttttcgttg ctgtccaccg cgttctcgat    1380
caggtctttg aacgtttccg actctttcat atcctccaga atgtcattag ttatttcgct   1440
gacatctatc gaggacgtgc ccatgatcca gtcggtccag tccccggcgt taccgatacg   1500
gtcaatcagg cgcgcgcggt accactggcg aacgccggca ggcatggggc catgctgata   1560
atctgcagcc gggtacggca ccaggaccag cagttcagga ttggcgtagt cggcagttgt   1620
ggcgcgctga atctctgtat aggccgtgtc gcctgagcca tccggaaatt tccaggtcag   1680
gtcgatatgc cagaccacat cttcggtcgc caggaagttg agcggagtac ccggttttcc   1740
cgttttaccg agagataag ttgtttcacc gtatcccat ggtgacgacg tatcctgcgc    1800
attcagcgcc cgtacgcgca cgtcatagct gcccgaataa atgccctgaa ccagaaaacc   1860
ctgcgcgctg gtaaccggaa cgtttatcca gtccccgttg tccttacgcc actgggcaac   1920
ataccggatt gcgccctcta ccttatccca tgacacgtcc aggcttgcta cagtcagccc   1980
ctgagacaca tgatcgctct cagtcaccac gatattcttc ggagcagaca ggacgcttat   2040
cggcgtgacg gtgatcgggg gagactcgac ccgaacgccg tcatcgatgt aacgatattt   2100
gtttggatcg tgctgaacgg ccgtaatagt gaaaccgcct gtactgtcgt cgttagccgc   2160
gattgaggtg accctgaagt actgtattgc gaggttatca ctgtctatcg cccaaacagc   2220
gcccgccaca ggaacctgac tgaatgccgt agccaccgtc accgttttt tatcggcgct   2280 caccgcgctg attgtccgcg tctgggcttt tccgtcggga aggttaacca ccagccggtc   2340
tttcgccgcg tagtctattt ctcgatcgag ggtaatttgg cggccgttgg ccgcgcttat   2400
acggcccccg ttctccttac cagagcggaa aggatcggcg acaccgataa tttcagcggg   2460
caaagggata taaccgtcca gccccacgcc aaacgatacg gtcccgtctt tggcattgga   2520
gagcaatacc cagcgaccgc gtcggtgcgc ttcactttgc gaggtgcagc cgattgcggt   2580
cagggacgtc tgccggacgt cgtaacgttc tacaagcgcc gaatcgtaaa cccccctcaac  2640 ggtatcgctg taatggttct gcggatcgga ccaggacacc aggcaggagc tgtagcgatt   2700
cttgtatgag ccgcccgcat aagtaaacag cccatcgata acgtttgaga cgttataaac   2760
```

```
ccagtcaaca tcgtcctgcg ggacgtctgc ctggacataa atctgatcgt ttccccagaa    2820
cgttattcca cgaaataccg cggcgagatc gttaagtacc tgccaggcgt cctcctggct    2880
ctgaatgaaa acgttgcagg tgaaacgcgg ttcggtgcca ccggcccgt cggaaaccat     2940 ttcgtcacag tactgggcga ttgaatacag cgcccactta tccaccatgg acgcatccac    3000
gcgcgtgccc atgccgtaaa tttcatccag aaccagatcg taaagatcc aggcagggtt    3060 attggaccat gccattttga acccgccgga ccatgaacca gataggttc gggttttcgg    3120 atcgtaatta tccggaacct taatcagctt gccttttatc ttacaggtca ctttcggcgc    3180
gctgccgttg aattggctgc tgtccacttc gacatacagg agcgctgtta aaggataacg    3240
aagcttgctg tcgatgactt ccgcatacga aaacaccttg aaggcgttaa ccagtttcga    3300
atttgatccg ctggcatcag ccgtaatacg cctgaccctg acagaccagc cggacgtgga    3360
ttttggcaga tcgatacggt ggtcacgctg atattccgtc gtggtctttc cgtcaaactt    3420
gccgtttaca accgttttcc aggcgccgcc gtccgttgat aaatcgatcg catactcggt    3480
gaccgtgccc accatatcgc cattatcttt atagagatac tggaccggaa ggctgagctt    3540
gatacggatg gcatccaggg aaaggtttgt aaactggcgc gtccagggcg cggtggtggt    3600
gacagttgtg cccacggcca gctcgttgtc gacctggggc atcccggcaa tataggtctg    3660
gtcctgtgtg cccttgcgga actcccattt cacgccgctg aagttgtatt ccccgctgtc    3720
gtttgccagc ggcgtatcgt tgagaaaaat gttctgagcg gtcaggtcgc cctgtatttc    3780
cccctcagaa acggcaatga gcattttaaa ttttgcgacc gacagcagat cgtcaggctg    3840
ctcaaccgga gtatgtgaac tgccacctcc ccctttggca ccctgcagga tggtttcttg    3900
tttaagaagc tgcattttt cacccat                                          3927

<210> SEQ ID NO 155
<211> LENGTH: 618
<212> TYPE: DNA
<213> ORGANISM: Escherichia coli

<400> SEQUENCE: 155
ctactgctga tcgctcgagt acataccggc gctgactatc gctcccctg cctcagtcag      60 accgtaggcc aggggacag gatgcccat agcgacggta ttgaccggcg ccccgaaggc      120
gtagttaggc gtgttgtccg tgctggagga tttacccgcg ccgaaggatg gctgggcgt     180 gagcatctgg acaacgcccc ccagcatcat cgacactccg acccctgtca gaattgacgt    240
ggcgctgata gctgttgcac tcatcgccgc gccccaggct gccatgctcg caccagcggt    300
aaagaatgca gcgaccagcg caacagcccc gacaactatc tgcaggacgc ccgaactttt    360
ggccccctca taaacgggca cgatccggta cacgcttcca ccgcgggtca tatcaaactc    420
ttccagcccg atattgttgc caccgttaaa aaaggcgaaa cggatcccct tcatatgagc    480
ttcagacata tattttttga atccgggaac ctgtgaacac atggccctga gcatctcgcg    540
caggtcggca acatcaaact gaacgcgttt accgaatttt tttgccattt taccttcgag    600
aataagcgtc ttaaccat                                                   618

<210> SEQ ID NO 156
<211> LENGTH: 720
<212> TYPE: DNA
<213> ORGANISM: Escherichia coli

<400> SEQUENCE: 156
```

```
ttaaccatgc attctgtcct tatgcctgac cacccggacc gttctgtcgc gataatattt    60
tccataaggc gttcgcgaag aaaggtgccc gaaaagatga tggagaatga tgttatcacc   120
cacatatacc gcggcgtgat tagtcaccga tgcctgcaca ctcatcatga tgatatctcc   180
gggctgcatt gcaccggcgg caatctcaac gaatccctca cgctcccagt tgtcgtcgta   240
gagacgctcc ttgccgctct cccaccattc gtaaggtact gaataattgc cgagaacaat   300
gccgtattcg cgcagataaa attcacggat aagcgaccag cagtcggcgt aacccagcac   360
ccactgccgc ccggcataat cccggtcttc acgcgggaa atcgtacaaa aatccccgtc    420
cggccaggac atgatccccc actcaatccc cgaccagtcg cactggatcc ggtccagctc   480
tgagggcacc agccgaacca catccggatg ggaatgaatg agcatgatga tctcaccgcg   540
cgcgcgggca gcgagctggt cttccgggga gagcgtgaat gtctcctcgg gtttatcggc   600
aatgttgcgg cagggaataa agatttgttg ctggcctgac tgaacaatca ggccgcaggc   660
ttctttgggg tattcagcag cgacgtgctg acggatagca tccagcaatt tttcacgcat   720

<210> SEQ ID NO 157
<211> LENGTH: 738
<212> TYPE: DNA
<213> ORGANISM: Escherichia coli

<400> SEQUENCE: 157
ttatttcccc tgcaggtttg cagccggaaa accgccgaac ggcagcggcg catccgggcc    60
gtgacgatcc tgacaatcct gccggcggcc gccacaaaca tctttcgacg ggtcatcggt   120
cggtgtaccg tctttggtaa agtatttcgt gccgttgtaa tcgcatccgg tcccgcttcg   180
gtaccagccc cgcatacacc aggtgcagac aggcgtaatc tgccgtgtcg gcagctgcag   240
gctctgaata tcgaaaggag aacacagctc gaaatcaacc tgtacccgcg tctctgcggt   300
tttagcattg acgtaaaaga gctgtaagcg ctcatcggcc gggctggcac ccggattacc   360 gttttttccag ttggcggcat cgagatactt cgaaagcgtg gtatggattt tgaccttagc   420
cctgaccata tcgtcatatt caagacacag cgcggtgaca tagtttccga cgttcccgac   480
ggacagcgtg ggcgttggct gggaacctgt actcgataac tccatcccct taagttcgta   540
gggatgggga tcgtactggt ttccctgcca gataatggcg ggcagatttt ctgcggcgaa   600
ggctgcccac ccctcttcct gaatattgtg cgcatgaaaa cgcagcacct gatccatacc   660
gaattcagtg ccgtcgatct caatcagctg aataacgctg ccgggctcaa gctgttgtat   720
gtctgccgta aaactcat                                                 738

<210> SEQ ID NO 158
<211> LENGTH: 339
<212> TYPE: DNA
<213> ORGANISM: Escherichia coli

<400> SEQUENCE: 158
tcagggcgcg aacgcctgtt caaaagtgaa ggccacagtg ctttttttcc cggtagggaa    60
agaaacgctg aacgaatcgg ccttcattct gaacagcttt ttttcacccc atggagtggt   120
ccaccagaac gatttagtaa cgtgagacat caggaaagcg cgcagcgcag ccgcctcctg   180
tctggtgccc gtccagtcca ggttccacgt ttcctgtttg tcgttgatcc ccatccccgc   240
tatctgtttg tagccatccc cgaactgggc ctgcagcgtt cgggctgttt cagtgccctg   300
cgctgttttt cgcgtgcgcc aggtaaacgt gtccgtcac                          339
```

<210> SEQ ID NO 159
<211> LENGTH: 3138
<212> TYPE: DNA
<213> ORGANISM: Escherichia coli

<400> SEQUENCE: 159

```
tcactgtgtc ctcctcgaat aaagcacgcc gcccgcggac atttcttttt tcagtcgctc      60
ggtgattgtc tgctgaacaa tcgcctgcag ctgtttcgcc gtccccgtgg cgttcgcctg     120
atttatgctt ccgtcactcc cctgctggct gatgctgact ggggcataaa cactgatccc     180
gcccatgcca gcaccggctg cgttcccgcc gccgaccaga ccacccgagg catacccgcg     240
catcaggcga tagagattag ccacgccgat gcggctggtt gattctttgg tgaagacgaa     300
ttccccgcgg tgaacgatac cggctggctc gtacttgccg ccgtgcccgg taaaaccgcc     360
cacgtcaaaa ccctgtggcc ggtatgacgg gaccgcgaat gactgaccgg cagaggaggt     420
tttcgccccg ccgctaaccc agcccattgc actctggatg gtgtaagcca ccagcagctg     480
gttgataacg gacacaatca ttttaaggat cgagctggtg aattccctga agctcgcctt     540
cccggttgtc gtcaggctgg taagctggcc cgccaacccg ctgaacgtag cctgagaaat     600
ctgctgaacg gagctgaaaa cgtttgtcgc tgaatcctga tattcggccc aaccctgttt     660
cgcaccggcc agccagtttg cacgcagggc atcttcagct tcgaacgtcg ccctttgctc     720
ttccagaacc ttttgctgcg cctgagggtt gtacgaatag ctttcgctga gacgctgcag     780
cgtagtttgt cgcccggctt cccgggtgga taacccctca gactgagcct gcaggcccgc     840
cctggcggct ttttgctgct gctcaaactt cacggcctga tcggccagct ggttgagctt     900
ttgctggctg gcaaccttat cgcccaggtc ggccagctgc gcttgtact cgagcgtttc     960
ttctttgtgc gccagcaggg attttttcctg cgccgtaagc tgacgacgcc cagcggcctc    1020
ctgcagaacg gtgaactgat tttcagtttg ccagagatcc tgacgctgtt tacttatgac    1080
gtcgttcacg ctggtatgct gctcaagcgt tttaagctgg gcctgaaggg tgagaagttc    1140
ggcctgcgcc ttttcctcgg ctttgtcccc ggcgggcgtt gagtagcttt tgcctttcgg    1200
tgttttttgga tccttccact gcttttcaat cccggcgcgg gccgcggcaa tgtccttttc    1260
agtccacagc gtggcgacac cgtctttcgc atcctggcgg ttttttctcaa taagctgact    1320
gagcttttc tctgctgaag cccgcttttc tgccgccgtc gcgccggact ccaccagctg    1380
gttaaactgc tgctggctgc ggattgcctg agcctgctgg tccgttcgca ttttttcccg    1440
cgcggctgcc agcccttcct gggcgtattg ctgatcggca agatcgtaag cctgcttttt    1500
cagctccacc tgctggcgcg cgtttctcag ccttttccgca tccgctttct gcagaacgtt    1560
gttaccggca taatccgggt cgaccttaag attgctggac agcgcgcggt actctttctc    1620
tgctgcctgc cactcagcaa aagagtcctg gcgcttcatc gcggtgtcag gattacgccc    1680
gacgcccagc atcgcatccc acgcaccgga ggcggcattc ttcacccagt tccaggcttt    1740
ttcgagggat ccgagattat cctcgaccgc accggcgcgc tgaatgaccg cgtcggaata    1800
tgcccgcatg ccagctcgg cagccttctg agaatccccc agcgcctgag cagaagctat    1860
ctgttcatac tgggtggctg tcagaaaatg aagggaatcg ttgagcgtcg cgaccgcgtt    1920
aaccggatca tccttcaggc gtttaaactg atttatggtt tcgtcaacgg cctgcccggt    1980
agcctgctgc agcctggcgg caacattgct gaccatgctg acgtcattac cgctgaacgc    2040
gccgctgcca cgacctgcg ccagcacgcc tgcagcggca tgctgagtga tgccattacc    2100
tgccagcgag cgcgccagcg cctgcagctg ccctgacgtt ttccccgcgt agttcccggt    2160
```

```
caggatcagc tgcctgttaa attcctcaga ctctttgctg ccgtcgtacc aggccttacc    2220
caacccgaat accgccgcgg caatccctcc gaccatgctg gcgatcccaa gaccgcgcag    2280
tgacagaagc tggtctatcc accctgcccg gttagccagc gtgatcccgg agccgcgcag    2340
cgcgccgaag ttaccgcgca tgacctcgcc gatcagtatt cccagttcct gccgggcggc    2400
ggcactttgc agccccagac cgtgcgtggc gactttggca gcttcgagct tgcggatata    2460
gacttcagcc gcatcgctgg caccgacctg cgccgccttc atgcgcagta gctcggtacc    2520
ggagagcttt tgctctgcaa cctgttgctt cagctggctg aggaatcgcg tgcgcgctgc    2580
ggccgatttt tcctccacga tctgcagttc ttttttgacgg ccgtggtgc gggaaataag     2640 ggcgagataa tcctgctggg ttatgttgcc ctgtgccctc gctgcgcgaa agcgcgcctg    2700
cacgttcgca agcgactgtg tttcaccatt gagctggcgt acgccgtcga tctggcggaa    2760
aaatgatgcc gcaagttcat cctgtcgacg ggcaagcgca gcggcctgcc cgtcattctc    2820
acgcatgcgc tgattaagct cggtcacgcg gcggtgagtt tcatcaacgg actttgaaac    2880
gttctgccag tctttggtaa gcccttccgt tgcggccgac tggcgggatt tcatatctgc    2940
ggcagccgcc gcgccagcgt cacccacggt tttaaacgca gccgcctgcc gctctgaagc    3000
gcgctgcatt cgcgtctgga cttttcaga gtcctcagcc atcccggtta gctggccctt     3060
tatgcgggca acctgctcac taaacgtggc gctgtcgacg tcaaggttga tgaccagatc    3120
gctaatctgc tgggccat                                                  3138

<210> SEQ ID NO 160
<211> LENGTH: 273
<212> TYPE: DNA
<213> ORGANISM: Escherichia coli

<400> SEQUENCE: 160
ctaatctgct gggccatatc ggataccctcc tgttatcccc tcagctgcgg ccatcagcgc      60
atcatcatcc ggctcgtcat cgctgatgac gataccggaa ggagaaagca ggctgaaatg     120
tgcgggggta agttccgggt cgcggaagaa aagagtggag atggaataaa gcagctctga    180
gaaatgcgca tcgagctgag cgtcctgaaa ataatgctcc cggtagaact ggtgccagtc    240
gcccagctca gtggaagtca ttccagccag cat                                 273

<210> SEQ ID NO 161
<211> LENGTH: 432
<212> TYPE: DNA
<213> ORGANISM: Escherichia coli

<400> SEQUENCE: 161
tcagctcgct ggcaagggct tttccgccgc aacgggttct gcgctttcgg cctccgctgg     60
ggcatccgga tcggcagctt tgtcatcctc aaccggaacg agcatgccgg agagcagctt    120
tatttccatt tctgctttac cgatcgcctc cggcggccag ccgctaagca cctgctggta    180
aagcgtctcc acatccgtgc cagccggatc gttatgccac aaagacatcg caatcaaacg    240
cgcaccgcag cgaatatttg agccaatcag cctggccgtc atttcctgat cgctgatgcc    300
gtcgctgtca gcgctgacgg ccttttcctc tgcggccata acgtgatgt actcaatacg     360 ctgaagcgcc gacagctcga agatggtcag tgattctttt tgccaggtga acttctcttt    420
tttcagaaac at                                                         432

<210> SEQ ID NO 162
<211> LENGTH: 744
```

<212> TYPE: DNA
<213> ORGANISM: Escherichia coli

<400> SEQUENCE: 162

```
ttacgctgca gttacggtaa ctttgcagac cgcaacgaaa ttaccgtcgc tggtcataac      60
aataacgtca gcggtgcctg ccgccacgcc ggtgacggtg atcgcattac cgctaacggt     120
gaccgttgct tttgccccgt ctgaggttgc cacacggaac gaggtatctg aggcactggc     180
tgggttaacc gtcacattga gcgttgtggt tgcgccgacg gccacgcttg ccgtggcttt     240
atcgagcgta acgcctgtca cggggatatt cggggtcccg ctttcttctg ccagttccgg     300
cttgccggta ttggtaattt tcgctgtacg ggttatgacc tcttttgccg gaatggcttt     360
acccaggctg ctgcaccagc cgcggaaaac gtcgacggta ccgttcgggt atttgatttt     420
gtaatagcgt actgagccat caataaacca tgcgacaagg tcttttttgcc cttcttcgcc     480
cggcttccag gcgagggtga acgaggtatc gccagcagat tttgcccccct gggccgtcgc     540
gttccagtcg gcatcctcgt cgtcgaggta agtgtcgtca tacgattcgg cggtcatttc     600
gcccggcgtc agctctttaa ttttcgccag gcggttccag tcgatatccg agagtggggtt    660
agcgaaagcg ttgcccgttc cggtgtaaag ccagagggtg gtaccggcac ctttcacagg     720
ggccagcggg tttggagtag gcat                                            744
```

<210> SEQ ID NO 163
<211> LENGTH: 402
<212> TYPE: DNA
<213> ORGANISM: Escherichia coli

<400> SEQUENCE: 163

```
ttaaattgaa taggtgatta agtacgtgaa atcgactgaa ccccaggtgg ccatttcatc      60
atcccgctga tagtcataac cctgcggggt gaacgtctcg accagttcgg tcagacctgg     120
gatgaaggcc attgccggat acactttctc ttccatccag gaatcaagcg cgctgtcggg     180
gctggaggct ttaagaaata cctcgatgtg aacaaccgcc tgccacgaat cttcgtcaag     240
cgaatcgccg gtgtactccg cgtcagaaag gtatacagcc acggcaggga gatcctgctc     300
ttcaagaaaa acagggcgcc cgtcaaacca ggtgaccgtg tcggtgatct cggctttcag     360
tttggccaga atggctgcac gaattgcgct gtgtctgttc at                        402
```

<210> SEQ ID NO 164
<211> LENGTH: 573
<212> TYPE: DNA
<213> ORGANISM: Escherichia coli

<400> SEQUENCE: 164

```
tcatcgcttc aggtggatcc tcagttggtt tttcagggct gcggaaagtt ctttgggcat      60
atcgctttca ataaggcgct ttgaaatagc ggtgaaggcc acggtgagcg gtgtctcaag     120
aggaactttg accacatcaa tcggataacg ggcctgacct acgcgccgca tgacctgcca     180
gcgcccgttc gcaagctgtt ggataaaagc gttacgaaag gtatagggcc cgattttaag     240
gacgctgccc gctccgtttc tggccccttt tttacgcgag agcctgacgc gcgccgtgcc     300
gagctttatc gcaggaagat taccgcggtt gattttttatc gacgcgaccg ggcgatcgtg     360
acgggccttg cgcagacggg aacgctggcg gaccagacga accggaagcc ccttttttccg     420
gttatcatca actgttgctt ctttcgctac agctttgctc ccctggctta tcgttcttct     480
ggccaccctg ttaagtgctt ttgcggttgc ctcaggaacg attaaccggc tgaggctgtt     540
```

```
caggttctga atagcccttt ccagtccttt cac                                  573
```

<210> SEQ ID NO 165
<211> LENGTH: 243
<212> TYPE: DNA
<213> ORGANISM: Escherichia coli

<400> SEQUENCE: 165

```
tcattcgaga tggatgcggg gttttccgtt gaacatgtca tagcgggtaa cgatcaggtt    60
cttaccgtcg tagtcgacgc tgtcgtttcg gcgtggctgg taaagctcag agaaaaccac   120
cagcgaagta cctgttcccg acaatggccc catttcctcg agttgctcgg cgggaacaac   180
gtcatagctg ctgccattga tgatcgctgt ctttcccatc ttttttatag tggccgcgtc   240
cat                                                                 243
```

<210> SEQ ID NO 166
<211> LENGTH: 327
<212> TYPE: DNA
<213> ORGANISM: Escherichia coli

<400> SEQUENCE: 166

```
ttaggcattg atcttaactt caacaacggt ggtgtttgcc cctgcatctt cccaggcgat    60
gcccgcggca acggcgtccg tttcttcgat cgtgattttg ccgtccttca gatacacctg   120
cgccccggca gtaaccgcat ctgcggatac ttttggcagg aggaaaacac cctcagtaaa   180
accgtccccg gtatcgccag ccgggatatc ggtaattgcc accgcgataa gttttccaac   240
aacaaccggg tcgccgctgt gaacatcggt tgcaccactg tttaccagag ggatcgtttt   300
cccgtcctgc gcatagttct tagccat                                       327
```

<210> SEQ ID NO 167
<211> LENGTH: 1947
<212> TYPE: DNA
<213> ORGANISM: Escherichia coli

<400> SEQUENCE: 167

```
ttactgacca gaggatttgg tcatgccgcg atagtccagc ggcgccacgc cagcatcaat    60
acgcactttc gtggcgatac catcagtggt gaagccttcc tgctgatcga tgtatggcgt   120
gtcgacgccg ttgagataag cgacctcaat ggtgtcggtg cccttcgcgg cagccagata   180
ccaggctttc gcatcagctt catccagacg tggttcggca atgacttctg caaagttctg   240
gatagggtta acgatcccgg cattgatgtc tgcaccttta acactggccg acttgatggt   300
ctgatttgcc agagtttcca gggcgacggg caccagcatg taggccggac ggatattcag   360
ggttcgctcc ccctccttct gcagacgcat cagcttgcgc gattcgtcca ggctggccac   420
agaaattgca cccgagctca ggttcttgtg atcggcatgg aacagcgcct ttccgtctga   480
gagtttcggg ttttggtca gaatggcgta aaccagatcg ccaatcgttg ctttcgccgc   540
gcgcccatc ttcatcggta cgtcggtaag ctggttcaga tcgtcgttga tgatcgcctg   600
gcgagttact gagaagattt caccatacgt ggcaagcgcg atggtttcgc ctttgtcact   660
ggtagtgatg tacttgtact cagccccttc gcgaacctgt cgcagagaag ggaacccacc   720
cataccgaca cgatgcgccg ttttgaagtc cgacagctgg ccttttttgg tccactgctc   780
gaaggtttcc tgcgcctcgt cccagccctg aatcagcgct tgttcgcaa catcaagcag   840
aatgttgcca aagtcagagg tgctgtgggt cagcgccagg ccaaccatct gcatcgggtt   900
gtagctggcc acgccgatac cttttttctgt cagggccata cgcgcatact cgcgcagcgt   960
```

```
cataccgtta taaacgttat cccgctcctg accttcgaac ccggcacgcg ccatcagtgc   1020
ctggcgaata ccatccgcga cgaagttacc gttgcccgca tgaatatgcg gctgagtggt   1080
tttattggac ggcgtggccg ttttaccgag ttctgccagc agcaaatctt tcgccttatc   1140
gacggagcaa tcagggtcgg ccacacactg attctgcagt tccatgtgct tattaccgaa   1200
catggcaaag agatcgccga tagcgttaac acgggttttc tgctcagcca cacctgcgc    1260 gcggatcgca ttttcatccg gtgccgggtc tgttttgcc tgcggtgcct gaggctgggt    1320
aataaccggg tcacgctggg tagtgttgcg cggcggggtg atcatgttgc gaatgcttt    1380 tggcatttt tcaaattcct caatacgttt tgaatgaata caggccatag cctgaaggga    1440
tggtgtcacc tggtcggcaa acccagttc aaggcactcg ctgccgttca tccaggtttc    1500
gtcctccagc attaccgcaa tttcttcggt ggattttccg gttttctgtg cataagccgg   1560
gataagaacg gattcaacct tgtcgagaag atccgcatag tcgcgcatat cgctcgcgtc   1620
accaccagca aaccccccagg gcttatggat catcatcatc gtgttttcag gcatgatgac   1680
cggattgcct accatcgcaa tcaccgaggc catggaggcc gccagaccgt cgatatgtac    1740
ggtaatcgcc gcgccgtggt gcttcagcgc gttataaata gcaattccgt cgaagacatc    1800
accaccgggc gagttgatat aaaggttgat gtgggtgacg tccccaagtg cccggagatc    1860
attgacgaac tgtttcgccg ttacgcccca gtacccgatt tcgtcataaa taaaaatgtc    1920
ggcctcactg ttattgctgg cctgcat                                        1947

<210> SEQ ID NO 168
<211> LENGTH: 1500
<212> TYPE: DNA
<213> ORGANISM: Escherichia coli

<400> SEQUENCE: 168 ttacttttg cgctggcttt cggacggtgg cgcgcccggt tctttggctt cggcactggt     60
gcctccttta tcattggcgg ggtcggtgtc aaacaccagg ccctgttcac ggttctcgtc    120
aacctcagct ttacggcgtg acttaacatc atccggggttg cgaccgctgg cacgtatcca    180
gtcggattca gtagcagcac cgccgcggat ctgcgttttc caggcattcg cttctttaac    240
gggatcaatc cacggcataa cgggccccga ataaaccgcg ttataaagcg agtccatatc    300
aatgcctctc ggcagcttga tttctccggc agcaatagcc atcttgagcc aggctcggta    360
catgggccgg tcactgaac cgatgaacca gtcctgaaga atcagatagc cgtcggttga    420
ctcgacaagc tcctgccgct gggcactgta cgttccgttg tagtttctgg atgtgctgga    480
aaagctgagg cgactgccgg cggacacggc acgcagctgt ccgttacgaa aagattcgag    540
gttagggttc gggcgatcgg atttaatcat cccgatttct tccccggcct gcagttcgtc    600
atagagcata ccgggctgaa tcatcagctc gcggtcatcg ctgcttgaat cagaatcgaa    660
gctctgtccg tcgcctttt tgatatacat gccgagtgcc gcagcaattc tggcagcagt    720
aagctccgag tcctcgtatt ctttcagcgc gctcagacgc atcagaacac cagacaaaag    780
agacgttccg cgggtctggt gcaggcgtcg ggtgaaatttg agatgcagca tgttctctgc    840
atctatctct ttggtatcaa actgacgccc ggatactggc aggcttttat agacctgata    900
ttttttcggg cgtccccagt tatcgacaaa aacgccctga ttgagctggg tggcagcatc    960
gctgttcatc ggcacaaagt ccggctccag cgcttccagc cagaacggca cgccagcaac   1020
cggctgaaga ccatttccgg taccgcgaac cagctgagca aataccctcac cgtcccggag   1080
```

```
ccacgttcgc agcatcagcc gctccagcat tgggcgggta aactgggttg tgacatctgg    1140
ccttacggac cattcgcccc actttcggcg gatatcagtg gccagctttt tagcgatctt    1200
cccgttactc agcatcggat gcggttcaac tatgatgccc ttcgcaccca ccacccttc     1260 ttccagcttg tcgaaaacgc cgatcaccag atcgtggttg ttatccagcc agcgcgcctg    1320
ctgcctcagc gaaaccgccc ccatctggct gagctgatcg gctgaacgat tttccttctg    1380
ggctttgtgg gtacgcgttt gctttaccgc ctcatacgct ttaataactg cgcgggcacg    1440
caggcgtgag gctttccagc ctggtgaaaa caggccaatc gcatcatcta aaaaactcat    1500
```

<210> SEQ ID NO 169
<211> LENGTH: 216
<212> TYPE: DNA
<213> ORGANISM: Escherichia coli

<400> SEQUENCE: 169

```
tcatccaaac ctcgccagcc tgtagccggg tcgcccacgg cgtttgttat tgagcgttgc      60
cagtcgtcgc tcccattcct gacgcctttt tctgatttcc gacaggtttt cgagcgtcat     120
ctgctgcccg ttgaaagtga ttgatttccc ctccagaaca gacagctcgg ctgcagcata     180
gcggtcgatc atgttttgaa tatctgctgg attcac                              216
```

<210> SEQ ID NO 170
<211> LENGTH: 2103
<212> TYPE: DNA
<213> ORGANISM: Escherichia coli

<400> SEQUENCE: 170

```
tcacacccaa cctcctgacg aagaccacgg attagcctgc tcggttacgg gcttctcacg      60
ttttggtttt ggtttagatt tcggcgcagg cggcggggat ggcatttcgc cagcttccgt     120
ctgcgtgtcc tcgatccacg tttcccgccg tgcccactca ggagctgacg gccatttgat     180 ttttcgtaa ccactaagga tggcgagcgc gtcggcataa acgagcaggt caaatgcttc      240
gtttgcgccc cggccgggct tactccattt ccttcattc gagcgttcct catacgtcag     300
ttcgtcatag aaccagctgc ccagccaggc ggggaaatgc acatagccag gcccgggtga    360
atcacgccac agcgcattat tcacccggtc tttaagggca tcggtctgga agagataaag    420
aggcacatca ccagtcgcct gtgcgcgcg cgttgatctg cccgtgttgt cgggaaacgt     480
tcgctggata agtttgctgc gcctgacgct gtcccctttg aagagataga tacgcttacc    540
cagcccctca cggcgacatc tgcgccagaa cttgtaggca ttatccgtca cgccatcttc    600 gcccccctgag tccacggcca tcgacatcag ccgcatgccc tttgatgggt cagctgcgag    660
cggccacgtt ttatcaaaga cgtcagtgag taaaagatcc cagtcctccg gatagctcgc    720
cggatccacc tgaatgcttt caccgttgcc gtcgcagcgc agcgaatgcc ggatgttgta    780
acggtcaact atccagcgct cacccatact tccataaccc gtaatctgca caacaaagcg    840
ccggttgcgc ccgcctgca cgtccacggt cgcagtgaga aactgcacgc cgttcggtac     900
cgaacgtttt gggacgtctt cggcacgctg ctcgagcaat tcacttttac gctgctccat    960
gctggctcgc ggcaaatagg gcctgccgaa atcggtgttg atcaccgtct tcagggtttc    1020
ttcgctgcgc gtggattcat attcctgctc ggcggtcaga aacttataaa taagctgcgc    1080
ccaggtctgg taagcagctg ccggaccttc catccagaag gaggcaatac gggaacgacg    1140
gccatcaccg ctaaccaggc cttcctgtc gatggtttgc ccgtcccgga gccagacaca    1200
tttcatgtta agcgcacgct tcatgtccgg tgtgatcctg cctttacagg cagggcactg    1260
```

```
aagaaacgcc gcttcgctgg caagcacagg atcgctgctg tcgcggtatc cggtcatatt    1320
gtccatttcc ggctggaaat attcgccgca atgcgggcat ggccagtaaa gacgacggcg    1380
gtcaccacgg ttatagagcg ataaaattcc ggtggtcgga ggggcttcat ggggcgtgga    1440
gcgccgccat tttgtgtctc tgatatccct cccgggcgag ctctcaacca gcgtcatccc    1500
ggaggacatg aatgtcgtgg ttcgtttcga tgccagtgaa aaagcatccc cctccccgtc    1560
gatatcttcc ggaaagcggt cataatccgt cagcgccaca cttttatagt ccgaggacga    1620
catgatattg acggatggcc agcccagctt cagatagtta ccggcgcgga atgtacggtc    1680
gtagacgttg ttatcgttac gtcttgggct tagcccgggt ttaacttcag gctacagcg     1740 aaaagtacgg tccaggcgtt ttttggaatg ctcgcgcgct ttttcctcag atacctgaat    1800
tacaagcata tctgccggat cgcagacaat gttataaacg atccagccgt caatcagccc    1860
gatggtttta cccgttcgcg ctgggcccac aaacacaacc gcatcgtatt cacgcgatgc    1920
cagacagttc atcggctcaa tcacataggg tgccagatcc ggatcccacg gaactgagtt    1980
tcccgccccc attggcacgc gcatataagt actgaccgca tcggccaccg gcatacgacg    2040
cggggctcgt aaaataccgg aaacatcgcg gcggatgtcc ctggcggatg cccgctttgc    2100
cat                                                                  2103

<210> SEQ ID NO 171
<211> LENGTH: 489
<212> TYPE: DNA
<213> ORGANISM: Escherichia coli

<400> SEQUENCE: 171
tcagtcctcc tcaggctgct cctcctcttt tccagcgtcc tgcaccttct ccgccatctg      60
gtcgcgcaga tcatcgataa cgctttgcac acgaactacc gcagcaggcg ttaaagcaca     120
gtcgcgctcg agcacatccg ggagggtttc aagtaccatg acgacggctt cgccatcaa     180 tgagaattct cgcgccactt catctgcggg tattaactgc cccgtatcct gttcgaactt    240
cagcctctcg ttctctgctt tccagtggga cagcctgtca gaaggggca tatcgtcgat    300 gttggccgaa acgtaggga tcatcagttc ggtcagaatg tcggtcacca gatagagctt     360
taacttgcta ttgctgcctg gagcaggttc aacattttc agtctcgcgg caaccgtctg    420
acggtgtacg ccggttatcc ctgccagctg gttgatattg agttttaaag tggcaatttc   480
ctggtccat                                                             489

<210> SEQ ID NO 172
<211> LENGTH: 729
<212> TYPE: DNA
<213> ORGANISM: Escherichia coli

<400> SEQUENCE: 172
ctatcgacgg cactgctgcc agataacacc accggggaaa cattccatca tgatggccgt      60
gcggacatag gaagccagtt catccatcgc tttcttgtct gctgccattt gctttgtgac    120
atccagcgcc gcacattcag cagcgttttt cagcgcgttt tcgatcaacg tttcaatgtt    180
ggtatcaaca ccaggtttaa cttgaactt atcggcactg acgttaccct tgttctgcgc    240
tggctcatca cgctggatac caaggctgat gttgtagata ttggtcaccg gctgaggtgt    300
ttcgattgcc gctgcgtgga tagcaccatt tgcgatagcg gcgtccttga tgaatgacac    360
tccattgcga ataagttcga aggagacggt gtcacgaatg cgctggtcca gctcgtcgat     420
```

```
tgccttttgt gcagcagagg tatcaatctc aacgccaagc gtcatcgaag cgcaatattg    480
ctgctcacca aaacgcgtat tgaccaggtg ttcaacggca aatttctgcc cttctgatgt    540
cagaaaggta aagtgatttt ctttctggta ttcagttgct gtgtgtctgg tttcagcaaa    600
accaagctcg cgcaattcgg ctgtgccaga tttagaaggc agatcaccag acagcaacgc    660
gccacggaaa acagcgcat  aaagcacttc attagcagcg ccagatagcg taatgatttt    720
gttactcat                                                            729
```

<210> SEQ ID NO 173
<211> LENGTH: 231
<212> TYPE: DNA
<213> ORGANISM: Escherichia coli

<400> SEQUENCE: 173

```
ctatttgtgg gtaaagttcg tagtgcgctg atcgtgcaaa atgatttag ttgggaacag     60 ttcgcaactc tgtcccataa aaatcagcat attcccatct atcccatatc cagcgcattg    120
accatcggga tactgaaggg agattccatc atctcttaga aagatcacca tctcttttgt    180
ttcaatttgc atatagctac ctggaggatt tatgaatgca aggattttca t             231
```

<210> SEQ ID NO 174
<211> LENGTH: 597
<212> TYPE: DNA
<213> ORGANISM: Escherichia coli

<400> SEQUENCE: 174

```
atggactatt accatgagat tgattttcca tctttattcg cgagagcagt ggaaagcgat     60
gacgatgtgg gtactacatt gcgcattcac ctactttgtg agcgcatggt cgaagcatgg    120
atatgcgcat gctgtgactg ccaagatctc tttggaagag ataaaaacaa acttttaatc    180
gaatgtaata ctaaaatatc catggcggga aacctgggaa tcccccccgga acttatgaaa    240 tcacttaaaa ccatcaactc aatgcgtaat gaccttgcac acaatccatc aatacaaagc    300
attgctgatt caaggatcca gagcctgaag gatactctga ctgaatactt taaacagcat    360
ccaacggaac ccagcatgga agaatcaaaa ctgggtattt ttaacgccga gaatcaatta    420
accgaagaag tttccttaga tagtgacagt tcaaaaaaca gacttaagtt aatcttgctg    480
ttcagcaagt taatgcaggc gttaatgcaa ttagttgcag ctaatcataa tgggcgctgg    540
gataaccaat ttagccaatt cgtttaccat gtgaccatga acgcaacaaa gagataa       597
```

<210> SEQ ID NO 175
<211> LENGTH: 198
<212> TYPE: DNA
<213> ORGANISM: Escherichia coli

<400> SEQUENCE: 175

```
ctagtcgtcg agttgcaaca caccgtgatc cagtgattct gaataggcga taagtccggt     60
ataaccgggg ataatctcac cattatcagc ttcaaattca ggaattgtgc cggtggtgat    120
ggtgtattga ggctggccat cttccttcgc gaaggctgcc aggtcttcaa tctgcttagc    180
tgtaagaact actgtcat                                                  198
```

<210> SEQ ID NO 176
<211> LENGTH: 480
<212> TYPE: DNA
<213> ORGANISM: Escherichia coli

<400> SEQUENCE: 176

```
ctattggtta ttcgacagtc gcactgattc gtaaatccgc tcacacgtca ttcctgcccg      60
gtagctttcg tcagatcgtc cagcataata tcgagctgct tctgcaaggc ttccgagcat     120
gtcggcaagc attgctgcgt tggctccggc tgttttgctt ctgacggaag tggcgagatc     180
tgcggtgtgc tttgcggcgt ccatgtgggt agcgagtttt gttgcttcgg cgcgcagctg     240
cttaacagtg gtagccaggc cagcagaagt aacggcagcg ctcgctgctt gagcttgagc     300
atctttaacg gcctcatccc gggcgattgt tcgcccttgt tcaatcatac gagctgcggt     360
ctgtgcattc gcttcctgtg aagattccgc gctatcccgg tcagcccact ttattttcca     420
gctgcggttc gtccactcac tgccagcgag aaacgaacct accaacgcaa caatcacaat     480
```

<210> SEQ ID NO 177
<211> LENGTH: 549
<212> TYPE: DNA
<213> ORGANISM: Escherichia coli

<400> SEQUENCE: 177

```
tcactggtct atcccccagc acgtcagtgc gctttcctgg tcccgccgtt ctacctgccc      60
ataacatcca tccttctggc ccttggtcag gcggcaatcg cggccaccgt ctttaatcca     120
ccagcggata gcttcacagg ctcctttcgt atcgccagca ttaattcgct tatagaacgt     180
agacgggaaa cattttccgg ggccgatgtt atatgggcag aaagaagcga tacccgcttt     240
ctgtggttcg gtcagtggta ctttgatatt tcggtcaacc cacgccagcg ccttgtcgcg     300
ttcaatggcg tttacctggg cgcatttctc agctgacagc ttcatgccct gtactactgg     360
cttgccatca accattgttg caccacggca atggtccag agtccgccgc cgtcgcgata     420
tgctgtcaag ctgttaccct ctttctcatc cagaaactga tcgagaatca cgggtgcgga     480
agccccggca agaatcaaac caacgaccgc tgcgctcaat ttattcttca gctttagaga     540
catagccat                                                              549
```

<210> SEQ ID NO 178
<211> LENGTH: 279
<212> TYPE: DNA
<213> ORGANISM: Escherichia coli

<400> SEQUENCE: 178

```
ttattcttca gctttagaga catagccatt gcgccgatcc tcccgttctt tccagcggaa      60
ataccagttc actgcacagg tgattaccgt gcatgcgata ccgacaataa ttgcccagtc     120
gctcaggctt aaccctgcaa ttctgtcggc caacatccag gacacctctt ttgctgtttt     180
agctgtttcg gcatatgcct tcgctgatac accgcagccg gcaagcgtgg ttcctgatcc     240
atatgaaagt ctgctgtaaa tggtgctcat tctggtcat                             279
```

<210> SEQ ID NO 179
<211> LENGTH: 1053
<212> TYPE: DNA
<213> ORGANISM: Escherichia coli

<400> SEQUENCE: 179

```
ttatgatttt ttcagttttt ccacctcttc ggtggtctgt ataaacctgt ctgcctccag      60
ttctacgccg atcgcccgac ggccaagttc tattgcagct ttcacagttg aaccagagcc     120
cataaagaaa tcggcaacga tatcccccgg tctgctgctg gcgctaatga tctgtttcag     180
catgtcggca ggttttttcgc atggatgttt gcctggataa aactgaacag gcttatgtgt     240
```

```
ccatacgtcg gtataaggaa caagagcgga aacagagaag cagcgccgaa ggattttgta      300
ttcctccagc aattctgaat acttgcggtt taatgactgg taggtagcca ccagctggtg      360
gtgaggatgt tcaagctttt gctgaatatg tttatcgatg gcgatccgcg tgaacagttc      420
ctgcaatttt cgatagtcca cttcattcgg tagttgccat tggcttgcac caaaccagtg      480
tgacgccatg ttttttcttc cggttgcctc agctatttct ttcgagctga cacccagtga      540
ttcacgggca ttacggaagt aatcaatcag cggcgtcata atgtgctgct ttagctctgt      600
gcttttcctt tcgtaaacat cctctttacc tgtatacggt ccaagatagt gctcagcaaa      660
caaaatccgt tccgtagatg gaaagtacgc acgcaggctt tctttattac atccattcca      720
gcggcccgat ggttttgccc aaatgatgtg attcaaaacg ttgaatcggg cgcgcatcat      780
aatctctata tctgaggcca gtcggtgacc gcaaaacagg tagatgctgc cagcaggttt      840
aagaacgcga gcatactcag ccaggcagct atcaagccag cgtaagtagt cctcgtcccc      900
cttccattgg ttgtcccagc cgttgggctt cactttgaag tacggaggat ccgtaactat      960
aagatcaata gagttatccg ggagggtggc gacgtaatgc agactatcag cgttgattaa     1020
ctcaacactg tttatttta cagtattttt cat                                   1053

<210> SEQ ID NO 180
<211> LENGTH: 192
<212> TYPE: DNA
<213> ORGANISM: Escherichia coli

<400> SEQUENCE: 180
ttactggagg cgtttataac atccgaactg gtaatcagat aaccccgcca tcaccagctg       60
cgtaagtatg agctggcaac gttcgtggct gaggtgggta ttctgtgcaa tctccccagc      120
cgttgctggt ttatcgctta attcattgaa acagcctttt gccgtttctg tcatatcttc      180
ctgatttagc at                                                          192

<210> SEQ ID NO 181
<211> LENGTH: 900
<212> TYPE: DNA
<213> ORGANISM: Escherichia coli

<400> SEQUENCE: 181
ttagcaaata ttccacatca tcgtactacc gttatggttt tcgataattt ttgcggctgg       60
gctagtacca aaagagtgca tatagcaatg atgaatagta aggaccagat cctgcaacgt      120
ttggtcactc tctagctcca tgatatttaa accaatattt tgagctttgt ccaaatgaat      180
atgtctggca tgtgcatacg ttgcttggtg gttgtttaac tcatcacata tacgcttagc      240
cttagcttca gcgtcagcct gacctgcgaa cataccagta caaagccatt tctggacaat      300
ttcgttcgcc cagagaattg cttttttcaca ctcgccaatc aacgttggat ttagttttg      360 gaacgtaaat tgccaccatt gcagtgcagc agggttggca aaaatttccg cttttgctct      420
ctcatactcc tcaataattg catgagatga taacccatta aactgtggat caattggccc      480
caagttcgac tgtttaccta aaacgatctg ctcagcacaa caagcaagca ttgtgccaca      540
actcattgaa atcataggta caatcgctcg gatattggtt ccgaactttg aacgaagata      600
atgaccaatt gattctagag ctgcgatatc gcctccagga gtatggagta agatatccaa      660
tcccagactc gtatctaacc cattgatagc agacataaga ccattttat catcatctga      720 catctggatc agatgttgaa acccaggccc cccttttga aggaagcctg agtaataaga      780
aattacattt cggccagtat gtttcgataa atcacgtaag tacttgtggc gaacctcatc      840
```

```
cgctggtgta cgttgagcga tagtacccat ctcacccaat acgtctatcc aatttggcat    900
```

<210> SEQ ID NO 182
<211> LENGTH: 207
<212> TYPE: DNA
<213> ORGANISM: Escherichia coli

<400> SEQUENCE: 182

```
tcagtatgag tacagttggt gagattgctg accgttctgc tcagtagtat ttggtgttac     60
tgtgctgtat gaatagagca caccacttct cacattcaga tcgttttgct gagcgagaac    120
acgcatagca aaatgctgta cggattcgcc ttttttgaaac tcttggggtt gtatgcccat   180
tttttcgtaa aattcagcag cgctcat                                         207
```

<210> SEQ ID NO 183
<211> LENGTH: 690
<212> TYPE: DNA
<213> ORGANISM: Escherichia coli

<400> SEQUENCE: 183

```
tcacatttct gccactttga gggcttcttc ttcctcatag tattcaagag ccatggccaa     60
cgcagattca tcaagctggg taaaagcggc ctttaaccca gcccagtgcc ctgaatagac    120
acgcaaccat gtcgaacggt caacgctaac catgcgggcc aacgctgcac cagcatagtc   180
tttataggtt tcattatttc tggttgcggc aatttcctgc cctgccagcc ataccaggcc   240
tatcagtttc tttactacgc gctcctgaag ggagttatca cccaggcatt tctgataagt   300
tttccagacg tattcacaca tcatcacctg gtgcttatag ctaaggtcaa aaccgtagca   360
gtaccgcaac caggcctgct ggtatccact aagcgcggac actgccctac gccacggcgc   420
ggactcaaat tccgcatctt ttatcggcgg cattggcctg cggcggctgc gtgtttccag   480
cacatacagt ggcgcggaaa gtgagttaac aaagcgtggc cccttctctc cttcgagttc   540
gacgagatga attccacggc gaggggtggc attttttgtct gctggtgggt gttcactgaa   600
agcctcaagc tgccctttg ttcccccaga caggtcaggt agcgcgcggc gcaattctat   660
tcttacaaaa ttcaggtctt gttgattcat                                     690
```

<210> SEQ ID NO 184
<211> LENGTH: 996
<212> TYPE: DNA
<213> ORGANISM: Escherichia coli

<400> SEQUENCE: 184

```
ttaagctttc gcaattacgc cgatcgccag cgcccgatcc ataaaacgca gtagcagctc     60
aagctgcgta ccatgcttct gctcgaatgc cggtacatcg gcgtgtaact cgtcgtggca   120
ctctctgcac agagggatca cgaagagatc atgggctttt gttgctgtcc cccccatacc   180
gtgccctacg atatggtgcg gatcatctgc tggccgtcgg caacactcac agggttgtgt   240
tttaacccag cgggtgtacg tctcatttat ccagcggcgt cgctttggcc tgagcatgaa   300
agattctgga gactccggat caacagagag cgtgaggatc ttcttcgcct tctcctgcac   360
gaggctggtt gcagaagcgg aaggcacaat gtcgctttcc ctcatgaccg agcggatctt   420
atcatccgga aggcgtagcc ccttgtgcgc aacgctttcc ggaataacat cagccaggtc   480
gtttctgacc atccaccagc acagttccgg aagcgtcagg atatgcgact cgggaaaacc   540
agaatcacgc cgaatgactt ccagaatcca ggataccagg tttcctgccg ctatacctgc   600
```

```
aagctgttcg gtatgctgcc ccgacaaagt gtgatcgcaa tgccagcaca ggcgaatact      660
tcctggtggg tgccgcattg ttgtgaagtt cttgtcgtgc cacgatgaat gtggccactg      720
gcattcaaac cgattactca accattgctc aagggaagga agcccaccag cacgctgaat      780
aacccgatca ttctcgaaga cctgccgcat taccggatca tcagccagcg gctgaatggc      840
ggcgggaaca gctcctgtac tgaatgacgc catttcttct ggttcaggct caagcagaac      900
gcgaccgcgc ataaagaggt gcatcagttc cgcgccggga cgaaacaaca caatccccat      960
acgatgggcg atctcggggg taagcagagc tctcac                                996
```

<210> SEQ ID NO 185
<211> LENGTH: 684
<212> TYPE: DNA
<213> ORGANISM: Escherichia coli

<400> SEQUENCE: 185

```
tcacgcgacc tgcccctgg caatgtgttc tgcccacagt ccaccaatcc agcgcacgcc       60
tttcgccgtg aaacgtgcct ggctgaatgc atgatttgag gttacggatg tgccggtttt      120
cacttcaaaa cggcccgcat caatatgctg atgccgtggg gtcatcgttc cgccaagacg      180
atacatgatg tcgttctcaa ggaggaataa ccgcagatcg ggctctttgg ccttaagcag      240
ttttgccacc tggcggaatg acattgaccc actggctgta cagtaccgat caacaaacgc      300
taccttcggc gccgcggcag ccagttcgtt agtcaactgc tgtttttgtt ctgcaaggtc      360
agctgcaaga cgtagggctt cagagaatga ttgaggaatc gtctgctgct gtgcctgctc      420
aagctcctgc cagcgatcaa ccagacgcgc ggtaaactcc ggcgacagct gcgcgacaac      480
gatataactg tcccgcttcc ctatcagata aaccgatacc gactgattga ggtgattttt      540
aacttccccc attgggggga gttcaataac ccgcgctct gccaggcgtt caatggaccg       600
tttaacatgg tcatgtcttg attccaccag ctcagcaata tcgctgctgg acatggttaa      660
cgctgttgtt gctaactggc tcat                                             684
```

<210> SEQ ID NO 186
<211> LENGTH: 387
<212> TYPE: DNA
<213> ORGANISM: Escherichia coli

<400> SEQUENCE: 186

```
tcaggcggct gcacccgccg gttcatatct gctgattgtt atctctaccc gacctttcgg      60
cacaacgggt ccccattcca ccagcatgcg cttaatctgg ctgtcgtctt cccagacacc      120
cgcatgcgtc agcgcgtcaa acagggcttt gttgtaatta tcgatatccc ggcggcgcgc      180
atccggcggg tacagagtga tttctaccgc tgccagttca gtcgatggct tcgggagacg      240
tcgtaattgc tcaatgatcg ccacgcaggc agcgctctgg tatttacggc cagcggcgct      300
aatgaggtga cgaccggcca gcggccccctt gttaggggcg cgccagtaag tgttcacgct      360
cggaggaaaa ggcaggatca gtttcac                                          387
```

<210> SEQ ID NO 187
<211> LENGTH: 1320
<212> TYPE: DNA
<213> ORGANISM: Escherichia coli

<400> SEQUENCE: 187

```
tcacgcggcc tctccccgca tattgcgaac aagttcagaa gcagcagtaa tgatttcgct      60
ggtggcagtc cgctccagcc agagttgatt gatattggct ttcagcttgt gttgcagtga      120
```

```
ctcatccagc atgtcagcac catccacctg gtcgaataca attctaacct ccagcggcca      180
gatacgggac tcgggaagcg gatccgatac tggtttagct ttctcacgaa tgtgcatgcg      240
gatctggcga atattggacc aactggaaac atccaggctt cccatggctg caatgaagtc      300
agtgctgttc atgccatatt caccggatgc ttcaagggac acagtgcgaa tacgttccga      360
catatccagg cgcacagcag cgtcatcgaa ttcaatcgac aacagccact catccacacc      420
gaacaaaata ctctcacgaa taagcagctt cgctttgtcg atcgttaaag gtgatacctg      480
agtgaattcc ggtgcttcga cagaatccgc cgcccaggta tgcccaaact tcgattcact      540
gaatgtgtat tcttctttat cgccaaacgc agctctaacg catgcccacg cctcgacacc      600
gctgatagca aaaatatctt tctgggtgag tggcaactct gcttctggct tatcagctgc      660
aggaggtgtg gcagttacag gttgagactt gctggcagca aattgtgcca aagccataaa      720
cgcccgccct tttgcctcca gttctgtgcg gttgatatag ctgaaccgct cgccacgcca      780
tgacttatcg aatacagcta tggcaccggc aaaaaacgcg ctggtgggtt tctgtttttc      840
gtcagcaggt acaaaccaca caggcagatc gaacccaatg cgcccgcgaa tgaatacaat      900
gtgatcggca tcttccggcc accacgtttc actcggcgcg gcttttatca ggaatacata      960
gcgaccgccc ttctcgcgct gggctgctgc gtagttcatg atgtgcgtca tgccggtgat     1020
cgcctgcttc tcgtggtact gcgaacggct atacggtggg ttgccatagc cagcgccacc     1080
cagttcagcc agacgttcag accagtcctg cgtcagcgcg ttatcttcgg cggtgtacca     1140
tgccgggcat ttcgcgttgt cgtcgtcagc aaacaaatcc agaactaatg gaccaaatag     1200
cgcgttgatc ccccaaaaaa gcagatccgg tgtccgccac tgatcgccaa cctctttcaa     1260
ttcgtgagct ggtttgctac gcagtgccgc cagcgcctgg caatatttat tggtcatcat     1320
```

<210> SEQ ID NO 188
<211> LENGTH: 882
<212> TYPE: DNA
<213> ORGANISM: Escherichia coli

<400> SEQUENCE: 188

```
tcatgaacgg aaccccgaat tttctggcag tgagtaatca acactctgga agtttgcgcg       60
gctggctgag ttagtctccc atttgccgtt aacgcgttca ggccggccag cactggacca      120
tttggtcgcg ctttgcaggt aaccagggaa gttttttgga atgaacagag ttgccgggcg      180
gaggtattgc gcctgctcgc tatcacgcca atcggcattt ttgtaatcca ctaccaagca      240
caggtcatca acagtgaatt gttcccgaag acgggcgcga atattctcca gcgacgtgct      300
gcatacctgg tagcgtgagc cagtagtctg attcaggtaa gacaaaacct gtctggcctg      360
atcagtaatc acaacctcag ggtcgggttg cgccgcaacc ggacaagagg gttttgaagt      420
tacttgtggt tcttgttttg attttactga cggatcccca ccagattctg acgggtcaaa      480
accgcctttt ttgctggatt tcgacgcctc aaattttgac gggtcggatt ttgatgcatc      540
agattttgat gggtcagatt ttgatgcgtc agattctgac aggtgagaaa aagcagcctc      600
tcgcaactta acgacgttaa gctgatatac gttcgatgcg ttacggttcc cattacggcg      660
ctgcttacgg gaaagccagc catccttctc aagctgagca agggccgtcc ttaccgtact      720
ttctccagca ccgatttgac gtgcgatcgt gccaatagac ggccagctaa caccctcatc      780
actactgaag tcgccagac gcgccatgat ggcaacgctg ataacttca tgcctgacga      840 agcgcatgca tcccatacgt aaccggttaa tttagtgctc at                         882
```

<210> SEQ ID NO 189
<211> LENGTH: 339
<212> TYPE: DNA
<213> ORGANISM: Escherichia coli

<400> SEQUENCE: 189

| ttaattctgt aaatttacgc tggaattgtt caagagggct gaagcactca tgatcgtacc | 60 |
| cttcgcgaag gtatataacg cgctgtgtat ctggctccca gcggacaact ctgacgggaa | 120 |
| ctccgtagtg atctctgaac cgccggttaa cttcagccat tcctcgcgcc ccttctcgtt | 180 |
| catctgaaca aatgcttcta ccatcaagtc tgctggctgg tagttgcctc catcagccgc | 240 |
| gttatttatg atttccacat agccgaactg ggcatcttta cccaccagcg gcaaacatct | 300 |
| gaattgctta gctggtctga atcggtttac actgttcat | 339 |

<210> SEQ ID NO 190
<211> LENGTH: 564
<212> TYPE: DNA
<213> ORGANISM: Escherichia coli

<400> SEQUENCE: 190

| tcatgcgtta gtttctccac tgatacgaca cgccaaggcg cccggagctg cacactcgcg | 60 |
| ggcgtcacct tttctgcctg ttgaaacgaa tacgtcaatc gcctgatctg aaacaccaac | 120 |
| cccataaagc gccataaatc ccaggaaccc gtgaatctgg tggcggagct tcttactgaa | 180 |
| taattctgaa agcattttgc gctctgatga atcaattacc ccatcagccg ctgctgccat | 240 |
| cttggcatta gccagctcac cagatgctgc tgccgctttc atctcaatgc tgtacagctc | 300 |
| aacgttatcc aggctctcag cagttggaac atccaccagc catttccctt ttcggttcgc | 360 |
| ctggtactcg gccaagtaac aagaaccaga caggtcctcc atccgttcca gttctgccaa | 420 |
| ggtaaagaac cgactgccac acttctggta caggtggttg tggaactggt cgatagtcat | 480 |
| ccctaaatcg gaagccatac ctaagcgacc atgcttgtgt gccttacaca tcaggcggat | 540 |
| tgctgtattt atgctgtcta ccat | 564 |

<210> SEQ ID NO 191
<211> LENGTH: 258
<212> TYPE: DNA
<213> ORGANISM: Escherichia coli

<400> SEQUENCE: 191

| ttaaagttga ctattgttgt tagcggaagg tatgccgtca tttttgttcg gataaatatc | 60 |
| aggtcgtaat tgatggggag ttactaccca tccgccccat tggcagagtt gaataactct | 120 |
| ttcagaaggt actcggttct ttgcaatcca gttcgcaaca gattgaactg attggaattc | 180 |
| aaaccgcctt gatacctctg aaatcgaccc gatcgccttc acagctttag ctgttacatt | 240 |
| cttgtgttga gatgacat | 258 |

<210> SEQ ID NO 192
<211> LENGTH: 711
<212> TYPE: DNA
<213> ORGANISM: Escherichia coli

<400> SEQUENCE: 192

| atgccttgtg cgcttaatct tctacttatg gtggaaaatg ctaaatacaa agactttgcc | 60 |
| gaaaggctaa acaggtctct ccaagagcaa tctattggag ttaaagaatt gtcagagttc | 120 |
| agtggtgtct cgtatgagat ggcgcggcgc tacactcttg gtactgcaaa gccgagagat | 180 |

```
gagaagatga ttcgaattgc agaaagactt gccgtctcac cggcttatct tgattatggt    240
gtgcctgtta atggtggcga cgcgccagcc aaaggcacgg tcagaataga caattggat     300 gttcatgctt cagccggttc cggatatata aaccaaccat tccctacaat agtgagctca    360
atagagattc cagaagagag gatcttcgag ttgtttggtc gtagaagcct tgatggcatc    420
gtcatgataa atgttgatgg cgatagcatg atgcccacgc tttgcccaaa ggacctgctt    480
ttcatagaca gcaaggttga acaattcagc ggcgacggcg tttatgtgtt caattttgaa    540
gacagtacgt tcgttaaacg tttgcagaag gtaaagggc gccgactggc agttctttca    600
gacaatgaac attacccgcc cttcttcata gaggagcatg aaatgaatga actatacata    660
ttcggcaagc taatcagatg cttacctcta aaaatgatag agtttggcta a             711

<210> SEQ ID NO 193
<211> LENGTH: 198
<212> TYPE: DNA
<213> ORGANISM: Escherichia coli

<400> SEQUENCE: 193
ctatttaaag agcttcttca gcttgtcctc aaccttcctg atttcggaag taagctggct     60
gctgttgaca ttgatagtag ctccacatcg acaagtgaaa cttttgttcg acttgagcca    120
agcgattttc ttcttcgtct tagtgccgca cttagggcat gcgggtaacg taatttcctg    180
gttatcaaaa gcgcccat                                                  198

<210> SEQ ID NO 194
<211> LENGTH: 918
<212> TYPE: DNA
<213> ORGANISM: Escherichia coli

<400> SEQUENCE: 194
atgaataatc cgttttttcaa aaatatgttg gtgtatcgca ttagtcgcga tttcaccatc     60
aaccaggaag agctggaaca gcagcttgaa ctatttcgct tcactccatg cggtagccag    120
gatatggcaa aaaccggttg ggtatcacca cttggtcagc tgtcagatcg cttgcatcac    180
actgtcaata atcaagtgtt gttggttatt cgccgggaag aaaaaatact gccatctcct    240
gtcattactg aagaactgcg caagcgtgtg tcgcgtctag aatccgatca ggggcgtcgc    300
ctcaaaaaaa ctgagaaaga ttcgctgcgt gatgaagtgt tgcactccct gcttcctcgg    360
gcgttctcca aaaactcgac tgttggtttg tggatcaacg tcaccgacgg tctgatcatg    420
gttgatgcag ccagcgctaa acgtgccgaa gactcactgg ccctgcttcg taaaactctc    480
ggttctctcc cggtggtacc gctgactatg aaacgccga tcgaactaac tatgaccgac    540
tgggttcgtt ccggtagtgc gcctgctggc tttggcctgg gtgatgaagc cgaactgaaa    600
gctattcttg aagatggcgg tattggacgc tttaaaaaac agactctggt cagtgacgaa    660
attcatgtgc atctggaagc tgcaaagta gttacaaagc tgtctatcga ctggcaacag    720
cgcattcagt tcgttctttg cgatgacggc agcatcaaac gccttaagtt ctctaatgag    780
attacagaac aaaacgacga tatcgaccgt gaggatgcgg ctcagcggtt cgacgctgac    840
tttgttctga tgaccggcga gcttatctct ctcattaacg gattaacaac ctctctcggc    900
ggcgaagcca agcgataa                                                  918

<210> SEQ ID NO 195
<211> LENGTH: 540
<212> TYPE: DNA
```

<213> ORGANISM: Escherichia coli

<400> SEQUENCE: 195

```
atgagctaca ttcagacatt atccggcaaa cattttaatt acctcgatat ccaacaggac    60
gatatcgtga tcgaggatat tgctaccgcg ttgtctcata tctgccgctt tgcagggcat   120
cttcctgagt tttacagtgt cggccagcat agcgttttaa ccagccacct cgttccgcag   180
gagtttgcat tagaagcact gcttcatgat gctgctgaag cctacctgca ggacatcccc   240
tccccactta agcgcctgct tccggattac caggcaatcg aagctcgtgt ggacgcagcc   300
attcggcaga agttcggtct accaactgag caacacccaa ccgtgaaata tgccgacctg   360
gtgatgctcg ccagcgaacg ccgcgatttt gagattgacg aaggttccat ttggccatgc   420
ctcgagggag ttgtcccaac ggatttattc attatcaacc cagttcgtcc tggccagtca   480
tacggcatgt tcatcaatcg ctttaacgag ttgatggagc agcgccaatg cgccgcatga   540
```

<210> SEQ ID NO 196
<211> LENGTH: 255
<212> TYPE: DNA
<213> ORGANISM: Escherichia coli

<400> SEQUENCE: 196

```
atgaccgtat ttgaatatct ccaggctcat ccgaatacca ccagcggtga atcgccaaa     60
ggtatgaaca aaaagacccc agcggtcgcc ggagcattat ctcagctcta tggcaccggt   120
cggatcgtga agtctggtgt tcgcaagggt attccaacat accgcattaa cgatatgccg   180
tttggttgca gtaacagcct aaccatgatg tttaaccagc tcttgagcag agccagacaa   240
ggagcagccc aatga                                                    255
```

<210> SEQ ID NO 197
<211> LENGTH: 348
<212> TYPE: DNA
<213> ORGANISM: Escherichia coli

<400> SEQUENCE: 197

```
atgacagcac tcaacaaaca ggcgctgcgt gaagaattcc agttcatgca ggacaactat    60
agcgacccgg cagaccacga tcggcaggtg atttacatcg aggcggaggc gctgctggat   120
gagttggaag ccaaagactc aacgatagca gcacaacaac atgagatccg tatgttgctg   180
aatgcgcttg aggaaaaacc atgcccgaaa tgcaacgaca caggaatgac tgatagtggc   240
ggcacgcagc catggggcga gccgattgag attgaatgcg actgccgaca gcaggatgcc   300
aacaccgcag aacttgtagc cgctggcatt ggcgtgaagg gggagtga                348
```

<210> SEQ ID NO 198
<211> LENGTH: 309
<212> TYPE: DNA
<213> ORGANISM: Escherichia coli

<400> SEQUENCE: 198

```
atggataaat taatcaaacc taccgccaaa ggtaaatatg acggttcatg tgattatctt    60
tgctcggaag atgcgcgatt catcgttatg cgcggcgatt atacggaagc ggaaataatt   120
caggcttctg tgtctcaaga tgtaatcgac tcggatggtg cggctgattt tgcaagtagc   180
gcccgctatt atcagtgctg gtacaaagtt agcccaatag gtggtcagga tggctattca   240
ggctggcatc atcctcgtga ttcgccgtgt cgcggtgcat atttcgcatc agttttgcaa   300
tgggattaa                                                           309
```

<210> SEQ ID NO 199
<211> LENGTH: 468
<212> TYPE: DNA
<213> ORGANISM: Escherichia coli

<400> SEQUENCE: 199

```
atgacaacta caaccaccc ggcgcacggt cctgtatcac tcgatcgcct gcaccagata      60
cgcgaacacc tgctgcatga tacccaatac tcaaacggcg ggaacagagc ctacattctc    120
gctgatgtat tgaaggtgat tgatggggct attgcccgcg agctggtacg ccgtgagcat    180
gcagcgtggt cacaggctac tttcggcgat gtcggtccag ttggtccgct gaagcacctt    240
tccaaagaag cgctcgaggc tgctgctgaa ccaggcgacc ttagcgaatg gctgacatg     300
caattcctgt tatgggatgc gcaacgtcgt gccggtatca gtgatgagca gattacccag    360
gcaatgataa aaaagctggc tataaataag gttcgccaat ggcctgagcc gaaagacggg    420
gaacctcgat tgcatatcaa agaacagtca gagcaggaga aaaaataa                 468
```

<210> SEQ ID NO 200
<211> LENGTH: 255
<212> TYPE: DNA
<213> ORGANISM: Escherichia coli

<400> SEQUENCE: 200

```
atgtttagcc tgattcggcg cggtcaaatc tacacggaca gtagcaactg gcccgtaatt     60
atccatagct gtagtgatca ctcggtccga attaaacgca atgatggcga gctgagaacg    120
attagcatca aacgctttaa cgaagatttt gaacgagtgg agcatgatga gtatcgcaaa    180
atatgtgccg aaatagagca ggaaacaaac ctgaaaaacc tacgtgcgat gcgtcgcggc    240
aagattactg aatag                                                     255
```

<210> SEQ ID NO 201
<211> LENGTH: 570
<212> TYPE: DNA
<213> ORGANISM: Escherichia coli

<400> SEQUENCE: 201

```
gtgaacaact taatgatcga ccttgagtcc atgggcaaaa aaccgaatgc ccctattgtc      60
tccattggtg ccgtattctt cgatccgcaa agcggtgaac tgggtcagga gttttacacc    120
gctgttaatc ttgaaagcgc tatggagcag ggagcggtgc cggatggtga cactattctg    180
tggtggttaa gacaaagctc agaagcacga tcagcaatct gtgttgatga tgcgatgccg    240
atatcatctg ccctatctga actgagccat tcattaatc ggcattctga taaccctaaa     300
tatttaaaag tttggggcaa tggagctact ttcgacaacg ttatattgcg cggcgcatat    360
gagcgtgccg gccaggtttg cccgtggcaa ttttggaatg atcacgacgt cagaaccatc    420
gtcacattag gcagatctgt aggtttcgat cctaagcgtg atatgccatt tgatggggtt    480
gcacataacg cactggctga tgcccgccac caggcgaaat atgtttcagc gatttggcag    540
aaactaatcc caaccaccag caacagctaa                                     570
```

<210> SEQ ID NO 202
<211> LENGTH: 237
<212> TYPE: DNA
<213> ORGANISM: Escherichia coli

<400> SEQUENCE: 202

```
atgagcaata ttttccagtt agctcccaac gattgggttt gtgaaagcgt tttgatcgcg      60
gttactgggc tcaaacccgg aaccatcctc cgtgccagaa aagaatgctg gatgattggg     120
agggagtata tccacgtatc gcctgacgga atcctaaac cttccagtga gtgcatgtat      180
aacagaaagg ctgtagatgc ctgggtcgct tcaatgaaaa gcaagcaacc agggtga       237
```

<210> SEQ ID NO 203
<211> LENGTH: 1314
<212> TYPE: DNA
<213> ORGANISM: Escherichia coli

<400> SEQUENCE: 203

```
atggataaag tcacatatcc aacaggcgtc gaaaaccacg gtggcacatt acgcatctgg     60
tttaatttta aggtaagcg tgtcagggaa agtctcggtg tccctgacac cgctaagaac     120
aggaagatag ccggggaact gcggacatca gtatgttttg ccatccgcac aggaaccttt    180
gattatgcaa cccagtttcc tgactcccct aacctcaagg cttttggtgt aagtaaaaaa    240
gacattacag tgaaagaact tgaagaaaaa tggctggatc tgaaacggat ggaaatctgc    300
gcgaacgcat ttaatcgcta tgaatctgtc gcaaggaata tggtgccgag atcggaggt    360 aatcgcctgg tgtcagcagt aaccaaagag gaattgctgt atctgaggaa atatttgcta    420
actggttatc agaatccgac gaaaaacaaa gccccggcaa aagggcgaag cgttgttact    480
gtgaactatt acatgacgac aatggccgga atgtttcagt ttgctgcgga tcacggttac    540
ttagaggtga acccattcga gggaattaag cctctgaaaa aagccagggc agaaccagat    600
cctctgtctc gtgatgaatt tattcgcctg atagatgcat gccggcatca gcagacgaaa    660
aacctgtggt cattagcagt gtacacagga atgcgtcacg gggaactggt ctccctggcc    720
tgggaagata tcgacctgaa ggctggaaca attaccgtca gacgtaatta tacgaaactt    780
ggtgagttca ctctaccgaa aaccgaggca agcacagatc gagtggtgca tcttatccag    840
cccgcaatca gtatcctgaa aaatcaggct gaaatgacaa ggctgggcag gcaatatcac    900
attgaagtgc agttacgtga gtacggccgt tcggtgaacc atgagtgtac attcgtcttt    960
aatccgcatg tggtcagacg cagtaagcag gtcggattta tctaccgggt cgattcagta   1020
ggcgactcat gggaagcggc acttaagcgt gcggggatca gacacagaaa ggcgtaccag   1080
tcacgacaca cctatgcgtg ctggtcatta tcagctggtg caaaccctag ttttattgcc   1140
agtcagatgg ggcatgcgag cgcgcagatg gtgttcaatg tttacggtgc atggatggct   1200
gacagcagcg cagagcagat cgcaatgctg aatcagaagc tggcagattt tgccccattg   1260
atgccccata gccacgagaa cagtacggga ggattattaa aatcagtaag ttaa         1314
```

<210> SEQ ID NO 204
<211> LENGTH: 726
<212> TYPE: DNA
<213> ORGANISM: Escherichia coli

<400> SEQUENCE: 204

```
gtggagggta acaccacgct ttatgccctg ccgaaacccg aggttgtcct gcgctggcgt     60
gagcagacca cagatgactt ccgcttctgt tttaagtttc cggcgaccat ttcgcatcag    120
gcagcattac ggcattgcga tgatttagtg actgaatttt tgacccgcat gtcaccgttg    180
gctccgcgca ttggacaata ctggctgcaa ctgcctgcca cattcggccc acgggagctg    240
cctgcgcttt ggcattttct cgattctctt cccggtgaat taattatgg ggtggaagtc    300 cgccatccac agtttttcgc caaaggggaa gaggaacaaa cgcttaatcg cggtttacat    360
```

```
cagcgcggcg ttaatcgggt gattttagac agccgcccgg ttcatgcagc acgtccatac    420
agtgaagcta ttcgcgacgc tcaacgaaaa aaacctaaag ttccggtaca tgctgtactg    480
acggcgaaaa atccactgat ccgtttatc ggtagtgatg atatgacgca aaaccgggaa    540
ttatttcagg tctggttaca aaaattagcg cagtggcatc agaccactac gccttatctt    600
tttttacata cgccagatat tgcccaggcc ccggaactgg tacataccct gtgggaagac    660
ttacgtaaaa cgcttccaga gatcggagca gttccggcta ttccacagca atcttctctt    720
ttctga                                                               726

<210> SEQ ID NO 205
<211> LENGTH: 396
<212> TYPE: DNA
<213> ORGANISM: Escherichia coli

<400> SEQUENCE: 205
atggtaagcg cgctgtatgc cgttttaagt gcgttgttat taatgaagtt ctcttttgat     60
gtcgttcgcc tgcgaatgca gtaccgcgtt gcctatggcg acggcggttt tagcgaactg    120
caaagcgcta ttcgcattca tggtaacgcg gtggaatata ttcctatcgc gattgtgttg    180
atgctgttta tggaaatgaa tggcgcagaa acctggatgg tgcatatttg cggcatcgtt    240
ttgcttgctg gtcgtctgat gcattattac ggttttcatc accgtctgtt ccgctggcga    300
cgttctggca tgagcgccac ctggtgtgcg ctgttgctga tggtgctggc gaatctttgg    360
tatatgccct gggagttggt tttctccctg cgttag                              396

<210> SEQ ID NO 206
<211> LENGTH: 744
<212> TYPE: DNA
<213> ORGANISM: Escherichia coli

<400> SEQUENCE: 206
atgtctcacc gcgacacgct attttctgcc cctatcgcca gactgggcga ctggaccttt     60
gatgaacggg tagctgaagt cttcccggat atgatccagc gttccgttcc cggctattcc    120
aatattattt ccatgattgg tatgttagcc gagcgcttcg ttcaacctgg tacgcaggtt    180
tacgatctgg gttgttctct gggcgcggcg acgctctcgg tgcgtcgcaa cattcatcat    240
gataattgca aaattattgc catcgacaac tccccggcga tgattgaacg ctgccgtcgt    300
catattgacg cctataaagc ccctacgcca gtagacgtta tgaaggtga tattcgcgat    360 atcgccattg aaaacgcatc gatggtggtg ctgaatttta ccctgcaatt cctggaacct    420
tccgagcgcc aggcgttact ggataaaatt tatcaagggc tgaacccggg cggtgcgctg    480
gtgctttcgg aaaaattcag tttcgaagat gccaagttg tgaactgct gttcaacatg    540 caccacgact taaacgtgc caacggttac agcgaactgg agatcagcca gaaacgcagc    600
atgctggaaa acgtgatgct gaccgattcc gtggaacccc ataaagcacg cctgcataaa    660
gccggttttg agcatagcga gctgtggttc cagtgcttta actttggttc actggtggca    720
ttaaaagcag aggacgctgc atga                                           744

<210> SEQ ID NO 207
<211> LENGTH: 972
<212> TYPE: DNA
<213> ORGANISM: Escherichia coli

<400> SEQUENCE: 207
```

```
atgatcgact ttggtaactt ttattctctg attgccaaaa atcatctttc acactggctc    60
gaaacgctgc ccgcgcagat tgctaactgg cagcgcgagc agcagcacgg gctgtttaag   120
cagtggtcca acgcggtgga atttctgcct gaaattaaac cgtatcgtct ggatttattg   180
catagcgtaa ccgccgaaag cgaagagcca ctgagcgccg ggcaaattaa gcgcattgaa   240
acgctgatgc gcaacctgat gccgtggcgc aaagggccgt tctcactgta tggcgtcaac   300
atcgataccg aatggcgttc cgactggaaa tgggatcgcg ttatgcccca tctttctgat   360
ttaaccgggc gcaccattct tgatgtcggc tgtggcagcg gttatcacat gtggcgcatg   420
attggcgcag gggcgcatct ggcggtgggt atcgatccca cgcagctatt cctctgccag   480
tttgaagcag tgcgtaaact gctgggtaac gatcagcgcg cacatttgtt accgttaggt   540
attgaacaac ttccggcact gaaagccttt gataccgtct tttcgatggg cgtgctttat   600
catcgtcgtt caccgctgga gcatctctgg cagttaaaag accaactggt gaatgaaggc   660
gaactggtgc tggaaacgct ggttattgat ggcgacgaaa acacggtgct ggtgccgggc   720
gatcgttacg ctcaaatgcg taatgtctat ttcattcctt ccgcgctggc gctgaaaaac   780
tggctgaaga gtgtggtttt tgttgatatt cgcattgcag atgtgagcgt taccaccaca   840
gaagagcagc gacgcaccga atggatggtc accgagtctc tggccgattt tctcgacccg   900
catgatccgg gtaaaacggg ggaaggttat cctgcgccta aacgcgcggt gctgattgcg   960
cgcaagccgt aa                                                       972
```

<210> SEQ ID NO 208
<211> LENGTH: 323
<212> TYPE: PRT
<213> ORGANISM: Escherichia coli

<400> SEQUENCE: 208

```
Met Glu Thr Lys Lys Asn Asn Ser Glu Tyr Ile Pro Glu Phe Asp Lys
1               5                   10                  15

Ser Phe Arg His Pro Arg Tyr Trp Gly Ala Trp Leu Gly Val Ala Ala
                20                  25                  30

Met Ala Gly Ile Ala Leu Thr Pro Pro Lys Phe Arg Asp Pro Ile Leu
            35                  40                  45

Ala Arg Leu Gly Arg Phe Ala Gly Arg Leu Gly Lys Ser Ser Arg Arg
        50                  55                  60

Arg Ala Leu Ile Asn Leu Ser Leu Cys Phe Pro Glu Arg Ser Glu Ala
65                  70                  75                  80

Glu Arg Glu Ala Ile Val Asp Glu Met Phe Ala Thr Ala Pro Gln Ala
                85                  90                  95

Met Val Met Met Ala Glu Leu Ala Ile Arg Gly Pro Glu Lys Ile Gln
            100                 105                 110

Pro Arg Val Asp Trp Gln Gly Leu Glu Ile Ile Glu Glu Ile Arg Arg
        115                 120                 125

Asn Asn Glu Lys Val Ile Phe Leu Val Pro His Gly Trp Ala Val Asp
    130                 135                 140

Ile Pro Ala Met Leu Met Ala Ser Gln Gly Gln Lys Met Ala Ala Met
145                 150                 155                 160

Phe His Asn Gln Gly Asn Pro Val Phe Asp Tyr Val Trp Asn Thr Val
                165                 170                 175

Arg Arg Arg Phe Gly Gly Arg Leu His Ala Arg Asn Asp Gly Ile Lys
            180                 185                 190

Pro Phe Ile Gln Ser Val Arg Gln Gly Tyr Trp Gly Tyr Tyr Leu Pro
```

```
            195                 200                 205
Asp Gln Asp His Gly Pro Glu His Ser Glu Phe Val Asp Phe Phe Ala
210                 215                 220

Thr Tyr Lys Ala Thr Leu Pro Ala Ile Gly Arg Leu Met Lys Val Cys
225                 230                 235                 240

Arg Ala Arg Val Val Pro Leu Phe Pro Ile Tyr Asp Gly Lys Thr His
                245                 250                 255

Arg Leu Thr Ile Gln Val Arg Pro Pro Met Asp Asp Leu Leu Glu Ala
            260                 265                 270

Asp Asp His Thr Ile Ala Arg Arg Met Asn Glu Glu Val Glu Ile Phe
        275                 280                 285

Val Gly Pro Arg Pro Glu Gln Tyr Thr Trp Ile Leu Lys Leu Leu Lys
290                 295                 300

Thr Arg Lys Pro Gly Glu Ile Gln Pro Tyr Lys Arg Lys Asp Leu Tyr
305                 310                 315                 320

Pro Ile Lys

<210> SEQ ID NO 209
<211> LENGTH: 440
<212> TYPE: PRT
<213> ORGANISM: Escherichia coli

<400> SEQUENCE: 209

Met Gln Gln Ile Ala Arg Ser Val Ala Leu Ala Phe Asn Asn Leu Pro
1               5                   10                  15

Arg Pro His Arg Val Met Leu Gly Ser Leu Thr Val Leu Thr Leu Ala
            20                  25                  30

Val Ala Val Trp Arg Pro Tyr Val Tyr His Arg Asp Ala Thr Pro Ile
        35                  40                  45

Val Lys Thr Ile Glu Leu Glu Gln Asn Glu Ile Arg Ser Leu Leu Pro
    50                  55                  60

Glu Ala Ser Glu Pro Ile Asp Gln Ala Ala Gln Glu Asp Glu Ala Ile
65                  70                  75                  80

Pro Gln Asp Glu Leu Asp Asp Lys Ile Ala Gly Glu Ala Gly Val His
                85                  90                  95

Glu Tyr Val Val Ser Thr Gly Asp Thr Leu Ser Ser Ile Leu Asn Gln
            100                 105                 110

Tyr Gly Ile Asp Met Gly Asp Ile Thr Gln Leu Ala Ala Ala Asp Lys
        115                 120                 125

Glu Leu Arg Asn Leu Lys Ile Gly Gln Gln Leu Ser Trp Thr Leu Thr
    130                 135                 140

Ala Asp Gly Glu Leu Gln Arg Leu Thr Trp Glu Val Ser Arg Arg Glu
145                 150                 155                 160

Thr Arg Thr Tyr Asp Arg Thr Ala Ala Asn Gly Phe Lys Met Thr Ser
                165                 170                 175

Glu Met Gln Gln Gly Glu Trp Val Asn Asn Leu Leu Lys Gly Thr Val
            180                 185                 190

Gly Gly Ser Phe Val Ala Ser Ala Arg Asn Ala Gly Leu Thr Ser Ala
        195                 200                 205

Glu Val Ser Ala Val Ile Lys Ala Met Gln Trp Gln Met Asp Phe Arg
    210                 215                 220

Lys Leu Lys Lys Gly Asp Glu Phe Ala Val Leu Met Ser Arg Glu Met
225                 230                 235                 240

Leu Asp Gly Lys Arg Glu Gln Ser Gln Leu Leu Gly Val Arg Leu Arg
```

```
                        245                 250                 255
Ser Glu Gly Lys Asp Tyr Tyr Ala Ile Arg Ala Glu Asp Gly Lys Phe
            260                 265                 270

Tyr Asp Arg Asn Gly Thr Gly Leu Ala Lys Gly Phe Leu Arg Phe Pro
        275                 280                 285

Thr Ala Lys Gln Phe Arg Ile Ser Ser Asn Phe Asn Pro Arg Arg Thr
    290                 295                 300

Asn Pro Val Thr Gly Arg Val Ala Pro His Arg Gly Val Asp Phe Ala
305                 310                 315                 320

Met Pro Gln Gly Thr Pro Val Leu Ser Val Gly Asp Gly Glu Val Val
            325                 330                 335

Val Ala Lys Arg Ser Gly Ala Ala Gly Tyr Tyr Val Ala Ile Arg His
        340                 345                 350

Gly Arg Ser Tyr Thr Thr Arg Tyr Met His Leu Arg Lys Ile Leu Val
    355                 360                 365

Lys Pro Gly Gln Lys Val Lys Arg Gly Asp Arg Ile Ala Leu Ser Gly
370                 375                 380

Asn Thr Gly Arg Ser Thr Gly Pro His Leu His Tyr Glu Val Trp Ile
385                 390                 395                 400

Asn Gln Gln Ala Val Asn Pro Leu Thr Ala Lys Leu Pro Arg Thr Glu
            405                 410                 415

Gly Leu Thr Gly Ser Asp Arg Arg Glu Phe Leu Ala Gln Ala Lys Glu
        420                 425                 430

Ile Val Pro Gln Leu Arg Phe Asp
    435                 440

<210> SEQ ID NO 210
<211> LENGTH: 310
<212> TYPE: PRT
<213> ORGANISM: Escherichia coli

<400> SEQUENCE: 210

Met Leu His Lys Lys Thr Leu Leu Phe Ala Ala Leu Ser Ala Ala Leu
1               5                   10                  15

Trp Gly Gly Ala Thr Gln Ala Ala Asp Ala Ala Val Val Ala Ser Leu
            20                  25                  30

Lys Pro Val Gly Phe Ile Ala Ser Ala Ile Ala Asp Gly Val Thr Glu
        35                  40                  45

Thr Glu Val Leu Leu Pro Asp Gly Ala Ser Glu His Asp Tyr Ser Leu
    50                  55                  60

Arg Pro Ser Asp Val Lys Arg Leu Gln Asn Ala Asp Leu Val Val Trp
65                  70                  75                  80

Val Gly Pro Glu Met Glu Ala Phe Met Gln Lys Pro Val Ser Lys Leu
            85                  90                  95

Pro Glu Ala Lys Gln Val Thr Ile Ala Gln Leu Glu Asn Val Lys Pro
        100                 105                 110

Leu Leu Met Lys Ser Ile His Gly Asp Asp Asp Asp His Asp His Ala
    115                 120                 125

Glu Lys Ser Asp Glu Asp His His Gly Asp Phe Asn Met His Leu
130                 135                 140

Trp Leu Ser Pro Glu Ile Ala Arg Ala Thr Ala Val Ala Ile His Gly
145                 150                 155                 160

Lys Leu Val Glu Leu Met Pro Gln Ser Arg Ala Lys Leu Asp Ala Asn
            165                 170                 175
```

Leu Lys Asp Phe Glu Ala Gln Leu Ala Ser Thr Glu Lys Gln Val Gly
            180                 185                 190

Asn Glu Leu Ala Pro Leu Lys Gly Lys Gly Tyr Phe Val Phe His Asp
        195                 200                 205

Ala Tyr Gly Tyr Phe Glu Lys Gln Phe Gly Leu Thr Pro Leu Gly His
    210                 215                 220

Phe Thr Val Asn Pro Glu Ile Gln Pro Gly Ala Gln Arg Leu His Glu
225                 230                 235                 240

Ile Arg Thr Gln Leu Val Glu Gln Lys Ala Thr Cys Val Phe Ala Glu
                245                 250                 255

Pro Gln Phe Arg Pro Ala Val Val Glu Ser Val Ala Arg Gly Thr Ser
            260                 265                 270

Val Arg Met Gly Thr Leu Asp Pro Leu Gly Thr Asn Ile Lys Leu Gly
        275                 280                 285

Lys Thr Ser Tyr Ser Glu Phe Leu Asn Gln Leu Ala Asn Gln Tyr Ala
    290                 295                 300

Ser Cys Leu Lys Gly Asp
305                 310

<210> SEQ ID NO 211
<211> LENGTH: 251
<212> TYPE: PRT
<213> ORGANISM: Escherichia coli

<400> SEQUENCE: 211

Met Thr Ser Leu Val Ser Leu Glu Asn Val Ser Val Ser Phe Gly Gln
1               5                   10                  15

Arg Arg Val Leu Ser Asp Val Ser Leu Glu Leu Lys Pro Gly Lys Ile
            20                  25                  30

Leu Thr Leu Leu Gly Pro Asn Gly Ala Gly Lys Ser Thr Leu Val Arg
        35                  40                  45

Val Val Leu Gly Leu Val Thr Pro Asp Glu Gly Val Ile Lys Arg Asn
    50                  55                  60

Gly Lys Leu Arg Ile Gly Tyr Val Pro Gln Lys Leu Tyr Leu Asp Thr
65                  70                  75                  80

Thr Leu Pro Leu Thr Val Asn Arg Phe Leu Arg Leu Arg Pro Gly Thr
                85                  90                  95

His Lys Glu Asp Ile Leu Pro Ala Leu Lys Arg Val Gln Ala Gly His
            100                 105                 110

Leu Ile Asn Ala Pro Met Gln Lys Leu Ser Gly Gly Glu Thr Gln Arg
        115                 120                 125

Val Leu Leu Ala Arg Ala Leu Leu Asn Arg Pro Gln Leu Leu Val Leu
    130                 135                 140

Asp Glu Pro Thr Gln Gly Val Asp Val Asn Gly Gln Val Ala Leu Tyr
145                 150                 155                 160

Asp Leu Ile Asp Gln Leu Arg Arg Glu Leu Asp Cys Gly Val Leu Met
                165                 170                 175

Val Ser His Asp Leu His Leu Val Met Ala Lys Thr Asp Glu Val Leu
            180                 185                 190

Cys Leu Asn His His Ile Cys Cys Ser Gly Thr Pro Glu Val Val Ser
        195                 200                 205

Leu His Pro Glu Phe Ile Ser Met Phe Gly Pro Arg Gly Ala Glu Gln
    210                 215                 220

Leu Gly Ile Tyr Arg His His Asn His Arg His Asp Leu Gln Gly
225                 230                 235                 240

-continued

```
Arg Ile Val Leu Arg Arg Gly Asn Asp Arg Ser
            245                 250

<210> SEQ ID NO 212
<211> LENGTH: 261
<212> TYPE: PRT
<213> ORGANISM: Escherichia coli

<400> SEQUENCE: 212

Met Ile Glu Leu Leu Phe Pro Gly Trp Leu Ala Gly Ile Met Leu Ala
1               5                   10                  15

Cys Ala Ala Gly Pro Leu Gly Ser Phe Val Val Trp Arg Arg Met Ser
            20                  25                  30

Tyr Phe Gly Asp Thr Leu Ala His Ala Ser Leu Leu Gly Val Ala Phe
        35                  40                  45

Gly Leu Leu Leu Asp Val Asn Pro Phe Tyr Ala Val Ile Ala Val Thr
    50                  55                  60

Leu Leu Leu Ala Gly Gly Leu Val Trp Leu Glu Lys Arg Pro Gln Leu
65                  70                  75                  80

Ala Ile Asp Thr Leu Leu Gly Ile Met Ala His Ser Ala Leu Ser Leu
                85                  90                  95

Gly Leu Val Val Val Ser Leu Met Ser Asn Ile Arg Val Asp Leu Met
            100                 105                 110

Ala Tyr Leu Phe Gly Asp Leu Leu Ala Val Thr Pro Glu Asp Leu Ile
        115                 120                 125

Ser Ile Ala Ile Gly Val Val Ile Val Ala Ile Leu Phe Trp Gln
    130                 135                 140

Trp Arg Asn Leu Leu Ser Met Thr Ile Ser Pro Asp Leu Ala Phe Val
145                 150                 155                 160

Asp Gly Val Lys Leu Gln Arg Val Lys Leu Leu Met Leu Val Thr
                165                 170                 175

Ala Leu Thr Ile Gly Val Ala Met Lys Phe Val Gly Ala Leu Ile Ile
            180                 185                 190

Thr Ser Leu Leu Ile Ile Pro Ala Ala Thr Ala Arg Arg Phe Ala Arg
        195                 200                 205

Thr Pro Glu Gln Met Ala Gly Val Ala Val Leu Val Gly Met Val Ala
    210                 215                 220

Val Thr Gly Gly Leu Thr Phe Ser Ala Phe Tyr Asp Thr Pro Ala Gly
225                 230                 235                 240

Pro Ser Val Val Leu Cys Ala Ala Leu Leu Phe Ile Ile Ser Met Met
                245                 250                 255

Lys Lys Gln Ala Ser
            260

<210> SEQ ID NO 213
<211> LENGTH: 336
<212> TYPE: PRT
<213> ORGANISM: Escherichia coli

<400> SEQUENCE: 213

Met Ile Glu Ala Asp Arg Leu Ile Ser Ala Gly Thr Thr Leu Pro Glu
1               5                   10                  15

Asp Val Ala Asp Arg Ala Ile Arg Pro Lys Leu Leu Glu Glu Tyr Val
            20                  25                  30

Gly Gln Pro Gln Val Arg Ser Gln Met Glu Ile Phe Ile Lys Ala Ala
        35                  40                  45
```

```
Lys Leu Arg Gly Asp Ala Leu Asp His Leu Leu Ile Phe Gly Pro Pro
         50                  55                  60

Gly Leu Gly Lys Thr Thr Leu Ala Asn Ile Val Ala Asn Glu Met Gly
 65                  70                  75                  80

Val Asn Leu Arg Thr Thr Ser Gly Pro Val Leu Glu Lys Ala Gly Asp
                 85                  90                  95

Leu Ala Ala Met Leu Thr Asn Leu Glu Pro His Asp Val Leu Phe Ile
            100                 105                 110

Asp Glu Ile His Arg Leu Ser Pro Val Val Glu Val Leu Tyr Pro
            115                 120                 125

Ala Met Glu Asp Tyr Gln Leu Asp Ile Met Ile Gly Glu Gly Pro Ala
        130                 135                 140

Ala Arg Ser Ile Lys Ile Asp Leu Pro Pro Phe Thr Leu Ile Gly Ala
145                 150                 155                 160

Thr Thr Arg Ala Gly Ser Leu Thr Ser Pro Leu Arg Asp Arg Phe Gly
                165                 170                 175

Ile Val Gln Arg Leu Glu Phe Tyr Gln Val Pro Asp Leu Gln Tyr Ile
                180                 185                 190

Val Ser Arg Ser Ala Arg Phe Met Gly Leu Glu Met Ser Asp Asp Gly
        195                 200                 205

Ala Leu Glu Val Ala Arg Arg Ala Arg Gly Thr Pro Arg Ile Ala Asn
    210                 215                 220

Arg Leu Leu Arg Arg Val Arg Asp Phe Ala Glu Val Lys His Asp Gly
225                 230                 235                 240

Thr Ile Ser Ala Asp Ile Ala Ala Gln Ala Leu Asp Met Leu Asn Val
                245                 250                 255

Asp Ala Glu Gly Phe Asp Tyr Met Asp Arg Lys Leu Leu Leu Ala Val
            260                 265                 270

Ile Asp Lys Phe Phe Gly Gly Pro Val Gly Leu Asp Asn Leu Ala Ala
        275                 280                 285

Ala Ile Gly Glu Glu Arg Glu Thr Ile Glu Asp Val Leu Glu Pro Tyr
    290                 295                 300

Leu Ile Gln Gln Gly Phe Leu Gln Arg Thr Pro Arg Gly Arg Met Ala
305                 310                 315                 320

Thr Val Arg Ala Trp Asn His Phe Gly Ile Thr Pro Pro Glu Met Pro
                325                 330                 335

<210> SEQ ID NO 214
<211> LENGTH: 203
<212> TYPE: PRT
<213> ORGANISM: Escherichia coli

<400> SEQUENCE: 214

Met Ile Gly Arg Leu Arg Gly Ile Ile Ile Glu Lys Gln Pro Pro Leu
 1               5                  10                  15

Val Leu Ile Glu Val Gly Gly Val Gly Tyr Glu Val His Met Pro Met
                20                  25                  30

Thr Cys Phe Tyr Glu Leu Pro Glu Ala Gly Gln Glu Ala Ile Val Phe
            35                  40                  45

Thr His Phe Val Val Arg Glu Asp Ala Gln Leu Leu Tyr Gly Phe Asn
        50                  55                  60

Asn Lys Gln Glu Arg Thr Leu Phe Lys Glu Leu Ile Lys Thr Asn Gly
 65                  70                  75                  80

Val Gly Pro Lys Leu Ala Leu Ala Ile Leu Ser Gly Met Ser Ala Gln
```

```
                    85                  90                  95

Gln Phe Val Asn Ala Val Glu Arg Glu Val Gly Ala Leu Val Lys
                   100                 105                 110

Leu Pro Gly Ile Gly Lys Lys Thr Ala Glu Arg Leu Ile Val Glu Met
            115                 120                 125

Lys Asp Arg Phe Lys Gly Leu His Gly Asp Leu Phe Thr Pro Ala Ala
        130                 135                 140

Asp Leu Val Leu Thr Ser Pro Ala Ser Pro Ala Thr Asp Asp Ala Glu
145                 150                 155                 160

Gln Glu Ala Val Ala Ala Leu Val Ala Leu Gly Tyr Lys Pro Gln Glu
                165                 170                 175

Ala Ser Arg Met Val Ser Lys Ile Ala Arg Pro Asp Ala Ser Ser Glu
            180                 185                 190

Thr Leu Ile Arg Glu Ala Leu Arg Ala Ala Leu
        195                 200

<210> SEQ ID NO 215
<211> LENGTH: 200
<212> TYPE: PRT
<213> ORGANISM: Escherichia coli

<400> SEQUENCE: 215

Met Asn Ile Asn Tyr Pro Ala Glu Tyr Glu Ile Gly Asp Ile Val Phe
1               5                   10                  15

Thr Cys Ile Ser Ala Ala Leu Phe Gly Gln Ile Ser Ala Ala Ser Asn
                20                  25                  30

Cys Trp Ser Asn His Val Gly Ile Ile Gly His Asn Gly Glu Asp
            35                  40                  45

Phe Leu Val Ala Glu Ser Arg Val Pro Leu Ser Thr Ile Thr Thr Leu
    50                  55                  60

Ser Arg Phe Ile Lys Arg Ser Ala Asn Gln Arg Tyr Ala Ile Lys Arg
65                  70                  75                  80

Leu Asp Ala Gly Leu Thr Glu Gln Gln Asn Gln Arg Ile Val Glu Gln
                85                  90                  95

Val Pro Ser Arg Leu Arg Lys Ile Tyr His Thr Gly Phe Lys Tyr Glu
                100                 105                 110

Ser Ser Arg Gln Phe Cys Ser Lys Phe Val Phe Asp Ile Tyr Lys Glu
            115                 120                 125

Ala Leu Cys Ile Pro Val Gly Glu Ile Glu Thr Phe Gly Glu Leu Leu
        130                 135                 140

Asn Ser Asn Pro Asn Ala Lys Leu Thr Phe Trp Lys Phe Trp Phe Leu
145                 150                 155                 160

Gly Ser Ile Pro Trp Glu Arg Lys Thr Val Thr Pro Ala Ser Leu Trp
                165                 170                 175

His His Pro Gly Leu Val Leu Ile His Ala Val Gly Val Glu Thr Pro
            180                 185                 190

Gln Pro Glu Leu Thr Glu Ala Val
        195                 200

<210> SEQ ID NO 216
<211> LENGTH: 173
<212> TYPE: PRT
<213> ORGANISM: Escherichia coli

<400> SEQUENCE: 216

Met Ala Ile Ile Leu Gly Ile Asp Pro Gly Ser Arg Val Thr Gly Tyr
```

-continued

```
1               5                   10                  15
Gly Val Ile Arg Gln Val Gly Arg Gln Leu Ser Tyr Leu Gly Ser Gly
            20                  25                  30

Cys Ile Arg Thr Lys Val Asp Asp Leu Pro Ser Arg Leu Lys Leu Ile
            35                  40                  45

Tyr Ala Gly Val Thr Glu Ile Ile Thr Gln Phe Gln Pro Asp Tyr Phe
 50                         55                  60

Ala Ile Glu Gln Val Phe Met Ala Lys Asn Ala Asp Ser Ala Leu Lys
 65                     70                  75                  80

Leu Gly Gln Ala Arg Gly Val Ala Ile Ala Ala Val Asn Gln Glu
                85                  90                  95

Leu Pro Val Phe Glu Tyr Ala Ala Arg Gln Val Lys Gln Thr Val Val
                100                 105                 110

Gly Ile Gly Ser Ala Glu Lys Ser Gln Val Gln His Met Val Arg Thr
                115                 120                 125

Leu Leu Lys Leu Pro Ala Asn Pro Gln Ala Asp Ala Ala Asp Ala Leu
 130                    135                 140

Ala Ile Ala Ile Thr His Cys His Val Ser Gln Asn Ala Met Gln Met
 145                    150                 155                 160

Ser Glu Ser Arg Leu Asn Leu Ala Arg Gly Arg Leu Arg
                165                 170
```

<210> SEQ ID NO 217
<211> LENGTH: 246
<212> TYPE: PRT
<213> ORGANISM: Escherichia coli

<400> SEQUENCE: 217

```
Met Ala Gly His Ser Lys Trp Ala Asn Thr Arg His Arg Lys Ala Ala
 1                  5                   10                  15

Gln Asp Ala Lys Arg Gly Lys Ile Phe Thr Lys Ile Ile Arg Glu Leu
                20                  25                  30

Val Thr Ala Ala Lys Leu Gly Gly Gly Asp Pro Asp Ala Asn Pro Arg
            35                  40                  45

Leu Arg Ala Ala Ile Asp Lys Ala Leu Ser Asn Asn Met Thr Arg Asp
 50                     55                  60

Thr Leu Asn Arg Ala Ile Ala Arg Gly Val Gly Gly Asp Asp Ala
 65                     70                  75                  80

Asn Met Glu Thr Ile Ile Tyr Glu Gly Tyr Gly Pro Gly Gly Thr Ala
                85                  90                  95

Ile Met Ile Glu Cys Leu Ser Asp Asn Arg Asn Arg Thr Val Ala Glu
                100                 105                 110

Val Arg His Ala Phe Ser Lys Cys Gly Gly Asn Leu Gly Thr Asp Gly
                115                 120                 125

Ser Val Ala Tyr Leu Phe Ser Lys Lys Gly Val Ile Ser Phe Glu Lys
 130                    135                 140

Gly Asp Glu Asp Thr Ile Met Glu Ala Ala Leu Glu Ala Gly Ala Glu
 145                    150                 155                 160

Asp Val Val Thr Tyr Asp Asp Gly Ala Ile Asp Val Tyr Thr Ala Trp
                165                 170                 175

Glu Glu Met Gly Lys Val Arg Asp Ala Leu Glu Ala Ala Gly Leu Lys
                180                 185                 190

Ala Asp Ser Ala Glu Val Ser Met Ile Pro Ser Thr Lys Ala Asp Met
 195                    200                 205
```

```
Asp Ala Glu Thr Ala Pro Lys Leu Met Arg Leu Ile Asp Met Leu Glu
    210                 215                 220
Asp Cys Asp Asp Val Gln Glu Val Tyr His Asn Gly Glu Ile Ser Asp
225                 230                 235                 240
Glu Val Ala Ala Thr Leu
                245

<210> SEQ ID NO 218
<211> LENGTH: 147
<212> TYPE: PRT
<213> ORGANISM: Escherichia coli

<400> SEQUENCE: 218

Met Ala Tyr Lys Arg Pro Val Ser Ile Leu Val Val Ile Tyr Ala Gln
1                 5                   10                  15
Asp Thr Lys Arg Val Leu Met Leu Gln Arg Arg Asp Asp Pro Asp Phe
                20                  25                  30
Trp Gln Ser Val Thr Gly Ser Val Glu Glu Gly Glu Thr Ala Pro Gln
            35                  40                  45
Ala Ala Met Arg Glu Val Lys Glu Glu Val Thr Ile Asp Val Val Ala
        50                  55                  60
Glu Gln Leu Thr Leu Ile Asp Cys Gln Arg Thr Val Glu Phe Glu Ile
65                  70                  75                  80
Phe Ser His Leu Arg His Arg Tyr Ala Pro Gly Val Thr Arg Asn Thr
                85                  90                  95
Glu Ser Trp Phe Cys Leu Ala Leu Pro His Glu Arg Gln Ile Val Phe
            100                 105                 110
Thr Glu His Leu Ala Tyr Lys Trp Leu Asp Ala Ser Ala Ala Ala Ala
        115                 120                 125
Leu Thr Lys Ser Trp Ser Asn Arg Gln Ala Ile Glu Gln Phe Val Ile
    130                 135                 140
Asn Ala Ala
145

<210> SEQ ID NO 219
<211> LENGTH: 590
<212> TYPE: PRT
<213> ORGANISM: Escherichia coli

<400> SEQUENCE: 219

Met Arg Thr Glu Tyr Cys Gly Gln Leu Arg Leu Ser His Val Gly Gln
1                 5                   10                  15
Gln Val Thr Leu Cys Gly Trp Val Asn Arg Arg Arg Asp Leu Gly Ser
                20                  25                  30
Leu Ile Phe Ile Asp Met Arg Asp Arg Glu Gly Ile Val Gln Val Phe
            35                  40                  45
Phe Asp Pro Asp Arg Ala Asp Ala Leu Lys Leu Ala Ser Glu Leu Arg
        50                  55                  60
Asn Glu Phe Cys Ile Gln Val Thr Gly Thr Val Arg Ala Arg Asp Glu
65                  70                  75                  80
Lys Asn Ile Asn Arg Asp Met Ala Thr Gly Glu Ile Glu Val Leu Ala
                85                  90                  95
Ser Ser Leu Thr Ile Ile Asn Arg Ala Asp Val Leu Pro Leu Asp Ser
            100                 105                 110
Asn His Val Asn Thr Glu Glu Ala Arg Leu Lys Tyr Arg Tyr Leu Asp
        115                 120                 125
```

```
Leu Arg Arg Pro Glu Met Ala Gln Arg Leu Lys Thr Arg Ala Lys Ile
130                 135                 140

Thr Ser Leu Val Arg Arg Phe Met Asp Asp His Gly Phe Leu Asp Ile
145                 150                 155                 160

Glu Thr Pro Met Leu Thr Lys Ala Thr Pro Glu Gly Ala Arg Asp Tyr
                165                 170                 175

Leu Val Pro Ser Arg Val His Lys Gly Lys Phe Tyr Ala Leu Pro Gln
                180                 185                 190

Ser Pro Gln Leu Phe Lys Gln Leu Leu Met Met Ser Gly Phe Asp Arg
        195                 200                 205

Tyr Tyr Gln Ile Val Lys Cys Phe Arg Asp Glu Asp Leu Arg Ala Asp
210                 215                 220

Arg Gln Pro Glu Phe Thr Gln Ile Asp Val Glu Thr Ser Phe Met Thr
225                 230                 235                 240

Ala Pro Gln Val Arg Glu Val Met Glu Ala Leu Val Arg His Leu Trp
                245                 250                 255

Leu Glu Val Lys Gly Val Asp Leu Gly Asp Phe Pro Val Met Thr Phe
                260                 265                 270

Ala Glu Ala Glu Arg Arg Tyr Gly Ser Asp Lys Pro Asp Leu Arg Asn
        275                 280                 285

Pro Met Glu Leu Thr Asp Val Ala Asp Leu Leu Lys Ser Val Glu Phe
290                 295                 300

Ala Val Phe Ala Gly Pro Ala Asn Asp Pro Lys Gly Arg Val Ala Ala
305                 310                 315                 320

Leu Arg Val Pro Gly Gly Ala Ser Leu Thr Arg Lys Gln Ile Asp Glu
                325                 330                 335

Tyr Gly Asn Phe Val Lys Ile Tyr Gly Ala Lys Gly Leu Ala Tyr Ile
                340                 345                 350

Lys Val Asn Glu Arg Ala Lys Gly Leu Glu Gly Ile Asn Ser Pro Val
        355                 360                 365

Ala Lys Phe Leu Asn Ala Glu Ile Ile Glu Ala Ile Leu Glu Arg Thr
370                 375                 380

Gly Ala Gln Asp Gly Asp Met Ile Phe Phe Gly Ala Asp Asn Lys Lys
385                 390                 395                 400

Ile Val Ala Asp Ala Met Gly Ala Leu Arg Leu Lys Val Gly Lys Asp
                405                 410                 415

Leu Gly Leu Thr Asp Glu Ser Lys Trp Ala Pro Leu Trp Val Ile Asp
                420                 425                 430

Phe Pro Met Phe Glu Asp Gly Glu Gly Leu Thr Ala Met His
        435                 440                 445

His Pro Phe Thr Ser Pro Lys Asp Met Thr Ala Ala Glu Leu Lys Ala
        450                 455                 460

Ala Pro Glu Asn Ala Val Ala Asn Ala Tyr Asp Met Val Ile Asn Gly
465                 470                 475                 480

Tyr Glu Val Gly Gly Gly Ser Val Arg Ile His Asn Gly Asp Met Gln
                485                 490                 495

Gln Thr Val Phe Gly Ile Leu Gly Ile Asn Glu Glu Glu Gln Arg Glu
                500                 505                 510

Lys Phe Gly Phe Leu Leu Asp Ala Leu Lys Tyr Gly Thr Pro Pro His
        515                 520                 525

Ala Gly Leu Ala Phe Gly Leu Asp Arg Leu Thr Met Leu Leu Thr Gly
530                 535                 540

Thr Asp Asn Ile Arg Asp Val Ile Ala Phe Pro Lys Thr Thr Ala Ala
```

```
                    545                 550                 555                 560
Ala Cys Leu Met Thr Glu Ala Pro Ser Phe Ala Asn Pro Thr Ala Leu
                565                 570                 575

Ala Glu Leu Ser Ile Gln Val Val Lys Lys Ala Glu Asn Asn
                580                 585                 590

<210> SEQ ID NO 220
<211> LENGTH: 188
<212> TYPE: PRT
<213> ORGANISM: Escherichia coli

<400> SEQUENCE: 220

Met Leu Glu Leu Asn Ala Lys Thr Thr Ala Leu Val Val Ile Asp Leu
1               5                   10                  15

Gln Glu Gly Ile Leu Pro Phe Ala Gly Gly Pro His Thr Ala Asp Glu
            20                  25                  30

Val Val Asn Arg Ala Gly Lys Leu Ala Ala Lys Phe Arg Ala Ser Gly
        35                  40                  45

Gln Pro Val Phe Leu Val Arg Val Gly Trp Ser Ala Asp Tyr Ala Glu
    50                  55                  60

Ala Leu Lys Gln Pro Val Asp Ala Pro Ser Pro Ala Lys Val Leu Pro
65                  70                  75                  80

Glu Asn Trp Trp Gln His Pro Ala Ala Leu Gly Ala Thr Asp Ser Asp
                85                  90                  95

Ile Glu Ile Ile Lys Arg Gln Trp Gly Ala Phe Tyr Gly Thr Asp Leu
            100                 105                 110

Glu Leu Gln Leu Arg Arg Arg Gly Ile Asp Thr Ile Val Leu Cys Gly
        115                 120                 125

Ile Ser Thr Asn Ile Gly Val Glu Ser Thr Ala Arg Asn Ala Trp Glu
130                 135                 140

Leu Gly Phe Asn Leu Val Ile Ala Glu Asp Ala Cys Ser Ala Ala Ser
145                 150                 155                 160

Ala Glu Gln His Asn Asn Ser Ile Asn His Ile Tyr Pro Arg Ile Ala
                165                 170                 175

Arg Val Arg Ser Val Glu Glu Ile Leu Asn Ala Leu
            180                 185

<210> SEQ ID NO 221
<211> LENGTH: 129
<212> TYPE: PRT
<213> ORGANISM: Escherichia coli

<400> SEQUENCE: 221

Met Gly Phe Pro Ser Pro Ala Ala Asp Tyr Val Glu Thr Arg Ile Ser
1               5                   10                  15

Leu Asp Gln Gln Leu Ile Ser Gln Pro Ala Ala Thr Tyr Phe Met Arg
            20                  25                  30

Ala Ser Arg Ser His Phe Arg Glu Gly Ile Ile Gln Gly Ala Leu Leu
        35                  40                  45

Val Val Asp Ala Ser Leu Thr Ala Cys Asp Gly Ser Leu Leu Ile Cys
    50                  55                  60

Ala Ile Asp Gly Glu Phe Arg Ile Lys Arg Tyr Arg Thr His Pro Gln
65                  70                  75                  80

Pro His Leu Val Asn Leu Asp Asn Gly Arg Arg Glu Ala Leu Pro Ala
                85                  90                  95

Asp Asp Asp Gly Tyr Ser Ser Ala Pro Ala Ile Phe Gly Val Ile Thr
```

```
                    100                 105                 110
Tyr Ile Ile Asn Asp Ala Arg Asn Ala Glu Phe Asp Asp Cys Pro Val
            115                 120                 125
Met

<210> SEQ ID NO 222
<211> LENGTH: 80
<212> TYPE: PRT
<213> ORGANISM: Escherichia coli

<400> SEQUENCE: 222

Met Phe Val Glu Leu Val Tyr Asp Lys Arg Asn Phe Asp Gly Leu Pro
1               5                   10                  15

Gly Ala Lys Asp Ile Ile Leu Gly Glu Leu Thr Lys Arg Val His Arg
            20                  25                  30

Ile Phe Pro Asp Ala Asp Val Arg Val Lys Pro Met Met Thr Leu Pro
        35                  40                  45

Ala Ile Asn Thr Asp Ala Ser Lys His Glu Lys Glu Gln Ile Ser Arg
    50                  55                  60

Thr Val Gln Glu Met Phe Glu Glu Ala Glu Phe Trp Leu Val Ser Glu
65                  70                  75                  80

<210> SEQ ID NO 223
<211> LENGTH: 126
<212> TYPE: PRT
<213> ORGANISM: Escherichia coli

<400> SEQUENCE: 223

Met Leu Trp Arg Ile Phe Ile Phe Val Asn Val Gly Leu Gly Glu Ala
1               5                   10                  15

Ala Lys Arg Asn Val Gly Thr Gly Glu Asn Gln Ile Pro Asp Met Ser
            20                  25                  30

Ala Phe Pro Ser Gly Asn Asn Trp Phe Gln Leu Pro Ser Gly His Ile
        35                  40                  45

Val Gln Ile Phe Ser Met Asn Val Leu Gly Ala Asp Ala Asn Gly Thr
    50                  55                  60

Ser Ala Asn Tyr Pro Ile Ala Phe Pro Thr Thr Met Ile Ala Val Ser
65                  70                  75                  80

Ala Leu Trp Ser Asp Gly Thr Val Ala Asn Ala Pro Thr Tyr Lys Met
            85                  90                  95

Met Gly Asn Thr Thr Asn Arg Thr Thr Leu Thr Ile Lys Val Ser Ala
            100                 105                 110

Ser Ser Gly Thr Tyr Gly Thr Met Ile Ile Ala Val Gly Arg
            115                 120                 125

<210> SEQ ID NO 224
<211> LENGTH: 147
<212> TYPE: PRT
<213> ORGANISM: Escherichia coli

<400> SEQUENCE: 224

Met Asn Lys Tyr Ser Tyr Ser Pro Ser Glu Asn Ala Phe Tyr Ala Val
1               5                   10                  15

Ala Leu Lys Asn Thr Tyr Glu Leu Ser Gly Thr Trp Pro Ala Asp Ala
            20                  25                  30

Leu Asp Ile Pro Asp Asp Ile Ser Val Lys Tyr Met Ala Glu Pro Pro
        35                  40                  45
```

```
Gln Gly Lys Ile Arg Val Ala Gly Glu Asn Gly Phe Pro Thr Trp Ala
 50                  55                  60
Glu Ile Pro Pro Ser His Glu Leu Ile Glu Gln Ala Glu Ser
 65              70                  75                  80
Glu Arg Gln Leu Leu Ile Asn Gln Ala Asn Glu Tyr Met Asn Ser Lys
                 85                  90                  95
Gln Trp Pro Gly Lys Ala Ala Ile Gly Arg Leu Lys Gly Glu Glu Leu
            100                 105                 110
Ala Gln Tyr Asn Ser Trp Leu Asp Tyr Leu Asp Ala Leu Glu Leu Val
            115                 120                 125
Asp Thr Ser Gly Thr Pro Asp Ile Glu Trp Pro Thr Pro Pro Ala Val
130                 135                 140
Gln Ala Arg
145

<210> SEQ ID NO 225
<211> LENGTH: 197
<212> TYPE: PRT
<213> ORGANISM: Escherichia coli

<400> SEQUENCE: 225

Met Lys Pro Val Phe Asp Glu Asn Gly Leu Ala Ala Val Pro Gly Asp
  1               5                  10                  15
Met Arg Cys Phe Tyr Tyr Asp Ala Val Thr Ser Glu Tyr Thr Gly Trp
                 20                  25                  30
Ser Asp Glu Tyr Ile Asn Thr Gly Val Ser Met Pro Ala Cys Ser Thr
             35                  40                  45
Gly Ile Asp Pro Asp Glu Asn Ile Pro Gly Arg Val Ala Val Phe Thr
 50                  55                  60
Gly Lys Gly Trp Ser His Glu Glu Asp His Arg Asn Glu Thr Val Tyr
 65                  70                  75                  80
Ser Ile Glu Asn Gly Ala Ala Val Thr Val Asp Tyr Ile Gly Ala Ile
                 85                  90                  95
Lys Asn Gly Tyr Val Thr Leu Ser Pro Leu Thr Pro Tyr Asp Lys Trp
            100                 105                 110
Asp Gly Glu Lys Trp Val Thr Asp Thr Glu Ala Gln His Gly Ala Ser
            115                 120                 125
Val Glu Ala Ala Glu Ala Gln Arg Gln Ser Leu Ile Asp Ala Ala Met
130                 135                 140
Ala Ser Ile Ser Leu Ile Gln Leu Lys Leu Gln Ala Gly Arg Lys Leu
145                 150                 155                 160
Thr Gln Ala Glu Thr Thr Arg Leu Asn Ala Val Leu Asp Tyr Ile Asp
                165                 170                 175
Ala Val Thr Ala Thr Asp Thr Ser Thr Ala Pro Asp Val Ile Trp Pro
            180                 185                 190
Glu Leu Pro Glu Ala
        195

<210> SEQ ID NO 226
<211> LENGTH: 310
<212> TYPE: PRT
<213> ORGANISM: Escherichia coli

<400> SEQUENCE: 226

Met Ile Tyr Ser Thr Gly Thr Ile Ser Ile Asn Gly Asn Thr Ala Thr
  1               5                  10                  15
```

Gly Ser Gly Thr Asn Trp Thr Ala Pro Ala Ser Gln Val Arg Ala Gly
            20                  25                  30

Gln Thr Ile Ile Val Met Ser Asn Pro Val Gln Leu Phe Gln Ile Ser
            35                  40                  45

Ser Val Asn Ser Ala Thr Ser Met Thr Val Thr Pro Ala Val Ser Pro
 50                  55                  60

Ala Leu Ser Gly Gln Lys Tyr Gly Ile Leu Val Ser Asp Asn Ile Ser
 65                  70                  75                  80

Val Asp Gly Leu Ala Gln Ala Met Ser Gln Leu Ile Lys Glu Tyr Asp
                85                  90                  95

Glu Asn Ile Gly Ala Trp Glu Thr Phe Ala Thr Thr Ser Ala Asn Gln
            100                 105                 110

Ser Ile Thr Val Thr Ile Asn Gly Thr Ala Val Thr Ile Pro Gly Ile
            115                 120                 125

Gly Lys Leu Ala Gln Lys Gly Ser Asn Gly Ala Val Thr Val Ala Asp
            130                 135                 140

Gly Gly Thr Gly Ala Thr Asn Ala Ala Asp Ala Arg Thr Asn Leu Gly
145                 150                 155                 160

Leu Gly Glu Gly Ser Pro Ala Ile Gly Val Pro Phe Trp Pro Ser
                165                 170                 175

Ala Ala Met Pro Asn Thr Val Ile Asp Ser Trp Ser Ser Met Val Phe
            180                 185                 190

Leu Lys Phe Asn Gly Ala Lys Phe Ser Ala Thr Asp Tyr Pro Val Leu
            195                 200                 205

Ala Lys Val Phe Pro Ser Leu Val Leu Pro Glu Ala Arg Gly Asp Phe
            210                 215                 220

Ile Arg Val Trp Asp Asp Gly Arg Gly Ala Asp Gly Gly Arg Glu Leu
225                 230                 235                 240

Leu Ser Trp Gln Glu Ala Thr Asn Phe Ser Gln Phe Ala Gly Asn Ile
                245                 250                 255

Gly Gly Gly Ala Gly His Ala Ile Asn Phe His Asp Gly Ile Ala Gly
            260                 265                 270

Asn Gln Pro Gly Phe Ser Arg Phe Asn Phe Asn Ser Asn Ser Val Gly
            275                 280                 285

Asp Gly Val Asn Phe Val Ala Val Arg Pro Arg Asn Ile Ala Phe Asn
            290                 295                 300

Phe Leu Val Arg Ala Lys
305                 310

<210> SEQ ID NO 227
<211> LENGTH: 1308
<212> TYPE: PRT
<213> ORGANISM: Escherichia coli

<400> SEQUENCE: 227

Met Gly Glu Lys Met Gln Leu Leu Lys Gln Glu Thr Ile Leu Gln Gly
1               5                   10                  15

Ala Lys Gly Gly Gly Ser Ser His Thr Pro Val Glu Gln Pro Asp
            20                  25                  30

Asp Leu Leu Ser Val Ala Lys Leu Lys Met Leu Ile Ala Val Ser Glu
            35                  40                  45

Gly Glu Ile Gln Gly Asp Leu Thr Ala Gln Asn Ile Phe Leu Asn Asp
 50                  55                  60

Thr Pro Leu Ala Asn Asp Ser Gly Glu Tyr Asn Phe Ser Gly Val Lys
 65                  70                  75                  80

```
Trp Glu Phe Arg Lys Gly Thr Gln Asp Gln Thr Tyr Ile Ala Gly Met
                85                  90                  95

Pro Gln Val Asp Asn Glu Leu Ala Val Gly Thr Val Thr Thr Thr
               100                 105                 110

Ala Pro Trp Thr Arg Gln Phe Thr Asn Leu Ser Leu Asp Ala Ile Arg
               115                 120                 125

Ile Lys Leu Ser Leu Pro Val Gln Tyr Leu Tyr Lys Asp Asn Gly Asp
130                 135                 140

Met Val Gly Thr Val Thr Glu Tyr Ala Ile Asp Leu Ser Thr Asp Gly
145                 150                 155                 160

Gly Ala Trp Lys Thr Val Val Asn Gly Lys Phe Asp Gly Lys Thr Thr
               165                 170                 175

Thr Glu Tyr Gln Arg Asp His Arg Ile Asp Leu Pro Lys Ser Thr Ser
               180                 185                 190

Gly Trp Ser Val Arg Val Arg Arg Ile Thr Ala Asp Ala Ser Gly Ser
               195                 200                 205

Asn Ser Lys Leu Val Asn Ala Phe Lys Val Phe Ser Tyr Ala Glu Val
               210                 215                 220

Ile Asp Ser Lys Leu Arg Tyr Pro Leu Thr Ala Leu Leu Tyr Val Glu
225                 230                 235                 240

Val Asp Ser Ser Gln Phe Asn Gly Ser Ala Pro Lys Val Thr Cys Lys
               245                 250                 255

Ile Lys Gly Lys Leu Ile Lys Val Pro Asp Asn Tyr Asp Pro Lys Thr
               260                 265                 270

Arg Thr Tyr Ser Gly Ser Trp Ser Gly Gly Phe Lys Met Ala Trp Ser
               275                 280                 285

Asn Asn Pro Ala Trp Ile Phe Tyr Asp Leu Val Leu Asp Glu Ile Tyr
               290                 295                 300

Gly Met Gly Thr Arg Val Asp Ala Ser Met Val Asp Lys Trp Ala Leu
305                 310                 315                 320

Tyr Ser Ile Ala Gln Tyr Cys Asp Glu Met Val Ser Asp Gly Ala Gly
               325                 330                 335

Gly Thr Glu Pro Arg Phe Thr Cys Asn Val Phe Ile Gln Ser Gln Glu
               340                 345                 350

Asp Ala Trp Gln Val Leu Asn Asp Leu Ala Ala Val Phe Arg Gly Ile
               355                 360                 365

Thr Phe Trp Gly Asn Asp Gln Ile Tyr Val Gln Ala Asp Val Pro Gln
370                 375                 380

Asp Asp Val Asp Trp Val Tyr Asn Val Ser Asn Val Ile Asp Gly Leu
385                 390                 395                 400

Phe Thr Tyr Ala Gly Gly Ser Tyr Lys Asn Arg Tyr Ser Ser Cys Leu
               405                 410                 415

Val Ser Trp Ser Asp Pro Gln Asn His Tyr Ser Asp Thr Val Glu Gly
               420                 425                 430

Val Tyr Asp Ser Ala Leu Val Glu Arg Tyr Asp Val Arg Gln Thr Ser
               435                 440                 445

Leu Thr Ala Ile Gly Cys Thr Ser Gln Ser Glu Ala His Arg Arg Gly
               450                 455                 460

Arg Trp Val Leu Leu Ser Asn Ala Lys Asp Gly Thr Val Ser Phe Gly
465                 470                 475                 480

Val Gly Leu Asp Gly Tyr Ile Pro Leu Pro Ala Glu Ile Ile Gly Val
               485                 490                 495
```

Ala Asp Pro Phe Arg Ser Gly Lys Glu Asn Gly Gly Arg Ile Ser Ala
            500                 505                 510

Ala Asn Gly Arg Gln Ile Thr Leu Asp Arg Glu Ile Asp Tyr Ala Ala
        515                 520                 525

Lys Asp Arg Leu Val Val Asn Leu Pro Asp Gly Lys Ala Gln Thr Arg
    530                 535                 540

Thr Ile Ser Ala Val Ser Ala Asp Lys Lys Thr Val Thr Val Ala Thr
545                 550                 555                 560

Ala Phe Ser Gln Val Pro Val Ala Gly Ala Val Trp Ala Ile Asp Ser
            565                 570                 575

Asp Asn Leu Ala Ile Gln Tyr Phe Arg Val Thr Ser Ile Ala Ala Asn
        580                 585                 590

Asp Asp Ser Thr Gly Gly Phe Thr Ile Thr Ala Val Gln His Asp Pro
    595                 600                 605

Asn Lys Tyr Arg Tyr Ile Asp Asp Gly Val Arg Val Glu Ser Pro Pro
610                 615                 620

Ile Thr Val Thr Pro Ile Ser Val Leu Ser Ala Pro Lys Asn Ile Val
625                 630                 635                 640

Val Thr Glu Ser Asp His Val Ser Gln Gly Leu Thr Val Ala Ser Leu
            645                 650                 655

Asp Val Ser Trp Asp Lys Val Glu Gly Ala Ile Arg Tyr Val Ala Gln
        660                 665                 670

Trp Arg Lys Asp Asn Gly Asp Trp Ile Asn Val Pro Val Thr Ser Ala
    675                 680                 685

Gln Gly Phe Ser Val Gln Gly Ile Tyr Ser Gly Ser Tyr Asp Val Arg
690                 695                 700

Val Arg Ala Leu Asn Ala Gln Asp Thr Ser Ser Pro Trp Gly Tyr Gly
705                 710                 715                 720

Glu Thr Thr Tyr Leu Ser Gly Lys Thr Gly Lys Pro Gly Thr Pro Leu
            725                 730                 735

Asn Phe Leu Ala Thr Glu Asp Val Val Trp His Ile Asp Leu Thr Trp
        740                 745                 750

Lys Phe Pro Asp Gly Ser Gly Asp Thr Ala Tyr Thr Glu Ile Gln Arg
    755                 760                 765

Ala Thr Thr Ala Asp Tyr Ala Asn Pro Glu Leu Leu Val Leu Val Pro
770                 775                 780

Tyr Pro Ala Ala Asp Tyr Gln His Gly Pro Met Pro Ala Gly Val Arg
785                 790                 795                 800

Gln Trp Tyr Arg Ala Arg Leu Ile Asp Arg Ile Gly Asn Ala Gly Asp
            805                 810                 815

Trp Thr Asp Trp Ile Met Gly Thr Ser Ser Ile Asp Val Ser Glu Ile
        820                 825                 830

Thr Asn Asp Ile Leu Glu Asp Met Lys Glu Ser Glu Thr Phe Lys Asp
    835                 840                 845

Leu Ile Glu Asn Ala Val Asp Ser Asn Glu Lys Ile Ala Gly Met Ala
850                 855                 860

Asn Asp Ile Lys Gln Ala Asn Asp Glu Leu Glu Gln Ala Lys Asp
865                 870                 875                 880

Ile Ala Lys Asn Ala Gln Asp Val Gly Lys Val Gln Thr Ser Val Asn
            885                 890                 895

Glu Leu Ser Ser Thr Val Gly Asn Val Ser Ser Leu Ser Gln Leu
        900                 905                 910

Glu Gln Thr Val Ala Thr Ala Asp Thr Ala Leu Gly Gln Arg Ile Asp

-continued

```
            915                 920                 925
Asn Ile Ser Val Ser Met Asp Gly Met Thr Gly Gly Val Lys Asn Ser
            930                 935                 940
Ala Ile Ala Ile Ile Gln Ala Asn Leu Ala Gln Val Ala Thr Arg Lys
945                 950                 955                 960
Thr Leu Ser Ala Ser Val Ala Gly Asn Ser Ala Asn Leu Asp Arg Leu
                965                 970                 975
Asp Glu Val Ile Val Ser Glu Lys Glu Ala Thr Ala Arg Ser Leu Leu
            980                 985                 990
Ser Leu Gln Thr Asp Val Asn Gly Asn Lys Ala Ser Ile Asn Ser Leu
            995                 1000                1005
Asn Gln Thr Leu Ser Asp Tyr Gln Gln Ala Thr Ala Thr Gln Ile
        1010                1015                1020
Asn Gly Ile Thr Ala Thr Val Asn Gly His Thr Ser Ala Ile Thr
        1025                1030                1035
Thr Asn Ala Gln Ala Ile Ala Asn Val Asn Gly Glu Leu Ser Ala
        1040                1045                1050
Met Tyr Asn Ile Lys Val Gly Val Ser Ser Asn Gly Gln Tyr Tyr
        1055                1060                1065
Ala Ala Gly Met Gly Ile Gly Val Glu Asn Thr Pro Ser Gly Met
        1070                1075                1080
Gln Ser Gln Val Ile Phe Leu Ala Asp Arg Phe Ala Val Thr Thr
        1085                1090                1095
Ala Ala Gly Asn Ser Val Ala Leu Pro Phe Val Ile Gln Asn Gly
        1100                1105                1110
Gln Thr Phe Ile Arg Ala Ser Phe Ile Gln Asp Gly Thr Ile Glu
        1115                1120                1125
Asn Ala Lys Ile Gly Asn Tyr Ile Gln Ser Asn Asn Tyr Ala Ala
        1130                1135                1140
Gly Ser Ala Gly Trp Lys Leu Asn Lys Ala Gly Asp Ala Glu Phe
        1145                1150                1155
Asn Asn Val Thr Val Arg Gly Val Val Tyr Ala Ser Gly Gly Ser
        1160                1165                1170
Phe Thr Gly Glu Ile Gln Ala Thr Ser Gly Lys Phe Lys Gly Thr
        1175                1180                1185
Val Glu Ala Gln Ser Phe Ile Gly Asp Ile Ala Asn Met His Thr
        1190                1195                1200
Gly Thr Asn Val Ser Arg Ser Ser Asp Gly Tyr Leu Glu Lys Val
        1205                1210                1215
Met Thr Tyr Asn Asp Ser Ser Ser Gly His Ala Arg His Val
        1220                1225                1230
Cys Val Ile Ala Asn Val Lys Gly Asn Gly Ala Gly Thr Ile Asp
        1235                1240                1245
Ile Asn Gly Asn Glu Ser Gly Ser Ser Val Gln Asp Met Glu Arg
        1250                1255                1260
Leu Ile Met His Ser Ala Val Val Thr Gly Pro Asn Val Thr Val
        1265                1270                1275
Arg Ile Lys Val Ser Ala Gln Asn Asn Arg Gly Ala Ser Ile Ser
        1280                1285                1290
Ser Pro Thr Ile Ile Val Ser His Gly Ser Gly Ser Phe Thr Gly
        1295                1300                1305
```

<210> SEQ ID NO 228

<211> LENGTH: 205
<212> TYPE: PRT
<213> ORGANISM: Escherichia coli

<400> SEQUENCE: 228

Met Val Lys Thr Leu Ile Leu Glu Gly Lys Met Ala Lys Lys Phe Gly
1               5                   10                  15

Lys Arg Val Gln Phe Asp Val Ala Asp Leu Arg Glu Met Leu Arg Ala
            20                  25                  30

Met Cys Ser Gln Val Pro Gly Phe Lys Lys Tyr Met Ser Glu Ala His
        35                  40                  45

Met Lys Gly Ile Arg Phe Ala Phe Phe Asn Gly Gly Asn Asn Ile Gly
    50                  55                  60

Leu Glu Glu Phe Asp Met Thr Arg Gly Gly Ser Val Tyr Arg Ile Val
65                  70                  75                  80

Pro Val Tyr Glu Gly Ala Lys Ser Ser Gly Val Leu Gln Ile Val Val
                85                  90                  95

Gly Ala Val Ala Leu Val Ala Ala Phe Phe Thr Ala Gly Ala Ser Met
            100                 105                 110

Ala Ala Trp Gly Ala Ala Met Ser Ala Thr Ala Ile Ser Ala Thr Ser
        115                 120                 125

Ile Leu Thr Gly Val Gly Val Ser Met Met Leu Gly Gly Val Val Gln
    130                 135                 140

Met Leu Thr Pro Gln Pro Ser Phe Gly Ala Gly Lys Ser Ser Ser Thr
145                 150                 155                 160

Asp Asn Thr Pro Asn Tyr Ala Phe Gly Ala Pro Val Asn Thr Val Ala
                165                 170                 175

Met Gly His Pro Val Pro Leu Ala Tyr Gly Leu Thr Glu Ala Gly Gly
            180                 185                 190

Ala Ile Val Ser Ala Gly Met Tyr Ser Ser Asp Gln Gln
        195                 200                 205

<210> SEQ ID NO 229
<211> LENGTH: 239
<212> TYPE: PRT
<213> ORGANISM: Escherichia coli

<400> SEQUENCE: 229

Met Arg Glu Lys Leu Leu Asp Ala Ile Arg Gln His Val Ala Ala Glu
1               5                   10                  15

Tyr Pro Lys Glu Ala Cys Gly Leu Ile Val Gln Ser Gly Gln Gln Gln
            20                  25                  30

Ile Phe Ile Pro Cys Arg Asn Ile Ala Asp Lys Pro Glu Glu Thr Phe
        35                  40                  45

Thr Leu Ser Pro Glu Asp Gln Leu Ala Ala Arg Ala Arg Gly Glu Ile
    50                  55                  60

Ile Met Leu Ile His Ser His Pro Asp Val Val Arg Leu Val Pro Ser
65                  70                  75                  80

Glu Leu Asp Arg Ile Gln Cys Asp Trp Ser Gly Ile Glu Trp Gly Ile
                85                  90                  95

Met Ser Trp Pro Asp Gly Asp Phe Cys Thr Ile Ser Pro Arg Glu Asp
            100                 105                 110

Arg Asp Tyr Ala Gly Arg Gln Trp Val Leu Gly Tyr Ala Asp Cys Trp
        115                 120                 125

Ser Leu Ile Arg Glu Phe Tyr Leu Arg Glu Tyr Gly Ile Val Leu Gly
    130                 135                 140

Asn Tyr Ser Val Pro Tyr Glu Trp Trp Glu Ser Gly Lys Glu Arg Leu
145                 150                 155                 160

Tyr Asp Asp Asn Trp Glu Arg Glu Gly Phe Val Glu Ile Ala Ala Gly
            165                 170                 175

Ala Met Gln Pro Gly Asp Ile Ile Met Met Ser Val Gln Ala Ser Val
        180                 185                 190

Thr Asn His Ala Ala Val Tyr Val Gly Asp Asn Ile Ile Leu His His
    195                 200                 205

Leu Phe Gly His Leu Ser Ser Arg Thr Pro Tyr Gly Lys Tyr Tyr Arg
210                 215                 220

Asp Arg Thr Val Arg Val Val Arg His Lys Asp Arg Met His Gly
225                 230                 235

<210> SEQ ID NO 230
<211> LENGTH: 245
<212> TYPE: PRT
<213> ORGANISM: Escherichia coli

<400> SEQUENCE: 230

Met Ser Phe Thr Ala Asp Ile Gln Gln Leu Glu Pro Gly Ser Val Ile
1               5                   10                  15

Gln Leu Ile Glu Ile Asp Gly Thr Glu Phe Gly Met Asp Gln Val Leu
            20                  25                  30

Arg Phe His Ala His Asn Ile Gln Glu Gly Trp Ala Ala Phe Ala
        35                  40                  45

Ala Glu Asn Leu Pro Ala Ile Ile Trp Gln Gly Asn Gln Tyr Asp Pro
    50                  55                  60

His Pro Tyr Glu Leu Lys Gly Met Glu Leu Ser Ser Thr Gly Ser Gln
65                  70                  75                  80

Pro Thr Pro Thr Leu Ser Val Gly Asn Val Gly Asn Tyr Val Thr Ala
                85                  90                  95

Leu Cys Leu Glu Tyr Asp Asp Met Val Arg Ala Lys Val Lys Ile His
            100                 105                 110

Thr Thr Leu Ser Lys Tyr Leu Asp Ala Ala Asn Trp Lys Asn Gly Asn
        115                 120                 125

Pro Gly Ala Ser Pro Ala Asp Glu Arg Leu Gln Leu Phe Tyr Val Asn
    130                 135                 140

Ala Lys Thr Ala Glu Thr Arg Val Gln Val Asp Phe Glu Leu Cys Ser
145                 150                 155                 160

Pro Phe Asp Ile Gln Ser Leu Gln Leu Pro Thr Arg Gln Ile Thr Pro
                165                 170                 175

Val Cys Thr Trp Cys Met Arg Gly Trp Tyr Arg Ser Gly Thr Gly Cys
            180                 185                 190

Asp Tyr Asn Gly Thr Lys Tyr Phe Thr Lys Asp Gly Thr Pro Thr Asp
        195                 200                 205

Asp Pro Ser Lys Asp Val Cys Gly Gly Arg Arg Gln Asp Cys Gln Asp
    210                 215                 220

Arg His Gly Pro Asp Ala Pro Leu Pro Phe Gly Gly Phe Pro Ala Ala
225                 230                 235                 240

Asn Leu Gln Gly Lys
                245

<210> SEQ ID NO 231
<211> LENGTH: 112
<212> TYPE: PRT

<213> ORGANISM: Escherichia coli

<400> SEQUENCE: 231

Met Thr Asp Thr Phe Thr Trp Arg Thr Arg Lys Thr Ala Gln Gly Thr
1               5                   10                  15

Glu Thr Ala Arg Thr Leu Gln Ala Gln Phe Gly Asp Gly Tyr Lys Gln
            20                  25                  30

Ile Ala Gly Met Gly Ile Asn Asp Lys Gln Glu Thr Trp Asn Leu Asp
        35                  40                  45

Trp Thr Gly Thr Arg Gln Glu Ala Ala Leu Arg Ala Phe Leu Met
    50                  55                  60

Ser His Val Thr Lys Ser Phe Trp Trp Thr Thr Pro Trp Gly Glu Lys
65                  70                  75                  80

Lys Leu Phe Arg Met Lys Ala Asp Ser Phe Ser Val Ser Phe Pro Thr
                85                  90                  95

Gly Lys Lys Ala Thr Val Ala Phe Thr Phe Glu Gln Ala Phe Ala Pro
            100                 105                 110

<210> SEQ ID NO 232
<211> LENGTH: 1045
<212> TYPE: PRT
<213> ORGANISM: Escherichia coli

<400> SEQUENCE: 232

Met Ala Gln Gln Ile Ser Asp Leu Val Ile Asn Leu Asp Val Asp Ser
1               5                   10                  15

Ala Thr Phe Ser Glu Gln Val Ala Arg Ile Lys Gly Gln Leu Thr Gly
            20                  25                  30

Met Ala Glu Asp Ser Glu Lys Val Gln Thr Arg Met Gln Arg Ala Ser
        35                  40                  45

Glu Arg Gln Ala Ala Ala Phe Lys Thr Val Gly Asp Ala Gly Ala Ala
    50                  55                  60

Ala Ala Ala Asp Met Lys Ser Arg Gln Ser Ala Ala Thr Glu Gly Leu
65                  70                  75                  80

Thr Lys Asp Trp Gln Asn Val Ser Lys Ser Val Asp Glu Thr His Arg
                85                  90                  95

Arg Val Thr Glu Leu Asn Gln Arg Met Arg Glu Asn Asp Gly Gln Ala
            100                 105                 110

Ala Ala Leu Ala Arg Arg Gln Asp Glu Leu Ala Ala Ser Phe Phe Arg
        115                 120                 125

Gln Ile Asp Gly Val Arg Gln Leu Asn Gly Glu Thr Gln Ser Leu Ala
    130                 135                 140

Asn Val Gln Ala Arg Phe Arg Ala Ala Arg Ala Gln Gly Asn Ile Thr
145                 150                 155                 160

Gln Gln Asp Tyr Leu Ala Leu Ile Ser Arg Thr Thr Ala Arg Gln Lys
                165                 170                 175

Glu Leu Gln Ile Val Glu Glu Lys Ser Ala Ala Ala Thr Arg Phe
            180                 185                 190

Leu Ser Gln Leu Lys Gln Gln Val Ala Glu Gln Lys Leu Ser Gly Thr
        195                 200                 205

Glu Leu Leu Arg Met Lys Ala Ala Gln Val Gly Ala Ser Asp Ala Ala
    210                 215                 220

Glu Val Tyr Ile Arg Lys Leu Glu Ala Ala Lys Val Ala Thr His Gly
225                 230                 235                 240

Leu Gly Leu Gln Ser Ala Ala Ala Arg Gln Glu Leu Gly Ile Leu Ile

```
                    245                 250                 255
Gly Glu Val Met Arg Gly Asn Phe Gly Ala Leu Arg Gly Ser Gly Ile
                260                 265                 270

Thr Leu Ala Asn Arg Ala Gly Trp Ile Asp Gln Leu Leu Ser Leu Arg
            275                 280                 285

Gly Leu Gly Ile Ala Ser Met Val Gly Ile Ala Ala Ala Val Phe
            290                 295                 300

Gly Leu Gly Lys Ala Trp Tyr Asp Gly Ser Lys Glu Ser Glu Phe
305                 310                 315                 320

Asn Arg Gln Leu Ile Leu Thr Gly Asn Tyr Ala Gly Lys Thr Ser Gly
                325                 330                 335

Gln Leu Gln Ala Leu Ala Arg Ser Leu Ala Gly Asn Gly Ile Thr Gln
            340                 345                 350

His Ala Ala Ala Gly Val Leu Ala Gln Val Val Gly Ser Gly Ala Phe
            355                 360                 365

Ser Gly Asn Asp Val Ser Met Val Ser Asn Val Ala Ala Arg Leu Gln
        370                 375                 380

Gln Ala Thr Gly Gln Ala Val Asp Glu Thr Ile Asn Gln Phe Lys Arg
385                 390                 395                 400

Leu Lys Asp Asp Pro Val Asn Ala Val Ala Thr Leu Asn Asp Ser Leu
                405                 410                 415

His Phe Leu Thr Ala Thr Gln Tyr Glu Gln Ile Ala Ser Ala Gln Ala
            420                 425                 430

Leu Gly Asp Ser Gln Lys Ala Ala Glu Leu Ala Met Arg Ala Tyr Ser
            435                 440                 445

Asp Ala Val Ile Gln Arg Ala Gly Ala Val Glu Asp Asn Leu Gly Ser
        450                 455                 460

Leu Glu Lys Ala Trp Asn Trp Val Lys Asn Ala Ala Ser Gly Ala Trp
465                 470                 475                 480

Asp Ala Met Leu Gly Val Gly Arg Asn Pro Asp Thr Ala Met Lys Arg
                485                 490                 495

Gln Asp Ser Phe Ala Glu Trp Gln Ala Ala Glu Lys Glu Tyr Arg Ala
            500                 505                 510

Leu Ser Ser Asn Leu Lys Val Asp Pro Asp Tyr Ala Gly Asn Asn Val
            515                 520                 525

Leu Gln Lys Ala Asp Ala Glu Arg Leu Arg Asn Ala Arg Gln Gln Val
        530                 535                 540

Glu Leu Lys Lys Gln Ala Tyr Asp Leu Ala Asp Gln Gln Tyr Ala Gln
545                 550                 555                 560

Glu Gly Leu Ala Ala Ala Arg Glu Lys Met Arg Thr Asp Gln Gln Ala
                565                 570                 575

Gln Ala Ile Arg Ser Gln Gln Phe Asn Gln Leu Val Glu Ser Gly
            580                 585                 590

Ala Thr Ala Ala Glu Lys Arg Ala Ser Ala Glu Lys Lys Leu Ser Gln
            595                 600                 605

Leu Ile Glu Lys Asn Arg Gln Asp Ala Lys Asp Gly Val Ala Thr Leu
        610                 615                 620

Trp Thr Glu Lys Asp Ile Ala Ala Arg Ala Gly Ile Glu Lys Gln
625                 630                 635                 640

Trp Lys Asp Pro Lys Thr Pro Lys Gly Lys Ser Tyr Ser Thr Pro Ala
                645                 650                 655

Gly Asp Lys Ala Glu Glu Lys Ala Gln Ala Glu Leu Leu Thr Leu Gln
            660                 665                 670
```

Ala Gln Leu Lys Thr Leu Glu Gln His Thr Ser Val Asn Asp Val Ile
              675                 680                 685

Ser Lys Gln Arg Gln Asp Leu Trp Gln Thr Glu Asn Gln Phe Thr Val
    690                 695                 700

Leu Gln Glu Ala Ala Gly Arg Arg Gln Leu Thr Ala Gln Glu Lys Ser
705                 710                 715                 720

Leu Leu Ala His Lys Glu Glu Thr Leu Glu Tyr Lys Arg Gln Leu Ala
                725                 730                 735

Asp Leu Gly Asp Lys Val Ala Ser Gln Gln Lys Leu Asn Gln Leu Ala
            740                 745                 750

Asp Gln Ala Val Lys Phe Glu Gln Gln Lys Ala Ala Arg Ala Gly
            755                 760                 765

Leu Gln Ala Gln Ser Glu Gly Leu Ser Thr Arg Glu Ala Gly Arg Gln
    770                 775                 780

Thr Thr Leu Gln Arg Leu Ser Glu Ser Tyr Ser Tyr Asn Pro Gln Ala
785                 790                 795                 800

Gln Gln Lys Val Leu Glu Gln Arg Ala Thr Phe Glu Ala Glu Asp
                805                 810                 815

Ala Leu Arg Ala Asn Trp Leu Ala Gly Ala Lys Gln Gly Trp Ala Glu
            820                 825                 830

Tyr Gln Asp Ser Ala Thr Asn Val Phe Ser Val Gln Gln Ile Ser
    835                 840                 845

Gln Ala Thr Phe Ser Gly Leu Ala Gly Gln Leu Thr Ser Leu Thr Thr
    850                 855                 860

Thr Gly Lys Ala Ser Phe Arg Glu Phe Thr Ser Ser Ile Leu Lys Met
865                 870                 875                 880

Ile Val Ser Val Ile Asn Gln Leu Leu Val Ala Tyr Thr Ile Gln Ser
                885                 890                 895

Ala Met Gly Trp Val Ser Gly Ala Lys Thr Ser Ser Ala Gly Gln
            900                 905                 910

Ser Phe Ala Val Pro Ser Tyr Arg Pro Gln Gly Phe Asp Val Gly Gly
    915                 920                 925

Phe Thr Gly His Gly Gly Lys Tyr Glu Pro Ala Gly Ile Val His Arg
    930                 935                 940

Gly Glu Phe Val Phe Thr Lys Glu Ser Thr Ser Arg Ile Gly Val Ala
945                 950                 955                 960

Asn Leu Tyr Arg Leu Met Arg Gly Tyr Ala Ser Gly Leu Val Gly
            965                 970                 975

Gly Gly Asn Ala Ala Gly Ala Gly Met Gly Gly Ile Ser Val Tyr Ala
            980                 985                 990

Pro Val Ser Ile Ser Gln Gln Gly Ser Asp Gly Ser Ile Asn Gln Ala
    995                 1000                1005

Asn Ala Thr Gly Thr Ala Lys Gln Leu Gln Ala Ile Val Gln Gln
    1010                1015                1020

Thr Ile Thr Glu Arg Leu Lys Lys Glu Met Ser Ala Gly Gly Val
    1025                1030                1035

Leu Tyr Ser Arg Arg Thr Gln
    1040                1045

<210> SEQ ID NO 233
<211> LENGTH: 90
<212> TYPE: PRT
<213> ORGANISM: Escherichia coli -continued

<400> SEQUENCE: 233

Met Leu Ala Gly Met Thr Ser Thr Glu Leu Gly Asp Trp His Gln Phe
1               5                   10                  15

Tyr Arg Glu His Tyr Phe Gln Asp Ala Gln Leu Asp Ala His Phe Ser
            20                  25                  30

Glu Leu Leu Tyr Ser Ile Ser Thr Leu Phe Phe Arg Asp Pro Glu Leu
        35                  40                  45

Thr Pro Ala His Phe Ser Leu Leu Ser Pro Ser Gly Ile Val Ile Ser
    50                  55                  60

Asp Asp Glu Pro Asp Asp Ala Leu Met Ala Ala Glu Gly Ile
65                  70                  75                  80

Thr Gly Gly Ile Arg Tyr Gly Pro Ala Asp
                85                  90

<210> SEQ ID NO 234
<211> LENGTH: 143
<212> TYPE: PRT
<213> ORGANISM: Escherichia coli

<400> SEQUENCE: 234

Met Phe Leu Lys Lys Glu Lys Phe Thr Trp Gln Lys Glu Ser Leu Thr
1               5                   10                  15

Ile Phe Glu Leu Ser Ala Leu Gln Arg Ile Glu Tyr Ile Thr Phe Met
            20                  25                  30

Ala Ala Glu Glu Lys Ala Val Ser Ala Ser Asp Ser Asp Gly Ile Ser Asp
        35                  40                  45

Gln Glu Met Thr Ala Arg Leu Ile Gly Ser Asn Ile Arg Cys Gly Ala
    50                  55                  60

Arg Leu Ile Ala Met Ser Leu Trp His Asn Asp Pro Ala Gly Thr Asp
65                  70                  75                  80

Val Glu Thr Leu Tyr Gln Gln Val Leu Ser Gly Trp Pro Pro Glu Ala
                85                  90                  95

Ile Gly Lys Ala Glu Met Glu Ile Lys Leu Leu Ser Gly Met Leu Val
            100                 105                 110

Pro Val Glu Asp Asp Lys Ala Ala Asp Pro Ala Pro Ala Glu Ala
        115                 120                 125

Glu Ser Ala Glu Pro Val Ala Ala Glu Lys Pro Leu Pro Ala Ser
    130                 135                 140

<210> SEQ ID NO 235
<211> LENGTH: 247
<212> TYPE: PRT
<213> ORGANISM: Escherichia coli

<400> SEQUENCE: 235

Met Pro Thr Pro Asn Pro Leu Ala Pro Val Lys Gly Ala Gly Thr Thr
1               5                   10                  15

Leu Trp Leu Tyr Thr Gly Thr Gly Asn Ala Phe Ala Asn Pro Leu Ser
            20                  25                  30

Asp Ile Asp Trp Asn Arg Leu Ala Lys Ile Lys Glu Leu Thr Pro Gly
        35                  40                  45

Glu Met Thr Ala Glu Ser Tyr Asp Asp Thr Tyr Leu Asp Asp Glu Asp
    50                  55                  60

Ala Asp Trp Asn Ala Thr Ala Gln Gly Ala Lys Ser Ala Gly Asp Thr
65                  70                  75                  80

Ser Phe Thr Leu Ala Trp Lys Pro Gly Glu Glu Gly Gln Lys Asp Leu

```
                  85                  90                  95

Val Ala Trp Phe Ile Asp Gly Ser Val Arg Tyr Tyr Lys Ile Lys Tyr
                 100                 105                 110

Pro Asn Gly Thr Val Asp Val Phe Arg Gly Trp Cys Ser Ser Leu Gly
                 115                 120                 125

Lys Ala Ile Pro Ala Lys Glu Val Ile Thr Arg Thr Ala Lys Ile Thr
                 130                 135                 140

Asn Thr Gly Lys Pro Glu Leu Ala Glu Ser Gly Thr Pro Asn Ile
145                 150                 155                 160

Pro Val Thr Gly Val Thr Leu Asp Lys Ala Thr Ala Ser Val Ala Val
                 165                 170                 175

Gly Ala Thr Thr Thr Leu Asn Val Thr Val Asn Pro Ala Ser Ala Ser
                 180                 185                 190

Asp Thr Ser Phe Arg Val Ala Ser Asp Gly Ala Lys Ala Thr Val
                 195                 200                 205

Thr Val Ser Gly Asn Ala Ile Thr Val Thr Gly Val Ala Ala Gly Thr
                 210                 215                 220

Ala Asp Val Ile Val Met Thr Ser Asp Gly Asn Phe Val Ala Val Cys
225                 230                 235                 240

Lys Val Thr Val Thr Ala Ala
                 245

<210> SEQ ID NO 236
<211> LENGTH: 133
<212> TYPE: PRT
<213> ORGANISM: Escherichia coli

<400> SEQUENCE: 236

Met Asn Arg His Ser Ala Ile Arg Ala Ala Ile Leu Ala Lys Leu Lys
1               5                   10                  15

Ala Glu Ile Thr Asp Thr Val Thr Trp Phe Asp Gly Arg Pro Val Phe
                 20                  25                  30

Leu Glu Glu Gln Asp Leu Pro Ala Val Ala Val Tyr Leu Ser Asp Ala
                 35                  40                  45

Glu Tyr Thr Gly Asp Ser Leu Asp Glu Asp Ser Trp Gln Ala Val Val
                 50                  55                  60

His Ile Glu Val Phe Leu Lys Ala Ser Ser Pro Asp Ser Ala Leu Asp
65                  70                  75                  80

Ser Trp Met Glu Glu Lys Val Tyr Pro Ala Met Ala Phe Ile Pro Gly
                 85                  90                  95

Leu Thr Glu Leu Val Glu Thr Phe Thr Pro Gln Gly Tyr Asp Tyr Gln
                 100                 105                 110

Arg Asp Asp Glu Met Ala Thr Trp Gly Ser Val Asp Phe Thr Tyr Leu
                 115                 120                 125

Ile Thr Tyr Ser Ile
    130

<210> SEQ ID NO 237
<211> LENGTH: 190
<212> TYPE: PRT
<213> ORGANISM: Escherichia coli

<400> SEQUENCE: 237

Met Lys Gly Leu Glu Arg Ala Ile Gln Asn Leu Asn Ser Leu Ser Arg
1               5                   10                  15

Leu Ile Val Pro Glu Ala Thr Ala Lys Ala Leu Asn Arg Val Ala Arg
```

```
                  20                  25                  30
Arg Thr Ile Ser Gln Gly Ser Lys Ala Val Ala Lys Glu Ala Thr Val
                35                  40                  45

Asp Asp Asn Arg Lys Lys Gly Leu Pro Val Arg Leu Val Arg Gln Arg
 50                  55                  60

Ser Arg Leu Arg Lys Ala Arg His Asp Arg Pro Val Ala Ser Ile Lys
 65                  70                  75                  80

Ile Asn Arg Gly Asn Leu Pro Ala Ile Lys Leu Gly Thr Ala Arg Val
                85                  90                  95

Arg Leu Ser Arg Lys Lys Gly Ala Arg Asn Gly Ala Gly Ser Val Leu
                100                 105                 110

Lys Ile Gly Pro Tyr Thr Phe Arg Asn Ala Phe Ile Gln Gln Leu Ala
                115                 120                 125

Asn Gly Arg Trp Gln Val Met Arg Arg Val Gly Gln Ala Arg Tyr Pro
                130                 135                 140

Ile Asp Val Val Lys Val Pro Leu Glu Thr Pro Leu Thr Val Ala Phe
145                 150                 155                 160

Thr Ala Ile Ser Lys Arg Leu Ile Glu Ser Asp Met Pro Lys Glu Leu
                165                 170                 175

Ser Ala Ala Leu Lys Asn Gln Leu Arg Ile His Leu Lys Arg
                180                 185                 190

<210> SEQ ID NO 238
<211> LENGTH: 80
<212> TYPE: PRT
<213> ORGANISM: Escherichia coli

<400> SEQUENCE: 238

Met Asp Ala Ala Thr Ile Lys Lys Met Gly Lys Thr Ala Ile Ile Asn
 1               5                  10                  15

Gly Ser Ser Tyr Asp Val Val Pro Ala Glu Gln Leu Glu Glu Met Gly
                20                  25                  30

Pro Leu Ser Gly Thr Gly Thr Ser Leu Val Val Phe Ser Glu Leu Tyr
                35                  40                  45

Gln Pro Arg Arg Asn Asp Ser Val Asp Tyr Asp Gly Lys Asn Leu Ile
                50                  55                  60

Val Thr Arg Tyr Asp Met Phe Asn Gly Lys Pro Arg Ile His Leu Glu
 65                  70                  75                  80

<210> SEQ ID NO 239
<211> LENGTH: 108
<212> TYPE: PRT
<213> ORGANISM: Escherichia coli

<400> SEQUENCE: 239

Met Ala Lys Asn Tyr Ala Gln Asp Gly Lys Thr Ile Pro Leu Val Asn
 1               5                  10                  15

Ser Gly Ala Thr Asp Val His Ser Gly Asp Pro Val Val Gly Lys
                20                  25                  30

Leu Ile Ala Val Ala Ile Thr Asp Ile Pro Ala Gly Asp Thr Gly Asp
                35                  40                  45

Gly Phe Thr Glu Gly Val Phe Leu Leu Pro Lys Val Ser Ala Asp Ala
                50                  55                  60

Val Thr Ala Gly Ala Gln Val Tyr Leu Lys Asp Gly Lys Ile Thr Ile
 65                  70                  75                  80

Glu Glu Thr Asp Ala Val Ala Ala Gly Ile Ala Trp Glu Asp Ala Gly
```

```
                85                  90                  95
Ala Asn Thr Thr Val Val Glu Val Lys Ile Asn Ala
                100                 105

<210> SEQ ID NO 240
<211> LENGTH: 648
<212> TYPE: PRT
<213> ORGANISM: Escherichia coli

<400> SEQUENCE: 240

Met Gln Ala Ser Asn Asn Ser Glu Ala Asp Ile Phe Ile Tyr Asp Glu
1               5                   10                  15

Ile Gly Tyr Trp Gly Val Thr Ala Lys Gln Phe Val Asn Asp Leu Arg
                20                  25                  30

Ala Leu Gly Asp Val Thr His Ile Asn Leu Tyr Ile Asn Ser Pro Gly
            35                  40                  45

Gly Asp Val Phe Asp Gly Ile Ala Ile Tyr Asn Ala Leu Lys His His
        50                  55                  60

Gly Ala Ala Ile Thr Val His Ile Asp Gly Leu Ala Ala Ser Met Ala
65                  70                  75                  80

Ser Val Ile Ala Met Val Gly Asn Pro Val Ile Met Pro Glu Asn Thr
                85                  90                  95

Met Met Met Ile His Lys Pro Trp Gly Phe Ala Gly Asp Ala Ser
                100                 105                 110

Asp Met Arg Asp Tyr Ala Asp Leu Leu Asp Lys Val Glu Ser Val Leu
            115                 120                 125

Ile Pro Ala Tyr Ala Gln Lys Thr Gly Lys Ser Thr Glu Glu Ile Ala
        130                 135                 140

Val Met Leu Glu Asp Glu Thr Trp Met Asn Gly Ser Glu Cys Leu Glu
145                 150                 155                 160

Leu Gly Phe Ala Asp Gln Val Thr Pro Ser Leu Gln Ala Met Ala Cys
                165                 170                 175

Ile His Ser Lys Arg Ile Glu Glu Phe Glu Lys Met Pro Lys Ser Ile
            180                 185                 190

Arg Asn Met Ile Thr Pro Pro Arg Asn Thr Thr Gln Arg Asp Pro Val
        195                 200                 205

Ile Thr Gln Pro Gln Ala Pro Gln Ala Lys Thr Asp Pro Ala Pro Asp
    210                 215                 220

Glu Asn Ala Ile Arg Ala Gln Val Leu Ala Glu Gln Lys Thr Arg Val
225                 230                 235                 240

Asn Ala Ile Gly Asp Leu Phe Ala Met Phe Gly Asn Lys His Met Glu
                245                 250                 255

Leu Gln Asn Gln Cys Val Ala Asp Pro Asp Cys Ser Val Asp Lys Ala
            260                 265                 270

Lys Asp Leu Leu Leu Ala Glu Leu Gly Lys Thr Ala Thr Pro Ser Asn
        275                 280                 285

Lys Thr Thr Gln Pro His Ile His Ala Gly Asn Gly Asn Phe Val Ala
    290                 295                 300

Asp Gly Ile Arg Gln Ala Leu Met Ala Arg Ala Gly Phe Glu Gly Gln
305                 310                 315                 320

Glu Arg Asp Asn Val Tyr Asn Gly Met Thr Leu Arg Glu Tyr Ala Arg
                325                 330                 335

Met Ala Leu Thr Glu Lys Gly Ile Gly Val Ala Ser Tyr Asn Pro Met
            340                 345                 350
```

Gln Met Val Gly Leu Ala Leu Thr His Ser Thr Ser Asp Phe Gly Asn
            355                 360                 365

Ile Leu Leu Asp Val Ala Asn Lys Ala Leu Ile Gln Gly Trp Asp Glu
        370                 375                 380

Ala Gln Glu Thr Phe Glu Gln Trp Thr Lys Lys Gly Gln Leu Ser Asp
385                 390                 395                 400

Phe Lys Thr Ala His Arg Val Gly Met Gly Gly Phe Pro Ser Leu Arg
                405                 410                 415

Gln Val Arg Glu Gly Ala Glu Tyr Lys Tyr Ile Thr Thr Ser Asp Lys
            420                 425                 430

Gly Glu Thr Ile Ala Leu Ala Thr Tyr Gly Glu Ile Phe Ser Val Thr
        435                 440                 445

Arg Gln Ala Ile Ile Asn Asp Asp Leu Asn Gln Leu Thr Asp Val Pro
450                 455                 460

Met Lys Met Gly Arg Ala Ala Lys Ala Thr Ile Gly Asp Leu Val Tyr
465                 470                 475                 480

Ala Ile Leu Thr Lys Asn Pro Lys Leu Ser Asp Gly Lys Ala Leu Phe
                485                 490                 495

His Ala Asp His Lys Asn Leu Ser Ser Gly Ala Ile Ser Val Ala Ser
            500                 505                 510

Leu Asp Glu Ser Arg Lys Leu Met Arg Leu Gln Lys Glu Gly Glu Arg
        515                 520                 525

Thr Leu Asn Ile Arg Pro Ala Tyr Met Leu Val Pro Val Ala Leu Glu
530                 535                 540

Thr Leu Ala Asn Gln Thr Ile Lys Ser Ala Ser Val Lys Gly Ala Asp
545                 550                 555                 560

Ile Asn Ala Gly Ile Val Asn Pro Ile Gln Asn Phe Ala Glu Val Ile
                565                 570                 575

Ala Glu Pro Arg Leu Asp Glu Ala Asp Ala Lys Ala Trp Tyr Leu Ala
            580                 585                 590

Ala Ala Lys Gly Thr Asp Thr Ile Glu Val Ala Tyr Leu Asn Gly Val
        595                 600                 605

Asp Thr Pro Tyr Ile Asp Gln Gln Glu Gly Phe Thr Thr Asp Gly Ile
610                 615                 620

Ala Thr Lys Val Arg Ile Asp Ala Gly Val Ala Pro Leu Asp Tyr Arg
625                 630                 635                 640

Gly Met Thr Lys Ser Ser Gly Gln
                645

<210> SEQ ID NO 241
<211> LENGTH: 499
<212> TYPE: PRT
<213> ORGANISM: Escherichia coli

<400> SEQUENCE: 241

Met Ser Phe Leu Asp Asp Ala Ile Gly Leu Phe Ser Pro Gly Trp Lys
1               5                   10                  15

Ala Ser Arg Leu Arg Ala Arg Ala Val Ile Lys Ala Tyr Glu Ala Val
            20                  25                  30

Lys Gln Thr Arg Thr His Lys Ala Gln Lys Glu Asn Arg Ser Ala Asp
        35                  40                  45

Gln Leu Ser Gln Met Gly Ala Val Ser Leu Arg Gln Gln Ala Arg Trp
    50                  55                  60

Leu Asp Asn Asn His Asp Leu Val Ile Gly Val Phe Lys Leu Glu
65                  70                  75                  80

-continued

Glu Arg Val Val Gly Ala Lys Gly Ile Ile Val Glu Pro His Pro Met
            85                  90                  95

Leu Ser Asn Gly Lys Ile Ala Lys Lys Leu Ala Thr Asp Ile Arg Arg
            100                 105                 110

Lys Trp Gly Glu Trp Ser Val Arg Pro Asp Val Thr Thr Gln Phe Thr
            115                 120                 125

Arg Pro Met Leu Glu Arg Leu Met Leu Arg Thr Trp Leu Arg Asp Gly
            130                 135                 140

Glu Val Phe Ala Gln Leu Val Arg Gly Thr Gly Asn Gly Leu Gln Pro
145                 150                 155                 160

Val Ala Gly Val Pro Phe Trp Leu Glu Ala Leu Glu Pro Asp Phe Val
            165                 170                 175

Pro Met Asn Ser Asp Ala Ala Thr Gln Leu Asn Gln Gly Val Phe Val
            180                 185                 190

Asp Asn Trp Gly Arg Pro Lys Lys Tyr Gln Val Tyr Lys Ser Leu Pro
            195                 200                 205

Val Ser Gly Arg Gln Phe Asp Thr Lys Glu Ile Asp Ala Glu Asn Met
210                 215                 220

Leu His Leu Lys Phe Thr Arg Arg Leu His Gln Thr Arg Gly Thr Ser
225                 230                 235                 240

Leu Leu Ser Gly Val Leu Met Arg Leu Ser Ala Leu Lys Glu Tyr Glu
            245                 250                 255

Asp Ser Glu Leu Thr Ala Ala Arg Ile Ala Ala Ala Leu Gly Met Tyr
            260                 265                 270

Ile Lys Lys Gly Asp Gly Gln Ser Phe Asp Ser Asp Ser Ser Ser Asp
            275                 280                 285

Asp Arg Glu Leu Met Ile Gln Pro Gly Met Leu Tyr Asp Glu Leu Gln
            290                 295                 300

Ala Gly Glu Glu Ile Gly Met Ile Lys Ser Asp Arg Pro Asn Pro Asn
305                 310                 315                 320

Leu Glu Ser Phe Arg Asn Gly Gln Leu Arg Ala Val Ser Ala Gly Ser
            325                 330                 335

Arg Leu Ser Phe Ser Ser Thr Ser Arg Asn Tyr Asn Gly Thr Tyr Ser
            340                 345                 350

Ala Gln Arg Gln Glu Leu Val Glu Ser Thr Asp Gly Tyr Leu Ile Leu
            355                 360                 365

Gln Asp Trp Phe Ile Gly Ser Val Thr Arg Pro Met Tyr Arg Ala Trp
            370                 375                 380

Leu Lys Met Ala Ile Ala Ala Gly Glu Ile Lys Leu Pro Arg Gly Ile
385                 390                 395                 400

Asp Met Asp Ser Leu Tyr Asn Ala Val Tyr Ser Gly Pro Val Met Pro
            405                 410                 415

Trp Ile Asp Pro Val Lys Glu Ala Asn Ala Trp Lys Thr Gln Ile Arg
            420                 425                 430

Gly Gly Ala Ala Thr Glu Ser Asp Trp Ile Arg Ala Ser Gly Arg Asn
            435                 440                 445

Pro Asp Asp Val Lys Ser Arg Arg Lys Ala Glu Val Asp Glu Asn Arg
450                 455                 460

Glu Gln Gly Leu Val Phe Asp Thr Asp Pro Ala Asn Asp Lys Gly Gly
465                 470                 475                 480

Thr Ser Ala Glu Ala Lys Glu Pro Gly Ala Pro Pro Ser Glu Ser Gln
            485                 490                 495

Arg Lys Lys

<210> SEQ ID NO 242
<211> LENGTH: 71
<212> TYPE: PRT
<213> ORGANISM: Escherichia coli

<400> SEQUENCE: 242

Met Asn Pro Ala Asp Ile Gln Asn Met Ile Asp Arg Tyr Ala Ala Ala
1               5                   10                  15

Glu Leu Ser Val Leu Glu Gly Lys Ser Ile Thr Phe Asn Gly Gln Gln
            20                  25                  30

Met Thr Leu Glu Asn Leu Ser Glu Ile Arg Lys Gly Arg Gln Glu Trp
        35                  40                  45

Glu Arg Arg Leu Ala Thr Leu Asn Asn Lys Arg Arg Gly Arg Pro Gly
    50                  55                  60

Tyr Arg Leu Ala Arg Phe Gly
65                  70

<210> SEQ ID NO 243
<211> LENGTH: 700
<212> TYPE: PRT
<213> ORGANISM: Escherichia coli

<400> SEQUENCE: 243

Met Ala Lys Arg Ala Ser Ala Arg Asp Ile Arg Arg Asp Val Ser Gly
1               5                   10                  15

Ile Leu Arg Ala Pro Arg Arg Met Pro Val Ala Asp Ala Val Ser Thr
            20                  25                  30

Tyr Met Arg Val Pro Met Gly Ala Gly Asn Ser Val Pro Trp Asp Pro
        35                  40                  45

Asp Leu Ala Pro Tyr Val Ile Glu Pro Met Asn Cys Leu Ala Ser Arg
    50                  55                  60

Glu Tyr Asp Ala Val Val Phe Val Gly Pro Ala Arg Thr Gly Lys Thr
65                  70                  75                  80

Ile Gly Leu Ile Asp Gly Trp Ile Val Tyr Asn Ile Val Cys Asp Pro
            85                  90                  95

Ala Asp Met Leu Val Ile Gln Val Ser Glu Glu Lys Ala Arg Glu His
        100                 105                 110

Ser Lys Lys Arg Leu Asp Arg Thr Phe Arg Cys Ser Pro Glu Val Lys
    115                 120                 125

Thr Arg Leu Ser Pro Arg Arg Asn Asp Asn Val Tyr Asp Arg Thr
130                 135                 140

Phe Arg Ala Gly Asn Tyr Leu Lys Leu Gly Trp Pro Ser Val Asn Ile
145                 150                 155                 160

Met Ser Ser Ser Asp Tyr Lys Ser Val Ala Leu Thr Asp Tyr Asp Arg
            165                 170                 175

Phe Pro Glu Asp Ile Asp Gly Glu Gly Asp Ala Phe Ser Leu Ala Ser
        180                 185                 190

Lys Arg Thr Thr Thr Phe Met Ser Ser Gly Met Thr Leu Val Glu Ser
    195                 200                 205

Ser Pro Gly Arg Asp Ile Arg Asp Thr Lys Trp Arg Arg Ser Thr Pro
210                 215                 220

His Glu Ala Pro Pro Thr Thr Gly Ile Leu Ser Leu Tyr Asn Arg Gly
225                 230                 235                 240

Asp Arg Arg Arg Leu Tyr Trp Pro Cys Pro His Cys Gly Glu Tyr Phe

```
                245                 250                 255
Gln Pro Glu Met Asp Asn Met Thr Gly Tyr Arg Asp Ser Ser Asp Pro
            260                 265                 270
Val Leu Ala Ser Glu Ala Ala Phe Leu Gln Cys Pro Ala Cys Lys Gly
            275                 280                 285
Arg Ile Thr Pro Asp Met Lys Arg Ala Leu Asn Met Lys Cys Val Trp
            290                 295                 300
Leu Arg Asp Gly Gln Thr Ile Asp Arg Lys Gly Leu Val Ser Gly Asp
305                 310                 315                 320
Gly Arg Arg Ser Arg Ile Ala Ser Phe Trp Met Glu Gly Pro Ala Ala
                325                 330                 335
Ala Tyr Gln Thr Trp Ala Gln Leu Ile Tyr Lys Phe Leu Thr Ala Glu
                340                 345                 350
Gln Glu Tyr Glu Ser Thr Arg Ser Glu Glu Thr Leu Lys Thr Val Ile
                355                 360                 365
Asn Thr Asp Phe Gly Arg Pro Tyr Leu Pro Arg Ala Ser Met Glu Gln
            370                 375                 380
Arg Lys Ser Glu Leu Leu Glu Gln Arg Ala Glu Asp Val Pro Lys Arg
385                 390                 395                 400
Ser Val Pro Asn Gly Val Gln Phe Leu Thr Ala Thr Val Asp Val Gln
                405                 410                 415
Ala Gly Arg Asn Arg Arg Phe Val Val Gln Ile Thr Gly Tyr Gly Ser
            420                 425                 430
Met Gly Glu Arg Trp Ile Val Asp Arg Tyr Asn Ile Arg His Ser Leu
            435                 440                 445
Arg Cys Asp Gly Asn Gly Glu Ser Ile Gln Val Asp Pro Ala Ser Tyr
        450                 455                 460
Pro Glu Asp Trp Asp Leu Leu Thr Asp Val Phe Asp Lys Thr Trp
465                 470                 475                 480
Pro Leu Ala Ala Asp Pro Ser Lys Gly Met Arg Leu Met Ser Met Ala
                485                 490                 495
Val Asp Ser Gly Gly Glu Asp Gly Val Thr Asp Asn Ala Tyr Lys Phe
            500                 505                 510
Trp Arg Arg Cys Arg Arg Glu Gly Leu Gly Lys Arg Ile Tyr Leu Phe
        515                 520                 525
Lys Gly Asp Ser Val Arg Arg Ser Lys Leu Ile Gln Arg Thr Phe Pro
        530                 535                 540
Asp Asn Thr Gly Arg Ser Thr Arg Arg Ala Gln Ala Thr Gly Asp Val
545                 550                 555                 560
Pro Leu Tyr Leu Leu Gln Thr Asp Ala Leu Lys Asp Arg Val Asn Asn
                565                 570                 575
Ala Leu Trp Arg Asp Ser Pro Gly Pro Gly Tyr Val His Phe Pro Ala
            580                 585                 590
Trp Leu Gly Ser Trp Phe Tyr Asp Glu Leu Thr Tyr Glu Glu Arg Ser
            595                 600                 605
Asn Glu Gly Lys Trp Ser Lys Pro Gly Arg Gly Ala Asn Glu Ala Phe
            610                 615                 620
Asp Leu Leu Val Tyr Ala Asp Ala Leu Ala Ile Leu Ser Gly Tyr Glu
625                 630                 635                 640
Lys Ile Lys Trp Pro Ser Ala Pro Glu Trp Ala Arg Arg Glu Thr Trp
                645                 650                 655
Ile Glu Asp Thr Gln Thr Glu Ala Gly Glu Met Pro Ser Pro Pro Pro
            660                 665                 670
```

```
Ala Pro Lys Ser Lys Pro Lys Pro Lys Arg Glu Lys Pro Val Thr Glu
        675                 680                 685

Gln Ala Asn Pro Trp Ser Ser Ser Gly Gly Trp Val
        690                 695                 700

<210> SEQ ID NO 244
<211> LENGTH: 162
<212> TYPE: PRT
<213> ORGANISM: Escherichia coli

<400> SEQUENCE: 244

Met Asp Gln Glu Ile Ala Thr Leu Lys Leu Asn Ile Asn Gln Leu Ala
1               5                   10                  15

Gly Ile Thr Gly Val His Arg Gln Thr Val Ala Ala Arg Leu Lys Asn
            20                  25                  30

Val Glu Pro Ala Pro Gly Ser Asn Ser Lys Leu Lys Leu Tyr Leu Val
        35                  40                  45

Thr Asp Ile Leu Thr Glu Leu Met Ile Pro Thr Val Ser Ala Asn Ile
    50                  55                  60

Asp Asp Met Pro Pro Ser Asp Arg Leu Ser His Trp Lys Ala Glu Asn
65                  70                  75                  80

Glu Arg Leu Lys Phe Glu Gln Asp Thr Gly Gln Leu Ile Pro Ala Asp
                85                  90                  95

Glu Val Ala Arg Glu Phe Ser Leu Met Ala Lys Ala Val Val Met Val
            100                 105                 110

Leu Glu Thr Leu Pro Asp Val Leu Glu Arg Asp Cys Ala Leu Thr Pro
        115                 120                 125

Ala Ala Val Val Arg Val Gln Ser Val Ile Asp Asp Leu Arg Asp Gln
    130                 135                 140

Met Ala Glu Lys Val Gln Asp Ala Gly Lys Glu Glu Glu Gln Pro Glu
145                 150                 155                 160

Glu Asp

<210> SEQ ID NO 245
<211> LENGTH: 242
<212> TYPE: PRT
<213> ORGANISM: Escherichia coli

<400> SEQUENCE: 245

Met Ser Asn Lys Ile Ile Thr Leu Ser Gly Ala Ala Asn Glu Val Leu
1               5                   10                  15

Tyr Ala Leu Phe Phe Arg Gly Ala Leu Leu Ser Gly Asp Leu Pro Ser
            20                  25                  30

Lys Ser Gly Thr Ala Glu Leu Arg Glu Leu Gly Phe Ala Glu Thr Arg
        35                  40                  45

His Thr Ala Thr Glu Tyr Gln Lys Glu Asn His Phe Thr Phe Leu Thr
    50                  55                  60

Ser Glu Gly Gln Lys Phe Ala Val Glu His Leu Val Asn Thr Arg Phe
65                  70                  75                  80

Gly Glu Gln Gln Tyr Cys Ala Ser Met Thr Leu Gly Val Glu Ile Asp
                85                  90                  95

Thr Ser Ala Ala Gln Lys Ala Ile Asp Glu Leu Asp Gln Arg Ile Arg
            100                 105                 110

Asp Thr Val Ser Phe Glu Leu Ile Arg Asn Gly Val Ser Phe Ile Lys
        115                 120                 125
```

```
Asp Ala Ala Ile Ala Asn Gly Ala Ile His Ala Ala Ile Glu Thr
    130                 135                 140

Pro Gln Pro Val Thr Asn Ile Tyr Asn Ile Ser Leu Gly Ile Gln Arg
145                 150                 155                 160

Asp Glu Pro Ala Gln Asn Lys Val Thr Val Ser Ala Asp Lys Phe Lys
                165                 170                 175

Val Lys Pro Gly Val Asp Thr Asn Ile Glu Thr Leu Ile Glu Asn Ala
            180                 185                 190

Leu Lys Asn Ala Ala Glu Cys Ala Leu Asp Val Thr Lys Gln Met
        195                 200                 205

Ala Ala Asp Lys Lys Ala Met Asp Glu Leu Ala Ser Tyr Val Arg Thr
    210                 215                 220

Ala Ile Met Met Glu Cys Phe Pro Gly Gly Val Ile Trp Gln Gln Cys
225                 230                 235                 240

Arg Arg
```

<210> SEQ ID NO 246
<211> LENGTH: 76
<212> TYPE: PRT
<213> ORGANISM: Escherichia coli

<400> SEQUENCE: 246

```
Met Lys Ile Leu Ala Phe Ile Asn Pro Pro Gly Ser Tyr Met Gln Ile
1               5                   10                  15

Glu Thr Lys Glu Met Val Ile Phe Leu Arg Asp Asp Gly Ile Ser Leu
            20                  25                  30

Gln Tyr Pro Asp Gly Gln Cys Ala Gly Tyr Gly Ile Asp Gly Asn Met
        35                  40                  45

Leu Ile Phe Met Gly Gln Ser Cys Glu Leu Phe Pro Thr Lys Ile Ile
    50                  55                  60

Leu His Asp Gln Arg Thr Thr Asn Phe Thr His Lys
65                  70                  75
```

<210> SEQ ID NO 247
<211> LENGTH: 198
<212> TYPE: PRT
<213> ORGANISM: Escherichia coli

<400> SEQUENCE: 247

```
Met Asp Tyr Tyr His Glu Ile Asp Phe Pro Ser Leu Phe Ala Arg Ala
1               5                   10                  15

Val Glu Ser Asp Asp Val Gly Thr Thr Leu Arg Ile His Leu Leu
            20                  25                  30

Cys Glu Arg Met Val Glu Ala Trp Ile Cys Ala Cys Asp Cys Gln
        35                  40                  45

Asp Leu Phe Gly Arg Asp Lys Asn Lys Leu Leu Ile Glu Cys Asn Thr
    50                  55                  60

Lys Ile Ser Met Ala Gly Asn Leu Gly Ile Pro Pro Glu Leu Met Lys
65                  70                  75                  80

Ser Leu Lys Thr Ile Asn Ser Met Arg Asn Asp Leu Ala His Asn Pro
                85                  90                  95

Ser Ile Gln Ser Ile Ala Asp Ser Arg Ile Gln Ser Leu Lys Asp Thr
            100                 105                 110

Leu Thr Glu Tyr Phe Lys Gln His Pro Thr Glu Pro Ser Met Glu Glu
        115                 120                 125

Ser Lys Leu Gly Ile Phe Asn Ala Glu Asn Gln Leu Thr Glu Glu Val
```

```
                130                 135                 140
Ser Leu Asp Ser Asp Ser Ser Lys Asn Arg Leu Lys Leu Ile Leu Leu
145                 150                 155                 160

Phe Ser Lys Leu Met Gln Ala Leu Met Gln Leu Val Ala Ala Asn His
                165                 170                 175

Asn Gly Arg Trp Asp Asn Gln Phe Ser Gln Phe Val Tyr His Val Thr
                180                 185                 190

Met Asn Ala Thr Lys Arg
        195

<210> SEQ ID NO 248
<211> LENGTH: 65
<212> TYPE: PRT
<213> ORGANISM: Escherichia coli

<400> SEQUENCE: 248

Met Thr Val Val Leu Thr Ala Lys Gln Ile Glu Asp Leu Ala Ala Phe
1               5                   10                  15

Ala Lys Glu Asp Gly Gln Pro Gln Tyr Thr Ile Thr Gly Thr Ile
                20                  25                  30

Pro Glu Phe Glu Ala Asp Asn Gly Glu Ile Ile Pro Gly Tyr Thr Gly
                35                  40                  45

Leu Ile Ala Tyr Ser Glu Ser Leu Asp His Gly Val Leu Gln Leu Asp
    50                  55                  60

Asp
65

<210> SEQ ID NO 249
<211> LENGTH: 159
<212> TYPE: PRT
<213> ORGANISM: Escherichia coli

<400> SEQUENCE: 249

Met Val Ile Val Ala Leu Val Gly Ser Phe Leu Ala Gly Ser Glu Trp
1               5                   10                  15

Thr Asn Arg Ser Trp Lys Ile Lys Trp Ala Asp Arg Asp Ser Ala Glu
                20                  25                  30

Ser Ser Gln Glu Ala Asn Ala Gln Thr Ala Ala Arg Met Ile Glu Gln
        35                  40                  45

Gly Arg Thr Ile Ala Arg Asp Glu Ala Val Lys Asp Ala Gln Ala Gln
    50                  55                  60

Ala Ala Ser Ala Ala Val Thr Ser Ala Gly Leu Ala Thr Thr Val Lys
65                  70                  75                  80

Gln Leu Arg Ala Glu Ala Thr Lys Leu Ala Thr His Met Asp Ala Ala
                85                  90                  95

Lys His Thr Ala Asp Leu Ala Thr Ser Val Arg Ser Lys Thr Ala Gly
                100                 105                 110

Ala Asn Ala Ala Met Leu Ala Asp Met Leu Gly Ser Leu Ala Glu Ala
        115                 120                 125

Ala Arg Tyr Tyr Ala Gly Arg Ser Asp Glu Ser Tyr Arg Ala Gly Met
    130                 135                 140

Thr Cys Glu Arg Ile Tyr Glu Ser Val Arg Leu Ser Asn Asn Gln
145                 150                 155

<210> SEQ ID NO 250
<211> LENGTH: 182
<212> TYPE: PRT
```

<213> ORGANISM: Escherichia coli

<400> SEQUENCE: 250

```
Met Ala Met Ser Leu Lys Leu Lys Asn Lys Leu Ser Ala Val Val
1               5                   10                  15

Gly Leu Ile Leu Ala Gly Ala Ser Ala Pro Val Ile Leu Asp Gln Phe
            20                  25                  30

Leu Asp Glu Lys Glu Gly Asn Ser Leu Thr Ala Tyr Arg Asp Gly Gly
        35                  40                  45

Gly Leu Trp Thr Ile Cys Arg Gly Ala Thr Met Val Asp Gly Lys Pro
    50                  55                  60

Val Val Gln Gly Met Lys Leu Ser Ala Glu Lys Cys Ala Gln Val Asn
65                  70                  75                  80

Ala Ile Glu Arg Asp Lys Ala Leu Ala Trp Val Asp Arg Asn Ile Lys
                85                  90                  95

Val Pro Leu Thr Glu Pro Gln Lys Ala Gly Ile Ala Ser Phe Cys Pro
            100                 105                 110

Tyr Asn Ile Gly Pro Gly Lys Cys Phe Pro Ser Thr Phe Tyr Lys Arg
        115                 120                 125

Ile Asn Ala Gly Asp Thr Lys Gly Ala Cys Glu Ala Ile Arg Trp Trp
    130                 135                 140

Ile Lys Asp Gly Gly Arg Asp Cys Arg Leu Thr Lys Gly Gln Lys Asp
145                 150                 155                 160

Gly Cys Tyr Gly Gln Val Glu Arg Arg Asp Gln Glu Ser Ala Leu Thr
                165                 170                 175

Cys Trp Gly Ile Asp Gln
            180
```

<210> SEQ ID NO 251
<211> LENGTH: 92
<212> TYPE: PRT
<213> ORGANISM: Escherichia coli

<400> SEQUENCE: 251

```
Met Thr Arg Met Ser Thr Ile Tyr Ser Arg Leu Ser Tyr Gly Ser Gly
1               5                   10                  15

Thr Thr Leu Ala Gly Cys Gly Val Ser Ala Lys Ala Tyr Ala Glu Thr
            20                  25                  30

Ala Lys Thr Ala Lys Glu Val Ser Trp Met Leu Ala Asp Arg Ile Ala
        35                  40                  45

Gly Leu Ser Leu Ser Asp Trp Ala Ile Ile Val Gly Ile Ala Cys Thr
    50                  55                  60

Val Ile Thr Cys Ala Val Asn Trp Tyr Phe Arg Trp Lys Glu Arg Glu
65                  70                  75                  80

Asp Arg Arg Asn Gly Tyr Val Ser Lys Ala Glu Glu
                85                  90
```

<210> SEQ ID NO 252
<211> LENGTH: 350
<212> TYPE: PRT
<213> ORGANISM: Escherichia coli

<400> SEQUENCE: 252

```
Met Lys Asn Thr Val Lys Ile Asn Ser Val Glu Leu Ile Asn Ala Asp
1               5                   10                  15

Ser Leu His Tyr Val Ala Thr Leu Pro Asp Asn Ser Ile Asp Leu Ile
            20                  25                  30
```

```
Val Thr Asp Pro Pro Tyr Phe Lys Val Lys Pro Asn Gly Trp Asp Asn
        35                  40                  45

Gln Trp Lys Gly Asp Glu Asp Tyr Leu Arg Trp Leu Asp Ser Cys Leu
    50                  55                  60

Ala Glu Tyr Ala Arg Val Leu Lys Pro Ala Gly Ser Ile Tyr Leu Phe
65                  70                  75                  80

Cys Gly His Arg Leu Ala Ser Asp Ile Glu Ile Met Met Arg Ala Arg
                85                  90                  95

Phe Asn Val Leu Asn His Ile Ile Trp Ala Lys Pro Ser Gly Arg Trp
            100                 105                 110

Asn Gly Cys Asn Lys Glu Ser Leu Arg Ala Tyr Phe Pro Ser Thr Glu
            115                 120                 125

Arg Ile Leu Phe Ala Glu His Tyr Leu Gly Pro Tyr Thr Gly Lys Glu
            130                 135                 140

Asp Val Tyr Glu Arg Lys Ser Thr Glu Leu Lys Gln His Ile Met Thr
145                 150                 155                 160

Pro Leu Ile Asp Tyr Phe Arg Asn Ala Arg Glu Ser Leu Gly Val Ser
                165                 170                 175

Ser Lys Glu Ile Ala Glu Ala Thr Gly Lys Lys Asn Met Ala Ser His
            180                 185                 190

Trp Phe Gly Ala Ser Gln Trp Gln Leu Pro Asn Glu Val Asp Tyr Arg
            195                 200                 205

Lys Leu Gln Glu Leu Phe Thr Arg Ile Ala Ile Asp Lys His Ile Gln
            210                 215                 220

Gln Lys Leu Glu His Pro His His Gln Leu Val Ala Thr Tyr Gln Ser
225                 230                 235                 240

Leu Asn Arg Lys Tyr Ser Glu Leu Leu Glu Glu Tyr Lys Ile Leu Arg
                245                 250                 255

Arg Cys Phe Ser Val Ser Ala Leu Val Pro Tyr Thr Asp Val Trp Thr
            260                 265                 270

His Lys Pro Val Gln Phe Tyr Pro Gly Lys His Pro Cys Glu Lys Pro
            275                 280                 285

Ala Asp Met Leu Lys Gln Ile Ile Ser Ala Ser Ser Arg Pro Gly Asp
            290                 295                 300

Ile Val Ala Asp Phe Phe Met Gly Ser Gly Ser Thr Val Lys Ala Ala
305                 310                 315                 320

Ile Glu Leu Gly Arg Arg Ala Ile Gly Val Glu Leu Glu Ala Asp Arg
                325                 330                 335

Phe Ile Gln Thr Thr Glu Glu Val Glu Lys Leu Lys Lys Ser
            340                 345                 350

<210> SEQ ID NO 253
<211> LENGTH: 63
<212> TYPE: PRT
<213> ORGANISM: Escherichia coli

<400> SEQUENCE: 253

Met Leu Asn Gln Glu Asp Met Thr Glu Thr Ala Lys Ala Val Phe Asn
1               5                   10                  15

Glu Leu Ser Asp Lys Pro Ala Thr Ala Gly Glu Ile Ala Gln Asn Thr
            20                  25                  30

His Leu Ser His Glu Arg Cys Gln Leu Ile Leu Thr Gln Leu Val Met
            35                  40                  45

Ala Gly Leu Ser Asp Tyr Gln Phe Gly Cys Tyr Lys Arg Leu Gln
```

<210> SEQ ID NO 254
<211> LENGTH: 299
<212> TYPE: PRT
<213> ORGANISM: Escherichia coli

<400> SEQUENCE: 254

Met Pro Asn Trp Ile Asp Val Leu Gly Glu Met Gly Thr Ile Ala Gln
1               5                   10                  15

Arg Thr Pro Ala Asp Glu Val Arg His Lys Tyr Leu Arg Asp Leu Ser
            20                  25                  30

Lys His Thr Gly Arg Asn Val Ile Ser Tyr Tyr Ser Gly Phe Leu Gln
        35                  40                  45

Lys Gly Gly Pro Gly Phe Gln His Leu Ile Gln Met Ser Asp Asp Asp
    50                  55                  60

Lys Asn Gly Leu Met Ser Ala Ile Asn Gly Leu Asp Thr Ser Leu Gly
65              70                  75                  80

Leu Asp Ile Leu Leu His Thr Pro Gly Gly Asp Ile Ala Ala Leu Glu
                85                  90                  95

Ser Ile Gly His Tyr Leu Arg Ser Lys Phe Gly Thr Asn Ile Arg Ala
            100                 105                 110

Ile Val Pro Met Ile Ser Met Ser Cys Gly Thr Met Leu Ala Cys Cys
        115                 120                 125

Ala Glu Gln Ile Val Leu Gly Lys Gln Ser Asn Leu Gly Pro Ile Asp
    130                 135                 140

Pro Gln Phe Asn Gly Leu Ser Ser His Ala Ile Ile Glu Glu Tyr Glu
145                 150                 155                 160

Arg Ala Lys Ala Glu Ile Phe Ala Asn Pro Ala Ala Leu Gln Trp Trp
                165                 170                 175

Gln Phe Thr Phe Gln Lys Leu Asn Pro Thr Leu Ile Gly Glu Cys Glu
            180                 185                 190

Lys Ala Ile Leu Trp Ala Asn Glu Ile Val Gln Lys Trp Leu Cys Thr
        195                 200                 205

Gly Met Phe Ala Gly Gln Ala Asp Ala Glu Ala Lys Ala Lys Arg Ile
    210                 215                 220

Cys Asp Glu Leu Asn Asn His Gln Ala Thr Tyr Ala His Ala Arg His
225                 230                 235                 240

Ile His Leu Asp Lys Ala Gln Asn Ile Gly Leu Asn Ile Met Glu Leu
                245                 250                 255

Glu Ser Asp Gln Thr Leu Gln Asp Leu Val Leu Thr Ile His His Cys
            260                 265                 270

Tyr Met His Ser Phe Gly Thr Ser Pro Ala Ala Lys Ile Ile Glu Asn
        275                 280                 285

His Asn Gly Ser Thr Met Met Trp Asn Ile Cys
    290                 295

<210> SEQ ID NO 255
<211> LENGTH: 68
<212> TYPE: PRT
<213> ORGANISM: Escherichia coli

<400> SEQUENCE: 255

Met Ser Ala Ala Glu Phe Tyr Glu Lys Met Gly Ile Gln Pro Gln Glu
1               5                   10                  15

Phe Gln Lys Gly Glu Ser Val Gln His Phe Ala Met Arg Val Leu Ala

```
                    20                  25                  30

Gln Gln Asn Asp Leu Asn Val Arg Ser Gly Val Leu Tyr Ser Tyr Ser
            35                  40                  45

Thr Val Thr Pro Asn Thr Thr Glu Gln Asn Gly Gln Gln Ser His Gln
        50                  55                  60

Leu Tyr Ser Tyr
65

<210> SEQ ID NO 256
<211> LENGTH: 229
<212> TYPE: PRT
<213> ORGANISM: Escherichia coli

<400> SEQUENCE: 256

Met Asn Gln Gln Asp Leu Asn Phe Val Arg Ile Glu Leu Arg Arg Ala
1               5                   10                  15

Leu Pro Asp Leu Ser Gly Gly Thr Lys Gly Gln Leu Glu Ala Phe Ser
            20                  25                  30

Glu His Pro Ala Asp Lys Asn Ala Thr Pro Arg Gly Ile His
        35                  40                  45

Leu Val Glu Leu Glu Gly Glu Lys Gly Pro Arg Phe Val Asn Ser Leu
    50                  55                  60

Ser Ala Pro Leu Tyr Val Leu Glu Thr Arg Ser Arg Arg Pro Met
65                  70                  75                  80

Pro Pro Ile Lys Asp Ala Glu Phe Glu Ser Ala Pro Trp Arg Arg Ala
                85                  90                  95

Val Ser Ala Leu Ser Gly Tyr Gln Gln Ala Trp Leu Arg Tyr Cys Tyr
            100                 105                 110

Gly Phe Asp Leu Ser Tyr Lys His Gln Val Met Met Cys Glu Tyr Val
        115                 120                 125

Trp Lys Thr Tyr Gln Lys Cys Leu Gly Asp Asn Ser Leu Gln Glu Arg
    130                 135                 140

Val Val Lys Lys Leu Ile Gly Leu Val Trp Leu Ala Gly Gln Glu Ile
145                 150                 155                 160

Ala Ala Thr Arg Asn Asn Glu Thr Tyr Lys Asp Tyr Ala Gly Ala Ala
                165                 170                 175

Leu Ala Arg Met Val Ser Val Asp Arg Ser Thr Trp Leu Arg Val Tyr
            180                 185                 190

Ser Gly His Trp Ala Gly Leu Lys Ala Ala Phe Thr Gln Leu Asp Glu
        195                 200                 205

Ser Ala Leu Ala Met Ala Leu Glu Tyr Tyr Glu Glu Glu Ala Leu
    210                 215                 220

Lys Val Ala Glu Met
225

<210> SEQ ID NO 257
<211> LENGTH: 331
<212> TYPE: PRT
<213> ORGANISM: Escherichia coli

<400> SEQUENCE: 257

Met Arg Ala Leu Leu Thr Pro Glu Ile Ala His Arg Met Gly Ile Val
1               5                   10                  15

Leu Phe Arg Pro Gly Ala Glu Leu Met His Leu Phe Met Arg Gly Arg
            20                  25                  30

Val Leu Leu Glu Pro Glu Pro Glu Glu Met Ala Ser Phe Ser Thr Gly
```

```
            35                 40                  45
Ala Val Pro Ala Ala Ile Gln Pro Leu Ala Asp Asp Pro Val Met Arg
 50                 55                 60
Gln Val Phe Glu Asn Asp Arg Val Ile Gln Arg Ala Gly Gly Leu Pro
65                 70                 75                  80
Ser Leu Glu Gln Trp Leu Ser Asn Arg Phe Glu Cys Gln Trp Pro His
                85                 90                 95
Ser Ser Trp His Asp Lys Asn Phe Thr Thr Met Arg His Pro Pro Gly
               100                105                110
Ser Ile Arg Leu Cys Trp His Cys Asp His Thr Leu Ser Gly Gln His
               115                120                125
Thr Glu Gln Leu Ala Gly Ile Ala Ala Gly Asn Leu Val Ser Trp Ile
130                135                140
Leu Glu Val Ile Arg Arg Asp Ser Gly Phe Pro Glu Ser His Ile Leu
145                150                155                 160
Thr Leu Pro Glu Leu Cys Trp Trp Met Val Arg Asn Asp Leu Ala Asp
                165                170                175
Val Ile Pro Glu Ser Val Ala His Lys Gly Leu Arg Leu Pro Asp Asp
                180                185                190
Lys Ile Arg Ser Val Met Arg Glu Ser Asp Ile Val Pro Ser Ala Ser
                195                200                205
Ala Thr Ser Leu Val Gln Glu Lys Ala Lys Ile Leu Thr Leu Ser
                210                215                220
Val Asp Pro Glu Ser Pro Glu Ser Phe Met Leu Arg Pro Lys Arg Arg
225                230                235                 240
Arg Trp Ile Asn Glu Thr Tyr Thr Arg Trp Val Lys Thr Gln Pro Cys
                245                250                255
Glu Cys Cys Arg Arg Pro Ala Asp Asp Pro His His Ile Val Gly His
                260                265                270
Gly Met Gly Gly Thr Ala Thr Lys Ala His Asp Leu Phe Val Ile Pro
                275                280                285
Leu Cys Arg Glu Cys His Asp Glu Leu His Ala Asp Val Pro Ala Phe
                290                295                300
Glu Gln Lys His Gly Thr Gln Leu Glu Leu Leu Arg Phe Met Asp
305                310                315                 320
Arg Ala Leu Ala Ile Gly Val Ile Ala Lys Ala
                325                330

<210> SEQ ID NO 258
<211> LENGTH: 227
<212> TYPE: PRT
<213> ORGANISM: Escherichia coli

<400> SEQUENCE: 258

Met Ser Gln Leu Ala Thr Thr Ala Leu Thr Met Ser Ser Ser Asp Ile
1                5                 10                 15
Ala Glu Leu Val Glu Ser Arg His Asp His Val Lys Arg Ser Ile Glu
                20                 25                 30
Arg Leu Ala Glu Arg Gly Val Ile Glu Leu Pro Pro Met Gly Glu Val
                35                 40                 45
Lys Asn His Leu Asn Gln Ser Val Ser Val Tyr Leu Ile Gly Lys Arg
                50                 55                 60
Asp Ser Tyr Ile Val Val Ala Gln Leu Ser Pro Glu Phe Thr Ala Arg
65                 70                 75                  80
```

-continued

Leu Val Asp Arg Trp Gln Glu Leu Glu Gln Ala Gln Gln Thr Ile
            85                  90                  95

Pro Gln Ser Phe Ser Glu Ala Leu Arg Leu Ala Ala Asp Leu Ala Glu
            100                 105                 110

Gln Lys Gln Gln Leu Thr Asn Glu Leu Ala Ala Ala Pro Lys Val
        115                 120                 125

Ala Phe Val Asp Arg Tyr Cys Thr Ala Ser Gly Ser Met Ser Phe Arg
        130                 135                 140

Gln Val Ala Lys Leu Leu Lys Ala Lys Glu Pro Asp Leu Arg Leu Phe
145                 150                 155                 160

Leu Leu Glu Asn Asp Ile Met Tyr Arg Leu Gly Gly Thr Met Thr Pro
                165                 170                 175

Arg His Gln His Ile Asp Ala Gly Arg Phe Glu Val Lys Thr Gly Thr
                180                 185                 190

Ser Val Thr Ser Asn His Ala Phe Ser Gln Ala Arg Phe Thr Ala Lys
            195                 200                 205

Gly Val Arg Trp Ile Gly Gly Leu Trp Ala Glu His Ile Ala Arg Gly
    210                 215                 220

Gln Val Ala
225

<210> SEQ ID NO 259
<211> LENGTH: 128
<212> TYPE: PRT
<213> ORGANISM: Escherichia coli

<400> SEQUENCE: 259

Met Lys Leu Ile Leu Pro Phe Pro Pro Ser Val Asn Thr Tyr Trp Arg
1               5                   10                  15

Ala Pro Asn Lys Gly Pro Leu Ala Gly Arg His Leu Ile Ser Ala Ala
            20                  25                  30

Gly Arg Lys Tyr Gln Ser Ala Ala Cys Val Ala Ile Ile Glu Gln Leu
        35                  40                  45

Arg Arg Leu Pro Lys Pro Ser Thr Glu Leu Ala Ala Val Glu Ile Thr
    50                  55                  60

Leu Tyr Pro Pro Asp Ala Arg Arg Asp Ile Asp Asn Tyr Asn Lys
65                  70                  75                  80

Ala Leu Phe Asp Ala Leu Thr His Ala Gly Val Trp Glu Asp Ser
                85                  90                  95

Gln Ile Lys Arg Met Leu Val Glu Trp Gly Pro Val Val Pro Lys Gly
            100                 105                 110

Arg Val Glu Ile Thr Ile Ser Arg Tyr Glu Pro Ala Gly Ala Ala Ala
        115                 120                 125

<210> SEQ ID NO 260
<211> LENGTH: 439
<212> TYPE: PRT
<213> ORGANISM: Escherichia coli

<400> SEQUENCE: 260

Met Met Thr Asn Lys Tyr Cys Gln Ala Leu Ala Ala Leu Arg Ser Lys
1               5                   10                  15

Pro Ala His Glu Leu Lys Glu Val Gly Asp Gln Trp Arg Thr Pro Asp
            20                  25                  30

Leu Leu Phe Trp Gly Ile Asn Ala Leu Phe Gly Pro Leu Val Leu Asp
        35                  40                  45

Leu Phe Ala Asp Asp Asn Ala Lys Cys Pro Ala Trp Tyr Thr Ala
 50                 55                  60

Glu Asp Asn Ala Leu Thr Gln Asp Trp Ser Glu Arg Leu Ala Glu Leu
 65                  70                  75                  80

Gly Gly Ala Gly Tyr Gly Asn Pro Pro Tyr Ser Arg Ser Gln Tyr His
                 85                  90                  95

Glu Lys Gln Ala Ile Thr Gly Met Thr His Ile Met Asn Tyr Ala Ala
            100                 105                 110

Ala Gln Arg Glu Lys Gly Arg Tyr Val Phe Leu Ile Lys Ala Ala
        115                 120                 125

Pro Ser Glu Thr Trp Trp Pro Glu Asp Ala Asp His Ile Val Phe Ile
130                 135                 140

Arg Gly Arg Ile Gly Phe Asp Leu Pro Val Trp Phe Val Pro Ala Asp
145                 150                 155                 160

Glu Lys Gln Lys Pro Thr Ser Ala Phe Phe Ala Gly Ala Ile Ala Val
                165                 170                 175

Phe Asp Lys Ser Trp Arg Gly Arg Phe Ser Tyr Ile Asn Arg Thr
            180                 185                 190

Glu Leu Glu Ala Lys Gly Arg Ala Phe Met Ala Leu Ala Gln Phe Ala
        195                 200                 205

Ala Ser Lys Ser Gln Pro Val Thr Ala Thr Pro Ala Ala Asp Lys
210                 215                 220

Pro Glu Ala Glu Leu Pro Leu Thr Gln Lys Asp Ile Phe Ala Ile Ser
225                 230                 235                 240

Gly Val Glu Ala Trp Ala Cys Val Arg Ala Ala Phe Gly Asp Lys Glu
                245                 250                 255

Glu Tyr Thr Phe Ser Glu Ser Lys Phe Gly His Thr Trp Ala Ala Asp
            260                 265                 270

Ser Val Glu Ala Pro Glu Phe Thr Gln Val Ser Pro Leu Thr Ile Asp
        275                 280                 285

Lys Ala Lys Leu Leu Ile Arg Glu Ser Ile Leu Phe Gly Val Asp Glu
290                 295                 300

Trp Leu Leu Ser Ile Glu Phe Asp Asp Ala Ala Val Arg Leu Asp Met
305                 310                 315                 320

Ser Glu Arg Ile Arg Thr Val Ala Leu Glu Ala Ser Gly Glu Tyr Gly
                325                 330                 335

Met Asn Ser Thr Asp Phe Ile Ala Ala Met Gly Ser Leu Asp Val Ser
            340                 345                 350

Ser Trp Ser Asn Ile Arg Gln Ile Arg Met His Ile Arg Glu Lys Ala
        355                 360                 365

Lys Pro Val Ser Asp Pro Leu Pro Glu Ser Arg Ile Trp Pro Leu Glu
370                 375                 380

Val Arg Ile Val Phe Asp Gln Val Asp Gly Ala Asp Met Leu Asp Glu
385                 390                 395                 400

Ser Leu Gln His Lys Leu Lys Ala Asn Ile Asn Gln Leu Trp Leu Glu
                405                 410                 415

Arg Thr Ala Thr Ser Glu Ile Ile Thr Ala Ala Ser Glu Leu Val Arg
            420                 425                 430

Asn Met Arg Gly Glu Ala Ala
        435

<210> SEQ ID NO 261
<211> LENGTH: 293
<212> TYPE: PRT

<213> ORGANISM: Escherichia coli

<400> SEQUENCE: 261

Met Ser Thr Lys Leu Thr Gly Tyr Val Trp Asp Ala Cys Ala Ser Ser
1               5                   10                  15

Gly Met Lys Leu Ser Ser Val Ala Ile Met Ala Arg Leu Ala Asp Phe
            20                  25                  30

Ser Ser Asp Glu Gly Val Ser Trp Pro Ser Ile Gly Thr Ile Ala Arg
        35                  40                  45

Gln Ile Gly Ala Gly Glu Ser Thr Val Arg Thr Ala Leu Ala Gln Leu
    50                  55                  60

Glu Lys Asp Gly Trp Leu Ser Arg Lys Gln Arg Arg Asn Gly Asn Arg
65                  70                  75                  80

Asn Ala Ser Asn Val Tyr Gln Leu Asn Val Val Lys Leu Arg Glu Ala
                85                  90                  95

Ala Phe Ser His Leu Ser Glu Ser Asp Ala Ser Lys Ser Asp Pro Ser
            100                 105                 110

Lys Ser Asp Ala Ser Lys Ser Asp Pro Ser Lys Phe Glu Ala Ser Lys
        115                 120                 125

Ser Ser Lys Lys Gly Gly Phe Asp Pro Ser Glu Ser Gly Gly Asp Pro
    130                 135                 140

Ser Val Lys Ser Lys Gln Glu Pro Gln Val Thr Ser Lys Pro Ser Cys
145                 150                 155                 160

Pro Val Ala Ala Gln Pro Asp Pro Glu Val Val Ile Thr Asp Gln Ala
                165                 170                 175

Arg Gln Val Leu Ser Tyr Leu Asn Gln Thr Thr Gly Ser Arg Tyr Gln
            180                 185                 190

Val Cys Ser Thr Ser Leu Glu Asn Ile Arg Ala Arg Leu Arg Glu Gln
        195                 200                 205

Phe Thr Val Asp Asp Leu Cys Leu Val Val Asp Tyr Lys Asn Ala Asp
    210                 215                 220

Trp Arg Asp Ser Glu Gln Ala Gln Tyr Leu Arg Pro Ala Thr Leu Phe
225                 230                 235                 240

Ile Pro Lys Asn Phe Pro Gly Tyr Leu Gln Ser Ala Thr Lys Trp Ser
                245                 250                 255

Ser Ala Gly Arg Pro Glu Arg Val Asn Gly Lys Trp Glu Thr Asn Ser
            260                 265                 270

Ala Ser Arg Ala Asn Phe Gln Ser Val Asp Tyr Ser Leu Pro Glu Asn
        275                 280                 285

Ser Gly Phe Arg Ser
    290

<210> SEQ ID NO 262
<211> LENGTH: 112
<212> TYPE: PRT
<213> ORGANISM: Escherichia coli

<400> SEQUENCE: 262

Met Asn Ser Val Asn Arg Phe Arg Pro Ala Lys Gln Phe Arg Cys Leu
1               5                   10                  15

Pro Leu Val Gly Lys Asp Ala Gln Phe Gly Tyr Val Glu Ile Ile Asn
            20                  25                  30

Asn Ala Ala Asp Gly Gly Asn Tyr Gln Pro Ala Asp Leu Met Val Glu
        35                  40                  45

Ala Phe Val Gln Met Asn Glu Lys Gly Arg Glu Glu Trp Leu Lys Leu

```
              50                  55                  60
Thr Gly Gly Ser Glu Ile Thr Thr Glu Phe Pro Ser Glu Leu Ser Ala
 65                  70                  75                  80

Gly Ser Gln Ile His Ser Ala Leu Tyr Thr Phe Ala Lys Gly Thr Ile
                     85                  90                  95

Met Ser Ala Ser Ala Leu Leu Asn Asn Ser Ser Val Asn Leu Gln Asn
                    100                 105                 110
```

<210> SEQ ID NO 263
<211> LENGTH: 187
<212> TYPE: PRT
<213> ORGANISM: Escherichia coli

<400> SEQUENCE: 263

```
Met Val Asp Ser Ile Asn Thr Ala Ile Arg Leu Met Cys Lys Ala His
 1               5                  10                  15

Lys His Gly Arg Leu Gly Met Ala Ser Asp Leu Gly Met Thr Ile Asp
                20                  25                  30

Gln Phe His Asn His Leu Tyr Gln Lys Cys Gly Ser Arg Phe Phe Thr
                35                  40                  45

Leu Ala Glu Leu Glu Arg Met Glu Asp Leu Ser Gly Ser Cys Tyr Leu
 50                  55                  60

Ala Glu Tyr Gln Ala Asn Arg Lys Gly Lys Trp Leu Val Asp Val Pro
 65                  70                  75                  80

Thr Ala Glu Ser Leu Asp Asn Val Glu Leu Tyr Ser Ile Glu Met Lys
                 85                  90                  95

Ala Ala Ala Ser Gly Glu Leu Asn Ala Lys Met Ala Ala
                100                 105                 110

Ala Asp Gly Val Ile Asp Ser Ser Glu Arg Lys Met Leu Ser Glu Leu
                115                 120                 125

Phe Ser Lys Lys Leu Arg His Gln Ile His Gly Phe Leu Gly Phe Met
130                 135                 140

Ala Leu Tyr Gly Val Gly Val Ser Asp Gln Ala Ile Asp Val Phe Val
145                 150                 155                 160

Ser Thr Gly Arg Lys Gly Asp Ala Arg Glu Cys Ala Ala Pro Gly Ala
                165                 170                 175

Leu Ala Cys Arg Ile Ser Gly Glu Thr Asn Ala
                180                 185
```

<210> SEQ ID NO 264
<211> LENGTH: 85
<212> TYPE: PRT
<213> ORGANISM: Escherichia coli

<400> SEQUENCE: 264

```
Met Ser Ser Gln His Lys Asn Val Thr Ala Lys Ala Val Lys Ala Ile
 1               5                  10                  15

Gly Ser Ile Ser Glu Val Ser Arg Arg Phe Glu Phe Gln Ser Val Gln
                20                  25                  30

Ser Val Ala Asn Trp Ile Ala Lys Asn Arg Val Pro Ser Glu Arg Val
                35                  40                  45

Ile Gln Leu Cys Gln Trp Gly Gly Trp Val Val Thr Pro His Gln Leu
                50                  55                  60

Arg Pro Asp Ile Tyr Pro Asn Lys Asn Asp Gly Ile Pro Ser Ala Asn
 65                  70                  75                  80

Asn Asn Ser Gln Leu
```

<210> SEQ ID NO 265
<211> LENGTH: 236
<212> TYPE: PRT
<213> ORGANISM: Escherichia coli

<400> SEQUENCE: 265

Met Pro Cys Ala Leu Asn Leu Leu Met Val Glu Asn Ala Lys Tyr
1               5                   10                  15

Lys Asp Phe Ala Glu Arg Leu Asn Arg Ser Leu Gln Glu Gln Ser Ile
            20                  25                  30

Gly Val Lys Glu Leu Ser Glu Phe Ser Gly Val Ser Tyr Glu Met Ala
        35                  40                  45

Arg Arg Tyr Thr Leu Gly Thr Ala Lys Pro Arg Asp Glu Lys Met Ile
50                  55                  60

Arg Ile Ala Glu Arg Leu Ala Val Ser Pro Ala Tyr Leu Asp Tyr Gly
65                  70                  75                  80

Val Pro Val Asn Gly Asp Ala Pro Ala Lys Gly Thr Val Arg Ile
                85                  90                  95

Glu Gln Leu Asp Val His Ala Ser Ala Gly Ser Gly Tyr Ile Asn Gln
            100                 105                 110

Pro Phe Pro Thr Ile Val Ser Ser Ile Glu Ile Pro Glu Glu Arg Ile
        115                 120                 125

Phe Glu Leu Phe Gly Arg Arg Ser Leu Asp Gly Ile Val Met Ile Asn
130                 135                 140

Val Asp Gly Asp Ser Met Met Pro Thr Leu Cys Pro Lys Asp Leu Leu
145                 150                 155                 160

Phe Ile Asp Ser Lys Val Glu Gln Phe Ser Gly Asp Gly Val Tyr Val
                165                 170                 175

Phe Asn Phe Glu Asp Ser Thr Phe Val Lys Arg Leu Gln Lys Val Lys
            180                 185                 190

Gly Arg Arg Leu Ala Val Leu Ser Asp Asn Glu His Tyr Pro Pro Phe
        195                 200                 205

Phe Ile Glu Glu His Glu Met Asn Glu Leu Tyr Ile Phe Gly Lys Leu
    210                 215                 220

Ile Arg Cys Leu Pro Leu Lys Met Ile Glu Phe Gly
225                 230                 235

<210> SEQ ID NO 266
<211> LENGTH: 65
<212> TYPE: PRT
<213> ORGANISM: Escherichia coli

<400> SEQUENCE: 266

Met Gly Ala Phe Asp Asn Gln Glu Ile Thr Leu Pro Ala Cys Pro Lys
1               5                   10                  15

Cys Gly Thr Lys Thr Lys Lys Ile Ala Trp Leu Lys Ser Asn Lys
            20                  25                  30

Ser Phe Thr Cys Arg Cys Gly Ala Thr Ile Asn Val Asn Ser Ser Gln
        35                  40                  45

Leu Thr Ser Glu Ile Arg Lys Val Glu Asp Lys Leu Lys Lys Leu Phe
50                  55                  60

Lys
65

```
<210> SEQ ID NO 267
<211> LENGTH: 305
<212> TYPE: PRT
<213> ORGANISM: Escherichia coli

<400> SEQUENCE: 267

Met Asn Pro Phe Phe Lys Asn Met Leu Val Tyr Arg Ile Ser Arg
1               5                   10                  15

Asp Phe Thr Ile Asn Gln Glu Glu Leu Glu Gln Gln Leu Glu Leu Phe
            20                  25                  30

Arg Phe Thr Pro Cys Gly Ser Gln Asp Met Ala Lys Thr Gly Trp Val
        35                  40                  45

Ser Pro Leu Gly Gln Leu Ser Asp Arg Leu His His Thr Val Asn Asn
    50                  55                  60

Gln Val Leu Leu Val Ile Arg Arg Glu Glu Lys Ile Leu Pro Ser Pro
65                  70                  75                  80

Val Ile Thr Glu Glu Leu Arg Lys Arg Val Ser Arg Leu Glu Ser Asp
                85                  90                  95

Gln Gly Arg Arg Leu Lys Lys Thr Glu Lys Asp Ser Leu Arg Asp Glu
            100                 105                 110

Val Leu His Ser Leu Leu Pro Arg Ala Phe Ser Lys Asn Ser Thr Val
        115                 120                 125

Gly Leu Trp Ile Asn Val Thr Asp Gly Leu Ile Met Val Asp Ala Ala
    130                 135                 140

Ser Ala Lys Arg Ala Glu Asp Ser Leu Ala Leu Leu Arg Lys Thr Leu
145                 150                 155                 160

Gly Ser Leu Pro Val Val Pro Leu Thr Met Glu Thr Pro Ile Glu Leu
                165                 170                 175

Thr Met Thr Asp Trp Val Arg Ser Gly Ser Ala Pro Ala Gly Phe Gly
            180                 185                 190

Leu Gly Asp Glu Ala Glu Leu Lys Ala Ile Leu Glu Asp Gly Gly Ile
        195                 200                 205

Gly Arg Phe Lys Lys Gln Thr Leu Val Ser Asp Glu Ile His Val His
    210                 215                 220

Leu Glu Ala Gly Lys Val Val Thr Lys Leu Ser Ile Asp Trp Gln Gln
225                 230                 235                 240

Arg Ile Gln Phe Val Leu Cys Asp Asp Gly Ser Ile Lys Arg Leu Lys
                245                 250                 255

Phe Ser Asn Glu Ile Thr Glu Gln Asn Asp Asp Ile Asp Arg Glu Asp
            260                 265                 270

Ala Ala Gln Arg Phe Asp Ala Asp Phe Val Leu Met Thr Gly Glu Leu
        275                 280                 285

Ile Ser Leu Ile Asn Gly Leu Thr Thr Ser Leu Gly Gly Glu Ala Lys
    290                 295                 300

Arg
305

<210> SEQ ID NO 268
<211> LENGTH: 179
<212> TYPE: PRT
<213> ORGANISM: Escherichia coli

<400> SEQUENCE: 268

Met Ser Tyr Ile Gln Thr Leu Ser Gly Lys His Phe Asn Tyr Leu Asp
1               5                   10                  15

Ile Gln Gln Asp Asp Ile Val Ile Glu Asp Ile Ala Thr Ala Leu Ser
```

```
                    20                  25                  30

His Ile Cys Arg Phe Ala Gly His Leu Pro Glu Phe Tyr Ser Val Gly
                35                  40                  45

Gln His Ser Val Leu Thr Ser His Leu Val Pro Gln Glu Phe Ala Leu
            50                  55                  60

Glu Ala Leu Leu His Asp Ala Ala Glu Ala Tyr Leu Gln Asp Ile Pro
65                  70                  75                  80

Ser Pro Leu Lys Arg Leu Leu Pro Asp Tyr Gln Ala Ile Glu Ala Arg
                85                  90                  95

Val Asp Ala Ala Ile Arg Gln Lys Phe Gly Leu Pro Thr Glu Gln His
            100                 105                 110

Pro Thr Val Lys Tyr Ala Asp Leu Val Met Leu Ala Ser Glu Arg Arg
        115                 120                 125

Asp Phe Glu Ile Asp Glu Gly Ser Ile Trp Pro Cys Leu Glu Gly Val
        130                 135                 140

Val Pro Thr Asp Leu Phe Ile Ile Asn Pro Val Arg Pro Gly Gln Ser
145                 150                 155                 160

Tyr Gly Met Phe Ile Asn Arg Phe Asn Glu Leu Met Glu Arg Gln
                165                 170                 175

Cys Ala Ala

<210> SEQ ID NO 269
<211> LENGTH: 84
<212> TYPE: PRT
<213> ORGANISM: Escherichia coli

<400> SEQUENCE: 269

Met Thr Val Phe Glu Tyr Leu Gln Ala His Pro Asn Thr Thr Ser Gly
1               5                   10                  15

Glu Ile Ala Lys Gly Met Asn Lys Lys Thr Pro Ala Val Ala Gly Ala
                20                  25                  30

Leu Ser Gln Leu Tyr Gly Thr Gly Arg Ile Val Lys Ser Gly Val Arg
            35                  40                  45

Lys Gly Ile Pro Thr Tyr Arg Ile Asn Asp Met Pro Phe Gly Cys Ser
        50                  55                  60

Asn Ser Leu Thr Met Met Phe Asn Gln Leu Leu Ser Arg Ala Arg Gln
65                  70                  75                  80

Gly Ala Ala Gln

<210> SEQ ID NO 270
<211> LENGTH: 115
<212> TYPE: PRT
<213> ORGANISM: Escherichia coli

<400> SEQUENCE: 270

Met Thr Ala Leu Asn Lys Gln Ala Leu Arg Glu Glu Phe Gln Phe Met
1               5                   10                  15

Gln Asp Asn Tyr Ser Asp Pro Ala Asp His Asp Arg Gln Val Ile Tyr
                20                  25                  30

Ile Glu Ala Glu Ala Leu Leu Asp Glu Leu Glu Ala Lys Asp Ser Thr
            35                  40                  45

Ile Ala Ala Gln Gln His Glu Ile Arg Met Leu Leu Asn Ala Leu Glu
        50                  55                  60

Glu Lys Pro Cys Pro Lys Cys Asn Asp Thr Gly Met Thr Asp Ser Gly
65                  70                  75                  80
```

```
Gly Thr Gln Pro Trp Gly Glu Pro Ile Glu Ile Glu Cys Asp Cys Arg
                85                  90                  95

Gln Gln Asp Ala Asn Thr Ala Glu Leu Val Ala Ala Gly Ile Gly Val
            100                 105                 110

Lys Gly Glu
        115

<210> SEQ ID NO 271
<211> LENGTH: 102
<212> TYPE: PRT
<213> ORGANISM: Escherichia coli

<400> SEQUENCE: 271

Met Asp Lys Leu Ile Lys Pro Thr Ala Lys Gly Lys Tyr Asp Gly Ser
1               5                   10                  15

Cys Asp Tyr Leu Cys Ser Glu Asp Ala Arg Phe Ile Val Met Arg Gly
            20                  25                  30

Asp Tyr Thr Glu Ala Glu Ile Ile Gln Ala Ser Val Ser Gln Asp Val
        35                  40                  45

Ile Asp Ser Asp Gly Ala Ala Asp Phe Ala Ser Ser Ala Arg Tyr Tyr
    50                  55                  60

Gln Cys Trp Tyr Lys Val Ser Pro Ile Gly Gly Gln Asp Gly Tyr Ser
65                  70                  75                  80

Gly Trp His His Pro Arg Asp Ser Pro Cys Arg Gly Ala Tyr Phe Ala
                85                  90                  95

Ser Val Leu Gln Trp Asp
            100

<210> SEQ ID NO 272
<211> LENGTH: 155
<212> TYPE: PRT
<213> ORGANISM: Escherichia coli

<400> SEQUENCE: 272

Met Thr Thr Asn Asn His Pro Ala His Gly Pro Val Ser Leu Asp Arg
1               5                   10                  15

Leu His Gln Ile Arg Glu His Leu Leu His Asp Thr Gln Tyr Ser Asn
            20                  25                  30

Gly Gly Asn Arg Ala Tyr Ile Leu Ala Asp Val Leu Lys Val Ile Asp
        35                  40                  45

Gly Ala Ile Ala Arg Glu Leu Val Arg Arg Glu His Ala Ala Trp Ser
    50                  55                  60

Gln Ala Thr Phe Gly Asp Val Gly Pro Val Gly Pro Leu Lys His Leu
65                  70                  75                  80

Ser Lys Glu Ala Leu Glu Ala Ala Glu Pro Gly Asp Leu Ser Glu
                85                  90                  95

Trp Ala Asp Met Gln Phe Leu Leu Trp Asp Ala Gln Arg Arg Ala Gly
            100                 105                 110

Ile Ser Asp Glu Gln Ile Thr Gln Ala Met Ile Lys Lys Leu Ala Ile
        115                 120                 125

Asn Lys Val Arg Gln Trp Pro Glu Pro Lys Asp Gly Glu Pro Arg Leu
    130                 135                 140

His Ile Lys Glu Gln Ser Glu Gln Glu Lys Lys
145                 150                 155

<210> SEQ ID NO 273
<211> LENGTH: 84
```

<212> TYPE: PRT
<213> ORGANISM: Escherichia coli

<400> SEQUENCE: 273

Met Phe Ser Leu Ile Arg Arg Gly Gln Ile Tyr Thr Asp Ser Ser Asn
1               5                   10                  15

Trp Pro Val Ile Ile His Ser Cys Ser Asp His Ser Val Arg Ile Lys
            20                  25                  30

Arg Asn Asp Gly Glu Leu Arg Thr Ile Ser Ile Lys Arg Phe Asn Glu
        35                  40                  45

Asp Phe Glu Arg Val Glu His Asp Gly Tyr Arg Lys Ile Cys Ala Glu
    50                  55                  60

Ile Glu Gln Glu Thr Asn Leu Lys Asn Leu Arg Ala Met Arg Arg Gly
65                  70                  75                  80

Lys Ile Thr Glu

<210> SEQ ID NO 274
<211> LENGTH: 189
<212> TYPE: PRT
<213> ORGANISM: Escherichia coli

<400> SEQUENCE: 274

Met Asn Asn Leu Met Ile Asp Leu Glu Ser Met Gly Lys Lys Pro Asn
1               5                   10                  15

Ala Pro Ile Val Ser Ile Gly Ala Val Phe Phe Asp Pro Gln Ser Gly
            20                  25                  30

Glu Leu Gly Gln Glu Phe Tyr Thr Ala Val Asn Leu Glu Ser Ala Met
        35                  40                  45

Glu Gln Gly Ala Val Pro Asp Gly Asp Thr Ile Leu Trp Trp Leu Arg
    50                  55                  60

Gln Ser Ser Glu Ala Arg Ser Ala Ile Cys Val Asp Asp Ala Met Pro
65                  70                  75                  80

Ile Ser Ser Ala Leu Ser Glu Leu Ser His Phe Ile Asn Arg His Ser
                85                  90                  95

Asp Asn Pro Lys Tyr Leu Lys Val Trp Gly Asn Gly Ala Thr Phe Asp
            100                 105                 110

Asn Val Ile Leu Arg Gly Ala Tyr Glu Arg Ala Gly Gln Val Cys Pro
        115                 120                 125

Trp Gln Phe Trp Asn Asp His Asp Val Arg Thr Ile Val Thr Leu Gly
    130                 135                 140

Arg Ser Val Gly Phe Asp Pro Lys Arg Asp Met Pro Phe Asp Gly Val
145                 150                 155                 160

Ala His Asn Ala Leu Ala Asp Ala Arg His Gln Ala Lys Tyr Val Ser
                165                 170                 175

Ala Ile Trp Gln Lys Leu Ile Pro Thr Thr Ser Asn Ser
            180                 185

<210> SEQ ID NO 275
<211> LENGTH: 78
<212> TYPE: PRT
<213> ORGANISM: Escherichia coli

<400> SEQUENCE: 275

Met Ser Asn Ile Phe Gln Leu Ala Pro Asn Asp Trp Val Cys Glu Ser
1               5                   10                  15

Val Leu Ile Ala Val Thr Gly Leu Lys Pro Gly Thr Ile Leu Arg Ala
            20                  25                  30

```
Arg Lys Glu Cys Trp Met Ile Gly Arg Glu Tyr Ile His Val Ser Pro
        35                  40                  45

Asp Gly Asn Pro Lys Pro Ser Ser Glu Cys Met Tyr Asn Arg Lys Ala
 50                  55                  60

Val Asp Ala Trp Val Ala Ser Met Lys Ser Lys Gln Pro Gly
 65                  70                  75

<210> SEQ ID NO 276
<211> LENGTH: 437
<212> TYPE: PRT
<213> ORGANISM: Escherichia coli

<400> SEQUENCE: 276

Met Asp Lys Val Thr Tyr Pro Thr Gly Val Glu Asn His Gly Gly Thr
 1               5                  10                  15

Leu Arg Ile Trp Phe Asn Phe Lys Gly Lys Arg Val Arg Glu Ser Leu
                20                  25                  30

Gly Val Pro Asp Thr Ala Lys Asn Arg Lys Ile Ala Gly Glu Leu Arg
            35                  40                  45

Thr Ser Val Cys Phe Ala Ile Arg Thr Gly Thr Phe Asp Tyr Ala Thr
 50                  55                  60

Gln Phe Pro Asp Ser Pro Asn Leu Lys Ala Phe Gly Val Ser Lys Lys
 65                  70                  75                  80

Asp Ile Thr Val Lys Glu Leu Glu Glu Lys Trp Leu Asp Leu Lys Arg
                85                  90                  95

Met Glu Ile Cys Ala Asn Ala Phe Asn Arg Tyr Glu Ser Val Ala Arg
            100                 105                 110

Asn Met Val Pro Arg Ile Gly Gly Asn Arg Leu Val Ser Ala Val Thr
        115                 120                 125

Lys Glu Glu Leu Leu Tyr Leu Arg Lys Tyr Leu Leu Thr Gly Tyr Gln
130                 135                 140

Asn Pro Thr Lys Asn Lys Ala Pro Ala Lys Gly Arg Ser Val Val Thr
145                 150                 155                 160

Val Asn Tyr Tyr Met Thr Thr Met Ala Gly Met Phe Gln Phe Ala Ala
                165                 170                 175

Asp His Gly Tyr Leu Glu Val Asn Pro Phe Glu Gly Ile Lys Pro Leu
            180                 185                 190

Lys Lys Ala Arg Ala Glu Pro Asp Pro Leu Ser Arg Asp Glu Phe Ile
        195                 200                 205

Arg Leu Ile Asp Ala Cys Arg His Gln Gln Thr Lys Asn Leu Trp Ser
210                 215                 220

Leu Ala Val Tyr Thr Gly Met Arg His Gly Glu Leu Val Ser Leu Ala
225                 230                 235                 240

Trp Glu Asp Ile Asp Leu Lys Ala Gly Thr Ile Thr Val Arg Arg Asn
                245                 250                 255

Tyr Thr Lys Leu Gly Glu Phe Thr Leu Pro Lys Thr Glu Ala Ser Thr
            260                 265                 270

Asp Arg Val Val His Leu Ile Gln Pro Ala Ile Ser Ile Leu Lys Asn
        275                 280                 285

Gln Ala Glu Met Thr Arg Leu Gly Arg Gln Tyr His Ile Glu Val Gln
    290                 295                 300

Leu Arg Glu Tyr Gly Arg Ser Val Asn His Glu Cys Thr Phe Val Phe
305                 310                 315                 320

Asn Pro His Val Val Arg Arg Ser Lys Gln Val Gly Phe Ile Tyr Arg
```

```
                    325                 330                 335
Val Asp Ser Val Gly Asp Ser Trp Glu Ala Ala Leu Lys Arg Ala Gly
                340                 345                 350

Ile Arg His Arg Lys Ala Tyr Gln Ser Arg His Thr Tyr Ala Cys Trp
            355                 360                 365

Ser Leu Ser Ala Gly Ala Asn Pro Ser Phe Ile Ala Ser Gln Met Gly
        370                 375                 380

His Ala Ser Ala Gln Met Val Phe Asn Val Tyr Gly Ala Trp Met Ala
385                 390                 395                 400

Asp Ser Ser Ala Glu Gln Ile Ala Met Leu Asn Gln Lys Leu Ala Asp
                405                 410                 415

Phe Ala Pro Leu Met Pro His Ser His Glu Asn Ser Thr Gly Gly Leu
                420                 425                 430

Leu Lys Ser Val Ser
            435

<210> SEQ ID NO 277
<211> LENGTH: 241
<212> TYPE: PRT
<213> ORGANISM: Escherichia coli

<400> SEQUENCE: 277

Met Glu Gly Asn Thr Thr Leu Tyr Ala Leu Pro Lys Pro Glu Val Val
1               5                   10                  15

Leu Arg Trp Arg Glu Gln Thr Thr Asp Asp Phe Arg Phe Cys Phe Lys
            20                  25                  30

Phe Pro Ala Thr Ile Ser His Gln Ala Ala Leu Arg His Cys Asp Asp
        35                  40                  45

Leu Val Thr Glu Phe Leu Thr Arg Met Ser Pro Leu Ala Pro Arg Ile
    50                  55                  60

Gly Gln Tyr Trp Leu Gln Leu Pro Ala Thr Phe Gly Pro Arg Glu Leu
65                  70                  75                  80

Pro Ala Leu Trp His Phe Leu Asp Ser Leu Pro Gly Glu Phe Asn Tyr
                85                  90                  95

Gly Val Glu Val Arg His Pro Gln Phe Phe Ala Lys Gly Glu Glu Glu
            100                 105                 110

Gln Thr Leu Asn Arg Gly Leu His Gln Arg Gly Val Asn Arg Val Ile
        115                 120                 125

Leu Asp Ser Arg Pro Val His Ala Ala Arg Pro Tyr Ser Glu Ala Ile
    130                 135                 140

Arg Asp Ala Gln Arg Lys Lys Pro Lys Val Pro Val His Ala Val Leu
145                 150                 155                 160

Thr Ala Lys Asn Pro Leu Ile Arg Phe Ile Gly Ser Asp Asp Met Thr
                165                 170                 175

Gln Asn Arg Glu Leu Phe Gln Val Trp Leu Gln Lys Leu Ala Gln Trp
            180                 185                 190

His Gln Thr Thr Thr Pro Tyr Leu Phe Leu His Thr Pro Asp Ile Ala
        195                 200                 205

Gln Ala Pro Glu Leu Val His Thr Leu Trp Glu Asp Leu Arg Lys Thr
    210                 215                 220

Leu Pro Glu Ile Gly Ala Val Pro Ala Ile Pro Gln Gln Ser Ser Leu
225                 230                 235                 240

Phe
```

<210> SEQ ID NO 278
<211> LENGTH: 131
<212> TYPE: PRT
<213> ORGANISM: Escherichia coli

<400> SEQUENCE: 278

Met Val Ser Ala Leu Tyr Ala Val Leu Ser Ala Leu Leu Met Lys
1               5                   10                  15

Phe Ser Phe Asp Val Val Arg Leu Arg Met Gln Tyr Arg Val Ala Tyr
            20                  25                  30

Gly Asp Gly Gly Phe Ser Glu Leu Gln Ser Ala Ile Arg Ile His Gly
        35                  40                  45

Asn Ala Val Glu Tyr Ile Pro Ile Ala Ile Val Leu Met Leu Phe Met
50                  55                  60

Glu Met Asn Gly Ala Glu Thr Trp Met Val His Ile Cys Gly Ile Val
65                  70                  75                  80

Leu Leu Ala Gly Arg Leu Met His Tyr Tyr Gly Phe His His Arg Leu
                85                  90                  95

Phe Arg Trp Arg Arg Ser Gly Met Ser Ala Thr Trp Cys Ala Leu Leu
            100                 105                 110

Leu Met Val Leu Ala Asn Leu Trp Tyr Met Pro Trp Glu Leu Val Phe
        115                 120                 125

Ser Leu Arg
    130

<210> SEQ ID NO 279
<211> LENGTH: 247
<212> TYPE: PRT
<213> ORGANISM: Escherichia coli

<400> SEQUENCE: 279

Met Ser His Arg Asp Thr Leu Phe Ser Ala Pro Ile Ala Arg Leu Gly
1               5                   10                  15

Asp Trp Thr Phe Asp Glu Arg Val Ala Glu Val Phe Pro Asp Met Ile
            20                  25                  30

Gln Arg Ser Val Pro Gly Tyr Ser Asn Ile Ile Ser Met Ile Gly Met
        35                  40                  45

Leu Ala Glu Arg Phe Val Gln Pro Gly Thr Gln Val Tyr Asp Leu Gly
50                  55                  60

Cys Ser Leu Gly Ala Ala Thr Leu Ser Val Arg Arg Asn Ile His His
65                  70                  75                  80

Asp Asn Cys Lys Ile Ile Ala Ile Asp Asn Ser Pro Ala Met Ile Glu
                85                  90                  95

Arg Cys Arg Arg His Ile Asp Ala Tyr Lys Ala Pro Thr Pro Val Asp
            100                 105                 110

Val Ile Glu Gly Asp Ile Arg Asp Ile Ala Ile Glu Asn Ala Ser Met
        115                 120                 125

Val Val Leu Asn Phe Thr Leu Gln Phe Leu Glu Pro Ser Glu Arg Gln
    130                 135                 140

Ala Leu Leu Asp Lys Ile Tyr Gln Gly Leu Asn Pro Gly Gly Ala Leu
145                 150                 155                 160

Val Leu Ser Glu Lys Phe Ser Phe Glu Asp Ala Lys Val Gly Glu Leu
                165                 170                 175

Leu Phe Asn Met His His Asp Phe Lys Arg Ala Asn Gly Tyr Ser Glu
            180                 185                 190

Leu Glu Ile Ser Gln Lys Arg Ser Met Leu Glu Asn Val Met Leu Thr 195                 200                 205
Asp Ser Val Glu Thr His Lys Ala Arg Leu His Lys Ala Gly Phe Glu
            210                 215                 220

His Ser Glu Leu Trp Phe Gln Cys Phe Asn Phe Gly Ser Leu Val Ala
225                 230                 235                 240

Leu Lys Ala Glu Asp Ala Ala
            245

<210> SEQ ID NO 280
<211> LENGTH: 323
<212> TYPE: PRT
<213> ORGANISM: Escherichia coli

<400> SEQUENCE: 280

Met Ile Asp Phe Gly Asn Phe Tyr Ser Leu Ile Ala Lys Asn His Leu
1               5                   10                  15

Ser His Trp Leu Glu Thr Leu Pro Ala Gln Ile Ala Asn Trp Gln Arg
            20                  25                  30

Glu Gln Gln His Gly Leu Phe Lys Gln Trp Ser Asn Ala Val Glu Phe
        35                  40                  45

Leu Pro Glu Ile Lys Pro Tyr Arg Leu Asp Leu Leu His Ser Val Thr
    50                  55                  60

Ala Glu Ser Glu Glu Pro Leu Ser Ala Gly Gln Ile Lys Arg Ile Glu
65                  70                  75                  80

Thr Leu Met Arg Asn Leu Met Pro Trp Arg Lys Gly Pro Phe Ser Leu
                85                  90                  95

Tyr Gly Val Asn Ile Asp Thr Glu Trp Arg Ser Asp Trp Lys Trp Asp
            100                 105                 110

Arg Val Met Pro His Leu Ser Asp Leu Thr Gly Arg Thr Ile Leu Asp
        115                 120                 125

Val Gly Cys Gly Ser Gly Tyr His Met Trp Arg Met Ile Gly Ala Gly
    130                 135                 140

Ala His Leu Ala Val Gly Ile Asp Pro Thr Gln Leu Phe Leu Cys Gln
145                 150                 155                 160

Phe Glu Ala Val Arg Lys Leu Leu Gly Asn Asp Gln Arg Ala His Leu
                165                 170                 175

Leu Pro Leu Gly Ile Glu Gln Leu Pro Ala Leu Lys Ala Phe Asp Thr
            180                 185                 190

Val Phe Ser Met Gly Val Leu Tyr His Arg Arg Ser Pro Leu Glu His
        195                 200                 205

Leu Trp Gln Leu Lys Asp Gln Leu Val Asn Glu Gly Glu Leu Val Leu
    210                 215                 220

Glu Thr Leu Val Ile Asp Gly Asp Glu Asn Thr Val Leu Val Pro Gly
225                 230                 235                 240

Asp Arg Tyr Ala Gln Met Arg Asn Val Tyr Phe Ile Pro Ser Ala Leu
                245                 250                 255

Ala Leu Lys Asn Trp Leu Lys Lys Cys Gly Phe Val Asp Ile Arg Ile
            260                 265                 270

Ala Asp Val Ser Val Thr Thr Thr Glu Glu Gln Arg Arg Thr Glu Trp
        275                 280                 285

Met Val Thr Glu Ser Leu Ala Asp Phe Leu Asp Pro His Asp Pro Gly
    290                 295                 300

Lys Thr Val Glu Gly Tyr Pro Ala Pro Lys Arg Ala Val Leu Ile Ala
305                 310                 315                 320

Arg Lys Pro

<210> SEQ ID NO 281
<211> LENGTH: 49496
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 281

| | | | | | |
|---|---|---|---|---|---|
| aggcctctcc | tcgcgagagg | cattttttat | ttgatgggat | aaagatcttt | gcgcttatac | 60 |
| ggttggattt | cgcccggttt | gcgagttttc | agcaatttta | atatccaggt | gtattgttct | 120 |
| ggtcgcggac | caacaaaaat | ctcgacttct | tcattcatcc | gccgcgcaat | cgtatgatca | 180 |
| tccgcctcta | acagatcatc | catcggtggg | cgcacctgaa | tcgtcagacg | atgcgtcttg | 240 |
| ccatcataaa | tcggaaatag | cggtacaacg | cgcgcacggc | acactttcat | caaacgacca | 300 |
| atcgcgggca | acgtcgcttt | ataggtggca | aagaaatcaa | caaattcgct | gtgttctggg | 360 |
| ccatgatcct | gatcgggtaa | ataatatccc | cagtaaccct | gacgtaccga | ctggatgaat | 420 |
| ggtttaatac | catcatttct | cgcatgcaga | cgaccaccaa | agcgacggcg | caccgtgttc | 480 |
| cagacataat | caaaaaccgg | gttgccctga | ttatggaaca | tcgctgccat | tttctgccct | 540 |
| tgcgaggcca | tcagcatggc | aggaatatcg | acggcccaac | cgtgcggcac | cagaaaaatc | 600 |
| actttctcgt | tattacgtcg | tatctcttcg | atgatctcca | gcccttgcca | gtcaacgcgc | 660 |
| ggctgaattt | tctccggccc | gcgtattgcc | aactcagcca | tcattaccat | cgcttgcggc | 720 |
| gcggtggcaa | acatctcatc | tacaatcgct | tcgcgttcag | cttcactacg | ttctggaaag | 780 |
| cagagcgaca | gattgattaa | cgcacgacgg | cgtgagcttt | ttcccagtcg | tccggcaaaa | 840 |
| cgtcccagcc | gtgccagaat | gggatcacgg | aactttggcg | gcgttaaagc | gatacccgcc | 900 |
| atcgctgcta | cgcccagcca | tgctccccag | tagcgcgggt | ggcgaaagga | tttatcaaac | 960 |
| tcaggaatgt | attcgctatt | attttttttc | gtttccatgc | ttttccagtt | tcggataagg | 1020 |
| caaaaatcaa | tctggtgata | gtgtagcggc | gcaacttgcc | ccgcaccaaa | taaaaaagcc | 1080 |
| ggtactgact | gcgtaccggc | tgcgaatgga | tgttaattaa | tcaaaccgta | gctgcggcac | 1140 |
| aatctctttg | gcctgtgcca | ggaattcgcg | acgatcggag | ccggtcagcc | cttcggtacg | 1200 |
| cggcagtttt | gccgtcagcg | ggtttacggc | ctgctggttt | atccatactt | catagtgcag | 1260 |
| atgcggcccg | gttgaacgtc | cggtattacc | ggaaagcgcg | atacggtcgc | cacgtttcac | 1320 |
| cttctgtccc | ggtttcacca | ggatcttgcg | caagtgcata | taacgcgtgg | tgtagctgcg | 1380 |
| accatgacga | atagccacat | aataacctgc | tgcgccacta | cgtttggcaa | ccaccacttc | 1440 |
| accgtcaccc | actgaaagca | ctggcgtacc | ttgtggcatg | gcaaaatcaa | cacctctgtg | 1500 |
| tggcgcaacg | cgaccggtca | ccggattagt | acgacgcggg | ttaaagttag | atgagatacg | 1560 |
| gaactgtttc | gccgtcggga | atcgcaagaa | tcctttcgcc | agaccagtac | cgttacgatc | 1620 |
| gtagaatttg | ccatcttcag | cgcggattgc | gtaataatct | ttaccttctg | aacgcaaacg | 1680 |
| tacgcccagc | agctggcttt | gctcacgttt | accatcaagc | atttctcgtg | acattaacac | 1740 |
| cgcaaattca | tcgccttttt | tcagtttgcg | gaaatccatt | tgccactgca | tggctttaat | 1800 |
| cactgcgctc | acttcggcgc | tggttaaacc | ggcgttctg | gcgctggcaa | caaagcttcc | 1860 |
| cccgacggta | cctttcagca | gattgttgac | ccactctcct | tgctgcattt | cgctggtcat | 1920 |
| tttaaaaccg | ttagcggcag | tacggtcata | ggttcgggtt | tcacgacgag | acacttccca | 1980 |

-continued

```
ggtgaggcgc tgcagttcgc cgtccgcggt taatgtccag gagagttgtt gaccgatttt    2040
caggttacgc aattctttgt cggcagcagc cagttgggtg atatcaccca tatcaatacc    2100
atactgattg agaatgctgc ttagcgtatc gccagtggaa acaacatatt catgcacgcc    2160
cgcttcaccg gcgattttgt catccagttc gtcctgggga atggcttcat cttcttgtgc    2220
agcttgatca atcggctcac tggcttcagg taagagcgaa cgaatttcgt tctgttccag    2280
ctcaatggtt ttgacaattg gcgtggcatc gcggtgataa acatagggcc gccagacagc    2340
gacggccaga gtaagaacgg tgagcgaccc aacataacg cggtgtggtc gcggtaaatt     2400
attaaacgcc agggcgacag agcgggctat ctgttgcacg taatcacttc ctcattaatc    2460
tcctttcagg cagctcgcat actggttggc taattgattc aggaattctg aatagcttgt    2520
tttacccagt tgatattcg tccccagggg atccaacgtt cccatacgaa cggatgtccc     2580
tcgtgcgacg ctctcaacga ccgctggcct gaactgtggc tcagcaaaaa cgcaggttgc    2640
tttttgctca accaactgtg ttcttatttc atgtaaacgc tgcgcgccag gttgaatctc    2700
agggttaacg gtaaaatgac caagcggtgt cagtccgaac tgttttcga aatagccgta     2760 agcatcgtga aaaacgaaat aacctttccc cttgagcggc gcgagctcgt taccaacctg    2820
cttttcggtt gaggctaatt gtgcctcaaa atccttcagg ttggcgtcaa gtttggctcg    2880
actttgcggc ataagttcca ctaatttcc atggattgca accgctgtag cccgcgctat     2940
ctctggggaa agccaaagat gcatgttgaa atcgccgtga tggtgatctt cgtcactttt    3000
ttccgcgtgg tcgtgatcat catcatcgcc gtgaatactt ttcatcagca gcggtttcac    3060
attctctagc tgcgcaatcg ttacctgttt cgcttcaggt aatttactta ccggtttttg    3120
catgaacgct tccatctccg ggccaaccca aacgactaag tccgcgttct gtaagcgttt    3180
tacatctgat ggacgcagtg aataatcatg ttctgaagcc ccgtcaggta gtaaaacctc    3240 cgttctgtt accccatcag caatggcaga agcgatgaac ccaacgggtt taagcgaagc     3300
gacaacggca gcatctgcgg cctgtgttgc accgccccag agagcggcgg ataatgctgc    3360
gaaaagaagc gttttttat gtaacataat gcgaccaatc atcgtaatga atatgagaag     3420
tgtgatatta taacatttca tgactactgc aagactaaaa ttaacatgac aagtctggtt    3480
tccctggaaa atgtctcggt ttcttttggc caacgccgcg tcctctctga tgtgtcgctg    3540
gaacttaaac ctggaaaaat tttgacttta cttgggccaa acggcgcagg taagtcgaca    3600
ctggtacggg tagtgctcgg gctggtaaca cccgatgaag gggttatcaa gcgcaacgga    3660
aaactgcgca tcggctatgt accgcagaag ctgtatctcg acaccacgtt gccactgacc    3720
gtaaaccgtt ttttacgctt acgccctggc acacataaag aagatatttt gcctgcactg    3780
aaacgtgtcc aggccgggca tctgattaac gcaccgatgc aaaagctctc gggtggcgaa    3840
acgcagcgtg tactgttagc gcgagcattg ttaaatcgac cgcaattatt agtgctggat    3900
gaacccactc agggcgtgga tgtgaatggt caggtggcgt tatatgacct tattgaccaa    3960
ctgcgtcgcg aactggattg tggcgtttta atggtatctc acgatctgca tctggtaatg    4020 gcaaaaccg atgaagtgct ttgcctgaat caccacattt gttgttccgg cacaccggaa     4080
gttgtttccc tgcatccgga gtttatttct atgtttggtc ctcgtggtgc tgaacaactg    4140
ggtatctatc gccatcatca taatcatcgt cacgatttac agggacgaat tgttttgcgt    4200
cggggaaatg atcgctcatg attgaattat tatttcccgg ttggttagcc gggatcatgc    4260
tcgcctgtgc cgcgggtccg ctgggttcgt ttgtagtctg gcgtcgtatg tcttatttcg    4320
```

```
gtgatacgct ggctcatgcc tcattacttg gcgtcgcgtt tggtttgttg ctggacgtga    4380
atccattcta tgcggtgatt gccgttacgc tgctgctggc gggcggtctg gtatggctgg    4440
agaagcgtcc acagctggcg atcgacacgt tattagggat tatggcgcac agtgccctgt    4500
cgctgggcct ggtggtcgtt agtctgatgt ctaatattcg tgttgatttg atggcttacc    4560
tgttcggtga tttactggca gtgacgccag aagatctcat ctctattgcg attggcgtgg    4620
tcatcgtggt ggctattttg ttctggcaat ggcgcaattt gctgtcgatg acgattagcc    4680
cggatctggc gtttgttgat ggtgtgaaat tacagcgcgt gaaattgttg ttgatgctgg    4740
tgacggcatt gacgattggt gtagcgatga aattcgtcgg cgcgttgatt attacttcac    4800
tgctgattat tcctgctgct actgcacgtc gctttgcccg cacgccggaa cagatggctg    4860
gtgtcgctgt tttggtgggg atggtggcag tgactggcgg tttaaccttt tccgcatttt    4920
acgatacacc tgcaggcccg tcggtggtgc tatgcgcggc actgttattt attatcagta    4980
tgatgaaaaa gcaggccagc taatctgtcg ctgaacacat ttgtcggatg cggcgcgagc    5040
gccttatccc acctgcggtt cgctatctct ggtaggcctg ataagacgcg aacagcgtcg    5100
catcaggcac actgccagtg tcggatgcgg ctcgagcgac caatccgact tacggcattt    5160
ctggcggcgt gatgccgaag tggttccacg cccgcactgt cgccatacgc ccgcgcggtg    5220
tacgctgcaa aaagccttgc tgaatcaaat aaggttccag tacatcctca atggtttcac    5280
gttcttcgcc aatggctgcc gccaggttat ccagacctac cggcccacca aagaacttat    5340
cgattaccgc cagcaacaat ttgcggtcca tataatcgaa accttcagca tcgacattca    5400
acatatccag cgcctgagca gcgatatctg ccgagatggt gccatcgtgc ttcacttcag    5460
cgaaatcacg cactcgacgc agcagacggt tggcaatacg tggcgtaccg cgcgcacgac    5520
gagcaacttc cagcgcgccg tcatcactca tctcaagccc cataaagcgt gcgctgcgac    5580
tgacgatata ttgcagatcc ggcacctgat aaaactccag acgttgcaca ataccaaaac    5640
gatcgcgcaa cggtgatgtc agcgaacctg cgcgcgtggt tgcaccaatc agggtaaacg    5700
gcggcaaatc aattttaatg gagcgtgccg ccggaccttc accaatcatg atatccagtt    5760
ggtaatcttc cattgccgga tacaacacct cttccaccac tggtgaaaga cggtggatct    5820
catcaataaa cagtacatcg tgtggttcaa ggttagtgag cattgctgcc agatcgcccg    5880
ccttttccag caccggacca gaagtcgtgc gtaaattaac gcccatttca ttggcgacaa    5940
tattggcaag cgtagtttta cccaaccccg gaggaccaaa aatcaataga tgatcgaggg    6000
catcgccgcg cagtttcgct gctttgatga aaatctccat ctgcgaacga acctgcggct    6060
gaccaacata ctcttccagt aatttagggc gaatggcgcg atctgccaca tcttccggca    6120
aagtggtacc ggcagaaatc agacggtctg cttcaatcat cctttacctc ataacgcggc    6180
gcgtagggct tcgcgaatta atgtttcact gctggcgtca gggcgagcga ttttgctcac    6240
catgcggctt gcttcttgtg gtttatagcc cagtgccacc agcgcagcaa ccgcttcctg    6300
ttcagcatcg tcggtcgccg ggctggcagg agacgtgagt accaggtcgg cggctggcgt    6360
aaagagatcg ccatgcaaac ctttaaatcg gtctttcatt tcgacaatca agcgttcggc    6420
ggttttttg ccaatacccg gcagtttcac cagtgccccc acttcttcac gctcaacggc    6480
attaacgaac tgctgcgctg acattccgga gaggatcgcc agcgccaact tcgggccgac    6540
gccgttggtt ttgatcaact ctttgaacaa cgtgcgctct tgtttattgt taaaaccgta    6600
cagcagttgc gcgtcttcac gcaccacaaa gtgggtgaaa acgatcgctt cctgacccgc    6660
ttcagggagt tcataaaaac aggtcatcgg catatgcact tcatagccta cgccgcccac    6720
```

-continued

```
ttcaattaac accagcgggg gttgtttttc aatgatgatg cctctgagtc tgcctatcac    6780
atgacgctcc tgcgtaatga atcaaagata atgctgtatg ataaaaaaat gctggataga    6840
tatccagcga aggatgaaga aaacttgcga ggtgtctcga tgatctgaaa aatggcgcag    6900
tataatttat tctacagatt atattggaag caaatattta aatattacat attcagcgaa    6960
gaaatgtgta ataaaaatac acattgcgac ccctgaaaaa aataaatttt ttatgctatt    7020
acgtatattc atatctattt caatggaatg acaacgtgaa tattaattat cctgctgaat    7080
atgaaattgg tgatatcgtc tttacatgta taagtgctgc cttatttggt caaatatcag    7140
ctgcatcaaa ttgctggagt aatcacgtcg ggatcattat cggtcataac ggtgaagact    7200
ttctggttgc agaaagccgt gttcccctct caaccatcac tacgctatcc cgtttttatta   7260
aacgctctgc taatcaacgc tatgctataa agcgattaga cgccggacta acagaacaac    7320
aaaatcaacg aattgttgaa caggttcctt cccggctacg caaaatttac cacaccggtt    7380
ttaaatacga atcttcgcgc cagttctgtt caaaatttgt ttttgatatt tataaagagg    7440
cgctatgtat tccggtgggt gaaatagaga cgtttggaga attgttaaat agcaatccaa    7500
atgcaaaact cactttctgg aaattctggt tcttaggttc tattccgtgg gagcgtaaaa    7560
ccgtcacgcc agccagtttg tggcatcatc cgggtttggt gttgattcac gcggtgggag    7620
ttgaaacgcc tcagcctgaa ctgaccgagg cggtataact taacgcagtc gccctctcgc    7680
caggttcagt cgcgattcgc tcatttgcat cgcattctga ctaacgtggc agtgggtgat    7740
ggcaatcgcc agcgcatcgg cggcatccgc ctgtggatta gcgggcagtt tcagcaaggt    7800
gcggaccata tgctgcacct ggcttttttc ggcactacca atacctacca ctgtttgctt    7860
tacctgacgt gccgcatatt caaataccgg caattcctga ttcaccgccg ccacaatcgc    7920
cacgccgcgc gcctgcccca gtttcagggc tgagtcagcg ttcttcgcca taaagacctg    7980
ttcaatggcg aaataatcag gctggaattg ggtgatgatt tccgtcacgc ccgcatagat    8040
gagcttcaga cgagacggta aatcatccac tttggtgcgt atgcatccgc tacccaggta    8100
ggacagttgc ctgcctacct ggcggatgac gccatagccg gtcacgcgcg aacccgggtc    8160
aatgccgaga ataatagcca tcacgcgtct ccgttttgct gtttagcagg cctcatcaga    8220
gagtcgctgc aacctcatca gagatttcac cgttatggta aacttcctgc acgtcgtcgc    8280
aatcttccag catatcgatc agacgcatca gtttcggtgc ggtttctgca tccatatcag    8340
ctttggtgga cgggatcatg gaaacttccg cgctgtctgc tttcagacct gccgcttcca    8400
gagcgtcgcg tactttgccc atttcttccc atgcagtgta gacatcaatc gcgccgtcat    8460
cataggtcac aacgtcttca gcaccggctt ccagggctgc ttccatgatg gtgtcttcat    8520
cgcctttctc gaaggagatc acgccttttt tgctgaacaa ataagctacg gaaccatcag    8580
taccgaggtt accgccacat ttgctgaatg catgacgcac ttcagcaacg gtacggttgc    8640
ggttgtcaga cagacattca atcatgattg ccgtgccgcc aggaccgtaa ccttcgtaga    8700
tgatggtttc catgtttgca tcatcatcac cgcccacacc tcgtgcaatt gcgcggttca    8760
gagtgtcacg ggtcatgttg ttagacagtg ctttatcaat tgctcacgc aaacgcgggt    8820
tagcgtccgg atcaccaccg cccagcttag ccgcggttac cagctcacga atgatttag    8880
tgaagatttt accgcgctta gcatcctgcg cagctttacg atgtctggtg ttggcccatt    8940
tactatgacc tgccataaaa atatctccag atagccctgc ctgttcaggc agcgttaatt    9000
acaaactgtt caatcgcctg ccggttgctc caggacttag tgagcgccgc cgcagcagac    9060
```

```
gcatcaagcc acttgtaagc cagatgttca gtgaaaacga tctggcgctc gtgcggaagc    9120
gcaagacaga accatgattc cgtattacgc gtcacgcccg gcgcatagcg atgacgtaaa    9180
tgtgaaaaaa tttcaaactc taccgtgcgc tgacagtcaa ttaaggtcag ttgttcagcg    9240
acaacatcaa tggtgacctc ttcctttact tcgcgcatgg cagcttgcgg cgcggtttca    9300
ccctcttcca cgctgccggt taccgactgc cagaaatcgg gatcgtcacg ccgctgcaac    9360
atcagcaccc gtttcgtatc ttgtgcgtag atgaccacta agatcgaaac gggacgctta    9420
taagccatat cagttattct cagccttctt cacaacctga atgctcagct cagccagtgc    9480
agtcgggtta gcaaagctcg gcgcttcagt catcaaacac gctgccgccg tggttttcgg    9540
gaaggcgata acgtcacgga tattgtcggt gccggtcagc agcatcgtca gacggtcaag    9600
accgaatgcc aaacctgcgt gcggcggagt accgtatttc agggcgtcga gcaggaagcc    9660
gaatttctcg cgctgttcct cttcgttgat acccagaata ccaaacaccg tctgctgcat    9720
atcaccatta tggatacgca cagaaccacc gcccacttcg taaccattga tgaccatatc    9780
gtaagcgtta gccaccgcat tttccggtgc agctttcagt tctgctgccg tcatgtcttt    9840
cggtgaggtg aacggatggt gcattgctgt caggccgcct tcaccgtcgt cttcaaacat    9900
cgggaagtcg ataaccccaca gcggtgccca tttgctttcg tcggtcagac caaggtcttt    9960
acccactttc aggcgcagtg cgcccatcgc gtcggcaaca attttcttgt tgtcggcacc    10020
gaagaaaatc atatcgccat cttgcgcgcc agtacgctcc aggatggctt cgatgatttc    10080
tgcattaagg aacttcgcta ccgggctatt gataccttcc agacctttcg cgcgttcgtt    10140
aactttgatg taagccagac ctttcgcgcc gtagatttta acgaagttac cgtattcgtc    10200
gatctgctta cgggtcaacg atgcgccgcc cggaacacgc agagcggcaa cacggccttt    10260
cggatcgttc gccggacctg caaatactgc aaactcaaca gatttcagca gatcggcaac    10320
gtcggtcagt tccatcgggt tacgcagatc cggtttatca gaaccataac ggcgttctgc    10380
ttctgcaaag gtcattaccg ggaaatcgcc cagatccacg cccttcactt ccagccacag    10440
atgacgcacc agcgcttcca tcacttcacg cacttgcggc gcggtcatga agaagtttc    10500 cacatcgatc tgagtaaatt caggctgacg gtcagcacgc aggtcttcgt cacggaagca    10560
tttaacgatc tgatagtagc ggtcaaagcc ggacatcatc agtagctgtt tgaacaactg    10620
cggggattgc ggcagcgcgt agaatttacc tttgtgcaca cgagaaggca ccaggtagtc    10680
acgcgcgcct tcaggcgtgg cttggtcag catcggagtt tcgatgtcga ggaagccgtg    10740
gtcatccata aaacggcgca ccaggctggt gattttagcg cgggttttca ggcgctgagc    10800
catttccggg cgacgcaggt cgaggtagcg gtatttcaga cgcgcttctt cggtgttgac    10860
gtggttagag tcaagcggca gaacatctgc acggttgatg atagtcagcg aggacgccag    10920
tacttcgatt tcgccagtcg ccatatcgcg gttaatattt ttttcgtcac gcgcacgtac    10980
ggtgcccgtg acctgaatgc agaactcatt acgcagttca gaggccagct ttaacgcgtc    11040
cgcacgatcc ggatcgaaaa atacctgcac gatacctcg cggtcgcgca tatcgatgaa    11100
gatcaggcta ccaagatcac gacgacggtt gacccaacca cacagagtca cctgctgccc    11160
cacgtgggac aaacggagct gtccacaata ttcgtacgc atgagatatc ccttaactta    11220
gctgccggcg gatgccccct gctgcgcagg tgaccaagtc gcagcgttag ctgtatgtca    11280
caactgaatg aaaaaaggcg gctattatac tggaaattct gccgcaccgt aagagcctgg    11340
cccgcgctgg aacgctcgt taccactta tatcgggcct gaaatcagac tctacgccag    11400
tttgctataa aggtgttgcc cgaactcata aaaattaaca aaatttgtcg ttccgccatc    11460
```

```
ggctaatcgc attaaggtga gaggcacgat tttgttttgt caggagtcat catgcttgaa    11520
cttaatgcta aaaccaccgc gctggtggtg attgatttac aagaaggcat cttgccttt     11580 gccggaggtc cacatactgc cgatgaggtg gttaatcgcg ccgggaagct ggcggcgaaa    11640
tttcgcgcca gcggtcagcc cgtgtttctg gtgcgcgttg gctggtctgc cgattacgcc    11700
gaagcattaa aacagccggt tgatgccccc tcccccgcaa aagtgttgcc cgaaaactgg    11760
tggcaacatc ctgctgcatt aggtgcaacc gacagcgata tcgaaatcat caaacgtcaa    11820
tggggtgcgt tttacggtac ggatctggag ttgcaattac gccgccgggg tatcgataca    11880
atagtgttat gtgggatctc gaccaatatc ggtgttgaat ccaccgcccg caatgcctgg    11940
gaactcggtt ttaatctggt gattgccgaa gatgcctgta gcgccgctag cgccgagcag    12000
cacaataaca gcattaatca tatctacccg cgcatcgccc gtgtgcgtag cgttgaagag    12060
atcctcaacg cgttatgatt tacatcggtt tgccacaatg gtcgcatcct aaatgggtgc    12120
ggttggggat caccagcctt gaagagtatg cccgccactt taactgcgtg acgcgggcat    12180
tttaaaaatc actaaagaac gcccaagagc atgtgttttc tttagtttat tcaatgcatt    12240
aaaaaatagt ttcgcatgaa attcggtaaa cttcatgtgt gcaataatgt cccattcatg    12300
ccccaaaatg ccccaaagca gacatttttg ccccaagtat gccccacaag tcacgtcttc    12360
aagtcgtcta tatccatagc acaccgagtt acattcttgc atccggggtg tcgacaatac    12420
ctactttatt gagtgtgcga gaattaccag gaacctttcc acaatgtagt agtctaatag    12480
tcgaatccat ctaacattaa gaagcgttat gatcactagc ctctcattga tatcttctgt    12540
aatagtcact ctatgtatca tggtgttcgc tacagtaaag gtagggattg gtttgtctaa    12600
caatccagac agaaatgata attaacctca accacgtaac cacacttcat acttcatact    12660
tcacttaaca gtgaagtgct cacatcaccg ggcagtcatc aaactccgca ttcctggcat    12720
cattaatgat gtacgtgatc actccaaata tagcgggtgc agaactgtaa ccatcatcat    12780
ctgctggcag cgcttccctt ctcccgttat ccagattaac caggtgcggc tgaggatgag    12840
tccgatatcg cttgatcctg aattccccgt cgattgcaca tatcagcagt gaaccatcgc    12900
aggcagtaag tgacgcatcc acaacaagca acgctccctg gattatccct tccctgaaat    12960
gtgaacgcga tgcccgcatg aaataagtcg ctgcgggctg actgattagc tgctgatcga    13020
gggagattcg tgtttcaaca taatctgccg caggtgaagg aaatcccatg tttacgccct    13080
ctcttgaata ccggataaaa acacagtata aatactgtat atccatccag caaagaggca    13140
atgagcaatg ttcgtggaac tcgtttatga caaaaggaat tttgatggtc tgcccggtgc    13200
aaaagatatc attctgggcg agttaactaa gagagttcac cggatcttcc ccgatgctga    13260
tgttcgggtt aaaccgatga tgacactgcc ggcgatcaac actgacgcca gcaagcatga    13320
gaaggaacag ataagccgta ctgttcagga aatgtttgaa gaggctgaat tctggttagt    13380
gagtgagtaa agattttcaa tgcccgccac agttacgtat tgattatgct gtggaggata    13440
ttcattttcg taaacgttgg tttgggagaa gcggcaaaac ggaatgtggg aacaggggaa    13500
aatcagatac cagatatgtc tgcatttcca tctggcaata actggtttca gttaccaagt    13560
ggacatatcg ttcagatatt ttccatgaac gttcttggtg cagatgctaa tggcacgtca    13620
gctaattacc ccattgcttt tccaacaacg atgattgctg tcagtgctct atggtctgat    13680
gggactgtag caaatgcacc gacatacaag atgatgggga acacgactaa cagaacaact    13740
ttgacgataa aagtatcagc cagctcaggt acttacggga caatgattat tgcggtggga    13800
```

```
cgataaatatg aataaataca gttactctcc ttcagaaaat gccttttatg ctgttgcgtt   13860
aaaaaatacc tatgaattga gtggcacatg gccagctgat gcattagata ttcctgatga   13920
catttctgta aaatatatgg cggaaccgcc acaagggaaa atccgagttg caggggaaaa   13980
tggttttccc acatgggctg aaatacctcc accatcacat gaggaactta ttgaacaggc   14040
cgaatcagag aggcaattat tgattaacca ggccaacgaa tacatgaaca gtaaacaatg   14100
gcccggtaaa gccgctattg gtcgtctgaa aggcgaggaa ctggcacaat ataattcgtg   14160
gctggattat ctggacgcac tggaactggt cgatacttcc ggtacgcccg atattgaatg   14220
gcctacgcct ccggcagttc aggccagatg acatccggcg cggtgctggt atctgttgca   14280
gtcaccgcgt caatgtaatc cagcacggcg ttaagtcggg ttgtttctgc ctgagtcagt   14340
ttccgtccgg cctgtaattt cagctgaatc agactaatgg aagccattgc tgcatcaatc   14400
agtgattggc gctgtgcttc tgccgcttct actgaggcac cgtgttgtgc ctcagtatct   14460
gtcacccatt tctcaccatc ccatttatca tatggcgtta acggtgaaag cgtgacataa   14520
ccgtttttga tggcaccgat ataatccact gtaacagctg cgccattttc gattgagtaa   14580
acagtctcat tgcgatggtc ttcctcatgg ctccatccct tacctgtaaa tactgccact   14640
cttcccggaa tgttttcgtc cgggtcaata ccagtggaac aggcgggcat acttacgcca   14700
gtattaatat attcatcaga ccagcccgta tattcagacg ttactgcatc ataataaaaa   14760
caacgcatat caccccggcac tgcagccagc ccatttttcat caaaaacagg tttcattatt   14820
tagccctcac cagaaagtta aatgcaatat ttcgcggtct gacagcaaca aaattcacac   14880
catcacccac agagttactg ttgaaattaa atcgtgaaaa tcctggctga tttccggcga   14940
tgccatcatg aaagttaatt gcgtgtccag cacctccgcc tatattcccg gcaaactgag   15000
aaaagtttgt agcttcctgc cagcttaata attcgcgacc accatctgca cctcgcccgt   15060
catcccagac acgaatgaaa tcaccgcggg cttcaggtaa taccagcgaa ggaaacactt   15120
tcgccagcac aggataatca gtggcagaga atttcgcgcc gttgaacttc aaaaacacca   15180
tactggacca gctgtcgatt acagtatttg gcattgcagc ggacggccag aagaacggaa   15240
cgccaatagc tggagaacct tctcccaaac caaggtttgt gcgagcgtct gcggcattcg   15300
ttgcgccggt tccgccgtct gcgacagtaa ccgcaccgtt gctcccttc tgcgcaagtt   15360 taccgatgcc tgggatggtt acggcggtgc cgttgatggt aactgtgatg ctttggtttg   15420
ctgaggtggt ggcgaacgtc tcccacgcgc caatattctc gtcgtactct ttgatgagct   15480
gtgacatggc ctgcgccagg ccgtcgactg agatattgtc cgacacaagg attccatact   15540
tctggccgct cagcgccggg gaaactgctg gcgtaaccgt cattgacgtg gcgctgttca   15600
cggatgaaat ctgaaacagc tgcaccgggt tagacatcac gataatcgtc tggccagcgc   15660
ggacctggct ggcgggagct gtccagtttg tgccggagcc ggttgcggta tttccgttaa   15720
tagagatagt tccggtgcta taaatcataa caactcctaa atttagacaa catgaagccc   15780
ggagaggtat ataaccctca ccagaaataa tttctgaatt ggttttaat acatgttggg   15840 caacgccagt gttggcatag ctatagttgt atcaaatgcc attgaccacc cacccaaata   15900
ataattgccg actactttat tcctttctgc tctgacattc ccacctgtca ttacaattcc   15960
tttataccta atatttccgt aaccaccaac gtgtcgacag ttagccccgg tataaacaat   16020
ctggcaaaat tcatcaccaa tattcaggtt cgcattggcg atatttattg tcccatcaaa   16080
aatgaatggc ttcgtgcaag taagaagacg tttgcgttga cgattggttt attcaatcca   16140
tcaactaaaa tatcatgtaa acgaattgcc ataacatttc ccactttatt ttacttactc   16200
```

```
aacacaacaa gtatattaaa attgaacctt gtcaacaaca caaaggagtc ccaatgaaac   16260
tcgctctaat tatgctgcca ttatgtctgt ccctcactgc atgtggtaat ggtttaaata   16320
ccggtaaacc aaattccggt gtcattccaa aacctttgga tcgagatggt aacggttctt   16380
taatttatga taccgaaaac cttccaatga cggggcagtg gtgtcacgag attgatcacg   16440
aataccgacg aatcggtagc ccttctaact gtgttataga ctactaaata ttaaccccctc  16500
aaaagagggg ttaatatttt aacctgtgaa tgaaccagat ccgtgtgata ctatgatagt   16560
aggcgaagaa attgacgcac ccctgttatt ttgagcggac actttaatac gcactgttac   16620
gtttggacct gttacaaccg cagaatgcat gataagtctc tccatgtctt gcacggatga   16680
accactctca ttgccgttaa tgtcgattgt tcctgcacca ttacctttaa cgtttgctat   16740
aacacagacg tgtcttgcgt gcccagaact ggatgaatca ttataagtca ttaccttttc   16800
taaatatccg tcactagacc gactcacatt cgtccctgtg tgcatatttg caatgtcccc   16860
gataaaactt tgggcttcca cagtcccttt gaatttaccg cttgttgctt ggatctcacc   16920
agtaaagcta ccgccactag catatactac acctctgacg gtcacattgt tgaattcagc   16980
atctccagct ttattcaact tccaaccagc agaaccagct gcatagttgt tggactggat   17040
atagttaccg attttgcgt tctcaatggt gccgtcctgg atgaagctgg cccggatgaa    17100
tgtctgcccg ttctggatca cgaacggcaa agctacgcta tttccggctg ccgtggtgac   17160
ggcgaagcgg tcagccagga agataacctg cgactgcatg ccggatggcg tattctccac   17220
gccgataccc atccccgcgg cgtaatactg cccgttgctg gagacaccaa ccttgatgtt   17280
gtacatcgcg ctgagttcgc cattaacgtt ggctatagcc tgagcgttag tggtgatggc   17340
ggaggtatgc ccgttcacgg tcgccgtgat gccgtttatc tgcgtggcgg tggcctgctg   17400
atagtcggag agcgtctgat tcaggctgtt gatggatgcc ttgttgccgt tgacgtccgt   17460
ctgcaggctc agcaatgaac gtgctgtggc ttccttctca ctgacgatca cctcgtcgag   17520
acggtccaga ttcgcgctgt tgccggcgac cgatgcagaa agggtttac gcgtggccac    17580
ctgagcgagg ttggcctgga ttatcgcaat tgcagagttc ttcaccccgc ccgtcatgcc   17640
gtccatagaa acgctgatgt tgtcgattcg ctggcccagg gcggtatcag ccgtcgcaac   17700
ggtctgctca agctgactga gtgaagacga acattcccg accgtgctgg aaagctcatt    17760
aacgctggtc tgaaccttcc cgacgtcctg ggcattttg gcgatatctt tcgcttgctg    17820
ctccagttcg tcgttggcct gtttgatatc gttagccatg ccagcaattt tttcgttgct   17880
gtccaccgcg ttctcgatca ggtctttgaa cgtttccgac tctttcatat cctccagaat   17940
gtcattagtt atttcgctga catctatcga ggacgtgccc atgatccagt cggtccagtc   18000
cccggcgtta ccgatacggt caatcaggcg cgcgcggtac cactggcgaa cgccggcagg   18060
catgggggcca tgctgataat ctgcagccgg gtacggcacc aggaccagca gttcaggatt   18120
ggcgtagtcg gcagttgtgg cgcgctgaat ctctgtatag gccgtgtcgc ctgagccatc   18180
cggaaatttc caggtcaggt cgatatgcca gaccacatct tcggtcgcca ggaagttgag   18240
cggagtaccc ggttttcccg ttttaccgga gagataagtt gtttcaccgt atccccatgg   18300
tgacgacgta tcctgcgcat tcagcgcccg tacgcgcacg tcatagctgc ccgaataaat   18360
gccctgaacc gagaaaccct gcgcgctggt aaccggaacg tttatccagt ccccgttgtc   18420
cttacgccac tgggcaacat accggattgc gccctctacc ttatcccatg acacgtccag   18480
gcttgctaca gtcagcccct gagacacatg atcgctctca gtcaccacga tattcttcgg   18540
```

```
agcagacagg acgcttatcg gcgtgacggt gatcggggga gactcgaccc gaacgccgtc   18600
atcgatgtaa cgatatttgt ttggatcgtg ctgaacggcc gtaatagtga aaccgcctgt   18660
actgtcgtcg ttagccgcga ttgaggtgac cctgaagtac tgtattgcga ggttatcact   18720
gtctatcgcc caaacagcgc ccgccacagg aacctgactg aatgccgtag ccaccgtcac   18780
cgttttttta tcggcgctca ccgcgctgat tgtccgcgtc tgggcttttc cgtcgggaag   18840
gttaaccacc agccggtctt tcgccgcgta gtctatttct cgatcgaggg taatttggcg   18900
gccgttggcc gcgcttatac ggcccccgtt ctccttacca gagcggaaag gatcggcgac   18960
accgataatt tcagcgggca aagggatata accgtccagc cccacgccaa acgatacggt   19020
cccgtctttg gcattggaga gcaatacccca gcgaccgcgt cggtgcgctt cactttgcga   19080
ggtgcagccg attgcggtca gggacgtctg ccggacgtcg taacgttcta caagcgccga   19140
atcgtaaacc ccctcaacgg tatcgctgta atggttctgc ggatcggacc aggacaccag   19200
gcaggagctg tagcgattct tgtatgagcc gcccgcataa gtaaacagcc catcgataac   19260
gtttgagacg ttataaaccc agtcaacatc gtcctgcggg acgtctgcct ggacataaat   19320
ctgatcgttt ccccagaacg ttattccacg aaataccgcg gcgagatcgt taagtacctg   19380
ccaggcgtcc tcctggctct gaatgaaaac gttgcaggtg aaacgcggtt cggtgccacc   19440
ggccccgtcg gaaaccattt cgtcacagta ctgggcgatt gaatacagcg cccacttatc   19500
caccatggac gcatccacgc gcgtgcccat gccgtaaatt tcatccagaa ccagatcgta   19560
aaagatccag gcagggttat tggaccatgc cattttgaac ccgccggacc atgaaccaga   19620
ataggttcgg gttttcggat cgtaattatc cggaacctta atcagcttgc cttttatctt   19680
acaggtcact ttcggcgcgc tgccgttgaa ttggctgctg tccacttcga catacaggag   19740
cgctgttaaa ggataacgaa gcttgctgtc gatgacttcc gcatacgaaa acaccttgaa   19800
ggcgttaacc agtttcgaat ttgatccgct ggcatcagcc gtaatacgcc tgaccctgac   19860
agaccagccg gacgtggatt ttggcagatc gatacggtgg tcacgctgat attccgtcgt   19920
ggtctttccg tcaaacttgc cgtttacaac cgttttccag gcgccgccgt ccgttgataa   19980
atcgatcgca tactcggtga ccgtgcccac catatcgcca ttatctttat agagatactg   20040
gaccggaagg ctgagcttga tacggatggc atccagggaa aggtttgtaa actggcgcgt   20100
ccagggcgcg gtggtggtga cagttgtgcc cacggccagc tcgttgtcga cctggggcat   20160
cccggcaata taggtctggt cctgtgtgcc cttgcggaac tcccatttca cgccgctgaa   20220
gttgtattcc ccgctgtcgt ttgccagcgg cgtatcgttg agaaaaatgt tctgagcggt   20280
caggtcgccc tgtatttccc cctcagaaac ggcaatgagc attttttaatt ttgcgaccga   20340 cagcagatcg tcaggctgct caaccggagt atgtgaactg ccacctcccc ctttggcacc   20400
ctgcaggatg gtttcttgtt taagaagctg catttttttca cccataaaaa aaggtgccga   20460 agcacccttta agttagtggc cgctggccta ctgctgatcg ctcgagtaca taccggcgct   20520
gactatcgct cccctgcct cagtcagacc gtaggccagg gggacaggat gccccatagc   20580
gacggtattg accggcgccc cgaaggcgta gttaggcgtg ttgtccgtgc tggaggattt   20640
acccgcgccg aaggatggct ggggcgtgag catctggaca acgccccca gcatcatcga   20700 cactccgacc cctgtcagaa ttgacgtggc gctgatagct gttgcactca tcgccgcgcc   20760
ccaggctgcc atgctcgcac cagcggtaaa gaatgcagcg accagcgcaa cagcccgac   20820 aactatctgc aggacgcccg aacttttggc ccctcataa acgggcacga tccggtacac   20880
gcttccaccg cgggtcatat caaactcttc cagcccgata ttgttgccac cgttaaaaaa   20940
```

```
ggcgaaacgg atcccctTca tatgagcttc agacatatat ttTtTgaatc cgggaacctg   21000
tgaacacatg gccctgagca tctcgcgcag gtcggcaaca tcaaactgaa cgcgtttacc   21060
gaatttTtTt gccattTtac cttcgagaat aagcgtctTa accatgcatt ctgtccttat   21120
gcctgaccac ccggaccgtt ctgtcgcgat aatattTtcc ataaggcgtt cgcgaagaaa   21180
ggtgcccgaa aagatgatgg agaatgatgt tatcacccac atataccgcg gcgtgattag   21240
tcaccgatgc ctgcacactc atcatgatga tatctccggg ctgcattgca ccggcggcaa   21300
tctcaacgaa tccctcacgc tcccagttgt cgtcgtagag acgctccttg ccgctctccc   21360
accattcgta aggtactgaa taattgccga gaacaatgcc gtattcgcgc agataaaatt   21420
cacggataag cgaccagcag tcggcgtaac ccagcaccca ctgccgcccg gcataatccc   21480
ggtcttcacg cggggaaatc gtacaaaaat ccccgtccgg ccaggacatg atcccccact   21540
caatccccga ccagtcgcac tggatccggt ccagctctga gggcaccagc cgaaccacat   21600
ccggatggga atgaatgagc atgatgatct caccgcgcgc gcgggcagcg agctggtctt   21660
ccggggagag cgtgaatgtc tcctcgggtt tatcggcaat gttgcggcag ggaataaaga   21720
tttgttgctg gcctgactga acaatcaggc cgcaggcttc tttggggtat tcagcagcga   21780
cgtgctgacg gatagcatcc agcaattTtt cacgcatTtt tatTtcccct gcaggtttgc   21840
agccggaaaa ccgccgaacg gcagcggcgc atccgggccg tgacgatcct gacaatcctg   21900
ccggcggccg ccacaaacat ctTtcgacgg gtcatcggtc ggtgtaccgt ctTtggtaaa   21960
gtatTtcgtg ccgttgtaat cgcatccggt cccgcttcgg taccagcccc gcatacacca   22020
ggtgcagaca ggcgtaatct gccgtgtcgg cagctgcagg ctctgaatat cgaaaggaga   22080
acacagctcg aaatcaacct gtacccgcgt ctctgcggtt ttagcattga cgtaaaagag   22140
ctgtaagcgc tcatcggccg ggctggcacc cggattaccg ttTtTccagt tggcggcatc   22200
gagatactTc gaaagcgtgg tatggattTt gaccttagcc ctgaccatat cgtcatattc   22260
aagacacagc gcggtgacat agttTccgac gttcccgacg gacagcgtgg gcgttggctg   22320
ggaacctgta ctcgataact ccatcccctt aagttcgtag ggatggggat cgtactggtt   22380
tccctgccag ataatggcgg gcagattTtt tgcggcgaag gctgcccacc cctcttcctg   22440
aatattgtgc gcatgaaaac gcagcacctg atccataccg aattcagtgc cgtcgatctc   22500
aatcagctga ataacgctgc cgggctcaag ctgttgtatg tctgccgtaa aactcatact   22560 cccccccataa aaaaagccg cccggaggca gctTtcagtg tttTtcgaga aaatcagggc   22620
gcgaacgcct gttcaaaagt gaaggccaca gtggctTtTt tcccggtagg gaagaaacg   22680 ctgaacgaat cggccTtcat tctgaacagc tTtTttTcac cccatggagt ggtccaccag   22740
aacgatTtag taacgtgaga catcaggaaa gcgcgcagcg cagccgcctc ctgtctggtg   22800
cccgtccagt ccaggtTcca cgtTtcctgt ttgtcgttga tccccatccc cgctatctgt   22860
ttgtagccat ccccgaactg ggcctgcagc gttcgggctg ttTcagtgcc ctgcgctgtt   22920
tTtcgcgtgc gccaggtaaa cgtgtccgtc actgtgtcct cctcgaataa agcacgccgc   22980
ccgcggacat ttctttTttc agtcgctcgg tgattgtctg ctgaacaatc gcctgcagct   23040
gtTtcgccgt ccccgtggcg ttcgcctgat tTtatgcttcc gtcactcccc tgctggctga   23100
tgctgactgg ggcataaaca ctgatcccgc ccatgccagc accggctgcg ttcccgccgc   23160
cgaccagacc acccgaggca tacccgcgca tcaggcgata gagattagcc acgccgatgc   23220
ggctggTtga ttcTtTggtg aagacgaatt ccccgcggtg aacgataccg ctggctcgt   23280
```

```
acttgccgcc gtgcccggta aaaccgccca cgtcaaaacc ctgtggccgg tatgacggga    23340
ccgcgaatga ctgaccggca gaggaggttt tcgccccgcc gctaacccag cccattgcac    23400
tctggatggt gtaagccacc agcagctggt tgataacgga cacaatcatt ttaaggatcg    23460
agctggtgaa ttccctgaag ctcgccttcc cggttgtcgt caggctggta agctggcccg    23520
ccaacccgct gaacgtagcc tgagaaatct gctgaacgga gctgaaaacg tttgtcgctg    23580
aatcctgata ttcggcccaa ccctgttccg caccggccag ccagtttgca cgcagggcat    23640
cttcagcttc gaacgtcgcc ctttgctctt ccagaacctt ttgctgcgcc tgagggttgt    23700
acgaatagct ttcgctgaga cgctgcagcg tagtttgtcg cccggcttcc cgggtggata    23760
accctcaga ctgagcctgc aggcccgccc tggcggcttt ttgctgctgc tcaaacttca     23820
cggcctgatc ggccagctgg ttgagctttt gctggctggc aaccttatcg cccaggtcgg    23880
ccagctgccg cttgtactcg agcgtttctt ctttgtgcgc cagcagggat ttttcctgcg    23940
ccgtaagctg acgacgccca gcggcctcct gcagaacggt gaactgattt tcagtttgcc    24000
agagatcctg acgctgttta cttatgacgt cgttcacgct ggtatgctgc tcaagcgttt    24060
taagctgggc ctgaagggtg agaagttcgg cctgcgcctt ttcctcggct ttgtccccgg    24120
cgggcgttga gtagcttttg cctttcggtg tttttggatc cttccactgc ttttcaatcc    24180
cggcgcgggc cgcggcaatg tccttttcag tccacagcgt ggcgacaccg tctttcgcat    24240
cctggcggtt tttctcaata agctgactga gcttttctc tgctgaagcc cgcttttctg     24300
ccgccgtcgc gccggactcc accagctggt taaactgctg ctggctgcgg attgcctgag    24360
cctgctggtc cgttcgcatt ttttcccgcg cggctgccag cccttcctgg gcgtattgct    24420
gatcggcaag atcgtaagcc tgcttttttca gctccacctg ctggcgcgcg tttctcagcc    24480
tttccgcatc cgctttctgc agaacgttgt taccggcata atccgggtcg accttaagat    24540
tgctggacag cgcgcggtac tctttctctg ctgcctgcca ctcagcaaaa gagtcctggc    24600
gcttcatcgc ggtgtcagga ttacgcccga cgcccagcat cgcatcccac gcaccggagg    24660
cggcattctt cacccagttc caggctttttt cgagggatcc gagattatcc tcgaccgcac    24720
cggcgcgctg aatgaccgcg tcggaatatg cccgcatggc cagctcggca gccttctgag    24780
aatcccccag cgcctgagca gaagctatct gttcatactg ggtggctgtc agaaaatgaa    24840
gggaatcgtt gagcgtcgcg accgcgttaa ccggatcatc cttcaggcgt ttaaactgat    24900
ttatggtttc gtcaacggcc tgcccggtag cctgctgcag cctggcggca acattgctga    24960
ccatgctgac gtcattaccg ctgaacgcgc cgctgccaac gacctgcgcc agcacgcctg    25020
cagcggcatg ctgagtgatg ccattacctg ccagcgagcg cgccagcgcc tgcagctgcc    25080
ctgacgtttt ccccgcgtag ttcccggtca ggatcagctg cctgttaaat tcctcagact    25140
ctttgctgcc gtcgtaccag gccttaccca acccgaatac cgccgcggca atccctccga    25200
ccatgctggc gatcccaaga ccgcgcagtg acagaagctg gtctatccac cctgcccggt    25260
tagccagcgt gatcccggag ccgcgcagcg cgccgaagtt accgcgcatg acctcgccga    25320
tcagtattcc cagttcctgc cgggcggcgg cactttgcag cccagaccg tgcgtggcga     25380
ctttggcagc ttcgagcttg cggatataga cttcagccgc atcgctggca ccgacctgcg    25440
ccgccttcat gcgcagtagc tcggtaccgg agagcttttg ctctgcaacc tgttgcttca    25500
gctggctgag gaatcgcgtg cgcgctgcgg ccgattttc ctccacgatc tgcagttctt      25560
tttgacgggc cgtggtgcgg gaaataaggg cgagataatc ctgctgggtt atgttgccct    25620
gtgccctcgc tgcgcgaaag cgcgcctgca cgttcgcaag cgactgtgtt tcaccattga    25680
```

```
gctggcgtac gccgtcgatc tggcggaaaa atgatgccgc aagttcatcc tgtcgacggg   25740
caagcgcagc ggcctgcccg tcattctcac gcatgcgctg attaagctcg gtcacgcggc   25800
ggtgagtttc atcaacggac tttgaaacgt tctgccagtc tttggtaagc ccttccgttg   25860
cggccgactg gcgggatttc atatctgcgg cagccgccgc gccagcgtca cccacggttt   25920
taaacgcagc cgcctgccgc tctgaagcgc gctgcattcg cgtctggact ttttcagagt   25980
cctcagccat cccggttagc tggcccttta tgcgggcaac ctgctcacta aacgtggcgc   26040
tgtcgacgtc aaggttgatg accagatcgc taatctgctg gccatatcg gataccctcct   26100 gttatcccct cagctgcggc catcagcgca tcatcatccg gctcgtcatc gctgatgacg   26160
ataccggaag gagaaagcag gctgaaatgt gcggggtaa gttccgggtc gcggaagaaa   26220
agagtggaga tggaataaag cagctctgag aaatgcgcat cgagctgagc gtcctgaaaa   26280
taatgctccc ggtagaactg gtgccagtcg cccagctcag tggaagtcat tccagccagc   26340
atggcgcgcc agtcgggtcg cccgaactcg cgcgccagat tcaggacaaa cttcagctcg   26400
ctggcaaggg cttttccgcc gcaacgggtt ctgcgctttc ggcctccgct ggggcatccg   26460
gatcggcagc tttgtcatcc tcaaccggaa cgagcatgcc ggagagcagc tttatttcca   26520
tttctgcttt accgatcgcc tccggcggcc agccgctaag cacctgctgg taaagcgtct   26580
ccacatccgt gccagccgga tcgttatgcc acaaagacat cgcaatcaaa cgcgcaccgc   26640
agcgaatatt tgagccaatc agcctggccg tcatttcctg atcgctgatg ccgtcgctgt   26700
cagcgctgac ggccttttcc tctgcggcca taaacgtgat gtactcaata cgctgaagcg   26760
ccgacagctc gaagatggtc agtgattctt tttgccaggt gaacttctct tttttcagaa   26820
acatgcgtcc ttccttacgc tgcagttacg gtaactttgc agaccgcaac gaaattaccg   26880
tcgctggtca taacaataac gtcagcggtg cctgccgcca cgccggtgac ggtgatcgca   26940
ttaccgctaa cggtgaccgt tgcttttgcc ccgtctgagg ttgccacacg gaacgaggta   27000
tctgaggcac tggctgggtt aaccgtcaca ttgagcgttg tggttgcgcc gacggccacg   27060
cttgccgtgg ctttatcgag cgtaacgcct gtcacgggga tattcggggt cccgcttttct   27120 tctgccagtt ccggcttgcc ggtattggta attttcgctg tacgggttat gacctctttt   27180
gccggaatgg cttacccag gctgctgcac cagccgcgga aaacgtcgac ggtaccgttc   27240
gggtatttga ttttgtaata gcgtactgag ccatcaataa accatgcgac aaggtctttt   27300
tgcccttctt cgcccggctt ccaggcgagg gtgaacgagg tatcgccagc agattttgcc   27360
ccctgggccg tcgcgttcca gtcggcatcc tcgtcgtcga ggtaagtgtc gtcatacgat   27420
tcggcggtca tttcgcccgg cgtcagctct ttaattttcg ccaggcggtt ccagtcgata   27480
tccgagagtg ggttagcgaa agcgttgccc gttccggtgt aaagccagag ggtggtaccg   27540
gcacctttca caggggccag cgggtttgga gtaggcataa gtacctctta aattgaatag   27600
gtgattaagt acgtgaaatc gactgaaccc caggtggcca tttcatcatc ccgctgatag   27660
tcataaccct gcggggtgaa cgtctcgacc agttcggtca gacctgggat gaaggccatt   27720
gccggataca ctttctcttc catccaggaa tcaagcgcgc tgtcgggcct ggaggcttta   27780
agaaatacct cgatgtgaac aaccgcctgc cacgaatctt cgtcaagcga ttacgtgtct   27840
tgagcgattg tgtaggctgg agctgcttcg aagttcctat actttctaga gaataggaac   27900
ttcggaatag gaactaagga ggatattcat atggaccatg gctaattccc atgtcagtcc   27960
agtgattctg aataggcgat aagtccggta taaccgggga taatctcacc attatcagct   28020
```

```
tcaaattcag gaattgtgcc ggtggtgatg gtgtattgag gctggccatc ttccttcgcg    28080
aaggctgcca ggtcttcaat ctgcttagct gtaagaacta ctgtcatgct cattcctcag    28140
ttgtaaaaaa gccccgcgag tgcgaggcga tttgattgaa ttctcggctc ttatctcagc    28200
gcagcccctt actgcgtgcc ggttgctcgg tgatgagcat cagcgatgag acattaaagc    28260
cgaccgaagg ccagcggcgt tcctcatgtt gccgacagag ccatatcgac aagaggacga    28320
aaactagcag catgaatcgc ctattggtta ttcgacagtc gcactgattc gtaaatccgc    28380
tcacacgtca ttcctgcccg gtagctttcg tcagatcgtc cagcataata tcgagctgct    28440
tctgcaaggc ttccgagcat gtcggcaagc attgctgcgt tggctccggc tgttttgctt    28500
ctgacggaag tggcgagatc tgcggtgtgc tttgcggcgt ccatgtgggt agcgagtttt    28560
gttgcttcgg cgcgcagctg cttaacagtg gtagccaggc cagcagaagt aacggcagcg    28620
ctcgctgctt gagcttgagc atctttaacg gcctcatccc gggcgattgt tcgcccttgt    28680
tcaatcatac gagctgcggt ctgtgcattc gcttcctgtg aagattccgc gctatcccgg    28740
tcagcccact ttattttcca gctgcggttc gtccactcac tgccgcgag aaacgaacct    28800 accaacgcaa caatcacaat gatgcagatg ccacccggct tcactggtct atccccagc    28860 acgtcagtgc gctttcctgg tcccgccgtt ctacctgccc ataacatcca tccttctggc    28920
ccttggtcag gcggcaatcg cggccaccgt ctttaatcca ccagcggata gcttcacagg    28980
ctcctttcgt atcgccagca ttaattcgct tatagaacgt agacgggaaa catttttccgg    29040 ggccgatgtt atatgggcag aaagaagcga tacccgcttt ctgtggttcg gtcagtggta    29100
ctttgatatt tcggtcaacc cacgccagcg ccttgtcgcg ttcaatggcg tttacctggg    29160
cgcatttctc agctgacagc ttcatgcccct gtactactgg cttgccatca accattgttg    29220
caccacggca aatggtccag agtccgccgc cgtcgcgata tgctgtcaag ctgttaccct    29280
ctttctcatc cagaaactga tcgagaatca cgggtgcgga agccccggca agaatcaaac    29340
caacgaccgc tgccgctcaat ttattcttca gctttagaga catagccatt gcgccgatcc    29400
tcccgttctt tccagcggaa ataccagttc actgcacagg tgattaccgt gcatgcgata    29460
ccgacaataa ttgcccagtc gctcaggctt aaccctgcaa ttctgtcggc caacatccag    29520
gacacctctt ttgctgtttt agctgtttcg gcatatgcct tcgctgatac accgcagccg    29580
gcaagcgtgg ttcctgatcc atatgaaagt ctgctgtaaa tggtgctcat tctggtcata    29640
gcctcacctc cgatagttcg gatggcgctg tgtgtgattg aagggggatca ggcaaccggg    29700 ctcttatgtt caagtaaaaa ttaaggatga ttcccggtgc ctgaagatgg tgatcaccac    29760
agcaacgggg gagcgtggtg atcgttatga ttttttcagt ttttccacct cttcggtggt    29820
ctgtataaac ctgtctgcct ccagttctac gccgatcgcc cgacggccaa gttctattgc    29880
agctttcaca gttgaaccag agcccataaa gaaatcggca acgatatccc ccggtctgct    29940
gctggcgcta atgatctgtt tcagcatgtc ggcaggtttt tcgcatggat gtttgcctgg    30000
ataaaactga acaggcttat gtgtccatac gtcggtataa ggaacaagag cggaaacaga    30060
gaagcagcgc cgaaggattt tgtattcctc cagcaattct gaatacttgc ggtttaatga    30120
ctggtaggta gccaccagct ggtggtgagg atgttcaagc ttttgctgaa tatgtttatc    30180
gatggcgatc cgcgtgaaca gttcctgcaa ttttcgatag tccacttcat tcggtagttg    30240
ccattggctt gcaccaaacc agtgtgacgc catgtttttc tttccggttg cctcagctat    30300
ttctttcgag ctgacaccca gtgattcacg ggcattacgg aagtaatcaa tcagcggcgt    30360
cataatgtgc tgctttagct ctgtgctttt cctttcgtaa acatcctctt tacctgtata    30420
```

```
cggtccaaga tagtgctcag caaacaaaat ccgttccgta gatggaaagt acgcacgcag   30480
gctttcttta ttacatccat tccagcggcc cgatggtttt gcccaaatga tgtgattcaa   30540
aacgttgaat cgggcgcgca tcataatctc tatatctgag gccagtcggt gaccgcaaaa   30600
caggtagatg ctgccagcag gtttaagaac gcgagcatac tcagccaggc agctatcaag   30660
ccagcgtaag tagtcctcgt cccccttcca ttggttgtcc cagccgttgg gcttcacttt   30720
gaagtacgga ggatccgtaa ctataagatc aatagagtta tccgggaggg tggcgacgta   30780
atgcagacta tcagcgttga ttaactcaac actgtttatt tttacagtat ttttcataga   30840
tcagtaagcg taactctgat aggctcacgt tgcttttgcg ctaaagcagt gggccttggt   30900
tagcttgtga cctgaaagca tgagctgatg gctggccggg tgcgctaaca cccaccagcc   30960
gcccatttcc acagcagaaa acccccatta ctggaggcgt ttataacatc cgaactggta   31020
atcagataac cccgccatca ccagctgcgt aagtatgagc tggcaacgtt cgtggctgag   31080
gtgggtattc tgtgcaatct ccccagccgt tgctggttta tcgcttaatt cattgaaaac   31140
agcctttgcc gtttctgtca tatcttcctg atttagcatg tctttacct aaaattagtt    31200 gcgtgacata cagataactc tggttggtga taccagcaag agaagaattt gattctgcaa   31260
ccaacaaggc ctttaggcat caggcaggaa tgagatgcaa taaaaaaacc acccgaaggt   31320
ggtcttatat gaatctttaa cgcggactta gcaaatattc cacatcatcg tactaccgtt   31380
atggttttcg ataattttg cggctgggct agtaccaaaa gagtgcatat agcaatgatg    31440
aatagtaagg accagatcct gcaacgtttg gtcactctct agctccatga tatttaaacc   31500
aatattttga gctttgtcca aatgaatatg tctggcatgt gcatacgttg cttggtggtt   31560
gtttaactca tcacatatac gcttagcctt agcttcagcg tcagcctgac ctgcgaacat   31620
accagtacaa agccatttct ggacaatttc gttcgcccag agaattgctt tttcacactc   31680
gccaatcaac gttggattta gttttttggaa cgtaaattgc caccattgca gtgcagcagg   31740
gttggcaaaa atttccgctt ttgctctctc atactcctca ataattgcat gagatgataa   31800
cccattaaac tgtggatcaa ttggccccaa gttcgactgt ttacctaaaa cgatctgctc   31860
agcacaacaa gcaagcattg tgccacaact cattgaaatc ataggtacaa tcgctcggat   31920
attggttccg aactttgaac gaagataatg accaattgat tctagagctg cgatatcgcc   31980
tccaggagta tggagtaaga tatccaatcc cagactcgta tctaacccat tgatagcaga   32040
cataagacca tttttatcat catctgacat ctggatcaga tgttgaaacc caggccccCC   32100 ttttgaagg aagcctgagt aataagaaat tacatttcgg ccagtatgtt tcgataaatc    32160
acgtaagtac ttgtggcgaa cctcatccgc tggtgtacgt tgagcgatag tacccatctc   32220
acccaatacg tctatccaat ttggcatgtt atcaatttat cagtatgagt acagttggtg   32280
agattgctga ccgttctgct cagtagtatt tggtgttact gtgctgtatg aatagagcac   32340
accacttctc acattcagat cgttttgctg agcgagaaca cgcatagcaa aatgctgtac   32400
ggattcgcct ttttgaaact cttggggttg tatgcccatt ttttcgtaaa attcagcagc   32460
gctcatgata tgtccctcgt ttttttctac atctatgcaa ttccaggagc catcaacaca   32520
agatgtagta gttagcagtc gtcaaataca cgaaaagcct caagatgagg cttaaaaaga   32580 ttcttttga taaagattta gccaaactat agcggtcaaa atgcagattt gacaagtata   32640
aaaagcactt aaagcctata aataggcagt ttttgagaat taaagcatct ttaatgaggt   32700
tgaacaaaat gcagtcttga cgctgaacag gactttactg gaacgtagag ctaaatggtt   32760
```

```
cgatttcatg aaccagttac aaaaaaaccc gctcatcggc gggtttataa aactttggca    32820
acatatcaaa tatgcttcaa atatggctta ttttgttgca ttttgcaagc gtgtttgaag    32880
gagatggtga aatttacttc acatttctgc cactttgagg gcttcttctt cctcatagta    32940
ttcaagagcc atggccaacg cagattcatc aagctgggta aaagcggcct ttaacccagc    33000
ccagtgccct gaatagacac gcaaccatgt cgaacggtca acgctaacca tgcgggccaa    33060
cgctgcacca gcatagtctt tataggtttc attatttctg gttgcggcaa tttcctgccc    33120
tgccagccat accaggccta tcagtttctt tactacgcgc tcctgaaggg agttatcacc    33180
caggcatttc tgataagttt tccagacgta ttcacacatc atcacctggt gcttatagct    33240
aaggtcaaaa ccgtagcagt accgcaacca ggcctgctgg tatccactaa gcgcggacac    33300
tgccctacgc cacggcgcgg actcaaattc cgcatctttt atcggcggca ttggcctgcg    33360
gcggctgcgt gtttccagca catacagtgg cgcggaaagt gagttaacaa agcgtggccc    33420
cttctctcct tcgagttcga cgagatgaat tccacggcga ggggtggcat ttttgtctgc    33480
tggtgggtgt tcactgaaag cctcaagctg cccttttgtt cccccagaca ggtcaggtag    33540
cgcgcggcgc aattctattc ttacaaaatt caggtcttgt tgattcatgc ttctttgcgc    33600
tccatacact taagctttcg caattacgcc gatcgccagc gcccgatcca taaaacgcag    33660
tagcagctca agctgcgtac catgcttctg ctcgaatgcc ggtacatcgg cgtgtaactc    33720
gtcgtggcac tctctgcaca gagggatcac gaagagatca tgggcttttg ttgctgtccc    33780
ccccataccg tgccctacga tatggtgcgg atcatctgct ggccgtcggc aacactcaca    33840
gggttgtgtt ttaacccagc gggtgtacgt ctcatttatc cagcggcgtc gctttggcct    33900
gagcatgaaa gattctggag actccggatc aacagagagc gtgaggatct tcttcgcctt    33960
ctcctgcacg aggctggttg cagaagcgga aggcacaatg tcgctttccc tcatgaccga    34020
gcggatctta tcatccggaa ggcgtagccc cttgtgcgca acgctttccg gaataacatc    34080
agccaggtcg tttctgacca tccaccagca cagttccgga agcgtcagga tatgcgactc    34140
gggaaaacca gaatcacgcc gaatgacttc cagaatccag gataccaggt ttcctgccgc    34200
tatacctgca agctgttcgg tatgctgccc cgacaaagtg tgatcgcaat gccagcacag    34260
gcgaatactt cctggtgggt gccgcattgt tgtgaagttc ttgtcgtgcc acgatgaatg    34320
tggccactgg cattcaaacc gattactcaa ccattgctca agggaaggaa gcccaccagc    34380
acgctgaata acccgatcat tctcgaagac ctgccgcatt accggatcat cagccagcgg    34440
ctgaatggcg gcgggaacag ctcctgtact gaatgacgcc atttcttctg gttcaggctc    34500
aagcagaacg cgaccgcgca taaagaggtg catcagttcc gcgccgggac gaaacaacac    34560
aatccccata cgatgggcga tctcgggggt aagcagagct ctcacgcgac ctgcccctg    34620 gcaatgtgtt ctgcccacag tccaccaatc cagcgcacgc ctttcgccgt gaaacgtgcc    34680
tggctgaatg catgatttga ggttacggat gtgccggttt tcacttcaaa cggcccgca    34740 tcaatatgct gatgccgtgg ggtcatcgtt ccgccaagac gatacatgat gtcgttctca    34800
aggaggaata accgcagatc gggctctttg gccttaagca gttttgccac ctggcggaat    34860
gacattgacc cactggctgt acagtaccga tcaacaaacg ctaccttcgg cgccgcggca    34920
gccagttcgt tagtcaactg ctgttttttgt tctgcaaggt cagctgcaag acgtagggct    34980
tcagagaatg attgaggaat cgtctgctgc tgtgcctgct caagctcctg ccagcgatca    35040
accagacgcg cggtaaactc cggcgacagc tgcgcgacaa cgatataact gtcccgcttc    35100
cctatcagat aaaccgatac cgactgattg aggtgatttt taacttcccc cattgggggg    35160
```

```
agttcaataa caccgcgctc tgccaggcgt tcaatggacc gtttaacatg gtcatgtctt    35220
gattccacca gctcagcaat atcgctgctg gacatggtta acgctgttgt tgctaactgg    35280
ctcatacttt tctccatatc aggcggctgc acccgccggt tcatatctgc tgattgttat    35340
ctctacccga cctttcggca caacgggtcc ccattccacc agcatgcgct taatctggct    35400
gtcgtcttcc cagacacccg catgcgtcag cgcgtcaaac agggctttgt tgtaattatc    35460
gatatcccgg cggcgcgcat ccggcgggta cagagtgatt tctaccgctg ccagttcagt    35520
cgatggcttc gggagacgtc gtaattgctc aatgatcgcc acgcaggcag cgctctggta    35580
tttacggcca gcgcgcgctaa tgaggtgacg accggccagc ggcccttgt taggggcgcg    35640
ccagtaagtg ttcacgctcg gaggaaaagg caggatcagt ttcacgcggc ctctccccgc    35700
atattgcgaa caagttcaga agcagcagta atgatttcgc tggtggcagt ccgctccagc    35760
cagagttgat tgatattggc tttcagcttg tgttgcagtg actcatccag catgtcagca    35820
ccatccacct ggtcgaatac aattctaacc tccagcggcc agatacggga ctcgggaagc    35880
ggatccgata ctggtttagc tttctcacga atgtgcatgc ggatctggcg aatattggac    35940
caactggaaa catccaggct tcccatggct gcaatgaagt cagtgctgtt catgccatat    36000
tcaccggatg cttcaagggc aacagtgcga atacgttccg acatatccag gcgcacagca    36060
gcgtcatcga attcaatcga caacagccac tcatccacac cgaacaaaat actctcacga    36120
ataagcagct tcgctttgtc gatcgttaaa ggtgatacct gagtgaattc cggtgcttcg    36180
acagaatccg ccgcccaggt atgcccaaac ttcgattcac tgaatgtgta ttcttcttta    36240
tcgccaaacg cagctctaac gcatgcccac gcctcgacac cgctgatagc aaaaatatct    36300
ttctgggtga gtggcaactc tgcttctggc ttatcagctg caggaggtgt ggcagttaca    36360
ggttgagact tgctggcagc aaattgtgcc aaagccataa acgcccgccc ttttgcctcc    36420
agttctgtgc ggttgatata gctgaaccgc tcgccacgcc atgacttatc gaatacagct    36480
atggcaccgg caaaaaacgc gctggtgggt ttctgttttt cgtcagcagg tacaaaccac    36540
acaggcagat cgaacccaat gcgcccgcga atgaatacaa tgtgatcggc atcttccggc    36600
caccacgttt cactcggcgc ggcttttatc aggaatacat agcgaccgcc cttctcgcgc    36660
tgggctgctg cgtagttcat gatgtgcgtc atgccggtga tcgcctgctt ctcgtggtac    36720
tgcgaacggc tatacggtgg gttgccatag ccagcgccac ccagttcagc cagacgttca    36780
gaccagtcct gcgtcagcgc gttatcttcg gcggtgtacc atgccgggca tttcgcgttg    36840
tcgtcgtcag caaacaaatc cagaactaat ggaccaaata gcgcgttgat cccccaaaaa    36900
agcagatccg gtgtccgcca ctgatcgcca acctctttca attcgtgagc tggtttgcta    36960
cgcagtgccg ccagcgcctg gcaatattta ttggtcatca tgaacggaac cccgaatttt    37020
ctggcagtga gtaatcaaca ctctggaagt ttgcgcggct ggctgagtta gtctcccatt    37080
tgccgttaac gcgttcaggc cggccagcac tggaccattt ggtcgcgctt tgcaggtaac    37140
cagggaagtt ttttggaatg aacagagttg ccgggcggag gtattgcgcc tgctcgctat    37200
cacgccaatc ggcattttg taatccacta ccaagcacag gtcatcaaca gtgaattgtt    37260
cccgaagacg ggcgcgaata ttctccagcg acgtgctgca tacctggtag cgtgagccag    37320
tagtctgatt caggtaagac aaaacctgtc tggcctgatc agtaatcaca acctcagggt    37380
cgggttgcgc cgcaaccgga caagagggtt ttgaagttac ttgtggttct tgttttgatt    37440
ttactgacgg atccccacca gattctgacg ggtcaaaacc gccttttttg ctggatttcg    37500
```

-continued

```
acgcctcaaa ttttgacggg tcggattttg atgcatcaga ttttgatggg tcagattttg    37560
atgcgtcaga ttctgacagg tgagaaaaag cagcctctcg caacttaacg acgttaagct    37620
gatatacgtt cgatgcgtta cggttcccat tacggcgctg cttacgggaa agccagccat    37680
ccttctcaag ctgagcaagg gccgtcctta ccgtactttc tccagcaccg atttgacgtg    37740
cgatcgtgcc aatagacggc cagctaacac cctcatcact actgaagtcg gccagacgcg    37800
ccatgatggc aacgctggat aacttcatgc ctgacgaagc gcatgcatcc catacgtaac    37860
cggttaattt agtgctcatg gtcgtccttt aattctgtaa atttacgctg gaattgttca    37920
agagggctga agcactcatg atcgtaccct tcgcgaaggt atataacgcg ctgtgtatct    37980
ggctcccagc ggacaactct gacgggaact ccgtagtgat ctctgaaccg ccggttaact    38040
tcagccattc ctcgcgcccc ttctcgttca tctgaacaaa tgcttctacc atcaagtctg    38100
ctggctggta gttgcctcca tcagccgcgt tatttatgat ttccacatag ccgaactggg    38160
catctttacc caccagcggc aaacatctga attgcttagc tggtctgaat cggtttacac    38220
tgttcatgcg ttagtttctc cactgatacg acacgccaag gcgcccggag ctgcactctc    38280
gcgggcgtca ccttttctgc ctgttgaaac gaatacgtca atcgcctgat ctgaaacacc    38340
aaccccataa agcgccataa atcccaggaa cccgtgaatc tggtggcgga gcttcttact    38400
gaataattct gaaagcattt tgcgctctga tgaatcaatt accccatcag ccgctgctgc    38460
catcttggca ttagccagct caccagatgc tgctgccgct ttcatctcaa tgctgtacag    38520
ctcaacgtta tccaggctct cagcagttgg aacatccacc agccatttcc cttttcggtt    38580
cgcctggtac tcgccaagt aacaagaacc agacaggtcc tccatccgtt ccagttctgc    38640
caaggtaaag aaccgactgc cacacttctg gtacaggtgg ttgtggaact ggtcgatagt    38700
catccctaaa tcggaagcca tacctaagcg accatgcttg tgtgccttac acatcaggcg    38760
gattgctgta tttatgctgt ctaccatgtt gatttccctc tggtagttaa taatcaactt    38820
aaagttgact attgttgtta gcggaaggta tgccgtcatt tttgttcgga taaatatcag    38880
gtcgtaattg atggggagtt actacccatc cgccccattg gcagagttga ataactcttt    38940
cagaaggtac tcggttcttt gcaatccagt tcgcaacaga ttgaactgat tggaattcaa    39000
accgccttga tacctctgaa atcgacccga tcgccttcac agctttagct gttacattct    39060
tgtgttgaga tgcatgtgt tctcctatga ctaagcctgc atcaatacta cttatagtag    39120
caattattag caacttaaaa tagaaatgac aactatgcct tgtgcgctta atcttctact    39180
tatggtggaa aatgctaaat acaaagactt tgccgaaagg ctaaacaggt ctctccaaga    39240
gcaatctatt ggagttaaag aattgtcaga gttcagtggt gtctcgtatg agatggcgcg    39300
gcgctacact cttggtactg caaagccgag agatgagaag atgattcgaa ttgcagaaag    39360
acttgccgtc tcaccggctt atcttgatta tggtgtgcct gttaatggtg gcgacgcgcc    39420
agccaaaggc acggtcagaa tagagcaatt ggatgttcat gcttcagccg gttccggata    39480
tataaaccaa ccattcccta caatagtgag ctcaatagag attccagaag agaggatctt    39540
cgagttgttt ggtcgtagaa gccttgatgg catcgtcatg ataaatgttg atggcgatag    39600
catgatgccc acgctttgcc caaggacct gcttttcata gacagcaagg ttgaacaatt    39660
cagcggcgac ggcgtttatg tgttcaattt tgaagacagt acgttcgtta aacgtttgca    39720
gaaggtaaaa gggcgccgac tggcagttct ttcagacaat gaacattacc cgcccttctt    39780
catagaggag catgaaatga atgaactata catattcggc aagctaatca gatgcttacc    39840
tctaaaaatg atagagtttg gctaataatt aattcatcaa gaaaccggcg aaagccggtt    39900
```

-continued

```
tttttacgc ctccaattcc tcacctcata acactacact actaaaaatt tcattttcta   39960 cttttttgttg ttgcaattat ctacttaaag tagctatagt cattgcatcg aaagcgaaca   40020
ggcaggacgc ccacgaagta gccgccggtg gcatatgaat aaccggatga ttcgctgaca   40080
gaaaacttag gttggggta gaggtttaca tgaatcattt attcacatgc tcattttgcg    40140
gagcaaccga actgggagcg ataaagatcg tcgcaaaagg tggtaaggac gaacctgcca   40200
tctgttcgga atgcgtagtc acatgtgtag aaaaaatgat cctgactaaa aaatcagagg   40260
ctgaaaaacc aacctctgat aacgaaataa tatcagtcga taaaaaacta tttaaagagc   40320
ttcttcagct tgtcctcaac cttcctgatt tcggaagtaa gctggctgct gttgacattg   40380
atagtagctc cacatcgaca agtgaaactt tgttcgact tgagccaagc gattttcttc    40440
ttcgtcttag tgccgcactt agggcatgcg ggtaacgtaa tttcctggtt atcaaaagcg   40500
cccataaaca tccctcttgg ttgtgtgaga acaccaagat accaccgcgc ctgatgtggt   40560
taaaagcagg ctaaagcaat aacaagtaac tccctgttct ggcggcccgg tgttttcccg   40620
tgtatttccg gtaaccgcca gccttttca gggcacaaca gaaaagggca tcaccgggcg    40680
acgggctcat aacccaatcc acccgggcaa aagaaaagcg gtctctgcaa gccgccgacc   40740
aatgcaggtg cccttctctg ttgtgtatgg agaaactaac ttttagcgt ctgtgcagat    40800 gcgctgagga accgagaatg aataatccgt ttttcaaaaa tatgttggtg tatcgcatta   40860
gtcgcgattt caccatcaac caggaagagc tggaacagca gcttgaacta tttcgcttca   40920
ctccatgcgg tagccaggat atggcaaaaa ccggttgggt atcaccactt ggtcagctgt   40980
cagatcgctt gcatcacact gtcaataatc aagtgttgtt ggttattcgc cgggaagaaa   41040
aaatactgcc atctcctgtc attactgaag aactgcgcaa gcgtgtgtcg cgtctagaat   41100
ccgatcaggg gcgtcgcctc aaaaaaactg agaaagattc gctgcgtgat gaagtgttgc   41160
actccctgct tcctcgggcg ttctccaaaa actcgactgt tggtttgtgg atcaacgtca   41220
ccgacggtct gatcatggtt gatgcagcca gcgctaaacg tgccgaagac tcactggccc   41280
tgcttcgtaa aactctcggt tctctcccgg tggtaccgct gactatggaa acgccgatcg   41340
aactaactat gaccgactgg gttcgttccg gtagtgcgcc tgctggcttt ggcctgggtg   41400
atgaagccga actgaaagct attcttgaag atggcggtat tggacgcttt aaaaaacaga   41460
ctctggtcag tgacgaaatt catgtgcatc tggaagctgg caaagtagtt acaaagctgt   41520
ctatcgactg gcaacagcgc attcagttcg ttctttgcga tgacggcagc atcaaacgcc   41580
ttaagttctc taatgagatt acagaacaaa acgacgatat cgaccgtgag gatgcggctc   41640
agcggttcga cgctgacttt gttctgatga ccggcgagct tatctctctc attaacggat   41700
taacaacctc tctcggcggc gaagccaagc gataaacacc aggcaacaat tacccccata   41760
agcatgggtt gggttgctgc acgctaaatt cagcaattca ttaatttaat ggcgcggtgc   41820
agcgcgccaa tatggagaaa accatgagct acattcagac attatccggc aaacatttta   41880
attacctcga tatccaacag gacgatatcg tgatcgagga tattgctacc gcgttgtctc   41940
atatctgccg ctttgcaggg catcttcctg agttttacag tgtcggccag catagcgttt   42000
taaccagcca cctcgttccg caggagtttg cattagaagc actgcttcat gatgctgctg   42060
aagcctacct gcaggacatc ccctccccac ttaagcgcct gcttccggat taccaggcaa   42120
tcgaagctcg tgtggacgca gccattcggc agaagttcgg tctaccaact gagcaacacc   42180
caaccgtgaa atatgccgac ctggtgatgc tcgccagcga acgccgcgat tttgagattg   42240
```

```
acgaaggttc catttggcca tgcctcgagg gagttgtccc aacggattta ttcattatca    42300
acccagttcg tcctggccag tcatacggca tgttcatcaa tcgctttaac gagttgatgg    42360
agcagcgcca atgcgccgca tgaaggtaaa agaactcgta gcggaggcgt ttgcctccgt    42420
tgctgaattg ccaccaaagc atgcgccgct tatgcgcgaa gtcgccacca gactggacgc    42480
tacgttcgca gcattaaaag agtctctggt gcaactggaa caggaacgta aagataaaac    42540
gccatgaccg tatttgaata tctccaggct catccgaata ccaccagcgg tgaaatcgcc    42600
aaaggtatga acaaaaagac cccagcggtc gccggagcat tatctcagct ctatggcacc    42660
ggtcggatcg tgaagtctgg tgttcgcaag ggtattccaa cataccgcat taacgatatg    42720
ccgtttggtt gcagtaacag cctaaccatg atgtttaacc agctcttgag cagagccaga    42780
caaggagcag cccaatgaca gcactcaaca aacaggcgct gcgtgaagaa ttccagttca    42840
tgcaggacaa ctatagcgac ccggcagacc acgatcggca ggtgatttac atcgaggcgg    42900
aggcgctgct ggatgagttg gaagccaaag actcaacgat agcagcacaa caacatgaga    42960
tccgtatgtt gctgaatgcg cttgaggaaa accatgccc gaaatgcaac gacacaggaa    43020
tgactgatag tggcggcacg cagccatggg gcgagccgat tgagattgaa tgcgactgcc    43080
gacagcagga tgccaacacc gcagaacttg tagccgctgg cattggcgtg aagggggagt    43140
gagatggata aattaatcaa acctaccgcc aaaggtaaat atgacggttc atgtgattat    43200 cttttgctcgg aagatgcgcg attcatcgtt atgcgcggcg attatcgga agcggaaata    43260 attcaggctt ctgtgtctca agatgtaatc gactcggatg gtgcggctga ttttgcaagt    43320
agcgcccgct attatcagtg ctggtacaaa gttagcccaa taggtggtca ggatggctat    43380
tcaggctggc atcatcctcg tgattcgccg tgtcgcggtg catatttcgc atcagttttg    43440
caatgggatt aaggaggact aacccatgac aactaacaac caccggcgc acggtcctgt    43500 atcactcgat cgcctgcacc agatacgcga acacctgctg catgataccc aatactcaaa    43560
cggcgggaac agagcctaca ttctcgctga tgtattgaag gtgattgatg gggctattgc    43620
ccgcgagctg gtacgccgtg agcatgcagc gtggtcacag gctactttcg gcgatgtcgg    43680
tccagttggt ccgctgaagc acctttccaa agaagcgctc gaggctgctg ctgaaccagg    43740
cgaccttagc gaatgggctg acatgcaatt cctgttatgg gatgcgcaac gtcgtgccgg    43800
tatcagtgat gagcagatta cccaggcaat gataaaaaag ctggctataa ataaggttcg    43860
ccaatggcct gagccgaaag acggggaacc tcgattgcat atcaaagaac agtcagagca    43920
ggagaaaaaa taagaatgtt tagcctgatt cggcgcggtc aaatctacac ggacagtagc    43980
aactggcccg taattatcca tagctgtagt gatcactcgg tccgaattaa acgcaatgat    44040
ggcgagctga gaacgattag catcaaacgc tttaacgaag attttgaacg agtgcagcat    44100
gatgagtatc gcaaaatatg tgccgaaata gagcaggaaa caaacctgaa aaacctacgt    44160
gcgatgcgtc gcggcaagat tactgaatag ccaaacagga gaatatttaa cgtgaacaac    44220
ttaatgatcg accttgagtc catgggcaaa aaaccgaatg cccctattgt ctccattggt    44280
gccgtattct tcgatccgca aagcggtgaa ctgggtcagg agttttacac cgctgttaat    44340
cttgaaagcg ctatggagca gggagcggtg ccggatggtg acactattct gtggtggtta    44400
agacaaagct cagaagcacg atcagcaatc tgtgttgatg atgcgatgcc gatatcatct    44460
gccctatctg aactgagcca tttcattaat cggcattctg ataacccta atatttaaaa    44520 gtttggggca atggagctac tttcgacaac gttatattgc gcggcgcata tgagcgtgcc    44580
ggccaggttt gcccgtggca attttggaat gatcacgacg tcagaaccat cgtcacatta    44640
```

```
ggcagatctg taggtttcga tcctaagcgt gatatgccat ttgatggggt tgcacataac   44700
gcactggctg atgcccgcca ccaggcgaaa tatgtttcag cgatttggca gaaactaatc   44760
ccaaccacca gcaacagcta aagttttccc cgggtgcagc cgggataatg gagaaataac   44820
tatgagcaat attttccagt tagctcccaa cgattgggtt tgtgaaagcg ttttgatcgc   44880
ggttactggg ctcaaacccg gaaccatcct ccgtgccaga aagaatgct ggatgattgg    44940 gagggagtat atccacgtat cgcctgacgg aaatcctaaa ccttccagtg agtgcatgta   45000
taacagaaag gctgtagatg cctgggtcgc ttcaatgaaa agcaagcaac cagggtgatt   45060
tgatgccatg aaaaaggtaa gctcgtatcg ctcttgggcg tctggaggta acaccaatgg   45120
ataaagtcac atatccaaca ggcgtcgaaa accacggtgg cacattacgc atctggttta   45180
attttaaagg taagcgtgtc agggaaagtc tcggtgtccc tgacaccgct aagaacagga   45240
agatagccgg ggaactgcgg acatcagtat gttttgccat ccgcacagga acctttgatt   45300
atgcaaccca gtttcctgac tcccctaacc tcaaggcttt tggtgtaagt aaaaaagaca   45360
ttacagtgaa agaacttgaa gaaaaatggc tggatctgaa acggatggaa atctgcgcga   45420
acgcatttaa tcgctatgaa tctgtcgcaa ggaatatggt gccgaggatc ggaggtaatc   45480
gcctggtgtc agcagtaacc aaagaggaat tgctgtatct gaggaaatat ttgctaactg   45540
gttatcagaa tccgacgaaa aacaaagccc cggcaaaagg gcgaagcgtt gttactgtga   45600
actattacat gacgacaatg gccggaatgt ttcagtttgc tgcggatcac ggttacttag   45660
aggtgaaccc attcgaggga attaagcctc tgaaaaaagc cagggcagaa ccagatcctc   45720
tgtctcgtga tgaatttatt cgcctgatag atgcatgccg gcatcagcag acgaaaaacc   45780
tgtggtcatt agcagtgtac acaggaatgc gtcacgggga actggtctcc ctggcctggg   45840
aagatatcga cctgaaggct ggaacaatta ccgtcagacg taattatacg aaacttggtg   45900
agttcactct accgaaaacc gaggcaagca cagatcgagt ggtgcatctt atccagcccg   45960
caatcagtat cctgaaaaat caggctgaaa tgacaaggct gggcaggcaa tatcacattg   46020
aagtgcagtt acgtgagtac ggccgttcgg tgaaccatga gtgtacattc gtctttaatc   46080
cgcatgtggt cagacgcagt aagcaggtcg gatttatcta ccgggtcgat tcagtaggcg   46140
actcatggga agcggcactt aagcgtgcgg ggatcagaca cagaaaggcg taccagtcac   46200
gacacaccta tgcgtgctgg tcattatcag ctggtgcaaa ccctagtttt attgccagtc   46260
agatggggca tgcgagcgcg cagatggtgt tcaatgttta cggtgcatgg atggctgaca   46320
gcagcgcaga gcagatcgca atgctgaatc agaagctggc agattttgcc ccattgatgc   46380
cccatagcca cgagaacagt acgggaggat tattaaaatc agtaagttaa cccctaacgc   46440
ccgtcatgtt aactgtgtgg agggtaacac cacgctttat gccctgccga aacccgaggt   46500
tgtcctgcgc tggcgtgagc agaccacaga tgacttccgc ttctgtttta gtttccggc   46560 gaccatttcg catcaggcag cattacggca ttgcgatgat ttagtgactg aattttgac    46620 ccgcatgtca ccgttggctc cgcgcattgg acaatactgg ctgcaactgc ctgccacatt   46680
cggcccacgg gagctgcctg cgcttttggca tttttctcgat tctcttcccg gtgaatttaa   46740
ttatggggtg gaagtccgcc atccacagtt tttcgccaaa ggggaagagg aacaaacgct   46800
taatcgcggt ttacatcagc gcggcgttaa tcgggtgatt ttagacagcc gcccggttca   46860
tgcagcacgt ccatacagtg aagctattcg cgacgctcaa cgaaaaaaac ctaaagttcc   46920
ggtacatgct gtactgacgg cgaaaaatcc actgatccgt tttatcggta gtgatgatat   46980
```

```
gacgcaaaac cgggaattat ttcaggtctg gttacaaaaa ttagcgcagt ggcatcagac    47040
cactacgcct tatcttttt tacatacgcc agatattgcc caggcccgg aactggtaca    47100 taccctgtgg gaagacttac gtaaaacgct tccagagatc ggagcagttc cggctattcc    47160
acagcaatct tctcttttct gaatttgcca cctatcatag acaggtgcca tcggccattt    47220
taaagggagt ttgtatggta agcgcgctgt atgccgtttt aagtgcgttg ttattaatga    47280
agttctcttt tgatgtcgtt cgcctgcgaa tgcagtaccg cgttgcctat ggcgacggcg    47340
gttttagcga actgcaaagc gctattcgca ttcatggtaa cgcggtggaa tatattccta    47400
tcgcgattgt gttgatgctg tttatggaaa tgaatggcgc agaaacctgg atggtgcata    47460
tttgcggcat cgttttgctt gctggtcgtc tgatgcatta ttacggtttt catcaccgtc    47520
tgttccgctg cgacgttct ggcatgagcg ccacctggtg tgcgctgttg ctgatggtgc    47580
tggcgaatct ttggtatatg ccctgggagt tggttttctc cctgcgttag cgcacaatac    47640
gccactttct ttttcccgga ttttacgtt atgtctcacc gcgacacgct attttctgcc    47700
cctatcgcca gactgggcga ctggaccttt gatgaacggg tagctgaagt cttcccggat    47760
atgatccagc gttccgttcc cggctattcc aatattattt ccatgattgg tatgttagcc    47820
gagcgcttcg ttcaacctgg tacgcaggtt tacgatctgg gttgttctct gggcgcggcg    47880
acgctctcgg tgcgtcgcaa cattcatcat gataattgca aaattattgc catcgacaac    47940
tccccggcga tgattgaacg ctgccgtcgt catattgacg cctataaagc ccctacgcca    48000
gtagacgtta ttgaaggtga tattcgcgat atcgccattg aaaacgcatc gatggtggtg    48060 ctgaattta ccctgcaatt cctggaacct tccgagcgcc aggcgttact ggataaaatt    48120
tatcaagggc tgaacccggg cggtgcgctg gtgctttcgg aaaaattcag tttcgaagat    48180
gccaaagttg gtgaactgct gttcaacatg caccacgact ttaaacgtgc caacggttac    48240
agcgaactgg agatcagcca gaaacgcagc atgctggaaa acgtgatgct gaccgattcc    48300
gtggaaaccc ataaagcacg cctgcataaa gccggttttg agcatagcga gctgtggttc    48360
cagtgcttta actttggttc actggtggca ttaaaagcag aggacgctgc atgatcgact    48420
ttggtaactt ttattctctg attgccaaaa atcatctttc acactggctc gaaacgctgc    48480
ccgcgcagat tgctaactgg cagcgcgagc agcagcacgg gctgtttaag cagtggtcca    48540
acgcggtgga atttctgcct gaaattaaac cgtatcgtct ggattattg catagcgtaa    48600 ccgccgaaag cgaagagcca ctgagcgccg ggcaaattaa gcgcattgaa acgctgatgc    48660
gcaacctgat gccgtggcgc aaagggccgt tctcactgta tggcgtcaac atcgataccg    48720
aatggcgttc cgactggaaa tgggatcgcg ttatgcccca tctttctgat ttaaccgggc    48780
gcaccattct tgatgtcggc tgtggcagcg gttatcacat gtggcgcatg attggcgcag    48840
gggcgcatct ggcggtgggt atcgatccca cgcagctatt cctctgccag tttgaagcag    48900
tgcgtaaact gctgggtaac gatcagcgcg cacatttgtt accgttaggt attgaacaac    48960
ttccggcact gaaagccttt gataccgtct tttcgatggg cgtgctttat catcgtcgtt    49020
caccgctgga gcatctctgg cagttaaaag accaactggt gaatgaaggc gaactggtgc    49080
tggaaacgct ggttattgat ggcgacgaaa acacggtgct ggtgccgggc gatcgttacg    49140
ctcaaatgcg taatgtctat ttcattcctt ccgcgctggc gctgaaaaac tggctgaaga    49200
agtgtggttt tgttgatatt cgcattgcag atgtgagcgt taccaccaca gaagagcagc    49260
gacgcaccga atggatggtc accgagtctc tggccgattt tctcgacccg catgatccgg    49320
gtaaaacggt ggaaggttat cctgcgccta aacgcgcggt gctgattgcg cgcaagccgt    49380
```

```
aaaggtctgg taatactgcc ggatgcggcg tgaacgcctt atccggccta caaagtcttg   49440
ctaattcaat atattgcagg ggctatgtag gcctgataag catagcgcat caggca       49496

<210> SEQ ID NO 282
<211> LENGTH: 290
<212> TYPE: DNA
<213> ORGANISM: Escherichia coli

<400> SEQUENCE: 282
gtcagcataa caccctgacc tctcattaat tgttcatgcc gggcggcact atcgtcgtcc     60
ggccttttcc tctcttactc tgctacgtac atctatttct ataaatccgt tcaatttgtc    120 tgtttttgc acaaacatga aatatcagac aattccgtga cttaagaaaa tttatacaaa     180
tcagcaatat accccttaag gagtatataa aggtgaattt gatttacatc aataagcggg    240
gttgctgaat cgttaaggta ggcggtaata gaaaagaaat cgaggcaaaa               290

<210> SEQ ID NO 283
<211> LENGTH: 173
<212> TYPE: DNA
<213> ORGANISM: Escherichia coli

<400> SEQUENCE: 283
atttcctctc atcccatccg gggtgagagt cttttccccc gacttatggc tcatgcatgc     60
atcaaaaaag atgtgagctt gatcaaaaac aaaaaatatt tcactcgaca ggagtattta    120
tattgcgccc gttacgtggg cttcgactgt aaatcagaaa ggagaaaaca cct           173

<210> SEQ ID NO 284
<211> LENGTH: 305
<212> TYPE: DNA
<213> ORGANISM: Escherichia coli

<400> SEQUENCE: 284
gtcagcataa caccctgacc tctcattaat tgttcatgcc gggcggcact atcgtcgtcc     60
ggccttttcc tctcttactc tgctacgtac atctatttct ataaatccgt tcaatttgtc    120 tgtttttgc acaaacatga aatatcagac aattccgtga cttaagaaaa tttatacaaa     180
tcagcaatat accccttaag gagtatataa aggtgaattt gatttacatc aataagcggg    240
gttgctgaat cgttaaggat ccctctagaa ataattttgt ttaactttaa gaaggagata    300
tacat                                                                305

<210> SEQ ID NO 285
<211> LENGTH: 180
<212> TYPE: DNA
<213> ORGANISM: Escherichia coli

<400> SEQUENCE: 285
catttcctct catcccatcc ggggtgagag tcttttcccc cgacttatgg ctcatgcatg     60
catcaaaaaa gatgtgagct tgatcaaaaa caaaaaatat ttcactcgac aggagtattt    120
atattgcgcc cggatccctc tagaaataat tttgtttaac tttaagaagg agatatacat    180

<210> SEQ ID NO 286
<211> LENGTH: 199
<212> TYPE: DNA
<213> ORGANISM: Escherichia coli

<400> SEQUENCE: 286
```

```
agttgttctt attggtggtg ttgctttatg gttgcatcgt agtaaatggt tgtaacaaaa    60 gcaattttc  cggctgtctg tatacaaaaa cgccgtaaag tttgagcgaa gtcaataaac   120
tctctaccca ttcagggcaa tatctctctt ggatccctct agaaataatt ttgtttaact   180
ttaagaagga gatatacat                                                199

<210> SEQ ID NO 287
<211> LENGTH: 117
<212> TYPE: DNA
<213> ORGANISM: Escherichia coli

<400> SEQUENCE: 287
atccccatca ctcttgatgg agatcaattc cccaagctgc tagagcgtta ccttgccctt    60
aaacattagc aatgtcgatt tatcagaggg ccgacaggct cccacaggag aaaaccg     117

<210> SEQ ID NO 288
<211> LENGTH: 108
<212> TYPE: DNA
<213> ORGANISM: Escherichia coli

<400> SEQUENCE: 288
ctcttgatcg ttatcaattc ccacgctgtt tcagagcgtt accttgccct taaacattag    60
caatgtcgat ttatcagagg gccgacaggc tcccacagga gaaaaccg               108

<210> SEQ ID NO 289
<211> LENGTH: 290
<212> TYPE: DNA
<213> ORGANISM: Escherichia coli

<400> SEQUENCE: 289
gtcagcataa caccctgacc tctcattaat tgttcatgcc gggcggcact atcgtcgtcc    60
ggccttttcc tctcttactc tgctacgtac atctatttct ataaatccgt tcaatttgtc   120
tgttttttgc acaaacatga atatcagac  aattccgtga cttaagaaaa tttatacaaa   180
tcagcaatat accccttaag gagtatataa aggtgaattt gatttacatc aataagcggg   240
gttgctgaat cgttaaggta ggcggtaata gaaaagaaat cgaggcaaaa              290

<210> SEQ ID NO 290
<211> LENGTH: 1485
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 290
ctcttgatcg ttatcaattc ccacgctgtt tcagagcgtt accttgccct taaacattag    60
caatgtcgat ttatcagagg gccgacaggc tcccacagga gaaaaccgat gaaaacgcg   120 tcaaccgtat cggaagatac tgcgtcgaat caagagccga cgcttcatcg cggattacat   180
aaccgtcata ttcaactgat tgcgttgggt ggcgcaattg gtactggtct gtttcttggc   240
attggcccgg cgattcagat ggcgggtccg gctgtattgc tgggctacgg cgtcgccggg   300
atcatcgctt tcctgattat cgccagcttg gcgaaatgg  tggttgagga gccggtatcc   360
ggttcatttg cccactttgc ctataaatac tggggaccgt tgcgggcttc cctctctggc   420
tggaactact gggtaatgtt cgtgctggtg ggaatggcag agctgaccgc tgcgggcatc   480
tatatgcagt actggttccc ggatgttcca acgtggattt gggctgccgc cttctttatt   540
```

```
atcatcaacg ccgttaacct ggtgaacgtg cgcttatatg gcgaaaccga gttctggttt      600
gcgttgatta aagtgctggc aatcatcggt atgatcggct ttggcctgtg gctgctgttt      660
tctggtcacg gcggcgagaa agccagtatc gacaacctct ggcgctacgg tggtttcttc      720
gccaccggct ggaatgggct gattttgtcg ctggcggtaa ttatgttctc cttcggcggt      780
ctggagctga ttgggattac tgccgctgaa gcgcgcgatc cggaaaaaag cattccaaaa      840
gcggtaaatc aggtggtgta tcgcatcctg ctgtttttaca tcggttcact ggtggtttta      900
ctggcgctct atccgtgggt ggaagtgaaa tccaacagta gcccgtttgt gatgattttc      960
cataatctcg acagcaacgt ggtagcttct gcgctgaact tcgtcattct ggtagcatcg     1020
ctgtcagtgt ataacagcgg ggtttactct aacagccgca tgctgtttgg cctttctgtg     1080
cagggtaatg cgccgaagtt tttgactcgc gtcagccgtc gcggtgtgcc gattaactcg     1140
ctgatgcttt ccggagcgat cacttcgctg gtggtgttaa tcaactatct gctgccgcaa     1200
aaagcgtttg gtctgctgat ggcgctggtg gtagcaacgc tgctgttgaa ctggattatg     1260
atctgtctgg cgcatctgcg ttttcgtgca gcgatgcgac gtcaggggcg tgaaacacag     1320
tttaaggcgc tgctctatcc gttcggcaac tatctctgca ttgccttcct cggcatgatt     1380
ttgctgctga tgtgcacgat ggatgatatg cgcttgtcag cgatcctgct gccggtgtgg     1440
attgtattcc tgtttatggc atttaaaacg ctgcgtcgga aataa                     1485

<210> SEQ ID NO 291
<211> LENGTH: 4323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
ctcttgatcg ttatcaattc ccacgctgtt tcagagcgtt accttgccct taaacattag       60
caatgtcgat ttatcagagg gccgacaggc tcccacagga gaaaaccgat gaaagctaaa      120
gatgttcagc caaccattat tattaataaa atggccttta tctctttgga agatatctat      180
gacattgcga taaaacaaaa aaaagtagaa atatcaacgg agatcactga acttttgacg      240
catggtcgtg aaaaattaga ggaaaaatta aattcaggag aggttatata tggaatcaat      300
acaggatttg gagggaatgc caatttagtt gtgccatttg agaaaatcgc agagcatcag      360
caaaatctgt taacttttct ttctgctggt actgggact atatgtccaa accttgtatt      420
aaagcgtcac aatttactat gttactttct gtttgcaaag gttggtctgc aaccagacca      480
attgtcgctc aagcaattgt tgatcatatt aatcatgaca ttgttcctct ggttcctcgc      540
tatggctcag tgggtgcaag cggtgattta attcctttat cttatattgc acgagcatta      600
tgtggtatcg gcaaagttta ttatatgggc gcagaaattg acgctgctga agcaattaaa      660
cgtgcagggt tgacaccatt atcgttaaaa gccaagaag tcttgctct gattaacggc      720 acccgggtaa tgtcaggaat cagtgcaatc accgtcatta aactggaaaa actatttaaa      780
gcctcaattt ctgcgattgc ccttgctgtt gaagcattac ttgcatctca tgaacattat      840
gatgcccgga ttcaacaagt aaaaaatcat cctggtcaaa acgcggtggc aagtgcattg      900
cgtaatttat tggcaggttc aacgcaggtt aatctattat ctggggttaa agaacaagcc      960
aataaagctt gtcgtcatca agaaattacc caactaaatg ataccttaca ggaagtttat     1020
```

```
tcaattcgct gtgcaccaca agtattaggt atagtgccag aatctttagc taccgctcgg    1080
aaaatattgg aacgggaagt tatctcagct aatgataatc cattgataga tccagaaaat    1140
ggcgatgttc tacacggtgg aaattttatg gggcaatatg tcgcccgaac aatggatgca    1200
ttaaaactgg atattgcttt aattgccaat catcttcacg ccattgtggc tcttatgatg    1260
gataaccgtt tctctcgtgg attacctaat tcactgagtc cgacacccgg catgtatcaa    1320
ggttttaaag gcgtccaact ttctcaaacc gctttagttg ctgcaattcg ccatgattgt    1380
gctgcatcag gtattcatac cctcgccaca gaacaataca atcaagatat tgtcagttta    1440
ggtctgcatg ccgctcaaga tgttttagag atggagcaga aattacgcaa tattgtttca    1500
atgacaattc tggtagtttg tcaggccatt catcttcgcg gcaatattag tgaaattgcg    1560
cctgaaactg ctaaatttta ccatgcagta cgcgaaatca gttctccttt gatcactgat    1620
cgtgcgttgg atgaagatat aatccgcatt gcggatgcaa ttattaatga tcaacttcct    1680
ctgccagaaa tcatgctgga agaataagct tggcgtaatc atggtcatag ctgtttcctg    1740
tgtgaaattg ttatccgctc acaattccac acaacatacg agccgaagc ataaagtgta    1800 aagcctgggg tgcctaatga gtgagctaac tcacattaat tgcgttgcgc tcactgcccg    1860
ctttccagtc gggaaacctg tcgtgccagc tgcattaatg aatcggccaa cgcgcgggga    1920
gaggcggttt gcgtattggg cgctcttccg cttcctcgct cactgactcg ctgcgctcgg    1980
tcgttcggct gcggcgagcg gtatcagctc actcaaaggc ggtaatacgg ttatccacag    2040
aatcagggga taacgcagga aagaacatgt gagcaaaagg ccagcaaaag gccaggaacc    2100
gtaaaaaggc cgcgttgctg gcgttttccc ataggctccg cccccctgac gagcatcaca    2160
aaaatcgacg ctcaagtcag aggtggcgaa acccgacagg actataaaga taccaggcgt    2220
ttccccctgg aagctccctc gtgcgctctc ctgttccgac cctgccgctt accggatacc    2280
tgtccgcctt tctcccttcg ggaagcgtgg cgctttctca tagctcacgc tgtaggtatc    2340
tcagttcggt gtaggtcgtt cgctccaagc tgggctgtgt gcacgaaccc cccgttcagc    2400
ccgaccgctg cgccttatcc ggtaactatc gtcttgagtc aacccggta agacacgact    2460 tatcgccact ggcagcagcc actggtaaca ggattagcag agcgaggtat gtaggcggtg    2520
ctacagagtt cttgaagtgg tggcctaact acggctacac tagaagaaca gtatttggta    2580
tctgcgctct gctgaagcca gttaccttcg gaaaaagagt tggtagctct tgatccggca    2640
aacaaaccac cgctggtagc ggtggttttt ttgtttgcaa gcagcagatt acgcgcagaa    2700
aaaaaggatc tcaagaagat cctttgatct tttctacggg gtctgacgct cagtggaacg    2760
aaaactcacg ttaagggatt ttggtcatga gattatcaaa aaggatcttc acctagatcc    2820
ttttaaatta aaaatgaagt tttaaatcaa tctaaagtat atatgagtaa acttggtctg    2880
acagttacca atgcttaatc agtgaggcac ctatctcagc gatctgtcta tttcgttcat    2940
ccatagttgc ctgactcccc gtcgtgtaga taactacgat acgggagggc ttaccatctg    3000
gccccagtgc tgcaatgata ccgcgagacc cacgctcacc ggctccagat ttatcagcaa    3060
taaaccagcc agccggaagg gccgagcgca gaagtggtcc tgcaacttta tccgcctcca    3120
tccagtctat taattgttgc cgggaagcta gagtaagtag ttcgccagtt aatagtttgc    3180
gcaacgttgt tgccattgct acaggcatcg tggtgtcacg ctcgtcgttt ggtatggctt    3240
cattcagctc cggttcccaa cgatcaaggc gagttacatg atccccatg ttgtgcaaaa    3300 aagcggttag ctccttcggt cctccgatcg ttgtcagaag taagttggcc gcagtgttat    3360
cactcatggt tatggcagca ctgcataatt ctcttactgt catgccatcc gtaagatgct    3420
```

```
tttctgtgac tggtgagtac tcaaccaagt cattctgaga atagtgtatg cggcgaccga    3480
gttgctcttg cccggcgtca atacgggata ataccgcgcc acatagcaga actttaaaag    3540
tgctcatcat tggaaaacgt tcttcggggc gaaaactctc aaggatctta ccgctgttga    3600
gatccagttc gatgtaaccc actcgtgcac ccaactgatc ttcagcatct tttactttca    3660
ccagcgtttc tgggtgagca aaaacaggaa ggcaaaatgc cgcaaaaaag gaataagggg    3720
cgacacggaa atgttgaata ctcatactct tcctttttca atattattga agcatttatc    3780
agggttattg tctcatgagc ggatacatat ttgaatgtat ttagaaaaat aaacaaatag    3840
gggttccgcg cacatttccc cgaaaagtgc cacctgacgt ctaagaaacc attattatca    3900
tgacattaac ctataaaaat aggcgtatca cgaggccctt tcgtctcgcg cgtttcggtg    3960
atgacggtga aaacctctga cacatgcagc tcccggagac ggtcacagct tgtctgtaag    4020
cggatgccgg gagcagacaa gcccgtcagg gcgcgtcagc gggtgttggc gggtgtcggg    4080
gctggcttaa ctatgcggca tcagagcaga ttgtactgag agtgcaccat atgcggtgtg    4140
aaataccgca cagatgcgta aggagaaaat accgcatcag gcgccattcg ccattcaggc    4200
tgcgcaactg ttgggaaggg cgatcggtgc gggcctcttc gctattacgc cagctggcga    4260
aagggggatg tgctgcaagg cgattaagtt gggtaacgcc agggttttcc cagtcacgac    4320
gtt                                                                  4323
```

<210> SEQ ID NO 292
<211> LENGTH: 5092
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 292

```
ctctagaaat aattttgttt aactttaaga aggagatata catatgaaaa cactatcaca      60
ggcccaatct aaaacttctt cacagcaatt cagctttacc gggaactcgt ctgcgaatgt     120
aattatcggc aatcaaaagc tgaccattaa tgatgtagct cgcgttgccc ggaatggcac     180
tttggtgtca ctgacgaaca ataccgacat tctgcaaggt attcaagcta gctgcgatta     240
tatcaataac gccgttgaat ctggcgagcc aatctacggg gtaacaagcg gttttggtgg     300
gatggcgaac gttgccatta gccgtgaaca ggcgagcgaa cttcagacca acctcgtttg     360
gttcctaaag acaggagctg gtaataagtt acctctggct gacgtaagag ccgcgatgct     420
gcttcgcgct aatagtcaca tgcgcggcgc cagtggtatc cgtcttgagc ttatcaagag     480
gatgaaaatc ttcctcaacg cgggtgtcac accatatgtt tatgagtttg gtagtatcgg     540
agccagtggt gatcttgttc ccctgagtta tattacgggt tcattgattg gtttagaccc     600
gtcctttaaa gtggatttta acgggaaaga aatggacgcc ccgaccgctt tacgacagct     660
taatctgagc ccacttactt tgctccctaa agaaggtctt gccatgatga atggcaccctc    720
tgtgatgact ggaattgccg cgaattgtgt gtatgacacg cagatcctaa cggccattgc     780
catgggtgtt cacgcgttgg acattcaagc cctgaatggt acaaaccagt cgtttcatcc     840
gtttatccat aattcaaaac cccatccggg acagctttgg gctgctgatc agatgatctc     900
actcctggcc aatagtcaac tggttcggga cgagctcgac ggcaaacatg attatcgcga     960
tcatgagctc atccaggacc ggtattcact tcgttgtctc ccacaatacc tggggcctat    1020
```

-continued

```
cgttgatggt atatctcaaa ttgcgaagca aattgaaatt gagatcaata gcgtaaccga    1080
caacccgctt atcgatgttg ataatcaggc ctcttatcac ggtggcaatt ttctgggcca    1140
gtatgttggt atggggatgg atcacctgcg gtactatatt gggcttctgg ctaaacatct    1200
tgatgtgcag attgccttat tagcttcacc agaattttca aatggactgc cgccatcatt    1260
gctcggtaac agagaaagga aagtaaatat gggccttaag ggccttcaga tatgtggtaa    1320
ctcaatcatg cccctcctga ccttttatgg gaactcaatt gctgatcgtt ttccgacaca    1380
tgctgaacag tttaaccaaa acattaactc acagggctat acatccgcga cgttagcgcg    1440
tcggtccgtg gatatcttcc agaattatgt tgctatcgct ctgatgttcg gcgtacaggc    1500
cgttgatttg cgcacttata aaaaaaccgg tcactacgat gctcgggctt gcctgtcgcc    1560
tgccaccgag cggctttata cgccgtacg tcatgttgtg ggtcagaaac cgacgtcgga    1620
ccgcccctat atttggaatg ataatgaaca agggctggat gaacacatcg cccggatatc    1680
tgccgatatt gccgccggag gtgtcatcgt ccaggcggta caagacatac ttccttgcct    1740
gcattaagct tggcgtaatc atggtcatag ctgtttcctg tgtgaaattg ttatccgctc    1800
acaattccac acaacatacg agccggaagc ataaagtgta aagcctgggg tgcctaatga    1860
gtgagctaac tcacattaat tgcgttgcgc tcactgcccg ctttccagtc gggaaacctg    1920
tcgtgccagc tgcattaatg aatcggccaa cgcgcgggga gaggcggttt gcgtattggg    1980
cgctcttccg cttcctcgct cactgactcg ctgcgctcgg tcgttcggct gcggcgagcg    2040
gtatcagctc actcaaaggc ggtaatacgg ttatccacag aatcagggga taacgcagga    2100
aagaacatgt gagcaaaagg ccagcaaaag gccaggaacc gtaaaaaggc cgcgttgctg    2160
gcgtttttcc ataggctccg cccccctgac gagcatcaca aaaatcgacg ctcaagtcag    2220
aggtggcgaa acccgacagg actataaaga taccaggcgt ttccccctgg aagctccctc    2280
gtgcgctctc ctgttccgac cctgccgctt accggatacc tgtccgcctt tctcccttcg    2340
ggaagcgtgg cgctttctca tagctcacgc tgtaggtatc tcagttcggt gtaggtcgtt    2400
cgctccaagc tgggctgtgt gcacgaaccc cccgttcagc ccgaccgctg cgccttatcc    2460
ggtaactatc gtcttgagtc caacccggta agacacgact tatcgccact ggcagcagcc    2520
actggtaaca ggattagcag agcgaggtat gtaggcggtg ctacagagtt cttgaagtgg    2580
tggcctaact acggctacac tagaagaaca gtatttggta tctgcgctct gctgaagcca    2640
gttaccttcg gaaaaagagt tggtagctct tgatccggca acaaaccacc gctggtagc    2700
ggtggttttt ttgtttgcaa gcagcagatt acgcgcagaa aaaaaggatc tcaagaagat    2760
cctttgatct tttctacggg gtctgacgct cagtggaacg aaaactcacg ttaagggatt    2820
ttggtcatga gattatcaaa aaggatcttc acctagatcc ttttaaatta aaaatgaagt    2880
tttaaatcaa tctaaagtat atatgagtaa acttggtctg acagttacca atgcttaatc    2940
agtgaggcac ctatctcagc gatctgtcta tttcgttcat ccatagttgc ctgactcccc    3000
gtcgtgtaga taactacgat acgggagggc ttaccatctg gccccagtgc tgcaatgata    3060
ccgcgagacc cacgctcacc ggctccagat ttatcagcaa taaaccagcc agccggaagg    3120
gccgagcgca gaagtggtcc tgcaacttta tccgcctcca tccagtctat taattgttgc    3180
cgggaagcta gagtaagtag ttcgccagtt aatagtttgc gcaacgttgt tgccattgct    3240
acaggcatcg tggtgtcacg ctcgtcgttt ggtatggctt cattcagctc cggttcccaa    3300
cgatcaaggc gagttacatg atcccccatg ttgtgcaaaa aagcggttag ctccttcggt    3360
cctccgatcg ttgtcagaag taagttggcc gcagtgttat cactcatggt tatggcagca    3420
```

```
ctgcataatt ctcttactgt catgccatcc gtaagatgct tttctgtgac tggtgagtac   3480
tcaaccaagt cattctgaga atagtgtatg cggcgaccga gttgctcttg cccggcgtca   3540
atacgggata ataccgcgcc acatagcaga actttaaaag tgctcatcat tggaaaacgt   3600
tcttcggggc gaaaactctc aaggatctta ccgctgttga gatccagttc gatgtaaccc   3660
actcgtgcac ccaactgatc ttcagcatct tttactttca ccagcgtttc tgggtgagca   3720
aaaacaggaa ggcaaaatgc cgcaaaaaag gaataagggc gacacggaaa tgttgaata    3780 ctcatactct tcctttttca atattattga agcatttatc agggttattg tctcatgagc   3840
ggatacatat ttgaatgtat ttagaaaaat aaacaaatag gggttccgcg cacatttccc   3900
cgaaaagtgc cacctgacgt ctaagaaacc attattatca tgacattaac ctataaaaat   3960
aggcgtatca cgaggccctt cgtctcgcg cgtttcggtg atgacggtga aaacctctga   4020
cacatgcagc tcccggagac ggtcacagct tgtctgtaag cggatgccgg gagcagacaa   4080
gcccgtcagg gcgcgtcagc gggtgttggc gggtgtcggg gctggcttaa ctatgcggca   4140
tcagagcaga ttgtactgag agtgcaccat atgcggtgtg aaataccgca cagatgcgta   4200
aggagaaaat accgcatcag cgccattcg ccattcaggc tgcgcaactg ttgggaaggg   4260
cgatcggtgc gggcctcttc gctattacgc cagctggcga aggggggatg tgctgcaagg   4320
cgattaagtt gggtaacgcc agggttttcc cagtcacgac gttgtaaaac gacgccagt    4380 gaattcgtta agacccactt tcacatttaa gttgttttc taatccgcat atgatcaatt    4440
caaggccgaa taagaaggct ggctctgcac cttggtgatc aaataattcg atagcttgtc   4500
gtaataatgg cggcatacta tcagtagtag gtgtttccct ttcttcttta gcgacttgat   4560
gctcttgatc ttccaatacg caacctaaag taaaatgccc cacagcgctg agtgcatata   4620
atgcattctc tagtgaaaaa ccttgttggc ataaaaggc taattgattt tcgagagttt    4680
catactgttt ttctgtaggc cgtgtaccta aatgtacttt tgctccatcg cgatgactta   4740
gtaaagcaca tctaaaactt ttagcgttat tacgtaaaaa atcttgccag ctttcccctt   4800
ctaaagggca aaagtgagta tggtgcctat ctaacatctc aatggctaag gcgtcgagca   4860
aagcccgctt atttttaca tgccaataca atgtaggctg ctctacacct agcttctggg   4920
cgagtttacg ggttgttaaa ccttcgattc cgacctcatt aagcagctct aatgcgctgt   4980
taatcacttt acttttatct aatctagaca tcattaattc ctaattttg ttgacactct   5040 atcattgata gagttatttt accactccct atcagtgata gagaaaagtg aa           5092
```

<210> SEQ ID NO 293
<211> LENGTH: 4987
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 293

```
ctctagaaat aattttgttt aactttaaga aggagatata catatgaaag ctaaagatgt     60
tcagccaacc attattatta ataaaaatgg ccttatctct ttggaagata tctatgacat    120
tgcgataaaa caaaaaaaag tagaaatatc aacggagatc actgaacttt tgacgcatgg    180
tcgtgaaaaa ttagaggaaa aattaaattc aggagaggtt atatatgaa tcaatacagg    240 atttggaggg aatgccaatt tagttgtgcc atttgagaaa atcgcagagc atcagcaaaa    300
```

```
tctgttaact tttctttctg ctggtactgg ggactatatg tccaaacctt gtattaaagc     360
gtcacaattt actatgttac tttctgtttg caaaggttgg tctgcaacca gaccaattgt     420
cgctcaagca attgttgatc atattaatca tgacattgtt cctctggttc ctcgctatgg     480
ctcagtgggt gcaagcggtg atttaattcc tttatcttat attgcacgag cattatgtgg     540
tatcggcaaa gtttattata tgggcgcaga aattgacgct gctgaagcaa ttaaacgtgc     600
agggttgaca ccattatcgt taaaagccaa agaaggtctt gctctgatta acggcacccg     660
ggtaatgtca ggaatcagtg caatcaccgt cattaaactg gaaaaactat ttaaagcctc     720
aatttctgcg attgcccttg ctgttgaagc attacttgca tctcatgaac attatgatgc     780
ccggattcaa caagtaaaaa atcatcctgg tcaaaacgcg gtggcaagtg cattgcgtaa     840
tttattggca ggttcaacgc aggttaatct attatctggg gttaaagaac aagccaataa     900
agcttgtcgt catcaagaaa ttacccaact aaatgatacc ttacaggaag tttattcaat     960
tcgctgtgca ccacaagtat taggtatagt gccagaatct ttagctaccg ctcggaaaat    1020
attggaacgg gaagttatct cagctaatga taatccattg atagatccag aaaatggcga    1080
tgttctacac ggtggaaatt ttatggggca atatgtcgcc cgaacaatgg atgcattaaa    1140
actggatatt gctttaattg ccaatcatct tcacgccatt gtggctctta tgatggataa    1200
ccgtttctct cgtggattac ctaattcact gagtccgaca cccggcatgt atcaaggttt    1260
taaaggcgtc caacttttctc aaaccgcttt agttgctgca attcgccatg attgtgctgc    1320
atcaggtatt catacccctcg ccacagaaca atacaatcaa gatattgtca gtttaggtct    1380
gcatgccgct caagatgttt tagagatgga gcagaaatta cgcaatattg tttcaatgac    1440
aattctggta gtttgtcagg ccattcatct tcgcggcaat attagtgaaa ttgcgcctga    1500
aactgctaaa ttttaccatg cagtacgcga aatcagttct cctttgatca ctgatcgtgc    1560
gttggatgaa gatataatcc gcattgcgga tgcaattatt aatgatcaac ttcctctgcc    1620
agaaatcatg ctggaagaat aagcttggcg taatcatggt catagctgtt tcctgtgtga    1680
aattgttatc cgctcacaat tccacacaac atacgagccg gaagcataaa gtgtaaagcc    1740
tggggtgcct aatgagtgag ctaactcaca ttaattgcgt tgcgctcact gcccgctttc    1800
cagtcgggaa acctgtcgtg ccagctgcat taatgaatcg gccaacgcgc ggggagaggc    1860
ggtttgcgta ttgggcgctc ttccgcttcc tcgctcactg actcgctgcg ctcggtcgtt    1920
cggctgcggc gagcggtatc agctcactca aaggcggtaa tacggttatc cacagaatca    1980
ggggataacg caggaaagaa catgtgagca aaaggccagc aaaaggccag gaaccgtaaa    2040
aaggccgcgt tgctggcgtt tttccatagg ctccgccccc ctgacgagca tcacaaaaat    2100
cgacgctcaa gtcagaggtg gcgaaacccg acaggactat aaagatacca ggcgtttccc    2160
cctggaagct ccctcgtgcg ctctcctgtt ccgaccctgc cgcttaccgg atacctgtcc    2220
gcctttctcc cttcgggaag cgtggcgctt tctcatagct cacgctgtag gtatctcagt    2280
tcggtgtagg tcgttcgctc caagctgggc tgtgtgcacg aacccccccgt tcagcccgac    2340 cgctgcgcct tatccggtaa ctatcgtctt gagtccaacc cggtaagaca cgacttatcg    2400
ccactggcag cagccactgg taacaggatt agcagagcga ggtatgtagg cggtgctaca    2460
gagttcttga agtggtggcc taactacggc tacactagaa gaacagtatt tggtatctgc    2520
gctctgctga agccagttac cttcggaaaa agagttggta gctcttgatc cggcaaacaa    2580
accaccgctg gtagcggtgg tttttttgtt tgcaagcagc agattacgcg cagaaaaaaa    2640
ggatctcaag aagatccttt gatcttttct acggggtctg acgctcagtg gaacgaaaac    2700
```

-continued

```
tcacgttaag ggattttggt catgagatta tcaaaaagga tcttcaccta gatccttta      2760 aattaaaaat gaagttttaa atcaatctaa agtatatatg agtaaacttg gtctgacagt     2820
taccaatgct taatcagtga ggcacctatc tcagcgatct gtctatttcg ttcatccata     2880
gttgcctgac tccccgtcgt gtagataact acgatacggg agggcttacc atctggcccc     2940
agtgctgcaa tgataccgcg agacccacgc tcaccggctc cagatttatc agcaataaac     3000
cagccagccg gaagggccga gcgcagaagt ggtcctgcaa ctttatccgc ctccatccag     3060
tctattaatt gttgccggga agctagagta agtagttcgc cagttaatag tttgcgcaac     3120
gttgttgcca ttgctacagg catcgtggtg tcacgctcgt cgtttggtat ggcttcattc     3180
agctccggtt cccaacgatc aaggcgagtt acatgatccc ccatgttgtg caaaaaagcg     3240
gttagctcct tcggtcctcc gatcgttgtc agaagtaagt tggccgcagt gttatcactc     3300
atggttatgg cagcactgca taattctctt actgtcatgc catccgtaag atgcttttct     3360
gtgactggtg agtactcaac caagtcattc tgagaatagt gtatgcggcg accgagttgc     3420
tcttgcccgg cgtcaatacg ggataatacc gcgccacata gcagaacttt aaaagtgctc     3480
atcattggaa aacgttcttc ggggcgaaaa ctctcaagga tcttaccgct gttgagatcc     3540
agttcgatgt aacccactcg tgcacccaac tgatcttcag catcttttac tttcaccagc     3600
gtttctgggt gagcaaaaac aggaaggcaa aatgccgcaa aaaagggaat aagggcgaca     3660
cggaaatgtt gaatactcat actcttcctt tttcaatatt attgaagcat ttatcagggt     3720
tattgtctca tgagcggata catatttgaa tgtatttaga aaataaaca aatagggtt      3780 ccgcgcacat ttccccgaaa agtgccacct gacgtctaag aaaccattat tatcatgaca     3840
ttaacctata aaaataggcg tatcacgagg ccctttcgtc tcgcgcgttt cggtgatgac     3900
ggtgaaaacc tctgacacat gcagctcccg gagacggtca gcttgtctt gtaagcggat      3960 gccgggagca gacaagcccg tcagggcgcg tcagcgggtg ttggcgggtg tcgggctgg      4020 cttaactatg cggcatcaga gcagattgta ctgagagtgc accatatgcg gtgtgaaata     4080
ccgcacagat gcgtaaggag aaaataccgc atcaggcgcc attcgccatt caggctgcgc     4140
aactgttggg aagggcgatc ggtgcgggcc tcttcgctat tacgcagct ggcgaaaggg      4200 ggatgtgctg caaggcgatt aagttgggta acgccaggt tttcccagtc acgacgttgt      4260
aaaacgacgg ccagtgaatt cgttaagacc cactttcaca tttaagttgt ttttctaatc     4320
cgcatatgat caattcaagg ccgaataaga aggctggctc tgcaccttgg tgatcaaata     4380
attcgatagc ttgtcgtaat aatggcggca tactatcagt agtaggtgtt tccctttctt     4440
ctttagcgac ttgatgctct tgatcttcca atacgcaacc taaagtaaaa tgccccacag     4500
cgctgagtgc atataatgca ttctctagtg aaaaaccttg ttggcataaa aaggctaatt     4560
gattttcgag agtttcatac tgtttttctg taggccgtgt acctaaatgt acttttgctc     4620
catcgcgatg acttagtaaa gcacatctaa aactttagc gttattacgt aaaaaatctt      4680
gccagctttc ccttctaaa gggcaaaagt gagtatggtg cctatctaac atctcaatgg      4740
ctaaggcgtc gagcaaagcc cgcttatttt ttacatgcca atacaatgta ggctgctcta     4800
cacctagctt ctgggcgagt ttacggggttg ttaaaccttc gattccgacc tcattaagca    4860
gctctaatgc gctgttaatc actttacttt tatctaatct agacatcatt aattcctaat     4920
ttttgttgac actctatcat tgatagagtt attttaccac tccctatcag tgatagagaa     4980
aagtgaa                                                               4987
```

-continued

<210> SEQ ID NO 294
<211> LENGTH: 5962
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 294

| | | | | | |
|---|---|---|---|---|---|
| ctcttgatcg | ttatcaattc | ccacgctgtt | tcagagcgtt | accttgccct | taaacattag | 60 |
| caatgtcgat | ttatcagagg | gccgacaggc | tcccacagga | gaaaaccgat | gaaaacacta | 120 |
| tcacaggccc | aatctaaaac | ttcttcacag | caattcagct | ttaccgggaa | ctcgtctgcg | 180 |
| aatgtaatta | tcggcaatca | aaagctgacc | attaatgatg | tagctcgcgt | tgcccggaat | 240 |
| ggcactttgg | tgtcactgac | gaacaatacc | gacattctgc | aaggtattca | agctagctgc | 300 |
| gattatatca | ataacgccgt | tgaatctggc | gagccaatct | acggggtaac | aagcggtttt | 360 |
| ggtgggatgg | cgaacgttgc | cattagccgt | gaacaggcga | gcgaacttca | gaccaacctc | 420 |
| gtttggttcc | taaagacagg | agctggtaat | aagttacctc | tggctgacgt | aagagccgcg | 480 |
| atgctgcttc | gcgctaatag | tcacatgcgc | ggcgccagtg | gtatccgtct | tgagcttatc | 540 |
| aagaggatgg | aaatcttcct | caacgcgggt | gtcacaccat | atgtttatga | gtttggtagt | 600 |
| atcggagcca | gtggtgatct | tgttcccctg | agttatatta | cgggttcatt | gattggttta | 660 |
| gacccgtcct | ttaaagtgga | ttttaacggg | aaagaaatgg | acgccccgac | cgctttacga | 720 |
| cagcttaatc | tgagcccact | tactttgctc | cctaaagaag | gtcttgccat | gatgaatggc | 780 |
| acctctgtga | tgactggaat | tgccgcgaat | tgtgtgtatg | acacgcagat | cctaacggcc | 840 |
| attgccatgg | gtgttcacgc | gttggacatt | caagccctga | atggtacaaa | ccagtcgttt | 900 |
| catccgttta | tccataattc | aaaaccccat | ccgggacagc | tttgggctgc | tgatcagatg | 960 |
| atctcactcc | tggccaatag | tcaactggtt | cgggacgagc | tcgacggcaa | acatgattat | 1020 |
| cgcgatcatg | agctcatcca | ggaccggtat | tcacttcgtt | gtctcccaca | atacctgggg | 1080 |
| cctatcgttg | atggtatatc | tcaaattgcg | aagcaaattg | aaattgagat | caatagcgta | 1140 |
| accgacaacc | cgcttatcga | tgttgataat | caggcctctt | atcacggtgg | caatttttctg | 1200 |
| ggccagtatt | ttggtatggg | gatggatcac | ctgcggtact | atattgggct | tctggctaaa | 1260 |
| catcttgatg | tgcagattgc | cttattagct | tcaccagaat | tttcaaatgg | actgccgcca | 1320 |
| tcattgctcg | gtaacagaga | aaggaaagta | aatatgggcc | ttaagggcct | tcagatatgt | 1380 |
| ggtaactcaa | tcatgcccct | cctgaccttt | tatgggaact | caattgctga | tcgttttccg | 1440 |
| acacatgctg | aacagtttaa | ccaaaacatt | aactcacagg | gctatacatc | cgcgacgtta | 1500 |
| gcgcgtcggt | ccgtggatat | cttccagaat | tatgttgcta | tcgctctgat | gttcggcgta | 1560 |
| caggccgttg | atttgcgcac | ttataaaaaa | accggtcact | acgatgctcg | ggcttgcctg | 1620 |
| tcgcctgcca | ccgagcggct | ttatagcgcc | gtacgtcatg | ttgtgggtca | gaaaccgacg | 1680 |
| tcggaccgcc | cctatatttg | gaatgataat | gaacaagggc | tggatgaaca | catcgcccgg | 1740 |
| atatctgccg | atattgccgc | cggaggtgtc | atcgtccagg | cggtacaaga | catacttcct | 1800 |
| tgcctgcatt | aagcttggcg | taatcatggt | catagctgtt | tcctgtgtga | aattgttatc | 1860 |
| cgctcacaat | tccacacaac | atacgagccg | gaagcataaa | gtgtaaagcc | tggggtgcct | 1920 |
| aatgagtgag | ctaactcaca | ttaattgcgt | tgcgctcact | gcccgctttc | cagtcgggaa | 1980 |
| acctgtcgtg | ccagctgcat | taatgaatcg | gccaacgcgc | ggggagaggc | ggtttgcgta | 2040 |

-continued

```
ttgggcgctc ttccgcttcc tcgctcactg actcgctgcg ctcggtcgtt cggctgcggc    2100
gagcggtatc agctcactca aaggcggtag tacgggtttt gctgcccgca aacgggctgt    2160
tctggtgttg ctagtttgtt atcagaatcg cagatccggc ttcaggtttg ccggctgaaa    2220
gcgctatttc ttccagaatt gccatgattt tttccccacg ggaggcgtca ctggctcccg    2280
tgttgtcggc agctttgatt cgataagcag catcgcctgt ttcaggctgt ctatgtgtga    2340
ctgttgagct gtaacaagtt gtctcaggtg ttcaatttca tgttctagtt gctttgtttt    2400
actggtttca cctgttctat taggtgttac atgctgttca tctgttacat tgtcgatctg    2460
ttcatggtga acagctttaa atgcaccaaa aactcgtaaa agctctgatg tatctatctt    2520
ttttacaccg ttttcatctg tgcatatgga cagttttccc tttgatatct aacggtgaac    2580
agttgttcta cttttgtttg ttagtcttga tgcttcactg atagatacaa gagccataag    2640
aacctcagat ccttccgtat ttagccagta tgttctctag tgtggttcgt tgttttttgcg   2700 tgagccatga gaacgaacca ttgagatcat gcttactttg catgtcactc aaaaattttg    2760
cctcaaaact ggtgagctga attttgcag ttaaagcatc gtgtagtgtt tttcttagtc     2820
cgttacgtag gtaggaatct gatgtaatgg ttgttggtat tttgtcacca ttcattttta    2880
tctggttgtt ctcaagttcg gttacgagat ccatttgtct atctagttca acttggaaaa    2940
tcaacgtatc agtcgggcgg cctcgcttat caaccaccaa tttcatattg ctgtaagtgt    3000
ttaaatcttt acttattggt ttcaaaaccc attggttaag ccttttaaac tcatggtagt    3060
tattttcaag cattaacatg aacttaaatt catcaaggct aatctctata tttgccttgt    3120
gagttttctt ttgtgttagt tctttttaata accactcata aatcctcata gagtatttgt    3180
tttcaaaaga cttaacatgt tccagattat attttatgaa ttttttttaac tggaaaagat    3240 aaggcaatat ctcttcacta aaaactaatt ctaattttc gcttgagaac ttggcatagt     3300
ttgtccactg gaaaatctca aagcctttaa ccaaaggatt cctgatttcc acagttctcg    3360
tcatcagctc tctggttgct ttagctaata caccataagc attttcccta ctgatgttca    3420
tcatctgagc gtattggtta taagtgaacg ataccgtccg ttctttcctt gtagggtttt    3480
caatcgtggg gttgagtagt gccacacagc ataaaattag cttggtttca tgctccgtta    3540
agtcatagcg actaatcgct agttcatttg ctttgaaaac aactaattca gacatacatc    3600
tcaattggtc taggtgattt taatcactat accaattgag atgggctagt caatgataat    3660
tactagtcct tttcctttga gttgtgggta tctgtaaatt ctgctagacc tttgctggaa    3720
aacttgtaaa ttctgctaga ccctctgtaa attccgctag acctttgtgt gttttttttg    3780
tttatattca agtggttata atttatagaa taaagaaaga ataaaaaaag ataaaaagaa    3840
tagatcccag ccctgtgtat aactcactac tttagtcagt tccgcagtat tacaaaagga    3900
tgtcgcaaac gctgtttgct cctctacaaa acagaccttta aaaccctaaa ggcttaagta   3960
gcaccctcgc aagctcgggc aaatcgctga atattccttt tgtctccgac catcaggcac    4020
ctgagtcgct gtcttttttcg tgacattcag ttcgctgcgc tcacggctct ggcagtgaat    4080
gggggtaaat ggcactacag gcgccttta tggattcatg caaggaaact acccataata     4140
caagaaaagc ccgtcacggg cttctcaggg cgttttatgg cgggtctgct atgtggtgct    4200
atctgacttt tgctgttca gcagttcctg ccctctgatt ttccagtctg accacttcgg     4260
attatcccgt gacaggtcat tcagactggc taatgcaccc agtaaggcag cggtatcatc    4320
aacaggctta cccgtcttac tgtcttttct acggggtctg acgctcagtg gaacgaaaac    4380
```

```
tcacgttaag ggattttggt catgagatta tcaaaaagga tcttcaccta gatccttta    4440 aattaaaaat gaagttttaa atcaatctaa agtatatatg agtaaacttg gtctgacagt    4500
taccaatgct taatcagtga ggcacctatc tcagcgatct gtctatttcg ttcatccata    4560
gttgcctgac tccccgtcgt gtagataact acgatacggg agggcttacc atctggcccc    4620
agtgctgcaa tgataccgcg agacccacgc tcaccggctc cagatttatc agcaataaac    4680
cagccagccg aagggccgag cgcagaagt ggtcctgcaa ctttatccgc ctccatccag    4740
tctattaatt gttgccggga agctagagta agtagttcgc cagttaatag tttgcgcaac    4800
gttgttgcca ttgctacagg catcgtggtg tcacgctcgt cgtttggtat ggcttcattc    4860
agctccggtt cccaacgatc aaggcgagtt acatgatccc ccatgttgtg caaaaaagcg    4920
gttagctcct tcggtcctcc gatcgttgtc agaagtaagt tggccgcagt gttatcactc    4980
atggttatgg cagcactgca taattctctt actgtcatgc catccgtaag atgcttttct    5040
gtgactggtg agtactcaac caagtcattc tgagaatagt gtatgcggcg accgagttgc    5100
tcttgcccgg cgtcaatacg ggataatacc gcgccacata gcagaacttt aaaagtgctc    5160
atcattggaa aacgttcttc ggggcgaaaa ctctcaagga tcttaccgct gttgagatcc    5220
agttcgatgt aacccactcg tgcacccaac tgatcttcag catctttac tttcaccagc     5280 gtttctggt gagcaaaaac aggaaggcaa atgccgcaa aaagggaat aagggcgaca      5340 cggaaatgtt gaatactcat actcttcctt tttcaatatt attgaagcat ttatcagggt    5400
tattgtctca tgagcggata catatttgaa tgtatttaga aaaataaaca ataggggtt     5460 ccgcgcacat ttccccgaaa agtgccacct gacgtctaag aaaccattat tatcatgaca    5520
ttaacctata aaaataggcg tatcacgagg ccctttcgtc tcgcgcgttt cggtgatgac    5580
ggtgaaaacc tctgacacat gcagctcccg gagacggtca cagcttgtct gtaagcggat    5640
gccgggagca gacaagcccg tcagggcgcg tcagcgggtg ttggcgggtg tcgggctgg    5700 cttaactatg cggcatcaga gcagattgta ctgagagtgc accatatgcg gtgtgaaata    5760
ccgcacagat gcgtaaggag aaaataccgc atcaggcgcc attcgccatt caggctgcgc    5820
aactgttggg aagggcgatc ggtgcgggcc tcttcgctat tacgccagct ggcgaaaggg    5880
ggatgtgctg caaggcgatt aagttgggta acgccagggt tttcccagtc acgacgttgt    5940
aaaacgacgg ccagtgaatt cg                                              5962
```

<210> SEQ ID NO 295
<211> LENGTH: 5857
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 295

```
ctcttgatcg ttatcaattc ccacgctgtt tcagagcgtt accttgccct taaacattag     60
caatgtcgat ttatcagagg gccgacaggc tcccacagga gaaaccgat gaaagctaaa    120 gatgttcagc caaccattat tattaataaa aatggcctta tctctttgga agatatctat    180
gacattgcga taaaacaaaa aaaagtagaa atatcaacgg agatcactga acttttgacg    240
catggtcgtg aaaaattaga ggaaaaatta aattcaggag aggttatata tggaatcaat    300
acaggatttg gagggaatgc caatttagtt gtgccatttg agaaaatcgc agagcatcag    360
caaaatctgt taactttct ttctgctggt actggggact atatgtccaa accttgtatt    420
```

-continued

```
aaagcgtcac aatttactat gttactttct gtttgcaaag gttggtctgc aaccagacca    480
attgtcgctc aagcaattgt tgatcatatt aatcatgaca ttgttcctct ggttcctcgc    540
tatggctcag tgggtgcaag cggtgattta attcctttat cttatattgc acgagcatta    600
tgtggtatcg gcaaagttta ttatatgggc gcagaaattg acgctgctga agcaattaaa    660
cgtgcagggt tgacaccatt atcgttaaaa gccaagaag gtcttgctct gattaacggc     720
acccgggtaa tgtcaggaat cagtgcaatc accgtcatta aactggaaaa actatttaaa    780
gcctcaattt ctgcgattgc ccttgctgtt gaagcattac ttgcatctca tgaacattat    840
gatgcccgga ttcaacaagt aaaaaatcat cctggtcaaa acgcggtggc aagtgcattg    900
cgtaatttat tggcaggttc aacgcaggtt aatctattat ctggggttaa agaacaagcc    960
aataaagctt gtcgtcatca agaaattacc caactaaatg ataccttaca ggaagtttat   1020
tcaattcgct gtgcaccaca agtattaggt atagtgccag aatctttagc taccgctcgg   1080
aaaatattgg aacgggaagt tatctcagct aatgataatc cattgataga tccagaaaat   1140
ggcgatgttc tacacggtgg aaattttatg gggcaatatg tcgcccgaac aatggatgca   1200
ttaaaactgg atattgcttt aattgccaat catcttcacg ccattgtggc tcttatgatg   1260
gataaccgtt tctctcgtgg attacctaat tcactgagtc cgacacccgg catgtatcaa   1320
ggttttaaag gcgtccaact ttctcaaacc gctttagttg ctgcaattcg ccatgattgt   1380
gctgcatcag gtattcatac cctcgccaca gaacaataca atcaagatat tgtcagttta   1440
ggtctgcatg ccgctcaaga tgttttagag atggagcaga aattacgcaa tattgtttca   1500
atgacaattc tggtagtttg tcaggccatt catcttcgcg gcaatattag tgaaattgcg   1560
cctgaaactg ctaaatttta ccatgcagta cgcgaaatca gttctccttt gatcactgat   1620
cgtgcgttgg atgaagatat aatccgcatt gcggatgcaa ttattaatga tcaacttcct   1680
ctgccagaaa tcatgctgga agaataagct tggcgtaatc atggtcatag ctgtttcctg   1740
tgtgaaattg ttatccgctc acaattccac acaacatacg agccggaagc ataaagtgta   1800
aagcctgggg tgcctaatga gtgagctaac tcacattaat tgcgttgcgc tcactgcccg   1860
ctttccagtc gggaaacctg tcgtgccagc tgcattaatg aatcggccaa cgcgcgggga   1920
gaggcggttt gcgtattggg cgctcttccg cttcctcgct cactgactcg ctgcgctcgg   1980
tcgttcggct gcggcgagcg gtatcagctc actcaaaggc ggtagtacgg ttttgctgc    2040 ccgcaaacgg gctgttctgg tgttgctagt ttgttatcag aatcgcagat ccggcttcag   2100
gtttgccggc tgaaagcgct atttcttcca gaattgccat gattttttcc ccacgggagg   2160
cgtcactggc tcccgtgttg tcggcagctt tgattcgata agcagcatcg cctgtttcag   2220
gctgtctatg tgtgactgtt gagctgtaac aagttgtctc aggtgttcaa tttcatgttc   2280
tagttgcttt gttttactgg tttcacctgt tctattaggt gttacatgct gttcatctgt   2340
tacattgtcg atctgttcat ggtgaacagc tttaaatgca ccaaaaactc gtaaaagctc   2400
tgatgtatct atcttttttta caccgttttc atctgtgcat atggacagtt tcccctttga   2460
tatctaacgg tgaacagttg ttctactttt gtttgttagt cttgatgctt cactgataga   2520
tacaagagcc ataagaacct cagatccttc cgtatttagc cagtatgttc tctagtgtgg   2580
ttcgttgttt ttgcgtgagc catgagaacg aaccattgag atcatgctta ctttgcatgt   2640
cactcaaaaa ttttgcctca aaactggtga gctgaatttt tgcagttaaa gcatcgtgta   2700
gtgtttttct tagtccgtta cgtaggtagg aatctgatgt aatggttgtt ggtattttgt   2760
```

-continued

```
caccattcat ttttatctgg ttgttctcaa gttcggttac gagatccatt tgtctatcta    2820
gttcaacttg gaaaatcaac gtatcagtcg ggcggcctcg cttatcaacc accaatttca    2880
tattgctgta agtgtttaaa tctttactta ttggtttcaa aacccattgg ttaagccttt    2940
taaactcatg gtagttattt tcaagcatta acatgaactt aaattcatca aggctaatct    3000
ctatatttgc cttgtgagtt ttcttttgtg ttagttcttt taataaccac tcataaatcc    3060
tcatagagta tttgttttca aaagacttaa catgttccag attatatttt atgaattttt    3120
ttaactggaa aagataaggc aatatctctt cactaaaaac taattctaat ttttcgcttg    3180
agaacttggc atagtttgtc cactggaaaa tctcaaagcc tttaaccaaa ggattcctga    3240
tttccacagt tctcgtcatc agctctctgg ttgctttagc taatacacca taagcatttt    3300
ccctactgat gttcatcatc tgagcgtatt ggttataagt gaacgatacc gtccgttctt    3360
tccttgtagg gttttcaatc gtggggttga gtagtgccac acagcataaa attagcttgg    3420
tttcatgctc cgttaagtca tagcgactaa tcgctagttc atttgctttg aaaacaacta    3480
attcagacat acatctcaat tggtctaggt gattttaatc actataccaa ttgagatggg    3540
ctagtcaatg ataattacta gtccttttcc tttgagttgt gggtatctgt aaattctgct    3600
agacctttgc tggaaaactt gtaaattctg ctagaccctc tgtaaattcc gctagacctt    3660
tgtgtgtttt ttttgtttat attcaagtgg ttataattta tagaataaag aaagaataaa    3720
aaagataaa aagaatagat cccagccctg tgtataactc actactttag tcagttccgc    3780
agtattacaa aaggatgtcg caaacgctgt ttgctcctct acaaaacaga ccttaaaacc    3840
ctaaaggctt aagtagcacc ctcgcaagct cgggcaaatc gctgaatatt ccttttgtct    3900
ccgaccatca ggcacctgag tcgctgtctt tttcgtgaca ttcagttcgc tgcgctcacg    3960
gctctggcag tgaatggggg taaatggcac tacaggcgcc ttttatggat tcatgcaagg    4020
aaactaccca taatacaaga aaagcccgtc acgggcttct cagggcgttt tatggcgggt    4080
ctgctatgtg gtgctatctg acttttttgct gttcagcagt tcctgccctc tgattttcca    4140
gtctgaccac ttcggattat cccgtgacag gtcattcaga ctggctaatg cacccagtaa    4200
ggcagcggta tcatcaacag gcttacccgt cttactgtct tttctacggg gtctgacgct    4260
cagtggaacg aaaactcacg ttaagggatt ttggtcatga gattatcaaa aaggatcttc    4320
acctagatcc ttttaaatta aaatgaagt tttaaatcaa tctaaagtat atatgagtaa    4380
acttggtctg acagttacca atgcttaatc agtgaggcac ctatctcagc gatctgtcta    4440
tttcgttcat ccatagttgc ctgactcccc gtcgtgtaga taactacgat acgggagggc    4500
ttaccatctg gccccagtgc tgcaatgata ccgcgagacc cacgctcacc ggctccagat    4560
ttatcagcaa taaccagcc agccggaagg gccgagcgca gaagtggtcc tgcaacttta    4620
tccgcctcca tccagtctat taattgttgc cgggaagcta gagtaagtag ttcgccagtt    4680
aatagtttgc gcaacgttgt tgccattgct acaggcatcg tggtgtcacg ctcgtcgttt    4740
ggtatggctt cattcagctc cggttcccaa cgatcaaggc gagttacatg atcccccatg    4800
ttgtgcaaaa aagcggttag ctccttcggt cctccgatcg ttgtcagaag taagttggcc    4860
gcagtgttat cactcatggt tatggcagca ctgcataatt ctcttactgt catgccatcc    4920
gtaagatgct tttctgtgac tggtgagtac tcaaccaagt cattctgaga atagtgtatg    4980
cggcgaccga gttgctcttg cccggcgtca atacgggata ataccgcgcc acatagcaga    5040
actttaaaag tgctcatcat tggaaaacgt tcttcgggc gaaaactctc aaggatctta    5100
ccgctgttga gatccagttc gatgtaaccc actcgtgcac ccaactgatc ttcagcatct    5160
```

-continued

```
tttactttca ccagcgtttc tgggtgagca aaaacaggaa ggcaaaatgc cgcaaaaaag    5220
ggaataaggg cgacacggaa atgttgaata ctcatactct tccttttca atattattga    5280 agcatttatc agggttattg tctcatgagc ggatacatat ttgaatgtat ttagaaaaat    5340
aaacaaatag gggttccgcg cacatttccc cgaaaagtgc cacctgacgt ctaagaaacc    5400
attattatca tgacattaac ctataaaaat aggcgtatca cgaggccctt tcgtctcgcg    5460
cgtttcggtg atgacggtga aaacctctga cacatgcagc tcccggagac ggtcacagct    5520
tgtctgtaag cggatgccgg gagcagacaa gcccgtcagg gcgcgtcagc gggtgttggc    5580
gggtgtcggg gctggcttaa ctatgcggca tcagagcaga ttgtactgag agtgcaccat    5640
atgcggtgtg aaataccgca cagatgcgta aggagaaaat accgcatcag gcgccattcg    5700
ccattcaggc tgcgcaactg ttgggaaggg cgatcggtgc gggcctcttc gctattacgc    5760
cagctggcga aggggggatg tgctgcaagg cgattaagtt gggtaacgcc agggttttcc    5820
cagtcacgac gttgtaaaac gacggccagt gaattcg                             5857
```

<210> SEQ ID NO 296
<211> LENGTH: 6602
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 296

```
accactccct atcagtgata gagaaaagtg aactctagaa ataattttgt ttaactttaa      60
gaaggagata tacatatgaa aacactatca caggcccaat ctaaaacttc ttcacagcaa     120
ttcagcttta ccgggaactc gtctgcgaat gtaattatcg gcaatcaaaa gctgaccatt     180
aatgatgtag ctcgcgttgc ccggaatggc actttggtgt cactgacgaa caataccgac     240
attctgcaag gtattcaagc tagctgcgat tatatcaata cgccgttga atctggcgag     300 ccaatctacg gggtaacaag cggttttggt gggatggcga acgttgccat tagccgtgaa     360
caggcgagcg aacttcagac caacctcgtt tggttcctaa agacaggagc tggtaataag     420
ttacctctgg ctgacgtaag agccgcgatg ctgcttcgcg ctaatagtca catgcgcggc     480
gccagtggta tccgtcttga gcttatcaag aggatgaaa tcttcctcaa cgcgggtgtc     540
acaccatatg tttatgagtt tggtagtatc ggagccagtg gtgatcttgt tcccctgagt     600
tatattacgg gttcattgat tggtttagac ccgtcctta aagtggattt taacgggaaa     660
gaaatggacg ccccgaccgc tttacgacag cttaatctga gcccacttac tttgctccct     720
aaagaaggtc ttgccatgat gaatggcacc tctgtgatga ctggaattgc cgcgaattgt     780
gtgtatgaca cgcagatcct aacggccatt gccatgggtg ttcacgcgtt ggacattcaa     840
gccctgaatg gtacaaacca gtcgtttcat ccgtttatcc ataattcaaa accccatccg     900
ggacagcttt gggctgctga tcagatgatc tcactcctgg ccaatagtca actggttcgg     960
gacgagctcg acggcaaaca tgattatcgc gatcatgagc tcatccagga ccggtattca    1020
cttcgttgtc tcccacaata cctggggcct atcgttgatg gtatatctca aattgcgaag    1080
caaattgaaa ttgagatcaa tagcgtaacc gacaacccgc ttatcgatgt tgataatcag    1140
gcctcttatc acggtggcaa ttttctgggc cagtatgttg gtatggggat ggatcacctg    1200
cggtactata ttgggcttct ggctaaacat cttgatgtgc agattgcctt attagcttca    1260
```

-continued

```
ccagaattttt caaatggact gccgccatca ttgctcggta acagagaaag gaaagtaaat      1320
atgggcctta agggccttca gatatgtggt aactcaatca tgcccctcct gacctttat        1380 gggaactcaa ttgctgatcg ttttccgaca catgctgaac agtttaacca aaacattaac       1440
tcacagggct atacatccgc gacgttagcg cgtcggtccg tggatatctt ccagaattat       1500
gttgctatcg ctctgatgtt cggcgtacag gccgttgatt tgcgcactta taaaaaaacc      1560
ggtcactacg atgctcgggc ttgcctgtcg cctgccaccg agcggcttta tagcgccgta      1620
cgtcatgttg tgggtcagaa accgacgtcg gaccgcccct atatttggaa tgataatgaa      1680
caagggctgg atgaacacat cgcccggata tctgccgata ttgccgccgg aggtgtcatc      1740
gtccaggcgg tacaagacat acttccttgc ctgcattaag cttggcgtaa tcatggtcat      1800
agctgtttcc tgtgtgaaat tgttatccgc tcacaattcc acacaacata cgagccggaa      1860
gcataaagtg taaagcctgg ggtgcctaat gagtgagcta actcacatta attgcgttgc      1920
gctcactgcc cgctttccag tcgggaaacc tgtcgtgcca gctgcattaa tgaatcggcc      1980
aacgcgcggg gagaggcggt ttgcgtattg ggcgctcttc cgcttcctcg ctcactgact      2040
cgctgcgctc ggtcgttcgg ctgcggcgag cggtatcagc tcactcaaag gcggtagtac      2100
gggttttgct gcccgcaaac gggctgttct ggtgttgcta gtttgttatc agaatcgcag      2160
atccggcttc aggtttgccg gctgaaagcg ctatttcttc cagaattgcc atgattttt       2220 ccccacggga ggcgtcactg gctcccgtgt tgtcggcagc tttgattcga taagcagcat      2280
cgcctgtttc aggctgtcta tgtgtgactg ttgagctgta acaagttgtc tcaggtgttc      2340
aatttcatgt tctagttgct ttgttttact ggtttcacct gttctattag gtgttacatg      2400
ctgttcatct gttacattgt cgatctgttc atggtgaaca gctttaaatg caccaaaaac      2460
tcgtaaaagc tctgatgtat ctatcttttt tacaccgttt tcatctgtgc atatggacag      2520
ttttcccttt gatatctaac ggtgaacagt tgttctactt tgtttgtta gtcttgatgc       2580 ttcactgata gatacaagag ccataagaac ctcagatcct tccgtattta gccagtatgt      2640
tctctagtgt ggttcgttgt ttttgcgtga gccatgagaa cgaaccattg agatcatgct      2700
tactttgcat gtcactcaaa aattttgcct caaaactggt gagctgaatt tttgcagtta      2760
aagcatcgtg tagtgttttt cttagtccgt tacgtaggta ggaatctgat gtaatggttg      2820
ttggtatttt gtcaccattc attttatct ggttgttctc aagttcggtt acgagatcca       2880
tttgtctatc tagttcaact tggaaaatca acgtatcagt cgggcggcct cgcttatcaa      2940
ccaccaattt catattgctg taagtgttta aatctttact tattggtttc aaaacccatt      3000
ggttaagcct tttaaactca tggtagttat tttcaagcat taacatgaac ttaaattcat      3060
caaggctaat ctctatattt gccttgtgag ttttcttttg tgttagttct tttaataacc      3120
actcataaat cctcatagag tatttgtttt caaaagactt aacatgttcc agattatatt      3180
ttatgaattt tttaactgg aaaagataag gcaatatctc ttcactaaaa actaattcta      3240
atttttcgct tgagaacttg gcatagtttg tccactggaa atctcaaag ccttaacca       3300 aaggattcct gatttccaca gttctcgtca tcagctctct ggttgcttta gctaatacac      3360
cataagcatt ttccctactg atgttcatca tctgagcgta ttggttataa gtgaacgata      3420
ccgtccgttc tttccttgta gggttttcaa tcgtggggtt gagtagtgcc acacagcata      3480
aaattagctt ggtttcatgc tccgttaagt catagcgact aatcgctagt tcatttgctt      3540
tgaaaacaac taattcagac atacatctca attggtctag gtgattttaa tcactatacc      3600
aattgagatg ggctagtcaa tgataattac tagtcctttt cctttgagtt gtgggtatct      3660
```

```
gtaaattctg ctagaccttt gctggaaaac ttgtaaattc tgctagaccc tctgtaaatt    3720
ccgctagacc tttgtgtgtt ttttttgttt atattcaagt ggttataatt tatagaataa    3780
agaaagaata aaaaagata aaaagaatag atcccagccc tgtgtataac tcactacttt    3840
agtcagttcc gcagtattac aaaaggatgt cgcaaacgct gtttgctcct ctacaaaaca    3900
gaccttaaaa ccctaaaggc ttaagtagca ccctcgcaag ctcgggcaaa tcgctgaata    3960
ttccttttgt ctccgaccat caggcacctg agtcgctgtc tttttcgtga cattcagttc    4020
gctgcgctca cggctctggc agtgaatggg ggtaaatggc actacaggcg cctttatgg     4080 attcatgcaa ggaaactacc cataatacaa gaaaagcccg tcacgggctt ctcagggcgt    4140
tttatggcgg gtctgctatg tggtgctatc tgactttttg ctgttcagca gttcctgccc    4200
tctgattttc cagtctgacc acttcggatt atcccgtgac aggtcattca gactggctaa    4260
tgcacccagt aaggcagcgg tatcatcaac aggcttaccc gtcttactgt cttttctacg    4320
gggtctgacg ctcagtggaa cgaaaactca cgttaaggga ttttggtcat gagattatca    4380 aaaggatct tcacctagat cctttaaat taaaaatgaa gttttaaatc aatctaaagt      4440
atatatgagt aaacttggtc tgacagttac caatgcttaa tcagtgaggc acctatctca    4500
gcgatctgtc tatttcgttc atccatagtt gcctgactcc ccgtcgtgta gataactacg    4560
atacgggagg gcttaccatc tggccccagt gctgcaatga taccgcgaga cccacgctca    4620
ccggctccag atttatcagc aataaaccag ccagccggaa gggccgagcg cagaagtggt    4680
cctgcaactt tatccgcctc catccagtct attaattgtt gccgggaagc tagagtaagt    4740
agttcgccag ttaatagttt gcgcaacgtt gttgccattg ctacaggcat cgtggtgtca    4800
cgctcgtcgt ttggtatggc ttcattcagc tccggttccc aacgatcaag gcgagttaca    4860
tgatccccca tgttgtgcaa aaaagcggtt agctccttcg gtcctccgat cgttgtcaga    4920
agtaagttgg ccgcagtgtt atcactcatg gttatggcag cactgcataa ttctcttact    4980
gtcatgccat ccgtaagatg cttttctgtg actggtgagt actcaaccaa gtcattctga    5040
gaatagtgta tgcggcgacc gagttgctct tgcccggcgt caatacggga taataccgcg    5100
ccacatagca gaactttaaa agtgctcatc attggaaaac gttcttcggg gcgaaaactc    5160
tcaaggatct taccgctgtt gagatccagt tcgatgtaac ccactcgtgc acccaactga    5220
tcttcagcat cttttacttt caccagcgtt tctgggtgag caaaaacagg aaggcaaaat    5280
gccgcaaaaa agggaataag ggcgacacgg aaatgttgaa tactcatact cttccttttt    5340
caatattatt gaagcattta tcagggttat tgtctcatga gcggatacat atttgaatgt    5400
atttagaaaa ataaacaaat aggggttccg cgcacatttc cccgaaaagt gccacctgac    5460
gtctaagaaa ccattattat catgacatta acctataaaa ataggcgtat cacgaggccc    5520
tttcgtctcg cgcgtttcgg tgatgacggt gaaaacctct gacacatgca gctcccggag    5580
acggtcacag cttgtctgta agcggatgcc gggagcagac aagcccgtca gggcgcgtca    5640
gcgggtgttg gcgggtgtcg ggctggctt aactatgcgg catcagagca gattgtactg     5700
agagtgcacc atatgcggtg tgaaataccg cacagatgcg taaggagaaa ataccgcatc    5760
aggcgccatt cgccattcag gctgcgcaac tgttgggaag ggcgatcggt gcgggcctct    5820
tcgctattac gccagctggc gaaaggggga tgtgctgcaa ggcgattaag ttgggtaacg    5880
ccagggtttt cccagtcacg acgttgtaaa acgacggcca gtgaattcgt taagacccac    5940
tttcacattt aagttgtttt tctaatccgc atatgatcaa ttcaaggccg aataagaagg    6000
```

```
ctggctctgc accttggtga tcaaataatt cgatagcttg tcgtaataat ggcggcatac    6060
tatcagtagt aggtgtttcc ctttcttctt tagcgacttg atgctcttga tcttccaata    6120
cgcaacctaa agtaaaatgc cccacagcgc tgagtgcata taatgcattc tctagtgaaa    6180
aaccttgttg gcataaaaag gctaattgat tttcgagagt ttcatactgt ttttctgtag    6240
gccgtgtacc taaatgtact tttgctccat cgcgatgact tagtaaagca catctaaaac    6300
ttttagcgtt attacgtaaa aaatcttgcc agctttcccc ttctaaaggg caaaagtgag    6360
tatggtgcct atctaacatc tcaatggcta aggcgtcgag caaagcccgc ttatttttta    6420
catgccaata caatgtaggc tgctctacac ctagcttctg ggcgagttta cgggttgtta    6480
aaccttcgat tccgacctca ttaagcagct ctaatgcgct gttaatcact ttacttttat    6540
ctaatctaga catcattaat tcctaatttt tgttgacact ctatcattga tagagttatt    6600
tt                                                                   6602
```

<210> SEQ ID NO 297
<211> LENGTH: 6497
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 297

```
accactccct atcagtgata gagaaaagtg aactctagaa ataatttttgt ttaactttaa     60 gaaggagata tacatatgaa agctaaagat gttcagccaa ccattattat taataaaaat    120
ggccttatct ctttggaaga tatctatgac attgcgataa acaaaaaaaa agtagaaata    180
tcaacggaga tcactgaact tttgacgcat ggtcgtgaaa aattagagga aaaattaaat    240
tcaggagagg ttatatatgg aatcaataca ggatttggag ggaatgccaa tttagttgtg    300
ccatttgaga aaatcgcaga gcatcagcaa aatctgttaa cttttctttc tgctggtact    360
ggggactata tgtccaaacc ttgtattaaa gcgtcacaat ttactatgtt actttctgtt    420
tgcaaaggtt ggtctgcaac cagaccaatt gtcgctcaag caattgttga tcatattaat    480
catgacattg ttcctctggt tcctcgctat ggctcagtgg gtgcaagcgg tgatttaatt    540
cctttatctt atattgcacg agcattatgt ggtatcggca agttttatta tatgggcgca    600
gaaattgacg ctgctgaagc aattaaacgt gcagggttga caccattatc gttaaaagcc    660
aaagaaggtc ttgctctgat taacggcacc cgggtaatgt caggaatcag tgcaatcacc    720
gtcattaaac tggaaaaact atttaaagcc tcaatttctg cgattgccct tgctgttgaa    780
gcattacttg catctcatga acattatgat gcccggattc aacaagtaaa aaatcatcct    840
ggtcaaaacg cggtggcaag tgcattgcgt aatttattgg caggttcaac gcaggttaat    900
ctattatctg ggttaaagaa acaagccaat aaagcttgtc gtcatcaaga aattacccaa    960
ctaaatgata ccttacagga gtttattcca attcgctgtg caccacaagt attaggtata   1020
gtgccagaat ctttagctac cgctcggaaa atattggaac gggaagttat ctcagctaat   1080
gataatccat tgatagatcc agaaaatggc gatgttctac acggtggaaa ttttatgggg   1140
caatatgtcg cccgaacaat ggatgcatta aaactggata ttgctttaat tgccaatcat   1200
cttcacgcca ttgtggctct tatgatggat aaccgtttct ctcgtggatt acctaattca   1260
ctgagtccga caccccggcat gtatcaaggt tttaaaggcg tccaactttc tcaaaccgct   1320
ttagttgctg caattcgcca tgattgtgct gcatcaggta ttcatacccct cgccacagaa   1380
```

```
caatacaatc aagatattgt cagtttaggt ctgcatgccg ctcaagatgt tttagagatg    1440
gagcagaaat tacgcaatat tgtttcaatg acaattctgg tagtttgtca ggccattcat    1500
cttcgcggca atattagtga aattgcgcct gaaactgcta aattttacca tgcagtacgc    1560
gaaatcagtt ctcctttgat cactgatcgt gcgttggatg aagatataat ccgcattgcg    1620
gatgcaatta ttaatgatca acttcctctg ccagaaatca tgctggaaga ataagcttgg    1680
cgtaatcatg gtcatagctg tttcctgtgt gaaattgtta tccgctcaca attccacaca    1740
acatacgagc cggaagcata agtgtaaag cctggggtgc ctaatgagtg agctaactca    1800
cattaattgc gttgcgctca ctgcccgctt tccagtcggg aaacctgtcg tgccagctgc    1860
attaatgaat cggccaacgc gcggggagag gcggtttgcg tattgggcgc tcttccgctt    1920
cctcgctcac tgactcgctg cgctcggtcg ttcggctgcg gcgagcggta tcagctcact    1980
caaaggcggt agtacgggtt ttgctgcccg caaacgggct gttctggtgt tgctagtttg    2040
ttatcagaat cgcagatccg gcttcaggtt tgccggctga aagcgctatt tcttccagaa    2100
ttgccatgat ttttccccca cgggaggcgt cactggctcc cgtgttgtcg gcagctttga    2160
ttcgataagc agcatcgcct gtttcaggct gtctatgtgt gactgttgag ctgtaacaag    2220
ttgtctcagg tgttcaattt catgttctag ttgctttgtt ttactggttt cacctgttct    2280
attaggtgtt acatgctgtt catctgttac attgtcgatc tgttcatggt gaacagcttt    2340
aaatgcacca aaaactcgta aaagctctga tgtatctatc ttttttacac cgttttcatc    2400
tgtgcatatg gacagttttc cctttgatat ctaacggtga acagttgttc tacttttgtt    2460
tgttagtctt gatgcttcac tgatagatac aagagccata agaacctcag atccttccgt    2520
atttagccag tatgttctct agtgtggttc gttgttttg cgtgagccat gagaacgaac    2580
cattgagatc atgcttactt tgcatgtcac tcaaaaattt tgcctcaaaa ctggtgagct    2640 gaattttgc agttaaagca tcgtgtagtg ttttttcttag tccgttacgt aggtaggaat    2700
ctgatgtaat ggttgttggt attttgtcac cattcatttt tatctggttg ttctcaagtt    2760
cggttacgag atccattttgt ctatctagtt caacttggaa aatcaacgta tcagtcgggc    2820
ggcctcgctt atcaaccacc aatttcatat tgctgtaagt gtttaaatct ttacttattg    2880
gtttcaaaac ccattggtta agccttttaa actcatggta gttattttca agcattaaca    2940
tgaacttaaa ttcatcaagg ctaatctcta tatttgcctt gtgagttttc ttttgtgtta    3000
gttcttttaa taaccactca taaatcctca tagagtattt gttttcaaaa gacttaacat    3060
gttccagatt atattttatg aatttttta actggaaaag ataaggcaat atctcttcac    3120
taaaaactaa ttctaatttt tcgcttgaga acttggcata gtttgtccac tggaaaatct    3180
caaagccttt aaccaaagga ttcctgattt ccacagttct cgtcatcagc tctctggttg    3240
ctttagctaa tacaccataa gcattttccc tactgatgtt catcatctga gcgtattggt    3300
tataagtgaa cgataccgtc cgttctttcc ttgtagggtt ttcaatcgtg gggttgagta    3360
gtgccacaca gcataaaatt agcttggttt catgctccgt taagtcatag cgactaatcg    3420
ctagttcatt tgcttgaaa acaactaatt cagacataca tctcaattgg tctaggtgat    3480
tttaatcact ataccaattg agatgggcta gtcaatgata attactagtc cttttccttt    3540
gagttgtggg tatctgtaaa ttctgctaga ccttgtctgg aaaacttgta aattctgcta    3600
gaccctctgt aaattccgct agacctttgt gtgttttttt tgtttatatt caagtggtta    3660
taatttatag aataagaaa gaataaaaaa agataaaag aatagatccc agccctgtgt    3720
```

```
ataactcact actttagtca gttccgcagt attacaaaag gatgtcgcaa acgctgtttg  3780
ctcctctaca aaacagacct taaaacccta aaggcttaag tagcaccctc gcaagctcgg  3840
gcaaatcgct gaatattcct tttgtctccg accatcaggc acctgagtcg ctgtcttttt  3900
cgtgacattc agttcgctgc gctcacggct ctggcagtga atgggggtaa atggcactac  3960
aggcgccttt tatggattca tgcaaggaaa ctacccataa tacaagaaaa gcccgtcacg  4020
ggcttctcag ggcgttttat ggcgggtctg ctatgtggtg ctatctgact ttttgctgtt  4080
cagcagttcc tgccctctga ttttccagtc tgaccacttc ggattatccc gtgacaggtc  4140
attcagactg gctaatgcac ccagtaaggc agcggtatca tcaacaggct tacccgtctt  4200
actgtctttt ctacggggtc tgacgctcag tggaacgaaa actcacgtta agggattttg  4260
gtcatgagat tatcaaaaag gatcttcacc tagatccttt taaattaaaa atgaagtttt  4320
aaatcaatct aaagtatata tgagtaaact tggtctgaca gttaccaatg cttaatcagt  4380
gaggcaccta tctcagcgat ctgtctattt cgttcatcca tagttgcctg actccccgtc  4440
gtgtagataa ctacgatacg ggagggctta ccatctggcc ccagtgctgc aatgataccg  4500
cgagacccac gctcaccggc tccagattta tcagcaataa accagccagc cggaagggcc  4560
gagcgcagaa gtggtcctgc aactttatcc gcctccatcc agtctattaa ttgttgccgg  4620
gaagctagag taagtagttc gccagttaat agtttgcgca acgttgttgc cattgctaca  4680
ggcatcgtgg tgtcacgctc gtcgtttggt atggcttcat tcagctccgg ttcccaacga  4740
tcaaggcgag ttacatgatc ccccatgttg tgcaaaaaag cggttagctc cttcggtcct  4800
ccgatcgttg tcagaagtaa gttggccgca gtgttatcac tcatggttat ggcagcactg  4860
cataattctc ttactgtcat gccatccgta agatgctttt ctgtgactgg tgagtactca  4920
accaagtcat tctgagaata gtgtatgcgg cgaccgagtt gctcttgccc ggcgtcaata  4980
cgggataata ccgcgccaca tagcagaact ttaaaagtgc tcatcattgg aaaacgttct  5040
tcggggcgaa aactctcaag gatcttaccg ctgttgagat ccagttcgat gtaacccact  5100
cgtgcaccca actgatcttc agcatctttt actttcacca gcgtttctgg gtgagcaaaa  5160
acaggaaggc aaaatgccgc aaaaaaggga ataagggcga cacggaaatg ttgaatactc  5220
atactcttcc ttttttcaata ttattgaagc atttatcagg gttattgtct catgagcgga  5280
tacatatttg aatgtatttta gaaaaataaa caaatagggg ttccgcgcac atttccccga  5340
aaagtgccac ctgacgtcta agaaaccatt attatcatga cattaaccta taaaaatagg  5400
cgtatcacga ggccctttcg tctcgcgcgt ttcggtgatg acggtgaaaa cctctgacac  5460
atgcagctcc cggagacggt cacagcttgt ctgtaagcgg atgccgggag cagacaagcc  5520
cgtcagggcg cgtcagcggg tgttggcggg tgtcggggct ggcttaacta tgcggcatca  5580
gagcagattg tactgagagt gcaccatatg cggtgtgaaa taccgcacag atgcgtaagg  5640
agaaaatacc gcatcaggcg ccattcgcca ttcaggctgc gcaactgttg ggaagggcga  5700
tcggtgcggg cctcttcgct attacgccag ctggcgaaag gggatgtgc tgcaaggcga  5760 ttaagttggg taacgccagg gttttcccag tcacgacgtt gtaaaacgac ggccagtgaa  5820
ttcgttaaga cccactttca catttaagtt gttttttctaa tccgcatatg atcaattcaa  5880
ggccgaataa gaaggctggc tctgcacctt ggtgatcaaa taattcgata gcttgtcgta  5940
ataatggcgg catactatca gtagtaggtg tttcccttc ttctttagcg acttgatgct  6000
cttgatcttc caatacgcaa cctaaagtaa aatgccccac agcgctgagt gcatataatg  6060
cattctctag tgaaaaacct tgttggcata aaaaggctaa ttgattttcg agagtttcat  6120
```

```
actgttttc tgtaggccgt gtacctaaat gtacttttgc tccatcgcga tgacttagta    6180
aagcacatct aaaacttta gcgttattac gtaaaaaatc ttgccagctt tccccttcta    6240
aagggcaaaa gtgagtatgg tgcctatcta acatctcaat ggctaaggcg tcgagcaaag    6300
cccgcttatt ttttacatgc caatacaatg taggctgctc tacacctagc ttctgggcga    6360
gtttacgggt tgttaaacct tcgattccga cctcattaag cagctctaat gcgctgttaa    6420
tcactttact tttatctaat ctagacatca ttaattccta attttgttg acactctatc     6480 attgatagag ttatttt                                                    6497
```

<210> SEQ ID NO 298
<211> LENGTH: 2137
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 298

```
ccagtgaatt cgttaagacc cactttcaca tttaagttgt ttttctaatc cgcatatgat      60
caattcaagg ccgaataaga aggctggctc tgcaccttgg tgatcaaata attcgatagc     120
ttgtcgtaat aatggcggca tactatcagt agtaggtgtt tccctttctt ctttagcgac     180
ttgatgctct tgatcttcca atacgcaacc taaagtaaaa tgccccacag cgctgagtgc     240
atataatgca ttctctagtg aaaaaccttg ttggcataaa aaggctaatt gattttcgag     300
agtttcatac tgttttctg taggccgtgt acctaaatgt acttttgctc catcgcgatg     360
acttagtaaa gcacatctaa aacttttagc gttattacgt aaaaaatctt gccagctttc     420
cccttctaaa gggcaaaagt gagtatggtg cctatctaac atctcaatgg ctaaggcgtc     480
gagcaaagcc cgcttatttt ttacatgcca atacaatgta ggctgctcta cacctagctt     540
ctgggcgagt ttacggggttg ttaaaccttc gattccgacc tcattaagca gctctaatgc     600
gctgttaatc actttacttt tatctaatct agacatcatt aattcctaat tttgttgac     660 actctatcat tgatagagtt attttaccac tccctatcag tgatagagaa agtgaactc     720 tagaaataat tttgtttaac tttaagaagg agatatacat atgaaaaacg cgtcaaccgt     780
atcggaagat actgcgtcga atcaagagcc gacgcttcat cgcggattac ataaccgtca     840
tattcaactg attgcgttgg gtggcgcaat tggtactggt ctgtttcttg gcattggccc     900
ggcgattcag atggcgggtc cggctgtatt gctgggctac ggcgtcgccg ggatcatcgc     960
tttcctgatt atgcgccagc ttggcgaaat ggtggttgag gagccggtat ccggttcatt    1020
tgcccacttt gcctataaat actggggacc gtttgcgggc ttcctctctg ctggaacta    1080 ctgggtaatg ttcgtgctgg tgggaatggc agagctgacc gctgcgggca tctatatgca    1140
gtactggttc ccggatgttc caacgtggat ttggctgcc gccttcttta ttatcatcaa    1200
cgccgttaac ctggtgaacg tgcgcttata tggcgaaacc gagttctggt ttgcgttgat    1260
taaagtgctg gcaatcatcg gtatgatcgg ctttggcctg tggctgctgt tttctggtca    1320
cggcggcgag aaagccagta tcgacaacct ctggcgctac ggtggtttct tcgccaccgg    1380
ctggaatggg ctgatttttgt cgctggcggt aattatgttc tccttcggcg gtctggagct    1440
gattgggatt actgccgctg aagcgcgcga tccggaaaaa agcattccaa aagcggtaaa    1500
tcaggtggtg tatcgcatcc tgctgttta catcggttca ctggtggttt actggcgct     1560
```

```
ctatccgtgg gtggaagtga atccaacag tagcccgttt gtgatgattt tccataatct    1620
cgacagcaac gtggtagctt ctgcgctgaa cttcgtcatt ctggtagcat cgctgtcagt    1680
gtataacagc ggggtttact ctaacagccg catgctgttt ggcctttctg tgcagggtaa    1740
tgcgccgaag tttttgactc gcgtcagccg tcgcggtgtg ccgattaact cgctgatgct    1800
ttccggagcg atcacttcgc tggtggtgtt aatcaactat ctgctgccgc aaaaagcgtt    1860
tggtctgctg atggcgctgg tggtagcaac gctgctgttg aactggatta tgatctgtct    1920
ggcgcatctg cgttttcgtg cagcgatgcg acgtcagggg cgtgaaacac agtttaaggc    1980
gctgctctat ccgttcggca actatctctg cattgccttc ctcggcatga tttttgctgct    2040 gatgtgcacg atggatgata tgcgcttgtc agcgatcctg ctgccggtgt ggattgtatt    2100
cctgtttatg gcatttaaaa cgctgcgtcg gaaataa                             2137
```

<210> SEQ ID NO 299
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Gly Gly Gly Gly Ser
1               5

<210> SEQ ID NO 300
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Lys Glu Ser Gly Ser Val Ser Ser Glu Gln Leu Ala Gln Phe Arg Ser
1               5                   10                  15

Leu Asp

<210> SEQ ID NO 301
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Glu Gly Lys Ser Ser Gly Ser Gly Ser Glu Ser Lys Ser Thr
1               5                   10

<210> SEQ ID NO 302
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

```
Gly Gly Gly Gly Gly Gly Gly Gly
1               5

<210> SEQ ID NO 303
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Gly Ser Ala Gly Ser Ala Ala Gly Ser Gly Glu Phe
1               5                   10

<210> SEQ ID NO 304
<211> LENGTH: 22
<212> TYPE: DNA
<213> ORGANISM: Escherichia coli

<400> SEQUENCE: 304
ggaattgtga gcgctcacaa tt                                                22
```

BACTERIA FOR THE TREATMENT OF DISORDERS

The instant application is a national stage application under 35 U.S.C. § 371 of international application number PCT/US2018/038840, filed Jun. 21, 2018, which designated the U.S. and hereby incorporates by reference U.S. Provisional Application No. 62/523,225, filed Jun. 21, 2017; U.S. Provisional Application No. 62/552,785, filed Aug. 31, 2017; U.S. Provisional Application No. 62/552,829, filed Aug. 31, 2017; U.S. Provisional Application No. 62/614,213, filed Jan. 5, 2018; U.S. Provisional Application No. 62/624,299, filed Jan. 31, 2018, and U.S. Provisional Application No. 62/523,202, filed Jun. 21, 2017, the entire contents of each of which are expressly incorporated herein by reference in their respective entireties.

A growing body of scientific evidence suggests that probiotic bacteria are beneficial in the treatment or prevention of various diseases or disorders associated with the gut, including, for example, gastrointestinal disorders such as Crohn's disease and inflammatory bowel syndrome. More recently, genetically engineered bacteria have emerged as a potential new therapeutic treatment modality for gastrointestinal diseases and have also opened the field of bacterial therapies to a large number of other indications, including metabolic diseases, inflammatory diseases, and cancer. One benefit of genetically engineered bacteria is the ability to specifically target one or more disease mechanisms. For example, for gastrointestinal disorders, bacteria can be engineered to contain genes for the expression of anti-inflammatory agents or agents that aid in the healing of a disrupted gut-barrier, such as the short chain fatty acid butyrate, e.g., as described in International Patent Publication WO2016141108. Genetically engineered bacteria may also be considered as a treatment modality for various metabolic disorders, including but not limited to rare metabolic disorders arising from inborn errors in metabolism or IEMs. For example, as described in International Patent Publication WO2016090343, bacteria have been genetically modified to treat phenylketonuria (PKU) by expressing one or more enzymes which metabolize phenylalanine and thereby consuming excess phenylalanine within the gastrointestinal tract.

Bacteriophage are the most common biological entity in the world, and it is well documented that a majority of bacterial species, both gram positive and gram negative, contain one or more DNA bacteriophages which are integrated as so-called prophages in the bacterial chromosome (Clokie et al, Phages in Nature, Bacteriophage. 2011 January-February; 1(1): 31-45).

DNA phages can be lytic or temperate. Lytic phages infect bacterial cells and then program the synthesis of progeny phages, which are then released from the lysed cell. Conversely, temperate DNA phages establish a stable relationship with their host bacteria in which the integrated phage DNA, i.e., the prophage, is replicated in concert with the host's genome, and any host-damaging phage genes are not expressed. However, bacteriophage particles can be released from cells containing an intact prophage by a process called induction, during which prophage genes required for lytic growth are turned on and progeny phage particles are produced and released from the cell through lysis of the cell (reviewed in Casjens, Prophages and bacterial genomics: what have we learned so far?; Mol Microbiol. 2003 July; 49(2):277-300). In some cases, induction can occur spontaneously and randomly in a small or large fraction of the bacteria that harbor the prophage. In other cases, specific, often undefined, environmental signals can cause simultaneous induction of a particular prophage in many cells, causing death of the bacterial cells.

Not all prophages have the ability to undergo a lytic cycle. Non-functional, i.e., defective or cryptic prophages can accrue to a high level of abundancy in many bacteria as a result of mutational decay and/or the loss of one or more genes essential to the lytic cycle over thousands of bacterial replication cycles (Bobay et al., Pervasive domestication of defective prophages by bacteria, Proc Natl Acad Sci USA. 2014 Aug. 19; 111(33): 12127-12132, and references therein).

SUMMARY

In some embodiments, the disclosure provides a bacterium comprising one or more phage genome(s), wherein one or more of the phage genomes are defective. In some embodiments, the disclosure provides a bacterium comprising one or more phage genome(s), wherein one or more of the phage genomes are defective such that lytic phage is not produced. In some embodiments, the disclosure provides a bacterium comprising one or more phage genome(s), wherein one or more of the phage genomes are defective in that one or more phage genes are not expressed. In some embodiments, the disclosure provides a bacterium comprising one or more phage genome(s), wherein one or more phage genes in the one or more phage genome(s) comprise one or more mutations. In some embodiments, the one or more phage genome(s) are present in the natural state of the probiotic bacterium. In some embodiments, the bacteria encode one or more lysogenic phage(s). In some embodiments, the bacteria encode one or more defective or cryptic phage(s) or satellite phage(s). In some embodiments, the bacteria encode one or more tailiocins or gene transfer agents.

In some of the embodiments of the disclosure, one or more of the phage genomes are mutated. Such mutations may include one or more deletion(s) of a part of or the complete sequence of one or more phage genes. Alternatively, the mutations may include one or more insertion(s) of one or more nucleotides into one or more phage genes. In another example, the mutations may include one or more substitution(s) of a part of or the complete sequence of one or more phage genes. In another example, the mutations include one or more inversion(s) of a part of or the complete sequence of one or more phage genes in the phage genome. Additionally, the mutations may include any combination of one or more deletions, insertions, substitutions or inversions. In certain embodiments, the one or more mutations reduce or prevent the production and release of phage particles from the bacterium relative to the same bacterium not having the one or more targeted mutations in the one or more phage genomes. In some embodiments, the bacterium is a probiotic bacterium. Non-limiting examples of such probiotic bacteria include *Bacteroides, Bifidobacterium, Clostridium, Escherichia, Lactobacillus,* and *Lactococcus*. In some embodiments, the bacterium is *Escherichia coli* strain Nissle. In some embodiments, the phage genome which is mutated is *E. coli* Nissle Phage 1 genome, the *E. coli* Nissle Phage 2 genome and/or the *E. coli* Nissle Phage 3 genome. In one embodiment, the mutated phage genome is the *E. coli* Nissle Phage 3 genome. In one embodiment, the mutations are located in or comprise one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the mutations, e.g., one or more deletions, are located in or comprise one or more genes selected from ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. pharmaceutically acceptable composition comprising the bacterium disclosed herein and a pharmaceutically acceptable carrier.

In some embodiments, the bacteria further comprise one or more circuits for the expression of one or more effector molecules.

In some embodiments, the disclosure relates to compositions and therapeutic methods for reducing hyperphenylalaninemia. In some embodiments, the compositions comprise a genetically engineered bacterium that is capable of expressing a phenylalanine metabolizing enzyme (PME). See, e.g., WO2017087580 A1, the contents of which are herein incorporated by reference in entirety. Phenylalanine is an essential amino acid primarily found in dietary protein. Typically, a small amount is utilized for protein synthesis, and the remainder is hydroxylated to tyrosine in an enzymatic pathway that requires phenylalanine hydroxylase (PAH) and the cofactor tetrahydrobiopterin. Hyperphenylalaninemia is a group of diseases associated with excess levels of phenylalanine, which can be toxic and cause brain damage. Primary hyperphenylalaninemia is caused by deficiencies in PAH activity that result from mutations in the PAH gene and/or a block in cofactor metabolism.

PKU is a severe form of hyperphenylalaninemia caused by mutations in the PAH gene. PKU is an autosomal recessive genetic disease that ranks as the most common inborn error of metabolism worldwide (1 in 3,000 births), and affects approximately 13,000 patients in the United States. More than 400 different PAH gene mutations have been identified (Hoeks et al., 2009). A buildup of phenylalanine (phe) in the blood can cause profound damage to the central nervous system in children and adults. If untreated in newborns, PKU can cause irreversible brain damage. Treatment for PKU currently involves complete exclusion of phenylalanine from the diet. Most natural sources of protein contain phenylalanine which is an essential amino acid and necessary for growth. In patients with PKU, this means that they rely on medical foods and phe-free protein supplements together with amino acid supplements to provide just enough phenylalanine for growth. This diet is difficult for patients and has an impact on quality of life.

Current PKU therapies require substantially modified diets consisting of protein restriction. Treatment from birth generally reduces brain damage and mental retardation (Hoeks et al., 2009; Sarkissian et al., 1999). However, the protein-restricted diet must be carefully monitored, and essential amino acids as well as vitamins must be supplemented in the diet. Furthermore, access to low protein foods is a challenge as they are more costly than their higher protein, nonmodified counterparts (Vockley et al., 2014). In children with PKU, growth retardation is common on a low-phenylalanine diet (Dobbelaere et al., 2003). In adulthood, new problems such as osteoporosis, maternal PKU, and vitamin deficiencies may occur (Hoeks et al., 2009). Excess levels of phenylalanine in the blood, which can freely penetrate the blood-brain barrier, can also lead to neurological impairment, behavioral problems (e.g., irritability, fatigue), and/or physical symptoms (e.g., convulsions, skin rashes, musty body odor). International guidelines recommend lifelong dietary phenylalanine restriction, which is widely regarded as difficult and unrealistic (Sarkissian et al., 1999), and "continued efforts are needed to overcome the biggest challenge to living with PKU—lifelong adherence to the low-phe diet" (Macleod et al., 2010).

In a subset of patients with residual PAH activity, oral administration of the cofactor tetrahydrobiopterin (also referred to as THB, BH4, Kuvan, or sapropterin) may be used together with dietary restriction to lower blood phenylalanine levels. However, cofactor therapy is costly and only suitable for mild forms of phenylketonuria. The annual cost of Kuvan, for example, may be as much as $57,000 per patient. Additionally, the side effects of Kuvan can include gastritis and severe allergic reactions (e.g., wheezing, light-headedness, nausea, flushing of the skin).

The enzyme phenylalanine ammonia lyase (PAL) is capable of metabolizing phenylalanine to non-toxic levels of ammonia and transcinnamic acid. Unlike PAH, PAL does not require THB cofactor activity in order to metabolize phenylalanine. Studies of oral enzyme therapy using PAL have been conducted, but "human and even the animal studies were not continued because PAL was not available in sufficient amounts at reasonable cost" (Sarkissian et al., 1999). A pegylated form of recombinant PAL (PEG-PAL) is also in development as an injectable form of treatment. However, most subjects dosed with PEG-PAL have suffered from injection site reactions and/or developed antibodies to this therapeutic enzyme (Longo et al., 2014). Thus, there is significant unmet need for effective, reliable, and/or long-term treatment for diseases associated with hyperphenylalaninemia, including PKU. There is an unmet need for a treatment that will control blood Phe levels in patients while allowing consumption of more natural protein.

In some embodiments, the disclosure provides genetically engineered bacteria that encode and express phenylalanine ammonia lyase and/or phenylalanine hydroxylase and/or L-aminoacid deaminase and are capable of reducing hyperphenylalaninemia. The enzyme phenylalanine ammonia lyase (PAL) is capable of metabolizing phenylalanine to non-toxic levels of ammonia and transcinnamic acid. Unlike PAH, PAL does not require THB cofactor activity in order to metabolize phenylalanine. L-amino acid deaminase (LAAD) catalyzes oxidative deamination of phenylalanine to generate phenylpyruvate, and trace amounts of ammonia and hydrogen peroxide. Phenylpyruvic acid (PPA) is widely used in the pharmaceutical, food, and chemical industries, and PPA is the starting material for the synthesis of D-phenylalanine, a raw intermediate in the production of many chiral drugs and food additives. LAAD has therefore been studied in the context of industrial PPA production (Hou et al. 2015, Appl Microbiol Biotechnol. 2015 October; 99(20): 8391-402; "Production of phenylpyruvic acid from L-phenylalanine using an L-amino acid deaminase from *Proteus mirabilis*: comparison of enzymatic and whole-cell biotransformation approaches"). Phenylpyruvate is unable to cross the blood brain barrier (Steele, Fed Proc. 1986 June; 45(7): 2060-4; "Blood-brain barrier transport of the alpha-keto acid analogs of amino acids." indicating that this conversion is useful in controlling the neurological phenotypes of PKU.

In certain aspects, the disclosure relates to genetically engineered bacteria that are capable of reducing hyperphenylalaninemia in a mammal. In certain aspects, the compositions and methods disclosed herein may be used for treating diseases associated with hyperphenylalaninemia, e.g., phenylketonuria. In certain embodiments, the genetically engineered bacteria are non-pathogenic and may be introduced into the gut in order to reduce toxic levels of phenylalanine. In certain embodiments, the phenylalanine ammonia lyase and/or phenylalanine hydroxylase and/or L-aminoacid deaminase is stably produced by the genetically engineered bacteria, and/or the genetically engineered bacteria are stably maintained in vivo and/or in vitro. In certain embodiments, the genetically engineered bacteria further comprise a phenylalanine transporter gene to increase their uptake of phenylalanine. The invention also provides pharmaceutical compositions comprising the genetically engineered bacteria, and methods of modulating and treating disorders associated with hyperphenylalaninemia.

The engineered bacteria may also contain one or more gene sequences relating to bio-safety and/or bio-containment, e.g., a kill-switch, gene guard system, and/or auxotrophy. In some embodiments, the engineered bacteria may contain an antibiotic resistance gene. The expression of any these gene sequence(s) may be regulated using a variety of promoter systems, such as any of the promoter systems disclosed herein, which promoter system may involve use of the same promoter to regulate one or more different genes, may involve use of a different copy of the same promoter to regulate different genes, and/or may involve the use of different promoters used in combination to regulate the expression of different genes. The use of different regulatory or promoter systems to control gene expression provides flexibility (e.g., the ability to differentially control gene expression under different environmental conditions and/or the ability to differentially control gene expression temporally) and also provides the ability to "fine-tune" gene expression, any or all of which regulation may serve to optimize gene expression and/or growth of the bacteria.

In some embodiments, the bacteria are capable of expressing any one or more effector molecules in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the circuits are present on one or more plasmids (e.g., high copy or low copy) or are integrated into one or more sites in the bacterial chromosome. Also, in some embodiments, the genetically engineered bacteria further comprise one or more of the following: (1) one or more auxotrophies, such as any auxotrophies known in the art and provided herein, e.g., thyA or dapB auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits. Compositions of the bacteria and methods for the treatment, prevention, or management of one or more diseases or disorders are also provided.

BRIEF DESCRIPTION OF THE FIGURES

FIG. 1B depicts a table describing 5 putative prophage in the Nissle genome (3 intact, 1 incomplete, and 1 questionable) according to PHASTER scoring.

FIG. 3 depicts a schematic showing 1 of 3 high-scoring phage in Nissle using the Phast tool, referred to herein as "Phage 2", and which contains all major components of a phage. Putative genes are labeled Hyp=Hypothetical, PLP=other phage like protein, Oth=Other, RNA=tRNA, TRA=transposase, Lys=Lysis, Ter=Terminase, Coa=Coat, Sha=Tail shaft, Fib=Tail fiber.

FIG. 4 depicts a schematic showing 1 of 3 high-scoring phage in Nissle using the Phast tool, referred to herein as "Phage 3", and which contains all major components of a phage. Putative genes are labeled Hyp=Hypothetical, PLP=other phage like protein, Oth=Other, RNA=tRNA, TRA=transposase, Lys=Lysis, Ter=Terminase, Coa=Coat, Sha=Tail shaft, Fib=Tail fiber.

FIG. 16A and FIG. 16B depict line graphs showing TCA production (FIG. 16A) and Phenylpyruvate production (FIG. 16B) in SYN-PKU-2002. Both are measures of the degradation of phenylalanine in vitro by SYN-PKU-2002. SYN-PKU-2002 was prepared by growth in Lysogeny Broth (LB) either aerobically (the uninduced state) or anaerobically with the addition of IPTG and arabinose (the induced state). In vitro, incubation of activated SYN-PKU-2002 in the presence of phenylalanine results in the production of TCA and PP over time, demonstrating that SYN-PKU-2002 is capable of metabolizing phenylalanine.

FIG. 17A and FIG. 17B depict the change in phenylalanine levels and hippurate recovery in mice gavaged with either streptomycin resistant Nissle or phage free strain SYN-PKU-2002 (which is phage free SYN-PKU-710). Mice were administered a single dose of phenylalanine (0.1 mg per gram body weight) by subcutaneous injection. At 1, 2 and 3 h post Phe challenge, the bacteria (or water no shown) were administered to mice by oral gavage (3×250 ul). Whole blood was collected via submandibular bleed at each time point and analyzed for phenylalanine levels. Urine collection in metabolic caging commenced immediately after the $1^{st}$ bacterial dose and continued to be collected for the duration of the study and analyzed for hippurate levels.

In FIG. 22A, fasted NHPs (n=6) were administered a 5 g peptide (left) or mock challenge (right) alone (black bars) or with $5×10^{11}$ cells of SYN-PKU-2002 (striped bars) and urine was collected for 6 h. Normalized HA recovery is shown as the average±standard deviation. Animals receiving SYN-PKU during the studies performed in FIG. 22A were also administered a dose of $^{13}$C-phenylalanine intravenously (IV) 1 h after peptide or mock challenge (FIG. 22B). Normalized urinary $^{13}$C-HA, which could only be derived from the IV administered $^{13}$C-Phe, was found in animals that received a peptide challenge and is displayed as black bars. No urinary $^{13}$C-HA was recovered in animals that remained fasting.

FIG. 26A depicts a graph showing normalized urinary HA recovery from dose groups shown as the average±standard deviation. FIG. 26B and FIG. 26C depict graphs showing the calculated AUCs for the concentrations of serum HA and. White bars represent the average AUC±standard deviation. FIG. 26D depicts a graph showing serum Phe concentration as determined at the indicated time points. The 3 highest doses administered in the dose response are shown compared to the No Cells control, as these 3 doses showed a significant reduction in serum Phe AUC (p<0.05).

FIG. 35A shows the effect of DAP auxotrophy on fecal clearance in group 1 mice (SYN-PKU901/SYN766).

DESCRIPTION OF EMBODIMENTS

Figure 1A:
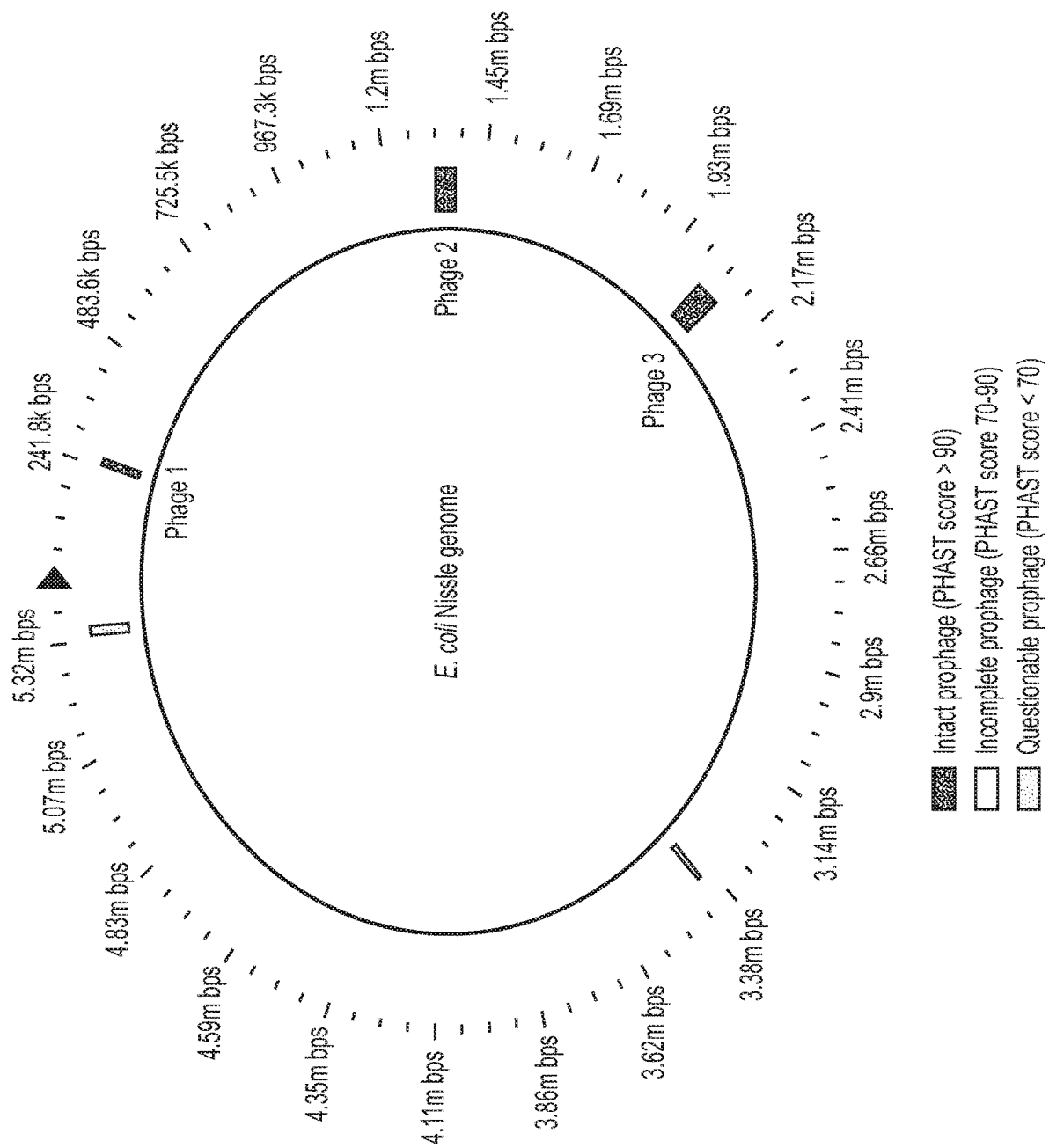
FIG. 1A depicts a schematic of locations of predicted phage on the EcN Genome (CP007799.1) from PHAST Analysis. The three high-scoring, intact phages are labeled as Phages 1-3. Phage 1 (PHAST score 110) is 18.8 kb long and stretches from coordinates 241,563-260,441 within the EcN genome. Phage 2 (PHAST score 150) is 52.4 kb long and stretches from 1,325,883-1,378,287. Phage 3 (PHAST score 150) is 59 kb long and stretches from 3,405,101-3, 418,180. Also identified were several low-scoring phage, designated as "incomplete" or "questionable" by the PHAST algorithm, which do not contain all the major components of a phage and could therefore represent partial phage, or false positive predictions. Abbreviations: EcN=*Escherichia coli* Nissle 1917; PHAST=Phage Search Tool software; kb=kilobases.

In one aspect, the disclosure provides bacteria which contain an endogenous phage and comprise one or more modifications to the phage sequence. In some embodiments, the modifications alter the properties of the prophage sequence. Such mutations include one or more partial or complete deletion(s) of one or more phage genes, one or more insertion(s) of one or more nucleotides into one or more phage genes, one or more partial or complete substitution(s) of one or more phage genes in the phage genome; one or more inversion(s) of one or more phage genes or combinations thereof.

This disclosure provides compositions comprising novel bacteria for the treatment of a disorder, which comprise one or more bacteriophages or prophages in their natural state. In some embodiments, the bacteria comprise one or more modifications to the genomes of the one or more phages. In some embodiments, the one or more modifications render the phage or prophage inactive. In some embodiments, these bacteria are further genetically modified to comprise one or more genes for the expression or production of one or more effector molecules. Methods for the production and use of these genetically engineered bacteria in novel therapies for the treatment of disorders are provided.

In one embodiment, *E. coli* Nissle is used as a starting point, parental strain or "chassis" for the genetically engineered bacteria. In one embodiment, the bacteriophage which is modified is a phage which is endogenous to *E. coli* Nissle in its phage is present in the bacteria in their natural state.

In some embodiments, the genetically engineered bacteria comprise one or more genes encoding one or more effectors, e.g., PME(s). In some embodiments, the genetically engineered bacteria comprise one or more genes encoding PAL. In some embodiments, the genetically engineered bacteria comprise one or more genes encoding LAAD. In some embodiments, the genetically engineered bacteria comprise one or more genes encoding PAL and one or more genes encoding LAAD. In some embodiments, the genetically engineered bacteria comprise one or more genes encoding a transporter, e.g., PheP. In some embodiments, the genetically engineered bacteria comprise one or more genes encoding a transporter, e.g., PheP and one or more genes encoding PAL. In some embodiments, the genetically engineered bacteria comprise one or more genes encoding a transporter, e.g., PheP and one or more genes encoding LAAD. In some embodiments, the genetically engineered bacteria comprise one or more genes encoding a transporter, e.g., PheP, one or more genes encoding LAAD, and one or more genes encoding PAL. In any of the preceding embodiments, the genetically engineered bacteria for the consumption of phenylalanine further comprise one or more relative to its original state. In some embodiments, the endogenous bacteriophage genomes. In some embodiments, the bacteriophage(s) have been mutated in one or more genes within the bacteriophage genome. Such mutations include deletions, insertions, substitutions and inversions and are located in or encompass one or more bacteriophage genes.

Bacteriophage are the most common biological entity in the world, and it is well documented that a majority of bacterial species, both gram positive and gram negative, contain one or more DNA bacteriophages which are integrated as so-called prophages in the bacterial chromosome (Clokie et al, Phages in Nature, Bacteriophage. 2011 January-February; 1(1): 31-45). For example, two separate studies on *E. coli* strains studies showed that 51 different functional phages were released from 27 *E. coli* strains analyzed, and 83 of 107 *E. coli* strains tested released at least one functional phage type (Casjens, Prophages and bacterial genomics: what have we learned so far?; Mol Microbiol. 2003 July; 49(2):277-300; Osawa et al., Genotypic variations of Shiga toxin-converting phages from enterohaemorrhagic *Escherichia coli* O157:H7 isolates; J Med Microbiol (2001) 49: 565-574, and Schicklmaier et al., A comparative study on the frequency of prophages among natural isolates of *Salmonella* and *Escherichia coli* with emphasis on generalized transducers. Antonie Van Leeuwenhoek (1998) 73: 49-54).

Figure 12:
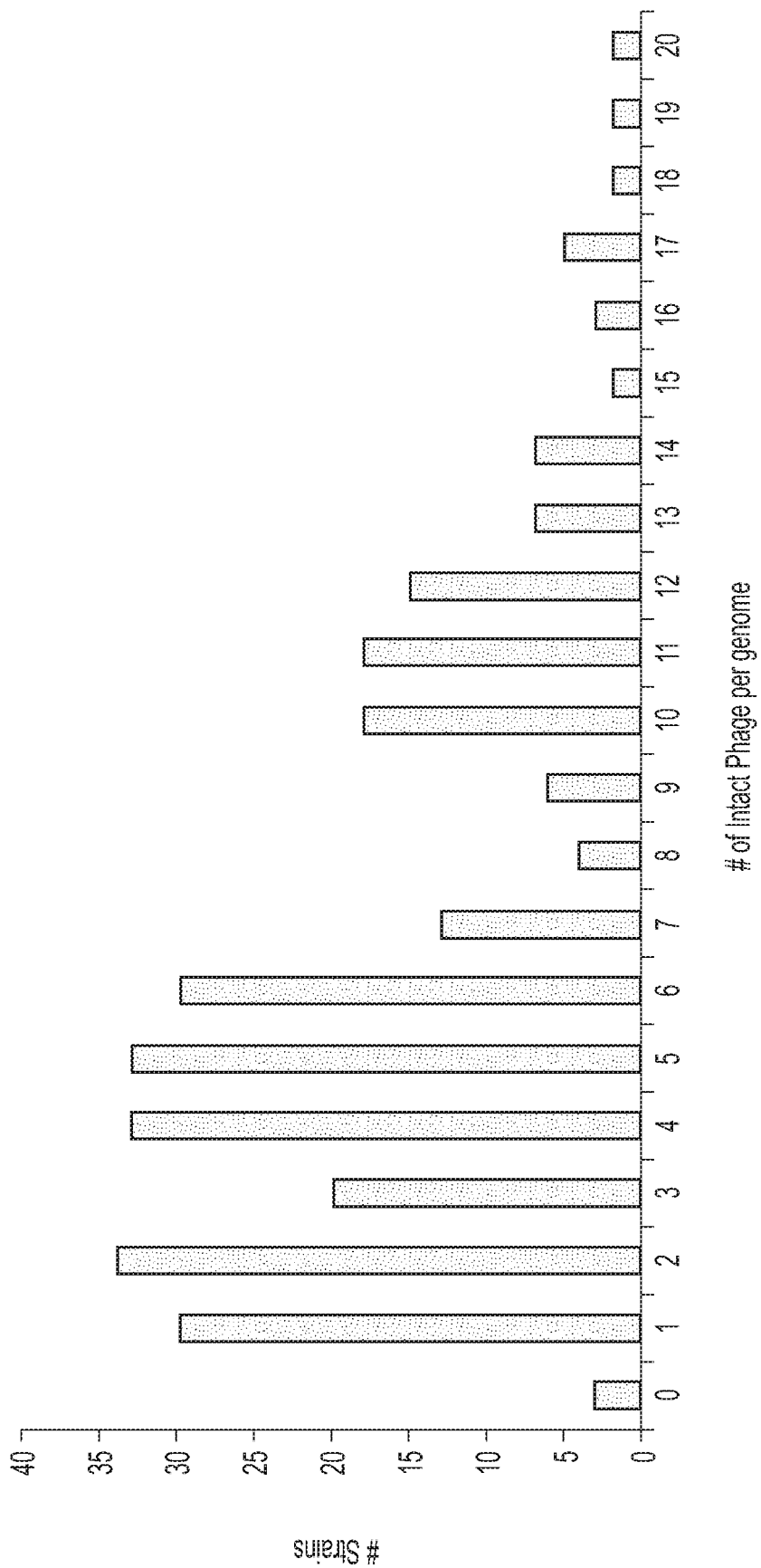
FIG. 12 depicts a bar graph showing the distribution of the number of predicted "intact" phage across a set of 287 *E. coli* genomes from Refseq. The Refseq database was analyzed for the number of intact phage that were present in published, complete *E. coli* genomes. The histogram displays a non-normal distribution, but it is clear that nearly all *E. coli* genomes contain intact prophage, and the majority of published, complete *E. coli* genomes contain more intact prophage than EcN. Abbreviations: *E. coli=Escherichia coli*; EcN=*Escherichia coli* Nissle 1917; Refseq=reference sequence.

As shown in FIG. 12, nearly all *E. coli* genomes contain intact prophage, and the majority of published, complete *E. coli* genomes contain more intact prophage than EcN. Abbreviations: *E. coli*=*Escherichia coli*; EcN=*Escherichia coli* Nissle 1917; Refseq=reference sequence.

Among Gram-positive bacteria, the genomes of *B. subtilis, Clostridium acetobutylicum, Lactococcus lactis*, and many others have been shown to include largely intact prophages (Kunst et al., 1997; Bolotin et al., The complete genome sequence of the gram-positive bacterium *Bacillus subtilis*. Nature (2001) 390: 249-256, Nolling et al., Genome sequence and comparative analysis of the solvent-producing bacterium *Clostridium acetobutylicum*. J Bacteriol (2001) 183: 4823-4838; Bolotin et al., The complete genome sequence of the lactic acid bacterium *Lactococcus lactis* ssp. *lactis* IL1403. Genome Res (2001) 11: 731-753).

DNA phages can be lytic or temperate. Lytic phages infect bacterial cells and then program the synthesis of progeny phages, which are then released from the lysed cell. Conversely, temperate DNA phages establish a stable relationship with their host bacteria in which the integrated phage DNA, i.e., the prophage, is replicated in concert with the host's genome, and any host-damaging phage genes are not expressed. However, bacteriophage particles can be released from cells containing an intact prophage by a process called induction, during which prophage genes required for lytic growth are turned on and progeny phage particles are produced and released from the cell through lysis of the cell (reviewed in Casjens, Prophages and bacterial genomics: what have we learned so far?; Mol Microbiol. 2003 July; 49(2):277-300). Induction can occur in some cases spontaneously and randomly in a small or large fraction of the bacteria that harbor the prophage, or specific, often undefined, environmental signals can cause simultaneous induction of a particular prophage in many cells, causing death of the bacterial cells. In some cases, presence of prophage sequences may also allow some bacteria to have properties they would not have without the phage, such as antibiotic resistance, the ability to exist in different environmental conditions, improved adhesion, pathogenicity or facilitated horizontal gene transfer (Casjens et al., 2001).

Not all prophage have the ability to undergo a lytic cycle. Non-functional, i.e., defective or cryptic prophages can accrue to a high level of abundancy in many bacteria as a result of mutational decay and/or the loss of one or more genes essential to the lytic cycle over thousands of bacterial replication cycles (Bobay et al., Pervasive domestication of defective prophages by bacteria, Proc Natl Acad Sci USA. 2014 Aug. 19; 111(33): 12127-12132, and references therein). Of note, defective prophages often also contain a number of genes that can provide advantageous functionality to the host, including genes encoding proteins with homologous recombination functions, prevention of further infection, or bacteriocins, which may be helpful in competition for nutrients, e.g., through growth inhibition of other neighboring bacterial species.

Phages can positively affect gene expression and fitness in *E. coli* in numerous ways. Cryptic, lysogenic, and lytic phages have been shown to provide multiple benefits to the host promoting survival in adverse environmental conditions. For example, gene sequences transferred to the bacterium by phages have been linked to adaptation to different nutrients or a different niche, or to increased ability to eliminate competing strains. Dormant prophage has also been shown to prevent superinfection with another, e.g., lytic, phage.

Several studies have shown that endogenous phages affect the ability of bacteria to grow in certain carbon sources. Along with lambda, active Mu, P1 and P2 prophages and cryptic prophage CP4-57 increase growth under glucose-limited and other growing conditions (Edlin, G., Lin, L. & Bitner, R. Reproductive fitness of P1, P2, and Mu lysogens of *Escherichia coli*. *J. Virol.* 21, 560-564 (1977); Edlin, G., Lin, L. & Kudmar, R. λ Lysogens of *E. coli* reproduce more rapidly than non-lysogens. Nature 255, 735-737 (1975); Wang, X., Kim, Y. & Wood, T. K. Control and benefits of CP4-57 prophage excision in *Escherichia coli* biofilms. ISME J. 3, 1164-4179 (2009). In another study, it was shown that when integrates into the *E. coli* genome, ability of the cell to grow on poor carbon sources is shut down. IN this case, limitation of metabolism may confer a survival benefit to the bacterium. Slowing bacterial growth in glucose-poor environments might help the bacterium, elude detection by the immune system, increasing the chances of survival.

Other survival properties may be affected as well. Wang et al created a single *E. coli* strain lacks all nine cryptic prophages. In this study, it was shown that these prophages are beneficial for withstanding osmotic, oxidative and acid stresses, for increasing growth under various conditions, enhancing phosphorus and nitrogen utilization, and for influencing biofilm formation (Wang et al., Cryptic prophages help bacteria cope with adverse environments; DOI: 10.1038/ncomms1146). In pathogenic bacteria prophage, several studies suggest that acquisition is associated with changes in pathogen virulence.

Accordingly, a skilled artisan might expect that modification, e.g., mutation or deletion of portions or entirety of an endogenous prophage may alter, e.g., negatively affect, bacterial fitness. Additionally, one might assume that endogenous prophage may alter, e.g., negatively affect, effector activity in a genetically engineered bacterium capable of producing this effector. This may be especially the case if the endogenous prophage is present in all specimen of a particular strain subtype—this would indicate that the bacterium comprising the prophage sequences evolutionarily was able to out compete a form of the bacterium that lacks the prophage.

As described further in this disclosure, a prophage in *E. coli* Nissle was identified, which is capable of undergoing lysis under certain conditions, and which is present in all specimens of *E. coli* Nissle. Surprisingly, testing of bacterial fitness, residence time, and activity showed that the bacterium comprising the mutation or deletion in the endogenous phage was essentially the same, e.g., at least the same order of magnitude.

Figure 19:
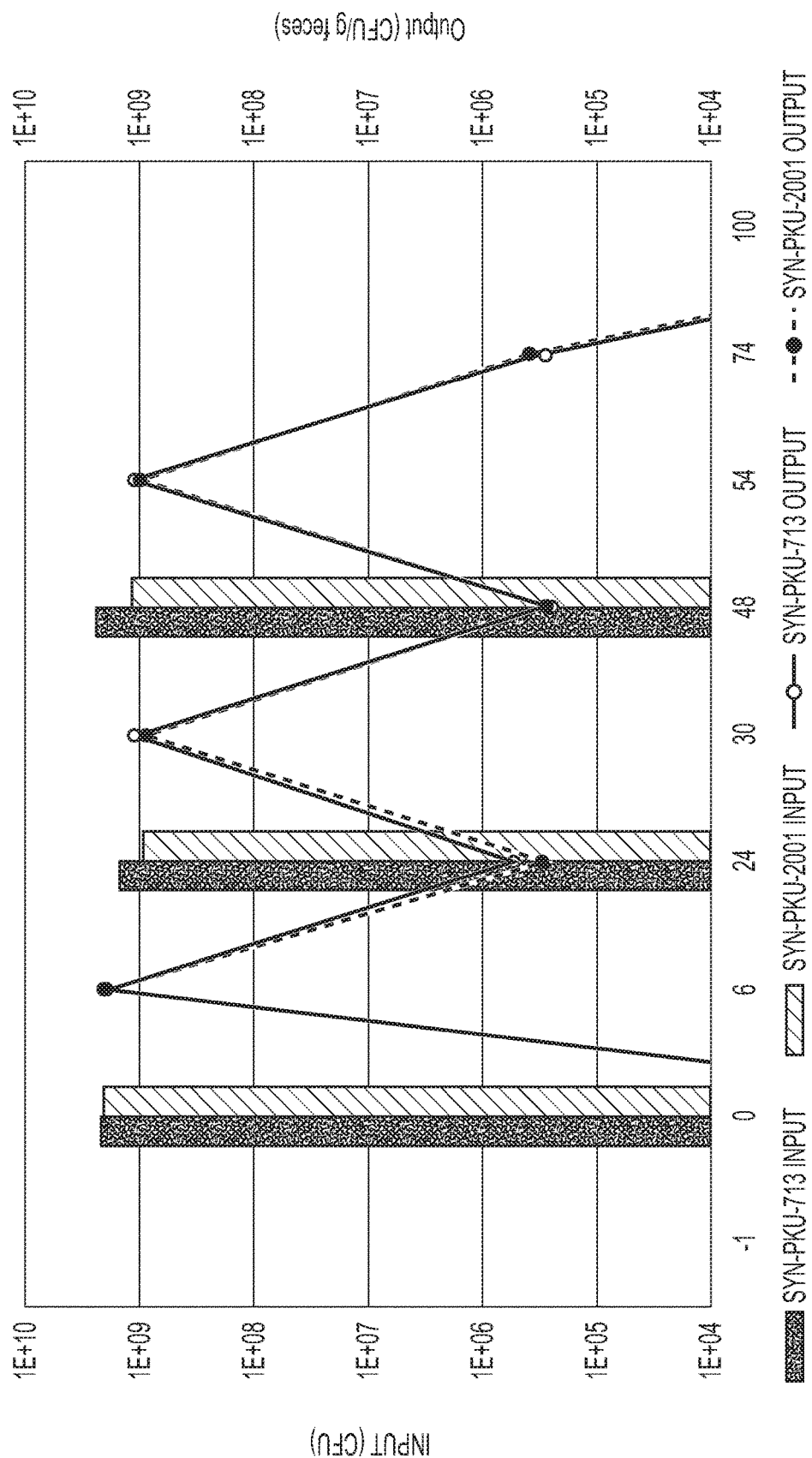
FIG. 19 depicts a graph showing the outcome of an in vivo competition study between phage containing and phage free strains SYN-PKU-713 and SYN-PKU-2001. Mice were administered equal amounts (approx. 3×10^9 of cells) daily for three days. Each day fecal pellets were collected and CFUs determined in plating assay based on the different antibiotic resistances of the two strains, as described in the Examples. Results indicate that there is no large difference in transit or colonization between the phage-free PKU strain of Nissle SYN-PKU-713 and SYN-PKU-2001.

Under similar assay conditions, there was no discernable difference in Phe degradation activity (in vitro or in vivo) between the strains. For example, under similar assay conditions, Phe consumption is within the same magnitude between the two strains (see., e.g., FIG. 15 and FIG. 17A). In vivo competition studies between phage containing and phage free strains indicate that there is no discernable difference in transit or colonization between the phage-free PKU strain of Nissle (see, e. g. FIG. 19).

Accordingly, in some embodiments, one or more modification(s), e.g., mutation(s) or deletion(s) or other modifications described herein, in the genome of a phage does not alter the bacterial fitness of the modified or genetically engineered bacterium. In some embodiments, the engineered bacteria comprising one or more phage modifications, e.g., mutation(s) or deletion(s) or other modifications described herein, have essentially the same or at least similar bacterial fitness as the corresponding isogenic strain in the absence of the phage mutation. In further embodiments, one or more modification(s), e.g., mutation(s) or deletion(s) or other modifications described herein in the genome of a phage does not alter the strain activity (e.g., effector activity or metabolic activity) of the engineered bacterium capable of producing the effector as compared to the corresponding isogenic strain without the phage mutation. In some embodiments, the unmodified or genetically engineered bacteria comprising one or more phage modifications, e.g., mutation(s) or deletion(s) or other modifications described herein, have essentially the same or at least similar bacterial strain activity (e.g., effector activity or metabolic activity) when compared to the corresponding isogenic strain without the phage mutation.

Additionally, in some embodiments, one or more modification(s), e.g., mutation(s) or deletion(s) or other modifications described herein, in the genome of a phage alters, e.g., increases or reduces, the bacterial fitness of the engineered bacterium. In some embodiments, the engineered bacteria comprising one or more phage modifications, e.g., mutation(s) or deletion(s) or other modifications described herein, have altered, e.g., reduced or increased, bacterial fitness as compared to the corresponding isogenic strain without the phage mutation. In some embodiments, the one or more modification(s), e.g., mutation(s) or deletion(s) or other modifications described herein in the genome of a phage alters, e.g., reduces or increases, strain activity (e.g., effector activity or metabolic activity) of the bacterium capable of producing the effector as compared to the corresponding isogenic strain without the phage mutation. In some embodiments, unmodified or genetically engineered bacteria comprising one or more phage modifications, e.g., mutation(s) or deletion(s) or other modifications described herein, have altered, e.g., reduced or increased, bacterial strain activity (e.g., effector activity or metabolic activity) as the corresponding isogenic strain without the phage mutation.

In some embodiments, the genetically engineered bacteria comprise one or more E. coli Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the one or more insertions comprise an antibiotic cassette. In some embodiments, the mutation is a deletion. In some embodiments, the genetically engineered bacteria comprise one or more deletions, which are located in or comprise one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise a modified phage genome sequence consisting of SEQ ID NO: 281.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Hyperphenylalaninemia," "hyperphenylalaninemic," and "excess phenylalanine" are used interchangeably herein to refer to increased or abnormally high concentrations of phenylalanine in the body. In some embodiments, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL. As used herein, diseases associated with hyperphenylalaninemia include, but are not limited to, phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. Affected individuals can suffer progressive and irreversible neurological deficits, mental retardation, encephalopathy, epilepsy, eczema, reduced growth, microcephaly, tremor, limb spasticity, and/or hypopigmentation (Leonard 2006). Hyperphenylalaninemia can also be secondary to other conditions, e.g., liver diseases.

"Phenylalanine ammonia lyase" and "PAL" are used to refer to a phenylalanine metabolizing enzyme (PME) that converts or processes phenylalanine to trans-cinnamic acid and ammonia. Trans-cinnamic acid has low toxicity and is converted by liver enzymes in mammals to hippuric acid, which is secreted in the urine. PAL may be substituted for the enzyme PAH to metabolize excess phenylalanine. PAL enzyme activity does not require THB cofactor activity. In some embodiments, PAL is encoded by a PAL gene derived from a prokaryotic species. In alternate embodiments, PAL is encoded by a PAL gene derived from a eukaryotic species. In some embodiments, PAL is encoded by a PAL gene derived from a bacterial species, including but not limited to, *Achromobacter xylosoxidans, Pseudomonas aeruginosa, Photorhabdus luminescens, Anabaena variabilis*, and *Agrobacterium tumefaciens*. In some embodiments, PAL is encoded by a PAL gene derived from *Anabaena variabilis* and referred to as "PAL1" herein (Moffitt et al., 2007). In some embodiments, PAL is encoded by a PAL gene derived from *Photorhabdus luminescens* and referred to as "PAL3" herein (Williams et al., 2005). In some embodiments, PAL is encoded by a PAL gene derived from a yeast species, e.g., *Rhodosporidium toruloides* (Gilbert et al., 1985). In some embodiments, PAL is encoded by a PAL gene derived from a plant species, e.g., *Arabidopsis thaliana* (Wanner et al., 1995). Any suitable nucleotide and amino acid sequences of PAL, or functional fragments thereof, may be used.

"Phenylalanine hydroxylase" and "PAH" are used to refer to an enzyme that catalyzes the hydroxylation of the aromatic side chain of phenylalanine to create tyrosine in the human body in conjunction with the cofactor tetrahydrobiopterin. The human gene encoding PAH is located on the long (q) arm of chromosome 12 between positions 22 and 24.2. The amino acid sequence of PAH is highly conserved among mammals Nucleic acid sequences for human and mammalian PAH are well known and widely available. The full-length human cDNA sequence for PAH was reported in 1985 (Kwok et al. 1985). Active fragments of PAH are also well known (e.g., Kobe et al. 1997).

"L-Aminoacid Deaminase" and "LAAD" are used to refer to an enzyme that catalyzes the stereospecific oxidative deamination of L-amino acids to generate their respective keto acids, ammonia, and hydrogen peroxide. For example, LAAD catalyzes the conversion of phenylalanine to phenylpyruvate. Multiple LAAD enzymes are known in the art, many of which are derived from bacteria, such as *Proteus, Providencia*, and *Morganella*, or venom. LAAD is characterized by fast reaction rate of phenylalanine degradation (Hou et al., Appl Microbiol Technol. 2015 October; 99(20): 8391-402; "Production of phenylpyruvic acid from L-phenylalanine using an L-amino acid deaminase from *Proteus mirabilis*: comparison of enzymatic and whole-cell biotransformation approaches"). Most eukaryotic and prokaryotic L-amino acid deaminases are extracellular; however, *Proteus* species LAAD are localized to the plasma membrane (inner membrane), facing outward into the periplasmic space, in which the enzymatic activity resides. As a consequence of this localization, phenylalanine transport through the inner membrane into the cytoplasm is not required for *Proteus* LAAD mediated phenylalanine degradation. Phenylalanine is readily taken up through the outer membrane into the periplasm without a transporter, eliminating the need for a transporter to improve substrate availability.

In some embodiments, the genetically engineered bacteria comprise a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the LAAD encoded by the genetically engineered bacteria is localized to the plasma membrane, facing into the periplasmic space and with the catalytic activity occurring in the periplasmic space.

"Phenylalanine metabolizing enzyme" or "PME" are used to refer to an enzyme which is able to degrade phenylalanine. Any phenylalanine metabolizing enzyme known in the art may be encoded by the genetically engineered bacteria. PMEs include, but are not limited to, phenylalanine hydroxylase (PAH), phenylalanine ammonia lyase (PAL), aminotransferase, L-amino acid deaminase (LAAD), and phenylalanine dehydrogenases.

Reactions with phenylalanine hydroxylases, phenylalanine dehydrogenases or aminotransferases require cofactors, while LAAD and PAL do not require any additional cofactors. In some embodiments, the PME encoded by the genetically engineered bacteria requires a cofactor. In some embodiments, this cofactor is provided concurrently or sequentially with the administration of the genetically engineered bacteria. In other embodiments, the genetically engineered bacteria can produce the cofactor. In some embodiments, the genetically engineered bacteria encode a phenylalanine hydroxylase. In some embodiments, the genetically engineered bacteria encode a phenylalanine dehydrogenase. In some embodiments, the genetically engineered bacteria encode an aminotransferase. In some embodiments, the PME encoded by the genetically engineered bacteria does not require a cofactor. Without wishing to be bound by theory, the lack of need for a cofactor means that the rate of phenylalanine degradation by the enzyme is dependent on the availability of the substrate and is not limited by the availability of the cofactor. In some embodiments, the PME produced by the genetically engineered bacteria is PAL. In some embodiments, the PME produced by the genetically engineered bacteria is LAAD. In some embodiments, the genetically engineered bacteria encode combinations of PMEs.

In some embodiments, the catalytic activity of the PME is dependent on oxygen levels. In some embodiments, the PME is catalytically active under microaerobic conditions. As a non-limiting example, LAAD catalytic activity is dependent on oxygen. In some embodiments, LAAD is active under low oxygen conditions, such as microaerobic conditions. In some embodiments, of the invention, the PME functions at very low levels of oxygen or in the absence of oxygen, e.g. as found in the colon. As a non-limiting example, PAL activity is not dependent on the presence of oxygen.

As used herein, "effector" or "effector molecule" can refers to a molecule, such as a metabolite or a polypeptide, which exerts a desired function. An effector may be encoded by a single gene. For example, a single gene can encode a polypeptide which is secreted or displayed. Alternatively, an effector may be synthesized by a biosynthetic pathway requiring multiple genes, e.g., butyrate. The polypeptides encoded by multiple genes within a biosynthetic pathway, e.g., which synthesizes a metabolite with desirable properties, may also be referred to as effectors. Similarly, polypeptides encoded by multiple genes within a catabolic pathway, e.g., for the breakdown of a toxic metabolite, may also be referred to as effectors. These effector molecules may also be referred to as "therapeutic metabolites", "therapeutic molecules" or "therapeutic polypeptides". Other terms that are used interchangeably herein with effector are "polypeptide of interest" or "polypeptides of interest", "protein of interest", "proteins of interest".

As used herein, "payload" refers to one or more polynucleotides and/or polypeptides of interest to be produced by a genetically engineered microorganism, such as a bacterium. In some embodiments, the payload is encoded by a gene or multiple genes or an operon. In some embodiments, the one or more genes and/or operon(s) comprising the payload are endogenous to the microorganism. In some embodiments, the one or more elements of the payload is derived from a different microorganism and/or organism. In some embodiments, the payload is a therapeutic payload. In some embodiments, the payload is encoded by genes for the biosynthesis of a molecule. In some embodiments, the payload is encoded by genes for the metabolism, catabolism, or degradation of a molecule. In some embodiments, the payload is encoded by genes for the importation of a molecule. In some embodiments, the payload is encoded by genes for the exportation of a molecule. In some embodiments, the payload is a regulatory molecule(s), e.g., a transcriptional regulator such as FNR. In some embodiments, the payload comprises a regulatory element, such as a promoter or a repressor. In some embodiments, the payload expression is driven from an inducible promoter, such as from FNRS. In some embodiments, payload expression is driven from a constitutive promoter. In some embodiments, the payload comprises a repressor element, such as a kill switch. In alternate embodiments, the payload is produced by a biosynthetic or biochemical pathway, wherein the biosynthetic or biochemical pathway may optionally be endogenous to the microorganism. In some embodiments, the genetically engineered microorganism comprises two or more payloads.

The present disclosure includes, inter alia, genetically engineered bacteria, pharmaceutical compositions thereof, and methods of modulating and treating disorders associated with hyperphenylalaninemia. In some embodiments, the genetically engineered bacteria comprise a gene encoding non-native phenylalanine ammonia lyase (PAL) and are capable of processing and reducing phenylalanine in a mammal. In some embodiments, the engineered bacteria further comprise a gene encoding a phenylalanine transporter. In some embodiments, the engineered bacteria may also comprise a gene encoding LAAD. The engineered bacteria may also contain one or more gene sequences relating to bio-safety and/or bio-containment, e.g., a kil-switch, gene guard system, and/or auxotrophy. The expression of these gene sequence(s) may be regulated using a variety of promoter systems, such as any of the promoter systems disclosed herein, which promoter may be the same promoter to regulate one or more different genes, may be a different copy of the same promoter to regulate different genes, or may involve the use of different promoters used in combination to regulate the expression of different genes. The use of different regulatory or promoter systems to control gene expression provides flexibility (e.g., the ability to differentially control gene expression under different environmental conditions and/or the ability to differentially control gene expression temporally) and also provides the ability to "fine-tune" gene expression, any or all of which regulation may serve to optimize gene expression and/or growth of the bacteria. The genetically engineered bacteria and pharmaceutical compositions comprising those bacteria may be used to metabolize phenylalanine in the body into non-toxic molecules in order to treat and/or prevent conditions associated with hyperphenylalaninemia, including PKU. In certain aspects, the compositions comprising the genetically engineered bacteria may be used in the methods of the disclosure to treat and/or prevent disorders associated with hyperphenylalaninemia.

Effector molecules also include anti-cancer molecules. "anti-cancer molecule" refers to one or more therapeutic substances or drugs of interest to be produced by a genetically engineered microorganism, e.g., engineered bacteria or engineered oncolytic virus, which are capable of reducing and/or inhibiting cell growth or replication. In some embodiments, the anti-cancer molecule is a therapeutic molecule that is useful for modulating or treating a cancer. In some embodiments, the anti-cancer molecule is a therapeutic molecule encoded by a gene. In alternate embodiments, the anti-cancer molecule is a therapeutic molecule produced by a biochemical or biosynthetic pathway, wherein the biosynthetic or biochemical pathway may optionally be endogenous to the microorganism. In some embodiments, the genetically engineered microorganism is capable of producing two or more anti-cancer molecules. Non-limiting examples of anti-cancer molecules include immune checkpoint inhibitors (e.g., CTLA-4 antibodies, PD-1 antibodies, PDL-1 antibodies), cytotoxic agents (e.g., Cly A, FASL, TRAIL, TNF-alpha), immunostimulatory cytokines and co-stimulatory molecules (e.g., OX40, CD28, ICOS, CCL21, IL-2, IL-18, IL-15, IL-12, IFN-gamma, IL-21, TNFs, GM-CSF), antigens and antibodies (e.g., tumor antigens, neoantigens, CtxB-PSA fusion protein, CPV-OmpA fusion protein, NY-ESO-1 tumor antigen, RAF1, antibodies against immune suppressor molecules, anti-VEGF, Anti-CXR4/CXCL12, anti-GLP1, anti-GLP2, anti-galectin1, anti-galectin3, anti-Tie2, anti-CD47, antibodies against immune checkpoints, antibodies against immunosuppressive cytokines and chemokines), DNA transfer vectors (e.g., endostatin, thrombospondin-1, TRAIL, SMAC, Stat3, Bcl2, FLT3L, GM-CSF, IL-12, AFP, VEGFR2), and enzymes (e.g., E. coli CD, HSV-TK). In some embodiments, the anti-cancer molecule includes nucleic acid molecules that mediate RNA interference, microRNA response or inhibition, TLR response, antisense gene regulation, target protein binding (aptamer or decoy oligos), gene editing, such as CRISPR interference. In some embodiments, bacteria or virus can be used as vectors to transfer DNA into mammalian cells, e.g., by bactofection (Bernardes et al., 2013).

Non-limiting examples of effector molecules include "anti-inflammation molecules" and/or "gut barrier function enhancer molecules". Anti-inflammation molecules and/or gut barrier function enhancer molecules include, but are not limited to, short-chain fatty acids, butyrate, propionate, acetate, IL-2, IL-22, superoxide dismutase (SOD), GLP-2 and analogs, GLP-1, IL-10, IL-27, TGF-β1, TGF-β2, N-acylphosphatidylethanolamines (NAPEs), elafin (also called peptidase inhibitor 3 and SKALP), trefoil factor, melatonin, tryptophan, $PGD_2$, and kynurenic acid, indole metabolites, and other tryptophan metabolites, as well as other molecules disclosed herein. Such molecules may also include compounds that inhibit pro-inflammatory molecules, e.g., a single-chain variable fragment (scFv), antisense RNA, siRNA, or shRNA that neutralizes TNF-α, IFN-γ, IL-1β, IL-6, IL-8, IL-17, and/or chemokines, e.g., CXCL-8 and CCL2. Such molecules also include AHR agonists (e.g., which result in IL-22 production, e.g., indole acetic acid, indole-3-aldehyde, and indole) and PXR agonists (e.g., IPA), as described herein. Such molecules also include HDAC inhibitors (e.g., butyrate), activators of GPR41 and/or GPR43 (e.g., butyrate and/or propionate and/or acetate), activators of GPR109A (e.g., butyrate), inhibitors of NF-kappaB signaling (e.g., butyrate), and modulators of PPARgamma (e.g., butyrate), activators of AMPK signaling (e.g., acetate), and modulators of GLP-1 secretion. Such molecules also include hydroxyl radical scavengers and antioxidants (e.g., IPA). A molecule may be primarily anti-inflammatory, e.g., IL-10, or primarily gut barrier function enhancing, e.g., GLP-2. A molecule may be both anti-inflammatory and gut barrier function enhancing.

An anti-inflammation and/or gut barrier function enhancer molecule may be encoded by a single gene, e.g., elafin is encoded by the PI3 gene. Alternatively, an anti-inflammation and/or gut barrier function enhancer molecule may be synthesized by a biosynthetic pathway requiring multiple genes, e.g., butyrate.

Effector molecules also include metabolic effector molecules. "Metabolic effector molecules" and/or "satiety effector molecules" include, but are not limited to, n-acyl-phophatidylethanolamines (NAPEs), n-acyl-ethanolamines (NAEs), ghrelin receptor antagonists, peptide YY3-36, cholecystokinin (CCK) family molecules, CCK58, CCK33, CCK22, CCK8, bombesin family molecules, bombesin, gastrin releasing peptide (GRP), neuromedin B (P), glucagon, GLP-1, GLP-2, apolipoprotein A-IV, amylin, somatostatin, enterostatin, oxyntomodulin, pancreatic peptide, short-chain fatty acids, butyrate, propionate, acetate, serotonin receptor agonists, nicotinamide adenine dinucleotide (NAD), nicotinamide mononucleotide (NMN), nucleotide riboside (NR), nicotinamide, and nicotinic acid (NA). Such molecules may also include compounds that inhibit a molecule that promotes metabolic disease, e.g., a single-chain variable fragment (scFv), antisense RNA, siRNA, or shRNA that inhibits dipeptidyl peptidase-4 (DPP4) or ghrelin receptor. A metabolic and/or satiety effector molecule may be encoded by a single gene, e.g., glucagon-like peptide 1 is encoded by the GLP-1 gene. In some embodiments, the genetically engineered bacteria comprising gene sequences comprising one or more circuits for the production or catabolism of tryptophan and/or one of its metabolites further comprise gene sequences for the expression of one or more metabolic effector molecule and/or satiety effector molecules.

Other non-limiting examples of effector molecules are described in in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

In certain embodiments, new or improved effectors (e.g., PMEs) can be identified according to methods known in the art or described herein, and are encoded by the genetically engineered bacteria. In some embodiments, the enzyme encoded by the genetically engineered bacteria is a wild type enzyme isolated from a viral, prokaryotic or eukaryotic organism. In some embodiments, the enzyme sequence has been further modified or mutated to increase one or more specific properties of the enzyme, such as stability or catalytic activity.

"Phenylalanine metabolite" refers to a metabolite that is generated as a result of the degradation of phenylalanine. The metabolite may be generated directly from phenylalanine, by the enzyme using phenylalanine as a substrate, or indirectly by a different enzyme downstream in the metabolic pathway, which acts on a phenylalanine metabolite substrate. In some embodiments, phenylalanine metabolites are produced by the genetically engineered bacteria encoding a PME.

In some embodiments, the phenylalanine metabolite results directly or indirectly from PAH activity, e.g., from PAH produced by the genetically engineered bacteria. In some embodiments, the metabolite is tyrosine. In some embodiments, the phenylalanine metabolite accumulates in the blood or the urine of a PKU patient, due to defective PAH activity. Non-limiting examples of such PKU metabolites are phenylpyruvic acid and phenyl-lactic acid. Other examples include phenylacetate, phenylethylamine, and phenylacetyl glutamine.

In some embodiments, the phenylalanine metabolite results directly or indirectly from PAL action, e.g., from PAL produced by the genetically engineered bacteria. Non-limiting examples of such PAL metabolites are trans-cinnamic acid and hippuric acid. In some embodiments, the phenylalanine metabolite results directly or indirectly from LAAD action, e.g., from LAAD produced by the genetically engineered bacteria. Examples of such LAAD metabolites are phenylpyruvate and phenyllactic acid.

"Phenylalanine transporter" is used to refer to a membrane transport protein that is capable of transporting phenylalanine into bacterial cells (see, e.g., Pi et al., 1991). In *Escherichia coli*, the pheP gene encodes a high affinity phenylalanine-specific permease responsible for phenylalanine transport (Pi et al., 1998). In some embodiments, the phenylalanine transporter is encoded by a pheP gene derived from a bacterial species, including but not limited to, *Acinetobacter calcoaceticus, Salmonella enterica*, and *Escherichia coli*. Other phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by a aroP gene derived from a bacterial species. In some embodiments, the phenylalanine transporter is encoded by LIV-binding protein and LS-binding protein and LivHMGF genes derived from a bacterial species. In some embodiments, the genetically engineered bacteria comprise more than one type of phenylalanine transporter, selected from pheP, aroP, and the LIV-I/LS system.

"Phenylalanine" and "Phe" are used to refer to an amino acid with the formula $C_6H_5CH_2CH(NH_2)COOH$. Phenylalanine is a precursor for tyrosine, dopamine, norepinephrine, and epinephrine. L-phenylalanine is an essential amino acid and the form of phenylalanine primarily found in dietary protein; the stereoisomer D-phenylalanine is found is lower amounts in dietary protein; DL-phenylalanine is a combination of both forms. Phenylalanine may refer to one or more of L-phenylalanine, D-phenylalanine, and DL-phenylalanine.

As used herein, the term "transporter" is meant to refer to a mechanism, e.g., protein, proteins, or protein complex, for importing a molecule, e.g., amino acid, peptide (di-peptide, tripeptide, polypeptide, etc.), toxin, metabolite, substrate, as well as other biomolecules into the microorganism from the extracellular milieu.

"Operably linked" refers a nucleic acid sequence, e.g., a gene encoding PAL, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

An "inducible promoter" refers to a regulatory region that is operably linked to one or more genes, wherein expression of the gene(s) is increased in the presence of an inducer of said regulatory region.

A "directly inducible promoter" refers to a regulatory region, wherein the regulatory region is operably linked to a gene encoding an effector molecule (e.g. a phenylalanine metabolizing enzyme, e.g. PAL) in the presence of an inducer of said regulatory region, the effector molecule is expressed. An "indirectly inducible promoter" refers to a regulatory system comprising two or more regulatory regions, for example, a first regulatory region that is operably linked to a gene encoding a first molecule, e.g., a transcriptional regulator, which is capable of regulating a second regulatory region that is operably linked to a gene encoding an effector molecule. In the presence of an inducer of the first regulatory region, the second regulatory region may be activated or repressed, thereby activating or repressing expression of the effector molecule. Both a directly inducible promoter and an indirectly inducible promoter are encompassed by "inducible promoter."

"Exogenous environmental condition(s)" or "environmental conditions" refer to settings or circumstances under which the promoter described herein is directly or indirectly induced. The phrase is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low-oxygen, microaerobic, or anaerobic conditions, such as the environment of the mammalian gut. In some embodiments, exogenous environmental conditions refer to the presence of molecules or metabolites that are specific to the mammalian gut in a healthy or disease-state, e.g., propionate. In some embodiments, the exogenous environmental conditions are specific to the tumor microenvironment. In some embodiments, exogenous environmental conditions are molecules or metabolites that are specific to the tumor microenvironment. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprises an oxygen level-dependent promoter. In some aspects, bacteria have evolved transcription factors that are capable of sensing oxygen levels. Different signaling pathways may be triggered by different oxygen levels and occur with different kinetics.

As used herein, "exogenous environmental conditions" or "environmental conditions" also refers to settings or circumstances or environmental conditions external to the engineered microorganism, which relate to in vitro culture conditions of the microorganism. "Exogenous environmental conditions" may also refer to the conditions during growth, production, and manufacture of the organism. Such conditions include aerobic culture conditions, anaerobic culture conditions, low oxygen culture conditions and other conditions under set oxygen concentrations. Such conditions also include the presence of a chemical and/or nutritional inducer, such as tetracycline, arabinose, IPTG, rhamnose, and the like in the culture medium. Such conditions also include the temperatures at which the microorganisms are grown prior to in vivo administration. For example, using certain promoter systems, certain temperatures are permissive to expression of a payload, while other temperatures are non-permissive. Oxygen levels, temperature and media composition influence such exogenous environmental conditions. Such conditions affect proliferation rate, rate of induction of the payload (e.g. PME, e.g. PAL or LAAD) or rate of induction of the transporter (e.g. PheP), and overall viability and metabolic activity of the strain during strain production.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003). Non-limiting examples are shown in Table 1.

In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic and/or low oxygen conditions by the global transcriptional regulator FNR that is naturally found in Nissle. Under anaerobic and/or low oxygen conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrS, FNR, P-FNRS promoter and other such related designations to indicate the promoter PfnrS.

TABLE 1

Examples of transcription factors and responsive genes and regulatory regions

| Transcription factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

As used herein, a "tunable regulatory region" refers to a nucleic acid sequence under direct or indirect control of a transcription factor and which is capable of activating, repressing, derepressing, or otherwise controlling gene expression relative to levels of an inducer. In some embodiments, the tunable regulatory region comprises a promoter sequence. The inducer may be RNS, or other inducer described herein, and the tunable regulatory region may be a RNS-responsive regulatory region or other responsive regulatory region described herein. The tunable regulatory region may be operatively linked to a gene sequence(s) or gene cassette for the production of one or more payloads, e.g., a butyrogenic or other gene cassette or gene sequence(s). For example, in one specific embodiment, the tunable regulatory region is a RNS-derepressible regulatory region, and when RNS is present, a RNS-sensing transcription factor no longer binds to and/or represses the regulatory region, thereby permitting expression of the operatively linked gene or gene cassette. In this instance, the tunable regulatory region derepresses gene or gene cassette expression relative to RNS levels. Each gene or gene cassette may be operatively linked to a tunable regulatory region that is directly or indirectly controlled by a transcription factor that is capable of sensing at least one RNS.

In some embodiments, the exogenous environmental conditions are the presence or absence of reactive oxygen species (ROS). In other embodiments, the exogenous environmental conditions are the presence or absence of reactive nitrogen species (RNS). In some embodiments, exogenous environmental conditions are biological molecules that are involved in the inflammatory response, for example, molecules present in an inflammatory disorder of the gut. In some embodiments, the exogenous environmental conditions or signals exist naturally or are naturally absent in the environment in which the recombinant bacterial cell resides. In some embodiments, the exogenous environmental conditions or signals are artificially created, for example, by the creation or removal of biological conditions and/or the administration or removal of biological molecules.

In some embodiments, the exogenous environmental condition(s) and/or signal(s) stimulates the activity of an inducible promoter. In some embodiments, the exogenous environmental condition(s) and/or signal(s) that serves to activate the inducible promoter is not naturally present within the gut of a mammal. In some embodiments, the inducible promoter is stimulated by a molecule or metabolite that is administered in combination with the pharmaceutical composition of the disclosure, for example, tetracycline, arabinose, or any biological molecule that serves to activate an inducible promoter. In some embodiments, the exogenous environmental condition(s) and/or signal(s) is added to culture media comprising a recombinant bacterial cell of the disclosure. In some embodiments, the exogenous environmental condition that serves to activate the inducible promoter is naturally present within the gut of a mammal (for example, low oxygen or anaerobic conditions, or biological molecules involved in an inflammatory response). In some embodiments, the loss of exposure to an exogenous environmental condition (for example, in vivo) inhibits the activity of an inducible promoter, as the exogenous environmental condition is not present to induce the promoter (for example, an aerobic environment outside the gut). As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the bacterium, wherein one or more copies of the regulatory region, promoter, gene, and/or gene cassette may be mutated or otherwise altered as described herein. In some embodiments, the genetically engineered bacteria are engineered to comprise multiple copies of the same regulatory region, promoter, gene, and/or gene cassette in order to enhance copy number or to comprise multiple different components of a gene cassette performing multiple different functions. In some embodiments, the genetically engineered bacteria of the invention comprise a gene encoding a effector molecule (e.g. PME) that is operably linked to a directly or indirectly inducible promoter that is not associated with said gene in nature, e.g., an FNR promoter operably linked to a gene encoding an effector molecule or a ParaBAD promoter operably linked to a second effector molecule.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* r promoter (e.g., promoter veg (BBa_K143013), promoter 43 (BBa_K143013), $P_{liaG}$ (BBa_K823000), $P_{kepA}$ (BBa_K823002), $P_{veg}$ (BBa_K823003)), a constitutive *Bacillus subtilis* e promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), a bacteriophage SP6 promoter (e.g., SP6 promoter (BBa_J64998)), and functional fragments thereof.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

In some embodiments, the genetically engineered bacteria are active (e.g., express one or more payloads (e.g. PME(s)) in the gut. In some embodiments, the genetically engineered bacteria are active (e.g., express one or more payloads) in the large intestine. In some embodiments, the genetically engineered bacteria are active (e.g., express one or more payloads) in the small intestine. In some embodiments, the genetically engineered bacteria are active in the small intestine and in the large intestine. Without wishing to be bound by theory, phenylalanine degradation may be every effective in the small intestine, because amino acid absorption, e.g., phenylalanine absorption, occurs in the small intestine. Through the prevention or reduction of phenylalanine uptake into the blood, increased levels and resulting Phe toxicity can be avoided. Additionally, extensive enterorecirculation of amino acids between the intestine and the body may allow the removal of systemic phenylalanine in PKU (e.g., described by Chang et al., in a rat model of PKU (Chang et al., A new theory of enterorecirculation of amino acids and its use for depleting unwanted amino acids using oral enzyme-artificial cells, as in removing phenylalanine in phenylketonuria; Artif Cells Blood Substit Immobil Biotechnol. 1995; 23(1):1-21)). Phenylalanine from the blood circulates into the small intestine (see, e.g., FIG. 15) and can be cleared by bacteria which are active at this location. In some embodiments, the genetically engineered bacteria transit through the small intestine. In some embodiments, the genetically engineered bacteria have increased residence time in the gut. In some embodiments, the genetically engineered bacteria colonize the small or large intestine. In some embodiments, the genetically engineered bacteria colonize the colon. In some embodiments, the genetically engineered bacteria have increased residence time in the gut. In some embodiments, the genetically engineered bacteria do not colonize the gut.

As used herein, the term "low oxygen" is meant to refer to a level, amount, or concentration of oxygen ($O_2$) that is lower than the level, amount, or concentration of oxygen that is present in the atmosphere (e.g., <21% $O_2$;<160 torr $O_{2j}$). Thus, the term "low oxygen condition or conditions" or "low oxygen environment" refers to conditions or environments containing lower levels of oxygen than are present in the atmosphere. In some embodiments, the term "low oxygen" is meant to refer to the level, amount, or concentration of oxygen ($O_2$) found in a mammalian gut, e.g., lumen, stomach, small intestine, duodenum, jejunum, ileum, large intestine, cecum, colon, distal sigmoid colon, rectum, and anal canal. In some embodiments, the term "low oxygen" is meant to refer to a level, amount, or concentration of $O_2$ that is 0-60 mmHg 02 (0-60 torr $O_{2j}$ (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 mmHg $O_2$), including any and all incremental fraction(s) thereof (e.g., 0.2 mmHg, 0.5 mmHg $O_2$, 0.75 mmHg 02, 1.25 mmHg $O_2$, 2.175 mmHg $O_2$, 3.45 mmHg 02, 3.75 mmHg $O_2$, 4.5 mmHg $O_2$, 6.8 mmHg $O_2$, 11.35 mmHg O2, 46.3 mmHg $O_2$, 58.75 mmHg, etc., which exemplary fractions are listed here for illustrative purposes and not meant to be limiting in any way). In some embodiments, "low oxygen" refers to about 60 mmHg $O_2$ or less (e.g., 0 to about 60 mmHg $O_{2j}$. The term "low oxygen" may also refer to a range of $O_2$ levels, amounts, or concentrations between 0-60 mmHg $O_2$ (inclusive), e.g., 0-5 mmHg $O_2$, <1.5 mmHg $O_2$, 6-10 mmHg, <8 mmHg, 47-60 mmHg, etc. which listed exemplary ranges are listed here for illustrative purposes and not meant to be limiting in any way. See, for example, Albenberg et al., Gastroenterology, 147(5): 1055-1063 (2014); Bergofsky et al., J Clin. Invest., 41(11): 1971-1980 (1962); Crompton et al., J Exp. Biol., 43: 473-478 (1965); He et al., PNAS (USA), 96: 4586-4591 (1999); McKeown, Br. J. Radiol., 87:20130676 (2014) (doi: 10.1259/brj.20130676), each of which discusses the oxygen levels found in the mammalian gut of various species and each of which are incorporated by reference herewith in their entireties. In some embodiments, the term "low oxygen" is meant to refer to the level, amount, or concentration of oxygen ($O_2$) found in a mammalian organ or tissue other than the gut, e.g., urogenital tract, tumor tissue, etc. in which oxygen is present at a reduced level, e.g., at a hypoxic or anoxic level. In some embodiments, "low oxygen" is meant to refer to the level, amount, or concentration of oxygen ($O_2$) present in partially aerobic, semi aerobic, microaerobic, nanoaerobic, microoxic, hypoxic, anoxic, and/or anaerobic conditions. For example, Table A summarizes the amount of oxygen present in various organs and tissues. In some embodiments, the level, amount, or concentration of oxygen ($O_2$) is expressed as the amount of dissolved oxygen ("DO") which refers to the level of free, non-compound oxygen ($O_2$) present in liquids and is typically reported in milligrams per liter (mg/L), parts per million (ppm; 1 mg/L=1 ppm), or in micromoles (umole) (1 umole $O_2$=0.022391 mg/L $O_2$). Fondriest Environmental, Inc., "Dissolved Oxygen", Fundamentals of Environmental Measurements, 19 Nov. 2013, www.fondriest.com/environmental-measurements/parameters/water-quality/dissolved-oxygen/>. In some embodiments, the term "low oxygen" is meant to refer to a level, amount, or concentration of oxygen ($O_2$) that is about 6.0 mg/L DO or less, e.g., 6.0 mg/L, 5.0 mg/L, 4.0 mg/L, 3.0 mg/L, 2.0 mg/L, 1.0 mg/L, or 0 mg/L, and any fraction therein, e.g., 3.25 mg/L, 2.5 mg/L, 1.75 mg/L, 1.5 mg/L, 1.25 mg/L, 0.9 mg/L, 0.8 mg/L, 0.7 mg/L, 0.6 mg/L, 0.5 mg/L, 0.4 mg/L, 0.3 mg/L, 0.2 mg/L and 0.1 mg/L DO, which exemplary fractions are listed here for illustrative purposes and not meant to be limiting in any way. The level of oxygen in a liquid or solution may also be reported as a percentage of air saturation or as a percentage of oxygen saturation (the ratio of the concentration of dissolved oxygen ($O_2$) in the solution to the maximum amount of oxygen that will dissolve in the solution at a certain temperature, pressure, and salinity under stable equilibrium). Well-aerated solutions (e.g., solutions subjected to mixing and/or stirring) without oxygen producers or consumers are 100% air saturated. In some embodiments, the term "low oxygen" is meant to refer to 40% air saturation or less, e.g., 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, and 0% air saturation, including any and all incremental fraction(s) thereof (e.g., 30.25%, 22.70%, 15.5%, 7.7%, 5.0%, 2.8%, 2.0%, 1.65%, 1.0%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of air saturation levels between 0-40%, inclusive (e.g., 0-5%, 0.05-0.1%, 0.1-0.2%, 0.1-0.5%, 0.5-2.0%, 0-10%, 5-10%, 10-15%, 15-20%, 20-25%, 25-30%, etc.). The exemplary fractions and ranges listed here are for illustrative purposes and not meant to be limiting in any way. In some embodiments, the term "low oxygen" is meant to refer to 9% $O_2$ saturation or less, e.g., 9%, 8%, 7%, 6%, 5%, 4%, 3%, 2%, 1%, 0%, $O_2$ saturation, including any and all incremental fraction(s) thereof (e.g., 6.5%, 5.0%, 2.2%, 1.7%, 1.4%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of $O_2$ saturation levels between 0-9%, inclusive (e.g., 0-5%, 0.05-0.1%, 0.1-0.2%, 0.1-0.5%, 0.5-2.0%, 0-8%, 5-7%, 0.3-4.2% $O_2$, etc.). The exemplary fractions and ranges listed here are for illustrative purposes and not meant to be limiting in any way.

TABLE A

Intestinal Oxygen Tension

| Compartment | Oxygen Tension |
| --- | --- |
| stomach | ~60 torr (e.g., 58 +/− 15 torr) |
| duodenum and first part of jejunum | ~30 torr (e.g., 32 +/− 8 torr); ~20% oxygen in ambient air |
| Ileum (mid- small intestine) | ~10 torr; ~6% oxygen in ambient air (e.g., 11 +/− 3 torr) |
| Distal sigmoid colon | ~3 torr (e.g., 3 +/− 1 torr) |
| colon | <2 torr |
| Lumen of cecum | <1 torr |
| tumor | <32 torr (most tumors are <15 torr) |

In some embodiments, a promoter described herein is directly or indirectly induced by conditions in a culture vessel (e.g., a flask or a fermenter or other appropriate culture vessel), in which the strain is grown or maintained prior to in vivo administration. Non-limiting examples of such conditions which are provided during culture of the strain prior to in vivo administration include low oxygen, anaerobic, microaerobic, or aerobic conditions, other defined oxygen levels (such as those exemplified below), presence of arabinose, presence of IPTG, rhamnose or other chemical and/or nutritional inducers described herein or known in the art. In some embodiments, the conditions in a culture vessel are set at certain oxygen levels, e.g., between 1% and 10% oxygen, between 10% and 20% oxygen, between 20% and 30% oxygen, between 30% and 40% oxygen, between 40% and 50% oxygen, between 60% and 70% oxygen, between 70% and 80% oxygen, between 80% and 90% oxygen, between 90% and 100% oxygen, and other levels of oxygen as described herein, at which point the promoter is directly or indirectly induced.

As used herein, the term "gene" or "gene sequence" is meant to refer to a genetic sequence, e.g., a nucleic acid sequence. The gene, gene sequence or genetic sequence is meant to include a complete gene sequence or a partial gene sequence. The gene, gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, yeast, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia, Lactobacillus, Lactococcus, Saccharomyces,* and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis,* and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human Some species, strains, and/or subtypes of non-pathogenic bacteria are currently recognized as probiotic. Examples of probiotic bacteria include, but are not limited to, *Bifidobacteria, Escherichia, Lactobacillus,* and *Saccharomyces*, e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum,* and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stably maintained" or "stable" bacterium is used to refer to a bacterial host cell carrying non-native genetic material, e.g., a gene encoding an effector molecule, which is incorporated into the host genome or propagated on a self-replicating extra-chromosomal plasmid, such that the non-native genetic material is retained, expressed, and/or propagated. The stable bacterium is capable of survival and/or growth in vitro, e.g., in medium, and/or in vivo, e.g., in the gut. For example, the stable bacterium may be a genetically modified bacterium comprising a gene encoding an effector molecule (e.g., a PAL), in which the plasmid or chromosome carrying the effector gene is stably maintained in the host cell, such that the effector can be expressed in the host cell, and the host cell is capable of survival and/or growth in vitro and/or in vivo. In some embodiments, copy number affects the stability of expression of the non-native genetic material, e.g. a PAL gene. In some embodiments, copy number affects the level of expression of the non-native genetic material, e.g. a PAL gene or a PAH gene.

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. Treating a disease, disorder, or condition may encompass reducing or eliminating an associated symptom without necessarily encompassing the elimination of the underlying disease. For example, primary hyperphenylalaninemia is caused by inborn genetic mutations for which there are no known cures. Hyperphenylalaninemia can also be secondary to other conditions, e.g., liver diseases. Treating hyperphenylalaninemia may encompass reducing or eliminating excess phenylalanine and/or associated symptoms, and does not necessarily encompass the elimination of the underlying disease. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition. A therapeutically effective amount may, for example, be sufficient to treat, prevent, reduce the severity, delay the onset, and/or reduce the risk of occurrence of one or more symptoms of a disease or condition. A therapeutically effective amount, as well as a therapeutically effective frequency of administration, can be determined by methods known in the art and discussed below.

As used herein, the term "antibody" or "antibodies" is meant to encompasses all variations of antibody and fragments thereof that possess one or more particular binding specificities. Thus, the term "antibody" or "antibodies" is meant to include full length antibodies, chimeric antibodies, humanized antibodies, single chain antibodies (ScFv, camelids), Fab, Fab', multimeric versions of these fragments (e.g., F(ab')2), single domain antibodies (sdAB, $V_HH$ fragments), heavy chain antibodies (HCAb), nanobodies, diabodies, and minibodies. Antibodies can have more than one binding specificity, e.g. be bispecific. The term "antibody" is also meant to include so-called antibody mimetics. Antibody mimetics refers to small molecules, e.g., 3-30 kDa, which can be single amino acid chain molecules, which can specifically bind antigens but do not have an antibody-related structure. Antibody mimetics, include, but are not limited to, Affibody molecules (Z domain of Protein A), Affilins (Gamma-B crystalline), Ubiquitin, Affimers (Cystatin), Affitins (Sac7d (from *Sulfolobus acidocaldarius*), Alphabodies (Triple helix coiled coil), Anticalins (Lipocalins), Avimers (domains of various membrane receptors), DARPins (Ankyrin repeat motif), Fynomers (SH3 domain of Fyn), Kunitz domain peptides Kunitz domains of various protease inhibitors), Ecallantide (Kalbitor), and Monobodies. In certain aspects, the term "antibody" or "antibodies" is meant to refer to a single chain antibody(ies), single domain antibody(ies), and camelid antibody(ies). Utility of antibodies in the treatment of cancer and additional anti cancer antibodies can for example be found in Scott et al., Antibody Therapy for Cancer, Nature Reviews Cancer April 2012 Volume 12, incorporated by reference in its entirety.

A "single-chain antibody" or "single-chain antibodies" typically refers to a peptide comprising a heavy chain of an immunoglobulin, a light chain of an immunoglobulin, and optionally a linker or bond, such as a disulfide bond. The single-chain antibody lacks the constant Fc region found in traditional antibodies. In some embodiments, the single-chain antibody is a naturally occurring single-chain antibody, e.g., a camelid antibody. In some embodiments, the single-chain antibody is a synthetic, engineered, or modified single-chain antibody. In some embodiments, the single-chain antibody is capable of retaining substantially the same antigen specificity as compared to the original immunoglobulin despite the addition of a linker and the removal of the constant regions. In some aspects, the single chain antibody can be a "scFv antibody", which refers to a fusion protein of the variable regions of the heavy (VH) and light chains (VL) of immunoglobulins (without any constant regions), optionally connected with a short linker peptide of ten to about 25 amino acids, as described, for example, in U.S. Pat. No. 4,946,778, the contents of which is herein incorporated by reference in its entirety. The Fv fragment is the smallest fragment that holds a binding site of an antibody, which binding site may, in some aspects, maintain the specificity of the original antibody. Techniques for the production of single chain antibodies are described in U.S. Pat. No. 4,946,778. The Vh and VL sequences of the scFv can be connected via the N-terminus of the VH connecting to the C-terminus of the VL or via the C-terminus of the VH connecting to the N-terminus of the VL. ScFv fragments are independent folding entities that can be fused indistinctively on either end to other epitope tags or protein domains. Linkers of varying length can be used to link the Vh and VL sequences, which the linkers can be glycine rich (provides flexibility) and serine or threonine rich (increases solubility). Short linkers may prevent association of the two domains and can result in multimers (diabodies, tribodies, etc.). Long linkers may result in proteolysis or weak domain association (described in Voelkel et al el., 2011). Linkers of length between 15 and 20 amino acids or 18 and 20 amino acids are most often used. Additional non-limiting examples of linkers, including other flexible linkers are described in Chen et al., 2013 (Adv Drug Deliv Rev. 2013 Oct. 15; 65(10): 1357-1369. Fusion Protein Linkers: Property, Design and Functionality), the contents of which is herein incorporated by reference in its entirety. Flexible linkers are also rich in small or polar amino acids such as Glycine and Serine, but can contain additional amino acids such as Threonine and Alanine to maintain flexibility, as well as polar amino acids such as Lysine and Glutamate to improve solubility. Exemplary linkers include, but are not limited to, (Gly-Gly-Gly-Gly-Ser)n, KESGSVSSEQLAQFRSLD and EGKSSGSGS-ESKST, (Gly)8, and Gly and Ser rich flexible linker, GSAGSAAGSGEF. "Single chain antibodies" as used herein also include single-domain antibodies, which include camelid antibodies and other heavy chain antibodies, light chain antibodies, including nanobodies and single domains VH or VL domains derived from human, mouse or other species. Single domain antibodies may be derived from any species including, but not limited to mouse, human, camel, llama, fish, shark, goat, rabbit, and bovine. Single domain antibodies include domain antigen-binding units which have a camelid scaffold, derived from camels, llamas, or alpacas. Camelids produce functional antibodies devoid of light chains. The heavy chain variable (VH) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies. Camelid scaffold-based antibodies can be produced using methods well known in the art. Cartilaginous fishes also have heavy-chain antibodies (IgNAR, 'immunoglobulin new antigen receptor'), from which single-domain antibodies called VNAR fragments can be obtained. Alternatively, the dimeric variable domains from IgG from humans or mice can be split into monomers. Nanobodies are single chain antibodies derived from light chains. The term "single chain antibody" also refers to antibody mimetics.

In some embodiments, the antibodies expressed by the engineered microorganisms are bispecific. In certain embodiments, a bispecific antibody molecule comprises a scFv, or fragment thereof, have binding specificity for a first epitope and a scFv, or fragment thereof, have binding specificity for a second epitope. Antigen-binding fragments or antibody portions include bivalent scFv (diabody), bispecific scFv antibodies where the antibody molecule recognizes two different epitopes, single binding domains (dAbs), and minibodies. Monomeric single-chain diabodies (scDb) are readily assembled in bacterial and mammalian cells and show improved stability under physiological conditions (Voelkel et al., 2001 and references therein; Protein Eng. (2001) 14 (10): 815-823 (describes optimized linker sequences for the expression of monomeric and dimeric bispecific single-chain diabodies).

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations. are referred to as unfolded. The term "peptide" or "polypeptide" may refer to an amino acid sequence that corresponds to a protein or a portion of a protein or may refer to an amino acid sequence that corresponds with non-protein sequence, a sequence selected from a regulatory peptide sequence, leader peptide sequence, signal peptide sequence, linker peptide sequence, and other peptide sequence.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins, Typically, fusion proteins result from well known in vitro recombination techniques. Fusion proteins may have a similar structural function (hut not necessarily to the same extent and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos. EMBO J. 8 (1989), 779-785. For example, amino acids belonging to one of the following groups represent conservative changes or substitutions: -Ala, Pro, Gly, Gin, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45% at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96 at least about 97 at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein the term "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. The term "codon-optimized" refers to the modification of codons in the gene or coding regions of a nucleic acid molecule to reflect the typical codon usage of the host organism without altering the polypeptide encoded by the nucleic acid molecule. Such optimization includes replacing at least one, or more than one, or a significant number, of codons with one or more codons that are more frequently used in the genes of the host organism. A "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. In some embodiments, the improvement of transcription and/or translation involves increasing the level of transcription and/or translation. In some embodiments, the improvement of transcription and/or translation involves decreasing the level of transcription and/or translation. In some embodiments, codon optimization is used to fine-tune the levels of expression from a construct of interest. Codon optimization includes, but is not limited to, processes including selecting codons for the coding sequence to suit the codon preference of the expression host organism. Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent, inter alia, on the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, the terms "secretion system" or "secretion protein" refers to a native or non-native secretion mechanism capable of secreting or exporting the protein(s) of interest or therapeutic protein(s) from the microbial, e.g., bacterial cytoplasm. The secretion system may comprise a single protein or may comprise two or more proteins assembled in a complex e.g., HlyBD. Non-limiting examples of secretion systems for gram negative bacteria include the modified type III flagellar, type I (e.g., hemolysin secretion system), type II, type IV, type V, type VI, and type VII secretion systems, resistance-nodulation-division (RND) multi-drug efflux pumps, various single membrane secretion systems. Non-liming examples of secretion systems for gram positive bacteria include Sec and TAT secretion systems. In some embodiments, the proteins of interest include a "secretion tag" of either RNA or peptide origin to direct the protein(s) of interest or therapeutic protein(s) to specific secretion systems. In some embodiments, the secretion system is able to remove this tag before secreting the protein(s) of interest from the engineered bacteria. For example, in Type V auto-secretion-mediated secretion the N-terminal peptide secretion tag is removed upon translocation of the "passenger" peptide from the cytoplasm into the periplasmic compartment by the native Sec system.

Further, once the auto-secretor is translocated across the outer membrane the C-terminal secretion tag can be removed by either an autocatalytic or protease-catalyzed e.g., OmpT cleavage thereby releasing the protein(s) of interest into the extracellular milieu.]]

As used herein, the term "transporter" is meant to refer to a mechanism, e.g., protein or proteins, for importing a molecule, e.g., amino acid, toxin, metabolite, substrate, etc. into the microorganism from the extracellular milieu. For example, a phenylalanine transporter such as PheP imports phenylalanine into the microorganism.

Effectors also include immune checkpoint inhibitors. An "immune checkpoint inhibitor" or "immune checkpoint" refers to a molecule that completely or partially reduces, inhibits, interferes with, or modulates one or more immune checkpoint proteins Immune checkpoint proteins regulate T-cell activation or function, and are known in the art. Non-limiting examples include CTLA-4 and its ligands CD 80 and CD86, and PD-1 and its ligands PD-L1 and PD-L2 Immune checkpoint proteins are responsible for co-stimulatory or inhibitory interactions of T-cell responses, and regulate and maintain self-tolerance and physiological immune responses. Systemic immunotherapy, e.g., using CTLA-4 inhibitors, may alter immunoregulation, provoke immune dysfunction, and result in opportunistic autoimmune disorders (see, e.g., Kong et al., 2014).

As used herein, a genetically engineered microorganism, e.g., engineered bacterium or phage, or molecule that "inhibits" a biological molecule refers to a bacterium or virus or molecule that is capable of reducing, decreasing, or eliminating the biological activity, biological function, and/or number of that biological molecule, as compared to control, e.g., an untreated control or an unmodified microorganism of the same subtype under the same conditions.

As used herein, a genetically engineered microorganism, e.g., engineered bacterium or phage molecule that "activates" or "stimulates" a biological molecule, refers to a bacterium or phage molecule that is capable of activating, increasing, enhancing, or promoting the biological activity, biological function, and/or number of that biological molecule, as compared to control, e.g., an untreated control or an unmodified microorganism of the same subtype under the same conditions.

The terms "phage" and "bacteriophage" are used interchangeably herein. Both terms refer to a virus that infects and replicates within a bacterium. As used herein "phage" or bacteriophage" collectively refers to prophage, lysogenic, dormant, temperate, intact, defective, cryptic, and satellite phage, phage tail bacteriocins, tailiocins, and gene transfer agents.

As used therein the term "prophage" refers to the genomic material of a bacteriophage, which is integrated into a replicon of the host cell and replicates along with the host. The prophage may be able to produce phages if specifically activated. In some cases, the prophage is not able to produce phages or has never done so (i.e., defective or cryptic prophages). In some cases, prophage also refers to satellite phages. The terms "prophage" and "endogenous phage" are used interchangeably herein.

As used herein, the term "temperate phage" or "temperate bacteriophage" or "prophage" are used interchangeably to refer to a phage which exists within the DNA of the bacterial host and replicate along with the host during the bacterial replication cycle and cell division.

As used herein the term "natural state" of a bacterium or organism or "native state" of a bacterium or refers to an organism which has not been modified by genetic engineering. In some cases, the term "natural state" of a bacterium or organism or "native state" of a bacterium refers to an organism which has not been modified by genetic engineering as compared to an isogenic strain that has been modified with respect to a defined element. As such, the bacterium may be in its natural state with respect to one defined element, but not in its natural state with respect to another defined element. In some embodiments, a bacterium may comprise one or more of the same or different phage(s) or prophage(s) in its natural or native state. In some embodiments, a bacterium, which in its native or natural state comprises one or more of the same or different types of phages or prophages, serves a progenitor strain for an engineered strain. Consequently, the same one or more endogenous phage(s) or prophage(s) may also be present in a genetically engineered bacterium, e.g., if the progenitor or parental strain contained such an endogenous phage or prophage in its native state. As such the genetically engineered bacterium also contains the prophage in its natural state (wherein the phage is the defined element that is in its natural state).

"Endogenous phage" or "endogenous prophage" also refers to a phage that is present in the natural state of a bacterium (and its parental strain).

As used herein the term "phage knockout" or "inactivated phage" refers to a phage which has been modified so that it can either no longer produce and/or package phage particles or it produces fewer phage particles than the wild type phage sequence. In some embodiments, the inactivated phage or phage knockout refers to the inactivation of a temperate phage in its lysogenic state, i.e., to a prophage. Such a modification refers to a mutation in the phage; such mutations include insertions, deletions (partial or complete deletion of phage genome), substitutions, inversions, at one or more positions within the phage genome, e.g., within one or more genes within the phage genome.

As used herein the term "isogenic" bacterial strains refers to bacterial strains that are genetically identical or that contain defined changes but are otherwise identical. For example, isogenic mutants typically refers to two strains that are identical except that one contains a defined mutation in one or more known genes or proteins. As such, a phage free or phage less strain has a corresponding isogenic strain which contains prophage which can be induced and release phage particles from the bacterial cell.

As used herein the adjectives "phage-free", "phage free" and "phageless" are used interchangeably to characterize a bacterium or strain which contains one or more prophages, one or more of which have been modified. The modification can result in a loss of the ability of the prophage to be induced or release phage particles. Alternatively, the modification can result in less efficient or less frequent induction or less efficient or less frequent phage release as compared to the isogenic strain without the modification. Ability to induce and release phage can be measured using a plaque assay as described herein.

As used herein, the term "lysogen" refers to a bacterium containing a prophage, which is in the lysogenic cycle, in which the phage genes required for lysis are not expressed.

As used herein phage induction refers to the part of the life cycle of a lysogenic prophage, in which the lytic phage genes are activated, phage particles are produced and lysis occurs.

As used herein, the term induction refers to the conversion of a lysogenic infection into a productive infection, i.e., the induced prophage initiates the production and release of phage particles. Induction often is stimulated by damage to bacterial DNA, and may or may not involve excision of the prophage from the bacterial chromosome.

In some embodiments, the genetically engineered bacteria are useful for the treatment, prevention, management, reduction in severity of, amelioration, cure a disorder, disease or condition. In some embodiments, the disorder is an autoimmune disorder. As used herein, "autoimmune disorders" include, but are not limited to, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, asthma, ulcerative colitis, undifferentiated connective tissue disease (UCTD), uveitis, vasculitis, vesiculobullous dermatosis, vitiligo, and Wegener's granulomatosis. In some embodiments, the disorder is graft vs host disease.

In some embodiments, the disease is a metabolic disease. As used herein, "metabolic diseases" include, but are not limited to, type 1 diabetes; type 2 diabetes; metabolic syndrome; Bardet-Biedel syndrome; Prader-Willi syndrome; non-alcoholic fatty liver disease; tuberous sclerosis; Albright hereditary osteodystrophy; brain-derived neurotrophic factor (BDNF) deficiency; Single-minded 1 (SIM1) deficiency; leptin deficiency; leptin receptor deficiency; pro-opiomelanocortin (POMC) defects; proprotein convertase subtilisin/kexin type 1 (PCSK1) deficiency; Src homology 2B1 (SH2B1) deficiency; pro-hormone convertase 1/3 deficiency; melanocortin-4-receptor (MC4R) deficiency; Wilms tumor, aniridia, genitourinary anomalies, and mental retardation (WAGR) syndrome; pseudohypoparathyroidism type 1A; Fragile X syndrome; Borjeson-Forsmann-Lehmann syndrome; Alstrom syndrome; Cohen syndrome; and ulnar-mammary syndrome.

In some embodiments, the disorder is cancer. "Cancer" or "cancerous" is used to refer to a physiological condition that is characterized by unregulated cell growth. In some embodiments, cancer refers to a tumor. "Tumor" is used to refer to any neoplastic cell growth or proliferation or any pre-cancerous or cancerous cell or tissue. A tumor may be malignant or benign. Types of cancer include, but are not limited to, adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, gestational trophoblastic disease, heart cancer, Kaposi sarcoma, kidney cancer, largyngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer, lymphoma (e.g., AIDS-related lymphoma, Burkitt lymphoma, cutaneous T cell lymphoma, Hodgkin lymphoma, Non-Hodgkin lymphoma, primary central nervous system lymphoma), malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), small intestine cancer, stomach cancer, teratoid tumor, testicular cancer, throat cancer, thymus cancer, thyroid cancer, unusual childhood cancers, urethral cancer, uterine cancer, uterine sarcoma, vaginal cancer, vulvar cancer, Waldenström macrogloblulinemia, and Wilms tumor. Side effects of cancer treatment may include, but are not limited to, opportunistic autoimmune disorder(s), systemic toxicity, anemia, loss of appetite, irritation of bladder lining, bleeding and bruising (thrombocytopenia), changes in taste or smell, constipation, diarrhea, dry mouth, dysphagia, edema, fatigue, hair loss (alopecia), infection, infertility, lymphedema, mouth sores, nausea, pain, peripheral neuropathy, tooth decay, urinary tract infections, and/or problems with memory and concentration (National Cancer Institute). In some embodiments, the disorder is a hyperammonemia disorder.

In some embodiments, the disorders are rare diseases, including but not limited to, hyperammonemia, ureacycle disorders, propionic acidemia, methylmalonic acidemia, maplesyrup urine disease, isovaleric acidemia, hyperoxaluria, phenylketonurea.

Exemplary circuitry for the treatment, prevention, reduction in severity, management, amelioration, cure of one or more of the disorders described above are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072. the contents of which are herein incorporated by reference in their entireties.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Bacteria

In some embodiments, the bacteria disclosed herein contain one or more mutations or modifications to an endogenous phage genome. In some embodiments, the bacterium comprises the bacteriophage in its natural or native state. In some embodiments, the phage is present in all isolates of a particular bacterium. In some embodiments, the phage is present in bacteria of the same species, strain, or substrain. In some embodiments, the phage is an intact prophage. In some embodiments, the phage is a defective prophage. In some embodiments, the one or more mutations renders the phage unable to enter the lytic cycle. In some embodiments, the one or more mutations affect the ability of the phage to undergo the lytic cycle, e.g., reduce the frequency or reduce the number of bacteria in a given population that can undergo the lytic stage. In some embodiments, the one or more mutations prevent the phage from infecting other bacteria. In some embodiments, the one or more mutations alters, e.g., increases or reduces, bacterial fitness. In some embodiments, the one or more mutations alters e.g., increases or reduces, effector function. In some embodiments, the one or more mutations do not alter bacterial fitness. In some embodiments, the one or more mutations do not alter effector function. In some embodiments, the one or more mutations improve the process by which the bacteria is manufactured or produced, including large-scale manufacturing. In any of these embodiments, the bacterium may otherwise be in its natural state. Alternatively, in any of these embodiments, the bacteria may be further genetically engineered to include gene sequence encoding one or more effector molecules.

In some embodiments, a bacterium comprising one or more mutated phages can be used as a bacterial chassis, to which genetic circuitry is added or modified.

In some embodiments, the bacteria are non-pathogenic bacteria. In some embodiments, the bacteria are commensal bacteria. In some embodiments, the bacteria are probiotic bacteria. In some embodiments, the bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to, *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*. In certain embodiments, the bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri*, and *Lactococcus lactis*.

In some embodiments, the bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added). Genomic sequencing confirmed that *E. coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and is not uropathogenic (Sonnenborn et al., 2009). As early as in 1917, *E. coli* Nissle was packaged into medicinal capsules, called Mutaflor, for therapeutic use. It is commonly accepted that *E. coli* Nissle's therapeutic efficacy and safety have convincingly been proven (Ukena et al., 2007).

In some embodiments, the bacteria of the disclosure or tumor-targeting bacteria. Tumor-targeting bacteria are described are described in International Patent Application PCT/US2017/013072, filed Jan. 11, 2017, published as WO2017/123675, the contents of which is herein incorporated by reference in its entirety.

One of ordinary skill in the art would appreciate that the genetic modifications disclosed herein may be adapted for other species, strains, and subtypes of bacteria. Furthermore, genes from one or more different species can be introduced into one another, e.g., the PAL gene from Rhodosporidium toruloides can be expressed in *Escherichia coli* (Sarkissian et al., 1999).

In any of these embodiments, any of the bacterial species disclosed herein or known in the art, and which may be used according to the disclosure, contain one or more mutations or modifications to one or more endogenous phage genomes. In some embodiments, the modifications to the endogenous phage genomes comprise one or more deletion(s), insertion(s), substitution(s) or inversions(s) or combinations thereof within the phage genomes. In some embodiments, the modification(s) is one or more deletions in the phage genome(s). In some embodiments, one or more phage genes are deleted. In some embodiments, one or more phage genes are partially deleted. In some embodiments, the modification(s) is one or more insertions in the phage genome(s). In some embodiments, the insertion comprises gene sequence encoding an antibiotic cassette as described herein. In some embodiments, one or more genes in the phage genome(s) are substituted with alternate gene sequence(s). In some embodiments, the substitution comprises gene sequence encoding an antibiotic cassette. In some embodiments, the entire sequence(s) of one or more phage genes is inverted. In some embodiments a partial sequence of one or more phage genes are inverted.

Unmodified *E. coli* Nissle and the genetically engineered bacteria of the invention may be destroyed, e.g., by defense factors in the gut or blood serum (Sonnenborn et al., 2009) or by activation of a kill switch, several hours or days after administration. Thus, the genetically engineered bacteria may require continued administration. In some embodiments, the residence time is calculated for a human subject. Residence time in vivo may be calculated for the genetically engineered bacteria of the invention (see, e.g., FIG. 68 of WO2017087580, the contents of which are herein incorporated by reference in their entirety).

In some embodiments, the genetically engineered bacteria comprise a gene encoding PAL, wherein the PAL gene is operably linked to a directly or indirectly inducible promoter. In some embodiments, the bacteria comprise a non-native PAL gene. In some embodiments, the bacteria comprise additional copies of a native PAL gene. In some embodiments, the promoter is not associated with the PAL gene in nature. In some embodiments, the promoter is any one or more of the promoters disclosed herein.

In some embodiments, the genetically engineered bacteria comprise a gene encoding PAH, wherein the PAH gene is operably linked to a directly or indirectly inducible promoter. In some embodiments, the bacteria comprise a non-native PAH gene. In some embodiments, the bacteria comprise additional copies of a native PAH gene. In some embodiments, the promoter is not associated with the PAH gene in nature. In some embodiments, the promoter is any one or more of the promoters disclosed herein.

In some embodiments, the genetically engineered bacteria comprise a gene encoding LAAD, wherein the LAAD gene is operably linked to a directly or indirectly inducible promoter. In some embodiments, the bacteria comprise a non-native LAAD gene. In some embodiments, the bacteria comprise additional copies of a native LAAD gene. In some embodiments, the promoter is not associated with the LAAD gene in nature. In some embodiments, the promoter is any one or more of the promoters disclosed herein.

In some embodiments, the genetically engineered bacteria further comprise a gene encoding a phenylalanine transporter (PheP). In certain embodiments, the bacteria comprise additional copies of a native gene encoding a phenylalanine transporter, wherein the phenylalanine transporter gene is operably linked to a directly or indirectly inducible promoter. In alternate embodiments, the bacteria comprise a gene encoding a non-native phenylalanine transporter, wherein the phenylalanine transporter gene is operably linked to a directly or indirectly inducible promoter. Both embodiments are encompassed by the term "non-native" phenylalanine transporter. In some embodiments, the promoter is not associated with the pheP gene in nature. In some embodiments, the same promoter controls expression of PheP and PAL and/or PAH and/or LAAD. In some embodiments, the promoter that controls expression of PheP differs from the promoter that controls expression of PAL and/or PAH and/or LAAD. In some embodiments, the promoter that controls the expression of PheP is any one or more of the promoters disclosed herein.

In some embodiments, the promoter that is operably linked to PAL, PAH, LAAD, and/or pheP is directly or indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by exogenous environmental conditions specific to the large intestine of a mammal. In some embodiments, the promoter is directly or indirectly induced by low-oxygen or anaerobic and/or low oxygen conditions such as the environment of the mammalian gut. In some embodiments, the promoter is directly or indirectly induced by the presence of molecules or metabolites that are specific to the gut of a mammal, e.g., propionate. In some embodiments, the promoter is directly or indirectly induced by exposure to tetracycline. In some embodiments, the promoter is directly or indirectly induced by exposure to arabinose. In some embodiments, the promoter is directly or indirectly induced by exposure to IPTG. In some embodiments, the promoter is directly or indirectly induced by exposure to rhamnose or other chemical and/or nutritional inducer known in the art. In some embodiments, the promoter is directly or indirectly regulated by the exogenous environmental temperature. In some embodiments, the promoter is directly or indirectly induced by exposure to IPTG or other laI binding compound. In some embodiments, the promoter is directly or indirectly induced by exposure to rhamnose. In some embodiments, the promoter is directly or indirectly induced by increase in temperature. In some embodiments, the promoter is directly or indirectly induced by decrease in temperature. In some embodiments, the promoter is directly or indirectly induced by a molecule that is co-administered with the genetically engineered bacteria of the invention. Such a molecule may be tetracycline or IPTG or arabinose or other chemical and/or nutritional inducer known in the art.

In some embodiments, the promoter is directly or indirectly induced prior to in vivo administration. Non-limiting examples of such conditions which are provided during culture of the strain prior to in vivo administration include low oxygen, anaerobic, microaerobic, or aerobic conditions, other defined oxygen levels (such as those exemplified below), presence of arabinose, presence of IPTG, rhamnose or other chemical and/or nutritional inducers described herein or known in the art. In some embodiments, the conditions in a culture vessel are set at certain oxygen levels, e.g. between 1% and 10% oxygen, between 10% and 20% oxygen, between 20% and 30% oxygen, between 30% and 40% oxygen, between 40% and 50% oxygen, between 60% and 70% oxygen, between 70% and 80% oxygen, between 80% and 90% oxygen, between 90% and 100% oxygen, and other levels of oxygen as described herein, at which point the promoter is directly or indirectly induced.

Bacteriophages

In some embodiments, the bacteria of the disclosure comprise one or more lysogenic, dormant, temperate, intact, defective, cryptic, or satellite phage or bacteriocins/phage tail or gene transfer agents in their natural state. In some embodiments, the prophage or bacteriophage exists in all isolates of a particular bacterium of interest. In some embodiments, the bacteria are probiotic bacteria. In some embodiments, the bacteria are genetically engineered derivatives of a parental strain comprising one or more of such bacteriophage. Accordingly, such bacteria of the disclosure may be in their natural state or be further genetically modified to contain circuitry for the expression or production of one or more effector molecules. In any of the embodiments described herein, the bacteria comprise one or more modifications or mutations within a prophage or bacteriophage genome which alters the properties or behavior of the bacteriophage. In some embodiments, the modifications or mutations prevent the prophage from entering or completing the lytic process. In some embodiments, the modifications or mutations prevent the phage from infecting other bacteria of the same or a different type.

In some embodiments, the modifications or mutations alter, e.g., reduce or increase, the fitness of the bacterial host. In some embodiments, the modifications or mutations alter, e.g., reduce or increase, desired effector function, e.g., of a genetically engineered bacterium. In some embodiments, the modifications or mutations do not alter, e.g., reduce or increase, the fitness of the bacterial host. In some embodiments, the modifications or mutations do not alter, e.g., reduce or increase, desired effector function, e.g., of a genetically engineered bacterium.

Phage genome size varies enormously, ranging from the smallest *Leuconostoc* phage L5 (2,435 bp), ~11.5 kbp (e.g. *Mycoplasma* phage P1), ~21 kbp (e.g. *Lactococcus* phage c2), and ~30 kbp (e.g. *Pasteurella* phage F108) to the almost 500 kbp genome of *Bacillus megaterium* phage G (Hatfull and Hendrix; Bacteriophages and their Genomes, Curr Opin Virol. 2011 Oct. 1; 1(4): 298-303, and references therein). Phage genomes may encode less than 10 genes up to several hundreds of genes. Temperate phages or prophages are typically integrated into the chromosome(s) of the bacterial host, although some examples of phages that are integrated into bacterial plasmids also exist (Little, Loysogeny, Prophage Induction, and Lysogenic Conversion. In: Waldor M K, Friedman D I, Adhya S, editors. Phages Their Role in Bacterial Pathogenesis and Biotechnology. Washington D.C.: ASM Press; 2005. pp. 37-54). In some cases, the phages are always located at the same position within the bacterial host chromosome(s), and this position is specific to each phage, i.e., different phages are located at different positions. Other phages are more permissive in that they can integrate at numerous different locations.

Accordingly, the bacteria of the disclosure comprise one or more phages genomes which may vary in length. In one embodiment, the genetically engineered bacteria comprise a bacteriophage genome ranging in length from at least about 1 bp to 10 kb. In one embodiment, the bacteria comprise a bacteriophage genome ranging in length from at least about 1 bp to 10 kb. In one embodiment, the genetically engineered bacteria comprise a bacteriophage genome ranging in length from at least about 10 kb to 20 kb. In one embodiment, the genetically engineered bacteria comprise a bacteriophage genome ranging in length from at least about 20 kb to 30 kb. In one embodiment, the genetically engineered bacteria comprise a bacteriophage genome ranging in length from at least about 30 kb to 40 kb. In one embodiment, the genetically engineered bacteria comprise a bacteriophage genome ranging in length from at least about 30 kb to 40 kb. In one embodiment, the genetically engineered bacteria comprise a bacteriophage genome ranging in length from at least about 40 kb to 50 kb. In one embodiment, the genetically engineered bacteria comprise a bacteriophage genome ranging in length from at least about 50 kb to 60 kb. In one embodiment, the genetically engineered bacteria comprise a bacteriophage genome ranging in length from at least about 60 kb to 70 kb. In one embodiment, the genetically engineered bacteria comprise a bacteriophage genome ranging in length from at least about 70 kb to 80 kb. In one embodiment, the genetically engineered bacteria comprise a bacteriophage genome ranging in length from at least about 80 kb to 90 kb. In one embodiment, the genetically engineered bacteria comprise a bacteriophage genome ranging in length from at least about 90 kb to 100 kb. In one embodiment, the genetically engineered bacteria comprise a bacteriophage genome ranging in length from at least about 100 kb to 120 kb. In one embodiment, the genetically engineered bacteria comprise a bacteriophage genome ranging in length from at least about 120 kb to 140 kb. In one embodiment, the genetically engineered bacteria comprise a bacteriophage genome ranging in length from at least about 140 kb to 160 kb. In one embodiment, the genetically engineered bacteria comprise a bacteriophage genome ranging in length from at least about 160 kb to 180 kb. In one embodiment, the genetically engineered bacteria comprise a bacteriophage genome ranging in length from at least about 180 kb to 200 kb. In one embodiment, the genetically engineered bacteria comprise a bacteriophage genome ranging in length from at least about 200 kb to 180 kb. In one embodiment, the genetically engineered bacteria comprise a bacteriophage genome ranging in length from at least about 160 kb to 250 kb. In one embodiment, the genetically engineered bacteria comprise a bacteriophage genome ranging in length from at least about 250 kb to 300 kb. In one embodiment, the genetically engineered bacteria comprise a bacteriophage genome ranging in length from at least about 300 kb to 350 kb. In one embodiment, the genetically engineered bacteria comprise a bacteriophage genome ranging in length from at least about 350 kb to 400 kb. In one embodiment, the genetically engineered bacteria comprise a bacteriophage genome ranging in length from at least about 400 kb to 500 kb. In one embodiment, the genetically engineered bacteria comprise a bacteriophage genome ranging in length from at least about 500 kb to 1000 kb. In one embodiment, the genetically engineered bacteria comprise a bacteriophage genome greater than 1000 kb in length.

In some embodiments, the bacteria of the disclosure comprise one or more phages genomes, which comprise one or more genes encoding one or more polypeptides. In one embodiment, the genetically engineered bacteria comprise a bacteriophage genome comprising at least about 1 to 5 genes. In one embodiment, the genetically engineered bacteria comprise a bacteriophage genome comprising at least about 5 to 10 genes. In one embodiment, the genetically engineered bacteria comprise a bacteriophage genome comprising at least about 10 to 15 genes. In one embodiment, the genetically engineered bacteria comprise a bacteriophage genome comprising at least about 15 to 20 genes. In one embodiment, the genetically engineered bacteria comprise a bacteriophage genome comprising at least about 20 to 25 genes. In one embodiment, the genetically engineered bacteria comprise a bacteriophage genome comprising at least about 25 to 30 genes. In one embodiment, the genetically engineered bacteria comprise a bacteriophage genome comprising at least about 30 to 35 genes. In one embodiment, the genetically engineered bacteria comprise a bacteriophage genome comprising at least about 35 to 40 genes. In one embodiment, the genetically engineered bacteria comprise a bacteriophage genome comprising at least about 40 to 45 genes. In one embodiment, the genetically engineered bacteria comprise a bacteriophage genome comprising at least about 45 to 50 genes. In one embodiment, the genetically engineered bacteria comprise a bacteriophage genome comprising at least about 50 to 55 genes. In one embodiment, the genetically engineered bacteria comprise a bacteriophage genome comprising at least about 55 to 60 genes. In one embodiment, the genetically engineered bacteria comprise a bacteriophage genome comprising at least about 60 to 65 genes. In one embodiment, the genetically engineered bacteria comprise a bacteriophage genome comprising at least about 65 to 70 genes. In one embodiment, the genetically engineered bacteria comprise a bacteriophage genome comprising at least about 70 to 75 genes. In one embodiment, the genetically engineered bacteria comprise a bacteriophage genome comprising at least about 75 to 80 genes. In one embodiment, the genetically engineered bacteria comprise a bacteriophage genome comprising at least about 80 to 85 genes. In one embodiment, the genetically engineered bacteria comprise a bacteriophage genome comprising at least about 85 to 90 genes. In one embodiment, the genetically engineered bacteria comprise a bacteriophage genome comprising at least about 90 to 95 genes. In one embodiment, the genetically engineered bacteria comprise a bacteriophage genome comprising at least about 95 to 100 genes. In one embodiment, the genetically engineered bacteria comprise a bacteriophage genome comprising at least about 100 to 115 genes. In one embodiment, the genetically engineered bacteria comprise a bacteriophage genome comprising at least about 115 to 120 genes. In one embodiment, the genetically engineered bacteria comprise a bacteriophage genome comprising at least about 120 to 125 genes. In one embodiment, the genetically engineered bacteria comprise a bacteriophage genome comprising at least about 125 to 130 genes. In one embodiment, the genetically engineered bacteria comprise a bacteriophage genome comprising at least about 130 to 135 genes. In one embodiment, the genetically engineered bacteria comprise a bacteriophage genome comprising at least about 135 to 140 genes. In one embodiment, the genetically engineered bacteria comprise a bacteriophage genome comprising at least about 140 to 145 genes. In one embodiment, the genetically engineered bacteria comprise a bacteriophage genome comprising at least about 145 to 150 genes. In one embodiment, the genetically engineered bacteria comprise a bacteriophage genome comprising at least about 150 to 160 genes. In one embodiment, the genetically engineered bacteria comprise a bacteriophage genome comprising at least about 160 to 170 genes. In one embodiment, the genetically engineered bacteria comprise a bacteriophage genome comprising at least about 170 to 180 genes. In one embodiment, the genetically engineered bacteria comprise a bacteriophage genome comprising at least about 180 to 190 genes. In one embodiment, the genetically engineered bacteria comprise a bacteriophage genome comprising at least about 190 to 200 genes. In one embodiment, the genetically engineered bacteria comprise a bacteriophage genome comprising at least about 200 to 300 genes. In one embodiment, the genetically engineered bacteria comprise a bacteriophage genome comprising more than about 300 genes.

In some embodiments, the phage is always or almost always located at the same location or position within the bacterial host chromosome(s) in a particular species. In some embodiments, the phages are found integrated at different locations within the host chromosome in a particular species. In some embodiments, the phage is located on a plasmid.

The presence of prophage sequences may also confer certain properties to the bacteria which are not present in an isogenic strain without the phage. For example, the prophage may in some cases allow bacteria to acquire antibiotic resistance, to exist in new environmental niches, to improve adhesion or to become pathogenic. Additionally, through the lytic process, DNA from one bacterium can be picked up and released in another bacterium, and phages therefore function as a vehicle for gene transfer.

Accordingly, in some embodiments, the bacteria comprise a phage which bestows antibiotic resistance to the bacterium. In some embodiments, the bacteria comprise a phage which bestows additional fitness to the bacterium. In some embodiments, the bacteria comprise a phage which bestows ability to grow in new environments to the bacterium. In some embodiments, the bacteria comprise a phage which bestows the ability to transfer host genetic material to another bacterium of the same or different species.

In some embodiments, the prophage may be a defective or a cryptic prophage. Defective prophages can no longer undergo a lytic cycle. Cryptic prophages may not be able to undergo a lytic cycle or never have undergone a lytic cycle. Functional studies of the full repertoire of prophages of bacterial genomes suggest that the majority of prophages are defective at some level: excision, virion formation, lysis, or infective ability (Bobay et al., 2014). Defective or cryptic prophages accrue to a high level of abundancy in many bacteria as a result of mutational decay and/or the loss of one or more genes essential to the lytic cycle over thousands of bacterial replication cycles. (Bobay et al., Pervasive domestication of defective prohages by bacteria, Proc Natl Acad Sci USA.). Of note, defective prophages often also contain a number of genes that can provide adaptive or advantageous functionality to the host, including genes encoding proteins with homologous recombination functions, mechanisms for prevention of further infection, or bacteriocins, which may be helpful in competition for nutrients, e.g., through growth inhibition of other neighboring bacterial species. For example, several defective prophages have been characterized in *E. coli* K-12 (e.g., Rac, e14, DLP12, and QIN) and in *Bacillus subtilis* (e.g., 186 and SKIN) (Casjens, 2001, and references therein). Each of these phage harbors some functional genes. For example, Rac encodes the RecE homologous recombination system.

Accordingly, in some embodiments, the bacteria comprise one or more defective or cryptic prophages. In some embodiments, the prophage genes confer homologous recombination functions. In some embodiments, the prophage genes confer the ability to prevent further infection. In some embodiments, the prophage genes confer bacteriocins. IN some embodiments, the phage genes promote growth under adverse conditions by increasing carbon utilization, improving resistance to osmotic, oxidative and acid stresses, for increasing growth under various conditions, enhancing phosphorus and nitrogen utilization, or influencing biofilm formation.

In some embodiments, the bacteria comprise one or more satellite phage genomes. Satellite phages are otherwise functional phages that do not carry their own structural protein genes, and have genomes that are configures for encapsulation by the structural proteins of other specific phages (Six and Klug Bacteriophage P4: a satellite virus depending on a helper such as prophage P2, Virology, Volume 51, Issue 2, February 1973, Pages 327-344). Accordingly, in some embodiments, the bacteria comprise phage genomes which do not carry their own structural genes.

In some embodiments, the bacteria comprise one or more tailiocins. Many bacteria, both gram positive and gram negative, produce a variety of particles resembling phage tails that are functional without an associated phage head (termed tailiocins), and many of which have been shown to have bacteriocin properties (reviewed in Ghequire and Mot. The Tailocin Tale: Peeling off Phage; Trends in Microbiology, October 2015, Vol. 23, No. 10). Phage tail-like bacteriocins are classified two different families: contractile phage tail-like (R-type) and noncontractile but flexible ones (F-type). Accordingly, in some embodiments, bacteria comprise one or more tailiocins which confer bacteriocin or other beneficial properties.

In some embodiments, the bacteria comprise one or more gene transfer agents. Gene transfer agents (GTAs) are phage-like elements that are encoded by some bacterial genomes. Although GTAs resemble phages, they lack the hallmark capabilities that define typical phages, and they package random fragments of the host cell DNA and then transfer them horizontally to other bacteria of the same species (reviewed in Lang et al., Gene transfer agents: phage-like elements of genetic exchange, Nat Rev Microbiol. 2012 Jun. 11; 10(7): 472-482). There, the DNA can replace the resident cognate chromosomal region by homologous recombination. However, these particles cannot propagate as viruses, as the vast majority of the particles do not carry the genes that encode the GTA.

In some embodiments, the bacteria comprise one or more filamentous virions. Filamentous virions integrate as dsDNA prophages (reviewed in Marvin D A, et al, Structure and assembly of filamentous bacteriophages, Prog Biophys Mol Biol. 2014 April; 114(2):80-122).

In any of the embodiments described herein, the genetically engineered bacteria described herein which express one or more enzymes and transporters (e.g. for the consumption of phenylalanine), comprise one or more modifications or mutations within an endogenous prophage or bacteriophage genome. These modifications may alter the properties or behavior of the prophage. In some embodiments, the modifications or mutations essentially have no effect on bacterial fitness, and the bacterial fitness is essentially the same as the fitness of the isogenic strain without the modifications or mutations. Prophages can be either identified experimentally or computationally. The experimental approach involves inducing the host bacteria to release phage particles by exposing them to UV light or other DNA-damaging conditions. However, in some cases, the conditions under which a prophage is induced is unknown, and therefore the absence of plaques in a plaque assay does not necessarily prove the absence of a prophage. Additionally, this approach can show only the existence of viable phages, but will not reveal defective prophages. As such, computational identification of prophages from genomic sequence data has become the most preferred route.

In some embodiments, the modifications or mutations essentially have no effect on effector function, and the effector function is essentially the same as the effector function of the isogenic strain without the modifications or mutations. Table H provides a list of non-limiting examples of probiotic bacteria and the number of potential bacteriophages contained in the bacterial genome as determined by Phaster scoring. Table I provides a list of Clostridial strains and potential phage genomes. Phaster is a web server for bioinformatically identifying Phage sequences in organisms (http://phaster.ca/). Phaster scoring is described in detail at phaster.ca and in Zhou, et al. ("PHAST: A Fast Phage Search Tool" Nucl. Acids Res. (2011) 39(suppl 2): W347-W352) and Arndt et al. (Arndt, et al. (2016) PHASTER: a better, faster version of the PHAST phage search tool. Nucleic Acids Res., 2016 May 3). In brief, three methods are applied with different criteria to score for prophage regions (as intact, questionable, or incomplete) within a provided bacterial genome sequence. In the first method, if the number of certain phage organism identified by Phaster is more than or equal to 100% of the total number of CDS of the region, the region is marked with total score 150. If less than 100%, method 2 and 3 is used. In method 2, if the number of certain phage organism identified by Phaster in the bacterial genome sequence provided is more than 50% of the total number of CDS of the region, that phage organism is considered as the major potential phage for that region; the percentage of the total number of that phage organism in this table in the total number of proteins of the region is calculated and then multiplied by 100; the percentage of the length of that phage organism in the length of the region is calculated and then multiplied by 50 (phage head's encapsulation capability is considered). In method 3, if any of the specific phage-related keywords (such as 'capsid', 'head', 'integrase', 'plate', 'tail', 'fiber', 'coat', 'transposase', 'portal', 'terminase', 'protease' or 'lysin') are present, the score is increased by 10 for each keyword found. If the size of the region is greater than 30 Kb, the score is increased by 10. If there are at least 40 proteins in the region, the score is increased by 10. If all of the phage-related proteins and hypothetical proteins constitute more than 70% of the total number of proteins in the region, the score is increased by 10. The total score of method 2 is compared with the total score of method 3, and the bigger one is chosen as the total score of the region. If the region's total score is less than 70, it is marked as incomplete; if between 70 to 90, it is marked as questionable; if greater than 90, it is marked as intact.

TABLE H

Matched Strains for Common Probiotics

| Organism | PHASTER Prophage (Intact) | PHASTER questionable/ incomplete (scores) | ACLAME Prediction |
|---|---|---|---|
| Bacillus coagulans | | | |
| Bacillus subtilis | | | |
| Bacillus cereus | | | |
| Bifidobacterium animalis | 0 | 0 | |
| Bifidobacterium bifidum | 0 | 2 (90, 30) | |
| Bifidobacterium breve | 1 | 0 | |
| Bifidobacterium infantis | | | |
| Bifidobacterium longum | 0 | 1 (70) | |
| Enterococcus faecium | | | |
| Enterococcus durans | | | |
| Lactobacillus caucasicus | | | |
| Lactobacillus acidophilus | 0 | 1 (20) | |
| Lactobacillus brevis | 1 | 1 (20) | 2 |
| Lactobacillus casei | | | 2 |
| Lactobacillus delbrueckii | 0 | 0 | |

TABLE H-continued

Matched Strains for Common Probiotics

| Organism | PHASTER Prophage (Intact) | PHASTER questionable/ incomplete (scores) | ACLAME Prediction |
|---|---|---|---|
| Lactobacillus fermentum | 1 | 1 (40) | |
| Lactobacillus gasseri | 1 | 2 (60, 40) | |
| Lactobacillus helveticus | | | |
| Lactobacillus paracasei | 2 | 1 (30) | |
| Lactobacillus plantarum | 2 | 0 | 3 |
| Lactobacillus reuteri | 3 | 4 (70, 60, 40, 30) | 4 |
| Lactobacillus rhamnosus | 2 | 3 (70, 60, 40) | |
| Lactobacillus salivarius | 2 | 2 (50, 20) | 3 |
| Lactobacillus thermophilus | | | |
| Lactococcus lactis | 6 | 0 | 5 |
| Leuconostoc mesenteroides | | | |
| Pediococcus acidilactici | | | |
| Streptococcus thermophilus | | | |

TABLE I

Clostridial Strains

| | Intact (phaster score) | Incomplete (phaster score) | Questionable (phaster score) |
|---|---|---|---|
| Clostridium butyricum 5521 | 1 (110) | 3 (40, 40, 20) | 2 (90, 70) |
| Clostridium butyricum E4 str. BoNT E BL5262 | 4 (150, 110, 130, 130) | 2 (50, 10) | 1 (70) |
| Clostridium tyrobutyricum UC7086 | | | |
| Clostridium butyricum strain KNU-L09 chromosome 1 | 2 | | |
| Clostridium butyricum strain CDC_51208 | 2 | | |
| Clostridium butyricum strain JKY6D1 chromosome 1 | 2 | | |
| Clostridium butyricum strain JKY6D1 chromosome 2 | 1 | | |
| Clostridium tyrobutyricum strain KCTC 5387 | 5 | | |
| Clostridium butyricum strain TOA chromosome 1 | 2 | | |
| Clostridium butyricum strain TOA chromosome 2 | 1 | | |

In any of these embodiments, the bacteria described herein comprise one or more modifications or mutations within an existing prophage or bacteriophage genome. These modifications alter the properties or behavior of the prophage. In some embodiments, the modifications or mutations prevent the prophage from entering or completing the lytic process. In some embodiments, the modifications or mutations prevent the phage from infecting other bacteria of the same or a different type.

In some embodiments, the modifications or mutations alter, e.g., reduce or increase, the fitness of the bacterial host. In some embodiments, the modifications or mutations alter, e.g., reduce or increase, desired effector function, e.g., of a genetically engineered bacterium. In some embodiments, the modifications or mutations do not alter, e.g., reduce or increase, the fitness of the bacterial host. In some embodiments, the modifications or mutations do not alter, e.g., reduce or increase, desired effector function, e.g., of a genetically engineered bacterium.

In some embodiments, the modifications or mutations improve phenylalanine consumption. In some embodiments, phenylalanine consumption remains similar to the levels observed in the isogenic strain comprising the unmodified phage. In some embodiments, the modifications or mutations essentially have no effect on bacterial fitness, and the bacterial fitness is essentially the same as the fitness of the isogenic strain without the modifications or mutations.

In some embodiments, the bacteria comprise at least about 1 to 2, at least about 2 to 3, at least about 3 to 4, at least about 4 to 5, at least about 5 to 6, at least about 6 to 7, at least about 7 to 8, at least about 8 to 9, at least about 9 to 10, at least about 10 to 11, at least about 11 to 12, at least about 12 to 13, at least about 13 to 14, at least about 14 to 15, at least about 15 to 16, at least about 16 to 17, at least about 17 to 18, at least about 18 to 19, at least about 19 to 20, at least about 20 to 21, at least about 21 to 22, at least about 22 to 23, at least about 23 to 24, at least about 24 to 25, at least about 25 to 26, at least about 26 to 27, at least about 27 to 28, at least about 28 to 29, at least about 29 to 30, at least about 30 to 31, at least about 31 to 32, at least about 32 to 33, at least about 33 to 34, at least about 34 to 35, at least about 35 to 36, at least about 36 to 37, at least about 37 to 38, at least about 38 to 39, at least about 39 to 40, at least about 40 to 41, at least about 41 to 42, at least about 42 to 43, at least about 43 to 44, at least about 44 to 45, at least about 45 to 46, at least about 46 to 47, at least about 47 to 48, at least about 48 to 49, at least about 49 to 50, at least about 50 to 51, at least about 51 to 52, at least about 52 to 53, at least about 53 to 54, at least about 54 to 55, at least about 55 to 56, at least about 56 to 57, at least about 57 to 58, at least about 58 to 59, at least about 59 to 60, at least about 60 to 61, at least about 61 to 62, at least about 62 to 63, at least about 63 to 64, at least about 64 to 65, at least about 65 to 66, at least about 66 to 67, at least about 67 to 68, at least about 68 to 69, at least about 69 to 70, at least about 70 to 71, at least about 71 to 72, at least about 72 to 73, at least about 73 to 74, at least about 74 to 75, at least about 75 to 76, at least about 76 to 77, at least about 77 to 78, at least about 78 to 79, at least about 79 to 80, at least about 80 to 81, at least about 81 to 82, at least about 82 to 83, at least about 83 to 84, at least about 84 to 85, at least about 85 to 86, at least about 86 to 87, at least about 87 to 88, at least about 88 to 89, at least about 89 to 90, at least about 90 to 91, at least about 91 to 92, at least about 92 to 93, at least about 93 to 94, at least about 94 to 95, at least about 95 to 96, at least about 96 to 97, at least about 97 to 98, at least about 98 to 99, at least about 99 to 100, or at least about 100 or more modifications or mutations to an existing prophage or bacteriophage genome.

In some embodiments, the modifications or mutations improve effector function, e.g., phenylalanine consumption. In some embodiments, effector function, e.g., phenylalanine consumption, remains similar to that observed in the isogenic strain comprising the unmodified phage. In some embodiments, the modifications or mutations essentially have no effect on bacterial fitness, and the bacterial fitness is essentially the same as the fitness of the isogenic strain without the modifications or mutations.

In some embodiments, the modifications or mutations reduce entry or completion of prophage lytic process at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold relative to the isogenic strain without the phage modification. In some embodiments, the modifications or mutations completely prevent entry or completion of prophage lytic process.

In some embodiments, the modifications or mutations reduce entry or completion of prophage lytic process by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% relative to the isogenic strain without the phage modification.

In some embodiments, the modifications or mutations prevent the phage from infecting other bacteria of the same or a different type by at least about 1- to 2-fold, at least about 2- to 3-fold, at least about 3- to 4-fold, at least about 4- to 5-fold, at least about 5- to 10-fold, at least about 10- to 100-fold, at least about 10- to 20-fold, at least about 20- to 30-fold, at least about 30- to 40-fold, at least about 40- to 50-fold, at least about 50- to 60-fold, at least about 60- to 70-fold, at least about 70- to 80-fold, at least about 80- to 90-fold, at least about 90- to 100-fold, or at least about 100- to 1000-fold relative to the isogenic strain without the phage modification. In some embodiments, the modifications or mutations completely prevent the phage from infecting other bacteria of the same or a different type. In some embodiments, the modifications or mutations prevent the phage from infecting other bacteria of the same or a different type by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100%.

In some embodiments, the modifications or mutations alters or alters, e.g., reduces or increases, the fitness of the bacterial host by at least about 1- to 2-fold, at least about 2- to 3-fold, at least about 3- to 4-fold, at least about 4- to 5-fold, at least about 5- to 10-fold, at least about 10- to 100-fold, or at least about 100- to 1000-fold relative to the isogenic strain without the phage modification. In some embodiments, the modifications or mutations alters, e.g., reduces or increases, the fitness of the bacterial host by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% relative to the isogenic strain without the phage modification as compared to the isogenic strain without the phage modification.

In some embodiments, the modifications or mutations alter, e.g., reduce or increase, the desired effector function, e.g., of a genetically engineered bacterium by at least about 1- to 2-fold, at least about 2- to 3-fold, at least about 3- to 4-fold, at least about 4- to 5-fold, at least about 5- to 10-fold, at least about 10- to 100-fold, or at least about 100- to 1000-fold. In some embodiments, the modifications or mutations alter, e.g., reduce or increase, the desired effector function, e.g., of a genetically engineered bacterium by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% relative to the isogenic strain without the phage modification.

In some embodiments, the mutations include one or more deletions within the phage genome sequence. As used herein, "deletion" refers to the removal of one or more nucleotides from a polynucleotide sequence. In some embodiments, the mutations include one or more insertions into the phage genome sequence. As used herein, "insertion" refers to the addition of one or more nucleotides to a polynucleotide sequence. In some embodiments, an antibiotic cassette can be inserted into one or more positions within the phage genome sequence. In some embodiments, the mutations include one or more substitutions within the phage genome sequence. As used herein, "substitution" refers to the replacement of one or more nucleotides with the same number of nucleotides within a polynucleotide sequence. In some embodiments, the mutations include one or more inversions within the phage genome sequence. As used herein, "inversion" refers to when a segment comprising 2 or more nucleotides is reversed end to end within a polynucleotide sequence. In some embodiments, the inversion may be governed by a specific flippase. Exemplary circuitry comprising multiple levels of control are exemplified herein and are also described in co-owned pending PCT Application PCT/US2016/039434, the contents of which is herein incorporated by reference in its entirety.

In some embodiments, the modifications within the phage genome are combinations of two or more of insertions, deletions, substitutions, or inversions within one or more phage genome genes.

In any of the embodiments described herein, the modifications may result in one or more frameshift mutations in one or more genes within the phage genome. As used herein, a frameshift mutation (also called a framing error or a reading frame shift) refers to a genetic mutation caused by indels (insertions or deletions) of a number of nucleotides in a DNA sequence that is not divisible by three. The earlier in the sequence the deletion or insertion occurs, the more altered the protein. In any of the embodiments described herein, the modifications may result in one or more missense mutation in one or more genes within the phage genome. As used herein, a missense mutation refers to when the change of a single base pair causes the substitution of a different amino acid in the resulting protein. This amino acid substitution may have no effect, or it may render the protein nonfunctional. In any of the embodiments described herein, the modifications may result in one or more nonsense mutations in one or more genes within the phage genome. As used herein, a nonsense mutation refers to a mutation in which a sense codon that corresponds to one of the twenty amino acids specified by the genetic code is changed to a chain-terminating codon and the polypeptide of interest is thereby truncated.

In some embodiments, the modifications within the phage genome are combinations of two or more frameshift, nonsense or missense mutations within one or more phage genome genes. In some embodiments, the bacteriophage that is modified is located on a bacterial chromosome. In some embodiments, the bacteriophage that is modified is located on a bacterial plasmid. In some embodiments, the plasmid is modified. In some embodiments, the plasmid is removed entirely. In some embodiments, the phage or prophage exists in all isolates of a particular species. In some embodiments, the prophage exists in all isolates of a particular phylum, order, sub order, family, class, subclass genus, species, sub species, or clade.

Mutations

In some embodiments, the one or more mutations comprise at least about 1-500 bp of the phage genome. In some embodiments, the one or more mutations comprise at least about 500-1000 bp of the phage genome. In some embodiments, the one or more mutations comprise at least about 1000-2000 bp of the phage genome. In some embodiments, the one or more mutations comprise at least about 1000-2000 bp of the phage genome. In some embodiments, the one or more mutations comprise at least about 2000-3000 bp of the phage genome. In some embodiments, the one or more mutations comprise at least about 3000-4000 bp of the phage genome. In some embodiments, the one or more mutations comprise at least about 4000-5000 bp of the phage genome. In some embodiments, the one or more mutations comprise at least about 5,000-6,000 bp of the phage genome. In some embodiments, the one or more mutations comprise at least about 6,000-7,000 bp of the phage genome. In some embodiments, the one or more mutations comprise at least about 7,000-8,000 bp of the phage genome. In some embodiments, the one or more mutations comprise at least about 8,000-9,000 bp of the phage genome. In some embodiments, the one or more mutations comprise at least about 9,000-10,000 bp of the phage genome. In some embodiments, the one or more mutations comprise at least about 10,000-15,000 bp of the phage genome. In some embodiments, the one or more mutations comprise at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are mutated. In some embodiments, the mutated nucleotides are interspersed. In some embodiments, the mutated nucleotides are consecutive. In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome is mutated. In some embodiments, at least about 30-40% of the phage genome is mutated. In some embodiments, at least about 40-50% of the phage genome is mutated. In some embodiments, at least about 50-60% of the phage genome is mutated. In some embodiments, at least about 60-70% of the phage genome is mutated. In some embodiments, at least about 70-80% of the phage genome is mutated. In some embodiments, at least about 80-90% of the phage genome is mutated. In some embodiments, at least about 90-100% of the phage genome is mutated.

In some embodiments, at least about 1, 2, 3, 4, 5, 6, 7, 8, 9, 10, 11, 12, 13, 14, 15, 16, 17, 18, 19, or 20 genes are mutated. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are mutated. In some embodiments, 13 genes are completely or partially mutated. In one embodiment, 74 genes are completely or partially mutated.

In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the phage genome are completely or partially mutated.

In some embodiments, the one or more mutations are located at the beginning or 5' end of the phage genome. In some embodiments, the one or more mutations are located at the end or 3' end of the phage genome. In some embodiments, the one or more mutations are located in the middle of the phage genome. In some embodiments, the phage genes are interspersed within the bacterial genome and the mutation are located in one or more of the interspersed positions.

In some embodiments, the region for an optimal mutation, i.e., to achieve a desired effect, can be determined through analysis of homology with other phages in other bacteria. Homologous conserved regions in phages may be suitable for mutation, as these are conserved and may comprise one or more essential genes. In some embodiments, regulatory elements, such as promoters, are mutated. In some embodiments, coding sequences are mutated. In some embodiments, the one or more mutated regions contain one or more genes essential for the lytic cycle.

In some embodiments, the mutations are located within or encompass one or more genes encoding lytic genes. In some embodiments, the mutations are located within or encompass one or more genes encoding one or more proteases or lysins. In some embodiments, the mutations are located within or encompass one or more genes encoding one or more toxins. In some embodiments, the mutations are located within or encompass one or more genes encoding one or more antibiotic resistance related proteins. In some embodiments, the mutations are located within or encompass one or phage translation related proteins. In some embodiments, the one or more mutations are located within or encompass one or more genes encoding structural proteins. Such structural genes include genes encoding polypeptides of the head, tail, collar, or coat. In some embodiments, the one or more mutations are located within or encompass one or more genes encoding polypeptides of the head structure. In some embodiments, the one or more mutations are located within or encompass one or more genes encoding polypeptides of the tail structure. In some embodiments, the one or more mutations are located within or encompass one or more genes encoding polypeptides of the collar structure. In some embodiments, the one or more mutations are located within or encompass one or more genes encoding tail proteins. In some embodiments, the one or more mutations are located within or encompass one or more genes encoding polypeptides of the coat structure. In some embodiments, the mutations are located within or encompass one or more genes encoding one or more plate proteins. In some embodiments, the mutations are located within or encompass one or more genes encoding one or more proteins require for assembly of the bacteriophage. In some embodiments, the mutations are located within or encompass one or more genes encoding one or more portal proteins. In some embodiments, the mutations are located within or encompass one or more genes encoding one or more polypeptides involved in recombination. In some embodiments, the mutations are located within or encompass one or more genes encoding one or more integrases. In some embodiments, the mutations are located within or encompass one or more genes encoding one or more invertases. In some embodiments, the mutations are located within or encompass one or more genes encoding one or more transposases. In some embodiments, the mutations are located with within or encompass one or more genes encoding one or more polypeptides involved in replication or translation. In some embodiments, the mutations are located within or encompass one or more genes encoding one or more primases. In some embodiments, the mutations are located within or encompass one or more genes encoding one or more tRNA related proteins. In some embodiments, the mutations are located within or encompass one or more genes encoding one or more polypeptides involved in phage insertion. In some embodiments, the mutations are located within or encompass one or more genes encoding an attachment site. In some embodiments, the mutations are located within or encompass one or more genes encoding one or more polypeptides involved in packaging. In some embodiments, the mutations are located within or encompass one or more genes encoding one or more terminases. In some embodiments, the mutations are located within or encompass one or more genes encoding one or more host genes.

In some embodiments, the mutations are located within or encompass genes encoding one or more polypeptides involved in one or more of cell lysis, phage structure, phage assembly, phage packaging recombination, replication or translation, phage insertion, or are host proteins, and combinations thereof.

In some embodiments, the mutations are located within or encompass genes encoding one or more polypeptides involved in one or more of cell lysis, phage structure, phage assembly, phage packaging recombination, replication or translation, phage insertion, and combinations thereof.

In some embodiments, the mutations are located within or encompass 1 genes encoding polypeptides involved in cell lysis, phage structure, phage assembly, phage packaging recombination, replication or translation, phage insertion, and combinations thereof. In some embodiments, the mutations are located within or encompass 2 genes encoding polypeptides involved in cell lysis, phage structure, phage assembly, phage packaging recombination, replication or translation, phage insertion, and combinations thereof. In some embodiments, the mutations are located within or encompass 3 genes encoding polypeptides involved in cell lysis, phage structure, phage assembly, phage packaging recombination, replication or translation, phage insertion, and combinations thereof. In some embodiments, the mutations are located within or encompass 4 genes encoding polypeptides involved in cell lysis, phage structure, phage assembly, phage packaging recombination, replication or translation, phage insertion, and combinations thereof. In some embodiments, the mutations are located within or encompass 2 genes encoding polypeptides involved in cell lysis, phage structure, phage assembly, phage packaging recombination, replication or translation, phage insertion, and combinations thereof. In some embodiments, the mutations are located within or encompass 5 genes encoding polypeptides involved in cell lysis, phage structure, phage assembly, phage packaging recombination, replication or translation, phage insertion, and combinations thereof. In some embodiments, the mutations are located within or encompass 6 genes encoding polypeptides involved in cell lysis, phage structure, phage assembly, phage packaging recombination, replication or translation, phage insertion, and combinations thereof. In some embodiments, the mutations are located within or encompass 7 genes encoding polypeptides involved in cell lysis, phage structure, phage assembly, phage packaging recombination, replication or translation, phage insertion, and combinations thereof. In some embodiments, the mutations are located within or encompass 8 genes encoding polypeptides involved in cell lysis, phage structure, phage assembly, phage packaging recombination, replication or translation, phage insertion, and combinations thereof. In some embodiments, the mutations are located within or encompass 9 genes encoding polypeptides involved in cell lysis, phage structure, phage assembly, phage packaging recombination, replication or translation, phage insertion, and combinations thereof. In some embodiments, the mutations are located within or encompass 10 genes encoding polypeptides involved in cell lysis, phage structure, phage assembly, phage packaging recombination, replication or translation, phage insertion, and combinations thereof. In some embodiments, the mutations are located within or encompass 11 genes encoding polypeptides involved in cell lysis, phage structure, phage assembly, phage packaging recombination, replication or translation, phage insertion, and combinations thereof. In some embodiments, the mutations are located within or encompass 12 genes encoding polypeptides involved in cell lysis, phage structure, phage assembly, phage packaging recombination, replication or translation, phage insertion, and combinations thereof. In some embodiments, the mutations are located within or encompass 13 genes encoding polypeptides involved in cell lysis, phage structure, phage assembly, phage packaging recombination, replication or translation, phage insertion, and combinations thereof. In some embodiments, the mutations are located within or encompass 14 genes encoding polypeptides involved in cell lysis, phage structure, phage assembly, phage packaging recombination, replication or translation, phage insertion, and combinations thereof. In some embodiments, the mutations are located within or encompass 15 genes encoding polypeptides involved in cell lysis, phage structure, phage assembly, phage packaging recombination, replication or translation, phage insertion, and combinations thereof. In some embodiments, the mutations are located within or encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the mutations are located within or encompass one or more host proteins within the phage genome.

Deletions

In some embodiments, the one or more deletions comprise at least about 1-500 bp of the phage genome. In some embodiments, the one or more deletions comprise at least about 500-1000 bp of the phage genome. In some embodiments, the one or more deletions comprise at least about 1000-2000 bp of the phage genome. In some embodiments, the one or more deletions comprise at least about 1000-2000 bp of the phage genome. In some embodiments, the one or more deletions comprise at least about 2000-3000 bp of the phage genome. In some embodiments, the one or more deletions comprise at least about 3000-4000 bp of the phage genome. In some embodiments, the one or more deletions comprise at least about 4000-5000 bp of the phage genome. In some embodiments, the one or more deletions comprise at least about 5,000-6,000 bp of the phage genome. In some embodiments, the one or more deletions comprise at least about 6,000-7,000 bp of the phage genome. In some embodiments, the one or more deletions comprise at least about 7,000-8,000 bp of the phage genome. In some embodiments, the one or more deletions comprise at least about 8,000-9,000 bp of the phage genome. In some embodiments, the one or more deletions comprise at least about 9,000-10,000 bp of the phage genome. In some embodiments, the one or more deletions comprise at least about 10,000-15,000 bp of the phage genome. In some embodiments, the one or more deletions comprise at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than 200,000 bp of the phage genome. In one specific embodiment, 9687 bp of the phage genome are deleted. In some embodiments, the deleted nucleotides are interspersed. In some embodiments, the deleted nucleotides are consecutive.

In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome is deleted. In some embodiments, at least about 30-40% of the phage genome is deleted. In some embodiments, at least about 40-50% of the phage genome is deleted. In some embodiments, at least about 50-60% of the phage genome is deleted. In some embodiments, at least about 60-70% of the phage genome is deleted. In some embodiments, at least about 70-80% of the phage genome is deleted. In some embodiments, at least about 80-90% of the phage genome is deleted. In some embodiments, at least about 90-100% of the phage genome is deleted.

In some embodiments, one or more genes are partially or completely deleted within the phage genome. In some embodiments, one or more genes are completely deleted and one or more genes are partially deleted. In one embodiment, there is one deletion within the phage genome and one or two genes at the ends of the deletion are partially deleted and the rest of the genes are completely deleted. In some embodiments, the deleted genes are adjacent to each other. In some embodiments, the deleted genes are not adjacent to each other.

In some embodiments, at least about 1, 2, 3, 4, 5, 6, 7, 8, 9, 10, 11, 12, 13, 14, 15, 16, 17, 18, 19, or 20 genes are deleted. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are deleted. In some embodiments, 13 genes are completely or partially deleted. In one embodiment, 74 genes are completely or partially deleted. In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the phage genome are completely or partially deleted.

In some embodiments, the one or more deletions are located at the beginning or 5' end of the phage genome. In some embodiments, the one or more deletions are located at the end or 3' end of the phage genome. In some embodiments, the one or more deletions are located in the middle of the phage genome. In some embodiments, the phage genes are interspersed within the bacterial genome and the deletion are located in one or more of the interspersed positions.

In some embodiments, the region for an optimal deletion, i.e., to achieve a desired effect, can be determined through analysis of homology with other phages is other bacteria. Homologous conserved regions in phages may be suitable for deletion, as these are conserved and may comprise one or more essential genes. In some embodiments, regulatory elements, such as promoters, are deleted. In some embodiments, coding sequences are deleted. In some embodiments, the one or more deleted regions contain one or more genes essential for the lytic cycle.

In some embodiments, the deletions are located within or encompass one or more genes encoding lytic genes. In some embodiments, the deletions are located within or encompass one or more genes encoding one or more proteases or lysins. In some embodiments, the deletions are located within or encompass one or more genes encoding one or more toxins. In some embodiments, the deletions are located within or encompass one or more genes encoding one or more antibiotic resistance related proteins. In some embodiments, the deletions are located within or encompass one or more genes encoding one or phage translation related proteins. In some embodiments, the one or more deletions are located within or encompass one or more genes encoding structural proteins. Such structural genes include genes encoding polypeptides of the head, tail, collar, or coat. In some embodiments, the one or more deletions are located within or encompass one or more genes encoding polypeptides of the head structure. In some embodiments, the one or more deletions are located within or encompass one or more genes encoding polypeptides of the tail structure. In some embodiments, the one or more deletions are located within or encompass one or more genes encoding polypeptides of the collar structure. In some embodiments, the one or more deletions are located within or encompass one or more genes encoding polypeptides of the coat structure. In some embodiments, the deletions are located within or encompass one or more genes encoding one or more plate proteins. In some embodiments, the deletions are located within or encompass one or more genes encoding one or more proteins require for assembly of the bacteriophage. In some embodiments, the deletions are located within or encompass one or more genes encoding one or more portal proteins. In some embodiments, the deletions are located within or encompass one or more genes encoding one or more polypeptides involved in recombination. In some embodiments, the deletions are located within or encompass one or more genes encoding one or more integrases. In some embodiments, the deletions are located within or encompass one or more genes encoding one or more invertases. In some embodiments, the deletions are located within or encompass one or more genes encoding one or more transposases. In some embodiments, the deletions are located with within or encompass one or more genes encoding one or more polypeptides involved in replication or translation. In some embodiments, the deletions are located within or encompass one or more genes encoding one or more primases. In some embodiments, the deletions are located within or encompass one or more genes encoding one or more tRNA related proteins. In some embodiments, the deletions are located within or encompass one or more genes encoding one or more polypeptides involved in phage insertion. In some embodiments, the deletions are located within or encompass one or more genes encoding an attachment site. In some embodiments, the deletions are located within or encompass one or more genes encoding one or more polypeptides involved in packaging. In some embodiments, the deletions are located within or encompass one or more genes encoding one or more terminases. In some embodiments, the deletions are located within or encompass one or more genes encoding one or more host genes.

In some embodiments, the deletions are located within or encompass genes encoding one or more polypeptides involved in one or more of cell lysis, phage structure, phage assembly, phage packaging recombination, replication or translation, phage insertion, or are host proteins, and combinations thereof.

In some embodiments, the deletions are located within or encompass genes encoding one or more polypeptides involved in one or more of cell lysis, phage structure, phage assembly, phage packaging recombination, replication or translation, phage insertion, and combinations thereof.

In some embodiments, the deletions are located within or encompass 1 genes encoding polypeptides involved in cell lysis, phage structure, phage assembly, phage packaging recombination, replication or translation, phage insertion, and combinations thereof. In some embodiments, the deletions are located within or encompass 2 genes encoding polypeptides involved in cell lysis, phage structure, phage assembly, phage packaging recombination, replication or translation, phage insertion, and combinations thereof. In some embodiments, the deletions are located within or encompass 3 genes encoding polypeptides involved in cell lysis, phage structure, phage assembly, phage packaging recombination, replication or translation, phage insertion, and combinations thereof. In some embodiments, the deletions are located within or encompass 4 genes encoding polypeptides involved in cell lysis, phage structure, phage assembly, phage packaging recombination, replication or translation, phage insertion, and combinations thereof. In some embodiments, the deletions are located within or encompass 2 genes encoding polypeptides involved in cell lysis, phage structure, phage assembly, phage packaging recombination, replication or translation, phage insertion, and combinations thereof. In some embodiments, the deletions are located within or encompass 5 genes encoding polypeptides involved in cell lysis, phage structure, phage assembly, phage packaging recombination, replication or translation, phage insertion, and combinations thereof. In some embodiments, the deletions are located within or encompass 6 genes encoding polypeptides involved in cell lysis, phage structure, phage assembly, phage packaging recombination, replication or translation, phage insertion, and combinations thereof. In some embodiments, the deletions are located within or encompass 7 genes encoding polypeptides involved in cell lysis, phage structure, phage assembly, phage packaging recombination, replication or translation, phage insertion, and combinations thereof. In some embodiments, the deletions are located within or encompass 8 genes encoding polypeptides involved in cell lysis, phage structure, phage assembly, phage packaging recombination, replication or translation, phage insertion, and combinations thereof. In some embodiments, the deletions are located within or encompass 9 genes encoding polypeptides involved in cell lysis, phage structure, phage assembly, phage packaging recombination, replication or translation, phage insertion, and combinations thereof. In some embodiments, the deletions are located within or encompass 10 genes encoding polypeptides involved in cell lysis, phage structure, phage assembly, phage packaging recombination, replication or translation, phage insertion, and combinations thereof. In some embodiments, the deletions are located within or encompass 11 genes encoding polypeptides involved in cell lysis, phage structure, phage assembly, phage packaging recombination, replication or translation, phage insertion, and combinations thereof. In some embodiments, the deletions are located within or encompass 12 genes encoding polypeptides involved in cell lysis, phage structure, phage assembly, phage packaging recombination, replication or translation, phage insertion, and combinations thereof. In some embodiments, the deletions are located within or encompass 13 genes encoding polypeptides involved in cell lysis, phage structure, phage assembly, phage packaging recombination, replication or translation, phage insertion, and combinations thereof. In some embodiments, the deletions are located within or encompass 14 genes encoding polypeptides involved in cell lysis, phage structure, phage assembly, phage packaging recombination, replication or translation, phage insertion, and combinations thereof. In some embodiments, the deletions are located within or encompass 15 genes encoding polypeptides involved in cell lysis, phage structure, phage assembly, phage packaging recombination, replication or translation, phage insertion, and combinations thereof. In some embodiments, the deletions are located within or encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the deletions are located within or encompass one or more host proteins within the phage genome.

Insertions

In some embodiments, the insertion is in a coding region of the phage genome. In some embodiments, the insertion is inserted into a regulatory region of the phage genome. In some embodiments, the insertions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more insertions comprise at least about 1-500 bp in length. In some embodiments, the one or more insertions comprise at least about 500-1000 bp in length. In some embodiments, the one or more insertions comprise at least about 1000-2000 bp in length. In some embodiments, the one or more insertions comprise at least about 2000-3000 bp in length. In some embodiments, the one or more insertions comprise at least about 3000-4000 bp in length. In some embodiments, the one or more insertions comprise at least about 4000-5000 bp in length. In some embodiments, the one or more insertions comprise at least about 5,000-6,000 bp in length. In some embodiments, the one or more insertions comprise at least about 6,000-7,000 bp in length. In some embodiments, the one or more insertions comprise at least about 7,000-8,000 bp in length. In some embodiments, the one or more insertions comprise at least about 8,000-9,000 bp in length. In some embodiments, the one or more insertions comprise at least about 9,000-10,000 bp in length. In some embodiments, the one or more insertions comprise at least about 10,000-15,000 bp in length. In some embodiments, the one or more insertions comprise at least about 10,000-15,000 bp in length, at least about 15,000-20,000 bp in length, at least about 20,000-25,000 bp in length, at least about 25,000-30,000 bp in length, at least about 30,000-35,000 bp in length, at least about 35,000-40,000 bp in length, at least about 40,000-45,000 bp in length, at least about 45,000-50,000 bp in length, at least about 50,000-55,000 bp in length, at least about 55,000-60,000 bp in length, at least about 60,000-65,000 bp in length, at least about 65,000-70,000 bp in length, at least about 70,000-75,000 bp in length, at least about 75,000-80,000 bp in length, at least about 80,000-85,000 bp in length, at least about 85,000-90,000 bp in length, at least about 90,000-95,000 bp in length, at least about 95,000-100,000 bp in length, at least about 100,000-110,000 bp in length, at least about 110,000-120,000 bp in length, at least about 120,000-130,000 bp in length, at least about 130,000-140,000 bp in length, at least about 140,000-150,000 bp in length, at least about 150,000-200,000 bp in length, or more than at least about 200,000 bp in length. In one specific embodiment, 9687 bp in length are inserted. In some embodiments, the inserted nucleotides are interspersed. In some embodiments, the inserted nucleotides are consecutive.

In some embodiments, the one or more insertions are located within 1-500 bp of the phage genome. In some embodiments, the one or more insertions are located within at least about 500-1000 bp of the phage genome. In some embodiments, the one or more insertions are located within at least about 1000-2000 bp of the phage genome. In some embodiments, the one or more insertions are located within at least about 1000-2000 bp of the phage genome. In some embodiments, the one or more insertions are located within at least about 2000-3000 bp of the phage genome. In some embodiments, the one or more insertions are located within at least about 3000-4000 bp of the phage genome. In some embodiments, the one or more insertions are located within at least about 4000-5000 bp of the phage genome. In some embodiments, the one or more insertions are located within at least about 5,000-6,000 bp of the phage genome. In some embodiments, the one or more insertions are located within at least about 6,000-7,000 bp of the phage genome. In some embodiments, the one or more insertions are located within at least about 7,000-8,000 bp of the phage genome. In some embodiments, the one or more insertions are located within at least about 8,000-9,000 bp of the phage genome. In some embodiments, the one or more insertions are located within at least about 9,000-10,000 bp of the phage genome. In some embodiments, the one or more insertions are located within at least about 10,000-15,000 bp of the phage genome. In some embodiments, the one or more insertions are located within at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are inserted. In some embodiments, the inserted nucleotides are interspersed. In some embodiments, the inserted nucleotides are consecutive.

In some embodiments, the insertions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome. In some embodiments, at least about 30-40% of the phage genome is inserted. In some embodiments, the insertions are located within at least about 40-50% of the phage genome. In some embodiments, the insertions are located within at least about 50-60% of the phage genome. In some embodiments, the insertions are located within at least about 60-70% of the phage genome. In some embodiments, the insertions are located within at least about 70-80% of the phage genome. In some embodiments, the insertions are located within at least about 80-90% of the phage genome. In some embodiments, the insertions are located within at least about 90-100% of the phage genome.

In some embodiments, at least about 1, 2, 3, 4, 5, 6, 7, 8, 9, 10, 11, 12, 13, 14, 15, 16, 17, 18, 19, or 20 genes comprise insertions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise insertions. In some embodiments, 13 genes comprise insertions. In one embodiment, 74 genes comprise insertions.

In some embodiments, the one or more insertions are located at the beginning or 5' end of the phage genome. In some embodiments, the one or more insertions are located at the end or 3' end of the phage genome. In some embodiments, the one or more insertions are located in the middle of the phage genome. In some embodiments, the phage genes are interspersed within the bacterial genome and the insertion are located in one or more of the interspersed positions.

In some embodiments, the region for an optimal insertion, i.e., to achieve a desired effect, can be determined through analysis of homology with other phages is other bacteria. Homologous conserved regions in phages may be suitable for insertion, as these are conserved and may comprise one or more essential genes. In some embodiments, regulatory elements, such as promoters, are inserted. In some embodiments, coding sequences are inserted. In some embodiments, the one or more inserted regions contain one or more genes essential for the lytic cycle.

In some embodiments, the insertions are located within one or more genes encoding lytic genes. In some embodiments, the insertions are located within one or more genes encoding one or more proteases or lysins. In some embodiments, the insertions are located within one or more genes encoding one or more toxins. In some embodiments, the insertions are located within one or more genes encoding one or more antibiotic resistance related proteins. In some embodiments, the insertions are located within one or more genes encoding one or phage translation related proteins. In some embodiments, the one or more insertions are located within one or more genes encoding structural proteins. Such structural genes include genes encoding polypeptides of the head, tail, collar, or coat. In some embodiments, the one or more insertions are located within one or more genes encoding polypeptides of the head structure. In some embodiments, the one or more insertions are located within one or more genes encoding polypeptides of the tail structure. In some embodiments, the one or more insertions are located within one or more genes encoding polypeptides of the collar structure. In some embodiments, the one or more insertions are located within one or more genes encoding polypeptides of the coat structure. In some embodiments, the insertions are located within one or more genes encoding one or more plate proteins. In some embodiments, the insertions are located within one or more genes encoding one or more proteins require for assembly of the bacteriophage. In some embodiments, the insertions are located within one or more genes encoding one or more portal proteins. In some embodiments, the insertions are located within one or more genes encoding one or more polypeptides involved in recombination. In some embodiments, the insertions are located within one or more genes encoding one or more integrases. In some embodiments, the insertions are located within one or more genes encoding one or more invertases. In some embodiments, the insertions are located within one or more genes encoding one or more transposases. In some embodiments, the insertions are located with within one or more genes encoding one or more polypeptides involved in replication or translation. In some embodiments, the insertions are located within one or more genes encoding one or more primases. In some embodiments, the insertions are located within one or more genes encoding one or more tRNA related proteins. In some embodiments, the insertions are located within one or more genes encoding one or more polypeptides involved in phage insertion. In some embodiments, the insertions are located within one or more genes encoding an attachment site. In some embodiments, the insertions are located within one or more genes encoding one or more polypeptides involved in packaging. In some embodiments, the insertions are located within one or more genes encoding one or more terminases. In some embodiments, the insertions are located within one or more genes encoding one or more host genes.

In some embodiments, the insertions are located within genes encoding one or more polypeptides involved in one or more of cell lysis, phage structure, phage assembly, phage packaging recombination, replication or translation, phage insertion, or are host proteins, and combinations thereof.

In some embodiments, the insertions are located within genes encoding one or more polypeptides involved in one or more of cell lysis, phage structure, phage assembly, phage packaging recombination, replication or translation, phage insertion, and combinations thereof.

In some embodiments, the insertions are located within 1 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 3 genes encoding polypeptides involved in cell lysis, phage structure, phage assembly, phage packaging recombination, replication or translation, phage insertion, and combinations thereof. In some embodiments, the insertions are located within 4 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 5 genes encoding polypeptides involved in cell lysis, phage structure, phage assembly, phage packaging recombination, replication or translation, phage insertion, and combinations thereof. In some embodiments, the insertions are located within 6 genes encoding polypeptides involved in cell lysis, phage structure, phage assembly, phage packaging recombination, replication or translation, phage insertion, and combinations thereof. In some embodiments, the insertions are located within 7 genes encoding polypeptides involved in cell lysis, phage structure, phage assembly, phage packaging recombination, replication or translation, phage insertion, and combinations thereof. In some embodiments, the insertions are located within 8 genes encoding polypeptides involved in cell lysis, phage structure, phage assembly, phage packaging recombination, replication or translation, phage insertion, and combinations thereof. In some embodiments, the insertions are located within 9 genes encoding polypeptides involved in cell lysis, phage structure, phage assembly, phage packaging recombination, replication or translation, phage insertion, and combinations thereof. In some embodiments, the insertions are located within 10 genes encoding polypeptides involved in cell lysis, phage structure, phage assembly, phage packaging recombination, replication or translation, phage insertion, and combinations thereof. In some embodiments, the insertions are located within 11 genes encoding polypeptides involved in cell lysis, phage structure, phage assembly, phage packaging recombination, replication or translation, phage insertion, and combinations thereof. In some embodiments, the insertions are located within 12 genes encoding polypeptides involved in cell lysis, phage structure, phage assembly, phage packaging recombination, replication or translation, phage insertion, and combinations thereof. In some embodiments, the insertions are located within 13 genes encoding polypeptides involved in cell lysis, phage structure, phage assembly, phage packaging recombination, replication or translation, phage insertion, and combinations thereof. In some embodiments, the insertions are located within 14 genes encoding polypeptides involved in cell lysis, phage structure, phage assembly, phage packaging recombination, replication or translation, phage insertion, and combinations thereof. In some embodiments, the insertions are located within 15 genes encoding polypeptides involved in cell lysis, phage structure, phage assembly, phage packaging recombination, replication or translation, phage insertion, and combinations thereof. In some embodiments, the insertions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the insertions are located within one or more host proteins within the phage genome.

Inversions

In some embodiments, the inversion is in a coding region of the phage genome. In some embodiments, the inversion is inverted into a regulatory region of the phage genome. In some embodiments, the inversions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more inversions comprise at least about 1-500 bp. In some embodiments, the one or more inversions comprise at least about 500-1000 bp. In some embodiments, the one or more inversions comprise at least about 1000-2000 bp. In some embodiments, the one or more inversions comprise at least about 2000-3000 bp. In some embodiments, the one or more inversions comprise at least about 3000-4000 bp. In some embodiments, the one or more inversions comprise at least about 4000-5000 bp. In some embodiments, the one or more inversions comprise at least about 5,000-6,000 bp. In some embodiments, the one or more inversions comprise at least about 6,000-7,000 bp. In some embodiments, the one or more inversions comprise at least about 7,000-8,000 bp. In some embodiments, the one or more inversions comprise at least about 8,000-9,000 bp. In some embodiments, the one or more inversions comprise at least about 9,000-10,000 bp. In some embodiments, the one or more inversions comprise at least about 10,000-15,000 bp. In some embodiments, the one or more inversions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, at least about 55,000-60,000 bp, at least about 60,000-65,000 bp, at least about 65,000-70,000 bp, at least about 70,000-75,000 bp, at least about 75,000-80,000 bp, at least about 80,000-85,000 bp, at least about 85,000-90,000 bp, at least about 90,000-95,000 bp, at least about 95,000-100,000 bp, at least about 100,000-110,000 bp, at least about 110,000-120,000 bp, at least about 120,000-130,000 bp, at least about 130,000-140,000 bp, at least about 140,000-150,000 bp, at least about 150,000-200,000 bp, or more than at least about 200,000 bp. In one specific embodiment, 9687 bp are inverted. In some embodiments, the inverted nucleotides are interspersed. In some embodiments, the inverted nucleotides are consecutive.

In some embodiments, the one or more inversions are located within at least about 1-500 bp of the phage genome. In some embodiments, the one or more inversions are located within at least about 500-1000 bp of the phage genome. In some embodiments, the one or more inversions are located within at least about 1000-2000 bp of the phage genome. In some embodiments, the one or more inversions are located within at least about 1000-2000 bp of the phage genome. In some embodiments, the one or more inversions are located within at least about 2000-3000 bp of the phage genome. In some embodiments, the one or more inversions are located within at least about 3000-4000 bp of the phage genome. In some embodiments, the one or more inversions are located within at least about 4000-5000 bp of the phage genome. In some embodiments, the one or more inversions are located within at least about 5,000-6,000 bp of the phage genome. In some embodiments, the one or more inversions are located within at least about 6,000-7,000 bp of the phage genome. In some embodiments, the one or more inversions are located within at least about 7,000-8,000 bp of the phage genome. In some embodiments, the one or more inversions are located within at least about 8,000-9,000 bp of the phage genome. In some embodiments, the one or more inversions are located within at least about 9,000-10,000 bp of the phage genome. In some embodiments, the one or more inversions are located within at least about 10,000-15,000 bp of the phage genome. In some embodiments, the one or more inversions are located within at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are inverted. In some embodiments, the inverted nucleotides are interspersed. In some embodiments, the inverted nucleotides are consecutive.

In some embodiments, the inversions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome. In some embodiments, at least about 30-40% of the phage genome is inverted. In some embodiments, the inversions are located within at least about 40-50% of the phage genome. In some embodiments, the inversions are located within at least about 50-60% of the phage genome. In some embodiments, the inversions are located within at least about 60-70% of the phage genome. In some embodiments, the inversions are located within at least about 70-80% of the phage genome. In some embodiments, the inversions are located within at least about 80-90% of the phage genome. In some embodiments, the inversions are located within at least about 90-100% of the phage genome.

In some embodiments, at least about 1, 2, 3, 4, 5, 6, 7, 8, 9, 10, 11, 12, 13, 14, 15, 16, 17, 18, 19, or 20 genes comprise inversions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise inversions. In some embodiments, 13 genes comprise inversions. In one embodiment, 74 genes comprise inversions.

In some embodiments, the one or more inversions are located at the beginning or 5' end of the phage genome. In some embodiments, the one or more inversions are located at the end or 3' end of the phage genome. In some embodiments, the one or more inversions are located in the middle of the phage genome. In some embodiments, the phage genes are interspersed within the bacterial genome and the inversion are located in one or more of the interspersed positions.

In some embodiments, the region for an optimal inversion, i.e., to achieve a desired effect, can be determined through analysis of homology with other phages is other bacteria. Homologous conserved regions in phages may be suitable for inversion, as these are conserved and may comprise one or more essential genes. In some embodiments, regulatory elements, such as promoters, are inverted. In some embodiments, coding sequences are inverted. In some embodiments, the one or more inverted regions contain one or more genes essential for the lytic cycle.

In some embodiments, the inversions are located within one or more genes encoding lytic genes. In some embodiments, the inversions are located within one or more genes encoding one or more proteases or lysins. In some embodiments, the inversions are located within one or more genes encoding one or more toxins. In some embodiments, the inversions are located within one or more genes encoding one or more antibiotic resistance related proteins. In some embodiments, the inversions are located within one or more genes encoding one or phage translation related proteins. In some embodiments, the one or more inversions are located within one or more genes encoding structural proteins. Such structural genes include genes encoding polypeptides of the head, tail, collar, or coat. In some embodiments, the inversions are located within one or more genes encoding one or more plate proteins. In some embodiments, the inversions are located within one or more genes encoding one or more proteins require for assembly of the bacteriophage. In some embodiments, the inversions are located within one or more genes encoding one or more portal proteins. In some embodiments, the inversions are located within one or more genes encoding one or more polypeptides involved in recombination. In some embodiments, the inversions are located within one or more genes encoding one or more integrases. In some embodiments, the inversions are located within one or more genes encoding one or more invertases. In some embodiments, the inversions are located within one or more genes encoding one or more transposases. In some embodiments, the inversions are located with within one or more genes encoding one or more polypeptides involved in replication or translation. In some embodiments, the inversions are located within one or more genes encoding one or more primases. In some embodiments, the inversions are located within one or more genes encoding one or more tRNA related proteins. In some embodiments, the inversions are located within one or more genes encoding one or more polypeptides involved in phage inversion. In some embodiments, the inversions are located within one or more genes encoding an attachment site. In some embodiments, the inversions are located within one or more genes encoding one or more polypeptides involved in packaging. In some embodiments, the inversions are located within one or more genes encoding one or more terminases. In some embodiments, the inversions are located within one or more genes encoding one or more host genes.

In some embodiments, the inversions are located within genes encoding one or more polypeptides involved in one or more of cell lysis, phage structure, phage assembly, phage packaging recombination, replication or translation, phage inversion, or are host proteins, and combinations thereof.

In some embodiments, the inversions are located within genes encoding one or more polypeptides involved in one or more of cell lysis, phage structure, phage assembly, phage packaging recombination, replication or translation, phage inversion, and combinations thereof.

In some embodiments, the inversions are located within 1 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 3 genes encoding polypeptides involved in cell lysis, phage structure, phage assembly, phage packaging recombination, replication or translation, phage inversion, and combinations thereof. In some embodiments, the inversions are located within 4 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 5 genes encoding polypeptides involved in cell lysis, phage structure, phage assembly, phage packaging recombination, replication or translation, phage inversion, and combinations thereof. In some embodiments, the inversions are located within 6 genes encoding polypeptides involved in cell lysis, phage structure, phage assembly, phage packaging recombination, replication or translation, phage inversion, and combinations thereof. In some embodiments, the inversions are located within 7 genes encoding polypeptides involved in cell lysis, phage structure, phage assembly, phage packaging recombination, replication or translation, phage inversion, and combinations thereof. In some embodiments, the inversions are located within 8 genes encoding polypeptides involved in cell lysis, phage structure, phage assembly, phage packaging recombination, replication or translation, phage inversion, and combinations thereof. In some embodiments, the inversions are located within 9 genes encoding polypeptides involved in cell lysis, phage structure, phage assembly, phage packaging recombination, replication or translation, phage inversion, and combinations thereof. In some embodiments, the inversions are located within 10 genes encoding polypeptides involved in cell lysis, phage structure, phage assembly, phage packaging recombination, replication or translation, phage inversion, and combinations thereof. In some embodiments, the inversions are located within 11 genes encoding polypeptides involved in cell lysis, phage structure, phage assembly, phage packaging recombination, replication or translation, phage inversion, and combinations thereof. In some embodiments, the inversions are located within 12 genes encoding polypeptides involved in cell lysis, phage structure, phage assembly, phage packaging recombination, replication or translation, phage inversion, and combinations thereof. In some embodiments, the inversions are located within 13 genes encoding polypeptides involved in cell lysis, phage structure, phage assembly, phage packaging recombination, replication or translation, phage inversion, and combinations thereof. In some embodiments, the inversions are located within 14 genes encoding polypeptides involved in cell lysis, phage structure, phage assembly, phage packaging recombination, replication or translation, phage inversion, and combinations thereof. In some embodiments, the inversions are located within 15 genes encoding polypeptides involved in cell lysis, phage structure, phage assembly, phage packaging recombination, replication or translation, phage inversion, and combinations thereof. In some embodiments, the inversions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage inversion, and combinations thereof. In some embodiments, the inversions are located within one or more host proteins within the phage genome.

Substitutions

In some embodiments, the substitution is in a coding region of the phage genome. In some embodiments, the substitution is substituted into a regulatory region of the phage genome. In some embodiments, the substitutions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more substitutions comprise at least about 1-500 bp. In some embodiments, the one or more substitutions comprise at least about 500-1000 bp. In some embodiments, the one or more substitutions comprise at least about 1000-2000 bp. In some embodiments, the one or more substitutions comprise at least about 2000-3000 bp. In some embodiments, the one or more substitutions comprise at least about 3000-4000 bp. In some embodiments, the one or more substitutions comprise at least about 4000-5000 bp. In some embodiments, the one or more substitutions comprise at least about 5,000-6,000 bp. In some embodiments, the one or more substitutions comprise at least about 6,000-7,000 bp. In some embodiments, the one or more substitutions comprise at least about 7,000-8,000 bp. In some embodiments, the one or more substitutions comprise at least about 8,000-9,000 bp. In some embodiments, the one or more substitutions comprise at least about 9,000-10,000 bp. In some embodiments, the one or more substitutions comprise at least about 10,000-15,000 bp. In some embodiments, the one or more substitutions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, at least about 55,000-60,000 bp, at least about 60,000-65,000 bp, at least about 65,000-70,000 bp, at least about 70,000-75,000 bp, at least about 75,000-80,000 bp, at least about 80,000-85,000 bp, at least about 85,000-90,000 bp, at least about 90,000-95,000 bp, at least about 95,000-100,000 bp, at least about 100,000-110,000 bp, at least about 110,000-120,000 bp, at least about 120,000-130,000 bp, at least about 130,000-140,000 bp, at least about 140,000-150,000 bp, at least about 150,000-200,000 bp, or more than at least about 200,000 bp. In one specific embodiment, 9687 bp are substituted. In some embodiments, the substituted nucleotides are interspersed. In some embodiments, the substituted nucleotides are consecutive.

In some embodiments, the one or more substitutions are located within 1-500 bp of the phage genome. In some embodiments, the one or more substitutions are located within at least about 500-1000 bp of the phage genome. In some embodiments, the one or more substitutions are located within at least about 1000-2000 bp of the phage genome. In some embodiments, the one or more substitutions are located within at least about 1000-2000 bp of the phage genome. In some embodiments, the one or more substitutions are located within at least about 2000-3000 bp of the phage genome. In some embodiments, the one or more substitutions are located within at least about 3000-4000 bp of the phage genome. In some embodiments, the one or more substitutions are located within at least about 4000-5000 bp of the phage genome. In some embodiments, the one or more substitutions are located within at least about 5,000-6,000 bp of the phage genome. In some embodiments, the one or more substitutions are located within at least about 6,000-7,000 bp of the phage genome. In some embodiments, the one or more substitutions are located within at least about 7,000-8,000 bp of the phage genome. In some embodiments, the one or more substitutions are located within at least about 8,000-9,000 bp of the phage genome. In some embodiments, the one or more substitutions are located within at least about 9,000-10,000 bp of the phage genome. In some embodiments, the one or more substitutions are located within at least about 10,000-15,000 bp of the phage genome. In some embodiments, the one or more substitutions are located within at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are substituted. In some embodiments, the substituted nucleotides are interspersed. In some embodiments, the substituted nucleotides are consecutive.

In some embodiments, the substitutions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome. In some embodiments, at least about 30-40% of the phage genome is substituted. In some embodiments, the substitutions are located within at least about 40-50% of the phage genome. In some embodiments, the substitutions are located within at least about 50-60% of the phage genome. In some embodiments, the substitutions are located within at least about 60-70% of the phage genome. In some embodiments, the substitutions are located within at least about 70-80% of the phage genome. In some embodiments, the substitutions are located within at least about 80-90% of the phage genome. In some embodiments, the substitutions are located within at least about 90-100% of the phage genome.

In some embodiments, at least about 1, 2, 3, 4, 5, 6, 7, 8, 9, 10, 11, 12, 13, 14, 15, 16, 17, 18, 19, or 20 genes comprise substitutions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise substitutions. In some embodiments, 13 genes comprise substitutions. In one embodiment, 74 genes comprise substitutions.

In some embodiments, the one or more substitutions are located at the beginning or 5' end of the phage genome. In some embodiments, the one or more substitutions are located at the end or 3' end of the phage genome. In some embodiments, the one or more substitutions are located in the middle of the phage genome. In some embodiments, the phage genes are interspersed within the bacterial genome and the substitution are located in one or more of the interspersed positions.

In some embodiments, the region for an optimal substitution, i.e., to achieve a desired effect, can be determined through analysis of homology with other phages is other bacteria. Homologous conserved regions in phages may be suitable for substitution, as these are conserved and may comprise one or more essential genes. In some embodiments, regulatory elements, such as promoters, are substituted. In some embodiments, coding sequences are substituted. In some embodiments, the one or more substituted regions contain one or more genes essential for the lytic cycle.

In some embodiments, the substitutions are located within one or more genes encoding lytic genes. In some embodiments, the substitutions are located within one or more genes encoding one or more proteases or lysins. In some embodiments, the substitutions are located within one or more genes encoding one or more toxins. In some embodiments, the substitutions are located within one or more genes encoding one or more antibiotic resistance related proteins. In some embodiments, the substitutions are located within one or more genes encoding one or phage translation related proteins. In some embodiments, the one or more substitutions are located within one or more genes encoding structural proteins. Such structural genes include genes encoding polypeptides of the head, tail, collar, or coat. In some embodiments, the substitutions are located within one or more genes encoding one or more plate proteins. In some embodiments, the substitutions are located within one or more genes encoding one or more proteins require for assembly of the bacteriophage. In some embodiments, the substitutions are located within one or more genes encoding one or more portal proteins. In some embodiments, the substitutions are located within one or more genes encoding one or more polypeptides involved in recombination. In some embodiments, the substitutions are located within one or more genes encoding one or more integrases. In some embodiments, the substitutions are located within one or more genes encoding one or more invertases. In some embodiments, the substitutions are located within one or more genes encoding one or more transposases. In some embodiments, the substitutions are located with within one or more genes encoding one or more polypeptides involved in replication or translation. In some embodiments, the substitutions are located within one or more genes encoding one or more primases. In some embodiments, the substitutions are located within one or more genes encoding one or more tRNA related proteins. In some embodiments, the substitutions are located within one or more genes encoding one or more polypeptides involved in phage substitution. In some embodiments, the substitutions are located within one or more genes encoding an attachment site. In some embodiments, the substitutions are located within one or more genes encoding one or more polypeptides involved in packaging. In some embodiments, the substitutions are located within one or more genes encoding one or more terminases. In some embodiments, the substitutions are located within one or more genes encoding one or more host genes.

In some embodiments, the substitutions are located within genes encoding one or more polypeptides involved in one or more of cell lysis, phage structure, phage assembly, phage packaging recombination, replication or translation, phage substitution, or are host proteins, and combinations thereof.

In some embodiments, the substitutions are located within genes encoding one or more polypeptides involved in one or more of cell lysis, phage structure, phage assembly, phage packaging recombination, replication or translation, phage substitution, and combinations thereof.

In some embodiments, the substitutions are located within 1 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 3 genes encoding polypeptides involved in cell lysis, phage structure, phage assembly, phage packaging recombination, replication or translation, phage substitution, and combinations thereof. In some embodiments, the substitutions are located within 4 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 5 genes encoding polypeptides involved in cell lysis, phage structure, phage assembly, phage packaging recombination, replication or translation, phage substitution, and combinations thereof. In some embodiments, the substitutions are located within 6 genes encoding polypeptides involved in cell lysis, phage structure, phage assembly, phage packaging recombination, replication or translation, phage substitution, and combinations thereof. In some embodiments, the substitutions are located within 7 genes encoding polypeptides involved in cell lysis, phage structure, phage assembly, phage packaging recombination, replication or translation, phage substitution, and combinations thereof. In some embodiments, the substitutions are located within 8 genes encoding polypeptides involved in cell lysis, phage structure, phage assembly, phage packaging recombination, replication or translation, phage substitution, and combinations thereof. In some embodiments, the substitutions are located within 9 genes encoding polypeptides involved in cell lysis, phage structure, phage assembly, phage packaging recombination, replication or translation, phage substitution, and combinations thereof. In some embodiments, the substitutions are located within 10 genes encoding polypeptides involved in cell lysis, phage structure, phage assembly, phage packaging recombination, replication or translation, phage substitution, and combinations thereof. In some embodiments, the substitutions are located within 11 genes encoding polypeptides involved in cell lysis, phage structure, phage assembly, phage packaging recombination, replication or translation, phage substitution, and combinations thereof. In some embodiments, the substitutions are located within 12 genes encoding polypeptides involved in cell lysis, phage structure, phage assembly, phage packaging recombination, replication or translation, phage substitution, and combinations thereof. In some embodiments, the substitutions are located within 13 genes encoding polypeptides involved in cell lysis, phage structure, phage assembly, phage packaging recombination, replication or translation, phage substitution, and combinations thereof. In some embodiments, the substitutions are located within 14 genes encoding polypeptides involved in cell lysis, phage structure, phage assembly, phage packaging recombination, replication or translation, phage substitution, and combinations thereof. In some embodiments, the substitutions are located within 15 genes encoding polypeptides involved in cell lysis, phage structure, phage assembly, phage packaging recombination, replication or translation, phage substitution, and combinations thereof. In some embodiments, the substitutions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage substitution, and combinations thereof. In some embodiments, the substitutions are located within one or more host proteins within the phage genome.

Phage in *E. coli* Nissle

Figure 3:
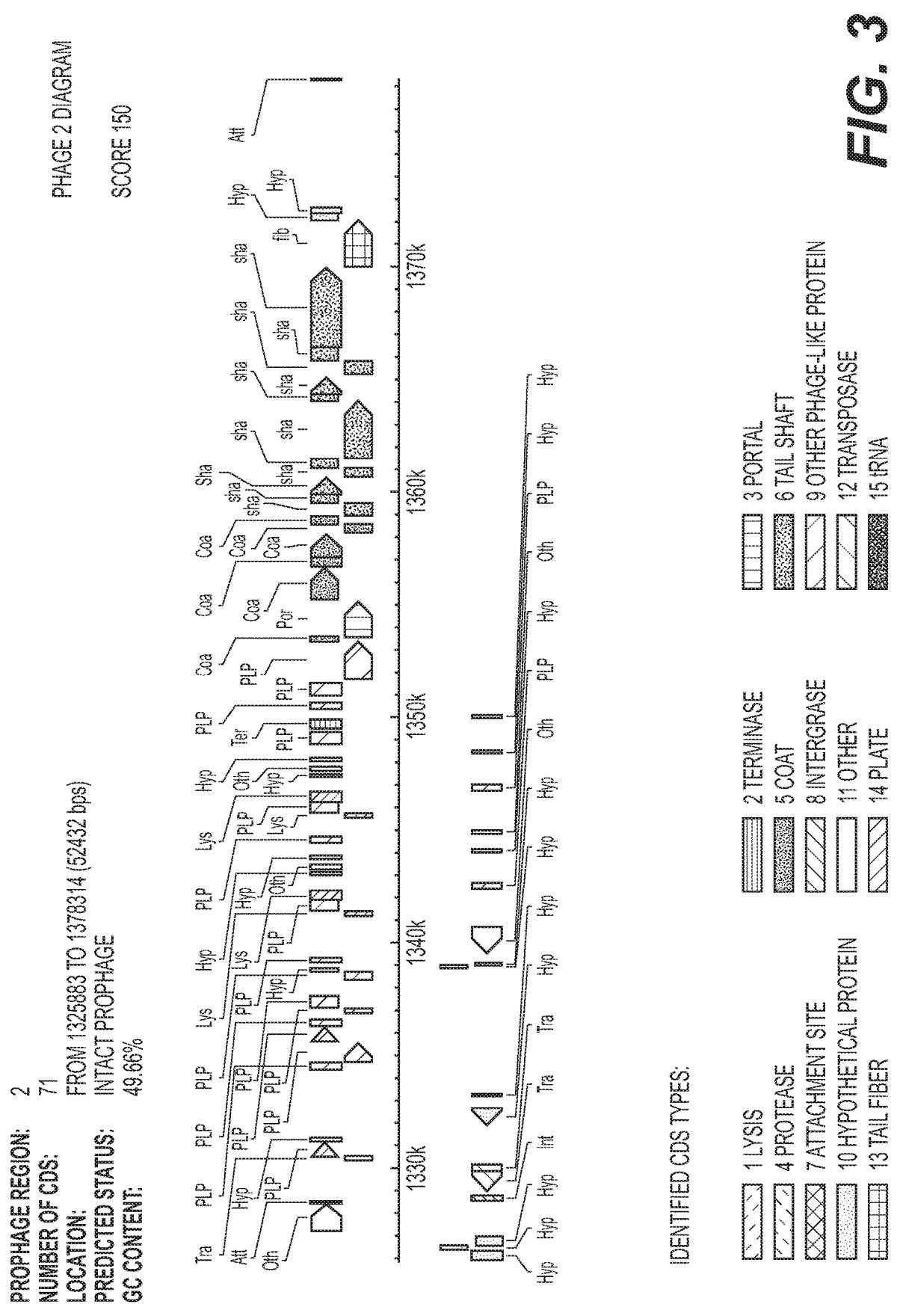
Figure 5A:
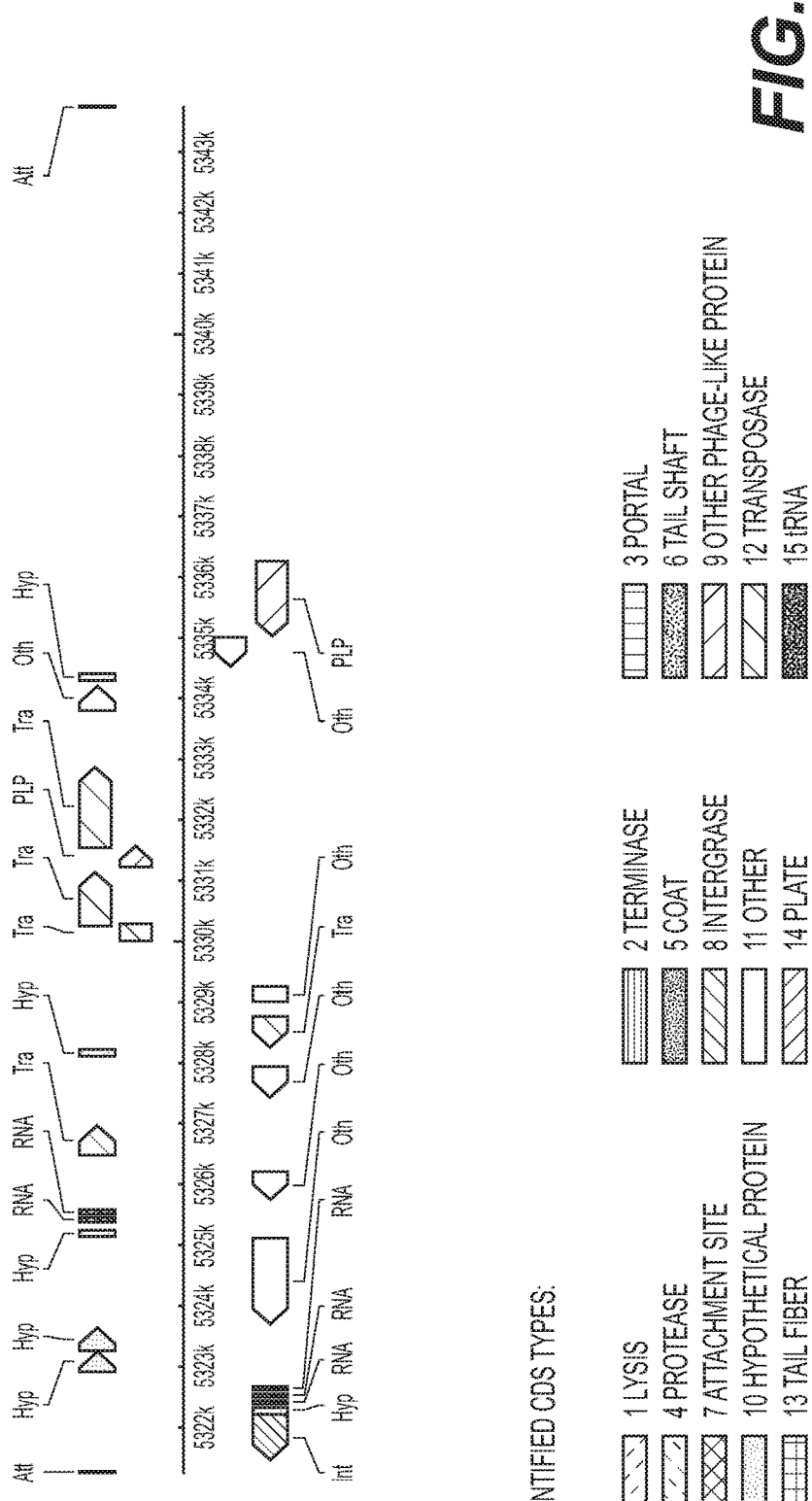
FIG. 5A depicts the first of 2 lower scoring "incomplete" or "questionable" phage identified using the Phast tool. Putative genes are labeled Hyp=Hypothetical, PLP=other phage like protein, Oth=Other, RNA=tRNA, TRA=transposase, int=Integrase, Att=attachment site.
Figure 5B:
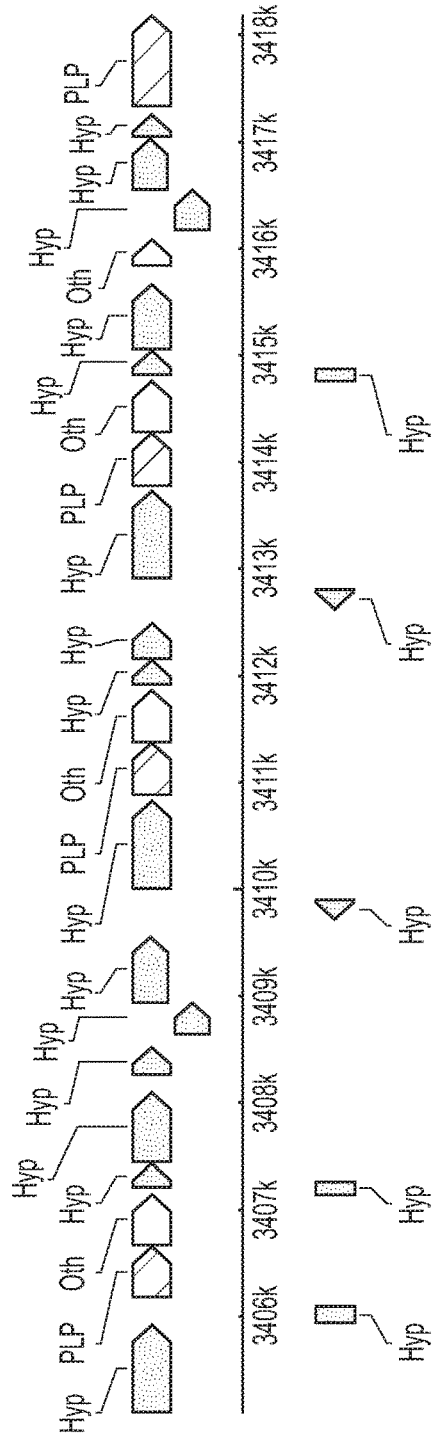
FIG. 5B depicts the second of 2 lower scoring "incomplete" or "questionable" phage identified using the Phast tool. Putative genes are labeled Hyp=Hypothetical, PLP=other phage like protein, Oth=Other.
Figure 6:
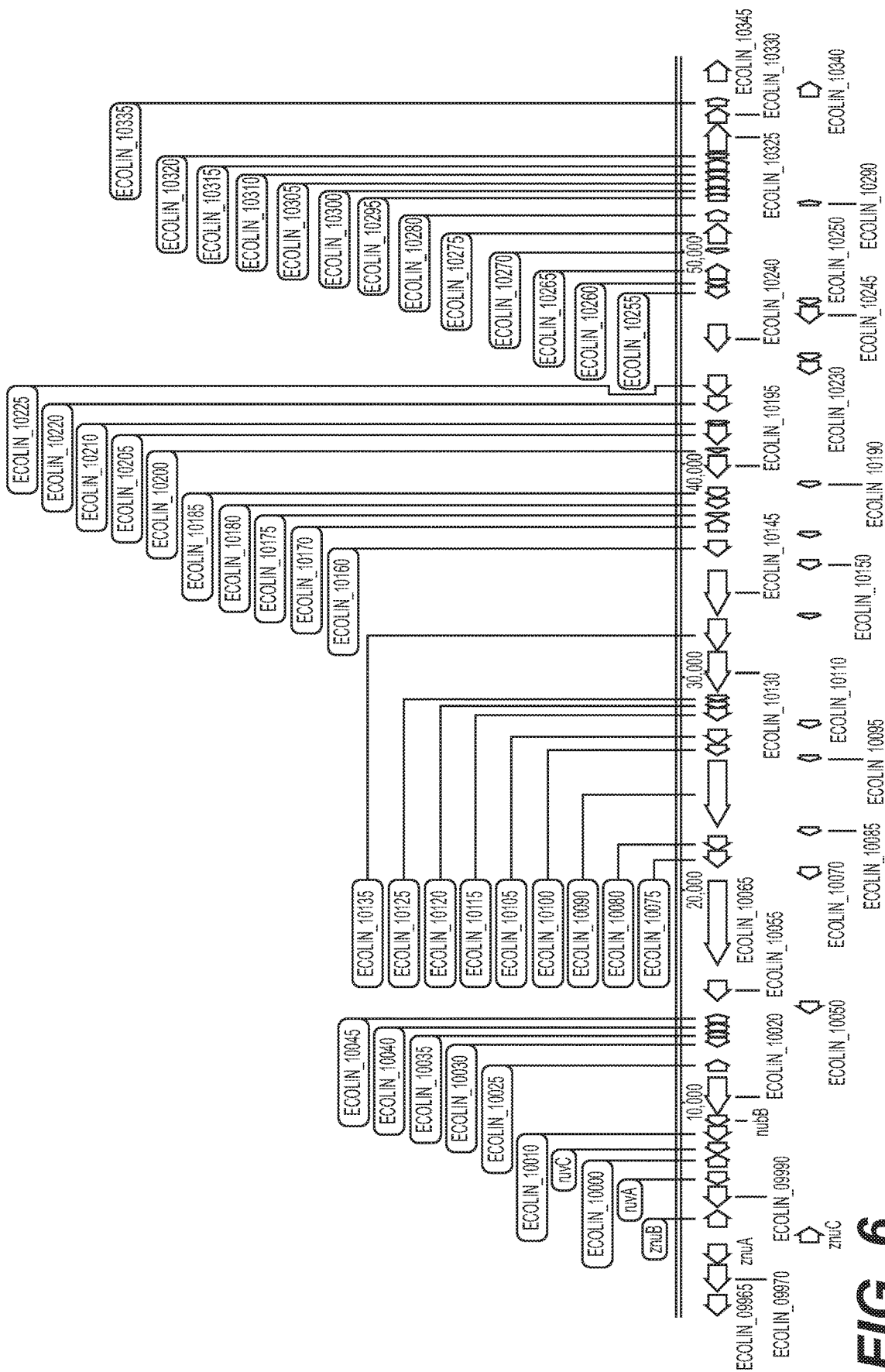
FIG. 6 depicts a schematic of the predicted Nissle Phage 3 sequence (59,056 bp).
Figure 7:
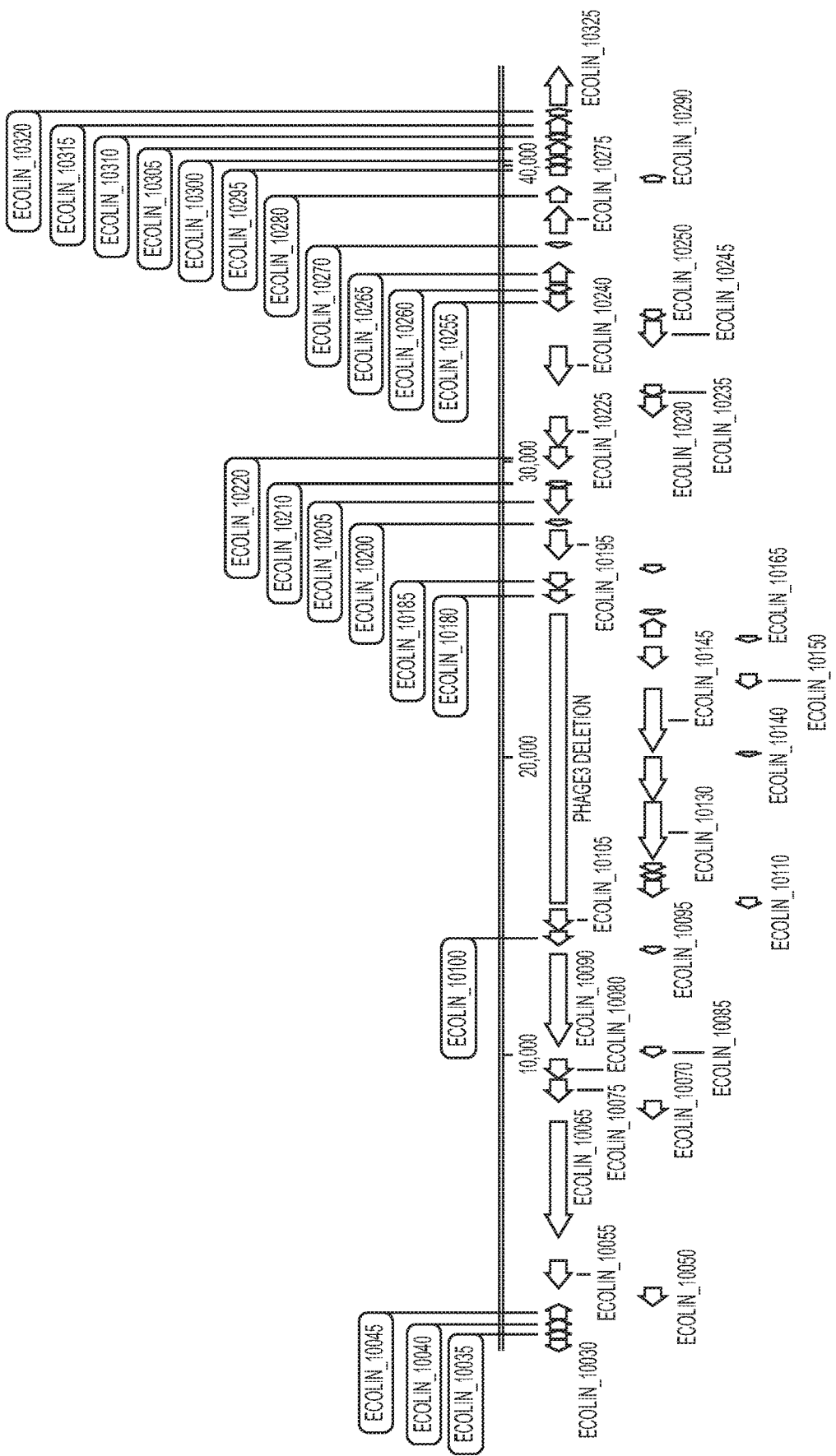
FIG. 7 depicts a schematic of the Phage 3 deletion within the Phage 3 genome used in SYN-PKU-2002.
Figure 8:
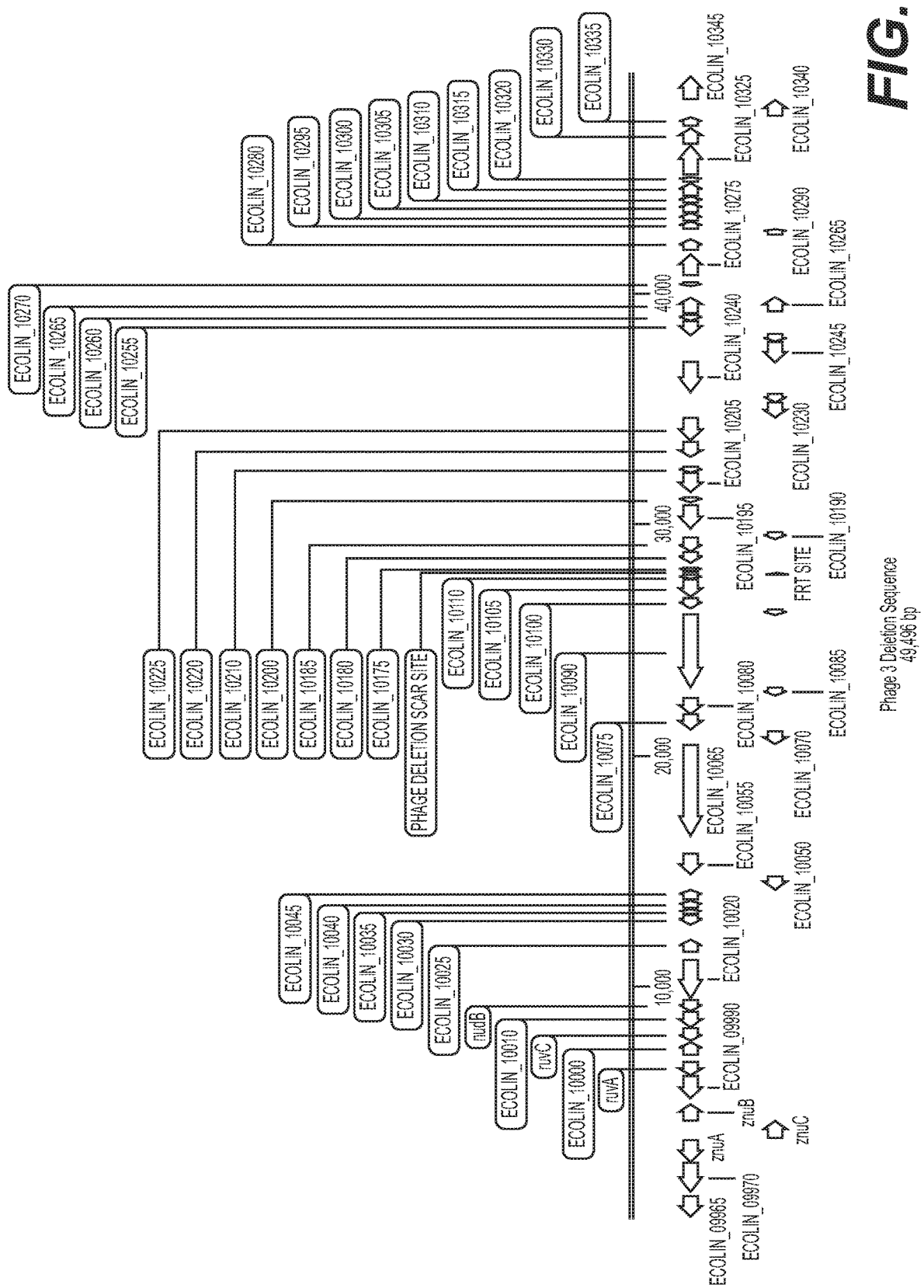
FIG. 8 depicts a schematic showing a 49,496 bp Phage 3 sequence comprising a knockout deletion, e.g., as comprised in SYN-PKU-2002.
Figure 9:
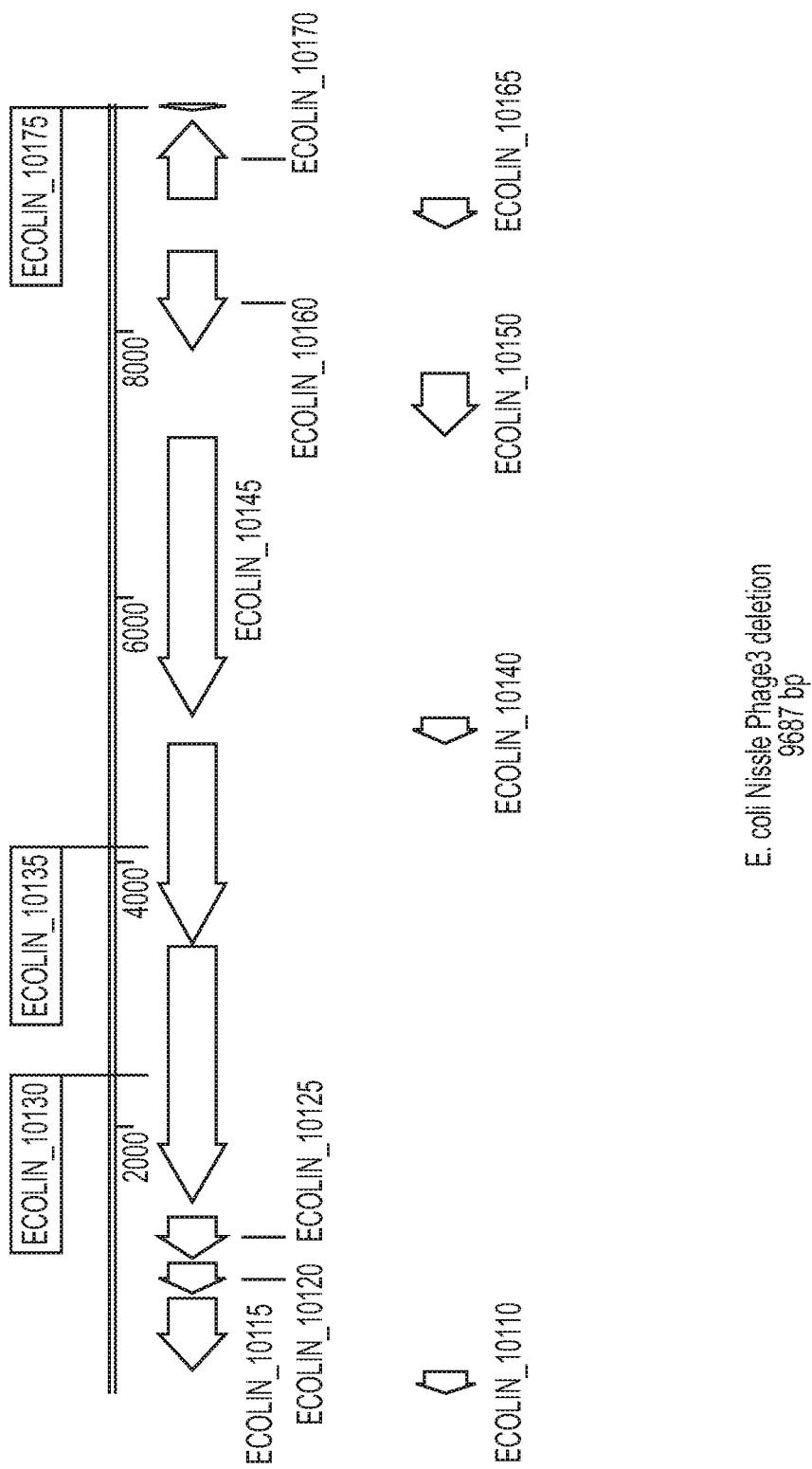
FIG. 9 depicts a schematic of the section of the phage that can be deleted to inactivate the phage, e.g., as deleted in SYN-PKU-2002.

In some embodiments, described herein genetically engineered bacteria are engineered *Escherichia coli* strain Nissle 1917 (*E. coli* Nissle). As described in more detail herein in the examples, routine testing procedures identified bacteriophage production from *Escherichia coli* Nissle 1917 (*E. coli* Nissle; *E. coli* Nissle) and related engineered derivatives. To determine the source of the bacteriophage, a collaborative bioinformatics assessment of the genomes of *E. coli* Nissle, and engineered derivatives was conducted to analyze genomic sequences of the strains for evidence of prophages, to assess any identified prophage elements for the likelihood of producing functional phage, to compare any functional phage elements with other known phage identified among bacterial genomic sequences, and to evaluate the frequency with which prophage elements are found in other sequenced *Escherichia coli* (*E. coli*) genomes. The assessment tools included phage prediction software (PHAST and PHASTER), SPAdes genome assembler software, software for mapping low-divergent sequences against a large reference genome (BWA MEM), genome sequence alignment software (MUMmer), and the National Center for Biotechnology Information (NCBI) nonredundant database. The assessment results show that *E. coli* Nissle and engineered derivatives analyzed contain three candidate prophage elements (FIG. 1), with two of the three (Phage 2 and Phage 3) containing most genetic features characteristic of intact phage genomes (FIG. 2, FIG. 3, and FIG. 4). Two other possible phage elements (FIG. 5A and FIG. 5B) were also identified. Of note, the engineered strains did not contain any additional phage elements that were not identified in parental *E. coli* Nissle, indicating that plaque-forming units produced by these strains originate from one of these endogenous phages. Further analysis described herein identified Phage 3 as the plaque-forming phage (Phage 3). Interestingly, Phage 3 is unique to *E. coli* Nissle among a collection of almost 6000 sequenced *E. coli* genomes, although related sequences limited to short regions of homology with other putative prophage elements are found in a small number of genomes. As described in more detail in the Examples, Phage 3, but not any of the other Phage was found to be inducible and result in bacterial lysis upon induction.

Prophages are very common among *E. coli* strains, with *E. coli* Nissle containing a relatively small number of prophage sequences compared to the average number found in a well-characterized set of sequenced *E. coli* genomes. As such, prophage presence in the engineered strains is part of the natural state of this species and the prophage features of the engineered strains analyzed were consistent with the progenitor strain, *E. coli* Nissle.

Table D lists the genes contained within the genome of Phage 3. Table E. Provides the sequence of Phage 3. Table F provides the sequences of the genes comprised in Phage 3 of *E. coli* Nissle. Table G. provides the sequences of the polypeptides encoded by the genome of *E. coli* Nissle Phage 3.

TABLE D

Phage 3 Genome

| Description | Position | Length | Orientation | GI Number | Protein ID | product |
|---|---|---|---|---|---|---|
| ECOLIN_09965 | 27 . . . 998 | 972 | <= | 660511998 | AID78889.1 | lipid A biosynthesis (KDO)2-(lauroyl)-lipid IVA acyltransferase |
| ECOLIN_09970 | 1117 . . . 2439 | 1323 | <= | 660511999 | AID78890.1 | peptidase |
| ECOLIN_09975 | 2455 . . . 3387 | 933 | <= | 660512000 | AID78891.1 | zinc ABC transporter substrate-binding protein |
| ECOLIN_09980 | 3466 . . . 4221 | 756 | => | 660512001 | AID78892.1 | zinc ABC transporter ATPase |
| ECOLIN_09985 | 4218 . . . 5003 | 786 | => | 660512002 | AID78893.1 | high-affinity zinc transporter membrane component |
| ECOLIN_09990 | 5150 . . . 6160 | 1011 | <= | 660512003 | AID78894.1 | ATP-dependent DNA helicase RuvB |
| ECOLIN_09995 | 6169 . . . 6780 | 612 | <= | 660512004 | AID78895.1 | ATP-dependent DNA helicase RuvA |
| ECOLIN_10000 | 7056 . . . 7658 | 603 | => | 660512005 | AID78896.1 | hypothetical protein |
| ECOLIN_10005 | 7660 . . . 8181 | 522 | <= | 660512006 | AID78897.1 | Holliday junction resolvase |
| ECOLIN_10010 | 8216 . . . 8956 | 741 | <= | 660512007 | AID78898.1 | hypothetical protein |
| ECOLIN_10015 | 8985 . . . 9428 | 444 | <= | 660512008 | AID78899.1 | dihydroneopterin triphosphate pyrophosphatase |
| ECOLIN_10020 | 9430 . . . 11,202 | 1773 | <= | 660512009 | AID78900.1 | aspartyl-tRNA synthetase |
| ECOLIN_10025 | 11,512 . . . 12,078 | 567 | => | 660512010 | AID78901.1 | hydrolase |
| ECOLIN_10030 | 12,680 . . . 13,069 | 390 | <= | 660512011 | AID78902.1 | DNA polymerase V ECOLIN_10030 |
| ECOLIN_10035 | 13,148 . . . 13,390 | 243 | => | 660512012 | AID78903.1 | MsgA |
| ECOLIN_10040 | 13,426 . . . 13,806 | 381 | => | 660512013 | AID78904.1 | hypothetical protein |
| ECOLIN_10045 | 13,808 . . . 14,251 | 444 | => | 660512014 | AID78905.1 | hypothetical protein |
| ECOLIN_10050 | 14,223 . . . 14,816 | 594 | <= | 660512015 | AID78906.1 | phage tail protein |
| ECOLIN_10055 | 14,816 . . . 15,748 | 933 | <= | 660512016 | AID78907.1 | tail protein |
| ECOLIN_10065 | 16,519 . . . 20,445 | 3927 | <= | 660512017 | AID78908.1 | host specificity protein |
| ECOLIN_10070 | 20,488 . . . 21,105 | 618 | <= | 660512018 | AID78909.1 | tail protein |

TABLE D-continued

Phage 3 Genome

| Description | Position | Length | Orientation | GI Number | Protein ID | product |
| --- | --- | --- | --- | --- | --- | --- |
| ECOLIN_10075 | 21,098 ... 21,817 | 720 | <= | 660512019 | AID78910.1 | peptidase P60 |
| ECOLIN_10080 | 21,820 ... 22,557 | 738 | <= | 660512020 | AID78911.1 | hypothetical protein |
| ECOLIN_10085 | 22,614 ... 22,952 | 339 | <= | 660512021 | AID78912.1 | tail protein |
| ECOLIN_10090 | 22,949 ... 26,086 | 3138 | <= | 660512022 | AID78913.1 | tail protein |
| ECOLIN_10095 | 26,070 ... 26,342 | 273 | <= | 660512023 | AID78914.1 | tail protein |
| ECOLIN_10100 | 26,393 ... 26,824 | 432 | <= | 660512024 | AID78915.1 | tail protein |
| ECOLIN_10105 | 26,835 ... 27,578 | 744 | <= | 660512025 | AID78916.1 | tail fiber protein |
| ECOLIN_10110 | 27,588 ... 27,989 | 402 | <= | 660512026 | AID78917.1 | Minor tail protein U |
| ECOLIN_10115 | 27,986 ... 28,558 | 573 | <= | 660512027 | AID78918.1 | tail protein |
| ECOLIN_10120 | 28,574 ... 28,816 | 243 | <= | 660512028 | AID78919.1 | DNA breaking-rejoining protein |
| ECOLIN_10125 | 28,842 ... 29,168 | 327 | <= | 660512029 | AID78920.1 | hypothetical protein |
| ECOLIN_10130 | 29,251 ... 31,197 | 1947 | <= | 660512030 | AID78921.1 | peptidase S14 |
| ECOLIN_10135 | 31,211 ... 32,710 | 1500 | <= | 660512031 | AID78922.1 | capsid protein |
| ECOLIN_10140 | 32,707 ... 32,922 | 216 | <= | 660512032 | AID78923.1 | hypothetical protein |
| ECOLIN_10145 | 32,919 ... 35,021 | 2103 | <= | 660512033 | AID78924.1 | DNA packaging protein |
| ECOLIN_10150 | 35,021 ... 35,509 | 489 | <= | 660512034 | AID78925.1 | terminase |
| ECOLIN_10160 | 35,693 ... 36,421 | 729 | <= | 660512035 | AID78926.1 | hypothetical protein |
| ECOLIN_10165 | 36,596 ... 36,826 | 231 | <= | 660512036 | AID78927.1 | hypothetical protein |
| ECOLIN_10170 | 36,825 ... 37,421 | 597 | => | 660512037 | AID78928.1 | hypothetical protein |
| ECOLIN_10175 | 37,490 ... 37,687 | 198 | <= | 660512038 | AID78929.1 | hypothetical protein |
| ECOLIN_10180 | 37,901 ... 38,380 | 480 | <= | 660512039 | AID78930.1 | hypothetical protein |
| ECOLIN_10185 | 38,401 ... 38,949 | 549 | <= | 660512040 | AID78931.1 | lysozyme |
| ECOLIN_10190 | 38,921 ... 39,199 | 279 | <= | 660512041 | AID78932.1 | holin |
| ECOLIN_10195 | 39,345 ... 40,397 | 1053 | <= | 660512042 | AID78933.1 | DNA adenine methylase |
| ECOLIN_10200 | 40,548 ... 40,739 | 192 | <= | 660512043 | AID78934.1 | hypothetical protein |
| ECOLIN_10205 | 40,908 ... 41,807 | 900 | <= | 660512044 | AID78935.1 | serine protease |
| ECOLIN_10210 | 41,820 ... 42,026 | 207 | <= | 660512045 | AID78936.1 | hypothetical protein |
| ECOLIN_10220 | 42,459 ... 43,148 | 690 | <= | 660512046 | AID78937.1 | antitermination protein |
| ECOLIN_10225 | 43,170 ... 44,165 | 996 | <= | 660512047 | AID78938.1 | hypothetical protein |
| ECOLIN_10230 | 44,162 ... 44,845 | 684 | <= | 660512048 | AID78939.1 | antirepressor |
| ECOLIN_10235 | 44,859 ... 45,245 | 387 | <= | 660512049 | AID78940.1 | crossover junction endodeoxyribonuclease |
| ECOLIN_10240 | 45,242 ... 46,561 | 1320 | <= | 660512050 | AID78941.1 | adenine methyltransferase, DNA methyltransferase ECOLIN_10240 |
| ECOLIN_10245 | 46,558 ... 47,439 | 882 | <= | 660512051 | AID78942.1 | GntR family transcriptional regulator ECOLIN_10245 |
| ECOLIN_10250 | 47,449 ... 47,787 | 339 | <= | 660512052 | AID78943.1 | hypothetical protein |

TABLE D-continued

| Phage 3 Genome | | | | | | |
|---|---|---|---|---|---|---|
| Description | Position | Length | Orientation | GI Number | Protein ID | product |
| ECOLIN_10255 | 47,784 ... 48,347 | 564 | <= | 660512053 | AID78944.1 | hypothetical protein, completely unknown |
| ECOLIN_10260 | 48,379 ... 48,636 | 258 | <= | 660512054 | AID78945.1 | hypothetical protein, cI repressor ECOLIN_10260 |
| ECOLIN_10265 | 48,715 ... 49,425 | 711 | => | 660512055 | AID78946.1 | hypothetical protein, Domain of unknown function (DUF4222); This short protein is likely to be of phage origin. For example it is found in Enterobacteria phage YYZ-2008. It is largely found in enteric bacteria. The molecular function of this protein is unknown. |
| ECOLIN_10270 | 49,868 ... 50,065 | 198 | <= | 660512056 | AID78947.1 | hypothetical protein |
| ECOLIN_10275 | 50,378 ... 51,295 | 918 | => | 660512057 | AID78948.1 | DNA recombinase In *Escherichia coli*, RdgC is required for growth in recombination-deficient exonuclease-depleted strains. Under these conditions, RdgC may act as an exonuclease to remove collapsed replication forks, in the absence of the normal repair mechanisms ECOLIN_10275 |
| ECOLIN_10280 | 51,404 ... 51,943 | 540 | => | 660512058 | AID78949.1 | hypothetical protein, 5' Deoxynucleotidase YfbR and HD superfamily hydrolases ECOLIN_10280 |
| ECOLIN_10290 | 52,104 ... 52,358 | 255 | => | 660512059 | AID78950.1 | hypothetical protein Multiple Antibiotic Resistance Regulator (MarR) family of transcriptional regulators |
| ECOLIN_10295 | 52,355 ... 52,702 | 348 | => | 660512060 | AID78951.1 | hypothetical protein, unknown ead like protein in P22 |
| ECOLIN_10300 | 52,704 ... 53,012 | 309 | => | 660512061 | AID78952.1 | hypothetical protein, totally unknown |

TABLE D-continued

Phage 3 Genome

| Description | Position | Length | Orientation | GI Number | Protein ID | product |
|---|---|---|---|---|---|---|
| ECOLIN_10305 | 53,026 . . . 53,493 | 468 | => | 660512062 | AID78953.1 | hypothetical protein, Protein of unknown function (DUF550); This family is found in a range of Proteobacteria and a few P-22 dsDNA virus particles. The function is currently not known. Similar to P22 EA gene ECOLIN_10305 |
| ECOLIN_10310 | 53,496 . . . 53,750 | 255 | => | 660512063 | AID78954.1 | hypothetical protein, Phage repressor protein C, contains Cro/C1-type HTH and peptisase s24 domains |
| ECOLIN_10315 | 53,772 . . . 54,341 | 570 | => | 660512064 | AID78955.1 | hypothetical protein, 3'-5' exonuclease ECOLIN_10315 |
| ECOLIN_10320 | 54,382 . . . 54,618 | 237 | => | 660512065 | AID78956.1 | excisionase ECOLIN_10320 |
| ECOLIN_10325 | 54,677 . . . 55,990 | 1314 | => | 660512066 | AID78957.1 | integrase, Phage integrase family; Members of this family cleave DNA substrates by a series of staggered XerC |
| ECOLIN_10330 | 56,017 . . . 56,742 | 726 | => | 660512067 | AID78958.1 | hypothetical protein |
| ECOLIN_10335 | 56,795 . . . 57,190 | 396 | => | 660512068 | AID78959.1 | membrane protein |
| ECOLIN_10340 | 57,231 . . . 57,974 | 744 | => | 660512069 | AID78960.1 | tRNA methyltransferase |
| ECOLIN_10345 | 57,971 . . . 58,942 | 972 | => | 660512070 | AID78961.1 | tRNA methyltransferase |

TABLE E

Phage 3 Genome Sequence
SEQ ID NO: 134

```
aggcctctcctcgcgagaggcatttttatttgatgggataaagatcttt
gcgcttatacggttggatttcgcccggtttgcgagttttcagcaatttta
atatccaggtgtattgttctggtcgcggaccaacaaaaatctcgacttct
tcattcatccgccgcgcaatcgtatgatcatccgcctctaacagatcatc
catcggtgggcgcacctgaatcgtcagacgatgcgtcttgccatcataaa
tcggaaatagcggtacaacgcgcgcacggcacacttttcatcaaacgacca
atcgcgggcaacgtcgctttataggtggcaaagaaatcaacaaattcgct
gtgttctgggccatgatcctgatcgggtaaataatatccccagtaaccct
gacgtaccgactggatgaatggtttaataccatcattttctcgcatgcaga
cgaccaccaaagcgacggcgcaccgtgttccagacataatcaaaaaccgg
gttgccctgattatggaacatcgctgccattttctgcccttgcgaggcca
tcagcatggcaggaatatcgacggcccaaccgtgcggcaccagaaaaatc
actttctcgttattacgtcgtatctcttcgatgatctccagcccttgcca
gtcaacgcgcggctgaattttctccggcccgcgtattgccaactcagcca
tcattaccatcgcttgcggcgcggtggcaaacatctcatctacaatcgct
tcgcgttcagcttcactacgttctggaaagcagagcgacagattgattaa
cgcacgacggcgtgagcttttccagtcgtccggcaaaacgtcccagcc
gtgccagaatgggatcacggaactttggcggcgttaaagcgatacccgcc
atcgctgctacgcccagccatgctccccagtagcgcgggtggcgaaagga
tttatcaaactcaggaatgtattcgctattattttttcgtttccatgc
ttttccagtttcggataaggcaaaaatcaatctggtgatagtgtagcggc
gcaacttgccccgcaccaaataaaaagccggtactgactgcgtaccggc
tgcgaatggatgttaattaatcaaaccgtagtcgggcacaatctctttg
gcctgtgccaggaattcgcgacgatcggagccggtcagccttcggtacg
cggcagttttgccgtcagcgggtttacggcctgctggtttatccatactt
catagtgcagatgcgggcccggttgaacgtccggtattaccggaaagcgcg
atacggtcgccacgtttcaccttctgtcccggtttcaccaggatcttgcg
caagtgcatataacgcgtggtgtagctgcgaccatgacgaatagccacat
aataacctgcgccactacgtttggcaaccaccacttcaccgtcaccc
actgaaagcactggctacctgtggcatggcaaaatcaacacctctgtg
tggcgcaacgcgaccggtcaccggattagtacgacgcgggtaaagttag
atgagatacggaactgttcgccgtcgggaatcgcaagaatcctttcgcc
agaccagtaccgttacgatcgtagaatttgccatcttcagcgcggattgc
gtaataatctttaccttctgaacgcaaacgtacgcccagcagctggctt
```

TABLE E-continued

Phage 3 Genome Sequence
SEQ ID NO: 134 gctcacgtttaccatcaagcatttctcgtgacattaacaccgcaaattca
tcgccttttttcagtttgcggaaatccatttgccactgcatggctttaat
cactgcgctcacttcggcgctggttaaaccggcgtttctggcgctggcaa
caaagcttcccccgacggtaccttcagcagattgttgacccactctcct
tgctgcatttcgctggtcattttaaaaccgttagcggcagtacggtcata
ggttcgggtttcacgacgagacacttcccaggtgaggcgctgcagttcgc
cgtccgcggttaatgtccaggagagttgttgaccgattttcaggttacgc
aattctttgtcggcagcagccagttgggtgatatcacccatatcaatacc
atactgattgagaatgctgcttagcgtatcgccagtggaacaacatatt
catgcacgcccgcttcaccggcgattttgtcatccagttcgtcctgggga
atggcttcatcttcttgtgcagcttgatcaatcggctcactggcttcagg
taagagcgaacgaatttcgttctgttccagctcaatggttttgacaattg
gcgtggcatcgcggtgataaacatagggccgcagacagcgacggccaga
gtaagaacggtgagcgacccaacataacgcggtgtggtcgcggtaaat
attaaacgccagggcgacagagcgggctatctgttgcacgtaatcacttc
ctcattaatctcctttcaggcagctcgcatactggttggctaattgattc
aggaattctgaatagcttgttttacccagtttgatattcgtccccagggg
atccaacgttcccatacgaacggatgtccctcgtgcgacgctctcaacga
ccgctggcctgaactgtggctcagcaaaaacgcaggttgcttttttgctca
accaactgtgttcttatttcatgtaaacgctgcgcgccaggttgaatctc
agggttaacggtaaaatgaccaagcggtgtcagtccgaactgtttttcga
aatagccgtaagcatcgtgaaaaacgaaataaccttttccccttgagcggc
gcgagctcgttaccaacctgcttttcggttgaggctaattgtgcctcaaa
atccttcaggttggcgtcaagtttggctcgactttgcggcataagttcca
ctaattttccatggattgcaaccgctgtagcccgcgctatctctgggaa
agccaaagatgcatgttgaaatcgccgtgatggtgatcttcgtcacttt
ttccgcgtggtcgtgatcatcatcatcgccgtgaatactttttcatcagca
gcggtttcacattctctagctgcgcaatcgttacctgtttcgcttcaggt
aatttacttaccggttttgcatgaacgcttccatctccgggccaaccca
aacgactaagtccgcgttctgtaagcgttttacatctgatggacgcagtg
aataatcatgttctgaagccccgtcaggtagtaaaacctccgtttctgtt
acccatcagcaatggcagaagcgatgaacccaacgggttttaagcgaagc
gacaacggcagcatctgcggcctgtgttgcaccgccccagagagcggcgg
ataatgctgcgaaaagaagcgttttttttatgtaacataatgcgaccaatc
atcgtaatgaatatgaagtgtgatattataacattttcatgactactgc
aagactaaaattaacgtgacaagtctggtttccctggaaaatgtctcggt
ttcttttggccaacgccgcgtcctctctgatgtgtcgctggaacttaaac
ctggaaaaattttgactttacttgggccaaacggcgcaggtaagtcgaca
ctggtacgggtagtgctcgggtcgtgtaacacccgatgaagggttatca
gcgcaacggaaaactgcgcatcggctatgtaccgcagaagctgtatctcg
acaccacgttgccactgaccgtaaaccgttttttacgcttacgccctggc
acacataaagaagatatttcgctgcactgaaacgtgtccaggccgggca
tctgattaacgcaccgatgcaaaagctctcgggtggcgaaacgcagcgtg
tactgttagcgcgagcattgttaaatcgaccgcaattattagtgctggat
gaacccactcagggcgtggatgtgaatggtcaggtggcgttatatgacct
tattgaccaactgcgtcgcgaactggattgtggcgttttaatggtatctc
acgatctgcatctgataatggcaaaaaccgatgaagtgctttcctgaat
caccacatttgttgttccggcacaccggaagttgtttccctgcatccgga
gtttatttctatgtttggtcctcgtggtgctgaacaactgggtatctatc
gccatcatcataatcatcgtcacgatttacagggacgaattgttttgcgt
cggggaaatgatcgctcatgattgaatttattttccggttggttagcc
gggatcatgctcgcctgtgccgcgggtccgctggtcgtttgtagtctg
gcgtcgtatgtcttatttcggtgatacgctggctcatgcctcattacttg
gcgtcgcgtttggtttgttgctggacgtgaatccattctatgcggtgatt
gccgttacgctgctgctggcggggcggtctggtatggctggagaagcgtcc
acagctggcgatcgacacgttattagggattatggcgcacaggtgccctgt
cgctgggcctggtggtcgttagtctgatgtctaatattcgtgttgatttg
atggcttacctgttcggtgatttactggcagtgacgccagaagatctcat
ctctattgcgattggcgtggtcatcgtggtggctattttgttctggcaat
ggcgcaatttgctgtcgatgacgattagcccggatctggcgtttgttgat
ggtgtgaaattacagcgcgtgaaattgttgttgatgctggtgacggcatt
gacgattggtgtagcgatgaaattcgtcggcgcgttgattattacttcac
tgctgattattcctgctgctactgcacgtcgctttgcccgcacgccgaa
cagatggctggtgtcgctgttttggtgggatggtggcagtgactggcgg
tttaaccttttccgcatttttacgatacacctgcaggcccgtcggtggtgc
tatgcgcggcactgttatttattatcagtatgatgaaaaagcaggccagc
taatctgtcgctgaacacatttgtcggatgcggcgcgagcgccttatccc
acctgcggttcgctatctctggtaggcctgataagacgcaaacgacgtcg
catcaggcacactgccagtgtcggatgcggctcgagcgaccaatccgact
tacggcatttctggcggtgtgatgccgaagtggttccacgcccgcactgt
cgccatacgcccgcggtgtacgctgcaaaaagccttgctgaatcaaat
aaggttccagtacatcctcaatggtttcacgttcttcgccaatggctgcc
gccaggttatccagacctaccggcccaccaaaagaacttatcgattacc
cagcaacaatttgcggtccatataatcgaaccttcagcatcgacattca
acatatccagcgctgagcagcgatatctgccgagatggtgccatcgtgc
ttcacttcagcgaaatcacgcactcgacgcagcagacggttggcaatacg
tggcgtaccgcgcgcacgacgagcaacttccagcgcgccgtcatcactca TABLE E-continued Phage 3 Genome Sequence
SEQ ID NO: 134 tctcaagcccccatcaaagcgtgcgctgcgactgacgatatattgcagatcc
ggcacctgataaaactccagacgttgcacaataccaaaacgatcgcgcaa
cggtgatgtcagcgaacctgcgcgcgtggttgcaccaatcagggtaaacg
gcggcaaatcaattttaatggagcgtgccgccggaccttcaccaatcatg
atatccagttggtaatcttccattgccggatacaacacctcttccaccac
tggtgaaagacggtggatctcatcaataacagtacatcgtgttggttcaa
ggttagtgagcattgctgccagatcgcccgccttttccagcaccggacca
gaagtcgtgcgtaaattaacgcccatttcattggcgacaatattggcaag
cgtagttttacccaaccccggaggaccaaaaatcaatagatgatcgaggg
catcgccgcgcagttcgctgctttgatgaaaatctccatctgcgaacga
acctgcggctgaccaacatactcttccagtaatttagggcgaatggcgcg
atctgccacatcttccggcaaagtggtaccggcagaaatcagacggtctg
cttcaatcatcctttacctcataacgcgcgcgtagggcttcgcgaatta
atgtttcactgctggcgtcggcgagcgattttgctcaccatgcgggctt
gcttcttgtggttatagcccagtgccaccagcgcagcaaccgcttcctg
ttcagcatcgtcggtcgccgggctggcaggagacgtgagtaccaggtcgg
cggctggcgtaaagagatcgccatgcaaacctttaaatcggtctttcatt
tcgacaatcaagcgttcggcggtttttttgccaatacccggcagtttcac
cagtgccccccacttcttcacgctcaacgcgcattaacgaactgctgcgctg
acattccggagaggatcgccagcgccaacttcgggccgacgccgttggtt
ttgatcaactctttgaacaacgtgcgctcttgtttattgttaaaaccgta
cagcagttgcgcgtcttcacgcaccacaaagtgggtgaaaacgatcgctt
cctgacccgcttcagggagttcataaaaacaggtcatcggcatatgcact
tcatagcctacgccgcccactcaattaacaccagcggggggttgttttt
aatgatgatgcctctgagtctgcctatcacatgacgctcctgcgtaatga
atcaaagataatgctgtatgataaaaaaatgctggatagatatccagcga
aggatgaagaaaacttgcgaggtgtctcgatgatctgaaaaatggcgcag
tataattattctacagattatattggaagcaaatatttaaatattacat
attcagcgaagaaatgtgtaataaaaatacacattgcgacccctgaaaaa
aataaatttttttatgctattacgtatattcatatctatttcaatggaatg
acaacgtcaataattaattatcctgctgaataatgaaattggtgatatcgtc
tttacatgtataagtgctgccttatttggtcaaatatcagctgcatcaaa
ttgctggagtaatcacgtcggatcattatcggtcataacggtgaagact
ttctggttgcagaaagccgtgttccctctcaaccatcactacgctatcc
cgttttattaaacgctctgctaatcaacgctatgctataaagcgattaga
cgccggactaacagaacaacaaatcaacgaattgttgaacaggttccctt
cccggctacgcaaaatttaccacaccggttttaaatacgaatcttcgcgc
cagttctgttcaaaatttgttttttgatatttataaagaggcgctatgtat
tccggtgggtgaatagagacgtttggagaattgttaaatagcaatgaa
atgcaaaactcactttctgaaattctggttcttaggttctattccgtgg
gagcgtaaaaccgtcacgccagccagtttgtggcatcatccggggtttggt
gttgattcacgcggtgggagttgaaacgcctcagcctgaactgaccgagg
cggtataacttaacgcagtcgccctctcgccaggttcagttcagtcgcgattcgc
tcatttgcatcgcattctgactaacgtgcagtgggtgatggcaatccgc
agcgcatcggcggcatccgcctgtggattagcgggcagtttcagcaaggt
gcggaccatatgctgcacctggctttttcggcactaccaatacctacca
ctgtttgctttacctgacgtgccgcatattcaaataccggcaattcctga
ttcaccgcgccacaatcgccacgccgcgcgcctgcccccagtttcagggc
tgagtcagcgttcttcgccataaagacctgttcaatggcgaaataatcag
gctggaattgggtgatgatttccgtcacgcccgcatagatgagcttcaga
cgagacggtaaatcatccactttggtgcgtatgcatccgctacccaggta
ggacagttgcctgcctacctggcggtgacgccatagccggtcacgcgcg
aacccgggtcaatgccgagaataatagccatcacgcgtctccgttttgct
gtttagcaggcctcatcagagagtcgctgcaacctcatcagagatttcac
cgttatggtaaacttcctgcacgtcgtcgcaatcttccagcatatcgatc
agacgcatcagtttcggtgcggttcctgcatccatatcagcttttggga
cgggatcatggaaacttccgcgctgtctgttttcagacctgccgcttcca
gagcgtcgcgtactttgcccatttcttcccatgcagtgtagacatcaatc
gcgccgtcatcataggtcacaacgtcttcagcaccggcttccagggctgc
ttccatgatgtgtcttcatcgccttttctcgaaggagatcacgccttttt
tgctgaacaaataagctacggaaccatcagtaccgaggttaccgccacat
ttgctgaatgcatgacgcacttcagcaacggtacggttgcggttgtcaga
cagacattcaatcatgattgccgtgccgccaggaccgtaaccttcgtaga
tgatggtttccatgtttgcatcatcaccgcccacacctcgtgcaatt
gcgcggttcagagtgtcacggtcatgtgttagacagtgctttatcaat
tgctgcacgcaaacgcgggttagcgtccgatcaccaccgccagcttag
ccgcggttaccagctcacgaatgattttagtgaagattttaccgcgctta
gcatcctgcggctttacgatgtctggtgttggcccatttactatgacc
tgccataaaaatatctccagatagccctgcctgttcaggcagcgttaatt
acaaactgttcaatcgcctgccggttgctccaggacttagtgagcgccgc
cgcagcagacgcatcaagccacttgtaagccagatgttcagtgaaaacga
tctgcgctgtcgtgaagcgcaagacagaaccatgattccgttcgattcga
gtcacgcccgtgccatagcgatgacgtaaatgtgaaaaaatttcaaactc
taccgtgcgctgacagtcaattaaggtcagttgttcagcgacaacatcaa
tggtgaccttcctttacttcgcgcatggcagcttgcggcgcggtttca
ccctcttccacgctgccggttaccgactgccagaaatcgggatcgtcacg
ccgctgcaacatcagcaccgtttcgtatcttgtgcgtagatgaccacta TABLE E-continued Phage 3 Genome Sequence
SEQ ID NO: 134 agatcgaaacgggacgcttataagccatatcagttattctcagccttctt
cacaacctgaatgctcagctcagccagtgcagtcgggttagcaaagctcg
gcgcttcagtcatcaaacacgctgccgccgtggttttcgggaaggcgata
acgtcacggatattgtcggtgccggtcagcagcatcgtcagacggtcaag
accgaatgccaaacctgcgtgcggcggagtaccgtatttcagggcgtcga
gcaggaagccgaatttctcgcgctgttcctcttcgttgatacccagaata
ccaaacaccgtctgctgcatatcaccattatggatacgcacagaaccacc
gcccacttcgtaaccattgatgaccatatcgtaagcgttagccaccgcat
tttccggtgcagctttcagttctgctgccgtcatgtctttcggtgaggtg
aacggatggtgcattgctgtcaggccgccttcaccgtcgtcttcaaacat
cgggaagtcgataacccacagcggtgcccatttgctttcgtcggtcagac
caaggtcttttacccactttcaggcgcagtgcgcccatcgcgtcggcaaca
attttcttgttgtcggcaccgaagaaaatcatatcgccatcttcgcgcgc
agtacgctccaggatggcttcgatgatttctgcattaaggaacttcgcta
ccgggctattgatacctcagacccttcgcgcgttcgttaactttgatg
taagccagacccttcgcgccgtagattttaacgaagttaccgtattcgtc
gatctgcttacgggtcaacgatgcgccgcccggaacacgcagagcggcaa
cacggcctttcggatcgttcgccggacctgcaaatactgcaaactcaaca
gattcagcagatcggcaacgtcggtcagttccatcgggttacgcagatc
cggtttatcagaaccataacggcgttctgcttctgcaaaggtcattaccg
ggaaatcgcccagatccacgcccttcacttccagccacagatgacgcacc
agcgcttccatcacttcacgcacttgcggcgcggtcatgaaagaagtttc
cacatcgatctgagtaaattcaggctgacggtcagcacgcaggtcttcgt
cacggaagcatttaacgatctgatagtagcggtcaaagccggacatcatc
agtagctgtttgaacaactgcggggattgcggcagcgcgtagaatttacc
tttgtgcacacgagaaggcaccaggtagtcacgcgcgccttcaggcgtgg
ctttggtcagcatcggagttcgatgtcgaggaagccgtggtcatccata
aaacggcgcaccaggctggtgatttagcgcgggttttcaggcgctgagc
catttccgggcgacgcaggtcgaggtagcggtatttcagacgcgcttct
cggtgttgacgtggttagagtcaagcggcagaacatctgcacggttgatg
atagtcagcgaggacgccagtacttcgatttcgccagtcgccatatcgcg
gttaatattttttttcgtcacgcacgtacgggtgccgtgacctgaatgc
agaactcattacgcagttcagaggccagctttaacgcgtccgcacgatcc
ggatcgaaaaatacctgcacgatacctcgcggtcgcgcatatcgatgaa
gatcaggctaccaagatcacgacgacggttgacccaaccacacagagtca
cctgctgccccacgtgggacaaacggagctgtccacaatattctgtacgc
atgagatatcccttaacttagctgccggcggatgccccctgctgcgcagg
tgaccaagtcgcagcgttagctgtatgtcacaactgaatgaaaaagcg
gctattatactggaaattctgccgcaccgtaagagcctggccgcgctgg
aacgcctcgttaccactttatatcgggcctgaaatcagactctacgccag
tttgctataaaggtgttgcccgaactcataaaaattaacaaaatttgtcg
ttccgccatcggctaatcgcattaaggtgagaggcacgattttgttttgt
caggagtcatcatgcttgaacttaatgctaaaaccaccgcggtggtgtcc
attgatttacaagaaggcatcttgccttttgccggaggtccacatactgc
cgatgaggtggttaatcgcgccgggaagctggcggcgaaatttcgccca
gcggtcagcccgtgtttctggtgcgcgttggctggtctgccgattacgc
gaagcattaaaacagccggttgatgccccctccccccgcaaaagtgttgcc
cgaaaactggtggcaacatcctgctgcattaggtgcaaccgacagcgata
tcgaaatcatcaaacgtcaatggggtgcgtttacggtacggatctggag
ttgcaattacgccgccgggtatcgatacaatagtgttatgtgggatctc
gaccaattacggtgttgaatccaccgccggcaatgcctgggaactcggtt
ttaatctggtgattgccgaagatgcctgtagcgccgctagcgccgagcag
cacaataacagcattaatcatatctacccgcgcatcgcccgtgtgcgtag
cgttgaagagatcctcaacgcgttatgattacatcggtttgccacaatg
gtcgcatcctaaatgggtgcggttggggatcaccagccttgaagagtatg
cccgccactttaactgtgacgcgggcattttaaaaatcactaaagaac
gcccaagagcatgtgttttctttagtttattcaatgcattaaaaaatagt
ttcgcatgaaattcggtaaacttcatgtgtgcaataatgtcccattcatg
ccccaaaatgccccaaagcagacatttttgccccaagtatgcccacaag
tcacgtcttcaagtcgtctatatccatagcacaccggattcattcttgc
atccggggtgtcgacaatacctacttttattgagtgtgcgagaattaccag
gaacctttccacaatgtagtagtctaatagtcgaatccatcaacattaa
gaagcgttatgatcactagcctctcattgatatcttctgtaatagtcact
ctatgtatcatggtgttcgctacagtaaaggtagggattggtttgtcaa
caatccagacagaaatgataattaacctcaacacgtaaccacacttcat
acttcatacttcacttaacagtgaagtgctcacatcaccgggcagtcatc
aaactccgcattcctggcatcattaatgatgtacgtgatcactccaaata
tagcgggtgcagaactgtaaccatcatcatcgctggtgcagccgcttccctt
ctcccgttatccagattaaccaggtgcggctgaggatgagtccgatcg
cttgatcctgaattcccgtcgattgcacatatcagcagtgaaccatcgc
aggcagtaagtgacgcatccacaacaagcaacgctccctggattatcct
tccctgaaatgtgaacgcatgcccgctaaaagaaaagtcgctgcgggctg
actgattagctgctgatcgagggagattcgtgtttcaacataatctgccg
caggtgaaggaaatcccatgtttacgccctctcttgaataccggataaa
acacagtataaaactgtatatccatccagcaaagaggcaatgagcaatg
ttcgtggaactcgtttatgacaaaaggaattttgatggtctgcccggtgc
aaaagatatcattctgggcgagttaactaagagagttcaccggatcttcc ccgatgctgatgttcgggttaaaccgatgatgacactgccggcgatcaac
actgacgccagcaagcatgagaaggaacagataagccgtactgttcagga
aatgtttgaagaggctgaattctggttagtgagtgagtaaagattttcaa
tgccgccacagttacgtattgattatgctgtggaggatattcattttcg
taaacgttggtttgggagaagcggcaaaacggaatgtgggaacaggggaa
aatcagataccagatatgtctgcatttccatctggcaataactggtttca
gttaccaagtggacatatcgttcagatattttccatgaacgttcttggtg
cagatgctaatggcacgtcagctaattacccccattgcttttccaacaacg
atgattgctgtcagtgctctatgtctgatgggactgtagcaaatgcacc
gacatacaagatgatggggaacacgactaacagaacaacttttgacgataa
aagtatcagccagctcaggtacttacgggacaatgattattgcggtggga
cgataatatgaataaatacagttactctccttcagaaaatgcctttatg
ctgttgcgttaaaaaatacctatgaattgagtggcacatggccagctgat
gcattagatattcctgatgacattcgttaaaatatatgcggaaccgcc
acaaggagaaaatccgagttgcaggggaaaatggtttttcccacatgggctg
aaatacctccaccatcacatgaggaacttattgaacaggccgaatcagag
aggcaattattgattaaccaggccaacgaatacatgaacagtaaacaatg
gcccggtaaagccgctattggtcgtctgaaaggcgaggaactggcacaat
ataattcgtggctggattatctggacgcactgaactggtcgatacttcc
ggtacgcccgatattgaatggcctacgcctccggcagttcaggccagatg
acatccggcgcggtgctggtatctgttgcagtcaccgcgtcaatgtaatc
cagcacggcgttaagtcgggttgtttctgcctgagtcagttcctgtccgg
cctgtaatttcagctgaatcagactaatgtgaagccattgctgcatcaatc
agtgattggcgctgtgcttctgccgcttctactgaggcaccgtgttgtgc
ctcagtatctgtcacccatttctcaccatcccatttatcatatggcgtta
acggtgaaagcgtgacataaccgttttgatggcaccgatataatccact
gtaacagctgcgccattttcgattgagtaaacagtctcattgcgatggtc
ttcctcatggctccatcccttacctgtaaatactgccactcttcccggaa
tgttttcgtccgggtcaataccagtggaacaggcgggcatacttacgcca
gtattaatatattcatcagaccagcccgtatattcagacgttactgcatc
ataataaaaacaacgcatatcacccggcactgcagccagcccattttcat
caaaaacaggtttcattatttagccctcaccagaaagttaaatgcaatat
ttcgcggtctgacagcaacaaaattcacaccatcacccacagagttactg
ttgaaatttaaatcgtgaaaatcctggctgatttccggcgatgccatcatg
aaagttaattgcgtgtccagcacctccgcctatattcccggcaaactgag
aaaagtttgtagcttcctgccagcttaataattcgcgaccaccatctgca
cctcgcccgtcatcccagacacgaatgaaatcaccgcgggcttcaggtaa
taccagcgaaggaaacactttcgccagcacaggataatcagtggcagaga
atttcgccgcgttgaacttcaaaacaccatactggaccagctgtcgaatt
acagtatttggcattgcagcggacggccagaagaaacggaacgccaatagc
tggagaacctcctcccaaaccaaggtttgtgcgagcgtctgcggcattcg
ttgcgccggttccgccgtctgcgacagtaaccgcaccgttgctccctttc
tgccgcaagttaccgatgcctggagtggttacggcggtgccgttgatggt
aactgtgatgcttggttttgctgaggtggtggcgaacgtctcccacgcgc
caatattccgtcgtactctttgatgagctgtgacatggcctgcgcagg
ccgtcgactgagatattgtccgacacaaggattccatacttctggccgct
cagcgccggggaaactgtgcgctaaccgtcattgacgtggcgctgttca
cggatgaaatctgaaacagctgcaccgggttagacatcacgataatcgtc
tggccagcgcggaacctggctgcgggagctgtccagtttgtgccggagcc
ggttgcggtatttccgttaatagagatagttccggtgctataaatcataa
caactcctaaatttagacaacatgaagcccggagaggtatataaccctca
ccagaaataatttctgaattggtttttaatacatgttgggcaacgccagt
gttggcatagctatagttgtatcaaatgccattgaccacccaaccccaaata
ataattgccgactactttattcctttctgctctgacattcccacctgtca
ttacaattcctttatacctaatattttccgtaaccaccaacgtgtcgacag
ttagccccggtataaacaatctggcaaattcatcaccaatattcaggtt
cgcattgccgatattttattgtcccatcaaaaatgaatggcttcgtgcaag
taagaagacgtttgcgttgacgattggtttattcaatggccatcaactaaaa
tatcatgtaaacgaattgccataacatttcccactttattttacttactc
aacacaacagtatattaaaattgaaccttgtcaacaacacaaaggagtc
ccaatgaaactcgctctaattatgctgccattatgtctgtcctcactgc
atgtggtaatggttaaataccggtaaaccaaattccggtgtcattccaa
aacctttggatcgagatggtaacggttctttaatttatgataccgaaaac
cttccaatgacgggaggtgcacgagattgatcacgaatacgaag
aatcggtagccttctaactgtgttatagactactaaatattaaccccctc
aaaagaggggttaatatttaacctgtgaatgaaccagatccgtgtgata
ctatgatagtaggcgaagaaattgacgcacccctgttattttgagcggac
acttaatacgcactgtacgtttggacctgttacaaccgcagaatgcat
gataagtctctccatgtcttgcacggatgaacactctcattgccgttaa
tgtcgattgttcctgcaccattaccttttaacgtttgctataacacagacg
tgtcttgcgtgcccagaactggatgaatcattataagtcattaccttttc
taaatatctcactagaccgcatcctgtcctgtgcataata
caatgtcccctaaaaactttgggcttccacagtccctttgaatttaccg
cttgttgcttggatctcaccagtaaagctaccgccactagcatatactac
acctctgacggtcacattgttgaattcagcatctccagctttattcaact
tccaaccagcagaaccagctgcatagttgttggactggatatagttaccg
attttttgcgttctcaatggtgccgtcctggatgaagctggcccggatgaa

TABLE E-continued

Phage 3 Genome Sequence
SEQ ID NO: 134 tgtctgcccgttctggatcacgaacggcaaagctacgctatttccggctg
ccgtggtgacggcgaagcggtcagccaggaagataacctgcgactgcatg
ccggatggcgtattctccacgccgatacccatccccgcggcgtaatactg
cccgttgctggagacaccaaccttgatgttgtacatcgcgctgagttcgc
cattaacgttggctatagcctgagcgttagtggtgatggcggaggtatgc
ccgttcacggtcgccgtgatgccgtttatctgcgtggcggtggcctgctg
atagtcggagagcgtctgattcaggctgttgatggatgcttgttgccgt
tgacgtccgtctgcaggctcagcaatgaacgtgctgtggcttccttctca
ctgacgatcacctcgtcgagacggtccagattcgcgctgttgccggcgac
cgatgcagaaagggttttacgcgtggccacctgagcggaggttggcctgga
ttatcgcaattgcagagttcttcacccgcccgtcatgccgtccatagaa
acgctgatgttgtcgattcgctggcccagggcggtatcagccgtcgcaac
ggtctgctcaagctgactgagtgaagacgaaacattcccgaccgtgctgg
aaagctcattaacgctgtctgaaccttcccgacgtcctgggcattttg
gcgatatctttcgcttgctgctccagttcgtcgttggcctgtttgatatc
gttagccatgccagcaattttttcgttgctgtccaccgcgttctcgatca
ggtctttgaacgtttccgactcttcatatcctcagaatgtcattagtt
atttcgctgacatctatcgaggacgtgcccatgatccagtcggtccagtc
cccgcgttaccgatacggtcaatcaggcgcgcgcgggtaccactggcgaa
cgccggcaggcatggggccatgctgataatctgcagccgggtacggcacc
aggaccagcagttcaggattggcgtagtcggcagttgtggcgcgctgaat
ctctgtataggccgtgtcgcctgagccatccggaaattccaggtcaggt
cgatatgccagaccacatcttcggtcgccaggaagttgagcggagtaccc
ggttttcccgttttaccggagagataagttgtttcaccgtatccccatgg
tgacgacgtatcctgcgcattcagcgcccgtacgcgcacgtcatagctgc
ccgaataaatgccctgaaccgagaaacccctgcgcgctggtaaccggaacg
ttttatccagtcccccgttgtccttacgccactgggcaacataccggattgc
gccctctaccttatcccatgacacgtccaggcttgctacagtcagcccct
gagacacatgatcgctctcagtcaccacgatattcttcggagcagacagg
acgctatcggcgtgacggtgatcggggggagactcgacccgaacgccgtc
atcgatgtaacgatatttgtttggatcgtgctgaacggccgtaatagtga
aaccgcctgtactgtcgtcgttagccgcgattgaggtgaccgtgaagtac
tgtattgcgaggttatcactgtctatcgcccaaacagcgcccgccacagg
aacctgactgaatgccgtagccaccgtcaccgttttttatcggcgctca
ccgcgctgattgtccgcgtctgggcttttccgtcgggaaggttaaccacc
agccggtctttcgccgcgtagtctatttctcgatcgaggttaatttggcg
gccgttggccgcgcttatacggcccccgttctccttaccagagcggaaag
gatcggcgacaccgataatttcagcggcaaagggatataaccgtccagc
cccacgccaaacgatacggtcccgtctttggcattggaaggcaatacccca
gcgaccgcgtcggtgcgcttcacttttgcgaggtgcagccgattgcggtca
gggacgtctgccggacgtcgtaacgttctacaagcgccgaatcgtaaacc
ccctcaacgtatcgctgtaatggtctgcggatcggaccaggacaccag
gcaggagctgatgtcttgtatgagccgcccgcataagtaaacagcc
catcgataacgtttgagacgttataaaaccccagtcaacatcgtcctgcgcg
acgtctgcctggacataaatctgatcgtttcccagaacgttattccacg
aaataccgcggcgagatcgttaagtacctgccaggcgtcctcctggctct
gaatgaaaacgttgcaggtgaaacgcggttcggtgccaccggcccgtcg
gaaaccatttcgtcacagtactgggcgattgaatacagcgcccacttatc
caccatggacgcatccacgcgcgtgcccatgccgtaaatttcatccagaa
ccagatcgtaaaagatccaggcaggggttattggaccatgccattttgaac
ccgccggaccatgaaccagaataggttcgggtttcggatcgtaattatc
cggaaccttaatcagcttgcctttactacaggtcacttctcggcgcgc
tgccgttgaattggctgctgtccacttcgacatacaggagcgctgttaaa
ggataacaagcttgctgtcgatgacttccgcatacgaaaacaccttgaa
ggcgttaaccagtttcgaatttgatccgctggcatcagccgtaatacgcc
tgaccctgacagaccagccggacgtggattttggcagctcgatacggtgg
tcacgctgatattccgtcgtggtctttccgtcaaacttgccgtttacaac
cgttttccaggcgccgcgtccgttgataaatcgatcgcatactcggtga
ccgtgcccaccatatcgccattatctttatagagatactggaccggaagg
ctgagcttgatacggatggcatccagggaaaggtttgtaaactggcgcgt
ccagggcgcggtggttggtgacagttgtgccacggccagctcgttgtcga
cctgggcatcccggcaatataggtctggtcctgtgtgccctgcggaac
tcccatttcacgccgctgaagttgtattccccgctgtcgtttgccagcgg
cgtatcgttgagaaaatgtttctgagcggtcaggtcggcctgtattggttt
cctcagaaacggcaatgagcattttaattttgcgaccgacacagcagatcg
tcaggctgctcaacggagtatgtgaactgccacctcccccttggcacc
ctgcaggatggtttcttgtttaagaagctgcattttttcacccataaaaa
aaggtgccgaagcaccttaagttagtggccgctggcctactgctgatg
ctcgagtacataccggctgactatcgtcccccctgcctcagtcagacc
gtaggcaggggacaggatgcccatagcgacggtgattgaccggcgccc
cgaaggcgtagttaggcgtgttgtccgtgctggaggatttacccgcgccg
aaggatggctggggcgtgagcatctggacaacgccccccagcatcactga
cactccgaccctgaagaattgacgtggcgctgatagctgttgcactca
tcgccgcgcccaggctgccatgctcgcaccagcggtaaagaatgcagcg
accagcgcaacagccccgacaactatctgcaggacgcccgaacttttggc
cccctcataaacgggcacgatccggtacacgcttccaccgcgggtcatat
caaactcttccagcccgatattgttgccaccgttaaaaaaggcgaaacgg
atcccccttcatatgagcttcagacatatattttttgaatccgggaacctg
tgaacacatggccctgagcatctcgcgcaggtcggcaacatcaaactgaa
cgcgtttaccgaattttttttgccatttttaccttcgagaataagcgtctta
accatgcattctgtccttatgcctgaccaccggaccgttctgtcgcgat
aatatttcataaggcgttcgcgaagaaaggtgcccgaaaagatgatgg
agaatgatgttatcacccacatataccgcgcgtgattagtcaccgatgc
ctgcacactcatcatgatgatatccgggctgcattgcaccggcggcaa
tctcaacgaatccctcacgctcccagttgtcgtcgtagagacgctccttg
ccgctctcccaccattcgtaaggtactgaataattgccgagaacaatgcc
gtattcgcgcagataaaattcacggataagcgaccagcagtcggcgtaac
ccagcacccactgccgcccggcataatcccggtcttcacgcggggaaatc
gtacaaaaatccccgtccggccaggacatgatccccactcaatcccga
ccagtcgcactggatccggtccagctctgagggcaccagccgaaccacat
ccggatgggaatgaatgacgcatgatgatctcaccgcgcgcgcgaggcagcg
agctggtcttccggggagagcgtgaatgtctcctcgggtttatcggcaat
gttgcgcaggaataaagatttgttgctggcctgactgaacaatcaggc
cgcaggcttctttggggtattcagcagcgacgtgctgacggatagcatcc
agcaattttcacgcattttatttcccctgcaggtttgcagccggaaaa
ccgccaacggcagcggcgcatccggggccgtgacgatcctgacaatcctg
ccggcggccgccacaaacatctttcgacgggtcatcggtcggtgtaccgt
ctttggtaaagtatttcgtgccgttgtaatcgcatccgtcccgcttcgg
taccagccccgcatacaccaggtgcagacaggcgtaatctgccgtgccgg
cagctgcaggctctgaatatcgaaaggagaacacagctcgaaatcaacct
gtacccgcgtctctgcggttttagcattgacgtaaaagagctgtaagcgc
tcatcggcgggctggcacccggattaccgttttttccagttggcggcatc
gagatacttcgaaagcgtggtatggattttgaccttagccctgaccatat
cgtcatattcaagacacagcggcggtgacatagtttccgacgttcccgacg
gacagctgggcgttggctgggaacctgtactcgataactccatccccctt
aagttcgtagggatggggatcgtactggtttccctgccagataatggcgg
gcagattttctgcggcgaaggctgcccaccctcttcctgaatattgtgc
gcatgaaaacgcagcaccctgatccataccgaattcagtgccgtcgatctc
aatcagctgaataacgctgccgggctcaagctgtgtatgtctgccgtaa
aactcatactcccccataaaaaaagccgcccggaggcagctttcagtg
tttttcgagaaaatcagggcgcgaacgcctgttcaaaagtgaaggccaca
gtggctttttcccggtagggaaagaaacgctgaacgaatcggccttgat
tctgaacagcttttttttcacccccatggagtggtccaccagaacgatttag
taacgtgagacatcaggaaagcgcgcagcgcagccgcctcctgtctggtg
cccgtccagtccaggttccacgttcctgtttgtcgttgatccccatccc
cgctatctgtttgtagccatccccgaactgggcctgcagcgtttcgggcctg
tttcagtgccctgcgctgttttcgcgtgcgcaggtaaacgtgtccgtc
actgtgtcctcctcgaataaagcacgccgccccgggacatttctttttc
agtcgctcggtgattgtctgctgaacaatcgcctgcagctgtttcgccgt
ccccgtggcgttcgctgatttatgcttccgtcactccctgctggctga
tgctgactggggcataaaacactgatcccgcccatgccagcaccggtgcg
ttcccgccgccgaccagaccaccgcgaggcatacccgcgcatcaggcgata
gagattagccacgccgatgcggctggttgattctttggtgaagacgaatt
ccccgcggtgaacgataccggctggctcgtacttgccgccgtgcccggta
aaaccgcccacgtcaaaaccctgtggccggtatgacgggaccgcgaatga
ctgaccggcagaggaggttttcgcccgccgctaacccagcccattgcac
tctggatggtgtaagccaccagcagctggttgataacggacacaatcatt
ttaaggatcgagctggtgaattccctgaagctcgcctttcccggttgtcgt
caggctggtaagctggcccgccaaccccgctgaacgtagctgcgagaaatct
gctgaacggagctgaaaacgtttgtcgctgaatcctgatattcggcccaa
ccctgtttcgcaccggccagcagtttgcacgcagggcatcttcagcttc
gaacgtcgcccttgctcttccagaaccttttgctgcgcctgagggttgt
acgaatagctttcgctggacgctgcagcgtagtttgtcgcccggcttc
cgggtggataaaccctcagactgagcgtgcaggccgcccgggcggcttt
ttgctgctgctcaaacttcacggcctgatcggcagctggttgagcttt
gctggctggcaaccttatcgcccaggtcggccagctgccgcttgtactcg
agcgtttctttttgtcgcgcagcagggattttttcctgcgccgttaagctg
acgacgcccagccgcctcctgcagaacggtgaactgattttcagtttgcc
agagatcctgacgctgtttacttatgacgtcgttcacgctggtatgctgc
tcaagcgttttaagctgggcctgaagggtgagaagttcggcctgcgcctt
ttcctcggctttgtcccccgccgggcgttggtagctttttgcctttccgtg
ttttcttcctcactgcttttcaatccggcgcgggcgcggcaatg
tcctttcagtccacagctggcgacaccgtctttcgcatcctggcggtt
tttctcaataagctgactgagcttttctctgctgaagcccgcttttctg
ccgccgtcgcgccgactccaccagctggttaaactgctgctgctgcgg
attgctgagcctgctggtccgttcgcattttttcccgcggctgccag
cccttcctgggcgtattcgtcgatcggcaagatcgtaagctgctttttca
gctccacctgctggcgcgcgtttctcagcctttccgcatccgctttctgc
agaacgttgtaccggcataatccgggtcgccattaagattgctggacag
cgcggtgtactcttctctgctgcctgccactcagcaaaagagtcctggc
gcttcatcgcggtgtcaggattacgcccgacgcccagcatcgcatcccac
gcaccggaggcggcattcttcacccagttccaggcttttttcgagggatcc
gagattatcctcgaccgcaccggcgcgctgaatgaccgcgtcggaatatg
cccgcatggccagctcggcagccttctgagaatccccagcgcctgagca

TABLE E-continued

Phage 3 Genome Sequence
SEQ ID NO: 134 gaagctatctgttcatactgggtgctgtcagaaaatgaagggaatcgtt
gagcgtcgcgaccgcgcgttaaccggatcatccttcaggcgttaaactgat
ttatggtttcgtcaacggcctgcccggtagcctgctgcagcctggcggca
acattgctgaccatgctgacgtcattaccgctgaacgcgccgctgccaac
gacctgcgccagcacgcctgcagcggcatgctgagtgatgccattacctg
ccagcgagcgcgccagcgcctgcagctgccctgacgtttcccgcgtag
ttccggtcaggatcagctgcctgttaaattcctcagactctttgctgcc
gtcgtaccaggcctacccaacccgaataccgcgcggcaatccctccga
ccatgctggcgatcccaagaccgcgcagtgacagaagctggtctatccac
cctgcccggttagccagcgtgatcccggagccgcgcagcgcgccgaagtt
accgcgcatgacctcgccgatcagtattcccagttcctgccgggcggcgg
cactttgcagcccagaccgtgcgtggcgactttggcagcttcgagcttg
cggatatagacttcagccgcatcgctggcaccgacctgcgccgccttcat
gcgcagtagctcggtaccggagagctttgctctgcaacctgtgaagccttcc
gctggctgaggaatcgcgtgcgcgctgcggccgattttcctccacgatc
tgcagttcttttgacgggccgtggtgcgggaaataagggcgagataatc
ctgctggttatgttgcctgtgccctcgctgcgcgaaagcgcgcctgca
cgttcgcaagcgactgtgtttcaccattgagctgcgtacgccgtcagtc
tggcgaaaaatgatgccgcaagttcatcctgtcgacgggcaagcgcagc
ggcctgcccgtcattctcacgcatgcgctgattaagctcggtcacgcggc
ggtgagtttcatcaacggactttgaaacgttctgccagtcttggtaagc
cctccgttgcggccgactggcggatctcatatctgcggcagccgccgc
gccagctcacccacggttttaaacgcagccgcctgccgctctgaagcgc
gctgcattcgcgtctggacttttcagagtcctcagccatcccggttagc
tggcccttatgcgggcaacctgctcactaaacgtggcgctgtcgacgtc
aaggttgatgaccagatcgctaatctgctgggccatatcggatacctcct
gttatccctcagctgcggccatcagcgcatcatcatccggctcgtcatc
gctgatgacgataccggaaggagaaagcaggctgaaatgtgcggggtaa
gttccgggtcgcggaagaaaagagtggagatggaataaagcagctctgag
aaatgcgcatcgagctgagcgtcctgaaaataatgctcccggtagaactg
gtgccagtcgccagctcagtggaagtcattccagccagcatggcggcgcc
agtcgggtcgcccgaactcgcgcgccagattcaggacaaacttcagctcg
ctggcaagggcttttccgccgcaacgggttctgcgctttcggcctccgct
ggggcatccggatcggcagctttgtcatcctcaaccggaacgagcatgcc
ggagagcagcttttatttccatttctgctttaccgatcgcctccggcgcc
agccgctaagcacctgctgttaaagcgtctccacatccgtgccagccgga
tcgttatgccacaaagacatcgcaatcaaacgcgcaccgcagcgaatatt
tgagccaatcagcctggccgtcatttcctgatcgctgatgccgtcgctgt
cagcgctgacggccttttcctctgcggccataaacgtgatgtacctcaata
cgctgaagcgccgacagctcgaagatggtcagtgattctttttgccaggt
gaacttctctttttttcagaaacatgcgtccttccttacgctgcagttacg
gtaactttcagaccgcaacgaaattaccgtcgctggtcataacaataac
gtcagcggtgcctgccgccacgccggtgacggtgatcgcattaccgctaa
cggtgaccgttgcttttgccccgtctgaggttgccacacggaacgaggta
tctgaggcactggctgggttaaccgtcacattgagcgttgtggttgcgc
gacggccacgcttgccgtggctttatcgagcgtaacgcctgtcacgggga
tattcggggtcccgctttcttctgccagttccggcttgccggtattggta
attttcgctgtacgggttatgacctcttttgccggaatggcttttacccag
gctgctgcaccagccgcggaaaacgtcgacggtaccgttcgggtatttga
ttttgtaatagcgtactgagccatcaataaaccatgcgacaaggtctttt
tgccctttcttcgcccggcttccaggcgagggtgaacgaggtatcgccagc
agattttgccccctgggccgtcgcgttccagtcggcatcctcgtcgtcga
ggtaagtgtcgtcatacgattcggcggtcatttcgcccggcgtcagctct
ttaattttcgccaggcggttccagtcgatatccgagagtgggttagcgaa
agcgttgcccgttccggtgtaaagcagagggtggtaccggccacctttca
caggggccagcgggtttggagtaggcataagtacctcttaaattgaatag
gtgattaagtacgtgaaatcgactgaacccccaggtggccatttcatcatc
ccgctgatagtcataaccctgcggggtgaacgtctcgaccagttcgtca
gacctgggatgaaggccattgccggatacactttctcttccatccaggaa
tcaagcgcgctgtcgggtcctggaggctttaagaaataacctcgatgtgaac
aaccgcctgccacgaatcttccgtcaagcgaatcgccggtgtactccgcgt
cagaaaggtatacagccacggcagggagatcctgctcttcaagaaaaaca
gggcgcccgtcaaaccaggtgaccgtgtcggtgatctcggctttcagttt
ggccagaatggctgcacgaattgcgctgtgtctgttcatcgcttcaggtg
gatcctcagttggttttcagggctgcggaaagttcttgggcatatcgc
tttcaataaggcgctttgaaatagcggtgaaggccacggtgagcggtgtc
tcaagaggaactttgaccacatcaatcggataacgggcctgacctacgcg
ccgcatgacctgccagcgccgttcgcaagctgttggataaacgttac
gaaaggtatagggccgatttaaggacgctgcccgctccgtttctggcc
cctttttttacgcgagagcctgacgcgccgtgccgagctttatcgcagg
aagattaccgcggttgattttatcgacgcgaccgggcgatcgtgacggg
ccttgcgcagacggggaacgctggcggaccagcaggtcggaagcccctt
ttccggttatcatcaactgttgcttcttcgctacagcttttgctccctg
gcttatcgttcttctggccaccctgttaagtgcttttgcggttgcctcag
gaacgattaaccggctgaggctgttcaggttctgaatagccctttccagt
cctttcacagacatagcgcctcctcattcgagatggatgcgggttttcc
gttgaacatgtcatagcgggtaacgatcaggttcttaccgtcgtagtcga
cgctgtcgtttcggcgtggctggtaaagctcagagaaaaccaccagcgaa
gtacctgttcccgacaatggccccatttcctcgagttgctcggcgggaac
aacgtcatagctgctgccattgatgatcgctgtctttcccatctttttta
tagtggccgcgtccatgcgcgccgccatccggtcaaaggagttaggcatt
gatcttaacttcaacaacggtggtgtttgcccctgcatcttcccaggcga
tgcccgcggcaacggcgtccgttttcttcgatcgtgattttgccgtccttc
agatacacctcgcgccccggcagtaaccgcatctgcggatacttttggcag
gaggaaaacaccctcagtaaaaccgtccccggtatcgccagccgggatat
cggtaattgccaccgcgataagttttccaacaacaaccgggtcgccgctg
tgaacatcggttgcaccactgttttaccagagggatcgttttcccgtcctg
cgcatagttcttagccataacttctccattcagcccctttcgaggctggt
ttcaggtataaaaaaagcccttacgggcgtctgttttgtcaggactgtttt
ttactgaccagaggggattggtcatgccgcgatagtccagcggcgccacgc
cagcatcaatacgcactttcgtggcgatcaccatcagtggtgaagccttcc
tgctgatcgatgatgccgtgtcgacgccgttgagataagcgacctcaat
ggtgtcggtgcccttcgcggcagccagataccaggcttctcgcatcagctt
catccagacgtggttcggcaatgacttctgcaaagttctggatagggtta
acgatcccggcattgatgtctgcacctttaacactggccgctttgatggt
ctgatttgccagagttccagggcgacgggcaccagcatgtaggccggac
ggatattcagggtcgctcccctccttctgcagacgcatcagctgcgc
gattcgtccaggctggccacagaaattgcacccgagctcaggttcttgtg
atcggcatggaacagccctttccgtctgagagtttcgggttttggtca
gaatggcgtaaaccagatcgccaatcgttgattcgccgcgcgcccatct
tcatcggtacgtcggtaagctggttcagatcgtcgttgatgatcgcctgg
cgagttactgagaagatttcaccatacgtggcaagcgcgatggtttcgcc
ttttgtcactggtagtgatgtacttgtactcagccccttcgcgaacctgtc
gcagagaagggaaccccaccataccgacacgatcgcgccgttttgaagtc
gacagctggcctttttttggtccactgctcgaaggtttcctgcgcctcgtc
ccagccctgaatcagcgctttgttcgcaacatcaagcagaatgttgccaa
agtcagaggtgctgtgggtcagcgccaggccaaccatctgcatcgggttg
tagctgccacgccgataccttttctgtcagggccatacgcgcatactc
gcgcagctcataccgttataaacgttatcccgctcctgaccttcgaacc
cggcacgcgccatcagtgcctggcgaataccatccgcgacgaagttaccg
ttgcccgcatgaatatgcggctgagtggtttttattggacggcgtggccgt
tttaccgagttctgccagcagcaaatcttccgcttatcgacggagcaat
caggtcggccacacactgattctgcagttccatgtgcttattaccgaac
atggcaaagagatcgccgatagcgttaacacgggttttctgctcagccaa
cacctgcgcgcgggatcgcattttcatccggtgccgggtctgtttttgcct
gcggtgcctgaggcgtgggtaataaccgggtcacgctgggtagtgttgcg
ggcggggtgatcatgttgcgaatgcttttttggcatttttttcaaattcctc
aatacgttttgaatgaatacaggccatagcctgaaagggatggtgtcacct
ggtcggcaaaacccagttcaaggcactcgctgccgttcatccaggttttcg
tcctccagcattaccgcaatttctctggtggattttccggttttctctgtgc
ataagccgggataagaacggattcaacctgtcgagaagatccgcatagt
cgcgcatatcgctcgcgtcaccaccagcaaaccccagggcttatggatc
atcatcatcgtgtttcaggcatgatgaccggattgcctaccatcgcaat
caccgaggccatggaggccgccagaccgtcgatatgtacggtaatgccgg
cgccgtggcttcagccgcttataaatagcaattccgtcgaagacatca
ccaccgggcgagttgatataaaggttgatgtgggtgacgtcccccaagtgc
ccggagatcattgacgaactgtttcgccgttacgccccagtaccccgattt
cgtcataaatacaaatgtcggcctcacggtgttattgctggcctgcatgcgg
aaccagaatttacttttttgcgctggctttcggacggtggcgcgccggtt
ctttggcttcggcactggtgcctcctttatcattggcggggtcggtgtca
aacaccaggcccctgttcacggttctcgtcaacctcagctttacggcgtga
cttaacatcatccgggttgcgaccgctggcacgtatccagtcggattcag
tagcagcaccgcgagccctgtcgttttccaggcattcgcttctttaacg
ggatcaatccacggcataacggcccgaataaaccgcgttatcaagcg
gtccatatcaatgcctctcggcagcttgatttctccggcagcaatagcca
tcttgagcaggctcggtacatgggccgggtcactgaaccgatgaaccag
tcctgaagaatcagatagccgtcggttgactcgacaagctcctgccgctg
ggcactgtacgttccgttgtagtttctggatgtgctgaaaagctgaggc
gactgccggcgacacggcacgcagctgtccgttacgaaaagattcgagg
ttagggttcgggcgatcggatttaatcatcccgatttcttccccggcctg
cagttcgtcataagcatccgggtgaatcatcagctcgcgtcatcgc
tgcttgaatcagaatcgaagctcgtccgtcgccttttttgatatacatg
ccgagtgccgcagcaattctggcagcagtaagctccgagtcctcgtattc
tttcagcgcgctcagacgcatcagaacaccagacaaaagagacgttccgc
gggtctggtgccggtcgggtgaatttgagatgcagcatgttcctgca
tctatctctttggtatcaaactgacgcccggatctggcaggctttata
gacctgatattttttcgggcgtcccagttatcgacaaaaacgccctgat
tgagctgggtggcagcatcgctgttcatcggcacaaagtccggctccagc
gcttccagccaacggcacgccagcaaccggctgaagaccattccggt
accgcgaaccagctgagcaaatacctcaccgtcccggagccacgttcgca
gcatcagccgctccagcattgggcgggtaaactgggtgtgacatcggc
cttacggaccattcgccccactttcggcggatatcagtggccagcttttt
agcgatcttcccgttactcagcatcggatgcggttcaactatgatgccct
tcgcacccaccaccccttttcttccagcttgtcgaaaacgccgatcaccaga TABLE E-continued Phage 3 Genome Sequence
SEQ ID NO: 134 tcgtggttgttatccagccagcgcgcctgctgcctcagcgaaaccgcccc
catctggctgagctgatcggctgaacgattttccttctgggctttgtggg
tacgcgtttgctttaccgcctcatacgcttttaataactgcgcgggcacgc
aggcgtgaggctttccagcctggtgaaaacaggccaatcgcatcatctaa
aaaactcatccaaacctcgccagcctgtagccgggtcgcccacggcgttt
gttattgagcgttgccagtcgtcgctcccattcctgacggccttttctga
tttccgacaggttttcgagcgtcatctgctgcccgttgaaagtgattgat
ttcccctccagaacagacagctcggctgcagcatagcggtcgatcatgtt
ttgaatatctgctggattcacacccaacctcctgacgaagaccacggatt
agcctgctcggttacgggcttctcacgttttggttttggtttagatttcg
gcgcaggcggcggggatggcatttcgccagcttccgtctgcgtgtcctcg
atccacgtttccgccgtgcccactcaggagctgacggccatttgatttt
ttcgtaaccactaaggatggcgagcgcgtcggcataaacgagcaggtcaa
atgcttcgtttgcgccccggccgggcttactccatttcccttcattcgag
cgttcctcatacgtcagttcgtcatagaaccagctgcccagccaggcggg
gaaatgcacatagccagggccgggtgaatcacgcacagcgcattattca
cccgtctcttaagggcatcggtctggagaagataaagaggcacatccacca
gtcgcctgtgcgcggcggttgatctgcccgtgttgcgcgggaaacgttcg
ctggataagtttgctgcgcctgacgctgtccccttgaagagatagatac
gcttacccagccccccacggcgacatctgcgccagaacttgtaggcatta
tccgtcacgccatcttcgcccctgagtccacggccatcgacatcagccg
catgcccttgatgggtcagctgcgagcggccacgttttatcaaagacgt
cagtgagtaaaagatcccagtcctccggatagctcgccggatccacctga
atgctttcaccgttgccgtcgcagcgcagcgaatgccggatgttgtaacg
gtcaactatccagcgctcacccatacttccataacccgtaatctgcacaa
caaagcgccggttgcgcccggcctgcacgtccacggtcgcagtgagaaac
tgcacgccgttcggtaccgaacgttttgggacgtcttcggcacgctgctc
gagcaattcacttttacgctgctccatgctggctcgcggcaaataggcc
tgccgaaatcggtgttgatcaccgtcttcagggtttcttcgctgcgcgtg
gattcatattcctgctcggcggtcagaaacttataaatagctgcgccca
ggtctggtaagcagctgccggacctcccatccagaaggaggcaatacggg
aacgacggccatcaccgctaaccaggccttcctgtcgatggtttgcccg
tcccggagccagacacatttcatgttaagcgcacgcttcatgtccggtgt
gatcctgcctttacaggcagggcactgaagaaacgccgcttcgctggcaa
gcacaggatcgctgctgtcgcggtatccggtcatattgtccattcccggc
tggaaatattcgccgcaatgcgggcatggccagtaaagacgacggcggtc
accacggttatagagcgataaaattccggtggtcggagggggcttcatggg
gcgtggagcgccgccattttgtgtctctgatatccctcccgggcgagctc
tcaaccagcgtcatcccggaggacatgatcgtggttcgttctgcagtgc
cagtgaaaaagcatccccctcccccgtcgatatcttccggaaagcggtcat
aatccgtcagcgccacacttttatagtccgaggacgacatgatattgacg
gatggccagcccagcttcagatagttaccggcgcggaatgtacggtcgta
gacgttgttatcgttacgtcttgggcttagccgggttttaacttcaggggc
tacagcgaaaagtacggtccaggcgtttttttggaatgctccgcgcttt
tcctcagatacctgaattacaagcatatctgccggatcgcagacaatgtt
ataaacgatccagccgtcaatcagcccgatggttttaccccgttcgcgctg
ggccacaaacacaaccgcatcgtattcacgcgatgccagacagttcatc
ggctcaatcacataggggtgccagatccggatcccacggaactgagtttcc
cgcccccattggcacgcgcatataagtactgaccgcatcggccaccggca
tacgacgcggggctcgtaaaataccggaaacatcgcggcggatgtccctg
gcggatgccgctttgccatcagtcctcctcaggctgctcctcctctttt
ccagcgtcctgcacctttcctccgccatctggtcgcgcagatcatcgataac
gctttgcacacgaactaccgcagcaggcgttaaagcacagtcgcgctcga
gcacatccgggagggtttcaagtaccatgacgacggctttcgccatcaat
gagaattctcgcgccacttcatctgcgggtattaactgccccgtatcctg
ttcgaacttcagcctctcgttctctgctttccagtgggacagccgtgtag
aaggggggcatatcgtcgatgttggcgaaacgtaggggatcatcagttcg
gtcagaatgtcggtcaccagatagagctttaacttgctattgctgcctgg
agcaggttcaacattttcagtctcgcggcaaccgtctgacggtgtacgc
cggttatccctgccagctggtttgatattgagtttaaagtggcgaagttcg
tggtccatgatggtgaacacttttttgaacgattctgacatgttgcgaaaat
ggcctctaattaaatcaaagacctgcgcacatgatgatgatgaccctgga
tccgaaaactagccgtttcccgcgagcacgccgccccgtggcagggtcc
ccctccgggagtacctttttgataataattatcaattgcacaattccatcatgatggccg
tcggacataggaagccagttcatccatcgctttcttgtctgctgccatt
tgctttgtgacatccagcgccgcacattcagcagcgttttttcagcgcgtt
ttcgatcaacgttttcaatgttggtatcaacaccaggttttaacttttgaact
tatcggcactgacggttaccttgttctgcgctggctcatcacgctggata
ccaaggctcgatgttgtagatattgtcaccggctgaggtgtttcgattgc
cgctgcgtggatagcaccatttgcgatagcggcgtccttgatgaatgaca
ctccattgcgaatagttcgaaggagagcggtcacgaatcgctggtcc
agctcgtcgattgccttttgtgcagcagaggtatcaatctcaacgccaag
cgtcatcgaagcgcaatattgctgctcaccaaaacgcgtattgaccaggt
gttcaacggcaaatttctgcccttctgatgtcagaaaggtaaagtgattt
tctttctggtattcagttgctgtgtgtctggtttcagcaaaaccaagctc
gcgcaattcggctgtgccagatttagaaggcagatcaccagacagcaacg cgccacggaaaaacagcgcataaagcacttcattagcagcgccagatagc
gtaatgattttgttactcatggaatatttccttttaggcgtgagcctgtc
gcacggcaatgccgcccgagaggtaaacgcaacctaacggcatcacccag
gctcactactgaaagactctctttgatgtgcgcgtgcgatgcgcgtagaa
gactgatttatcaacctgtctttatatcaggattcattacctgactattt
gtgggtaaagttcgtagtgcgctgatcgtgcaaaatgattttagttggga
acagttcgcaactctgtcccataaaaatcagcatattcccatctatccca
tatccagcgcattgaccatcgggatactgaagggagattccatcatctct
tagaaagatcaccatctcttttgtttcaatttgcatatagctacctggag
gatttatgaatgcaaggattttcatggactattaccatgagatttgatttt
ccatctttattcgcgagagcagtggaaagcgatgacgatgtgggtactac
attgcgcattcacctacttttgtgagcgcatggtcgaagcatggatatgcg
catgctgtgactgccaagatctctttggaagagataaaaacaaacttttta
atcgaatgtaatactaaaatatccatggcgggaaacctgggaatccccccc
ggaacttatgaaatcacttaaaaccatcaactcaatgcgtaatgaccttg
cacacaatccatcaatacaaagcattgctgattcaaggatccagagcctg
aaggatactctgactgaatactttaaacagcatccaacggaacccagcat
ggaagaatcaaaactgggtattttttaacgccgagaatcaattaaccgaag
aagtttccttagatagtgacagttcaaaaaacagacttaagttaatcttg
ctgttcagcaagttaatgcaggcgttaatgcaattagttgcagctaatca
taatgggcgctgggataaccaatttagccaattcgtttaccatgtgacca
tgaacgcaacaaaagagataaatccaagcccgttttgtacgggctgttgca
ttatcacaggcactcagtgaatgcctgctgtaatgccgctagtcgtcgag
ttgcaacacaccgtgatccagtgattctgaataggcgataagtccggtat
aaccggggataatctcaccattatcagcttcaaattcaggaattgtgccg
gtggtgatggtgtattgaggctggccatcttccttcgcgaaggctgccag
gtcttcaatctgcttagctgtaagaactactgtcatgctcattcctcagt
tgtaaaaaagccccgcgagtgcgaggcgatttgattgaattctcggctct
tatctcagcgcagcccttactgcgtgccggttgctcggtgatgagcatc
agcgatgagacattaaagccgaccgaaggccagcggcgttcctcatgttg
ccgacagaccatcaccagaggacgaaaactagcagcatgaatcgcc
tattggttattcgacagtcgcactgattcgtaaatccgctcacacgtcat
tcctgcccggtagctttcgtcagatcgtccagcataatatcgagctgctt
ctgcaaggcttccgagcatgtcggcaagcattgctgcgttggctccggct
gttttgcttctgacggaagtggcagatctgcggtgtgctttgcggcgtc
catgtgggtagcgagttttgttgcttcggcgcgcagctgcttaacagtgg
tagccaggccagcagaagtaacgcagcgctcgctgcttgagcttgagca
tcttttaacggcctcatcccgggcgattgttcgcccttgttcaatcatacg
agctgcgtctgtgcattcgcttcctgtgaagattccgcgctatcccggt
cagccacttttattttccagctgcgttcgtccactcactgccagcgaga
aacgaacctaccaacgcaacaatcacaatgatgcagatgccacccggctt
cactggtctatcccccagcacgtcagtgcgctttcctggtcccgccgttc
tacctgcccataacatccatcctctggcccttggtcaggcggcaatcgc
ggccacctgtcttcaatccaccagcggatagcttcacaggctcctttcgta
tcgccagcattaattcgcttatagaacgtagacgggaaacattttccggg
gccgatgttatatgggcagaaagaagcgatacccgctttctgtggttcgg
tcagtggtactttgatatttcggtcaacccacgccagccgccttgtccgt
tcaatggcgtttacctgggcgcatttctcagctgacagcttcatgccctg
tactactggcttgccatcaaccattgttgcaccacgcaaatggtccaga
gtccgccgccgtcgcgatatgctgtcaagctgttaccctcttttctcatcc
agaaactgatcgagaatcacggtgcggaagccccgcaagaatcaaacc
aacgaccgctgcgtcaattattcttcagctttagagacatagccattg
cgccgatcctcccgttctttccagcggaaataccagttcactgcacaggt
gattaccgtgcatgcgataccgacaataattgcccagtcgctcaggctta
accctgcaattctgtcggccaacatccaggacacctctttttgctgtttta
gctgtttcggcatatgccttcgctgatacaccgcagccggcaagcgtggt
tcctgatccatatgaaagtctgctgtaaatggtgctcattctgctcatag
cctcacctccgatagttcggatgcgctgtgtgattgaaggggatcag
gcaaccgggctcttatgttcaagtaaaaattaaggatgattcccggtgcc
tgaagatggtgatcaccacgacaacgggagcgtggtgatcgttatgat
ttttcagttttccacctcttcggtggtctgtataaacctgtctgcctc
cagtctacgccgatcgcccgacggccaagttctattgcagcttttcacag
ttgaaccagagcccataaagaaatcggcaacgatatcccccggtctgctg
ctgcgctaatgatctgttttcagcatgtcggcaggtttttcgcatgagtg
tttgcctggataaaactgaacaggcctatgtgtccatacgtcggtataag
gaacaagagcggaaacagagaaggcagcgccgaaggatttttgtattcctcc
agcaattctgaatacttgcggtttaatgactggtaggtagccaccagctg
gtggtgaggatgttcaagctttttgctgaatatgtttatcgatggcgatcc
gcgtgaacagttcctgcaattttcgatagtccacttcattcggtagttgc
cattggcttgcaccaaaccagtgtgacgccatgtttttctttccggttgc
ctcagctatttctttcgagctgacacccagtgattcacgggcattacgga
agtaatcaatcagcggcgtcataatgtcgctgcttagctctgtgctttt
ctttcgtaaacatcctctttaccgtataacgtccaagatagtgctcagc
aaacaaaatccgttccgtagatggaaagtacgcacgcaggctttctttat
tacatccattccagcgcccgatggtttttgcccaaatgatgtgattcaaa
acgttgaatcgggcgcgcatcataatctctatatctgaggccagtcggtg
accgcaaaacaggtagatgctgccagcaggtttaagaacgcgagcatact TABLE E-continued Phage 3 Genome Sequence
SEQ ID NO: 134 cagccaggcagctatcaagccagcgtaagtagtcctcgtcccccttccat
tggttgtcccagccgttgggcttcactttgaagtacggaggatccgtaac
tataagatcaatagagttatccggagggtggcgacgtaatgcagactat
cagcgttgattaactcaacactgtttattttttacagtattttttcatagat
cagtaagcgtaactctgataggctcacgttgcttttgcgctaaagcagtg
ggccttggttagcttgtgacctgaaagcatgagctgatggctggccgggt
gcgctaacacccaccagccgcccatttccacagcagaaaaccccccattac
tggaggcgtttataacatccgaactggtaatcagataaccccgccatcac
cagctgcgtaagtatgagctggcaacgttcgtggctgaggtgggtattct
gtgcaatctcccagccgttgctggtttatcgcttaattcattgaaaaca
gcctttgccgtttctgtcatatcttcctgatttagcatgtcttttaccta
aaattagttgcgtgacatacagataactctggttggtgataccagcaaga
gaagaatttgattctgcaaccaacaaggcctttaggcatcaggcaggaat
gagatgcaataaaaaaaccaccccgaaggtggtcttatatgaatctttaac
gcggacttagcaaatattccacatcatcgtactaccgttatggttttcga
taatttttgcggctgggctagtaccaaaagagtgcatatagcaatgatga
atagtaaggaccagatcctgcaacgtttggtcactctctagctccatgat
attttaaaccaatattttgagctttgtccaaatgaatatgtctggcatgtg
catacgttgcttggtggttgtttaactcatcacatatacgcttagccta
gcttcagcgtcagcctgacctgcgaacataccagtacaaagccatttctg
gacaatttcgttcgcccagagaattgcttttttcacactcgccaatcaacg
ttggatttagtttttggaacgtaaattgccaccattgcagtgcagcaggg
ttggcaaaaattttccgcttttgctctctcatactcctcaataattgcatg
agatgataacccattaaactgtggatcaattggccccaagttcgactgtt
tacctaaaacgatctgctcagcacaacaagcaagcattgtgccacaactc
attgaaatcataggtacaatcgctcggatattggttccgaactttgaacg
aagataatgaccaattgattctagagctgcgatatcgcctccaggagtat
ggagtaagatatccaatcccgactcgtatctaacccattgatagcagac
ataagaccatttttatcatcatctgacatctggatcagatgttgaaaccc
aggcccccctttttgaaggaagcctgagtaataagaaattacatttcggc
cagtatgtttcgataaatcacgtaagtacttgtggcgaacctcatccgct
ggtgtacgttgagcgatagtacccatctcacccaatacgtctatccaatt
tggcatgttatcaatttatcagtatgagtacagttggtgagattgctgac
cgttctgctcagtagtatttggtgttactgtgctgtatgaatagagcaca
ccacttctcaaacttcagatcgttttgcgagcgagaacacgcatagaaa
atgctgtacggattcgccttttttgaaactcttggggttgtatgcccattt
tttcgtaaaattcagcagcgctcatgatatgtccctcgttttttttctaca
tctatgcaattccaggagccatcaacacaagatgtagtagttagcagtcg
tcaaatacacgaaaagcctcaagatgaggcttaaaaagattcttttttgat
aaagatttagccaaactatagcggtcaaaatcagatttgacaagtataa
aaagcacttaaagcctataaataggcagttttttgagaattaaagcatctt
taatgaggttgaacaaaatgcagtcttgacgctgaacaggactttactgg
aacgtagagctaaatggttcgatttcatgaaccagattacaaaaaaaccg
ctcatcggcgggtttataaaacttttggcaacatatcaaatatgcttcaaa
tatggcttattttgttgcattttgcaagcgtgtttgaaggagatggtgaa
atttacttcacatttctgccactttgagggcttcttcttcctcatagtat
tcaagagccatggccaacgcagattcatcaagctgggtaaaaagcggcctt
taacccagcccagtgccctgaatagacacgcaaccatgtcgaacggtcaa
cgctaaccatgcgggcaacgctgcaccagcatagtcttttataggtttca
ttatttctggttgcggcaatttcctgccctgccagccataccaggcctat
cagttcttttactacgcgctcctgaagggagttatcaccacaggcattct
gataagtttccagacgtattcacacatcatccacctggtgcttatagcta
aaggtcaaaaccgtagcagtaccgcaaccaggcctgctggtatccactaag
cgcggacactgccctacgccacggcgcggactcaaattccgcatctttta
tcggcggcattggcctgcggcggctgcgtgtttccagcacatacagtggc
gcggaaagtgagttaacaaagcgtggccccttctctccttcggttcgac
gagatgaattccacggcgaggggtggcattttttgtctgctggtgggtgtt
cactgaaagcctcaagctgccctttgttccccagacaggtcaggtagc
gcgcggcgcaattctattcttacaaaattcaggtcttgttgattcatgct
tctttggcgctccatactaccttaagcttcgcaattacgcgcgatcgccagg
cccgatccataaaacgcagtagcagctcaagctgcgtaccatgcttctgc
tcgaatgccggtacatcggcgtgtaactcgtcgtggcactctctgcacag
agggatcacgaagagatcatgggcttttgttgctgtcccccccataccgt
gccctacgatatggtgcagatcatctgctggcgtcggcaacactcacag
ggttgtgttttaaccagcggggtacgtctcatttatccagcggcgtcg
cttggcctgagcatgaaagattctggagactccggatcaacagagagcg
tgaggatcttcttcgccttctcctgcacgaggctggttgcagaagcggaa
ggcacaatgtcgcttcctcatgaccgagcggctttatcatccggaag
gcgtagcccttgtgcgcaacgctttccggaataacatcagccaggtcgt
ttctgaccatccaccagcacagttccggaagcgtcaggatatgcgactg
ggaaaaccagaatcacgccgaatgacttccagaatccaggataccaggtt
tcctgccgctatacctgcaagctgttcggtatgctgccccgacaaagtgt
gatcgcaatgccagcacaggcgaatacttcctggtgggtgccgcattgtt
gtgaagttcttgtcgtgccacgatgaatgtggccactggcattcaaaccg
attactcaaccattgctcaagggaaggaagcccaccagcacgctgaataa
cccgatcattctcgaagacctgccgcattaccggatcatcagccagcggc
tgaatggcggcgggaacagcctcctgtactgaatgacgccatttcttctgg ttcaggctcaagcagaacgcgaccgcgcataaagaggtgcatcagttccg
cgccgggacgaaacaacacaatccccatacgatgggcgatctcgggggta
agcagagctctcacgcgacctgcccctggcaatgtgttctgcccacagt
ccaccaatccagcgcacgcctttcgccgtgaaacgtgcctggctgaatgc
atgatttgaggttacggatgtgccggttttcacttcaaaacggcccgcat
caatatgctgatgccgtggggtcatcgttccgccaagacgatacatgatg
tcgttctcaaggaggaataaccgcagatcgggctctctttggccttaagcag
ttttgccacctggcggaatgacattgacccactggctgtacagtaccgat
caacaaacgctaccttcggcgccgcggcagccagttcgttagtcaactgc
tgtttttgttctgcaaggtcagctgcaagacgtagggcttcagagaatga
ttgaggaatcgtctgctgctgtgcctgctcaagctcctgccagcgatcaa
ccagacgcgcggtaaactccggcgacagctgcgcgacaacgatataactg
tcccgcttccctatcagataaaccgataccgactgattgaggtgattttt
aacttcccccattgggggagttcaataacaccgcgctctgccaggcgtt
caatgaccgtttaacatggtcatgtcttgattccaccagctcagcaata
tcgctgctggacatggttaacgctgttgttgctaactggctcatacttttt
ctccatatcaggcggctgcacccgccggttcatatctgctgattgttatc
tctaccgaccttcggcacacagggtccccattccaccagcatgcgctt
aatctggctgtcgtcttcccagacaccgcatgcgtcagcgcgtcaaaca
gggcttgttgtaattatcgatatcccgggcgcgcatccggcgggtac
agagtgatttctaccgctgccagttcagtcgatggcttcgggagacgtcg
taattgctcaatgatcgccacgcaggcagcgctctggtatttacggccag
cggcgctaatgaggtgacgaccggccacgcggcccctttgttaggggcgc
cagtaagtgttcacgctcggaggaaaaggcaggatcagtttcacgcggcc
tctccccgcatattgcgaacaagttcagaagcagcagtaatgatttcgct
ggtggcaggtccgctccagccagaagttgattgatattggctttcagcttgt
gttgcagtgactcatccagcatgtcagcaccattccacctggtcgaataca
attctaaccctccagcggccagatacgggactcgggaagcggatccgatac
tggtttagcttttctcacgaatgtgcatgcggatctggcgaatattggacc
aactggaaacatccaggctttcccatggctgcaatgaagtcagtgctgttc
atgccatattcaccggatgcttcaagggcaacagtgcgaatacgttccga
catatccaggcgcacagcagcgtcatcgaattcaatcgacaacagccact
catcccacaccgaacaaaatactctcacgaataagcagcttcgctttgtcg
atcgttaaaggtgatacctgagtgaattccggtgcttcgacagaatccgc
cgcccaggtatgcccaaacttcagtcactgaatgtgtattcttcttttat
cgccaaacgcagctctaacgcatgcccacgcctcgacaccgctgatagca
aaaatatctttctgggtgagtggcaactctgcttctggcttatcagctgc
aggaggtgtggcagttacaggttgagacttgctggcagcaaattgtgcca
aagccataaacgcccgccctttttgcctccagttctgtcgcggttgatatag
ctgaaccgtcgccacgccatgacttatcgaatacagctatggcgaccggc
aaaaaacgcgctggtgggtttctgtttttcgtcagcaggtacaaaccaca
caggcagatcgaacccaatgcgcccgcgaatgaataacaatgtgatcggca
tcttccggccaccagtttcactcggcgcggcttttatcaggaatacata
gcgaccgccttctccgcgctgggctgctgcgtagttcatgatgtgcgtca
tgccggtgatcgcctgcttctcgtggtactgcgaacggctatacggtggg
ttgccatagccagcgccacccagttcagccagacgttcagaccagtcctg
cgtcagccgcgttatcttcggcggtgtaccatgccgggcagttttcgcgttgt
cgtcgtcagcaaacaaatccagaactaatgaccaaatagcgcgttgatc
ccccaaaaaagcagatccggtgtccgccactgatcgccaacctctttcaa
ttcgtgagctggtttgctacgcagtccgccagcgcctggcaatatttat
tggtcatcatgaacggaacccgaattttctggcagtgagtaatcaacac
tctggaagttttgcgcggctggctgagttagtctcccatttgccgttaacg
cgttcaggccggccagcactggacccattggtcgcgctttgcaggtaacc
agggaagtttttttggaatgaacagagttgccgggcggaggtattgcgcct
gctcgctatcacgccaatcggcatttttgtaatccactaccaagcacagg
tcatcaacagtgaattgttcccgaacagggcgggaatattctccaggcga
cgtgctgcatacctggtagcgtgagccagtagtcgattcaggtaagaca
aaacctgtctgcctgatcagtaatcacaacctcagggtcgggttgcgcc
gcaaccggacaagaggggtttgaagttacttgtggttcttgtttttgattt
tactgacggatccccaccagattctgacgggtcaaaaccgccttttttgc
tggatttcgacgcctcaaattttgacgggtcggattttgatgcatcagat
tttgatgggtcagattttgatgcgtcagattctgacaggtgagaaaaagc
agcctctcgcaacttaacgacgttaagctgatatacgttcgatgcgttac
ggttcccattacggcgctgcttacgggaaagccagccatccttctcaagc
tgagcaagggcgtcctctaccgtacttctccagcaccgatttgacgtgc
gatcgtgccaatagacggccagctaacaccctcatcactactgaagtcgg
ccagacgcgccatgatggcaacgctggataacttcatgcctgacgaagcg
catgcatcccatacgtaaccgttaatttagtgctcatgcatggtcgtcttta
attctgtaaattttacgctggaattgttcaagagggctgaagcactcatga
tcgtacccttcgcgaaggtatataacgcgctgtgtatctggctcccagcg
gacaactctgacgggaactccgtagtgatctctgaaccgccggttaactt
cagccattcctcgcgccccttctcgttcatctgaacaaatgcttctacca
tcaagtctgctggtagttgcctccatcagccgcgttattatgatt
tccacatagccgaactgggcatctttacccaccagcggcaaaatctgaa
ttgcttagctggtctgaatcggtttacactgttcatgcgttagtttctcc
actgatacgacacgccaaggcgcccggagctgcacactcgcgggcgtcac
cttttctgcctgttgaaacgaatacgtcaatcgcctgatctgaaacacca TABLE E-continued Phage 3 Genome Sequence
SEQ ID NO: 134 acccccataaagcgccataaatcccaggaacccgtgaatctggtggcggag
cttcttactgaataattctgaaagcattttgcgctctgatgaatcaatta
ccccatcagccgctgctgccatcttggcattagccagctcaccagatgct
gctgccgctttcatctcaatgctgtacagctcaacgttatccaggctctc
agcagttggaacatccaccagccatttcccttttcggttcgcctggtact
cggcaagtaacaagaaccagacaggtcctccatccgttccagttctgcc
aaggtaaagaaccgactgccacacttctggtacaggtggttgtggaactg
gtcgatagtcatccctaaatcggaagccataccttaagcgaccatgcttgt
gtgccttacacatcaggcggattgctgtatttatgctgtctaccatgttg
atttccctctggtagttaataatcaacttaaagttgactattgttgttag
cggaaggtatgccgtcatttttgttcggataaatatcaggtcgtaattga
tggggagttactacccatccgccccattggcagagttgaataactctttc
agaaggtactcggttctttgcaatccagttcgcaacagattgaactgatt
ggaattcaaaccgccttgatacctctgaaatcgacccgatcgccttcaca
gctttagctgttacattcttgtgttgagatgacatgtgttctcctatgac
taagcctgcatcaatactacttatagtagcaattattagcaacttaaaat
agaaatgacaactatgccttgtgcgcttaatcttctacttatggtggaaa
atgctaaatacaaagactttgccgaaaggctaaacaggtctctccaagag
caatctattggagttaaagaattgtcagagttcagtggtgtctcgtatga
gatggcgcggcgctacactcttggtactgcaaagccgagagatgagaaga
tgattcgaattgcagaaagacttgccgtctcaccggcttatcttgattat
ggtgtgcctgttaattggtggcgacgcgccagccaaaggcacgctcagaat
agagcaattggatgttcatgcttcagccggttccggatatataaaccaac
cattccctacaatagtgagctcaatagagattccagaagagaggatcttc
gagttgtttggtcgtagaagccttgatggcatcgtcatgataaatgttga
tggcgatagcatgatgcccacgctttgcccaaaggacctgcttttcatag
acagcaaggttgaacaattcagcggcgacggcgttatgtgttcaatttt
gaagacagtacgttcgttaaacgtttgcagaaggtaaaagggcgccgact
ggcagttctttcagacaatgaacattacccgcccttcttcatagaggagc
atgaaatgaatgaactatacatattcggcaagctaatcagatgcttacct
ctaaaaatgataagagttttggctaataattaattcatcaagaaaccgga
aagccggttttttttttacgcctccaattcctcacctcataacactacacta
ctaaaaatttcattttctacttttttgttgttgcaattatctacttaaagt
agctatagtcattgcatcgaaagcgaacaggcaggacgcccacgaagtag
ccgccggtgcatatgaataaccggatgattcgctgacagaaaacttagg
ttgggggtagaggtttacatgaatcatttattcacatgctcattttgcgg
agcaaccgaactgggagcgataaaagatcgtcgcaaaaggtggtaaggacg
aacctgccatctgttcggaatgcgtagtcacatgtgtagaaaaaatgatc
ctgactaaaaaatcagaggctgaaaaaccaacctctgataaacgaaaat
atcagtcgataaaaaactatttaaagagctctcttcagcttgtcctcaacc
ttcctgatttcggaagtaagctggctgctgttgacattgatagtagctcc
acatcgacaagtgaaacttttgttcgacttgagccaagcgattttcttct
tcgtcttagtgccgcacttagggcatgcgggtaacgtaatttcgttgtta
tcaaaagcgcccataaacatccctcttggttgtgtgagaacaccaagata
ccaccgcgcctgatgtggttaaaagcaggctaaagcaataacaagtaact
ccctgttctggcggccggtgtttcccgtgtatttccggtaaccgccag
ccttttcagggcacaacagaaaagggcatcaccgggcgacgggctcata
acccaatccaccccgggcaaaaagaaacggctctctgcaagccgccgacca
atgcaggtgcccttctctgttgtgtatgagaaactaactttttagcgtc
tgtgcagatgcgctgaggaaccgagaatgaataatccgttttttcaaaaat
atgttggtgtatcgcattagtcgcgatttccaccatcaaccaggaagagct
ggaacagcagcttgaactatttcgcttcactccatgcggtagccaggata
tggcaaaaccggttgggtatcaccacttggtcagctgtcagatcgcttg
catcacactgtcaataatcaagtgttgttggttattcgccgggaagaaaa
aatactgccatctcctgtcattactgaagaactgcgcaagcgtgtgtcgc
gtctagaatccgatcaggggcgtcgcctcaaaaaaactgagaaagattcg
ctgcgtgatgaagtgttgcactccctgcttcctcgggcgttctccaaaaa
ctcgactgttggtttgtggatcaacgtcaccgacggtctgatcatggttg
atgcagccagcgctaaacgtgccgaagactcactggccctgcttcgtaaa
actctcggttctctcccggtggtaccgctgactatggaaacgccgatcga
actaactatgaccgctgggttcgttccggtagtgcgcctgctgctttg
gcctgggtgatgaagccgaactgaaagctattcttgaagatggcggtatt
ggacgctttaaaaaacagactctggtcagtgacgaaattcatgtgcatct
ggaagctggcaaagtagttacaaagctgtctatcgactggcaacagcga
ttcagttcgttcttttgcgatgacggcagcatcaaacgccttaagttctct
aatgagattacagaacaaaacgacgatatcgaccgtgaggatgcggctca
gcggttcgacgctgactttgttctgatgaccggcgagcttatctctctca
ttaacggattaacaacctctctcggcggcgaaggccaagcagtcaaacacca
ggcaacaattacccccataagctgggttgggttgctgcacgctaaattc
agcaattcattaatttaatggcgcggtgcagcgcgccaatatggagaaaa
ccatgagctacattcagacattatccggcaaacattttaattacctcgat
atccaacaggacgatatcgtgatcgaggtatgctaccgcgttgtctca
tatctgccgctttcaggggcatcttcctgagttttacagtgtcggccagc
atagcgttttaaccagccacctcgttccgcaggagtttgcattagaagca
ctgcttcatgatgctgctgaagcctacctgcaggacatcccctcccact
taagcgcctgcttccggattaccaggcaatcgaagctcgtgtggacgcag
ccattcggcagaagttcggtctaccaactgagcaacacccaaccgtgaaa
tatgccgacctggtgatgctcgccagcgaacgccgcgattttgagattga
cgaaggttccatttggccatgcctcgagggagttgtcccaacggatttat
tcattatcaacccagttcgtcctggccagtcatacggcatgttcatcaat
cgctttaacgagttgatggagcagcgccaatgcgccgcatgaaggtaaaa
gaactcgtagcggaggcgtttgcctccgttgctgaattgccaccaaagca
tgcgccgcttatgcgcgaagtcgccaccagactggacgctacgttcgcag
cattaaaagagtctctggtgcaactggaacaggaacgtaaagataaaacg
ccatgaccgtatttgaatatctccaggctcatccgaataccaccagcggt
gaaatcgccaaaggtatgaacaaaaagaccccagcggtcgccggagcatt
atctcagctctatggcaccggtcggatcgtgaagtctggtgttcgcaagg
gtattccaacataccgcattaacgatatgccgtttggttgcagtaacagc
ctaaccatgatgtttaaccagctcttgagcagagccagacaaggagcagc
ccaatgacagcactcaacaaacaggcgctgcgtgaagaattccagttcat
gcaggacaactatagcgacccggcagaccacgatcggcaggtgatttaca
tcgaggcggaggcgctgctggatgagttggaagcaaagactcaacgata
gcagcacaacaacatgagatccgtatgttgctgaatgcgcttgaggaaaa
accatgcccgaaatgcaacgacacaggaatgactgatagtggcggcacgc
agccatggggcgagccgattgagattgaagctgcactgccgacagcaggat
gccaacaccgcagaacttgtagccgctggcattggcgtgaaggggaagtg
agatggataaaattaatcaaacctaccgccaaaggtaaatatgacggttca
tgtgattatctttgctcggaagatgcgcgattcatcgttatgcgcggcga
ttatacggaagcgggaaatattcaggcttctgtgtctcaagatgcaatcg
actccgatggtgcggctgattttgcaagtagcgccgctattatcagtcgt
tggtacaaagtagcccaataggtggtcaggatggctattcaggctggca
tcatcctcgtgattcgccgtgtcgcggtgcatatttcgcatcagttttgc
aatgggattaaggaggactaacccatgacaactaacaaccaccccggcgca
cggtcctgtatcactcgatcgcctgcaccagatacgcgaacacctgctgc
atgataccaatactcaaacggcgggaacagagcctacattctcgctgat
gtattgaaggtgattgatggggctattgcccgcgagctggtacgccgtga
gcatgcagcgtggtcacaggctactttcggcgatgtcggtccagttggtc
cgctgaagcaccttctccaagaagcgctcgaggctgctgctgaaccaggc
gaccttagcgaatgggctgacatgcaattcctgttatgggatgcgcaacg
tcgtgccggtatcagtgatgagcagattacccaggcaatgataaaaagc
tggctataaataaggttcgccaatggcctgagccgaaagacggggaacct
cgattgcatatcaaagaacagtcagagcaggagaaaaaataagaatgttt
agcctgattcggcgcggtcaaatctacacggacagtagcaactggcccgt
aattatccatagctgtagtgatcactcggtccgaattaaacgcaatgatg
gcgagctgagaacgattagcatcaaacgctttaacgaagattttgaacga
gtggagcatgatgagtatcgcgaaaatatgtgccgaaatagacaggaaac
aaacctgaaaaacctacgtgcgatgcgtcgcgcaagattactgaatagc
caaacaggagaatatttaacgtgaacaacttaatgatcgaccttgagtcc
atgggcaaaaaaccgaatgcccctattgtctccattggtgccgtattctt
cgatccgcaaagcggtaactgggtcaggagttttacaccgctgttaatc
ttgaaagcgctatggagcagggagcggtgccggatggtgacactattctg
tggtggttaagacaaagctcagaagcacgatcagcaatctgtgttgatga
tgcgatgccgatatcatctgccctatctgaactgagccatttcattaatc
ggcattctgataaccctaaatatttaaaagtttggggcaatggagctact
ttcgacaacgttatattgcgcggcgcatatgagcgtgccggccaggtttg
cccgtggcaattttggaatgatcacgacgtcagaaccatcgtcacattag
gcagatctgtaggtttcgatcctaagcgtgatatgccattgatgggtt
gcacataacgcactgcctggtgatgcccgccaccagggaaatatgtttcagc
gatttggcgaaactaatccaaccaccagcaacagctaaagttttcccc
gggtgcagccgggataatggagaaataactatgagcaatattttccagtt
agctcccaacgatgggtttgtgaaagcgttttgatcgcggttactgggc
tcaaacccggaaccatcctccgtgccagaaaagaatgctggatgattggg
agggagtatatccacgtatcgcctgaccggaaatcctaaacctccagtga
gtgcatgtataacagaaaaggctgtagatgcctgggtcgctcaatgaaaa
gcaagcaaccagggtgatttgatgccatgaaaaaggtaagctcgtatcgc
tcttgggcgtctggaggtaacaccaatggataaagtcacatatccaacag
gcgtcgaaaaccacggtggcacattacgcatctggttttaatttaaaggt
aagcgtgtcagggaaagtctcggtgtccctgacaccgctaagaacgaga
gatagccggggaactgcggacatcagtatgttttgccatccgcacaggaa
cctttgattatgcaacccagtttcctgactccctaacctcaaggcttt
ggtgtaagtaaaaaagacattacagtgaaagaacttgaagaaaaaggct
ggatctgaaacggatggaaatctgcgcgaacgcattttaatcgctatgaat
ctgtcgcaaggaatggtgccgaggatcggaggtaatcgcctggtgtca
gcagtaaccaaagaggaattgctgtatctgaggaaatatttgctaactgg
ttatcagaatccgacgaaaaacgcccccggcaaaagggcgaagcgttg
ttactgtgaactattacatgacgacaatggccggaatgtttcagtttgct
gcggatcacggttacttagaggtgaacccattcgagggaattaagcctct
gaaaaaagccagggcagaaccagatcctctgtctcgtgatgaatttattc
gcctgatagatgcatgccggccatcagacagacgaaaaaacctggtcatta
gcagtgtacacaggaatggtcacgggggaactggtctccctggcctggga
agatatcgacctgaaggctggaacaattaccgtcagacgtaattatacga
aacttggtgagttcactctaccgaaaaccgaggcaagcacagatcgagtg
gtgcatcttatccagcccgcaatcagtatcctgaaaaatcaggctgaaat
gacaaggctgggcaggcaatatcacattgaagtgcagttacgtgagtacg

TABLE E-continued

Phage 3 Genome Sequence
SEQ ID NO: 134

```
gccgttcggtgaaccatgagtgtacattcgtctttaatccgcatgtggtc
agacgcagtaagcaggtcggatttatctaccgggtcgattcagtaggcga
ctcatgggaagcggcacttaagcgtgcggggatcagacacagaaaggcgt
accagtcacgacacacctatgcgtgctggtcattatcagctggtgcaaac
cctagttttattgccagtcagatggggcatgcgagcgcgcagatggtgtt
caatgtttacggtgcatggatggctgacagcagcgcagagcagatcgcaa
tgctgaatcagaagctggcagattttgccccattgatgcccatagccac
gagaacagtacgggaggattattaaaatcagtaagttaaccctaacgcc
cgtcatgttaactgtgtggagggtaacaccacgctttatgccctgccgaa
acccgaggttgtcctgcgctggcgtgagcagaccacagatgacttccgct
tctgttttaagtttccggcgaccatttcgcatcaggcagcattacggcat
tgcgatgatttagtgactgaattttttgacccgcatgtcaccgttggctcc
gcgcattggacaatactggctgcaactgcctgccacattcggcccacggg
agctgcctgcgctttggcattttctcgattctcttcccggtgaatttaat
tatggggtggaagtccgccatccacagttttttcgccaaaggggaagagga
acaaaacgcttaatcgcggtttacatcagcgcggcgttaatcgggtgattt
tagacagccgcccggttcatgcagcacgtccatacagtgaagctattcgc
gacgctcaacgaaaaaaacctaaagttccggtacatgctgtactgacggc
gaaaaatccactgatccgttttatcggtagtgatgatatgacgcaaaacc
gggaattatttcaggtctggttacaaaaattagcgcagtggcatcagacc
actacgcctatctttttttacatacgccagatattgcccaggccccgga
actgtacatacccctgtgggaagacttacgtaaaacgcttccaggatcg
gagcagttccggctattccacagcaatcttctctttttctgaatttgccac
ctatcatagacaggtgccatccggccattttaaaggggagtttgtatggtaa
gcgcgctgtatgccgttttaagtgcgttgttattaatgaagttctctttt
gatgtcgttcgcctgcgaatgcagtaccgccgttgcctatggcgacggcgg
ttttagcgaactgcaaagcgcattcgcattcatggtaacgcggtggaat
atattcctatcgcgattgtgttgatgctgtttatggaaatgaatggcgca
gaaacctggatggtgcatatttgcggcatcgttttgcttgctggtcgtct
gatgcattattacggttttcatcaccgtctgttccgctggcgacgttctg
gcatgagcgccacctggtgtcgctgttgctgatggtgctggcgaatctt
tggtatatgccctgggagttggttttctccctgcgttagcgcacaatacg
ccacttttcttttcccggattttttacgttatgtctcaccgcgacacgcta
ttttctgccccctatcgccagactgggcgactggacctttgatgaacgggt
agctgaagtcttcccggatatgatccagcgttccgttcccggctattcca
atattatttccatgattggtatgttagccgagcgcttcgttcaacctggt
acgcaggtttacgatctgggttgttctctgggcgcggcgacgctctcggt
gcgtcgcaacattcatcatgataattgcaaaatttattgccatcgacaact
ccccggcgatgattgaacgctgccgtcgtcatattgacgcctataaagcc
cctacgccagtagacgttattgaaggtgatattcgcgatatcgccattga
aaacgcatcgatggtggtgctgaattttaccctgcaattcctggaacctt
ccgagcgccaggcgttactggataaaattatcaaggagctgaaccccggc
ggtgcgctggtgctttcggaaaaattcagtttcgaagatgccaaagttgg
tgaactgctgttcaacatgccaccgactttaaacgtgccaacggttaca
gcgaactggagatcagccagaaacgcagcatgctggaaaacgtgatgctg
accgattccgtgaaacccataaagcacgcctgcataaagccggttttga
gcatagcgagctgtggttccagtgcttttaactttggttcactggtggcat
taaaagcagaggacgctgcatgatcgactttggtaacttttattctctga
ttgccaaaaatcatctttcacactggctcgaaacgctgcccgcgcagatt
gctaactggcagcgcgagcagcagcacgggcgtgtttaagcagtggtccaa
cgcggtggaatttctgcctgaaattaaaccgtatcgtctggatttattgc
atagcgtaaccgccgaaagcgaagagccactgagcgccgggcaaattaag
cgcattgaaacgctgatgcgcaacctgatgccgtggcgcaaagggccgtt
ctcactgtatggcgtcaacatcgataccgaatggcgttccgactggaaat
gggatcgcgttatgccccatctttctgatttaaccgggcgcaccattctt
gatgtcggctgtggcagcggttatcacatgtggcgcatgattggcgcagg
ggcgcatcggcggtgggtatcgatcccacgcagctattcctctgccagt
ttgaagcagtcgtaaactgctgggtaacgatcagcgcgcacatttgtta
ccgttaggtattgaacaacttccggcactgaaagcctttgataccgtctt
ttcgatggcgtgctttatcatcgtcgttcaccgctggagcatctctggc
agttaaaagaccaactggtgaatgaaggcgaactggtgctggaaacgctg
gttattgatggcgacgaaaacacggtgctggtgccgggcgatcgttacgc
tcaaatgcgtaatgtctatttcattccttccgcgctggcgctgaaaaact
ggctgaagaagtgtggttttgttgatattcgcattgcagatgtgagcgtt
accaccacagaagagcagcgacgcaccgaatggatggtcaccgagtctct
ggccgattttctcgacccgcatgatccgggtaaaacggtggaaggttatc
ctgcgcctaaacgcgcggtgctgattgcgcgcaagccgtaaaggtctggt
aatactgccggatgcggcgtaacgccttatccggcctacaaagtcttgc
taattcaatatattgcaggggctatgtaggcctgataagcatagcgcatc
aggca
```

TABLE F

Sequences of the genes comprised in Phage 3 of *E. coli* Nissle

| Description | Sequence | SEQ ID NO |
|---|---|---|
| ECOLIN_09965 | ttatttgatgggataaagatctttgcgcttatacggttggatttcgcccggtttgcgagttttca gcaattttaatatccaggtgtattgttctggtcgcggaccaacaaaaatctcgacttcttcatt catccgccgcgcaatcgtatgatcatccgcctctaacagatcatccatcggtgggcgcac ctgaatcgtcagacgatgcgtcttgccatcataaatcggaaatagcggtacaacgcgcgc acggcacactttcatcaaacgaccaatcgcgggcaacgtcgctttataggtggcaaagaa atcaacaaattcgctgtgttctgggccatgatcctgatcgggtaaataatatccccagtaac cctgacgtaccgactggatgaatggtttaataccatcatttctcgcatgcagacgaccacc aaagcgacggcgcaccgtgttccagacattaatcaaaaaccgggttgccctgattatgga acatcgctgccatttctgcccttgcgaggccatcagcatgcaggaatatcgacggccc aaccgtcgcgcaccagaaaaatcactttctcgttattacgtcgtatctcttcgatgatctcca gcccttgccagtcaacgcgcggctgaatttctccggcccgcgtattgccaactcagccat cattaccatcgcttgcggcgcggtggcaaacatctcatctacaatcgcttcgcgttcagctt cactacgttctggaaagcagagcgacagattgattaacgcacgacggcgtgagcttttc ccagtcgtccggcaaaacgtcccagccgtgccagaatgggatcacggaacttttggcgg cgttaaagcgataccgccatcgctgctacgcccagccatgctccccagtagcgcgggt ggcgaaaggatttatcaaactcaggaatgtattcgctattatttttttcgtttccat | 135 |
| ECOLIN_09970 | ttaatcaaaccgtagctgcggcacaatctctttggcctgtgccaggaattcgcgacgatcg gagccggtcagcccttcggtacgcggcagttttgcgtcagcgggtttacggcctgctgg tttatccatacttcatagtgcagatgcggcccggttgaacgtccggtattaccggaaagcg cgatacggtcgccacgtttcaccttctgtcccggtttcaccaggatcttgcgcaagtcgcata taacgcgtggtgtagctgcgaccatgacgaatagccacataataacctgctgcgccacta cgtttggcaaccaccacttcaccgtcacccactgaaagcactggcgtaccttgtggcatg gcaaaatcaacacctctgtgtggcgcaacgcgaccggtcaccggattagtacgacgcg gttaaagttagatgagatacggaactgttcgccgtcgggaatcgcaagaatcctttcgc cagaccagtaccgttacgatcgtagaatttgccatcttcagcgcggattgcgtaataatctttt accttctgaacgcaaactgcgccagccggctttgctcacgtttaccatcaagcatttt ctcgtgacattaacaccgcaaattcatcgccttttttcagtttgcggaaatccatttgccactg catgctttaatcactgcgctcacttcggcgctggttaaaccggcgtttctggcgctggca acaaagcttcccccgacggtaccttcagcagattgttgacccactctccttgctgcatttcg ctggtcatttttaaaaccgttagcggcagtacggtcataggttcgggtttcacgacgagaca cttcccaggtgaggcgctgcagttcgccgtccgcggttaatgtccaggagagttgttgac | 136 |

TABLE F-continued

Sequences of the genes comprised in Phage 3 of E. coli Nissle

| Description | Sequence | SEQ ID NO |
|---|---|---|
| | cgattttcaggttacgcaattctttgtcggcagcagccagttgggtgatatcacccatatcaa<br>taccatactgattgagaatgctgcttagcgtatcgccagtggaaacaacatattcatgcacg<br>cccgcttcaccggcgatttttgtcatccagttcgtcctggggaatggcttcatcttcttgtgca<br>gcttgatcaatcggctcactggcttcaggtaagagcgaacgaatttcgttctgttccagctc<br>aatggttttgacaattggcgtggcatcgcggtgataaacatagggccgccagacagcga<br>cggccagagtaagaacggtgagcgaccccaacataacgcggtgtggtcgcggtaaatt<br>attaaacgccagggcgacagagcgggctatctgttgcac | |
| ECOLIN_09975 | ttaatctcctttcaggcagctcgcatactggttggctaattgattcaggaattctgaatagctt<br>gttttacccagtttgatattcgtccccaggggatccaacgttcccatacgaacggatgtccc<br>tcgtgcgacgctctcaacgaccgctggcctgaactgtggctcagcaaaaacgcaggttg<br>cttttttgctcaaccaactgtgttcttatttcatgtaaacgctgcgcgccaggttgaatctcagg<br>gttaacggtaaaatgaccaagcggtgtcagtccgaactgttttttcgaaatagccgtaagca<br>tcgtgaaaaacgaaataaccctttcccctttgagcggcgcgagctcgttaccaacctgcttttc<br>ggttgaggctaattgtgcctcaaaatccttcaggttggcgtcaagtttggctcgactttgcg<br>gcataagttccactaattttccatggattgcaaccgctgtagcccgcgctatctctggggaa<br>agccaaagatgcatgttgaaatcgccgtgatggtgatcttcgtcactttttttccgcgtggtcg<br>tgatcatcatcatcgccgtgaatacttttcatcagcagcggtttcacattctctagctgcgca<br>atcgttacctgtttcgcttcaggtaatttacttaccggttttttgcatgaacgcttccatctccgg<br>gccaacccaaacgactaagtccgcgttctgtaagcgttttacatctgatggacgcagtgaa<br>taatcatgttctgaagcccgtcaggtagtaaaaacctccgttctgttaccccatcagcaatg<br>gcagaagcgatgaacccaacgggtttaagcgaagcgacaacggcagcatctgcggcct<br>gtgttgcaccgccccagagagcggcggataatgctgcgaaaagaagcgtttttttatgtaa<br>cat | 137 |
| ECOLIN_09980 | atgacaagtctggtttccctggaaaatgtctcggtttcttttggccaacgccgcgtcctctct<br>gatgtgtcgctggaacttaaacctggaaaaattttgactttacttgggccaaacggcgcag<br>gtaagtcgacactggtacgggtagtgctcgggctggtaacacccgatgaaggggttatc<br>aagcgcaacggaaaactgcgcatcggctatgtaccgcagaagctgtatctcgacaccac<br>gttgccactgaccgtaaaccgttttttacgcttacgccctggcacacataaagaagatatttt<br>gcctgcactgaaacgtgtccaggccgggcatctgattaacgcaccgatgcaaaagctct<br>cgggtggcgaaacgcagcgtgtactgttagcgcgagcattgttaaatcgaccgcaattatt<br>agtgctggatgaacccactcagggcgtggatgtgaatggtcaggtggcgttatatgacctt<br>attgaccaactgcgtcgcgaactggattgtggcgttttaatggtatctcacgatctgcatctg<br>gtaatggcaaaaaccgatgaagtgcttgcctgaatcaccacatttgttgttccggcacacc<br>ggaagttgtttccctgcatccggagtttatttctatgtttggtcctcgtggtgctgaacaactg<br>ggtatctatcgccatcatcataatcatcgtcacgatttacagggacgaattgttttgcgtcgg<br>ggaaatgatcgctcatga | 138 |
| ECOLIN_09985 | atgattgaattattatttcccggttggttagccgggatcatgctcgcctgtgccgcgggtcc<br>gctgggttcgtttgtagtctggcgtcgtatgtcttatttcggtgatacgctggctcatgcctca<br>ttacttggcgtcgcgtttggtttgttgctggacgtgaatccattctatgcggtgattgccgtta<br>cgctgctgctggcgggcggtctggtatggctggagaagcgtccacagctggcgatcga<br>cacgttattagggattatggcgcacagtgccctgtcgctgggcctggtggtcgttagtctg<br>atgtctaatattcgtgttgatttgatgcttacctgttcggtgatttactggcagtgacgccag<br>aagatctcatctctattgcgattggcgtggtcatcgtggtggctattttgttctggcaatgcg<br>gcaatttgctgtcgatgacgattagccggatctggcgtttgttgatggtgtgaaattacag<br>cgcgtgaaattgttgttgatgctggtgacggcattgacgattggtgtagcgatgaaattcgt<br>cggcgcgttgattattacttcactgctgattattcctgctgctactgcacgtcgctttgcccgc<br>acgccggaacagatggctggtgtcgctgttttggtggggatggtggcagtgactggcgg<br>tttaacctttccgcattttacgatacacctgcaggcccgtcggtggtgctatgcgcggcac<br>tgttatttattatcagtatgatgaaaaagcaggccagctaa | 139 |
| ECOLIN_09990 | ttacggcatttctggcggcgtgatgccgaagtggttccacgcccgcactgtcgccatacg<br>cccgcgcggtgtacgctgcaaaaagccttgctgaatcaaataaggttccagtacatcctc<br>aatggtttcacgttcttcgccaatggctgccgccaggttatccagacctaccggcccacca<br>aagaacttatcgattaccgccagcaacaatttgcggtccatataatcgaaaccttcagcatc<br>gacattcaacatatccagcgcctgagcagcgatatctgccgagatggtgccatcgtgcttc<br>acttcagcgaaatcacgcactcgacgcagcagacggttggcacatcgtggcgtaccgc<br>gcgcacgacgagcaacttccagcgcgccgtcatcactcatctcaagcccataaagcgt<br>gcgctgcgactgacgatatattgcagatccggcacctgataaaactccagacgttgcaca<br>ataccaaaacgatcgcgcaacggtgatgtcagcgaacctgcgcgcgtggttgcaccaat<br>cagggtaaacggcggcaaatcaattttaatggagcgtgccgccggaccttcaccaatcat<br>gatatccagttggtaatcttccattgccggatacaacacctcttccaccactggtgaaagac<br>ggtggatctcatcaataaacagtacatcgtgtggttcaaggttagtgagcattgctgccag<br>atcgcccgccttttccagcaccggaccagaagtcgtgcgtaaattaacgcccatttcattg<br>gcgacaatattggcagcgtagttttacccaacccggaggaccaaaaatcaatagatga<br>tcgagggcatcgccgcgcagtttcgctgctttgatgaaaatctccatctgcgaacgaacct<br>gcgggctgaccaacatactcttccagtaatttagggcgaatggcgcgatctgccacatcttc<br>cggcaaagtggtaccggcagaaatcagacggtctgcttcaatcat | 140 |
| ECOLIN_09995 | tcataacgcggcgcgtagggcttcgcgaattaatgttttcactgctggcgtcagggcgagc<br>gattttgctcaccatgcggcttgcttcttgtggtttatagcccagtgccaccagcgcagcaa<br>ccgcttcctgttcagcatcgtcggtcgccgggctggcaggagacgtgagtaccaggtcg<br>gcggctggcgtaaagagatcgccatgcaaacctttaaatcggtctttcatttcgacaatcaa<br>gcgttcggcggttttttttgccaatacccggcagtttcaccagtgccccacttcttcacgctc | 141 |

TABLE F-continued

Sequences of the genes comprised in Phage 3 of E. coli Nissle

| Description | Sequence | SEQ ID NO |
|---|---|---|
| | aacggcattaacgaactgctgcgctgacattccggagaggatcgccagcgccaacttcg<br>ggccgacgccgttggttttgatcaactctttgaacaacgtgcgctcttgtttattgttaaaacc<br>gtacagcagttgcgcgtcttcacgcaccacaaagtgggtgaaaacgatcgcttcctgacc<br>cgcttcagggagttcataaaaacaggtcatcggcatatgcacttcatagcctacgccgcc<br>cacttcaattaacaccagcgggggtgtttttcaatgatgatgcctctgagtctgcctatcac | |
| ECOLIN_10000 | gtgaatattaattatcctgctgaatatgaaattggtgatatcgtctttacatgtataagtgctgc<br>cttatttggtcaaatatcagctgcatcaaattgctggagtaatcacgtcgggatcattatcgg<br>tcataacggtgaagactttctggttgcagaaagccgtgttccctctcaaccatcactacgc<br>tatcccgttttattaaacgctctgctaatcaacgctatgctataaagcgattagacgccggac<br>taacagaacaacaaaatcaacgaattgttgaacaggttccttcccggctacgcaaaattta<br>ccacaccggttttaaatacgaatcttcgcgccagttctgttcaaaatttgtttttgatatttataa<br>agaggcgctatgtattccggtgggtgaaatagagacgtttggagaattgttaaatagcaat<br>ccaaatgcaaaactcactttctggaaattctggttcttaggttctattccgtgggagcgtaaa<br>accgtcacgccagccagtttgtggcatcatccgggtttggtgttgattcacgcggtgggag<br>ttgaaacgcctcagcctgaactgaccgaggcggtataa | 142 |
| ECOLIN_10005 | ttaacgcagtcgccctctcgccaggttcagtcgcgattcgctcatttgcatcgcattctgact<br>aacgtggcagtgggtgatggcaatcgccagcgcatcggcggcatccgcctgtggattag<br>cgggcagtttcagcaaggtgcggaccatatgctgcacctggctttttcggcactaccaat<br>acctaccactgtttgctttacctgacgtgccgcatattcaaataccggcaattcctgattcac<br>cgccgccacaatcgccacgccgcgcgcctgccccagtttcagggctgagtcagcgttct<br>tcgccataaagacctgttcaatggcgaaataatcaggctggaattgggtgatgatttccgtc<br>acgcccgcatagatgagcttcagacgagacggtaaatcatccactttggtgcgtatgcatc<br>cgctacccaggtaggacagttgcctgcctacctggcggatgacgccatagccggtcacg<br>cgcgaacccgggtcaatgccgagaataatagccat | 143 |
| ECOLIN_10010 | tcagagagtcgctgcaacctcatcagagatttcaccgttatggtaaacttcctgcacgtcgt<br>cgcaatcttccagcatatcgatcagacgcatcagtttcggtgcggtttctgcatccatatca<br>gctttggtggacgggatcatgaaacttccgcgctgtctgcttttcagacctgccgcttcca<br>gagcgtcgcgtactttgcccattttctccccatgcagtgtagacatcaatcgcgccgtcatca<br>taggtcacaacgtcttcagcaccggcttccagggctgcttccatgatggtgtcttcatcgcc<br>tttctcgaaggagatcacgcctttttttgctgaacaaataagctacggaaccatcagtaccga<br>ggttaccgccacatttgctgaatgcatgacgcactttcagcaacggtacggttgcggttgtc<br>agacagacattcaatcatgattgccgtgccgccaggaccgtaaccttcgtagatgatggtt<br>tccatgtttgcatcatcatcaccgcccacacctcgtgcaattgcgcggttcagagtgtcacg<br>ggtcatgttgttagacagtgctttatcaattgctgcacgcaaacgcgggttagcgtccggat<br>caccaccgcccagctagccgcggttaccagctcacgaatgattttagtgaagattttacc<br>gcgcttagcatcctgcgcagattacgatgtctggtgaggcccatttactatgacctgccat | 144 |
| nudB | tcaggcagcgttaattacaaactgttcaatcgcctgccggttgctccaggacttagtgagc<br>gccgccgcagcagacgcatcaagccacttgtaagccagatgttcagtgaaaacgatctg<br>gcgctcgtgcggaagcgcaagacagaaccatgattccgtattacgcgtcacgcccggc<br>gcatagcgatgacgtaaatgtgaaaaaatttcaaactctaccgtgcgctgacagtcaatta<br>aggtcagttgttcagcgacaacatcaatggtgacctcttcctttacttcgcgcatggcagctt<br>gcggcgcggtttcaccctcttccacgctgccggttaccgactgccagaaatcgggatcgt<br>cacgccgctgcaacatcagcaccccgtttcgtatcttgtgcgtagatgaccactaagatcga<br>aacgggacgcttataagccat | 145 |
| ECOLIN_10020 | tcagttattctcagcctttcttcacaacctgaatgctcagctcagccagtgcagtcgggttag<br>caaagctcggcgcttcagtcatcaaacacgctgccgccgtggttttcgggaaggcgataa<br>cgtcacggatattgtcggtgccggtcagcagcatcgtcagacggtcaagaccgaatgcc<br>aaacctgcgtgcggcggagtaccgtatttcagggcgtcgagcaggaagccgaatttctc<br>gcgctgacctatcgttgatacccagaataccaaacaccgtctgctgcatatcaccattatg<br>gatacgcacagaaccaccgcccacttcgtaaccattgatgaccatatcgtaagcgttagc<br>caccgcattttccggtgcagctttcagttctgctgccgtcatgtcttttcggtgaggtgaacg<br>gatggtgcattgctgtcaggccgccttcaccgtcgtcttcaaacatcgggaagtcgataac<br>ccacagcggtgcccatttgctttcgtcggtcagaccaaggtctttacccactttcaggcgc<br>agtgcgcccatcgcgtcggcaacaattttctcttgttgtcggcaccgaagaaaatcatatcgc<br>catcttgcgcgccagtacgctccaggatggcttcgatgatttctgcattaaggaacttcgct<br>accgggctattgataccttccagaccttccgcgcgttcgttaactttgatgtaagccagacct<br>ttcgcgccgtagatttttaacgaagttaccgtattcgtcgatctgcttacgggtcaacgatgc<br>gccgcccggaacacgcagagcggcaacacggcctttcggatcgttcgccggacctgca<br>aatactgcaaactcaacagatttcagcagatcggcaacgtcggtcagttccatcgggttac<br>gcagatccggtttatcagaaccataacggcgttctgcttctgcaaaggtcattaccgggaa<br>atcgcccagatccacgcccttcacttccagccacagatgacgcaccagcgcttccatcac<br>ttcacgcacttgcggcgcagtcatgaaagaagtttccacatcgatctgagtaaattcaggc<br>tgacggtcagcacgcaggtcttcgtcacggaagcatttaacgatctgatagtagcggtca<br>aagccggacatcatcagtagctgtttgaacaactgcggggattgcggcagcgcgtagaa<br>tttacctttgtgcacacgagaaggcaccaggtagtcacgcgcgccttcaggcgtggctttg<br>gtcagcatcggagtttcatgtcgaggaagccgtggtcatccataaaacgcgcaccag<br>gctggtgattttagcgcgggttttcaggcgctgagccatttccgggcgacgcaggtcgag<br>gtagcggtatttcagacgcgcttcttcggtgttgacgtggttagagtcaagcggcagaaca<br>tctgcacggttgatgatagtcagcgaggacgccagtacttcgatttcgccagtcgccatat<br>cgcggttaatattttttttcgtcacgcgcacgtacggtgcccgtgacctgaatgcagaactca<br>ttacgcagttcagaggccagctttaacgcgtccgcacgatccggatcgaaaaatacctgc | 146 |

TABLE F-continued

Sequences of the genes comprised in Phage 3 of *E. coli* Nissle

| Description | Sequence | SEQ ID NO |
|---|---|---|
| | acgataccttcgcggtcgcgcatatcgatgaagatcaggctaccaagatcacgacgacg<br>gttgacccaaccacacagagtcacctgctgccccacgtgggacaaacggagctgtcca<br>caatattctgtacgcat | |
| ECOLIN_10025 | atgcttgaacttaatgctaaaaccaccgcgctggtggtgattgatttacaagaaggcatctt<br>gccttttgccggaggtccacatactgccgatgaggtggttaatcgcgccgggaagctgg<br>cggcgaaatttcgcgccagcggtcagcccgtgtttctggtgcgcgttggctggtctgccg<br>attacgccgaagcattaaaacagccggttgatgcccctcccccgcaaaagtgttgcccg<br>aaaaactggtggcaacatcctgctgcattaggtgcaaccgacagcgatatcgaaatcatca<br>aacgtcaatggggtgcgttttacggtacggatctggagttgcaattacgccgccgggtat<br>cgatacaatagtgttatgtgggatctcgaccaatatcggtgttgaatccaccgcccgcaat<br>gcctgggaactcggttttaatctggtgattgccgaagatgcctgtagcgccgctagcgcc<br>gagcagcacaataacagcattaatcatatctacccgcgcatcgcccgtgtgcgtagcgtt<br>gaagagatcctcaacgcgttatga | 147 |
| ECOLIN_10030 | tcacatcaccgggcagtcatcaaactccgcattcctggcatcattaatgatgtacgtgatca<br>ctccaaatatagcggggtgcagaactgtaaccatcatcatctgctggcagcgcttcccttctc<br>ccgttatccagattaaccaggtgcggctgaggatgagtccgatatcgcttgatcctgaattc<br>cccgtcgattgcacatatcagcagtgaaccatcgcaggcagtaagtgacgcatccacaa<br>caagcaacgctccctggattatcccttccctgaaatgtgaacgcgatgcccgcatgaaata<br>agtcgctgcgggctgactgattagctgctgatcgagggagattcgtgtttcaacataatctg<br>ccgcaggtgaaggaaatcccat | 148 |
| ECOLIN_10035 | atgttcgtggaactcgtttatgacaaaaggaattttgatggtctgcccggtgcaaaagatat<br>cattctgggcgagttaactaagagagttcaccggatcttccccgatgctgatgttcgggtta<br>aaccgatgatgacactgccggcgatcaacactgacgccagcaagcatgagaaggaaca<br>gataagccgtactgttcaggaaatgtttgaagaggctgaattctggttagtgagtgagtaa | 149 |
| ECOLIN_10040 | atgctgtggaggatattcattttcgtaaacgttggtttgggagaagcggcaaaacggaatg<br>tgggaacagggggaaaatcagatacagatatgtctgcatttccatctggcaataactggttt<br>cagttaccaagtggacatatcgttcagatattttccatgaacgttcttggtgcagatgctaat<br>ggcacgtcagctaattaccccattgcttttccaacaacgatgattgctgtcagtgctctatgg<br>tctgatgggactgtagcaaatgcaccgacatacaagatgatggggaacacgactaacag<br>aacaactttgacgataaaagtatcagccagctcaggtacttacgggacaatgattattgcg<br>gtgggacgataa | 150 |
| ECOLIN_10045 | atgaataaatacagttactctccttcagaaaatgccttttatgctgttgcgttaaaaaatacct<br>atgaattgagtggcacatggccagctgatgcattagatattcctgatgacatttctgtaaaat<br>atatggcggaaccgccacaagggaaaatccgagttgcaggggaaaatggttttcccaca<br>tgggctgaaatacctccaccatcacatgaggaacttattgaacaggccgaatcagagag<br>gcaattattgattaaccaggccaacgaatacatgaacagtaaacaatggcccggtaaagc<br>cgctattggtcgtctgaaaggcgaggaactggcacaatataattcgtggctggattatctg<br>gacgcactggaactggtcgatacttccggtacgcccgatattgaatggcctacgcctccg<br>gcagttcaggccagatga | 151 |
| ECOLIN_10050 | ctacgcctccgcagttcaggccagatgacatccggcgcggtgctggtatctgttgcagt<br>caccgcgtcaatgtaatccagcacggcgttaagtcgggttgtttctgcctgagtcagtttcc<br>gtccggcctgtaatttcagctgaatcagactaatggaagccattgctgcatcaatcagtgat<br>tggcgctgtgcttctgccgcttctactgaggcaccgtgttgtgcctcagtatctgtcacccat<br>ttctcaccatcccatttatcatatggcgttaacggtgaaagcgtgacataaccgtttttgatg<br>gcaccgatataatccactgtaacagctgcgccattttcgattgagtgtaaacagtctccattgcg<br>atggtcttcctcatggctccatcccttacctgtaaatactgccactcttcccggaatgttttcgt<br>ccgggtcaataccagtggaacaggcgggcatacttacgccagtattaatatattcatcaga<br>ccagcccgtatattcagacgttactgcatcataataaaaacaacgcatatcacccggcact<br>gcagccagcccatttcatcaaaaacaggtttcat | 152 |
| ECOLIN_10055 | ttatttagccctcaccagaaagttaaatgcaatatttcgcggtctgacagcaacaaaattca<br>caccatcacccacagagttactgttgaaattaaatcgtgaaaatcctggctgatttccggcg<br>atgccatcatgaaagttaattgcgtgtccagcacctccgcctatattcccggcaaactgag<br>aaaagtttgtagcttcctgccagcttaataattcgcgaccaccatctgcacctcgcccgtca<br>tcccagacacgaatgaaatcaccgcgggcttcaggtaataccagcgaaggaaacacttt<br>cgccagcacaggataatcagtggcagagaatttcgcgccgttgaacttcaaaaacaccat<br>actggaccagctgtcgattacagtatttggcattgcagcggacggcagaagaacggaa<br>cgccaatagctggagaaccttctcccaaaccaaggtttgtgcgagcgtctgcggcattcg<br>ttgcgccggttccgccgtctgcgacagtaaccgcaccgttgctccctttctgcgcaagttta<br>ccgatgcctgggatggttacggcggtgccgttgatggtaactgtgatgctttggtttgctga<br>ggtggtggcgaacgtctcccacgcgccaatattctcgtcgtactcttttgatgagctgtgac<br>atggcctgcgccaggccgtcgactgagatattgtccgacacaaggattccatacttctgg<br>ccgtcagcgccggggaaactgctggcgtaaccgtcattgacgtggcgctgttcacgga<br>tgaaatctgaaacagctgcaccgggttagacatcacgataatcgtctggccagcgcgga<br>cctggctggcgggagctgtccagttgtgccggagccggttgcggtatttccgttaataga<br>gatagttccggtgctataaatcat | 153 |
| ECOLIN_10065 | ttaacctgtgaatgaaccagatccgtgtgatactatgatagtaggcgaagaaattgacgca<br>cccctgttatttgagcggacactttaatacgcactgttacgtttggacctgttacaaccgca<br>gaatgcatgataagtctctccatgtcttgcacggatgaaccactctcattgccgttaatgtcg | 154 |

TABLE F-continued

Sequences of the genes comprised in Phage 3 of *E. coli* Nissle

| Description | Sequence | SEQ ID NO |
|---|---|---|
| | attgttcctgcaccattacctttaacgtttgctataacacagacgtgtcttgcgtgcccagaa<br>ctggatgaatcattataagtcattaccttttctaaatatccgtcactagaccgactcacattcg<br>tccctgtgtgcatatttgcaatgtccccgataaaactttgggcttccacagtcccttgaattt<br>accgcttgttgcttggatctcaccagtaaagctaccgccactagcatatactacacctctga<br>cggtcacattgttgaattcagcatctccagctttattcaacttccaaccagcagaaccagct<br>gcatagttgttggactggatatagttaccgattttgcgttctcaatggtgccgtcctggatga<br>agctggcccggatgaatgtctgcccgttctggatcacgaacggcaaagctacgctatttc<br>cggctgccgtggtgacggcgaagcggtcagccaggaagataacctgcgactgcatgcc<br>ggatggcgtattctccacgccgatacccatccccgcggcgtaatactgcccgttgctgga<br>gacaccaaccttgatgttgtacatcgcgctgagttcgccattaacgttggctatagcctgag<br>cgttagtggtgatggcggaggtatgcccgttcacggtcgccgtgatgccgtttatctgcgt<br>ggcggtggcctgctgatagtcggagagcgtctgattcaggctgttgatggatgccttgttg<br>ccgttgacgtccgtctgcaggctcagcaatgaacgtgctgtggcttccttctcactgacgat<br>cacctcgtcgagacggtccagattcgcgctgttgccggcgaccgatgcagaaagggtttt<br>acgcgtggccacctgagcgaggttggcctggattatcgcaattgcagagttcttcacccc<br>gcccgtcatgccgtccatagaaacgctgatgttgtcgattcgctggcccagggcggtatc<br>agccgtcgcaacggtctgctcaagctgactgagtgaagacgaaacattcccgaccgtgc<br>tggaaagctcattaacgctggtctgaaccttcccgacgtcctgggcatttttggcgatatctt<br>tcgcttgctgctccagttcgtcgttggcctgtttgatatcgttagccatgccagcaatttttcg<br>ttgctgtccaccgcgttctcgatcaggtctttgaacgtttccgactcttcatatcctccagaa<br>tgtcattagttatttcgctgacatctatcgaggacgtgccatgatccagtcggtccagtccc<br>cggcgttaccgatacggtcaatcaggcgcgcgcggtaccactggcgaacgccggcag<br>gcatggggccatgctgataatctgcagccgggtacggcaccaggaccagcagttcagg<br>attggcgtagtcggcagttgtggcgcgctgaatctctgtataggccgtgtcgcctgagcca<br>tccggaaatttccaggtcaggtcgatatgccagaccacatcttcggtcgccaggaagttg<br>agcggagtacccggttttcccgttttaccggagagataagttgtttcaccgtatccccatgg<br>tgacgacgtatcctgcgcattcagcgcccgtacgcgcacgtcatagctgcccgaataaat<br>gccctgaaccgagaaacccctgcgcgctggtaaccggaacgtttatccagtccccgttgtc<br>cttacgccactgggcaacataccggattgcgccctctaccttatcccatgacacgtccagg<br>cttgctacagtcagcccctgagacacatgatcgctctcagtcaccacgatattcttcggag<br>cagacaggacgcttatcggcgtgacggtgatcggggagactcgacccgaacgccgtc<br>atcgatgtaacgatatttgtttggatcgtgctgaacggccgtaatagtgaaaccgcctgtac<br>tgtcgtcgttagccgcgattgaggtgaccctgaagtactgtattgcgaggttatcactgtct<br>atcgcccaaacagccgcccgcacaggaacctgactgaatgccgtagccaccgtcaccg<br>tttttttatcggcgctcaccgcgctgattgtccgcgtctgggcttttccgtcgggaaggttaa<br>ccaccagccggtctttcgccgcgtagtctatttctcgatcgagggtaatttggcggccgttg<br>gccgcgcttatacggccccgttctccttaccagagcggaaaggatcggcgacaccgat<br>aatttcagcgggcaaagggtataaccgtccagcccacgccaaacgatacggtcccgt<br>ctttggcattggagagcaatacccagcgaccgcgtcggtgcgcttcactttgcgaggtgc<br>agccgattgcggtcagggacgtctgccggacgtcgtaacgttctacaagcgccgaatcg<br>taaaccccctcaacggtatcgctgtaatggttctgcggatcggaccaggacaccaggca<br>ggagctgtagcgattcttgtatgagccgcccgcataagtaaacagcccatcgataacgttt<br>gagacgttataaaccagtcaacatcgtcctgcgggacgtctgcctggacataaatctgat<br>cgtttccccagaacgttattccacgaaataccgcggcgagatcgttaagtacctgccagg<br>cgtcctcctggctctgaatgaaaacgttgcaggtgaaacgcggttcggtgccaccggcc<br>ccgtcggaaaccatttcgtcacagtactgggcgattgaatacagcgcccacttatccacca<br>tggacgcatccacgcgcgtgcccatgccgtaaatttcatccagaaccagatcgtaaaaga<br>tccaggcagggttattggaccatgccattttgaacccgccggaaccatgaaccagaatagg<br>ttcgggttttcggatcgtaattatccggaaccttaatcagcttgcctttatcttacaggtcact<br>ttcggcgcgctgccgttgaattggctgctgtccacttcgacatacaggagcgctgttaaag<br>gataacgaagcttgctgtcgatgacttccgcatacgaaaacaccttgaaggcgttaacca<br>gtttcgaatttgatccgctggcatcagccgtaatacgcctgaccctgacagaccagccgg<br>acgtggattttggcagatcgatacggtggtcacgctgatattccgtcgtggtctttccgtca<br>aacttgccgtttacaaccgttttccaggcgccgccgtccgttgataaatcgatcgcatactc<br>ggtgaccgtgccaccatatcgccattatctttatagagatactggaccggaaggctgag<br>cttgatacggatggcatccagggaaaggtttgtaaactggcgcgtccagggcgcggtgg<br>tggtgacagttgtgcccacggccagctcgttgtcgacctggggcatcccggcaatatagg<br>tctggtcctgtgtgcccttgcggaactcccattcacgccgctgaagttgtattccccgctgt<br>cgtttgccagcggcgtatcgttgagaaaaatgttctgagcggtcaggtcgccctgtatttcc<br>ccctcagaaacggcaatgagcatttttaattttgcgaccgacagcagatcgtcaggctgct<br>caaccggagtatgtgaactgccacctcccccttttggcaccctgcaggatggtttcttgttta<br>agaagctgcattttttcacccat | |
| ECOLIN_10070 | ctactgctgatcgctcgagtacataccggcgctgactatcgctcccccctgcctcagtcaga<br>ccgtaggccaggggacaggatgccccatagcgacggtattgaccggcgccccgaag<br>gcgtagttaggcgtgttgtccgtgctggaggatttacccgcgccgaaggatggctgggg<br>cgtgagcatctggacaacgccccccagcatcatcgacactccgaccctgtcagaattg<br>acgtggcgctgatagctgttgcactcatcgccgcgcccaggctgccatgctcgcacca<br>gcggtaaagaatgcagcgaccagcgcaacagcccgacaactatctgcaggacgccc<br>gaactttggcccctcataaacgggcacgatccggtacacgcttccaccgcgggtcata<br>tcaaactcttccagcccgatattgttgccaccgttaaaaaaggcgaaacggatcccttcat<br>atgagcttcagacatatatttttgaatccgggaacctgtgaacacatggccctgagcatct<br>cgcgcaggtcggcaacatcaaactgaacgcgtttaccgaatttttttgccatttaccttcga<br>gaataagcgtcttaaccat | 155 |

TABLE F-continued

Sequences of the genes comprised in Phage 3 of *E. coli* Nissle

| Description | Sequence | SEQ ID NO |
| --- | --- | --- |
| ECOLIN_10075 | ttaaccatgcattctgtccttatgcctgaccacccggaccgttctgtcgcgataatattttcca<br>taaggcgttcgcgaagaaaggtgcccgaaaagatgatggagaatgatgttatcacccac<br>atataccgcggcgtgattagtcaccgatgcctgcacactcatcatgatgatatctccgggc<br>tgcattgcaccggcggcaatctcaacgaatccctcacgctcccagttgtcgtcgtagaga<br>cgctccttgccgctctcccaccattcgtaaggtactgaataattgccgagaacaatgccgt<br>attcgcgcagataaaattcacggataagcgaccagcagtcggcgtaacccagcacccac<br>tgccgcccggcataatcccggtcttcacgcggggaaatcgtacaaaaatccccgtccgg<br>ccaggacatgatcccccactcaatccccgaccagtcgcactggatccggtccagctctg<br>agggcaccagccgaaccacatccggatgggaatgaatgagcatgatgatctcaccgcg<br>cgcgcgggcagcgagctggtcttccggggagagcgtgaatgtctcctcgggtttatcgg<br>caatgttgcggcagggaataaagatttgttgctggcctgactgaacaatcaggccgcagg<br>cttctttggggtattcagcagcgacgtgctgacggatagcatccagcaattttttcacgcat | 156 |
| ECOLIN_10080 | ttatttcccctgcaggtttgcagccggaaaaccgccgaacggcagcggcgcatccgggc<br>cgtgacgatcctgacaatcctgccggcggccgccacaaacatctttcgacgggtcatcg<br>gtcggtgtaccgtctttggtaaagtatttcgtgccgttgtaatcgcatccggtcccgcttcgg<br>taccagccccgcatacaccaggtgcagacaggcgtaatctgccgtgtcggcagctgca<br>ggctctgaatatcgaaaggagaacacagctcgaaatcaacctgtacccgcgtctctgcg<br>gttttagcattgacgtaaaagagctgtaagcgctcatcggccgggctggcacccggatta<br>ccgttttttccagttggcggcatcgagatacttcgaaagcgtggtatggattttgaccttagcc<br>ctgaccatatcgtcatattcaagacacagcgcggtgacatagtttccgacgttcccgacgg<br>acagcgtgggcgttggctgggaacctgtactcgataactccatcccccttaagttcgtaggg<br>atggggatcgtactggtttccctgccagataatggcgggcagattttctgcgcgcgaaggct<br>gcccacccctcttcctgaatattgtgcgcatgaaaacgcagcacctgatccataccgaatt<br>cagtgccgtcgatctcaatcagctgaataacgctgccgggctcaagctgttgtatgtctgc<br>cgtaaaactcat | 157 |
| ECOLIN_10085 | tcagggcgcgaacgcctgttcaaaagtgaaggccacagtggcttttttcccggtagggaa<br>agaaacgctgaacgaatcggccttcattctgaacagctttttttcacccatggagtggtcc<br>accagaacgatttagtaacgtgagacatcaggaaagcgcgcagcgcagccgcctcctgt<br>ctggtgcccgtccagtccaggttccacgttcctgtttgtcgttgatccccatccccgctatc<br>tgtttgtagccatccccgaactgggcctgcagcgttcgggctgtttcagtgccctgcgctgt<br>ttttcgcgtgcgccaggtaaacgtgtccgtcac | 158 |
| ECOLIN_10090 | tcactgtgtcctcctcgaataaagcacgccgcccgcggacatttcttttttcagtcgctcggt<br>gattgtctgctgaacaatcgcctgcagctgtttcgccgtccccgtggcgttcgcctgatttat<br>gcttccgtcactcccctgctggctgatgctgactggggcataaacactgatcccgcccatg<br>ccagcaccggctgcgttcccgccgccgaccagaccaccgagggcatacccgcgcatc<br>aggcgatagagattagccacgccgatgcggctggttgattctttggtgaagacgaattcc<br>ccgcggtgaacgataccggctggctcgtacttgccgccgtgcccggtaaaaccgccca<br>cgtcaaaaccctgtggccggtatgacgggaccgcgaatgactgaccggcagaggaggt<br>tttcgcccccgccgctaacccagcccattgcactctggatggtgtaagccaccagcagctg<br>gttgataacggacacaatcattttaaggatcgagctggtgaattccctgaagctcgccttcc<br>cggttgtcgtcaggctggtaagctggcccgccaacccgctgaacgtagcctgagaaatc<br>tgctgaacggagctgaaaacgtttgtcgctgaatcctgatattcggcccaaccctgtttcgc<br>accggccagccagtttgcacgcagggcatcttcagcttcgaacgtcgcccttgctcttcc<br>agaacttttgctgcgcctgagggttgtacgaatagctttcgctgagacgctgcagcgtag<br>tttgtcgcccggcttcccggtggataaccctcagactgagcctgcaggcccgcctg<br>gcggcttttgctgctgctcaaacttcacggcctgatcggccagctggttgagcttttgctg<br>gctggcaaccttatcgcccaggtcggccagctgccgcttgtactcgagcgttcttctttgt<br>gcgccagcagggattttcctgcgccgtaagctgacgacgcccagcggcctcctgcaga<br>acggtgaactgattttcagtttgccagagatcctgacgctgtttacttatgacgtcgttcacg<br>ctggtatgctgctcaagcgttttaagctgggcctgaagggtgagaagttcggcctgcgcct<br>tttcctcggctttgtccccggcgggcgttgagtagcttttgccttcggtgttttggatccttc<br>cactgcttttcaatcccggcgcgggccgcggcaatgtcctttcagtccacagcgtggcg<br>acaccgtctttcgcatcctggcggttttttctcaataagctgactgagcttttctctgctgaag<br>cccgctttctgccgccgtcgcgccggactccaccagctggttaaactgctgctggctgc<br>ggattgcctgagcctgctggtccgttcgcatttttttccccgcggctgccagccctttcctgg<br>gcgtattgctgatcggcaagatcgtaagcctgcttttttcagctccacctgctggcgcgtt<br>tctcagccttttccgcatccgctttctgcagaacgttgttaccggcataatccgggtcgacctt<br>aagattgctggacagcgcgcggtactctttctctgctgcctgccactcagcaaaagagtcc<br>tggcgcttcatcgcggtgtcaggattacgcccgagcatcgcatcccacgcacc<br>ggaggcggcattcttcacccagttccaggctttttcgagggatccgagattatcctcgacc<br>gcaccggcgcgctgaatgaccgcgtcggaatatgcccgcatgccagctcggcagcct<br>tctgagaatcccccagcgcctgagcagaagctatctgttcatactgggtggctgtcagaa<br>aatgaagggaatcgttgagcgtcgcgaccgcgttaaccggatcatccttcaggcgtttaa<br>actgatttatggtttcgtcaacggcctgcccggtagcctgctgcagcctggcggcaacatt<br>gctgaccatgctgacgtcattaccgctgaacgcgccgctgccaacgacctgcgccagca<br>cgcctgcagcggcatgctgagtgatgccattacctgccagcgagcgcgccagcgcctg<br>cagctgccctgacgttttccccgcgtagttcccggtcaggatcagctgcctgttaaattcct<br>cagactctttgctgccgtcgtaccaggccttacccaacccgaataccgccgcggcaatcc<br>ctccgaccatgctggcgatcccaagaccgcgcagtgacagaagctggtctatccaccct<br>gcccggttagccagcgtgatcccggagccgcgcagcgcgccgaagttaccgcgcatg<br>acctcgccgatcagtattcccagttcctgccgggcggcggcactttgcagcccagacc<br>gtgcgtggcgactttggcagcttcgagcttgcggatatagacttcagccgcatcgctggc | 159 |

TABLE F-continued

Sequences of the genes comprised in Phage 3 of E. coli Nissle

| Description | Sequence | SEQ ID NO |
|---|---|---|
| | accgacctgcgccgcctttcatgcgcagtagctcggtaccggagagcttttgctctgcaac<br>ctgttgcttcagctggctgaggaatcgcgtgcgcgctgcggccgattttttcctccacgatct<br>gcagttctttttgacgggccgtggtgcgggaaataagggcgagataatcctgctgggttat<br>gttgccctgtgccctcgctgcgcgaaagcgcgcctgcacgttcgcaagcgactgtgtttc<br>accattgagctggcgtacgccgtcgatctggcggaaaaatgatgccgcaagttcatcctg<br>tcgacgggcaagcgcagcggcctgcccgtcattctcacgcatgcgctgattaagctcgg<br>tcacgcggcggtgagtttcatcaacggactttgaaacgttctgccagtctttggtaagccct<br>tccgttgcggccgactggcgggatttcatatctgcggcagccgccgcgccagcgtcacc<br>cacggttttaaacgcagccgcctgccgctctgaagcgcgctgcattcgcgtctggacttttt<br>cagagtcctcagccatcccggttagctggccctttatgcgggcaacctgctcactaaacgt<br>ggcgctgtcgacgtcaaggttgatgaccagatcgctaatctgctgggccat | |
| ECOLIN_10095 | ctaatctgctgggccatatcggataccctcctgttatcccctcagctgcggccatcagcgcat<br>catcatccggctcgtcatcgctgatgacgataccggaaggagaaagcaggctgaaatgt<br>gcgggggtaagttccgggtcgcggaagaaaaagagtggagatggaataaagcagctctg<br>agaaatgcgcatcgagctgagcgtcctgaaaataatgctcccggtagaactggtgccagt<br>cgcccagctcagtggaagtcattccagccagcat | 160 |
| ECOLIN_10100 | tcagctcgctggcaagggcttttccgccgcaacgggttctgcgctttcggcctccgctgg<br>ggcatccggatcggcagctttgtcatcctcaaccggaacgagcatgccggagagcagct<br>ttatttccatttctgctttaccgatcgcctccggcggccagccgctaagcacctgctggtaa<br>agcgtctccacatccgtgccagccggatcgttatgccacaaagacatcgcaatcaaacg<br>cgcaccgcagcgaatatttgagccaatcagcctggccgtcatttcctgatcgctgatgccg<br>tcgctgtcagcgctgacggccttttcctctgcggccataaacgtgatgtactcaatacgctg<br>aagcgccgacagctcgaagatggtcagtgattcttttttgccaggtgaacttctctttttttcag<br>aaacat | 161 |
| ECOLIN_10105 | ttacgctgcagttacggtaactttgcagaccgcaacgaaattaccgtcgctggtcataaca<br>ataacgtcagcggtgcctgccgccacgccggtgacggtgatcgcattaccgctaacggt<br>gaccgttgcttttgccccgtctgaggttgccacacggaacgaggtatctgaggcactggc<br>tgggttaaccgtcacattgagcgttgtggttgcgccgacggccacgcttgccgtggcttta<br>tcgagcgtaacgcctgtcacggggatattcggggtcccgcttcttctgccagttccggctt<br>gccggtattggtaattttcgctgtacgggttatgacctcttttgccggaatggctttacccag<br>gctgctgcaccagccgcggaaaacgtcgacggttccggtatttgattttgtaatag<br>cgtactgagccatcaataaaccatgcgacaaggtcttttgcccttcttcgcccggcttcca<br>ggcgagggtgaacgaggtatcgccagcagattttgcccctgggccgtcgcgttccagt<br>cggcatcctcgtcgtcgaggtaagtgtcgtcatacgattcggcggtcatttcgcccggcgt<br>cagctcttttaattttcgccaggcggttccagtcgatatccgagagtgggttagcgaaagcg<br>ttgcccgttccggtgtaaagcagagggtggtaccggcacctttcacaggggcagcgg<br>gtttggagtaggcat | 162 |
| ECOLIN_10110 | ttaaattgaataggtgattaagtacgtgaaatcgactgaaccccaggtggccatttcatcat<br>cccgctgatagtcataaccctgcggggtgaacgtctcgaccagttcggtcagacctggg<br>atgaaggccattgccggatacactttctcttccatccaggaatcaagcgcgctgtcggg<br>ctggaggctttaagaaataccctcgatgtgaacaaccgcctgccacgaatcttcgtcaagc<br>gaatcgccggtgtactccgcgtcagaaaggtatacagccacggcagggagatcctgctc<br>ttcaagaaaaacagggcgcccgtcaaaccaggtgaccgtgtcggtgatctcggctttcag<br>tttggccagaatggctgcacgaattgcgctgtgtctgttcat | 163 |
| ECOLIN_10115 | tcatcgcttcaggtggatcctcagttggttttttcagggctgcggaaagttctttgggcatatc<br>gctttcaataagcgctttgaaatagcggtgaaggccacggtgagcggtgtctcaagag<br>gaactttgaccacatcaatcggataacgggcctgacctacgcgccgcatgacctgccag<br>cgcccgttcgcaagctgttggataaaagcgttacgaaaggtatagggcccgattttaagg<br>acgctgcccgctccgtttctggccccttttttacgcgagagcctgacgcgcgccgtgccg<br>agctttatcgcaggaagattaccgcggttgatttttatcgacgcgaccgggcgatcgtgac<br>gggccttgcgcagacgggaacgctggcggaccagacgaaccggaagcccctttttccg<br>gttatcatcaactgttgcttctttgctacagctttgctccctggcttatcgttcttctggccac<br>cctgttaagtgctttgcggttgcctcaggaacgattaaccggctgaggctgttcaggttct<br>gaatagccctttccagtcctttcac | 164 |
| ECOLIN_10120 | tcattcgagatggatgcggggttttccgttgaacatgtcatagcgggtaacgatcaggttct<br>taccgtcgtagtcgacgctgtcgtttcggcgtggctggtaaagctcagagaaaaccacca<br>gcgaagtacctgttcccgacaatggcccccatttcctcgagtttgctcggcgggaacaacgt<br>catagctgctgccattgatgatcgctgtctttcccatcttttttatagtggccgcgtccat | 165 |
| ECOLIN_10125 | ttaggcattgatcttaacttcaacaacggtggtgtttgcccctgcatcttcccaggcgatgcc<br>cgcggcaacgcctccgtttcttcgatcgtgattttgccgtccttcagatacacctgcgccc<br>cggcagtaaccgcatctgcggatacttttggcaggaggaaaacaccctcagtaaaaccg<br>tccccggtatcgccagccgggatatcggtaattgccaccgcgataagttttccaacaaca<br>accgggtcgccgctgtgaacatcggttgcaccactgtttaccagagggatcgttttcccgt<br>cctgcgcatagttcttagccat | 166 |
| ECOLIN_10130 | ttactgaccagaggatttggtcatgccgcgatagtccagcggcgccacgccagcatcaat<br>acgcactttcgtggcgataccatcagtggtgaagccttcctgctgatcgatgtatggcgtgt<br>cgacgccgttgagataagcgaccctcaatggtgtcggtgcccttcgcggcagccagatac<br>caggctttcgcatcagcttcatccagacgtggttcggcaatgacttctgcaaagttctggat | 167 |

TABLE F-continued

Sequences of the genes comprised in Phage 3 of *E. coli* Nissle

| Description | Sequence | SEQ ID NO |
|---|---|---|
| | agggttaacgatcccggcattgatgtctgcacctttaacactggccgacttgatggtctgat ttgccagagtttccagggcgacgggcaccagcatgtaggccggacggatattcagggtt cgctcccctccttctgcagacgcatcagcttgcgcgattcgtccaggctggccacagaa attgcacccgagctcaggttcttgtgatcggcatggaacagcgccttccgtctgagagttt cgggttttggtcagaatggcgtaaaccagatcgccaatcgttgctttcgccgcgcgcccc atcttcatcggtacgtcggtaagctggttcagatcgtcgttgatgatcgcctggcgagttac tgagaagatttcaccatacgtggcaagcgcgatggtttcgcctttgtcactggtagtgatgt acttgtactcagcccctttcgcgaacctgtcgcagagaagggaacccacccataccgaca cgatgcgccgttttgaagtccgacagctggccttttttggtccactgctcgaaggtttcctgc gcctcgtcccagccctgaatcagcgctttgttcgcaacatcaagcagaatgttgccaaagt cagaggtgctgtgggtcagcgccaggccaaccatctgcatcgggttgtagctggccacg ccgatacctttttctgtcagggccatacgcgcatactcgcgcagcgtcataccgttataaac gttatcccgctcctgacctcgaacccggcacgcgccatcagtgcctggcgaataccatc cgcgacgaagttaccgttgcccgcatgaatatgcggctgagtggttttattggacggcgtg gccgttttaccgagttctgccagcagcaaatctttcgcctatcgacggagcaatcagggt cggccacacactgattctgcagttccatgtgcttattaccgaacatgcaaagagatcgcc gatagcgttaacacgggttttctgctcagcaacacctgcgcgcgggatcgcattttcatcc ggtgccgggtctgttttcgctgcggtgcctgaggctgggtaataaccgggtcacgctgg gtagtgttgcgcggcgggtgatcatgttgcgaatgcttttggcatttttcaaattcctcaa tacgttttgaatgaatacaggccatagcctgaagggatggtgtcacctggtcggcaaaac ccagttcaaggcactcgctgccgttcatccaggtttcgtcctccagcattaccgcaatttctt cggtggattttccggttttctgtgcataagccgggataagaacggattcaaccttgtcgaga agatccgcatagtcgcgcatatcgctcgcgtcaccaccagcaaaccccaggggcttatg gatcatcatcatcgtgttttcaggcatgatgaccggattgcctaccatcgcaatcaccgag gccatggaggccgccagaccgtcgatatgtacggtaatcgccgcgccgtggtgcttcag cgcgttataaatagcaattccgtcgaagacatcaccaccgggcgagttgatataaaggttg atgtgggtgacgtccccaagtgcccggagatcattgacgaactgtttcgccgttacgccc cagtacccgatttcgtcataaataaaaatgtcggcctcactgttattgctggcctgcat | |
| ECOLIN_10135 | ttacttttttgcgctggctttcggacggtggcgcgcccggttctttggcttcggcactggtgc ctcctttatcattggcggggtcggtgtcaaacaccaggccctgttcacggttctcgtcaacc tcagctttacggcgtgacttaacatcatccgggttgcgaccgctggcacgtatccagtcgg attcagtagcagcaccgccgcgatctgcgttttccaggcattcgcttctttaacgggatca atccacgcgcataacgggccccgaataaaccgcgttataaagcgagtccatatcaatgcct ctcggcagcttgatttctccggcagcaatagccatcttgagccaggctcggtacatgggc cgggtcactgaaccgatgaaccagtcctgaagaatcagatagccgtcggttgactcgac aagctcctgccgctgggcactgtacgttccgttgtagtttctggatgtgctggaaaagctga ggcgactgccggcggacacggcacgcagctgtccgttacgaaaagattcgaggttagg gttcgggcgatcggatttaatcatcccgatttcttccccggcctgcagttcgtcatagagca taccgggctgaatcatcagctcgcggtcatcgctgcttgaatcagaatcgaagctctgtcc gtcgcctttttttgatatacatgccgagtgccgcagcaattctggcagcagtaagctccgagt cctcgtattcttttcagcgcgctcagacgcatcagaacaccagcaaaagagacgttccgc gggtctggtgcaggcgtcggtgaatttgagatgcagcatgttctctgcatctatctctttg gtatcaaactgacgcccggatactggcaggcttttatagacctgatattttttcgggcgtcc ccagttatcgacaaaaacgccctgattgagctgggtggcagcatcgctgttcatcggcac aaagtccggctccagcgcttccagcagaacggcacgccagcaaccggctgaagacc atttccggtaccgcgaaccagctgagcaaatacctcaccgtcccggagccacgttcgca gcatcagccgctccagcattgggcgggtaaactgggttgtgacatctggccttacggacc attcgccccactttcggcggatatcagtggccagcttttagcgatcttcccgttactcagca tcggatgcggttcaactatgatgcccttcgcacccaccacccttcttccagcttgtcgaaa acgccgatcaccagatcgtggttgttatccagccagcgcgcctgctgcctcagcgaaac cgcccccatctggctgagctgatcggctgaacgattttccttctgggctttgtgggtacgcg tttgctttaccgcctcatacgctttaataactgcgcgggcacgcaggcgtgaggctttccag cctggtgaaaacaggccaatcgcatcatctaaaaaactcat | 168 |
| ECOLIN_10140 | tcatccaaacctcgccagcctgtagccgggtcgcccacggcgtttgttattgagcgttgcc agtcgtcgctcccattcctgacggccttttctgatttccgacaggttttcgagcgtcatctgct gcccgttgaaagtgattgatttcccctccagaacagacagctcggctgcagcatagcggt cgatcatgttttgaatatctgctggattcac | 169 |
| ECOLIN_10145 | tcacacccaacctcctgacgaagaccacggattagcctgctcggttacgggcttctcacg ttttggttttggtttagatttcggcgcaggcggcggggatggcatttcgccagcttccgtctg cgtgtcctcgatccacgtttcccgccgtgcccactcaggagctgacggccatttgattttttc gtaaccactaaggatggcgagcgcgtcggcataaacgagcaggtcaaatgcttcgtttg cgcccggccgggcttactccatttcccttcattcgagcgttcctcatacgtcagttcgtcat agaaccagctgcccagccaggcggggaaatgcacatagccagggcgggtgaatcac gccacagcgcattattcaccggtctttaagggcatcggtctggagaagataaagaggca catcaccagtcgcctgtgcgcggcgcgttgatctgcccgtgttgtcgggaaacgttcgct ggataagtttgctgcgcctgacgctgtcccctttgaagagatagatacgcttacccagccc ctcacggcgacatctgcgccagaacttgtaggcattatccgtcacgccatcttcgcccct gagtccacggccatcgacatcagccgcatgccctttgatggtgacgctgcgagcggcca cgtttttatcaaagacgtcagtgagtaaaagatcccagtcctccggatagctcgccggatcc acctgaatgctttcaccgttgccgtcgcagcgcagcgaatgccggatgttgtaacggtca actatccagcgctcacccatacttccataacccgtaatctgcacaacaaagcgccggttgc gcccggcctgcacgtccacggtcgcagtgagaaactgcacgccgttcggtaccgaacg ttttgggacgtcttcggcacgctgctcgagcaattcacttttacgctgctccatgctggctcg | 170 |

TABLE F-continued

Sequences of the genes comprised in Phage 3 of E. coli Nissle

| Description | Sequence | SEQ ID NO |
|---|---|---|
| | cggcaaatagggcctgccgaaatcggtgttgatcaccgtcttcagggtttcttcgctgcgc<br>gtggattcatattcctgctcggcggtcagaaacttataaataagctgcgcccaggtctggta<br>agcagctgccggaccttccatccagaaggaggcaatacgggaacgacggccatcacc<br>gctaaccaggcctttcctgtcgatggtttgcccgtcccggagccagacacatttcatgttaa<br>gcgcacgcttcatgtccggtgtgatcctgcctttacaggcagggcactgaagaaacgcc<br>gcttcgctggcaagcacaggatcgctgctgtcgcggtatccggtcatattgtccatttccg<br>gctggaaatattcgccgcaatgcgggcatggccagtaaagacgacggcggtcaccacg<br>gttatagagcgataaaattccggtggtcggaggggcttcatggggcgtggagcgccgcc<br>attttgtgtctctgatatccctcccgggcgagctctcaaccagcgtcatcccggaggacat<br>gaatgtcgtggttcgtttcgatgccagtgaaaaagcatcccctccccgtcgatatcttccg<br>gaaagcggtcataatccgtcagcgccacacttttatagtccgaggacgacatgatattgac<br>ggatggccagcccagcttcagatagttaccggcgcggaatgtacggtcgtagacgttgtt<br>atcgttacgtcttgggcttagccgggtttaacttcagggctacagcgaaaagtacggtcc<br>aggcgttttttggaatgctcgcgcgcttttttcctcagatacctgaattacaagcatatctgcc<br>ggatcgcagacaatgttataaacgatccagccgtcaatcagcccgatggttttacccgttc<br>gcgctgggcccacaaacacaaccgcatcgtattcacgcgatgccagacagttcatcggc<br>tcaatcacataggqtgccagatccggatcccacggaactgagtttcccgcccccattggc<br>acgcgcatataagtactgaccgcatcggccaccggcatacgacgcggggctcgtaaaat<br>accggaaacatcgcggcggatgtccctggcggatgcccgctttgccat | |
| ECOLIN_10150 | tcagtcctcctcaggctgctcctcctcttttccagcgtcctgcacctttctccgccatctggtc<br>gcgcagatcatcgataacgctttgcacacgaactaccgcagcaggcgttaaagcacagt<br>cgcgctcgagcacatccgggagggtttcaagtaccatgacgacggctttcgccatcaatg<br>agaattctcgcgccacttcatctgcgggtattaactgcccccgtatcctgttcgaacttcagc<br>ctctcgttctctgctttccagtgggacagcctgtcagaaggggggcatatcgtcgatgttggc<br>cgaaacggtagggatcatcagttcggtcagaatgtcggtcaccagatagagctttaacttg<br>ctattgctgcctggagcaggttcaacatttttcagtctcgcggcaaccgtctgacggtgtac<br>gccggttatccctgccagctggttgatattgagttttaaagtggcaatttcctggtccat | 171 |
| ECOLIN_10160 | ctatcgacggcactgctgccagataacaccaccggggaaacattccatcatgatggccgt<br>gcgcacataggaagccagttcatccatcgctttcttgtctgctgccatttgctttgtgacatc<br>cagcgccgcacattcagcagcgttttttcagcgcgttttttcgatcaacgtttcaatgttggtatc<br>aacaccaggtttaactttgaacttatcggcactgacggttaccttgttctgcgctggctcatc<br>acgctggataccaaggctgatgtgtagatattggtcaccggctgaggtgtttcgattgcc<br>gctgcgtggatagcaccatttgcgatagcggcgtccttgatgaatgacactccattgcgaa<br>taagttcgaaggagacggtgtcacgaatgcgctggtccagctcgtcgattgccttttgtgc<br>agcagaggtatcaatctcaacgccaagcgtcatcgaagcgcaatattgctgctcaccaaa<br>acgcgtattgaccaggtgttcaacggcaaatttctgccctttctgatgtcagaaaggtaaagt<br>gattttcttttctggtattcagttgctgtgtgtctggtttcagcaaaaccaagctcgcgcaattc<br>ggctgtgccagatttagaaggcagatcaccagacagcaacgcgccacggaaaaacag<br>cgcataaagcacttcattagcagcgccagatagcgtaatgattttgttactcat | 172 |
| ECOLIN_10165 | ctatttgtgggtaaagttcgtagtgcgctgatcgtgcaaaatgatttttagttgggaacagttc<br>gcaactctgtcccataaaaatcagcatattccatctatcccatatccagcgcattgaccat<br>cgggatactgaagggagattccatcatctcttagaaagatcaccatctctttttgtttcaatttg<br>catatagctacctggaggattatgaatgcaaggattttcat | 173 |
| ECOLIN_10170 | atggactattaccatgagattgattttccatctttattcgcgagagcagtggaaagcgatga<br>cgatgtgggtactacattgcgcattcacctactttgtgagcgcatggtcgaagcatggatat<br>gcgcatgctgtgactgccaagatctctttggaagagataaaaacaaactttaatcgaatgt<br>aatactaaaatatccatggcgggaaacctgggaatcccccgqaacttatgaaatcactta<br>aaaccatcaactcaatgcgtaatgaccttgcacacaatccatcaatacaaagcattgctgat<br>tcaaggatccagagcctgaaggatactctgactgaatactttaaacagcatccaacggaa<br>cccagcatggaagaatcaaaactgggtattttaacgccgagaatcaattaaccgaagaa<br>gtttccttagatagtgacagttcaaaaaacagacttaagttaatcttgctgttcagcaagtta<br>tgcaggcgttaatgcaattagttgcagctaatcataatgggcgctgggataaccaatttagc<br>caattcgtttaccatgtgaccatgaacgcaacaaagagataa | 174 |
| ECOLIN_10175 | ctagtcgtcgagttgcaacacaccgtgatccagtgattctgaataggcgataagtccggta<br>taaccggggataatctcaccattatcagcttcaaattcaggaattgtgccggtggtgatggt<br>gtattgaggctggccatcttccttcgcgaaggctgccaggtcttcaatctgcttagctgtaa<br>gaactactgtcat | 175 |
| ECOLIN_10180 | ctattggttattcgacagtcgcactgattcgtaaatccgctcacacgtcattcctgcccggta<br>gctttcgtcagatcgtccagcataatatcgagctgcttctgcaaggcttccgagcatgtcgg<br>caagcattgctgcgttggctccggctgttttgcttctgacggaagtggcgagatcgcggt<br>gtgctttgcggcgtccatgtgggtagcgagttttgttgcttcggcgcgcagctgcttaacag<br>tggtagccaggccagcagaagtaacggcagcgctcgctgcttgagcttgagcatcttttaa<br>cggcctcatcccgggcgattgttcgcccttgttcaatcatacgagctgcggtctgtgcattc<br>gcttcctgtgaagattccgcgctatcccggtcagcccacttttattttccagctgcggttcgtc<br>cactcactgccagcgagaaacgaacctaccaacgcaacaatcacaat | 176 |
| ECOLIN_10185 | tcactggtctatcccccagcacgtcagtgcgctttcctggtcccgccgttctacctgccat<br>aacatccatccttctggcccttggtcaggcggcaatcgcggccaccgtctttaatccacca<br>gcggatagcttcacaggtcctttcgtatcgccagcattaattcgcttatagaacgtagacg<br>ggaaacatttccggggccgatgttatatgggcagaaagaagcgatacccgctttctgtg | 177 |

TABLE F-continued

Sequences of the genes comprised in Phage 3 of E. coli Nissle

| Description | Sequence | SEQ ID NO |
|---|---|---|
| | gttcggtcagtggtactttgatatttcggtcaacccacgccagcgccttgtcgcgttcaatg gcgtttacctgggcgcatttctcagctgacagcttcatgccctgtactactggcttgccatca accattgttgcaccacggcaaatggtccagagtccgccgccgtcgcgatatgctgtcaag ctgttaccctctttctcatccagaaactgatcgagaatcacgggtgcggaagcccggca agaatcaaaccaacgaccgctgcgctcaatttattcttcagctttagagacatagccat | |
| ECOLIN_10190 | ttattcttcagctttagagacatagccattgcgccgatcctcccgttcttccagcggaaata ccagttcactgcacaggtgattaccgtgcatgcgataccgacaataattgcccagtcgctc aggcttaaccctgcaattctgtcggccaacatccaggacacctcttttgctgttttagctgttt cggcatatgccttcgctgatacaccgcagccggcaagcgtggttcctgatccatatgaaa gtctgctgtaaatggtgctcattctggtcat | 178 |
| ECOLIN_10195 | ttatgattttttcagttttttccacctcttcggtggtctgtataaacctgtctgcctccagttctacg ccgatcgcccgacggccaagttctattgcagctttcacagttgaaccagagcccataaag aaatcggcaacgatatccccggtctgctgctggcgctaatgatctgtttcagcatgtcgg caggtttttcgcatggatgtttgcctggataaaactgaacaggcttatgtgtccatacgtcgg tataaggaacaagagcggaaacagagaagcagcgccgaaggattttgtattcctccagc aattctgaatacttgcggtttaatgactggtaggtagccaccagctggtggtgaggatgttc aagcttttgctgaatatgtttatcgatggcgatccgcgtgaacagttcctgcaattttcgatag tccacttcattcggtagttgccattggcttgcaccaaaccagtgtgacgccatgtttttctttc cggttgcctcagctatttctttcgagctgacacccagtgattcacgggcattacggaagtaa tcaatcagcggcgtcataatgtgctgctttagctctgtgcttttcctttcgtaaacatcctctttta cctgtatacggtccaagatagtgctcagcaaacaaaatccgttccgtagatggaaagtac gcacgcaggctttctttattacatccattccagcggcccgatggttttgcccaaatgatgtga ttcaaaacgttgaatcgggcgcgcatcataatctctatatctgaggccagtcggtgaccgc aaaacaggtagatgctgccagcaggtttaagaacgcgagcatactcagccaggcagcta tcaagccagcgtaagtagtcctcgtcccccttccattggttgtcccagccgttgggcttcac tttgaagtacggaggatccgtaactataagatcaatagagttatccgggagggtggcgac gtaatgcagactatcagcgttgattaactcaacactgtttattttacagtattttcat | 179 |
| ECOLIN_10200 | ttactggaggcgtttataacatccgaactggtaatcagataaccccgccatcaccagctgc gtaagtatgagctggcaacgttcgtggctgaggtgggtattctgtgcaatctccccagccg ttgctggtttatcgcttaattcattgaaaacagccttttgccgtttctgtcatatcttcctgatttag cat | 180 |
| ECOLIN_10205 | ttagcaaatattccacatcatcgtactaccgttatggttttcgataattttttgcggctgggctag taccaaaagagtgcatatagcaatgatgaatagtaaggaccagatcctgcaacgtttggtc actctctagctccatgatatttaaaccaatatttgagcttttgtccaaatgaatatgtctggcat gtgcatacgttgcttggtggttgtttaactcatcacatatacgcttagccttagcttcagcgtc agcctgacctgcgaacataccagtacaaagccatttctggacaatttcgttcgcccagaga attgcttttcacactcgccaatcaacgttggattagttttttggaacgtaaattgccaccattg cagtgcagcagggttggcaaaaattccgcttttgctctctcatactcctcaataattgcatg agatgataacccattaaactgtggatcaattggccccaagttcgactgtttacctaaaacga tctgctcagcacaacaagcaagcattgtgccacaactcattgaaatcataggtacaatcgc tcggatattggttccgaacttttgaacgaagataatgaccaattgattctagagctgcgatatc gcctccaggagtatggagtaagatatccaatcccagactcgtatctaacccattgatagca gacataagaccatttttatcatcatctgacatctggatcagatgttgaaacccaggccccccc ttttttgaaggaagcctgagtaataagaaattacatttcggccagtatgtttcgataaatcacg taagtacttgtggcgaacctcatccgctggtgtacgttgagcgatagtacccatctcaccc aatacgtctatccaatttggcat | 181 |
| ECOLIN_10210 | tcagtatgagtacagttggtgagattgctgaccgttctgctcagtagtatttggtgttactgtg ctgtatgaatagagcacaccacttctcacattcagatcgttttgctgagcgagaacacgcat agcaaaatgctgtacggattcgccttttgaaactcttggggttgtatgcccattttttcgtaa aattcagcagcgctcat | 182 |
| ECOLIN_10220 | tcacatttctgccactttgagggcttcttcttcctcatagtattcaagagccatggccaacgc agattcatcaagctgggtaaaagcggccctttaacccagcccagtgccctgaatagacacg caaccatgtcgaacggtcaacgctaaccatgcgggcaacgctgcaccagcatagtcttt ataggtttcattatttctggttgcggcaatttcctgccctgccagccataccaggcctatcag tttctttactacgcgctcctgaagggagttatcacccaggcatttctgataagttttccagac gtattcacacatcatcacctggtgcttatagctaaggtcaaaaccgtagcagtaccgcaac caggcctgctggtatccactaagcgcggacactgccctacgccacggcgcggactcaa attccgcatctttatcggcggcattggcctgcggcggctgcgtgtttccagcacatacagt ggcgcggaaagtgagttaacaaagcgtggccccttctctccttcgagttcgacgagatga attccacggcgaggggtggcattttttgtctgctggtgggtgttcactgaaagcctcaagct gcccttttgttcccccagacaggtcaggtagcgcgcggcgcaattctattcttacaaaattc aggtcttgttgattcat | 183 |
| ECOLIN_10225 | ttaagctttcgcaattacgccgatcgccagcgcccgatccataaaacgcagtagcagctc aagctgcgtaccatgcttctgctgaatgccggtacatcggcgtgtaactcgtcgtggcac tctctgcacagagggatcacgaagagatcatgggcttgttgctgtccccccatacccgt gccctacgatatggtgcggatcatctgctggccgtcggcaacactcacagggttgtgttttt aacccagcgggtgtacgtctcatttatccagcggcgtcgctttggcctgagcatgaaagat tctggagactccggatcaacagagagcgtgaggatcttcttcgccttctcctgcacgagg ctggttgcagaagcggaaggcacaatgtcgctttccctcatgaccgagcggatcttatcat | 184 |

TABLE F-continued

Sequences of the genes comprised in Phage 3 of E. coli Nissle

| Description | Sequence | SEQ ID NO |
|---|---|---|
| | ccggaaggcgtagcccccttgtgcgcaacgctttccggaataacatcagccaggtcgtttc<br>tgaccatccaccagcacagttccggaagcgtcaggatatgcgactcgggaaaaccaga<br>atcacgccgaatgacttccagaatccaggataccaggtttcctgccgctatacctgcaagc<br>tgttcggtatgctgccccgacaaagtgtgatcgcaatgccagcacaggcgaatacttcct<br>ggtgggtgccgcattgttgtgaagttcttgtcgtgccacgatgaatgtggccactggcattc<br>aaaccgattactcaaccattgctcaagggaaggaagcccaccagcacgctgaataaccc<br>gatcattctcgaagacctgccgcattaccggatcatcagccagcggctgaatggcggcg<br>ggaacagctcctgtactgaatgacgccatttcttctggttcaggctcaagcagaacgcgac<br>cgcgcataaagaggtgcatcagttccgcgcgggacgaaacaacacaatccccatacg<br>atgggcgatctcgggggtaagcagagctctcac | |
| ECOLIN_10230 | tcacgcgacctgcccctggcaatgtgttctgcccacagtccaccaatccagcgcacgc<br>ctttcgccgtgaaacgtgcctggctgaatgcatgattttgaggttacggatgtgccggttttc<br>acttcaaaacggcccgcatcaatatgctgatgccgtggggtcatcgttccgccaagacga<br>tacatgatgtcgttctcaaggaggaataaccgcagatcgggctctttggccttaagcagttt<br>tgccacctggcggaatgacattgacccactggctgtacagtaccgatcaacaaacgctac<br>cttcggcgccgcggcagccagttcgttagtcaactgctgttttttgttctgcaaggtcagctg<br>caagacgtagggcttcagagaatgattgaggaatcgtctgctgctgtgcctgctcaagctc<br>ctgccagcgatcaaccagacgcgcggtaaactccggcgacagctgcgcgacaacgat<br>ataactgtcccgcttccctatcagataaaccgataccgactgattgaggtgattttaacttc<br>ccccattgggggagttcaataacaccgcgctctgccaggcgttcaatggaccgtttaac<br>atggtcatgtcttgattccaccagctcagcaatatcgctgctggacatggttaacgctgttgt<br>tgctaactggctcat | 185 |
| ECOLIN_10235 | tcaggcggctgcacccgccggttcatatctgctgattgttatctctacccgacctttcggca<br>caacgggtccccattccaccagcatgcgcttaatctggctgtcgtcttcccagacacccgc<br>atgcgtcagcgcgtcaaacagggctttgttgtaattatcgatatcccggcggcgcgcatcc<br>ggcgggtacagagtgatttctaccgctgccagttcagtcgatggcttcgggagacgtcgt<br>aattgctcaatgatcgccacgcaggcagcgctctggtatttacggccagcggcgctaatg<br>aggtgacgaccggccagcggccccttgttaggggcgcgccagtaagtgttcacgctcg<br>gaggaaaaggcaggatcagtttcac | 186 |
| ECOLIN_10240 | tcacgcggcctctccccgcatattgcgaacaagttcagaagcagcagtaatgatttcgctg<br>gtggcagtccgctccagcagagttgattgatattggctttgtgttgcagtgactc<br>atccagcatgtcagcaccatccacctggtcgaatacaattctaacctccagcggccagat<br>acgggactcgggaagcggatccgatactggtttagcttttctcacgaatgtgcatgcggat<br>ctggcgaatattggaccaactggaaacatccaggcttcccatggctgcaatgaagtcagt<br>gctgttcatgccatattcaccggatgcttcaagggcaacagtgcgaatacgttccgacata<br>tccaggcgcacagcagcgtcatcgaattcaatcgacaacagccactcatccacaccgaa<br>caaaatactctcacgaataagcagcttcgctttgtcgatcgttaaaggtgatacctgagtga<br>attccggtgcttcgacagaatccgccgcccaggtatgcccaaacttcgattcactgaatgt<br>gtattcttctttatcgccaaacgcagctctaacgcatgcccacgcctcgacaccgctgata<br>gcaaaaatatcttttctgggtgagtgcaactctgcttctggcttatcagctgcaggaggtgt<br>ggcagttacaggttgagacttgctggcagcaaattgtgccaaagccataaacgcccgcc<br>cttttgcctccagttctgtgcggttgatatagctgaaccgctcgccacgccatgacttatcga<br>atacagctatggcaccggcaaaaaacgcgctggtgggtttctgttttttcgtcagcaggtac<br>aaaccacacaggcagatcgaacccaatgcgcccgcgaatgaatacaatgtgatcggcat<br>cttccggccaccacgtttcactcggcgcggttttatcaggaatacatagcgaccgcccctt<br>ctcgcgctgggctgctgcgtagttcatgatgtgcgtcatgccggtgatcgcctgcttctcgt<br>ggtactgcgaacggctatacggtgggttgccatagccagcgccacccagttcagccaga<br>cgttcagaccagtcctgcgtcagcgcgttatcttcggcggtgtaccatgccgggcatttcg<br>cgttgtcgtcgtcagcaaacaaatccagaactaatggaccaaatagcgcgttgatccccc<br>aaaaaagcagatccggtgtccgccactgatcgccaacctcttttcaattcgtgagctggttt<br>gctacgcagtgccgccagcgcctggcaatatttattggtcatcat | 187 |
| ECOLIN_10245 | tcatgaacggaaccccgaattttctggcagtgagtaatcaacactctggaagtttgcgcgg<br>ctggctgagttagtctcccatttgccgttaacgcgttcaggccggccagcactggaccattt<br>ggtcgcgctttgcaggtaaccagggaagttttttggaatgaacagagttgccgggcggag<br>gtattgcgcctgctcgctatcacgccaatcggcattttttgtaatccactaccaagcacaggt<br>catcaacagtgaattgttcccgaagacgggcgcgaatattctccagcgacgtgctgcata<br>cctggtagcgtgagccagtagtctgattcaggtaagacaaaacctgtctggcctgatcagt<br>aatcacaacctcagggtcgggttgcgccgcaaccggacaagagggttttgaagttacttg<br>tggttcttgtttgattttactgacggatccccaccagattctgacgggtcaaaaccgcctttt<br>tgctggatttcgacgcctcaaattttgacgggtcggatttgatgcatcagattttgatgggtc<br>agattttgatgcgtcagattctgacaggtgagaaaaagcagcctctcgcaacttaacgacg<br>ttaagctgatatacgttcgatgcgttacggttcccattacggcgctgcttacgggaaagcca<br>gccatccttctcaagctgagcaagggccgtccttaccgtacttctccagcaccgatttgac<br>gtgcgatcgtgccaatagacggccagctaacacccctcatcactactgaagtcggccaga<br>cgccgcatgatggcaacgctggataacttcatgcctgacgaagcgcatgcatcccatac<br>gtaaccggttaatttagtgctcat | 188 |
| ECOLIN_10250 | ttaattctgtaaatttacgctggaattgttcaagagggctgaagcactcatgatcgtacccttt<br>cgcgaaggtatataacgcgctgtgtatctggctcccagcggacaactctgacgggaactc<br>cgtagtgatctctgaaccgccggttaacttcagccattcctcgcgcccttctcgttcatctg | 189 |

TABLE F-continued

Sequences of the genes comprised in Phage 3 of E. coli Nissle

| Description | Sequence | SEQ ID NO |
|---|---|---|
| | aacaaatgcttctaccatcaagtctgctggctggtagttgcctccatcagccgcgttatttat gatttccacatagccgaactgggcatctttacccaccagcggcaaacatctgaattgctta gctggtctgaatcggtttacactgttcat | |
| ECOLIN_10255 | tcatgcgttagtttctccactgatacgacacgccaaggcgcccggagctgcacactcgcg ggcgtcacctttctgcctgttgaaacgaatacgtcaatcgcctgatctgaaacaccaacc ccataaagcgccataaatcccaggaacccgtgaatctggtggcggagcttcttactgaat aattctgaaagcattttgcgctctgatgaatcaattacccccatcagccgctgctgccatcttg gcattagccagctcaccagatgctgctgccgctttcatctcaatgctgtacagctcaacgtt atccaggctctcagcagttggaacatccaccagccatttcccttttcggttcgcctggtact cggccaagtaacaagaaccagacaggtcctccatccgttccagttctgccaaggtaaag aaccgactgccacacttctggtacaggtggttgtggaactggtcgatagtcatccctaaat cggaagccatacctaagcgaccatgcttgtgtgccttacacatcaggcggattgctgtattt atgctgtctaccat | 190 |
| ECOLIN_10260 | ttaaagttgactattgttgttagcggaaggtatgccgtcattttttgttcggataaatatcaggtc gtaattgatggggagttactacccatccgcccccattggcaggttgaataactctttcagaa ggtactccggttctttgcaatccagttcgcaacagattgaactgattggaattcaaaccgcctt gatacctctgaaatcgacccgatcgccttcacagctttagctgttacattcttgtgttgagat gacat | 191 |
| ECOLIN_10265 | atgccttgtgcgcttaatcttctacttatggtggaaaatgctaaatacaaagactttgccgaa aggctaaacaggtctctccaagagcaatctattggagttaaagaattgtcagagttcagtg gtgtctcgtatgagatggcgcggcgctacactcttggtactgcaaagccgagagatgaga agatgattcgaattgcagaaagacttgccgtctcaccggctatcttgattatggtgtgcctg ttaatggtggcgacgcgccagccaaaggcacggtcagaatagagcaattggatgttcat gcttcagccggttccggatatataaaccaaccattccctacaatagtgagctcaatagaga ttccagaagagaggatcttcgagttgtttggtcgtagaagccttgatggcatcgtcatgata aatgttgatggcgatagcatgatgcccacgctttgcccaaaggacctgcttttcatagaca gcaaggttgaacaattcagcggcgacggcgtttatgtgttcaattttgaagacagtcgttc gttaaacgtttgcagaaggtaaaagggcgccgactggcagttcttttcagacaatgaacatt acccgcccttcttcatagaggagcatgaaatgaatgaactatacatattcggcaagctaat cagatgcttacctctaaaaatgatagagtttggctaa | 192 |
| ECOLIN_10270 | ctatttaaagagcttcttcagcttgtcctcaaccttcctgatttcggaagtaagctggctgctg ttgacattgatagtagctccacatcgacaagtgaaactttttgttcgacttgagccaagcgatt ttcttcttcgtcttagtgccgcacttagggcatgcgggtaacgtaatttcctggttatcaaaag cgcccat | 193 |
| ECOLIN_10275 | atgaataatccgtttttcaaaaatatgttggtgtatcgcattagtcgcgatttcaccatcaacc aggaagagctggaacagcagcttgaactatttcgcttcactccatgcggtagccaggata tggcaaaaaccggttgggtatcaccacttggtcagctgtcagatcgcttgcatcacactgt caataatcaagtgttgttggttattcgccgggaagaaaaaatactgccatctcctgtcattac tgaagaactgcgcaagcgtgtgtcgcgtctagaatccgatcaggggcgtcgcctcaaaa aaactgagaaagattcgctgcgtgatgaagtgttgcactccctgcttcctcgggcgttctcc aaaaactcgactgttggtttgtggatcaacgtcaccgacggtctgatcatggttgatgcag ccagcgctaaacgtgccgaagactcactggccctgcttcgtaaaactctcggttctctccc ggtggtaccgctgactatggaaacgccgatcgaactaactatgaccgactgggttcgttc cggtagtgcgcctgctggctttggcctgggtgatgaagccgaactgaaagctattcttgaa gatggcggtattggacgcgtttaaaaaaacagactctggtcagtgacgaaattcatgtcgatct ggaagctggcaaagtagttacaaagctgtctatcgactggcaacagcgcattcagttcgtt cttttgcgatgacggcagcatcaaacgccttaagttctctaatgagattacagaacaaacg acgatatcgaccgtgaggatgcggctcagcggttcgacgctgactttgttctgatgaccg gcgagcttatctctctcattaacggattaacaacctctctcggcggcgaagccaagcgata a | 194 |
| ECOLIN_10280 | atgagctacattcagacattatccggcaaacattttaattacctcgatatccaacaggacga tatcgtgatcgaggatattgctaccgcgttgtctcatatctgccgctttgcagggcatcttcct gagttttacagtgtcggccagcatagcgttttaaccagccaccctcgttccgcaggagtttgc attagaagcactgcttcatgatgctgctgaagcctaccgcaggacatcccctccccactt aagcgcctgcttccggattaccaggcaatcgaagctcgtgtggacgcagccattcggca gaagttcggtctaccaactgagcaacacccaaccgtgaaatatgccgacctggtgatgct cgccagcgaacgccgcgattttgagattgacgaaggttccatttggccatgcctcgaggg agtttgtcccaacggatttattcattatcaacccagttcgtcctggccagtcatacggcatgtt catcaatcgctttaacgagttgatggagcagcgccaatgcgccgcatga | 195 |
| ECOLIN_10290 | atgaccgtatttgaatatctccaggctcatccgaataccaccagcggtgaaatcgccaaag gtatgaacaaaaagaccccagcggtcgccggagcattatctcagctctatggcaccggt cggatcgtgaagtctggtgttcgcaagggtattccaacataccgcattaacgatatgccgtt tggttgcagtaacagcctaaccatgatgtttaaccagctcttgagcagagccagacaagg agcagcccaatga | 196 |
| ECOLIN_10295 | atgacagcactcaacaaacaggcgctgcgtgaagaattccagttcatgcaggacaactat agcgaccggcagaccacgatcggcaggtgatttacatcgaggcggaggcgctgctg gatgagttggaagccaaagactcaacgatagcagcacaacaacatgagatccgtatgtt gctgaatgcgcttgaggaaaaaccatgcccgaaatgcaacgacacaggaatgactgata | 197 |

TABLE F-continued

Sequences of the genes comprised in Phage 3 of *E. coli* Nissle

| Description | Sequence | SEQ ID NO |
|---|---|---|
| | gtggcggcacgcagccatggggcgagccgattgagattgaatgcgactgccgacagc<br>aggatgccaacaccgcagaacttgtagccgctggcattggcgtgaagggggagtga | |
| ECOLIN_10300 | atggataaattaatcaaacctaccgccaaaggtaaatatgacggttcatgtgattatctttgc<br>tcggaagatgcgcgattcatcgttatgcgcggcgattatacggaagcggaaataattcag<br>gcttctgtgtctcaagatgtaatcgactcggatggtgcggctgattttgcaagtagcgcccg<br>ctattatcagtgctggtacaaagttagcccaataggtggtcaggatggctattcaggctgg<br>catcatcctcgtgattcgccgtgtcgcggtgcatatttcgcatcagttttgcaatgggattaa | 198 |
| ECOLIN_10305 | atgacaactaacaaccaccggcgcacggtcctgtatcactcgatcgcctgcaccagata<br>cgcgaacacctgctgcatgatacccaatactcaaacggcgggaacagagcctacattct<br>cgctgatgtattgaaggtgattgatgggctattgcccgcgagctggtacgccgtgagca<br>tgcagcgtggtcacaggctactttcggcgatgtcggtccagttggtccgctgaagcaccttt<br>tccaaagaagcgctcgaggctgctgctgaaccaggcgaccttagcgaatgggctgacat<br>gcaattcctgttatgggatgcgcaacgtcgtgccggtatcagtgatgagcagattacccag<br>gcaatgataaaaagctggctataaataaggttcgccaatggcctgagccgaaagacgg<br>ggaacctcgattgcatatcaaagaacagtcagagcaggagaaaaaataa | 199 |
| ECOLIN_10310 | atgtttagcctgattcggcgcggtcaaatctacacggacagtagcaactggcccgtaatta<br>tccatagctgtagtgatcactcggtccgaattaaacgcaatgatggcgagctgagaacga<br>ttagcatcaaacgctttaacgaagattttgaacgagtggagcatgatgagtatcgcaaaat<br>atgtgccgaaatagagcaggaaacaaacctgaaaaacctacgtgcgatgcgtcgcggc<br>aagattactgaatag | 200 |
| ECOLIN_10315 | gtgaacaacttaatgatcgaccttgagtccatgggcaaaaaaccgaatgcccctattgtct<br>ccattggtgccgtattcttcgatccgcaaagcggtgaactgggtcaggagttttacaccgc<br>tgttaatcttgaaagcgctatggagcagggagcggtgccggatggtgacactattctgtg<br>gtggttaagacaaagctcagaagcacgatcagcaatctgtgttgatgatgcgatgccgat<br>atcatctgccctatctgaactgagccatttcattaatcggcattctgataaccctaaatatttaa<br>aagtttggggcaatgagctactttcgacaacgttatattgcgcggcgcatatgagcgtgc<br>cggccaggtttgcccgtggcaattttggaatgatcacgacgtcagaaccatcgtcacatta<br>ggcagatctgtaggtttcgatcctaagcgtgatatgccatttgatggggttgcacataacgc<br>actggctgatgcccgccaccaggcgaaatatgtttcagcgatttggcagaaactaatccc<br>aaccaccagcaacagctaa | 201 |
| ECOLIN_10320 | atgagcaatattttccagttagctcccaacgattgggtttgtgaaagcgttttgatcgcggtt<br>actgggctcaaacccggaaccatcctccgtgccagaaaagaatgctggatgattgggag<br>ggagtatatccacgtatcgcctgacggaaatcctaaaccttccagtgagtgcatgtataac<br>agaaaggctgtagatgcctgggtcgcttcaatgaaaagcaagcaaccagggtga | 202 |
| ECOLIN_10325 | atggataaagtcacatatccaacaggcgtcgaaaaccacggtggcacattacgcatctgg<br>tttaattttaaaggtaagcgtgtcagggaaagtctcggtgtccctgacaccgctaagaaca<br>ggaagatagccggggaactgcggacatcagtatgttttgccatccgcacaggaacctttg<br>attatgcaacccagtttcctgactcccctaacctcaaggcttttggtgtaagtaaaaaagac<br>attacagtgaaagaacttgaagaaaaatggctggatctgaaacggatggaaatctgcgcg<br>aacgcatttaatcgctatgaatctgtcgcaaggaatatggtgcgaggatcggaggtaatc<br>gcctggtgtcagcagtaaccaaagaggaattgctgtatctgaggaaatatttgctaactgg<br>ttatcagaatccgacgaaaaacaaagcccccggcaaagggcgaagcgttgttactgtga<br>actattacatgacgacaatggccggaatgtttcagtttgctgcggatcacggttacttagag<br>gtgaacccattcgagggaattaagcctctgaaaaaagcaggggcagaaccagatcctct<br>gtctcgtgatgaatttattcgcctgatagatgcatgccggcatcagcagacgaaaaacctg<br>tggtcattagcagtgtacacaggaatgcgtcacggggaactggtctccctggcctgggaa<br>gatatcgacctgaaggctggaacaattaccgtcagacgtaattatacgaaacttggtgagt<br>tcactctaccgaaaaccgaggcaagcacagatcgagtggtgcatcttatccagcccgca<br>atcagtatcctgaaaaatcaggctgaaatgacaaggctgggcaggcaatatcacattgaa<br>gtgcagttacgtgagtacggccgttcggtgaaccatgagtgtacattcgtctcttaatccgca<br>tgtggtcagacgcagtaagcaggtcggatttatctaccgggtcgattcagtaggcgactc<br>atgggaagcggcacttaagcgtgcgggatcagacacagaaaggcgtaccagtcacg<br>acacacctatgcgtgctggtcattatcagctggtgcaaaccctagttttattgccagtcagat<br>ggggcatgcgagcgcgcagatggtgttcaatgtttacggtgcatggatggctgacagca<br>gcgcagagcagatcgcaatgctgaatcagaagctggcagattttgccccattgatgcccc<br>atagccacgagaacagtacgggaggattattaaaatcagtaagttaa | 203 |
| ECOLIN_10330 | gtggagggtaacaccacgctttatgccctgccgaaacccgaggttgtcctgcgctggcgt<br>gagcagaccacagatgacttccgcttctgtttttaagtttccggcgaccattcgcatcaggc<br>agcattacggcattgcgatgatttagtgactgaattttttgacccgcatgtcaccgttggctcc<br>gcgcattggacaatactggctgcaactgcctgccacattccgccacgggagctgcctg<br>cgctttggcatttctcgattctcttcccggtgaatttaattatggggtggaagtccgccatcc<br>acagttttcgccaaaggggaagaggaacaaacgcttaatcgcggtttacatcagcgcgg<br>cgttaatcgggtgattttagacagccgcccggttcatgcagcacgtccatacagtgaagct<br>attcgcgacgctcaacgaaaaaaacctaaagttccggtacatgctgtactgacggcgaaa<br>aatccactgatccgtttttatcggtagtgatgatatgacgcaaaaccgggaattattcaggtc<br>tggttacaaaaattagcgcagtggcatcagaccactacgccttatctttttttacatacgcca<br>gatattgcccaggccccggaactggtacataccctgtgggaagacttacgtaaaacgctt<br>ccagagatcggagcagttccggctattccacagcaatcttctcttttctga | 204 |

TABLE F-continued

Sequences of the genes comprised in Phage 3 of *E. coli* Nissle

| Description | Sequence | SEQ ID NO |
|---|---|---|
| ECOLIN_10335 | atggtaagcgcgctgtatgccgttttaagtgcgttgttattaatgaagttctcttttgatgtcgtt cgcctgcgaatgcagtaccgcgttgcctatggcgacggcggttttagcgaactgcaaag cgctattcgcattcatggtaacgcggtggaatatattcctatcgcgattgtgttgatgctgttt atggaaatgaatggcgcagaaacctggatggtgcatatttgcggcatcgttttgcttgctg gtcgtctgatgcattattacggttttcatcaccgtctgttccgctggcgacgttctggcatga gcgccacctggtgtgcgctgttgctgatggtgctggcgaatctttggtatatgccctggga gttggttttctccctgcgttag | 205 |
| ECOLIN_10340 | atgtctcaccgcgacacgctatttctgccccatcgccagactgggcgactggacctttg atgaacgggtagctgaagtcttcccggatatgatccagcgttccgttcccggctattccaat attatttccatgattggtatgttagccgagcgcttcgttcaacctggtacgcaggtttacgatc tgggttgttctctgggcgcggcgacgctctcggtgcgtcgcaacattcatcatgataattgc aaaattattgccatcgacaactccccggcgatgattgaacgctgccgtcgtcatattgacg cctataaagcccctacgccagtagacgttattgaaggtgatattcgcgatatcgccattgaa aacgcatcgatggtggtgctgaattttaccctgcaattcctggaaccttccgagcgccagg cgttactggataaaatttatcaagggctgaacccgggcggtgcgctggtgctttcggaaa aattcagtttcgaagatgccaaagttggtgaactgctgttcaacatgcaccacgactttaaa cgtgccaacggttacagcgaactggagatcagccagaaacgcagcatgctggaaaacg tgatgctgaccgattccgtggaaacccataaagcacgcctgcataaagccggttttgagc atagcgagctgtggttccagtgctttaactttggttcactggtggcattaaaagcagaggac gctgcatga | 206 |
| ECOLIN_10345 | atgatcgactttggtaactttttattctctgattgccaaaaatcatctttcacactggctcgaaac gctgcccgcgcagattgctaactggcagcgcgagcagcagcacgggctgtttaagcag tggtccaacgcggtggaatttctgcctgaaattaaaccgtatcgtctggatttattgcatagc gtaaccgccgaaagcgaagagccactgagcgccgggcaaattaagcgcattgaaacg ctgatgcgcaacctgatgccgtggcgcaaagggccgttctcactgtatggcgtcaacatc gataccgaatggcgttccgactggaaatgggatcgcgttatgccccatctttctgatttaac cgggcgcaccattcttgatgtcggctgtggcagcggttatcacatggcgcatgattggc gcaggggcgcatctggcggtgggtatcgatcccacgcagctattcctctgccagtttgaa gcagtgcgtaaactgctgggtaacgatcagcgcgcacatttgttaccgttaggtattgaac aacttccggcactgaaagcctttgataccgtcttttcgatgggcgtgctttatcatcgtcgttc accgctggagcatctctggcagttaaaagaccaactggtgaatgaaggcgaactggtgc tggaaacgctggttattgatggcgacgaaaacacggtgctggtgccgggcgatcgttac gctcaaatgcgtaatgtctatttcattccttccgcgctggcgctgaaaaactggctgaagaa gtgtggttttgttgatattcgcattgcagatgtgagcgttaccaccacagaagagcagcga cgcaccgaatggatggtcaccgagtctctggccgattttctcgacccgcatgatccgggt aaaacggtggaaggttatcctgcgcctaaacgcgcggtgctgattgcgcgcaagccgta a | 207 |

TABLE G

Polypeptide sequences encoded by the genome of *E. coli* Nissle Phage 3.

| ECOLIN_09965 | METKKNNSEYIPEFDKSFRHPRYWGAWLGVAAMAGIALTPPKFRD PILARLGRFAGRLGKSSRRRALINLSLCFPERSEAEREAIVDEMFAT APQAMVMMAELAIRGPEKIQPRVDWQGLEIIEEIRRNNEKVIFLVP HGWAVDIPAMLMASQGQKMAAMFHNQGNPVFDYVWNTVRRRF GGRLHARNDGIKPFIQSVRQGYWGYYLPDQDHGPEHSEFVDFFAT YKATLPAIGRLMKVCRARVVPLFPIYDGKTHRLTIQVRPPMDDLLE ADDHTIARRMNEEVEIFVGPRPEQYTWILKLLKTRKPGEIQPYKRK DLYPIK* | 208 |
|---|---|---|
| ECOLIN_09970 | MQQIARSVALAFNNLPRPHRVMLGSLTVLTLAVAVWRPYVYHRD ATPIVKTIELEQNEIRSLLPEASEPIDQAAQEDEAIPQDELDDKIAGE AGVHEYVVSTGDTLSSILNQYGIDMGDITQLAAADKELRNLKIGQ QLSWTLTADGELQRLTWEVSRRETRTYDRTAANGFKMTSEMQQG EWVNNLLKGTVGGSFVASARNAGLTSAEVSAVIKAMQWQMDFR KLKKGDEFAVLMSREMLDGKREQSQLLGVRLRSEGKDYYAIRAE DGKFYDRNGTGLAKGFLRFPTAKQFRISSNFNPRRTNPVTGRVAPH RGVDFAMPQGTPVLSVGDGEVVVAKRSGAAGYYVAIRHGRSYTT RYMHLRKILVKPGQKVKRGDRIALSGNTGRSTGPHLHYEVWINQQ AVNPLTAKLPRTEGLTGSDRREFLAQAKEIVPQLRFD* | 209 |
| ECOLIN_09975 | MLHKKTLLFAALSAALWGGATQAADAAVVASLKPVGFIASAIAD GVTETEVLLPDGASEHDYSLRPSDVKRLQNADLVVWVGPEMEAF MQKPVSKLPEAKQVTIAQLENVKPLLMKSIHGDDDDHDHAEKSDE DHHHGDFNMHLWLSPEIARATAVAIHGKLVELMPQSRAKLDANL KDFEAQLASTEKQVGNELAPLKGKGYFVFHDAYGYFEKQFGLTPL GHFTVNPEIQPGAQRLHEIRTQLVEQKATCVFAEPQFRPAVVESVA RGTSVRMGTLDPLGTNIKLGKTSYSEFLNQLANQYASCLKGD* | 210 |

TABLE G-continued

Polypeptide sequences encoded by the genome of E. coli Nissle Phage 3.

| | | |
|---|---|---|
| ECOLIN_09980 | MTSLVSLENVSVSFGQRRVLSDVSLELKPGKILTLLGPNGAGKSTL VRVVLGLVTPDEGVIKRNGKLRIGYVPQKLYLDTTLPLTVNRFLRL RPGTHKEDILPALKRVQAGHLINAPMQKLSGGETQRVLLARALLN RPQLLVLDEPTQGVDVNGQVALYDLIDQLRRELDCGVLMVSHDL HLVMAKTDEVLCLNHHICCSGTPEVVSLHPEFISMFGPRGAEQLGI YRHHHNHRHDLQGRIVLRRGNDRS* | 211 |
| ECOLIN_09985 | MIELLFPGWLAGIMLACAAGPLGSFVVWRRMSYFGDTLAHASLLG VAFGLLLDVNPFYAVIAVTLLLAGGLVWLEKRPQLAIDTLLGIMA HSALSLGLVVVSLMSNIRVDLMAYLFGDLLAVTPEDLISIAIGVVI V VAILFWQWRNLLSMTISPDLAFVDGVKLQRVKLLLMLVTALTIGV AMKFVGALIITSLLIIPAATARRFARTPEQMAGVAVLVGMVAVTG GLTFSAFYDTPAGPSVVLCAALLFIISMMKKQAS* | 212 |
| ECOLIN_09990 | MIEADRLISAGTTLPEDVADRAIRPKLLEEYVGQPQVRSQMEIFIKA AKLRGDALDHLLIFGPPGLGKTTLANIVANEMGVNLRTTSGPVLE KAGDLAAMLTNLEPHDVLFIDEIHRLSPVVEEVLYPAMEDYQLDI MIGEGPAARSIKIDLPPFTLIGATTRAGSLTSPLRDRFGIVQRLEFYQ VPDLQYIVSRSARFMGLEMSDDGALEVARRARGTPRIANRLLRRV RDFAEVKHDGTISADIAAQALDMLNVDAEGFDYMDRKLLLAVID KFFGGPVGLDNLAAAIGEERETIEDVLEPYLIQQGFLQRTPRGRMA TVRAWNHFGITPPEMP* | 213 |
| ECOLIN_09995 | MIGRLRGIIIEKQPPLVLIEVGGVGYEVHMPMTCFYELPEAGQEAIV FTHFVVREDAQLLYGFNNKQERTLFKELIKTNGVGPKLALAILSGM SAQQFVNAVEREEVGALVKLPGIGKKTAERLIVEMKDRFKGLHGD LFTPAADLVLTSPASPATDDAEQEAVAALVALGYKPQEASRMVSK IARPDASSETLIREALRAAL* | 214 |
| ECOLIN_10000 | MNINYPAEYEIGDIVFTCISAALFGQISAASNCWSNHVGIIIGHNGE DFLVAESRVPLSTITTLSRFIKRSANQRYAIKRLDAGLTEQQNQRIV EQVPSRLRKIYHTGFKYESSRQFCSKFVFDIYKEALCIPVGEIETFGE LLNSNPNAKLTFWKFWFLGSIPWERKTVTPASLWHHPGLVLIHAV GVETPQPELTEAV* | 215 |
| ECOLIN_10005 | MAIILGIDPGSRVTGYGVIRQVGRQLSYLGSGCIRTKVDDLPSRLKL IYAGVTEIITQFQPDYFAIEQVFMAKNADSALKLGQARGVAIVAAV NQELPVFEYAARQVKQTVVGIGSAEKSQVQHMVRTLLKLPANPQ ADAADALAIAITHCHVSQNAMQMSESRLNLARGRLR* | 216 |
| ECOLIN_10010 | MAGHSKWANTRHRKAAQDAKRGKIFTKIIRELVTAAKLGGGDPD ANPRLRAAIDKALSNNMTRDTLNRAIARGVGGDDDANMETIIYEG YGPGGTAIMIECLSDNRNRTVAEVRHAFSKCGGNLGTDGSVAYLF SKKGVISFEKGDEDTIMEAALEAGAEDVVTYDDGAIDVYTAWEE MGKVRDALEAAGLKADSAEVSMIPSTKADMDAETAPKLMRLIDM LEDCDDVQEVYHNGEISDEVAATL* | 217 |
| ECOLIN_10015 | MAYKRPVSILVVIYAQDTKRVLMLQRRDDPDFWQSVTGSVEEGET APQAAMREVKEEVTIDVVAEQLTLIDCQRTVEFEIFSHLRHRYAPG VTRNTESWFCLALPHERQIVFTEHLAYKWLDASAAAALTKSWSNR QAIEQFVINAA* | 218 |
| ECOLIN_10020 | MRTEYCGQLRLSHVGQQVTLCGWVNRRRDLGSLIFIDMRDREGIV QVFFDPDRADALKLASELRNEFCIQVTGTVRARDEKNINRDMATG EIEVLASSLTIINRADVLPLDSNHVNTEEARLKYRYLDLRRPEMAQ RLKTRAKITSLVRRFMDDHGFLDIETPMLTKATPEGARDYLVPSRV HKGKFYALPQSPQLFKQLLMMSGFDRYYQIVKCFRDEDLRADRQP EFTQIDVETSFMTAPQVREVMEALVRHLWLEVKGVDLGDFPVMT FAEAERRYGSDKPDLRNPMELTDVADLLKSVEFAVFAGPANDPKG RVAALRVPGGASLTRKQIDEYGNFVKIYGAKGLAYIKVNERAKGL EGINSPVAKFLNAEIIEAILERTGAQDGDMIFFGADNKKIVADAMG ALRLKVGKDLGLTDESKWAPLWVIDFPMFEDDGEGGLTAMHHPF TSPKDMTAAELKAAPENAVANAYDMVINGYEVGGGSVRIHNGD MQQTVFGILGINEEEQREKFGFLLDALKYGTPPHAGLAFGLDRLT MLLTGTDNIRDVIAFPKTTAAACLMTEAPSFANPTALAELSIQVVK KAENN* | 219 |
| ECOLIN_10025 | MLELNAKTTALVVIDLQEGILPFAGGPHTADEVVNRAGKLAAKFR ASGQPVFLVRVGWSADYAEALKQPVDAPSPAKVLPENWWQHPA ALGATDSDIEIIKRQWGAFYGTDLELQLRRRGIDTIVLCGISTNIGVE STARNAWELGFNLVIAEDACSAASAEQHNNSINHIYPRIARVRSVE EILNAL* | 220 |
| ECOLIN_10030 | MGFPSPAADYVETRISLDQQLISQPAATYFMRASRSHFREGIIQGAL LVVDASLTACDGSLLICAIDGEFRIKRYRTHPQPHLVNLDNGRREA LPADDDGYSSAPAIFGVITYIINDARNAEFDDCPVM* | 221 |

TABLE G-continued

Polypeptide sequences encoded by the genome of E. coli Nissle Phage 3.

| | | |
|---|---|---|
| ECOLIN_10035 | MFVELVYDKRNFDGLPGAKDIILGELTKRVHRIFPDADVRVKPMM TLPAINTDASKHEKEQISRTVQEMFEEAEFWLVSE* | 222 |
| ECOLIN_10040 | MLWRIFIFVNVGLGEAAKRNVGTGENQIPDMSAFPSGNNWFQLPS GHIVQIFSMNVLGADANGTSANYPIAFPTTMIAVSALWSDGTVAN APTYKMMGNTTNRTTLTIKVSASSGTYGTMIIAVGR* | 223 |
| ECOLIN_10045 | MNKYSYSPSENAFYAVALKNTYELSGTWPADALDIPDDISVKYMA EPPQGKIRVAGENGFPTWAEIPPPSHEELIEQAESERQLLINQANEY MNSKQWPGKAAIGRLKGEELAQYNSWLDYLDALELVDTSGTPDIE WPTPPAVQAR* | 224 |
| ECOLIN_10050 | MKPVFDENGLAAVPGDMRCFYYDAVTSEYTGWSDEYINTGVSMP ACSTGIDPDENIPGRVAVFTGKGWSHEEDHRNETVYSIENGAAVT VDYIGAIKNGYVTLSPLTPYDKWDGEKWVTDTEAQHGASVEAAE AQRQSLIDAAMASISLIQLKLQAGRKLTQAETTRLNAVLDYIDAVT ATDTSTAPDVIWPELPEA* | 225 |
| ECOLIN_10055 | MIYSTGTISINGNTATGSGTNWTAPASQVRAGQTIIVMSNPVQLFQI SSVNSATSMTVTPAVSPALSGQKYGILVSDNISVDGLAQAMSQLIK EYDENIGAWETFATTSANQSITVTINGTAVTIPGIGKLAQKGSNGA VTVADGGTGATNAADARTNLGLGEGSPAIGVPFFWPSAAMPNTVI DSWSSMVFLKFNGAKFSATDYPVLAKVFPSLVLPEARGDFIRVWD DGRGADGGRELLSWQEATNFSQFAGNIGGGAGHAINFHDGIAGNQ PGFSRFNFNSNSVGDGVNFVAVRPRNIAFNFLVRAK* | 226 |
| ECOLIN_10065 | MGEKMQLLKQETILQGAKGGGGSSHTPVEQPDDLLSVAKLKMLIA VSEGEIQGDLTAQNIFLNDTPLANDSGEYNFSGVKWEFRKGTQDQ TYIAGMPQVDNELAVGTTVTTTAPWTRQFTNLSLDAIRIKLSLPVQ YLYKDNGDMVGTVTEYAIDLSTDGGAWKTVVNGKFDGKTTTEY QRDHRIDLPKSTSGWSVRVRRITADASGSNSKLVNAFKVFSYAEVI DSKLRYPLTALLYVEVDSSQFNGSAPKVTCKIKGKLIKVPDNYDPK TRTYSGSWSGGFKMAWSNNPAWIFYDLVLDEIYGMGTRVDASMV DKWALYSIAQYCDEMVSDGAGGTEPRFTCNVFIQSQEDAWQVLN DLAAVFRGITFWGNDQIYVQADVPQDDVDWVYNVSNVIDGLFTY AGGSYKNRYSSCLVSWSDPQNHYSDTVEGVYDSALVERYDVRQT SLTAIGCTSQSEAHRRGRWVLLSNAKDGTVSFGVGLDGYIPLPAEII GVADPFRSGKENGGRISAANGRQITLDREIDYAAKDRLVVNLPDG KAQTRTISAVSADKKTVTVATAFSQVPVAGAVWAIDSDNLAIQYF RVTSIAANDDSTGGFTITAVQHDPNKYRYIDDGVRVESPPITVTPIS VLSAPKNIVVTESDHVSQGLTVASLDVSWDKVEGAIRYVAQWRK DNGDWINVPVTSAQGFSVQGIYSGSYDVRVRALNAQDTSSPWGY GETTYLSGKTGKPGTPLNFLATEDVVWHIDLTWKFPDGSGDTAYT EIQRATTADYANPELLVLVPYPAADYQHGPMPAGVRQWYRARLI DRIGNAGDWTDWIMGTSSIDVSEITNDILEDMKESETFKDLIENAV DSNEKIAGMANDIKQANDELEQQAKDIAKNAQDVGKVQTSVNEL SSTVGNVSSSLSQLEQTVATADTALGQRIDNISVSMDGMTGGVKN SAIAIIQANLAQVATRKTLSASVAGNSANLDRLDEVIVSEKEATAR SLLLSLQTDVNGNKASINSLNQTLSDYQQATATQINGITATVNGHTS AITTNAQAIANVNGELSAMYNIKVGVSSNGQYYAAGMGIGVENTP SGMQSQVIFLADRFAVTTAAGNSVALPFVIQNGQTFIRASFIQDGTI ENAKIGNYIQSNNYAAGSAGWKLNKAGDAEFNNVTVRGVVYASG GSFTGEIQATSGKFKGTVEAQSFIGDIANMHTGTNVSRSSDGYLEK VMTYNDSSSSGHARHVCVIANVKGNGAGTIDINGNESGSSVQDME RLIMHSAVVTGPNVTVRIKVSAQNNRGASISSPTIIVSHGSGSFTG* | 227 |
| ECOLIN_10070 | MVKTLILEGKMAKKFGKRVQFDVADLREMLRAMCSQVPGFKKY MSEAHMKGIRFAFFNGGNNIGLEEFDMTRGGSVYRIVPVYEGAKS SGVLQIVVGAVALVAAFFTAGASMAAWGAAMSATAISATSILTGV GVSMMLGGVVQMLTPQPSFGAGKSSSTDNTPNYAFGAPVNTVAM GHPVPLAYGLTEAGGAIVSAGMYSSDQQ* | 228 |
| ECOLIN_10075 | MREKLLDAIRQHVAAEYPKEACGLIVQSGQQQIFIPCRNIADKPEET FTLSPEDQLAARARGEIIMLIHSHPDVVRLVPSELDRIQCDWSGIEW GIMSWPDGDFCTISPREDRDYAGRQWVLGYADCWSLIREFYLREY GIVLGNYSVPYEWWESGKERLYDDNWEREGFVEIAAGAMQPGDII MMSVQASVTNHAAVYVGDNIILHHLFGHLSSRTPYGKYYRDRTV RVVRHKDRMHG* | 229 |
| ECOLIN_10080 | MSFTADIQQLEPGSVIQLIEIDGTEFGMDQVLRFHAHNIQEEGWAA FAAENLPAIIWQGNQYDPHPYELKGMELSSTGSQPTPTLSVGNVGN YVTALCLEYDDMVRAKVKIHTTLSKYLDAANWKNGNPGASPADE RLQLFYVNAKTAETRVQVDFELCSPFDIQSLQLPTRQITPVCTWCM RGWYRSGTGCDYNGTKYFTKDGTPTDDPSKDVCGGRRQDCQDR HGPDAPLPFGGFPAANLQGK* | 230 |

TABLE G-continued

Polypeptide sequences encoded by the genome of *E. coli* Nissle Phage 3.

| | | |
|---|---|---|
| ECOLIN_10085 | MTDTFTWRTRKTAQGTETARTLQAQFGDGYKQIAGMGINDKQET WNLDWTGTRQEAAALRAFLMSHVTKSFWWTTPWGEKKLFRMK ADSFSVSFPTGKKATVAFTFEQAFAP* | 231 |
| ECOLIN_10090 | MAQQISDLVINLDVDSATFSEQVARIKGQLTGMAEDSEKVQTRMQ RASERQAAAFKTVGDAGAAAAADMKSRQSAATEGLTKDWQNVS KSVDETHRRVTELNQRMRENDGQAAALARRQDELAASFFRQIDG VRQLNGETQSLANVQARFRAARAQGNITQQDYLALISRTTARQKE LQIVEEKSAAARTRFLSQLKQQVAEQKLSGTELLRMKAAQVGASD AAEVYIRKLEAAKVATHGLGLQSAAARQELGILIGEVMRGNFGAL RGSGITLANRAGWIDQLLSLRGLGIASMVGGIAAAVFGLGKAWYD GSKESEEFNRQLILTGNYAGKTSGQLQALARSLAGNGITQHAAAG VLAQVVGSGAFSGNDVSMVSNVAARLQQATGQAVDETINQFKRL KDDPVNAVATLNDSLHFLTATQYEQIASAQALGDSQKAAELAMR AYSDAVIQRAGAVEDNLGSLEKAWNWVKNAASGAWDAMLGVG RNPDTAMKRQDSFAEWQAAEKEYRALSSNLKVDPDYAGNNVLQ KADAERLRNARQQVELKKQAYDLADQQYAQEGLAAAREKMRTD QQAQAIRSQQQFNQLVESGATAAEKRASAEKKLSQLIEKNRQDAK DGVATLWTEKDIAAARAGIEKQWKDPKTPKGKSYSTPAGDKAEE KAQAELLTLQAQLKTLEQHTSVNDVISKQRQDLWQTENQFTVLQE AAGRRQLTAQEKSLLAHKEETLEYKRQLADLGDKVASQQKLNQL ADQAVKFEQQQKAARAGLQAQSEGLSTREAGRQTTLQRLSESYSY NPQAQQKVLEEQRATFEAEDALRANWLAGAKQGWAEYQDSATN VFSSVQQISQATFSGLAGQLTSLTTTGKASFREFTSSILKMIVSVINQ LLVAYTIQSAMGWVSGGAKTSSAGQSFAVPSYRPQGFDVGGFTGH GGKYEPAGIVHRGEFVFTKESTSRIGVANLYRLMRGYASGGLVGG GNAAGAGMGGISVYAPVSISQQGSDGSINQANATGTAKQLQAIVQ QTITERLKKEMSAGGVLYSRRTQ* | 232 |
| ECOLIN_10095 | MLAGMTSTELGDWHQFYREHYFQDAQLDAHFSELLYSISTLFFRD PELTPAHFSLLSPSGIVISDDEPDDDALMAAAEGITGGIRYGPAD* | 233 |
| ECOLIN_10100 | MFLKKEKFTWQKESLTIFELSALQRIEYITFMAAEEKAVSADSDGIS DQEMTARLIGSNIRCGARLIAMSLWHNDPAGTDVETLYQQVLSG WPPEAIGKAEMEIKLLSGMLVPVEDDKAADPDAPAEAESAEPVAA EKPLPAS* | 234 |
| ECOLIN_10105 | MPTPNPLAPVKGAGTTLWLYTGTGNAFANPLSDIDWNRLAKIKEL TPGEMTAESYDDTYLDDEDADWNATAQGAKSAGDTSFTLAWKP GEEGQKDLVAWFIDGSVRYYKIKYPNGTVDVFRGWCSSLGKAIPA KEVITRTAKITNTGKPELAEEESGTPNIPVTGVTLDKATASVAVGATT TLNVTVNPASASDTSFRVATSDGAKATVTVSGNAITVTGVAAGTA DVIVMTSDGNFVAVCKVTVTAA* | 235 |
| ECOLIN_10110 | MNRHSAIRAAILAKLKAEITDTVTWFDGRPVFLEEQDLPAVAVYLS DAEYTGDSLDEDSWQAVVHIEVFLKASSPDSALDSWMEEKVYPA MAFIPGLTELVETFTPQGYDYQRDDEMATWGSVDFTYLITYSI* | 236 |
| ECOLIN_10115 | MKGLERAIQNLNSLSRLIVPEATAKALNRVARRTISQGSKAVAKEA TVDDNRKKGLPVRLVRQRSRLRKARHDRPVASIKINRGNLPAIKLG TARVRLSRKKGARNGAGSVLKIGPYTFRNAFIQQLANGRWQVMR RVGQARYPIDVVKVPLETPLTVAFTAISKRLIESDMPKELSAALKN QLRIHLKR* | 237 |
| ECOLIN_10120 | MDAATIKKMGKTAIINGSSYDVVPAEQLEEMGPLSGTGTSLVVFSE LYQPRRNDSVDYDGKNLIVTRYDMFNGKPRIHLE* | 238 |
| ECOLIN_10125 | MAKNYAQDGKTIPLVNSGATDVHSGDPVVVGKLIAVAITDIPAGD TGDGFTEGVFLLPKVSADAVTAGAQVYLKDGKITIEETDAVAAGI AWEDAGANTTVVEVKINA* | 239 |
| ECOLIN_10130 | MQASNNSEADIFIYDEIGYWGVTAKQFVNDLRALGDVTHINLYINS PGGDVFDGIAIYNALKHHGAAITVHIDGLAASMSASVIAMVGNPVI MPENTMMMIHKPWGFAGGDASDMRDYADLLDKVESVLIPAYAQ KTGKSTEEIAVMLEDETWMNGSECLELGFADQVTPSLQAMACIHS KRIEEFEKMPKSIRNMITPPRNTTQRDPVITQPQAPQAKTDPAPDEN AIRAQVLAEQKTRVNAIGDLFAMFGNKHMELQNQCVADPDCSVD KAKDLLLAELGKTATPSNKTTQPHIHAGNGNFVADGIRQALMARA GFEGQERDNVYNGMTLREYARMALTEKGIGVASYNPMQMVGLA LTHSTSDFGNILLDVANKALIQGWDEAQETFEQWTKKGQLSDFKT AHRVGMGGFPSLRQVREGAEYKYITTSDKGETIALATYGEIFSVTR QAIIINDDLNQLTDVPMKMGRAAKATIGDLVYAILTKNPKLSDGA LFHADHKNLSSGAISVASLDESRKLMRLQKEGERTLNIRPAYMLVP VALETLANQSSIKSASVKGADINAGIVNPIQNFAEVIAEPRLDEADAK AWYLAAAKGTDTIEVAYLNGVDTPYIDQQEGFTTDGIATKVRIDA GVAPLDYRGMTKSSGQ* | 240 |

TABLE G-continued

Polypeptide sequences encoded by the genome of *E. coli* Nissle Phage 3.

| | | |
|---|---|---|
| ECOLIN_<br>10135 | MSFLDDAIGLFSPGWKASRLRARAVIKAYEAVKQTRTHKAQKENR<br>SADQLSQMGAVSLRQQARWLDNNHDLVIGVFDKLEERVVGAKGI<br>IVEPHPMLSNGKIAKKLATDIRRKWGEWSVRPDVTTQFTRPMLER<br>LMLRTWLRDGEVFAQLVRGTGNGLQPVAGVPFWLEALEPDFVPM<br>NSDAATQLNQGVFVDNWGRPKKYQVYKSLPVSGRQFDTKEIDAE<br>NMLHLKFTRRLHQTRGTSLLSGVLMRLSALKEYEDSELTAARIAA<br>ALGMYIKKGDGQSFDSDSSSDDRELMIQPGMLYDELQAGEEIGMI<br>KSDRPNPNLESFRNGQLRAVSAGSRLSFSSTSRNYNGTYSAQRQEL<br>VESTDGYLILQDWFIGSVTRPMYRAWLKMAIAAGEIKLPRGIDMD<br>SLYNAVYSGPVMPWIDPVKEANAWKTQIRGGAATESDWIRASGR<br>NPDDVKSRRKAEVDENREQGLVFDTDPANDKG6TSAEAKEPGAP<br>PSESQRKK* | 241 |
| ECOLIN_<br>10140 | MNPADIQNMIDRYAAAELSVLEGKSITFNGQQMTLENLSEIRKGRQ<br>EWERRLATLNNKRRGRPGYRLARFG* | 242 |
| ECOLIN_<br>10145 | MAKRASARDIRRDVSGILRAPRRMPVADAVSTYMRVPMGAGNSV<br>PWDPDLAPYVIEPMNCLASREYDAVVFVGPARTGKTIGLIDGWIV<br>YNIVCDPADMLVIQVSEEKAREHSKKRLDRTFRCSPEVKTRLSPRR<br>NDNNVYDRTFRAGNYLKLGWPSVNIMSSSDYKSVALTDYDRFPE<br>DIDGEGDAFSLASKRTTTFMSSGMTLVESSPGRDIRDTKWRRSTPH<br>EAPPTTGILSLYNRGDRRRLYWPCPHCGEYFQPEMDNMTGYRDSS<br>DPVLASEAAFLQCPACKGRITPDMKRALNMKCVWLRDGQTIDRK<br>GLVSGDGRRSRIASFWMEGPAAAYQTWAQLIYKFLTAEQEYESTR<br>SEETLKTVINTDFGRPYLPRASMEQRKSELLEQRAEDVPKRSVPNG<br>VQFLTATVDVQAGRNRRFVVQITGYGSMGERWIVDRYNIRHSLRC<br>DGNGESIQVDPASYPEDWDLLLTDVFDKTWPLAADPSKGMRLMS<br>MAVDSGGEDGVTDNAYKFWRRCRREGLGKRIYLFKGDSVRRSKL<br>IQRTFPDNTGRSTRRAQATGDVPLYLLQTDALKDRVNNALWRDSP<br>GPGYVHFPAWLGSWFYDELTYEERSNEGKWSKPGRGANEAFDLL<br>VYADALAILSGYEKIKWPSAPEWARRETWIEDTQTEAGEMPSPPPA<br>PKSKPKPKREKPVTEQANPWSSSGGWV* | 243 |
| ECOLIN_<br>10150 | MDQEIATLKLNINQLAGITGVHRQTVAARLKNVEPAPGSNSKLKL<br>YLVTDILTELMIPTVSANIDDMPPSDRLSHWKAENERLKFEQDTGQ<br>LIPADEVAREFSLMAKAVVMVLETLPDVLERDCALTPAAVVRVQS<br>VIDDLRDQMAEKVQDAGKEEEQPEED* | 244 |
| ECOLIN_<br>10160 | MSNKIITLSGAANEVLYALFFRGALLSGDLPSKSGTAELRELGFAET<br>RHTATEYQKENHFTFLTSEGQKFAVEHLVNTRFGEQQYCASMTLG<br>VEIDTSAAQKAIDELDQRIRDTVSFELIRNGVSFIKDAAIANGAIHA<br>AAIETPQPVTNIYNISLGIQRDEPAQNKVTVSADKFKVKPGVDTNIE<br>TLIENALKNAAECAALDVTKQMAADKKAMDELASYVRTAIMMEC<br>FPGGVIWQQCRR* | 245 |
| ECOLIN_<br>10165 | MKILAFINPPGSYMQIETKEMVIFLRDDGISLQYPDGQCAGYGIDG<br>NMLIFMGQSCELFPTKIILHDQRTTNFTHK* | 246 |
| ECOLIN_<br>10170 | MDYYHEIDFPSLFARAVESDDDVGTTLRIHLLCERMVEAWICACC<br>DCQDLFGRDKNKLLIECNTKISMAGNLGIPPELMKSLKTINSMRND<br>LAHNPSIQSIADSRIQSLKDTLTEYFKQHPTEPSMEESKLGIFNAENQ<br>LTEEVSLDSDSSKNRLKLILLFSKLMQALMQLVAANHNGRWDNQF<br>SQFVYHVTMNATKR* | 247 |
| ECOLIN_<br>71015 | MTVVLTAKQIEDLAAFAKEDGQPQYTITTGTIPEFEADNGEIIPGYT<br>GLIAYSESLDHGVLQLDD* | 248 |
| ECOLIN_<br>10180 | MVIVALVGSFLAGSEWTNRSWKIKWADRDSAESSQEANAQTAAR<br>MIEQGRTIARDEAVKDAQAQAASAAVTSAGLATTVKQLRAEATK<br>LATHMDAAKHTADLATSVRSKTAGANAAMLADMLGSLAEAARY<br>YAGRSDESYRAGMTCERIYESVRLSNNQ* | 249 |
| ECOLIN_<br>10185 | MAMSLKLKNKLSAAVVGLILAGASAPVILDQFLDEKEGNSLTAYR<br>DGGGLWTICRGATMVDGKPVVQGMKLSAEKCAQVNAIERDKAL<br>AWVDRNIKVPLTEPQKAGIASFCPYNIGPGKCFPSTFYKRINAGDT<br>KGACEAIRWWIKDGGRDCRLTKGQKDGCYGQVERRDQESALTC<br>WGIDQ* | 250 |
| ECOLIN_<br>10190 | MTRMSTIYSRLSYGSGTTLAGCGVSAKAYAETAKTAKEVSWMLA<br>DRIAGLSLSDWAIIVGIACTVITCAVNWYFRWKEREDRRNGYVSK<br>AEE* | 251 |
| ECOLIN_<br>10195 | MKNTVKINSVELINADSLHYVATLPDNSIDLIVTDPPYFKVKPNGW<br>DNQWKGDEDYLRWLDSCLAEYARVLKPAGSIYLFCGHRLASDIEI<br>MMRARFNVLNHIIWAKPSGRWNGCNKESLRAYFPSTERILFAEHY<br>LGPYTGKEDVYERKSTELKQHIMTPLIDYFRNARESLGVSSKEIAE<br>ATGKKNMASHWFGASQWQLPNEVDYRKLQELFTRIAIDKHIQQK<br>LEHPHHQLVATYQSLNRKYSELLEEYKILRRCFSVSALVPYTDVW | 252 |

TABLE G-continued

Polypeptide sequences encoded by the genome of E. coli Nissle Phage 3.

| | | |
|---|---|---|
| | THKPVQFYPGKHPCEKPADMLKQIISASSRPGDIVADFFMGSGSTV KAAIELGRRAIGVELEADRFIQTTEEVEKLKKS* | |
| ECOLIN_10200 | MLNQEDMTETAKAVFNELSDKPATAGEIAQNTHLSHERCQLILTQ LVMAGLSDYQFGCYKRLQ* | 253 |
| ECOLIN_10205 | MPNWIDVLGEMGTIAQRTPADEVRHKYLRDLSKHTGRNVISYYSG FLQKGGPGFQHLIQMSDDDKNGLMSAINGLDTSLGLDILLHTPGG DIAALESIGHYLRSKFGTNIRAIVPMISMSCGTMLACCAEQIVLGKQ SNLGPIDPQFNGLSSHAIIEEYERAKAEIFANPAALQWWQFTFQKL NPTLIGECEKAILWANEIVQKWLCTGMFAGQADAEAKAKRICDEL NNHQATYAHARHIHLDKAQNIGLNIMELESDQTLQDLVLTIHHCY MHSFGTSPAAKIIENHNGSTMMWNIC* | 254 |
| ECOLIN_10210 | MSAAEFYEKMGIQPQEFQKGESVQHFAMRVLAQQNDLNVRSGVL YSYSTVTPNTTEQNGQQSHQLYSY* | 255 |
| ECOLIN_10220 | MNQQDLNFVRIELRRALPDLSGGTKGQLEAFSEHPPADKNATPRR GIHLVELEGEKGPRFVNSLSAPLYVLETRSRRRPMPPIKDAEFESAP WRRAVSALSGYQQAWLRYCYGFDLSYKHQVMMCEYVWKTYQK CLGDNSLQERVVKKLIGLVWLAGQEIAATRNNETYKDYAGAALA RMVSVDRSTWLRVYSGHWAGLKAAFTQLDESALAMALEYYEEE EALKVAEM* | 256 |
| ECOLIN_10225 | MRALLTPEIAHRMGIVLFRPGAELMHLFMRGRVLLEPEPEEMASFS TGAVPAAIQPLADDPVMRQVFENDRVIQRAGGLPSLEQWLSNRFE CQWPHSSWHDKNFTTMRHPPGSIRLCWHCDHTLSGQHTEQLAGIA AGNLVSWILEVIRRDSGFPPESHILTLPELCWWMVRNDLADVIPESV AHKGLRLPDDKIRSVMRESDIVPSASATSLVQEKAKKILTLSVDPES PESFMLRPKRRRWINETYTRWVKTQPCECCRRPADDPHHIVGHGM GGTATKAHDLFVIPLCRECHDELHADVPAFEQKHGTQLELLLRFM DRALAIGVIAKA* | 257 |
| ECOLIN_10230 | MSQLATTALTMSSSDIAELVESRHDHVKRSIERLAERGVIELPPMG EVKNHLNQSVSVYLIGKRDSYIVVAQLSPEFTARLVDRWQELEQA QQQTIPQSFSEALRLAADLAEQKQQLTNELAAAAPKVAFVDRYCT ASGSMSFRQVAKLLKAKEPDLRLFLLENDIMYRLGGTMTPRHQHI DAGRFEVKTGTSVTSNHAFSQARFTAKGVRWIGGLWAEHIARGQ VA* | 258 |
| ECOLIN_10235 | MKLILPFPPSVNTYWRAPNKGPLAGRHLISAAGRKYQSAACVAIIE QLRRLPKPSTELAAVEITLYPPDARRRDIDNYNKALFDALTHAGV WEDDSQIKRMLVEWGPVVPKGRVEITISRYEPAGAAA* | 259 |
| ECOLIN_10240 | MMTNKYCQALAALRSKPAHELKEVGDQWRTPDLLFWGINALFGP LVLDLFADDDNAKCPAWYTAEDNALTQDWSERLAELGGAGYGN PPYSRSQYHEKQAITGMTHIMNYAAAQREKGGRYVFLIKAAPSET WWPEDADHIVFIRGRIGFDLPVWFVPADEKQKPTSAFFAGAIAVFD KSWRGERFSYINRTELEAKGRAFMALAQFAASKSQPVTATPPAAD KPEAELPLTQKDIFAISGVEAWACVRAAFGDKEEYTFSESKFGHTW AADSVEAPEFTQVSPLTIDKAKLLIRESILFGVDEWLLSIEFDDAAV RLDMSERIRTVALEASGEYGMNSTDFIAAMGSLDVSSWSNIRQIRM HIREKAKPVSDPLPESRIWPLEVRIVFDQVDGADMLDESLQHKLKA NINQLWLERTATSEIITAASELVRNMRGEAA* | 260 |
| ECOLIN_10245 | MSTKLTGYVWDACASSGMKLSSVAIMARLADFSSDEGVSWPSIGT IARQIGAGESTVRTALAQLEKDGWLSRKQRRNGNRNASNVYQLN VVKLREAAFSHLSESDASKSDPSKSDASKSDPSKFEASKSSKKGGF DPSESGGDPSVKSKQEPQVTSKPSCPVAAQPDPEVVITDQARQVLS YLNQTTGSRYQVCSTSLENIRARLREQFTVDDLCLVVDYKNADWR DSEQAQYLRPATLFIPKNFPGYLQSATKWSSAGRPERVNGKWETN SASRANFQSVDYSLPENSGFRS* | 261 |
| ECOLIN_10250 | MNSVNRFRPAKQFRCLPLVGKDAQFGYVEIINNAADGGNYQPADL MVEAFVQMNEKGREEWLKLTGGSEITTEFPSELSAGSQIHSALYTF AKGTIMSASALLNNSSVNLQN* | 262 |
| ECOLIN_10255 | MVDSINTAIRLMCKAHKHGRLGMASDLGMTIDQFHNHLYQKCGS RFFTLAELERMEDLSGSCYLAEYQANRKGKWLVDVPTAESLDNV ELYSIEMKAAAASGELANAKMAAAADGVIDSSERKMLSELFSKKL RHQIHGFLGFMALYGVGVSDQAIDVFVSTGRKGDARECAAPGAL ACRISGETNA* | 263 |
| ECOLIN_10260 | MSSQHKNVTAKAVKAIGSISEVSRRFEFQSVQSVANWIAKNRVPSE RVIQLCQWGGWVVTPHQLRPDIYPNKNDGIPSANNNSQL* | 264 |
| ECOLIN_10265 | MPCALNLLLMVENAKYKDFAERLNRSLQEQSIGVKELSEFSGVSY EMARRYTLGTAKPRDEKMIRIAERLAVSPAYLDYGVPVNGGDAPA | 265 |

TABLE G-continued

Polypeptide sequences encoded by the genome of *E. coli* Nissle Phage 3.

| | | |
|---|---|---|
| | KGTVRIEQLDVHASAGSGYINQPFPTIVSSIEIPEERIFELFGRRSLDG IVMINVDGDSMMPTLCPKDLLFIDSKVEQFSGDGVYVFNFEDSTFV KRLQKVKGRRLAVLSDNEHYPPFFIEEHEMNELYIFGKLIRCLPLK MIEFG* | |
| ECOLIN_10270 | MGAFDNQEITLPACPKCGTKTKKKIAWLKSNKSFTCRCGATINVN SSQLTSEIRKVEDKLKKLFK* | 266 |
| ECOLIN_10275 | MNNPFFKNMLVYRISRDFTINQEELEQQLELFRFTPCGSQDMAKTG WVSPLGQLSDRLHHTVNNQVLLVIRREEKILPSPVITEELRKRVSRL ESDQGRRLKKTEKDSLRDEVLHSLLPRAFSKNSTVGLWINVTDGLI MVDAASAKRAEDSLALLRKTLGSLPVVPLTMETPIELTMTDWVRS GSAPAGFGLGDEAELKAILEDGGIGRFKKQTLVSDEIHVHLEAGKV VTKLSIDWQQRIQFVLCDDGSIKRLKFSNEITEQNDDIDREDAAQRF DADFVLMTGELISLINGLTTSLGGEAKR* | 267 |
| ECOLIN_10280 | MSYIQTLSGKHFNYLDIQQDDIVIEDIATALSHICRFAGHLPEFYSV GQHSVLTSHLVPQEFALEALLHDAAEAYLQDIPSPLKRLLPDYQAI EARVDAAIRQKFGLPTEQHPTVKYADLVMLASERRDFEIDEGSIWP CLEGVVPTDLFIINPVRPGQSYGMFINRFNELMEQRQCAA* | 268 |
| ECOLIN_10290 | MTVFEYLQAHPNTTSGEIAKGMNKKTPAVAGALSQLYGTGRIVKS GVRKGIPTYRINDMPFGCSNSLTMMFNQLLSRARQGAAQ* | 269 |
| ECOLIN_10295 | MTALNKQALREEFQFMQDNYSDPADHDRQVIYIEAEALLDELEAK DSTIAAQQHEIRMLLNALEEKPCPKCNDTGMTDSGGTQPWGEPIEI ECDCRQQDANTAELVAAGIGVKGE* | 270 |
| ECOLIN_10300 | MDKLIKPTAKGKYDGSCDYLCSEDARFIVMRGDYTEAEIIQASVSQ DVIDSDGAADFASSARYYQCWYKVSPIGGQDGYSGWHHPRDSPC RGAYFASVLQWD* | 271 |
| ECOLIN_10305 | MTTNNHPAHGPVSLDRLHQIREHLLHDTQYSNGGNRAYILADVLK VIDGAIARELVRREHAAWSQATFGDVGPVGPLKHLSKEALEAAAE PGDLSEWADMQFLLWDAQRRAGISDEQITQAMIKKLAINKVRQW PEPKDGEPRLHIKEQSEQEKK* | 272 |
| ECOLIN_10310 | MFSLIRRGQIYTDSSNWPVIIHSCSDHSVRIKRNDGELRTISIKRFNE DFERVEHDEYRKICAEIEQETNLKNLRAMRRGKITE* | 273 |
| ECOLIN_10315 | MNNLMIDLESMGKKPNAPIVSIGAVFFDPQSGELGQEFYTAVNLES AMEQGAVPDGDTILWWLRQSSEARSAICVDDAMPISSALSELSHFI NRHSDNPKYLKVWGNGATFDNVILRGAYERAGQVCPWQFWNDH DVRTIVTLGRSVGFDPKRDMPFDGVAHNALADARHQAKYVSAIW QKLIPTTSNS* | 274 |
| ECOLIN_10320 | MSNIFQLAPNDWVCESVLIAVTGLKPGTILRARKECWMIGREYIHV SPDGNPKPSSECMYNRKAVDAWVASMKSKQPG* | 275 |
| ECOLIN_10325 | MDKVTYPTGVENHGGTLRIWFNFKGKRVRESLGVPDTAKNRKIA GELRTSVCFAIRTGTFDYATQFPDSPNLKAFGVSKKDITVKELEEK WLDLKRMEICANAFNRYESVARNMVPRIGGNRLVSAVTKEELLYL RKYLLTGYQNPTKNKAPAKGRSVVTVNYYMTTMAGMFQFAADH GYLEVNPFEGIKPLKKARAEPDPLSRDEFIRLIDACRHQQTKNLWS LAVYTGMRHGELVSLAWEDIDLKAGTITVRRNYTKLGEFTLPKTE ASTDRVVHLIQPAISILKNQAEMTRLGRQYHIEVQLREYGRSVNHE CTFVFNPHVVRRSKQVGFIYRVDSVGDSWEAALKRAGIRHRKAYQ SRHTYACWSLSAGANPSFIASQMGHASAQMVFNVYGAWMADSS AEQIAMLNQKLADFAPLMPHSHENSTGGLLKSVS* | 276 |
| ECOLIN_10330 | MEGNTTLYALPKPEVVLRWREQTTDDFRFCFKFPATISHQAALRH CDDLVTEFLTRMSPLAPRIGQYWLQLPATFGPRELPALWHFLDSLP GEFNYGVEVRHPQFFAKGEEEQTLNRGLHQRGVNRVILDSRPVHA ARPYSEAIRDAQRKKPKVPVHAVLTAKNPLIRFIGSDDMTQNRELF QVWLQKLAQWHQTTTPYLFLHTPDIAQAPELVHTLWEDLRKTLPE IGAVPAIPQQSSLF* | 277 |
| ECOLIN_10335 | MVSALYAVLSALLLMKFSFDVVRLRMQYRVAYGDGGFSELQSAI RIHGNAVEYIPIAIVLMLFMEMNGAETWMVHICGIVLLAGRLMKL YGFHHRLFRWRRSGMSATWCALLLMVLANLWYMPWELVFSLR* | 278 |
| ECOLIN_10340 | MSHRDTLFSAPIARLGDWTFDERVAEVFPDMIQRSVPGYSNIISMIG MLAERFVQPGTQVYDLGCSLGAATLSVRRNIHHDNCKIIAIDNSPA MIERCRRHIDAYKAPTPVDVIEGDIRDIAIENASMVVLNFTLQFLEP SERQALLDKIYQGLNPGGALVLSEKFSFEDAKVGELLFNMHHDFK RANGYSELEISQKRSMLENVMLTDSVETHKARLHKAGFEHSELWF QCFNFGSLVALKAEDAA* | 279 |

TABLE G-continued

Polypeptide sequences encoded by the genome of *E. coli* Nissle Phage 3.

| | | |
|---|---|---|
| ECOLIN_<br>10345 | MIDFGNFYSLIAKNHLSHWLETLPAQIANWQREQQHGLFKQWSNA<br>VEFLPEIKPYRLDLLHSVTAESEEPLSAGQIKRIETLMRNLMPWRK<br>GPFSLYGVNIDTEWRSDWKWDRVMPHLSDLTGRTILDVGCGSGY<br>HMWRMIGAGAHLAVGIDPTQLFLCQFEAVRKLLGNDQRAHLLPL<br>GIEQLPALKAFDTVFSMGVLYHRRSPLEHLWQLKDQLVNEGELVL<br>ETLVIDGDENTVLVPGDRYAQMRNVYFIPSALALKNWLKKCGFV<br>DIRIADVSVTTTEEQRRTEWMVTESLADFLDPHDPGKTVEGYPAPK<br>RAVLIARKP* | 280 |

In any of these embodiments, the bacteria described herein comprise one or more modifications or mutations within the *E. coli* Nissle Phage 3 genome. In some embodiments, the modifications alter the properties or behavior of the Phage 3. In some embodiments, the modifications or mutations prevent Phage 3 from entering or completing the lytic process. In some embodiments, the modifications or mutations reduce the ability of Phage 3 to enter the lytic process. In some embodiments, the modifications or mutations prevent the *E. coli* Nissle Phage 3 from infecting other bacteria of the same or a different type.

In some embodiments, the modifications or mutations alter, e.g., increase or reduce, the fitness of the bacterial host. In some embodiments, the modifications or mutations essentially have no effect on bacterial fitness, and the bacterial fitness is essentially the same as the fitness of the isogenic strain without the modifications or mutations. In some embodiments, the modifications or mutations alter, e.g., increase or reduce, the desired effector function, e.g., of a genetically engineered bacterium. In some embodiments, the modifications or mutations improve the desired effector function, e.g., of a genetically engineered bacterium. In some embodiments, the modifications or mutations essentially have no effect on effector function, and the effector function is essentially the same as effector function of the isogenic strain without the modifications or mutations. In some embodiments, the effector circuits are engineered into the genome first and then the phage is modified. In some embodiments, a new chassis with a modified Phage 3 is generated prior the engineering of the effector function(s).

In some embodiments, the bacteria comprise at least about 1 to 2, at least about 2 to 3, at least about 3 to 4, at least about 4 to 5, at least about 5 to 6, at least about 6 to 7, at least about 7 to 8, at least about 8 to 9, at least about 9 to 10, at least about 10 to 11, at least about 11 to 12, at least about 12 to 13, at least about 13 to 14, at least about 14 to 15, at least about 15 to 16, at least about 16 to 17, at least about 17 to 18, at least about 18 to 19, at least about 19 to 20, at least about 20 to 21, at least about 21 to 22, at least about 22 to 23, at least about 23 to 24, at least about 24 to 25, at least about 25 to 26, at least about 26 to 27, at least about 27 to 28, at least about 28 to 29, at least about 29 to 30, at least about 30 to 31, at least about 31 to 32, at least about 32 to 33, at least about 33 to 34, at least about 34 to 35, at least about 35 to 36, at least about 36 to 37, at least about 37 to 38, at least about 38 to 39, at least about 39 to 40, at least about 40 to 41, at least about 41 to 42, at least about 42 to 43, at least about 43 to 44, at least about 44 to 45, at least about 45 to 46, at least about 46 to 47, at least about 47 to 48, at least about 48 to 49, at least about 49 to 50, at least about 50 to 51, at least about 51 to 52, at least about 52 to 53, at least about 53 to 54, at least about 54 to 55, at least about 55 to 56, at least about 56 to 57, at least about 57 to 58, at least about 58 to 59, at least about 59 to 60, at least about 60 to 61, at least about 61 to 62, at least about 62 to 63, at least about 63 to 64, at least about 64 to 65, at least about 65 to 66, at least about 66 to 67, at least about 67 to 68, at least about 68 to 69, at least about 69 to 70, at least about 70 to 71, at least about 71 to 72, at least about 72 to 73, at least about 73 to 74, at least about 74 to 75, at least about 75 to 76, at least about 76 to 77, at least about 77 to 78, at least about 78 to 79, at least about 79 to 80, at least about 80 to 81, at least about 81 to 82, at least about 82 to 83, at least about 83 to 84, at least about 84 to 85, at least about 85 to 86, at least about 86 to 87, at least about 87 to 88, at least about 88 to 89, at least about 89 to 90, at least about 90 to 91, at least about 91 to 92, at least about 92 to 93, at least about 93 to 94, at least about 94 to 95, at least about 95 to 96, at least about 96 to 97, at least about 97 to 98, at least about 98 to 99, at least about 99 to 100, or at least about 100 or more modifications or mutations.

In some embodiments, the modifications or mutations reduce entry or completion of Phage 3 lytic process by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold. In some embodiments, the modifications or mutations reduce entry or completion of Phage 3 lytic process completely.

In some embodiments, the modifications or mutations reduce entry or completion of Phage 3 lytic process by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100%.

In some embodiments, the modifications or mutations prevent *E. coli* Nissle Phage 3 genome from infecting other bacteria of the same or a different by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold. In some embodiments, the modifications or mutations prevent the *E. coli* Nissle Phage 3 from infecting other bacteria of the same or a different type completely. In some embodiments, the modifications or mutations prevent the *E. coli* Nissle Phage 3 from infecting other bacteria of the same or a different type by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100%.

In some embodiments, the modifications or mutations alters, increases or reduces, the fitness of the bacterial host by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold as compared to the same isogenic strain without the phage modification. In some embodiments, the modifications or mutations alters, increases or reduces, the fitness of the bacterial host by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% as compared to the same isogenic strain without the phage modification.

In some embodiments, the modifications or mutations alters, e.g., increases or reduces, the desired effector function, e.g., of a genetically engineered bacterium by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold as compared to the same isogenic strain without the phage modification. In some embodiments, the modifications or mutations alter, e.g., increase or reduce, the desired effector function, e.g., of a genetically engineered bacterium by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% as compared to the same isogenic strain without the phage modification.

In some embodiments, the mutations include one or more deletions within the *E. coli* Nissle Phage 3 genome sequence. In some embodiments, the mutations include one or more insertions into the *E. coli* Nissle Phage 3 genome sequence. In some embodiments, an antibiotic cassette can be inserted into one or more positions within the *E. coli* Nissle Phage 3 genome sequence. In some embodiments, the mutations include one or more substitutions within the *E. coli* Nissle Phage 3 genome sequence. In some embodiments, the mutations include one or more inversions within the *E. coli* Nissle Phage 3 genome sequence. In some embodiments, the inversion may be governed by a specific flippase. Exemplary circuitry comprising multiple levels of control are exemplified herein and are also described in co-owned pending International Patent Application PCT/US2016/039434, the contents of which is herein incorporated by reference in its entirety.

In some embodiments, the modifications within the *E. coli* Nissle Phage 3 genome are combinations of two or more of insertions, deletions, substitutions, or inversions within one or more *E. coli* Nissle Phage 3 genome genes.

In any of the embodiments described herein, the modifications may result in one or more frameshift mutations in one or more genes within the *E. coli* Nissle Phage 3 genome. In any of the embodiments described herein, the modifications may result in one or more missense mutation in one or more genes within the *E. coli* Nissle Phage 3 genome. In any of the embodiments described herein, the modifications may result in one or more nonsense mutations in one or more genes within the *E. coli* Nissle Phage 3 genome.

In some embodiments, the modifications within the *E. coli* Nissle Phage 3 genome are combinations of two or more frameshift, nonsense or missense mutations within one or more *E. coli* Nissle Phage 3 genome genes.

Mutations

In some embodiments, the one or more mutations comprise at least about 1-500 bp of the *E. coli* Nissle Phage 3 genome. In some embodiments, the one or more mutations comprise at least about 500-1000 bp of the *E. coli* Nissle Phage 3 genome. In some embodiments, the one or more mutations comprise at least about 1000-2000 bp of the *E. coli* Nissle Phage 3 genome. In some embodiments, the one or more mutations comprise at least about 1000-2000 bp of the *E. coli* Nissle Phage 3 genome. In some embodiments, the one or more mutations comprise at least about 2000-3000 bp of the *E. coli* Nissle Phage 3 genome. In some embodiments, the one or more mutations comprise at least about 3000-4000 bp of the *E. coli* Nissle Phage 3 genome. In some embodiments, the one or more mutations comprise at least about 4000-5000 bp of the *E. coli* Nissle Phage 3 genome. In some embodiments, the one or more mutations comprise at least about 5,000-6,000 bp of the *E. coli* Nissle Phage 3 genome. In some embodiments, the one or more mutations comprise at least about 6,000-7,000 bp of the *E. coli* Nissle Phage 3 genome. In some embodiments, the one or more mutations comprise at least about 7,000-8,000 bp of the *E. coli* Nissle Phage 3 genome. In some embodiments, the one or more mutations comprise at least about 8,000-9,000 bp of the *E. coli* Nissle Phage 3 genome. In some embodiments, the one or more mutations comprise at least about 9,000-10,000 bp of the *E. coli* Nissle Phage 3 genome. In some embodiments, the one or more mutations comprise at least about 10,000-15,000 bp of the *E. coli* Nissle Phage 3 genome. In some embodiments, the one or more mutations comprise at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In one specific embodiment, 9687 bp of the *E. coli* Nissle Phage 3 genome are mutated. In some embodiments, the mutated nucleotides are interspersed. In some embodiments, the mutated nucleotides are consecutive.

In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome is mutated. In some embodiments, at least about 30-40% of the *E. coli* Nissle Phage 3 genome is mutated. In some embodiments, at least about 40-50% of the *E. coli* Nissle Phage 3 genome is mutated. In some embodiments, at least about 50-60% of the *E. coli* Nissle Phage 3 genome is mutated. In some embodiments, at least about 60-70% of the *E. coli* Nissle Phage 3 genome is mutated. In some embodiments, at least about 70-80% of the *E. coli* Nissle Phage 3 genome is mutated. In some embodiments, at least about 80-90% of the *E. coli* Nissle Phage 3 genome is mutated. In some embodiments, 90-100% of the *E. coli* Nissle Phage 3 genome is mutated.

In some embodiments, at least about 1, 2, 3, 4, 5, 6, 7, 8, 9, 10, 11, 12, 13, 14, 15, 16, 17, 18, 19, or 20 genes are mutated. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are mutated. In some embodiments, 13 genes are completely or partially mutated. In one embodiment, 74 genes are completely or partially mutated.

In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the *E. coli* Nissle Phage 3 genome are completely or partially mutated.

In some embodiments, the one or more mutations are located at the beginning or 5' end of the *E. coli* Nissle Phage 3 genome. In some embodiments, the one or more mutations are located at the end or 3' end of the *E. coli* Nissle Phage 3 genome. In some embodiments, the one or more mutations are located in the middle of the *E. coli* Nissle Phage 3 genome. In some embodiments, the *E. coli* Nissle Phage 3 genes are interspersed within the bacterial genome and the mutation are located in one or more of the interspersed positions.

In some embodiments, the mutations are located within or encompass one or more genes encoding lytic genes. In some embodiments, the mutations are located within or encompass one or more genes encoding one or more proteases or lysins. In some embodiments, the mutations are located within or encompass one or more genes encoding one or more toxins. In some embodiments, the mutations are located within or encompass one or more genes encoding one or more antibiotic resistance related proteins. In some embodiments, the mutations are located within or encompass one or more genes encoding one or phage translation related proteins. In some embodiments, the one or more mutations are located within or encompass one or more genes encoding structural proteins. Such structural genes include genes encoding polypeptides of the head, tail, collar, or coat. In some embodiments, the one or more mutations are located within or encompass one or more genes encoding head proteins. In some embodiments, the one or more mutations are located within or encompass one or more genes encoding tail proteins. In some embodiments, the one or more mutations are located within or encompass one or more genes encoding collar proteins. In some embodiments, the one or more mutations are located within or encompass one or more genes encoding coat proteins. In some embodiments, the mutations are located within or encompass one or more genes encoding one or more plate proteins. In some embodiments, the mutations are located within or encompass one or more genes encoding one or more proteins require for assembly of the bacteriophage. In some embodiments, the mutations are located within or encompass one or more genes encoding one or more portal proteins. In some embodiments, the mutations are located within or encompass one or more genes encoding one or more polypeptides involved in recombination. In some embodiments, the mutations are located within or encompass one or more genes encoding one or more integrases. In some embodiments, the mutations are located within or encompass one or more genes encoding one or more invertases. In some embodiments, the mutations are located within or encompass one or more genes encoding one or more transposases. In some embodiments, the mutations are located with within or encompass one or more genes encoding one or more polypeptides involved in replication or translation. In some embodiments, the mutations are located within or encompass one or more genes encoding one or more primases. In some embodiments, the mutations are located within or encompass one or more genes encoding one or more tRNA related proteins. In some embodiments, the mutations are located within or encompass one or more genes encoding one or more polypeptides involved in phage insertion. In some embodiments, the mutations are located within or encompass one or more genes encoding an attachment site. In some embodiments, the mutations are located within or encompass one or more genes encoding one or more polypeptides involved in packaging. In some embodiments, the mutations are located within or encompass one or more genes encoding one or more terminases. In some embodiments, the mutations are located within or encompass one or more genes encoding one or more host genes.

In some embodiments, the mutations are located within or encompass genes encoding one or more polypeptides involved in one or more of cell lysis, phage structure, phage assembly, phage packaging recombination, replication or translation, phage insertion, or are host proteins, and combinations thereof.

In some embodiments, the mutations are located within or encompass genes encoding one or more polypeptides involved in one or more of cell lysis, phage structure, phage assembly, phage packaging recombination, replication or translation, phage insertion, and combinations thereof.

In some embodiments, the mutations are located within or encompass 1 genes encoding polypeptides involved in cell lysis, phage structure, phage assembly, phage packaging recombination, replication or translation, phage insertion, and combinations thereof. In some embodiments, the mutations are located within or encompass 2 genes encoding polypeptides involved in cell lysis, phage structure, phage assembly, phage packaging recombination, replication or translation, phage insertion, and combinations thereof. In some embodiments, the mutations are located within or encompass 3 genes encoding polypeptides involved in cell lysis, phage structure, phage assembly, phage packaging recombination, replication or translation, phage insertion, and combinations thereof. In some embodiments, the mutations are located within or encompass 4 genes encoding polypeptides involved in cell lysis, phage structure, phage assembly, phage packaging recombination, replication or translation, phage insertion, and combinations thereof. In some embodiments, the mutations are located within or encompass 2 genes encoding polypeptides involved in cell lysis, phage structure, phage assembly, phage packaging recombination, replication or translation, phage insertion, and combinations thereof. In some embodiments, the mutations are located within or encompass 5 genes encoding polypeptides involved in cell lysis, phage structure, phage assembly, phage packaging recombination, replication or translation, phage insertion, and combinations thereof. In some embodiments, the mutations are located within or encompass 6 genes encoding polypeptides involved in cell lysis, phage structure, phage assembly, phage packaging recombination, replication or translation, phage insertion, and combinations thereof. In some embodiments, the mutations are located within or encompass 7 genes encoding polypeptides involved in cell lysis, phage structure, phage assembly, phage packaging recombination, replication or translation, phage insertion, and combinations thereof. In some embodiments, the mutations are located within or encompass 8 genes encoding polypeptides involved in cell lysis, phage structure, phage assembly, phage packaging recombination, replication or translation, phage insertion, and combinations thereof. In some embodiments, the mutations are located within or encompass 9 genes encoding polypeptides involved in cell lysis, phage structure, phage assembly, phage packaging recombination, replication or translation, phage insertion, and combinations thereof. In some embodiments, the mutations are located within or encompass 10 genes encoding polypeptides involved in cell lysis, phage structure, phage assembly, phage packaging recombination, replication or translation, phage insertion, and combinations thereof. In some embodiments, the mutations are located within or encompass 11 genes encoding polypeptides involved in cell lysis, phage structure, phage assembly, phage packaging recombination, replication or translation, phage insertion, and combinations thereof. In some embodiments, the mutations are located within or encompass 12 genes encoding polypeptides involved in cell lysis, phage structure, phage assembly, phage packaging recombination, replication or translation, phage insertion, and combinations thereof. In some embodiments, the muta-
tions are located within or encompass 13 genes encoding polypeptides involved in cell lysis, phage structure, phage assembly, phage packaging recombination, replication or translation, phage insertion, and combinations thereof. In some embodiments, the mutations are located within or encompass 14 genes encoding polypeptides involved in cell lysis, phage structure, phage assembly, phage packaging recombination, replication or translation, phage insertion, and combinations thereof. In some embodiments, the mutations are located within or encompass 15 genes encoding polypeptides involved in cell lysis, phage structure, phage assembly, phage packaging recombination, replication or translation, phage insertion, and combinations thereof. In some embodiments, the mutations are located within or encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the mutations are located within or encompass one or more host proteins within the phage genome.

In any of the embodiments described herein, the modifications encompass are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more mutations encompass or are located in ECOLIN_09965. In some embodiments, one or more mutations encompass or are located in ECOLIN_09970. In some embodiments, one or more mutations encompass or are located in ECOLIN_09975. In some embodiments, one or more mutations encompass or are located in ECOLIN_09980. In some embodiments, one or more mutations encompass or are located in ECOLIN_09985. In some embodiments, one or more mutations encompass or are located in ECOLIN_09990. In some embodiments, one or more mutations encompass or are located in ECOLIN_09995. In some embodiments, one or more mutations encompass or are located in ECOLIN_10000. In some embodiments, one or more mutations encompass or are located in ECOLIN_10005. In some embodiments, one or more mutations encompass or are located in ECOLIN_10010. In some embodiments, one or more mutations encompass or are located in ECOLIN_10015. In some embodiments, one or more mutations encompass or are located in ECOLIN_10020. In some embodiments, one or more mutations encompass or are located in ECOLIN_10025. In some embodiments, one or more mutations encompass or are located in ECOLIN_10030. In some embodiments, one or more mutations encompass or are located in ECOLIN_10035. In some embodiments, one or more mutations encompass or are located in ECOLIN_10040. In some embodiments, one or more mutations encompass or are located in ECOLIN_10045. In some embodiments, one or more mutations encompass or are located in ECOLIN_10050. In some embodiments, one or more mutations encompass or are located in ECOLIN_10055. In some embodiments, one or more mutations encompass or are located in ECOLIN_10065. In some embodiments, one or more mutations encompass or are located in ECOLIN_10070. In some embodiments, one or more mutations encompass or are located in ECOLIN_10075. In some embodiments, one or more mutations encompass or are located in ECOLIN_10080. In some embodiments, one or more mutations encompass or are located in ECOLIN_10085. In some embodiments, one or more mutations encompass or are located in ECOLIN_10090. In some embodiments, one or more mutations encompass or are located in ECOLIN_10095. In some embodiments, one or more mutations encompass or are located in ECOLIN_10100. In some embodiments, one or more mutations encompass or are located in ECOLIN_10105. In some embodiments, one or more mutations encompass or are located in ECOLIN_10110. In some embodiments, one or more mutations encompass or are located in ECOLIN_10115. In some embodiments, one or more mutations encompass or are located in ECOLIN_10120. In some embodiments, one or more mutations encompass or are located in ECOLIN_10125. In some embodiments, one or more mutations encompass or are located in ECOLIN_10130. In some embodiments, one or more mutations encompass or are located in ECOLIN_10135. In some embodiments, one or more mutations encompass or are located in ECOLIN_10140. In some embodiments, one or more mutations encompass or are located in ECOLIN_10145. In some embodiments, one or more mutations encompass or are located in ECOLIN_10150. In some embodiments, one or more mutations encompass or are located in ECOLIN_10160. In some embodiments, one or more mutations encompass or are located in ECOLIN_10165. In some embodiments, one or more mutations encompass or are located in ECOLIN_10170. In some embodiments, one or more mutations encompass or are located in ECOLIN_10175. In some embodiments, one or more mutations encompass or are located in ECOLIN_10180. In some embodiments, one or more mutations encompass or are located in ECOLIN_10185. In some embodiments, one or more mutations encompass or are located in ECOLIN_10190. In some embodiments, one or more mutations encompass or are located in ECOLIN_10195. In some embodiments, one or more mutations encompass or are located in ECOLIN_10200. In some embodiments, one or more mutations encompass or are located in ECOLIN_10205. In some embodiments, one or more mutations encompass or are located in ECOLIN_10210. In some embodiments, one or more mutations encompass or are located in ECOLIN_10220. In some embodiments, one or more mutations encompass or are located in ECOLIN_10225. In some embodiments, one or more mutations encompass or are located in ECOLIN_10230. In some embodiments, one or more mutations encompass or are located in ECOLIN_10235. In some embodiments, one or more mutations encompass or are located in ECOLIN_10240. In some embodiments, one or more mutations encompass or are located in ECOLIN_10245. In some embodiments, one or more mutations encompass or are located in ECOLIN_10250. In some embodiments, one or more mutations encompass or are located in ECOLIN_10255. In some embodiments, one or more mutations encompass or are located in ECOLIN_10260. In some embodiments, one or more mutations encompass or are located in ECOLIN_10265. In some embodiments, one or more mutations encompass or are located in ECOLIN_10270. In some embodiments, one or more mutations encompass or are located in ECOLIN_10275. In some embodiments, one or more mutations encompass or are located in ECOLIN_10280. In some embodiments, one or more mutations encompass or are located in ECOLIN_10290. In some embodiments, one or more mutations encompass or are located in ECOLIN_10295. In some embodiments, one or more mutations encompass or are located in ECOLIN_10300. In some embodiments, one or more mutations encompass or are located in ECOLIN_10305. In some embodiments, one or more mutations encompass or are located in ECOLIN_10310. In some embodiments, one or more mutations encompass or are located in ECOLIN_10315. In some embodiments, one or more mutations encompass or are located in ECOLIN_10320. In some embodiments, one or more mutations encompass or are located in ECOLIN_10325. In some embodiments, one or more mutations encompass or are located in ECOLIN_10330. In some embodiments, one or more mutations encompass or are located in ECOLIN_10335. In some embodiments, one or more mutations encompass or are located in ECOLIN_10340. In some embodiments, one or more mutations encompass or are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase are mutated.

In one embodiment, the mutation is a complete or partial mutation of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the mutation is a complete or partial mutation of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the mutation is a complete mutation of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial mutation of ECOLIN_10175. In one embodiment, the sequence of SEQ ID NO: 130 is mutated from the Phage 3 genome. In one embodiment, a sequence comprising SEQ ID NO: 130 is mutated from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Deletions

In some embodiments, the one or more deletions comprise at least about 1-500 bp of the *E. coli* Nissle Phage 3 genome. In some embodiments, the one or more deletions comprise at least about 500-1000 bp of the *E. coli* Nissle Phage 3 genome. In some embodiments, the one or more deletions comprise at least about 1000-2000 bp of the *E. coli* Nissle Phage 3 genome. In some embodiments, the one or more deletions comprise at least about 1000-2000 bp of the *E. coli* Nissle Phage 3 genome. In some embodiments, the one or more deletions comprise at least about 2000-3000 bp of the *E. coli* Nissle Phage 3 genome. In some embodiments, the one or more deletions comprise at least about 3000-4000 bp of the *E. coli* Nissle Phage 3 genome. In some embodiments, the one or more deletions comprise at least about 4000-5000 bp of the *E. coli* Nissle Phage 3 genome. In some embodiments, the one or more deletions comprise at least about 5,000-6,000 bp of the *E. coli* Nissle Phage 3 genome. In some embodiments, the one or more deletions comprise at least about 6,000-7,000 bp of the *E. coli* Nissle Phage 3 genome. In some embodiments, the one or more deletions comprise at least about 7,000-8,000 bp of the *E. coli* Nissle Phage 3 genome. In some embodiments, the one or more deletions comprise at least about 8,000-9,000 bp of the *E. coli* Nissle Phage 3 genome. In some embodiments, the one or more deletions comprise at least about 9,000-10,000 bp of the *E. coli* Nissle Phage 3 genome. In some embodiments, the one or more deletions comprise at least about 10,000-15,000 bp of the *E. coli* Nissle Phage 3 genome. In some embodiments, the one or more deletions comprise at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In one specific embodiment, 9687 bp of the *E. coli* Nissle Phage 3 genome are deleted. In some embodiments, the deleted nucleotides are interspersed. In some embodiments, the deleted nucleotides are consecutive.

In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome is deleted. In some embodiments, at least about 30-40% of the *E. coli* Nissle Phage 3 genome is deleted. In some embodiments, at least about 40-50% of the *E. coli* Nissle Phage 3 genome is deleted. In some embodiments, at least about 50-60% of the *E. coli* Nissle Phage 3 genome is deleted. In some embodiments, at least about 60-70% of the *E. coli* Nissle Phage 3 genome is deleted. In some embodiments, at least about 70-80% of the *E. coli* Nissle Phage 3 genome is deleted. In some embodiments, at least about 80-90% of the *E. coli* Nissle Phage 3 genome is deleted. In some embodiments, at least about 90-100% of the *E. coli* Nissle Phage 3 genome is deleted.

In some embodiments, one or more genes are partially or completely deleted within the *E. coli* Nissle Phage 3 genome. In some embodiments, one or more genes are completely deleted and one or more genes are partially deleted. In one embodiment, there is one deletion within the *E. coli* Nissle Phage 3 genome and one or two genes at the ends of the deletion are partially deleted and the rest of the genes are completely deleted. In some embodiments, the deleted genes are adjacent to each other. In some embodiments, the deleted genes are not adjacent to each other.

In some embodiments, at least about 1, 2, 3, 4, 5, 6, 7, 8, 9, 10, 11, 12, 13, 14, 15, 16, 17, 18, 19, or 20 genes are deleted. In some embodiments, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are deleted. In some embodiments, 13 genes are completely or partially deleted. In one embodiment, 74 genes are completely or partially deleted.

In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the E. coli Nissle Phage 3 genome are completely or partially deleted.

In some embodiments, the one or more deletions are located at the beginning or 5' end of the E. coli Nissle Phage 3 genome. In some embodiments, the one or more deletions are located at the end or 3' end of the E. coli Nissle Phage 3 genome. In some embodiments, the one or more deletions are located in the middle of the E. coli Nissle Phage 3 genome. In some embodiments, the E. coli Nissle Phage 3 genes are interspersed within the bacterial genome and the deletion are located in one or more of the interspersed positions.

In some embodiments, the region for an optimal deletion, i.e., to achieve a desired effect, can be determined through analysis of homology with other phages in other bacteria, e.g., other E. coli strains. Homologous conserved regions in E. coli Nissle Phage 3 may be suitable for deletion, as these are conserved and may comprise one or more essential genes. In some embodiments, regulatory elements, such as promoters, are deleted. In some embodiments, coding sequences are deleted. In some embodiments, the one or more deleted regions contain one or more genes essential for the lytic cycle.

In some embodiments, the deletions are located within or encompass one or more genes encoding lytic genes. In some embodiments, the deletions are located within or encompass one or more genes encoding one or more proteases or lysins. In some embodiments, the deletions are located within or encompass one or more genes encoding one or more toxins. In some embodiments, the deletions are located within or encompass one or more genes encoding one or more antibiotic resistance related proteins. In some embodiments, the deletions are located within or encompass one or more genes encoding one or phage translation related proteins. In some embodiments, the one or more deletions are located within or encompass one or more genes encoding structural proteins. Such structural genes include genes encoding polypeptides of the head, tail, collar, or coat. In some embodiments, the deletions are located within or encompass one or more genes encoding one or more head proteins. In some embodiments, the deletions are located within or encompass one or more genes encoding one or more tail proteins. In some embodiments, the deletions are located within or encompass one or more genes encoding one or more collar proteins. In some embodiments, the deletions are located within or encompass one or more genes encoding one or more coat proteins. In some embodiments, the deletions are located within or encompass one or more genes encoding one or more plate proteins. In some embodiments, the deletions are located within or encompass one or more genes encoding one or more proteins require for assembly of the bacteriophage. In some embodiments, the deletions are located within or encompass one or more genes encoding one or more portal proteins. In some embodiments, the deletions are located within or encompass one or more genes encoding one or more polypeptides involved in recombination. In some embodiments, the deletions are located within or encompass one or more genes encoding one or more integrases. In some embodiments, the deletions are located within or encompass one or more genes encoding one or more invertases. In some embodiments, the deletions are located within or encompass one or more genes encoding one or more transposases. In some embodiments, the deletions are located with within or encompass one or more genes encoding one or more polypeptides involved in replication or translation. In some embodiments, the deletions are located within or encompass one or more genes encoding one or more primases. In some embodiments, the deletions are located within or encompass one or more genes encoding one or more tRNA related proteins. In some embodiments, the deletions are located within or encompass one or more genes encoding one or more polypeptides involved in phage insertion. In some embodiments, the deletions are located within or encompass one or more genes encoding an attachment site. In some embodiments, the deletions are located within or encompass one or more genes encoding one or more polypeptides involved in packaging. In some embodiments, the deletions are located within or encompass one or more genes encoding one or more terminases. In some embodiments, the deletions are located within or encompass one or more genes encoding one or more host genes.

In some embodiments, the deletions are located within or encompass genes encoding one or more polypeptides involved in one or more of cell lysis, phage structure, phage assembly, phage packaging recombination, replication or translation, phage insertion, or are host proteins, and combinations thereof.

In some embodiments, the deletions are located within or encompass genes encoding one or more polypeptides involved in one or more of cell lysis, phage structure, phage assembly, phage packaging recombination, replication or translation, phage insertion, and combinations thereof.

In some embodiments, the deletions are located within or encompass 1 genes encoding polypeptides involved in cell lysis, phage structure, phage assembly, phage packaging recombination, replication or translation, phage insertion, and combinations thereof. In some embodiments, the deletions are located within or encompass 2 genes encoding polypeptides involved in cell lysis, phage structure, phage assembly, phage packaging recombination, replication or translation, phage insertion, and combinations thereof. In some embodiments, the deletions are located within or encompass 3 genes encoding polypeptides involved in cell lysis, phage structure, phage assembly, phage packaging recombination, replication or translation, phage insertion, and combinations thereof. In some embodiments, the deletions are located within or encompass 4 genes encoding polypeptides involved in cell lysis, phage structure, phage assembly, phage packaging recombination, replication or translation, phage insertion, and combinations thereof. In some embodiments, the deletions are located within or encompass 2 genes encoding polypeptides involved in cell lysis, phage structure, phage assembly, phage packaging recombination, replication or translation, phage insertion, and combinations thereof. In some embodiments, the deletions are located within or encompass 5 genes encoding polypeptides involved in cell lysis, phage structure, phage assembly, phage packaging recombination, replication or translation, phage insertion, and combinations thereof. In some embodiments, the deletions are located within or encompass 6 genes encoding polypeptides involved in cell lysis, phage structure, phage assembly, phage packaging recombination, replication or translation, phage insertion, and combinations thereof. In some embodiments, the deletions are located within or encompass 7 genes encoding polypeptides involved in cell lysis, phage structure, phage assembly, phage packaging recombination, replication or translation, phage insertion, and combinations thereof. In some embodiments, the deletions are located within or encompass 8 genes encoding polypeptides involved in cell lysis, phage structure, phage assembly, phage packaging recombination, replication or translation, phage insertion, and combinations thereof. In some embodiments, the deletions are located within or encompass 9 genes encoding polypeptides involved in cell lysis, phage structure, phage assembly, phage packaging recombination, replication or translation, phage insertion, and combinations thereof. In some embodiments, the deletions are located within or encompass 10 genes encoding polypeptides involved in cell lysis, phage structure, phage assembly, phage packaging recombination, replication or translation, phage insertion, and combinations thereof. In some embodiments, the deletions are located within or encompass 11 genes encoding polypeptides involved in cell lysis, phage structure, phage assembly, phage packaging recombination, replication or translation, phage insertion, and combinations thereof. In some embodiments, the deletions are located within or encompass 12 genes encoding polypeptides involved in cell lysis, phage structure, phage assembly, phage packaging recombination, replication or translation, phage insertion, and combinations thereof. In some embodiments, the deletions are located within or encompass 13 genes encoding polypeptides involved in cell lysis, phage structure, phage assembly, phage packaging recombination, replication or translation, phage insertion, and combinations thereof. In some embodiments, the deletions are located within or encompass 14 genes encoding polypeptides involved in cell lysis, phage structure, phage assembly, phage packaging recombination, replication or translation, phage insertion, and combinations thereof. In some embodiments, the deletions are located within or encompass 15 genes encoding polypeptides involved in cell lysis, phage structure, phage assembly, phage packaging recombination, replication or translation, phage insertion, and combinations thereof. In some embodiments, the deletions are located within or encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the deletions are located within or encompass one or more host proteins within the phage genome.

In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more deletions encompass (completely or partially) or are located in ECOLIN_09965. In some embodiments, one or more deletions encompass (completely or partially) or are located in ECOLIN_09970. In some embodiments, one or more deletions encompass (completely or partially) or are located in ECOLIN_09975. In some embodiments, one or more deletions encompass (completely or partially) or are located in ECOLIN_09980. In some embodiments, one or more deletions encompass (completely or partially) or are located in ECOLIN_09985. In some embodiments, one or more deletions encompass (completely or partially) or are located in ECOLIN_09990. In some embodiments, one or more deletions encompass (completely or partially) or are located in ECOLIN_09995. In some embodiments, one or more deletions encompass (completely or partially) or are located in ECOLIN_10000. In some embodiments, one or more deletions encompass (completely or partially) or are located in ECOLIN_10005. In some embodiments, one or more deletions encompass (completely or partially) or are located in ECOLIN_10010. In some embodiments, one or more deletions encompass (completely or partially) or are located in ECOLIN_10015. In some embodiments, one or more deletions encompass (completely or partially) or are located in ECOLIN_10020. In some embodiments, one or more deletions encompass (completely or partially) or are located in ECOLIN_10025. In some embodiments, one or more deletions encompass (completely or partially) or are located in ECOLIN_10030. In some embodiments, one or more deletions encompass (completely or partially) or are located in ECOLIN_10035. In some embodiments, one or more deletions encompass (completely or partially) or are located in ECOLIN_10040. In some embodiments, one or more deletions encompass (completely or partially) or are located in ECOLIN_10045. In some embodiments, one or more deletions encompass (completely or partially) or are located in ECOLIN_10050. In some embodiments, one or more deletions encompass (completely or partially) or are located in ECOLIN_10055. In some embodiments, one or more deletions encompass (completely or partially) or are located in ECOLIN_10065. In some embodiments, one or more deletions encompass (completely or partially) or are located in ECOLIN_10070. In some embodiments, one or more deletions encompass (completely or partially) or are located in ECOLIN_10075. In some embodiments, one or more deletions encompass (completely or partially) or are located in ECOLIN_10080. In some embodiments, one or more deletions encompass (completely or partially) or are located in ECOLIN_10085. In some embodiments, one or more deletions encompass (completely or partially) or are located in ECOLIN_10090. In some embodiments, one or more deletions encompass (completely or partially) or are located in ECOLIN_10095. In some embodiments, one or more deletions encompass (completely or partially) or are located in ECOLIN_10100. In some embodiments, one or more deletions encompass (completely or partially) or are located in ECOLIN_10105. In some embodiments, one or more deletions encompass (completely or partially) or are located in ECOLIN_10110. In some embodiments, one or more deletions encompass (completely or partially) or are located in ECOLIN_10115. In some embodiments, one or more deletions encompass (completely or partially) or are located in ECOLIN_10120. In some embodiments, one or more deletions encompass (completely or partially) or are located in ECOLIN_10125. In some embodiments, one or more deletions encompass (completely or partially) or are located in ECOLIN_10130. In some embodiments, one or more deletions encompass (completely or partially) or are located in ECOLIN_10135. In some embodiments, one or more deletions encompass (completely or partially) or are located in ECOLIN_10140. In some embodiments, one or more deletions encompass (completely or partially) or are located in ECOLIN_10145. In some embodiments, one or more deletions encompass (completely or partially) or are located in ECOLIN_10150. In some embodiments, one or more deletions encompass (completely or partially) or are located in ECOLIN_10160. In some embodiments, one or more deletions encompass (completely or partially) or are located in ECOLIN_10165. In some embodiments, one or more deletions encompass (completely or partially) or are located in ECOLIN_10170. In some embodiments, one or more deletions encompass (completely or partially) or are located in ECOLIN_10175. In some embodiments, one or more deletions encompass (completely or partially) or are located in ECOLIN_10180. In some embodiments, one or more deletions encompass (completely or partially) or are located in ECOLIN_10185. In some embodiments, one or more deletions encompass (completely or partially) or are located in ECOLIN_10190. In some embodiments, one or more deletions encompass (completely or partially) or are located in ECOLIN_10195. In some embodiments, one or more deletions encompass (completely or partially) or are located in ECOLIN_10200. In some embodiments, one or more deletions encompass (completely or partially) or are located in ECOLIN_10205. In some embodiments, one or more deletions encompass (completely or partially) or are located in ECOLIN_10210. In some embodiments, one or more deletions encompass (completely or partially) or are located in ECOLIN_10220. In some embodiments, one or more deletions encompass (completely or partially) or are located in ECOLIN_10225. In some embodiments, one or more deletions encompass (completely or partially) or are located in ECOLIN_10230. In some embodiments, one or more deletions encompass (completely or partially) or are located in ECOLIN_10235. In some embodiments, one or more deletions encompass (completely or partially) or are located in ECOLIN_10240. In some embodiments, one or more deletions encompass (completely or partially) or are located in ECOLIN_10245. In some embodiments, one or more deletions encompass (completely or partially) or are located in ECOLIN_10250. In some embodiments, one or more deletions encompass (completely or partially) or are located in ECOLIN_10255. In some embodiments, one or more deletions encompass (completely or partially) or are located in ECOLIN_10260. In some embodiments, one or more deletions encompass (completely or partially) or are located in ECOLIN_10265. In some embodiments, one or more deletions encompass (completely or partially) or are located in ECOLIN_10270. In some embodiments, one or more deletions encompass (completely or partially) or are located in ECOLIN_10275. In some embodiments, one or more deletions encompass (completely or partially) or are located in ECOLIN_10280. In some embodiments, one or more deletions encompass (completely or partially) or are located in ECOLIN_10290. In some embodiments, one or more deletions encompass (completely or partially) or are located in ECOLIN_10295. In some embodiments, one or more deletions encompass (completely or partially) or are located in ECOLIN_10300. In some embodiments, one or more deletions encompass (completely or partially) or are located in ECOLIN_10305. In some embodiments, one or more deletions encompass (completely or partially) or are located in ECOLIN_10310. In some embodiments, one or more deletions encompass (completely or partially) or are located in ECOLIN_10315. In some embodiments, one or more deletions encompass (completely or partially) or are located in ECOLIN_10320. In some embodiments, one or more deletions encompass (completely or partially) or are located in ECOLIN_10325. In some embodiments, one or more deletions encompass (completely or partially) or are located in ECOLIN_10330. In some embodiments, one or more deletions encompass (completely or partially) or are located in ECOLIN_10335. In some embodiments, one or more deletions encompass (completely or partially) or are located in ECOLIN_10340. In some embodiments, one or more deletions encompass (completely or partially) or are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase are deleted.

In one specific embodiment, a Minor tail protein U, a tail protein, a DNA breaking-rejoining protein, a peptidase S14, a capsid protein, a DNA packaging protein, and a terminase are deleted. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Insertions

In some embodiments, the insertion is in a coding region of the *E. coli* Nissle Phage 3 genome. In some embodiments, the insertion is inserted into a regulatory region of the *E. coli* Nissle Phage 3 genome. In some embodiments, the inserted polynucleotides comprise one or more antibiotic cassette(s). Suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more inserted polynucleotides comprise at least about 1-500 bp in length. In some embodiments, the one or more inserted polynucleotides comprise at least about 500-1000 bp in length. In some embodiments, the one or more inserted polynucleotides comprise at least about 1000-2000 bp in length. In some embodiments, the one or more inserted polynucleotides comprise at least about 1000-2000 bp in length. In some embodiments, the one or more inserted polynucleotides comprise at least about 2000-3000 bp in length. In some embodiments, the one or more inserted polynucleotides comprise at least about 3000-4000 bp in length. In some embodiments, the one or more inserted polynucleotides comprise at least about 4000-5000 bp in length. In some embodiments, the one or more inserted polynucleotides comprise at least about 5,000-6,000 bp in length. In some embodiments, the one or more inserted polynucleotides comprise at least about 6,000-7,000 bp in length. In some embodiments, the one or more inserted polynucleotides comprise at least about 7,000-8,000 bp in length. In some embodiments, the one or more inserted polynucleotides comprise at least about 8,000-9,000 bp in length. In some embodiments, the one or more inserted polynucleotides comprise at least about 9,000-10,000 bp in length. In some embodiments, the one or more inserted polynucleotides comprise at least about 10,000-15,000 bp in length. In some embodiments, the one or more inserted polynucleotides comprise at least about 10,000-15,000 bp in length, at least about 15,000-20,000 bp in length, at least about 20,000-25,000 bp in length, at least about 25,000-30,000 bp in length, at least about 30,000-35,000 bp in length, at least about 35,000-40,000 bp in length, at least about 40,000-45,000 bp in length, at least about 45,000-50,000 bp in length, at least about 50,000-55,000 bp in length, at least about 55,000-60,000 bp in length, at least about 60,000-65,000 bp in length, at least about 65,000-70,000 bp in length, at least about 70,000-75,000 bp in length, at least about 75,000-80,000 bp in length, at least about 80,000-85,000 bp in length, at least about 85,000-90,000 bp in length, at least about 90,000-95,000 bp in length, 95,000-100,000 bp in length, at least about 100,000-110,000 bp in length, at least about 110,000-120,000 bp in length, at least about 120,000-130,000 bp in length, at least about 130,000-140,000 bp in length, at least about 140,000-150,000 bp in length, at least about 150,000-200,000 bp in length, or more than at least about 200,000 bp in length. In one specific embodiment, at least about 9687 bp in length are inserted.

In some embodiments, the one or more insertions are located within at least about 1-500 bp of the *E. coli* Nissle Phage 3 genome. In some embodiments, the one or more insertions are located within at least about 500-1000 bp of the *E. coli* Nissle Phage 3 genome. In some embodiments, the one or more insertions are located within at least about 1000-2000 bp of the *E. coli* Nissle Phage 3 genome. In some embodiments, the one or more insertions are located within at least about 1000-2000 bp of the *E. coli* Nissle Phage 3 genome. In some embodiments, the one or more insertions are located within at least about 2000-3000 bp of the *E. coli* Nissle Phage 3 genome. In some embodiments, the one or more insertions are located within at least about 3000-4000 bp of the *E. coli* Nissle Phage 3 genome. In some embodiments, the one or more insertions are located within at least about 4000-5000 bp of the *E. coli* Nissle Phage 3 genome. In some embodiments, the one or more insertions are located within at least about 5,000-6,000 bp of the *E. coli* Nissle Phage 3 genome. In some embodiments, the one or more insertions are located within at least about 6,000-7,000 bp of the *E. coli* Nissle Phage 3 genome. In some embodiments, the one or more insertions are located within at least about 7,000-8,000 bp of the *E. coli* Nissle Phage 3 genome. In some embodiments, the one or more insertions are located within at least about 8,000-9,000 bp of the *E. coli* Nissle Phage 3 genome. In some embodiments, the one or more insertions are located within at least about 9,000-10,000 bp of the *E. coli* Nissle Phage 3 genome. In some embodiments, the one or more insertions are located within at least about 10,000-15,000 bp of the *E. coli* Nissle Phage 3 genome. In some embodiments, the one or more insertions are located within at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In one specific embodiment, 9687 bp of the *E. coli* Nissle Phage 3 genome are inserted. In some embodiments, the inserted nucleotides are interspersed. In some embodiments, the inserted nucleotides are consecutive.

In some embodiments, the insertions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome. In some embodiments, at least about 30-40% of the *E. coli* Nissle Phage 3 genome is inserted. In some embodiments, the insertions are located within at least about 40-50% of the *E. coli* Nissle Phage 3 genome. In some embodiments, the insertions are located within at least about 50-60% of the *E. coli* Nissle Phage 3 genome. In some embodiments, the insertions are located within at least about 60-70% of the *E. coli* Nissle Phage 3 genome. In some embodiments, the insertions are located within at least about 70-80% of the *E. coli* Nissle Phage 3 genome. In some embodiments, the insertions are located within at least about 80-90% of the *E. coli* Nissle Phage 3 genome. In some embodiments, the insertions are located within at least about 90-100% of the *E. coli* Nissle Phage 3 genome.

In some embodiments, at least about 1, 2, 3, 4, 5, 6, 7, 8, 9, 10, 11, 12, 13, 14, 15, 16, 17, 18, 19, or 20 genes comprise insertions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise insertions. In some embodiments, 13 genes comprise insertions. In one embodiment, 74 genes comprise insertions.

In some embodiments, the one or more insertions are located at the beginning or 5' end of the *E. coli* Nissle Phage 3 genome. In some embodiments, the one or more insertions are located at the end or 3' end of the *E. coli* Nissle Phage 3 genome. In some embodiments, the one or more insertions are located in the middle of the *E. coli* Nissle Phage 3 genome. In some embodiments, the *E. coli* Nissle Phage 3 genes are interspersed within the bacterial genome and the insertion are located in one or more of the interspersed positions.

In some embodiments, the region for an optimal insertion, i.e., to achieve a desired effect, can be determined through analysis of homology with other phages in other bacteria. Homologous conserved regions in phages may be suitable for insertion, as these are conserved and may comprise one or more essential genes. In some embodiments, regulatory elements, such as promoters, are inserted. In some embodiments, coding sequences are inserted. In some embodiments, the one or more inserted regions contain one or more genes essential for the lytic cycle.

In some embodiments, the insertions are located within one or more genes encoding lytic genes. In some embodiments, the insertions are located within one or more genes encoding one or more proteases or lysins. In some embodiments, the insertions are located within one or more genes encoding one or more toxins. In some embodiments, the insertions are located within one or more genes encoding one or more antibiotic resistance related proteins. In some embodiments, the insertions are located within one or more genes encoding one or phage translation related proteins. In some embodiments, the one or more insertions are located within one or more genes encoding structural proteins. Such structural genes include genes encoding polypeptides of the head, tail, collar, or coat. In some embodiments, the one or more mutations are located within or encompass one or more genes encoding head proteins. In some embodiments, the one or more mutations are located within or encompass one or more genes encoding tail proteins. In some embodiments, the one or more mutations are located within or encompass one or more genes encoding collar proteins. In some embodiments, the one or more mutations are located within or encompass one or more genes encoding coat proteins. In some embodiments, the insertions are located within one or more genes encoding one or more plate proteins. In some embodiments, the insertions are located within one or more genes encoding one or more proteins require for assembly of the bacteriophage. In some embodiments, the insertions are located within one or more genes encoding one or more portal proteins. In some embodiments, the insertions are located within one or more genes encoding one or more polypeptides involved in recombination. In some embodiments, the insertions are located within one or more genes encoding one or more integrases. In some embodiments, the insertions are located within one or more genes encoding one or more invertases. In some embodiments, the insertions are located within one or more genes encoding one or more transposases. In some embodiments, the insertions are located with within one or more genes encoding one or more polypeptides involved in replication or translation. In some embodiments, the insertions are located within one or more genes encoding one or more primases. In some embodiments, the insertions are located within one or more genes encoding one or more tRNA related proteins. In some embodiments, the insertions are located within one or more genes encoding one or more polypeptides involved in phage insertion. In some embodiments, the insertions are located within one or more genes encoding an attachment site. In some embodiments, the insertions are located within one or more genes encoding one or more polypeptides involved in packaging. In some embodiments, the insertions are located within one or more genes encoding one or more terminases. In some embodiments, the insertions are located within one or more genes encoding one or more host genes.

In some embodiments, the insertions are located within genes encoding one or more polypeptides involved in one or more of cell lysis, phage structure, phage assembly, phage packaging recombination, replication or translation, phage insertion, or are host proteins, and combinations thereof.

In some embodiments, the insertions are located within genes encoding one or more polypeptides involved in one or more of cell lysis, phage structure, phage assembly, phage packaging recombination, replication or translation, phage insertion, and combinations thereof.

In some embodiments, the insertions are located within 1 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 3 genes encoding polypeptides involved in cell lysis, phage structure, phage assembly, phage packaging recombination, replication or translation, phage insertion, and combinations thereof. In some embodiments, the insertions are located within 4 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 5 genes encoding polypeptides involved in cell lysis, phage structure, phage assembly, phage packaging recombination, replication or translation, phage insertion, and combinations thereof. In some embodiments, the insertions are located within 6 genes encoding polypeptides involved in cell lysis, phage structure, phage assembly, phage packaging recombination, replication or translation, phage insertion, and combinations thereof. In some embodiments, the insertions are located within 7 genes encoding polypeptides involved in cell lysis, phage structure, phage assembly, phage packaging recombination, replication or translation, phage insertion, and combinations thereof. In some embodiments, the insertions are located within 8 genes encoding polypeptides involved in cell lysis, phage structure, phage assembly, phage packaging recombination, replication or translation, phage insertion, and combinations thereof. In some embodiments, the insertions are located within 9 genes encoding polypeptides involved in cell lysis, phage structure, phage assembly, phage packaging recombination, replication or translation, phage insertion, and combinations thereof. In some embodiments, the insertions are located within 10 genes encoding polypeptides involved in cell lysis, phage structure, phage assembly, phage packaging recombination, replication or translation, phage insertion, and combinations thereof. In some embodiments, the insertions are located within 11 genes encoding polypeptides involved in cell lysis, phage structure, phage assembly, phage packaging recombination, replication or translation, phage insertion, and combinations thereof. In some embodiments, the insertions are located within 12 genes encoding polypeptides involved in cell lysis, phage structure, phage assembly, phage packaging recombination, replication or translation, phage insertion, and combinations thereof. In some embodiments, the insertions are located within 13 genes encoding polypeptides involved in cell lysis, phage structure, phage assembly, phage packaging recombination, replication or translation, phage insertion, and combinations thereof. In some embodiments, the insertions are located within 14 genes encoding polypeptides involved in cell lysis, phage structure, phage assembly, phage packaging recombination, replication or translation, phage insertion, and combinations thereof. In some embodiments, the insertions are located within 15 genes encoding polypeptides involved in cell lysis, phage structure, phage assembly, phage packaging recombination, replication or translation, phage insertion, and combinations thereof. In some embodiments, the insertions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the insertions are located within one or more host proteins within the phage genome.

In any of the embodiments described herein, the insertions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more insertions are located in ECOLIN_09965. In some embodiments, one or more insertions are located in ECOLIN_09970. In some embodiments, one or more insertions are located in ECOLIN_09975. In some embodiments, one or more insertions are located in ECOLIN_09980. In some embodiments, one or more insertions are located in ECOLIN_09985. In some embodiments, one or more insertions are located in ECOLIN_09990. In some embodiments, one or more insertions are located in ECOLIN_09995. In some embodiments, one or more insertions are located in ECOLIN_10000. In some embodiments, one or more insertions are located in ECOLIN_10005. In some embodiments, one or more insertions are located in ECOLIN_10010. In some embodiments, one or more insertions are located in ECOLIN_10015. In some embodiments, one or more insertions are located in ECOLIN_10020. In some embodiments, one or more insertions are located in ECOLIN_10025. In some embodiments, one or more insertions are located in ECOLIN_10030. In some embodiments, one or more insertions are located in ECOLIN_10035. In some embodiments, one or more insertions are located in ECOLIN_10040. In some embodiments, one or more insertions are located in ECOLIN_10045. In some embodiments, one or more insertions are located in ECOLIN_10050. In some embodiments, one or more insertions are located in ECOLIN_10055. In some embodiments, one or more insertions are located in ECOLIN_10065. In some embodiments, one or more insertions are located in ECOLIN_10070. In some embodiments, one or more insertions are located in ECOLIN_10075. In some embodiments, one or more insertions are located in ECOLIN_10080. In some embodiments, one or more insertions are located in ECOLIN_10085. In some embodiments, one or more insertions are located in ECOLIN_10090. In some embodiments, one or more insertions are located in ECOLIN_10095. In some embodiments, one or more insertions are located in ECOLIN_10100. In some embodiments, one or more insertions are located in ECOLIN_10105. In some embodiments, one or more insertions are located in ECOLIN_10110. In some embodiments, one or more insertions are located in ECOLIN_10115. In some embodiments, one or more insertions are located in ECOLIN_10120. In some embodiments, one or more insertions are located in ECOLIN_10125. In some embodiments, one or more insertions are located in ECOLIN_10130. In some embodiments, one or more insertions are located in ECOLIN_10135. In some embodiments, one or more insertions are located in ECOLIN_10140. In some embodiments, one or more insertions are located in ECOLIN_10145. In some embodiments, one or more insertions are located in ECOLIN_10150. In some embodiments, one or more insertions are located in ECOLIN_10160. In some embodiments, one or more insertions are located in ECOLIN_10165. In some embodiments, one or more insertions are located in ECOLIN_10170. In some embodiments, one or more insertions are located in ECOLIN_10175. In some embodiments, one or more insertions are located in ECOLIN_10180. In some embodiments, one or more insertions are located in ECOLIN_10185. In some embodiments, one or more insertions are located in ECOLIN_10190. In some embodiments, one or more insertions are located in ECOLIN_10195. In some embodiments, one or more insertions are located in ECOLIN_10200. In some embodiments, one or more insertions are located in ECOLIN_10205. In some embodiments, one or more insertions are located in ECOLIN_10210. In some embodiments, one or more insertions are located in ECOLIN_10220. In some embodiments, one or more insertions are located in ECOLIN_10225. In some embodiments, one or more insertions are located in ECOLIN_10230. In some embodiments, one or more insertions are located in ECOLIN_10235. In some embodiments, one or more insertions are located in ECOLIN_10240. In some embodiments, one or more insertions are located in ECOLIN_10245. In some embodiments, one or more insertions are located in ECOLIN_10250. In some embodiments, one or more insertions are located in ECOLIN_10255. In some embodiments, one or more insertions are located in ECOLIN_10260. In some embodiments, one or more insertions are located in ECOLIN_10265. In some embodiments, one or more insertions are located in ECOLIN_10270. In some embodiments, one or more insertions are located in ECOLIN_10275. In some embodiments, one or more insertions are located in ECOLIN_10280. In some embodiments, one or more insertions are located in ECOLIN_10290. In some embodiments, one or more insertions are located in ECOLIN_10295. In some embodiments, one or more insertions are located in ECOLIN_10300. In some embodiments, one or more insertions are located in ECOLIN_10305. In some embodiments, one or more insertions are located in ECOLIN_10310. In some embodiments, one or more insertions are located in ECOLIN_10315. In some embodiments, one or more insertions are located in ECOLIN_10320. In some embodiments, one or more insertions are located in ECOLIN_10325. In some embodiments, one or more insertions are located in ECOLIN_10330. In some embodiments, one or more insertions are located in ECOLIN_10335. In some embodiments, one or more insertions are located in ECOLIN_10340. In some embodiments, one or more insertions are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase contain one or more insertions. In one specific embodiment, a Minor tail protein U, a tail protein, a DNA breaking-rejoining protein, a peptidase S14, a capsid protein, a DNA packaging protein, and a terminase contain one or more insertions.

In one embodiment one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175 comprise an insertion.

Inversions

In some embodiments, the inversion is in a coding region of the *E. coli* Nissle Phage 3 genome. In some embodiments, the inversion is inverted into a regulatory region of the *E. coli* Nissle Phage 3 genome. In some embodiments, the inversions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more inversions comprise 1-500 bp. In some embodiments, the one or more inversions comprise at least about 500-1000 bp. In some embodiments, the one or more inversions comprise at least about 1000-2000 bp. In some embodiments, the one or more inversions comprise at least about 2000-3000 bp. In some embodiments, the one or more inversions comprise at least about 3000-4000 bp. In some embodiments, the one or more inversions comprise at least about 4000-5000 bp. In some embodiments, the one or more inversions comprise at least about 5,000-6,000 bp. In some embodiments, the one or more inversions comprise at least about 6,000-7,000 bp. In some embodiments, the one or more inversions comprise at least about 7,000-8,000 bp. In some embodiments, the one or more inversions comprise at least about 8,000-9,000 bp. In some embodiments, the one or more inversions comprise at least about 9,000-10,000 bp. In some embodiments, the one or more inversions comprise at least about 10,000-15,000 bp. In some embodiments, the one or more inversions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, or at least about 55,000-60,000 bp. In one specific embodiment, 9687 bp are inverted. In some embodiments, the inverted nucleotides are interspersed. In some embodiments, the inverted nucleotides are consecutive.

In some embodiments, the one or more inversions are located within at least about 1-500 bp of the *E. coli* Nissle Phage 3 genome. In some embodiments, the one or more inversions are located within at least about 500-1000 bp of the *E. coli* Nissle Phage 3 genome. In some embodiments, the one or more inversions are located within at least about 1000-2000 bp of the *E. coli* Nissle Phage 3 genome. In some embodiments, the one or more inversions are located within at least about 1000-2000 bp of the *E. coli* Nissle Phage 3 genome. In some embodiments, the one or more inversions are located within at least about 2000-3000 bp of the *E. coli* Nissle Phage 3 genome. In some embodiments, the one or more inversions are located within at least about 3000-4000 bp of the *E. coli* Nissle Phage 3 genome. In some embodiments, the one or more inversions are located within at least about 4000-5000 bp of the *E. coli* Nissle Phage 3 genome. In some embodiments, the one or more inversions are located within at least about 5,000-6,000 bp of the *E. coli* Nissle Phage 3 genome. In some embodiments, the one or more inversions are located within at least about 6,000-7,000 bp of the *E. coli* Nissle Phage 3 genome. In some embodiments, the one or more inversions are located within at least about 7,000-8,000 bp of the *E. coli* Nissle Phage 3 genome. In some embodiments, the one or more inversions are located within at least about 8,000-9,000 bp of the *E. coli* Nissle Phage 3 genome. In some embodiments, the one or more inversions are located within at least about 9,000-10,000 bp of the *E. coli* Nissle Phage 3 genome. In some embodiments, the one or more inversions are located within at least about 10,000-15,000 bp of the *E. coli* Nissle Phage 3 genome. In some embodiments, the one or more inversions are located within at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In some embodiments, the inverted nucleotides are interspersed. In some embodiments, the inverted nucleotides are consecutive.

In some embodiments, the inversions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome. In some embodiments, at least about 30-40% of the *E. coli* Nissle Phage 3 genome is inverted. In some embodiments, the inversions are located within at least about 40-50% of the *E. coli* Nissle Phage 3 genome. In some embodiments, the inversions are located within at least about 50-60% of the *E. coli* Nissle Phage 3 genome. In some embodiments, the inversions are located within at least about 60-70% of the *E. coli* Nissle Phage 3 genome. In some embodiments, the inversions are located within at least about 70-80% of the *E. coli* Nissle Phage 3 genome. In some embodiments, the inversions are located within at least about 80-90% of the *E. coli* Nissle Phage 3 genome. In some embodiments, the inversions are located within at least about 90-100% of the *E. coli* Nissle Phage 3 genome.

In some embodiments, at least about 1, 2, 3, 4, 5, 6, 7, 8, 9, 10, 11, 12, 13, 14, 15, 16, 17, 18, 19, or 20 genes comprise inversions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise inversions. In some embodiments, 13 genes comprise inversions. In one embodiment, 74 genes comprise inversions.

In some embodiments, the one or more inversions are located at the beginning or 5' end of the *E. coli* Nissle Phage 3 genome. In some embodiments, the one or more inversions are located at the end or 3' end of the *E. coli* Nissle Phage 3 genome. In some embodiments, the one or more inversions are located in the middle of the *E. coli* Nissle Phage 3 genome. In some embodiments, the *E. coli* Nissle Phage 3 genes are interspersed within the bacterial genome and the inversion are located in one or more of the interspersed positions.

In some embodiments, the region for an optimal inversion, i.e., to achieve a desired effect, can be determined through analysis of homology with other phages in other bacteria. Homologous conserved regions in phages may be suitable for inversion, as these are conserved and may comprise one or more essential genes. In some embodiments, regulatory elements, such as promoters, are inverted. In some embodiments, coding sequences are inverted. In some embodiments, the one or more inverted regions contain one or more genes essential for the lytic cycle.

In some embodiments, the inversions are located within one or more genes encoding lytic genes. In some embodiments, the inversions are located within one or more genes encoding one or more proteases or lysins. In some embodiments, the inversions are located within one or more genes encoding one or more toxins. In some embodiments, the inversions are located within one or more genes encoding one or more antibiotic resistance related proteins. In some embodiments, the inversions are located within one or more genes encoding one or phage translation related proteins. In some embodiments, the one or more inversions are located within one or more genes encoding structural proteins. Such structural genes include genes encoding polypeptides of the head, tail, collar, or coat. In some embodiments, the one or more mutations are located within or encompass one or more genes encoding head proteins. In some embodiments, the one or more mutations are located within or encompass one or more genes encoding tail proteins. In some embodiments, the one or more mutations are located within or encompass one or more genes encoding collar proteins. In some embodiments, the one or more mutations are located within or encompass one or more genes encoding coat proteins. In some embodiments, the inversions are located within one or more genes encoding one or more plate proteins. In some embodiments, the inversions are located within one or more genes encoding one or more proteins require for assembly of the bacteriophage. In some embodiments, the inversions are located within one or more genes encoding one or more portal proteins. In some embodiments, the inversions are located within one or more genes encoding one or more polypeptides involved in recombination. In some embodiments, the inversions are located within one or more genes encoding one or more integrases. In some embodiments, the inversions are located within one or more genes encoding one or more invertases. In some embodiments, the inversions are located within one or more genes encoding one or more transposases. In some embodiments, the inversions are located with within one or more genes encoding one or more polypeptides involved in replication or translation. In some embodiments, the inversions are located within one or more genes encoding one or more primases. In some embodiments, the inversions are located within one or more genes encoding one or more tRNA related proteins. In some embodiments, the inversions are located within one or more genes encoding one or more polypeptides involved in phage inversion. In some embodiments, the inversions are located within one or more genes encoding an attachment site. In some embodiments, the inversions are located within one or more genes encoding one or more polypeptides involved in packaging. In some embodiments, the inversions are located within one or more genes encoding one or more terminases. In some embodiments, the inversions are located within one or more genes encoding one or more host genes.

In some embodiments, the inversions are located within genes encoding one or more polypeptides involved in one or more of cell lysis, phage structure, phage assembly, phage packaging recombination, replication or translation, phage inversion, or are host proteins, and combinations thereof.

In some embodiments, the inversions are located within genes encoding one or more polypeptides involved in one or more of cell lysis, phage structure, phage assembly, phage packaging recombination, replication or translation, phage inversion, and combinations thereof.

In some embodiments, the inversions are located within 1 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 3 genes encoding polypeptides involved in cell lysis, phage structure, phage assembly, phage packaging recombination, replication or translation, phage inversion, and combinations thereof. In some embodiments, the inversions are located within 4 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 5 genes encoding polypeptides involved in cell lysis, phage structure, phage assembly, phage packaging recombination, replication or translation, phage inversion, and combinations thereof. In some embodiments, the inversions are located within 6 genes encoding polypeptides involved in cell lysis, phage structure, phage assembly, phage packaging recombination, replication or translation, phage inversion, and combinations thereof. In some embodiments, the inversions are located within 7 genes encoding polypeptides involved in cell lysis, phage structure, phage assembly, phage packaging recombination, replication or translation, phage inversion, and combinations thereof. In some embodiments, the inversions are located within 8 genes encoding polypeptides involved in cell lysis, phage structure, phage assembly, phage packaging recombination, replication or translation, phage inversion, and combinations thereof. In some embodiments, the inversions are located within 9 genes encoding polypeptides involved in cell lysis, phage structure, phage assembly, phage packaging recombination, replication or translation, phage inversion, and combinations thereof. In some embodiments, the inversions are located within 10 genes encoding polypeptides involved in cell lysis, phage structure, phage assembly, phage packaging recombination, replication or translation, phage inversion, and combinations thereof. In some embodiments, the inversions are located within 11 genes encoding polypeptides involved in cell lysis, phage structure, phage assembly, phage packaging recombination, replication or translation, phage inversion, and combinations thereof. In some embodiments, the inversions are located within 12 genes encoding polypeptides involved in cell lysis, phage structure, phage assembly, phage packaging recombination, replication or translation, phage inversion, and combinations thereof. In some embodiments, the inversions are located within 13 genes encoding polypeptides involved in cell lysis, phage structure, phage assembly, phage packaging recombination, replication or translation, phage inversion, and combinations thereof. In some embodiments, the inversions are located within 14 genes encoding polypeptides involved in cell lysis, phage structure, phage assembly, phage packaging recombination, replication or translation, phage inversion, and combinations thereof. In some embodiments, the inversions are located within 15 genes encoding polypeptides involved in cell lysis, phage structure, phage assembly, phage packaging recombination, replication or translation, phage inversion, and combinations thereof. In some embodiments, the inversions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage inversion, and combinations thereof. In some embodiments, the inversions are located within one or more host proteins within the phage genome.

In any of the embodiments described herein, the inversions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more inversions encompass (completely or partially) or are located in ECOLIN_09965.
In some embodiments, one or more inversions encompass (completely or partially) or are located in ECOLIN_09970.
In some embodiments, one or more inversions encompass (completely or partially) or are located in ECOLIN_09975.
In some embodiments, one or more inversions encompass (completely or partially) or are located in ECOLIN_09980.
In some embodiments, one or more inversions encompass (completely or partially) or are located in ECOLIN_09985.
In some embodiments, one or more inversions encompass (completely or partially) or are located in ECOLIN_09990.
In some embodiments, one or more inversions encompass (completely or partially) or are located in ECOLIN_09995.
In some embodiments, one or more inversions encompass (completely or partially) or are located in ECOLIN_10000.
In some embodiments, one or more inversions encompass (completely or partially) or are located in ECOLIN_10005.
In some embodiments, one or more inversions encompass (completely or partially) or are located in ECOLIN_10010.
In some embodiments, one or more inversions encompass (completely or partially) or are located in ECOLIN_10015.
In some embodiments, one or more inversions encompass (completely or partially) or are located in ECOLIN_10020.
In some embodiments, one or more inversions encompass (completely or partially) or are located in ECOLIN_10025.
In some embodiments, one or more inversions encompass (completely or partially) or are located in ECOLIN_10030.
In some embodiments, one or more inversions encompass (completely or partially) or are located in ECOLIN_10035.
In some embodiments, one or more inversions encompass (completely or partially) or are located in ECOLIN_10040.
In some embodiments, one or more inversions encompass (completely or partially) or are located in ECOLIN_10045.
In some embodiments, one or more inversions encompass (completely or partially) or are located in ECOLIN_10050.
In some embodiments, one or more inversions encompass (completely or partially) or are located in ECOLIN_10055.
In some embodiments, one or more inversions encompass (completely or partially) or are located in ECOLIN_10065.
In some embodiments, one or more inversions encompass (completely or partially) or are located in ECOLIN_10070.
In some embodiments, one or more inversions encompass (completely or partially) or are located in ECOLIN_10075.
In some embodiments, one or more inversions encompass (completely or partially) or are located in ECOLIN_10080.
In some embodiments, one or more inversions encompass (completely or partially) or are located in ECOLIN_10085.
In some embodiments, one or more inversions encompass (completely or partially) or are located in ECOLIN_10090.
In some embodiments, one or more inversions encompass (completely or partially) or are located in ECOLIN_10095.
In some embodiments, one or more inversions encompass (completely or partially) or are located in ECOLIN_10100.
In some embodiments, one or more inversions encompass (completely or partially) or are located in ECOLIN_10105.
In some embodiments, one or more inversions encompass (completely or partially) or are located in ECOLIN_10110.
In some embodiments, one or more inversions encompass (completely or partially) or are located in ECOLIN_10115.
In some embodiments, one or more inversions encompass (completely or partially) or are located in ECOLIN_10120.
In some embodiments, one or more inversions encompass (completely or partially) or are located in ECOLIN_10125.
In some embodiments, one or more inversions encompass (completely or partially) or are located in ECOLIN_10130.
In some embodiments, one or more inversions encompass (completely or partially) or are located in ECOLIN_10135.
In some embodiments, one or more inversions encompass (completely or partially) or are located in ECOLIN_10140.
In some embodiments, one or more inversions encompass (completely or partially) or are located in ECOLIN_10145.
In some embodiments, one or more inversions encompass (completely or partially) or are located in ECOLIN_10150.
In some embodiments, one or more inversions encompass (completely or partially) or are located in ECOLIN_10160.
In some embodiments, one or more inversions encompass (completely or partially) or are located in ECOLIN_10165.
In some embodiments, one or more inversions encompass (completely or partially) or are located in ECOLIN_10170.
In some embodiments, one or more inversions encompass (completely or partially) or are located in ECOLIN_10175.
In some embodiments, one or more inversions encompass (completely or partially) or are located in ECOLIN_10180.
In some embodiments, one or more inversions encompass (completely or partially) or are located in ECOLIN_10185.
In some embodiments, one or more inversions encompass (completely or partially) or are located in ECOLIN_10190.
In some embodiments, one or more inversions encompass (completely or partially) or are located in ECOLIN_10195.
In some embodiments, one or more inversions encompass (completely or partially) or are located in ECOLIN_10200.
In some embodiments, one or more inversions encompass (completely or partially) or are located in ECOLIN_10205.
In some embodiments, one or more inversions encompass (completely or partially) or are located in ECOLIN_10210.
In some embodiments, one or more inversions encompass (completely or partially) or are located in ECOLIN_10220.
In some embodiments, one or more inversions encompass (completely or partially) or are located in ECOLIN_10225.
In some embodiments, one or more inversions encompass (completely or partially) or are located in ECOLIN_10230.
In some embodiments, one or more inversions encompass (completely or partially) or are located in ECOLIN_10235.
In some embodiments, one or more inversions encompass (completely or partially) or are located in ECOLIN_10240.
In some embodiments, one or more inversions encompass (completely or partially) or are located in ECOLIN_10245.
In some embodiments, one or more inversions encompass (completely or partially) or are located in ECOLIN_10250.
In some embodiments, one or more inversions encompass (completely or partially) or are located in ECOLIN_10255.

In some embodiments, one or more inversions encompass (completely or partially) or are located in ECOLIN_10260. In some embodiments, one or more inversions encompass (completely or partially) or are located in ECOLIN_10265. In some embodiments, one or more inversions encompass (completely or partially) or are located in ECOLIN_10270. In some embodiments, one or more inversions encompass (completely or partially) or are located in ECOLIN_10275. In some embodiments, one or more inversions encompass (completely or partially) or are located in ECOLIN_10280. In some embodiments, one or more inversions encompass (completely or partially) or are located in ECOLIN_10290. In some embodiments, one or more inversions encompass (completely or partially) or are located in ECOLIN_10295. In some embodiments, one or more inversions encompass (completely or partially) or are located in ECOLIN_10300. In some embodiments, one or more inversions encompass (completely or partially) or are located in ECOLIN_10305. In some embodiments, one or more inversions encompass (completely or partially) or are located in ECOLIN_10310. In some embodiments, one or more inversions encompass (completely or partially) or are located in ECOLIN_10315. In some embodiments, one or more inversions encompass (completely or partially) or are located in ECOLIN_10320. In some embodiments, one or more inversions encompass (completely or partially) or are located in ECOLIN_10325. In some embodiments, one or more inversions encompass (completely or partially) or are located in ECOLIN_10330. In some embodiments, one or more inversions encompass (completely or partially) or are located in ECOLIN_10335. In some embodiments, one or more inversions encompass (completely or partially) or are located in ECOLIN_10340. In some embodiments, one or more inversions encompass (completely or partially) or are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase are inverted. In one specific embodiment, a Minor tail protein U, a tail protein, a DNA breaking-rejoining protein, a peptidase S14, a capsid protein, a DNA packaging protein, and a terminase are inverted.

In one embodiment, the inversion is a complete or partial inversion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the inversion is a complete or partial inversion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the inversion is a complete inversion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial inversion of ECOLIN_10175. In one embodiment, the sequence of SEQ ID NO: 130 is inverted from the Phage 3 genome. In one embodiment, a sequence comprising SEQ ID NO: 130 is inverted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Substitutions

In some embodiments, the substitution is in a coding region of the *E. coli* Nissle Phage 3 genome. In some embodiments, the substitution is substituted into a regulatory region of the *E. coli* Nissle Phage 3 genome. In some embodiments, the substitutions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more substitutions comprise at least about 1-500 bp. In some embodiments, the one or more substitutions comprise at least about 500-1000 bp. In some embodiments, the one or more substitutions comprise at least about 1000-2000 bp. In some embodiments, the one or more substitutions comprise at least about 2000-3000 bp. In some embodiments, the one or more substitutions comprise at least about 3000-4000 bp. In some embodiments, the one or more substitutions comprise at least about 4000-5000 bp. In some embodiments, the one or more substitutions comprise at least about 5,000-6,000 bp. In some embodiments, the one or more substitutions comprise at least about 6,000-7,000 bp. In some embodiments, the one or more substitutions comprise at least about 7,000-8,000 bp. In some embodiments, the one or more substitutions comprise at least about 8,000-9,000 bp. In some embodiments, the one or more substitutions comprise at least about 9,000-10,000 bp. In some embodiments, the one or more substitutions comprise at least about 10,000-15,000 bp. In some embodiments, the one or more substitutions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, at least about 55,000-60,000 bp, at least about 60,000-65,000 bp, at least about 65,000-70,000 bp, at least about 70,000-75,000 bp, at least about 75,000-80,000 bp, at least about 80,000-85,000 bp, at least about 85,000-90,000 bp, at least about 90,000-95,000 bp, at least about 95,000-100,000 bp, at least about 100,000-110,000 bp, at least about 110,000-120,000 bp, at least about 120,000-130,000 bp, at least about 130,000-140,000 bp, at least about 140,000-150,000 bp, at least about 150,000-200,000 bp, or more than at least about 200,000 bp. In one specific embodiment, 9687 bp are substituted. In some embodiments, the substituted nucleotides are interspersed. In some embodiments, the substituted nucleotides are consecutive.

In some embodiments, the one or more substitutions are located within 1-500 bp of the E. coli Nissle Phage 3 genome. In some embodiments, the one or more substitutions are located within 500-1000 bp of the E. coli Nissle Phage 3 genome. In some embodiments, the one or more substitutions are located within at least about 1000-2000 bp of the E. coli Nissle Phage 3 genome. In some embodiments, the one or more substitutions are located within at least about 1000-2000 bp of the E. coli Nissle Phage 3 genome. In some embodiments, the one or more substitutions are located within at least about 2000-3000 bp of the E. coli Nissle Phage 3 genome. In some embodiments, the one or more substitutions are located within at least about 3000-4000 bp of the E. coli Nissle Phage 3 genome. In some embodiments, the one or more substitutions are located within at least about 4000-5000 bp of the E. coli Nissle Phage 3 genome. In some embodiments, the one or more substitutions are located within at least about 5,000-6,000 bp of the E. coli Nissle Phage 3 genome. In some embodiments, the one or more substitutions are located within at least about 6,000-7,000 bp of the E. coli Nissle Phage 3 genome. In some embodiments, the one or more substitutions are located within at least about 7,000-8,000 bp of the E. coli Nissle Phage 3 genome. In some embodiments, the one or more substitutions are located within at least about 8,000-9,000 bp of the E. coli Nissle Phage 3 genome. In some embodiments, the one or more substitutions are located within at least about 9,000-10,000 bp of the E. coli Nissle Phage 3 genome. In some embodiments, the one or more substitutions are located within at least about 10,000-15,000 bp of the E. coli Nissle Phage 3 genome. In some embodiments, the one or more substitutions are located within at least about 10,000-15,000 bp of the E. coli Nissle Phage 3 genome, at least about 15,000-20,000 bp of the E. coli Nissle Phage 3 genome, at least about 20,000-25,000 bp of the E. coli Nissle Phage 3 genome, at least about 25,000-30,000 bp of the E. coli Nissle Phage 3 genome, at least about 30,000-35,000 bp of the E. coli Nissle Phage 3 genome, at least about 35,000-40,000 bp of the E. coli Nissle Phage 3 genome, 40,000-45,000 bp of the E. coli Nissle Phage 3 genome, at least about 45,000-50,000 bp of the E. coli Nissle Phage 3 genome, at least about 50,000-55,000 bp of the E. coli Nissle Phage 3 genome, or at least about 55,000-60,000 bp of the E. coli Nissle Phage 3 genome In one specific embodiment, 9687 bp of the E. coli Nissle Phage 3 genome are substituted. In some embodiments, the substituted nucleotides are interspersed. In some embodiments, the substituted nucleotides are consecutive.

In some embodiments, the substitutions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the E. coli Nissle Phage 3 genome. In some embodiments, at least about 30-40% of the E. coli Nissle Phage 3 genome is substituted. In some embodiments, the substitutions are located within at least about 40-50% of the E. coli Nissle Phage 3 genome. In some embodiments, the substitutions are located within at least about 50-60% of the E. coli Nissle Phage 3 genome. In some embodiments, the substitutions are located within at least about 60-70% of the E. coli Nissle Phage 3 genome. In some embodiments, the substitutions are located within at least about 70-80% of the E. coli Nissle Phage 3 genome. In some embodiments, the substitutions are located within at least about 80-90% of the E. coli Nissle Phage 3 genome. In some embodiments, the substitutions are located within at least about 90-100% of the E. coli Nissle Phage 3 genome.

In some embodiments, at least about 1, 2, 3, 4, 5, 6, 7, 8, 9, 10, 11, 12, 13, 14, 15, 16, 17, 18, 19, or 20 genes comprise substitutions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise substitutions. In some embodiments, 13 genes comprise substitutions. In one embodiment, 74 genes comprise substitutions.

In some embodiments, the one or more substitutions are located at the beginning or 5' end of the E. coli Nissle Phage 3 genome. In some embodiments, the one or more substitutions are located at the end or 3' end of the E. coli Nissle Phage 3 genome. In some embodiments, the one or more substitutions are located in the middle of the E. coli Nissle Phage 3 genome. In some embodiments, the E. coli Nissle Phage 3 genes are interspersed within the bacterial genome and the substitution are located in one or more of the interspersed positions.

In some embodiments, the region for an optimal substitution, i.e., to achieve a desired effect, can be determined through analysis of homology with other phages is other bacteria. Homologous conserved regions in phages may be suitable for substitution, as these are conserved and may comprise one or more essential genes. In some embodiments, regulatory elements, such as promoters, are substituted. In some embodiments, coding sequences are substituted. In some embodiments, the one or more substituted regions contain one or more genes essential for the lytic cycle.

In some embodiments, the substitutions are located within one or more genes encoding lytic genes. In some embodiments, the substitutions are located within one or more genes encoding one or more proteases or lysins. In some embodiments, the substitutions are located within one or more genes encoding one or more toxins. In some embodiments, the substitutions are located within one or more genes encoding one or more antibiotic resistance related proteins. In some embodiments, the substitutions are located within one or more genes encoding one or phage translation related proteins. In some embodiments, the one or more substitutions are located within one or more genes encoding structural proteins. Such structural genes include genes encoding polypeptides of the head, tail, collar, or coat. In some embodiments, the substitutions are located within one or more genes encoding one or more plate proteins. In some embodiments, the substitutions are located within one or more genes encoding one or more proteins require for assembly of the bacteriophage. In some embodiments, the substitutions are located within one or more genes encoding one or more portal proteins. In some embodiments, the substitutions are located within one or more genes encoding one or more polypeptides involved in recombination. In some embodiments, the substitutions are located within one or more genes encoding one or more integrases. In some embodiments, the substitutions are located within one or more genes encoding one or more invertases. In some embodiments, the substitutions are located within one or more genes encoding one or more transposases. In some embodiments, the substitutions are located with within one or more genes encoding one or more polypeptides involved in replication or translation. In some embodiments, the substitutions are located within one or more genes encoding one or more primases. In some embodiments, the substitutions are located within one or more genes encoding one or more tRNA related proteins. In some embodiments, the substitutions are located within one or more genes encoding one or more polypeptides involved in phage substitution. In some embodiments, the substitutions are located within one or more genes encoding an attachment site. In some embodiments, the substitutions are located within one or more genes encoding one or more polypeptides involved in packaging. In some embodiments, the substitutions are located within one or more genes encoding one or more terminases. In some embodiments, the substitutions are located within one or more genes encoding one or more host genes.

In some embodiments, the substitutions are located within genes encoding one or more polypeptides involved in one or more of cell lysis, phage structure, phage assembly, phage packaging recombination, replication or translation, phage substitution, or are host proteins, and combinations thereof.

In some embodiments, the substitutions are located within genes encoding one or more polypeptides involved in one or more of cell lysis, phage structure, phage assembly, phage packaging recombination, replication or translation, phage substitution, and combinations thereof.

In some embodiments, the substitutions are located within 1 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 3 genes encoding polypeptides involved in cell lysis, phage structure, phage assembly, phage packaging recombination, replication or translation, phage substitution, and combinations thereof. In some embodiments, the substitutions are located within 4 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 5 genes encoding polypeptides involved in cell lysis, phage structure, phage assembly, phage packaging recombination, replication or translation, phage substitution, and combinations thereof. In some embodiments, the substitutions are located within 6 genes encoding polypeptides involved in cell lysis, phage structure, phage assembly, phage packaging recombination, replication or translation, phage substitution, and combinations thereof. In some embodiments, the substitutions are located within 7 genes encoding polypeptides involved in cell lysis, phage structure, phage assembly, phage packaging recombination, replication or translation, phage substitution, and combinations thereof. In some embodiments, the substitutions are located within 8 genes encoding polypeptides involved in cell lysis, phage structure, phage assembly, phage packaging recombination, replication or translation, phage substitution, and combinations thereof. In some embodiments, the substitutions are located within 9 genes encoding polypeptides involved in cell lysis, phage structure, phage assembly, phage packaging recombination, replication or translation, phage substitution, and combinations thereof. In some embodiments, the substitutions are located within 10 genes encoding polypeptides involved in cell lysis, phage structure, phage assembly, phage packaging recombination, replication or translation, phage substitution, and combinations thereof. In some embodiments, the substitutions are located within 11 genes encoding polypeptides involved in cell lysis, phage structure, phage assembly, phage packaging recombination, replication or translation, phage substitution, and combinations thereof. In some embodiments, the substitutions are located within 12 genes encoding polypeptides involved in cell lysis, phage structure, phage assembly, phage packaging recombination, replication or translation, phage substitution, and combinations thereof. In some embodiments, the substitutions are located within 13 genes encoding polypeptides involved in cell lysis, phage structure, phage assembly, phage packaging recombination, replication or translation, phage substitution, and combinations thereof. In some embodiments, the substitutions are located within 14 genes encoding polypeptides involved in cell lysis, phage structure, phage assembly, phage packaging recombination, replication or translation, phage substitution, and combinations thereof. In some embodiments, the substitutions are located within 15 genes encoding polypeptides involved in cell lysis, phage structure, phage assembly, phage packaging recombination, replication or translation, phage substitution, and combinations thereof. In some embodiments, the substitutions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage substitution, and combinations thereof. In some embodiments, the substitutions are located within one or more host proteins within the phage genome.

In any of the embodiments described herein, the substitutions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more substitutions are located in ECOLIN_09965. In some embodiments, one or more substitutions are located in ECOLIN_09970. In some embodiments, one or more substitutions are located in ECOLIN_09975. In some embodiments, one or more substitutions are located in ECOLIN_09980. In some embodiments, one or more substitutions are located in ECOLIN_09985. In some embodiments, one or more substitutions are located in ECOLIN_09990. In some embodiments, one or more substitutions are located in ECOLIN_09995. In some embodiments, one or more substitutions are located in ECOLIN_10000. In some embodiments, one or more substitutions are located in ECOLIN_10005. In some embodiments, one or more substitutions are located in ECOLIN_10010. In some embodiments, one or more substitutions are located in ECOLIN_10015. In some embodiments, one or more substitutions are located in ECOLIN_10020. In some embodiments, one or more substitutions are located in ECOLIN_10025. In some embodiments, one or more substitutions are located in ECOLIN_10030. In some embodiments, one or more substitutions are located in ECOLIN_10035. In some embodiments, one or more substitutions are located in ECOLIN_10040. In some embodiments, one or more substitutions are located in ECOLIN_10045. In some embodiments, one or more substitutions are located in ECOLIN_10050. In some embodiments, one or more substitutions are located in ECOLIN_10055. In some embodiments, one or more substitutions are located in ECOLIN_10065. In some embodiments, one or more substitutions are located in ECOLIN_10070. In some embodiments, one or more substitutions are located in ECOLIN_10075. In some embodiments, one or more substitutions are located in ECOLIN_10080. In some embodiments, one or more substitutions are located in ECOLIN_10085. In some embodiments, one or more substitutions are located in ECOLIN_10090. In some embodiments, one or more substitutions are located in ECOLIN_10095. In some embodiments, one or more substitutions are located in ECOLIN_10100. In some embodiments, one or more substitutions are located in ECOLIN_10105. In some embodiments, one or more substitutions are located in ECOLIN_10110. In some embodiments, one or more substitutions are located in ECOLIN_10115. In some embodiments, one or more substitutions are located in ECOLIN_10120. In some embodiments, one or more substitutions are located in ECOLIN_10125. In some embodiments, one or more substitutions are located in ECOLIN_10130. In some embodiments, one or more substitutions are located in ECOLIN_10135. In some embodiments, one or more substitutions are located in ECOLIN_10140. In some embodiments, one or more substitutions are located in ECOLIN_10145. In some embodiments, one or more substitutions are located in ECOLIN_10150. In some embodiments, one or more substitutions are located in ECOLIN_10160. In some embodiments, one or more substitutions are located in ECOLIN_10165. In some embodiments, one or more substitutions are located in ECOLIN_10170. In some embodiments, one or more substitutions are located in ECOLIN_10175. In some embodiments, one or more substitutions are located in ECOLIN_10180. In some embodiments, one or more substitutions are located in ECOLIN_10185. In some embodiments, one or more substitutions are located in ECOLIN_10190. In some embodiments, one or more substitutions are located in ECOLIN_10195. In some embodiments, one or more substitutions are located in ECOLIN_10200. In some embodiments, one or more substitutions are located in ECOLIN_10205. In some embodiments, one or more substitutions are located in ECOLIN_10210. In some embodiments, one or more substitutions are located in ECOLIN_10220. In some embodiments, one or more substitutions are located in ECOLIN_10225. In some embodiments, one or more substitutions are located in ECOLIN_10230. In some embodiments, one or more substitutions are located in ECOLIN_10235. In some embodiments, one or more substitutions are located in ECOLIN_10240. In some embodiments, one or more substitutions are located in ECOLIN_10245. In some embodiments, one or more substitutions are located in ECOLIN_10250. In some embodiments, one or more substitutions are located in ECOLIN_10255. In some embodiments, one or more substitutions are located in ECOLIN_10260. In some embodiments, one or more substitutions are located in ECOLIN_10265. In some embodiments, one or more substitutions are located in ECOLIN_10270. In some embodiments, one or more substitutions are located in ECOLIN_10275. In some embodiments, one or more substitutions are located in ECOLIN_10280. In some embodiments, one or more substitutions are located in ECOLIN_10290. In some embodiments, one or more substitutions are located in ECOLIN_10295. In some embodiments, one or more substitutions are located in ECOLIN_10300. In some embodiments, one or more substitutions are located in ECOLIN_10305. In some embodiments, one or more substitutions are located in ECOLIN_10310. In some embodiments, one or more substitutions are located in ECOLIN_10315. In some embodiments, one or more substitutions are located in ECOLIN_10320. In some embodiments, one or more substitutions are located in ECOLIN_10325. In some embodiments, one or more substitutions are located in ECOLIN_10330. In some embodiments, one or more substitutions are located in ECOLIN_10335. In some embodiments, one or more substitutions are located in ECOLIN_10340. In some embodiments, one or more substitutions are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase contain one or more substitutions. In one specific embodiment, a Minor tail protein U, a tail protein, a DNA breaking-rejoining protein, a peptidase S14, a capsid protein, a DNA packaging protein, and a terminase contain one or more substitutions.

In one embodiment, the substitution is a complete or partial substitution of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the substitution is a complete or partial substitution of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the substitution is a complete substitution of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial substitution of ECOLIN_10175. In one embodiment, the sequence of SEQ ID NO: 130 is substituted from the Phage 3 genome. In one embodiment, a sequence comprising SEQ ID NO: 130 is substituted from the Phage 3 genome.

Regulation of Effector Molecules and Payloads Expression

In some embodiments, the bacterial cell which comprises a mutated endogenous phage further comprises a stably maintained plasmid or chromosome carrying the gene(s) encoding payload (s), such that the payload(s) can be expressed in the host cell, and the host cell is capable of survival and/or growth in vitro, e.g., in medium, and/or in vivo, e.g., in the gut or the tumor microenvironment. In some embodiments, bacterial cell comprises two or more distinct payloads or operons, e.g., two or more payload genes. In some embodiments, bacterial cell comprises three or more distinct transporters or operons, e.g., three or more payload genes. In some embodiments, bacterial cell comprises at least about 4, 5, 6, 7, 8, 9, 10, or more distinct payloads or operons, e.g., at least about 4, 5, 6, 7, 8, 9, 10, or more payload genes.

In one embodiment, the genetically engineered bacteria of the invention comprise a gene encoding a phenylalanine-metabolizing enzyme (PME). In some embodiments, the genetically engineered bacteria comprise a gene encoding a phenylalanine-metabolizing enzyme (PME) and are capable of reducing hyperphenylalaninemia.

Examples of phenylalanine metabolizing enzymes include, but are not limited to, phenylalanine hydroxylase (PAH), phenylalanine ammonia lyase (PAL), aminotransferases, L-amino acid deaminase (LAAD), and phenylalanine dehydrogenases. Reactions with phenylalanine hydroxylases, phenylalanine dehydrogenases or aminotransferases require cofactors, while LAAD and PAL do not require any extra cofactor. Without wishing to be bound by theory, the lack of need for a cofactor means that phenylalanine degradation by the enzyme encoded by the genetically engineered bacteria is dependent on the availability of the substrate and is not limited by the availability of the cofactor.

In some embodiments, the engineered bacteria comprise gene sequence encoding one or more phenylalanine hydroxylase (PAH) polypeptides. In some embodiments, the engineered bacteria comprise gene sequence encoding one or more phenylalanine ammonia lyase (PAL) polypeptides. Phenylalanine ammonia lyase (PAL; EC 4.3.1.24) is an enzyme that catalyzes a reaction converting L-phenylalanine to ammonia and trans-cinnamic acid. Phenylalanine ammonia lyase is specific for L-Phe, and to a lesser extent, L-Tyrosine. The reaction catalyzed by PAL is the spontaneous, non-oxidative deamination of L-phenylalanine to yield trans-cinnamic acid and ammonia. Unlike the mammalian enzyme (PAH), PAL is a monomer and requires no cofactors (MacDonald et al., Biochem Cell Biol 2007; 85:273-82. A modern view of phenylalanine ammonia lyase). In microorganisms, it has a catabolic role, allowing them to utilize L-phenylalanine (L-Phe) as a sole source of carbon and nitrogen. In one embodiment, the genetically engineered bacteria of the invention comprise a PAL gene. PAL is capable of converting phenylalanine to non-toxic levels of transcinnamic acid and ammonia. Trans-cinnamic acid (TCA) can further be converted to TCA metabolites benzoic and hippuric acids (Sarkissian et al., J Mass Spectrom. 2007 June; 42(6):811-7; Quantitation of phenylalanine and its trans-cinnamic, benzoic and hippuric acid metabolites in biological fluids in a single GC-MS analysis). PAL enzyme activity does not require THB cofactor activity.

In some embodiments, PAL is encoded by a PAL gene derived from a bacterial species, including but not limited to, *Achromobacter xylosoxidans*, *Pseudomonas aeruginosa*, *Photorhabdus luminescens*, *Anabaena variabilis*, and *Agrobacterium tumefaciens*. In some embodiments, the bacterial species is *Photorhabdus luminescens*. In some embodiments, the bacterial species is *Anabaena variabilis*. In some embodiments, PAL is encoded by a PAL gene derived from a eukaryotic species, e.g., a yeast species, a plant species. Multiple distinct PAL proteins are known in the art. The genetically engineered bacteria convert more phenylalanine when the PAL gene is expressed than unmodified bacteria of the same bacterial subtype under the same conditions. Thus, the genetically engineered bacteria comprising PAL may be used to metabolize phenylalanine in the body into non-toxic molecules in order to treat conditions associated with hyperphenylalaninemia, including PKU. In some embodiments, the genetically engineered bacteria express *Anabaena variabilis* PAL ("PAL1"). In some embodiments, the genetically engineered bacteria express *Photorhabdus luminescens* PAL ("PAL3"). Non-limiting examples of PAL sequences of interest are shown in Table 2.

In some embodiments, the engineered bacteria comprise gene sequence encoding one or more LAAD polypeptides. In some embodiments, the engineered bacteria comprise gene sequence encoding one or more PAL polypeptides and one or more LAAD polypeptides. LAAD catalyzes the stereospecific oxidative, i.e., oxygen consuming, deamination of L-amino acids to α-keto acids along with the production of ammonia and hydrogen peroxide via an imino acid intermediate. LAADs are found in snake venoms, and in many bacteria (Bifulco et al. 2013), specifically in the cytomembranes of the *Proteus, Providencia*, and *Morganella* bacteria. LAADs (EC 1.4.3.2) are flavoenzymes with a dimeric structure. Each subunit contains a non-covalently-bound flavin adenine dinucleotide (FAD) cofactor) and do not require any external cofactors. *Proteus mirabilis* contains two types of LAADs (Duerre and Chakrabarty 1975). One has broad substrate specificity and catalyzes the oxidation of aliphatic and aromatic L-amino acids to keto acids, typically L-phenylalanine (GenBank: U35383.1) (Baek et al., Journal of Basic Microbiology 2011, 51, 129-135; "Expression and characterization of a second L-amino acid deaminase isolated from *Proteus mirabilis* in *Escherichia coli*"). The other type acts mainly on basic L-amino acids (GenBank: EU669819.1). LAADs from bacterial, fungal, and plant sources appear to be involved in the utilization of L-amino acids (i.e., ammonia produced by the enzymatic activity) as a nitrogen source. Most eukaryotic and prokaryotic L-amino acid deaminases are extracellularly secreted, with the exception of from *Proteus* species LAADs, which are membrane-bound. In *Proteus mirabilis*, LAADs have been reported to be located in the plasma membrane, facing outward into the periplasmic space, in which the enzymatic activity resides (Pelmont J et al., (1972) "L-amino acid oxidases of *Proteus mirabilis*: general properties" Biochimie 54: 1359-1374).

In one embodiment, the genetically engineered bacteria of the invention comprise a LAAD gene. LAAD is capable of converting phenylalanine to non-toxic levels of phenylpyruvate, which can also further be degraded, e.g., by liver enzymes, to phenyllactate. Phenylpyruvate cannot cross the blood brain barrier, which allows LAAD to reduce the levels of phenylalanine in the brain without allowing the accumulation of another potentially toxic metabolite. In some embodiments, LAAD is encoded by a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the genetically engineered bacteria express *Proteus mirabilis* LAAD enzyme GenBank: U35383.1. Non-limiting examples of LAAD sequences of interest are shown in Table 2. In some embodiments, the LAAD enzyme is derived from snake venom. According to the invention, genetically engineered bacteria convert more phenylalanine when the LAAD gene is expressed than unmodified bacteria of the same bacterial subtype under the same conditions. Thus, the genetically engineered bacteria comprising LAAD may be used to metabolize phenylalanine in the body into non-toxic molecules in order to treat conditions associated with hyperphenylalaninemia, including PKU.

In some embodiments, the genetically engineered bacteria encode a wild type enzyme as it occurs in nature. In some embodiments, the genetically engineered bacteria encode an enzyme which comprises mutations relative to the wild type sequence. In some embodiments, the mutations increase stability of the enzyme. In some embodiments, the mutations increase the catalytic activity of the enzyme. In some embodiments, the genetically engineered bacteria comprise a gene encoding one or more of the proteins listed in Table 2. In some embodiments, the genetically engineered bacteria comprise gene sequence(s) encoding one or more of the polypeptides comprising sequence of any of SEQ ID Nos: 1-8. In some embodiments, the genetically engineered bacteria comprise gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID Nos: 1-8. In some embodiments, the genetically engineered bacteria encode one or more enzymes from Table 2, which comprise a mutation. In some embodiments, the genetically engineered bacteria comprise a gene encoding wild type PAH. In some embodiments, the genetically engineered bacteria encode a mutated PAH with increased stability and/or activity. In some embodiments, the genetically engineered bacteria comprise a gene encoding wild type PAL. In some embodiments, the genetically engineered bacteria encode a mutated PAL with increased stability and/or activity. In some embodiments, the genetically engineered bacteria comprise a gene encoding wild type LAAD. In some embodiments, the genetically engineered bacteria encode a mutated LAAD with increased stability and/or activity. Methods for screening for enzymes with desirable properties are known in the art and described herein.

TABLE 2

Sequences of Phenylalanine Metabolizing Enzymes

| Description | Sequence | SEQ ID NO |
|---|---|---|
| Phenylalanine ammonia-lyase (*Anabaena variabilis*) Acc. No.: Q3M5Z3.1 | MKTLSQAQSKTSSQQFSFTGNSSANVIIGNQKLTINDVA RVARNGTLVSLTNNTDILQGIQASCDYINNAVESGEPIY GVTSGFGGMANVAISREQASELQTNLVWFLKTGAGNKL PLADVRAAMLLRANSHMRGASGIRLELIKRMEIFLNAG VTPYVYEFGSIGASGDLVPLSYITGSLIGLDPSFKVDFNG KEMDAPTALRQLNLSPLTLLPKEGLAMMNGTSVMTGIA ANCVYDTQILTAIAMGVHALDIQALNGTNQSFHPFIHNS KPHPGQLWAADQMISLLANSQLVRDELDGKHDYRDHE LIQDRYSLRCLPQYLGPIVDGISQIAKQIEIEINSVTDNPLI DVDNQASYHGGNFLGQYVGMGMDHLRYYIGLLAKHL DVQIALLASPEFSNGLPPSLLGNRERKVNMGLKGLQICG NSIMPLLTFYGNSIADRFPTHAEQFNQNINSQGYTSATLA RRSVDIFQNYVAIALMFGVQAVDLRTYKKTGHYDARA CLSPATERLYSAVRHVVGQKPTSDRPYIWNDNEQGLDE HIARISADIAAGGVIVQAVQDILPCLH | SEQ ID NO: 1 |
| histidine ammonia- | MKTLSQAQSKTSSQQFSFTGNSSANVIIGNQKLTINDVA RVARNGTLVSLTNNTDILQGIQASCDYINNAVESGEPIY | SEQ ID NO: 2 |

TABLE 2-continued

Sequences of Phenylalanine Metabolizing Enzymes

| Description | Sequence | SEQ ID NO |
|---|---|---|
| lyase [Anabaena variabilis ATCC 29413] (Acc. NO: ABA23593.1) | GVTSGFGGMANVAISREQASELQTNLVWFLKTGAGNKL PLADVRAAMLLRANSHMRGASGIRLELIKRMEIFLNAG VTPYVYEFGSIGASGDLVPLSYITGSLIGLDPSFKVDFNG KEMDAPTALRQLNLSPLTLLPKEGLAMMNGTSVMTGIA ANCVYDTQILTAIAMGVHALDIQALNGTNQSFHPFIHNS KPHPGQLWAADQMISLLANSQLVRDELDGKHDYRDHE LIQDRYSLRCLPQYLGPIVDGISQIAKQIEIEINSVTDNPLI DVDNQASYHGGNFLGQYVGMGMDHLRYYIGLLAKHL DVQIALLASPEFSNGLPPSLLGNRERKVNMGLKGLQICG NSIMPLLTFYGNSIADRFPTHAEQFNQNINSQGYTSATLA RRSVDIFQNYVAIALMFGVQAVDLRTYKKTGHYDARA CLSPATERLYSAVRHVVGQKPTSDRPYIWNDNEQGLDE HIARISADIAAGGVIVQAVQDILPCLH | |
| histidine ammonia- lyase [Photorhabdus luminescens] (WP_ 011146484) | MKAKDVQPTIIINKNGLISLEDIYDIAIKQKKVEISTEITEL LTHGREKLEEKLNSGEVIYGINTGFGGNANLVVPFEKIA EHQQNLLTFLSAGTGDYMSKPCIKASQFTMLLSVCKGW SATRPIVAQAIVDHINHDIVPLVPRYGSVGASGDLIPLSYI ARALCGIGKVYYMGAEIDAAEAIKRAGLTPLSLKAKEG LALINGTRVMSGISAITVIKLEKLFKASISAIALAVEALLA SHEHYDARIQQVKNHPGQNAVASALRNLLAGSTQVNLL SGVKEQANKACRHQEITQLNDTLQEVYSIRCAPQVLGIV PESLATARKILEREVISANDNPLIDPENGDVLHGGNFMG QYVARTMDALKLDIALIANHLHAIVALMMDNRFSRGLP NSLSPTPGMYQGFKGVQLSQTALVAAIRHDCAASGIHTL ATEQYNQDIVSLGLHAAQDVLEMEQKLRNIVSMTILVV CQAIHLRGNISEIAPETAKFYHAVREISSPLITDRALDEDII RIADAIINDQLPLPEIMLEE | SEQ ID NO: 3 |
| Histidine ammonia lyase (Photorhabdus luminescens) Acc. NO: CAE15566 | MKQLTIYPGKLTLDELRQVYLQPVKITLDSQIFPAIERSV ECVNAILAENRTAYGINTGFGLLASTRIEEDNLEKLQRSL VVSHAAGVGKALDDNMTRLIMVLKINSLSRGYSGIRLA VIQALIALVNAEIYPHIPCKGSVGASGDLAPLAHMSLLLL GEGQARYQGEWLPAKEALAKANLQPITLAAKEGLALLN GTQVSTAFALRGLFEAEDLLAAAIVCGSLSVEAALGSRK PFDARVHVVRGQQGQIDVAALYRHVLEESSELSDSHINC PKVQDPYSLRCQPQVMGACLTQLRHAADVILTEANAVS DNPLVFAEQGEVISGGNFHAEPVAMASDNLALVLAEIG ALSERRIALLMDSHMSQLPPFLVENGGVNSGFMIAQVTA AALASENKALAHPASVDSLPTSANQEDHVSMAPAAGRR LWEMAENTRGILAIEWLSACQGIDFRNGLKSSPILEEAR VILRAKVDYYDQDRFFAPDIDAAVKLLAEQHLSSLLPSG QILQRKNNR | SEQ ID NO: 4 |
| amino acid deaminase (Proteus mirabilis) Acc. No: ACD36582 | MAISRRKFILGGTVVAVAAGAGVLTPMLTREGRFVPGT PRHGFVEGTGGPLPKQDDVVVIGAGILGIMTAINLAERG LSVTIVEKGNIAGEQSSRFYGQAISYKMPDETFLLHHLG KHRWREMNAKVGIDTTYRTQGRVEVPLDEEDLENVRK WIDAKSKDVGSDIPFRTKMIEGAELKQRLRGATTDWKI AGFEEDSGSFDPEVATFVMAEYAKKMGIKIFTNCAARG LETQAGVISDVVTEKGPIKTSRVVVAGGVGSRLFMQNL NVDVPTLPAYQSQQLISAAPNAPGGNVALPGGIFFRDQA DGTYATSPRVIVAPVVKESFTYGYKYLPLLALPDFPVHIS LNEQLINSFMQSTHWDLNEESPFEKYRDMTALPDLPELN ASLEKLKKEFPAFKESTLIDQWSGAMAIAPDENPIISDVK EYPGLVINTATGWMTESPVSAEITADLLLGKKPVLDAK PFSLYRF | SEQ ID NO: 5 |
| amino acid deaminase [Proteus mirabilis HI4320]) Acc. No.: AAA86752.1 | MNISRRKLLLGVGAAGVLAGGAALVPMVRRDGKFVEA KSRASFVEGTQGALPKEADVVIIGAGIQGIMTAINLAERG MSVTILEKGQIAGEQSGRAYSQIISYQTSPEIFPPLHHYGKI LWRGMNEKIGADTSYRTQGRVEALADEKALDKAQAWI KTAKEAAGFDTPLNTRIIKGEELSNRLVGAQTPWTVAAF EEDSGSVDPETGTPALARYAKQIGVKIYTNCAVRGIETA GGKISDVVSEKGAIKTSQVVLAGGIWSRLFMGNMGIDIP TLNVYLSQQRVSGVPGAPRGNVHLPNGIHFREQADGTY AVAPRIFTSSIVKDSFLLGPKFMHLLGGGELPLEFSIGEDL FNSFKMPTSWNLDEKTPFEQFRVATATQNTQHLDAVFQ RMKTEFPVFEKSEVVERWGAVVSPTFDELPIISEVKEYP GLVINTATVWGMTEGPAAGEVTADIVMGKKPVIDPTPF SLDRFKK | SEQ ID NO: 6 |
| LAAD from Proteus vulgaris; | MAISRRKFIIGGTVVAVAAGAGILTPMLTREGRFVPGTP RHGFVEGTEGALPKQADVVVVGAGILGIMTAINLVERG LSVVIVEKGNIAGEQSSRFYGQAISYKMPDETFLLHHLG | SEQ ID NO: 7 |

TABLE 2-continued

Sequences of Phenylalanine Metabolizing Enzymes

| Description | Sequence | SEQ ID NO |
|---|---|---|
| (Acc. NO: BAA90864) | KHRWREMNAKVGIDTTYRTQGRVEVPLDEEDLVNVRK WIDERSKNVGSDIPFKTRIIEGAELNQRLRGATTDWKIAG FEEDSGSFDPEVATFVMAEYAKKMGVRIYTQCAARGLE TQAGVISDVVTEKGAIKTSQVVVAGGVWSRLFMQNLN VDVPTLPAYQSQQLISGSPTAPGGNVALPGGIFFREQAD GTYATSPRVIVAPVVKESFTYGYKYLPLLALPDFPVHISL NEQLINSFMQSTHWNLDEVSPFEQFRNMTALPDLPELNA SLEKLKAEFPAFKESKLIDQWSGAMAIAPDENPIISEVKE YPGLVINTATGWGMTESPVSAELTADLLLGKKPVLDPK PFSLYRF | |
| Phenylalanine hydroxylase [Homo sapiens] (Acc. No. AAH26251 | MSTAVLENPGLGRKLSDFGQETSYIEDNCNQNGAISLIFS LKEEVGALAKVLRLFEENDVNLTHIESRPSRLKKDEYEF FTHLDKRSLPALTNIIKILRHDIGATVHELSRDKKKDTVP WFPRTIQELDRFANQILSYGAELDADHPGFKDPVYRARR KQFADIAYNYRHGQPIPRVEYMEEGKKTWGTVFKTLKS LYKTHACYEYNHIFPLLEKYCGFHEDNIPQLEDVSQFLQ TCTGFRLRPVAGLLSSRDFLGGLAFRVFHCTQYIRHGSK PMYTPEPDICHELLGHVPLFSDRSFAQFSQEIGLASLGAP DEYIEKLATIYWFTVEFGLCKQGDSIKAYGAGLLSSFGE LQYCLSEKPKLLPLELEKTAIQNYTVTEFQPLYYVAESF NDAKEKVRNFAATIPRPFSVRYDPYTQRIEVLDNTQQLK ILADSINSEIGILCSALQKIK | SEQ ID NO: 8 |

The PME, e.g., PAL, LAAD, or PAH, gene(s) may be present on a plasmid or chromosome in the genetically engineered bacteria. In some embodiments, the PME gene sequence(s) are expressed under the control of one or more constitutive promoter(s). In some embodiments, the PME gene is expressed under the control of a promoter that is directly or indirectly induced by exogenous environmental conditions, as described herein. In some embodiments, the PME gene is expressed under the control of a promoter that is directly or indirectly induced by exogenous environmental conditions, such as in the presence of molecules or metabolites specific to the gut of a mammal. In one embodiment, the PME gene is expressed under the control of a promoter that is directly or indirectly induced by low-oxygen, microaerobic, or anaerobic conditions, wherein expression of the PME gene, e.g., the PAL gene, is activated under low-oxygen or anaerobic environments, such as the environment of the mammalian gut.

In some embodiments, the genetically engineered bacteria comprise gene sequence encoding one or more PAL polypeptide sequence(s). In some embodiments, the engineered bacteria comprise gene sequence encoding one or more PAL polypeptide sequence(s) in which the gene sequence(s) is directly or indirectly induced by low-oxygen or anaerobic conditions, such as the mammalian gut. In some embodiments, the engineered bacteria comprise gene sequence encoding one or more LAAD polypeptides. In some embodiments, the engineered bacteria comprise gene sequence encoding one or more LAAD polypeptides, in which the gene sequence(s) is directly or indirectly induced by oxygenated, low oxygen, or microaerobic conditions, such as conditions found in the proximal intestine, including but not limited to the stomach, duodenum, and ileum. In other embodiments, the engineered bacteria comprise gene sequence(s) encoding one or more PME polypeptide sequences(s) in which the gene sequene(s) is directly or indirectly induced by an environmental factor that is naturally present in a mammalian gut. In other embodiments, the genetically engineered bacteria encode one or more PME gene sequences(s) which are directly or indirectly induced by an environmental factor that is not naturally present in a mammalian gut, e.g., arabinose or IPTG. In other embodiments, the genetically engineered bacteria encode one or more PME gene sequences(s) which are directly or indirectly induced by an environmental factor that is naturally present in a mammalian gut under inflammatory conditions. In some embodiments, the engineered bacteria comprise gene sequence(s) encoding one or more PAL polypeptides and gene sequence(s) encoding one or more LAAD polypeptides in which the gene sequences are under the control of the same promoter or a different copy of the same promoter, which is directly or indirectly induced by exogenous environmental conditions, such as any of the environmental conditions discussed herein and such as any of the promoters discussed herein. In some embodiments, the engineered bacteria comprise gene sequence(s) encoding one or more PAL polypeptides and gene sequence(s) encoding one or more LAAD polypeptides in which the gene sequences are under the control of a different promoter, which is directly or indirectly induced by exogenous environmental conditions, such as any of the environmental conditions discussed herein and such as any of the promoters discussed herein. In some embodiments, the engineered bacteria comprise gene sequence(s) encoding one or more PAL polypeptides and gene sequence(s) encoding one or more LAAD polypeptides in which the gene sequences are under the control of a constitutive promoter. In some embodiments, the engineered bacteria comprise gene sequence(s) encoding one or more PAL polypeptides and gene sequence(s) encoding one or more LAAD polypeptides in which the PAL gene sequences are under the control of a constitutive promoter and the LAAD gene sequence(s) are under the control of an inducible promoter. In some embodiments, the engineered bacteria comprise gene sequence(s) encoding one or more PAL polypeptides and gene sequence(s) encoding one or more LAAD polypeptides in which the LAAD gene sequences are under the control of a constitutive promoter and the PAL gene sequence(s) are under the control of an inducible promoter. In any of these embodiments, the bacteria may further comprise gene sequence encoding one or more Phe transporter polypeptides, which gene sequence(s) may be under the control of a constitutive or inducible promoter and may be the same or different promoter from the promoter controlling the Pal and/or LAAD gene sequence(s).

In other embodiments, the engineered bacteria encode one or more PME gene sequence(s) which are directly or indirectly induced prior to in vivo administration during bacterial cell culture; i.e., one or more PME gene sequence(s) are expressed under the control of an inducible promoter that is responsive to specific molecules or metabolites, temperature, oxygen levels or other parameters provided in the culture of the bacterium as it is grown in a flask, fermenter, or other culture vessel. In some embodiments, the engineered bacteria encode one or more PME gene sequence(s) which are directly or indirectly induced prior to in vivo administration during bacterial cell culture; wherein the one or more PME gene sequence(s) are expressed under low oxygen or anaerobic conditions. In some embodiments, the engineered bacteria encode one or more PME gene sequence(s) which are directly or indirectly induced prior to in vivo administration during bacterial cell culture; wherein the one or more PME gene sequence(s) are expressed under aerobic conditions. In some embodiments, the engineered bacteria encode one or more PME gene sequence(s) which are directly or indirectly induced prior to in vivo administration during bacterial cell culture; wherein the one or more PME gene sequence(s) are expressed under microaerobic conditions. In some embodiments, the engineered bacteria encode one or more PME gene sequence(s) which are directly or indirectly induced prior to in vivo administration during bacterial cell culture; wherein the one or more PME gene sequence(s) are expressed in the presence of arabinose. In some embodiments, the engineered bacteria encode one or more PME gene sequence(s) which are directly or indirectly induced prior to in vivo administration during bacterial cell culture; wherein the one or more PME gene sequence(s) are expressed in the presence of IPTG.

Payload (and/or polypeptides of interest and/or proteins of interest and/or therapeutic polypeptides and/or therapeutic proteins and/or therapeutic peptides and/or effector and/or effector molecules) include any of the metabolites described herein and/or any of the enzyme(s) or polypeptide(s) which function as enzymes for the production or catabolism of such effector molecules. Effector molecules and payloads include but are not limited to anti-cancer molecules, immune modulators, gut barrier enhancer molecules, anti-inflammatory molecules, satiety molecules or neuromodulatory effectors. Non-limiting examples of payloads are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

As used herein, the term "gene of interest" or "gene sequence of interest" includes any or a plurality of any of the gene(s) an/or gene sequence(s) and or gene cassette(s) encoding one or more effector molecules and payloads include but are not limited to anti-cancer molecules, immune modulators, gut barrier enhancer molecules, anti-inflammatory molecules, satiety molecules or effectors, neuromodulatory molecules described herein, e.g., kynureninase, tryptophan production enzymes, tryptophan degradation enzymes, one or more kynurenine production enzymes, serotonin or melatonin production or degradation enzymes, indole metabolite production or degradation enzymes (described herein) KP metabolite production or degradation enzymes. Non-limiting examples of additional genes of interest are described in Non-limiting examples of payloads are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

In some embodiments, the genetically engineered bacteria comprise multiple copies of the same payload gene(s). In some embodiments, the gene encoding the payload is present on a plasmid and operably linked to a directly or indirectly inducible promoter. In some embodiments, the gene encoding the payload is present on a plasmid and operably linked to a constitutive promoter. In some embodiments, the gene encoding the payload is present on a plasmid and operably linked to a promoter that is induced under low-oxygen or anaerobic conditions. In some embodiments, the gene encoding the payload is present on plasmid and operably linked to a promoter that is induced by exposure to tetracycline or arabinose, or another chemical or nutritional inducer described herein.

In some embodiments, the gene encoding the payload is present on a chromosome and operably linked to a directly or indirectly inducible promoter. In some embodiments, the gene encoding the payload is present on a chromosome and operably linked to a constitutive promoter. In some embodiments, the gene encoding the payload is present in the chromosome and operably linked to a promoter that is induced under low-oxygen or anaerobic conditions. In some embodiments, the gene encoding the payload is present on chromosome and operably linked to a promoter that is induced by exposure to tetracycline or arabinose, or another chemical or nutritional inducer described herein.

In some embodiments, the genetically engineered bacteria comprise two or more payloads, all of which are present on the chromosome. In some embodiments, the genetically engineered bacteria comprise two or more payloads, all of which are present on one or more same or different plasmids. In some embodiments, the genetically engineered bacteria comprise two or more payloads, some of which are present on the chromosome and some of which are present on one or more same or different plasmids.

In any of the nucleic acid embodiments, described above, the one or more payload(s) for producing a polypeptide of interest combinations are operably linked to one or more directly or indirectly inducible promoter(s). In some embodiments, the one or more payload(s) are operably linked to a directly or indirectly inducible promoter that is induced under exogeneous environmental conditions, e.g., conditions found in the gut, the tumor microenvironment, or other tissue specific conditions. In some embodiments, the one or more payload(s) are operably linked to a directly or indirectly inducible promoter that is induced by metabolites found in the gut, the tumor microenvironment, or other specific conditions. In some embodiments, the one or more payload(s) are operably linked to a directly or indirectly inducible promoter that is induced under low-oxygen or anaerobic conditions. In some embodiments, the one or more payload(s) are operably linked to a directly or indirectly inducible promoter that is induced under inflammatory conditions (e.g., RNS, ROS), as described herein. In some embodiments, the one or more payload(s) are operably linked to a directly or indirectly inducible promoter that is induced under immunosuppressive conditions, e.g., as found in the tumor, or other specific tissues, as described herein. In some embodiments, the two or more gene sequence(s) are linked to a directly or indirectly inducible promoter that is induced by exposure a chemical or nutritional inducer, which may or may not be present under in vivo conditions and which may be present during in vitro conditions (such as strain culture, expansion, manufacture), such as tetracycline or arabinose, or others described herein. In some embodiments, the two or more payloads are all linked to a constitutive promoter.

In a non-limiting example, the genetically engineered bacteria may comprise two payloads, one of which is linked to a constitutive promoter, and one of which is linked to a directly or indirectly inducible promoter. In a non-limiting example, the genetically engineered bacteria may comprise three payloads, one of which is linked to a constitutive promoter, and one of which is linked to a directly or indirectly inducible promoter and one of which is linked to a second, different directly or indirectly inducible promoter.

In some embodiments, the promoter is induced under in vivo conditions, e.g., the gut, as described herein. In some embodiments, the promoters are induced under in vitro conditions, e.g., various cell culture and/or cell manufacturing conditions, as described herein. In some embodiments, the promoter is induced under in vivo conditions, e.g., the gut, as described herein, and under in vitro conditions, e.g., various cell culture and/or cell production and/or manufacturing conditions, as described herein.

In some embodiments, the promoter that is operably linked to the gene encoding the payload is directly induced by exogenous environmental conditions (e.g., in vivo and/or in vitro and/or production/manufacturing conditions). In some embodiments, the promoter that is operably linked to the gene encoding the payload is indirectly induced by exogenous environmental conditions (e.g., in vivo and/or in vitro and/or production/manufacturing conditions).

In some embodiments, the promoter is directly or indirectly induced by exogenous environmental conditions specific to the gut of a mammal. In some embodiments, the promoter is directly or indirectly induced by exogenous environmental conditions specific to the hypoxic environment of a tumor and/or the small intestine of a mammal. In some embodiments, the promoter is directly or indirectly induced by low-oxygen or anaerobic conditions such as the hypoxic environment of a tumor and/or the environment of the mammalian gut. In some embodiments, the promoter is directly or indirectly induced by molecules or metabolites that are specific to the tumor, a particular tissue, or the gut of a mammal. In some embodiments, the promoter is directly or indirectly induced by a molecule that is co-administered with the bacterial cell.

FNR Dependent Regulation

The genetically engineered bacteria of the invention comprise a gene or gene cassette for producing a polypeptide of interest, wherein the gene or gene cassette is operably linked to a directly or indirectly inducible promoter that is controlled by exogenous environmental condition(s). In some embodiments, the inducible promoter is an oxygen level-dependent promoter and a polypeptide of interest is expressed in low-oxygen, microaerobic, or anaerobic conditions. For example, in low oxygen conditions, the oxygen level-dependent promoter is activated by a corresponding oxygen level-sensing transcription factor, thereby driving production of the polypeptide of interest.

Bacteria have evolved transcription factors that are capable of sensing oxygen levels. Different signaling pathways may be triggered by different oxygen levels and occur with different kinetics. An oxygen level-dependent promoter is a nucleic acid sequence to which one or more oxygen level-sensing transcription factors is capable of binding, wherein the binding and/or activation of the corresponding transcription factor activates downstream gene expression. In one embodiment, the genetically engineered bacteria comprise a gene or gene cassette for producing a payload under the control of an oxygen level-dependent promoter. In a more specific aspect, the genetically engineered bacteria comprise a gene or gene cassette for producing a payload under the control of an oxygen level-dependent promoter that is activated under low-oxygen or anaerobic environments, such as the hypoxic environment of a tumor and/or the environment of the mammalian gut, and/or other specific tissues.

In certain embodiments, the bacterial cell comprises a gene encoding a payload expressed under the control of a fumarate and nitrate reductase regulator (FNR) responsive promoter. In *E. coli*, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. FNR responsive promoters include, but are not limited to, the FNR responsive promoters listed in Table 3 below. Underlined sequences are predicted ribosome binding sites, and bolded sequences are restriction sites used for cloning.

TABLE 3

FNR Promoter Sequences

| FNR Responsive Promoter | Sequence |
|---|---|
| SEQ ID NO: 1A | GTCAGCATAACACCCTGACCTCTCATTAATTGTTCATGCCGGGCG GCACTATCGTCGTCCGGCCTTTTCCTCTCTTACTCTGCTACGTAC ATCTATTTCTATAAATCCGTTCAATTTGTCTGTTTTTTGCACAAAC ATGAAATATCAGACAATTCCGTGACTTAAGAAAATTTATACAAA TCAGCAATATACCCCTTAAGGAGTATATAAGGTGAATTTGATT TACATCAATAAGCGGGGTTGCTGAATCGTTAAGGTAGGCGGTAA TAGAAAAGAAATCGAGGCAAAA |

TABLE 3-continued

FNR Promoter Sequences

| FNR Responsive Promoter | Sequence |
| --- | --- |
| SEQ ID NO: 2A | ATTTCCTCTCATCCCATCCGGGGTGAGAGTCTTTTCCCCCGACTT<br>ATGGCTCATGCATGCATCAAAAAAGATGTGAGCTTGATCAAAAA<br>CAAAAAATATTTCACTCGACAGGAGTATTTATATTGCGCCCGTT<br>ACGTGGGCTTCGACTGTAAATC<u>AGAAAGGAGAAAACACCT</u> |
| SEQ ID NO: 3A | GTCAGCATAACACCCTGACCTCTCATTAATTGTTCATGCCGGGCG<br>GCACTATCGTCGTCCGGCCTTTTCCTCTCTTACTCTGCTACGTAC<br>ATCTATTTCTATAAATCCGTTCAATTTGTCTGTTTTTTGCACAAAC<br>ATGAAATATCAGACAATTCCGTGACTTAAGAAAATTTATACAAA<br>TCAGCAATATACCCCTTAAGGAGTATATAAAGGTGAATTTGATT<br>TACATCAATAAGCGGGGTTGCTGAATCGTTAAGGATCCCTCTAG<br><u>AAATAATTTTGTTTAACTTTAAGAAGGAGATATACAT</u> |
| SEQ ID NO: 4A | CATTTCCTCTCATCCCATCCGGGGTGAGAGTCTTTTCCCCCGACT<br>TATGGCTCATGCATGCATCAAAAAAGATGTGAGCTTGATCAAAA<br>ACAAAAAATATTTCACTCGACAGGAGTATTTATATTGCGCCCGG<br>ATCCCTCTAGAAATAATTTTGTTTAACTTTAAGAAGGAGATATA<br><u>CAT</u> |
| SEQ ID NO: 5A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGTAAAGTTTGAGCGAAGTCAATAAACTCTCTACCCATTC<br>AGGGCAATATCTCTCTTGGATCCCTCTAGAAATAATTTTGTTTA<br><u>ACTTTAAGAAGGAGATATACAT</u> |
| SEQ ID NO: 6A | ATCCCCATCACTCTTGATGGAGATCAATTCCCCAAGCTGCTAGAG<br>CGTTACCTTGCCCTTAAACATTAGCAATGTCGATTTATCAGAGGG<br>CCGACAGGCTCCCACAGGAGAAAACCG |
| SEQ ID NO: 7A | CTCTTGATCGTTATCAATTCCCACGCTGTTTCAGAGCGTTACCTT<br>GCCCTTAAACATTAGCAATGTCGATTTATCAGAGGGCCGACAGG<br>CTCCCACAGGAGAAAACCG |
| nirB1<br>SEQ ID NO: 8A | GTCAGCATAACACCCTGACCTCTCATTAATTGTTCATGCCGGGCG<br>GCACTATCGTCGTCCGGCCTTTTCCTCTCTTACTCTGCTACGTACA<br>TCTATTTCTATAAATCCGTTCAATTTGTCTGTTTTTTGCACAAACA<br>TGAAATATCAGACAATTCCGTGACTTAAGAAAATTTATACAAAT<br>CAGCAATATACCCCTTAAGGAGTATATAAAGGTGAATTTGATTT<br>ACATCAATAAGCGGGGTTGCTGAATCGTTAAGGTAGGCGGTAAT<br>AG<u>AAAAGAAATCGAGGCAAAA</u> |
| nirB2<br>SEQ ID NO: 9A | CGGCCCGATCGTTGAACATAGCGGTCCGCAGGCGGCACTGCTTA<br>CAGCAAACGGTCTGTACGCTGTCGTCTTTGTGATGTGCTTCCTGT<br>TAGGGTTTCGTCAGCCGTCACCGTCAGCATAACACCCTGACCTCTC<br>ATTAATTGCTCATGCCGGACGGCACTATCGTCGTCCGGCCTTTTC<br>CTCTCTTCCCCCGCTACGTGCATCTATTTCTATAAACCCGCTCATT<br>TTGTCTATTTTTTGCACAAACATGAAATATCAGACAATTCCGTGA<br>CTTAAGAAAATTTATACAAATCAGCAATATACCCATTAAGGAGT<br>ATATAAAGGTGAATTTGATTTACATCAATAAGCGGGGTTGCTGA<br>ATCGTTAAGGTAGGCGGTAATAGAAAAGAAATCGAGGCAAAAat<br>gtttgtttaactttaagaaggagatatacat |
| nirB3<br>SEQ ID NO: 10A | GTCAGCATAACACCCTGACCTCTCATTAATTGCTCATGCCGGACG<br>GCACTATCGTCGTCCGGCCTTTTCCTCTCTTCCCCCGCTACGTGC<br>ATCTATTTCTATAAACCCGCTCATTTGTCTATTTTTTGCACAAAC<br>ATGAAATATCAGACAATTCCGTGACTTAAGAAAATTTATACAAA<br>TCAGCAATATACCCATTAAGGAGTATATAAAGGTGAATTTGATT<br>TACATCAATAAGCGGGGTTGCTGAATCGTTAAGGTAGGCGGTAA<br>TAGAAAAGAAATCGAGGCAAAA |
| ydfZ<br>SEQ ID NO: 11A | ATTTCCTCTCATCCCATCCGGGGTGAGAGTCTTTTCCCCCGACTT<br>ATGGCTCATGCATGCATCAAAAAAGATGTGAGCTTGATCAAAAA<br>CAAAAAATATTTCACTCGACAGGAGTATTTATATTGCGCCCGTTA<br>CGTGGGCTTCGACTGTAAATC<u>AGAAAGGAGAAAACACCT</u> |
| nirB + RBS<br>SEQ ID NO: 12A | GTCAGCATAACACCCTGACCTCTCATTAATTGTTCATGCCGGGCG<br>GCACTATCGTCGTCCGGCCTTTTCCTCTCTTACTCTGCTACGTACA<br>TCTATTTCTATAAATCCGTTCAATTTGTCTGTTTTTTGCACAAACA<br>TGAAATATCAGACAATTCCGTGACTTAAGAAAATTTATACAAAT<br>CAGCAATATACCCCTTAAGGAGTATATAAAGGTGAATTTGATTT<br>ACATCAATAAGCGGGGTTGCTGAATCGTTAAGGATCCCTCTAGA<br><u>AATAATTTTGTTTAACTTTAAGAAGGAGATATACAT</u> |
| ydfZ + RBS<br>SEQ ID NO: 13A | CATTTCCTCTCATCCCATCCGGGGTGAGAGTCTTTTCCCCCGACT<br>TATGGCTCATGCATGCATCAAAAAAGATGTGAGCTTGATCAAAA |

TABLE 3-continued

FNR Promoter Sequences

| FNR Responsive Promoter | Sequence |
|---|---|
| | ACAAAAAATATTTCACTCGACAGGAGTATTTATATTGCGCCCGG<br>ATCCCTCTAGAAATAATTTTGTTTAACTTTAAGAAGGAGATATA<br>CAT |
| fnrS1<br>SEQ ID NO: 14A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGTAAAGTTTGAGCGAAGTCAATAAACTCTCTACCCATTC<br>AGGGCAATATCTCTCTTGGATCCCTCTAGAAATAATTTTGTTTAA<br>CTTTAAGAAGGAGATATACAT |
| fnrS2<br>SEQ ID NO: 15A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGCAAAGTTTGAGCGAAGTCAATAAACTCTCTACCCATTC<br>AGGGCAATATCTCTCTTGGATCCAAAGTGAACTCTAGAAATAAT<br>TTTGTTTAACTTTAAGAAGGAGATATACAT |
| nirB + crp<br>SEQ ID NO: 16A | TCGTCTTTGTGATGTGCTTCCTGTTAGGTTTCGTCAGCCGTCACC<br>GTCAGCATAACACCCTGACCTCTCATTAATTGCTCATGCCGGACG<br>GCACTATCGTCGTCCGGCCTTTTCCTCTCTTCCCCCGCTACGTGC<br>ATCTATTTCTATAAACCCGCTCATTTTGTCTATTTTTTGCACAAAC<br>ATGAAATATCAGACAATTCCGTGACTTAAGAAAATTTATACAAA<br>TCAGCAATATACCCATTAAGGAGTATATAAAGGTGAATTTGATT<br>TACATCAATAAGCGGGGTTGCTGAATCGTTAAGGTAGaaatgtgatcta<br>gttcacatttGCGGTAATAGAAAAGAAATCGAGGCAAAAatgtttgtttaacttta<br>agaaggagatatacat |
| fnrS + crp<br>SEQ ID NO: 17A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGCAAAGTTTGAGCGAAGTCAATAAACTCTCTACCCATTC<br>AGGGCAATATCTCTCaaatgtgatctagttcacattttttgtttaactttaagaaggagatatac<br>at |

FNR promoter sequences are known in the art, and any suitable FNR promoter sequence(s) may be used in the genetically engineered bacteria of the invention. Any suitable FNR promoter(s) may be combined with any suitable payload.

Non-limiting FNR promoter sequences are provided in Table 3, which depicts the nucleic acid sequences of exemplary regulatory region sequences comprising a FNR-responsive promoter sequence. Underlined sequences are predicted ribosome binding sites, and bolded sequences are restriction sites used for cloning. In some embodiments, the genetically engineered bacteria of the invention comprise one or more of: SEQ ID NO: 1A, SEQ ID NO: 2A, SEQ ID NO: 3A, SEQ ID NO: 4A, SEQ ID NO: 5A, SEQ ID NO: 6A, SEQ ID NO: 7A, nirB1 promoter (SEQ ID NO: 8A), nirB2 promoter (SEQ ID NO: 9A), nirB3 promoter (SEQ ID NO: 10A), ydfZ promoter (SEQ ID NO: 11A), nirB promoter fused to a strong ribosome binding site (SEQ ID NO: 12A), ydfZ promoter fused to a strong ribosome binding site (SEQ ID NO: 13A), fnrS, an anaerobically induced small RNA gene (fnrS1 promoter SEQ ID NO: 14A or fnrS2 promoter SEQ ID NO: 15A), nirB promoter fused to a crp binding site (SEQ ID NO: 16A), and fnrS fused to a crp binding site (SEQ ID NO: 17A). In some embodiments, the FNR-responsive promoter is at least about 80%, at least about 85%, at least about 90%, at least about 95%, or at least about 99% homologous to the sequence of any one of SEQ ID NOs: 1A-17A.

In some embodiments, multiple distinct FNR nucleic acid sequences are inserted in the genetically engineered bacteria. In alternate embodiments, the genetically engineered bacteria comprise a gene encoding a payload (e.g. PME e.g. PAL) expressed under the control of an alternate oxygen level-dependent promoter, e.g., DNR (Trunk et al., 2010) or ANR (Ray et al., 1997). In these embodiments, expression of the payload gene is particularly activated in a low-oxygen or anaerobic environment, such as in the gut. In some embodiments, gene expression is further optimized by methods known in the art, e.g., by optimizing ribosomal binding sites and/or increasing mRNA stability. In one embodiment, the mammalian gut is a human mammalian gut.

Any suitable FNR promoter(s) may be combined with any suitable PAL. Non-limiting FNR promoter sequences are provided in Table 3, and non-limiting PAL sequences are also provided herein. In some embodiments, the genetically engineered bacteria of the invention comprise one or more of of the following SEQ ID NOs disclosed in WO2017087580, the contents of which are herein incorporated by reference in their entirety: SEQ ID NO: 9, SEQ ID NO: 10, nirB1 promoter (SEQ ID NO: 11), nirB2 promoter (SEQ ID NO: 12), nirB3 promoter (SEQ ID NO: 13), ydfZ promoter (SEQ ID NO: 14), nirB promoter fused to a strong ribosome binding site (SEQ ID NO: 15), ydfZ promoter fused to a strong ribosome binding site (SEQ ID NO: 16), fnrS, an anaerobically induced small RNA gene (fnrS1 promoter SEQ ID NO: 9 or fnrS2 promoter SEQ ID NO: 17), nirB promoter fused to a crp binding site (SEQ ID NO: 18), and fnrS fused to a crp binding site (SEQ ID NO: 19).

In another embodiment, the genetically engineered bacteria comprise the gene or gene cassette for producing the payload expressed under the control of anaerobic regulation of arginine deiminiase and nitrate reduction transcriptional regulator (ANR). In *P. aeruginosa*, ANR is "required for the expression of physiological functions which are inducible under oxygen-limiting or anaerobic conditions" (Winteler et al., 1996; Sawers 1991). *P. aeruginosa* ANR is homologous with *E. coli* FNR, and "the consensus FNR site (TTGAT-ATCAA) was recognized efficiently by ANR and FNR"

(Winteler et al., 1996). Like FNR, in the anaerobic state, ANR activates numerous genes responsible for adapting to anaerobic growth. In the aerobic state, ANR is inactive. *Pseudomonas fluorescens, Pseudomonas putida, Pseudomonas syringae*, and *Pseudomonas mendocina* all have functional analogs of ANR (Zimmermann et al., 1991). Promoters that are regulated by ANR are known in the art, e.g., the promoter of the arcDABC operon (see, e.g., Hasegawa et al., 1998).

The FNR family also includes the dissimilatory nitrate respiration regulator (DNR) (Arai et al., 1995), a transcriptional regulator which is required in conjunction with ANR for "anaerobic nitrate respiration of *Pseudomonas aeruginosa*" (Hasegawa et al., 1998). For certain genes, the FNR-binding motifs "are probably recognized only by DNR" (Hasegawa et al., 1998). Any suitable transcriptional regulator that is controlled by exogenous environmental conditions and corresponding regulatory region may be used. Non-limiting examples include ArcA/B, ResD/E, NreA/B/C, and AirSR, and others are known in the art.

In other embodiments, the one or more gene sequence(s) for producing a payload (e.g. a PME e.g. PAL) are expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism, and assimilation of less favorable carbon sources when rapidly metabolizable carbohydrates, such as glucose, are present (Wu et al., 2015). This preference for glucose has been termed glucose repression, as well as carbon catabolite repression (Deutscher, 2008; Görke and Stulke, 2008). In some embodiments, the gene or gene cassette for producing a payload molecule is controlled by an oxygen level-dependent promoter fused to a CRP binding site. In some embodiments, the one or more gene sequence(s) for a payload are controlled by an FNR promoter fused to a CRP binding site. In these embodiments, cyclic AMP binds to CRP when no glucose is present in the environment. This binding causes a conformational change in CRP, and allows CRP to bind tightly to its binding site. CRP binding then activates transcription of the gene or gene cassette by recruiting RNA polymerase to the FNR promoter via direct protein-protein interactions. In the presence of glucose, cyclic AMP does not bind to CRP and transcription of the gene or gene cassette for producing a payload is repressed. In some embodiments, an oxygen level-dependent promoter (e.g., an FNR promoter) fused to a binding site for a transcriptional activator is used to ensure that the gene or gene cassette for producing a payload is not expressed under anaerobic conditions when sufficient amounts of glucose are present, e.g., by adding glucose to growth media in vitro.

In some embodiments, the genetically engineered bacteria comprise an oxygen level-dependent promoter from a different species, strain, or substrain of bacteria. In some embodiments, the genetically engineered bacteria comprise an oxygen level-sensing transcription factor, e.g., FNR, ANR or DNR, from a different species, strain, or substrain of bacteria. In some embodiments, the genetically engineered bacteria comprise an oxygen level-sensing transcription factor and corresponding promoter from a different species, strain, or substrain of bacteria. The heterologous oxygen-level dependent transcriptional regulator and/or promoter increases the transcription of genes operably linked to said promoter, e.g., one or more gene sequence(s) for producing the payload(s) in a low-oxygen or anaerobic environment, as compared to the native gene(s) and promoter in the bacteria under the same conditions. In certain embodiments, the non-native oxygen-level dependent transcriptional regulator is an FNR protein from *N. gonorrhoeae* (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., the gene encoding the payload, in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., the gene encoding the payload, in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., (2006). In some embodiments, both the oxygen level-sensing transcriptional regulator and corresponding promoter are mutated relative to the wild-type sequences from bacteria of the same subtype in order to increase expression of the payload in low-oxygen conditions.

In some embodiments, the bacterial cells comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding the payload are present on different plasmids. In some embodiments, the gene encoding the oxygen level-sensing transcriptional regulator and the gene encoding the payload are present on the same plasmid.

In some embodiments, the gene encoding the oxygen level-sensing transcriptional regulator is present on a chromosome. In some embodiments, the gene encoding the oxygen level-sensing transcriptional regulator and the gene encoding the payload are present on different chromosomes. In some embodiments, the gene encoding the oxygen level-sensing transcriptional regulator and the gene encoding the payload are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene encoding the payload. In some embodiments, expression of the transcriptional regulator is controlled by the same promoter that controls expression of the payload. In some embodiments, the transcriptional regulator and the payload are divergently transcribed from a promoter region.

Oxygen Level Independent Inducible Promoters

Oxygen Level Independent Inducible Promoters systems, such as systems including FNRS24Y, are described in PCT/US2016/062369, filed Nov. 16, 2016 and published as WO2017087580, the contents of which is herein incorporated by reference in its entirety.

In addition to promoters that are induced in response to oxygen levels, the PME gene(s) and/or Phe transporter gene(s) can be regulated by promoters that are induced in response to inflammatory conditions, such as in presence of reactive nitrogen species or in the presence of reactive oxygen species. Examples of such inducible promoters are found in co-pending, co-owned International Application PCT/US2016/050836, filed Sep. 8, 2016, the contents of which are hereby incorporated by reference in their entirety.

In any of the embodiments described herein, the genetically engineered bacteria comprising one or more PME and/or one or more phe transporters under control of an oxygen independent promoter further comprise one or more bacteriophages. In some embodiments, the bacteriophages have been mutated in one or more genes within the bacteriophage genome. Such mutations include deletions, insertions, substitutions and inversions and are located in or encompass one or more bacteriophage genes.

In some embodiments, the genetically engineered bacteria comprise one or more E. coliIn some embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

RNS-Dependent Regulation

In some embodiments, the genetically engineered bacteria or genetically engineered virus comprise a gene encoding a payload that is expressed under the control of an inducible promoter. In some embodiments, the genetically engineered bacterium or genetically engineered virus that expresses a payload under the control of a promoter that is activated by inflammatory conditions. In one embodiment, the gene for producing the payload is expressed under the control of an inflammatory-dependent promoter that is activated in inflammatory environments, e.g., a reactive nitrogen species or RNS promoter. In some embodiments, the genetically engineered bacteria of the invention comprise a tunable regulatory region that is directly or indirectly controlled by a transcription factor that is capable of sensing at least one reactive nitrogen species. Suitable RNS inducible promoters, e.g., inducible by reactive nitrogen species are described in International Patent Application PCT/US2016/062369, filed Nov. 16, 2016 and published as WO2017087580, published as WO2017/123675, the contents of which is herein incorporated by reference in its entirety.

ROS-Dependent Regulation

In some embodiments, the genetically engineered bacteria or genetically engineered virus comprise a gene for producing a payload that is expressed under the control of an inducible promoter. In some embodiments, the genetically engineered bacterium or genetically engineered virus that expresses a payload under the control of a promoter that is activated by conditions of cellular damage. In one embodiment, the gene for producing the payload is expressed under the control of a cellular damaged-dependent promoter that is activated in environments in which there is cellular or tissue damage, e.g., a reactive oxygen species or ROS promoter. In some embodiments, the genetically engineered bacteria of the invention comprise a tunable regulatory region that is directly or indirectly controlled by a transcription factor that is capable of sensing at least one reactive oxygen species. Suitable ROS inducible promoters, e.g., inducible by reactive oxygen species are described in International Patent Application PCT/US2017/013072, filed Jan. 11, 2017, published as WO2017/123675, International Patent Applications PCT/US2016/032562, filed May 13, 2016, published as WO2016183531, and PCT/US2016/062369, filed Nov. 16, 2016 and published as WO2017087580, the contents of each of which are herein incorporated by reference in their entireties.

TABLE 17

Nucleotide sequences of exemplary OxyR-regulated regulatory regions

| Regulatory Sequence | sequence |
|---|---|
| katG (SEQ ID | TGTGGCTTTTATGAAAATCACACAGTGATCACAAATTTTAAACAGAGC ACAAAATGCTGCCTCGAAATGAGGGCGGGAAAATAAGGTTATCAGCC |

TABLE 17-continued

Nucleotide sequences of exemplary OxyR-regulated regulatory regions

| Regulatory Sequence | sequence |
|---|---|
| NO: 18C) | TTGTTTTCTCCCTCATTACTTGAAGGATATGAAGCTAAAACCCTTTTTT<br>ATAAAGCATTTGTCCGAATTCGGACATAATCAAAAAAGCTTAATTAAG<br>ATCAATTTGATCTACATCTCTTTAACCAACAATATGTAAGATCTCAACT<br>ATCGCATCCGTGGATTAATTCAATTATAACTTCTCTCTAACGCTGTGTA<br>TCGTAACGGTAACACTGTAGAGGGGAGCACATTGATGCGAATTCATTA<br>AAGAGGAGAAAGGTACC |
| dps<br>(SEQ ID<br>NO: 19C) | TTCCGAAAATTCCTGGCGAGCAGATAAATAAGAATTGTTCTTATCAAT<br>ATATCTAACTCATTGAATCTTTATTAGTTTTGTTTTTCACGCTTGTTACC<br>ACTATTAGTGTGATAGGAACAGCCAGAATAGCGGAACACATAGCCGG<br>TGCTATACTTAATCTCGTTAATTACTGGGACATAACATCAAGAGGATA<br>TGAAATTCGAATTCATTAAAGAGGAGAAAGGTACC |
| ahpC<br>(SEQ ID<br>NO: 20C) | GCTTAGATCAGGTGATTGCCCTTTGTTTATGAGGGTGTTGTAATCCATG<br>TCGTTGTTGCATTTGTAAGGGCAACACCTCAGCCTGCAGGCAGGCACT<br>GAAGATACCAAAGGGTAGTTCAGATTACACGGTCACCTGGAAAGGGG<br>GCCATTTTACTTTTTATCGCCGCTGGCGGTGCAAAGTTCACAAAGTTGT<br>CTTACGAAGGTTGTAAGGTAAAACTTATCGATTTGATAATGGAAACGC<br>ATTAGCCGAATCGGCAAAAATTGGTTACCTTACATCTCATCGAAAACA<br>CGGAGGAAGTATAGATGCGAATTCATTAAAGAGGAGAAAGGTACC |
| oxyS<br>(SEQ ID<br>NO: 21C) | CTCGAGTTCATTATCCATCCTCCATCGCCACGATAGTTCATGGCGATA<br>GGTAGAATAGCAATGAACGATTATCCCTATCAAGCATTCTGACTGATA<br>ATTGCTCACACGAATTCATTAAAGAGGAGAAAGGTACC |

In some embodiments, the regulatory region sequence is at least about 80%, at least about 85%, at least about 90%, at least about 95%, or at least about 99% homologous to the sequence of SEQ ID NO: 18C, SEQ ID NO: 19C, SEQ ID NO: 20C, and/or SEQ ID NO: 21C.

Propionate and Other Promoters

In some embodiments, the genetically engineered bacteria comprise the gene or gene cassette for producing one or more payload genes expressed under the control of an inducible promoter that is responsive to specific molecules or metabolites in the environment, e.g., the tumor microenvironment, a specific tissue, or the mammalian gut. For example, the short-chain fatty acid propionate is a major microbial fermentation metabolite localized to the gut (Hosseini et al., 2011). In one embodiment, the gene or gene cassette for producing a payload is under the control of a propionate-inducible promoter. In a more specific embodiment, the gene or gene cassette for producing the payload is under the control of a propionate-inducible promoter that is activated by the presence of propionate in the mammalian gut. Any molecule or metabolite found in the mammalian gut, in a healthy and/or disease state, may be used to induce payload expression. Non-limiting examples of inducers include propionate, bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese. In alternate embodiments, the gene or gene cassette for producing therapeutic polypeptide is under the control of a pAraBAD promoter, which is activated in the presence of the sugar arabinose.

In some embodiments, the gene or gene cassette for producing the polypeptide of interest is present on a plasmid and operably linked to a promoter that is induced under low-oxygen or anaerobic conditions. In some embodiments, the gene or gene cassette for producing polypeptide of interest is present in the chromosome and operably linked to a promoter that is induced under low-oxygen or anaerobic conditions. In some embodiments, the gene or gene cassette for producing a polypeptide of interest is present on a plasmid and operably linked to a promoter that is induced by molecules or metabolites that are specific to the to the tumor and/or the mammalian gut. In some embodiments, the gene or gene cassette for producing polypeptide of interest is present on a chromosome and operably linked to a promoter that is induced by molecules or metabolites that are specific to the tumor and/or the mammalian gut. In some embodiments, the gene or gene cassette for producing polypeptide of interest is present on a chromosome and operably linked to a promoter that is induced by exposure to tetracycline. In some embodiments, the gene or gene cassette for producing polypeptide of interest is present on a plasmid and operably linked to a promoter that is induced by exposure to tetracycline.

In some embodiments, gene expression is further optimized by methods known in the art, e.g., by optimizing ribosomal binding sites (RBS), manipulating transcriptional regulators, and/or increasing mRNA stability. Bioinformatics tools for the fine tuning and optimization of RBS are known in the art.

In any of the embodiments described herein above (and elsewhere herein), the engineered bacteria may additionally comprise gene sequence(s) encoding one or more gene sequence(s) under the control of any of the promoters discussed herein. In some embodiments, the genetically engineered bacteria comprise a stably maintained plasmid or chromosome carrying the gene or gene cassette for producing the polypeptide of interest, such that the gene or gene cassette can be expressed in the host cell, and the host cell is capable of survival and/or growth in vitro, e.g., in medium, and/or in vivo, e.g., in the gut or the tumor microenvironment. In some embodiments, a bacterium may comprise multiple copies of the gene or gene cassette for producing a polypeptide of interest. In some embodiments, gene or gene cassette for producing the payload is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, gene or gene cassette for producing a polypeptide of interest is expressed on a high-copy plasmid. In some embodiments, the high-copy plasmid may be useful for increasing gene or gene cassette expression. In some embodiments, gene or gene cassette for producing a polypeptide of interest is expressed on a chromosome.

Other Inducible Promoters

In some embodiments, the gene encoding a polypeptide of interest is present on a plasmid and operably linked to a promoter that is induced by one or more nutritional and/or chemical inducer(s) and/or metabolite(s). In some embodiments, the gene encoding a polypeptide of interest is present in the chromosome and operably linked to a promoter that is induced by one or more nutritional and/or chemical inducer(s) and/or metabolite(s).

In some embodiments, the bacterial cell comprises a stably maintained plasmid or chromosome carrying the one or more gene sequences(s), inducible by one or more nutritional and/or chemical inducer(s) and/or metabolite(s), encoding a polypeptide of interest, such that a polypeptide of interest can be expressed in the host cell, and the host cell is capable of survival and/or growth in vitro, e.g., in medium, and/or in vivo, e.g., in the tumor or in the gut. In some embodiments, bacterial cell comprises two or more distinct copies of the one or more gene sequences(s) encoding a polypeptide of interest, which is controlled by a promoter inducible one or more nutritional and/or chemical inducer(s) and/or metabolite(s). In some embodiments, the genetically engineered bacteria comprise multiple copies of the one or more gene sequences(s) encoding a polypeptide of interest, which is controlled by a promoter inducible by one or more nutritional and/or chemical inducer(s) and/or metabolite(s). In some embodiments, the one or more gene sequences(s) encoding a polypeptide of interest(s), is present on a plasmid and operably linked to a directly or indirectly inducible promoter inducible by one or more nutritional and/or chemical inducer(s) and/or metabolite(s). In some embodiments, the one or more gene sequences(s) encoding a polypeptide of interest, is present on a chromosome and operably linked to a directly or indirectly inducible promoter. In some embodiments, the one or more gene sequence(s) encoding a polypeptide of interest is induced by one or more nutritional and/or chemical inducer(s) and/or metabolites.

In some embodiments, one or more gene sequence(s) encoding polypeptides of interest described herein is present on a plasmid and operably linked to promoter a directly or indirectly inducible by one or more nutritional and/or chemical inducer(s) and/or metabolite(s). In some embodiments, the bacterial cell comprises a stably maintained plasmid or chromosome carrying the gene encoding a polypeptide of interest, which is induced by one or more nutritional and/or chemical inducer(s) and/or metabolite(s), such that a polypeptide of interest can be expressed in the host cell, and the host cell is capable of survival and/or growth in vitro, e.g., under culture conditions, and/or in vivo, e.g., in the gut or the tumor microenvironment. In some embodiments, bacterial cell comprises two or more gene sequence(s) for the production of a polypeptide of interest, one or more of which are induced by one or more nutritional and/or chemical inducer(s) and/or metabolite(s). In some embodiments, the genetically engineered bacteria comprise multiple copies of the same gene sequence(s) for the production of a polypeptide of interest which are induced by one or more nutritional and/or chemical inducer(s) and/or metabolite(s). In some embodiments, the genetically engineered bacteria comprise multiple copies of different gene sequence(s) for the production of a polypeptide of interest, one or more of which are induced by one or more nutritional and/or chemical inducer(s) and/or metabolite(s).

In some embodiments, the gene sequence(s) for the production of a polypeptide of interest is present on a plasmid and operably linked to a promoter that is induced by one or more nutritional and/or chemical inducer(s) and/or metabolite(s). In some embodiments, gene sequence(s) for the production of a polypeptide of interest is present in the chromosome and operably linked to a promoter that is induced by one or more nutritional and/or chemical inducer(s) and/or metabolite(s).

In some embodiments, the genetically engineered bacteria comprise two or more distinct PAL genes. In some embodiments, the genetically engineered bacteria comprise multiple copies of the same PAL gene. In some embodiments, the PAL gene is present on a plasmid and operably linked to a directly or indirectly inducible promoter. In some embodiments, the PAL gene is present on a plasmid and operably linked to a promoter that is induced under low-oxygen or anaerobic conditions. In some embodiments, the PAL gene is present on a chromosome and operably linked to a directly or indirectly inducible promoter. In some embodiments, the PAL gene is present in the chromosome and operably linked to a promoter that is induced under low-oxygen or anaerobic conditions. In some embodiments, the PAL gene is present on a plasmid and operably linked to a promoter that is induced by exposure to tetracycline. In some embodiments, the PAL gene is present on a plasmid and operably linked to a promoter that is induced by exposure to arabinose. In some embodiments, the PAL gene is present on a plasmid and operably linked to a promoter that is induced by exposure to IPTG or another LacI inducer. In some embodiments, the PAL gene is present on a plasmid and operably linked to a promoter that is induced by exposure to rhamnose. In some embodiments, the PAL gene is present on a plasmid and operably linked to a promoter that is induced by exposure to tetracycline. In some embodiments, the PAL gene is present on a plasmid and operably linked to a promoter that is induced by change in temperature from a non-permissive temperature to a permissive temperature. In some embodiments, the PAL gene is present on a chromosome and operably linked to a promoter that is induced by exposure to arabinose. In some embodiments, the PAL gene is present on a chromosome and operably linked to a promoter that is induced by exposure to IPTG or another LacI inducer. In some embodiments, the PAL gene is present on a chromosome and operably linked to a promoter that is induced by exposure to rhamnose. In some embodiments, the PAL gene is present on a chromosome and operably linked to a promoter that is induced by exposure to tetracycline. In some embodiments, the PAL gene is present on a chromosome and operably linked to a promoter that is induced by change in temperature from a non-permissive temperature to a permissive temperature.

In some embodiments, the genetically engineered bacteria comprise a stably maintained plasmid or chromosome carrying the LAAD gene, such that LAAD can be expressed in the host cell, and the host cell is capable of survival and/or growth in vitro, e.g., in medium, and/or in vivo, e.g., in the gut. In some embodiments, the genetically engineered bacteria comprise two or more distinct LAAD genes. In some embodiments, the genetically engineered bacteria comprise multiple copies of the same LAAD gene. In some embodiments, the LAAD gene is present on a plasmid and operably linked to a directly or indirectly inducible promoter. In some embodiments, the LAAD gene is present on a plasmid and operably linked to a promoter that is inducible, e.g., by arabinose or tetracycline. In some embodiments, the LAAD gene is present on a chromosome and operably linked to a directly or indirectly inducible promoter. In some embodiments, the LAAD gene is present in the chromosome and operably linked to a promoter that is induced, e.g., by arabinose or tetracycline. In some embodiments, the LAAD gene is present on a plasmid and operably linked to a promoter that is induced by exposure to tetracycline. In some embodiments, the LAAD gene is present on a plasmid and operably linked to a promoter that is induced by exposure to arabinose. In some embodiments, the LAAD gene is present on a plasmid and operably linked to a promoter that is induced by exposure to IPTG or another Lad inducer. In some embodiments, the LAAD gene is present on a plasmid and operably linked to a promoter that is induced by exposure to rhamnose. In some embodiments, the LAAD gene is present on a plasmid and operably linked to a promoter that is induced by change in temperature from a non-permissive temperature to a permissive temperature. In some embodiments, the LAAD gene is present on a plasmid and operably linked to a constitutive promoter. In some embodiments, the LAAD gene is present on a plasmid and operably linked to a promoter that is induced by exposure to tetracycline. In some embodiments, the LAAD gene is present on a chromosome and operably linked to a promoter that is induced by exposure to arabinose. In some embodiments, the LAAD gene is present on a chromosome and operably linked to a promoter that is induced by exposure to IPTG or another Lad inducer. In some embodiments, the LAAD gene is present on a chromosome and operably linked to a promoter that is induced by exposure to rhamnose. In some embodiments, the LAAD gene is present on a chromosome and operably linked to a promoter that is induced by change in temperature from a non-permissive temperature to a permissive temperature. In some embodiments, the LAAD gene is present on a chromosome and operably linked to a constitutive promoter.

In any of these embodiments of bacteria comprising PME gene(s), e.g., PAL, PAH, and/or LAAD, the bacteria may further comprise gene sequence encoding one or more Phe transporters, which Phe transporter gene sequence(s) may be present on a plasmid or chromosome, which may be the same or a different plasmid or chromosome from the location of the PME gene. The Phe transporter gene sequence(s) may be under the control of the same or a different promoter from the PMR gene sequence(s).

In some embodiments, the genetically engineered bacteria comprise an oxygen-level dependent transcriptional regulator, e.g., FNR, ANR, or DNR, and corresponding promoter from a different bacterial species. The non-native oxygen-level dependent transcriptional regulator and promoter increase the transcription of genes operably linked to said promoter, e.g., PAL or PAH, in a low-oxygen or anaerobic environment, as compared to the native transcriptional regulator and promoter in the bacteria under the same conditions. PAL or PAH, in a low-oxygen or anaerobic environment, as compared to the wild-type promoter under the same conditions. PAL or PAH, in a low-oxygen or anaerobic environment, as compared to the wild-type transcriptional regulator under the same conditions. 2006).

In some embodiments, the genetically engineered bacteria of the invention comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding PAL are present on different plasmids. In some embodiments, the gene encoding the oxygen level-sensing transcriptional regulator and the gene encoding PAL are present on the same plasmid. In some embodiments, the gene encoding the oxygen level-sensing transcriptional regulator is present on a chromosome. In some embodiments, the gene encoding the oxygen level-sensing transcriptional regulator and the gene encoding PAL are present on different chromosomes. In some embodiments, the gene encoding the oxygen level-sensing transcriptional regulator and the gene encoding PAL are present on the same chromosome.

In one embodiment, LAAD expression is under the control of the $P_{araBAD}$ promoter. In one embodiment, expression of LAAD occurs under aerobic or microaerobic conditions. In one embodiment, PAL expression is under the control of the $P_{araBAD}$ promoter. In one embodiment, PAL expression occurs under aerobic or microaerobic conditions. In one embodiment, PAL expression occurs under anaerobic or low oxygen conditions and LADD expression occurs under aerobic or microaerobic conditions. In one embodiment, PAL expression occurs under anaerobic or low oxygen conditions and LADD expression is under the control of the $P_{araBAD}$ promoter.

In some embodiments, one or more gene(s) or gene cassette(s) for producing polypeptide(s) of interest (e.g., PAL and LAAD gene) are present, and each gene is expressed under the control of different promoters, such as any of the promoters discussed in this paragraph and elsewhere herein.

In some embodiments, the one or more PME genes, e.g., PAL and/or LAAD gene are expressed under the control of a promoter that is induced by exposure to arabinose. In some embodiments, the one or more PME genes, e.g., PAL and/or LAAD gene are expressed under the control of a promoter that is induced by exposure to IPTG or other Lad inducer. In some embodiments, the one or more PME genes, e.g., PAL and/or LAAD gene are expressed under the control of a promoter that is induced by exposure to rhamnose. In some embodiments, the one or more PME genes, e.g., PAL and/or LAAD gene are expressed under the control of a promoter that is induced by a change in temperature from a non-permissive temperature to a permissive temperature.

In some embodiments, the promoter that is operably linked to the gene encoding polypeptide of interest is directly or indirectly induced by one or more nutritional and/or chemical inducer(s) and/or metabolite(s).

In some embodiments, one or more inducible promoter(s) are useful for or induced during in vivo expression of the one or more protein(s) of interest. In some embodiments, the promoters are induced during in vivo expression of one or more anti-cancer, satiety, gut barrier enhancer, immune modulatory and/or neuromodulatory molecules and/or other polypeptide(s) of interest. In some embodiments, expression of one or more a polypeptide of interest(s) and/or other polypeptide(s) of interest is driven directly or indirectly by one or more arabinose inducible promoter(s) in vivo. In some embodiments, the promoter is directly or indirectly induced by a chemical and/or nutritional inducer and/or metabolite which is co-administered with the genetically engineered bacteria of the invention.

In some embodiments, expression of one or more a polypeptide of interest and/or other polypeptide(s) of interest, is driven directly or indirectly by one or more promoter(s) induced by a chemical and/or nutritional inducer and/or metabolite during in vitro growth, preparation, or manufacturing of the strain prior to in vivo administration. In some embodiments, the promoter(s) induced by a chemical and/or nutritional inducer and/or metabolite are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with a polypeptide of interest(s) and/or other polypeptide(s) of interest prior to administration. In some embodiments, the cultures, which are induced by a chemical and/or nutritional inducer and/or metabolite, are grown aerobically. In some embodiments, the cultures, which are induced by a chemical and/or nutritional inducer and/or metabolite, are grown anaerobically.

The genes of arabinose metabolism are organized in one operon, AraBAD, which is controlled by the PAraBAD promoter. The PAraBAD (or Para) promoter suitably fulfills the criteria of inducible expression systems. PAraBAD displays tighter control of payload gene expression than many other systems, likely due to the dual regulatory role of AraC, which functions both as an inducer and as a repressor. Additionally, the level of ParaBAD-based expression can be modulated over a wide range of L-arabinose concentrations to fine-tune levels of expression of the payload. However, the cell population exposed to sub-saturating L-arabinose concentrations is divided into two subpopulations of induced and uninduced cells, which is determined by the differences between individual cells in the availability of L-arabinose transporter (Zhang et al., Development and Application of an Arabinose-Inducible Expression System by Facilitating Inducer Uptake in *Corynebacterium glutamicum*; Appl. Environ. Microbiol. August 2012 vol. 78 no. 16 5831-5838). Alternatively, inducible expression from the ParaBad can be controlled or fine-tuned through the optimization of the ribosome binding site (RBS), as described herein.

In one embodiment, expression of one or more polypeptides of interest, e.g., one or more therapeutic polypeptide(s), is driven directly or indirectly by one or more arabinose inducible promoter(s).

In some embodiments, the arabinose inducible promoter is useful for or induced during in vivo expression of the one or more protein(s) of interest. In some embodiments, expression of one or more protein(s) of interest is driven directly or indirectly by one or more arabinose inducible promoter(s) in vivo. In some embodiments, the promoter is directly or indirectly induced by a molecule that is co-administered with the genetically engineered bacteria of the invention, e.g., arabinose.

In some embodiments, expression of one or more protein(s) of interest, is driven directly or indirectly by one or more arabinose inducible promoter(s) during in vitro growth, preparation, or manufacturing of the strain prior to in vivo administration. In some embodiments, the arabinose inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., arabinose. In some embodiments, the cultures, which are induced by arabinose, are grown aerobically. In some embodiments, the cultures, which are induced by arabinose, are grown anaerobically.

In one embodiment, the arabinose inducible promoter drives the expression of a construct comprising one or more protein(s) of interest, jointly with a second promoter, e.g., a second constitutive or inducible promoter. In some embodiments, two promoters are positioned proximally to the construct and drive its expression, wherein the arabinose inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., arabinose and IPTG). In another non-limiting example, the first inducing conditions may be culture conditions, e.g., including arabinose presence, and the second inducing conditions may be in vivo conditions. Such in vivo conditions include low-oxygen, microaerobic, or anaerobic conditions, presence of gut metabolites, and/or metabolites administered in combination with the bacterial strain. In some embodiments, the one or more arabinose promoters drive expression of one or more protein(s) of interest, in combination with the FNR promoter driving the expression of the same gene sequence(s).

In some embodiments, the arabinose inducible promoter drives the expression of one or more protein(s) of interest from a low-copy plasmid or a high copy plasmid or a biosafety system plasmid described herein. In some embodiments, the arabinose inducible promoter drives the expression of one or more protein(s) of interest from a construct which is integrated into the bacterial chromosome. Exemplary insertion sites are described herein.

In some embodiments, one or more protein(s) of interest are knocked into the arabinose operon and are driven by the native arabinose inducible promoter In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 23 of Table 18. In some embodiments, the arabinose inducible construct further comprises a gene encoding AraC, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 24 of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 25 of Table 18.

In some embodiments, the genetically engineered bacteria comprise one or more gene sequence(s) which are inducible through a rhamnose inducible system. The genes rhaBAD are organized in one operon which is controlled by the rhaP BAD promoter. The rhaP BAD promoter is regulated by two activators, RhaS and RhaR, and the corresponding genes belong to one transcription unit which divergently transcribed in the opposite direction of rhaBAD. In the presence of L-rhamnose, RhaR binds to the rhaP RS promoter and activates the production of RhaR and RhaS. RhaS together with L-rhamnose then bind to the rhaP BAD and the rhaP T promoter and activate the transcription of the structural genes. In contrast to the arabinose system, in which AraC is provided and divergently transcribed in the gene sequence(s), it is not necessary to express the regulatory proteins in larger quantities in the rhamnose expression system because the amounts expressed from the chromosome are sufficient to activate transcription even on multi-copy plasmids. Therefore, only the rhaP BAD promoter is cloned upstream of the gene that is to be expressed. Full induction of rhaBAD transcription also requires binding of the CRP-cAMP complex, which is a key regulator of catabolite repression. Alternatively, inducible expression from the rhaBAD can be controlled or fine-tuned through the optimization of the ribosome binding site (RBS), as described herein. In one embodiment, expression of one or more protein(s) of interest is driven directly or indirectly by one or more rhamnose inducible promoter(s). In one embodiment, expression of the payload is driven directly or indirectly by a rhamnose inducible promoter.

In some embodiments, the rhamnose inducible promoter is useful for or induced during in vivo expression of the one or more protein(s) of interest. In some embodiments, expression of one or more protein(s) of interest is driven directly or indirectly by one or more rhamnose inducible promoter(s) in vivo. In some embodiments, the promoter is directly or indirectly induced by a molecule that is co-administered with the genetically engineered bacteria of the invention, e.g., rhamnose In some embodiments, expression of one or more protein(s), is driven directly or indirectly by one or more rhamnose inducible promoter(s) during in vitro growth, preparation, or manufacturing of the strain prior to in vivo administration. In some embodiments, the rhamnose inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., rhamnose. In some embodiments, the cultures, which are induced by rhamnose, are grown arerobically. In some embodiments, the cultures, which are induced by rhamnose, are grown anaerobically.

In one embodiment, the rhamnose inducible promoter drives the expression of a construct comprising one or more protein(s) of interest jointly with a second promoter, e.g., a second constitutive or inducible promoter. In some embodiments, two promoters are positioned proximally to the construct and drive its expression, wherein the rhamnose inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., rhamnose and arabinose). In another non-limiting example, the first inducing conditions may be culture conditions, e.g., including rhamnose presence, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more rhamnose promoters drive expression of one or more protein(s) of interest and/or transcriptional regulator(s), e.g., FNRS24Y, in combination with the FNR promoter driving the expression of the same gene sequence(s).

In some embodiments, the rhamnose inducible promoter drives the expression of one or more protein(s) of interest, from a low-copy plasmid or a high copy plasmid or a biosafety system plasmid described herein. In some embodiments, the rhamnose inducible promoter drives the expression of one or more protein(s) of interest, from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 26 of Table 18.

In some embodiments, the genetically engineered bacteria comprise one or more gene sequence(s) which are inducible through an Isopropyl β-D-1-thiogalactopyranoside (IPTG) inducible system or other compound which induced transcription from the Lac Promoter. IPTG is a molecular mimic of allolactose, a lactose metabolite that activates transcription of the lac operon. In contrast to allolactose, the sulfur atom in IPTG creates a non-hydrolyzable chemical blond, which prevents the degradation of IPTG, allowing the concentration to remain constant. IPTG binds to the lac repressor and releases the tetrameric repressor (lad) from the lac operator in an allosteric manner, thereby allowing the transcription of genes in the lac operon. Since IPTG is not metabolized by $E.\ coli$, its concentration stays constant and the rate of expression of Lac promoter-controlled is tightly controlled, both in vivo and in vitro. IPTG intake is independent on the action of lactose permease, since other transport pathways are also involved. Inducible expression from the PLac can be controlled or fine-tuned through the optimization of the ribosome binding site (RBS), as described herein. Other compounds which inactivate Lad, can be used instead of IPTG in a similar manner.

In one embodiment, expression of one or more protein(s) of interest is driven directly or indirectly by one or more IPTG inducible promoter(s).

In some embodiments, the IPTG inducible promoter is useful for or induced during in vivo expression of the one or more protein(s) of interest. In some embodiments, expression of one or more protein(s) of interest is driven directly or indirectly by one or more IPTG inducible promoter(s) in vivo. In some embodiments, the promoter is directly or indirectly induced by a molecule that is co-administered with the genetically engineered bacteria of the invention, e.g., IPTG.

In some embodiments, expression of one or more protein(s) of interest is driven directly or indirectly by one or more IPTG inducible promoter(s) during in vitro growth, preparation, or manufacturing of the strain prior to in vivo administration. In some embodiments, the IPTG inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., IPTG. In some embodiments, the cultures, which are induced by IPTG, are grown arerobically. In some embodiments, the cultures, which are induced by IPTG, are grown anaerobically.

In one embodiment, the IPTG inducible promoter drives the expression of a construct comprising one or more protein(s) of interest jointly with a second promoter, e.g., a second constitutive or inducible promoter. In some embodiments, two promoters are positioned proximally to the construct and drive its expression, wherein the IPTG inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., arabinose and IPTG). In another non-limiting example, the first inducing conditions may be culture conditions, e.g., including IPTG presence, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more IPTG inducible promoters drive expression of one or more protein(s) of interest in combination with the FNR promoter driving the expression of the same gene sequence(s).

In some embodiments, the IPTG inducible promoter drives the expression of one or more protein(s) of interest from a low-copy plasmid or a high copy plasmid or a biosafety system plasmid described herein. In some embodiments, the IPTG inducible promoter drives the expression of one or more protein(s) of interest from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 27 of Table 18. In some embodiments, the IPTG inducible construct further comprises a gene encoding lacI, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 28 of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 29 of Table 18.

In some embodiments, the genetically engineered bacteria comprise one or more gene sequence(s) which are inducible through a tetracycline inducible system. The initial system Gossen and Bujard (Tight Control of gene expression in mammalian cells by tetracycline-responsive promoters. Gossen M & Bujard H. *PNAS*, 1992 Jun. 15; 89(12):5547-51) developed is known as tetracycline off: in the presence of tetracycline, expression from a tet-inducible promoter is reduced. Tetracycline-controlled transactivator (tTA) was created by fusing tetR with the C-terminal domain of VP16 (virion protein 16) from herpes simplex virus. In the absence of tetracycline, the tetR portion of tTA will bind tetO sequences in the tet promoter, and the activation domain promotes expression. In the presence of tetracycline, tetracycline binds to tetR, precluding tTA from binding to the tetO sequences. Next, a reverse Tet repressor (rTetR), was developed which created a reliance on the presence of tetracycline for induction, rather than repression. The new transactivator rtTA (reverse tetracycline-controlled transactivator) was created by fusing rTetR with VP16. The tetracycline on system is also known as the rtTA-dependent system.

In one embodiment, expression of one or more protein(s) of interest is driven directly or indirectly by one or more tetracycline inducible promoter(s). In some embodiments, the tetracycline inducible promoter is useful for or induced during in vivo expression of the one or more protein(s) of interest. In some embodiments, expression of one or more protein(s) of interest and/or transcriptional regulator(s), e.g., FNRS24Y, is driven directly or indirectly by one or more tetracycline inducible promoter(s) in vivo. In some embodiments, the promoter is directly or indirectly induced by a molecule that is co-administered with the genetically engineered bacteria of the invention, e.g., tetracycline In some embodiments, expression of one or more protein(s) of interest is driven directly or indirectly by one or more tetracycline inducible promoter(s) during in vitro growth, preparation, or manufacturing of the strain prior to in vivo administration. In some embodiments, the tetracycline inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., tetracycline. In some embodiments, the cultures, which are induced by tetracycline, are grown arerobically. In some embodiments, the cultures, which are induced by tetracycline, are grown anaerobically.

In one embodiment, the tetracycline inducible promoter drives the expression of a construct comprising one or more protein(s) of interest jointly with a second promoter, e.g., a second constitutive or inducible promoter. In some embodiments, two promoters are positioned proximally to the construct and drive its expression, wherein the tetracycline inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., tetracycline and IPTG). In another non-limiting example, the first inducing conditions may be culture conditions, e.g., including tetracycline presence, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more tetracycline promoters drive expression of one or more protein(s) of interest in combination with the FNR promoter driving the expression of the same gene sequence(s).

In some embodiments, the tetracycline inducible promoter drives the expression of one or more protein(s) of interest from a low-copy plasmid or a high copy plasmid or a biosafety system plasmid described herein. In some embodiments, the tetracycline inducible promoter drives the expression of one or more protein(s) of interest from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the bolded sequences of SEQ ID NO: 34 (tet promoter is in bold) of Table 18. In some embodiments, the tetracycline inducible construct further comprises a gene encoding AraC, which is divergently transcribed from the same promoter as the one or more one or more protein(s) of interest In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 34 in italics (Tet repressor is in italics) of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 34 in italics (Tet repressor is in italics) of Table 18.

In some embodiments, the genetically engineered bacteria comprise one or more gene sequence(s) whose expression is controlled by a temperature sensitive mechanism. Thermoregulators are advantageous because of strong transcriptional control without the use of external chemicals or specialized media (see, e.g., Nemani et al., Magnetic nanoparticle hyperthermia induced cytosine deaminase expression in microencapsulated *E. coli* for enzyme-prodrug therapy; J Biotechnol. 2015 Jun. 10; 203: 32-40, and references therein). Thermoregulated protein expression using the mutant c1857 repressor and the pL and/or pR phage λ promoters have been used to engineer recombinant bacterial strains. The gene of interest cloned downstream of the promoters can then be efficiently regulated by the mutant thermolabile c1857 repressor of bacteriophage. At temperatures below 37° C., c1857 binds to the oL or oR regions of the pR promoter and blocks transcription by RNA polymerase. At higher temperatures, the functional c1857 dimer is destabilized, binding to the oL or oR DNA sequences is abrogated, and mRNA transcription is initiated. An exemplary construct is depicted in FIG. 88A of WO2017087580, the contents of which are herein incorporated by reference in their entirety. Inducible expression from the ParaBad can be controlled or further fine-tuned through the optimization of the ribosome binding site (RBS), as described herein.

In one embodiment, expression of one or more protein(s) of interest is driven directly or indirectly by one or more thermoregulated promoter(s). In some embodiments, thermoregulated promoter is useful for or induced during in vivo expression of the one or more protein(s) of interest. In some embodiments, expression of one or more protein(s) of interest is driven directly or indirectly by one or more thermoregulated promoter(s) in vivo. In some embodiments, the promoter is directly or indirectly induced by a molecule that is co-administered with the genetically engineered bacteria of the invention, e.g., temperature.

In some embodiments, expression of one or more protein(s) of interest is driven directly or indirectly by one or more thermoregulated promoter(s) during in vitro growth, preparation, or manufacturing of the strain prior to in vivo administration. In some embodiments, it may be advantageous to shup off production of the one or more protein(s) of interest. This can be done in a thermoregulated system by growing the strain at lower temperatures, e.g., 30 C. Expression can then be induced by elevating the temperature to 37 C and/or 42 C. In some embodiments, thermoregulated promoter(s) are induced in culture, e.g., grown in a flask, fermenter or other appropriate culture vessel, e.g., used during cell growth, cell expansion, fermentation, recovery, purification, formulation, and/or manufacture. In some embodiments, the cultures, which are induced by temperatures between 37 C and 42 C, are grown arerobically. In some embodiments, the cultures, which are induced by induced by temperatures between 37 C and 42 C, are grown anaerobically.

In one embodiment, thermoregulated promoter drives the expression of a construct comprising one or more protein(s) of interest jointly with a second promoter, e.g., a second constitutive or inducible promoter. In some embodiments, two promoters are positioned proximally to the construct and drive its expression, wherein thermoregulated promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., thermoregulation and arabinose). In another non-limiting example, the first inducing conditions may be culture conditions, e.g., permissive temperature, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more thermoregulated promoters drive expression of one or more protein(s) of interest in combination with the FNR promoter driving the expression of the same gene sequence(s).

In some embodiments, thermoregulated promoter drives the expression of one or more protein(s) of interest from a low-copy plasmid or a high copy plasmid or a biosafety system plasmid described herein. In some embodiments, thermoregulated promoter drives the expression of one or more protein(s) of interest from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 30 of Table 18. In some embodiments, thermoregulated construct further comprises a gene encoding mutant c1857 repressor, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 31 of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 33 of Table 18.

In some embodiments, the genetically engineered bacteria comprise one or more gene sequence(s) which are indirectly inducible through a system driven by the PssB promoter. The Pssb promoter is active under aerobic conditions, and shuts off under anaerobic conditions.

This promoter can be used to express a gene of interest under aerobic conditions. This promoter can also be used to tightly control the expression of a gene product such that it is only expressed under anaerobic conditions. In this case, the oxygen induced PssB promoter induces the expression of a repressor, which represses the expression of a gene of interest. As a result, the gene of interest is only expressed in the absence of the repressor, i.e., under anaerobic conditions. This strategy has the advantage of an additional level of control for improved fine-tuning and tighter control. FIG. 89A of WO2017087580, the contents of which are herein incorporated by reference in their entirety depicts a schematic of the gene organization of a PssB promoter.

In one embodiment, expression of one or more protein(s) of interest is indirectly regulated by a repressor expressed under the control of one or more PssB promoter(s).

In some embodiments, induction of the PssB promoter(s) indirectly drives the in vivo expression of one or more protein(s) of interest. In some embodiments, induction of the PssB promoter(s) indirectly drives the expression of one or more protein(s) of interest during in vitro growth, preparation, or manufacturing of the strain prior to in vivo administration. In some embodiments, conditions for induction of the PssB promoter(s) are provided in culture, e.g., in a flask, fermenter or other appropriate culture vessel, e.g., used during cell growth, cell expansion, fermentation, recovery, purification, formulation, and/or manufacture.

In some embodiments, the PssB promoter indirectly drives the expression of one or more protein(s) of interest from a low-copy plasmid or a high copy plasmid or a biosafety system plasmid described herein. In some embodiments, the PssB promoter indirectly drives the expression of one or more protein(s) of interest from a construct which is integrated into the bacterial chromosome. Exemplary insertion sites are described herein.

In another non-limiting example, this strategy can be used to control expression of thyA and/or dapA, e.g., to make a conditional auxotroph. The chromosomal copy of dapA or ThyA is knocked out. Under anaerobic conditions, dapA or thyA as the case may be are expressed, and the strain can grow in the absence of dap or thymidine. Under aerobic conditions, dapA or thyA expression is shut off, and the strain cannot grow in the absence of dap or thymidine. Such a strategy can, for example be employed to allow survival of bacteria under anaerobic conditions, e.g., the gut and/or conditions of the tumor microenvironment, but prevent survival under aerobic conditions (biosafety switch). In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 35 of Table 18.

Sequences useful for expression from inducible promoters are listed in Table 18.

TABLE 18

| Inducible promoter construct sequences | |
|---|---|
| Description | Sequence |
| Arabinose Promoter region SEQ ID NO: 23 | CAGACATTGCCGTCACTGCGTCTTTTACTGGCTCTTCTCGCTAAC CCAACCGGTAACCCCGCTTATTAAAAGCATTCTGTAACAAAGCG GGACCAAAGCCATGACAAAAACGCGTAACAAAAGTGTCTATAA TCACGGCAGAAAAGTCCACATTGATTATTTGCACGGCGTCACAC TTTGCTATGCCATAGCATTTTTATCCATAAGATTAGCGGATCCA GCCTGACGCTTTTTTTCGCAACTCTCTACTGTTTCTCCATACCTC TAGAAATAATTTTGTTTAACTTTAAGAAGGAGATATACAT |
| AraC (reverse orientation) SEQ ID NO: 24 | TTATTCACAACCTGCCCTAAACTCGCTCGGACTCGCCCCGGTGC ATTTTTTAAATACTCGCGAGAAATAGAGTTGATCGTCAAAACCG ACATTGCGACCGACGGTGGCGATAGGCATCCGGGTGGTGCTCA AAAGCAGCTTCGCCTGACTGATGCGCTGGTCCTCGCGCCAGCTT AATACGCTAATCCCTAACTGCTGGCGGAACAAATGCGACAGAC GCGACGGCGACAGGCAGACATGCTGTGCGACGCTGGCGATATC AAAATTACTGTCTGCCAGGTGATCGCTGATGTACTGACAAGCCT CGCGTACCCGATTATCCATCGGTGGATGGAGCGACTCGTTAATC GCTTCCATGCGCCGCAGTAACAATTGCTCAAGCAGATTTATCGC CAGCAATTCCGAATAGCGCCCTTCCCCTTGTCCGGCATTAATGA TTTGCCCAAACAGGTCGCTGAAATGCGGCTGGTGCGCTTCATCC GGGCGAAAGAAACCGGTATTGGCAAATATCGACGGCCAGTTAA GCCATTCATGCCAGTAGGCGCGCGGACGAAAGTAAACCCACTG GTGATACCATTCGTGAGCCTCCGGATGACGACCGTAGTGATGA ATCTCTCCAGGCGGGAACAGCAAAATATCACCCGGTCGGCAGA CAAATTCTCGTCCCTGATTTTTCACCACCCCCTGACCGCGAATG GTGAGATTGAGAATATAACCTTTCATTCCCAGCGGTCGGTCGAT AAAAAAATCGAGATAACCGTTGGCCTCAATCGGCGTTAAACCC GCCACCAGATGGGCGTTAAACGAGTATCCCGGCAGCAGGGGAT CATTTTGCGCTTCAGCCATACTTTTCATACTCCCGCCATTCAGAG AAGAAACCAATTGTCCATATTGCAT |
| AraC polypeptide SEQ ID NO: 25 | MQYGQLVSSLNGGSMKSMAEAQNDPLLPGYSFNAHLVAGLTPIE ANGYLDFFIDRPLGMKGYILNLTIRGQGVVKNQGREFVCRPGDILL FPPGEIHHYGRHPEAHEWYHQWVYFRPRAYWHEWLNWPSIFANT GFFRPDEAHQPHFSDLFGQIINAGQGEGRYSELLAINLLEQLLLRRM EAINESLHPPMDNRVREACQYISDHLADSNFDIASVAQHVCLSPSR LSHLFRQQLGISVLSWREDQRISQAKLLLSTTRMPIATVGRNVGFD DQLYFSRVFKKCTGASPSEFRAGCE* |

TABLE 18-continued

Inducible promoter construct sequences

| Description | Sequence |
|---|---|
| Region comprising rhamnose inducible promoter SEQ ID NO: 26 | CGGTGAGCATCACATCACCACAATTCAGCAAATTGTGAACATC<br>ATCACGTTCATCTTTCCCTGGTTGCCAATGGCCCATTTTCCTGTC<br>AGTAACGAGAAGGTCGCGAATCAGGCGCTTTTTAGACTGGTCG<br>TAATGAAATTCAGCTGTCACCGGATGTGCTTTCCGGTCTGATGA<br>GTCCGTGAGGACGAAACAGCCTCTACAAATAATTTTGTTTAAAA<br>CAACACCCACTAAGATAACTCTAGAAATAATTTTGTTTAACTTT<br>AAGAAGGAGATATACAT |
| Lac Promoter region SEQ ID NO: 27 | ATTCACCACCCTGAATTGACTCTCTTCCGGGCGCTATCATGCCA<br>TACCGCGAAAGGTTTTGCGCCATTCGATGGCGCGCCGCTTCGTC<br>AGGCCACATAGCTTTCTTGTTCTGATCGGAACGATCGTTGGCTG<br>TGTTGACAATTAATCATCGGCTCGTATAATGTGTGGAATTGTGA<br>GCGCTCACAATTAGCTGTCACCGGATGTGCTTTCCGGTCTGATG<br>AGTCCGTGAGGACGAAACAGCCTCTACAAATAATTTTGTTTAAA<br>CAACACCCACTAAGATAACTCTAGAAATAATTTTGTTTAACTT<br>TAAGAAGGAGATATACAT |
| LacO | GGAATTGTGAGCGCTCACAATT |
| LacI (in reverse orientation) SEQ ID NO: 28 | TCACTGCCCGCTTTCCAGTCGGGAAACCTGTCGTGCCAGCTGCA<br>TTAATGAATCGGCCAACGCGCGGGGAGAGGCGGTTTGCGTATT<br>GGGCGCCAGGGTGGTTTTTCTTTTCACCAGTGAGACTGGCAACA<br>GCTGATTGCCCTTCACCGCCTGGCCCTGAGAGAGTTGCAGCAAG<br>CGGTCCACGCTGGTTTGCCCCAGCAGGCGAAAATCCTGTTTGAT<br>GGTGGTTAACGGCGGGATATAACATGAGCTATCTTCGGTATCGT<br>CGTATCCCACTACCGAGATATCCGCACCAACGCGCAGCCCGGA<br>CTCGGTAATGGCGCGCATTGCGCCCAGCGCCATCTGATCGTTGG<br>CAACCAGCATCGCAGTGGGAACGATGCCCTCATTCAGCATTTGC<br>ATGGTTTGTTGAAAACCGGACATGGCACTCCAGTCGCCTTCCCG<br>TTCCGCTATCGGCTGAATTTGATTGCGAGTGAGATATTTATGCC<br>AGCCAGCCAGACGCAGACGCGCCGAGACAGAACTTAATGGGCC<br>CGCTAACAGCGCGATTTGCTGGTGACCCAATGCGACCAGATGCT<br>CCACGCCCAGTCGCGTACCGTCCTCATGGGAGAAAATAATACT<br>GTTGATGGGTGTCTGGTCAGAGACATCAAGAAATAACGCCGGA<br>ACATTAGTGCAGGCAGCTTCCACAGCAATGGCATCCTGGTCATC<br>CAGCGGATAGTTAATGATCAGCCCACTGACGCGTTGCGCGAGA<br>AGATTGTGCACCGCCGCTTTACAGGCTTCGACGCCGCTTCGTTC<br>TACCATCGACACCACCACGCTGGCACCCAGTTGATCGGCGCGA<br>GATTTAATCGCCGCGACAATTTGCGACGGCGCGTGCAGGGCCA<br>GACTGGAGGTGGCAACGCCAATCAGCAACGACTGTTTGCCCGC<br>CAGTTGTTGTGCCACGCGGTTGGGAATGTAATTCAGCTCCGCCA<br>TCGCCGCTTCCACTTTTTCCCGCGTTTTCGCAGAAACGTGGCTG<br>GCCTGGTTCACCACGCGGGAAACGGTCTGATAAGAGACACCGG<br>CATACTCTGCGACATCGTATAACGTTACTGGTTTCAT |
| LacI polypeptide sequence SEQ ID NO: 29 | MKPVTLYDVAEYAGVSYQTVSRVVNQASHVSAKTREKVEAAMA<br>ELNYIPNRVAQQLAGKQSLLIGVATSSSLALHAPSQIVAAIKSRADQ<br>LGASVVVSMVERSGVEACKAAVHNLLAQRVSGLIINYPLDDQDAI<br>AVEAACTNVPALFLDVSDQTPINSIIFSHEDGTRLGVEHLVALGHQ<br>QIALLAGPLSSVSARLRLAGWHKYLTRNQIQPIAEREGDWSAMSG<br>FQQTMQMLNEGIVPTAMLVANDQMALGAMRAITESGLRVGADIS<br>VVGYDDTEDSSCYIPPLTTIKQDFRLLGQTSVDRLLQLSQGQAVKG<br>NQLLPVSLVKRKTTLAPNTQTASPRALADSLMQLARQVSRLESGQ |
| Region comprising Temperature sensitive promoter SEQ ID NO: 30 | ACGTTAAATCTATCACCGCAAGGGATAAATATCTAACACCGTGC<br>GTGTTGACTATTTTACCTCTGGCGGTGATAATGGTTGCATAGCT<br>GTCACCGGATGTGCTTTCCGGTCTGATGAGTCCGTGAGGACGAA<br>ACAGCCTCTACAAATAATTTTGTTTAAAACAACACCCACTAAGA<br>TAACTCTAGAAATAATTTTGTTTAACTTTAAGAAGGAGATATAC<br>AT |
| mutant cI857 repressor SEQ ID NO: 31 | TCAGCCAAACGTCTCTTCAGGCCACTGACTAGCGATAACTTTCC<br>CCACAACGGAACAACTCTCATTGCATGGGATCATTGGGTACTGT<br>GGGTTTAGTGGTTGTAAAAACACCTGACCGCTATCCCTGATCAG<br>TTTCTTGAAGGTAAACTCATCACCCCCAAGTCTGGCTATGCAGA<br>AATCACCTGGCTCAACAGCCTGCTCAGGGTCAACGAGAATTAA<br>CATTCCGTCAGGAAAGCTTGGCTTGGAGCCTGTTGGTGCGGTCA<br>TGGAATTACCTTCAACCTCAAGCCAGAATGCAGAATCACTGGCT<br>TTTTTGGTTGTGCTTACCCATCTCTCCGCATCACCTTTGGTAAAG<br>GTTCTAAGCTTAGGTGAGAACATCCCTGCCTGAACATGAGAAA<br>AAACAGGGTACTCATACTCACTTCTAAGTGACGGCTGCATACTA<br>ACCGCTTCATACATCTCGTAGATTTCTCTGGCGATTGAAGGGCT<br>AAATTCTTCAACGCTAACTTTGAGAATTTTTGTAAGCAATGCGG<br>CGTTATAAGCATTTAATGCATTGATGCCATTAAATAAAGCACCA<br>ACGCCTGACTGCCCCATCCCCATCTTGTCTGCGACAGATTCCTG<br>GGATAAGCCAAGTTCATTTTTCTTTTTTTCATAAAATTGCTTTAAG |

TABLE 18-continued

Inducible promoter construct sequences

| Description | Sequence |
| --- | --- |
| | GCGACGTGCGTCCTCAAGCTGCTCTTGTGTTAATGGTTTCTTTTT<br>TGTGCTCAT |
| RBS and leader region<br>SEQ ID NO: 32 | CTCTAGAAATAATTTTGTTTAACTTTAAGAAGGAGATATACAT |
| mutant cI857 repressor polypeptide sequence<br>SEQ ID NO: 33 | MSTKKKPLTQEQLEDARRLKAIYEKKKNELGLSQESVADKMGMG<br>QSGVGALFNGINALNAYNAALLTKILKVSVEEFSPSIAREIYEMYE<br>AVSMQPSLRSEYEYPVFSHVQAGMFSPKLRTFTKGDAERWVSTTK<br>KASDSAFWLEVEGNSMTAPTGSKPSFPDGMLILVDPEQAVEPGDF<br>CIARLGGDEFTFKKLIRDSGQVFLQPLNPQYPMIPCNESCSVVGKVI<br>ASQWPEETFG |
| TetR-Tet promoter construct<br>SEQ ID NO: 34 | *Ttaagacccactttcacatttaagttgtattctaatccgcatatgatcaattcaaggccgaataagaagg<br>ctggctctgcaccttggtgatcaaataattcgatagcttgtcgtaataatggcggcatactatcagtagta<br>ggtgtttccctttcttctttagcgacttgatgctcttgatcttccaatacgcaacctaaagtaaaatgcccca<br>cagcgctgagtgcatataatgcattctctagtgaaaaaccttgttggcataaaaaggctaattgattttcg<br>agagtttcatactgttatctgtaggccgtgtacctaaatgtactttttgctccatcgcgatgacttagtaaag<br>cacatctaaaacttttagcgttattacgtaaaaaatcttgccagctttcccttctaaagggcaaaagtga<br>gtatggtgcctatctaacatctcaatggctaaggcgtcgagcaaagcccgcttattttttacatgccaata<br>caatgtaggctgctctacacctagcttctgggcgagtttacggttgttaaaccttcgattccgacctcatt<br>aagcagctctaatgcgctgttaatcactttactttttatctaatctagacatcattaattcctaattttt*gttgaca<br>ctctatcattgatagagttatttt*taccactccctatcagtgatagagaaaagt*gaa**ctctagaaataatt<br>ttgtttaactttaagaaggagatatacat* |
| PssB promoter<br>SEQ ID NO: 35 | tcacctttcccggattaaacgctttttttgcccggtggcatggtgctaccggcgatcacaaacggttaattatg<br>acacaaattgacctgaatgaatatacagtattggaatgcattacccggagtgttgtgtaacaatgtctggcca<br>ggtttgtttcccggaaccgaggtcacaacatagtaaaagcgctattggtaatggtacaatcgcgcgtttaca<br>cttattc |

Constitutive Promoters

In some embodiments, the gene encoding the payload is present on a plasmid and operably linked to a constitutive promoter. In some embodiments, the gene encoding the payload is present on a chromosome and operably linked to a promoter that is induced by change in temperature from a non-permissive temperature to a permissive temperature. In some embodiments, the gene encoding the payload is present on a chromosome and operably linked to a constitutive promoter.

In some embodiments, the constitutive promoter is active under in vivo conditions, e.g., the gut and/or conditions of the tumor microenvironment, as described herein. In some embodiments, the promoters are active under in vitro conditions, e.g., various cell culture and/or cell manufacturing conditions, as described herein. In some embodiments, the constitutive promoter is active under in vivo conditions, e.g., the gut and/or conditions of the tumor microenvironment, as described herein, and under in vitro conditions, e.g., various cell culture and/or cell production and/or manufacturing conditions, as described herein.

In some embodiments, the constitutive promoter that is operably linked to the gene encoding the payload is active in various exogenous environmental conditions (e.g., in vivo and/or in vitro and/or production/manufacturing conditions). In some embodiments, the constitutive promoter is active in exogenous environmental conditions specific to the gut of a mammal and/or specific to conditions of the tumor microenvironment. In some embodiments, the constitutive promoter is active in exogenous environmental conditions specific to the small intestine of a mammal. In some embodiments, the constitutive promoter is active in low-oxygen or anaerobic conditions such as the environment of the mammalian gut and/or conditions of the tumor microenvironment. In some embodiments, the constitutive promoter is active in the presence of molecules or metabolites that are specific to the gut of a mammal and/or conditions of the tumor microenvironment. In some embodiments, the constitutive promoter is directly or indirectly induced by a molecule that is co-administered with the bacterial cell. In some embodiments, the constitutive promoter is active in the presence of molecules or metabolites or other conditions, that are present during in vitro culture, cell production and/or manufacturing conditions.

Bacterial constitutive promoters are known in the art and are described in International Patent Application PCT/US2017/013072, filed Jan. 11, 2017, published as WO2017/123675, the contents of which is herein incorporated by reference in its entirety.

Ribosome Binding Sites

In some embodiments, ribosome binding sites are added, switched out or replaced. By testing a few ribosome binding sites, expression levels can be fine-tuned to the desired level. Non-limiting examples of RBS are listed at Registry of standard biological parts and are described in are described in International Patent Application PCT/US2017/013072, filed Jan. 11, 2017, published as WO2017/123675, the contents of which is herein incorporated by reference in its entirety.

Induction of Payloads During Strain Culture

Induction of payloads during culture is described in International Patent Application PCT/US2017/013072, filed Jan. 11, 2017, published as WO2017/123675, International Patent Applications PCT/US2016/032562, filed May 13, 2016, published as WO2016183531, and PCT/US2016/062369, filed Nov. 16, 2016 and published as WO2017087580, the contents of each of which are herein incorporated by reference in their entireties.

In some embodiments, it is desirable to pre-induce payload or protein of interest expression and/or payload activity prior to administration. Such payload or protein of interest may be an effector intended for secretion or may be an enzyme which catalyzes a metabolic reaction to produce an effector. In other embodiments, the protein of interest is an enzyme which catabolizes a harmful metabolite. In such situations, the strains are pre-loaded with active payload or protein of interest. In such instances, the genetically engineered bacteria of the invention express one or more protein(s) of interest, under conditions provided in bacterial culture during cell growth, expansion, purification, fermentation, and/or manufacture prior to administration in vivo. Such culture conditions can be provided in a flask, fermenter or other appropriate culture vessel, e.g., used during cell growth, cell expansion, fermentation, recovery, purification, formulation, and/or manufacture. As used herein, the term "bacterial culture" or bacterial cell culture" or "culture" refers to bacterial cells or microorganisms, which are maintained or grown in vitro during several production processes, including cell growth, cell expansion, recovery, purification, fermentation, and/or manufacture. As used herein, the term "fermentation" refers to the growth, expansion, and maintenance of bacteria under defined conditions. Fermentation may occur under a number of cell culture conditions, including anaerobic or low oxygen or oxygenated conditions, in the presence of inducers, nutrients, at defined temperatures, and the like.

Culture conditions are selected to achieve optimal activity and viability of the cells, while maintaining a high cell density (high biomass) yield. A number of cell culture conditions and operating parameters are monitored and adjusted to achieve optimal activity, high yield and high viability, including oxygen levels (e.g., low oxygen, microaerobic, aerobic), temperature of the medium, and nutrients and/or different growth media, chemical and/or nutritional inducers and other components provided in the medium.

In some embodiments, the one or more protein(s) of interest and are directly or indirectly induced, while the strains is grown up for in vivo administration. Without wishing to be bound by theory, pre-induction may boost in vivo activity, e.g., in the gut or a tumor. If the bacterial residence time in a particular gut compartment is relatively short, the bacteria may pass through the small intestine without reaching full in vivo induction capacity. In contrast, if a strain is pre-induced and preloaded, the strains are already fully active, allowing for greater activity more quickly as the bacteria reach the intestine. Ergo, no transit time is "wasted", in which the strain is not optimally active. As the bacteria continue to move through the intestine, in vivo induction occurs under environmental conditions of the gut (e.g., low oxygen, or in the presence of gut metabolites). Similarly, if a tumor targeting or other bacterium is pre-induced and preloaded, this may allow for greater activity more quickly as the bacteria reach the the gut or the tumor, either through systemic administration or intratumor injection, as described herein. Once in the gut or the tumor, in vivo induction occurs, e.g., under conditions of the tumor microenvironment.

In one embodiment, expression of one or more payload(s), is induced during cell growth, cell expansion, fermentation, recovery, purification, formulation, and/or manufacture. In one embodiment, expression of several different proteins of interest is induced during cell growth, cell expansion, fermentation, recovery, purification, formulation, and/or manufacture.

In some embodiments, the strains are administered without any pre-induction protocols during strain growth prior to in vivo administration.

Anaerobic Induction

In some embodiments, cells are induced under anaerobic or low oxygen conditions in culture. In such instances, cells are grown (e.g., for 1.5 to 3 hours) until they have reached a certain OD, e.g., ODs within the range of 0.1 to 10, indicating a certain density e.g., ranging from $1\times10^8$ to $1\times10^{11}$, and exponential growth and are then switched to anaerobic or low oxygen conditions for approximately 3 to 5 hours. In some embodiments, strains are induced under anaerobic or low oxygen conditions, e.g. to induce FNR promoter activity and drive expression of one or more payload(s) and/or transporters under the control of one or more FNR promoters.

In one embodiment, expression of one or more payload(s), is under the control of one or more FNR promoter(s) and is induced during cell growth, cell expansion, fermentation, recovery, purification, formulation, and/or manufacture under anaerobic or low oxygen conditions. In one embodiment, expression of several different proteins of interest is under the control of one or more FNR promoter(s) and is induced during cell growth, cell expansion, fermentation, recovery, purification, formulation, and/or manufacture under anaerobic or low oxygen conditions.

Without wishing to be bound by theory, strains that comprise one or more payload(s) under the control of an FNR promoter, may allow expression of payload(s) from these promoters in vitro, under anaerobic or low oxygen culture conditions, and in vivo, under the low oxygen conditions found in the gut and/or conditions of the tumor microenvironment.

In some embodiments, promoters linked to the payload of interest may be inducible by arabinose, cumate, and salicylate, IPTG, rhamnose, tetracycline, and/or other chemical and/or nutritional inducers can be induced under anaerobic or low oxygen conditions in the presence of the chemical and/or nutritional inducer. In particular, strains may comprise a combination of gene sequence(s), some of which are under control of FNR promoters and others which are under control of promoters induced by chemical and/or nutritional inducers. In some embodiments, strains may comprise one or more payload gene sequence(s) and/or under the control of one or more FNR promoter(s), and one or more payload gene sequence(s) under the control of a one or more constitutive promoter(s) described herein.

Aerobic Induction

In some embodiments, it is desirable to prepare, pre-load and pre-induce the strains under aerobic conditions. This allows more efficient growth and viability, and, in some cases, reduces the build-up of toxic metabolites. In such instances, cells are grown (e.g., for 1.5 to 3 hours) until they have reached a certain OD, e.g., ODs within the range of 0.1 to 10, indicating a certain density e.g., ranging from $1\times10^8$ to $1\times10^{11}$, and exponential growth and are then induced through the addition of the inducer or through other means, such as shift to a permissive temperature, for approximately 3 to 5 hours.

In some embodiments, promoters inducible by arabinose, cumate, and salicylate, IPTG, rhamnose, tetracycline, and/or other chemical and/or nutritional inducers described herein or known in the art can be induced under aerobic conditions in the presence of the chemical and/or nutritional inducer during cell growth, cell expansion, fermentation, recovery, purification, formulation, and/or manufacture. In one embodiment, expression of one or more payload(s) is under the control of one or more promoter(s) regulated by chemical and/or nutritional inducers and is induced during cell growth, cell expansion, fermentation, recovery, purification, formulation, and/or manufacture under aerobic conditions.

In some embodiments, genetically engineered strains comprise gene sequence(s) which are induced under aerobic culture conditions. In some embodiments, these strains further comprise FNR inducible gene sequence(s) for in vivo activation in the gut and/or conditions of the tumor microenvironment. In some embodiments, these strains do not further comprise FNR inducible gene sequence(s) for in vivo activation in the gut and/or conditions of the tumor microenvironment.

Microaerobic Induction

In some embodiments, viability, growth, and activity are optimized by pre-inducing the bacterial strain under microaerobic conditions. In some embodiments, microaerobic conditions are best suited to "strike a balance" between optimal growth, activity and viability conditions and optimal conditions for induction; in particular, if the expression of the one or more payload(s) are driven by an anaerobic and/or low oxygen promoter, e.g., a FNR promoter. In such instances, cells are for example grown (e.g., for 1.5 to 3 hours) until they have reached a certain OD, e.g., ODs within the range of 0.1 to 10, indicating a certain density e.g., ranging from $1 \times 10^8$ to $1 \times 10^{11}$, and exponential growth and are then induced through the addition of the inducer or through other means, such as shift to at a permissive temperature, for approximately 3 to 5 hours.

In one embodiment, expression of one or more payload(s) is under the control of one or more FNR promoter(s) and is induced during cell growth, cell expansion, fermentation, recovery, purification, formulation, and/or manufacture under microaerobic conditions.

Without wishing to be bound by theory, strains that comprise one or more payload(s) under the control of an FNR promoter, may allow expression of payload(s) from these promoters in vitro, under microaerobic culture conditions, and in vivo, under the low oxygen conditions found in the gut and/or conditions of the tumor microenvironment.

In some embodiments, promoters inducible by arabinose, cumate, and salicylate, IPTG, rhamnose, tetracycline, and/or other chemical and/or nutritional inducers can be induced under microaerobic conditions in the presence of the chemical and/or nutritional inducer. In particular, strains may comprise a combination of gene sequence(s), some of which are under control of FNR promoters and others which are under control of promoters induced by chemical and/or nutritional inducers. In some embodiments, strains may comprise one or more payload gene sequence(s) under the control of one or more FNR promoter(s), and one or more payload gene sequence(s) under the control of a one or more constitutive promoter(s) described herein.

In one embodiment, expression of one or more payload(s) is under the control of one or more promoter(s) regulated by chemical and/or nutritional inducers and is induced during cell growth, cell expansion, fermentation, recovery, purification, formulation, and/or manufacture under microaerobic conditions.

In some embodiments, it is desirable to pre-induce payload or protein of interest expression and/or payload activity prior to administration. Such payload or protein of interest may be an effector intended for secretion or may be an enzyme which catalyzes a metabolic reaction to produce an effector. In other embodiments, the protein of interest is an enzyme which catabolizes a harmful metabolite. In such situations, the strains are pre-loaded with active payload or Generation of Bacterial Strains with Enhanced Ability to Transport Biomolecules Due to their ease of culture, short generation times, very high population densities and small genomes, microbes can be evolved to unique phenotypes in abbreviated timescales. Adaptive laboratory evolution (ALE) is the process of passaging microbes under selective pressure to evolve a strain with a preferred phenotype. Most commonly, this is applied to increase utilization of carbon/energy sources or adapting a strain to environmental stresses (e.g., temperature, pH), whereby mutant strains more capable of growth on the carbon substrate or under stress will outcompete the less adapted strains in the population and will eventually come to dominate the population.

This same process can be extended to any essential metabolite by creating an auxotroph. An auxotroph is a strain incapable of synthesizing an essential metabolite and must therefore have the metabolite provided in the media to grow. In this scenario, by making an auxotroph and passaging it on decreasing amounts of the metabolite, the resulting dominant strains should be more capable of obtaining and incorporating this essential metabolite.

For example, if the biosynthetic pathway for producing an amino acid is disrupted a strain capable of high-affinity capture of said amino acid can be evolved via ALE. First, the strain is grown in varying concentrations of the auxotrophic amino acid, until a minimum concentration to support growth is established. The strain is then passaged at that concentration, and diluted into lowering concentrations of the amino acid at regular intervals. Over time, cells that are most competitive for the amino acid—at growth-limiting concentrations—will come to dominate the population. These strains will likely have mutations in their amino acid-transporters resulting in increased ability to import the essential and limiting amino acid.

Similarly, by using an auxotroph that cannot use an upstream metabolite to form an amino acid, a strain can be evolved that not only can more efficiently import the upstream metabolite, but also convert the metabolite into the essential downstream metabolite. These strains will also evolve mutations to increase import of the upstream metabolite, but may also contain mutations which increase expression or reaction kinetics of downstream enzymes, or that reduce competitive substrate utilization pathways.

In the previous examples, a metabolite innate to the microbe was made essential via mutational auxotrophy and selection was applied with growth-limiting supplementation of the endogenous metabolite. However, phenotypes capable of consuming non-native compounds can be evolved by tying their consumption to the production of an essential compound. For example, if a gene from a different organism is isolated which can produce an essential compound or a precursor to an essential compound this gene can be recombinantly introduced and expressed in the heterologous host. This new host strain will now have the ability to synthesize an essential nutrient from a previously non-metabolizable substrate. Hereby, a similar ALE process can be applied by creating an auxotroph incapable of converting an immediately downstream metabolite and selecting in growth-limiting amounts of the non-native compound with concurrent expression of the recombinant enzyme. This will result in mutations in the transport of the non-native substrate, expression and activity of the heterologous enzyme and expression and activity of downstream native enzymes. It should be emphasized that the key requirement in this process is the ability to tether the consumption of the non-native metabolite to the production of a metabolite essential to growth.

Once the basis of the selection mechanism is established and minimum levels of supplementation have been established, the actual ALE experimentation can proceed. Throughout this process several parameters must be vigilantly monitored. It is important that the cultures are maintained in an exponential growth phase and not allowed to reach saturation/stationary phase. This means that growth rates must be check during each passaging and subsequent dilutions adjusted accordingly. If growth rate improves to such a degree that dilutions become large, then the concentration of auxotrophic supplementation should be decreased such that growth rate is slowed, selection pressure is increased and dilutions are not so severe as to heavily bias subpopulations during passaging. In addition, at regular intervals cells should be diluted, grown on solid media and individual clones tested to confirm growth rate phenotypes observed in the ALE cultures.

Predicting when to halt the stop the ALE experiment also requires vigilance. As the success of directing evolution is tied directly to the number of mutations "screened" throughout the experiment and mutations are generally a function of errors during DNA replication, the cumulative cell divisions (CCD) acts as a proxy for total mutants which have been screened. Previous studies have shown that beneficial phenotypes for growth on different carbon sources can be isolated in about $10^{11.2}$ CCD$^1$. This rate can be accelerated by the addition of chemical mutagens to the cultures—such as N-methyl-N-nitro-N-nitrosoguanidine (NTG)—which causes increased DNA replication errors. However, when continued passaging leads to marginal or no improvement in growth rate the population has converged to some fitness maximum and the ALE experiment can be halted.

At the conclusion of the ALE experiment, the cells should be diluted, isolated on solid media and assayed for growth phenotypes matching that of the culture flask. Best performers from those selected are then prepped for genomic DNA and sent for whole genome sequencing. Sequencing with reveal mutations occurring around the genome capable of providing improved phenotypes, but will also contain silent mutations (those which provide no benefit but do not detract from desired phenotype). In cultures evolved in the presence of NTG or other chemical mutagen, there will be significantly more silent, background mutations. If satisfied with the best performing strain in its current state, the user can proceed to application with that strain. Otherwise the contributing mutations can be deconvoluted from the evolved strain by reintroducing the mutations to the parent strain by genome engineering techniques. See Lee, D.-H., Feist, A. M., Barrett, C. L. & Palsson, B. . Cumulative Number of Cell Divisions as a Meaningful Timescale for Adaptive Laboratory Evolution of *Escherichia coli*. *PLoS ONE* 6, e26172 (2011).

Metabolite Transport

In some embodiments, the genetically engineered bacteria further comprise a gene encoding a transporter. Transporters may be expressed or modified in the genetically engineered bacteria of the invention in order to enhance phenylalanine transport into the cell. Non-limiting examples of such transporters are described in pending International Patent Application PCT/US2016/032565, the contents of which is herein incorporated by reference in its entirety.

Such transporters are membrane transport protein that is capable of transporting metabolites into bacterial cells. In some embodiments, the gene encoding the transporter in the genetically modified bacteria of the invention is not modified. In some embodiments, the genetically engineered bacteria of the invention comprise multiple copies of the transporter gene. In some embodiments, the genetically engineered bacteria of the invention comprise multiple copies of a non-native transporter gene. In some embodiments, the genetically engineered bacteria of the invention comprise a transporter gene that is controlled by its native promoter, an inducible promoter, a promoter that is stronger than the native promoter, e.g., the GlnRS promoter or the P(Bla) promoter, or a constitutive promoter. In some embodiments, the promoter is induced under conditions during manufacture or other in vitro conditions. In some embodiments, expression of the transporter gene is controlled by a different promoter than the promoter that controls expression of the gene encoding the one or more effector molecule. In some embodiments, expression of the transporter gene is controlled by the same promoter that controls expression of the one or more effector molecules. In some embodiments, the transporter gene and the one or more effector molecules are divergently transcribed from a promoter region.

In some embodiments, the native transporter gene is mutagenized, mutants exhibiting increased transport are selected, and the mutagenized transporter gene is isolated and inserted into the genetically engineered bacteria (see, e.g., Pi et al., 1996; Pi et al., 1998).

In some embodiments, the genetically engineered bacteria of the invention produce PAL under exogenous environmental conditions, such as the low-oxygen environment of the mammalian gut, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. In some embodiments, the genetically engineered bacteria of the invention produce PAL under exogenous environmental conditions, such as the low-oxygen environment of the mammalian gut, and increase hippuric acid in the urine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing to hippurate. In embodiments using genetically modified forms of these bacteria, PAL-mediated processing of phenylalanine will be appreciable under exogenous environmental conditions.

Figure 16B:
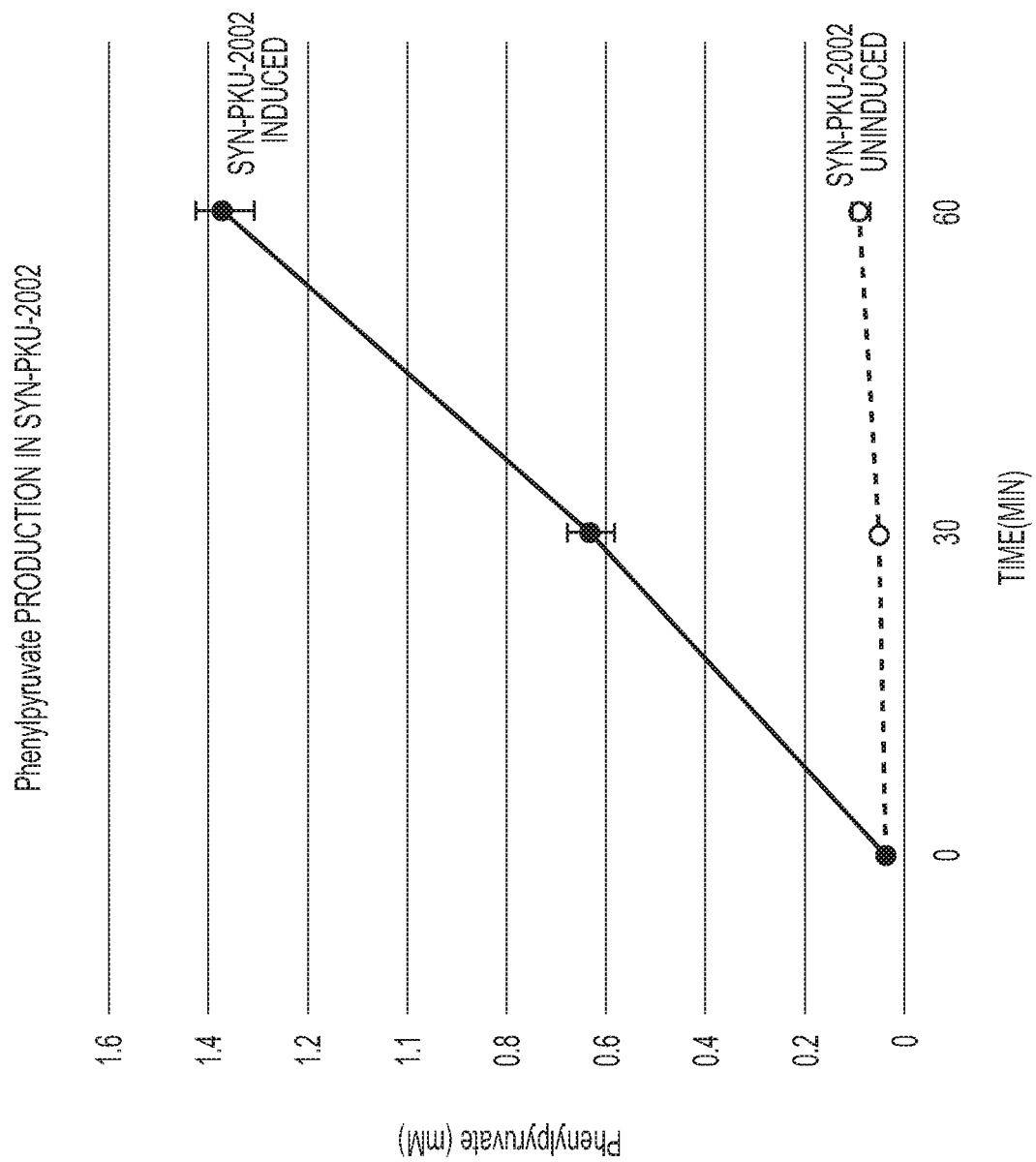

In some embodiments, the genetically engineered bacteria of the invention produce PAL under exogenous environmental conditions, such as under bacterial culture conditions in vitro, and increase transcinnamic acid in the media by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Phenylalanine may be measured by methods known in the art, e.g., blood sampling and mass spectrometry. In some embodiments, cinnamate is measured by methods known in the art to assess PAL activity. Cinnamate production is directly correlated with phenylalanine degradation, and in some embodiments, that cinnamate may be used as an alternative biomarker for strain activity (FIG. 16B). Cinnamate can be further degraded to hippuric acid by liver enzymes; both can be measured as described in Example 24-26. As shown herein, TCA is rapidly converted to hippuric acid in vivo, and hippuric acid subsequently accumulates in the urine. Therefore, hippurate, in blood and in particular in the urine, may be an even better biomarker for phenylalanine degradation in vivo. In some embodiments, PAL expression is measured by methods known in the art, e.g., measurement of blood phenylalanine levels. Hippuric acid may be measured according to methods described herein in the Examples, and methods known in the art.

In some embodiments, the genetically engineered bacteria of the invention produce LAAD, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing. In embodiments using genetically modified forms of these bacteria, LAAD-mediated processing of phenylalanine will be appreciable under exogenous environmental conditions. Phenylalanine may be measured by methods known in the art, e.g., blood sampling and mass spectrometry. Pyruvic acid and phenylpyruvate, the LAAD generated degradation products can be measured using masspectrometry as described in Examples 24-26, and can be used as an additional readout of LAAD activity.

In some embodiments, the genetically engineered bacteria of the invention produce more than one PME, e.g., PAL, PAH, and/or LAAD, under exogenous environmental conditions, such as in vivo or under bacterial culture conditions in vitro, and reduce blood phenylalanine and/or increase transcinnamic acid in the media by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. In any of these embodiments, the bacteria may further comprise gene sequence(s) encoding one or more Phe transporter polypeptides.

In some embodiments, one or more PME(s), e.g., PAL, LAAD, and/or PAH, are expressed on a low-copy plasmid.

In some embodiments, the gene(s) encoding the one or more transporter(s) is located on a plasmid or in the chromosome and expression may be regulated by any of the promoters disclosed herein.

In other embodiments, the genetically engineered bacteria encode one or more transporter(s) which are directly or indirectly induced in vivo administration, e.g., are expressed under the control of an inducible promoter that is responsive conditions or to specific molecules or metabolites in the exogenous in vivo environment, e.g., the gut. In some embodiments, the promoter is induced by gut specific molecules, or low oxygen conditions. In some embodiments, the bacterial strains are administered in combination with a chemical and/or nutritional inducer.

Figure 15:
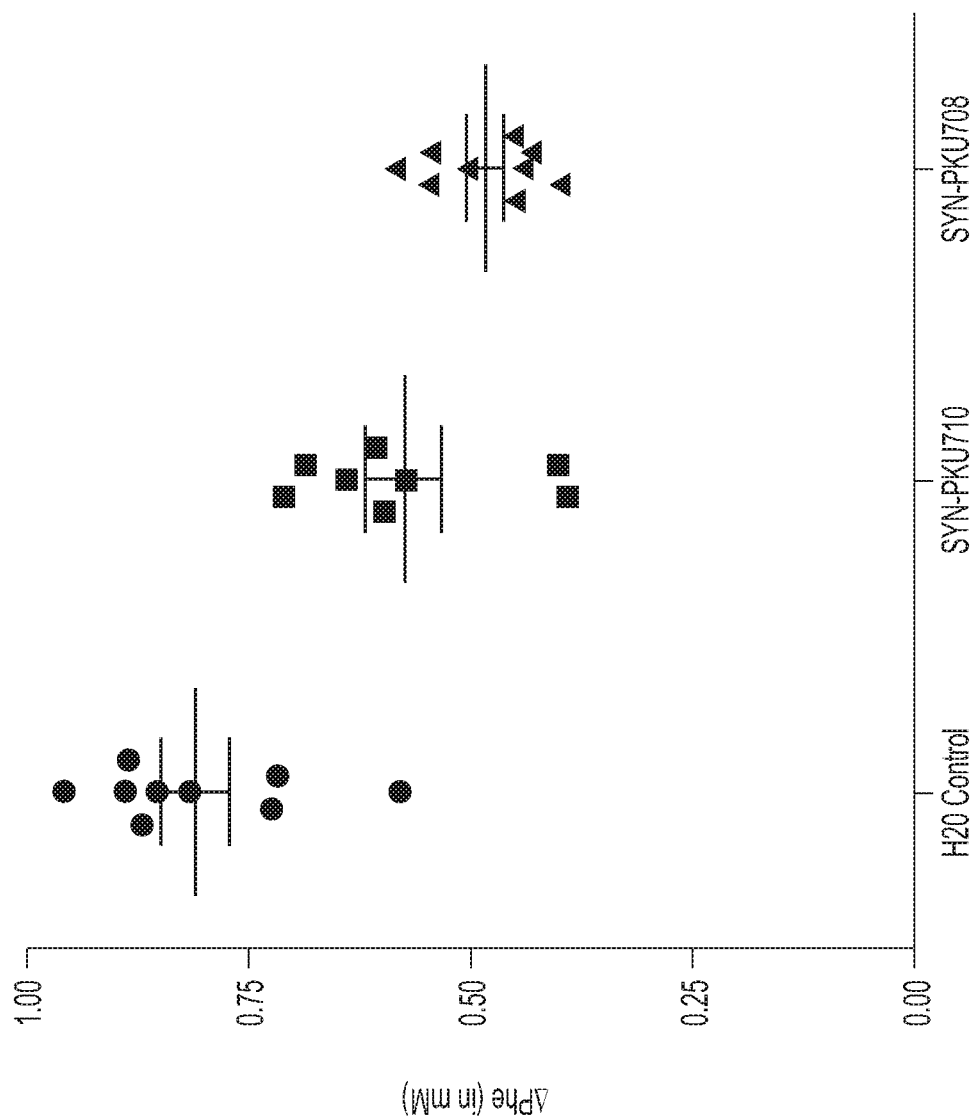
FIG. 15 depicts blood phenylalanine concentrations relative to baseline at 4 hours post SC phenylalanine injection, comparing strains SYN-PKU710 and SYN-PKU708. Mice were administered single dose of phenylalanine by subcutaneous injection at 0.1 mg per gram body weight. At 1, 2 and 3 h post Phe challenge, the bacteria (or water) were administered to mice by oral gavage (300 ul/dose, total of 3Xe10 cfu/mouse). The percentage decrease in deltaPhe SYN-PKU710 and SYN-PKU708 were calculated to be 29% and 40%, respectively.

In some embodiments, one or more PME(s), e.g., PAL, LAAD, and/or PAH, are expressed on a high-copy plasmid. In some embodiments, the high-copy plasmid may be useful for increasing the PME, e.g., PAL, LAAD, and/or PAH, expression, thereby increasing the metabolism of phenylalanine and reducing hyperphenylalaninemia. In some embodiments, a genetically engineered bacterium comprising a the PME, e.g., PAL, LAAD, and/or PAH, expressed on a high-copy plasmid does not increase phenylalanine metabolism or decrease phenylalanine levels as compared to a genetically engineered bacterium comprising the same PME, e.g., PAL, LAAD, and/or PAH, expressed on a low-copy plasmid in the absence of heterologous pheP and additional copies of a native pheP. Genetically engineered bacteria comprising the same the PME gene(s), e.g., PAL, LAAD, and/or PAH gene(s) on high and low copy plasmids were generated. For example, either PAL1 or PAL3 on a high-copy plasmid and a low-copy plasmid were generated, and each metabolized and reduced phenylalanine to similar levels (FIG. 15). Thus, in some embodiments, the rate-limiting step of phenylalanine metabolism is phenylalanine availability (see, e.g., FIG. 16). In these embodiments, it may be advantageous to increase phenylalanine transport into the cell, thereby enhancing phenylalanine metabolism. In conjunction with pheP, even low-copy PAL plasmids are capable of almost completely eliminating Phe from a test sample (see, e.g., FIG. 16A). Furthermore, in some embodiments, that incorporate pheP, there may be additional advantages to using a low-copy PAL-expressing plasmid in conjunction in order to enhance the stability of PAL expression while maintaining high phenylalanine metabolism, and to reduce negative selection pressure on the transformed bacterium. In alternate embodiments, the phenylalanine transporter is used in conjunction with the high-copy plasmid.

In some embodiments, a transporter may not increase phenylalanine degradation. For example, *Proteus mirabilis* LAAD is localized to the plasma membrane, with the enzymatic catalysis occurring in the periplasm. Phenylalanine can readily traverse the outer membrane without the need of a transporter. Therefore, in embodiments, in which the genetically engineered bacteria express LAAD, a transporter may not be needed or improve phenylalanine metabolism.

In some embodiments, the PME(s), e.g., PAL, LAAD, and/or PAH, gene(s) are expressed on a chromosome. In some embodiments, expression from the chromosome may be useful for increasing stability of expression of the PME. In some embodiments, the PME gene, e.g., PAL, LAAD, and/or PAH gene(s), is integrated into the bacterial chromosome at one or more integration sites in the genetically engineered bacteria. In some embodiments, the PME gene, e.g., PAL, LAAD, and/or PAH gene(s) is inserted into the bacterial genome at one or more of the following insertion sites in *E. coli* Nissle: malE/K, insB/I, araC/BAD, lacZ, agaI/rsmI, thyA, and malP/T. Any suitable insertion site may be used (see, e.g., FIG. 66 of WO2017087580, the contents of which are herein incorporated by reference in their entirety). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. In some embodiments, more than one copy, e.g., two, three, four, five, six, seven, eight, nine, ten or more copies of the PME gene, e.g., PAL, PAH, and/or LAAD is integrated into the bacterial chromosome at one or more integration sites in the genetically engineered bacteria. The more than one copy of a PME gene may be more than one copy of the same PME gene or more than one copy of different PME genes.

Exemplary constructs are shown in Tables 4-13 below. Table 4 shows the sequence of an exemplary construct comprising a gene encoding PheP and an FNR promoter sequence for chromosomal insertion (SEQ ID NO: 21B), with the pheP sequence underlined and the FNR promoter sequence bolded. Table 5 shows the sequence of an exemplary construct comprising a gene encoding PAL1 and an FNR promoter sequence on a high-copy plasmid (SEQ ID NO: 22B), with the PAL1 sequence underlined and the FNR promoter sequence bolded. Table 6 shows the sequence of an exemplary construct comprising a gene encoding PAL3 and an FNR promoter sequence on a high-copy plasmid (SEQ ID NO: 23B), with the PAL3 sequence underlined and the FNR promoter sequence bolded. Table 7 shows the sequence of an exemplary construct comprising a gene encoding PAL1 and a Tet promoter sequence on a high-copy plasmid (SEQ ID NO: 24B), with the PAL1 sequence underlined and the Tet promoter sequence bolded. Table 8 shows the sequence of an exemplary construct comprising a gene encoding PAL3 and a Tet promoter sequence on a high-copy plasmid (SEQ ID NO: 25B), with the PAL3 sequence underlined and the Tet promoter sequence bolded. Table 9 shows the sequence of an exemplary construct comprising a gene encoding PAL1 and an FNR promoter sequence on a low-copy plasmid (SEQ ID NO: 26B), with the PAL1 sequence underlined and the FNR promoter sequence bolded. Table 10 shows the sequence of an exemplary construct comprising a gene encoding PAL3 and an FNR promoter sequence on a low-copy plasmid (SEQ ID NO: 27B), with the PAL3 sequence underlined and the FNR promoter sequence bolded. Table 11 shows the sequence of an exemplary construct comprising a gene encoding PAL1 and a Tet promoter sequence on a low-copy plasmid (SEQ ID NO: 28B), with the PAL1 sequence underlined and the Tet promoter sequence bolded. Table 12 shows the sequence of an exemplary construct comprising a gene encoding PAL3 and a Tet promoter sequence on a low-copy plasmid (SEQ ID NO: 29B), with the PAL3 sequence underlined and the Tet promoter sequence bolded. Table 13 shows the sequence of an exemplary construct comprising a gene encoding PheP, a gene coding TetR, and a Tet promoter sequence for chromosomal insertion (SEQ ID NO: 30B), with the pheP sequence underlined, the TetR sequence boxed, and the FNR promoter sequence bolded.

TABLE 4

Nucleotide sequences of FNR promoter-PheP construct (SEQ ID NO: 21B)

CTCTTGATCGTTATCAATTCCCACGCTGTTTCAGAGCGTTACCTTGCCCTT

AAACATTAGCAATGTCGATTTATCAGAGGGCCGACAGGCTCCCACAGGAGA

AAACCGATGAAAAACGCGTCAACCGTATCGGAAGATACTGCGTCGAATCAA

GAGCCGACGCTTCATCGCGGATTACATAACCGTCATATTCAACTGATTGCG

TTGGGTGGCGCAATTGGTACTGGTCTGTTTCTTGGCATTGGCCCGGCGATT

CAGATGGCGGGTCCGGCTGTATTGCTGGGCTACGGCGTCGCCGGGATCATC

GCTTTCCTGATTATGCGCCAGCTTGGCGAAATGGTGGTTGAGGAGCCGGTA

TABLE 4-continued

Nucleotide sequences of FNR promoter-PheP construct (SEQ ID NO: 21B)

TCCGGTTCATTTGCCCACTTTGCCTATAAATACTGGGGACCGTTTGCGGGC

TTCCTCTCTGGCTGGAACTACTGGGTAATGTTCGTGCTGGTGGGAATGGCA

GAGCTGACCGCTGCGGGCATCTATATGCAGTACTGGTTCCCGGATGTTCCA

ACGTGGATTTGGGCTGCCGCCTTCTTTATTATCATCAACGCCGTTAACCTG

GTGAACGTGCGCTTATATGGCGAAACCGAGTTCTGGTTTGCGTTGATTAAA

GTGCTGGCAATCATCGGTATGATCGGCTTTGGCCTGTGGCTGCTGTTTTCT

GGTCACGGCGGCGAGAAAGCCAGTATCGACAACCTCTGGCGCTACGGTGGT

TTCTTCGCCACCGGCTGGAATGGGCTGATTTTGTCGCTGGCGGTAATTATG

TTCTCCTTCGGCGGTCTGGAGCTGATTGGGATTACTGCCGCTGAAGCGCGC

GATCCGGAAAAAAGCATTCCAAAAGCGGTAAATCAGGTGGTGTATCGCATC

CTGCTGTTTTACATCGGTTCACTGGTGGTTTTACTGGCGCTCTATCCGTGG

GTGGAAGTGAAATCCAACAGTAGCCCGTTTGTGATGATTTTCCATAATCTC

GACAGCAACGTGGTAGCTTCTGCGCTGAACTTCGTCATTCTGGTAGCATCG

CTGTCAGTGTATAACAGCGGGGTTTACTCTAACAGCCGCATGCTGTTTGGC

CTTTCTGTGCAGGGTAATGCGCCGAAGTTTTTGACTCGCGTCAGCCGTCGC

GGTGTGCCGATTAACTCGCTGATGCTTTCCGGAGCGATCACTTCGCTGGTG

GTGTTAATCAACTATCTGCTGCCGCAAAAAGCGTTTGGTCTGCTGATGGCG

CTGGTGGTAGCAACGCTGCTGTTGAACTGGATTATGATCTGTCTGGCGCAT

CTGCGTTTTCGTGCAGCGATGCGACGTCAGGGGCGTGAAACACAGTTTAAG

GCGCTGCTCTATCCGTTCGGCAACTATCTCTGCATTGCCTTCCTCGGCATG

ATTTTGCTGCTGATGTGCACGATGGATGATATGCGCTTGTCAGCGATCCTG

CTGCCGGTGTGGATTGTATTCCTGTTTATGGCATTTAAAACGCTGCGTCGG

AAATAA

TABLE 5

Nucleotide sequences of FNR promoter-PAL1 construct, high-copy (SEQ ID NO: 22B)

CTCTTGATCGTTATCAATTCCCACGCTGTTTCAGAGCGTTACCTTGCCCTT

AAACATTAGCAATGTCGATTTATCAGAGGGCCGACAGGCTCCCACAGGAGA

AAACCGATGAAAACACTATCACAGGCCCAATCTAAAACTTCTTCACAGCAA

TTCAGCTTTACCGGGAACTCGTCTGCGAATGTAATTATCGGCAATCAAAAG

CTGACCATTAATGATGTAGCTCGCGTTGCCCGGAATGGCACTTTGGTGTCA

CTGACGAACAATACCGACATTCTGCAAGGTATTCAAGCTAGCTGCGATTAT

ATCAATAACGCCGTTGAATCTGGCGAGCCAATCTACGGGGTAACAAGCGGT

TTTGGTGGGATGGCGAACGTTGCCATTAGCCGTGAACAGGCGAGCGAACTT

CAGACCAACCTCGTTTGGTTCCTAAAGACAGGAGCTGGTAATAAGTTACCT

CTGGCTGACGTAAGAGCCGCGATGCTGCTTCGCGCTAATAGTCACATGCGC

GGCGCCAGTGGTATCCGTCTTGAGCTTATCAAGAGGATGGAAATCTTCCTC

AACGCGGGTGTCACACCATATGTTTATGAGTTTGGTAGTATCGGAGCCAGT

TABLE 5-continued

Nucleotide sequences of FNR promoter-PAL1 construct, high-copy (SEQ ID NO: 22B)

GGTGATCTTGTTCCCCTGAGTTATATTACGGGTTCATTGATTGGTTTAGAC
CCGTCCTTTAAAGTGGATTTTAACGGGAAAGAAATGGACGCCCCGACCGCT
TTACGACAGCTTAATCTGAGCCCACTTACTTTGCTCCCTAAAGAAGGTCTT
GCCATGATGAATGGCACCTCTGTGATGACTGGAATTGCCGCGAATTGTGTG
TATGACACGCAGATCCTAACGGCCATTGCCATGGGTGTTCACGCGTTGGAC
ATTCAAGCCCTGAATGGTACAAACCAGTCGTTTCATCCGTTTATCCATAAT
TCAAAACCCCATCCGGGACAGCTTTGGGCTGCTGATCAGATGATCTCACTC
CTGGCCAATAGTCAACTGGTTCGGGACGAGCTCGACGGCAAACATGATTAT
CGCGATCATGAGCTCATCCAGGACCGGTATTCACTTCGTTGTCTCCCACAA
TACCTGGGGCCTATCGTTGATGGTATATCTCAAATTGCGAAGCAAATTGAA
ATTGAGATCAATAGCGTAACCGACAACCCGCTTATCGATGTTGATAATCAG
GCCTCTTATCACGGTGGCAATTTTCTGGGCCAGTATGTTGGTATGGGGATG
GATCACCTGCGGTACTATATTGGGCTTCTGGCTAAACATCTTGATGTGCAG
ATTGCCTTATTAGCTTCACCAGAATTTTCAAATGGACTGCCGCCATCATTG
CTCGGTAACAGAGAAAGGAAAGTAAATATGGGCCTTAAGGGCCTTCAGATA
TGTGGTAACTCAATCATGCCCCTCCTGACCTTTTATGGGAACTCAATTGCT
GATCGTTTTCCGACACATGCTGAACAGTTTAACCAAAACATTAACTCACAG
GGCTATACATCCGCGACGTTAGCGCGTCGGTCCGTGGATATCTTCCAGAAT
TATGTTGCTATCGCTCTGATGTTCGGCGTACAGGCCGTTGATTTGCGCACT
TATAAAAAACCGGTCACTACGATGCTCGGGCTTGCCTGTCGCCTGCCACC
GAGCGGCTTTATAGCGCCGTACGTCATGTTGTGGGTCAGAAACCGACGTCG
GACCGCCCCTATATTTGGAATGATAATGAACAAGGGCTGGATGAACACATC
GCCCGGATATCTGCCGATATTGCCGCCGGAGGTGTCATCGTCCAGGCGGTA
CAAGACATACTTCCTTGCCTGCATTAAGCTTGGCGTAATCATGGTCATAGC
TGTTTCCTGTGTGAAATTGTTATCCGCTCACAATTCCACACAACATACGAG
CCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACC
CGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCTC
AGTGGAACGAAAACTCACGTTAAGGGATTTTGGTCATGAGATTATCAAAAA
GGATCTTCACCTAGATCCTTTTAAATTAAAAATGAAGTTTTAAATCAATCT
AAAGTATATATGAGTAAACTTGGTCTGACAGTTACCAATGCTTAATCAGTG
AGGCACCTATCTCAGCGATCTGTCTATTTCGTTCATCCATAGTTGCCTGAC
TCCCCGTCGTGTAGATAACTACGATACGGGAGGGCTTACCATCTGGCCCCA
GTGCTGCAATGATACCGCGAGACCCACGCTCACCGGCTCCAGATTTATCAG
CAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATCG
TGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCAC
TCATGGTTATGGCAGCACTGCATAATTCTCTTACTGTCATGCCATCCGTAA
GATGCTTTTCTGTGACTGGTGAGTACTCAACCAAGTCATTCTGAGAATAGT
GTATGCGGCGACCGAGTTGCTCTTGCCCGGCGTCAATACGGGATAATACCG
CGCCACATAGCAGAACTTTAAAAGTGCTCATCATTGGAAAACGTTCTTCGG
GGCGAAAACTCTCAAGGATCTTACCGCTGTTGAGATCCAGTTCGATGTAAC
CCACTCGTGCACCCAACTGATCTTCAGCATCTTTTACTTTCACCAGCGTTT
CTGGGTGAGCAAAAACAGGAAGGCAAAATGCCGCAAAAAAGGGAATAAGGG
CGACACGGAAATGTTGAATACTCATACTCTTCCTTTTTCAATATTATTGAA
GCATTTATCAGGGTTATTGTCTCATGAGCGGATACATATTTGAATGTATTT
AGAAAAATAAACAAATAGGGGTTCCGCGCACATTTCCCCGAAAAGTGCCAC
CTGACGTCTAAGAAACCATTATTATCATGACATTAACCTATAAAAATAGGC
GTATCACGAGGCCCTTTCGTCTCGCGCGTTTCGGTGATGACGGTGAAAACC
TCTGACACATGCAGCTCCCGGAGACGGTCACAGCTTGTCTGTAAGCGGATG
CCGGGAGCAGACAAGCCCGTCAGGGCGCGTCAGCGGGTGTTGGCGGGTGTC
GGGGCTGGCTTAACTATGCGGCATCAGAGCAGATTGTACTGAGAGTGCACC
ATATGCGGTGTGAAATACCGCACAGATGCGTAAGGAGAAAATACCGCATCA
GGCGCCATTCGCCATTCAGGCTGCGCAACTGTTGGGAAGGGCGATCGGTGC
GGGCCTCTTCGCTATTACGCCAGCTGGCGAAAGGGGGATGTGCTGCAAGGC
GATTAAGTTGGGTAACGCCAGGGTTTTCCCAGTCACGACGTT

TABLE 6

Nucleotide sequences of FNR promoter-PAL3 construct, high-copy (SEQ ID NO: 23B)

**CTCTTGATCGTTATCAATTCCCACGCTGTTTCAGAGCGTTACCTTGCCCTT
AAACATTAGCAATGTCGATTTATCAGAGGGCCGACAGGCTCCCACAGGAGA
AAACCG**ATGAAAGCTAAAGATGTTCAGCCAACCATTATTATTAATAAAAAT
GGCCTTATCTCTTTGGAAGATATCTATGACATTGCGATAAAACAAAAAAAA
GTAGAAATATCAACGGAGATCACTGAACTTTTGACGCATGGTCGTGAAAAA
TTAGAGGAAAAATTAAATTCAGGAGAGGTTATATATGGAATCAATACAGGA
TTTGGAGGGAATGCCAATTTAGTTGTGCCATTTGAGAAAATCGCAGAGCAT
CAGCAAAATCTGTTAACTTTTCTTTCTGCTGGTACTGGGGACTATATGTCC
AAACCTTGTATTAAAGCGTCACAATTTACTATGTTACTTTCTGTTTGCAAA
GGTTGGTCTGCAACCAGACCAATTGTCGCTCAAGCAATTGTTGATCATATT
AATCATGACATTGTTCCTCTGGTTCCTCGCTATGGCTCAGTGGGTGCAAGC
GGTGATTTAATTCCTTTATCTTATATTGCACGAGCATTATGTGGTATCGGC
AAAGTTTATTATATGGGCGCAGAAATTGACGCTGCTGAAGCAATTAAACGT
GCAGGGTTGACACCATTATCGTTAAAAGCCAAAGAAGGTCTTGCTCTGATT
AACGGCACCCGGGTAATGTCAGGAATCAGTGCAATCACCGTCATTAAACTG
GAAAAACTATTTAAAGCCTCAATTTCTGCGATTGCCCTTGCTGTTGAAGCA
TTACTTGCATCTCATGAACATTATGATGCCCGGATTCAACAAGTAAAAAAT
CATCCTGGTCAAAACGCGGTGGCAAGTGCATTGCGTAATTTATTGGCAGGT
TCAACGCAGGTTAATCTATTATCTGGGGTTAAAGAACAAGCCAATAAAGCT
TGTCGTCATCAAGAAATTACCCAACTAAATGATACCTTACAGGAAGTTTAT
TCAATTCGCTGTGCACCACAAGTATTAGGTATAGTGCCAGAATCTTTAGCT
ACCGCTCGGAAAATATTGGAACGGGAAGTTATCTCAGCTAATGATAATCCA
TTGATAGATCCAGAAAATGGCGATGTTCTACACGGTGGAAATTTTATGGGG
CAATATGTCGCCCGAACAATGGATGCATTAAAACTGGATATTGCTTTAATT
GCCAATCATCTTCACGCCATTGTGGCTCTTATGATGGATAACCGTTTCTCT
CGTGGATTACCTAATTCACTGAGTCCGACACCCGGCATGTATCAAGGTTTT
AAAGGCGTCCAACTTTCTCAAACCGCTTTAGTTGCTGCAATTCGCCATGAT
TGTGCTGCATCAGGTATTCATACCCTCGCCACAGAACAATACAATCAAGAT
ATTGTCAGTTTAGGTCTGCATGCCGCTCAAGATGTTTTAGAGATGGAGCAG
AAATTACGCAATATTGTTTCAATGACAATTCTGGTAGTTTGTCAGGCCATT
CATCTTCGCGGCAATATTAGTGAAATTGCGCCTGAAACTGCTAAATTTTAC
CATGCAGTACGCGAAATCAGTTCTCCTTTGATCACTGATCGTGCGTTGGAT
GAAGATATAATCCGCATTGCGGATGCAATTATTAATGATCAACTTCCTCTG
CCAGAAATCATGCTGGAAGAATAAGCTTGGCGTAATCATGGTCATAGCTGT
TTCCTGTGTGAAATTGTTATCCGCTCACAATTCCACACAACATACGAGCCG
GAAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGC
TGCGGCGAGCGGTATCAGCTCACTCAAAGGCGGTAATACGGTTATCCACAG
AATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGG
TAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAG
TTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGT
GGAACGAAAACTCACGTTAAGGGATTTTGGTCATGAGATTATCAAAAAGGA
TCTTCACCTAGATCCTTTTAAATTAAAAATGAAGTTTTAAATCAATCTAAA
GTATATATGAGTAAACTTGGTCTGACAGTTACCAATGCTTAATCAGTGAGG
CACCTATCTCAGCGATCTGTCTATTTCGTTCATCCATAGTTGCCTGACTCC
CCGTCGTGTAGATAACTACGATACGGGAGGGCTTACCATCTGGCCCCAGTG
CTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCT
TCGGTCCTCCGATCGTTGTCAGAAGTAAGTTGGCCGCAGTGTTATCACTCA
TGGTTATGGCAGCACTGCATAATTCTCTTACTGTCATGCCATCCGTAAGAT
GCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGC
CACATAGCAGAACTTTAAAAGTGCTCATCATTGGAAAACGTTCTTCGGGGC
GAAAACTCTCAAGGATCTTACCGCTGTTGAGATCCAGTTCGATGTAACCCA
CTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGA
CACGGAAATGTTGAATACTCATACTCTTCCTTTTTCAATATTATTGAAGCA
TTTATCAGGGTTATTGTCTCATGAGCGGATACATATTTGAATGTATTTAGA
AAAATAAACAAATAGGGGTTCCGCGCACATTTCCCCGAAAAGTGCCACCTG
ACGTCTAAGAAACCATTATTATCATGACATTAACCTATAAAAATAGGCGTA

TABLE 6-continued

Nucleotide sequences of FNR promoter-PAL3 construct, high-copy (SEQ ID NO: 23B)

TCACGAGGCCCTTTCGTCTCGCGTTTCGGTGATGACGGTGAAAACCTCT

GACACATGCAGCTCCCGGAGACGGTCACAGCTTGTCTGTAAGCGGATGCCG

GGAGCAGACAAGCCCGTCAGGGCGCGTCAGCGGGTGTTGGCGGGTGTCGGG

GCTGGCTTAACTATGCGGCATCAGAGCAGATTGTACTGAGAGTGCACCATA

TGCGGTGTGAAATACCGCACAGATGCGTAAGGAGAAAATACCGCATCAGGC

GCCATTCGCCATTCAGGCTGCGCAACTGTTGGGAAGGGCGATCGGTGCGGG

CCTCTTCGCTATTACGCCAGCTGGCGAAAGGGGGATGTGCTGCAAGGCGAT

TAAGTTGGGTAACGCCAGGGTTTTCCCAGTCACGACGTT

TABLE 7

Nucleotide sequences of Tet promoter-PAL1 construct, high-copy (SEQ ID NO: 24B)

CTCTAGAAATAATTTTGTTTAACTTTAAGAAGGAGATATACATATGAAAAC

ACTATCACAGGCCCAATCTAAAACTTCTTCACAGCAATTCAGCTTTACCGG

GAACTCGTCTGCGAATGTAATTATCGGCAATCAAAAGCTGACCATTAATGA

TGTAGCTCGCGTTGCCCGGAATGGCACTTTGGTGTCACTGACGAACAATAC

CGACATTCTGCAAGGTATTCAAGCTAGCTGCGATTATATCAATAACGCCGT

TGAATCTGGCGAGCCAATCTACGGGGTAACAAGCGGTTTTGGTGGGATGGC

GAACGTTGCCATTAGCCGTGAACAGGCGAGCGAACTTCAGACCAACCTCGT

TTGGTTCCTAAAGACAGGAGCTGGTAATAAGTTACCTCTGGCTGACGTAAG

AGCCGCGATGCTGCTTCGCGCTAATAGTCACATGCGCGGCGCCAGTGGTAT

CCGTCTTGAGCTTATCAAGAGGATGGAAATCTTCCTCAACGCGGGTGTCAC

ACCATATGTTTATGAGTTTGGTAGTATCGGAGCCAGTGGTGATCTTGTTCC

CCTGAGTTATATTACGGGTTCATTGATTGGTTTAGACCCGTCCTTTAAAGT

GGATTTTAACGGGAAAGAAATGGACGCCCCGACCGCTTTACGACAGCTTAA

TCTGAGCCCACTTACTTTGCTCCCTAAAGAAGGTCTTGCCATGATGAATGG

CACCTCTGTGATGACTGGAATTGCCGCGAATTGTGTGTATGACACGCAGAT

CCTAACGGCCATTGCCATGGGTGTTCACGCGTTGGACATTCAAGCCCTGAA

TGGTACAAACCAGTCGTTTCATCCGTTTATCCATAATTCAAAACCCCATCC

GGGACAGCTTTGGGCTGCTGATCAGATGATCTCACTCCTGGCCAATAGTCA

ACTGGTTCGGGACGAGCTCGACGGCAAACATGATTATCGCGATCATGAGCT

CATCCAGGACCGGTATTCACTTCGTTGTCTCCCACAATACCTGGGGCCTAT

CGTTGATGGTATATCTCAAATTGCGAAGCAAATTGAAATTGAGATCAATAG

CGTAACCGACAACCCGCTTATCGATGTTGATAATCAGGCCTCTTATCACGG

TGGCAATTTTCTGGGCCAGTATGTTGGTATGGGGATGGATCACCTGCGGTA

CTATATTGGGCTTCTGGCTAAACATCTTGATGTGCAGATTGCCTTATTAGC

TTACCAGAATTTTCAAATGGACTGCCGCCATCATTGCTCGGTAACAGAGA

AAGGAAAGTAAAATGGGCCTTAAGGGCCTTCAGATATGTGGTAACTCAAT

CATGCCCCTCCTGACCTTTTATGGGAACTCAATTGCTGATCGTTTTCCGAC

TABLE 7-continued

Nucleotide sequences of Tet promoter-PAL1 construct, high-copy (SEQ ID NO: 24B)

ACATGCTGAACAGTTTAACCAAAACATTAACTCACAGGGCTATACATCCGC

GACGTTAGCGCGTCGGTCCGTGGATATCTTCCAGAATTATGTTGCTATCGC

TCTGATGTTCGGCGTACAGGCCGTTGATTTGCGCACTTATAAAAAAACCGG

TCACTACGATGCTCGGGCTTGCCTGTCGCCTGCCACCGAGCGGCTTTATAG

CGCCGTACGTCATGTTGTGGGTCAGAAACCGACGTCGGACCGCCCCTATAT

TTGGAATGATAATGAACAAGGGCTGGATGAACACATCGCCCGGATATCTGC

CGATATTGCCGCCGGAGGTGTCATCGTCCAGGCGGTACAAGACATACTTCC

TTGCCTGCATTAAGCTTGGCGTAATCATGGTCATAGCTGTTTCCTGTGTGA

AATTGTTATCCGCTCACAATTCCACACAACATACGAGCCGGAAGCATAAAG

TGTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTAA

TGAATCGGCCAACGCGCGGGGAGAGGCGGTTTGCGTATTGGGCGCTCTTCC

GCTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGT

AAAAAGGCCGCGTTGCTGGCGTTTTTCCATAGGCTCCGCCCCCCTGACGAG

CATCACAAAAATCGACGCTCAAGTCAGAGGTGGCGAAACCCGACAGGACTA

TAAAGATACCAGGCGTTTCCCCCTGGAAGCTCCCTCGTGCGCTCTCCTGTT

CCGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGTC

GTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGAC

TTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACT

AGAAGAACAGTATTTGGTATCTGCGCTCTGCTGAAGCCAGTTACCTTCGGA

AAAAGAGTTGGTAGCTCTTGATCCGGCAAACAAACCACCGCTGGTAGCGGT

GGTTTTTTTGTTTGCAAGCAGCAGATTACGCGCAGAAAAAAAGGATCTCAA

GAAGATCCTTTGATCTTTTCTACGGGGTCTGACGCTCAGTGGAACGAAAAC

TCACGTTAAGGGATTTTGGTCATGAGATTATCAAAAAGGATCTTCACCTAG

ATCCTTTTAAATTAAAAATGAAGTTTTAAATCAATCTAAAGTATATATGAG

TAAACTTGGTCTGACAGTTACCAATGCTTAATCAGTGAGGCACCTATCTCA

GCGATCTGTCTATTTCGTTCATCCATAGTTGCCTGACTCCCCGTCGTGTAG

ATAACTACGATACGGGAGGGCTTACCATCTGGCCCCAGTGCTGCAATGATA

CCGCGAGACCCACGCTCACCGGCTCCAGATTTATCAGCAATAAACCAGCCA

GCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAAT

AGTTTGCGCAACGTTGTTGCCATTGCTACAGGCATCGTGGTGTCACGCTCG

TCGTTTGGTATGGCTTCATTCAGCTCCGGTTCCCAACGATCAAGGCGAGTT

TABLE 7-continued

Nucleotide sequences of Tet promoter-PAL1 construct, high-copy (SEQ ID NO: 24B)

ACATGATCCCCCATGTTGTGCAAAAAAGCGGTTAGCTCCTTCGGTCCTCCG
ATCGTTGTCAGAAGTAAGTTGGCCGCAGTGTTATCACTCATGGTTATGGCA
GCACTGCATAATTCTCTTACTGTCATGCCATCCGTAAGATGCTTTTCTGTG
ACTGGTGAGTACTCAACCAAGTCATTCTGAGAATAGTGTATGCGGCGACCG
AGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCC
AACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGT
TGAATACTCATACTCTTCCTTTTTCAATATTATTGAAGCATTTATCAGGGT
TATTGTCTCATGAGCGGATACATATTTGAATGTATTTAGAAAAATAAACAA
ATAGGGGTTCCGCGCACATTTCCCCGAAAAGTGCCACCTGACGTCTAAGAA
ACCATTATTATCATGACATTAACCTATAAAAATAGGCGTATCACGAGGCCC
TTTCGTCTCGCGCGTTTCGGTGATGACGGTGAAAACCTCTGACACATGCAG
CTCCCGGAGACGGTCACAGCTTGTCTGTAAGCGGATGCCGGGAGCAGACAA
GCCCGTCAGGGCGCGTCAGCGGGTGTTGGCGGGTGTCGGGGCTGGCTTAAC
TATGCGGCATCAGAGCAGATTGTACTGAGAGTGCACCATATGCGGTGTGAA
ATACCGCACAGATGCGTAAGGAGAAAATACCGCATCAGGCGCCATTCGCCA
TTCAGGCTGCGCAACTGTTGGGAAGGGCGATCGGTGCGGGCCTCTTCGCTA
TTACGCCAGCTGGCGAAAGGGGGATGTGCTGCAAGGCGATTAAGTTGGGTA
ACGCCAGGGTTTTCCCAGTCACGACGTTGTAAAACGACGGCCAGTGAATTC
GTTAAGACCCACTTTCACATTTAAGTTGTTTTTCTAATCCGCATATGATCA
ATTCAAGGCCGAATAAGAAGGCTGGCTCTGCACCTTGGTGATCAAATAATT
CGATAGCTTGTCGTAATAATGGCGGCATACTATCAGTAGTAGGTGTTTCCC
TTTCTTCTTTAGCGACTTGATGCTCTTGATCTTCCAATACGCAACCTAAAG
TAAAATGCCCCACAGCGCTGAGTGCATATAATGCATTCTCTAGTGAAAAAC
CTTGTTGGCATAAAAAGGCTAATTGATTTTCGAGAGTTTCATACTGTTTTT
CTGTAGGCCGTGTACCTAAATGTACTTTTGCTCCATCGCGATGACTTAGTA
AAGCACATCTAAAACTTTTAGCGTTATTACGTAAAAAATCTTGCCAGCTTT
CCCCTTCTAAAGGGCAAAAGTGAGTATGGTGCCTATCTAACATCTCAATGG
CTAAGGCGTCGAGCAAAGCCCGCTTATTTTTTACATGCCAATACAATGTAG
GCTGCTCTACACCTAGCTTCTGGGCGAGTTTACGGGTTGTTAAACCTTCGA
TTCCGACCTCATTAAGCAGCTCTAATGCGCTGTTAATCACTTTACTTTTAT
CTAATCTAGACATCATTAATTCCTAATTTTT**GTTGACACTCTATCATTGAT
AGAGTTATTTTACCACTCCCTATCAGTGATAGAGAA**AAGTGAA

TABLE 8

Nucleotide sequences of Tet promoter-PAL3, high-copy construct (SEQ ID NO: 25B)

CTCTAGAAATAATTTTGTTTAACTTTAAGAAGGAGATATACAT<u>ATGAAAGC
TAAAGATGTTCAGCCAACCATTATTATTAATAAAAATGGCCTTATCTCTTT
GGAAGATATCTATGACATTGCGATAAAACAAAAAAAAGTAGAAATATCAAC
GGAGATCACTGAACTTTTGACGCATGGTCGTGAAAAATTAGAGGAAAAATT
AAATTCAGGAGAGGTTATATATGGAATCAATACAGGATTTGGAGGGAATGC
CAATTTAGTTGTGCCATTTGAGAAAATCGCAGAGCATCAGCAAAATCTGTT
AACTTTTCTTTCTGCTGGTACTGGGGACTATATGTCCAAACCTTGTATTAA
AGCGTCACAATTTACTATGTTACTTTCTGTTTGCAAAGGTTGGTCTGCAAC
CAGACCAATTGTCGCTCAAGCAATTGTTGATCATATTAATCATGACATTGT
TCCTCTGGTTCCTCGCTATGGCTCAGTGGGTGCAAGCGGTGATTTAATTCC
TTTATCTTATATTGCACGAGCATTATGTGGTATCGGCAAAGTTTATTATAT
GGGCGCAGAAATTGACGCTGCTGAAGCAATTAAACGTGCAGGGTTGACACC
ATTATCGTTAAAAGCCAAAGAAGGTCTTGCTCTGATTAACGGCACCCGGGT
AATGTCAGGAATCAGTGCAATCACCGTCATTAAACTGGAAAAACTATTTAA
AGCCTCAATTTCTGCGATTGCCCTTGCTGTTGAAGCATTACTTGCATCTCA
TGAACATTATGATGCCCGGATTCAACAAGTAAAAAATCATCCTGGTCAAAA
CGCGGTGGCAAGTGCATTGCGTAATTTATTGGCAGGTTCAACGCAGGTTAA
TCTATTATCTGGGGTTAAAGAACAAGCCAATAAAGCTTGTCGTCATCAAGA
AATTACCCAACTAAATGATACCTTACAGGAAGTTTATTCAATTCGCTGTGC
ACCACAAGTATTAGGTATAGTGCCAGAATCTTTAGCTACCGCTCGGAAAAT
ATTGGAACGGGAAGTTATCTCAGCTAATGATAATCCATTGATAGATCCAGA
AAATGGCGATGTTCTACACGGTGGAAATTTTATGGGGCAATATGTCGCCCG
AACAATGGATGCATTAAAACTGGATATTGCTTTAATTGCCAATCATCTTCA
CGCCATTGTGGCTCTTATGATGGATAACCGTTTCTCTCGTGGATTACCTAA
TTCACTGAGTCCGACACCCGGCATGTATCAAGGTTTTAAAGGCGTCCAACT
TTCTCAAACCGCTTTAGTTGCTGCAATTCGCCATGATTGTGCTGCATCAGG
TATTCATACCCTCGCCACAGAACAATACAATCAAGATATTGTCAGTTTAGG
TCTGCATGCCGCTCAAGATGTTTTAGAGATGGAGCAGAAATTACGCAATAT
TGTTTCAATGACAATTCTGGTAGTTTGTCAGGCCATTCATCTTCGCGGCAA
TATTAGTGAAATTGCGCCTGAAACTGCTAAATTTTACCATGCAGTACGCGA
AATCAGTTCTCCTTTGATCACTGATCGTGCGTTGGATGAAGATATAATCCG
CATTGCGGATGCAATTATTAATGATCAACTTCCTCTGCCAGAAATCATGCT
GGAAGAATAAGCTTGGCGTAATCATGGTCATAGCTGTTTCCTGTGTGAAAT</u>
TGTTATCCGCTCACAATTCCACACAACATACGAGCCGGAAGCATAAAGTGT
AAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGCT
TCCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAAC

TABLE 8-continued

Nucleotide sequences of Tet promoter-PAL3, high-copy construct (SEQ ID NO: 25B)

GCAGGAAAGAACATGTGAGCAAAAGGCCAGCAAAAGGCCAGGAACCGTAAA

AAGGCCGCGTTGCTGGCGTTTTTCCATAGGCTCCGCCCCCCTGACGAGCAT

CACAAAAATCGACGCTCAAGTCAGAGGTGGCGAAACCCGACAGGACTATAA

AGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGC

GCCTTATCCGGTAACTATCGTCTTGAGTCCAACCCGGTAAGACACGACTTA

TCGCCACTGGCAGCAGCCACTGGTAACAGGATTAGCAGAGCGAGGTATGTA

GGCGGTGCTACAGAGTTCTTGAAGTGGTGGCCTAACTACGGCTACACTAGA

AGAACAGTATTTGGTATCTGCGCTCTGCTGAAGCCAGTTACCTTCGGAAAA

AGAGTTGGTAGCTCTTGATCCGGCAAACAAACCACCGCTGGTAGCGGTGGT

TTTTTTGTTTGCAAGCAGCAGATTACGCGCAGAAAAAAAGGATCTCAAGAA

GATCCTTTGATCTTTTCTACGGGGTCTGACGCTCAGTGGAACGAAAACTCA

CGTTAAGGGATTTTGGTCATGAGATTATCAAAAGGATCTTCACCTAGATC

CTTTTAAATTAAAAATGAAGTTTTAAATCAATCTAAAGTATATATGAGTAA

ACTTGGTCTGACAGTTACCAATGCTTAATCAGTGAGGCACCTATCTCAGCG

ATCTGTCTATTTCGTTCATCCATAGTTGCCTGACTCCCCGTCGTGTAGATA

ACTACGATACGGGAGGGCTTACCATCTGGCCCCAGTGCTGCAATGATACCG

CGAGACCCACGCTCACCGGCTCCAGATTTATCAGCAATAAACCAGCCAGCC

GGAAGGGCCGAGCGCAGAAGTGGTCCTGCAACTTTATCCGCCTCCATCCAG

TCTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTCG

TTTGGTATGGCTTCATTCAGCTCCGGTTCCCAACGATCAAGGCGAGTTACA

TGATCCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCA

CTGCATAATTCTCTTACTGTCATGCCATCCGTAAGATGCTTTTCTGTGACT

GGTGAGTACTCAACCAAGTCATTCTGAGAATAGTGTATGCGGCGACCGAGT

TGCTCTTGCCCGGCGTCAATACGGGATAATACCGCGCCACATAGCAGAACT

TTAAAAGTGCTCATCATTGGAAAACGTTCTTCGGGGCGAAAACTCTCAAGG

ATCTTACCGCTGTTGAGATCCAGTTCGATGTAACCCACTCGTGCACCCAAC

TGATCTTCAGCATCTTTTACTTTCACCAGCGTTTCTGGGTGAGCAAAAACA

GGAAGGCAAAATGCCGCAAAAAAGGGAATAAGGGCGACACGGAAATGTTGA

ATACTCATACTCTTCCTTTTTCAATATTATTGAAGCATTTATCAGGGTTAT

TGTCTCATGAGCGGATACATATTTGAATGTATTTAGAAAAATAAACAAATA

GGGGTTCCGCGCACATTTCCCCGAAAAGTGCCACCTGACGTCTAAGAAACC

ATTATTATCATGACATTAACCTATAAAAATAGGCGTATCACGAGGCCCTTT

CGTCTCGCGCGTTTCGGTGATGACGGTGAAAACCTCTGACACATGCAGCTC

TABLE 8-continued

Nucleotide sequences of Tet promoter-PAL3, high-copy construct (SEQ ID NO: 25B)

CCGGAGACGGTCACAGCTTGTCTGTAAGCGGATGCCGGGAGCAGACAAGCC

CGTCAGGGCGCGTCAGCGGGTGTTGGCGGGTGTCGGGGCTGGCTTAACTAT

GCGGCATCAGAGCAGATTGTACTGAGAGTGCACCATATGCGGTGTGAAATA

CCGCACAGATGCGTAAGGAGAAAATACCGCATCAGGCGCCATTCGCCATTC

AGGCTGCGCAACTGTTGGGAAGGGCGATCGGTGCGGGCCTCTTCGCTATTA

CGCCAGCTGGCGAAAGGGGGATGTGCTGCAAGGCGATTAAGTTGGGTAACG

CCAGGGTTTTCCCAGTCACGACGTTGTAAAACGACGGCCAGTGAATTCGTT

AAGACCCACTTTCACATTTAAGTTGTTTTTCTAATCCGCATATGATCAATT

CAAGGCCGAATAAGAAGGCTGGCTCTGCACCTTGGTGATCAAATAATTCGA

TAGCTTGTCGTAATAATGGCGGCATACTATCAGTAGTAGGTGTTTCCCTTT

CTTCTTTAGCGACTTGATGCTCTTGATCTTCCAATACGCAACCTAAAGTAA

AATGCCCCACAGCGCTGAGTGCATATAATGCATTCTCTAGTGAAAAACCTT

GTTGGCATAAAAAGGCTAATTGATTTTCGAGAGTTTCATACTGTTTTTCTG

TAGGCCGTGTACCTAAATGTACTTTTGCTCCATCGCGATGACTTAGTAAAG

CACATCTAAAACTTTTAGCGTTATTACGTAAAAAATCTTGCCAGCTTTCCC

CTTCTAAAGGGCAAAAGTGAGTATGGTGCCTATCTAACATCTCAATGGCTA

AGGCGTCGAGCAAAGCCCGCTTATTTTTTACATGCCAATACAATGTAGGCT

GCTCTACACCTAGCTTCTGGGCGAGTTTACGGGTTGTTAAACCTTCGATTC

CGACCTCATTAAGCAGCTCTAATGCGCTGTTAATCACTTTACTTTTATCTA

ATCTAGACATCATTAATTCCTAATTTTTGTTGACACTCTATCATTGATAGA

GTTATTTTACCACTCCCTATCAGTGATAGAGAAAAGTGAA

TABLE 9

Nucleotide sequences of FNR promoter-PAL1 construct, low-copy (SEQ ID NO: 26B)

CTCTTGATCGTTATCAATTCCCACGCTGTTTCAGAGCGTTACCTTGCCCTT

AAACATTAGCAATGTCGATTTATCAGAGGGCCGACAGGCTCCCACAGGAGA

AAACCGATGAAAACACTATCACAGGCCCAATCTAAAACTTCTTCACAGCAA

TTCAGCTTTACCGGGAACTCGTCTGCGAATGTAATTATCGGCAATCAAAAG

CTGACCATTAATGATGTAGCTCGCGTTGCCCGGAATGGCACTTTGGTGTCA

CTGACGAACAATACCGACATTCTGCAAGGTATTCAAGCTAGCTGCGATTAT

ATCAATAACGCCGTTGAATCTGGCGAGCCAATCTACGGGGTAACAAGCGGT

TTTGGTGGGATGGCGAACGTTGCCATTAGCCGTGAACAGGCGAGCGAACTT

CAGACCAACCTCGTTTGGTTCCTAAAGACAGGAGCTGGTAATAAGTTACCT

CTGGCTGACGTAAGAGCCGCGATGCTGCTTCGCGCTAATAGTCACATGCGC

GGCGCCAGTGGTATCCGTCTTGAGCTTATCAAGAGGATGGAAATCTTCCTC

AACGCGGGTGTCACACCATATGTTTATGAGTTTGGTAGTATCGGAGCCAGT

GGTGATCTTGTTCCCCTGAGTTATATTACGGGTTCATTGATTGGTTTAGAC

CCGTCCTTTAAAGTGGATTTTAACGGGAAAGAAATGGACGCCCCGACCGCT

TABLE 9-continued

Nucleotide sequences of FNR promoter-PAL1 construct, low-copy (SEQ ID NO: 26B)

TTACGACAGCTTAATCTGAGCCCACTTACTTTGCTCCCTAAAGAAGGTCTT
GCCATGATGAATGGCACCTCTGTGATGACTGGAATTGCCGCGAATTGTGTG
TATGACACGCAGATCCTAACGGCCATTGCCATGGGTGTTCACGCGTTGGAC
ATTCAAGCCCTGAATGGTACAAACCAGTCGTTTCATCCGTTTATCCATAAT
TCAAAACCCCATCCGGGACAGCTTTGGGCTGCTGATCAGATGATCTCACTC
CTGGCCAATAGTCAACTGGTTCGGGACGAGCTCGACGGCAAACATGATTAT
CGCGATCATGAGCTCATCCAGGACCGGTATTCACTTCGTTGTCTCCCACAA
TACCTGGGGCCTATCGTTGATGGTATATCTCAAATTGCGAAGCAAATTGAA
ATTGAGATCAATAGCGTAACCGACAACCCGCTTATCGATGTTGATAATCAG
GCCTCTTATCACGGTGGCAATTTTCTGGGCCAGTATGTTGGTATGGGATG
GATCACCTGCGGTACTATATTGGGCTTCTGGCTAAACATCTTGATGTGCAG
ATTGCCTTATTAGCTTCACCAGAATTTTCAAATGGACTGCCGCCATCATTG
CTCGGTAACAGAGAAAGGAAAGTAAATATGGGCCTTAAGGGCCTTCAGATA
TGTGGTAACTCAATCATGCCCCTCCTGACCTTTTATGGGAACTCAATTGCT
GATCGTTTTCCGACACATGCTGAACAGTTTAACCAAAACATTAACTCACAG
GGCTATACATCCGCGACGTTAGCGCGTCGGTCCGTGGATATCTTCCAGAAT
TATGTTGCTATCGCTCTGATGTTCGGCGTACAGGCCGTTGATTTGCGCACT
TATAAAAAAACCGGTCACTACGATGCTCGGGCTTGCCTGTCGCCTGCCACC
GAGCGGCTTTATAGCGCCGTACGTCATGTTGTGGGTCAGAAACCGACGTCG
GACCGCCCCTATATTTGGAATGATAATGAACAAGGGCTGGATGAACACATC
GCCCGGATATCTGCCGATATTGCCGCCGGAGGTGTCATCGTCCAGGCGGTA
CAAGACATACTTCCTTGCCTGCATTAAGCTTGGCGTAATCATGGTCATAGC
TGTTTCCTGTGTGAAATTGTTATCCGCTCACAATTCCACACAACATACGAG
CCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTC
GGCTGCGGCGAGCGGTATCAGCTCACTCAAAGGCGGTAGTACGGGTTTTGC
TGCCCGCAAACGGGCTGTTCTGGTGTTGCTAGTTTGTTATCAGAATCGCAG
ATCCGGCTTCAGGTTTGCCGGCTGAAAGCGCTATTTCTTCCAGAATTGCCA
TGATTTTTTCCCCACGGGAGGCGTCACTGGCTCCCGTGTTGTCGGCAGCTT
TGATTCGATAAGCAGCATCGCCTGTTTCAGGCTGTCTATGTGTGACTGTTG
AGCTGTAACAAGTTGTCTCAGGTGTTCAATTTCATGTTCTAGTTGCTTTGT
TTTACTGGTTTCACCTGTTCTATTAGGTGTTACATGCTGTTCATCTGTTAC
ATTGTCGATCTGTTCATGGTGAACAGCTTTAAATGCACCAAAAACTCGTAA
AAGCTCTGATGTATCTATCTTTTTTACACCGTTTTCATCTGTGCATATGGA
CAGTTTTCCCTTTGATATCTAACGGTGAACAGTTGTTCTACTTTTGTTTGT
TAGTCTTGATGCTTCACTGATAGATACAAGAGCCATAAGAACCCTCAGATCC

TTCCGTATTTAGCCAGTATGTTCTCTAGTGTGGTTCGTTGTTTTTGCGTGA
GCCATGAGAACGAACCATTGAGATCATGCTTACTTTGCATGTCACTCAAAA
ATTTTGCCTCAAAACTGGTGAGCTGAATTTTTGCAGTTAAAGCATCGTGTA
GTGTTTTTCTTAGTCCGTTACGTAGGTAGGAATCTGATGTAATGGTTGTTG
GTATTTTGTCACCATTCATTTTTATCTGGTTGTTCTCAAGTTCGGTTACGA
GATCCATTTGTCTATCTAGTTCAACTTGGAAAATCAACGTATCAGTCGGGC
GGCCTCGCTTATCAACCACCAATTTCATATTGCTGTAAGTGTTTAAATCTT
TACTTATTGGTTTCAAAACCCATTGGTTAAGCCTTTTAAACTCATGGTAGT
TATTTTCAAGCATTAACATGAACTTAAATTCATCAAGGCTAATCTCTATAT
TTGCCTTGTGAGTTTTCTTTTGTGTTAGTTCTTTTAATAACCACTCATAAA
TCCTCATAGAGTATTTGTTTTCAAAAGACTTAACATGTTCCAGATTATATT
TTATGAATTTTTTTAACTGGAAAAGATAAGGCAATATCTCTTCACTAAAAA
CTAATTCTAATTTTTCGCTTGAGAACTTGGCATAGTTTGTCCACTGGAAAA
TCTCAAAGCCTTTAACCAAAGGATTCCTGATTTCCACAGTTCTCGTCATCA
GCTCTCTGGTTGCTTTAGCTAATACACCATAAGCATTTTCCCTACTGATGT
TCATCATCTGAGCGTATTGGTTATAAGTGAACGATACCGTCCGTTCTTTCC
TTGTAGGGTTTTCAATCGTGGGGTTGAGTAGTGCCACACAGCATAAAATTA
GCTTGGTTTCATGCTCCGTTAAGTCATAGCGACTAATCGCTAGTTCATTTG
CTTTGAAAACAACTAATTCAGACATACATCTCAATTGGTCTAGGTGATTTT
AATCACTATACCAATTGAGATGGGCTAGTCAATGATAATTACTAGTCCTTT
TCCTTTGAGTTGTGGGTATCTGTAAATTCTGCTAGACCTTTGCTGGAAAAC
TTGTAAATTCTGCTAGACCCTCTGTAAATTCCGCTAGACCTTTGTGTGTTT
TTTTTGTTTATATTCAAGTGGTTATAATTTATAGAATAAAGAAAGAATAAA
AAAAGATAAAAAGAATAGATCCCAGCCCTGTGTATAACTCACTACTTTAGT
CAGTTCCGCAGTATTACAAAAGGATGTCGCAAACGCTGTTTGCTCCTCTAC
AAAACAGACCTTAAAACCCTAAAGGCTTAAGTAGCACCCTCGCAAGCTCGG
GCAAATCGCTGAATATTCCTTTTGTCTCCGACCATCAGGCACCTGAGTCGC
TGTCTTTTTCGTGACATTCAGTTCGCTGCGCTCACGGCTCTGGCAGTGAAT
GGGGGTAAATGGCACTACAGGCGCCTTTTATGGATTCATGCAAGGAAACTA
CCCATAATACAAGAAAAGCCCGTCACGGGCTTCTCAGGGCGTTTTATGGCG
GGTCTGCTATGTGGTGCTATCTGACTTTTTGCTGTTCAGCAGTTCCTGCCC
TCTGATTTTCCAGTCTGACCACTTCGGATTATCCCGTGACAGGTCATTCAG
ACTGGCTAATGCACCCAGTAAGGCAGCGGTATCATCAACAGGCTTACCCGT
CTTACTGTCTTTTCTACGGGGTCTGACGCTCAGTGGAACGAAAACTCACGT
TAAGGGATTTTGGTCATGAGATTATCAAAAAGGATCTTCACCTAGATCCTT
TTAAATTAAAAATGAAGTTTTAAATCAATCTAAAGTATATATGAGTAAACT
TGGTCTGACAGTTACCAATGCTTAATCAGTGAGGCACCTATCTCAGCGATC
TGTCTATTTCGTTCATCCATAGTTGCCTGACTCCCCGTCGTGTAGATAACT
ACGATACGGGAGGGCTTACCATCTGGCCCCAGTGCTGCAATGATACCGCGA

TABLE 9-continued

Nucleotide sequences of FNR promoter-PAL1 construct, low-copy (SEQ ID NO: 26B)

GACCCACGCTCACCGGCTCCAGATTTATCAGCAATAAACCAGCCAGCCGA
AGGGCCGAGCGCAGAAGTGGTCCTGCAACTTTATCCGCCTCCATCCAGTCT
ATTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGA
TCCCCCATGTTGTGCAAAAAAGCGGTTAGCTCCTTCGGTCCTCCGATCGTT
GTCAGAAGTAAGTTGGCCGCAGTGTTATCACTCATGGTTATGGCAGCACTG
CATAATTCTCTTACTGTCATGCCATCCGTAAGATGCTTTTCTGTGACTGGT
GAGTACTCAACCAAGTCATTCTGAGAATAGTGTATGCGGCGACCGAGTTGC
TCTTGCCCGGCGTCAATACGGGATAATACCGCGCCACATAGCAGAACTTTA
AAAGTGCTCATCATTGGAAAACGTTCTTCGGGGCGAAAACTCTCAAGGATC
TTACCGCTGTTGAGATCCAGTTCGATGTAACCCACTCGTGCACCCAACTGA
TCTTCAGCATCTTTTACTTTCACCAGCGTTTCTGGGTGAGCAAAAACAGGA
AGGCAAAATGCCGCAAAAAAGGGAATAAGGGCGACACGGAAATGTTGAATA
CTCATACTCTTCCTTTTTCAATATTATTGAAGCATTTATCAGGGTTATTGT
CTCATGAGCGGATACATATTTGAATGTATTTAGAAAAATAAACAAATAGGG
GTTCCGCGCACATTTCCCCGAAAAGTGCCACCTGACGTCTAAGAAACCATT
ATTATCATGACATTAACCTATAAAAATAGGCGTATCACGAGGCCCTTTCGT
CTCGCGCGTTTCGGTGATGACGGTGAAAACCTCTGACACATGCAGCTCCCG
GAGACGGTCACAGCTTGTCTGTAAGCGGATGCCGGGAGCAGACAAGCCCGT
CAGGGCGCGTCAGCGGGTGTTGGCGGGTGTCGGGGCTGGCTTAACTATGCG
GCATCAGAGCAGATTGTACTGAGAGTGCACCATATGCGGTGTGAAATACCG
CACAGATGCGTAAGGAGAAAATACCGCATCAGGCGCCATTCGCCATTCAGG
CTGCGCAACTGTTGGGAAGGGCGATCGGTGCGGGCCTCTTCGCTATTACGC
CAGCTGGCGAAAGGGGGATGTGCTGCAAGGCGATTAAGTTGGGTAACGCCA
GGGTTTTCCCAGTCACGACGTTGTAAAACGACGGCCAGTGAATTCG

TABLE 10

Nucleotide sequences of FNR promoter-PAL3 construct, low-copy (SEQ ID NO: 27B)

CTCTTGATCGTTATCAATTCCCACGCTGTTTCAGAGCGTTACCTTGCCCTT
AAACATTAGCAATGTCGATTTATCAGAGGGCCGACAGGCTCCCACAGGAGA
AAACCGATGAAAGCTAAAGATGTTCAGCCAACCATTATTATTAATAAAAAT
GGCCTTATCTCTTTGGAAGATATCTATGACATTGCGATAAAACAAAAAAAA
GTAGAAAATATCAACGGAGATCACTGAACTTTTGACGCATGGTCGTGAAAAA
TTAGAGGAAAAATTAAATTCAGGAGAGGTTATATATGGAATCAATACAGGA
TTTGGAGGGAATGCCAATTTAGTTGTGCCATTTGAGAAAATCGCAGAGCAT
CAGCAAAATCTGTTAACTTTTCTTTCTGCTGGTACTGGGGACTATATGTCC

TABLE 10-continued

Nucleotide sequences of FNR promoter-PAL3 construct, low-copy (SEQ ID NO: 27B)

AAACCTTGTATTAAAGCGTCACAATTTACTATGTTACTTTCTGTTTGCAAA
GGTTGGTCTGCAACCAGACCAATTGTCGCTCAAGCAATTGTTGATCATATT
AATCATGACATTGTTCCTCTGGTTCCTCGCTATGGCTCAGTGGGTGCAAGC
GGTGATTTAATTCCTTTATCTTATATTGCACGAGCATTATGTGGTATCGGC
AAAGTTTATTATATGGGCGCAGAAATTGACGCTGCTGAAGCAATTAAACGT
GCAGGGTTGACACCATTATCGTTAAAAGCCAAAGAAGGTCTTGCTCTGATT
AACGGCACCCGGGTAATGTCAGGAATCAGTGCAATCACCGTCATTAAACTG
GAAAAACTATTTAAAGCCTCAATTTCTGCGATTGCCCTTGCTGTTGAAGCA
TTACTTGCATCTCATGAACATTATGATGCCCGGATTCAACAAGTAAAAAAT
CATCCTGGTCAAAACGCGGTGGCAAGTGCATTGCGTAATTTATTGGCAGGT
TCAACGCAGGTTAATCTATTATCTGGGGTTAAAGAACAAGCCAATAAAGCT
TGTCGTCATCAAGAAATTACCCAACTAAATGATACCTTACAGGAAGTTTAT
TCAATTCGCTGTGCACCACAAGTATTAGGTATAGTGCCAGAATCTTTAGCT
ACCGCTCGGAAAATATTGGAACGGGAAGTTATCTCAGCTAATGATAATCCA
TTGATAGATCCAGAAAATGGCGATGTTCTACACGGTGGAAATTTTATGGGG
CAATATGTCGCCCGAACAATGGATGCATTAAAACTGGATATTGCTTTAATT
GCCAATCATCTTCACGCCATTGTGGCTCTTATGATGGATAACCGTTTCTCT
CGTGGATTACCTAATTCACTGAGTCCGACACCCGGCATGTATCAAGGTTTT
AAAGGCGTCCAACTTTCTCAAACCGCTTTAGTTGCTGCAATTCGCCATGAT
TGTGCTGCATCAGGTATTCATACCCTCGCCACAGAACAATACAATCAAGAT
ATTGTCAGTTTAGGTCTGCATGCCGCTCAAGATGTTTTAGAGATGGAGCAG
AAATTACGCAATATTGTTTCAATGACAATTCTGGTAGTTTGTCAGGCCATT
CATCTTCGCGGCAATATTAGTGAAATTGCGCCTGAAACTGCTAAATTTTAC
CATGCAGTACGCGAAATCAGTTCTCCTTTGATCACTGATCGTGCGTTGGAT
GAAGATATAATCCGCATTGCGGATGCAATTATTAATGATCAACTTCCTCTG
CCAGAAATCATGCTGGAAGAATAAGCTTGGCGTAATCATGGTCATAGCTGT
TTCCTGTGTGAAATTGTTATCCGCTCACAATTCCACACAACATACGAGCCG
GAAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGC
TGCGGCGAGCGGTATCAGCTCACTCAAAGGCGGTAGTACGGGTTTTGCTGC
CCGCAAACGGGCTGTTCTGGTGTTGCTAGTTTGTTATCAGAATCGCAGATC
CGGCTTCAGGTTTGCCGGCTGAAAGCGCTATTTCTTCCAGAATTGCCATGA
TTTTTTCCCCACGGGAGGCGTCACTGGCTCCCGTGTTGTCGGCAGCTTTGA
TTCGATAAGCAGCATCGCCTGTTTCAGGCTGTCTATGTGTGACTGTTGAGC
TGTAACAAGTTGTCTCAGGTGTTCAATTTCATGTTCTAGTTGCTTTGTTTT
ACTGGTTTCACCTGTTCTATTAGGTGTTACATGCTGTTCATCTGTTACATT
GTCGATCTGTTCATGGTGAACAGCTTTAAATGCACCAAAAACTCGTAAAAG

TABLE 10-continued

Nucleotide sequences of FNR promoter-PAL3 construct, low-copy (SEQ ID NO: 27B)

CTCTGATGTATCTATCTTTTTTACACCGTTTTCATCTGTGCATATGGACAG
TTTTTCCCTTTGATATCTAACGGTGAACAGTTGTTCTACTTTTGTTTGTTAG
TCTTGATGCTTCACTGATAGATACAAGAGCCATAAGAACCTCAGATCCTTC
CGTATTTAGCCAGTATGTTCTCTAGTGTGGTTCGTTGTTTTTGCGTGAGCC
ATGAGAACGAACCATTGAGATCATGCTTACTTTGCATGTCACTCAAAAATT
TTGCCTCAAAACTGGTGAGCTGAATTTTTGCAGTTAAAGCATCGTGTAGTG
TTTTTCTTAGTCCGTTACGTAGGTAGGAATCTGATGTAATGGTTGTTGGTA
TTTTGTCACCATTCATTTTTATCTGGTTGTTCTCAAGTTCGGTTACGAGAT
CCATTTGTCTATCTAGTTCAACTTGGAAAATCAACGTATCAGTCGGGCGGC
CTCGCTTATCAACCACCAATTTCATATTGCTGTAAGTGTTTAAATCTTTAC
TTATTGGTTTCAAAACCCATTGGTTAAGCCTTTTAAACTCATGGTAGTTAT
TTTCAAGCATTAACATGAACTTAAATTCATCAAGGCTAATCTCTATATTTG
CCTTGTGAGTTTTCTTTTGTGTTAGTTCTTTTAATAACCACTCATAAATCC
TCATAGAGTATTTGTTTTCAAAAGACTTAACATGTTCCAGATTATATTTTA
TGAATTTTTTTAACTGGAAAAGATAAGGCAATATCTCTTCACTAAAAACTA
ATTCTAATTTTTCGCTTGAGAACTTGGCATAGTTTGTCCACTGGAAAATCT
CAAAGCCTTTAACCAAAGGATTCCTGATTTCCACAGTTCTCGTCATCAGCT
CTCTGGTTGCTTTAGCTAATACACCATAAGCATTTTCCCTACTGATGTTCA
TCATCTGAGCGTATTGGTTATAAGTGAACGATACCGTCCGTTCTTTCCTTG
TAGGGTTTTCAATCGTGGGGTTGAGTAGTGCCACACAGCATAAAATTAGCT
TGGTTTCATGCTCCGTTAAGTCATAGCGACTAATCGCTAGTTCATTTGCTT
TGAAAACAACTAATTCAGACATACATCTCAATTGGTCTAGGTGATTTTAAT
CACTATACCAATTGAGATGGGCTAGTCAATGATAATTACTAGTCCTTTTCC
TTTGAGTTGTGGGTATCTGTAAATTCTGCTAGACCTTTGCTGGAAAACTTG
TAAATTCTGCTAGACCCTCTGTAAATTCCGCTAGACCTTTGTGTGTTTTTT
TTGTTTATATTCAAGTGGTTATAATTTATAGAATAAAGAAAGAATAAAAAA
AGATAAAAAGAATAGATCCCAGCCCTGTGTATAACTCACTACTTTAGTCAG
TTCCGCAGTATTACAAAAGGATGTCGCAAACGCTGTTTGCTCCTCTACAAA
ACAGACCTTAAAACCCTAAAGGCTTAAGTAGCACCCTCGCAAGCTCGGGCA
AATCGCTGAATATTCCTTTTGTCTCCGACCATCAGGCACCTGAGTCGCTGT
CTTTTTCGTGACATTCAGTTCGCTGCGCTCACGGCTCTGGCAGTGAATGGG
GGTAAATGGCACTACAGGCGCCTTTTATGGATTCATGCAAGGAAACTACCC
ATAATACAAGAAAGCCCGTCACGGGCTTCTCAGGGCGTTTTATGGCGGGT
CTGCTATGTGGTGCTATCTGACTTTTTGCTGTTCAGCAGTTCCTGCCCTCT
GATTTTCCAGTCTGACCACTTCGGATTATCCCGTGACAGGTCATTCAGACT
GGCTAATGCACCCAGTAAGGCAGCGGTATCATCAACAGGCTTACCCGTCTT
ACTGTCTTTTCTACGGGGTCTGACGCTCAGTGGAACGAAAACTCACGTTAA
GGGATTTTGGTCATGAGATTATCAAAAAGGATCTTCACCTAGATCCTTTTA

TABLE 10-continued

Nucleotide sequences of FNR promoter-PAL3 construct, low-copy (SEQ ID NO: 27B)

AATTAAAAATGAAGTTTTAAATCAATCTAAAGTATATATGAGTAAACTTGG
TCTGACAGTTACCAATGCTTAATCAGTGAGGCACCTATCTCAGCGATCTGT
CTATTTCGTTCATCCATAGTTGCCTGACTCCCCGTCGTGTAGATAACTACG
ATACGGGAGGGCTTACCATCTGGCCCCAGTGCTGCAATGATACCGCGAGAC
CCACGCTCACCGGCTCCAGATTTATCAGCAATAAACCAGCCAGCCGGAAGG
GCCGAGCGCAGAAGTGGTCCTGCAACTTTATCCGCCTCCATCCAGTCTATT
AATTGTTGCCGGGAAGCTAGAGTAAGTAGTTCGCCAGTTAATAGTTTGCGC
AACGTTGTTGCCATTGCTACAGGCATCGTGGTGTCACGCTCGTCGTTTGGT
ATGGCTTCATTCAGCTCCGGTTCCCAACGATCAAGGCGAGTTACATGATCC
CCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCAT
AATTCTCTTACTGTCATGCCATCCGTAAGATGCTTTTCTGTGACTGGTGAG
TACTCAACCAAGTCATTCTGAGAATAGTGTATGCGGCGACCGAGTTGCTCT
TGCCCGGCGTCAATACGGGATAATACCGCGCCACATAGCAGAACTTTAAA
GTGCTCATCATTGGAAAACGTTCTTCGGGGCGAAAACTCTCAAGGATCTTA
CCGCTGTTGAGATCCAGTTCGATGTAACCCACTCGTGCACCCAACTGATCT
TCAGCATCTTTTACTTTCACCAGCGTTTCTGGGTGAGCAAAAACAGGAAGG
CAAAATGCCGCAAAAAAGGGAATAAGGGCGACACGGAAATGTTGAATACTC
ATACTCTTCCTTTTTCAATATTATTGAAGCATTTATCAGGGTTATTGTCTC
ATGAGCGGATACATATTTGAATGTATTTAGAAAAATAAACAAATAGGGGTT
CCGCGCACATTTCCCCGAAAAGTGCCACCTGACGTCTAAGAAACCATTATT
ATCATGACATTAACCTATAAAAATAGGCGTATCACGAGGCCCTTTCGTCTC
GCGCGTTTCGGTGATGACGGTGAAAACCTCTGACACATGCAGCTCCCGGAG
ACGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGCA
TCAGAGCAGATTGTACTGAGAGTGCACCATATGCGGTGTGAAATACCGCAC
AGATGCGTAAGGAGAAAATACCGCATCAGGCGCCATTCGCCATTCAGGCTG
CGCAACTGTTGGGAAGGGCGATCGGTGCGGGCCTCTTCGCTATTACGCCAG
CTGGCGAAAGGGGGATGTGCTGCAAGGCGATTAAGTTGGGTAACGCCAGGG
TTTTCCCAGTCACGACGTTGTAAAACGACGGCCAGTGAATTCG

TABLE 11

Nucleotide sequences of Tet promoter-PAL1 construct, low-copy (SEQ ID NO: 28B)

ACCACTCCCTATCAGTGATAGAGAAAAGTGAACTCTAGAAATAATTTTGTT
TAACTTTAAGAAGGAGATATACAT<u>ATGAAAACACTATCACAGGCCCAATCT</u>
<u>AAAACTTCTTCACAGCAATTCAGCTTTACCGGGAACTCGTCTGCGAATGTA</u>
<u>ATTATCGGCAATCAAAAGCTGACCATTAATGATGTAGCTCGCGTTGCCCGG</u>
<u>AATGGCACTTTGGTGTCACTGACGAACAATACCGACATTCTGCAAGGTATT</u>

TABLE 11-continued

Nucleotide sequences of Tet promoter-PAL1 construct, low-copy (SEQ ID NO: 28B)

CAAGCTAGCTGCGATTATATCAATAACGCCGTTGAATCTGGCGAGCCAATC
TACGGGGTAACAAGCGGTTTTGGTGGGATGGCGAACGTTGCCATTAGCCGT
GAACAGGCGAGCGAACTTCAGACCAACCTCGTTTGGTTCCTAAAGACAGGA
GCTGGTAATAAGTTACCTCTGGCTGACGTAAGAGCCGCGATGCTGCTTCGC
GCTAATAGTCACATGCGCGGCGCCAGTGGTATCCGTCTTGAGCTTATCAAG
AGGATGGAAATCTTCCTCAACGCGGGTGTCACACCATATGTTTATGAGTTT
GGTAGTATCGGAGCCAGTGGTGATCTTGTTCCCCTGAGTTATATTACGGGT
TCATTGATTGGTTTAGACCCGTCCTTTAAAGTGGATTTTAACGGGAAAGAA
ATGGACGCCCCGACCGCTTTACGACAGCTTAATCTGAGCCCACTTACTTTG
CTCCCTAAAGAAGGTCTTGCCATGATGAATGGCACCTCTGTGATGACTGGA
ATTGCCGCGAATTGTGTGTATGACACGCAGATCCTAACGGCCATTGCCATG
GGTGTTCACGCGTTGGACATTCAAGCCCTGAATGGTACAAACCAGTCGTTT
CATCCGTTTATCCATAATTCAAAACCCCATCCGGGACAGCTTTGGGCTGCT
GATCAGATGATCTCACTCCTGGCCAATAGTCAACTGGTTCGGGACGAGCTC
GACGGCAAACATGATTATCGCGATCATGAGCTCATCCAGGACCGGTATTCA
CTTCGTTGTCTCCCACAATACCTGGGGCCTATCGTTGATGGTATATCTCAA
ATTGCGAAGCAAATTGAAATTGAGATCAATAGCGTAACCGACAACCCGCTT
ATCGATGTTGATAATCAGGCCTCTTATCACGGTGGCAATTTTCTGGGCCAG
TATGTTGGTATGGGGATGGATCACCTGCGGTACTATATTGGGCTTCTGGCT
AAACATCTTGATGTGCAGATTGCCTTATTAGCTTCACCAGAATTTTCAAAT
GGACTGCCGCCATCATTGCTCGGTAACAGAGAAAGGAAAGTAAATATGGGC
CTTAAGGGCCTTCAGATATGTGGTAACTCAATCATGCCCCTCCTGACCTTT
TATGGGAACTCAATTGCTGATCGTTTTCCGACACATGCTGAACAGTTTAAC
CAAAACATTAACTCACAGGGCTATACATCCGCGACGTTAGCGCGTCGGTCC
GTGGATATCTTCCAGAATTATGTTGCTATCGCTCTGATGTTCGGCGTACAG
GCCGTTGATTTGCGCACTTATAAAAAAACCGGTCACTACGATGCTCGGGCT
TGCCTGTCGCCTGCCACCGAGCGGCTTTATAGCGCCGTACGTCATGTTGTG
GGTCAGAAACCGACGTCGGACCGCCCCTATATTTGGAATGATAATGAACAA
GGGCTGGATGAACACATCGCCCGGATATCTGCCGATATTGCCGCCGGAGGT
GTCATCGTCCAGGCGGTACAAGACATACTTCCTTGCCTGCATTAAGCTTGG
CGTAATCATGGTCATAGCTGTTTCCTGTGTGAAATTGTTATCCGCTCACAA
TTCCACACAACATACGAGCCGGAAGCATAAAGTGTAAAGCCTGGGGTGCCT
AATGAGTGAGCTAACTCACATTAATTGCGTTGCGCTCACTGCCCGCTTTCC
AGTCGGGAAACCTGTCGTGCCAGCTGCATTAATGAATCGGCCAACGCGCGG
GGAGAGGCGGTTTGCGTATTGGGCGCTCTTCCGCTTCCTCGCTCACTGACT
CGCTGCGCTCGGTCGTTCGGCTGCGGCGAGCGGTATCAGCTCACTCAAAGG
CGGTAGTACGGGTTTTGCTGCCCGCAAACGGGCTGTTCTGGTGTTGCTAGT
TTGTTATCAGAATCGCAGATCCGGCTTCAGGTTTGCCGGCTGAAAGCGCTA

TABLE 11-continued

Nucleotide sequences of Tet promoter-PAL1 construct, low-copy (SEQ ID NO: 28B)

TTTCTTCCAGAATTGCCATGATTTTTTCCCCACGGGAGGCGTCACTGGCTC
CCGTGTTGTCGGCAGCTTTGATTCGATAAGCAGCATCGCCTGTTTCAGGCT
GTCTATGTGTGACTGTTGAGCTGTAACAAGTTGTCTCAGGTGTTCAATTTC
ATGTTCTAGTTGCTTTGTTTTACTGGTTTCACCTGTTCTATTAGGTGTTAC
ATGCTGTTCATCTGTTACATTGTCGATCTGTTCATGGTGAACAGCTTTAAA
TGCACCAAAAACTCGTAAAAGCTCTGATGTATCTATCTTTTTTACACCGTT
TTCATCTGTGCATATGGACAGTTTTCCCTTTGATATCTAACGGTGAACAGT
TGTTCTACTTTTGTTTGTTAGTCTTGATGCTTCACTGATAGATACAAGAGC
CATAAGAACCTCAGATCCTTCCGTATTTAGCCAGTATGTTCTCTAGTGTGG
TTCGTTGTTTTGCGTGAGCCATGAGAACGAACCATTGAGATCATGCTTAC
TTTGCATGTCACTCAAAAATTTTGCCTCAAAACTGGTGAGCTGAATTTTTG
CAGTTAAAGCATCGTGTAGTGTTTTCTTAGTCCGTTACGTAGGTAGGAAT
CTGATGTAATGGTTGTTGGTATTTTGTCACCATTCATTTTTATCTGGTTGT
TCTCAAGTTCGGTTACGAGATCCATTTGTCTATCTAGTTCAACTTGGAAAA
TCAACGTATCAGTCGGGCGGCCTCGCTTATCAACCACCAATTTCATATTGC
TGTAAGTGTTTAAATCTTTACTTATTGGTTTCAAAACCCATTGGTTAAGCC
TTTTAAACTCATGGTAGTTATTTTCAAGCATTAACATGAACTTAAATTCAT
CAAGGCTAATCTCTATATTTGCCTTGTGAGTTTTCTTTTGTGTTAGTTCTT
TTAATAACCACTCATAAATCCTCATAGAGTATTTGTTTTCAAAAGACTTAA
CATGTTCCAGATTATATTTTATGAATTTTTTTAACTGGAAAAGATAAGGCA
ATATCTCTTCACTAAAAACTAATTCTAATTTTTCGCTTGAGAACTTGGCAT
AGTTTGTCCACTGGAAAATCTCAAAGCCTTTAACCAAAGGATTCCTGATTT
CCACAGTTCTCGTCATCAGCTCTCTGGTTGCTTTAGCTAATACACCATAAG
CATTTTCCCTACTGATGTTCATCATCTGAGCGTATTGGTTATAAGTGAACG
ATACCGTCCGTTCTTTCCTTGTAGGGTTTTCAATCGTGGGGTTGAGTAGTG
CCACACAGCATAAAATTAGCTTGGTTTCATGCTCCGTTAAGTCATAGCGAC
TAATCGCTAGTTCATTTGCTTTGAAAACAACTAATTCAGACATACATCTCA
ATTGGTCTAGGTGATTTTAATCACTATACCAATTGAGATGGGCTAGTCAAT
GATAATTACTAGTCCTTTTCCTTTGAGTTGTGGGTATCTGTAAATTCTGCT
AGACCTTTGCTGGAAAACTTGTAAATTCTGCTAGACCCTCTGTAAATTCCG
CTAGACCTTTGTGTGTTTTTTTTGTTTATATTCAAGTGGTTATAATTTATA
GAATAAAGAAAGAATAAAAAAAGATAAAAAGAATAGATCCCAGCCCTGTGT
ATAACTCACTACTTTAGTCAGTTCCGCAGTATTACAAAAGGATGTCGCAAA
CGCTGTTTGCTCCTCTACAAAACAGACCTTAAAACCCTAAAGGCTTAAGTA
GCACCCTCGCAAGCTCGGGCAAATCGCTGAATATTCCTTTTGTCTCCGACC
ATCAGGCACCTGAGTCGCTGTCTTTTTCGTGACATTCAGTTCGCTGCGCTC
ACGGCTCTGGCAGTGAATGGGGGTAAATGGCACTACAGGCGCCTTTTATGG
ATTCATGCAAGGAAACTACCCATAATACAAGAAAAGCCCGTCACGGGCTTC
TCAGGGCGTTTTATGGCGGGTCTGCTATGTGGTGCTATCTGACTTTTTGCT

TABLE 11-continued

Nucleotide sequences of Tet promoter-PAL1 construct, low-copy (SEQ ID NO: 28B)

GTTCAGCAGTTCCTGCCCTCTGATTTTCCAGTCTGACCACTTCGGATTATC

CCGTGACAGGTCATTCAGACTGGCTAATGCACCCAGTAAGGCAGCGGTATC

ATCAACAGGCTTACCCGTCTTACTGTCTTTTCTACGGGGTCTGACGCTCAG

TGGAACGAAAACTCACGTTAAGGGATTTTGGTCATGAGATTATCAAAAAGG

ATCTTCACCTAGATCCTTTTAAATTAAAAATGAAGTTTTAAATCAATCTAA

AGTATATATGAGTAAACTTGGTCTGACAGTTACCAATGCTTAATCAGTGAG

GCACCTATCTCAGCGATCTGTCTATTTCGTTCATCCATAGTTGCCTGACTC

CCCGTCGTGTAGATAACTACGATACGGGAGGGCTTACCATCTGGCCCCAGT

GCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTA

TCCGCCTCCATCCAGTCTATTAATTGTTGCCGGGAAGCTAGAGTAAGTAGT

TCGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACGA

TCAAGGCGAGTTACATGATCCCCCATGTTGTGCAAAAAAGCGGTTAGCTCC

TTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGA

TGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCG

CCACATAGCAGAACTTTAAAAGTGCTCATCATTGGAAAACGTTCTTCGGGG

CGAAAACTCTCAAGGATCTTACCGCTGTTGAGATCCAGTTCGATGTAACCC

ACTCGTGCACCCAACTGATCTTCAGCATCTTTTACTTTCACCAGCGTTTCT

GGGTGAGCAAAAACAGGAAGGCAAAATGCCGCAAAAAAGGGAATAAGGGCG

ACACGGAAATGTTGAATACTCATACTCTTCCTTTTTCAATATTATTGAAGC

ATTTATCAGGGTTATTGTCTCATGAGCGGATACATATTTGAATGTATTTAG

AAAAATAAACAAATAGGGGTTCCGCGCACATTTCCCCGAAAAGTGCCACCT

GACGTCTAAGAAACCATTATTATCATGACATTAACCTATAAAAATAGGCGT

ATCACGAGGCCCTTTCGTCTCGCGCGTTTCGGTGATGACGGTGAAAACCTC

TGACACATGCAGCTCCCGGAGACGGTCACAGCTTGTCTGTAAGCGGATGCC

GGGAGCAGACAAGCCCGTCAGGGCGCGTCAGCGGGTGTTGGCGGGTGTCGG

GGCTGGCTTAACTATGCGGCATCAGAGCAGATTGTACTGAGAGTGCACCAT

ATGCGGTGTGAAATACCGCACAGATGCGTAAGGAGAAAATACCGCATCAGG

CGCCATTCGCCATTCAGGCTGCGCAACTGTTGGGAAGGGCGATCGGTGCGG

GCCTCTTCGCTATTACGCCAGCTGGCGAAAGGGGGATGTGCTGCAAGGCGA

TTAAGTTGGGTAACGCCAGGGTTTTCCCAGTCACGACGTTGTAAAACGACG

GCCAGTGAATTCGTTAAGACCCACTTTCACATTTAAGTTGTTTTTCTAATC

CGCATATGATCAATTCAAGGCCGAATAAGAAGGCTGGCTCTGCACCTTGGT

GATCAAATAATTCGATAGCTTGTCGTAATAATGGCGGCATACTATCAGTAG

TAGGTGTTTCCCTTTCTTCTTTAGCGACTTGATGCTCTTGATCTTCCAATA

TABLE 11-continued

Nucleotide sequences of Tet promoter-PAL1 construct, low-copy (SEQ ID NO: 28B)

CGCAACCTAAAGTAAAATGCCCCACAGCGCTGAGTGCATATAATGCATTCT

CTAGTGAAAAACCTTGTTGGCATAAAAAGGCTAATTGATTTTCGAGAGTTT

CATACTGTTTTTCTGTAGGCCGTGTACCTAAATGTACTTTTGCTCCATCGC

GATGACTTAGTAAAGCACATCTAAAACTTTTAGCGTTATTACGTAAAAAAT

CTTGCCAGCTTTCCCCTTCTAAAGGGCAAAAGTGAGTATGGTGCCTATCTA

ACATCTCAATGGCTAAGGCGTCGAGCAAAGCCCGCTTATTTTTTACATGCC

AATACAATGTAGGCTGCTCTACACCTAGCTTCTGGGCGAGTTTACGGGTTG

TTAAACCTTCGATTCCGACCTCATTAAGCAGCTCTAATGCGCTGTTAATCA

CTTTACTTTTATCTAATCTAGACATCATTAATTCCTAATTTTTGTTGACAC

TCTATCATTGATAGAGTTATTTT

TABLE 12

Nucleotide sequences of Tet promoter-PAL3 construct, low-copy (SEQ ID NO: 29B)

ACCACTCCCTATCAGTGATAGAGAAAAGTGAACTCTAGAAATAATTTTGTT

TAACTTTAAGAAGGAGATATACATATGAAAGCTAAAGATGTTCAGCCAACC

ATTATTATTAATAAAAATGGCCTTATCTCTTTGGAAGATATCTATGACATT

GCGATAAACAAAAAAAGTAGAAATATCAACGGAGATCACTGAACTTTTG

ACGCATGGTCGTGAAAAATTAGAGGAAAAATTAAATTCAGGAGAGGTTATA

TATGGAATCAATACAGGATTTGGAGGGAATGCCAATTTAGTTGTGCCATTT

GAGAAAATCGCAGAGCATCAGCAAAATCTGTTAACTTTTCTTTCTGCTGGT

ACTGGGGACTATATGTCCAAACCTTGTATTAAAGCGTCACAATTTACTATG

TTACTTTCTGTTTGCAAAGGTTGGTCTGCAACCAGACCAATTGTCGCTCAA

GCAATTGTTGATCATATTAATCATGACATTGTTCCTCTGGTTCCTCGCTAT

GGCTCAGTGGGTGCAAGCGGTGATTTAATTCCTTTATCTTATATTGCACGA

GCATTATGTGGTATCGGCAAAGTTTATTATATGGGCGCAGAAATTGACGCT

GCTGAAGCAATTAAACGTGCAGGGTTGACACCATTATCGTTAAAAGCCAAA

GAAGGTCTTGCTCTGATTAACGGCACCCGGGTAATGTCAGGAATCAGTGCA

ATCACCGTCATTAAACTGGAAAAACTATTTAAAGCCTCAATTTCTGCGATT

GCCCTTGCTGTTGAAGCATTACTTGCATCTCATGAACATTATGATGCCCGG

ATTCAACAAGTAAAAAATCATCCTGGTCAAAACGCGGTGGCAAGTGCATTG

CGTAATTTATTGGCAGGTTCAACGCAGGTTAATCTATTATCTGGGGTTAAA

GAACAAGCCAATAAAGCTTGTCGTCATCAAGAAATTACCCAACTAAATGAT

ACCTTACAGGAAGTTTATTCAATTCGCTGTGCACCACAAGTATTAGGTATA

GTGCCAGAATCTTTAGCTACCGCTCGGAAAATATTGGAACGGGAAGTTATC

TCAGCTAATGATAATCCATTGATAGATCCAGAAAATGGCGATGTTCTACAC

GGTGGAAATTTTATGGGGCAATATGTCGCCCGAACAATGGATGCATTAAAA

CTGGATATTGCTTTAATTGCCAATCATCTTCACGCCATTGTGGCTCTTATG

ATGGATAACCGTTTCTCTCGTGGATTACCTAATTCACTGAGTCCGACACCC

TABLE 12-continued

Nucleotide sequences of Tet promoter-PAL3 construct, low-copy (SEQ ID NO: 29B)

GGCATGTATCAAGGTTTTAAAGGCGTCCAACTTTCTCAAACCGCTTTAGTT

GCTGCAATTCGCCATGATTGTGCTGCATCAGGTATTCATACCCTCGCCACA

GAACAATACAATCAAGATATTGTCAGTTTAGGTCTGCATGCCGCTCAAGAT

GTTTTAGAGATGGAGCAGAAATTACGCAATATTGTTTCAATGACAATTCTG

GTAGTTTGTCAGGCCATTCATCTTCGCGGCAATATTAGTGAAATTGCGCCT

GAAACTGCTAAATTTTACCATGCAGTACGCGAAATCAGTTCTCCTTTGATC

ACTGATCGTGCGTTGGATGAAGATATAATCCGCATTGCGGATGCAATTATT

AATGATCAACTTCCTCTGCCAGAAATCATGCTGGAAGAATAAGCTTGGCGT

AATCATGGTCATAGCTGTTTCCTGTGTGAATTGTTATCCGCTCACAATTC

CACACAACATACGAGCCGGAAGCATAAAGTGTAAAGCCTGGGGTGCCTAAT

GAGTGAGCTAACTCACATTAATTGCGTTGCGCTCACTGCCCGCTTTCCAGT

CGGGAAACCTGTCGTGCCAGCTGCATTAATGAATCGGCCAACGCGCGGGA

GAGGCGGTTTGCGTATTGGGCGCTCTTCCGCTTCCTCGCTCACTGACTCGC

TGCGCTCGGTCGTTCGGCTGCGGCGAGCGGTATCAGCTCACTCAAAGGCGG

TAGTACGGGTTTTGCTGCCCGCAAACGGGCTGTTCTGGTGTTGCTAGTTTG

TTATCAGAATCGCAGATCCGGCTTCAGGTTTGCCGGCTGAAAGCGCTATTT

CTTCCAGAATTGCCATGATTTTTTCCCCACGGGAGGCGTCACTGGCTCCCG

TGTTGTCGGCAGCTTTGATTCGATAAGCAGCATCGCCTGTTTCAGGCTGTC

TATGTGTGACTGTTGAGCTGTAACAAGTTGTCTCAGGTGTTCAATTTCATG

TTCTAGTTGCTTTGTTTTACTGGTTTCACCTGTTCTATTAGGTGTTACATG

CTGTTCATCTGTTACATTGTCGATCTGTTCATGGTGAACAGCTTTAAATGC

ACCAAAAACTCGTAAAAGCTCTGATGTATCTATCTTTTTTACACCGTTTTC

ATCTGTGCATATGGACAGTTTTCCCTTTGATATCTAACGGTGAACAGTTGT

TCTACTTTTGTTTGTTAGTCTTGATGCTTCACTGATAGATACAAGAGCCAT

AAGAACCTCAGATCCTTCCGTATTTAGCCAGTATGTTCTCTAGTGTGGTTC

GTTGTTTTGCGTGAGCCATGAGAACGAACCATTGAGATCATGCTTACTTT

GCATGTCACTCAAAAATTTGCCTCAAAACTGGTGAGCTGAATTTTTGCAG

TTAAAGCATCGTGTAGTGTTTTTCTTAGTCCGTTACGTAGGTAGGAATCTG

ATGTAATGGTTGTTGGTATTTTGTCACCATTCATTTTTATCTGGTTGTTCT

CAAGTTCGGTTACGAGATCCATTTGTCTATCTAGTTCAACTTGGAAAATCA

ACGTATCAGTCGGGCGGCCTCGCTTATCAACCACCAATTTCATATTGCTGT

AAGTGTTTAAATCTTTACTTATTGGTTTCAAAACCCATTGGTTAAGCCTTT

TAAACTCATGGTAGTTATTTTCAAGCATTAACATGAACTTAAATTCATCAA

GGCTAATCTCTATATTTGCCTTGTGAGTTTTCTTTTGTGTTAGTTCTTTTA

ATAACCACTCATAAATCCTCATAGAGTATTTGTTTTCAAAAGACTTAACAT

GTTCCAGATTATATTTTATGAATTTTTTTAACTGGAAAAGATAAGGCAATA

TCTCTTCACTAAAAACTAATTCTAATTTTTCGCTTGAGAACTTGGCATAGT

TTGTCCACTGGAAAATCTCAAAGCCTTTAACCAAAGGATTCCTGATTTCCA

CAGTTCTCGTCATCAGCTCTCTGGTTGCTTTAGCTAATACACCCATAAGCAT

TTTCCCTACTGATGTTCATCATCTGAGCGTATTGGTTATAAGTGAACGATA

CCGTCCGTTCTTTCCTTGTAGGGTTTTCAATCGTGGGGTTGAGTAGTGCCA

CACAGCATAAAATTAGCTTGGTTTCATGCTCCGTTAAGTCATAGCGACTAA

TCGCTAGTTCATTTGCTTTGAAAACAACTAATTCAGACATACATCTCAATT

GGTCTAGGTGATTTTAATCACTATACCAATTGAGATGGGCTAGTCAATGAT

AATTACTAGTCCTTTTCCTTTGAGTTGTGGGTATCTGTAAATTCTGCTAGA

CCTTTGCTGGAAAACTTGTAAATTCTGCTAGACCCTCTGTAAATTCCGCTA

GACCTTTGTGTGTTTTTTTGTTTATATTCAAGTGGTTATAATTTATAGAA

TAAAGAAAGAATAAAAAAAGATAAAAAGAATAGATCCCAGCCCTGTGTATA

ACTCACTACTTTAGTCAGTTCCGCAGTATTACAAAAGGATGTCGCAAACGC

TGTTTGCTCCTCTACAAAACAGACCTTAAAACCCTAAAGGCTTAAGTAGCA

CCCTCGCAAGCTCGGGCAAATCGCTGAATATTCCTTTTGTCTCCGACCATC

AGGCACCTGAGTCGCTGTCTTTTTCGTGACATTCAGTTCGCTGCGCTCACG

GCTCTGGCAGTGAATGGGGGTAAATGGCACTACAGGCGCCTTTTATGGATT

CATGCAAGGAAACTACCCATAATACAAGAAAAGCCCGTCACGGGCTTCTCA

GGGCGTTTATGGCGGGTCTGCTATGTGGTGCTATCTGACTTTTTGCTGTT

CAGCAGTTCCTGCCCTCTGATTTTCCAGTCTGACCACTTCGGATTATCCCG

TGACAGGTCATTCAGACTGGCTAATGCACCCAGTAAGGCAGCGGTATCATC

AACAGGCTTACCCGTCTTACTGTCTTTTCTACGGGGTCTGACGCTCAGTGG

AACGAAAACTCACGTTAAGGGATTTTGGTCATGAGATTATCAAAAAGGATC

TTCACCTAGATCCTTTTAAATTAAAAATGAAGTTTTAAATCAATCTAAAGT

ATATATGAGTAAACTTGGTCTGACAGTTACCAATGCTTAATCAGTGAGGCA

CCTATCTCAGCGATCTGTCTATTTCGTTCATCCATAGTTGCCTGACTCCCC

GTCGTGTAGATAACTACGATACGGGAGGGCTTACCATCTGGCCCCAGTGCT

GCAATGATACCGCGAGACCCACGCTCACCGGCTCCAGATTTATCAGCAATA

AACCAGCCAGCCGGAAGGGCCGAGCGCAGAAGTGGTCCTGCAACTTTATCC

GCCTCCATCCAGTCTATTAATTGTTGCCGGGAAGCTAGAGTAAGTAGTTCG

CCAGTTAATAGTTTGCGCAACGTTGTTGCCATTGCTACAGGCATCGTGGTG

TCACGCTCGTCGTTTGGTATGGCTTCATTCAGCTCCGGTTCCCAACGATCA

AGGCGAGTTACATGATCCCCCATGTTGTGCAAAAAAGCGGTTAGCTCCTTC

GGTCCTCCGATCGTTGTCAGAAGTAAGTTGGCCGCAGTGTTATCACTCATG

GTTATGGCAGCACTGCATAATTCTCTTACTGTCATGCCATCCGTAAGATGC

TTTTCTGTGACTGGTGAGTACTCAACCAAGTCATTCTGAGAATAGTGTATG

CGGCGACCGAGTTGCTCTTGCCCGGCGTCAATACGGGATAATACCGCGCCA

CATAGCAGAACTTTAAAAGTGCTCATCATTGGAAAACGTTCTTCGGGGCGA

AAACTCTCAAGGATCTTACCGCTGTTGAGATCCAGTTCGATGTAACCCACT

CGTGCACCCAACTGATCTTCAGCATCTTTTACTTTCACCAGCGTTTCTGGG

TGAGCAAAAACAGGAAGGCAAAATGCCGCAAAAAAGGGAATAAGGGCGACA

TABLE 12-continued

Nucleotide sequences of Tet promoter-PAL3 construct, low-copy (SEQ ID NO: 29B)

CGGAAATGTTGAATACTCATACTCTTCCTTTTTCAATATTATTGAAGCATT
TATCAGGGTTATTGTCTCATGAGCGGATACATATTTGAATGTATTTAGAAA
AATAAACAAATAGGGGTTCCGCGCACATTTCCCCGAAAAGTGCCACCTGAC
GTCTAAGAAACCATTATTATCATGACATTAACCTATAAAAATAGGCGTATC
ACGAGGCCCTTTCGTCTCGCGCGTTTCGGTGATGACGGTGAAAACCTCTGA
CACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGGGC
TGGCTTAACTATGCGGCATCAGAGCAGATTGTACTGAGAGTGCACCATATG
CGGTGTGAAATACCGCACAGATGCGTAAGGAGAAAATACCGCATCAGGCGC
CATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTA
AGTTGGGTAACGCCAGGGTTTTCCCAGTCACGACGTTGTAAAACGACGGCC
AGTGAATTCGTTAAGACCCACTTTCACATTTAAGTTGTTTTTCTAATCCGC
ATATGATCAATTCAAGGCCGAATAAGAAGGCTGGCTCTGCACCTTGGTGAT
CAAATAATTCGATAGCTTGTCGTAATAATGGCGGCATACTATCAGTAGTAG
GTGTTTCCCTTTCTTCTTTAGCGACTTGATGCTCTTGATCTTCCAATACGC
AACCTAAAGTAAAATGCCCCACAGCGCTGAGTGCATATAATGCATTCTCTA
GTGAAAAACCTTGTTGGCATAAAAAGGCTAATTGATTTTCGAGAGTTTCAT
ACTGTTTTTCTGTAGGCCGTGTACCTAAATGTACTTTTGCTCCATCGCGAT
GACTTAGTAAAGCACATCTAAAACTTTTAGCGTTATTACGTAAAAAATCTT
GCCAGCTTTCCCCTTCTAAAGGGCAAAAGTGAGTATGGTGCCTATCTAACA
TCTCAATGGCTAAGGCGTCGAGCAAAGCCCGCTTATTTTTTACATGCCAAT
ACAATGTAGGCTGCTCTACACCTAGCTTCTGGGCGAGTTTACGGGTTGTTA
AACCTTCGATTCCGACCTCATTAAGCAGCTCTAATGCGCTGTTAATCACTT
TACTTTTATCTAATCTAGACATCATTAATTCCTAATTTTTGTTGACACTCT
ATCATTGATAGAGTTATTTT

TABLE 13

Nucleotide sequences of TetR-PheP construct, low-copy (SEQ ID NO: 30B)

ccagtgaattcg<u>ttaagacccactttcacatttaagttgttttttctaatc</u>
<u>cgcatatgatcaattcaaggccgaataagaaggctggctctgcaccttgg</u>
<u>tgatcaaataattcgatagcttgtcgtaataatggcggcatactatcagt</u>
<u>agtaggtgtttccctttcttctttagcgacttgatgctcttgatcttcca</u>
<u>atacgcaacctaaagtaaaatgccccacagcgctgagtgcatataatgca</u>

TABLE 13-continued

Nucleotide sequences of TetR-PheP construct, low-copy (SEQ ID NO: 30B)

<u>ttctctagtgaaaaaccttgttggcataaaaaggctaattgattttcgag</u>
<u>agtttcatactgtttttctgtaggccgtgtacctaaatgtacttttgctc</u>
<u>catcgcgatgacttagtaaagcacatctaaaacttttagcgttattacgt</u>
<u>aaaaaatcttgccagctttccccttctaaagggcaaaagtgagtatggtg</u>
<u>cctatctaacatctcaatggctaaggcgtcgagcaaagcccgcttatttt</u>
<u>ttacatgccaatacaatgtaggctgctctacacctagcttctgggcgagt</u>
<u>ttacggggttgttaaaccttcgattccgacctcattaagcagctctaatgc</u>
<u>gctgttaatcactttacttttatctaatctagacat</u>cattaattcctaat
tttgttgacactctatcattgatagagttattttaccactccctatcagt
gatagagaaaagtgaactctagaaataattttgtttaactttaagaagga
gatatacat<u>ATGAAAAACGCGTCAACCGTATCGGAAGATACTGCGTCGAA</u>
<u>TCAAGAGCCGACGCTTCATCGCGGATTACATAACCGTCATATTCAACTGA</u>
<u>TTGCGTTGGGTGGCGCAATTGGTACTGGTCTGTTTCTTGGCATTGGCCCG</u>
<u>GCGATTCAGATGGCGGGTCCGGCTGTATTGCTGGGCTACGGCGTCGCCGG</u>
<u>GATCATCGCTTTCCTGATTATGCGCCAGCTTGGCGAAATGGTGGTTGAGG</u>
<u>AGCCGGTATCCGGTTCATTTGCCCACTTTGCCTATAAATACTGGGGACCG</u>
<u>TTTGCGGGCTTCCTCTCTGGCTGGAACTACTGGGTAATGTTCGTGCTGGT</u>
<u>GGGAATGGCAGAGCTGACCGCTGCGGGCATCTATATGCAGTACTGGTTCC</u>
<u>CGGATGTTCCAACGTGGATTTGGGCTGCCGCCTTCTTTATTATCATCAAC</u>
<u>GCCGTTAACCTGGTGAACGTGCGCTTATATGGCGAAACCGAGTTCTGGTT</u>
<u>TGCGTTGATTAAAGTGCTGGCAATCATCGGTATGATCGGCTTTGGCCTGT</u>
<u>GGCTGCTGTTTTCTGGTCACGGCGGCGAGAAAGCCAGTATCGACAACCTC</u>
<u>TGGCGCTACGGTGGTTTCTTCGCCACCGGCTGGAATGGGCTGATTTTGTC</u>
<u>GCTGGCGGTAATTATGTTCTCCTTCGGCGGTCTGGAGCTGATTGGGATTA</u>
<u>CTGCCGCTGAAGCGCGCGATCCGGAAAAAAGCATTCCAAAAGCGGTAAAT</u>
<u>CAGGTGGTGTATCGCATCCTGCTGTTTTACATCGGTTCACTGGTGGTTTT</u>
<u>ACTGGCGCTCTATCCGTGGGTGGAAGTGAAATCCAACAGTAGCCCGTTTG</u>
<u>TGATGATTTTCCATAATCTCGACAGCAACGTGGTAGCTTCTGCGCTGAAC</u>
<u>TTCGTCATTCTGGTAGCATCGCTGTCAGTGTATAACAGCGGGGTTTACTC</u>
<u>TAACAGCCGCATGCTGTTTGGCCTTTCTGTGCAGGGTAATGCGCCGAAGT</u>
<u>TTTTGACTCGCGTCAGCCGTCGCGGTGTGCCGATTAACTCGCTGATGCTT</u>
<u>TCCGGAGCGATCACTTCGCTGGTGGTGTTAATCAACTATCTGCTGCCGCA</u>
<u>AAAAGCGTTTGGTCTGCTGATGGCGCTGGTGGTAGCAACGCTGCTGTTGA</u>
<u>ACTGGATTATGATCTGTCTGGCGCATCTGCGTTTTCGTGCAGCGATGCGA</u>

TABLE 13-continued

Nucleotide sequences of TetR-PheP construct, low-copy (SEQ ID NO: 30B)

CGTCAGGGGCGTGAAACACAGTTTAAGGCGCTGCTCTATCCGTTCGGCAA

CTATCTCTGCATTGCCTTCCTCGGCATGATTTTGCTGCTGATGTGCACGA

TGGATGATATGCGCTTGTCAGCGATCCTGCTGCCGGTGTGGATTGTATTC

CTGTTTATGGCATTTAAAACGCTGCGTCGGAAATAA

In some embodiments, the genetically engineered bacteria contain gene sequence(s) comprising one or more sequence(s) of any of SEQ ID Nos: 21B-30B. In some embodiments, the genetically engineered bacteria contain gene sequence(s) comprising one or more sequence(s) having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID Nos: 21B-30B.

In any of the embodiments described herein, the genetically engineered bacteria comprising one or more genes encoding one or more PME(s) further comprise one or more endogenous bacteriophage genomes. In some embodiments, the bacteriophage has been mutated in one or more genes within the bacteriophage genome. Such mutations include deletions, insertions, substitutions and inversions and may be located in or encompass one or more bacteriophage genes.

In one embodiment, E. coli Nissle is used as a starting point, parental strain or "chassis" for the genetically engineered bacteria comprising one or more PME(s). In one embodiment, the bacteriophage which is modified is a phage which is endogenous to E. coli Nissle in its natural state.

In some embodiments, the genetically engineered bacteria comprise one or more E. coli. Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some of the preceding embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10215, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one embodiment, the genetically engineered bacteria comprise a complete or partial deletion of one or more ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Oxygen Consuming Enzymes

LAAD catalytic activity is dependent on oxygen, and therefore may not be active in anaerobic and/or low oxygen environments in the intestine, e.g., the colon. Oxygen is present in more proximal compartments of the GI tract.

The oxygen tension as measured in healthy mice is shown in Table 17A. He et al., Proc Natl Acad Sci USA. 1999 Apr. 13; 96(8):4586-91; "Noninvasive measurement of anatomic structure and intraluminal oxygenation in the gastrointestinal tract of living mice with spatial and spectral EPR imaging", the contents of which is herein incorporated by reference in its entirety. A marked oxygen gradient from the proximal to the distal GI tract. As noted by He, the observed oxygen gradient seen along the GI tract can be explained by a combination of processes. Without wishing to be bound by theory, food, when swallowed, is initially equilibrated with the oxygen tension of ambient room air. On passage to the stomach and later the small intestine, the oxygen levels may fall as oxygen diffuses across the mucosal membrane. A gradual process of equilibration with the capillary levels of oxygen (i.e., 5-10 torr; ref. 9) may occur. On passage to the colon, with its heavy bacterial colonization, further decreases in oxygenation occur. Finally, the lumen of the distal colon displays marked hypoxia, as expected, based on the abundance of anaerobic bacteria at this site.

TABLE 17A

Oxygen Tension in Gastrointestinal Tract Compartments

| Compartment | Oxygen Tension |
| --- | --- |
| Ambient Air | 159 Torr |
| stomach | ~60 torr |

TABLE 17A-continued

Oxygen Tension in Gastrointestinal Tract Compartments

| Compartment | Oxygen Tension |
| --- | --- |
| duodenum and first part of jejunum | (~30 torr); ~20% oxygen in ambient air |
| Ileum | (~10 torr); ~6% oxygen in ambient air |
| colon | (<2 torr) |

As shown in FIG. 25B, LAAD activity is retained in microaerobic conditions, albeit at lower levels than under aerobic conditions (FIG. 25A and FIG. 25B). LAAD therefore may be active in the more proximal areas of the intestine, such as stomach, duodenum, jejunum, and ileum. It is contemplated as part of this disclosure that LAAD expressed by the genetically engineered bacteria may advantageously be active in a different compartment than PAL, which may be expressed in the colon if under the control of an FNR promoter. In one embodiment, the genetically engineered bacteria express two enzymes, which have different oxygen requirements and/or are induced under different oxygen conditions, such that an PME is expressed and active throughout the entire gastrointestinal system. For example, the first enzyme, e.g., LAAD, which is dependent on the presence of oxygen, is expressed in one or more of stomach, duodenum and ileum under the control of a constitutive or inducible promoter (such as ParaBAD), and the second enzyme, e.g., PAL, is expressed in the colon under the control of an FNR promoter. In some embodiments, PAL is expressed under the conditions found in the small intestine, e.g. under the control of an FNR promoter, constitutive promoter, or a different inducible promoter described herein. In some embodiments, PAL and/or LAAD are pre-induced prior to in vivo administration, and are expressed and active in the proximal part of the intestine. In some embodiments, PAL and/or LAAD are pre-induced (aerobically or anaerobically, or with or without chemical and/or nutritional inducer, as described herein) prior to in vivo administration, and are expressed and active in the distal part of the intestine.

Several strategies can be employed to further increase LAAD activity under oxygen limiting conditions. For example, the activity of other enzymes that consume large amounts of oxygen can be reduced or extinguished. One such enzyme is NADH dehydrogenase. E. coli has two NADH dehydrogenases; nuo and ndh2, and is has been shown that knock out of both of these enzymes reduces oxygen consumption by 80%. In some embodiments, additional measures are taken to conserve limiting oxygen, i.e., to allow LAAD to function under lower exogenous oxygen conditions in the genetically engineered bacteria expressing LAAD. In some embodiments, the genetically engineered bacteria further comprise a mutation in one or more genes involved in oxygen consumption. In some embodiments, one or both E. coli NADH dehydrogenases are knocked out. In some embodiments, the knocked out NADH dehydrogenase is nuo. In some embodiments, the knocked out NADH dehydrogenase is ndh2. In some embodiments nuo and ndh2 are knocked out. Other enzymes involved in E. coli oxygen metabolism may also be knocked out, including enzymes in the respiratory chain, such as cydB (a subunit of high affinity terminal oxidase), cydD (an enzyme required to make cytochrome D), and cyoABC (subunits of low affinity cytochrome oxidase). In some embodiments, the genetically engineered bacteria harbor a knock out mutation/deletion in one more genes selected from cydB, cydD, and cyoABC.

In one embodiment, the one or more PME encoded by the genetically engineered bacteria are expressed and show activity in the stomach. In one embodiment, the one or more PME encoded by the genetically engineered bacteria are expressed and show activity in the duodenum. In one embodiment, the one or more PME encoded by the genetically engineered bacteria are expressed and show activity in the jejunum. In one embodiment, the one or more PME encoded by the genetically engineered bacteria are expressed and show activity in the ileum. In one embodiment, the one or more PME encoded by the genetically engineered bacteria are expressed and show activity in the colon.

Phenylalanine Transport

In some embodiments wherein the bacterium comprises a gene encoding a PME, the bacterium may further comprise a gene encoding a phenylalanine transporter. Phenylalanine transporters may be expressed or modified in the genetically engineered bacteria of the invention in order to enhance phenylalanine transport into the cell.

PheP is a membrane transport protein that is capable of transporting phenylalanine into bacterial cells (see, e.g., Pi et al., 1991). In some embodiments, the native pheP gene in the genetically modified bacteria of the invention is not modified. In some embodiments, the genetically engineered bacteria of the invention comprise multiple copies of the native pheP gene. In some embodiments, the genetically engineered bacteria of the invention comprise multiple copies of a non-native pheP gene. In some embodiments, the genetically engineered bacteria of the invention comprise a pheP gene that is controlled by its native promoter, an inducible promoter, a promoter that is stronger than the native promoter, e.g., the GlnRS promoter or the P(Bla) promoter, or a constitutive promoter. In some embodiments, expression of the pheP gene is controlled by a different promoter than the promoter that controls expression of the gene encoding the phenylalanine-metabolizing enzyme and/or the transcriptional regulator. In some embodiments, expression of the pheP gene is controlled by the same promoter that controls expression of the phenylalanine-metabolizing enzyme and/or the transcriptional regulator. In some embodiments, the pheP gene and the phenylalanine-metabolizing enzyme and/or the transcriptional regulator are divergently transcribed from a promoter region. In some embodiments, expression of each of the genes encoding PheP, the phenylalanine-metabolizing enzyme, and the transcriptional regulator is controlled by a different promoter. In some embodiments, expression of the genes encoding PheP, the phenylalanine-metabolizing enzyme, and the transcriptional regulator is controlled by the same promoter.

In some embodiments, the native pheP gene in the genetically modified bacteria is not modified, and one or more additional copies of the native pheP gene are inserted into the genome under the control of the same inducible promoter that controls expression of PAL, e.g., the FNR promoter, or a different inducible promoter than the one that controls expression of PAL, or a constitutive promoter. In alternate embodiments, the native pheP gene is not modified, and a copy of a non-native pheP gene from a different bacterial species is inserted into the genome under the control of the same inducible promoter that controls expression of PAL, e.g., the FNR promoter, or a different inducible promoter than the one that controls expression of PAL, or a constitutive promoter.

In some embodiments, the native pheP gene in the genetically modified bacteria is not modified, and one or more additional copies of the native pheP gene are present in the bacteria on a plasmid and under the control of the same inducible promoter that controls expression of PAL, e.g., the FNR promoter, or a different inducible promoter than the one that controls expression of the PME, or a constitutive promoter. In alternate embodiments, the native pheP gene is not modified, and a copy of a non-native pheP gene from a different bacterial species is present in the bacteria on a plasmid and under the control of the same inducible promoter that controls expression of PAL, e.g., the FNR promoter, or a different inducible promoter than the one that controls expression of PAL, or a constitutive promoter.

In some embodiments, the native pheP gene is mutagenized, mutants exhibiting increased phenylalanine transport are selected, and the mutagenized pheP. The phenylalanine transporter modifications described herein may be present on a plasmid or chromosome.

In some embodiments, the genetically engineered bacterium is E. coli Nissle, and the native pheP gene in E. coli Nissle is not modified; one or more additional copies the native E. coli Nissle pheP genes are inserted into the E. coli Nissle genome under the control of the same inducible promoter that controls expression of PAL, e.g., the FNR promoter, or a different inducible promoter than the one that controls expression of PAL, or a constitutive promoter. In an alternate embodiment, the native pheP gene in E. coli Nissle is not modified, and a copy of a non-native pheP gene from a different bacterium is inserted into the E. coli Nissle genome under the control of the same inducible promoter that controls expression of PAL, e.g., the FNR promoter, or a different inducible promoter than the one that controls expression of PAL, or a constitutive promoter. In some embodiments, the genetically engineered bacterium is E. coli Nissle, and the native pheP gene in E. coli Nissle is not modified; one or more additional copies the native E. coli Nissle pheP genes are present in the bacterium on a plasmid and under the control of the same inducible promoter that controls expression of PAL, e.g., the FNR promoter, or a different inducible promoter than the one that controls expression of PAL, or a constitutive promoter. In an alternate embodiment, the native pheP gene in E. coli Nissle is not modified, and a copy of a non-native pheP gene from a different bacterium, are present in the bacterium on a plasmid and under the control of the same inducible promoter that controls expression of PAL, e.g., the FNR promoter, or a different inducible promoter than the one that controls expression of PAL, or a constitutive promoter.

In other embodiments, the gene(s) encoding the one or more Phe transporter(s) may be located on a plasmid or in the chromosome and the gene expression may be regulated by any of the promoters disclosed herein, which may be the same or different from the promoters regulating the PME gene(s).

It has been reported that Escherichia coli has five distinct transport systems (AroP, Mtr, PheP, TnaB, and TyrP) for the accumulation of aromatic amino acids. A general amino acid permease, encoded by the aroP gene, transports three aromatic amino acids, including phenylalanine, with high affinity, and is thought, together with PheP, responsible for the lion share of phenylalanine import. Additionally, a low level of accumulation of phenylalanine was observed in an aromatic amino acid transporter-deficient E. coli strain (AaroP ApheP Amtr Atna AtyrP), and was traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF (Koyanagi et al., and references therein; Identification of the LIV-I/LS System as the Third Phenylalanine Transporter in Escherichia coli K-12).

In some embodiments, the genetically engineered bacteria comprise an aroP gene. In some embodiments, the genetically engineered bacterium is E. coli Nissle, and the native aroP gene in E. coli Nissle is not modified; one or more additional copies of the native E. coli Nissle aroP genes are present in the bacterium on a plasmid or in the chromosome and under the control of the same inducible promoter that controls expression of the PME, e.g., the FNR promoter, or the araBAD promoter, a different inducible promoter than the one that controls expression of the PME, or a constitutive promoter. In an alternate embodiment, the native aroP gene in E. coli Nissle is not modified, and a copy of a non-native aroP gene from a different bacterium, are present in the bacterium on a plasmid or in the chromosome and under the control of the same inducible promoter that controls expression of the PME, e.g., the FNR promoter or the AraBAD promoter, or a different inducible promoter than the one that controls expression of the PME, or a constitutive promoter.

In other embodiments, the genetically engineered bacteria comprise AroP and PheP, under the control of the same or different inducible or constitutive promoters.

In some embodiments, the pheP gene is expressed on a chromosome. In some embodiments, expression from the chromosome may be useful for increasing stability of expression of pheP. In some embodiments, the pheP gene is integrated into the bacterial chromosome at one or more integration sites in the genetically engineered bacteria. In some embodiments, the pheP gene is inserted into the bacterial genome at one or more of the following insertion sites in E. coli Nissle: malE/K, insB/I, araC/BAD, lacZ, agaI/rsmI, thyA, and malP/T. Any suitable insertion site may be used (see, e.g., FIG. 66 of WO2017087580, the contents of which are herein incorporated by reference in their entirety). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacteria encode one or more Phe transporter(s) which are directly or indirectly pre-induced prior to in vivo administration, e.g., are expressed under the control of an inducible promoter that is responsive to specific molecules or metabolites in the provided in the culture of the bacterium in a flask, fermenter, or other culture vessel, during production of the strain prior to in vivo administration.

In other embodiments, the genetically engineered bacteria encode one or more Phe transporter(s) which are directly or indirectly induced in vivo administration, e.g., are expressed under the control of an inducible promoter that is responsive conditions or to specific molecules or metabolites in the exogenous in vivo environment, e.g., the gut. In some embodiments, the promoter is induced by gut specific molecules, or low oxygen conditions. In some embodiments, the bacterial strains are administered in combination with a chemical and/or nutritional inducer.

In some embodiments, the genetically engineered bacterium comprises multiple mechanisms of action and/or one or more auxotrophies. In certain embodiments, the bacteria are genetically engineered to comprise five copies of PAL under the control of an oxygen level-dependent promoter (e.g., $P_{fnrS}$-PAL3) inserted at different integration sites on the chromosome (e.g., malE/K, yicS/nepI, malP/T, agaI/rsmI, and cea), and one copy of a phenylalanine transporter gene under the control of an oxygen level-dependent promoter (e.g., $P_{fnrS}$-pheP) inserted at a different integration site on the chromosome (e.g., lacZ). In a more specific aspect, the bacteria are genetically engineered to further include a kanamycin resistance gene, and a thyA auxotrophy, in which the thyA gene is deleted and/or replaced with an unrelated gene.

In any of the embodiments described herein, the genetically engineered bacteria comprising one or more genes encoding one or more phenylalanine transporters further comprise one or more endogenous bacteriophages. In some embodiments, the bacteriophage(s) have been mutated in one or more genes within the bacteriophage genome. Such mutations include deletions, insertions, substitutions and inversions and are located in or encompass one or more bacteriophage genes.

In some embodiments, expression of the pheP gene is controlled by a different promoter than the promoter that controls expression of the gene encoding the phenylalanine-metabolizing enzyme and/or the transcriptional regulator. In some embodiments, expression of the pheP gene is controlled by the same promoter that controls expression of the phenylalanine-metabolizing enzyme and/or the transcriptional regulator. In some embodiments, the pheP gene and the phenylalanine-metabolizing enzyme and/or the transcriptional regulator are divergently transcribed from a promoter region. In some embodiments, expression of each of the genes encoding PheP, the phenylalanine-metabolizing enzyme, and the transcriptional regulator is controlled by a different promoter. In some embodiments, expression of the genes encoding PheP, the phenylalanine-metabolizing enzyme, and the transcriptional regulator is controlled by the same promoter.

In some embodiments, the native pheP gene in the genetically modified bacteria is not modified, and one or more additional copies of the native pheP gene are inserted into the genome under the control of the same inducible promoter that controls expression of PAL, e.g., the FNR promoter, or a different inducible promoter than the one that controls expression of PAL, or a constitutive promoter. In alternate embodiments, the native pheP gene is not modified, and a copy of a non-native pheP gene from a different bacterial species is inserted into the genome under the control of the same inducible promoter that controls expression of PAL, e.g., the FNR promoter, or a different inducible promoter than the one that controls expression of PAL, or a constitutive promoter.

In some embodiments, the native pheP gene in the genetically modified bacteria is not modified, and one or more additional copies of the native pheP gene are present in the bacteria on a plasmid and under the control of the same inducible promoter that controls expression of PAL, e.g., the FNR promoter, or a different inducible promoter than the one that controls expression of the PME, or a constitutive promoter. In alternate embodiments, the native pheP gene is not modified, and a copy of a non-native pheP gene from a different bacterial species is present in the bacteria on a plasmid and under the control of the same inducible promoter that controls expression of PAL, e.g., the FNR promoter, or a different inducible promoter than the one that controls expression of PAL, or a constitutive promoter.

In some embodiments, the native pheP gene is mutagenized, mutants exhibiting increased phenylalanine transport are selected, and the mutagenized pheP The phenylalanine transporter modifications described herein may be present on a plasmid or chromosome.

In some embodiments, the genetically engineered bacterium is *E. coli* Nissle, and the native pheP gene in *E. coli* Nissle is not modified; one or more additional copies the native *E. coli* Nissle pheP genes are inserted into the *E. coli* Nissle genome under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium is inserted into the *E. coli* Nissle genome under the control of the same inducible promoter that controls expression of PAL, e.g., the FNR promoter, or a different inducible promoter than the one that controls expression of PAL, or a constitutive promoter. In some embodiments, the genetically engineered bacterium is *E. coli* Nissle, and the native pheP gene in *E. coli* Nissle is not modified; one or more additional copies the native *E. coli* Nissle pheP genes are present in the bacterium on a plasmid and under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium, are present in the bacterium on a plasmid and under the control of the same inducible promoter that controls expression of PAL, e.g., the FNR promoter, or a different inducible promoter than the one that controls expression of PAL, or a constitutive promoter.

In other embodiments, the gene(s) encoding the one or more Phe transporter(s) may be located on a plasmid or in the chromosome and the gene expression may be regulated by any of the promoters disclosed herein, which may be the same or different from the promoters regulating the PME gene(s).

It has been reported that *Escherichia coli* has five distinct transport systems (AroP, Mtr, PheP, TnaB, and TyrP) for the accumulation of aromatic amino acids. A general amino acid permease, encoded by the aroP gene, transports three aromatic amino acids, including phenylalanine, with high affinity, and is thought, together with PheP, responsible for the lion share of phenylalanine import. Additionally, a low level of accumulation of phenylalanine was observed in an aromatic amino acid transporter-deficient *E. coli* strain (AaroP ApheP Amtr Atna AtyrP), and was traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF (Koyanagi et al., and references therein; Identification of the LIV-I/LS System as the Third Phenylalanine Transporter in *Escherichia coli* K-12).

In some embodiments, the genetically engineered bacteria comprise an aroP gene. In some embodiments, the genetically engineered bacterium is *E. coli* Nissle, and the native aroP gene in *E. coli* Nissle is not modified; one or more additional copies of the native *E. coli* Nissle aroP genes are present in the bacterium on a plasmid or in the chromosome and under the control of the same inducible promoter that controls expression of the PME, e.g., the FNR promoter, or the araBAD promoter, a different inducible promoter than the one that controls expression of the PME, or a constitutive promoter. In an alternate embodiment, the native aroP gene in *E. coli* Nissle is not modified, and a copy of a non-native aroP gene from a different bacterium, are present in the bacterium on a plasmid or in the chromosome and under the control of the same inducible promoter that controls expression of the PME, e.g., the FNR promoter or the AraBAD promoter, or a different inducible promoter than the one that controls expression of the PME, or a constitutive promoter.

In other embodiments, the genetically engineered bacteria comprise AroP and PheP, under the control of the same or different inducible or constitutive promoters.

In some embodiments, the pheP gene is expressed on a chromosome. In some embodiments, expression from the chromosome may be useful for increasing stability of expression of pheP. In some embodiments, the pheP gene is integrated into the bacterial chromosome at one or more integration sites in the genetically engineered bacteria. In some embodiments, the pheP gene is inserted into the bacterial genome at one or more of the following insertion sites in E. coli Nissle: malE/K, insB/I, araC/BAD, lacZ, agaI/rsmI, thyA, and malP/T. Any suitable insertion site may be used (see, e.g., FIG. 66 of WO2017087580, the contents of which are herein incorporated by reference in their entirety). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacteria encode one or more Phe transporter(s) which are directly or indirectly pre-induced prior to in vivo administration, e.g., are expressed under the control of an inducible promoter that is responsive to specific molecules or metabolites in the provided in the culture of the bacterium in a flask, fermenter, or other culture vessel, during production of the strain prior to in vivo administration.

In other embodiments, the genetically engineered bacteria encode one or more Phe transporter(s) which are directly or indirectly induced in vivo administration, e.g., are expressed under the control of an inducible promoter that is responsive conditions or to specific molecules or metabolites in the exogenous in vivo environment, e.g., the gut. In some embodiments, the promoter is induced by gut specific molecules, or low oxygen conditions. In some embodiments, the bacterial strains are administered in combination with a chemical and/or nutritional inducer.

In some embodiments, the genetically engineered bacterium comprises multiple mechanisms of action and/or one or more auxotrophies. In certain embodiments, the bacteria are genetically engineered to comprise five copies of PAL under the control of an oxygen level-dependent promoter (e.g., $P_{fnrS}$-PAL3) inserted at different integration sites on the chromosome (e.g., malE/K, yicS/nepI, malP/T, agaI/rsmI, and cea), and one copy of a phenylalanine transporter gene under the control of an oxygen level-dependent promoter (e.g., $P_{fnrS}$-pheP) inserted at a different integration site on the chromosome (e.g., lacZ). In a more specific aspect, the bacteria are genetically engineered to further include a kanamycin resistance gene, and a thyA auxotrophy, in which the thyA gene is deleted and/or replaced with an unrelated gene.

In any of the embodiments described herein, the genetically engineered bacteria comprising one or more genes encoding one or more phenylalanine transporters further comprise one or more endogenous bacteriophages. In some embodiments, the bacteriophage(s) have been mutated in one or more genes within the bacteriophage genome. Such mutations include deletions, insertions, substitutions and inversions and are located in or encompass one or more bacteriophage genes.

In one embodiment, E. coli Nissle is used as a starting point, parental strain or "chassis" for the genetically engineered bacteria. In one embodiment, the bacteriophage which is modified is a phage which is endogenous to E. coli Nissle in its natural state.

In some embodiments, the genetically engineered bacteria comprise one or more E. coli Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some embodiments, the mutation is a deletion. In some embodiments, the genetically engineered bacteria comprise one or more deletions Multiple Mechanisms of Action In some embodiments of the disclosure, modifications to the genome of EcN have been made to enhance phenylalanine degradation under the low oxygen conditions found in the gut while augmenting biologic containment through diaminopimelate auxotrophy. These genetically engineered bacteria further comprise one or more modifications to endogenous EcN phage 3.

Figure 13:
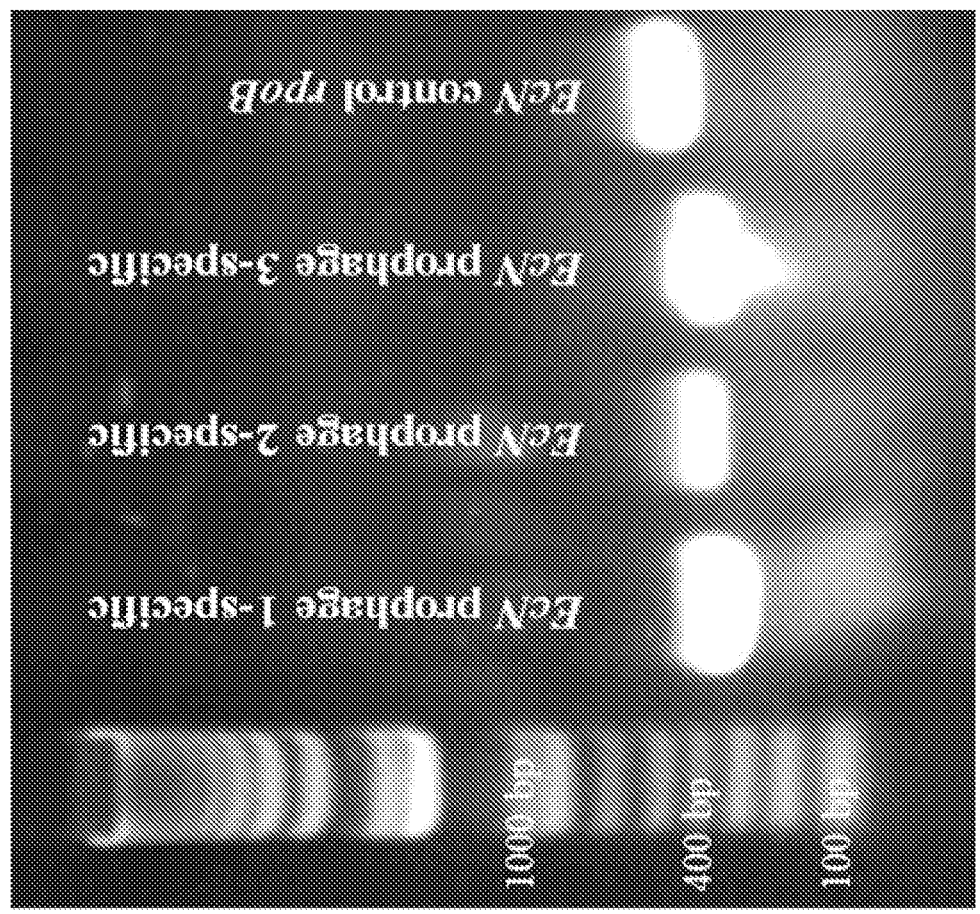
FIG. 13 depicts an DNA gel electrophoresis study verifying phage-specific PCR Primers. The performance of PCR primer pairs for Phages 1, 2 and 3 and rpoB against EcN genomic DNA is shown. Abbreviations: bp=base pair; EcN=*E. coli* Nissle; rpoB=β subunit of bacterial RNA polymerase.

In some embodiments, the bacteria are genetically engineered to include multiple mechanisms of action (MoAs), e.g., circuits producing multiple copies of the same product (e.g., to enhance copy number) or circuits performing multiple different functions. Examples of insertion sites include, but are not limited to, malE/K, yicS/nepI, insB/I, araC/BAD, lacZ, agaI/rsmI, thyA, malP/T, dapA, and cea, and others shown in FIG. 66 of WO2017087580, the contents of which are herein incorporated by reference in their entirety. For example, the genetically engineered bacteria may include four copies of a payload inserted at four different insertion sites, e.g., malE/K, insB/I, araC/BAD, and lacZ. The genetically engineered bacteria may also include four copies of the same or different payload inserted at four different insertion sites, e.g., malE/K, yicS/nepI, agaI/rsmI, and cea, and one copy a third same or different gene inserted at a different insertion site, e.g., lacZ (FIG. 13B of WO2017087580, the contents of which are herein incorporated by reference in their entirety). Alternatively, the genetically engineered bacteria may include three copies of a payload inserted at three different insertion sites, e.g., malE/K, insB/I, and lacZ.

In some embodiments, the genetically engineered bacteria are capable of expressing any one or more of the described circuits in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the described circuits are present on one or more plasmids (e.g., high copy or low copy) or are integrated into one or more sites in the bacterial chromosome. Also, in some embodiments, the genetically engineered bacteria are further capable of expressing any one or more of the described circuits and further comprise one or more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

In some embodiments, under conditions where the gene sequence(s) for producing the payload(s), are expressed, the bacterium produces an effector or metabolizes a substrate at levels at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold greater as compared to unmodified bacteria of the same subtype under the same conditions.

In any of these embodiments, the genetically engineered bacteria further contain one or more mutations or modifications to an endogenous phage genome. In some embodiments, the mutations are deletion, insertion, substitution or inversions within the phage genome. IN some embodiments, the mutations are deletions. In some embodiments, the deletions comprise one or more phage genes. In some embodiments, phage genes are partially deleted. In some embodiments, the mutations are insertions. In some embodiments, the insertion comprises an antibiotic cassette as described herein. IN some embodiments, one or more genes are substituted. In some embodiments, the substitution comprises an antibiotic cassette. In some embodiments, one or more phage genes are inverted. In some embodiments parts or one or more phage genes are inverted.

In one embodiment, the E. coli Nissle bacteria described herein comprise one or more modifications or mutations, e.g., deletion, insertion, substitution or inversion, within the E. coli Nissle Phage 3 genome. In some embodiments, the mutation is an insertion. In some embodiments, the insertion comprises an antibiotic cassette as described herein. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Induction of PMEs and/or Phe Transporters During Strain Culture

For induction and preinduction of PME's and/or Phe Transporters described herein, protocols and strategies were employed as described in PCT/WO2017/087580 A1, the entire contents of which are expressly incorporated herein by reference in its entirety.

In any of the embodiments described herein, the genetically engineered bacteria comprise one or more PMEs and/or one or more transporters which are induced under manufacturing conditions (e.g., aerobic, anaerobic, low-oxygen, or microaerobic) comprise one or more endogenous bacteriophage genomes. In some embodiments, the bacteriophage(s) have been mutated in one or more genes within the bacteriophage genome. Such mutations include deletions, insertions, substitutions and inversions and are located in or encompass one or more bacteriophage genes.

In some embodiments, the genetically engineered bacteria comprise one or more E. coli Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Measurement of Pre-Induction

In some embodiments, such culture conditions, in which expression of the PME(s) and or PheP are induced result in the reduction of phenylalanine in the culture by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions, or as compared to the baseline levels. In some embodiments, such culture conditions, in which expression of the PME(s) and or PheP are induced result in the production of transcinnamic acid (TCA) in the culture by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions, or as compared to the baseline levels.

In some embodiments, cinnamate accumulation in the bacterial cultures is measured by methods known in the art and described herein. Cinnamate production is directly correlated with phenylalanine degradation, and in some embodiments, cinnamate may be used as an indicator for strain activity during strain growth, production and manufacture. Measurement of a reduction in phenylalanine and or the production of TCA therefore may be used to measure and monitor, and fine tune the induction of a therapeutic strain prior to administration in vivo.

Phage 3

PAL inserted at four different insertion sites, e.g., malE/K, araC/BAD, and lacZ. The genetically engineered bacteria may also include four copies of PAL inserted at four different insertion sites, e.g., malE/K, yicS/nepI, agaI/rsmI, and cea, and one copy of a phenylalanine transporter gene inserted at a different insertion site, e.g., lacZ (FIG. 13B). Alternatively, the genetically engineered bacteria may include three copies of PAL inserted at three different insertion sites, e.g., malE/K, insB/I, and lacZ, and three copies of a phenylalanine transporter gene inserted at three different insertion sites, e.g., dapA, cea, and araC/BAD. In any of these embodiments, the genetically engineered bacteria further contain one or more mutations or modifications to EcN endogenous Phage 3.

In some embodiments, the genetically engineered bacteria comprise one or more gene sequence(s) encoding one or more of (1) PAL, PAH, and/or LAAD for degradation of phenylalanine, in wild type or in a mutated form (for increased stability or metabolic activity) (2) transporter PheP and/or AroP for uptake of phenylalanine, in wild type or in mutated form (for increased stability or metabolic activity) (3) PAL, PAH, LAAD, and/or PheP for secretion and extracellular phenylalanine degradation, (4) components of secretion machinery, as described herein (5) Auxotrophy, e.g., deltaThyA and/or deltadapA (6) antibiotic resistance, including but not limited to, kanamycin or chloramphenicol resistance (7) mutations/deletions in genes involved in oxygen metabolism, as described herein and (8) mutations/deletions in genes of the endogenous Nissle phenylalanine synthesis pathway (e.g., delta PheA for Phe auxotrophy) (9) one or more biosafety systems constructs and/or kill switches (10) one or more other regulatory factors, e.g., FNRS24Y (11) one or more modifications or mutations, e.g., deletion, insertion, substitution or inversion, within the E. coli Nissle Phage 3 genome.

In any of the embodiments described herein, the genetically engineered bacteria for the consumption of phenylalanine further comprise one or more endogenous bacteriophage genomes. In some embodiments, the bacteriophage(s) have been mutated in one or more genes within the bacteriophage genome. Such mutations include deletions, insertions, substitutions and inversions and are located in or encompass one or more bacteriophage genes.

In some embodiments, the genetically engineered bacteria comprise one or more E. coli Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, under conditions where the gene sequence(s) for producing the payload(s), e.g., the PME(s), Phe tranporter(s), and/or transcriptional regulator(s) are expressed, the genetically engineered bacteria of the disclosure both degrade phenylalanine and generate TCA at levels at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold greater as compared to unmodified bacteria of the same subtype under the same conditions.

In some embodiments, under conditions where the gene sequence(s) for producing the payload(s), e.g., the PME(s), Phe tranporter(s), and/or transcriptional regulator(s) are expressed, the genetically engineered bacteria of the disclosure both degrade phenylalanine and generate hippurate at levels at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold greater as compared to unmodified bacteria of the same subtype under the same conditions.

In some embodiments, the gene sequence(s) encoding the PME(s) and/or Phe transporters, e.g., PheP, and/or other regulatory proteins, e.g., FNRS24Y are expressed under the control of a constitutive promoter. In another embodiment, the gene sequence(s) encoding the one or more PME(s) and/or Phe transporters, e.g., PheP, and/or other regulatory proteins, e.g., FNRS24Y are expressed under the control of an inducible promoter. In some embodiments, the gene sequence(s) encoding the one or more PME(s) and/or Phe transporters, e.g., PheP, and/or other regulatory proteins, e.g., FNRS24Y, are expressed under the control of a promoter that is directly or indirectly induced by exogenous environmental conditions. In one embodiment, the gene sequence(s) encoding the one or more PME(s) and/or Phe transporters, e.g., PheP, and/or other regulatory proteins, e.g., FNRS24Y, are expressed under the control of a promoter that is directly or indirectly induced by low-oxygen or anaerobic conditions, wherein expression of the gene sequence(s) encoding the PME(s) and/or Phe transporters, e.g., PheP, and/or other regulatory proteins, e.g., FNRS24Y, are activated under low-oxygen or anaerobic environments, such as the environment of the mammalian gut. Exemplary inducible promoters described herein include oxygen level-dependent promoters (e.g., FNR-inducible promoter) arabinose, tetracycline, IPTG, rhamnose, and other chemical and/or nutritional inducers. In some embodiments, such inducible promoters described herein, are induced under in vitro culture conditions, as strains are prepared prior to in vivo administration, as described herein. Examples of inducible promoters include, but are not limited to, an FNR responsive promoter, a $P_{araBAD}$ promoter, and a $P_{TetR}$ promoter, Plac promoter, the rhaP BAD (rhamnose) promtoer, each of which are described in more detail herein. Inducible promoters are described in more detail infra.

The at least one gene encoding the one or more PME(s) and/or Phe transporters, e.g., PheP, and/or other regulatory proteins, e.g., FNRS24Y, may be present on a plasmid or chromosome in the bacterial cell. In one embodiment, the gene sequence(s) encoding the one or more PME(s) and/or Phe transporters, e.g., PheP, and/or other regulatory proteins, e.g., FNRS24Y, are located on a plasmid in the bacterial cell. In another embodiment, the gene sequence(s) encoding the one or more PME(s) and/or Phe transporters, e.g., PheP, and/or other regulatory proteins, e.g., FNRS24Y, are located in the chromosome of the bacterial cell. In yet another embodiment, a native copy of the gene sequence(s) encoding the one or more PME(s) and/or Phe transporters, e.g., PheP, and/or other regulatory proteins, e.g., FNRS24Y, are located in the chromosome of the bacterial cell, and one or more gene(s) encoding one or more PME(s) and/or Phe transporters, e.g., PheP, and/or other regulatory proteins, e.g., FNRS24Y, are located on a plasmid in the bacterial cell. In yet another embodiment, a native copy of the gene sequence(s) encoding the one or more PME(s) and/or Phe transporters, e.g., PheP, and/or other regulatory proteins, e.g., FNRS24Y, are located on a plasmid in the bacterial cell, and at least one gene encoding the at least one or more PME(s) and/or Phe transporters, e.g., PheP, and/or other regulatory proteins, e.g., FNRS24Y, from a different species of bacteria are located on a plasmid in the bacterial cell. In yet another embodiment, a native copy of the gene sequence(s) encoding the one or more PME(s) and/or Phe transporters, e.g., PheP, and/or other regulatory proteins, e.g., FNRS24Y, are located in the chromosome of the bacterial cell, and the one or more gene(s) encoding the one or more PME(s) and/or Phe transporters, e.g., PheP, and/or other regulatory proteins, e.g., FNRS24Y, from a different species of bacteria are located in the chromosome of the bacterial cell. In some embodiments, the gene sequence(s) encoding the one or more PME(s) and/or Phe transporters, e.g., PheP, and/or other regulatory proteins, e.g., FNRS24Y, are expressed on a low-copy plasmid. In some embodiments, the gene sequence(s) encoding the one or more PME(s) and/or Phe transporters, e.g., PheP, and/or other regulatory proteins, e.g., FNRS24Y, are expressed on a high-copy plasmid. In some embodiments, the high-copy plasmid may be useful for increasing expression of the at least one PME(s) and/or Phe transporters, e.g., PheP, and/or other regulatory proteins, e.g., FNRS24Y. In some embodiments, the genetically engineered bacteria described above further comprise one or more of the modifications, mutations, and/or deletions in endogenous genes described herein. In any of the embodiments described herein, the genetically engineered bacteria comprise one or more endogenous bacteriophage genomes. In some embodiments, the bacteriophage(s) have been mutated in one or more genes within the bacteriophage genome. Such mutations include deletions, insertions, substitutions and inversions and may be located in or encompass one or more bacteriophage genes.

In some embodiments, the genetically engineered bacteria comprise one or more E. coli Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one embodiment, the genetically engineered bacterial strain comprises three chromosomal insertions of FNR driven PAL3 (3× fnrS-PAL (malP/T, yicS/nepI, malE/K), e.g., SEQ ID NO: 38 of WO2017087580, the contents of which are herein incorporated by reference in their entirety) and two copies of FNR driven pheP (2× fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y The strain further comprises one copy of LAAD knocked into the arabinose operon with expression driven by the native Para promoter (Para::FNRS24Y, e.g., SEQ ID NO: 64 of WO2017087580, the contents of which are herein incorporated by reference in their entirety). In one embodiment, the genetically engineered bacterial strain is SYN-PKU707.

In one embodiment, the genetically engineered bacterial strain comprises three chromosomal insertions of FNR driven PAL3 (3× fnrS-PAL (malP/T, yicS/nepI, malE/K), e.g., SEQ ID NO: 38 of WO2017087580, the contents of which are herein incorporated by reference in their entirety) and two copies of FNR driven pheP (2× fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y knocked into the arabinose operon with expression driven by the native Para promoter (Para::FNRS24Y e.g., SEQ ID NO: 64 of WO2017087580, the contents of which are herein incorporated by reference in their entirety). The genome is further engineered to include a dapA auxotrophy, in which the dapA gene is deleted. In one embodiment, the genetically engineered bacterial strain is SYN-PKU712.

In one embodiment, the genetically engineered bacterial strain comprises a bacterial chromosome with three chromosomal insertions of FNR driven PAL3 (3× fnrS-PAL (malP/T, yicS/nepI, malE/K), e.g., SEQ ID NO: 38 of WO2017087580, the contents of which are herein incorporated by reference in their entirety) and two copies of FNR driven pheP (2× fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y knocked into the arabinose operon with expression driven by the native Para promoter and one copy of LAAD inserted at the same insertion site (Para::FNRS24Y-LAAD, e.g., SEQ ID NO: 73 of WO2017087580, the contents of which are herein incorporated by reference in their entirety), which is transcribed as a bicistronic message from the endogenous arabinose promoter. The genome is further engineered to include a dapA auxotrophy, in which the dapA gene is deleted. In one embodiment, the genetically engineered bacterial strain is SYN-PKU708.

In one embodiment, the genetically engineered bacterial strain comprises a bacterial chromosome with three chromosomal insertions of FNR driven PAL3 (3× fnrS-PAL (malP/T, yicS/nepI, malE/K), e.g., SEQ ID NO: 38 of WO2017087580, the contents of which are herein incorporated by reference in their entirety) and two copies of FNR driven pheP (2× fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y knocked into the arabinose operon with expression driven by the native Para promoter and one copy of LAAD inserted at the same insertion site (Para::FNRS24Y-LAAD, e.g., SEQ ID NO: 73 of WO2017087580, the contents of which are herein incorporated by reference in their entirety), which is transcribed as a bicistronic message from the endogenous arabinose promoter. In one embodiment, the genetically engineered bacterial strain is SYN-PKU711.

In one embodiment, the genetically engineered bacterial strain comprises a bacterial chromosome comprising three chromosomal insertions of FNR driven PAL3 (3× fnrS-PAL (malP/T, yicS/nepI, malE/K), e.g., SEQ ID NO: 38 of WO2017087580, the contents of which are herein incorporated by reference in their entirety) and two copies of FNR driven pheP (2× fnrS-pheP (lacZ, agaI/rsmI), e.g., SEQ ID NO: 62 of WO2017087580, the contents of which are herein incorporated by reference in their entirety). The strain further comprises one copy of LAAD knocked into the arabinose operon with expression driven by the native Para promoter (Para::LAAD, e.g., SEQ ID NO: 40 of WO2017087580, the contents of which are herein incorporated by reference in their entirety). The genome is further engineered to include a dapA auxotrophy, in which the dapA gene is deleted. In one embodiment, the genetically engineered bacterial strain is SYN-PKU709.

In one embodiment, the genetically engineered bacterial strain comprises a bacterial chromosome comprising three chromosomal insertions of FNR driven PAL3 (3× fnrS-PAL (malP/T, yicS/nepI, malE/K), e.g., SEQ ID NO: 38 of WO2017087580, the contents of which are herein incorporated by reference in their entirety) and two copies of FNR driven pheP (2× fnrS-pheP (lacZ, agaI/rsmI), e.g., SEQ ID NO: 62 of WO2017087580, the contents of which are herein incorporated by reference in their entirety). The strain further comprises one copy of the LAAD knocked into the arabinose operon with expression driven by the native Para promoter (Para::LAAD, e.g., SEQ ID NO: 40 of WO2017087580, the contents of which are herein incorporated by reference in their entirety). SYN-PKU710 further comprises two copies of IPTG inducible PAL3 (2×LacIPAL, exo/cea and rhtC/rhtB, e.g., SEQ ID NO: 74 of WO2017087580, the contents of which are herein incorporated by reference in their entirety), a dapA auxotrophy and is cured of all antibiotic resistances. In one embodiment, the genetically engineered bacterial strain is SYN-PKU710.

In any of these embodiments, the any of the genetically engineered described herein and depicted in FIG. 47 of WO2017087580, the contents of which are herein incorporated by reference in their entirety further comprise a bacteriophage genome described herein, which further comprises one or more mutations described herein. In any of these embodiments, the genetically engineered bacteria are derived from E. coli Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In one embodiment, the genetically engineered bacteria comprise two additional copies of PheP (in addition to the wild type gene). This provides redundancy, in case one of the PheP genes acquires a mutation. In one embodiment, the PheP genes are inserted at lacZ and agaI/rsml. In one embodiment, the two copies of PheP are under the control of the PfnrS promoter. In one embodiment, the genetically engineered bacteria comprise three copies of PAL3. In one embodiment, the genetically engineered bacteria comprise three copies of PAL3, inserted at malEK, malPT, yicS/nepI. In one embodiment, the expression of the three copies of PAL3 is under the control of the PfnrS promoter. In one embodiment, the genetically engineered bacteria comprise one or more copies of LAAD. In one embodiment, the genetically engineered bacteria comprise one copy of LAAD, inserted in the arabinose operon. In one embodiment, LAAD is under the control of the endogenous ParaBAD promoter. In one embodiment, the genetically engineered bacteria comprise an auxotrophy, e.g., deltaThyA. In one embodiment, the genetically engineered bacteria comprise an antibiotic resistance. In one embodiment, the genetically engineered bacteria comprise an antibiotic resistance and an auxotrophy, e.g., deltaThyA. In one embodiment, the genetically engineered bacteria do not comprise an auxotrophy, e.g., deltaThyA. In one embodiment, the genetically engineered bacteria do not comprise an antibiotic resistance. In one embodiment, the genetically engineered bacteria comprise neither an antibiotic resistance nor an auxotrophy, e.g., deltaThyA.

In one embodiment, the genetically engineered bacteria comprise three copies of PAL, e.g., PAL3, 2 copies of PheP (in addition to the endogenous PheP), and one copy of LAAD. In one embodiment, the genetically engineered bacteria comprise three copies of PAL, e.g., PAL3, 2 copies of PheP (in addition to the endogenous PheP), and one copy of LAAD, and an auxotrophy, e.g., delta ThyA. In one embodiment, the genetically engineered bacteria comprise three copies of PAL, 2 copies of PheP (in addition to the endogenous PheP), and one copy of LAAD, and an antibiotic resistance gene. In one embodiment, the genetically engineered bacteria comprise three copies of PAL, 2 copies of PheP (in addition to the endogenous PheP), and one copy of LAAD, and an antibiotic resistance gene and an auxotrophy, e.g., delta ThyA.

In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter). In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an antibiotic resistance. In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an auxotrophy, e.g., delta dapA. In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an antibiotic resistance and an auxotrophy, e.g., deltadapA.

In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsml sites), and one copy of LAAD (under the control of the endogenous ParaBAD promoter, and inserted in the endogenous arabinose operon). In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsml sites), and one copy of LAAD (under the control of the endogenous ParaBAD promoter, and inserted in the endogenous arabinose operon), and further comprise an antibiotic resistance. In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsml sites), and one copy of LAAD (under the control of the endogenous ParaBAD promoter, and inserted in the endogenous arabinose operon) and further comprise an auxotrophy, e.g., deltadapA. In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsml sites), and one copy of LAAD (under the control of the endogenous ParaBAD promoter, and inserted in the endogenous arabinose operon), and further comprise an antibiotic resistance and an auxotrophy, e.g., deltadapA.

In one embodiment, the genetically engineered bacteria are SYN-PKU705. In one embodiment, SYN-PKU705 further comprises an antibiotic resistance. In one embodiment, SYN-PKU705 further comprises an auxotrophy, e.g., deltaThyA. In one embodiment, SYN-PKU705 further comprises an antibiotic resistance and auxotrophy, e.g., deltaThyA. In any of these embodiments, the any of the genetically engineered described in the preceeding paragraphs further comprise a bacteriophage genome described herein, which further comprises one or more mutations described herein. In any of these embodiments, the genetically engineered bacteria are derived from E. coli Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1001.

In one embodiment, the genetically engineered bacterium comprises two chromosomal copies of pheP (lacZ::PfnrS-pheP, agaI/rsmt:PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO:98 of WO2017087580, the contents of which are herein incorporated by reference in their entirety). In one embodiment, the strain is SYN-PKU1002.

In one embodiment, the genetically engineered bacterium comprises two chromosomal copies of pheP (lacZ::PfnrS-pheP, agaI/rsmt:PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1003.

In one embodiment, the genetically engineered bacterium comprises two chromosomal copies of pheP (lacZ::PfnrS-pheP, agaI/rsmt:PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1004.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1005

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1006.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1007.

In one embodiment, the genetically engineered bacterium comprises two chromosomal copies of pheP (lacZ::PfnrS-pheP, agaI/rsmt:PfnrS-pheP) and a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1008.

In one embodiment, the genetically engineered bacterium a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1009.

In one embodiment, the genetically engineered bacterium a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1010.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1011.

In one embodiment, the genetically engineered bacterium a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-Kis antitoxin). The strain further comprises a plasmid shown in FIG. 61A, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1012.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1013.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1014.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1015.

In one embodiment, the genetically engineered bacterium comprises a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1016.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1017.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1018.

In one embodiment, the genetically engineered bacterium comprises two chromosomal copies of pheP (lacZ::PfnrS-pheP, agaI/rsmt:PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1019.

In one embodiment, the genetically engineered bacterium comprises two chromosomal copies of pheP (lacZ::PfnrS-pheP, agaI/rsmt:PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1020.

In one embodiment, the genetically engineered bacterium comprises two chromosomal copies of pheP (lacZ::PfnrS-pheP, agaI/rsmt:PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1021.

In one embodiment, the genetically engineered bacterium comprises two chromosomal copies of pheP (lacZ::PfnrS-pheP, agaI/rsmt:PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1022.

In one embodiment, the genetically engineered bacterium comprises two chromosomal copies of pheP (lacZ::PfnrS-pheP, agaI/rsmt:PfnrS-pheP) and a construct shown in FIG. 61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1023.

In one embodiment, the genetically engineered bacterium comprises two chromosomal copies of pheP (lacZ::PfnrS-pheP, agaI/rsmt:PfnrS-pheP) and a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1024.

In one embodiment, the genetically engineered bacterium a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1025.

In one embodiment, the genetically engineered bacterium a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1026.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1027.

In one embodiment, the genetically engineered bacterium a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1028.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA:: constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1029.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA:: constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1030.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1032.

In one embodiment, the genetically engineered bacterium comprises a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1032. In any of these embodiments, the any of the genetically engineered described herein comprising an AIPS system further comprise a bacteriophage genome described herein, which further comprises one or more mutations described herein.

In any of these embodiments, the genetically engineered bacteria are derived from E. coli Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In any of the preceeding embodiments, the bacteria described herein comprise one or more modifications or mutations, e.g., deletion, insertion, substitution or inversion, within the E. coli Nissle Phage 3 genome. In some embodiments, the mutation is an insertion. In some embodiments, the insertion comprises an antibiotic cassette as described herein. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one embodiment, the genetically engineered bacteria comprise one or more copies of PAL3, (e.g., under the control of a Pfnr promoter) and one or more copies of PAL1 (e.g. under the control of a Pfnr promoter). In one embodiment, the genetically engineered bacteria comprise one or more copies of PAL3, (e.g., under the control of a Pfnr promoter) and one or more copies of PAL1 (e.g. under the control of a Pfnr promoter); and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of LAAD (e.g., under the control of the ParaBAD promoter). In one embodiment, the genetically engineered bacteria comprise one or more copies of PAL3, (e.g., under the control of a Pfnr promoter) and one or more copies of LAAD (e.g., under the control of the ParaBAD promoter); and are derived from E. coli Nissle and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of PAH. In one embodiment, the genetically engineered bacteria comprise one or more copies of PAL3, (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAL1, (e.g., under the control of a Pfnr promoter) and one or more copies of LAAD (e.g., under the control of the ParaBAD promoter). In one embodiment, the genetically engineered bacteria comprise one or more copies of PAL1, (e.g., under the control of a Pfnr promoter) and one or more copies of LAAD (e.g., under the control of the ParaBAD promoter); and further comprises one or more copies of a phenylalanine transporter (e.g., PheP and/or AroP, e.g., under the control of a Pfnr promoter). In one embodiment, the genetically engineered bacteria comprise one or more copies of PAL1 (e.g., under the control of a Pfnr promoter) and one or more copies of PAH. In one embodiment, the genetically engineered bacteria comprise one or more copies of PAL1 (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAH and one or more copies of LAAD (e.g., under the control of the ParaBAD promoter). In one embodiment, the genetically engineered bacteria comprise one or more copies of PAH and one or more copies of LAAD (e.g., under the control of the ParaBAD promoter); and further comprises one or more copies of a phenylalanine transporter (e.g., PheP and/or AroP, e.g., under the control of a Pfnr promoter). PMEs and transporters may be integrated into any of the insertion sites described herein. In any of these embodiments, the any of the genetically engineered described in the preceding paragraph further comprise a bacteriophage genome described herein, which further comprises one or more mutations described herein. In any of these embodiments, the genetically engineered bacteria are derived from E. coli Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter); and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH. In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter); and further comprise one or more copies of a phenylalanine transporter (e.g., PheP and/or AroP, e.g., under the control of a Pfnr promoter). PMEs and/or transporters may be integrated into any of the insertion sites described herein. Alternatively, PMEs and/or transporters may be comprised on low or high copy plasmids. PMEs and/or transporters may be integrated into any of the insertion sites described herein in combination with PMEs and/or transporters that are comprised on low or high copy plasmids. In any of these embodiments, the any of the genetically engineered described in the preceding paragraph further comprise a bacteriophage genome described herein, which further comprises one or more mutations described herein. In any of these embodiments, the genetically engineered bacteria are derived from E. coli Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). PMEs and transporters may be integrated into any of the insertion sites described herein. Alternatively, PMEs and/or transporters may be comprised on low or high copy plasmids. In any of these embodiments, the any of the genetically engineered described in the preceding paragraph further comprise a bacteriophage genome described herein, which further comprises one or more mutations described herein. In any of these embodiments, the genetically engineered bacteria are derived from E. coli Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). PMEs and transporters may be integrated into any of the insertion sites described herein. Alternatively, located PMEs and/or transporters may be comprised on low or high copy plasmids. In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise two copies of PAL (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and one copy of LAAD (e.g., under the control of the ParaBAD promoter). In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In any of these embodiments, the genetically engineered bacteria further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In any of these embodiments, the bacteria described herein comprise one or more modifications or mutations, e.g., deletion, insertion, substitution or inversion, within the E. coli Nissle Phage 3 genome. In some embodiments, the mutation is an insertion. In some embodiments, the insertion comprises an antibiotic cassette as described herein. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:
  a) One or more additional copies of an endogenous Nissle gene encoding a high affinity phenylalanine transporter (PheP);
  b) One more copies of a gene encoding phenylalanine ammonia lyase (PAL) derived from *Photorhabdus*;
  c) One or more gene encoding L-amino acid deaminase (LAAD) derived from *Proteus mirabilis*;
  d) One or more deletion of endogenous genes to generate an auxotrophy, e.g., dapA or ThyA;
  e) Antibiotic resistance; and
  f) One or more modifications or mutations, e.g., deletion, insertion, substitution or inversion, within the E. coli Nissle Phage 3 genome In any of the preceding embodiments, the mutation in Phage 3 is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:
  a) One or more additional copies of an endogenous Nissle gene encoding a high affinity phenylalanine transporter (PheP);
  b) One more copies of a gene encoding phenylalanine ammonia lyase (PAL) derived from *Photorhabdus*;
  c) One or more gene encoding L-amino acid deaminase (LAAD) derived from *Proteus mirabilis*;
  d) One or more deletion of endogenous genes to generate an auxotrophy, e.g., dapA or ThyA; and
  e) One or more modifications or mutations, e.g., deletion, insertion, substitution or inversion, within the *E. coli* Nissle Phage 3 genome.

In any of the preceding embodiments, the mutation in Phage 3 is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise the following elements:
  a) One or more additional copies of an endogenous Nissle gene encoding a high affinity phenylalanine transporter (PheP);
  b) One more copies of a gene encoding phenylalanine ammonia lyase (PAL) derived from *Photorhabdus*;
  c) One or more gene encoding L-amino acid deaminase (LAAD) derived from *Proteus mirabilis*;
  d) One or more deletion of endogenous genes to generate an auxotrophy, e.g., dapA or ThyA; and
  e) One or more modifications or mutations, e.g., deletion, insertion, substitution or inversion, within the *E. coli* Nissle Phage 3 genome.

In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:
 a) One or more additional copies of an endogenous Nissle gene encoding a high affinity phenylalanine transporter (PheP) under the regulatory control of an promoter inducible under exogenous environmental conditions;
 b) One more copies of a gene encoding phenylalanine ammonia lyase (PAL) derived from *Photorhabdus luminescens* inducible under exogenous environmental conditions;
 c) One or more copies of the gene encoding PAL under the regulatory control of a promoter inducible by a chemical or nutritional inducer;
 d) One or more gene encoding L-amino acid deaminase (LAAD) derived from *Proteus mirabilis* under the regulatory control of a promoter inducible by a chemical inducer, which is the same or different from the chemical inducer that induces expression of PAL;
 e) One or more deletion of endogenous genes to generate an auxotrophy, e.g., dapA or ThyA; and
 f) One or more modifications or mutations, e.g., deletion, insertion, substitution or inversion, within the *E. coli* Nissle Phage 3 genome In any of the preceding embodiments, the mutation in Phage 3 is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise the following elements:
 a) One or more additional copies of an endogenous Nissle gene encoding a high affinity phenylalanine transporter (PheP) under the regulatory control of an promoter inducible under exogenous environmental conditions;
 b) One more copies of a gene encoding phenylalanine ammonia lyase (PAL) derived from *Photorhabdus luminescens* inducible under exogenous environmental conditions;
 c) One or more copies of the gene encoding PAL under the regulatory control of a promoter inducible by a chemical or nutritional inducer;
 d) One or more gene encoding L-amino acid deaminase (LAAD) derived from *Proteus mirabilis* under the regulatory control of a promoter inducible by a chemical inducer, which is the same or different from the chemical inducer that induces expression of PAL;
 e) One or more deletion of endogenous genes to generate an auxotrophy, e.g., dapA or ThyA; and
 f) One or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise the following elements:
a) Two additional copies of an endogenous Nissle gene encoding a high affinity phenylalanine transporter (PheP) under the regulatory control of an promoter inducible under exogenous environmental conditions;
b) Three copies of a gene encoding phenylalanine ammonia lyase (PAL) derived from *Photorhabdus luminescens* inducible under exogenous environmental conditions;
c) Two copies of the gene encoding PAL under the regulatory control of a promoter inducible by a chemical or nutritional inducer;
d) One copy of the gene encoding L-amino acid deaminase (LAAD) derived from *Proteus mirabilis* under the regulatory control of a promoter inducible by a chemical inducer, which is the same or different from the chemical inducer that induces expression of PAL;
e) One or more deletion of endogenous dapA to generate an auxotrophy; and f) one or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:
a) One or more additional copies of an endogenous Nissle gene encoding a high affinity phenylalanine transporter (PheP) under the regulatory control of an anaerobic-inducible promoter (PfnrS) and the anaerobic-responsive transcriptional activator FNR;

b) One more copies of a gene encoding phenylalanine ammonia lyase (PAL) derived from *Photorhabdus luminescens* under the regulatory control of PfnrS and FNR;
c) One or more copies of the gene encoding PAL under the regulatory control of a synthetic promoter (Ptac) and the lactose-responsive transcriptional repressor LacI;
d) One or more gene encoding L-amino acid deaminase (LAAD) derived from *Proteus mirabilis* under the regulatory control of the arabinose-inducible promoter (PBAD) and the arabinose-responsive transcriptional activator AraC;
e) One or more deletion of endogenous genes to generate an auxotrophy, e.g., dapA or ThyA; and
f) one or more modifications or mutations, e.g., deletion, insertion, substitution or inversion, within the *E. coli* Nissle Phage 3 genome.

In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacterium comprises the following elements:
a) One or more additional copies of an endogenous Nissle gene encoding a high affinity phenylalanine transporter (PheP) under the regulatory control of an anaerobic-inducible promoter (PfnrS) and the anaerobic-responsive transcriptional activator FNR;
b) One more copies of a gene encoding phenylalanine ammonia lyase (PAL) derived from *Photorhabdus luminescens* under the regulatory control of PfnrS and FNR;
c) One or more copies of the gene encoding PAL under the regulatory control of a synthetic promoter (Ptac) and the lactose-responsive transcriptional repressor LacI;
d) One or more gene encoding L-amino acid deaminase (LAAD) derived from *Proteus mirabilis* under the regulatory control of the arabinose-inducible promoter (PBAD) and the arabinose-responsive transcriptional activator AraC;
e) One or more deletion of endogenous genes to generate an auxotrophy, e.g., dapA or ThyA; and
f) one or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one specific embodiment, the genetically engineered bacteria comprise each of the following elements:
- a) two additional copies of the endogenous Nissle gene encoding the high affinity phenylalanine transporter (PheP) under the regulatory control of an anaerobic-inducible promoter (PfnrS) and the anaerobic-responsive transcriptional activator FNR, inserted into the chromosome at the lacZ and the agaI/rsml loci;
- b) three copies of a gene encoding phenylalanine ammonia lyase (PAL) derived from *Photorhabdus luminescens* under the regulatory control of PfnrS and FNR, inserted into the chromosome at the malEK, malPT, and yicS/nepI loci;
- c) two additional copies of the gene encoding PAL under the regulatory control of a synthetic promoter (Plac) and the lactose-responsive transcriptional repressor LacI, inserted at the exo/cea and the rhtC/rhtB loci;
- d)
- e) one copy of a gene encoding L-amino acid deaminase (LAAD) derived from *Proteus mirabilis* under the regulatory control of the arabinose-inducible promoter (PBAD) and the arabinose-responsive transcriptional activator AraC, with LAAD under the native arabinose promoter;
- f) a deletion of the dapA gene that encodes 4-hydroxy-tetrahydropicolinate synthase to create a diaminopimelate auxotroph; andOne or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one specific embodiment, the genetically engineered bacteria comprise each of the following elements:
- a) Two additional copies of the endogenous Nissle gene encoding the high affinity phenylalanine transporter (PheP) under the regulatory control of an anaerobic-inducible promoter (PfnrS) and the anaerobic-responsive transcriptional activator FNR, inserted into the chromosome at the lacZ and the agalksml loci;
- b) Three copies of a gene encoding phenylalanine ammonia lyase (PAL) derived from *Photorhabdus luminescens* under the regulatory control of PfnrS and FNR, inserted into the chromosome at the malEK, malPT, and yicS/nepI loci;
- c) Two additional copies of the gene encoding PAL under the regulatory control of a synthetic promoter (Plac) and the lactose-responsive transcriptional repressor LacI, inserted at the exo/cea and the rhtC/rhtB loci;
- d) One copy of a gene encoding L-amino acid deaminase (LAAD) derived from *Proteus mirabilis* under the regulatory control of the arabinose-inducible promoter (PBAD) and the arabinose-responsive transcriptional activator AraC, with LAAD under the native arabinose promoter;
- e) A deletion of the dapA gene that encodes 4-hydroxy-tetrahydropicolinate synthase to create a diaminopimelate auxotroph; and
- f) A deletion of a region within the *E. coli* Nissle Phage 3 genome, wherein deleted region comprises ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, and partially ECOLIN_10165.

In one specific embodiment, the genetically engineered bacteria comprise each of the following elements:
  a) two additional copies of the endogenous Nissle gene encoding the high affinity phenylalanine transporter (PheP) under the regulatory control of an anaerobic-inducible promoter (PfnrS) and the anaerobic-responsive transcriptional activator FNR, inserted into the chromosome at the lacZ and the agaI/rsml loci;
  b) three copies of a gene encoding phenylalanine ammonia lyase (PAL) derived from Photorhabdus luminescens under the regulatory control of PfnrS and FNR, inserted into the chromosome at the malEK, malPT, and yicS/nepI loci;
  c) two additional copies of the gene encoding PAL under the regulatory control of a synthetic promoter (Plac) and the lactose-responsive transcriptional repressor LacI, inserted at the exo/cea and the rhtC/rhtB loci;
  d) one copy of a gene encoding L-amino acid deaminase (LAAD) derived from Proteus mirabilis under the regulatory control of the arabinose-inducible promoter (PBAD) and the arabinose-responsive transcriptional activator AraC, with LAAD under the native arabinose promoter;
  e) a deletion of the dapA gene that encodes 4-hydroxy-tetrahydropicolinate synthase to create a diaminopimelate auxotroph; and
  g) a deletion of a region within the E. coli Nissle Phage 3 genome, wherein deleted region consists of SEQ ID NO: 130.

In one embodiment, the genetically engineered bacterium is E. coli Nissle. In some embodiments, the strain comprises the same modifications as SYN-PKU-2002. In some embodiments, the strain is SYN-PKU-2002.

Table 14 contains non-limiting examples of the genetically engineered bacteria of the disclosure. In certain embodiments, the genetically engineered bacteria of Table 14 further contain a PME for secretion.

TABLE 14

Non-limiting Examples of Embodiments of the Disclosure

| Strain Name | Genotype |
| --- | --- |
| SYN-PKU101 | Low copy pSC101-Ptet::PAL1, ampicillin resistant |
| SYN-PKU102 | High copy pColE1-Ptet::PAL1, ampicillin resistant, |
| SYN-PKU201 | Low copy pSC101-Ptet::PAL3, ampicillin resistant |
| SYN-PKU202 | High copy pColE1-Ptet::PAL3, ampicillin resistant, |
| SYN-PKU203 | lacZ::Ptet-pheP::cam |
| SYN-PKU401 | Low copy pSC101-Ptet::PAL1, ampicillin resistant, chromosomal lacZ::Ptet-pheP::cam |
| SYN-PKU402 | High copy pColE1-Ptet::PAL1, ampicillin resistant, chromosomal lacZ::Ptet-pheP::cam |
| SYN-PKU302 | Low Copy pSC101-Ptet::PAL3, ampicillin resistant; chromosomal lacZ::Ptet-pheP::cam |
| SYN-PKU303 | High copy pColE1-Ptet::PAL3, ampicillin resistant, chromosomal lacZ::Ptet-pheP::cam |
| SYN-PKU304 | Low Copy pSC101-PfnrS-PAL3, ampicillin resistant; chromosomal lacZ::PfnrS-pheP::cam |
| SYN-PKU305 | Low Copy pSC101-PfnrS-PAL3, kanamycin resistant; chromosomal lacZ::PfnrS-pheP::cam |
| SYN-PKU306 | Low Copy pSC101-PfnrS-PAL3, kanamycin resistant; thyA |
| SYN-PKU307 | Low Copy pSC101-PfnrS-PAL3, ampicillin resistant; |
| SYN-PKU308 | Low Copy pSC101-PfnrS-PAL3, kanamycin resistant; |
| SYN-PKU401 | High Copy pUC57-Ptet-LAAD; kanamycin resistant |
| SYN-PKU501 | malPT:: PfnrS-PAL3::kan |
| SYN-PKU502 | malPT:: PfnrS-PAL3::kan; bicistronic lacZ:: PfnrS-PAL3-pheP::cam |
| SYN-PKU503 | malEK::PfnrS-PAL3::cam |
| SYN-PKU504 | agaI/rsmI::PfnrS-PAL3 |
| SYN-PKU505 | cea::PfnrS-PAL3 |
| SYN-PKU506 | malEK::PfnrS-PAL3; agaI/rsmI::PfnrS-PAL3; cea::PfnrS-PAL3 |
| SYN-PKU507 | malEK::PfnrS-PAL3; agaI/rsmI::PfnrS-PAL3; cea::PfnrS-PAL3; lacZ::PfnrS-pheP::cam |
| SYN-PKU508 | malEK::PfnrS-PAL3; pheA auxotroph |
| SYN-PKU509 | malEK::PfnrS-PAL3; agaI/rsmI::PfnrS-PAL3; cea::PfnrS-PAL3; lacZ::PfnrS-pheP::cam |
| SYN-PKU601 | malPT::PfnrS-INT5::kan, rrnBUP -[PAL3]; lacZ::PfnrS-pheP::cam (recombinase based strain) |
| SYN-PKU510 | malEK::PfnrS-PAL3; agaI/rsmI::PfnrS-PAL3; cea::PfnrS-PAL3; |
| SYN-PKU511 | malEK:: PfnrS-PAL3; agaI/rsmI::PfnrS-PAL3; cea::PfnrS-PAL3; yicS/nepI::PfnrS-PAL3::kan; malPT::PfnrS-PAL3; lacZ::PfnrS-pheP; ΔthyA |
| SYN-PKU204 | lacZ::PfnrS-pheP::cam |
| SYN-PKU512 | malEK::PfnrS-PAL3; agaI/rsmI::PfnrS-PAL3; cea::PfnrS-PAL3; malPT::PfnrS-PAL3; lacZ::PfnrS-pheP::cam; ΔthyA |
| SYN-PKU513 | malEK:: PfnrS-PAL3; agaI/rsmI::PfnrS-PAL3; cea::PfnrS-PAL3; lacZ::PfnrS-pheP; ΔthyA |
| SYN-PKU514 | malEK:: PfnrS-PAL3; agaI/rsmI:PfnrS-PAL3; cea::PfnrS-PAL3; malPT::PfnrS-PAL3; ΔthyA |
| SYN-PKU515 | malEK:: PfnrS-PAL3; agaI/rsmI::PfnrS-PAL3; cea::PfnrS-PAL3; ΔthyA |
| SYN-PKU516 | agaI/rsmI::PfnrS-PAL3::kan |
| SYN-PKU517 | malEK:: PfnrS-PAL3::cam; malPT::PfnrS-PAL3::kan; lacZ::PfnrS-pheP; ΔthyA |
| SYN-PKU518 | malEK-PfnrS-PAL3::cam; PfnrS::pheP::kan |
| SYN-PKU519 | ParaBC-PAL3::cam; PfnrS-pheP::kan |
| SYN-PKU520 | agaI/rsmI:PfnrS-PAL3::kan; PfnrS-PheP::cam |
| SYN-PKU801 | ΔargR; thyA::cam |
| SYN-PKU701 | ParaBC-LAAD::cam; malEK-PfnrS-PAL3; malPT::PfnrS-PAL3::kan; PfnrS-pheP |
| SYN-PKU521 | yicS/nepI::PfnrS-PAL3::kan; lacZ::PfnrS-pheP::cam |
| SYN-PKU522 | cea::PfnrS-PAL3::kan; lacZ::PfnrS-pheP::cam |
| SYN-PKU523 | malPT::PfnrS-PAL3::kan; lacZ::PfnrS-pheP::cam |
| SYN-PKU524 | malEK:: PfnrS-PAL3; malPT::PfnrS-PAL3; lacZ::PfnrS-pheP |
| SYN-PKU702 | malEK:: PfnrS-PAL3; lacZ::PfnrS-pheP; Para::LAAD |
| SYN-PKU703 | malEK:: PfnrS-PAL3; malPT::PfnrS-PAL3; lacZ::PfnrS-pheP; agaI/rsmI:PfnrS::pheP; Para::LAAD |
| SYN-PKU704 | malEK:: PfnrS-PAL3; malPT::PfnrS-PAL3; yicS/nepI::PfnrS-PAL3; lacZ::PfnrS-pheP; Para::LAAD |
| SYN-PKU705 | malEK:: PfnrS-PAL3; malPT::PfnrS-PAL3; yicS/nepI::PfnrS-PAL3::kan; lacZ::PfnrS-pheP; agaI/rsmI:PfnrS::pheP Para::LAAD |
| SYN-PKU602 | malEK:: PT7::PAL3; Para::INT5::cam (recombinase); lacZ::PfnrS-pheP; malPT::Pconstitutive::T7 polymerase (unflipped); |
| SYN-PKU901 | Nissle with streptomycin resistance |
| SYN001 | WT Nissle |
| SYN-902 | WT nissle that has the pKD46 plasmid |
| SYN-903 | WT nissle that has the pKD46 plasmid and with phage knockout |
| SYN-PKU713 | LacZ::PfnrS-PAL3::pheP |
| SYN-PKU706 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD, ΔdapA::cm |
| SYN-PKU707 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y::cm |
| SYN-PKU708 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y-LAAD; ΔdapA |
| SYN-PKU-709 | malEK:: PfnrS-PAL3; malPT::PfnrS-PAL3; yicS/nepI:: PfnrS-PAL3; lacZ::PfnrS-pheP, agaI/rsmI::PfnrS-pheP; Para-LAAD; ΔdapA |
| SYN-PKU-710 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB::LacIPAL3; ΔdapA |

TABLE 14-continued

Non-limiting Examples of Embodiments of the Disclosure

| Strain Name | Genotype |
|---|---|
| SYN-PKU711 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y-LAAD; |
| SYN-PKU-712 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y; ΔDapA |
| SYN-PKU-713 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3:cm; rhtC/rhtB::LacIPAL3:kn; ΔdapA (chloramphenicol and kanamycin resistance) |
| SYN-PKU-2002 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB::LacIPAL3; ΔdapA ; phage free (deletion of SEQ ID NO: 130) |
| SYN-PKU-2001 | Parental strain of SYN2002 with insertion of phage3 KO frag::cm and cured of pKD46 (not cured of chloramphenicol resistance); malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB::LacIPAL3; ΔdapA) with insertion of phage3 KO frag::cm and cured of pKD46 (not cured of chloramphenicol resistance) |
| SYN3282 | E. coli Nissle 1917, lacZ::P$_{fnrS}$-PheP, ΔlacZ, malEK::P$_{fnrS}$-PAL, araBC::P$_{BAD}$-LAAD, malPT::P$_{fnrS}$-PAL, yicS/nepI::P$_{fnrS}$-PAL, agaI/rsmI::P$_{fnrS}$-PheP, exo/cea::P$_{tac}$-PAL, rhtBC::P$_{tac}$-PAL, ΔΦ, chloramphenicol resistant<br>Note: DAP prototrophic strain genetically engineered to encode Phe-degrading activity |
| SYN766 | E. coli Nissle 1917, ΔdapA, chloramphenicol resistant. |

In any of the embodiments, described herein, in which the genetically engineered organism, e.g., engineered bacteria or engineered OV, produces a protein, polypeptide, peptide, or other anti-cancer, gut barrier enhancer, anti-inflammatory, neuromodulatory, satiety effector, DNA, RNA, small molecule or other molecule intended to be secreted from the microorganism, the engineered microorganism may comprise a secretion mechanism and corresponding gene sequence(s) encoding the secretion system.

| | |
|---|---|
| SYN-PKU-1035 | SYN-PKU-1033 cured entirely |
| SYN-PKU-1036 | SYN-PKU-1034 cured entirely |

In one embodiment, the genetically engineered bacteria comprise one or more PMEs for metabolizing phenylalanine in combination with one or more PMEs for secretion. In one embodiment, the genetically engineered bacteria comprise one or more PMEs for metabolizing phenylalanine and a phenylalanine transporter in combination with one or more PMEs for secretion. In one embodiment, the genetically engineered bacteria comprise one or more PMEs for metabolizing phenylalanine and a phenylalanine transporter in combination with one or more PMEs for secretion, and also include an auxotrophy and/or an antibiotic resistance. Secretion systems described herein are utilized to secrete the PMEs in the genetically engineered bacteria with multiple mechanisms of action.

In any of these embodiments, the bacteria described herein comprise one or more modifications or mutations, e.g., deletion, insertion, substitution or inversion, within the E. coli Nissle Phage 3 genome. In some embodiments, the mutation is an insertion. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Secretion

In any of the embodiments described herein, in which the genetically engineered microorganism produces a protein, polypeptide, peptide, or other anti-cancer, immune modulatory, DNA, RNA, small molecule or other molecule intended to be secreted from the microorganism, the engineered microorganism may comprise a secretion mechanism and corresponding gene sequence(s) encoding the secretion system.

In some embodiments, the genetically engineered bacteria further comprise a native secretion mechanism or non-native secretion mechanism that is capable of secreting the anti-cancer molecule from the bacterial cytoplasm in the extracellular environment. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane.

In Gram-negative bacteria, secretion machineries may span one or both of the inner and outer membranes.

In order to translocate a protein, e.g., therapeutic polypeptide, to the extracellular space, the polypeptide must first be translated intracellularly, mobilized across the inner membrane and finally mobilized across the outer membrane. Many effector proteins (e.g., therapeutic polypeptides)—particularly those of eukaryotic origin—contain disulphide bonds to stabilize the tertiary and quaternary structures. While these bonds are capable of correctly forming in the oxidizing periplasmic compartment with the help of periplasmic chaperones, in order to translocate the polypeptide across the outer membrane the disulphide bonds must be reduced and the protein unfolded again.

Suitable secretion systems for secretion of heterologous polypeptides, e.g., effector molecules, from gram negative and gram positive bacteria are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

Surface Display

In some embodiments, the genetically engineered bacteria and/or microorganisms encode one or more gene(s) and/or gene cassette(s) encoding a polypeptide of interest described herein which is anchored or displayed on the surface of the bacteria and/or microorganisms. Examples of the payload molecules which are displayed or anchored to the bacteria and/or microorganism, are any of the payload molecules or other effectors described herein, and include but are not limited to enzymes (e.g., PME(s) or kynureninase), antibodies, e.g., scFv fragments, and tumor-specific antigens or neoantigens.

Suitable systems for surface display of heterologous polypeptides, e.g., effector molecules, on the surface of gram negative and gram positive bacteria are described in International Patent Application PCT/US2017/013072, filed Jan. 11, 2017, published as WO2017/123675, the contents of which is herein incorporated by reference in its entirety The Essential Genes and Auxotrophs As used herein, the term "essential gene" refers to a gene that is necessary for cell growth and/or survival. Bacterial essential genes are well known to one of ordinary skill in the art, and can be identified by directed deletion of genes and/or random mutagenesis and screening (see, e.g., Zhang and Lin, "DEG 5.0, a database of essential genes in both prokaryotes and eukaryotes," Nucl Acids Res, 2009; 37:D455-D458 and Gerdes et al., "Essential genes on metabolic maps," Curr Opin Biotechnol, 2006; 17(5):448-456, the entire contents of each of which are expressly incorporated herein by reference).

An "essential gene" may be dependent on the circumstances and environment in which an organism lives. For example, a mutation of, modification of, or excision of an essential gene may result in the genetically engineered bacteria of the disclosure becoming an auxotroph. An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thiI, as long as the corresponding wild-type gene product is not produced in the bacteria. Table 18A lists exemplary bacterial genes which may be disrupted or deleted to produce an auxotrophic strain. These include, but are not limited to, genes required for oligonucleotide synthesis, amino acid synthesis, and cell wall synthesis.

TABLE 18A

Non-limiting Examples of Bacterial Genes
Useful for Generation of an Auxotroph

| Amino Acid | Oligonucleotide | Cell Wall |
|---|---|---|
| cysE | thyA | dapA |
| glnA | uraA | dapB |
| ilvD |  | dapD |
| leuB |  | dapE |
| lysA |  | dapF |
| serA |  |  |
| metA |  |  |
| glyA |  |  |
| hisB |  |  |
| ilvA |  |  |
| pheA |  |  |
| proA |  |  |
| thrC |  |  |
| trpC |  |  |
| tyrA |  |  |

Table 19A shows the survival of various amino acid auxotrophs in the mouse gut, as detected 24 hrs and 48 hrs post-gavage. These auxotrophs were generated using BW25113, a non-Nissle strain of E. coli.

TABLE 19A

Survival of amino acid auxotrophs in the mouse gut

| Gene | AA Auxotroph | Pre-Gavage | 24 hours | 48 hours |
|---|---|---|---|---|
| argA | Arginine | Present | Present | Absent |
| cysE | Cysteine | Present | Present | Absent |
| glnA | Glutamine | Present | Present | Absent |
| glyA | Glycine | Present | Present | Absent |
| hisB | Histidine | Present | Present | Present |
| ilvA | Isoleucine | Present | Present | Absent |
| leuB | Leucine | Present | Present | Absent |
| lysA | Lysine | Present | Present | Absent |
| metA | Methionine | Present | Present | Present |
| pheA | Phenylalanine | Present | Present | Present |
| proA | Proline | Present | Present | Absent |
| serA | Serine | Present | Present | Present |
| thrC | Threonine | Present | Present | Present |
| trpC | Tryptophan | Present | Present | Present |
| tyrA | Tyrosine | Present | Present | Present |
| ilvD | Valine/Isoleucine/Leucine | Present | Present | Absent |

TABLE 19A-continued

Survival of amino acid auxotrophs in the mouse gut

| Gene | AA Auxotroph | Pre-Gavage | 24 hours | 48 hours |
|------|--------------|------------|----------|----------|
| thyA | Thiamine | Present | Absent | Absent |
| uraA | Uracil | Present | Absent | Absent |
| flhD | FlhD | Present | Present | Present |

For example, thymine is a nucleic acid that is required for bacterial cell growth; in its absence, bacteria undergo cell death. The thyA gene encodes thymidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro, or in the presence of high DAP levels found naturally in the human gut in vivo. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro, or in the presence of high uracil levels found naturally in the human gut in vivo. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to, yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, mc, ftsB, eno, pyrG, chpR, lgt, fbaA, pgk, yqgD, metK, yqgF, plsC, ygiT, pare, ribB, cca, ygjD, tdcF, yraL, yihA, ftsN, murl, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsl, murE, murF, mraY, murD, ftsW, murG, murC, ftsQ, ftsA, ftsZ, lpxC, secM, secA, can, folK, hemL, yadR, dapD, map, rpsB, infB, nusA, ftsH, obgE, rpmA, rplU, ispB, murA, yrbB, yrbK, yhbN, rpsI, rplM, degS, mreD, mreC, mreB, accB, accC, yrdC, def, fort, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf, pyrH, olA, rlpB, leuS, lnt, glnS, fldA, cydA, infA, cydC, ftsK, lolA, serS, rpsA, msbA, lpxK, kdsB, mukF, mukE, mukB, asnS, fabA, mviN, me, yceQ, fabD, fabG, acpP, tmk, holB, lolC, lolD, lolE, purB, ymfK, minE, mind, pth, rsA, ispE, lolB, hemA, prfA, prmC, kdsA, topA, ribA, fabl, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson, "Synthetic Auxotrophs with Ligand-Dependent Essential Genes for a BL21 (DE3) Biosafety Strain," ACS Synth Biol 2015; 4(12):1279-1286, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG, and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A, and F40G. In some embodiments, the essential gene is tyrS comprising the mutations L36V, C38A, and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L51, and L6G. In some embodiments, the essential gene is adk comprising the mutations I4L, L51, and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid, or L-histidine methyl ester. Bacterial cells comprising mutations in dnaN (H191N, R240C, I317S, F319V, L340T, V347I, and S345C) are complemented by benzothiazole, indole, or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using the arabinose system shown in FIGS. 85-86 of WO2017087580.

In some embodiments, the genetically engineered bacterium of the disclosure is an auxotroph and also comprises kill switch circuitry, such as any of the kill switch components and systems described herein. For example, the genetically engineered bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synth Biol, 2015; 4(3):307-316, the entire contents of which are expressly incorporated herein by reference). In some embodiments, the genetically engineered bacterium of the disclosure is an auxotroph and also comprises kill switch circuitry, such as any of the kill switch components and systems described herein, as well as another biosecurity system, such a conditional origin of replication (Wright et al., 2015). In one embodiment, a genetically engineered bacterium, comprises one or more AIPS constructs integrated into the bacterial chromosome in combination with one or more biosafety plasmid(s). In some embodiments, the plasmid comprises a conditional origin of replication (COR), for which the plasmid replication initiator protein is provided in trans, i.e., is encoded by the chromosomally integrated biosafety construct. In some embodiments, the chromosomally integrated construct is further introduced into the host such that an auxotrophy results (e.g., dapA or thyA auxotrophy), which in turn is complemented by a gene product expressed from the biosafety plasmid construct. In some embodiments, the biosafety plasmid further encodes a broad-spectrum toxin (e.g., Kis), while the integrated biosafety construct encodes an anti-toxin (e.g., anti-Kis), permitting propagation of the plasmid in the bacterial cell containing both constructs. Without wishing to be bound by theory, this mechanism functions to select against plasmid spread by making the plasmid DNA itself disadvantageous to maintain by a wild-type bacterium. A non-limiting example of such a biosafety system is shown in FIG. 61A, FIG. 61B, FIG. 61C, and FIG. 61D of WO2017087580, the contents of which are herein incorporated by reference in their entirety.

In some embodiments, the genetically engineered bacteria comprise a chromosomally inserted biosafety construct nucleic acid sequence (to be combined with a plasmid based biosafety construct) that is at least about 80%, at least about 85%, at least about 90%, at least about 95%, or at least about 99% homologous to the DNA sequence of SEQ ID NO: 81, 82, 83, 84, 85 of WO2017087580, the contents of which are herein incorporated by reference in their entirety, or a functional fragment thereof. In some embodiments, the genetically engineered bacteria comprise a chromosomally inserted biosafety construct nucleic acid sequence (to be combined with a plasmid based biosafety construct) encoding a polypeptide sequence that is at least about 80%, at least about 85%, at least about 90%, at least about 95%, or at least about 99% homologous to the polypeptide sequence of SEQ ID NO: 86, 87, 88 of WO2017087580, the contents of which are herein incorporated by reference in their entirety, or a functional fragment thereof.

In some embodiments, the genetically engineered bacteria comprise a chromosome based biosafety construct nucleic acid sequence (to be combined with a plasmid based biosafety construct) that is at least about 80%, at least about 85%, at least about 90%, at least about 95%, or at least about 99% homologous to the DNA sequence of SEQ ID NO: 89, 90, 91, 92, 93, 94 of WO2017087580, the contents of which are herein incorporated by reference in their entirety or a functional fragment thereof. In some embodiments, the genetically engineered bacteria comprise a chromosome based biosafety construct nucleic acid sequence (to be combined with a plasmid based biosafety construct) encoding a polypeptide sequence that is at least about 80%, at least about 85%, at least about 90%, at least about 95%, or at least about 99% homologous to the polypeptide sequence encoded by the DNA sequence of SEQ ID NO: 89, 90, 91, 92, 93, 94 of WO2017087580, the contents of which are herein incorporated by reference in their entirety or a functional fragment thereof.

In some embodiments, the genetically engineered bacteria comprise a plasmid based biosafety construct payload nucleic acid sequence at least about 80%, at least about 85%, at least about 90%, at least about 95%, or at least about 99% homologous to the DNA sequence of SEQ ID NO: 36, 37, 74, 95, 96, 98, 99, 100, 113 of WO2017087580, the contents of which are herein incorporated by reference in their entirety or a functional fragment thereof. In some embodiments, the genetically engineered bacteria comprise a plasmid based biosafety construct payload nucleic acid sequence encoding a polypeptide which is at least about 80%, at least about 85%, at least about 90%, at least about 95%, or at least about 99% homologous to the polypeptide encoded by the DNA sequence of SEQ ID NO: 36, 37, 74, 95, 96, 98, 99, 100, 113 of WO2017087580, the contents of which are herein incorporated by reference in their entirety or a functional fragment thereof. In some embodiments, the plasmid based construct comprises one or more copies of PAL. In some embodiments, the plasmid based construct comprises one or more copies of PheP. In some embodiments, the plasmid based construct comprises one or more copies of LAAD. In some embodiments, the plasmid based construct comprises one or more copies of PAL and one or more copies of PheP. In some embodiments, the plasmid based construct comprises one or more copies of PAL and one or more copies of LAAD. In some embodiments, the plasmid based construct comprises one or more copies of LAAD and one or more copies of PheP. In some embodiments, the plasmid based construct comprises one or more copies of PAL and one or more copies of PheP and one or more copies of LAAD. In some embodiments, the phenylalanine catabolizing plasmid payload(s) (i.e., PAL, PheP, and/or LAAD) are under the control of one or more constitutive or inducible promoter(s) as described herein (e.g., low oxygen, arabinose, IPTG inducible, or a combination thereof). In some embodiments, the promoter is useful for pre-induction. In some embodiments, the promoter is useful for in vivo activation. In some embodiments, the promoter is useful for pre-induction and in vivo activity. In some embodiments, the construct comprises two or more promoters, some of which are useful for preinduction, and some of which are useful for in vivo activity.

In some embodiments, the genetically engineered bacteria comprise a plasmid based biosafety construct nucleic acid sequence (to be combined with a chromosome based biosafety construct), e.g., that comprises a payload construct for the catabolism of phenylalanine. In some embodiments, the plasmid based construct comprises one or more copies of PAL. In some embodiments, the plasmid based construct comprises one or more copies of PheP. In some embodiments, the plasmid based construct comprises one or more copies of LAAD. In some embodiments, the plasmid based construct comprises one or more copies of PAL and one or more copies of PheP. In some embodiments, the plasmid based construct comprises one or more copies of PAL and one or more copies of LAAD. In some embodiments, the plasmid based construct comprises one or more copies of LAAD and one or more copies of PheP. In some embodiments, the plasmid based construct comprises one or more copies of PAL and one or more copies of PheP and one or more copies of LAAD. In some embodiments, the phenylalanine catabolizing plasmid payload(s) (i.e., PAL, PheP, and/or LAAD) are under the control of one or more constitutive or inducible promoter(s) as described herein (e.g., low oxygen, arabinose, IPTG inducible, or a combination thereof). In some embodiments, the promoter is useful for pre-induction. In some embodiments, the promoter is useful for in vivo activation. In some embodiments, the promoter is useful for pre-induction and in vivo activity. In some embodiments, the construct comprises two or more promoters, some of which are useful for preOinduction, and some of which are useful for in vivo activity.

In any of these embodiments, the genetically engineered bacteria comprising an auxotrophy contain one or more mutations or modifications to an endogenous phage genome. In some embodiments, the modifications to the endogenous phage genome are one or more deletion(s), insertion(s), substitution(s) or inversions(s) or combinations thereof within the phage genome. In some embodiments, the mutations are deletions. In some embodiments, the deletions comprise one or more phage genes. In some embodiments, phage genes are partially deleted. In some embodiments, the mutations are insertions. In some embodiments, the insertion comprises an antibiotic cassette as described herein. In some embodiments, one or more genes are substituted. In some embodiments, the substitution comprises an antibiotic cassette. In some embodiments, one or more phage genes are inverted. In some embodiments parts of one or more phage genes are inverted.

In some embodiments, the genetically engineered bacteria are derived from E. coli Nissle and comprise one or more E. coli Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some of the preceding embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281. In some embodiments, the genetically engineered bacteria further comprise one or more circuits comprising one or more gene(s) encoding one or more effector molecules. In some embodiments, the genetically engineered bacteria are capable of expressing any one or more of the circuits in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the described circuits are present on one or more plasmids (e.g., high copy or low copy) or are integrated into one or more sites in the bacterial chromosome. Also, in some embodiments, the genetically engineered bacteria are further capable of expressing any one or more of the described circuits and further comprise one or more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

The addition of a Phe-auxotrophy may also have utility for increasing the rate of phenylalanine degradation. For example, the deletion of the pheA gene confers phenylalanine auxotrophy. By turning off endogenous bacterial phenylalanine production, this may drive increased uptake from the environment and also result in increased degradation of phenylalanine taken up from the environment.

Genetic Regulatory Circuits

In some embodiments, the genetically engineered bacteria comprise multi-layered genetic regulatory circuits for expressing the constructs described herein. Suitable multi-layered genetic regulatory circuits are described in International Patent Application PCT/US2016/39434, filed on Jun. 24, 2016, published as WO2016/210378, the contents of which is herein incorporated by reference in its entirety. The genetic regulatory circuits are useful to screen for mutant bacteria that produce an anti-cancer molecule or rescue an auxotroph. In certain embodiments, the invention provides methods for selecting genetically engineered bacteria that produce one or more genes of interest.

Host-Plasmid Mutual Dependency

In some embodiments, the genetically engineered bacteria of the invention also comprise a plasmid that has been modified to create a host-plasmid mutual dependency. In certain embodiments, the mutually dependent host-plasmid platform is an antibiotic independent plasmid system (AIPS) (Wright et al., 2015). These and other systems and platforms are described in International Patent Application PCT/US2017/013072, filed Jan. 11, 2017, published as WO2017/123675, the contents of which is herein incorporated by reference in its entirety. Kill Switch In some embodiments, the genetically engineered bacteria of the invention also comprise a kill switch. The kill switch is intended to actively kill genetically engineered bacteria in response to external stimuli. As opposed to an auxotrophic mutation where bacteria die because they lack an essential nutrient for survival, the kill switch is triggered by a particular factor in the environment that induces the production of toxic molecules within the microbe that cause cell death. Suitable kill switches are described in PCT/US2016/039427, filed Jun. 24, 2016 and published as WO2016210373, the contents of which is herein incorporated by reference in its entirety.

Pharmaceutical Compositions and Formulations

Pharmaceutical compositions comprising the genetically engineered bacteria of the invention may be used to treat, manage, ameliorate, and/or prevent diseases associated with hyperphenylalaninemia, e.g., PKU. Pharmaceutical compositions of the invention comprising one or more genetically engineered bacteria, alone or in combination with prophylactic agents, therapeutic agents, and/or and pharmaceutically acceptable carriers are provided. In certain embodiments, the pharmaceutical composition comprises one species, strain, or subtype of bacteria that are engineered to comprise the genetic modifications described herein. In alternate embodiments, the pharmaceutical composition comprises two or more species, strains, and/or subtypes of bacteria that are each engineered to comprise the genetic modifications described herein.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, PA). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the genetically engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{11}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The genetically engineered bacteria may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered bacteria disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, PA In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered bacteria disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered bacteria are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered bacteria described herein.

In one embodiment, the genetically engineered bacteria of the disclosure may be formulated in a composition suitable for administration to pediatric subjects. As is well known in the art, children differ from adults in many aspects, including different rates of gastric emptying, pH, gastrointestinal permeability, etc. (Ivanovska et al., 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered bacteria may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. See, e.g., US 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered bacteria described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered bacteria may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-coglycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{\_}/ED_{50}$) may be calculated as therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Methods of Treatment

Another aspect of the disclosure provides methods of treating a disease comprising administering to a subject in need thereof a composition comprising an engineered bacteria disclosed herein. In some embodiments, the disclosure provides a method for treating a disease comprising administering to a subject in need thereof a composition comprising an engineered bacteria comprising a modification in an endogenous or native phage genome.

Another aspect of the disclosure provides methods of treating a disease associated with hyperphenylalaninemia or symptom(s) associated with hyperphenylalaninemia. In some embodiments, the disclosure provides a method for treating a disease associated with hyperphenylalaninemia or symptom(s) associated with hyperphenylalaninemia comprising administering to a subject in need thereof a composition comprising an engineered bacteria disclosed herein. In some embodiments, the disclosure provides a method for treating a disease associated with hyperphenylalaninemia or symptom(s) associated with hyperphenylalaninemia comprising administering to a subject in need thereof a composition comprising an engineered bacteria comprising gene sequence encoding one or PMEs, e.g., PAH and/or PAH, and/or LAAD. In some embodiments, the engineered bacteria may comprise a modification in an endogenous or native phage genome. In some embodiments, the genetically engineered bacteria further comprise one or more circuits comprising one or more gene(s) encoding one or more effector molecules (e.g. one or more PMEs, e.g., PAH and/or PAH, and/or LAAD and/or gene sequence encoding one or more Phe transporters). In some embodiments, the genetically engineered bacteria are capable of expressing any one or more of the circuits in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the described circuits are present on one or more plasmids (e.g., high copy or low copy) or are integrated into one or more sites in the bacterial chromosome. Also, in some embodiments, the genetically engineered bacteria are further capable of expressing any one or more of the described circuits and further comprise one or more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits. In any of these embodiments, the modifications to the endogenous phage genome are one or more deletion(s), insertion(s), substitution(s) or inversions(s) or combinations thereof within the phage genome. In some embodiments, the mutations are deletions. In some embodiments, the deletions comprise one or more phage genes. In some embodiments, phage genes are partially deleted. In some embodiments, the mutations are insertions. In some embodiments, the insertion comprises an antibiotic cassette as described herein. IN some embodiments, one or more genes are substituted. In some embodiments, the substitution comprises an antibiotic cassette. In some embodiments, one or more phage genes are inverted. In some embodiments parts of one or more phage genes are inverted.

In some embodiments, the disclosure provides a method for treating a disease associated with hyperphenylalaninemia or symptom(s) associated with hyperphenylalaninemia comprising administering to a subject in need thereof a composition comprising an engineered bacteria comprising gene sequence encoding one or more PMEs, e.g., PAH and/or PAH, and/or LAAD and optionally gene sequence encoding one or more Phe transporters, wherein the gene sequence(s) encoding the one or more PMES are under the control of an inducible promoter, and the gene sequence encoding the one or more Phe transporters are under the control of an inducible promoter, such as any of the inducible promoters disclosed herein. The gene sequence(s) may be under the control of the same or different inducible promoters. In some embodiments, one or more of the gene sequence encoding the one or more PMEs, e.g., PAH and/or PAH, and/or LAAD are under the control of constitutive promoter. In some embodiments, one or more of the gene sequence encoding the one or more Phe transporters are under the control of constitutive promoter. In other embodiments, the bacteria may comprise one or more of the following: one or more auxotrophies, one or more killswitches, gene guard components, and/or antibiotic resistance. In some embodiments, the insertion comprises an antibiotic cassette as described herein.

In some embodiments, the disease is selected from the group consisting of: classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, autoimmune disorders, cancer, tumors, metabolic disease (e.g., type 2 diabetes, obesity, hepatic encephalopathy, non-alcoholic fatty liver diease, and associated or related disorders), Segawa's disease, and rare disorders of metabolism. Non-limiting examples of such rare disorder of metabolism include maple sirup urine disease, isovereric acidemia, methylmalonic acidemia, propionic acidemia, hyperoxalurea, phenylketonuria, and hyperammonemia). In some embodiments, hyperphenylalaninemia is secondary to other conditions, e.g., liver diseases. In some embodiments, the invention provides methods for reducing, ameliorating, or eliminating one or more symptom(s) associated with these diseases, including but not limited to neurological deficits, mental retardation, encephalopathy, epilepsy, eczema, reduced growth, microcephaly, tremor, limb spasticity, and/or hypopigmentation. In some embodiments, the subject to be treated is a human patient.

In certain embodiments, the genetically engineered bacteria are capable of metabolizing a meabolite in the diet in order to treat a disease or disorder associated with accumulation of the metabolite (e.g., hyperphenylalaninemia, e.g., PKU). In some embodiments, the genetically engineered bacteria are delivered simultaneously with dietary protein. In other embodiments, the genetically engineered bacteria are not delivered simultaneously with dietary protein. Studies have shown that pancreatic and other glandular secretions into the intestine contain high levels of proteins, enzymes, and polypeptides, and that the amino acids produced as a result of their catabolism are reabsorbed back into the blood in a process known as "enterorecirculation" (Chang, 2007; Sarkissian et al., 1999). Thus, high intestinal levels of phenylalanine may be partially independent of food intake, and are available for breakdown by PAL. In some embodiments, the genetically engineered bacteria and dietary protein are delivered after a period of fasting or phenylalanine-restricted dieting. In these embodiments, a patient suffering from hyperphenylalaninemia may be able to resume a substantially normal diet, or a diet that is less restrictive than a phenylalanine-free diet. In some embodiments, the genetically engineered bacteria may be capable of metabolizing phenylalanine from additional sources, e.g., the blood, in order to treat a disease associated with hyperphenylalaninemia, e.g., PKU. In these embodiments, the genetically engineered bacteria need not be delivered simultaneously with dietary protein, and a phenylalanine gradient is generated, e.g., from blood to gut, and the genetically engineered bacteria metabolize phenylalanine and reduce phenylalaninemia.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally, e.g., in a liquid suspension. In some embodiments, the genetically engineered bacteria of the invention are lyophilized in a gel cap and administered orally. In some embodiments, the genetically engineered bacteria of the invention are administered via a feeding tube or gastric shunt. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, the pharmaceutical composition described herein is administered to reduce levels of a certain metabolite or other type of biomarker molecule or molecule associated with or causative of the disorder in a subject. In some embodiments, the methods of the present disclosure reduce the phenylalanine levels in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the phenylalanine level in a subject before and after administration of the pharmaceutical composition. In some embodiments, the method of treating or ameliorating hyperphenylalaninemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, levels of a certain metabolite or other type of biomarker molecule or molecule associated with or causative of the disorder (e.g. phenylalnine) in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce levels of a certain metabolite (e.g. phenylalanine) or other type of biomarker molecule or molecule associated with or causative of the disorder. In some embodiments, the methods may include administration of the compositions of the invention to reduce the metabolite or other type of molecule to undetectable levels in a subject. In some embodiments, the methods may include administration of the compositions of the invention to reduce concentrations of the metabolite or other type of molecule to undetectable levels, or to less than about 1%, 2%, 5%, 10%, 20%, 25%, 30%, 40%, 50%, 60%, 70%, 75%, or 80% of the subject's levels prior to treatment.

Levels of a metabolite or other type of molecule that accumulates in response to the administration of the genetically engineered bacteria upon induction of the circuitry in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods described herein may include administration of the compositions of the invention to reduce levels of a certain metabolite or other type of biomarker molecule or molecule associated with or causative of the disorder and resulting in increased levels of a metabolite or other type of molecule which accumulates as a result of the administration of the genetically engineered bacteria. In some embodiments, the methods may include administration of the compositions of the invention to reduce one metabolite or other type of molecule to undetectable levels in a subject, and concurrently and proportionately increase levels of another metabolite or other type of molecule. In some embodiments, the methods may include administration of the compositions of the invention, leading to an increase concentrations of a metabolite or other type of molecule to more than about 1%, 2%, 5%, 10%, 20%, 25%, 30%, 40%, 50%, 60%, 70%, 75%, 80%, 90%, 95%, or up to 99% or up to 100% of the subject's levels of the metabolite prior to treatment. Such increases may be measured for example in the urine, the blood, the feces, or in a tumor.

In some embodiments, the activity of genetically engineered bacteria expressing PAL (e.g., phenylalanine degrading activity) can be detected in the urine of a mammalian subject, e.g., an animal model or a human, by measuring the amounts of hippurate produced and the rate of its accumulation. Hippurate is a PAL specific breakdown product, and is normally present in human urine at low concentrations. It is the end product of metabolism of phenylalanine via the PAL pathway. Phenylalanine ammonia lyase mediates the conversion of phenylalanine to cinnamate. When cinnamate is produced in the gut, is absorbed and quickly converted to hippurate in the liver and excreted in the liver (Hoskins JA and Gray Phenylalanine ammonia lyase in the management of phenylketonuria: the relationship between ingested cinnamate and urinary hippurate in humans. J Res Commun Chem Pathol Pharmacol. 1982 February; 35(2):275-82). Phenylalainine is converted to hippurate in a 1:1 ratio, i.e., 1 mole of Phe is converted into 1 mol of hippurate. Thus, changes in urinary hippurate levels can be used as a non-invasive measure of the effect of therapies that utilize this mechanism.

Hippuric acid thus has the potential to function as a biomarker allowing monitoring of dietary adherence and treatment effect in patients receiving PAL-based regimens. It can be used as an adjunct to measurement of blood Phe levels in the management of patients and because it is a urinary biomarker, it can have advantages particularly in children to adjust protein intake—which can be challenging as needs vary based on growth.

In some embodiments, the methods of the present disclosure increase the hippurate levels in the urine of a subject by at least about 10%, 20%, 25%, 30%, 40%, 50%, 60%, 70%, 75%, 80%, 85%, 90%, 95%, 96%, 97%, 98%, 99% or more as compared to levels in an untreated or control subject. In some embodiments, the increase is measured by comparing the hippurate level in a subject before and after administration of the pharmaceutical composition of the disclosure.

In this section, the term "PAL-based drug" refers to any drug, polypeptide, biologic, or treatment regimen that has PAL activity, for example, PEG-PAL, Kuvan, a composition comprising a bacteria of the present disclosure, e.g., bacteria encoding PAL and optionally PheP transporter. In some embodiments, the disclosure provides a method for measuring PAL activity in vivo by administering to a subject, e.g., a mammalian subject, a PAL-based drug and measuring the amount of hippurate produced in the subject as a measure of PAL activity. In some embodiments, the disclosure provides a method for monitoring the therapeutic activity of a PAL-based drug by administering to a subject, e.g., a mammalian subject, the PAL-based drug and measuring the amount of hippurate produced in the subject as a measure of PAL therapeutic activity. In some embodiments, the disclosure provides a method for adjusting the dosage of a PAL-based drug by administering to a subject, e.g., a mammalian subject, the PAL-based drug, measuring the amount of hippurate produced in the subject to determine PAL activity, and adjusting (e.g., increasing or decreasing) the dosage of the drug to increase or decrease the PAL activity in the subject. In some embodiments, the disclosure provides a method for adjusting the protein intake and/or diet of a subject having hyperphenylalanemia comprising administering to the subject a PAL-based drug, measuring the amount of hippurate produced in the subject, and adjusting (e.g., increasing or decreasing) the protein intake or otherwise adjusting the diet of the subject to increase or decrease the PAL activity in the subject. In some embodiments, the disclosure provides a method for confirming adherence to a protein intake and/or diet regimen of a subject having hyperphenylalanemia comprising administering to the subject a PAL-based drug, measuring the amount of hippurate produced in the subject, and measuring PAL activity in the subject.

In some embodiments of the methods disclosed herein, both blood phenylalanine levels and urine hippurate levels are monitored in a subject. In some embodiments, blood phenylalanine and hippurate in the urine are measured at multiple time points, to determine the rate of phenylalanine breakdown. In some embodiments, hippurate levels in the urine are used evaluate PAL activity or strain activity in animal models.

In some embodiments, hippuric acid measurements in the urine, alone or in combination with blood phenylalanine measurements, are used to the strain prove mechanism of action. In some embodiments, hippuric acid measurements in the urine, alone or in combination with blood phenylalanine measurements, are used as a tool to differentiate between PAL and LAAD activity in a strain, and allow to determine the contribution of each enzyme to the overall strain activity.

In some embodiments, hippuric acid measurements in the urine, alone or in combination with blood phenylalanine measurements, are used evaluate safety in animal models and human subjects. In some embodiments, hippuric acid measurements in the urine, alone or in combination with blood phenylalanine measurements, are used in the evaluation of dose-response and optimal regimen for the desired pharmacologic effect and safety. In some embodiments, hippuric acid measurements in the urine, alone or in combination with blood phenylalanine measurements, are used as surrogate endpoint for efficacy and/or toxicity. In some embodiments, hippuric acid measurements in the urine, alone or in combination with blood phenylalanine measurements, are used to predict patients' response to a regimen comprising a therapeutic strain. In some embodiments, hippuric acid measurements in the urine, alone or in combination with blood phenylalanine measurements, are used for the identification of certain patient populations that are more likely to respond to the drug therapy. In some embodiments, hippuric acid measurements in the urine, alone or in combination with blood phenylalanine measurements, are used to avoid specific adverse events. In some embodiments, hippuric acid measurements in the urine, alone or in combination with blood phenylalanine measurements, are useful for patient selection.

In some embodiments, hippuric acid measurements in the urine, alone or in combination with blood phenylalanine measurements, are used as one method for adjusting protein intake/diet of PKU patient on a regimen which includes the administration of a therapeutic PKU strain expressing PAL.

In some embodiments, measurement of urine levels of hippuric acid, alone or in combination with blood phenylalanine measurements, is used to measure and/or monitor the activity of recombinant PAL. In some embodiments, measurement of urine levels of hippuric acid is used to measure and/or monitor the activity of recombinant pegylated PAL (Peg-PAL). In some embodiments, measurement of urine levels of hippuric acid, alone or in combination with blood phenylalanine measurements, is used to measure and/or monitor the activity of recombinant PAL administered in combination with a therapeutic strain as described herein.

In some embodiments, hippuric acid measurements in the urine, alone or in combination with blood phenylalanine measurements, are used in combination with other biomarkers, e.g., clinical safety biomarkers. In some embodiments, measurement of increases and/or decreases in certain metabolites or other types of morlecules are used thein combination with measurements of other biomarkers, e.g., clinical safety biomarkers. Non-limiting examples of such safety markers include physical examination, vital signs, and electrocardiogram (ECG). Other non-limiting examples include liver safety tests known in the art, e.g., serum aspartate transaminase (AST), alanine transaminase (ALT), alkaline phosphatase (ALP), gamma-glutamyl transferase (GGT), and bilirubin. Such biosafety markers also include renal safety tests, e.g., those known in the art, e.g., blood urea nitrogen (BUN), serum creatinine, glomerular filtration rate (GFR), creatinine clearance, serum electrolytes (sodium, potassium, chloride, and bicarbonate), and complete urine analysis (color, pH, specific gravity, glucose, proteins, ketone bodies, and microscopic exam for blood, leukocytes, casts), as well as Cystatin-c, β 2-microglobulin, uric acid, clusterin, N-acetyl-beta-dglucosaminidase, neutrophil gelatinase-associated lipocalin (NGAL), N-acetyl-β-dglucosaminidase (NAG), and kidney injury molecule-1 (KIM-1). Other non-limiting examples include Hematology safety biomarkers known in the art, e.g., Complete blood count, total hemoglobin, hematocrit, red cell count, mean red cell volume, mean cell hemoglobin, red cell distribution width %, mean cell hemoglobin concentration, total white cell count, differential white cell count (Neutrophils, lymphocytes, basophils, esinophils, and monocytes), and platelets. Other no-liming examples include bone safety markers known in the art, e.g., Serum calcium and inorganic phosphates. Other non-limiting examples include basic metabolic safety biomarkers known in the art, e.g., blood glucose, triglycerides (TG), total cholesterol, low density lipoprotein cholesterol (LDLc), and high density lipoprotein cholesterol (HDL-c). Other specific safety biomarkers known in the art include, e.g., serum immunoglobulin levels, C-reactive protein (CRP), fibrinogen, thyroid stimulating hormone (TSH), thyroxine, testosterone, insulin, lactate dehydrogenase (LDH), creatine kinase (CK) and its isoenzymes, cardiac troponin (cTn), and methemoglobin.

In some embodiments, the activity of genetically engineered bacteria expressing LAAD can be specifically detected in the feces and differentiated from other E. coli strains. A Phenylalanine Deaminase Test "Phenylalanine Agar Slant" can be used for this purpose. Phenylalanine agar used to determine whether the microbe can use phenylalanine and convert it to phenyl pyruvate. When the test chemicals are added to the tube containing the sample on the phenylalanine agar, phenylpyruvate is converted to a green compound, indicating a positive test. Wild type E. coli does not produce phenylpyruvate, since they do not encode an enzyme, which can produce phenylpyruvate from phenylalanine, allowing differentiation from other E. coli strains. The genetically engineered bacteria can be differentiated from other bacterial species which are able to produce phenylpyruvate by PCR-based tests known in the art. For example, species specific sequences can be amplified. For example, universal PCR that amplifies conserved regions in various bacteria is ideal to detect any pathogen in screening of specimens. For this purpose, the conserved region of the 16S rRNA gene can be used as a target gene for the universal PCR; the 16S rRNA gene contains species-specific regions by which a large number of bacterial species can be differentiated.

In some embodiments, the Phenylalanine Deaminase Test can be used to detect the genetically engineered bacteria in a feces sample. In some embodiments, PCR-based tests can be conducted to differentiate the genetically engineered bacteria from other bacterial species.

In some embodiments, quantitative PCR (qPCR) is used to amplify, detect, and/or quantify mRNA expression levels of the gene, gene(s), or gene cassettes for producing the payloads, e.g., PME(s) and/or PheP. Primers may be designed and used to detect mRNA in a sample according to methods known in the art. In some embodiments, a fluorophore is added to a sample reaction mixture that may contain payload RNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the payload(s).

In some embodiments, quantitative PCR (qPCR) is used to amplify, detect, and/or quantify mRNA expression levels of the payload(s). Primers may be designed and used to detect mRNA in a sample according to methods known in the art. In some embodiments, a fluorophore is added to a sample reaction mixture that may contain payload, payloads, e.g., PME(s) and/or PheP and/or FNRS24Y, mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the payload(s) e.g., PME(s) and/or PheP and/or FNRS24Y.

In certain embodiments, the genetically engineered bacteria are *E. coli* Nissle in which endogenous or native *E. coli* Nissle Phage 3 has been modified as described herein. In some embodiments, Phage 3 can no longer undergo the lytic cycle due to the modification. In some embodiments, the lytic cycle is reduced or less frequent due to the modification. The genetically engineered bacteria may be destroyed, e.g., by defense factors in the gut or blood serum (Sonnenborn et al., 2009) or by activation of a kill switch, several hours or days after administration. Thus, the pharmaceutical composition comprising the genetically engineered bacteria may be re-administered at a therapeutically effective dose and frequency. Length of Nissle residence in vivo in mice is shown in FIG. 68 of WO2017087580, the contents of which are herein incorporated by reference in their entirety. In alternate embodiments, the genetically engineered bacteria are not destroyed within hours or days after administration and may propagate and colonize the gut.

The methods of the invention may comprise administration of the pharmaceutical composition alone or in combination with one or more additional therapeutic agents. In some embodiments for the treatment of hyperphenylalaninemia, the pharmaceutical composition may be administered in conjunction with the cofactor tetrahydrobiopterin (e.g., Kuvan/sapropterin), large neutral amino acids (e.g., tyrosine, tryptophan), glycomacropeptides, a probiotic (e.g., VSL3), an enzyme (e.g., pegylated-PAL), and/or other agents used in the treatment of phenylketonuria (Al Hafid and Christodoulou, 2015). See, e.g., WO2017087580 A1, the entire contents of which are incorporated by reference in its entirety.

An important consideration in the selection of the one or more additional therapeutic agents is that the agent(s) should be compatible with the genetically engineered bacteria of the invention, e.g., the agent(s) must not interfere with or kill the bacteria. In some embodiments, the pharmaceutical composition is administered with food. In alternate embodiments, the pharmaceutical composition is administered before or after eating food. The pharmaceutical composition may be administered in combination with one or more dietary modifications, e.g., low-phenylalanine diet. The dosage of the pharmaceutical composition and the frequency of administration may be selected based on the severity of the symptoms and the progression of the disease. The appropriate therapeutically effective dose and/or frequency of administration can be selected by a treating clinician. The methods of the invention also include kits comprising the pharmaceutical composition described herein. The kit can include one or more other elements including, but not limited to: instructions for use; other reagents, e.g., a label, an additional therapeutic agent; devices or materials for measuring levels of metabolites or other types of molecules associated with the disorder, in a subject; devices or other materials for preparing the pharmaceutical composition of the invention for administration; and devices or other materials for administration to a subject. Instructions for use can include guidance for therapeutic application, such as suggested dosages and/or modes of administration, e.g., in a patient with the disorder. The kit can further contain at least one additional therapeutic agent, and/or one or more additional genetically engineered bacterial strains of the invention, formulated as appropriate, in one or more separate pharmaceutical preparations.

In some embodiments, the kit is used for administration of the pharmaceutical composition to a subject. In some embodiments, the kit is used for administration of the pharmaceutical composition, alone or in combination with one or more additional therapeutic agents, to a subject. In some embodiments, the kit is used for measuring levels of metabolites or other types of molecules in a subject before, during, or after administration of the pharmaceutical composition to the subject. In certain embodiments, the kit is used for administration and/or re-administration of the pharmaceutical composition, alone or in combination with one or more additional therapeutic agents, when levels of metabolites or other types of molecules are increased or abnormally high. In some embodiments involving hyperphenylalaninemia, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL.

In some embodiments, the genetically engineered bacteria achieve a target degradation rate of about 0.15 to about 8.01 $\mu$mol/$10^9$ CFUs/hr. In some embodiments, the genetically engineered bacteria achieve a target degradation rate of about 0.15 to about 2 $\mu$mol/$10^9$ CFUs/hr. In some embodiments, the genetically engineered bacteria achieve a target degradation rate of about 0.6 to about 8.01 $\mu$mol/$10^9$ CFUs/hr. In some embodiments, the genetically engineered bacteria achieve a target degradation rate of about 0.2 to about 2.67 $\mu$mol/$10^9$ CFUs/hr.

In some embodiments, the genetically engineered bacteria achieve a target degradation rate of about 0.15 to about 0.6 $\mu$mol/$10^9$ CFUs/hr. In some embodiments, the genetically engineered bacteria achieve a target degradation rate of about 0.22 to about 0.9 $\mu$mol/$10^9$ CFUs/hr. In some embodiments, the genetically engineered bacteria achieve a target degradation rate of about 0.3 to about 1.21 $\mu$mol/$10^9$ CFUs/hr. In some embodiments, the genetically engineered bacteria achieve a target degradation rate of about 0.54 to about 2.16 $\mu$mol/$10^9$ CFUs/hr. In some embodiments, the genetically engineered bacteria achieve a target degradation rate of about 1.13 to about 4.53 $\mu$mol/$10^9$ CFUs/hr. In some embodiments, the genetically engineered bacteria achieve a target degradation rate of about 1.84 to about 7.38 $\mu$mol/$10^9$ CFUs/hr. In some embodiments, the genetically engineered bacteria achieve a target degradation rate of about 1.61 to about 6.43 $\mu$mol/$10^9$ CFUs/hr. In some embodiments, the genetically engineered bacteria achieve a target degradation rate of about 2 to about 8.01 µmol/$10^9$ CFUs/hr.

In some embodiments, the genetically engineered bacteria achieve a target degradation rate of about 0.1 to about 1 µmol/$10^9$ CFUs/hr. In some embodiments, the genetically engineered bacteria achieve a target degradation rate of about 1 to about 2 µmol/$10^9$ CFUs/hr. In some embodiments, the genetically engineered bacteria achieve a target degradation rate of about 2 to about 3 µmol/$10^9$ CFUs/hr. In some embodiments, the genetically engineered bacteria achieve a target degradation rate of about 3 to about 4 µmol/$10^9$ CFUs/hr. In some embodiments, the genetically engineered bacteria achieve a target degradation rate of about 4 to about 5 µmol/$10^9$ CFUs/hr. In some embodiments, the genetically engineered bacteria achieve a target degradation rate of about 5 to about 6 µmol/$10^9$ CFUs/hr. In some embodiments, the genetically engineered bacteria achieve a target degradation rate of about 6 to about 7 µmol/$10^9$ CFUs/hr. In some embodiments, the genetically engineered bacteria achieve a target degradation rate of about 7 to about 8 µmol/$10^9$ CFUs/hr.

In some embodiments, the genetically engineered bacteria achieve a target reduction rate of less than 0.15 µmol/$10^9$ CFUs/hr. In some embodiments, the genetically engineered bacteria achieve a target degradation rate of greater than 8.01 µmol/$10^9$ CFUs/hr.

In some embodiments, the genetically engineered bacteria achieve a target reduction of between about 178 mg and 2382 mg. In some embodiments, the genetically engineered bacteria achieve a target reduction of 1.08 mmol to 14.42 mmol. In some embodiments, the reduction is less than 1.08 mmol. In some embodiments, the reduction is greater than 14.42 mmol.

In some embodiments, target reduction and target degradation rates are based on classical PKU phenylalanine levels. In some embodiments, the target reduction and target degradation rates are based on phenylalanine levels observed in mild PKU. In some embodiments, target reduction and target degradation rates are based on phenylalanine levels observed in mild hyperphenylalaninemia.

Figure 28:
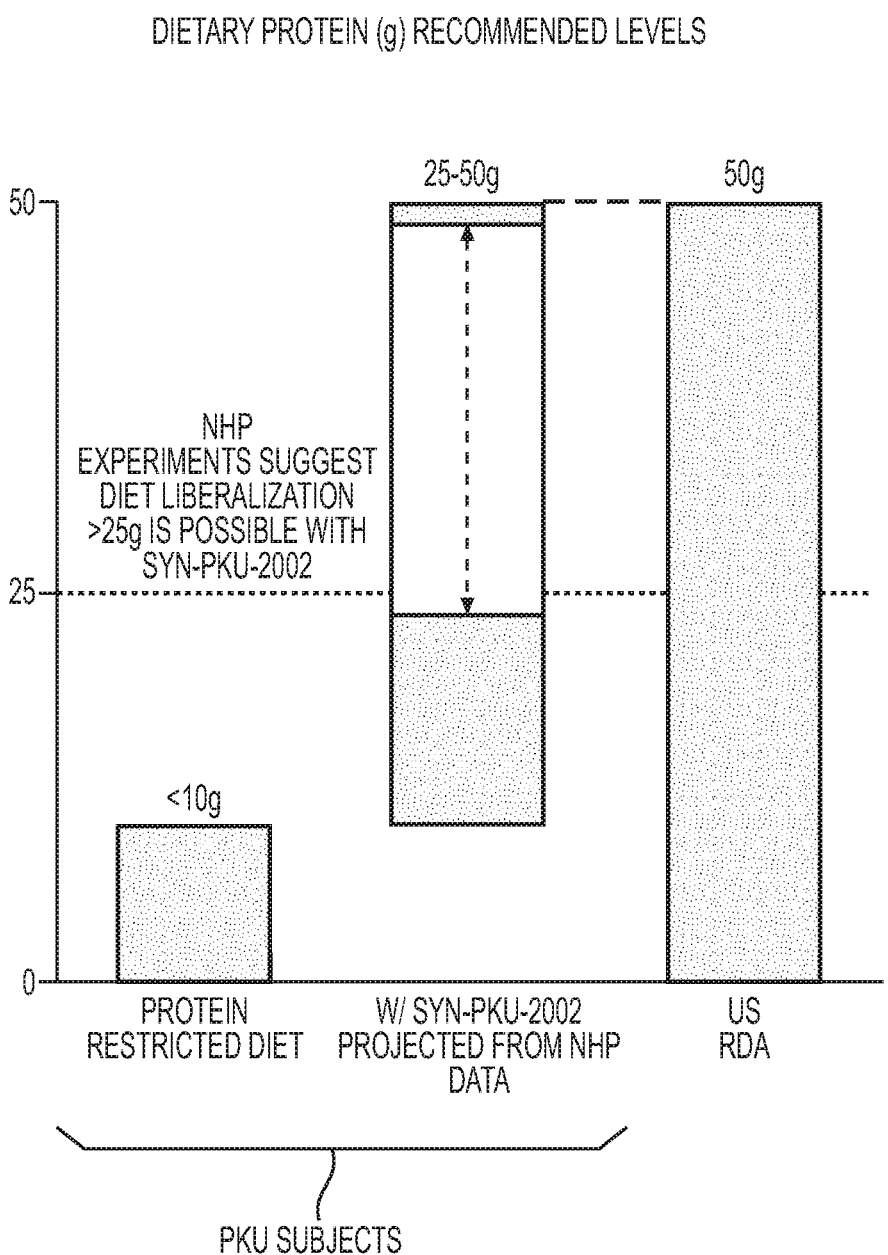
FIG. 28 depicts a graph showing SYN-PKU-2002 conversion of Phe in an NHP resulting in an increase in protein intake, which would correspond to a 2.5 fold increase in protein intake in a PKU patient.
Figure 29:
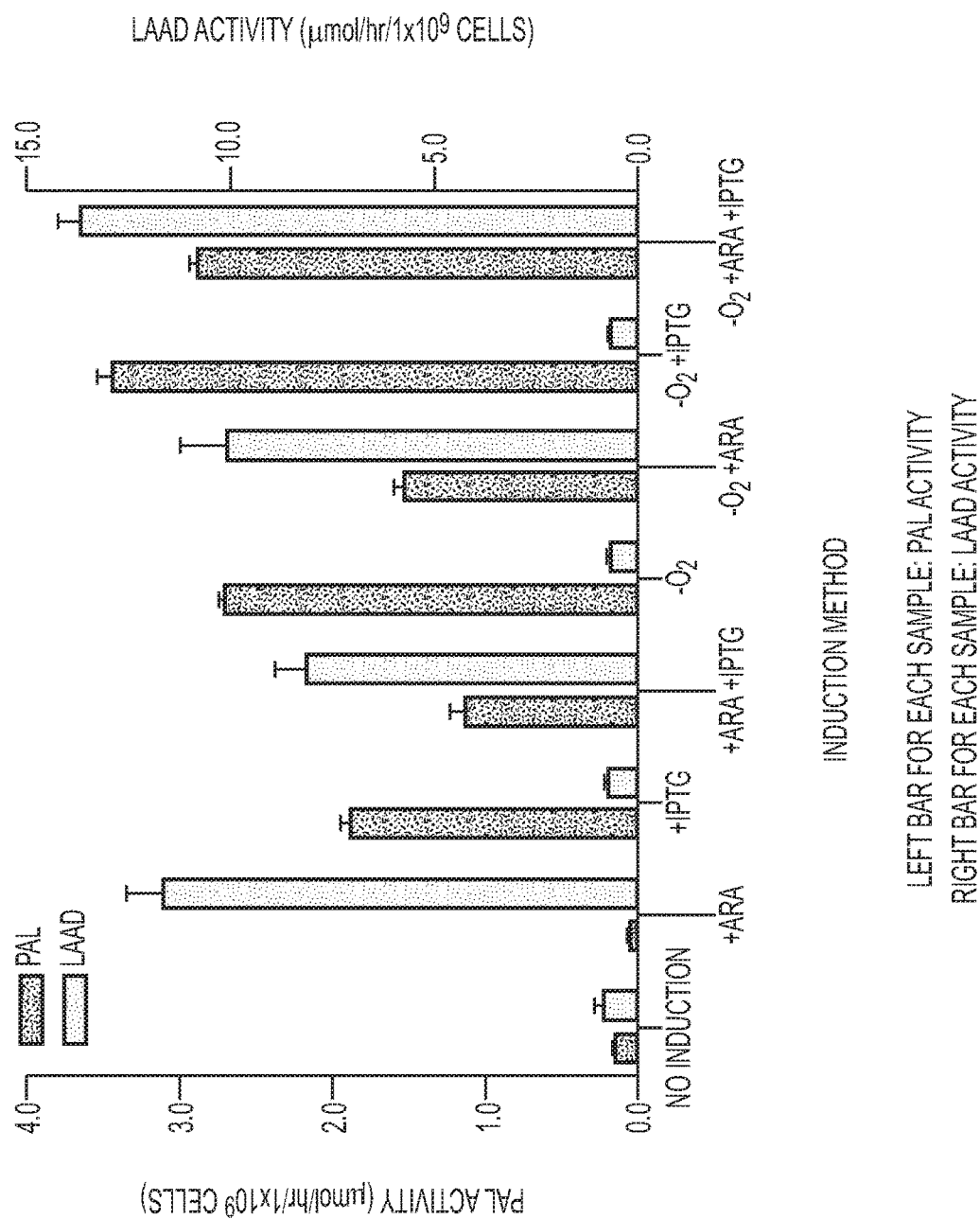
FIG. 29 depicts a graph showing in vitro activity of SYN-PKU-2002. $1 \times 10^8$ activated cells were analyzed in 50 mM Phe assay buffer for PAL (dark blue bars, left y-axis) and LAAD (light blue bars, right y-axis) activity. Cells were pre-induced with L-arabinose (+ara), IPTG (+IPTG) or in an anaerobic chamber ($-O_2$) and rates of TCA and PP were calculated by linear regression of TCA and PP production over time. The graph displays the average and standard deviation of three biological replicates.
Figure 30:
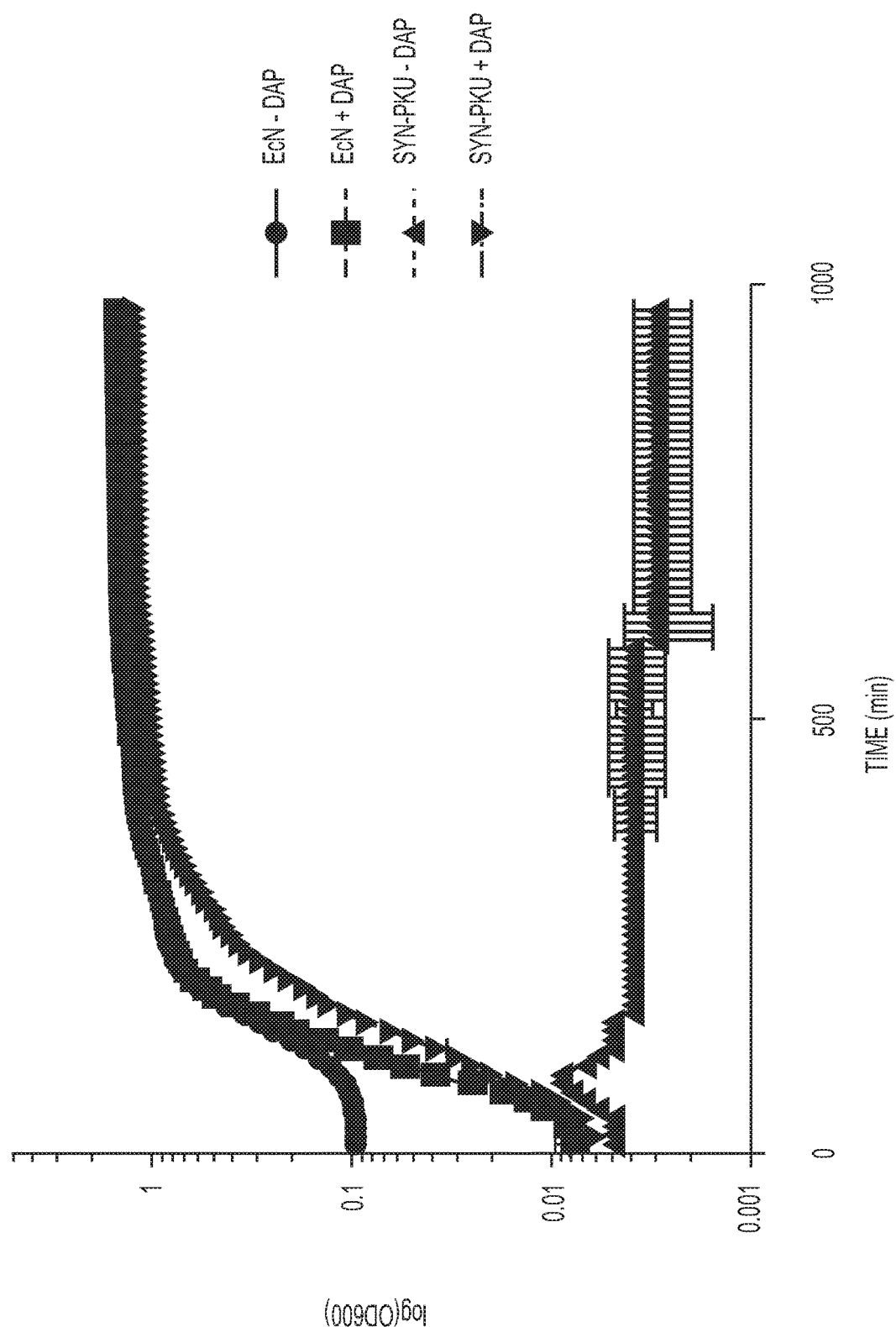
FIG. 30 depicts a graph showing the effect of dapA deletion on SYN-PKU-2002 growth in vitro. To characterize the growth of E. coli Nissle (EcN) and SYN-PKU-2002, which contains a mutation in the dapA gene, both strains were incubated in LB that did (+) or did not (−) contain diaminopimelic acid (DAP; 100 µg/mL) at 37° C. for 960 minutes under constant shaking. The OD600 was measured every 10 minutes to assess cell growth over time. The average of three biological replicates and two technical replicates is plotted for each time point. Data shows that SYN-PKU-2002 is unable to grow without the addition of exogenous DAP to the growth media.

In some embodiments, administration of the genetically engineered bacteria allow for diet liberalization (partial or complete) (see FIG. 28).

Treatment In Vivo

The genetically engineered bacteria of the invention may be evaluated in vivo, e.g., in an animal model. Any suitable animal model of the disease or condition may be used. In some embodiments, the animal model is a mouse model. See e.g. WO2017/087580 A1, the entire contents of which are incorporated by reference in its entirety.

In some embodiments, pharmacokinetics and pharmacodynamic studies may be conducted in non-human primates to determine any potential toxicities arising from administration of the genetically engineered bacteria. Non-limiting examples of such studies are described in Examples 30 and 31.

Screening Methods

In some embodiments, of the disclosure a genetically engineered strain may be improved upon by using screening and selection methods, e.g., to increase activity of an effector (e.g. to increase PME enzymatic activity) or to increase the ability of a strain to take up a metabolite (e.g. increased ability to take up phenylalanine). In some embodiments, the screen serves to generate a bacterial strain with improved effector activity. In some embodiments, the screen serves to generate a bacterial strain which has improved ability to take up a metabolite. In some embodiments, the screen may identify a bacterial strain with both improved effector activity and enhanced substrate import. Non-limiting examples of methods of screening which can be used are described herein.

Generation of Bacterial Strains with Enhance Ability to Transport Biomolecules

In some embodiments, the ALE method can be used to identify genetically engineered bacteria with improved phenylalanine uptake.

Specific Screen to Improve PME Activity

Screens using genetic selection are conducted to improve phenylalanine consumption in the genetically engineered bacteria. Toxic phenylalanine analogs exert their mechanism of action (MOA) by being incorporated into cellular protein, causing cell death. These compounds, such as paralog p-fluoro-DL-phenylalanine and ortholog o-fluoro-DL-phenylalanine have utility in an untargeted approach to select PAL enzymes with increased activity. Assuming that these toxic compounds can be metabolized by PAL into a non-toxic metabolite, rather than being incorporated into cellular protein, genetically engineered bacteria which have improved phenylalanine degradation activity can tolerate higher levels of these compounds and can be screened for and selected on this basis.

REFERENCES

Al Hafid N, Christodoulou J. Phenylketonuria: a review of current and future treatments. Transl Pediatr. 2015 October; 4(4):304-317. PMID: 26835392;

Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-229. PMID: 15039098;

Andersen et al. Uracil uptake in *Escherichia coli* K-12: isolation of uraA mutants and cloning of the gene. J Bacteriol. 1995 April; 177(8):2008-2013. PMID: 7721693;

Arai et al. Expression of the nir and nor genes for denitrification of *Pseudomonas aeruginosa* requires a novel CRP/FNR-related transcriptional regulator, DNR, in addition to ANR. FEBS Lett. 1995 Aug. 28; 371(1):73-76. PMID: 7664887;

Arthur et al. Intestinal inflammation targets cancer-inducing activity of the microbiota. Science. 2012 Oct. 5; 338 (6103):120-123. PMID: 22903521;

Callura et al. Tracking, Tuning and terminating microbial physiology using synthetic riboregulators. Proc Natl Acad Sci USA. 2010; 27(36):15898-15903. PMID: 20713708;

Castiglione et al. The transcription factor DNR from *Pseudomonas aeruginosa* specifically requires nitric oxide and haem for the activation of a target promoter in *Escherichia coli*. Microbiology. 2009 September; 155(Pt 9):2838-2844. PMID: 19477902;

Chang, ed. (2007) "Use of Enzyme Artificial Cells for Genetic Enzyme Defects." In Artificial Cells: Biotechnology, Nanomedicine, Regenerative Medicine, Blood Substitutes, Bioencapsulation, and Cell/Stem Cell Therapy. World Scientific Publishing, pp. 147-159;

Clarkson et al. Diaminopimelic acid and lysine auxotrophs of *Pseudomonas aeruginosa* 8602. J Gen Microbiol. 1971 May; 66(2):161-169. PMID: 4999073;

Cuevas-Ramos et al. *Escherichia coli* induces DNA damage in vivo and triggers genomic instability in mammalian cells. Proc Natl Acad Sci USA. 2010 Jun. 22; 107(25): 11537-11542. PMID: 20534522;

Danino et al. Programmable probiotics for detection of cancer in urine. Sci Transl Med. 2015 May 27; 7(289): 289ra84. PMID: 26019220;

Deutscher. The mechanisms of carbon catabolite repression in bacteria. Curr Opin Microbiol. 2008 April; 11(2):87-93. PMID: 18359269;

Dinleyici et al. *Saccharomyces boulardii* CNCM 1-745 in different clinical conditions. Expert Opin Biol Ther. 2014 November; 14(11):1593-1609. PMID: 24995675;

Dobbelaere et al. Evaluation of nutritional status and pathophysiology of growth retardation in patients with phenylketonuria. J Inherit Metab Dis. 2003; 26(1):1-11. PMID: 12872834;

Eiglmeier et al. Molecular genetic analysis of FNR-dependent promoters. Mol Microbiol. 1989 July; 3(7):869-878. PMID: 2677602;

Estrem et al. Identification of an UP element consensus sequence for bacterial promoters. Proc Natl Acad Sci USA. 1998 Aug. 18; 95(17):9761-9766. PMID: 9707549;

Galimand et al. Positive FNR-like control of anaerobic arginine degradation and nitrate respiration in *Pseudomonas aeruginosa*. J Bacteriol. 1991 March; 173(5):1598-1606. PMID: 1900277;

Gardner et al. Construction of a genetic toggle switch in *Escherichia coli*. Nature. 2000; 403:339-342. PMID: 10659857;

Gerdes et al. Essential genes on metabolic maps. Curr Opin Biotechnol. 2006 October; 17(5):448-456. PMID: 16978855;

Gilbert et al. Molecular cloning of the phenylalanine ammonia lyase gene from Rhodosporidium toruloides in *Escherichia coli* K-12. J Bacteriol. 1985 January; 161(1): 314-320. PMID: 2981805;

Görke B, Stulke J. Carbon catabolite repression in bacteria: many ways to make the most out of nutrients. Nat Rev Microbiol. 2008 August; 6(8):613-624. PMID: 18628769;

Hasegawa et al. Activation of a consensus FNR-dependent promoter by DNR of *Pseudomonas aeruginosa* in response to nitrite. FEMS Microbiol Lett. 1998 Sep. 15; 166(2):213-217. PMID: 9770276;

Hoeks et al. Adult issues in phenylketonuria. Neth J Med. 2009 January; 67(1):2-7. PMID: 19155540;

Hoeren et al. Sequence and expression of the gene encoding the respiratory nitrous-oxide reductase from *Paracoccus denitrificans*. Eur J Biochem. 1993 Nov. 15; 218(1):49-57. PMID: 8243476;

Hosseini et al. Propionate as a health-promoting microbial metabolite in the human gut. Nutr Rev. 2011 May; 69(5): 245-258. PMID: 21521227;

Isabella et al. Deep sequencing-based analysis of the anaerobic stimulon in *Neisseria gonorrhoeae*. BMC Genomics. 2011 Jan. 20; 12:51. PMID: 21251255;

Ivanovska et al. Pediatric drug formulations: a review of challenges and progress. Pediatrics. 2014 August; 134(2): 361-372. PMID: 25022739; Kobe et al. Regulation and crystallization of phosphorylated and dephosphorylated forms of truncated dimeric phenylalanine hydroxylase. Protein Sci. 1997 June; 6(6):1352-1357. PMID: 9194198;

Kwok et al. Nucleotide sequence of a full-length complementary DNA clone and amino acid sequence of human phenylalanine hydroxylase. Biochemistry 1985 Jan. 29; 24(3):556-561. PMID: 2986678;

Leonard J V (2006). Disorders of the urea cycle and related enzymes. Inborn Metabolic Diseases, 4$^{th}$ ed (pp. 263-272). Springer Medizin Verlag Heidelberg;

Longo et al. Phase 1 Trial of Subcutaneous rAvPAL-PEG in Subjects with Phenylketonuria. Lancet. 2014 Jul. 5; 384 (9937):37-44;

Lopez G, Anderson J C. Synthetic Auxotrophs with Ligand-Dependent Essential Genes for a BL21(DE3) Biosafety Strain. ACS Synth Biol. 2015 Dec. 18; 4(12):1279-1286. PMID: 26072987;

Macleod et al. Nutritional Management of Phenylketonuria. Ann Nestle Eng. 2010 June; 68(2):58-69. PMID: 22475869;

Meadow et al. Biosynthesis of diaminopimelic acid and lysine in *Escherichia coli*. Biochem J. 1959 July; 72(3): 396-400. PMID: 16748796;

Miller (1972) Experiments in Molecular Genetics. Cold Spring Harbor Laboratory Press, Cold Spring Harbor, NY;

Moffitt et al. Discovery of two cyanobacterial phenylalanine ammonia lyases: kinetic and structural characterization. Biochemistry. 2007 Jan. 30; 46(4):1004-1012. PMID: 17240984;

Moore et al. Regulation of FNR dimerization by subunit charge repulsion. J Biol Chem. 2006 Nov. 3; 281(44): 33268-33275. PMID: 16959764;

Nougayrede et al. *Escherichia coli* induces DNA double-strand breaks in eukaryotic cells. Science. 2006 Aug. 11; 313(5788):848-51. PMID: 16902142;

Olier et al. Genotoxicity of *Escherichia coli* Nissle 1917 strain cannot be dissociated from its probiotic activity. Gut Microbes. 2012 November-December; 3(6):501-509. PMID: 22895085;

Pi et al. Cloning and sequencing of the pheP gene, which encodes the phenylalanine-specific transport system of *Escherichia coli*. J Bacteriol. 1991 June; 173(12):3622-3629. PMID: 1711024;

Pi et al. Topology of the phenylalanine-specific permease of *Escherichia coli*. J Bacteriol. 1996 May; 178(9):2650-2655. PMID: 8626334;

Pi et al. Functional consequences of changing proline residues in the phenylalanine-specific permease of *Escherichia coli*. J Bacteriol. 1998 November; 180(21):5515-5519. PMID: 9791098;

Purcell et al. Towards a whole-cell modeling approach for synthetic biology. Chaos. 2013 June; 23(2):025112. PMID: 23822510;

Ray et al. The effects of mutation of the anr gene on the aerobic respiratory chain of *Pseudomonas aeruginosa*. FEMS Microbiol Lett. 1997 Nov. 15; 156(2):227-232. PMID: 9513270;

Reister et al. Complete genome sequence of the Gram-negative probiotic *Escherichia coli* strain Nissle 1917. J Biotechnol. 2014 Oct. 10; 187:106-107. PMID: 25093936;

Rembacken et al. Non-pathogenic *Escherichia coli* versus mesalazine for the treatment of ulcerative colitis: a randomised trial. Lancet. 1999 Aug. 21; 354(9179):635-639. PMID: 10466665;

Remington's Pharmaceutical Sciences (2012), 22$^{nd}$ ed. Mack Publishing Co, Easton, PA Salmon et al. Global gene expression profiling in *Escherichia coli* K12. The effects of oxygen availability and FNR. J Biol Chem. 2003 Aug. 8; 278(32):29837-29855. PMID: 12754220;

Sarkissian et al. A different approach to treatment of phenylketonuria: phenylalanine degradation with recombinant phenylalanine ammonia lyase. Proc Natl Acad Sci USA. 1999 Mar. 2; 96(5):2339-2344. PMID: 10051643;

Sat et al. The *Escherichia coli* mazEF suicide module mediates thymineless death. J Bacteriol. 2003 March; 185(6):1803-1807. PMID: 12618443;

Sawers. Identification and molecular characterization of a transcriptional regulator from *Pseudomonas aeruginosa* PAO1 exhibiting structural and functional similarity to the FNR protein of *Escherichia coli*. Mol Microbiol. 1991 June; 5(6):1469-1481. PMID: 1787797;

Schultz. Clinical use of *E. coli* Nissle 1917 in inflammatory bowel disease. Inflamm Bowel Dis. 2008 July; 14(7): 1012-1018. PMID: 18240278;

Sonnenborn et al. The non-pathogenic *Escherichia coli* strain Nissle 1917—features of a versatile probiotic. Microbial Ecology in Health and Disease. 2009; 21:122-158;

Trunk et al. Anaerobic adaptation in *Pseudomonas aeruginosa*: definition of the Anr and Dnr regulons. Environ Microbiol. 2010 June; 12(6):1719-1733. PMID: 20553552;

Ukena et al. Probiotic *Escherichia coli* Nissle 1917 inhibits leaky gut by enhancing mucosal integrity. PLoS One. 2007 Dec. 12; 2(12):e1308. PMID: 18074031;

Unden et al. Alternative respiratory pathways of *Escherichia coli*: energetics and transcriptional regulation in response to electron acceptors. Biochim Biophys Acta. 1997 Jul. 4; 1320(3):217-234. PMID: 9230919;

Vockley et al. Phenylalanine hydroxylase deficiency: diagnosis and management guideline. Genet Med. 2014 February; 16(2):188-200. PMID: 24385074;

Wanner et al. The phenylalanine ammonia-lyase gene family in *Arabidopsis thaliana*. Plant Mol Biol. 1995 January; 27(2):327-338. PMID: 7888622;

Williams et al. The gene stlA encodes a phenylalanine ammonia-lyase that is involved in the production of a stilbene antibiotic in *Photorhabdus luminescens* TT01. Microbiology. 2005 August; 151(Pt 8):2543-2550. PMID: 16079333.

Winteler et al. The homologous regulators ANR of *Pseudomonas aeruginosa* and FNR of *Escherichia coli* have overlapping but distinct specificities for anaerobically inducible promoters. Microbiology. 1996 March; 142 (Pt 3):685-693. PMID: 8868444;

Wright et al. GeneGuard: A Modular Plasmid System Designed for Biosafety. ACS Synth Biol. 2015 Mar. 20; 4(3):307-316. PMID: 24847673;

Wu et al. Direct regulation of the natural competence regulator gene tfoX by cyclic AMP (cAMP) and cAMP receptor protein in Vibrios. Sci Rep. 2015 Oct. 7; 5:14921. PMID: 26442598;

Xiang L, Moore B S. Biochemical characterization of a prokaryotic phenylalanine ammonia lyase. J Bacteriol. 2005 June; 187(12):4286-4289. PMID: 15937191;

Zhang R, Lin Y. DEG 5.0, a database of essential genes in both prokaryotes and eukaryotes. Nucleic Acids Res. 2009 January; 37(Database issue):D455-D458. PMID: 18974178;

Zimmermann et al. Anaerobic growth and cyanide synthesis of *Pseudomonas aeruginosa* depend on anr, a regulatory gene homologous with fnr of *Escherichia coli*. Mol Microbiol. 1991 June; 5(6):1483-1490. PMID: 1787798.

EXAMPLES

Example 3. Metabolite Measurements

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Phenylalanine Quantification (Dansyl-Chloride Derivatization)

For in vitro and in vivo assays described herein, which assess the ability of the genetically engineered bacteria to degrade phenylalanine and which require quantification of phenylalanine levels in the sample, a dansyl-chloride derivatization protocol was employed as described in co-owned, pending International Patent Applications PCT/US2016/032562, filed May 13, 2016 and PCT/US2016/062369, the contents of each of which is herein incorporated by reference in its entirety.

Trans-Cinnamic Acid Quantification (Trifluoroethylamine Derivatization)

For in vitro and in vivo assays described herein, which assess the ability of the genetically engineered bacteria to degrade phenylalanine and which require quantification of Trans-cinnamic acid levels in the sample, a trifluoroethylamine derivatization protocol was employed as as described in co-owned, pending PCT/US2016/032562, filed May 13, 2016 and PCT/US2016/062369, the contents of each of which is herein incorporated by reference in its entirety.

Phenylalanine, Trans-Cinnamic Acid, Phenylacetic Acid, Phenylpyruvic Acid, Phenyllactic Acid, Hippuric Acid and Benzoic Acid Quantification (2-Hydrazinoquinoline Derivatization)

For in vitro and in vivo assays described herein, which assess the ability of the genetically engineered bacteria to degrade phenylalanine and which require quantification of phenylalanine, trans-cinnamic acid, phenylacetic acid, phenylpyruvic acid, phenyllactic acid, hippuric acid, and benzoic acid levels in the sample, a 2-Hydrazinoquinoline derivatization protocol was employed as as described in co-owned, pending International Patent Applications PCT/US2016/032562, filed May 13, 2016 and PCT/US2016/062369, the contents of each of which is herein incorporated by reference in its entirety.

Hippuric Acid, Trans-Cinnamic Acid, Phenylalanine, and Phenylpyruvate Quantification in Plasma and Urine by LC-MS/MS Hippuric acid, Trans-cinnamic acid, Phenylalanine, and Phenylpyruvate Quantification in Plasma and Urine by LC-MS/MS were measured as described in in co-owned, pending International Patent Applications PCT/US2016/032562, filed May 13, 2016 and PCT/US2016/062369, the contents of each of which is herein incorporated by reference in its entirety.

Examples 1-55 of PCT/US2016/062369, filed Nov. 16, 2016, the contents of each of which is herein incorporated by reference in its entierety describe the construction and activity of various Phe consuming strains.

Example 27. In Vitro Activity of SYN-PKU-710

SYN-PKU-710 is an engineered bacterium derived from *Escherichia coli* Nissle 1917 (EcN) (ref) that has been designed to treat hyperphenylalaninemia by consuming and converting phenylalanine to the non-toxic metabolites trans-cinnamate (TCA) and phenylpyruvate (PP). It works by intercepting and degrading phenylalanine found in the intestine, which decreases the flux of phenylalanine into the blood. SYN-PKU-710 was created by a series of genetic manipulations that allowed for the degradation of phenylalanine in the microaerobic (low oxygen) environment of the human gut. The following modifications to the genome of EcN have been made to enhance phenylalanine degradation under the low oxygen conditions found in the gut while augmenting biologic containment through diaminopimelate auxotrophy:

a. Insertion of two additional copies of an endogenous Nissle gene encoding a high affinity phenylalanine transporter (PheP) under the regulatory control of an anaerobic-inducible promoter (PfnrS) and the anaerobic-responsive transcriptional activator FNR
b. Insertion of three copies of a gene encoding phenylalanine ammonia lyase (PAL) derived from *Photorhabdus luminescens* under the regulatory control of PfnrS and FNR
c. Insertion of two additional copies of the gene encoding PAL under the regulatory control of a synthetic promoter (Plac) and the lactose-responsive transcriptional repressor LacI
d. Insertion of the gene encoding L-amino acid deaminase (LAAD) derived from *Proteus mirabilis* under the regulatory control of the arabinose-inducible promoter (PBAD) and the arabinose-responsive transcriptional activator AraC
e. Deletion of the dapA gene that encodes 4-hydroxy-tetrahydropicolinate synthase to create a diaminopimelate auxotroph SYN-PKU-710 was derived from EcN in a series of genetic manipulations designed to allow degradation of phenylalanine in the microaerobic (low oxygen) environment of the human gut. Genomic insertions of two additional copies of the endogenous gene encoding PheP, a high affinity phenylalanine transporter, were made within the EcN chromosome. This transporter allows the uptake of environmental phenylalanine into the bacterial cell. In addition, three copies of a gene encoding phenylalanine ammonia lyase (PAL), derived from the organism *Photorhabdus luminescens*, were chromosomally integrated. PAL catalyzes the conversion of phenylalanine into the non-toxic product trans-cinnamate. The genes encoding PheP and PAL were placed under the regulatory control of an anaerobic-inducible promoter (PfnrS) and the anaerobic-responsive transcriptional activator FNR. These regulatory components ensure that phenylalanine degradation machinery are produced in the anoxic environment of the human gut. Additional copies of the gene encoding PAL were inserted into the Nissle chromosome under the control of a synthetic promoter (Plac) and the LacI transcriptional repressor. These copies may be induced for expression when lactose or a lactose analog is used to alleviate transcriptional repression, and are envisioned to be utilized for the induction of phenylalanine degradation activity during the production of drug material. In this manner, initial strain potency from LacI-mediated induction will allow for immediate activity upon SYN-PKU-710 administration, while PfnrS-mediated induction will allow for de novo potency induction post-administration. A second pathway of phenylalanine degradation in SYN-PKU-710 was introduced through the chromosomal insertion of the gene encoding L-amino acid deaminase (LAAD), derived from the organism *Proteus mirabilis*, which converts phenylalanine into phenylpyruvate in the presence of oxygen. This gene was inserted downstream of the endogenous Nissle araC gene in a manner that allows the expression of LAAD to be induced by AraC in response to arabinose during production of drug material. The activity of PAL and LAAD have shown to be additive. The inclusion of LAAD is a mechanism to capitalize on the available oxygen expected to be found in greater abundance in the proximal GI tract.

SYN-PKU-710 was also modified with a deletion of the diaminopimelate (dapA) gene that encodes 4-hydroxy-tetrahydropicolinate synthase, which is essential for bacterial growth. This deletion renders SYN-PKU-710 unable to synthesize diaminopimelate, thereby preventing the proper formation of bacterial cell wall unless the strain is supplemented with diaminopimelate exogenously. For external manufacturing purposes, SYN-PKU-710 was also modified with a deletion of a portion of its endogenous prophage (0) which removes its ability to express phage particles. The strain comprising the deletion of a portion of its endogenous prophage is referred to herein as SYN-PKU-2002.

Sequences and additional details relating toe SYN-PKU-710 are described in International Patent Applications PCT/US2016/032562, filed May 13, 2016 and PCT/US2016/062369, filed Nov. 16, 2016, the contents of each of which are herein incorporated by reference in their entireties.

To measure in vitro activity, overnight cultures were diluted 1:100 in LB and grown with shaking (250 rpm) at 37° C. After 1.5 hrs of growth, cultures were placed in a Coy anaerobic chamber supplying 90% $N_2$, 5% $CO_2$, 5% H2. After 4 hrs of induction, bacteria were pelleted, washed in PBS, and resuspended in assay buffer (M9 minimal media with 0.5% glucose, 8.4% sodium bicarbonate, and 4 mM Phe). Rates of phenylalanine degradation (i.e., disappearance from the assay solution) or cinnamate accumulation from 30 to 90 min were normalized to 1e9 cells. Table 59 shows the normalized rates for all strains and describes genotypes and the activities of non-limiting examples of engineered plasmid-bearing strains and engineered strains comprising chromosomal insertions.

TABLE 59

Genotype and Activity of engineered plasmid-bearing strains and engineered strains comprising chromosomal insertions.

| Strain Name | Genotype | PAL Activity (umol/hr./10^9 cells) | LAAD activity (umol/hr./10^9 cells) |
|---|---|---|---|
| | Plasmid-based strains | | |
| SYN-PKU101 | Low copy pSC101-Ptet::PAL1, ampicillin resistant | ND | NA |
| SYN-PKU102 | High copy pColE1-Ptet::PAL1, ampicillin resistant, | ND | NA |
| SYN-PKU201 | Low copy pSC101-Ptet::PAL3, ampicillin resistant | ND | NA |
| SYN-PKU202 | High copy pColE1-Ptet::PAL3, ampicillin resistant, | ND | NA |
| SYN-PKU203 | lacZ::Ptet-pheP::cam | 0 | NA |
| SYN-PKU401 | Low copy pSC101-Ptet::PAL1, ampicillin resistant, chromosomal lacZ::Ptet-pheP::cam | 1.1 | NA |
| SYN-PKU402 | High copy pColE1-Ptet::PAL1, ampicillin resistant, chromosomal lacZ::Ptet-pheP::cam | 0.8 | NA |

TABLE 59-continued

Genotype and Activity of engineered plasmid-bearing strains and engineered strains comprising chromosomal insertions.

| Strain Name | Genotype | PAL Activity (umol/hr./10^9 cells) | LAAD activity (umol/hr./10^9 cells) |
|---|---|---|---|
| SYN-PKU302 | Low Copy pSC101-Ptet::PAL3, ampicillin resistant; chromosomal lacZ::Ptet-pheP::cam | 2.2 | NA |
| SYN-PKU303 | High copy pColE1-Ptet::PAL3, ampicillin resistant, chromosomal lacZ::Ptet-pheP::cam | 7.1 | NA |
| SYN-PKU304 | Low Copy pSC101-PfnrS-PAL3, ampicillin resistant; chromosomal lacZ::PfnrS-pheP::cam | 3 | NA |
| SYN-PKU305 | Low Copy pSC101-PfnrS-PAL3, kanamycin resistant; chromosomal lacZ::PfnrS-pheP::cam | 3 | NA |
| SYN-PKU306 | Low Copy pSC101-PfnrS-PAL3, kanamycin resistant; thyA | 0.3 | NA |
| SYN-PKU307 | Low Copy pSC101-PfnrS-PAL3, ampicillin resistant; | 0.3 | NA |
| SYN-PKU308 | Low Copy pSC101-PfnrS-PAL3, kanamycin resistant; | 0.3 | NA |
| SYN-PKU401 | High Copy pUC57-Ptet::LAAD; kanamycin resistant | NA | 50 ($^+O_2$), 0 ($^-O_2$) |
| Integrated strains | | | |
| SYN-PKU501 | malPT:: PfnrS-PAL3::kan | 0.3 | NA |
| SYN-PKU502 | malPT:: PfnrS-PAL3::kan; bicistronic lacZ:: PfnrS-PAL3-pheP::cam | ND | NA |
| SYN-PKU503 | malEK::PfnrS-PAL3::cam | 0.3 | NA |
| SYN-PKU504 | agaI/rsmI::PfnrS-PAL3 | 0.3 | NA |
| SYN-PKU505 | cea::PfnrS-PAL3 | 0.3 | NA |
| SYN-PKU506 | malEK::PfnrS-PAL3::agaI/rsmI::PfnrS-PAL3; cea::PfnrS-PAL3 | 0.7 | NA |
| SYN-PKU507 | malEK:: PfnrS-PAL3; agaI/rsmI::PfnrS-PAL3; cea::PfnrS-PAL3; lacZ::PfnrS-pheP::cam | 5.2 | NA |
| SYN-PKU508 | malEK::PfnrS-PAL3; pheA auxotroph | 0.4 | NA |
| SYN-PKU509 | malEK::PfnrS-PAL3; agaI/rsmI::PfnrS-PAL3; cea::PfnrS-PAL3; lacZ::PfnrS-pheP::cam | 4.9 | NA |
| SYN-PKU601 | malPT::PfrnS::INT5::kan, rrnBUP -[PAL3]; lacZ::PfnrS-pheP::cam (recombinase based strain) | 0.9 | NA |
| SYN-PKU510 | malEK::PfnrS-PAL3; agaI/rsmI::PfnrS-PAL3; cea::PfnrS-PAL3; | 0.6 | NA |
| SYN-PKU511 | malEK:: PfnrS-PAL3; agaI/rsmI::PfnrS-PAL3; cea::PfnrS-PAL3; yicS/nepI::PfnrS-PAL3::kan; malPT::PfnrS-PAL3; lacZ::PfnrS-pheP; ΔthyA | 7.7 | NA |
| SYN-PKU204 | lacZ::PfnrS -pheP::cam | ND | NA |
| SYN-PKU512 | malEK::PfnrS-PAL3; agaI/rsmI::PfnrS-PAL3; cea::PfnrS-PAL3; malPT::PfnrS-PAL3; lacZ::PfnrS-pheP::cam; ΔthyA | 6.7 | NA |
| SYN-PKU513 | malEK:: PfnrS-PAL3; agaI/rsmI::PfnrS-PAL3; cea::PfnrS-PAL3; lacZ::PfnrS-pheP; ΔthyA | 4.9 | NA |
| SYN-PKU514 | malEK:: PfnrS-PAL3; agaI/rsmI::PfnrS-PAL3; cea::PfnrS-PAL3; malPT::PfnrS-PAL3:: ΔthyA | 0.8 | NA |
| SYN-PKU515 | malEK:: PfnrS-PAL3; agaI/rsmI::PfnrS-PAL3; cea::PfnrS-PAL3; ΔthyA | 0.7 | NA |
| SYN-PKU516 | agaI/rsmI::PfnrS-PAL3::kan | 0.3 | NA |
| SYN-PKU517 | malEK:: PfnrS-PAL3::cam; malPT::PfnrS-PAL3::kan, lacZ::PfnrS-pheP; ΔthyA | 2.9 | NA |
| SYN-PKU518 | malEK-PfnrS-PAL3::cam; PfnrS::pheP::kan | 1.7 | NA |
| SYN-PKU519 | ParaBC-PAL3::cam; PfnrS-pheP::kan | 1.3 | NA |
| SYN-PKU520 | agaI/rsmI::PfnrS-PAL3::kan; PfnrS-PheP::cam | 2.0 | NA |
| SYN-PKU801 | ΔargR; thyA::cam | ND | NA |
| SYN-PKU701 | ParaBC-LAAD::cam; malEK-PfnrS-PAL3; malPT::PfnrS-PAL3::kan; PfnrS-pheP | 2.7 | 28 ($^+O_2$), 0 ($^-O_2$) |
| SYN-PKU521 | yicS/nepI::PfnrS-PAL3::kan; lacZ::PfnrS-pheP::cam | 2.4 | NA |
| SYN-PKU522 | cea::PfnrS-PAL3::kan; lacZ::PfnrS-pheP::cam | ND | NA |
| SYN-PKU523 | malPT::PfrnS-PAL3::kan; lacZ::PfnrS-pheP::cam | 0.5 | NA |
| SYN-PKU524 | malEK:: PfnrS-PAL3; malPT::PfnrS-PAL3; lacZ::PfnrS-pheP | 2.9 | NA |
| SYN-PKU702 | malEK:: PfnrS-PAL3; lacZ::PfnrS-pheP; Para::LAAD | 1.5 | ND |
| SYN-PKU703 | malEK:: PfnrS-PAL3; malPT::PfnrS-PAL3; lacZ::PfnrS-pheP; agaI/rsmI::PfnrS::pheP; Para::LAAD | 3.1 | ND |

TABLE 59-continued

Genotype and Activity of engineered plasmid-bearing strains and engineered strains comprising chromosomal insertions.

| Strain Name | Genotype | PAL Activity (umol/hr./10^9 cells) | LAAD activity (umol/hr./10^9 cells) |
|---|---|---|---|
| SYN-PKU704 | malEK:: PfnrS-PAL3; malPT::PfnrS-PAL3; yicS/nepI::PfnrS-PAL3; lacZ::PfnrS-pheP; Para::LAAD | 3.5 | ND |
| SYN-PKU705 | malEK:: PfnrS-PAL3; malPT::PfnrS-PAL3; yicS/nepI::PfnrS-PAL3::kan; lacZ::PfnrS-pheP; agaI/rsmI::PfnrS::pheP Para::LAAD | 3.7 | ND |
| SYN-PKU602 | malEK:: PT7::PAL3; Para::INT5::cam (recombinase); lacZ::PfnrS-pheP; malPT::Pconstitutive::T7 polymerase (unflipped); | 2.4 | NA |
| SYN-PKU901 | Nissle with streptomycin resistance | NA | NA |
| SYN-PKU713 | LacZ::PfnrS-PAL3::pheP | NA | NA |
| SYN-PKU706 | malEK::PfnrS-PAL3; malPT::PfnrS-PAL3; yicS/nepI:: PfnrS-PAL3; lacZ::PfnrS-pheP, agaI/rsmI::PfnrS-pheP; Para::LAAD, ΔthyA::cm | ND | ND |
| SYN-PKU707 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y::cm | 4.0 | NA |
| SYN-PKU708 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y-LAAD; ΔdapA | 4.0 | 44 (+O2), 0 (-O2) |
| SYN-PKU-709 | malEK:: PfnrS-PAL3; malPT::PfnrS-PAL3; yicS/nepI:: PfnrS-PAL3; lacZ::PfnrS-pheP, agaI/rsmI::PfnrS-pheP; Para-LAAD; ΔdapA | ND | NA |
| SYN-PKU-710 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB::LacIPAL3; ΔdapA | 4.4 | 40 (+O2), 0 (-O2) |
| SYN-PKU711 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y-LAAD; | ND | ND |
| SYN-PKU-712 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::FNRS24Y; ΔDapA | ND | ND |
| SYN-PKU-714 | lacZ::PfnrS-pheP, agaI/rsmI::PfnrS-pheP | ND | ND |

| Description | Sequence | SEQ ID NO |
|---|---|---|
| FNRS24Y (bold) driven by the arabinose inducible promoter (underlined) and araC in reverse direction (italic). RBS is underlined and bolded (see FIG. 48A of WO2017087580) | TTATTCACAACCTGCCCTAAACTCGCTCGGACTCGCCCCGGTGCATT TTTTAAATACTCGCGAGAAATAGAGTTGATCGTCAAAACCGACATTG CGACCGACGGTGGCGATAGGCATCCGGGTGGTGCTCAAAAGCAGC TTCGCCTGACTGATGCGCTGGTCCTCGCGCCAGCTTAATACGCTAAT CCCTAACTGCTGGCGGAACAAATGCGACAGACGCGACGGCGACAG GCAGACATGCTGTGCGACGCTGGCGATATCAAAATTACTGTCTGCC AGGTGATCGCTGATGTACTGACAAGCCTCGCGTACCCGATTATCCAT CGGTGGATGGAGCGACTCGTTAATCGCTTCCATGCGCGCAGTAAC AATTGCTCAAGCAGATTTATCGCCAGCAATTCCGAATAGCGCCCTTC CCCTTGTCCGGCATTAATGATTTGCCCAAACAGGTCGCTGAAATGCG GCTGGTGCGCTTCATCCGGGCGAAAGAAACCGGTATTGGCAAATAT CGACGGCCAGTTAAGCCATTCATGCCAGTAGGCGCGCGGACGAAA GTAAACCCACTGGTGATACCATTCGTGAGCCTCCGGATGACGACCG TAGTGATGAATCTCTCAGGCGGGAACAGCAAATATCACCCGGTC GGCAGACAAATTCTCGTCCCTGATTTTTCACCACCCCTGACCGCGA ATGGTGAGATTGAGAATATAACCTTTCATTCCCAGCGGTCGGTCGAT AAAAAATCGAGATAACCGTTGGCCTCAATCGGCGTTAAACCCGCCA CCAGATGGGCGTTAAACGAGTATCCCGGCAGCAGGGGATCATTTTG CGCTTCAGCCATACTTTTCATACTCCCGCCATTCAGAGAAGAAACCA ATTGTCCATATTGCATCAGACATTGCCGTCACTGCGTCTTTTACTG GCTCTTCTCGCTAACCCAACCGGTAACCCCGCTTATTAAAAGCA TTCTGTAACAAAGCGGGACCAAAGCCATGACAAAAACGCGTAA CAAAAGTGTCTATAATCACGGCAGAAAAGTCCACATTGATTATT TGCACGGCGTCACACTTTGCTATGCCATAGCATTTTTATCCATA AGATTAGCGGATCCAGCCTGACGCTTTTTTTCGCAACTCTCTAC | 64 |

| Description | Sequence | SEQ ID NO |
|---|---|---|
| | TGTTTCTCCATACCTCTAGAAATAATTTTGTTTAACTTTAAGA<br>AGGAGATATACATATGATCCCGGAAAAGCGAATTATACGGC<br>GCATTCAGTCTGGCGGTTGTGCTATCCATTGCCAGGATTGC<br>TATATCAGCCAGCTTTGCATCCCGTTCACACTCAACGAACAT<br>GAGCTTGATCAGCTTGATAATATCATTGAGCGGAAGAAGCC<br>TATTCAGAAAGGCCAGACGCTGTTTAAGGCTGGAGATGAAC<br>TTAAATCGCTTTATGCCATCCGCTCCGGTACGATTAAAAGTT<br>ATACCATCACTGAGCAAGGCGACGAGCAAATCACTGGTTTC<br>CATTTAGCAGGCGATCTGGTGGGATTTGATGCCATCGGCAG<br>CGGTCATCACCCGAGTTTCGCGCAGGCGCTGGAAACCTCGA<br>TGGTATGTGAAATCCCGTTCGAAACGCTGGACGATTTGTCT<br>GGTAAAATGCCGAATCTGCGTCAGCAGATGATGCGTCTGAT<br>GAGCGGTGAAATCAAAGGCGATCAGGACATGATCCTGCTGT<br>TGTCGAAGAAAAATGCCGAGGAACGTCTGGCTGCATTCATC<br>TACAACCTGTCCCGTCGTTTTGCCCAACGCGGCTTCTCCCCT<br>CGTGAATTCCGCCTGACGATGACTCGTGGTGATATCGGTAA<br>CTATCTGGGCCTGACGGTTGAAACCATCAGCCGTCTGCTGG<br>GTCGCTTCCAGAAAAGCGGTATGCTGGCAGTCAAAGGTAAA<br>TACATCACTATCGAAAATAACGATGCGCTGGCCCAGCTTGC<br>TGGTCATACGCGTAACGTTGCCTGA | |
| FNRS24Y | ATGATCCCGGAAAAGCGAATTATACGGCGCATTCAGTCTGGCG<br>GTTGTGCTATCCATTGCCAGGATTGCTATATCAGCCAGCTTTGC<br>ATCCCGTTCACACTCAACGAACATGAGCTTGATCAGCTTGATAA<br>TATCATTGAGCGGAAGAAGCCTATTCAGAAAGGCCAGACGCTG<br>TTTAAGGCTGGAGATGAACTTAAATCGCTTTATGCCATCCGCTC<br>CGGTACGATTAAAAGTTATACCATCACTGAGCAAGGCGACGAG<br>CAAATCACTGGTTTCCATTTAGCAGGCGATCTGGTGGGATTTGA<br>TGCCATCGGCAGCGGTCATCACCCGAGTTTCGCGCAGGCGCTGG<br>AAACCTCGATGGTATGTGAAATCCCGTTCGAAACGCTGGACGA<br>TTTGTCTGGTAAAATGCCGAATCTGCGTCAGCAGATGATGCGTC<br>TGATGAGCGGTGAAATCAAAGGCGATCAGGACATGATCCTGCT<br>GTTGTCGAAGAAAAATGCCGAGGAACGTCTGGCTGCATTCATCT<br>ACAACCTGTCCCGTCGTTTTGCCCAACGCGGCTTCTCCCCTCGT<br>GAATTCCGCCTGACGATGACTCGTGGTGATATCGGTAACTATCT<br>GGGCCTGACGGTTGAAACCATCAGCCGTCTGCTGGGTCGCTTCC<br>AGAAAAGCGGTATGCTGGCAGTCAAAGGTAAATACATCACTAT<br>CGAAAATAACGATGCGCTGGCCCAGCTTGCTGGTCATACGCGT<br>AACGTTGCCTGA | 65 |
| AraC (reverse orientation) | TTATTCACAACCTGCCCTAAACTCGCTCGGACTCGCCCCGGTGC<br>ATTTTTTAAATACTCGCGAGAAATAGAGTTGATCGTCAAAACCG<br>ACATTGCGACCGACGGTGGCGATAGGCATCCGGGTGGTGCTCA<br>AAAGCAGCTTCGCCTGACTGATGCGCTGGTCCTCGCGCCAGCTT<br>AATACGCTAATCCCTAACTGCTGGCGGAACAAATGCGACAGAC<br>GCGACGGCGACAGGCAGACATGCTGTGCGACGCTGGCGATATC<br>AAAATTACTGTCTGCCAGGTGATCGCTGATGTACTGACAAGCCT<br>CGCGTACCCGATTATCCATCGGTGGATGGAGCGACTCGTTAATC<br>GCTTCCATGCGCCGCAGTAACAATTGCTCAAGCAGATTTATCGC<br>CAGCAATTCCGAATAGCGCCCTTCCCCTTGTCCGGCATTAATGA<br>TTTGCCCAAACAGGTCGCTGAAATGCGGCTGGTGCGCTTCATCC<br>GGGCGAAAGAAACCGGTATTGGCAAATATCGACGGCCAGTTAA<br>GCCATTCATGCCAGTAGGCGCGCGGACGAAAGTAAACCCACTG<br>GTGATACCATTCGTGAGCCTCCGGATGACGACCGTAGTGATGA<br>ATCTCTCCAGGCGGGAACAGCAAAATATCACCCGGTCGGCAGA<br>CAAATTCTCGTCCCTGATTTTTCACCACCCCTGACCGCGAATG<br>GTGAGATTGAGAATATAACCTTTCATTCCCAGCGGTCGGTCGAT<br>AAAAAAATCGAGATAACCGTTGGCCTCAATCGGCGTTAAACCC<br>GCCACCAGATGGGCGTTAAACGAGTATCCCGGCAGCAGGGGAT<br>CATTTTGCGCTTCAGCCATACTTTTCATACTCCCGCCATTCAGAG<br>AAGAAACCAATTGTCCATATTGCAT | 66 |
| Promoter region | CAGACATTGCCGTCACTGCGTCTTTTACTGGCTCTTCTCGCTAAC<br>CCAACCGGTAACCCCGCTTATTAAAAGCATTCTGTAACAAAGCG<br>GGACCAAAGCCATGACAAAAACGCGTAACAAAAGTGTCTATAA<br>TCACGGCAGAAAAGTCCACATTGATTATTTGCACGGCGTCACAC<br>TTTGCTATGCCATAGCATTTTTATCCATAAGATTAGCGGATCCA<br>GCCTGACGCTTTTTTTCGCAACTCTCTACTGTTTCTCCATACCTC<br>TAGAAATAATTTTGTTTAACTTTAAGAAGGAGATATACAT | 67 |
| RBS and Leader Region | CTCTAGAAATAATTTTGTTTAACTTTAAGAAGGAGATATACAT | 68 |
| FNRS24Y Polypeptide | MIPEKRIIRRIQSGGCAIHCQDCYISQLCIPFTLNEHELDQLDNIIERK<br>KPIQKGQTLFKAGDELKSLYAIRSGTIKSYTITEQGDEQITGFHLAG | 69 |

| Description | Sequence | SEQ ID NO |
|---|---|---|
| | DLVGFDAIGSGHHPSFAQALETSMVCEIPFETLDDLSGKMPNLRQQ<br>MMRLMSGEIKGDQDMILLLSKKNAEERLAAFIYNLSRRFAQRGFS<br>PREFRLTMTRGDIGNYLGLTVETISRLLGRFQKSGMLAVKGKYITIE<br>NNDALAQLAGHTRNVA | |
| AraC polypeptide | MQYGQLVSSLNGGSMKSMAEAQNDPLLPGYSFNAHLVAGLTPIE<br>ANGYLDFFIDRPLGMKGYILNLTIRGQGVVKNQGREFVCRPGDILL<br>FPPGEIHHYGRHPEAHEWYHQWVYFRPRAYWHEWLNWPSIFANT<br>GFFRPDEAHQPHFSDLFGQIINAGQGEGRYSELLAINLLEQLLLRRM<br>EAINESLHPPMDNRVREACQYISDHLADSNFDIASVAQHVCLSPSR<br>LSHLFRQQLGISVLSWREDQRISQAKLLLSTTRMPIATVGRNVGFD<br>DQLYFSRVFKKCTGASPSEFRAGCE* | 70 |
| Wild Type FNR | ATGATCCCGGAAAAGCGAATTATACGGCGCATTCAGTCTGGCG<br>GTTGTGCTATCCATTGCCAGGATTGCACGATCAGCCAGCTTTGC<br>ATCCCGTTCACACTCAACGAACATGAGCTTGATCAGCTTGATAA<br>TATCATTGAGCGGAAGAAGCCTATTCAGAAAGGCCAGACGCTG<br>TTTAAGGCTGGAGATGAACTTAAATCGCTTTATGCCATCCGCTC<br>CGGTACGATTAAAAGTTATACCATCACTGAGCAAGGCGACGAG<br>CAAATCACTGGTTTCCATTTAGCAGGCGATCTGGTGGGATTTGA<br>TGCCATCGGCAGCGGTCATCACCCGAGTTTCGCGCAGGCGCTGG<br>AAACCTCGATGGTATGTGAAATCCCGTTCGAAACGCTGGACGA<br>TTTGTCTGGTAAAATGCCGAATCTGCGTCAGCAGATGATGCGTC<br>TGATGAGCGGTGAAATCAAAGGCGATCAGGACATGATCCTGCT<br>GTTGTCGAAGAAAAATGCCGAGGAACGTCTGGCTGCATTCATCT<br>ACAACCTGTCCCGTCGTTTTGCCCAACGCGGCTTCTCCCCTCGT<br>GAATTCCGCCTGACGATGACTCGTGGTGATATCGGTAACTATCT<br>GGGCCTGACGGTTGAAACCATCAGCCGTCTGCTGGGTCGCTTCC<br>AGAAAAGCGGTATGCTGGCAGTCAAAGGTAAATACATCACTAT<br>CGAAAATAACGATGCGCTGGCCCAGCTTGCTGGTCATACGCGT<br>AACGTTGCCTGA | 71 |
| Wild Type FNR polypeptide | MIPEKRIIRRIQSGGCAIHCQDCSISQLCIPFTLNEHELDQLDNIIERK<br>KPIQKGQTLFKAGDELKSLYAIRSGTIKSYTITEQGDEQITGFHLAG<br>DLVGFDAIGSGHHPSFAQALETSMVCEIPFETLDDLSGKMPNLRQQ<br>MMRLMSGEIKGDQDMILLLSKKNAEERLAAFIYNLSRRFAQRGFS<br>PREFRLTMTRGDIGNYLGLTVETISRLLGRFQKSGMLAVKGKYITIE<br>NNDALAQLAGHTRNVA | 72 |

TABLE 77

Biosafety System Constructs and Sequence Components

| Description | Sequence | SEQ ID NO |
|---|---|---|
| Biosafety Plasmid System Component- dap A Biosafety Plasmid System Vector sequences, comprising dapA, Kid Toxin and R6K minimal ori, and promoter elements driving expression of these components, as shown in FIG. 61A of WO2017087580, | ACTCTTCCTTTTTCAATATTATTGAAGCATTTATCAGGGT<br>TATTGTCTCATGAGCGGATACATATTTGAATGTATTTAG<br>AAAAATAAACAAATAGGGGAATTAAAAAAAAGCCCGCT<br>CATTAGGCGGGCTACTACCTAGGCCGCGGCCGCGCGAAT<br>TCGAGCTCGGTACCCGGGGATCCTCTAGAGTCGACCTGC<br>AGGCATGCAAGCTTGCGGCCGCGTCGTGACTGGGAAAA<br>CCCTGGCGACTAGTCTTGGACTCCTGTTGATAGATCCAG<br>TAATGACCTCAGAACTCCATCTGGATTTGTTCAGAACGC<br>TCGGTTGCCGCCGGGCGTTTTTTATTGGTGAGAATCCAG<br>GGGTCCCCAATAATTACGATTTAAATCACAGCAAACACC<br>ACGTCGGCCCTATCAGCTGCGTGCTTTCTATGAGTCGTTG<br>CTGCATAACTTGACAATTAACATCCGGCTCGTAGGGTTT<br>GTGGAGGGCCCAAGTTCACTTAAAAAGGAGATCAACAA<br>TGAAAGCAATTTTCGTACTGAAACATCTTAATCATGCTG<br>GGGAGGGTTTCTAATGTTCACGGGAAGTATTGTCGCGAT<br>TGTTACTCCGATGGATGAAAAAGGTAATGTCTGTCGGGC<br>TAGCTTGAAAAAACTGATTGATTATCATGTCGCCAGCGG<br>TACTTCGGCGATCGTTTCTGTTGGCACCACTGGCGAGTC<br>CGCTACCTTAAATCATGACGAACATGCTGATGTGGTGAT<br>GATGACGCTGGATCTGGCTGATGGGCGCATTCCGGTAAT<br>TGCCGGGACCGGCGCTAACGCTACTGCGGAAGCCATTAG<br>CCTGACGCAGCGCTTCAATGACAGTGGTATCGTCGGCTG<br>CCTGACGGTAACCCCTTACTACAATCGTCCGTCGCAAGA<br>AGGTTTGTATCAGCATTTCAAAGCCATCGCTGAGCATAC<br>TGACCTGCCGCAAATTCTGTATAATGTGCCGTCCCGTAC<br>TGGCTGCGATCTGCTCCCGGAAACGGTGGGCCGTCTGGC<br>GAAAGTAAAAAATATTATCGGAATCAAAGAGGCAACAG | 81 |

TABLE 77-continued

Biosafety System Constructs and Sequence Components

| Description | Sequence | SEQ ID NO |
|---|---|---|
| | GGAACTTAACGCGTGTAAACCAGATCAAAGAGCTGGTTT<br>CAGATGATTTTGTTCTGCTGAGCGGCGATGATGCGAGCG<br>CGCTGGACTTCATGCAATTGGGCGGTCATGGGGTTATTT<br>CCGTTACGGCTAACGTCGCAGCGCGTGATATGGCCCAGA<br>TGTGCAAACTGGCAGCAGAAGGGCATTTTGCCGAGGCA<br>CGCGTTATTAATCAGCGTCTGATGCCATTACACAACAAA<br>CTATTTGTCGAACCCAATCCAATCCCGGTGAAATGGGCA<br>TGTAAGGAACTGGGTCTTGTGGCGACCGATACGCTGCGC<br>CTGCCAATGACACCAATCACCGACAGTGGCCGTGAGAC<br>GGTCAGAGCGGCGCTTAAACATGCCGGTTTGCTGTAAGA<br>CTTTTGTCAGGTTCCTACTGTGACGACTACCACCGATAG<br>ACTGGAGTGTTGCTGCGAAAAAACCCCGCCGAAGCGGG<br>GTTTTTTGCGAGAAGTCACCACGATTGTGCTTTACACGG<br>AGTAGTCGGCAGTTCCTTAAGTCAGAATAGTGGACAGGC<br>GGCCAAGAACTTCGTTCATGATAGTCTCCGGAACCCGTT<br>CGAGTCGTTTTCCGCCCCGTGCTTTCATATCAATTGTCCG<br>GGGTTGATCGCAACGTACAACACCTGTGGTACGTATGCC<br>AACACCATCCAACGACACCGCAAAGCCGGCAGTGCGGG<br>CAAAATTGCCTCCGCTGGTTACGGGCACAACAACAGGCA<br>GGCGGGTCACGCGATTAAAGGCCGCCGGTGTGACAATC<br>AGCACCGGCCGCGTTCCCTGCTGCTCATGACCTGCGGTA<br>GGATCAAGCGAGACAAGCCAGATTTCCCCTCTTTCCATC<br>TAGTATAACTATTGTTTCTCTAGTAACATTTATTGTACAA<br>CACGAGCCCATTTTTGTCAAATAAATTTTAAATTATATCA<br>ACGTTAATAAGACGTTGTCAATAAAATTATTTTGACAAA<br>ATTGGCCGGCCGGCGCGCCGATCTGAAGATCAGCAGTTC<br>AACCTGTTGATAGTACGTACTAAGCTCTCATGTTTCACGT<br>ACTAAGCTCTCATGTTTAACGTACTAAGCTCTCATGTTTA<br>ACGAACTAAACCCTCATGGCTAACGTACTAAGCTCTCAT<br>GGCTAACGTACTAAGCTCTCATGTTTCACGTACTAAGCT<br>CTCATGTTTGAACAATAAAATTAATATAAATCAGCAACT<br>TAAATAGCCTCTAAGGTTTTAAGTTTTATAAGAAAAAAA<br>AGAATATATAAGGCTTTTAAAGCCTTTAAGGTTTAACGG<br>TTGTGGACAACAAGCCAGGGATGTAACGCACTGAGAAG<br>CCCTTAGAGCCTCTCAAAGCAATTTTGAGTGACACAGGA<br>ACACTTAACGGCTGACATGGGGCGCGCCCAGCTGTCTAG<br>GGCGGCGGATTTGTCCTACTCAGGAGAGCGTTCACCGAC<br>AAACAACAGATAAAACGAAAGGCCCAGTCTTTCGACTG<br>AGCCTTTCGTTTTATTTGATGCCT | |
| Biosafety Plasmid<br>System Component-<br>ThyA<br>Biosafety Plasmid<br>System Vector<br>sequences,<br>comprising ThyA,<br>Kid Toxin and R6K<br>minimal ori, and<br>promoter elements<br>driving expression<br>of these<br>components, as<br>shown in FIG. 61B<br>of WO2017087580 | ACTCTTCCTTTTTCAATATTATTGAAGCATTTATCAGGGT<br>TATTGTCTCATGAGCGGATACATATTTGAATGTATTTAG<br>AAAAATAAACAAATAGGGGAATTAAAAAAAAGCCCGCT<br>CATTAGGCGGGCTACTACCTAGGCCGCGGCCGCGCGAAT<br>TCGAGCTCGGTACCCGGGGATCCTCTAGAGTCGACCTGC<br>AGGCATGCAAGCTTGCGGCCGCGTCGTGACTGGGAAAA<br>CCCTGGCGACTAGTCTTGGACTCCTGTTGATAGATCCAG<br>TAATGACCTCAGAACTCCATCTGGATTTGTTCAGAACGC<br>TCGGTTGCCGCCGGGCGTTTTTTATTGGTGAGAATCCAG<br>GGGTCCCCAATAATTACGATTTAAATCACAGCAAACACC<br>ACGTCGGCCCTATCAGCTGCGTGCTTTCTATGAGTCGTTG<br>CTGCATAACTTGACAATTAATCATCCGGCTCGTAGGGTT<br>TGTGGAGGGCCCAAGTTCACTTAAAAAGGAGATCAACA<br>ATGAAAGCAATTTTCGTACTGAAACATCTTAATCATGCT<br>GGGGAGGGTTTCTAATGAAACAGTATTTAGAACTGATGC<br>AAAAAGTGCTCGACGAAGGCACACAGAAAAACGACCGT<br>ACCGGAACCGGAACGCTTTCCATTTTTGGTCATCAGATG<br>CGTTTTAACCTGCAAGATGGATTCCCGCTGGTGACAACT<br>AAACGTTGCCACCTGCGTTCCATCATCCATGAACTGCTG<br>TGGTTTCTTCAGGGCGACACTAACATTGCTTATCTACAC<br>GAAAACAATGTCACCATCTGGGACGAATGGGCCGATGA<br>AAACGGCGACCTCGGGCCAGTGTATGGTAAACAGTGGC<br>GTGCCTGGCCAACGCCAGATGGTCGTCATATTGACCAGA<br>TCACTACGGTACTGAACCAGCTGAAAAACGACCCGGATT<br>CGCGCCGCATTATTGTTTCAGCGTGGAACGTAGGCGAAC<br>TGGATAAAATGGCGCTGGCACCGTGCGCCATGCATTCTTCC<br>AGTTCTATGTGGCAGACGGCAAACTCTCTTGCCAGCTTT<br>ATCAGCGCTCCTGTGACGTCTTCCTCGGCCTGCCGTTCAA<br>CATTGCCAGCTACGCGTTATTGGTGCATATGATGGCGCA<br>GCAGTGCGATCTGGAAGTGGGTGATTTTGTCTGGACCGG<br>TGGCGACACGCATCTGTACAGCAACCATATGGATCAAAC<br>TCATCTGCAATTAAGCCGCGAACCGCGTCCGCTGCCGAA<br>GTTGATTATCAAACGTAAACCCGAATCCATCTTCGACTA<br>CCGTTTCGAAGACTTTGAGATTGAAGGCTACGATCCGCA<br>TCCGGGCATTAAAGCGCCGGTGGCTATCTAAGACTTTTG | 82 |

TABLE 77-continued

Biosafety System Constructs and Sequence Components

| Description | Sequence | SEQ ID NO |
|---|---|---|
| | TCAGGTTCCTACTGTGACGACTACCACCGATAGACTGGA<br>GTGTTGCTGCGAAAAAACCCCGCCGAAGCGGGGTTTTTT<br>GCGAGAAGTCACCACGATTGTGCTTTACACGGAGTAGTC<br>GGCAGTTCCTTAAGTCAGAATAGTGGACAGGCGGCCAA<br>GAACTTCGTTCATGATAGTCTCCGGAACCCGTTCGAGTC<br>GTTTTCCGCCCCGTGCTTTCATATCAATTGTCCGGGGTTG<br>ATCGCAACGTACAACACCTGTGGTACGTATGCCAACACC<br>ATCCAACGACACCGCAAAGCCGGCAGTGCGGGCAAAAT<br>TGCCTCCGCTGGTTACGGGCACAACAACAGGCAGGCGG<br>GTCACGCGATTAAAGGCCGCCGGTGTGACAATCAGCACC<br>GGCCGCGTTCCCTGCTGCTCATGACCTGCGGTAGGATCA<br>AGCGAGACAAGCCAGATTTCCCCTCTTTCCATCTAGTAT<br>AACTATTGTTTCTCTAGTAACATTTATTGTACAACACGAG<br>CCCATTTTTGTCAAATAAATTTTAAATTATATCAACGTTA<br>ATAAGACGTTGTCAATAAAATTATTTTGACAAAATTGGC<br>CGGCCGGCGCGCCGATCTGAAGATCAGCAGTTCAACCTG<br>TTGATAGTACGTACTAAGCTCTCATGTTTCACGTACTAA<br>GCTCTCATGTTTAACGTACTAAGCTCTCATGTTTAACGAA<br>CTAAACCCTCATGGCTAACGTACTAAGCTCTCATGGCTA<br>ACGTACTAAGCTCTCATGTTTCACGTACTAAGCTCTCATG<br>TTTGAACAATAAAATTAATATAAATCAGCAACTTAAATA<br>GCCTCTAAGGTTTTAAGTTTTATAAGAAAAAAAAGAATA<br>TATAAGGCTTTTAAAGCCTTTAAGGTTTAACGGTTGTGG<br>ACAACAAGCCAGGGATGTAACGCACTGAGAAGCCCTTA<br>GAGCCTCTCAAAGCAATTTTGAGTGACACAGGAACACTT<br>AACGGCTGACATGGGGCGCGCCCAGCTGTCTAGGGCGG<br>CGGATTTGTCCTACTCAGGAGAGCGTTCACCGACAAACA<br>ACAGATAAAACGAAAGGCCCAGTCTTTCGACTGAGCCTT<br>TCGTTTTATTTGATGCCT | |
| Kid toxin (reverse orientation) | TTAAGTCAGAATAGTGGACAGGCGGCCAAGAACTTCGTT<br>CATGATAGTCTCCGGAACCCGTTCGAGTCGTTTTCCGCC<br>CCGTGCTTTCATATCAATTGTCCGGGGTTGATCGCAACG<br>TACAACACCTGTGGTACGTATGCCAACACCATCCAACGA<br>CACCGCAAAGCCGGCAGTGCGGGCAAAATTGCCTCCGCT<br>GGTTACGGGCACAACAACAGGCAGGCGGGTCACGCGAT<br>TAAAGGCCGCCGGTGTGACAATCAGCACCGGCCGCGTTC<br>CCTGCTGCTCATGACCTGCGGTAGGATCAAGCGAGACAA<br>GCCAGATTTCCCCTCTTTCCAT | 83 |
| dapA | ATGTTCACGGGAAGTATTGTCGCGATTGTTACTCCGATG<br>GATGAAAAAGGTAATGTCTGTCGGGCTAGCTTGAAAAA<br>ACTGATTGATTATCATGTCGCCAGCGGTACTTCGGCGAT<br>CGTTTCTGTTGGCACCACTGGCGAGTCCGCTACCTTAAA<br>TCATGACGAACATGCTGATGTGGTGATGATGACGCTGGA<br>TCTGGCTGATGGGCGCATTCCGGTAATTGCCGGGACCGG<br>CGCTAACGCTACTGCGGAAGCCATTAGCCTGACGCAGCG<br>CTTCAATGACAGTGGTATCGTCGGCTGCCTGACGGTAAC<br>CCCTTACTACAATCGTCCGTCGCAAGAAGGTTTGTATCA<br>GCATTTCAAAGCCATCGCTGAGCATACTGACCTGCCGCA<br>AATTCTGTATAATGTGCCGTCCCGTACTGGCTGCGATCT<br>GCTCCCGGAAACGGTGGCCGTCTGGCGAAAGTAAAAA<br>ATATTATCGGAATCAAAGAGGCAACAGGGAACTTAACG<br>CGTGTAAACCAGATCAAAGAGCTGGTTTCAGATGATTTT<br>GTTCTGCTGAGCGGCGATGATGCGAGCGCGCTGGACTTC<br>ATGCAATTGGGCGGTCATGGGTTATTTCCGTTACGGCT<br>AACGTCGCAGCGCGTGATATGGCCCAGATGTGCAAACTG<br>GCAGCAGAAGGGCATTTTGCCGAGGCACGCGTTATTAAT<br>CAGCGTCTGATGCCATTACACAACAAACTATTTGTCGAA<br>CCCAATCCAATCCCGGTGAAATGGGCATGTAAGGAACTG<br>GGTCTTGTGGCGACCGATACGCTGCGCCTGCCAATGACA<br>CCAATCACCGACAGTGGCCGTGAGACGGTCAGAGCGGC<br>GCTTAAACATGCCGGTTTGCTGTAA | 84 |
| thyA | ATGAAACAGTATTTAGAACTGATGCAAAAAGTGCTCGAC<br>GAAGGCACACAGAAAAACGACCGTACCGGAACCGGAAC<br>GCTTTCCATTTTTGGTCATCAGATGCGTTTTAACCTGCAA<br>GATGGATTCCCGCTGGTGACAACTAAACGTTGCCACCTG<br>CGTTCCATCATCCATGAACTGCTGTGGTTTCTTCAGGGCG<br>ACACTAACATTGCTTATCTACACGAAAACAATGTCACCA<br>TCTGGGACGAATGGGCCGATGAAAACGGCGACCTCGGG<br>CCAGTGTATGGTAAACAGTGGCGTGCCTGGCCAACGCCA<br>GATGGTCGTCATATTGACCAGATCACTACGGTACTGAAC<br>CAGCTGAAAAACGACCCGGATTCGCGCCGCATTATTGTT<br>TCAGCGTGGAACGTAGGCGAACTGGATAAAATGGCGCT | 85 |

TABLE 77-continued

Biosafety System Constructs and Sequence Components

| Description | Sequence | SEQ ID NO |
|---|---|---|
| | GGCACCGTGCCATGCATTCTTCCAGTTCTATGTGGCAGA<br>CGGCAAACTCTCTTGCCAGCTTTATCAGCGCTCCTGTGA<br>CGTCTTCCTCGGCCTGCCGTTCAACATTGCCAGCTACGC<br>GTTATTGGTGCATATGATGGCGCAGCAGTGCGATCTGGA<br>AGTGGGTGATTTTGTCTGGACCGGTGGCGACACGCATCT<br>GTACAGCAACCATATGGATCAAACTCATCTGCAATTAAG<br>CCGCGAACCGCGTCCGCTGCCGAAGTTGATTATCAAACG<br>TAAACCCGAATCCATCTTCGACTACCGTTTCGAAGACTT<br>TGAGATTGAAGGCTACGATCCGCATCCGGGCATTAAAGC<br>GCCGGTGGCTATCTAA | |
| Kid toxin polypeptide | MERGEIWLVSLDPTAGHEQQGTRPVLIVTPAAFNRVTRLPV<br>VVPVTSGGNFARTAGFAVSLDGVGIRTTGVVRCDQPRTID<br>MKARGGKRLERVPETIMNEVLGRLSTILT* | 86 |
| dapA polypeptide | MFTGSIVAIVTPMDEKGNVCRASLKKLIDYHVASGTSAIVS<br>VGTTGESATLNHDEHADVVMMTLDLADGRIPVIAGTGAN<br>ATAEAISLTQRFNDSGIVGCLTVTPYYNRPSQEGLYQHFKAI<br>AEHTDLPQILYNVPSRTGCDLLPETVGRLAKVKNIIGIKEAT<br>GNLTRVNQIKELVSDDFVLLSGDDASALDFMQLGGHGVIS<br>VTANVAARDMAQMCKLAAEGHFAEARVINQRLMPLHNK<br>LFVEPNPIPVKWACKELGLVATDTLRLPMTPITDSGRETVR<br>AALKHAGLL | 87 |
| ThyA polypeptide | MKQYLELMQKVLDEGTQKNDRTGTGTLSIFGHQMRFNLQ<br>DGFPLVTTKRCHLRSIIHELLWFLQGDTNIAYLHENNVTIW<br>DEWADENGDLGPVYGKQWRAWPTPDGRHIDQITTVLNQL<br>KNDPDSRRIIVSAWNVGELDKMALAPCHAFFQFYVADGKL<br>SCQLYQRSCDVFLGLPFNIASYALLVHMMAQQCDLEVGDF<br>VWTGGDTHLYSNHMDQTHLQLSREPRPLPKLIIKRKPESIF<br>DYRFEDFEIEGYDPHPGIKAPVAI* | 88 |

I. Example 55. Prophage Bioinformatic Analysis of *Escherichia coli* Nissle 1917 and its Engineered Derivatives A. Synopsis Objective: Routine testing procedures identified bacteriophage production from *Escherichia coli* Nissle 1917 (*E. coli* Nissle; *E. coli* Nissle) and related engineered derivatives. In an effort to determine the source of the bacteriophage, a collaborative bioinformatics assessment of the genomes of *E. coli* Nissle, and engineered derivatives was conducted to analyze genomic sequences of the strains for evidence of prophages, to assess any identified prophage elements for the likelihood of producing functional phage, to compare any functional phage elements with other known phage identified among bacterial genomic sequences, and to evaluate the frequency with which prophage elements are found in other sequenced *Escherichia coli* (*E. coli*) genomes.

Experimental Procedures

1. Bioanalytical Methods
a. Phage Prediction

The phage prediction software (PHAST) (Zhou, et al., "PHAST: A Fast Phage Search Tool" Nucl. Acids Res. (2011) 39(suppl 2): W347-W352) was used to search for prophage within the published and publicly available *E. coli* Nissle genome (Genbank accession NZ_CP007799.1) (Reister et al., Complete genome sequence of the gram-negative probiotic *Escherichia coli* strain Nissle 1917; J Biotechnol. 2014 Oct. 10; 187:106-7), as well as within SYN001—*E. coli* Nissle 1917, a research cell bank produced from a single expansion of *E. coli* Nissle derived from DSM 6601, lot # Jul91 (DSMZ, Braunschweig, Germany), and the genome of the genetically engineered strains.

b. DNA Sequencing and Assembly

The genome sequences of the genetically engineered strains were generated by an external resource (GENEWIZ, Boston Mass.) using an Illumina MiSeq DNA sequencer. To examine the sequences for phage sequences, it was first necessary to assemble the genomic sequencing reads using genome assembler software (SPAdes) version 3.9.1, using default parameters (Nurk et al., Assembling single-cell genomes and mini-metagenomes from chimeric MDA products; J Comput Biol. 2013 October; 20(10):714-37). Scaffolds with lengths less than 500 nucleotides were discarded.

c. Identification of Potential Sequence Regions Specific to a Genetically Engineered Strain In order to identify any sequences which could be potentially present in the engineered strains but not present in the original *E. coli* Nissle strain, the raw read data were aligned to each of three reference genomes using software for mapping low-divergent sequences against a large reference genome (BWA MEM) (Li and Durbin, Fast and accurate short read alignment with Burrows-Wheeler transform; Bioinformatics. 2009 Jul. 15; 25(14):1754-60). The three reference genomes were the published sequences and publicly available *E. coli* Nissle genome (Genbank accession NZ_CP007799.1) (Reister et al., Complete genome sequence of the gram-negative probiotic *Escherichia coli* strain Nissle 1917; J Biotechnol. 2014 Oct. 10; 187:106-7), the SYN001 (wild type *E. coli* Nissle) version of the *E. coli* Nissle genome that was sequenced by Genewiz, and the expected sequence for the genome of engineered strain which was based on the sequence of SYN001 along with changes resulting from specific engineering steps used to create the engineered strain. To focus on those sequences that did not correspond to the expected sequence of the engineered strain, the reads were aligned to each reference, and those that aligned to each reference separately according to the software Samtools (Li et al., The Sequence Alignment/Map format and SAMtools; Bioinformatics. 2009 Aug. 15; 25(16):2078-9) were discarded, and the remaining reads that did not align to each reference genome were further analyzed. The same process was used to identify unique sequences in the engineered strains.

The reads that did not map to each of the three references were assembled using the genome assembler software SPAdes version 3.9.1, with default parameters (Nurk et al., Assembling single-cell genomes and mini-metagenomes from chimeric MDA products; J Comput Biol. 2013 October; 20(10):714-37). These assembled scaffolds were used to check for the presence of phage-related sequences by comparing them against the nonredundant database in the National Center for Biotechnology Information (NCBI) using the Blast tool (Altschul et al., Basic local alignment search tool; J Mol Biol. 1990 Oct. 5; 215(3):403-10).

To verify these results, a whole-genome alignment was performed between the entire assembly of the genetically engineered strain and the publicly available CP007799.1 reference genome using genome sequence alignment software (MUMmer) (Delcher et al., Fast algorithms for large-scale genome alignment and comparison; Nucleic Acids Res. 2002 Jun. 1; 30(11):2478-83). These alignments identified unique sequences from the new assembly that did not map to the reference assembly. The unique sequences were again compared against the non-redundant database in NCBI using the Blast tool (Altschul et al., Basic local alignment search tool; J Mol Biol. 1990 Oct. 5; 215(3):403-10) to check for the presence of phage-related sequence. The approach resulted in the identification of three potential phages.

d. Search for Matches to Phage 3 in Other Genomes

To further refine the size of the Phage 3 sequence identified by the PHAST bioinformatic tool, the core region of the Phage 3 sequence was determined by aligning the 59 kilobase (kb) region of Phage 3 in *E. coli* Nissle to the closely-related genome of *E. coli* BW25113, which does not contain Phage 3. Regions at the left- and right-hand ends of the 59 kb Phage 3 sequence from *E. coli* Nissle matched the genomic organization of genes in *E. coli* BW25113 which likely corresponded to host chromosomal (non-phage) sequences; however a 43 kb region in the middle of the Phage 3 sequence from *E. coli* Nissle was not present in *E. coli* BW25113 and appeared as an insertion between two host chromosomal genes present in *E. coli* BW25113. Therefore, by this alignment, a 43 kb core Phage 3 region was observed which was unique to *E. coli* Nissle and likely contains the true limits of Phage 3. This 43 kb core Phage 3 sequence was then compared for alignment against a comprehensive set of 5691 *E. coli* and *Shigella* assemblies downloaded from NCBI using the MUMmer alignment software DElcher et al., Fast algorithms for large-scale genome alignment and comparison; Nucleic Acids Res. 2002 Jun. 1; 30(11):2478-83). To identify instances of Phage 3 outside of *E. coli*, the entire 43 kb core Phage 3 region was compared against the nonredundant NCBI database using the Blast tool (Altschul et al., Basic local alignment search tool; *J Mol Biol.* 1990 Oct. 5; 215(3):403-10).

To determine whether partial hits to Phage 3 in other genomes were part of larger phage elements, the scaffolds with partial matches to Phage 3 were extracted from the other genomes and PHAST (Zhou, et al., "PHAST: A Fast Phage Search Tool" Nucl. Acids Res. (2011) 39(suppl 2): W347-W352) was used to predict the presence of prophage within these regions.

e. Large-Scale Phage Prediction Across *E. coli*

To assess the frequency with which prophages of any type are found among sequenced *E. coli* strains, a newly published, more efficient version of PHAST (PHASTER) Arndt D., et al., PHASTER: a better, faster version of the PHAST phage search tool. Nucleic Acids Res. 44, W16-W21(2016)) was used to search for the presence of any prophage elements within a large set of *E. coli* genomes. Because the accuracy of phage prediction algorithms is dependent on the use of high-quality genomes, a set of 287 high-quality reference sequence (Refseq) *E. coli* genomes was used for this search.

B. Results

1. Phage Content of *E. coli* Nissle

Figure 2:
FIG. 2 depicts a schematic showing 1 of 3 high-scoring phage in Nissle using the Phast tool, referred to herein as "Phage 1", and which contains all major components of a phage. Putative genes are labeled Hyp=Hypothetical, PLP=other phage like protein, Oth=Other, RNA=tRNA, TRA=transposase.

Three high-confidence, predicted prophage sequences were found within each version of the *E. coli* Nissle genome, referred herein to as Phage 1, Phage 2, and Phage 3 (FIG. 1). All three of these high-scoring phage were designated by PHAST as "intact" phage, indicating that they contain all of the major components of a phage (FIG. 1). The longest predicted phage in *E. coli* Nissle (Phage 3) contains a total of 68 proteins, and includes a phage tail, head, portal, terminase, lysin, capsid, and integrase, all of which appear to be intact. Phage 2 contains a total of 69 proteins, and includes phage transposase, lysis, terminase, head, portal, capsid, and tail proteins. Closer inspection of Phage 2 revealed that the int/xis gene pair have been disrupted by a mobile genetic element, and that the cl repressor has been fragmented into separate DNA-binding and sensing peptides, which would be expected to prevent induction of this phage. The shortest of the intact phages predicted in *E. coli* Nissle, Phage 1, contains a total of 32 proteins, and includes lysis and transposase functionality. However, the absence of many structural genes within the putative prophage element termed Phage 1 calls into question its potential to release viable phage particles. Features of Phage 1-3 are summarized in Table 84.

i.

TABLE 84

Summary of Putative Phage Features

| Feature | Phage 1 | Phage 2 | Phage 3 |
| --- | --- | --- | --- |
| Nissle coordinates | 241563-260441 | 1325883-1378287 | 2023188-2082243 |
| Phast score | 110 | 150 | 150 |
| Intact designation (score greater or equal 90) | "intact" | "intact" | "intact" |

TABLE 84-continued

Summary of Putative Phage Features

| Feature | Phage 1 | Phage 2 | Phage 3 |
|---|---|---|---|
| Length | 18.8 kb, | 52.4 kb | 59 kb |
| Top hit | PHAGE_Stx2_c_1717_NC_011357 | PHAGE_Entero_lambda_NC_001416 | PH AGE_Entero_c_1_NC_019706 |
| Encoded essential phage genes | Contains a lysin and a transposase | Contains transposase, lysis, terminase, head, portal, capsid, tail | Contains tail, head, portal, terminase, lysin, capsid, integrase |
| Total number of Proteins | 32 | 69 | 68 |
| Number of proteins classified as phage | 18 | 52 | 59 |
| Number of proteins which are "hypothetical" | 12 | 12 | 8 |

2. Engineered Strain has the Same Phage Content as *E. coli* Nissle

Within the assembled genome of the engineered strain, PHAST predicted the same phage content as had been predicted in the original *E. coli* Nissle genome. All three of the phage that were identified as "intact" phage within *E. coli* Nissle were also identified within the genome of the engineered strain (Phages 1-3).

3. Engineered Strain Contains No Additional Prophage Elements

The vast majority of the raw sequencing reads of the engineered strain mapped to the reference genomes, and there were very few sequences that were unique to the engineered strain genome. There was no evidence for phage sequence within the small amount of unique sequence. When assembled, these unique sequences resulted in only 3 scaffolds, each with length <2 kb, and no similarity to known phage sequence. This result was confirmed by performing a whole-genome alignment of the complete engineered strain assembly to the *E. coli* Nissle reference genome, and identifying regions within the engineered strain which did not map to the reference. Using this procedure, two of the same short sequences were identified. None of these short sequences had any similarity to any known phage sequence. These very short sequences unique to the engineered strain likely represent spurious DNA in the samples, and not phage.

4. Phage 3 is Specific to *E. coli* Nissle

Figure 10:
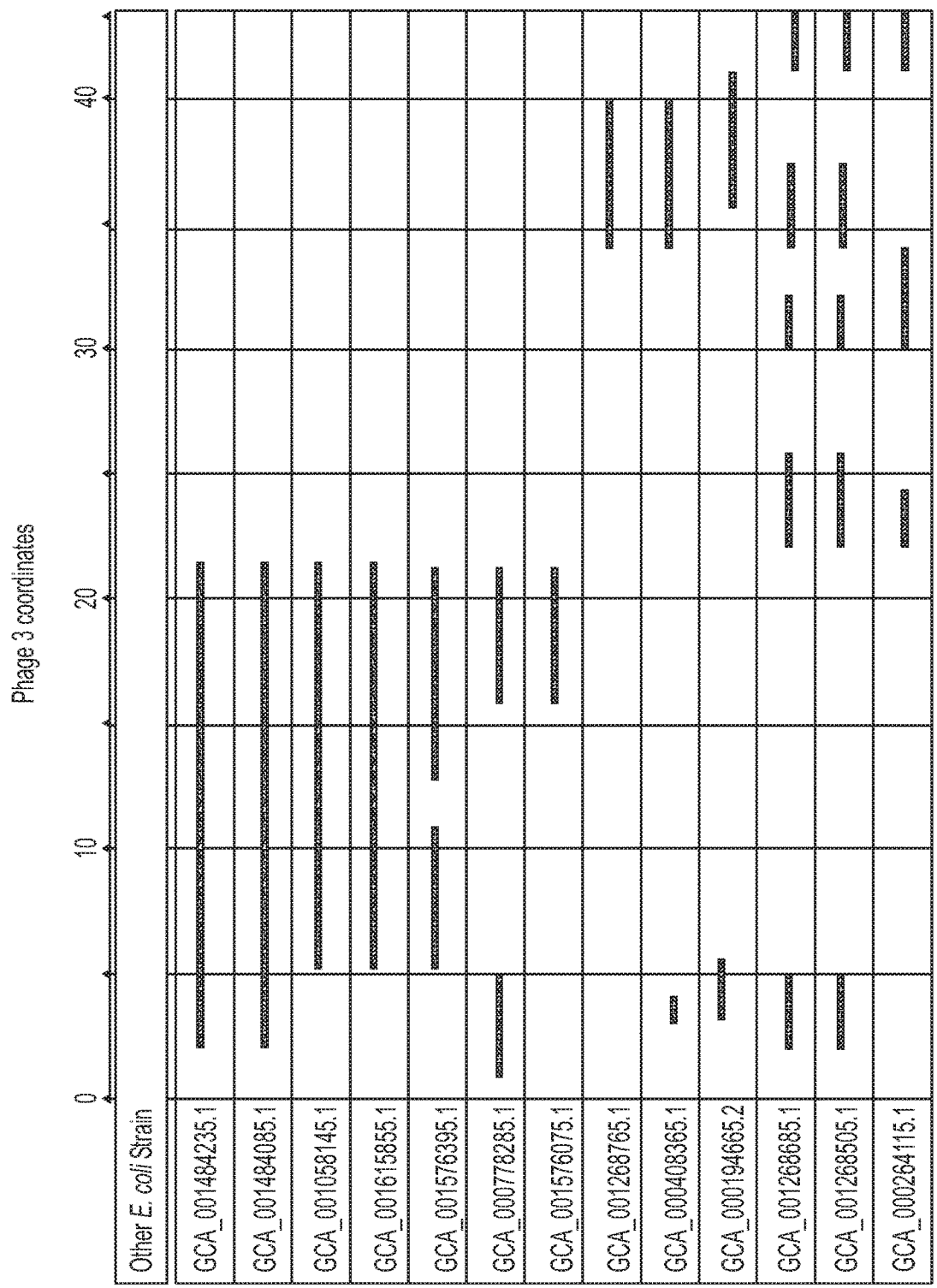
FIG. 10 depicts a schematic showing partial regions within the 43 kb Phage 3 sequence that align to sequence in other *E. coli* strains. The sequence identified as Phage 3 was compared against 5691 *E. coli* and *Shigella* genome assemblies downloaded from NCBI. Listed in the column on the left are the accession numbers of the *E. coli* genomes that were positive in the analysis. Across the top of the Figure are the coordinates of the DNA sequence according to the number of kb from the start of the sequence. The lines depict the sequence from each specific *E. coli* genome that align with the DNA sequence of Phage 3. Abbreviations: *E. coli=Escherichia coli*; kb=kilobase; NCBI=National Center for Biotechnology Information; DNA=deoxyribonucleic acid.
Figure 11:
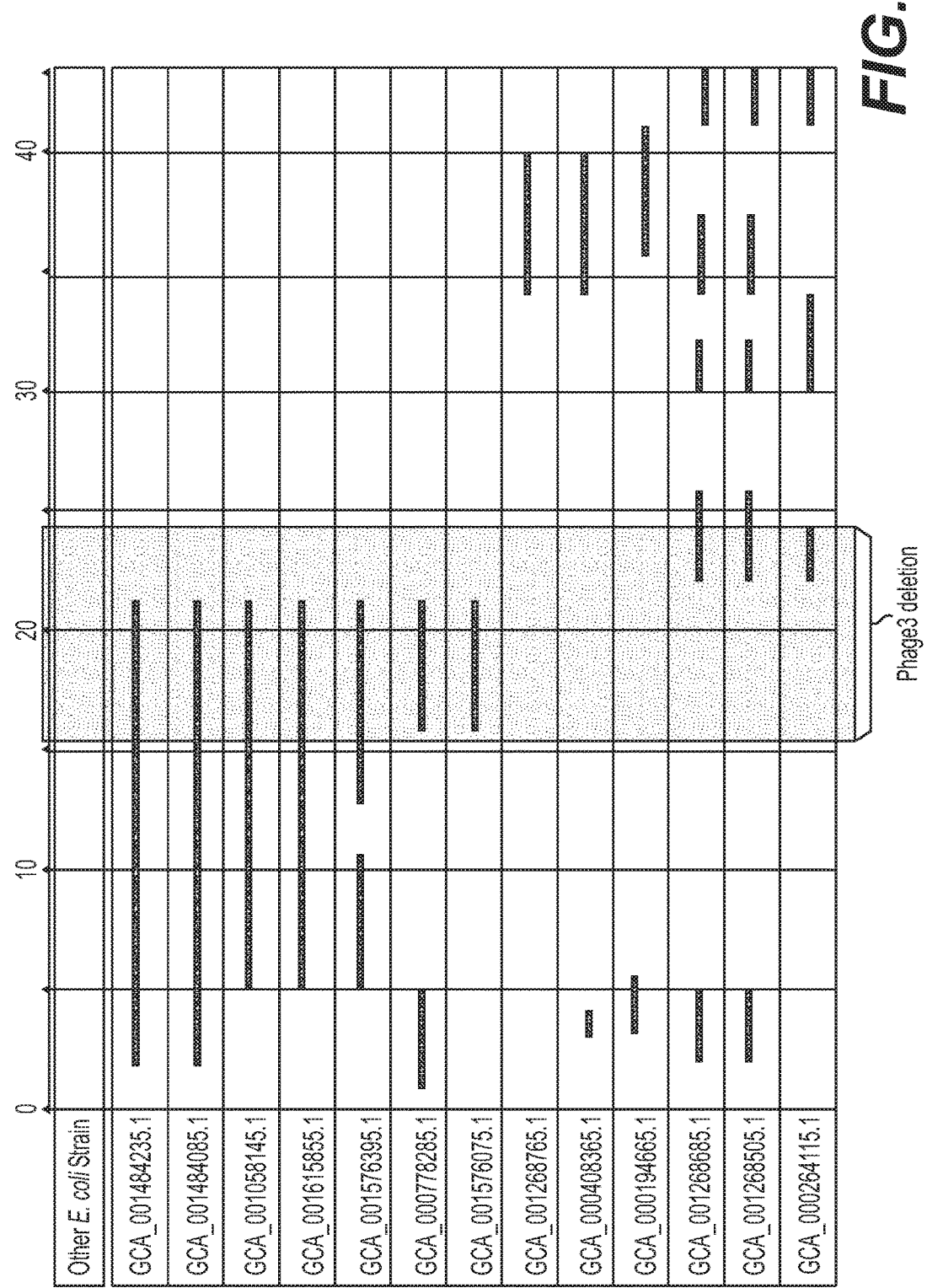
FIG. 11 depicts a schematic showing partial regions within the 43 kb Phage 3 sequence that align to sequence in other *E. coli* strains. The area in the shaded box was chosen as a site for deletion in the Phage 3 knockout strategy.

Laboratory studies have determined that the plaque-forming phage particles released by *E. coli* Nissle, and the engineered strain were exclusively derived from Phage 3 (SYN-17.002). Therefore, an assessment of the presence of Phage 3 (as a prophage) in other *E. coli* genomes was conducted. Within an extensive data set of 5691 *E. coli* and *Shigella* genome assemblies downloaded from NCBI, full-length Phage 3 was only found in *E. coli* Nissle. There were only two full-length, 43 kb matches covering the entire length of Phage 3 with 100% identity, and both of these corresponded to different versions of the *E. coli* Nissle genome (GCA_000333215.1 and GCA_000714595.1). There were five additional long partial matches (14-20 kb, with 97-99.6% identity), and four other shorter partial matches (5-10 kb, 95-98% identity) in other *E. coli* genomes within the data set (FIG. 10). Several other shorter fragments, split between multiple scaffolds of the same assembly, were also identified. The partial matches map to different regions of Phage 3 and are displayed in FIG. 10.

The scaffolds containing these partial matches in other genomes were extracted and used to determine that each partial match to Phage 3 comprises a fragment of a longer prophage within the other genome that had no other similarity to Phage 3. These regions were always part of a longer, high-scoring, "intact" phage prediction in the other genomes. These phage outside of *E. coli* Nissle corresponded to "hybrid" phage, where part of the sequence matches to Phage 3, and the rest corresponds to phage sequence which are different from Phage 3. These results indicate that the closest related phage present in *E. coli* share up to approximately half of their genome with the Phage 3 DNA sequence. Outside of *E. coli*, several partial matches were identified within more distantly related *Enterobacter*, 10-18 kb long, with 96-97% identity.

5. Distribution of Predicted Phage Across *E. coli*

Phage are very common in *E. coli*. Almost all of the *E. coli* genomes in the Refseq database contained at least one "intact", high-scoring phage as assessed using the PHASTER phage prediction software tool, and some have up to 20 (FIG. 12). The average number of predicted phage in an *E. coli* genome is 6.4, which is substantially higher than the number predicted for *E. coli* Nissle by PHASTER. Using this newer phage prediction tool, only the two longer phage are identified in *E. coli* Nissle (those referred to herein as Phage 2 and Phage 3). Therefore, *E. coli* Nissle has substantially fewer predicted phage than most other *E. coli*.

C. Conclusions

Conclusions of the bioinformatics analyses are as follows: First, *E. coli* Nissle and the engineered derivatives contain three candidate prophage elements, with two of the three (Phage 2 and Phage 3) containing most genetic features characteristic of intact phage genomes. Additionally, Phage 3 is unique to *E. coli* Nissle among a collection of almost 6000 sequenced *E. coli* genomes, although related sequences limited to short regions of homology with other putative prophage elements are found in a small number of genomes. Fourth, prophages are very common among *E. coli* strains, with *E. coli* Nissle containing a relatively small number as compared to the average found in a well-characterized set of sequenced *E. coli* genomes. These data support the conclusion that prophage presence in an engineered strain of *E. coli* Nissle is a consequence of the natural state of this species and the prophage features of such the engineered strains analyzed were consistent with the progenitor strain, *E. coli* Nissle.

Example 56. General Protocol for the Detection and Characterization Of Bacteriophage from *E. coli* Nissle and Genetically Engineered Derivatives

*Escherichia coli* Nissle 1917 (*E. coli* Nissle) and engineered derivatives test positive for a low level presence of phage 3 in a validated bacteriophage plaque assay. Bacteriophage plaque assays were conducted to determine presence and levels of bacteriophage. In brief, supernatants from cultures of test bacteria that were grown overnight were mixed with a phage-sensitive indicator strain and plated in soft agar to detect the formation of plaques, indicative of the presence of bacteriophage. Polymerase chain reaction (PCR) primers were designed to detect the three different endogenous prophages identified in the bioinformatics analyses, and were used to assess plaques for the presence of phage-specific DNA.

D. Experimental Procedures

1. Phage Testing Protocol: Plaque Assay of Bacterial Virus from *Escherichia coli* Using Mitomycin C Induction Data Analysis The cell lines were analyzed for the production of phage using the mitomycin C phage induction procedure (Method STM-V-708, Plaque Assay of Bacterial Virus from *Escherichia coli* (*E. coli*). Using Mitomycin C Induction, as described in Sinsheimer RL. Purification and Properties of Bacteriophage X174. J. Mol. Biol. 1959; 1:37-42, and Clowes, R C and Hayes, W. Experiments in microbial genetics. John Wiley & Sons, N Y. 1968, the contents of each of which is herein incorporated by reference in its entireties). Briefly, sample (with thymidine supplemented media to support cell expansion, as appropriate) and control cells were grown overnight. A portion of the sample, positive control (*E. coli*, EMG 2: K (lambda), ATCC 23716, or equivalent) and negative control (*E. coli*, ATCC 13706, or equivalent) were removed and centrifuged, and each supernatant examined in a plaque assay for the presence of bacteriophage. Mitomycin C, at a final concentration of 2 µg/mL, was added to the remaining sample, positive and negative bacterial cultures. The cultures were then placed at 37±2° C. and shaken at 300-400 RPM until lysis occured in the positive control (~4.5 hours). Each culture was treated with chloroform, centrifuged, and a 0.1 mL aliquot of the supernatant was examined for the presence of bacteriophage. To accomplish this, supernatants were mixed with phage-sensitive *E. coli* strain ATCC 13706, mixed with 0.7% agarose solution, and plated as a lawn atop lysogeny broth (LB) agar. The test was considered valid if plaques were present in the positive control and no plaques were present in the negative control.

2. PCR Detection of Specific Bacteriophage a. Selection of Phage-Specific PCR Primers Oligonucleotide polymerase chain reaction (PCR) primers were designed with specificity to each of the three putative prophage regions of *E. coli* Nissle, and ordered from Integrated DNA Technologies (IDT, Skokie, IL). The primers were selected after careful examination of the Nissle genome, and designed to bind completely within unique regions predicted to encode phage-specific proteins (Table 85).

TABLE 85

Phage-specific and Control Primers for *E. coli* Nissle

| Primer Description: | Primer Sequence: | Predicted Fragment Size: | SEQ ID NO |
|---|---|---|---|
| Putative Prophage 1 Forward | 5'-agtgcctgtacca gacgttc-3' | 366 bp | SEQ ID NO: 118 |
| Putative Prophage 1 Reverse | 5'-agaaatgacaacc agagagc-3' |  | SEQ ID NO: 119 |
| Putative Prophage 2 Forward | 5'-ttgagtttaatat ggcagaac-3' | 379 bp | SEQ ID NO: 120 |
| Putative Prophage 2 Reverse | 5'-aaatgatcatcgc gtcatc-3' |  | SEQ ID NO: 121 |
| Putative Prophage 3 Forward | 5'-gcatcaatcagtg attggc-3' | 349 bp | SEQ ID NO: 122 |
| Putative Prophage 3 Reverse | 5'-acgtctgaatata cgggctg-3' |  | SEQ ID NO: 123 |
| Control rpoB Forward | 5'-tccagcttgactc gtttcag-3' | 424 bp | SEQ ID NO: 124 |
| Control rpoB Reverse | 5'-agcaccttacccg aagagt-3' |  | SEQ ID NO: 125 |

Abbreviations: bp = basepair; *E. coli* Nissle = *Escherichia coli* Nissle 1917; rpoB = β subunit of bacterial RNA polymerases An additional pair of oligonucleotide PCR primers was designed that specifically bound to rpoB, an essential bacterial-specific gene found within the *E. coli* Nissle genome and related strains but located outside of the three phage elements. The primer set that bound to rpoB served as a positive control for both the quality of the genomic DNA preparations, and the effectiveness of the PCR protocol. Additionally, phage DNA should not contain the rpoB gene, therefore these primers also served as a control for the purity of the phage-plaque picking technique. It was determined that while 25 PCR reaction cycles was sufficient to produce a strong band with a specific Phage PCR primer pair for plaques produced by that corresponding phage, only a weak or often no band, was observed with the rpoB primers using the same plaque DNA with 25 cycles (data not shown). For this reason, PCR analysis of plaque samples was conducted for 25 cycles.

b. PCR Reaction Conditions and Confirmation of Primer Specificity

Using the oligonucleotide primers described supra, PCR was performed against *E. coli* Nissle genomic DNA (gDNA) to determine whether the expected PCR products for Phage 1, 2, and 3 as well as the rpoB host genomic control were produced. The phage-negative strain ATCC 13706 served as a negative control for the PCR reaction. To prepare gDNA template for the PCR reaction, *E. coli* Nissle was grown in LB medium at 37±2° C. and shaken at 250 rotations per minute (rpm) overnight. One hundred (100) µL of stationary phase culture was added to a 1.5 mL microcentrifuge tube and spun at >20,000×g (15,000 rpm) in a microcentrifuge for 30 seconds. The supernatant was removed and the cell pellet was resuspended in 100 µL of sterile water. This 100 µL suspension was moved to a 0.2 mL thin wall tube and heated at 98° C. in an Eppendorf Mastercycler Pro thermocycler for 10 minutes. The resulting solution contained gDNA that was suitable for a PCR reaction. Polymerase chain reaction was performed using MyTaq™ Red Mix (Bioline) as the source of DNA nucleotides and polymerase to support DNA amplification, with E. coli Nissle gDNA as the DNA template, and mixed according to the conditions in Table 86. Polymerase chain reactions were performed in an Eppendorf Mastercycler Pro thermocycler as described in Table 87. Upon completion of PCR, 5 µL of reactions or DNA standard (1 kB+ ladder, Invitrogen) were loaded onto a 0.8% agarose gel for separation by electrophoresis and visualization using a Syngene ultra violet (UV) transilluminator.

TABLE 86

PCR Preparation to Amplify Putative Prophage Regions from E. coli Nissle

| Reagent | Per Reaction (µL) | Final Concentration |
| --- | --- | --- |
| Nuclease-free sterile water | 23 | N/A |
| Forward primer (100 µM) | 0.5 | 1 µM |
| Reverse primer (100 µM) | 0.5 | 1 µM |
| gDNA template | 1 | N/A |
| 2X MyTaq ™ Red Mix | 25 | 0.2 U/µL |

Abbreviation: E. coli Nissle = Escherichia coli;
gDNA = genomic deoxyribonucleic acid;
N/A = not applicable;
PCR = polymerase chain reaction;
U = unit;
µL = microliter;
µM = micromolar

TABLE 87

PCR Reaction Cycle for Amplifying Prophage Regions from E. coli Nissle

| Stage | Temperature (° C.) | Time (min:sec) |
| --- | --- | --- |
| 1 | 95 | 1:00 |
| 2 | 95 | 0:15 |
|   | 58 | 0:15 |
|   | 72 | 0:10 |
| 3 | Repeat Stage 2: 30x | NA |
| 4 | 72 | 1:00 |
| 5 | 4 | Infinity |

Abbreviation: ° C. = degrees Celsius;
E. coli Nissle = Escherichia coli;
min = minute;
PCR = polymerase chain reaction;
sec = second(s);
NA = not applicable 3. Testing of Individual Plaques for Specific Phages Bacteriophage titer assays were performed using a validated method. PCR analysis was conducted on supernatants of resulting phage titer plates that contained enumerable bacteriophage plaques (when applicable) derived from E. coli Nissle, or an engineered strain. The identity of the phage that generated the plaques was determined by PCR. Agar plugs of individual plaques were removed from the culture plates with 2 µL pipet tips. Each plug was resuspended in 0.5 mL of sterile distilled water. The plug resuspensions were vortexed for 15 seconds, then 1 µL was added to PCR reactions as the DNA template. The phage-specific PCR reactions were performed with MyTaq™ Red Mix (Bioline) as the source of DNA nucleotides and polymerase to support DNA amplification, with the plug resuspensions as the DNA template, and mixed according to the conditions in Table 5. Each set of primers from Table 85, supra was used in a separate PCR reaction to identify each of the three putative phage, with E. coli Nissle and ATCC 13706 gDNAs serving as positive and negative controls. The PCR reactions were performed according to the conditions in Table 89, and were performed for a limiting number of cycles (25 cycles) to prevent the amplification of any residual host chromosomal DNA present in the plaques. Upon completion of PCR, 5 µL of reactions or DNA standard (1 kB+ ladder, Invitrogen) were loaded onto a 0.8% agarose gel for separation by electrophoresis and visualization using a Syngene UV transilluminator.

TABLE 88

PCR Reaction Conditions to Amplify E. coli Nissle Specific Phage from Plaque Plugs

| Reagent | Per Reaction (µL) | Final Concentration |
| --- | --- | --- |
| Nuclease-free sterile water | 23 | N/A |
| Forward primer (100 µM) | 0.5 | 1 µM |
| Reverse primer (100 µM) | 0.5 | 1 µM |
| plaque plug or gDNA template (control) | 1 | N/A |
| 2X MyTaq ™ Red Mix | 25 | 0.2 U/gL |

Abbreviation: E. coli Nissle = Escherichia coli;
gDNA = genomic deoxyribonucleic acid;
N/A = not applicable;
PCR = polymerase chain reaction;
rxn = reaction;
U = unit;
µL = microliter;
µM = micromolar

TABLE 89

PCR Reaction Cycle for Amplifying Prophage Regions from Plaque Plugs

| Stage | Temperature (° C.) | Time (min:sec) |
| --- | --- | --- |
| 1 | 95 | 5:00 |
| 2 | 95 | 0:15 |
|   | 58 | 0:15 |
|   | 72 | 0:10 |
| 3 | Repeat Stage 2: 24x | NA |
| 4 | 72 | 1:00 |
| 5 | 4 | Infinity |

Abbreviation: ° C. = degrees Celsius;
min = minute(s);
PCR = polymerase chain reaction;
sec = second(s);
NA = not applicable Example 57. Testing of E. coli Nissle and Mutaflor for Presence of Phage 4. Summary of Phage Testing Data Independent analyses to detect the presence of phage in several samples was conducted. The analyses showed that the Cell bank sample of E. coli Nissle from the German Collection of Microorganisms and Cell Culture (referred to herein as SYN001), and capsules of Mutaflor which contain E. coli Nissle, variably express a low level of phage under the uninduced and induced (mitomycin C treatment) conditions (Table 90).

Interestingly, E. coli Nissle strains are not always inducible as seen by the CTM lot demonstrating no phage in either condition. Additionally, even when inducible E. coli Nissle cells (Mutaflor and SYN001) express detectable phage, the levels are similar to the maximum levels seen under uninduced or induced conditions for other E. coli Nissle strains.

In contrast, a positive control strain, ATCC 23716,[2] which is an E. coli K-12 strain that contains a bacteriophage lambda prophage, produced 5-6 orders of magnitude more phage than E. coli Nissle or its derivatives following induction. This demonstrates an obvious lack of inducibility of E. coli Nissle strains, for reasons that are not yet understood.

TABLE 90

Summary of Phage Plaque Assay Testing Results

| | Phage Titer | |
|---|---|---|
| Strain | Uninduced (pfu/mL) | Induced (pfu/mL) |
| E. coli Nissle - Mutaflor capsule | 0 | $2.5 \times 10^4$ |
| E. coli Nissle - SYN001 | 0 | $2.0 \times 10^4$ |
| ATCC 23716 (positive control) | $3.0 \times 10^4$ | $3.2 \times 10^9$ |

Abbreviations: CTM = clinical trial material; E. coli Nissle = Escherichia coli Nissle 1917; MCB = master cell bank; pfu = plaque forming unit; SYN001 = Escherichia coli Nissle 1917 from the German Collection of Microorganisms and Cell Cultures. Note that most strains were evaluated in separate experiments, and that the ATCC 23716 positive control strain was run as a control in each assay. The data above for ATCC23716 are the average of positive control strain for these assays.

5. Verification of Phage-specific Primers Against E. coli Nissle Genomic DNA

To verify that the PCR analysis method could identify plaque-producing phage, PCR analysis was performed against E. coli Nissle gDNA using the primers specific for either Prophage 1, 2, 3, or the host rpoB gene (Table 85). Although not shown here, a similar analysis with the same primers against the indicator strain ATCC 13706 gave no band for the Phage primers and faint band for rpoB, consistent with this strain lacking the three E. coli Nissle prophages but containing an rpoB gene with some sequence similarity to the E. coli Nissle gene. Each primer set produced a single DNA product of the correct size as judged by agarose gel electrophoresis, which is displayed in FIG. 13. Based on this result, these primer pairs were used to assess phage DNA from individual plaques from the analyses summarized in Table 90 for the presence of the different phages.

6. Analysis of Individual Plaques for the Presence of Phages 1, 2, and 3

Figure 14:
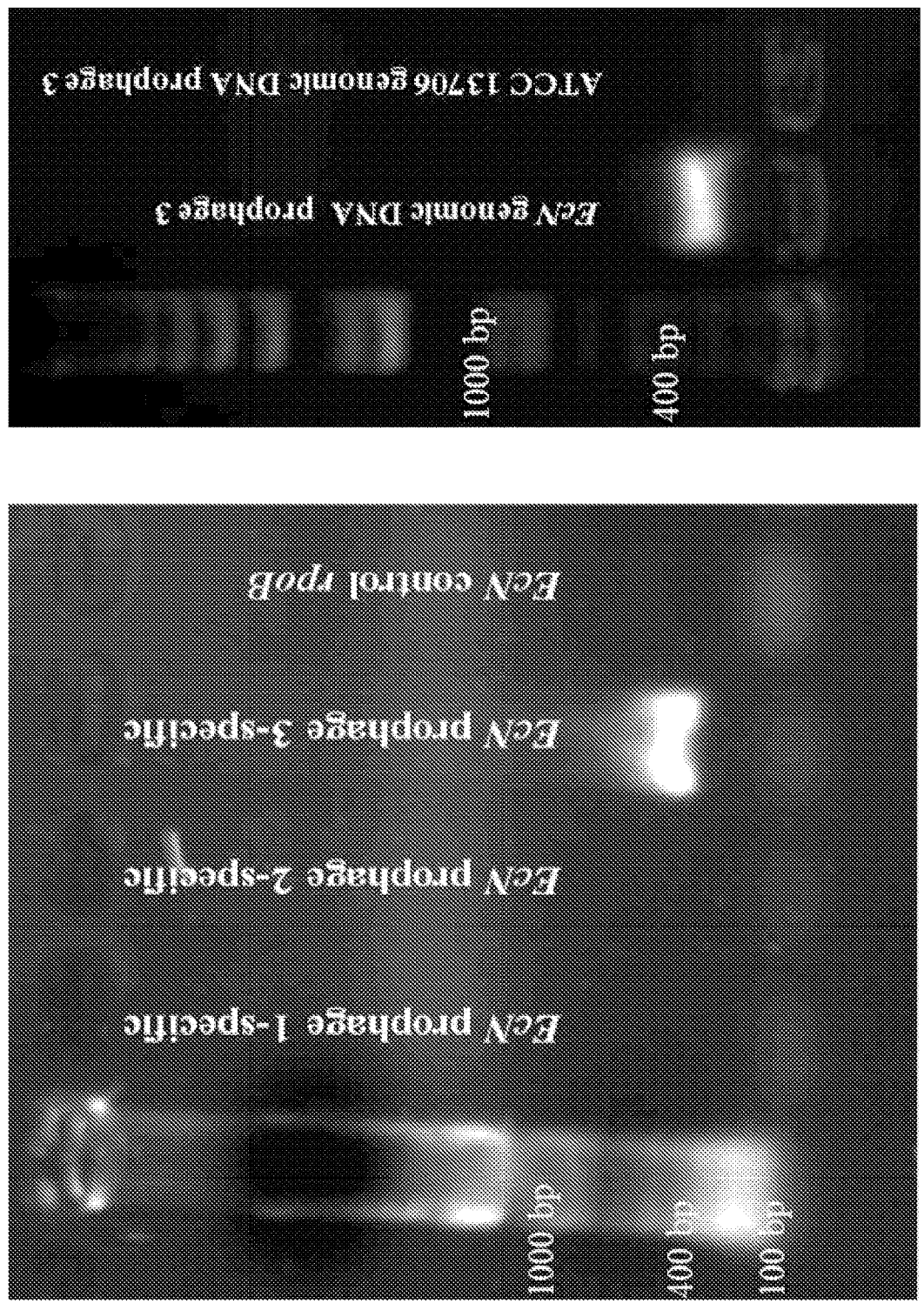
FIG. 14 depicts DNA gel electrophoresis study showing EcN Prophage Regions Amplified from ATCC 13706 Plaque Plugs. Abbreviations: bp=base pairs; EcN=*Escherichia coli* Nissle 1917; rpoB=β subunit of bacterial RNA polymerase.

Plates with enumerable plaques from the plaque assays were analyzed by PCR analysis. Polymerase chain reaction analysis was performed against ten plaques from plates with enumerable plaques using the primers specific for either prophage 1, 2, 3, or the host rpoB gene to determine the identity of the phage that created the plaques. In some cases, plates with clearly enumerable plaques contained fewer than ten plaques, in which case all plaques were used. However, at least 6 plaques were tested for every analysis. In every PCR reaction that was run, only the primers specific for prophage 3 produced a PCR product, and this was true in all cases for each test strain and batch listed in Table 90. A representative gel analysis of this data is displayed in FIG. 14; the left panel of FIG. 14 shows a representative set of PCR reactions visualized for an individual plaque plug taken from an assay of E. coli Nissle-Mutaflor. The right panel shows a control experiment using gDNA from either E. coli Nissle or ATCC13706, the phage-negative indicator strain used in the CRL phage assay, and which does not contain a resident prophage 3. This latter finding confirms that the positive results observed in the phage plaque PCR analysis is not the result of a cross-reaction with sequences in the ATCC13706 plating strain.

E. CONCLUSIONS

In conclusion, these data demonstrate that an expressible prophage element resides in the E. coli Nissle and Mutaflor strains evaluated. This indicates that an expressible prophage is present in E. coli Nissle. In the uninduced state, E. coli Nissle and Mutaflor produce no or low-level detectable plaques. The levels of phage produced in all cases was 5-6 orders of magnitude lower than for the positive control strain ATCC23716. Based on bioinformatics analyses of these bacterial genomes, PCR assays were developed to determine if any of the three endogenous prophage elements identified in these strains were the source of the active phage particles. The results show that the plaques derived from E. coli Nissle result from only one of the three prophage elements identified bioinformatically, referred to herein as Phage 3, as this prophage genome was uniquely amplified from plaques formed on the phage-sensitive E. coli strain ATCC 13706 (which does not natively contain the Phage 3 sequence). Taken together, these data strongly support the conclusions that Phage 3 is the responsible agent for positive phage test results, and that there appear to be no observable differences in phage production among these strains. This information also establishes that the phage produced by these strains is the result of a prophage element native to E. coli Nissle, including commercial Mutaflor capsules.

1. Summary of Results and Conclusions:

In conclusion, these data demonstrate that an expressible prophage element is endogenous to E. coli Nissle. The frequencies with which phage particles were produced by the tested strains, as determined by the validated plaque assay, were quantitatively at a similar low level, indicating that a generally expressible prophage is present in E. coli Nissle. Based on bioinformatics analyses of these bacterial genomes (Example 55), PCR assays were developed to determine if any of the three endogenous prophage elements identified in E. coli Nissle were the source of the plaque-forming phage particles. The results show that the plaques, when expressed from E. coli Nissle result from only one of the three prophage elements identified bioinformatically, prophage 3. This prophage genome was uniquely amplified by PCR from plaques formed on the phage-sensitive Escherichia coli (E. coli) strain ATCC 13706 (which does not natively contain the prophage 3 sequence). Taken together, these data strongly support the conclusions that prophage 3 is the responsible agent for positive phage test results, and that there appear to be no observable differences in phage production among these strains. This information also establishes that the phage produced by these strains is the result of a prophage element native to E. coli Nissle, including commercial Mutaflor.

Example 58. Phage Testing of SYN001, SYN-PKU-710, SYN-PKU1033, and SYN-PKU1034

In this study, plaque assays on E. coli Nissle, and engineered strains comprising phenylalanine consuming circuitry, SYN-PKU-710, SYN-PKU1033 and SYN-PKU1034, were conducted to determine levels of phage produced by each strain. Table 91 provides descriptions of the strains used in this study.

TABLE 91

Strain Descriptions

| Stain Designation | Strain Description |
|---|---|
| SYN-PKU-710 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB::LacIPAL3; ΔdapA. |
| SYN-PKU1033 | Phenylalanine consuming strain which has an Antibiotic Independent Plasmid System (AIPS) comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU1034 has a weaker RBS upstream of the pheP portion of the PAL-pheP gene cassette in the AIP plasmid compared to SYN-PKU1033 |
| SYN-PKU1034 | phenylalanine consuming strain which has an AIPS comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU1034 has a weaker RBS upstream of the pheP portion of the PAL-pheP gene cassette in the AIP plasmid compared to SYN-PKU1033 |

Each strain was tested with and without mitomycin C in log phase, and without mitomycin C from stationary overnights. CFU counts were determined before supernatants were processed for the plaque assay, in order to determine the amount of plaques produced per cell.

The following test strains were grown overnight in LB (with DAP 100 ug/mL where appropriate), 3 mL in a 14 mL culture tube shaking at 250 rpm at 37 C: SYN01 (Nissle); ATC13706 (negative control); SYN-PKU-710; SYN-PKU1033, and SYN-PKU1034. An additional 20 mL culture of ATCC13706 was grown in LB in a 125 mL baffled flask (37C, 250 rpm) for use as the sensitive plaque indicator strain. These overnight cultures were used to inoculate 10 mL cultures in LB at a 1:100 dilution (DAP 100 ug/mL where appropriate) in 125 mL baffled flasks in duplicate. For each strain, one flask contained 2 ug/mL of mitomycin C and the other culture was used as a log phase uninduced control. All flasks were grown at 37 C shaking (250 rpm) for 4.5 hours. Next, cultures and stationary uninduced overnight cultures were diluted 10-fold in PBS in a 96-well plate and plated for determination of cell counts. Ten ul of spot dilutions spanning the 10^3 to the 10^-8 dilutions were plated per plate (LB plates-DAP 100 ug/mL where appropriate), in duplicate, for each strain.

After counting the cells, 1 mL from each culture (3 cultures per strain) was transferred into 1.5 mL microcentrifuge tubes and 50 uL of chloroform was added. Tubes were vortexed for 15-30 seconds, cells were spun down in a microcentrifuge for 2 minutes at maximum speed.

Supernatants were diluted in 96-well plates containing 180 uL of LB per well. 200 uL of neat supernatant for each strain was added to a first well, and 10-fold dilutions were performed with a multichanel pipette. To prepare sensitive control strain, 10 mL ATCC13706 were spun down at 4000×g in a 15 mL falcon tube, supernatant was decanted, and cells were resuspended in an equal volume of 10 mM magnesium sulfate.

Fourteen mL culture tubes containing 100 ul of ATCC13706 cell suspension were prepared for the appropriate strains and dilution of supernatants. Neat supernatant and supernatant dilutions were added to the tubes and the cell/supernatant mixture was incubated for a minimum of 5 min.

After incubation, 3 mL of liquid top agar composed of 7 g/L agar in LB media lacking yeast extract was added to tubes and the mixture was immediately poured evenly onto appropriately labelled LB plate. After plates dried, they were moved the 37C static incubator, inverted, and incubated overnight. Plaque counts are shown in Table 92.

TABLE 92

Plaque Counts

| | supernatant dilution | | | | | cfu/mL |
|---|---|---|---|---|---|---|
| | 0 | −1 | −2 | −3 | −4 | |
| | final dilution (for calculating pfu/mL) | | | | | |
| | −1 | −2 | −3 | −4 | −5 | culture |
| ATCC13706 uninduced stationary | N | N | | | | 3.1 × 10^9 |
| ATCC13706 uninduced log | N | N | | | | 3.2 × 10^9 |
| ATCC13706 + MC log | N | N | | | | 2.4 × 10^8 |
| SYN001 uninduced stationary | 4 | 1 | N | | | 2.4 × 10^9 |
| SYN001 uninduced log | 16 | N | N | | | 4.7 × 10^9 |
| SYN001 + MC log | TMTC | 46 | 1 | | | 0 |
| SYN-PKU-710 uninduced stationary | TMTC | 39 | 4 | N | N | 1.45 × 10^9 |
| SYN-PKU-710 uninduced log | TMTC | 118 | 13 | N | N | 3.0 × 10^9 |
| SYN-PKU-710 + MC log | TMTC | TMTC | 261 | 34 | 3 | 0 |
| SYN-PKU1033 uninduced stationary | 27 | 2 | N | N | N | 7.5 × 10^8 |
| SYN-PKU1033 uninduced log | 4 | N | N | N | N | 7.4 × 10^8 |
| SYN-PKU1033 + MC log | 30 | 4 | 1 | N | N | 0 |
| SYN-PKU1034 uninduced stationary | 6 | 1 | N | N | N | 1.2 × 10^9 |
| SYN-PKU1034 uninduced log | 6 | 1 | N | N | N | 5.5 × 10^8 |
| SYN-PKU1034 + MC log | 31 | 3 | N | N | N | 0 |

TMTC = too many to count;
N = none

Colony counting showed that 2 ug/mL of mitomycin C was completely lethal for all Nissle strains but not for ATCC13706, in which 2 ug/mL killed approximately 90% of cells.

PCR analysis was conducted to confirm that phage 3 DNA was present using primers specific to Phage 3 (not shown).

Example 59. Deactivating Phage Production from *E. coli* Nissle Using Chromosomal Insertion of an Antibiotic Cassette Bioinformatic approaches helped identify 3 regions of the genome putatively containing active phage (see Example 55). Using an in-house developed PCR method, it was shown that the active phage originated from a genomic locus between bases 2,035,867 and 2,079,177 of the *E. coli* Nissle genome.

F. Knock-Out Primer Design

To inactivate the phage, lambda red recombineering was used to make a 9,687 base pair deletion. Lambda red recombineering is a procedure using recombination enzymes from a bacteriophage lambda to insert a piece of custom DNA into the chromosome of *E. coli* directed by flanking homology. First, primers were designed and synthesized to amplify a chloramphenicol acetyltransferase (CAT) gene flanked by flippase recognition sites (FRT) from the plasmid pKD3 (Table 93). When introduced into Nissle, this cassette provides resistance to the antibiotic chloramphenicol. In addition, these primers contain 60 base pairs of homology to the genome which directs the antibiotic cassette into the Phage loci. The Phage 3 KO FWD and Phage 3 KO REV primers were used to PCR amplify a 1178 base pair linear DNA fragment, which was PCR purified. The resulting DNA template was used in recombineering.

TABLE 93

Primers used in the inactivation of Phage3

| Primer Name | Sequence | SEQ ID NO |
|---|---|---|
| Phage3 KO FWD | TGGAGGCTTTAAGAAATACCTCGATGTG AACAACCGCCTGCCACGAATCTTCGTCA AGCG_ATTACACGTCTTGAGCGAT_ | SEQ ID NO: 126 |
| Phage3 KO REV | GATAATGGTGAGATTATCCCCGGTTATA CCGGACTTATCGCCTATTCAGAATCACT GGAT_CTGACATGGGAATTAGCCA_ | SEQ ID NO: 127 |

Bold = Homology to Nissle genome; Italicized = Homology to pKD3

G. Introduction of Lambda Red System

To prepare a strain of Nissle for deletion of phage, first the lambda red system was introduced, by transforming a pKD46 plasmid into the *E. coli* Nissle host strain. *E. coli* Nissle cells were grown overnight in LB media. The overnight culture was diluted 1:100 in 5 mL of LB media and grown until it reached an $OD_{600}$ of 0.4-0.6. All tubes, solutions, and cuvettes were pre-chilled to 4° C. The *E. coli* cells were centrifuged at 2,000 rpm for 5 min. at 4° C., the supernatant was removed, and the cells were resuspended in 1 mL of 4° C. water. The *E. coli* cells were centrifuged at 2,000 rpm for 5 min. at 4° C., the supernatant was removed, and the cells were resuspended in 0.5 mL of 4° C. water. The *E. coli* cells were centrifuged at 2,000 rpm for 5 min. at 4° C., the supernatant is removed, and the cells are resuspended in 0.1 mL of 4° C. water. The electroporator was set to 2.5 kV. One ng of pKD46 plasmid DNA was added to the *E. coli* cells, mixed by pipetting, and pipetted into a sterile, chilled cuvette. The dry cuvette was placed into the sample chamber, and the electric pulse was applied. One mL of room-temperature SOC media was immediately added, and the mixture was transferred to a culture tube and incubated at 30° C. for 1 hr. The cells were spread out on a selective media plate and incubated overnight at 30° C.

H. Lambda Red Inactivation of Phage in Nissle

The recombineering construct was transformed into *E. coli* Nissle comprising pKD46 to delete the phage sequence. All tubes, solutions, and cuvettes were pre-chilled to 4° C. An overnight culture was diluted 1:100 in 5 mL of LB media containing carbenicillin and grown until it reached an OD600 of 0.1. Next, 0.05 mL of 100× L-arabinose stock solution was added to induce pKD46 lambda red expression. The culture was grown until it reached an OD600 of 0.4-0.6. The *E. coli* cells were then centrifuged at 2,000 rpm for 5 min. at 4° C., the supernatant was removed, and the cells were resuspended in 1 mL of 4° C. water. The *E. coli* cells were centrifuged at 2,000 rpm for 5 min. at 4° C., the supernatant was removed, and the cells were resuspended in 0.5 mL of 4° C. water. The *E. coli* were centrifuged at 2,000 rpm for 5 min. at 4° C., the supernatant was removed, and the cells were resuspended in 0.1 mL of 4° C. water. The electroporator was set to 2.5 kV, and 0.5 µg of the recombineering construct was added to the cells, mixed by pipetting, and pipetted into a sterile, chilled cuvette. The dry cuvette was placed into the sample chamber, and the electric pulse was applied. 1 mL of room-temperature SOC media was immediately added, and the mixture was transferred to a culture tube and incubated at 37° C. for 1 hr. The cells were spread out on an LB plate containing 35 µg/mL chloramphenicol and incubated overnight.

I. Verification of Mutation

The presence of the mutation was verified by colony PCR. Colonies were picked with a pipette tip and resuspended in 20 µl of cold ddH2O by pipetting up and down. Three µl of the suspension was pipetted onto an index plate with appropriate antibiotic for later use. The index plate was grown at 37° C. overnight. A PCR master mix was made using 5 µl of 10×PCR buffer, 0.6 µl of 10 mM dNTPs, 0.4 µl of 50 mM Mg2SO4, 6.0 µl of 10× enhancer, and 3.0 µl of ddH2O (15 µl of master mix per PCR reaction). A 10 µM primer mix was made by mixing 2 µL of a primer unique to the CAT gene (100 µM stock) or genomic sequence neighboring the inserted CAT gene (100 µM stock) into 16 µL of ddH2O. Sequence of primers used is shown in Table 94. For each 20 µl reaction, 15 µL of the PCR master mix, 2.0 µL of the colony suspension (template), 2.0 µL of the primer mix, and 1.0 µL of Pfx Platinum DNA Pol were mixed in a PCR tube. The PCR thermocycler was programmed as follows, with steps 2-4 repeating 34 times: 1) 94° C. at 5:00 min., 2) 94° C. at 0:15 min., 3) 55° C. at 0:30 min, 4) 68° C. at 2:00 min., 5) 68° C. at 7:00 min., and then cooled to 4° C. The PCR products were analyzed by gel electrophoresis using 10 µL of each amplicon and 2.5 µL, 5× dye. The PCR product only forms if the CAT gene has inserted into the genome (thereby deleting and inactivating the Phage).

TABLE 94

Primers for Verifying Deletion of Phage3

| Primer Name | Sequence | SEQ ID NO |
|---|---|---|
| Phage3 KO verify FWD | TGGAGGCTTTAAGAAATACC | SEQ ID NO: 128 |
| Phage3 KO verify REV | GCTGGCGATTCAGGTTCATC | SEQ ID NO: 129 |

J. Removal of Antibiotic Resistances from Mutant

The antibiotic resistance gene was removed with the plasmid pCP20. Plasmid pCP20 is a temperature-sensitive plasmid that expresses the Flippase recombinase that will recombine the FRT-sites thereby removing the CAT gene. The strain with deleted phage sequence was grown in LB media containing antibiotics at 37° C. until it reached an OD600 of 0.4-0.6. All tubes, solutions, and cuvettes were pre-chilled to 4° C. The cells were centrifuged at 2,000 rpm for 5 min. at 4° C., the supernatant was removed, and the cells were resuspended in 1 mL of 4° C. water. Cells were centrifuged at 2,000 rpm for 5 min. at 4° C., the supernatant was removed, and the cells were resuspended in 0.5 mL of 4° C. water. Cells were centrifuged at 2,000 rpm for 5 min. at 4° C., the supernatant was removed, and the cells were resuspended in 0.1 mL of 4° C. water. The electroporator was set to 2.5 kV, and 1 ng of pCP20 plasmid DNA was added to the cells, mixed by pipetting, and pipetted into a sterile, chilled cuvette. The dry cuvette was placed into the sample chamber, and the electric pulse was applied. One mL of room-temperature SOC media was immediately added, and the mixture was transferred to a culture tube and incubated at 30° C. for 1-3 hrs. Next, 200 µL of cells were spread on carbenicillin plates, 200 µL of cells were spread on chloramphenicol plates, and both were grown at 37° C. overnight. The carbenicillin plate contain cells with pCP20. The cells were incubated overnight, and colonies that did not grow to a sufficient OD600 overnight were further incubated for an additional 24 hrs. The chloramphenicol plate provides an indication of how many cells survived the electroporation. Transformants from the carbenicillin plate were purified non-selectively at 43° C. and allowed to grow overnight.

The purified transformants were tested for sensitivity to carbenicillin and chloramphenicol. A colony from the plate grown at 43° C. was picked and resuspended in 10 µL of LB media. Three µL of the cell suspension was pipetted onto each of three plates: 1) an LB plate with chloramphenicol incubated at 37° C., which tests for the presence or absence of the CAT gene in the genome of the host strain; 2) an LB plate with carbenicillin incubated at 30° C., which tests for the presence or absence of the beta-lactamase (CarbR) gene from the pCP20 plasmid; and 3) an LB plate without antibiotic incubated at 37° C. If no growth was observed on the chloramphenicol or carbenicillin plates for a colony, then both the CAT gene and the pCP20 plasmid were lost, and the colony was saved for further analysis. The saved colonies were restreaked onto an LB plate to obtain single colonies and grown overnight at 37° C. The deletion of the phage sequence was confirmed by sequencing the phage loci region of the genome and, more importantly, by phenotypically verifying the absence of plaque formation (essentially following the protocol as described in Examples 57 or 58, and as described for example in Example 60).

Table 95. lists the portion of the *E. coli* Nissle Phage 3 removed for inactivation of the Phage 3.

TABLE 95

Sequence removed from Phage 3

SEQ ID NO: 130 aatcgccggtgtactccgcgtcagaaaggtatacagccacggcagggagatcctgctcttcaagaaaaacagggcgcccgtcaaaccag gtgaccgtgtcggtgatctcggctttcagtttggccagaatggctgcacgaattgcgctgtgtctgttcatcgcttcaggtggatcctcagttggt ttttcagggctgcggaaagttctttgggcatatcgctttcaataaggcgctttgaaatagcggtgaaggccacggtgagcggtgtctcaagag gaactttgaccacatcaatcggataacgggcctgacctacgcgccgcatgacctgccagcgcccgttcgcaagctgttggataaaagcgtta cgaaaggtatagggcccgattttaaggacgctgcccgctccgtttctggccccttttttacgcgagagcctgacgcgcgccgtgccgagcttt atcgcaggaagattaccgcggttgattttatcgacgcgaccgggcgatcgtgacgggccttgcgcagacgggaacgctggcggaccaga cgaaccggaagccccttttccggttatcatcaactgttgcttctttcgctacagctttgctccctggcttatcgttcttctggccaccctgttaagt gcttttgcggttgcctcaggaacgattaaccggctgaggctgttcaggttctgaatagccctttccagtcctttcacagacatagcgcctcctca ttcgagatggatgcggggttttccgttgaacatgtcatagcgggtaacgatcaggttcttaccgtcgtagtcgacgctgtcgtttcggcgtggct ggtaaagctcagagaaaaccaccagcgaagtacctgttcccgacaatggccccatttcctcgagttgctcggcgggaacaacgtcatagct gctgccattgatgatcgctgtctttcccatctttttttatagtggccgcgtccatgcgcgcgccatccggtcaaaggagttaggcattgatcttaa cttcaacaacggtggtgtttgccctgcatcttcccaggcgatgcccgcggcaacggcgtccgtttcttcgatcgtgattttgccgtccttcaga tacacctgcgccccggcagtaaccgcatctgcggatacttttggcaggaggaaaacaccctcagtaaaaccgtccccggtatcgccagccg ggatatcggtaattgccaccgcgataagttttccaacaacaaccgggtcgccgctgtgaacatcggttgcaccactgtttaccagagggatcg ttttcccgtcctgcgcatagttcttagccataacttctccattcagccccttccgaggctggtttcaggtataaaaaaagcccttacgggcgtctgt ttgtcaggactgttttttactgaccagaggatttggtcatgccgcgatagtccagcggcgccacgccagcatcaatacgcactttcgtggcgat accatcagtggtgaagccttcctgctgatcgatgtatggcgtgtcgacgccgttgagataagcgacctcaatggtgtcggtgccttcgcggc agccagataccaggctttcgcatcagcttcatccagacgtggttcggcaatgacttctgcaaagttctggatagggttaacgatcccggcattg atgtctgcacctttaacactggccgacttgatggtctgatttgccagagtttccagggcgacgggcaccagcatgtaggccggacggatattc agggttcgctccccctccttctgcagacgcatcagcttgcgcgattcgtccaggctggccacagaaattgcacccgagctcaggttcttgtga tcggcatggaacagcgcctttccgtctgagagtttcgggttttggtcagaatggcgtaaaccagatcgccaatcgttgctttcgccgcgcc ccatcttcatcggtacgtcggtaagctggttcagatcgtcgttgatgatcgcctggcgagttactgagaagatttcaccatacgtggcaagcgc gatggtttcgcctttgtcactggtagtgatgtacttgtactcagccccttcgcgaacctgtcgcagagaagggaacccaccatacc gacacg atgcgccgttttgaagtccgacagctggcctttttggtccactgctcgaaggtttcctgcgcctcgtcccagccctgaatcagcgctttgttcgc aacatcaagcagaatgttgccaaagtcagaggtgctgtgggcagcgccaggccaaccatctgcatcgggttgtagctggccacgccgata cctttttctgtcagggccatacgcgcatactcgcgcagcgtcataccgttataaacgttatccc gctcctgaccttcgaacccggcacgcgcca tcagtgcctggcgaataccatccgcgacgaagttaccgttgcccgcatgaatatgcggctgagtggttttattggacggcgtggccgttttacc gagttctgccagcagcaaatctttcgccttatcgacggagcaatcagggtcggccacacactgattctgcagttccatgtgcttattaccgaac atggcaaagagatcgccgatacgcttaacacgggttttctgctcagccaacacctgcgcgcggatcgcattttcatccggtgccgggtctgtt tttgcctgcggtgcctgaggctgggtaataaccgggtcacgctgggtagtgttgcgcggcggggtgatcatgttgcgaatgcttttttggcatttt ttcaaattcctcaatacgttttgaatgaatacaggccatagcctgaagggatggtgtcacctggtcggcaaaacccagttcaaggcactcgctg ccgttcatccaggtttcgtcctccagcattaccgcaatttcttcggtggattttccggttttctgtgcataagccgggataagaacggattcaacct tgtcgagaagatccgcatagtcgcgcatatcgctcgcgtcaccaccagcaaaccccagggcttatggatcatcatcatcgtgttttcaggca tgatgaccggattgcctaccatcgcaatcaccgaggccatggaggccgccagaccgtcgatatgtacggtaatcgccgcgccgtggtgctt cagcgcgttataaatagcaattccgtcgaagacatcaccaccgggcgagttgatataaaggttgatgtgggtgacgtccccaagtgcccgga gatcattgacgaactgtttcgccgttacgcccagtacccgatttcgtcataaataaaaatgtcggcctcactgttattgctggcctgcatgcgg aaccacgaattactttttgcgctggctttcggacggtggcgcgcccggttctttggcttcggcactggtgcctccttttcattggcggggtcgg tgtcaaacaccaggccctgttcacggttctcgtcaacctcagctttacggcgtgacttaacatcatccgggttgcgaccgctggcacgtatcca gtcggattcagtagcagcaccgccgcggatctgcgttttccaggcattcgcttctttaacgggatcaatccacggcataacgggccccgaata TABLE 95-continued Sequence removed from Phage 3 aaccgcgttataaagcgagtccatatcaatgcctctcggcagcttgatttctccggcagcaatagccatcttgagccaggctcggtacatggg ccgggtcactgaaccgatgaaccagtcctgaagaatcagatagccgtcggttgactcgacaagctcctgccgctgggcactgtacgttccgt tgtagtttctggatgtgctggaaaagctgaggcgactgccggcggacacggcacgcagctgtccgttacgaaaagattcgaggttagggttc gggcgatcggatttaatcatcccgatttcttccccggcctgcagttcgtcatagagcataccggctgaatcatcagctcgcggtcatcgctgc ttgaatcagaatcgaagctctgtccgtcgccttttttgatatacatgccgagtgccgcagcaattctggcagcagtaagctccgagtcctcgtat tctttcagcgcgctcagacgcatcagaacaccagacaaaagagacgttccgcgggtctggtgcaggcgtcgggtgaatttgagatgcagca tgttctctgcatctatctctttggtatcaaactgacgcccggatactggcaggcttttatagacctgatattttttcgggcgtccccagttatcgaca aaaacgccctgattgagctgggtggcagcatcgctgttcatcggcacaaagtccggctccagcgcttccagccagaacggcacgccagca accggctgaagaccatttccggtaccgcgaaccagctgagcaaatacctcaccgtcccggagccacgttcgcagcatcagccgctccagc attgggcgggtaaactgggttgtgacatctggccttacggaccattcgcccacttttcggcggatatcagtggccagcttttttagcgatcttccc gttactcagcatcggatgcggttcaactatgatgcccttcgcacccaccaccccttttcttccagcttgtcgaaaacgccgatcaccagatcgtgg ttgttatccagccagcgcgcctgctgcctcagcgaaaccgcccccatctggctgagctgatcggctgaacgattttccttctgggctttgtggg tacgcgtttgctttaccgcctcatacgctttaataactgcgcgggcacgcaggcgtgaggctttccagcctggtgaaaacaggccaatcgcat catctaaaaaactcatccaaacctcgccagcctgtagccgggtcgcccacggcgtttgttattgagcgttgccagtcgtcgctcccattcctga cggccttttctgatttccgacaggttttcgagcgtcatctgctgcccgttgaaagtgattgatttcccctccagaacagacagctcggctgcagc atagcggtcgatcatgttttgaatatctgctggattcacacccaacctcctgacgaagaccacggattagcctgctcggttacgggcttctcac gttttggttttggtttagatttcggcgcaggcggcggggatggcatttcgccagcttccgtctgcgtgtcctcgatccacgtttcccgccgtgcc cactcaggagctgacggccatttgatttttcgtaaccactaaggatggcgagcgcgtcggcataaacgagcaggtcaaatgcttcgtttgcg ccccggccgggcttactccatttcccttcattcgagcgttcctcatacgtcagttcgtcatagaaccagctgcccagccaggcggggaaatgc acatagccagggccgggtgaatcacgccacagcgcattattcacccggtctttaagggcatcggtctggagaagataaagaggcacatcac cagtcgcctgtgcgcggcgcgttgatctgcccgtgttgtcgggaaacgttcgctggataagtttgctgcgcctgacgctgtccccttttgaaga gatagatacgcttacccagcccctcacggcgacatctgcgccagaacttgtaggcattatccgtcacgccatcttcgcccctgagtccacg gccatcgacatcagccgcatgcccttgatgggtcagctgcgagcggccacgttttatcaaagacgtcagtgagtaaaagatcccagtcctc cggatagctcgccggatccacctgaatgctttcaccgttgccgtcgcagcgcagcgaatgccggatgttgtaacggtcaactatccagcgct cacccatacttccataaccccgtaatctgcacaacaaagcgccggttgcgcccggcctgcacgtccacggtcgcagtgagaaactgcacgc cgttcggtaccgaacgttttgggacgtcttcggcacgctgctcgagcaattcacttttacgctgctccatgctggctcgcggcaaatagggcct gccgaaatcggtgttgatcaccgtcttcagggtttcttcgctgcgcgtggattcatattcctgctcggcggtcagaaacttataaataagctgcg cccaggtctggtaagcagctgccggaccttccatccagaaggaggcaatacgggaacgacggccatcaccgctaaccaggcctttcctgt cgatggtttgcccgtcccggagccagacacatttcatgttaagcgcacgcttcatgtccggtgtgatcctgcctttacaggcagggcactgaa gaaacgccgcttcgctggcaagcacaggatcgctgctgtcgcggtatccggtcatattgtccatttccggctggaaatattcgccgcaatgcg ggcatggccagtaaagacgacggcggtcaccacggttatagagcgataaaattccggtggtcggagggcttcatgggcgtggagcgc cgccattttgtgtctctgatatccctcccgggcgagctctcaaccagcgtcatcccggaggacatgaatgtcgtggttcgtttcgatgccagtg aaaaagcatcccctcccgtcgatatcttccggaaagcggtcataatccgtcagcgccacacttttatagtccgaggacgacatgatattga cggatggccagcccagcttcagatagttaccggcgcggaatgtacggtcgtagacgttgttatcgttacgtcttgggcttagccgggttttaac ttcagggctacagcgaaaagtacggtccaggcgttttttggaatgctcgcgcgcttttttcctcagatacctgaattacaagcatatctgccggat cgcagacaatgttataaacgatccagccgtcaatcagcccgatggttttacccgttcgcgctgggcccacaaacacaaccgcatcgtattcac gcgatgccagacagttcatcggctcaatcacataggtgccagatccggatcccacggaactgagtttcccgcccccattggcacgcgcat ataagtactgaccgcatcggccaccggcatacgacgcggggctcgtaaaataccggaaacatcgcggcggatgtccctggcggatgccc gctttgccatcagtcctcctcaggctgctcctcctcttttccagcgtcctgcaccttctccgccatctggtcgcgcagatcatcgataacgctttg TABLE 95-continued Sequence removed from Phage 3 cacacgaactaccgcagcaggcgttaaagcacagtcgcgctcgagcacatccgggagggtttcaagtaccatgacgacggctttcgccat
caatgagaattctcgcgccacttcatctgcgggtattaactgccccgtatcctgttcgaacttcagcctctcgttctctgctttccagtgggacag
cctgtcagaaggggggcatatcgtcgatgttggccgaaacggtagggatcatcagttcggtcagaatgtcggtcaccagatagagctttaactt
gctattgctgcctggagcaggttcaacattttcagtctcgcggcaaccgtctgacggtgtacgccggttatccctgccagctggttgatattga
gttttaaagtggcaatttcctggtccatgatggtgaacacttttgaacgattcgacatgttgcgaaaatggcctctaattaaatcaaagacctgc
gcacatgatgatgatgaccctggatccgaaaaactagccgtttcccgcgagcacgccgcccgtggcagggtcccctccgggagtacctt
ttgataataattatcaattgcacactatcgacggcactgctgccagataacaccaccggggaaacattccatcatgatggccgtgcggacata
ggaagccagttcatccatcgctttcttgtctgctgccatttgctttgtgacatccagcgccgcacattcagcagcgttttcagcgcgttttcgatc
aacgtttcaatgttggtatcaacaccaggtttaactttgaacttatcggcactgacggttaccttgttctgcgctggctcatcacgctggatacca
aggctgatgttgtagatattggtcaccggctgaggtgtttcgattgccgctgcgtggatagcaccatttgcgatagcggcgtccttgatgaatg
acactccattgcgaataagttcgaaggagacggtgtcacgaatgcgctggtccagctcgtcgattgccttttgtgcagcagaggtatcaatctc
aacgccaagcgtcatcgaagcgcaatattgctgctcaccaaaacgcgtattgaccaggtgttcaacggcaaatttctgcccttctgatgtcag
aaaggtaaagtgattttcttctggtattcagttgctgtgtgtctggtttcagcaaaaccaagctcgcgcaattcggctgtgccagatttagaagg
cagatcaccagacagcaacgcgccacggaaaaacagcgcataaagcacttcattagcagcgccagatagcgtaatgattttgttactcatgg
aatatttccttttaggcgtgagcctgtcgcacggcaatgccgcccgagaggtaaacgcaacctaacggcatcacccaggctcactactgaaa
gactctctttgatgtgcgcgtgcgatgcgcgtagaagactgatttatcaacctgtctttatatcaggattcattacctgactatttgtgggtaaagtt
cgtagtgcgctgatcgtgcaaaatgattttagttgggaacagttcgcaactctgtcccataaaaatcagcatattcccatctatcccatatccagc
gcattgaccatcgggatactgaagggagattccatcatctcttagaaagatcaccatctcttttgtttcaatttgcatatagctacctggaggattt
atgaatgcaaggattttcatggactattaccatgagattgattttccatctttattcgcgagagcagtggaaagcgatgacgatgtgggtactaca
ttgcgcattcacctactttgtgagcgcatggtcgaagcatggatatgcgcatgctgtgactgccaagatctctttggaagagataaaaacaaac
ttttaatcgaatgtaatactaaaatatccatggcgggaaacctgggaatcccccggaacttatgaaatcacttaaaaccatcaactcaatgcgt
aatgaccttgcacacaatccatcaatacaaagcattgctgattcaaggatccagagcctgaaggatactctgactgaatactttaaacagcatc
caacggaacccagcatggaagaatcaaaactgggtattttttaacgccgagaatcaattaaccgaagaagtttccttagatagtgacagttcaa
aaaacagacttaagttaatcttgctgttcagcaagttaatgcaggcgttaatgcaattagttgcagctaatcataatgggcgctgggataaccaa
tttagccaattcgtttaccatgtgaccatgaacgcaacaaagagataaatccaagcccgttttgtacgggctgttgcattatcacaggcactcag
tgaatgcctgctgtaatgccgctagtcgtcgagttgcaacacaccgtg Table E. lists the Phage 3 genes that were inactivated by the deletion.

TABLE E

| Phage 3 Genes inactivated by the deletion | | | | |
|---|---|---|---|---|
| ECOLIN_10110 | 1 ... 160 | Minor tail protein U | GI: 660512026 | |
| ECOLIN_10115 | 157 ... 729 | tail protein | GI: 660512027 | |
| ECOLIN_10120 | 745 ... 987 | DNA breaking-rejoining protein | GI: 660512028 | |
| ECOLIN_10125 | 1013 ... 1339 | hypothetical protein | GI: 660512029 | |
| ECOLIN_10130 | 1422 ... 3368 | peptidase S14 | GI: 660512030 | |
| ECOLIN_10135 | 3382 ... 4881 | capsid protein | GI: 660512031 | |

TABLE E-continued

| Phage 3 Genes inactivated by the deletion | | | |
|---|---|---|---|
| ECOLIN_10140 | 4878 ... 5093 | hypothetical protein | GI: 660512032 |
| ECOLIN_10145 | 5090 ... 7192 | DNA packaging protein | GI: 660512033 |
| ECOLIN_10150 | 7192 ... 7680 | terminase | GI: 660512034 |
| ECOLIN_10160 | 7864 ... 8592 | hypothetical protein | GI: 660512035 |
| ECOLIN_10165 | 8767 ... 8997 | hypothetical protein | GI: 660512036 |
| ECOLIN_10170 | 8996 ... 9592 | hypothetical protein | GI: 660512037 |
| ECOLIN_10175 | 9661 ... 9687 | hypothetical protein | GI: 660512038 |

Table F. shows the sequence of Phage 3 comprising the deletion.

TABLE F

Phage 3 sequence with Deletion

SEQ ID NO: 281 aggcctctcctcgcgagaggcattttttatttgatgggataaagatctttgcgcttatacggttggatttcgcccggtttgcgagttttcagcaattttt a
atatccaggtgtattgttctggtcgcggaccaacaaaaatctcgacttcttcattcatccgccgcgcaatcgtatgatcatccgcctctaacagatca
tccatcggtgggcgcacctgaatcgtcagacgatgcgtcttgccatcataaatcggaaatagcggtacaacgcgcgcacggcacactttcatca
aacgaccaatcgcgggcaacgtcgctttataggtggcaaagaaatcaacaaattcgctgtgttctgggccatgatcctgatcgggtaaataatat
ccccagtaaccctgacgtaccgactggatgaatggtttaataccatcatttctcgcatgcagacgaccaccaaagcgacggcgcaccgtgttcc
agacataatcaaaaaccgggttgccctgattatggaacatcgctgccattttctgcccttgcgaggccatcagcatggcaggaatatcgacggcc
caaccgtgcggcaccagaaaaatcactttctcgttattacgtcgtatctcttcgatgatctccagcccttgccagtcaacgcgcggctgaattttctc
cggcccgcgtattgccaactcagccatcattaccatcgcttgcggcgcggtggcaaacatctcatctacaatcgcttcgcgttcagcttcactacg
ttctggaaagcagagcgacagattgattaacgcacgacggcgtgagcttttcccagtcgtccggcaaaacgtcccagccgtgccagaatggg
atcacgaactttggcggcgttaaagcgatacccgccatcgctgctacgcccagccatgctcccagtagcgcgggtggcgaaaggatttatc
aaactcaggaatgtattcgctattatttttttcgtttccatgcttttccagtttcggataaggcaaaaatcaatctggtgatagtgtagcggcgcaactt
gccccgcaccaaataaaaagccggtactgactgcgtaccggctgcgaatggatgttaattaatcaaaccgtagctgcggcacaatctctttgg
cctgtgccaggaattcgcgacgatcggagccggtcagcccttcggtacgcggcagttttgccgtcagcgggtttacggcctgctggtttatccat
acttcatagtgcagatgcggcccggttgaacgtccggtattaccggaaagcgcgatacggtcgccacgtttcaccttctgtcccggtttcaccag
gatcttgcgcaagtgcatataacgcgtggtgtagctgcgaccatgacgaatagccacataataacctgctgcgccactacgtttggcaaccacc
acttcaccgtcacccactgaaagcactggcgtaccttgtggcatggcaaaatcaacacctctgtgtggcgcaacgcgaccggtcaccggatta
gtacgacgcgggttaaagttagatgagatacggaactgtttcgccgtcgggaatcgcaagaatcctttcgccagaccagtaccgttacgatcgta
gaatttgccatcttcagcgcggattgcgtaataatctttaccttctgaacgcaaacgtacgcccagcagctggctttgctcacgtttaccatcaagc
atttctcgtgacattaacaccgcaaattcatcgcctttttcagtttgcggaaatccatttgccactgcatggctttaatcactgcgctcacttcggcgc
tggttaaaccggcgtttctggcgctggcaacaaagcttcccccgacggtacctttcagcagattgttgacccactctccttgctgcatttcgctggt
cattttaaaaccgttagcggcagtacggtcataggttcgggtttcacgacgagacacttcccaggtgaggcgctgcagttcgccgtccgcggtta
atgtccaggagagttgttgaccgattttcaggttacgcaattctttgtcggcagcagccagttgggtgatatcacccatatcaataccatactgattg
agaatgctgcttagcgtatcgccagtggaaacaacatattcatgcacgcccgcttcaccggcgattttgtcatccagttcgtcctggggaatggct
tcatcttcttgtgcagcttgatcaatcggctcactggcttcaggtaagagcgaacgaatttcgttctgttccagctcaatggttttgacaattggcgtg
gcatcgcggtgataaacataggccgccagacagcgacggccagagtaagaacggtgagcgaccccaacataacgcggtgtggtcgcggt
aaattattaaacgccagggcgacagagcgggctatctgttgcacgtaatcacttcctcattaatctccttttcaggcagctcgcatactggttggcta
attgattcaggaattctgaatagcttgttttacccagtttgatattcgtccccagggatccaacgttcccatacgaacggatgtccctcgtgcgacg
ctctcaacgaccgctggcctgaactgtggctcagcaaaaacgcaggttgcttttgctcaaccaactgtgttcttatttcatgtaaacgctgcgcgc
caggttgaatctcagggttaacggtaaaatgaccaagcggtgtcagtccgaactgttttcgaaatagccgtaagcatcgtgaaaaacgaaataa
cctttccccttgagcggcgcgagctcgttaccaacctgcttttcggttgaggctaattgtgcctcaaaatccttcaggttggcgtcaagtttggctcg
actttgcggcataagttccactaattttccatggattgcaaccgctgtagcccgcgctatctctggggaaagccaaagatgcatgttgaaatcgcc
gtgatggtgatcttcgtcactttttccgcgtggtcgtgatcatcatcatcgccgtgaatacttttcatcagcagcggtttcacattctctagctgcgca
atcgttacctgtttcgcttcaggtaatttacttaccggttttgcatgaacgcttccatctccgggccaacccaaacgactaagtccgcgttctgtaag
cgttttacatctgatggacgcagtgaataatcatgttctgaagcccgtcaggtagtaaaacctccgtttctgttacccatcagcaatggcagaag
cgatgaacccaacgggtttaagcgaagcgacaacggcagcatctgcggcctgtgttgcaccgcccagagagcggcggataatgctgcgaa
aagaagcgttttttatgtaacataatgcgaccaatcatcgtaatgaatatgagaagtgtgatattataacatttcatgactactgcaagactaaaatta
acatgacaagtctggtttccctggaaaatgtctcggtttcttttggccaacgccgcgtcctctctgatgtgtcgctggaacttaaacctggaaaaatt
ttgactttacttgggccaaacggcgcaggtaagtcgacactggtacgggtagtgctcgggctggtaacacccgatgaaggggttatcaagcgc
aacggaaaactgcgcatcggctatgtaccgcagaagctgtatctcgacaccacgttgccactgaccgtaaaccgttttttacgcttacgccctgg TABLE F-continued Phage 3 sequence with Deletion cacacataaagaagatattttgcctgcactgaaacgtgtccaggccgggcatctgattaacgcaccgatgcaaaagctctcgggtggcgaaac gcagcgtgtactgttagcgcgagcattgttaaatcgaccgcaattattagtgctggatgaacccactcagggcgtggatgtgaatggtcaggtgg cgttatatgaccttattgaccaactgcgtcgcgaactggattgtggcgttttaatggtatctcacgatctgcatctggtaatggcaaaaaccgatgaa gtgctttgcctgaatcaccacatttgttgttccggcacaccggaagttgtttccctgcatccggagtttatttctatgtttggtcctcgtggtgctgaac aactgggtatctatcgccatcatcataatcatcgtcacgatttacagggacgaattgttttgcgtcggggaaatgatcgctcatgattgaattattattt cccggttggttagccgggatcatgctcgcctgtgccgcgggtccgctgggttcgtttgtagtctggcgtcgtatgtcttatttcggtgatacgctgg ctcatgcctcattacttggcgtcgcgtttggtttgttgctggacgtgaatccattctatgcggtgattgccgttacgctgctgctggcgggcggtctg gtatggctggagaagcgtccacagctggcgatcgacacgttattagggattatggcgcacagtgccctgtcgctgggcctggtggtcgttagtc tgatgtctaatattcgtgttgatttgatggcttacctgttcggtgatttactggcagtgacgccagaagatctcatctctattgcgattggcgtggtcat cgtggtggctattttgttctggcaatggcgcaatttgctgtcgatgacgattagcccggatctggcgtttgttgatggtgtgaaattacagcgcgtga aattgttgttgatgctggtgacggcattgacgattggtgtagcgatgaaattcgtcggcgcgttgattattacttcactgctgattattcctgctgctac tgcacgtcgctttgcccgcacgccggaacagatggctggtgtcgctgttttggtggggatggtggcagtgactggcggtttaaccttttccgcatt ttacgatacacctgcaggcccgtcggtggtgctatgcgcggcactgttatttattatcagtatgatgaaaaagcaggccagctaatctgtcgctga acacatttgtcggatgcggcgcgagcgccttatcccacctgcggttcgctatctctggtaggcctgataagacgcgaacagcgtcgcatcaggc acactgccagtgtcggatgcggctcgagcgaccaatccgacttacggcatttctggcggcgtgatgccgaagtggttccacgcccgcactgtc gccatacgcccgcgcggtgtacgctgcaaaaagccttgctgaatcaaataaggttccagtacatcctcaatggtttcacgttcttcgccaatggct gccgccaggttatccagacctaccggcccaccaaagaacttatcgattaccgccagcaacaatttgcggtccatataatcgaaaccttcagcatc gacattcaacatatccagcgcctgagcagcgatatctgccgagatggtgccatcgtgcttcacttcagcgaaatcacgcactcgacgcagcaga cggttggcaatacgtggcgtaccgcgcgcacgacgagcaacttccagcgcgccgtcatcactcatctcaagcccataaagcgtgcgctgcg actgacgatatattgcagatccggcacctgataaaactccagacgttgcacaataccaaaacgatcgcgcaacgtgatgtcagcgaacctgc gcgcgtggttgcaccaatcagggtaaacggcggcaaatcaattttaatggagcgtgccgccggaccttcaccaatcatgatatccagttggtaat cttccattgccggatacaacacctcttccaccactggtgaaagacggtggatctcatcaataaacagtacatcgtgtggttcaaggttagtgagca ttgctgccagatcgcccgcctttccagcaccggaccagaagtcgtgcgtaaattaacgcccatttcattggcgacaatattggcaagcgtagtttt acccaaccccggaggaccaaaaatcaatagatgatcgagggcatcgccgcgcagtttcgctgctttgatgaaaatctccatctgcgaacgaac ctgccggctgaccaacatactcttccagtaatttagggcgaatggcgcgatctgccacatcttccggcaaagtggtaccggcagaaatcagacgg tctgcttcaatcatcctttacctcataacgcggcgcgtagggcttcgcgaattaatgtttcactgctggcgtcagggcgagcgattttgctcaccat gcggcttgcttcttgtggtttatagcccagtgccaccagcgcagcaaccgcttcctgttcagcatcgtcggtcgccgggctggcaggagacgtg agtaccaggtcggcggctggcgtaaagagatcgccatgcaaacctttaaatcggtctttcatttcgacaatcaagcgttcggcggttttttttgccaa tacccggcagtttcaccagtgcccccacttcttcacgctcaacggcattaacgaactgctgcgctgacattccggagaggatcgccagcgccaa cttcgggccgacgccgttggttttgatcaactctttgaacaacgtgcgctcttgtttattgttaaaaccgtacagcagttgcgcgtcttcacgcacca caaagtgggtgaaaacgatcgcttcctgacccgcttcagggagttcataaaaacaggtcatcggcatatgcacttcatagcctacgccgcccac ttcaattaacaccagcggggttgtttttcaatgatgatgcctctgagtctgcctatcacatgacgctcctgcgtaatgaatcaaagataatgctgtat gataaaaaatgctggatagatatccagcgaaggatgaagaaaacttgcgaggtgtctcgatgatctgaaaaatggcgcagtataatttattctac agattatattggaagcaaatatttaaatattacatattcagcgaagaaatgtgtaataaaaatacacattgcgaccccctgaaaaaaataaatttttttatg ctattacgtatattcatatctatttcaatggaatgacaacgtgaatattaattatcctgctgaatatgaaattggtgatatcgtctttacatgtataagtgct gccttatttggtcaaatatcagctgcatcaaattgctggagtaatcacgtcgggatcattatcggtcataacggtgaagactttctggttgcagaaa gccgtgttcccctctcaaccatcactacgctatcccgttttattaaacgctctgctaatcaacgctatgctataaagcgattagacgccggactaac agaacaacaaaatcaacgaattgttgaacaggttccttcccggctacgcaaaatttaccacaccggttttaaatacgaatcttcgcgccagttctgt tcaaaatttgttttgatatttataaagaggcgctatgtattccggtgggtgaaatagagacgtttggagaattgttaaatagcaatccaaatgcaaaa TABLE F-continued Phage 3 sequence with Deletion ctcactttctggaaattctggttcttaggttctattccgtgggagcgtaaaaccgtcacgccagccagtttgtggcatcatccgggtttggtgttgatt
cacgcggtgggagttgaaacgcctcagcctgaactgaccgaggcggtataacttaacgcagtcgccctctcgccaggttcagtcgcgattcgc
tcatttgcatcgcattctgactaacgtggcagtgggtgatggcaatcgccagcgcatcggcggcatccgcctgtggattagcgggcagtttcag
caaggtgcggaccatatgctgcacctggctttttcggcactaccaatacctaccactgtttgctttacctgacgtgccgcatattcaaataccggc
aattcctgattcaccgccgccacaatcgccacgccgcgcctgccccagtttcagggctgagtcagcgttcttcgccataaagacctgttcaat
ggcgaaataatcaggctggaattgggtgatgatttccgtcacgcccgcatagatgagcttcagacgagacggtaaatcatccactttggtgcgta
tgcatccgctacccaggtaggacagttgcctgcctacctggcggatgacgccatagccggtcacgcgcgaacccgggtcaatgccgagaata
atagccatcacgcgtctccgttttgctgtttagcaggcctcatcagagagtcgctgcaacctcatcagagatttcaccgttatggtaaacttcctgca
cgtcgtcgcaatcttccagcatatcgatcagacgcatcagtttcggtgcggtttctgcatccatatcagctttggtggacgggatcatggaaacttc
cgcgctgtctgctttcagacctgccgcttccagagcgtcgcgtactttgcccatttcttcccatgcagtgtagacatcaatcgcgccgtcatcatag
gtcacaacgtcttcagcaccggcttccagggctgcttccatgatggtgtcttcatcgcctttctcgaaggagatcacgcctttttttgctgaacaaata
agctacggaaccatcagtaccgaggttaccgccacatttgctgaatgcatgacgcacttcagcaacggtacggttgcggttgtcagacagacat
tcaatcatgattgccgtgccgccaggaccgtaaccttcgtagatgatggtttccatgtttgcatcatcatcaccgcccacacctcgtgcaattgcgc
ggttcagagtgtcacgggtcatgttgttagacagtgctttatcaattgctgcacgcaaacgcgggttagcgtccggatcaccaccgcccagctta
gccgcggttaccagctcacgaatgattttagtgaagattttaccgcgcttagcatcctgcgcagcttttacgatgtctggtgttggcccatttactatg
acctgccataaaaatatctccagatagccctgcctgttcaggcagcgttaattacaaactgttcaatcgcctgccggttgctccaggacttagtga
gcgccgccgcagcagacgcatcaagccacttgtaagccagatgttcagtgaaaacgatctggcgctcgtgcggaagcgcaagacagaacca
tgattccgtattacgcgtcacgcccggcgcatagcgatgacgtaaatgtgaaaaaatttcaaactctaccgtgcgctgacagtcaattaaggtca
gttgttcagcgacaacatcaatggtgacctcttcctttacttcgcgcatggcagcttgcggcgcggtttcaccctcttccacgctgccggttaccga
ctgccagaaatcgggatcgtcacgccgctgcaacatcagcacccgtttcgtatcttgtgcgtagatgaccactaagatcgaaacgggacgcttat
aagccatatcagttattctcagccttcttcacaacctgaatgctcagctcagccagtgcagtcgggttagcaaagctcggcgcttcagtcatcaaa
cacgctgccgccgtggttttcgggaaggcgataacgtcacggatattgtcggtgccggtcagcagcatcgtcagacggtcaagaccgaatgcc
aaacctgcgtgcggcggagtaccgtatttcagggcgtcgagcaggaagccgaatttctcgcgctgttcctcttcgttgatcccagaataccaaa
caccgtctgctgcatatcaccattatggatacgcacagaaccaccgcccacttcgtaaccattgatgaccatatcgtaagcgttagccaccgcatt
ttccggtgcagctttcagttctgctgccgtcatgtctttcggtgaggtgaacggatggtgcattgctgtcaggccgccttcaccgtcgtcttcaaac
atcgggaagtcgataacccacagcggtgcccatttgctttcgtcggtcagaccaaggtctttacccactttcaggcgcagtgcgcccatcgcgtc
ggcaacaattttcttgttgtcggcaccgaagaaaatcatatcgccatcttgcgcgccagtacgctccaggatggcttcgatgatttctgcattaagg
aacttcgctaccgggctattgataccttccagacctttcgcgcgttcgttaactttgatgtaagccagacctttcgcgccgtagattttaacgaagtta
ccgtattcgtcgatctgcttacgggtcaacgatgcgccgcccggaacacgcagagcggcaacacggcctttcggatcgttcgccggacctgca
aatactgcaaactcaacagatttcagcagatcggcaacgtcggtcagttccatcgggttacgcagatccggtttatcagaaccataacggcgttct
gcttctgcaaaggtcattaccgggaaatcgcccagatccacgcccttcacttccagccacagatgacgcaccagcgcttccatcacttcacgca
cttgcggcgcggtcatgaaagaagtttccacatcgatctgagtaaattcaggctgacggtcagcacgcaggtcttcgtcacggaagcatttaacg
atctgatagtagcggtcaaagccgacatcatcagtagctgtttgaacaactgcggggattgcggcagcgcgtagaatttacctttgtgcacacg
agaaggcaccaggtagtcacgcgcgccttcaggcgtggctttggtcagcatcggagtttcgatgtcgaggaagccgtggtcatccataaaacg
gcgcaccaggctggtgattttagcgcgggttttcaggcgctgagccatttccgggcgacgcaggtcgaggtagcggtatttcagacgcgcttct
tcggtgttgacgtggttagagtcaagcggcagaacatctgcacggttgatgatagtcagcgaggacgccagtacttcgatttcgccagtcgccat
atcgcggttaatatttttttcgtcacgcgcacgtacggtgcccgtgacctgaatgcagaactcattacgcagttcagaggccagctttaacgcgtc
cgcacgatccggatcgaaaaatacctgcacgataccttcgcggtcgcgcatatcgatgaagatcaggctaccaagatcacgacgacggttgac
ccaaccacacagagtcacctgctgccccacgtgggacaaacggagctgtccacaatattctgtacgcatgagatatcccttaacttagctgccg TABLE F-continued Phage 3 sequence with Deletion

```
gcggatgccccctgctgcgcaggtgaccaagtcgcagcgttagctgtatgtcacaactgaatgaaaaaaggcggctattatactggaaattctg
ccgcaccgtaagagcctggcccgcgctggaacgcctcgttaccactttatatcgggcctgaaatcagactctacgccagtttgctataaaggtgt
tgcccgaactcataaaaattaacaaaatttgtcgttccgccatcggctaatcgcattaaggtgagaggcacgattttgttttgtcaggagtcatcatg
cttgaacttaatgctaaaaccaccgcgctggtggtgattgatttacaagaaggcatcttgccttttgccggaggtccacatactgccgatgaggtg
gttaatcgcgccgggaagctggcggcgaaatttcgcgccagcggtcagcccgtgtttctggtgcgcgttggctggtctgccgattacgccgaa
gcattaaaacagccggttgatgcccctcccccgcaaaagtgttgcccgaaaactggtggcaacatcctgctgcattaggtgcaaccgacagc
gatatcgaaatcatcaaacgtcaatgggggtgcgttttacggtacggatctggagttgcaattacgccgcggggtatcgatacaatagtgttatgt
gggatctcgaccaatatcggtgttgaatccaccgcccgcaatgcctgggaactcggttttaatctggtgattgccgaagatgcctgtagcgccgc
tagcgccgagcagcacaataacagcattaatcatatctacccgcgcatcgcccgtgtgcgtagcgttgaagagatcctcaacgcgttatgattta
catcggtttgccacaatggtcgcatcctaaatgggtgcggttggggatcaccagccttgaagagtatgcccgccactttaactgcgtgacgcgg
gcattttaaaaatcactaaagaacgcccaagagcatgtgttttctttagtttattcaatgcattaaaaaatagtttcgcatgaaattcggtaaacttcat
gtgtgcaataatgtcccattcatgccccaaaatgccccaaagcagacattttttgccccaagtatgccccacaagtcacgtcttcaagtcgtctatat
ccatagcacaccgagttacattcttgcatccggggtgtcgacaatacctactttattgagtgtgcgagaattaccaggaaccttttccacaatgtagt
agtctaatagtcgaatccatctaacattaagaagcgttatgatcactagcctctcattgatatcttctgtaatagtcactctatgtatcatggtgttcgct
acagtaaaggtagggattggtttgtctaacaatccagacagaaatgataattaacctcaaccacgtaaccacacttcatacttcatacttcacttaac
agtgaagtgctcacatcaccgggcagtcatcaaactccgcattcctggcatcattaatgatgtacgtgatcactccaaatatagcgggtgcagaa
ctgtaaccatcatcatctgctggcagcgcttcccttctcccgttatccagattaaccaggtgcggctgaggatgagtccgatatcgcttgatcctga
attccccgtcgattgcacatatcagcagtgaaccatcgcaggcagtaagtgacgcatccacaacaagcaacgctccctggattatcccttccctg
aaatgtgaacgcgatgcccgcatgaaataagtcgctgcgggctgactgattagctgctgatcgagggagattcgtgtttcaacataatctgccgc
aggtgaaggaaatcccatgtttacgccctctcttgaataccggataaaaacacagtataaatactgtatatccatccagcaaagaggcaatgagc
aatgttcgtggaactcgtttatgacaaaaggaattttgatggtctgcccggtgcaaaagatatcattctgggcgagttaactaagagagttcaccg
gatcttccccgatgctgatgttcgggttaaaccgatgatgacactgccggcgatcaacactgacgccagcaagcatgagaaggaacagataag
ccgtactgttcaggaaatgtttgaagaggctgaattctggttagtgagtgagtaaagattttcaatgcccgccacagttacgtattgattatgctgtg
gaggatattcattttcgtaaacgttggtttgggagaagcggcaaaacggaatgtgggaacaggggaaaatcagataccagatatgtctgcatttc
catctggcaataactggtttcagttaccaagtggacatatcgttcagatattttccatgaacgttcttggtgcagatgctaatggcacgtcagctaatt
accccattgcttttccaacaacgatgattgctgtcagtgctctatggtctgatgggactgtagcaaatgcaccgacatacaagatgatgggaaca
cgactaacagaacaactttgacgataaaagtatcagccagctcaggtacttacgggacaatgattattgcggtgggacgataatatgaataaata
cagttactctccttcagaaaatgccttttatgctgttgcgttaaaaaatacctatgaattgagtggcacatggccagctgatgcattagatattcctgat
gacatttctgtaaaatatatggcggaaccgccacaagggaaaatccgagttgcagggggaaatggttttcccacatgggctgaaatacctccac
catcacatgaggaacttattgaacaggccgaatcagagaggcaattattgattaaccaggccaacgaatacatgaacagtaaacaatggcccg
gtaaagccgctattggtcgtctgaaaggcgaggaactggcacaatataattcgtggctggattatctggacgcactggaactggtcgatacttcc
ggtacgcccgatattgaatggcctacgcctccggcagttcaggccagatgacatccggcgcggtgctggtatctgttgcagtcaccgcgtcaat
gtaatccagcacggcgttaagtcgggttgtttctgcctgagtcagtttccgtccggcctgtaatttcagctgaatcagactaatggaagccattgct
gcatcaatcagtgattggcgctgtgcttctgccgcttctactgaggcaccgtgttgtgcctcagtatctgtcacccatttctcaccatcccatttatcat
atggcgttaacggtgaaagcgtgacataaccgttttttgatggcaccgatataatccactgtaacagctgcgccattttcgattgagtaaacagtctc
attgcgatggtcttcctcatggctccatcccttacctgtaaatactgccactcttcccgaatgttttcgtccgggtcaataccagtggaacaggcg
ggcatacttacgccagtattaatatattcatcagaccagcccgtatattcagacgttactgcatcataataaaaacaacgcatatcacccggcactg
cagccagcccatttctcaaaaacaggtttcattatttagccctcaccagaaagttaaatgcaatatttcgcggtctgacagcaacaaaattcaca
ccatcacccacagagttactgttgaaattaaatcgtgaaaatcctggctgatttccggcgatgccatcatgaaagttaattgcgtgtccagcacctc
```

TABLE F-continued

Phage 3 sequence with Deletion cgcctatattcccggcaaactgagaaaagtttgtagcttcctgccagcttaataattcgcgaccaccatctgcacctcgcccgtcatcccagacac
gaatgaaatcaccgcgggcttcaggtaataccagcgaaggaaacactttcgccagcacaggataatcagtggcagagaatttcgcgccgttga
acttcaaaaacaccatactggaccagctgtcgattacagtatttggcattgcagcggacggccagaagaacggaacgccaatagctggagaac
cttctcccaaaccaaggtttgtgcgagcgtctgcggcattcgttgcgccggttccgccgtctgcgacagtaaccgcaccgttgctccctttctgcg
caagtttaccgatgcctgggatggttacggcggtgccgttgatggtaactgtgatgctttggtttgctgaggtggtggcgaacgtctcccacgcg
ccaatattctcgtcgtactctttgatgagctgtgacatggcctgcgccaggccgtcgactgagatattgtccgacacaaggattccatacttctggc
cgctcagcgccggggaaactgctggcgtaaccgtcattgacgtggcgctgttcacggatgaaatctgaaacagctgcaccgggttagacatca
cgataatcgtctggccagcgcggacctggctggcgggagctgtccagtttgtgccggagccggttgcggtatttccgttaatagagatagttcc
ggtgctataaatcataacaactcctaaatttagacaacatgaagcccggagaggtatataaccctcaccagaaataatttctgaattggttttaata
catgttgggcaacgccagtgttggcatagctatagttgtatcaaatgccattgaccaccacccaataataattgccgactactttattcctttctgc
tctgacattcccacctgtcattacaattcctttatacctaatatttccgtaaccaccaacgtgtcgacagttagcccggtataaacaatctggcaaaa
ttcatcaccaatattcaggttcgcattggcgatatttattgtcccatcaaaaatgaatggcttcgtgcaagtaagaagacgtttgcgttgacgattggt
ttattcaatccatcaactaaaatatcatgtaaacgaattgccataacatttcccacttttattttacttactcaacacaacaagtatattaaaattgaacctt
gtcaacaacacaaaggagtcccaatgaaactcgctctaattatgctgccattatgtctgtccctcactgcatgtggtaatggtttaaataccggtaa
accaaattccggtgtcattccaaaaccttggatcgagatggtaacggttctttaatttatgataccgaaaaccttccaatgacggggcagtggtgt
cacgagattgatcacgaataccgacgaatcggtagcccttctaactgtgttatagactactaaatattaaccccctcaaaagaggggttaatattttaa
cctgtgaatgaaccagatccgtgtgatactatgatagtaggcgaagaaattgacgcaccccgttattttgagcggacactttaatacgcactgtta
cgtttggacctgttacaaccgcagaatgcatgataagtctctccatgtcttgcacggatgaaccactctcattgccgttaatgtcgattgttcctgca
ccattacctttaacgtttgctataacacagacgtgtcttgcgtgcccagaactggatgaatcattataagtcattaccttttctaaatatccgtcactag
accgactcacattcgtccctgtgtgcatatttgcaatgtccccgataaaactttgggcttccacagtcccctttgaatttaccgcttgttgcttggatctc
accagtaaagctaccgccactagcatatactacacctctgacggtcacattgttgaattcagcatctccagctttattcaacttccaaccagcagaa
ccagctgcatagttgttggactggatatagttaccgattttgcgttctcaatggtgccgtcctggatgaagctggcccggatgaatgtctgcccgtt
ctggatcacgaacggcaaagctacgctatttccggctgccgtggtgacggcgaagcggtcagccaggaagataacctgcgactgcatgccg
gatggcgtattctccacgccgatacccatccccgcggcgtaatactgcccgttgctggagacaccaaccttgatgttgtacatcgcgctgagttc
gccattaacgttggctatagcctgagcgttagtggtgatggcggaggtatgcccgttcacggtcgccgtgatgccgtttatctgcgtggcggtgg
cctgctgatagtcggagagcgtctgattcaggctgttgatggatgccttgttgccgttgacgtccgtctgcaggctcagcaatgaacgtgctgtgg
cttccttctcactgacgatcacctcgtcgagacggtccagattcgcgctgttgccggcgaccgatgcagaaagggttttacgcgtggccacctga
gcgaggttggcctggattatcgcaattgcagagttcttcaccccgcccgtcatgccgtccatagaaacgctgatgttgtcgattcgctgcccag
ggcggtatcagccgtcgcaacggtctgctcaagctgactgagtgaagacgaaacattcccgaccgtgctggaaagctcattaacgctggtctg
aaccttcccgacgtcctgggcattttggcgatatctttcgcttgctgctccagttcgtcgttggcctgtttgatatcgttagccatgccagcaatttttt
cgttgctgtccaccgcgttctcgatcaggtctttgaacgtttccgactctttcatatcctccagaatgtcattagttatttcgctgacatctatcgagga
cgtgcccatgatccagtcggtccagtccccggcgttaccgatacggtcaatcaggcgcgcgcggtaccactggcgaacgccggcaggcatg
gggccatgctgataatctgcagccgggtacggcaccaggaccagcagttcaggattggcgtagtcggcagttgtggcgcgctgaatctctgta
taggccgtgtcgcctgagccatccggaaatttccaggtcaggtcgatatgccagaccacatcttcggtcgccaggaagttgagcggagtaccc
ggttttcccgttttaccggagagataagttgtttcaccgtatccccatggtgacgacgtatcctgcgcattcagcgcccgtacgcgcacgtcatag
ctgcccgaataaatgccctgaaccgagaaaccctgcgcgctggtaaccggaacgtttatccagtccccgttgtccttacgccactgggcaacat
accggattgcgccctctacccttatcccatgacacgtccaggcttgctacagtcagcccctgagacacatgatcgctctcagtcaccacgatattct
tcggagcagacaggacgcttatcggcgtgacggtgatcggggagactcgacccgaacgccgtcatcgatgtaacgatatttgtttggatcgt
gctgaacggccgtaatagtgaaaccgcctgtactgtcgtcgttagccgcgattgaggtgaccctgaagtactgtattgcgaggttatcactgtcta TABLE F-continued Phage 3 sequence with Deletion tcgcccaaacagcgcccgccacaggaacctgactgaatgccgtagccaccgtcaccgttttttatcggcgctcaccgcgctgattgtccgcgt
ctgggcttttccgtcgggaaggttaaccaccagccggtctttcgccgcgtagtctatttctcgatcgagggtaatttggcggccgttggccgcgct
tatacggcccccgttctccttaccagagcggaaaggatcggcgacaccgataatttcagcgggcaaagggatataaccgtccagccccacgc
caaacgatacggtcccgtctttggcattggagagcaatacccagcgaccgcgtcggtgcgcttcactttgcgaggtgcagccgattgcggtca
gggacgtctgccggacgtcgtaacgttctacaagcgccgaatcgtaaaccccctcaacggtatcgctgtaatggttctgcggatcggaccagg
acaccaggcaggagctgtagcgattcttgtatgagccgcccgcataagtaaacagcccatcgataacgtttgagacgttataaacccagtcaac
atcgtcctgcgggacgtctgcctggacataaatctgatcgtttccccagaacgttattccacgaaataccgcggcgagatcgttaagtacctgcc
aggcgtcctcctggctctgaatgaaaacgttgcaggtgaaacgcggttcggtgccaccggccccgtcggaaaccatttcgtcacagtactggg
cgattgaatacagcgcccacttatccaccatggacgcatccacgcgcgtgcccatgccgtaaatttcatccagaaccagatcgtaaaagatcca
ggcagggttattggaccatgccattttgaacccgccggaccatgaaccagaataggttcgggttttcggatcgtaattatccggaaccttaatcag
cttgccttttatcttacaggtcactttcggcgcgctgccgttgaattggctgctgtccacttcgacatacaggagcgctgttaaaggataacgaagc
ttgctgtcgatgacttccgcatacgaaaacaccttgaaggcgttaaccagtttcgaatttgatccgctggcatcagccgtaatacgcctgaccctg
acagaccagccggacgtggattttggcagatcgatacggtggtcacgctgatattccgtcgtggtctttccgtcaaacttgccgtttacaaccgttt
tccaggcgccgccgtccgttgataaatcgatcgcatactcggtgaccgtgcccaccatatcgccattatctttatagagatactggaccggaagg
ctgagcttgatacggatggcatccagggaaaggtttgtaaactggcgcgtccagggcgcggtggtggtgacagttgtgcccacggccagctc
gttgtcgacctggggcatcccggcaatataggtctggtcctgtgtgcccttgcggaactcccatttcacgccgctgaagttgtattcccgctgtc
gtttgccagcggcgtatcgttgagaaaaatgttctgagcggtcaggtcgccctgtatttccccctcagaaacggcaatgagcatttttaattttgcg
accgacagcagatcgtcaggctgctcaaccggagtatgtgaactgccacctcccccttggcaccctgcaggatggtttcttgtttaagaagctg
cattttttcacccataaaaaaaggtgccgaagcacctttaagttagtggccgctggcctactgctgatcgctcgagtacataccggcgctgactat
cgctcccccctgcctcagtcagaccgtaggccaggggacaggatgccccatagcgacggtattgaccggcgccccgaaggcgtagttaggc
gtgttgtccgtgctggaggatttacccgcgccgaaggatggctggggcgtgagcatctggacaacgccccccagcatcatcgacactccgac
ccctgtcagaattgacgtggcgctgatagctgttgcactcatcgccgcgccccaggctgccatgctcgcaccagcggtaaagaatgcagcgac
cagcgcaacagccccgacaactatctgcaggacgcccgaacttttggccccctcataaacgggcacgatccggtacacgcttccaccgcggg
tcatatcaaactcttccagcccgatattgttgccaccgttaaaaaaggcgaaacggatccccttcatatgagcttcagacatatatttttttgaatccg
ggaacctgtgaacacatggccctgagcatctcgcgcaggtcggcaacatcaaactgaacgcgtttaccgaattttttttgccatttttaccttcgaga
ataagcgtcttaaccatgcattctgtccttatgcctgaccacccggaccgttctgtcgcgataatattttccataaggcgttcgcgaagaaaggtgc
ccgaaaagatgatggagaatgatgttatcacccacatataccgcggcgtgattagtcaccgatgcctgcacactcatcatgatgatatctccggg
ctgcattgcaccggcggcaatctcaacgaatccctcacgctcccagttgtcgtcgtagagacgctccttgccgctctcccaccattcgtaaggta
ctgaataattgccgagaacaatgccgtattcgcgcagataaaattcacggataagcgaccagcagtcggcgtaacccagcacccactgccgcc
cggcataatcccggtcttcacgcggggaaatcgtacaaaaatcccgtccggccaggacatgatcccccactcaatcccgaccagtcgcact
ggatccggtccagctctgagggcaccagccgaaccacatccggatgggaatgaatgagcatgatgatctcaccgcgcgcgcgggcagcga
gctggtcttccggggagagcgtgaatgtctcctcgggtttatcggcaatgttgcggcagggaataaagatttgttgctggcctgactgaacaatc
aggccgcaggcttctttggggtattcagcagcgacgtgctgacggatagcatccagcaatttttcacgcatttttatttcccctgcaggtttgcagc
cggaaaaccgccgaacggcagcggcgcatccgggccgtgacgatcctgacaatcctgccggcggccgccacaaacatctttcgacgggtc
atcggtcggtgtaccgtctttggtaaagtatttcgtgccgttgtaatcgcatccggtcccgcttcggtaccagccccgcatacaccaggtgcagac
aggcgtaatctgccgtgtcggcagctgcaggtctgaatatcgaaaggagaacacagctcgaaatcaacctgtacccgcgtctctgcggttta
gcattgacgtaaaagagctgtaagcgctcatcggccgggctggcaccggattaccgttttccagttggcggcatcgagatacttcgaaagcg
tggtatggattttgaccttagccctgaccatatcgtcatattcaagacacagcgcggtgacatagtttccgacgttcccgacggacagcgtgggc
gttggctgggaacctgtactcgataactccatccccttaagttcgtagggatggggatcgtactggtttccctgccagataatggcgggcagatttt TABLE F-continued Phage 3 sequence with Deletion ctgcggcgaaggctgcccaccccctcttcctgaatattgtgcgcatgaaaacgcagcacctgatccataccgaattcagtgccgtcgatctcaatc
agctgaataacgctgccgggctcaagctgttgtatgtctgccgtaaaactcatactcccccccataaaaaaaagccgcccggaggcagctttcag
tgtttttcgagaaaatcagggcgcgaacgcctgttcaaaagtgaaggccacagtggcttttttcccggtagggaaagaaacgctgaacgaatcg
gccttcattctgaacagcttttttttcaccccatggagtggtccaccagaacgatttagtaacgtgagacatcaggaaagcgcgcagcgcagccgc
ctcctgtctggtgcccgtccagtccaggttccacgtttcctgtttgtcgttgatccccatccccgctatctgtttgtagccatcccgaactgggcct
gcagcgttcgggctgtttcagtgccctgcgctgttttcgcgtgcgccaggtaaacgtgtccgtcactgtgtcctcctcgaataaagcacgccgcc
cgcggacatttcttttttcagtcgctcggtgattgtctgctgaacaatcgcctgcagctgtttcgccgtcccgtggcgttcgcctgatttatgcttcc
gtcactcccctgctggctgatgctgactggggcataaacactgatcccgcccatgccagcaccggctgcgttcccgccgccgaccagaccac
ccgaggcatacccgcgcatcaggcgatagagattagccacgccgatgcggctggttgattctttggtgaagacgaattccccgcggtgaacga
taccggctggctcgtacttgccgccgtgcccggtaaaaccgcccacgtcaaaaccctgtggccggtatgacgggaccgcgaatgactgaccg
gcagaggaggttttcgccccgccgctaacccagcccattgcactctggatggtgtaagccaccagcagctggttgataacggacacaatcattt
taaggatcgagctggtgaattccctgaagctcgccttcccggttgtcgtcaggctggtaagctggcccgccaacccgctgaacgtagcctgaga
aatctgctgaacggagctgaaaacgtttgtcgctgaatcctgatattcggcccaaccctgtttcgcaccggccagccagtttgcacgcagggcat
cttcagcttcgaacgtcgccctttgctcttccagaaccttttgctgcgcctgagggttgtacgaatagctttcgctgagacgctgcagcgtagtttgt
cgcccggcttcccggggtggataaaccctcagactgagcctgcaggcccgccctggcggcttttgctgctgctcaaacttcacggcctgatcgg
ccagctggttgagcttttgctggctggcaaccttatcgcccaggtcggccagctgccgcttgtactcgagcgtttcttctttgtgcgccagcaggg
attttttcctgcgccgtaagctgacgacgcccagcggcctcctgcagaacggtgaactgattttcagtttgccagagatcctgacgctgtttacttat
gacgtcgttcacgctggtatgctgctcaagcgttttaagctgggcctgaagggtgagaagttcggcctgcgccttttcctcggctttgtcccggc
gggcgttgagtagcttttgcctttcggtgtttttggatccttccactgcttttcaatcccggcgcgggccgcggcaatgtccttttcagtccacagcgt
ggcgacaccgtctttcgcatcctggcggtttttctcaataagctgactgagcttttctctgctgaagcccgcttttctgccgccgtcgcgccggact
ccaccagctggttaaactgctgctggctgcggattgcctgagcctgctggtccgttcgcattttttcccgcgcggctgccagcccttcctgggcgt
attgctgatcggcaagatcgtaagcctgcttttttcagctccacctgctggcgcgcgtttctcagcctttccgcatccgctttctgcagaacgttgtta
ccggcataatccgggtcgaccttaagattgctggacagcgcgcggtactctttctctgctgcctgccactcagcaaaagagtcctggcgcttcat
cgcggtgtcaggattacgcccgacgcccagcatcgcatcccacgcaccggaggcggcattcttcacccagttccaggcttttttcgagggatcc
gagattatcctcgaccgcaccggcgcgctgaatgaccgcgtcggaatatgcccgcatggccagctcggcagccttctgagaatcccccagcg
cctgagcagaagctatctgttcatactgggtggctgtcagaaaatgaagggaatcgttgagcgtcgcgaccgcgttaaccggatcatccttcag
gcgtttaaactgatttatggtttcgtcaacgcctgcccggtagcctgctgcagcctggcggcaacattgctgaccatgctgacgtcattaccgct
gaacgcgccgctgccaacgacctgcgccagcacgcctgcagcggcatgctgagtgatgccattacctgccagcgagcgcgccagcgcctg
cagctgcctgacgttttccccgcgtagttcccggtcaggatcagctgcctgttaaattcctcagactctttgctgccgtcgtaccaggccttaccc
aacccgaataccgccgcggcaatccctccgaccatgctggcgatcccaagaccgcgcagtgacagaagctggtctatccaccctgcccggtt
agccagcgtgatcccggagccgcgcagcgcgccgaagttaccgcgcatgacctcgccgatcagtattcccagttcctgccgggcggcggca
ctttgcagcccagaccgtgcgtggcgactttggcagcttcgagcttgcggatatagacttcagccgcatcgctggcaccgacctgcgccgcct
tcatgcgcagtagctcggtaccggagagcttttgctctgcaacctgttgcttcagctggctgaggaatcgcgtgcgcgctgcggccgattttcct
ccacgatctgcagttctttttgacgggccgtggtgcgggaaataagggcgagataatcctgctgggttatgttgccctgtgcctcgctgcgcga
aagcgcgcctgcacgttcgcaagcgactgtgtttcaccattgagctggcgtacgccgtcgatctggcggaaaaatgatgccgcaagttcatcct
gtcgacgggcaagcgcagcggcctgcccgtcattctcacgcatgcgctgattaagctcggtcacgcggcggtgagtttcatcaacggactttg
aaacgttctgccagtctttggtaagcccttccgttgcggccgactggcgggatttcatatctgcggcagccgccgcgccagcgtcacccacggt
tttaaacgcagccgcctgccgctctgaagcgcgctgcattcgcgtctggacttttcagagtcctcagccatcccggttagctggcccttttatgcg
ggcaacctgctcactaaacgtggcgctgtcgacgtcaaggttgatgaccagatcgctaatctgctgggccatatcggataccctcctgttatccct TABLE F-continued Phage 3 sequence with Deletion cagctgcggccatcagcgcatcatcatccggctcgtcatcgctgatgacgataccggaaggagaaagcaggctgaaatgtgcggggtaagt
tccgggtcgcggaagaaaagagtggagatggaataaagcagctctgagaaatgcgcatcgagctgagcgtcctgaaaataatgctcccggta
gaactggtgccagtcgcccagctcagtggaagtcattccagccagcatggcgcgccagtcgggtcgcccgaactcgcgcgccagattcagg
acaaacttcagctcgctggcaagggcttttccgccgcaacgggttctgcgctttcggcctccgctggggcatccggatcggcagctttgtcatcc
tcaaccggaacgagcatgccggagagcagctttatttccatttctgctttaccgatcgcctccggcggccagccgctaagcacctgctggtaaa
gcgtctccacatccgtgccagccggatcgttatgccacaaagacatcgcaatcaaacgcgcaccgcagcgaatatttgagccaatcagcctgg
ccgtcatttcctgatcgctgatgccgtcgctgtcagcgctgacggccttttcctctgcggccataaacgtgatgtactcaatacgctgaagcgccg
acagctcgaagatggtcagtgattcttttttgccaggtgaacttctctttttttcagaaacatgcgtccttccttacgctgcagttacggtaactttgcaga
ccgcaacgaaattaccgtcgctggtcataacaataacgtcagcggtgcctgccgccacgccggtgacggtgatcgcattaccgctaacggtga
ccgttgcttttgccccgtctgaggttgccacacggaacgaggtatctgaggcactggctgggttaaccgtcacattgagcgttgtggttgcgccg
acggccacgcttgccgtggcttatcgagcgtaacgcctgtcacggggatattcggggtcccgctttcttctgccagttccggcttgccggtattg
gtaattttcgctgtacgggttatgacctcttttgccggaatggctttacccaggctgctgcaccagccgcggaaaacgtcgacggtaccgttcgg
gtatttgattttgtaatagcgtactgagccatcaataaaccatgcgacaaggtcttttgccttcttcgcccggcttccaggcgagggtgaacgag
gtatcgccagcagattttgcccctgggccgtcgcgttccagtcggcatcctcgtcgtcgaggtaagtgtcgtcatacgattcggcggtcatttcg
cccgcgtcagctcttaattttcgccaggcggttccagtcgatatccgagagtgggttagcgaaagcgttgcccgttccggtgtaaagccagag
ggtggtaccggcacctttcacaggggccagcgggtttggagtaggcataagtacctcttaaattgaataggtgattaagtacgtgaaatcgactg
aaccccaggtggccatttcatcatcccgctgatagtcataaccctgcggggtgaacgtctcgaccagttcggtcagacctgggatgaaggccat
tgccggatacactttctcttccatccaggaatcaagcgcgctgtcggggctggaggctttaagaaatacctcgatgtgaacaaccgcctgccac
gaatcttcgtcaagcgattacacgtcttgagcgattgtgtaggctggagctgcttcgaagttcctatactttctagagaataggaacttcggaatag
gaactaaggaggatattcatatggaccatggctaattcccatgtcagtccagtgattctgaataggcgataagtccggtataaccggggataatct
caccattatcagcttcaaattcaggaattgtgccggtggtgatggtgtattgaggctggccatcttccttcgcgaaggctgccaggtcttcaatctg
cttagctgtaagaactactgtcatgctcattcctcagttgtaaaaaagccccgcgagtgcgaggcgatttgattgaattctcggctcttatctcagcg
cagccccttactgcgtgccggttgctcggtgatgagcatcagcgatgagacattaaagccgaccgaaggccagcggcgttcctcatgttgccg
acagagccatatcgacaagaggacgaaaactagcagcatgaatcgcctattggttattcgacagtcgcactgattcgtaaatccgctcacacgtc
attcctgcccggtagctttcgtcagatcgtccagcataatatcgagctgcttctgcaaggcttccgagcatgtcggcaagcattgctgcgttggctc
cggctgttttgcttctgacggaagtggcgagatctgcggtgtgctttgcggcgtccatgtgggtagcgagttttgttgcttcggcgcgcagctgctt
aacagtggtagccaggccagcagaagtaacggcagcgctcgctgcttgagcttgagcatctttaacggcctcatcccgggcgattgttcgccct
tgttcaatcatacgagctgcggtctgtgcattcgcttcctgtgaagattccgcgctatcccggtcagcccactttatttttccagctgcggttcgtcca
ctcactgccagcgagaaacgaacctaccaacgcaacaatcacaatgatgcagatgccacccggcttcactggtctatccccagcacgtcagt
gcgctttcctggtcccgccgttctacctgcccataacatccatccttctggcccttggtcaggcggcaatcgcggccaccgtctttaatccaccag
cggatagcttcacaggctcctttcgtatcgccagcattaattcgcttatagaacgtagacgggaaacattttccggggccgatgttatatgggcag
aaagaagcgatacccgctttctgtggttcggtcagtggtactttgatatttcggtcaaccacgccagcgccttgtcgcgttcaatggcgtttacct
gggcgcatttctcagctgacagcttcatgccctgtactactggcttgccatcaaccattgttgcaccacggcaaatggtccagagtccgccgccg
tcgcgatatgctgtcaagctgttaccctcttttctcatccagaaactgatcgaatcacgggtgcggaagccccggcaagaatcaaaccaacga
ccgctgcgctcaatttattcttcagctttagagacatagccattgcgccgatcctcccgttctttccagcggaaataccagttcactgcacaggtgat
taccgtgcatgcgataccgacaataattgcccagtcgctcaggcttaaccctgcaattctgtcggccaacatccaggacacctcttttgctgtttta
gctgtttcggcatatgccttcgctgatacaccgcagccggcaagcgtggttcctgatccatatgaaagtctgctgtaaatggtgctcattctggtca
tagcctcacctccgatagtcggatggcgctgtgtgtgattgaagggatcaggcaaccgggctcttatgttcaagtaaaaattaaggatgattcc
cggtgcctgaagatggtgatcaccacagcaacggggagcgtggtgatcgttatgattttttcagttttttccacctcttcggtggtctgtataaacct TABLE F-continued Phage 3 sequence with Deletion

```
gtctgcctccagttctacgccgatcgcccgacggccaagttctattgcagctttcacagttgaaccagagcccataaagaaatcggcaacgatat
cccccggtctgctgctggcgctaatgatctgtttcagcatgtcggcaggttttcgcatggatgtttgcctggataaaactgaacaggcttatgtgtc
catacgtcggtataaggaacaagagcggaaacagagaagcagcgccgaaggattttgtattcctccagcaattctgaatacttgcggtttaatga
ctggtaggtagccaccagctggtggtgaggatgttcaagcttttgctgaatatgtttatcgatggcgatccgcgtgaacagttcctgcaattttcgat
agtccacttcattcggtagttgccattggcttgcaccaaaccagtgtgacgccatgttttctttccggttgcctcagctatttctttcgagctgacacc
cagtgattcacgggcattacggaagtaatcaatcagcggcgtcataatgtgctgctttagctctgtgcttttccttttcgtaaacatcctctttacctgta
tacggtccaagatagtgctcagcaaacaaaatccgttccgtagatggaaagtacgcacgcaggctttctttattacatccattccagcggcccgat
ggttttgcccaaatgatgtgattcaaaacgttgaatcgggcgcgcatcataatctctatatctgaggccagtcggtgaccgcaaaacaggtagat
gctgccagcaggtttaagaacgcgagcatactcagccaggcagctatcaagccagcgtaagtagtcctcgtccccttccattggttgtcccag
ccgttgggcttcactttgaagtacggaggatccgtaactataagatcaatagagttatccgggagggtggcgacgtaatgcagactatcagcgtt
gattaactcaacactgtttattttacagtattttcatagatcagtaagcgtaactctgataggctcacgttgcttttgcgctaaagcagtgggccttg
gttagcttgtgacctgaaagcatgagctgatggctggccgggtgcgctaacaccccaccagccgcccatttccacagcagaaaaccccattact
ggaggcgtttataacatccgaactggtaatcagataaccccgccatcaccagctgcgtaagtatgagctggcaacgttcgtggctgaggtgggt
attctgtgcaatctccccagccgttgctggtttatcgcttaattcattgaaaacagcctttgccgtttctgtcatatcttcctgatttagcatgtcttttacc
taaaattagttgcgtgacatacagataactctggttggtgataccagcaagagaagaatttgattctgcaaccaacaaggcctttaggcatcaggc
aggaatgagatgcaataaaaaaaccacccgaaggtggtcttatatgaatctttaacgcggacttagcaaatattccacatcatcgtactaccgttat
ggttttcgataattttgcggctgggctagtaccaaaagagtgcatatagcaatgatgaatagtaaggaccagatcctgcaacgtttggtcactctc
tagctccatgatatttaaaccaatattttgagctttgtccaaatgaatatgtctggcatgtgcatacgttgcttggtggttgtttaactcatcacatatac
gcttagccttagcttcagcgtcagcctgacctgcgaacataccagtacaaagccatttctggacaatttcgttcgcccagagaattgcttttcaca
ctcgccaatcaacgttggatttagttttggaacgtaaattgccaccattgcagtgcagcagggttggcaaaaatttccgcttttgctctctcatactc
ctcaataattgcatgagatgataacccattaaactgtggatcaattggccccaagttcgactgtttacctaaaacgatctgctcagcacaacaagca
agcattgtgccacaactcattgaaatcataggtacaatcgctcggatattggttccgaactttgaacgaagataatgaccaattgattctagagctg
cgatatcgcctccaggagtatggagtaagatatccaatcccagactcgtatctaacccattgatagcagacataagaccatttttatcatcatctga
catctggatcagatgttgaaacccaggcccccttttgaaggaagcctgagtaataagaaattacatttcggccagtatgtttcgataaatcacgt
aagtacttgtggcgaacctcatccgctggtgtacgttgagcgatagtacccatctcacccaatacgtctatccaatttggcatgttatcaatttatca
gtatgagtacagttggtgagattgctgaccgttctgctcagtagtatttggtgttactgtgctgtatgaatagagcacaccacttctcacattcagatc
gttttgctgagcgagaacacgcatagcaaaatgctgtacggattcgccttttgaaactcttggggttgtatgcccattttttcgtaaaattcagcagc
gctcatgatatgtccctcgttttttctacatctatgcaattccaggagccatcaacacaagatgtagtagttagcagtcgtcaaatacacgaaaagc
ctcaagatgaggcttaaaaagattcttttgataaagatttagccaaactatagcggtcaaaatgcagatttgacaagtataaaaagcacttaaagc
ctataaataggcagttttgagaattaaagcatctttaatgaggttgaacaaaatgcagtcttgacgctgaacaggactttactggaacgtagagct
aaaatggttcgatttcatgaaccagttacaaaaaaaccccgctcatcggcgggtttataaaactttggcaacatatcaaatatgcttcaaatatggctta
ttttgttgcatttgcaagcgtgtttgaaggagatggtgaaatttacttcacatttctgccactttgagggcttcttcttcctcatagtattcaagagccat
ggccaacgcagattcatcaagctgggtaaaagcggcctttaacccagcccagtgccctgaatagacacgcaaccatgtcgaacggtcaacgc
taaccatgcgggccaacgctgcaccagcatagtctttataggtttcattatttctggttgcggcaatttcctgccctgccagccataccaggcctatc
agtttcttactacgcgctcctgaagggagttatcacccaggcatttctgataagttttccagacgtattcacacatcatccctggtgcttatagcta
aggtcaaaaccgtagcagtaccgcaaccaggcctgctggtatccactaagcgcggacactgccctacgccacggcgcggactcaaattccgc
atcttttatcggcggcattggcctgcggcggctgcgtgtttccagcacatacagtggcgcggaaagtgagttaacaaagcgtggccccttctctc
cttcgagttcgacgagatgaattccacggcgaggggtggcattttgtctgctggtgggtgttcactgaaagcctcaagctgccctttgttccccc
agacaggtcaggtagcgcgcggcgcaattctattcttacaaaattcaggtcttgttgattcatgcttctttgcgctccatacacttaagctttcgcaat
```

TABLE F-continued

Phage 3 sequence with Deletion

```
tacgccgatcgccagcgcccgatccataaaacgcagtagcagctcaagctgcgtaccatgcttctgctcgaatgccggtacatcggcgtgtaa
ctcgtcgtggcactctctgcacagagggatcacgaagagatcatgggcttttgttgctgtccccccataccgtgccctacgatatggtgcggat
catctgctggccgtcggcaacactcacagggttgtgttttaacccagcgggtgtacgtctcatttatccagcggcgtcgctttggcctgagcatga
aagattctggagactccggatcaacagagagcgtgaggatcttcttcgccttctcctgcacgaggctggttgcagaagcggaaggcacaatgtc
gctttccctcatgaccgagcggatcttatcatccggaaggcgtagccccttgtgcgcaacgctttccggaataacatcagccaggtcgtttctgac
catccaccagcacagttccggaagcgtcaggatatgcgactcggaaaaccagaatcacgccgaatgacttccagaatccaggataccaggt
ttcctgccgctatacctgcaagctgttcggtatgctgccccgacaaagtgtgatcgcaatgccagcacaggcgaatacttcctggtgggtgccgc
attgttgtgaagttcttgtcgtgccacgatgaatgtggccactggcattcaaaccgattactcaaccattgctcaagggaaggaagcccaccagc
acgctgaataacccgatcattctcgaagacctgccgcattaccggatcatcagccagcggctgaatggcggcgggaacagctcctgtactgaa
tgacgccatttcttctggttcaggctcaagcagaacgcgaccgcgcataaagaggtgcatcagttccgcgccgggacgaaacaacacaatccc
catacgatgggcgatctcgggggtaagcagagctctcacgcgacctgccccctggcaatgtgttctgcccacagtccaccaatccagcgcac
gcctttcgccgtgaaacgtgcctggctgaatgcatgatttgaggttacggatgtgccggttttcacttcaaaacggcccgcatcaatatgctgatg
ccgtggggtcatcgttccgccaagacgatacatgatgtcgttctcaaggaggaataaccgcagatcgggctctttggccttaagcagttttgcca
cctggcggaatgacattgacccactggctgtacagtaccgatcaacaaacgctaccttcggcgccgcggcagccagttcgttagtcaactgctg
ttttgttctgcaaggtcagctgcaagacgtagggcttcagagaatgattgaggaatcgtctgctgctgtgcctgctcaagctcctgccagcgatc
aaccagacgcgcggtaaactccggcgacagctgcgcgacaacgatataactgtcccgcttccctatcagataaaccgataccgactgattgag
gtgatttttaacttcccccattgggggagttcaataacaccgcgctctgccaggcgttcaatgaccgtttaacatggtcatgtcttgattccacca
gctcagcaatatcgctgctggacatggttaacgctgttgttgctaactggctcatacttttctccatatcaggcggctgcacccgccggttcatatct
gctgattgttatctctacccgacctttcggcacaacgggtccccattccaccagcatgcgcttaatctggctgtcgtcttcccagacacccgcatgc
gtcagcgcgtcaaacagggctttgttgtaattatcgatatcccggcggcgcgcatccggcgggtacagagtgatttctaccgctgccagttcagt
cgatggcttcgggagacgtcgtaattgctcaatgatcgccacgcaggcagcgctctggtatttacggccagcggcgctaatgaggtgacgacc
ggccagcggccccttgttaggggcgcgccagtaagtgttcacgctcggaggaaaaggcaggatcagtttcacgcggcctctccccgcatattg
cgaacaagttcagaagcagcagtaatgatttcgctggtggcagtccgctccagccagagttgattgatattggctttcagcttgtgttgcagtgact
catccagcatgtcagcaccatccacctggtcgaatacaattctaacctccagcggccagatacgggactcgggaagcggatccgatactggttt
agctttctcacgaatgtgcatgcggatctggcgaatattggaccaactggaaacatccaggcttcccatggctgcaatgaagtcagtgctgttcat
gccatattcaccggatgcttcaagggcaacagtgcgaatacgttccgacatatccaggcgcacagcagcgtcatcgaattcaatcgacaacag
ccactcatccacaccgaacaaaatactctcacgaataagcagcttcgctttgtcgatcgttaaaggtgatacctgagtgaattccggtgcttcgac
agaatccgccgcccaggtatgcccaaacttcgattcactgaatgtgtattcttctttatcgccaaacgcagctctaacgcatgcccacgcctcgac
accgctgatagcaaaaatatctttctgggtgagtggcaactctgcttctggcttatcagctgcaggaggtgtggcagttacaggttgagacttgct
ggcagcaaattgtgccaaagccataaacgcccgccctttgcctccagttctgtgcggttgatatagctgaaccgctcgccacgccatgacttatc
gaatacagctatggcaccggcaaaaaacgcgctggtgggtttctgttttcgtcagcaggtacaaaccacacaggcagatcgaacccaatgcg
cccgcgaatgaatacaatgtgatcggcatcttccggccaccacgtttcactcggcgcggcttttatcaggaatacatagcgaccgcccttctcgc
gctgggctgctgcgtagttcatgatgtgcgtcatgccggtgatcgcctgcttctcgtggtactgcgaacggctatacggtgggttgccatagcca
gcgccacccagttcagccagacgttcagaccagtcctgcgtcagcgcgttatcttcggcggtgtaccatgccgggcatttcgcgttgtcgtcgtc
agcaaacaaatccagaactaatggaccaaatagcgcgttgatccccaaaaaagcagatccggtgtccgccactgatcgccaacctcttttcaat
tcgtgagctggtttgctacgcagtccgccagcgcctggcaatatttattggtcatcatgaacggaaccccgaatttctggcagtgagtaatcaa
cactctggaagtttgcgcggctggctgagttagtctcccatttgccgttaacgcgttcaggccggccagcactggaccattggtcgcgctttgca
ggtaaccagggaagttttttggaatgaacagagttgccgggcggaggtattgcgcctgctcgctatcacgccaatcggcattttgtaatccacta
ccaagcacaggtcatcaacagtgaattgttcccgaagacgggcgcgaatattctccagcgacgtgctgcataccttggtagcgtgagccagtag
```

TABLE F-continued

Phage 3 sequence with Deletion tctgattcaggtaagacaaaacctgtctggcctgatcagtaatcacaacctcagggtcgggttgcgccgcaaccggacaagagggttttgaagtt
acttgtggttcttgttttgattttactgacggatccccaccagattctgacgggtcaaaaccgccttttttgctggatttcgacgcctcaaattttgacg
ggtcggattttgatgcatcagattttgatgggtcagattttgatgcgtcagattctgacaggtgagaaaaagcagcctctcgcaacttaacgacgtt
aagctgatatacgttcgatgcgttacggttcccattacggcgctgcttacgggaaagccagccatccttctcaagctgagcaagggccgtcctta
ccgtactttctccagcaccgatttgacgtgcgatcgtgccaatagacggccagctaacaccctcatcactactgaagtcggccagacgcgccat
gatggcaacgctggataacttcatgcctgacgaagcgcatgcatcccatacgtaaccggttaatttagtgctcatggtcgtcctttaattctgtaaat
ttacgctggaattgttcaagagggctgaagcactcatgatcgtacccttcgcgaaggtatataacgcgctgtgtatctggctcccagcggacaac
tctgacgggaactccgtagtgatctctgaaccgccggttaacttcagccattcctcgcgccccttctcgttcatctgaacaaatgcttctaccatcaa
gtctgctggctggtagttgcctccatcagccgcgttatttatgatttccacatagccgaactgggcatctttacccaccagcggcaaacatctgaat
tgcttagctggtctgaatcggtttacactgttcatgcgttagtttctccactgatacgacacgccaaggcgcccggagctgcacactcgcgggcgt
cacctttctgcctgttgaaacgaatacgtcaatcgcctgatctgaaacaccaacccataaagcgccataaatcccaggaacccgtgaatctgg
tggcggagcttcttactgaataattctgaaagcattttgcgctctgatgaatcaattaccccatcagccgctgctgccatcttggcattagccagctc
accagatgctgctgccgctttcatctcaatgctgtacagctcaacgttatccaggctctcagcagttggaacatccaccagccatttcccttttcggt
tcgcctggtactcggccaagtaacaagaaccagacaggtcctccatccgttccagttctgccaaggtaaagaaccgactgccacacttctggta
caggtggttgtggaactggtcgatagtcatccctaaatcggaagccatacctaagcgaccatgcttgtgtgccttacacatcaggcggattgctgt
atttatgctgtctaccatgttgatttccctctggtagttaataatcaacttaaagttgactattgttgttagcggaaggtatgccgtcatttttgttcggata
aatatcaggtcgtaattgatggggagttactacccatccgccccattggcagagttgaataactctttcagaaggtactcggttctttgcaatccagt
tcgcaacagattgaactgattggaattcaaaccgccttgatacctctgaaatcgacccgatcgccttcacagctttagctgttacattcttgtgttga
gatgacatgtgttctcctatgactaagcctgcatcaatactacttatagtagcaattattagcaacttaaaatagaaatgacaactatgccttgtgcgc
ttaatcttctacttatggtggaaaatgctaaatacaaagactttgccgaaaggctaaacaggtctctccaagagcaatctattggagttaaagaattg
tcagagttcagtggtgtctcgtatgagatggcgcggcgctacactcttggtactgcaaagccgagagatgagaagatgattcgaattgcagaaa
gacttgccgtctcaccggcttatcttgattatggtgtgcctgttaatggtggcgacgcgccagccaaaggcacggtcagaatagagcaattggat
gttcatgcttcagccggttccggatatataaaccaaccattccctacaatagtgagctcaatagagattccagaagagaggatcttcgagttgtttg
gtcgtagaagccttgatggcatcgtcatgatgaaatgttgatggcgatagcatgatgcccacgctttgcccaaaggacctgcttttcatagacagca
aggttgaacaattcagcggcgacggctgtttatgtgttcaattttgaagacagtacgttcgttaaacgtttgcagaaggtaaaagggcgccgactg
gcagttctttcagacaatgaacattacccgcccttcttcatagaggagcatgaaatgaatgaactatacatattcggcaagctaatcagatgcttac
ctctaaaaatgatagagtttggctaataattaattcatcaagaaaccggcgaaagccggttttttttacgcctccaattcctcacctcataacactaca
ctactaaaaatttcattttctacttttttgttgttgcaattatctacttaaagtagctatagtcattgcatcgaaagcgaacaggcaggacgcccacgaa
gtagccgccggtggcatatgaataaccggatgattcgctgacagaaaacttaggttgggggtagaggtttacatgaatcatttattcacatgctca
ttttgcggagcaaccgaactgggagcgataaagatcgtcgcaaaaggtggtaaggacgaacctgccatctgttcggaatgcgtagtcacatgt
gtagaaaaatgatcctgactaaaaaatcagaggctgaaaaaccaacctctgataacgaaataatatcagtcgataaaaaactatttaaagagctt
cttcagcttgtcctcaaccttcctgatttcggaagtaagctggctgctgttgacattgatagtagctccacatcgacaagtgaaacttttgttcgactt
gagccaagcgatttcttcttcgtcttagtgccgcacttagggcatgcgggtaacgtaatttcctggttatcaaaagcgcccataaacatccctcttg
gttgtgtgagaacaccaagataccaccgcgcctgatgtggttaaaagcaggctaaagcaataacaagtaactccctgttctggcggcccggtgt
tttcccgtgtatttccggtaaccgccagcctttttcagggcacaacagaaagggcatcaccgggcgacgggctcataacccaatccacccgg
gcaaaagaaagcggtctctgcaagccgccgaccaatgcaggtgcccttctctgttgtgtatggagaaactaacttttttagcgtctgtgcagatg
cgctgaggaaccgagaatgaataatccgttttttcaaaaatatgttggtgtatcgcattagtcgcgatttcaccatcaaccaggaagagctggaaca
gcagcttgaactatttcgcttcactccatgcggtagccaggatatggcaaaaaccggttgggtatcaccacttggtcagctgtcagatcgcttgca
tcacactgtcaataatcaagtgttgttggttattcgccgggaagaaaaaaatactgccatctcctgtcattactgaagaactgcgcaagcgtgtgtcg TABLE F-continued Phage 3 sequence with Deletion cgtctagaatccgatcaggggcgtcgcctcaaaaaaactgagaaagattcgctgcgtgatgaagtgttgcactccctgcttcctcgggcgttctc
caaaaactcgactgttggtttgtggatcaacgtcaccgacggtctgatcatggttgatgcagccagcgctaaacgtgccgaagactcactggcc
ctgcttcgtaaaactctcggttctctcccggtggtaccgctgactatggaaacgccgatcgaactaactatgaccgactgggttcgttccggtagt
gcgcctgctggctttggcctgggtgatgaagccgaactgaaagctattcttgaagatggcggtattggacgctttaaaaaacagactctggtcag
tgacgaaattcatgtgcatctggaagctggcaaagtagttacaaagctgtctatcgactggcaacagcgcattcagttcgttctttgcgatgacgg
cagcatcaaacgccttaagttctctaatgagattacagaacaaaacgacgatatcgaccgtgaggatgcggctcagcggttcgacgctgactttg
ttctgatgaccggcgagcttatctctctcattaacggattaacaacctctctcggcggcgaagccaagcgataaacaccaggcaacaattcccc
cataagcatgggtgggttgctgcacgctaaattcagcaattcattaatttaatggcgcggtgcagcgcgccaatatggagaaaaccatgagcta
cattcagacattatccggcaaacattttaattacctcgatatccaacaggacgatatcgtgatcgaggatattgctaccgcgttgtctcatatctgcc
gctttgcagggcatcttcctgagttttacagtgtcggccagcatagcgttttaaccagccacctcgttccgcaggagtttgcattagaagcactgct
tcatgatgctgctgaagcctacctgcaggacatcccctccccacttaagcgcctgcttccggattaccaggcaatcgaagctcgtgtggacgca
gccattcggcagaagttcggtctaccaactgagcaacacccaaccgtgaaatatgccgacctggtgatgctcgccagcgaacgccgcgatttt
gagattgacgaaggttccatttggccatgcctcgaggagttgtcccaacggatttattcattatcaacccagttcgtcctggccagtcatacggc
atgttcatcaatcgctttaacgagttgatggagcagcgccaatgcgccgcatgaaggtaaaagaactcgtagcggaggcgtttgcctccgttgct
gaattgccaccaaagcatgcgccgcttatgcgcgaagtcgccaccagactggacgctacgttcgcagcattaaaagagtctctggtgcaactg
gaacaggaacgtaaagataaaacgccatgaccgtatttgaatatctccaggctcatccgaataccaccagcggtgaaatcgccaaaggtatga
acaaaagaccccagcggtcgccggagcattatctcagctctatggcaccggtcggatcgtgaagtctggtgttcgcaagggtattccaacata
ccgcattaacgatatgccgtttggttgcagtaacagcctaaccatgatgtttaaccagctcttgagcagagccagacaaggagcagcccaatga
cagcactcaacaaacaggcgctgcgtgaagaattccagttcatgcaggacaactatagcgacccggcagaccacgatcggcaggtgatttac
atcgaggcggaggcgctgctggatgagttggaagccaaagactcaacgatagcagcacaacaacatgagatccgtatgttgctgaatgcgctt
gaggaaaaaccatgcccgaaatgcaacgacacaggaatgactgatagtggcggcacgcagccatggggcgagccgattgagattgaatgc
gactgccgacagcaggatgccaacaccgcagaacttgtagccgctggcattggcgtgaaggggagtgagatggataaattaatcaaaccta
ccgcaaaggtaaatatgacggttcatgtgattatctttgctcggaagatgcgcgattcatcgttatgcgcggcgattatacggaagcggaaataa
ttcaggcttctgtgtctcaagatgtaatcgactcggatggtgcggctgattttgcaagtagcgcccgctattatcagtgctggtacaaagttagccc
aataggtggtcaggatggctattcaggctggcatcatcctcgtgattcgccgtgtcgcggtgcatatttcgcatcagttttgcaatgggattaagga
ggactaacccatgacaactaacaaccacccggcgcacggtcctgtatcactcgatcgcctgcaccagatacgcgaacacctgctgcatgatac
ccaatactcaaacggcgggaacagagcctacattctcgctgatgtattgaaggtgattgatggggctattgcccgcgagctggtacgccgtgag
catgcagcgtggtcacaggctactttcggcgatgtcggtccagttggtccgctgaagcacctttccaaagaagcgctcgaggctgctgctgaac
caggcgaccttagcgaatgggctgacatgcaattcctgttatgggatgcgcaacgtcgtgccggtatcagtgatgagcagattacccaggcaat
gataaaaagctggctataaataaggttcgccaatggcctgagccgaaagacggggaacctcgattgcatatcaaagaacagtcagagcagg
agaaaaaataagaatgtttagcctgattcggcgcggtcaaatctacacggacagtagcaactggcccgtaattatccatagctgtagtgatcactc
ggtccgaattaaacgcaatgatggcgagctgagaacgattagcatcaaacgctttaacgaagattttgaacgagtggagcatgatgagtatcgc
aaaatatgtgccgaaatagagcaggaaacaaacctgaaaaacctacgtgcgatgcgtcgcggcaagattactgaatagccaaacaggagaat
atttaacgtgaacaacttaatgatcgaccttgagtccatgggcaaaaaaccgaatgcccctattgtctccattggtgccgtattcttcgatccgcaa
agcggtgaactgggtcaggagttttacaccgctgttaatcttgaaagcgctatggagcagggagcggtgccggatggtgacactattctgtggt
ggttaagacaaagctcagaagcacgatcagcaatctgtgttgatgatgcgatgccgtatcatctgccctatctgaactgagccatttcattaatcg
gcattctgataaccctaaatatttaaaagtttggggcaatggagctactttcgacaacgttatattgcgcggcgcatatgagcgtgccggccaggtt
tgcccgtggcaattttggaatgatcacgacgtcagaaccatcgtcacattaggcagatctgtaggtttcgatcctaagcgtgatatgccatttgatg
gggttgcacataacgcactggctgatgcccgccaccaggcgaaatatgtttcagcgatttggcagaaactaatcccaaccaccagcaacagct TABLE F-continued Phage 3 sequence with Deletion aaagttttcccgggtgcagccgggataatggagaaataactatgagcaatattttccagttagctcccaacgattgggtttgtgaaagcgttttga
tcgcggttactgggctcaaacccggaaccatcctccgtgccagaaaagaatgctggatgattgggagggagtatatccacgtatcgcctgacg
gaaatcctaaaccttccagtgagtgcatgtataacagaaaggctgtagatgcctgggtcgcttcaatgaaaagcaagcaaccagggtgatttgat
gccatgaaaaaggtaagctcgtatcgctcttgggcgtctggaggtaacaccaatggataaagtcacatatccaacaggcgtcgaaaaccacgg
tggcacattacgcatctggtttaattttaaaggtaagcgtgtcagggaaagtctcggtgtccctgacaccgctaagaacaggaagatagccggg
gaactgcggacatcagtatgttttgccatccgcacaggaacctttgattatgcaacccagtttcctgactcccctaacctcaaggcttttggtgtaag
taaaaaagacattacagtgaaagaacttgaagaaaaatggctggatctgaaacggatggaaatctgcgcgaacgcatttaatcgctatgaatctg
tcgcaaggaatatggtgccgaggatcggaggtaatcgcctggtgtcagcagtaaccaaagaggaattgctgtatctgaggaaatatttgctaact
ggttatcagaatccgacgaaaaacaaagccccggcaaaagggcgaagcgttgttactgtgaactattacatgacgacaatggccggaatgtttc
agtttgctgcggatcacggttacttagaggtgaacccattcgagggaattaagcctctgaaaaaagccagggcagaaccagatcctctgtctcgt
gatgaatttattcgcctgatagatgcatgccggcatcagcagacgaaaaacctgtggtcattagcagtgtacacaggaatgcgtcacggggaac
tggtctccctggcctgggaagatatcgacctgaaggctggaacaattaccgtcagacgtaattatacgaaacttggtgagttcactctaccgaaa
accgaggcaagcacagatcgagtggtgcatcttatccagcccgcaatcagtatcctgaaaaatcaggctgaaatgacaaggctgggcaggca
atatcacattgaagtgcagttacgtgagtacggccgttcggtgaaccatgagtgtacattcgtctttaatccgcatgtggtcagacgcagtaagca
ggtcggatttatctaccgggtcgattcagtaggcgactcatgggaagcggcacttaagcgtgcggggatcagacacagaaaggcgtaccagt
cacgacacacctatgcgtgctggtcattatcagctggtgcaaaccctagttttattgccagtcagatggggcatgcgagcgcgcagatggtgttc
aatgtttacggtgcatggatggctgacagcagcgcagagcagatcgcaatgctgaatcagaagctggcagattttgccccattgatgccccata
gccacgagaacagtacgggaggattattaaaatcagtaagttaaccctaacgcccgtcatgttaactgtgtggagggtaacaccacgctttatg
ccctgccgaaacccgaggttgtcctgcgctggcgtgagcagaccacagatgacttccgcttctgttttaagtttccggcgaccatttcgcatcag
gcagcattacggcattgcgatgatttagtgactgaattttgacccgcatgtcaccgttggctccgcgcattggacaatactggctgcaactgcctg
ccacattcggcccacgggagctgcctgcgctttggcattttctcgattctcttcccggtgaatttaattatggggtggaagtccgccatccacagttt
ttcgccaaaggggaagaggaacaaacgcttaatcgcggtttacatcagcgcggcgttaatcgggtgattttagacagccgcccggttcatgcag
cacgtccatacagtgaagctattcgcgacgctcaacgaaaaaaacctaaagttccggtacatgctgtactgacggcgaaaaatccactgatccg
ttttatcggtagtgatgatatgacgcaaaaccgggaattatttcaggtctggttacaaaaattagcgcagtggcatcagaccactacgccttatctttt
tttacatacgccagatattgcccaggccccggaactggtacataccctgtgggaagacttacgtaaaacgcttccagagatcggagcagttccg
gctattccacagcaatcttctcttttctgaatttgccacctatcatagacaggtgccatcggccattttaaagggagtttgtatggtaagcgcgctgta
tgccgttttaagtgcgttgttattaatgaagttctcttttgatgtcgttcgcctgcgaatgcagtaccgcgttgcctatggcgacggcggttttagcga
actgcaaagcgctattcgcattcatggtaacgcggtggaatatattcctatcgcgattgtgttgatgctgtttatggaaatgaatggcgcagaaacc
tggatggtgcatatttgcggcatcgttttgcttgctggtcgtctgatgcattattacggttttcatcaccgtctgttccgctggcgacgttctggcatga
gcgccacctggtgtgcgctgttgctgatggtgctggcgaatctttggtatatgccctgggagttggttttctccctgcgttagcgcacaatacgcca
cttctttttcccggattttttacgttatgtctcaccgcgacacgctattttctgccctatcgccagactgggcgactggacctttgatgaacgggtag
ctgaagtcttcccggatatgatccagcgttccgttcccggctattccaatattatttccatgattggtatgttagccgagcgcttcgttcaacctggta
cgcaggtttacgatctgggttgttctctgggcgcggcgacgctctcggtgcgtcgcaacattcatcatgataattgcaaaattattgccatcgacaa
ctccccggcgatgattgaacgctgccgtcgtcatattgacgcctataaagcccctacgccagtagacgttattgaaggtgatattcgcgatatcgc
cattgaaaacgcatcgatggtggtgctgaattttaccctgcaattcctggaaccttccgagcgccaggcgttactggataaaatttatcaagggct
gaacccggcggtgcgctggtgctttcggaaaaattcagtttcgaagatgccaaagttggtgaactgctgttcaacatgcaccacgactttaaac
gtgccaacggttacagcgaactggagatcagccagaaacgcagcatgctggaaaacgtgatgctgaccgattccgtggaaacccataaagca
cgcctgcataaagccggttttgagcatagcgagctgtggttccagtgcttttaactttggttcactggtggcattaaaagcagaggacgctgcatga
tcgactttggtaacttttattctctgattgccaaaaatcatctttcacactggctcgaaacgctgcccgcgcagattgctaactggcagcgcgagca TABLE F-continued Phage 3 sequence with Deletion

```
gcagcacgggctgtttaagcagtggtccaacgcggtggaatttctgcctgaaattaaaccgtatcgtctggatttattgcatagcgtaaccgccga
aagcgaagagccactgagcgccgggcaaattaagcgcattgaaacgctgatgcgcaacctgatgccgtggcgcaaagggccgttctcactgt
atggcgtcaacatcgataccgaatggcgttccgactggaaatgggatcgcgttatgcccatctttctgatttaaccgggcgcaccattcttgatgt
cggctgtggcagcggttatcacatgtggcgcatgattggcgcaggggcgcatctggcggtgggtatcgatcccacgcagctattcctctgcca
gtttgaagcagtgcgtaaactgctgggtaacgatcagcgcgcacatttgttaccgttaggtattgaacaacttccggcactgaaagcctttgatac
cgtcttttcgatgggcgtgctttatcatcgtcgttcaccgctggagcatctctggcagttaaaagaccaactggtgaatgaaggcgaactggtgct
ggaaacgctggttattgatggcgacgaaaacacggtgctggtgccgggcgatcgttacgctcaaatgcgtaatgtctatttcattccttccgcgct
ggcgctgaaaaactggctgaagaagtgtggttttgttgatattcgcattgcagatgtgagcgttaccaccacagaagagcagcgacgcaccgaa
tggatggtcaccgagtctctggccgattttctcgacccgcatgatccgggtaaaacggtggaaggttatcctgcgcctaaacgcgcggtgctgat
tgcgcgcaagccgtaaaggtctggtaatactgccggatgcggcgtgaacgccttatccggcctacaaagtcttgctaattcaatatattgcaggg
gctatgtaggcctgataagcatagcgcatcaggca
```

Example 60. Testing of a Phage 3 Knockout of Wild Type E. coli Nissle (Prior to Removal of Chloramphenicol Cassette)

As described in Example 59, primers with 40 bp overhangs and homology to pKD3 had been used to create a knock out targeting a 10 kB region of the phage genome (lambda red recombineering followed by selecting for chloramphenicol resistance). Four clones obtained were selected. Using primers for to screen for the presence of an insertion of a chloramphenicol cassette in the phage 3 genome, the expected the 200 bp band was seen for all four clones indicating a positive insertion specific to the phage 3 genome.

The same 4 chloramphenicol resistant colonies were resuspended in 1 mL of LB in 14 mL culture tubes. Tubes were grown shaking at 37 C, 250 rpm. When cells reached early log phase, the cultures were split into two 500 ul aliquots; one aliquot was treated with mitomycin C (2 ug/mL); the other was left untreated. After 3.5 hrs, 400 ul of each culture was removed and 20 ul of chloroform was added. Samples were vortexed for 15 seconds and spun down in a centrifuge at max speed for 1 min. Table 96 shows the number of plaques counted. SYN-902 is WT Nissle comprising the pKD46 plasmid.
i.

TABLE 96

| Plaque Counts | | | |
|---|---|---|---|
| supernatant dilution | 0 | −1 | −2 |
| SYN-902 Φ3 knockout 1 no induction | 0 | | |
| SYN-902 Φ3 knockout 1 + MC | 0 | | |

TABLE 96-continued

| Plaque Counts | | | |
|---|---|---|---|
| supernatant dilution | 0 | −1 | −2 |
| SYN-902 Φ3 knockout 2 no induction | 0 | | |
| SYN-902 Φ3 knockout 2 + MC | 0 | | |
| SYN-902 Φ3 knockout 3 no induction | 0 | | |
| SYN-902 Φ3 knockout 3 + MC | 0 | | |
| SYN-902 Φ3 knockout 4 no induction | 0 | | |
| SYN-902 Φ3 knockout 4 + MC | 0 | | |
| ATCC13706 (negative control) | 0 | | |
| SYN-PKU-710 + MC (positive control) | TMTC | not plated | TMTC |

TMTC: too many to count

In conclusion, no plaques were observed in any of the knock out strains, while the positive control produced a large number of plaques. These results indicate that deletion of a 10 kb internal region of phage 3 in wild type E. coli Nissle prevents the formation of plaques following mitomycin C treatment.

Example 61. Phage Detection Assay in a Phage 3 Knockout Strain (Wild Type Nissle and SYN-PKU-1034)

This study was conducted to test whether A phage 3 knockout in wild type Nissle and in SYN-PKU-1034 results in a negative test in a plaque assay. Table 97 describes the strains used in this study.

TABLE 97

Strain Descriptions

| Strain Name | Description |
|---|---|
| SYN-PKU-1034 | Phenylalanine consuming strain which has a AIPS comprising the plasmid and genomic components shown in FIG. 61 of WO2017087580, the contents of which are herein incorporated by reference in their entirety. The plasmid comprising the toxin is |

TABLE 97-continued

Strain Descriptions

| Strain Name | Description |
|---|---|
| | medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD: ΔthyA; dapA::antitoxin) |
| SYN-PKU-1034d"phi"3 | SYN-PKU-1034 with phage knockout |
| SYN001 | Wild type E. coli Nissle |
| SYN-903 | SYN001 with phage knockout |

In this study, supernatants from E. coli Nissle (SYN01), SYN-903 (the phage 3 knockout in the Nissle background), SYN-PKU-1034d"phi"3 (phage 3 knockout in negative strain), SYN-PKU-710 (positive control), and ATCC13706 (negative control) were tested for the presence of phage.

PCR analysis using a primer set specific to a chloramphenicol (cm) cassette on one end and Phage 3 on the other had previously shown that the clone SYN-PKU-1034 phage 3 KO tested positive for the correct insertion of the chloramphenicol cassette (data not shown). Insertion of the CM cassette was performed as described above in Example 59.

For phage testing, strains (SYN01 (Nissle), ATC13706 (negative control), SYN-PKU-710, SYN-PKU-1033, SYN-PKU-1034, ATCC13706 (sensitive plaque indicator strain) were grown overnight in LB (with DAP 100 ug/mL where appropriate), 3 mL in a 14 mL culture tube shaking at 250 rpm at 37 C. Top agar composed of 7 g/L agar in LB media lacking yeast extract is prepared, melted, and kept at 45 C to maintain liquid.

Overnight cultures were used to inoculate 10 LB with DAP 100 ug/mL where appropriate in 125 mL baffled flasks at a 1:100 dilution. Each test strain was inoculated into 2 10 mL cultures: one flask with 2 ug/mL of mitomycin C to induce the phage and the second flask as a log phase uninduced control. All flasks were grown at 37 C shaking (250 rpm). All cultures were grown for 4.5 hours, diluted 10-fold in PBS in a 96-well plate, and plated for determination of cell counts. Spot dilutions (10 ul) spanning the $10^{-3}$ to the $10^{-8}$ dilutions were plated per plate (LB plates-DAP 100 ug/mL where appropriate), in duplicate, for each strain.

After completion of the cell counts, 1 mL from each culture (3 cultures per strain) was removed and placed in a 1.5 mL Eppendorf, 50 uL of chloroform was added, and tubes were vortexed for 15-30 seconds. Cells were spun down in a microcentrifuge for 2 minutes at maximum speed. Meanwhile, a 96-well plate was prepared to contain 180 uL of LB per well in columns 2-5 and 8-11. Dilutions of supernatant were performed in this plate. 200 uL of neat supernatant for each strain was added to column 1 for samples 1-8 and column 7 for samples 9-15. 10-fold dilutions were performed with a multi-channel pipette from columns 2-5 and 8-11.

To prepare sensitive control strain, 10 mL ATCC13706 was spun down at 4000×g in 15 mL falcon tube, supernatant was decanted and cells were resuspended in an equal volume of 10 mM magnesium sulfate. 14 mL culture tubes were set up and labelled for the appropriate strain and dilution of supernatant was added. To each tube, 100 ul of ATCC13706 cell suspension was added. Neat supernatant and its dilutions were added to the appropriate tubes and the cell/supernatant mixture was incubated for a minimum of 5 min.

After incubation, 3 mL of top agar was added to tubes and the mixture was immediately spread (by pouring) onto labelled LB plates. Plates were allowed to dry and then moved to a 37C static incubator, inverted, and incubated overnight. Results are shown in Table 987.

TABLE 98

Plaque Counts

| | Supernatant dilution | | | | | |
|---|---|---|---|---|---|---|
| | 0 | −1 | −2 | −3 | −4 | |
| | Final dilution (for calculating pfu/mL) | | | | | cfu/mL |
| | −1 | −2 | −3 | −4 | −5 | culture |
| ATCC13706 uninduced stationary | 0 | 0 | | | | $3.3 \times 10^{9}$ |
| ATCC13706 + MC log | 0 | 0 | 0 | | | $1.8 \times 10^{7}$ |
| SYN001 uninduced stationary | 20 | 3 | | | | $1.8 \times 10^{\wedge}$ |
| SYN001 + MC log | 249 | 18 | 2 | | | 0 |
| SYN-903 uninduced stationary | 0 | 0 | | | | 3.5e9 |
| SYN-903 + MC log | 0 | 0 | 0 | | | $1.5 \times 10^{4}$ |
| SYN-PKU-1034dphi3 uninduced stationary | 0 | 0 | | | | $1.8 \times 10^{9}$ |
| SYN-PKU-1034dphi3 + MC log | 0 | 0 | 0 | | | 0 |
| SYN-PKU-710 uninduced stationary | TMTC | 65 | 2 | | | $2.1 \times 10^{9}$ |
| SYN-PKU-710 + MC log | TMTC | TMTC | 289 | 72 | 3 | 0 |

TMTC = too many to count

As seen in the Table above, phage 3 is responsible for plaque formation, and a deletion in central genes within the phage chromosome can inhibit the formation of plaques. Gross observation did not suggest any sort of growth defect caused by deletion of the phage sequences.

Example 62. Phage Testing of SYN-PKU-2001, SYN-PKU-1035, and SYN-PKU-1036

This study was conducted to assess the phage production in various phenylalanine strains in which the antibiotic cassette has been removed from the plasmid background, and to confirm that removal of this cassette does not allow for reformation of phage particles.

Additionally, a phage-3 knockout version of SYN-PKU-710, but still containing the cm cassette was tested. Table 99 describes the strains used in this study and related background strains.

TABLE 99

Strain Descriptions

| Name | Description |
| --- | --- |
| SYN-PKU-710 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB::LacIPAL3; ΔdapA. |
| SYN-PKU-2001 | SYN-PKU-710 with deltaphage3::cm |
| SYN-PKU1033 | Phenylalanine consuming strain which has a kill switch system comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU-1034has a weaker RBS upstream of the pheP portion of the PAL-pheP gene cassette in the AIP plasmid compared to SYN-PKU1033 |
| SYN-PKU-1035 | SYN-PKU1033deltaphage 3 cured entirely |
| SYN-PKU-1034 | Phenylalanine consuming strain which has a kill switch system comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU-1034has a weaker RBS upstream of the pheP portion of the PAL-pheP gene cassette in the AIP plasmid compared to SYN-PKU1033 |
| SYN-PKU-1036 | SYN-PKU-1034deltaphage 3 cured entirely |

Cultures of ATCC13706 control, SYN-PKU-2001, SYN-PKU-1035, and SYN-PKU-1036 were grown overnight in 3 mL cultures in 14 mL tubes shaking at 37 C. Cells were then diluted into fresh media with mitomycin C (2 ug/mL). Plaque assays were performed essentially as described in Example 58. Plaque counts are shown in Table 100.

TABLE 100

Plaque Counts

| | Supernatant Dilution | | | | |
| --- | --- | --- | --- | --- | --- |
| | 0 | −1 | −2 | −3 | −4 |
| | Final Dilution (for calculating pfu/mL) | | | | |
| | −1 | −2 | −3 | −4 | −5 |
| ATCC13706 uninduced stationary | 0 | 0 | N/T | N/T | N/T |
| ATCC13706 + MC log | 0 | 0 | N/T | N/T | N/T |
| SYN-PKU-2001 uninduced stationary | 0 | 0 | N/T | N/T | N/T |
| SYN-PKU-2001 + MC log | 0 | 0 | N/T | N/T | N/T |
| SYN-PKU-1035 uninduced stationary | 0 | 0 | N/T | N/T | N/T |
| SYN-PKU-1035 + MC log | 0 | 0 | N/T | N/T | N/T |
| SYN-PKU-1036 uninduced stationary | 0 | 0 | N/T | N/T | N/T |
| SYN-PKU-1036 + MC log | 0 | 0 | N/T | N/T | N/T |
| SYN-PKU-710 uninduced stationary | TMTC | 57 | 3 | 0 | N/T |
| SYN-PKU-710 + MC log | TMTC | TMTC | 42 | 4 | 1 |

N/T—not tested;
MC—mitomycin C at 2 ug/mL

These results show that the knockout of phage 3 in SYN-PKU-710 resulted in no pfu from supernatant. Curing cassette from phage 3 knockout in plasmid strains also led to no pfu formation in supernatant.

Example 63. Generation and Analysis of SYN-PKU-2002

A version of the phenylalanine consuming strain SYN-PKU-710 in which phage 3 has been knocked out and the chloramphenicol cassette has been cured was analyzed. First, plaque formation was assessed in a plaque assay. Next, the ability of the strain to produce transcinnamic acid (TCA) was compared with SYN-PKU-710 to determine whether removal of the phage would cause any changes in phenylalanine consumption activity in vitro. Sanger sequencing of the relevant Phe degrading regions was performed to confirm that phenylalanine consuming circuitry.

First, to cure the chloramphenicol cassette, SYN-PKU-2001 (SYN-PKU-7103 with a delta phage 3::cm insertion) was transformed with pCP20, and 4 carbenicillin resistant transformants were selected for analysis. Removal of the chloramphenicol cassette was first confirmed by PCR. These transformants were grown overnight at 42 degrees to cure the pCP20 plasmid and were then streaked on LB plates (plain LB plates as control to ensure no growth, LB plus carbenicillin to confirm loss of plasmid and LB chloramphenicol to confirm removal of the chromosomal Cm cassette respectively, and LB Dap, on which the strains grow (dap auxotrophy)). Cells were also streaked on Phe agar and spotted ferric chloride to ensure LAAD activity was still present. All 4 clones turned dark green immediately, signifying a positive LAAD result. One clone was maintained for further analysis and named SYN-PKU-2002.

Next SYN-PKU-2002 was prepared for phage testing using ATCC13706 as a negative control and SYN-PKU-710 as a positive control. Plaque assay was carried out essentially as described in Example 58. Phage testing results showed no plaques in uninduced and mitomycin C induced supernatants from SYN-PKU-2002 (data not shown).

Next, flasks were prepared for testing activity of SYN-PKU-2002. Activity was tested with or without IPTG induction (aerobically), and with anaerobic induction. To perform this assay, an overnight culture of SYN-PKU-2002 was back-diluted 1:100 in 10 mL cultures in 125 mL baffled flasks (3 flasks inoculated, 1 for each condition). Cells were allowed to grow for 1 hr and 40 minutes, at which point they had entered early log phase. One flask remained untouched, the other received IPTG at 1 mM final concentration, and third flask was moved to the anaerobic chamber supplying 90% $N_2$, 5% $CO_2$, and 5% $H_2$. The cells were allowed to induce for 4.5 hours. The TCA production assay was then performed according to the standard protocol as described elsewhere herein. Essentially, bacteria were resuspended in assay buffer containing 50 mM phenylalanine. Aliquots were removed from cell assays every 20 min for 1.5 hrs for trans-cinnamate quantification by absorbance at 290 nm.

As seen in Table 101, both IPTG and anaerobic induction of SYN-PKU-2002 was observed.

TABLE 101

In vitro Activity Measurements

| Strain | CFU/ASSAY | 30 | 60 | rate (umol/hr/1e9cells) |
|---|---|---|---|---|
| SYN-PKU-2002 – IPTG A | 8.16E+07 | 0.00488 | 0.015122 | 0.19 |
| SYN-PKU-2002 – IPTG B | 8.57E+07 | 0.00267 | 0.009158 | 0.11 |
| SYN-PKU-2002 + IPTG A | 8.00E+07 | 0.1345 | 0.273565 | 3.42 |

TABLE 101-continued

In vitro Activity Measurements

| Strain | CFU/ASSAY | 30 | 60 | rate (umol/hr/1e9cells) |
|---|---|---|---|---|
| SYN-PKU-2002 + IPTG B | 8.93E+07 | 0.13411 | 0.263227 | 2.95 |
| SYN-PKU-2002 – O2 A | 7.25E+07 | 0.09474 | 0.170983 | 2.36 |
| SYN-PKU-2002 – O2 B | 8.62E+07 | 0.08878 | 0.176152 | 2.04 |

All samples were sent for Sanger sequencing and confirmed that all of the Phe-degrading relevant regions in SYN-PKU-2002 were sequence accurate.

In conclusion, SYN-PKU-2002 does not produce plaque forming units (pfus) against ATCC13706, when supernatant was used form cultures that were uninduced or induced with mitomycin C. SYN-PKU-2002 contains no antibiotic markers and no plasmids. It also has phenylalanine degrading activity both with IPTG and anaerobic induction. All of the relevant regions involved in phenylalanine degradation were sequenced. Therefore, SYN-PKU-2002 appears functionally equivalent to SYN2619 except that it does not produce phage.

Example 64. SYN-PKU-2002 in Vitro Activity Measurements

A 1:100 back-dilution from overnight culture of SYN-PKU-2002 was grown to early log phase for 1.5 h before moving to the anaerobic chamber for 4 hours in the presence of 1 mM IPTG and 0.1% arabinose for induction as described herein. To perform activity assay, 1e8 cells were resuspended and incubated in assay buffer (M9 media with 0.5% glucose, 50 mM Phe, and 50 mM MOPS with 50 mM phenylalanine). Supernatant samples were taken over time and TCA (the product of PAL) was measured by absorbance at 290 nm to determine the rate of TCA production/PAL activity. Phenylpyruvate was measured using LCMS methods described herein. Results are shown in FIG. 16A and FIG. 16B.

Example 65. Analysis of Activity of SYN-PKU-2002 in Vivo—the Effect of Phage 3 Deletion from SYN-PKU-710 on in Vivo Activity in the Enterorecirculaton Model of Phenylketonuria (PKU)

The activity of SYN-PKU-2002 to produce hippurate in vivo is assessed. In this study, SYN-PKU-710 and SYN-PKU-2002 are grown in flasks and induced anaerobically, and the effect of the phage deletion on the ability of the SYN-PKU-2002 to produce hippurate and reduce serum Phe is assessed through comparison with the isogenic phage containing strain SYN-PKU-710 in vivo.

SYN-PKU-710 and SYN-PKU-2002 overnight cultures are each used to inoculate 4 2 L flasks containing 500 mL of LB with DAP100 ug/mL. These cultures are grown for 1 hr and 45 min and then moved to the anaerobic chamber supplying 90% $N_2$, 5% $CO_2$, and 5% $H_2$ for 4 hours. Cells are then spun down at 4600× G for 12 min and resuspended in 10 mL of formulation buffer (Glycerol: 15% (v/v), Sucrose: 10% (w/v) (100 g/L), MOPS: 10 mM (2.1 g/L), NaCl: 25 mM (1.46 g/L)). Several 40 ul aliquots are removed to be used for cell counting and activity determination. Activity is determined essentially as described in Example 63 and is measured for SYN-PKU-710 and SYN-PKU-2002, respectively. The viability as determined by cellometer count for SYN-PKU-710 and SYN-PKU-2002. SYN-PKU901 (streptomycin resistant Nissle, 8e10 cfu/ml) is used as a control. Cells are brought up to 10 ml with PBS, and then mixed 9:1 with 1 M bicarbonate to achieve a final concentration of 100 mM bicarbonate, in preparation for daily gavage of 4e10 cells (3×300 ul doses).

To compare the efficacy of phage positive SYN-PKU-710 vs isogenic phageless strain SYN-PKU-2002 in vivo, strains are administered to in enu2 mice. SYN-PKU901 is administered as a control. Female BTBR-Pah enu2 mice (20-35 g) from CRL (GEMS) within 6-18 wks of age are allowed to acclimate to facility for at least 2 days Animals are placed on phenylalanine deficient diet (Teklad TD.97152) and are given a phenylalanine enriched water at 0.5 g/L of L-Phenylalanine (Sigma) and 5% sucrose/L (Sigma) at least 2 days prior to starting study. Phenylalanine enriched water is removed for duration of study and is replaced with normal water.

On the day of the study, mice are randomized into treatment groups according to weight as follows: Group 1: $H_2O$ (n=9); Group 2: SYN-PKU901 (n=9); Group 3: SYN-PKU-710 (n=9); Group 4: SYN-PKU-2002 (n=9). Blood samples are collected by sub-mandibular skin puncture to determine baseline phenylalanine levels. Mice are then administered single dose of phenylalanine by subcutaneous injection at 0.1 mg per gram body weight, according to the average group weight. At 1, 2 and 3 h post Phe challenge, the bacteria (or water) are administered to mice by oral gavage (3×300 ul). Animals are bled and urine is collected from all animals up to 4 h post Phe challenge. Blood samples are kept on ice until processing for plasma in a centrifuge (2000 g for 10 min at 4 C) within 20 min of collection. Plasma is then transferred into a 96-well plate for MS analysis. Urine is collected in 5 mL tubes and volumes are recorded before transferring samples to MS for hippurate analysis.

Example 66. In Vivo Serum Phe and Hippurate Measurements Upon Administration of SYN-PKU-2002

The activity of SYN-PKU-2002 was assessed in vivo. To prepare the cells for the study, SYN-PKU901 and SYN-PKU-2002 overnight cultures were each used to inoculate 4 2 L flasks containing 500 mL of LB with DAP100 ug/mL. These cultures were grown for 1 hr and 45 min and then moved to the anaerobic chamber supplying 90% $N_2$, 5% $CO_2$, and 5% $H_2$ for 4 hours. Cells were then spun down at 4600×G for 12 min and resuspended in 10 mL of formulation buffer (Glycerol: 15% (v/v), Sucrose: 10% (w/v) (100 g/L), MOPS: 10 mM (2.1 g/L), NaCl: 25 mM (1.46 g/L)). Several 40 ul aliquots were removed to be used for cell counting and activity determination. The viability as determined by cellometer count (in quadruplicate) 6.94e10 cfu/ml (+/−5.78e9).

Activity was determined using a plate based assay. Briefly, 1×10$^8$ cfu as determined by cellometer were added to 1 ml of prewarmed assay buffer (1× M9 minimal media containing 0.5% glucose, 50 mM MOPS, and 50 mM phenylalanine) in a microfuge tube, vortexed briefly, and immediately placed in a heat block or water bath at 37 degrees Celsius for static incubation (t=0). Supernatant samples from cells re-suspended in assay buffer were analyzed for the abundance of TCA over several time points using spectrophotometer at an absorbance of 290 nm. The accurate OD290 window for TCA detection occurs in a relatively narrow concentration range. For this reason, supernatant samples were diluted to ensure that the absorbance measurement fell into the linear range for detection. Measurements were compared to a TCA standard curve. Activity was determined to be 2.72 umol/hr/1e9 cfu (+/−0.15 umol/hr/1e9 cfu).

Beginning 4 days prior to the study (i.e., Days −4-1), Pah ENU2/2 mice (~11-15 weeks of age) were maintained on phenylalanine-free chow and water that was supplemented with 0.5 grams/L phenylalanine. On the day of the study, mice were randomized into treatment groups according to weight as follows: Group 1: SYN-PKU901 (n=9); Group 2: Group 2: SYN-PKU-2002 (n=9). Blood samples were collected by sub-mandibular skin puncture to determine baseline phenylalanine levels. Mice were then administered single dose of phenylalanine by subcutaneous injection at 0.1 mg per gram body weight, according to the average group weight. At 1, 2 and 3 h post Phe challenge, the bacteria (or water) were administered to mice by oral gavage (3×250 ul). Whole blood was collected via submandibular bleed at each time point. Urine collection in metabolic caging commenced immediately after the 1$^{st}$ bacterial dose and continued to be collected for the duration of the study (4 hours).

Figure 17B:
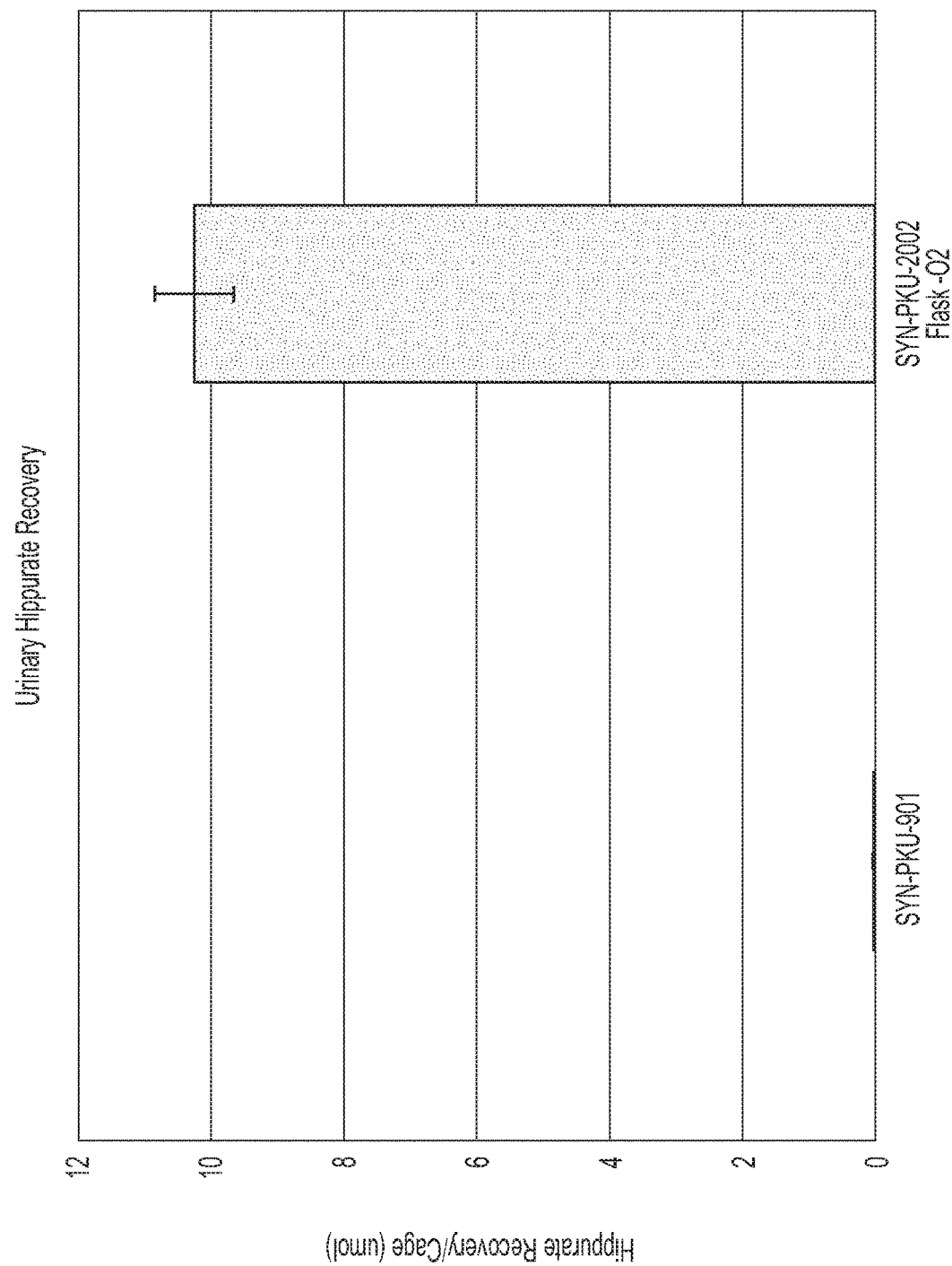

Blood samples were kept on ice until processing for plasma in a centrifuge (2000 g for 10 min at 4 C) within 20 min of collection. Plasma was then transferred into a 96-well plate for MS analysis. Urine was collected in 5 mL tubes and volumes were recorded before transferring samples to MS for analysis. Results are shown in FIG. 17A and FIG. 17B and show that SYN-PKU-2002 causes decreased changes in phenylalanine post-Phe injection and produces hippurate, in a similar manner as SYN-PKU-710.

Example 67. Efficacy of SYN-PKU-2002 in the ENU2 Murine Model of Phenylketonuria The objective of this study was to examine the dose dependent in vivo activity of the phenylalanine (Phe)-degrading probiotic SYN-PKU-2002 in the ENU2 murine model of phenylketonuria (PKU), as measured by the generation of urinary hippurate (HA), trans-cinnamate (TCA), and phenylalanine (Phe) following oral SYN-PKU-2002 administration. Efficacy of SYN-PKU-2002 as it relates to PKU was measured by the ability of orally administered SYN-PKU-2002 to decrease plasma Phe levels in Pah$^{enu2/enu2}$ mice independent of dietary Phe intake, in conjunction with the appearance of plasma TCA and HA, and was also assessed by measuring these metabolites in the plasma following Phe administration by subcutaneous (SQ) injection.

In the initial study, female Pah$^{enu2/enu2}$ mice maintained on Phe-deficient diet were weighed and then randomized by weight into 2 treatment groups (n=9 each). Blood (lithium heparin used as anticoagulant) was obtained from each mouse via submandibular bleed (T=0 h). Mice then received an SQ injection of Phe (0.1 mg/g) and were immediately placed in metabolic cages (3 mice/cage) for collection of urine. At 1, 2, and 3 h post Phe injection, mice were gavaged orally with either control SYN-PKU901 (Group 1) or SYN-PKU-2002 (Group 2) cells that had been grown and pre-induced in shake flasks (5×10$^{10}$ cells total dose, evenly split across the 3 hourly gavages). At 4 h post-injection, plasma (lithium heparin used as anticoagulant) was obtained by submandibular bleed and the urine was collected. Liquid chromatography-tandem mass spectroscopy (LC-MS/MS) was used to measure concentrations of Phe, TCA, and HA in plasma and urine.

The study was performed similarly to the study described in Example 65 with the exception that the SYN-PKU-2002 test article used to gavage mice was grown and activated in a bioreactor using a process similar to the one intended for scale up of drug substance. Female ENU2 mice (n=63) maintained on Phe deficient diet were weighed and then randomized by weight into 7 treatment groups (n=9 each). Mice were then given a SQ injection with Phe (0.1 mg/g) and immediately placed in metabolic cages for urine collection. SYN-PKU-2002 was gavaged orally at 1, 2, and 3 h post Phe injection to 6 dose groups (n=9/dose group split into 3 metabolic cages of 3 mice/cage). Dose groups received $1\times10^{11}$, $5\times10^{10}$, $2.5\times10^{10}$, $1.25\times10^{10}$, $6.25\times10^{9}$, or $3.13\times10^{9}$ cells in total, equally split across the 3 hourly gavages. SYN-PKU901 was gavaged to a control group (n=9) at the highest dose of $1\times10^{11}$ cells. Urine was collected over 4 h. Plasma (lithium heparin used as anticoagulant). was obtained by submandibular bleed at T=0 h and at T=4 h at the highest dose group ($1\times10^{11}$ cells) for both SYN-PKU-2002 and SYN-PKU901-treated mice for the determination of plasma Phe changes. LC-MS/MS was used to measure plasma and urinary Phe, HA, and TCA. A quantitative LC-MS/MS method was not available to measure phenylpyruvate in plasma or urine.

Figure 18A:
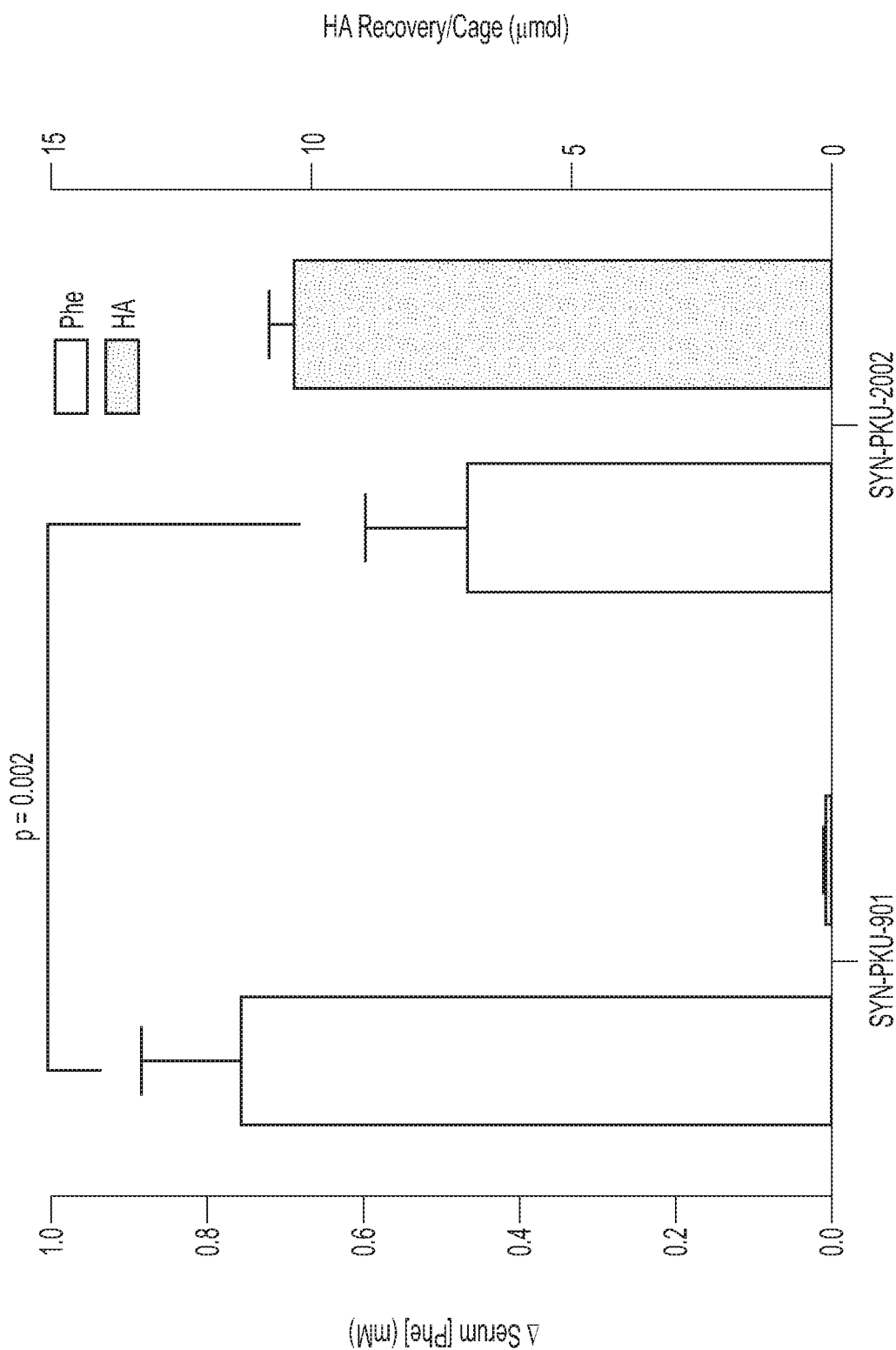
FIG. 18A and FIG. 18B depicts a graph showing changes in phenylalanine levels post Phe challenge (FIG. 18A) and hippurate recovery (FIG. 18B) from urine collected from animals treated with the indicated doses of SYN-PKU-2002. In brief, animals were transferred to metabolic cages (3 mice per cage, 2 cages per group) and administered single dose of phenylalanine by subcutaneous injection (0.1 mg per gram body weight). At 1, 2 and 3 h post Phe challenge, bacteria were administered to mice by oral gavage at the doses $1×10^{11}$, $5×10^{10}$, $2.5×10^{10}$, $1.25×10^{10}$, $6.25×10^{9}$, or $3.13×10^{9}$ cells. SYN-PKU901 was gavaged to a control group (n=9) at the highest dose of $1×10^{11}$ cells. Urine was collected from all animals up to 4 h post Phe challenge. Blood was obtained by submandibular bleed at T=0 h and at T=4 h at the highest dose group (1×10" cells) for both SYN-PKU-2002 and SYN-PKU901-treated mice for the determination of changes in serum Phe.
Figure 18B:
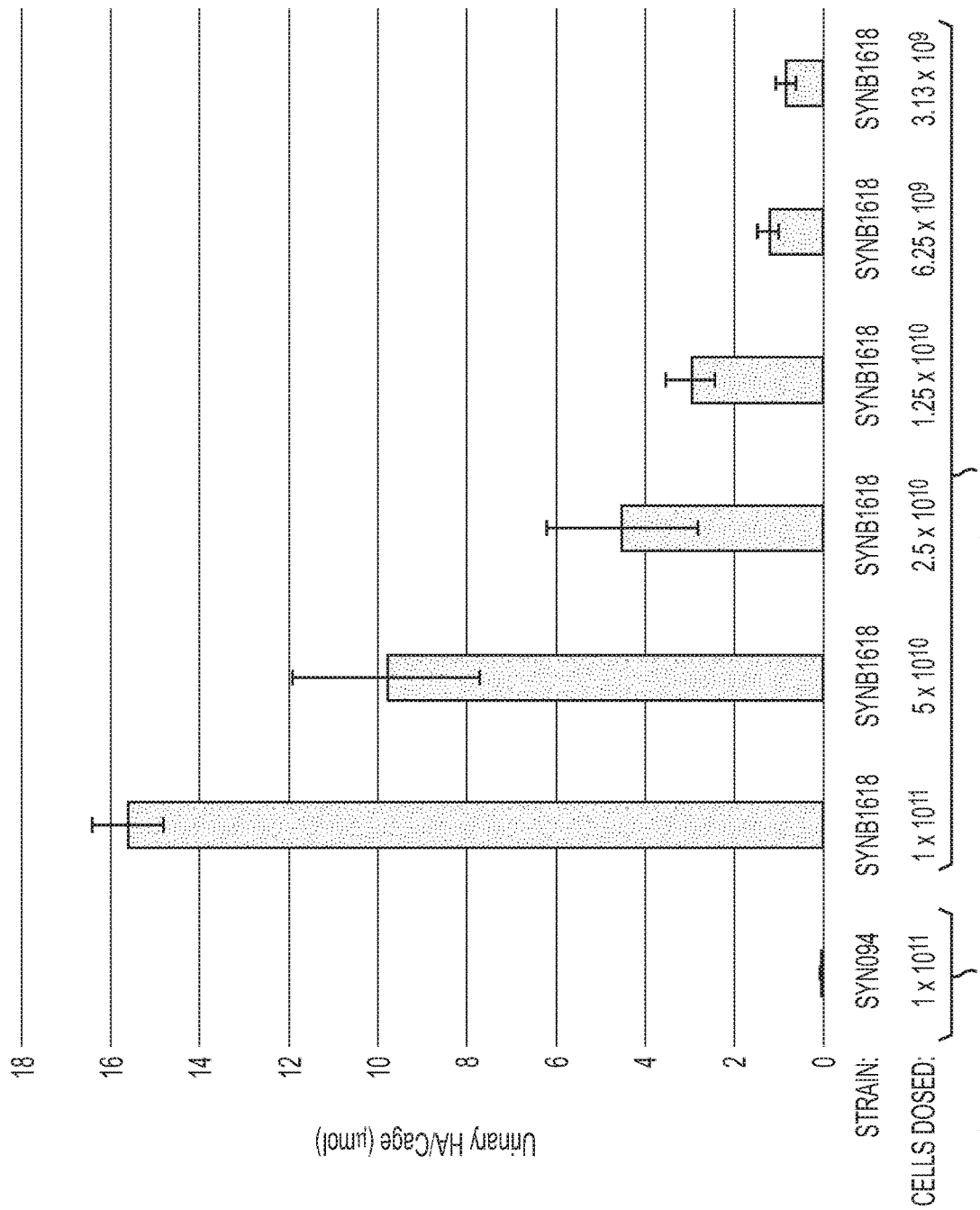

Results are shown in FIG. 17A and FIG. 18B. In the first study, following SQ Phe injection (0.1 mg/g), a plasma Phe increase was significantly blunted in ENU2 mice that received an oral dose of $5\times10^{10}$ SYN-PKU-2002 cells compared to an equal dose of the control strain SYN-PKU901 (37.7% decrease, p=0.0002). The quantity of urinary HA excreted during the 0-4 h sampling period of the study was determined by multiplying the urinary HA concentration by the volume of urine collected. Urinary HA concentrations were below the lower limit of quantitation (BLLOQ; <0.04 mM) in mice treated with the control strain SYN-PKU901, while concentrations in mice administered SYN-PKU-2002 were high (ranging from 6.59-7.97 mM), resulting in measurable HA excretion over 4 hours (10.24±0.59 μmol). TCA and HA were not observed in the plasma of any of the mice at T=0 but were detected 4 h post administration in the group receiving SYN-PKU-2002. TCA and HA were not measurable in the plasma of mice treated with the control strain SYN-PKU901 at any time point, indicating that TCA increases were due to SYN-PKU-2002 activity and demonstrating SYN-PKU-2002 function in vivo. Urinary concentrations of Phe and TCA were BLLOQ in all samples.

In the second study, efficacy was also observed when SYN-PKU-2002 was grown in a bioreactor under conditions similar to the process used for scale-up of drug substance. Following SQ Phe injection (0.1 mg/g) in ENU2 mice, a plasma Phe increase was significantly blunted in the group that received an oral dose of $1\times10^{11}$ SYN-PKU-2002 cells compared to an equal dose of SYN-PKU901 cells (29.3% decrease, p=0.02). Additionally, increases in urinary HA excretion were observed in mice treated with SYN-PKU-2002 in a dose-dependent manner (15.61±0.81, 9.81±2.11, 4.52±1.70, 2.97±0.55, 1.24±0.23, and 0.86±0.25 μmol of HA were excreted in mice dosed with $1\times10^{11}$, $5\times10^{10}$, $2.5\times10^{10}$, $1.25\times10^{10}$, $6.25\times10^{9}$, or $3.13\times10^{9}$ SYN-PKU-2002 cells, respectively). Mice treated with $1\times10^{11}$ SYN-PKU901 cells, the highest dose used for SYN-PKU-2002, did not excrete a large amount of HA (0.08±0.02 μmol). Similar to the first study, TCA and HA were not observed in the plasma of any of the mice at T=0, but were detected at 4 h post-administration in the group receiving SYN-PKU-2002 and not in animals receiving SYN-PKU901. HA excretion in urine correlated well with the amount of SYN-PKU-2002 cells dosed, indicating that the metabolite HA is a promising biomarker of in vivo SYN-PKU-2002 activity.

In conclusion, these data demonstrate the Phe-metabolizing activity of SYN-PKU-2002 in vivo by increasing the circulation of plasma TCA and HA and greatly increasing the amount SYN-PKU-2002 activity in the ENU2 mouse model. The second part of the study showed that SYN-PKU-2002 grown in a bioreactor using a process intended for the scale-up of drug substance was active in vivo. In this experiment, plasma Phe levels increased in mice when given an SQ injection of Phe along with orally administered control strain SYN-PKU901; however, mice orally dosed with SYN-PKU-2002 had a significantly blunted spike in plasma Phe concentrations following SQ Phe injection. Importantly, this result indicates that systemically circulating Phe reaches the intestine through enterorecirculation and is subsequently broken down by orally administered SYN-PKU-2002 in the gastrointestinal (GI) tract. This experiment demonstrated that SYN-PKU-2002 can decrease circulating Phe levels in blood, independent of the dietary intake of protein Example 68. Viability Comparison Between Phage Containing and Phage Free Phenylalanine Consuming Strains in Vivo To identify potential differences in viability, transit or colonization between the phage containing phenylalanine strain SYN-PKU-710 and its phage-free counterpart SYN-PKU-2002, an in vivo competition study was conducted and a competitive index of SYN-PKU-710 vs the isogenic phageless SYN-PKU-2002 strain was generated. Because neither SYN-PKU-710 or SYN-PKU-2002 have antibiotic cassettes, marked strains that are uncured of antibiotic resistance were used in this study. For SYN-PKU-710, the chloramphenicol/kanamycin (cm/kan) marked strain SYN-PKU-713 was used. For SYN-PKU-2002, the chloramphenicol (cm) marked strain SYN-PKU-2001 was used. Table 102 lists strains relevant to this study.

TABLE 102

Strain Descriptions

| Strain Name | Description |
|---|---|
| SYN-PKU-710 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB::LacIPAL3; ΔdapA. |
| SYN-PKU-713 | malEK:: PfnrS-PAL3; malPT:: PfnrS-PAL3; yicS/nepI:: PfnrS-PAL3; lacZ::PfnrS-pheP, agaI/rsmI::PfnrS-pheP; Para::LAAD; exo/cea:: LacIPAL3:cm; rhtC/rhtB::LacIPAL3:kn; ΔdapA (chloramphenicol and kanamycin resistance) |

TABLE 102-continued

Strain Descriptions

| Strain Name | Description |
|---|---|
| SYN-PKU-2002 | malEK:: PfnrS-PAL3; malPT::PfnrS-PAL3; yicS/nepI:: PfnrS-PAL3; lacZ::PfnrS-pheP, agaI/rsmI:PfnrS-pheP; Para::LAAD; exo/cea:: LacIPAL3; rhtC/rhtB::LacIPAL3; AdapA; with phage3 KO, cured of cm resistance |
| SYN-PKU-2001 | malEK:: PfnrS-PAL3; malPT::PfnrS-PAL3; yicS/nepI:: PfnrS-PAL3; lacZ::PfnrS-pheP, agaI/rsmI::PfnrS-pheP; Para::LAAD; exo/cea:: LacIPAL3; rhtC/rhtB: :LacIPAL3; AdapA; with insertion of phage3 KO frag::cm and cured of pKD46 (not cured of chloramphenicol resistance; with chloraphenico resistance |

Briefly, overnight cultures of SYN-PKU-713 and SYN-PKU-2001 were used to inoculate 100 mL of LB (also containing DAP 100 ug/mL and appropriate antibiotics) in 500 mL baffled flasks. The cultures were grown for 6 h, at which point they were spun down in a centrifuge at 4000×g for 15 minutes for collection. Supernatant was discarded. Cells were resuspended in approximately 7 mL of formulation buffer (Glycerol: 15% (v/v), Sucrose: 10% (w/v) (100 g/L), MOPS: 10 mM (2.1 g/L), NaCl: 25 mM (1.46 g/L)). Cells were aliquoted into 650 uL aliquots and frozen at −80C. Smaller aliquots were removed for cell plating and viability determination. Using a cellometer, viability was shown to be very high, and cell numbers fairly comparable between the strains.

All cell counts for this study (including input) were obtained by plating so that input (gavage) and output (feces) could be consistently compared. The two 650 uL aliquots were thawed on ice, mixed 1:1, diluted in sodium bicarbonate (9 parts cells:1 part 1M bicarbonate (144 uL), and then plated out in quadruplicate for quantitation on kan/cm and cm (from −8→−10 dilution by 10-fold 10 uL spot plating).

On Day 1, wild type B6 mice (n=6) were gavaged with 200 ul cells (approximately 3×10^9 of each strain). Fecal pellets were collected 6 hours prior and 6 hours post gavage. On days 2 and 3, mice were gavaged with 200 ul cells and fecal pellets were collected 6 hours prior and 6 hours post gavage. On days 4 and 5, fecal pellets were collected.

Each day, collected fecal pellets were weighed in tubes containing 1 ml PBS and homogenized. To determine the CFU of Nissle in the fecal pellet, the homogenized fecal pellet was serially diluted, and each sample was plated onto LB plates containing chloramphenicol and plates containing kanamycin. The plates were incubated at 37° C. overnight, and colonies were counted. To determine the amount of the two strains in the feces, total recombinant Nissle was counted on cm plates, and the number of SYN-PKU-713 obtained on kan plates was subtracted from the total amount to determine the number of SYN-PKU-2001 CFUs.

Results are shown in FIG. 19 and the competitive index (SYN-PKU-713 input/SYN-PKU-2001 output are shown in Table 103.

TABLE 103

Competitive Index of Output
Competitive index of output (SYN-PKU-713 output/SYN-PKU-2001 output):

| Time (h) | M1 | M2 | M3 | M4 | M5 | M6 | AVG |
|---|---|---|---|---|---|---|---|
| 6 | 0.6 | 1.1 | 2.1 | 1.6 | 1.8 | 1.4 | 1.4 |
| 24 | 1.7 | 1.2 | 1.2 | 22.5 | 2.9 | 1 | 5.1 |
| 30 | 1.2 | 1 | 0.9 | 1.5 | 1.8 | 0.9 | 1.2 |

TABLE 103-continued

Competitive Index of Output
Competitive index of output (SYN-PKU-713 output/SYN-PKU-2001 output):

| Time (h) | M1 | M2 | M3 | M4 | M5 | M6 | AVG |
|---|---|---|---|---|---|---|---|
| 48 | 1.5 | 1.1 | 1 | 1.1 | 1.5 | 0.1 | 1.1 |
| 54 | 1 | 1.2 | 0.9 | 1.1 | 1.2 | 1.8 | 1.2 |
| 74 | 0.4 | 0.4 | 0.8 | 1.8 | 1.6 | 0.7 | 0.9 |
| 100 | NA | NA | NA | NA | NA | NA | NA |

Results indicate that there is no large difference in transit or colonization between the phage-free PKU strain of Nissle SYN-PKU-713 and SYN-PKU-2001.

Example 69. General Bacteriophage Testing Protocol for Strains Derived from *E. coli* Nissle The following procedure detects a DNA sequence found in EcN prophage/phage. It amplifies phage and prophage DNA within the EcN genome in SYN-PKU-2002 as the primers amplify outside of the region of prophage deleted to generate the bacterial strain for SYN-PKU-2002.

The validated bacteriophage (phage) method, GP-V708, Plaque Assay of Bacterial Virus from *E. coli* Using Mitomycin C Induction, measures the presence of phage using a plaque assay. Testing confirms that phage detected is from the endogenous EcN prophage and not from a contaminating phage, or adventitious agent.

The plaque assay starts with a loopful or scrape of frozen sample, negative and positive bacterial cultures which are grown in enriched medium supplemented with 10 mM thymidine at 37±2° C. and shaken at 200-300 RPM overnight. A portion of the sample, positive control (*E. coli*, EMG 2: K [lambda], ATCC 23716, or equivalent) and negative control (*E. coli*, ATCC 13706, or equivalent) is removed and centrifuged, and each supernatant examined in a plaque assay for the presence of bacteriophage. Mitomycin C, at a final concentration of 2 μg/mL, is added to the remaining sample, positive and negative bacterial cultures. The cultures are then placed at 37±2° C. and shaken at 300-400 RPM until lysis occurs in the positive control (~4.5 hours). Each culture is treated with chloroform, centrifuged, and a 0.1 mL aliquot of the supernatant is examined for the presence of bacteriophage. To accomplish this, supernatants are mixed with phage-sensitive *E. coli* strain ATCC 13706, mixed with 0.7% agarose solution, and plated as a lawn atop LB agar. The test is considered valid if plaques are present in the positive control and no plaques are present in the negative control.

Plates containing the strain of interest that contain enumerable plaques are identity tested by end point PCR to confirm that plaques are from phage generated from the endogenous EcN prophage. This is accomplished by first creating an agar plug of individual plaques with a 2 µL pipet tip and resuspending each plug in 0.5 mL of deionized water. Plug resuspensions are vortexed for 15 sec and 1 µL is used as template for PCR. As a negative control, an agar plug from the same plates is created from an area which does not contain plaques. A total of 10 plaques are tested per sample, when available. In cases when less than 10 plaques are formed per sample, all plaques are analyzed. One (1) negative control plug is tested per sample. As additional controls, pure broth cultures of EcN and ATCC 13706 are grown overnight in enriched medium at 37±2° C. with shaking at 200-300 RPM. One hundred (100) µL of stationary cultures are added to 0.2 mL thin wall tubes and heated at 98° C. in an Eppendorf Mastercycler Pro thermocycler for 10 min to prepare genomic lysate to be used as template for PCR.

Overall samples and controls used as template for each PCR assay were:

a. Sample: 1 µL of up to 10 resuspended plaques picked from an enumerable plate
b. Negative control: 1 µL of 1 plug picked from a non-plaque area from the enumerable sample plate
c. Negative control: 1 µL from lysed stationary culture of *E. coli*, ATCC 13706, or equivalent strain (plaque indicator strain)
d. Positive control: 1 µL from lysed stationary culture of the strain of interest cells PCR is used to amplify a region of EcN-specific phage followed by detection of PCR amplified fragment at the endpoint of the reaction via gel electrophoresis. Primers (Integrated DNA Technologies, Skokie, IL) used for the amplification of EcN-specific phage are shown in Table 104. The primers were selected after careful examination of the EcN phage and amplify a region within the EcN-specific phage but do not bind to any region in the genomic DNA within the phage-sensitive *E. coli* strain ATCC 13706 that is used for plaque detection.

TABLE 104

EcN-Phage-specific PCR Primers

| Primer description | Primer sequence | SEQ ID NO |
|---|---|---|
| EcN phage forward primer | 5-gcatcaatcagtgattggc-3 | SEQ ID NO: 132 |
| EcN phage reverse primer | 5-ACGTCTGAATATACGGGCTG-3 | SEQ ID NO: 133 |

Abbreviations: EcN = *E. coli* Nissle 1917

The reactions are carried out in 0.2 mL thin wall tubes using an Eppendorf Mastercycler Pro PCR machine. A master mix is prepared for the phage-specific primers. Primers are reconstituted to a final concentration of 100 µM in nuclease-free sterile water. Master mixes are prepared per the recipe in Table 105.

TABLE 105

PCR Master Mix Preparation

| Reagent | Per rxn (µL) | Final Concentration |
|---|---|---|
| Nuclease-free sterile water | 8.8 | N/A |
| Forward primer (10 µM) | 0.1 | 0.12 µM |

TABLE 105-continued

PCR Master Mix Preparation

| Reagent | Per rxn (µL) | Final Concentration |
|---|---|---|
| Reverse primer (10 µM) | 0.1 | 0.12 µM |
| 2X MyTaq ™ Red Mix | 10 | 0.2 U/µL |

Abbreviations:
N/A = not applicable;
PCR = polymerase chain reaction;
rxn = reaction Nineteen (19) µL of PCR master mix is added to each 0.2 mL PCR tube followed by addition of 1 µL of PCR template into individual tubes. The tubes are capped, placed in the PCR machine, and the reaction cycle run following parameters in Table 106.

TABLE 106

PCR Reaction Cycle

| Stage | Temperature (° C.) | Time (min:sec) |
|---|---|---|
| 1 | 95 | 5:00 |
| 2 | 95 | 0:15 |
|  | 58 | 0:15 |
|  | 72 | 0:10 |
| 3 | Repeat Stage 2: 25 cycles | N/A |
| 4 | 72 | 1:00 |
| 5 | 45 | N/A |

Abbreviations:
° C. = degrees Celsius;
min = minute(s);
PCR = polymerase chain reaction;
sec = second(s)

Five µL of each standard, sample, or control reaction are loaded onto a 0.8% agarose gel for separation by electrophoresis and visualization using a Syngene UV transilluminator. The approximate size of the amplified band is 350 bp for the presence of EcN-specific phage while the negative control does not produce any bands.

Example 70. SYN-PKU-2002 Toxicology Study

The dosing duration for the GLP toxicology study is 28 days in male and female CD-1 mice with BID dosing (twice daily). Doses cover an approximate range of $1\times10^9$, $1\times10^{10}$, and $1\times10^{11}$ CFUs. The highest concentration is the maximum feasible dose. Mice are assessed for test article related mortality, clinical observations, body weight, hematology, clinical chemistry, and macroscopic and microscopic pathology. Following cessation of dosing, fecal samples are taken from mice for several days to assay for the presence of SYN-PKU-2002 DNA using qPCR analysis to determine the decrease in SYN-PKU-2002 over time. Blood also is evaluated for the presence of SYN-PKU-2002 DNA using qPCR. The design fo the 28-Day Mouse GLP Toxicology Study is outlined in Table 107.

TABLE 107

Design for 28-Day Mouse GLP Toxicology Study
4-Week GLP Toxicity Study of SYN-PKU-2002 in Mice with 2-Week Recovery Phase

| | |
|---|---|
| Purpose | Determine subchronic toxicity of test compound |
| | Determine reversibility of test compound effects |
| | Determine TK profile and exposures associated with findings |
| | Determine excretion/clearance of SYN-PKU-2002 in feces |
| GLP Status | GLP |
| Species, Strain | Mouse, CD1 |
| Test Article | SYN-PKU-2002 |
| Route/Number Doses | Oral (PO)/twice daily (BID, 6-8 hours between the doses) |
| Treatment Duration | 28 days |
| Recovery | 14 days |

| Study Design | Group | Dose/day (CFU)* | Numbers of Animals M | F |
|---|---|---|---|---|
| | 1 (Control) | 0 | 12 MS + 6 Rec | 12 MS + 6 Rec |
| | 2 | ~2 × $10^9$ CFU | 12 MS + 6 Rec | 12 MS + 6 Rec |
| | 3 | ~2 × $10^{10}$ CFU | 12 MS | 12 MS |
| | 4 | ~2 × $10^{11}$ CFU (maximum feasible dose) | 12 MS | 12 MS |

MS = main study; Rec = recovery
*draft doses estimated based on prior programs
CFU = colony forming units

| | |
|---|---|
| Mortality | All animals, 2X daily (AM, PM) |
| Clinical Observation | MS animals, 1X daily, detailed observations |
| Body Weight | All animals - pretest, weekly, and prior to necropsy (fasted) |
| Food Consumption | MS animals, weekly |
| Veterinary Exams | MS animals, standard assessments |
| Ophthalmology | All animals - pretest and prior to necropsy (Main study animals. Recovery animals if significant ophthalmic changes are noted at end-of-dosing. |
| Hematology/Serum Chemistry | MS animals - at least 3/sex/group for hematology |
| | MS animals - at least 3/sex/group for clinical chemistry |
| | Recovery - at least 3/sex/group for hematology |
| | Recovery - at least 3/sex/group for clinical chemistry |
| Urinalysis | Main study and recovery animals (Week 4 and Week 6) |
| Necropsy | Day 28 (Main study animals) and Day 42 (Recovery animals) |
| Fecal Excretion of SYN-PKU-2002 (non-GLP) | Fecal samples will be collected from all animals predose, Days 7, 14, 21, 28, and from recovery animals Days 30, 35 and 40 and SYN-PKU-2002 DNA will be quantified using a qPCR method (Taqman chemistry) that uses primers specific for SYN-PKU-2002 |
| Gross Necropsy/Organ Weights | All animals, standard organ list |
| Histopathology | All animals, standard tissue list, evaluate control and high dose animals, read down when findings are seen. |
| Toxicokinetics | A sample of blood will be collected on Day 28 just prior to necropsy and analyzed for the presence of SYN-PKU-2002 DNA using a qPCR method (Taqman chemistry) that uses primers specific for SYN-PKU-2002 |

24. Example 71 Assessment of Gastric Phenylpyruvate in a Pig Model

Levels of gastric phenylpyruvate in two pigs (which had a duodenal canula) at various times prior and post administration of SYN-PKU-2002.

Two days prior to administration of of SYN-PKU-2002, two pigs were put on liquid diet with protein shake/apple juice for 2 days. On day 0, pigs were anesthetized and intubated, and ~250 ml (~50 g) Peptone, 3×10e12 bacteria (SYN-PKU-2001 in 30 ml)+24 ml 1M bicarbonate flush (2 g) were instilled at T=0.

Figure 20:
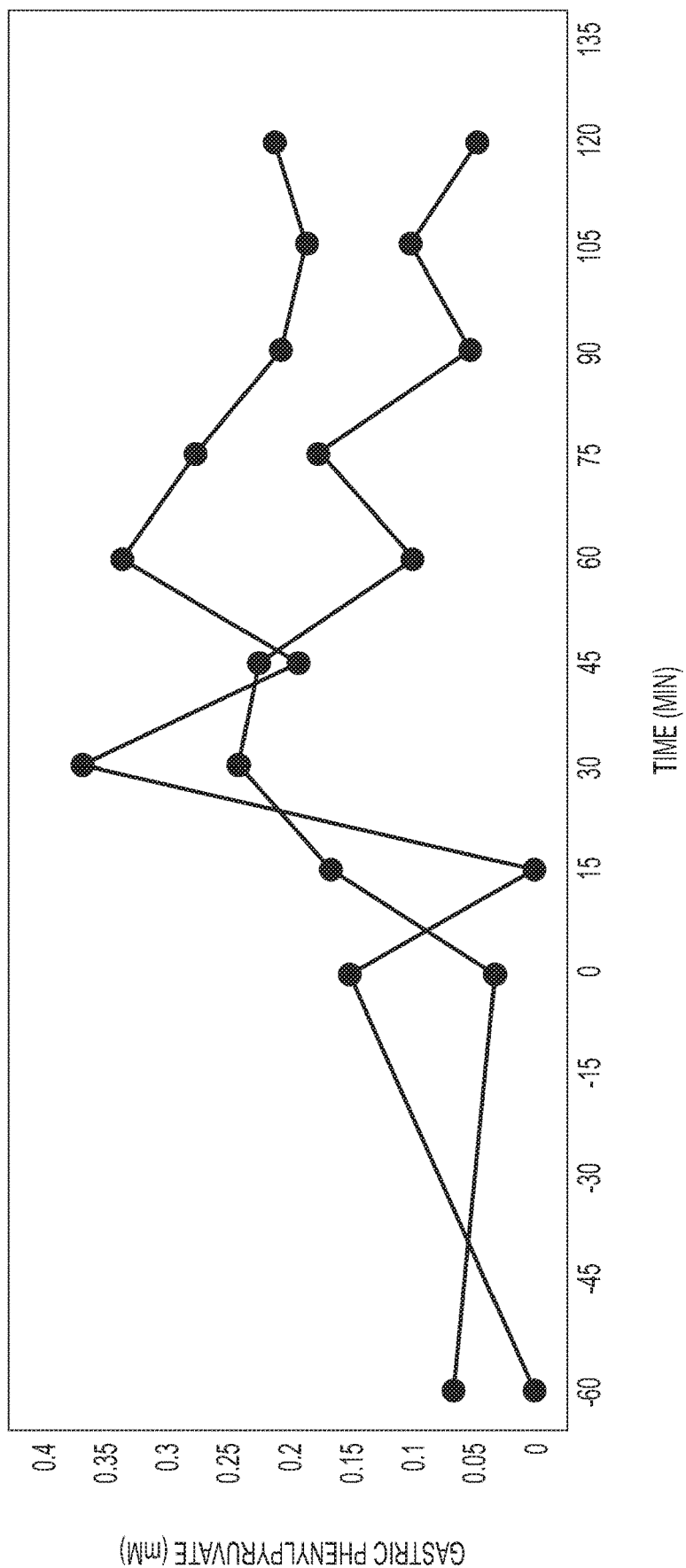
FIG. 20 depicts a graph showing measurements of gastric phenylpyruvate in two pigs at various times prior and post administration of SYN-PKU-2001.

Next, 1 ml gastric samples were taked at T=0, 15 min, 30 min, 45 min, 60 min, 75 min, 90 min, 105 min, 120 min. Samples were immediately spun down, the supernatant frozen and the tube with the pellet put at 4 C. Additionally, 1 ml blood samples were taken at T=0, 30 min, 60 min, 90 min, and 120 min, collected in heparinized tubes, spun, plasma collected and frozen. When possible, urine was collected and frozen. Results are shown in FIG. 20 and indicate that LAAD is active in the stomach.

Example 72. Conversion Efficiency of Oral Trans-Cinnamate to Urinary Hippurate in Non-Human Primates Studies of SYN-PKU-2002 activity and efficacy were next extended to fasted healthy non-human primates (NHPs), a translational model with more relevant metabolism and GI physiology to the human. A cohort of 6 Cynomolgus monkeys (2.5-4 kg) was used. Though not a PKU phenotype, healthy NHP physiology is helpful for informing future clinical studies that will likely initially be performed in healthy humans.

All NHP studies described herein were performed at Charles River Labs (Shrewsbury, MA) in compliance with all applicable sections of the Final Rules of the Animal Welfare Act regulations (Code of Federal Regulations, Title 9), the Public Health Service Policy on Humane Care and Use of Laboratory Animals from the Office of Laboratory Animal Welfare, and the Guide for the Care and Use of Laboratory Animals from the National Research Council. Six male NHP subjects aged 2 to 5 years were used (2.5-4 kg), and were maintained on International Certified Primate Chow (PMI nutrition, 5048). Subjects were fasted overnight (16 h) before initiation of all studies. For all studies, immediately prior to dosing, animals were separated into individual cages and an angled pan was inserted at the bottom of each cage to aid in the collection of urine. Orogastric tubes were used for all oral dosing.

Figure 21:
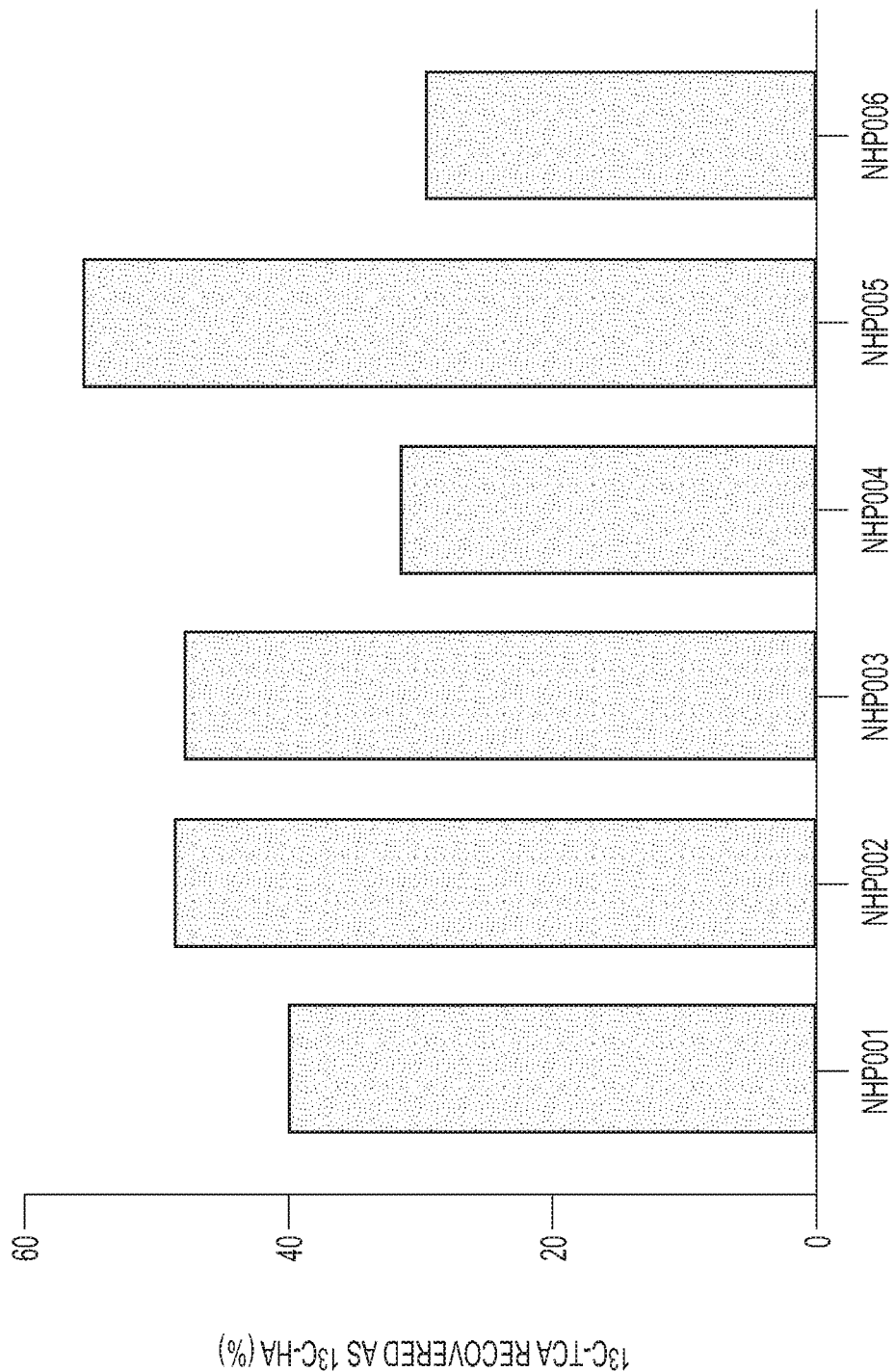
FIG. 21 depicts a graph showing conversion efficiency of oral trans-cinnamate to urinary hippurate in non-human primates. NHPs (n=6) were orally administered "C-trans-cinnamate ($^{13}$C-TCA) and urine was collected over 6 h. $^{13}$C-Hippurate ($^{13}$C-HA) was measured by mass spectroscopy. The percentage of urinary $^{13}$C-HA recovered as a function of $^{13}$C-TCA administered was calculated and used as a normalization factor for HA recovery in subsequent experiments. This factor accounts for TCA that is not converted to HA or that is lost to incomplete urinary collection, thus allowing a more accurate description of strain activity.

First, the conversion efficiency of orally administered TCA to urinary HA in monkeys was measured for calculation of a normalization factor to use in subsequent experiments. Each NHP was orally administered 10 mL of Peptone from meat (500 g/L; Sigma, 70174) and 15 mL of $^{13}$C-TCA (12.5 mg/mL; Cambridge Isotopes Lab, CLM-7498-PK) dissolved in 120 mM sodium bicarbonate, followed by a 2 mL water flush. In this manner, the in vivo PAL/Phe degradation activity of SYN-PKU could be inferred from urinary HA recovery. Isotopically labeled $^{13}$C-TCA was orally administered and urinary $^{13}$C-HA was measured. An average of 41.9±10.3% of the orally administered $^{13}$C-TCA was recovered as urinary $^{13}$C-HA (FIG. 21).

Example 73. Profiling and Efficacy in Non-Human Primates (NHPs)

Efficacy of SYN-PKU-2002 in a non-human primate model was assessed.

In all studies described herein animals were separated into individual cages and an angled pan was inserted at the bottom of each cage to aid in the collection of urine immediately prior to dosing. Orogastric tubes were used for all oral dosing.

NHPs were orally administered 10 mL of Peptone from meat (500 g/mL) or water as a mock. Next, NHPs were administered 10 mL of SYN-PKU-2002 resuspended in formulation buffer (previously grown in activated in a bioreactor and thawed on ice) or formulation buffer alone as a mock. Finally, NHPs were administered 5 mL of 0.36M sodium bicarbonate followed by a flush with 2 mL of water. Where applicable, 1 h post dosing regimen, animals were injected intravenously with 12.5 mL of $^{13}$C-Phe (20 mg/mL). Animals were bled at 0, 0.5, 1, 2, 4, and 6 h by venipuncture. Where applicable, animals were given 3.5 mL of $d_5$-Phe (20 mg/mL; CDN Isotopes, D-1589) following mock protein dose. At 6 h post dosing, the urine collection pan was removed and the contents poured into a graduated cylinder for volume measurement. All samples were stored at –80° C. until LC-MS/MS analysis.

Phe area under the curves (AUC) were calculated with the linear-trapezoidal method using R and the PKNCA package (Denny W, D. S., and Buckeridge C. Simple, automatic, noncompartmental analysis: The PKNCA R package. *J Pharmk PharmD* 42.1, 11-107, doi:10.1007/s10928-015-9432-2 (2015)), and models to describe the AUCs were estimated with the rstanarm package. AUCO-last for $d_5$-Phe were calculated with the linear-up/log-down method. Mean and credible intervals for labeled Phe AUC and the treatment difference were calculated using a hierarchical Bayesian model with a fixed effect for treatment (vehicle or cells) and a random effect per animal.

For growth and induction of strains in bioreactors, a sterile loop was used to inoculate cells in 50 mL of FM2 medium (Supplementary Table 2) in a 500 mL Ultra-Yield™ flask (Thomson). Cells were grown at 37° C. with shaking at 350 rpm until an OD$_{600}$ of ~5 was reached, at which point 30 mL of the culture was used to inoculate 4 L of FM2 in an Eppendorf BioFlow 115 bioreactor (starting OD$_{600}$ of ~0.02). The fermenter was controlled at 60% dissolved oxygen with agitation, air, and oxygen supplementation, and controlled to pH 7 using ammonium hydroxide. At OD$_{600}$ of ~1.5, cells were activated by creation of a low oxygen environment (10% dissolved oxygen), and the addition of IPTG (1 mM). At OD$_{600}$ of ~20, L-arabinose (0.15% final concentration) was added and the cells were grown for an additional hour. Cells were harvested by centrifugation at 4,500×G for 30 min at 4° C., resuspended in formulation buffer, and stored at –80° C. until the day of testing.

Figure 22D:
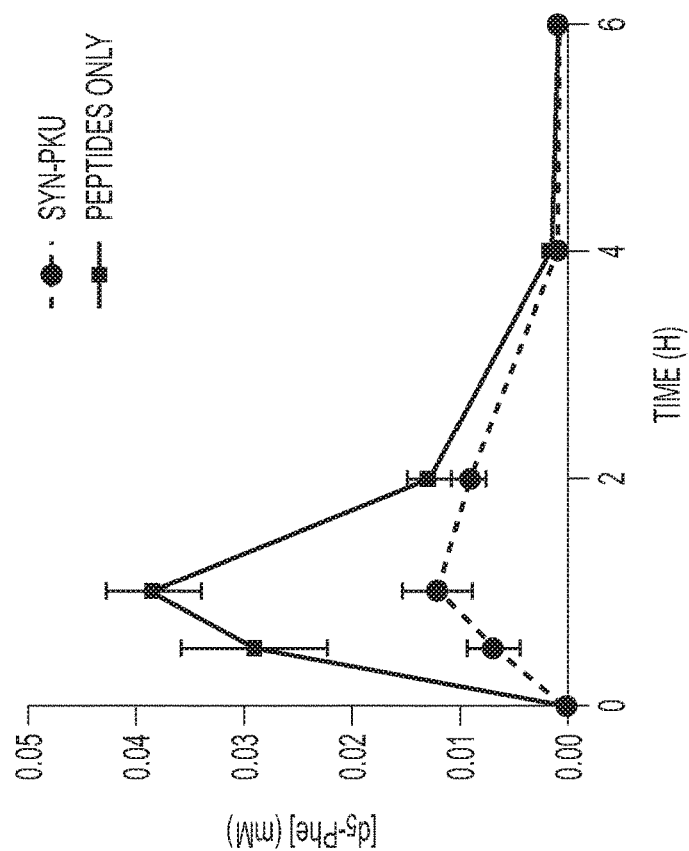
FIGS. 22A, B, C, D, and E depict graphs showing profiling and efficacy in non-human primates (NHPs).
In FIG. 22C, fasted NHPs were administered an oral dose of $d_5$-phenylalanine ($d_5$-Phe) with or without administration of SYN-PKU-2002. The dashed line represents the quantity of $d_5$-Phe administered. $d_5$-hippurate ($d_5$-HA) was only found in animals that received SYN-PKU-2002 (striped bar). Data is representative of the average normalized $d_5$-HA recovery±standard deviation (n=6). Serum $d_5$-Phe was measured in NHPs that received SYN-PKU-2002 (light grey line) or mock administration (dark gray line) (FIG. 22D). Data represent the average $d_5$-Phe concentration±standard deviation (n=6) In FIG. 22E, NHPs received a $d_5$-Phe alone or with $5 \times 10^{11}$ cells of SYN-PKU-2002. Blood was collected over 6 h and areas under the curve for serum $d_5$-Phe were calculated. Data show AUCs plus and minus the upper and lower bounds of the 90% credible level respectively.

First, fasted monkeys were administered a 5 g peptide challenge with and without SYN-PKU-2002 administration and urinary HA was measured. All animals showed a significant HA response when treated with SYN-PKU-2002 compared to baseline levels without cell administration (FIG. 22A, left). Interestingly, significant HA was recovered in fasted monkeys that did not receive a peptide challenge (FIG. 22A, right), suggesting that, the primate GI tract may be a reservoir for Phe. In both preceding experiments (FIG. 22A), to examine the process of enterorecirculation in monkeys, subjects that received SYN-PKU-2002 were also injected with $^{13}$C-Phe intravenously 1 h following peptide challenge and $^{13}$C-HA was measured in urine (FIG. 22B). No $^{13}$C-HA was detected in the group that did not receive peptide, however, $^{13}$C-HA was detected in the group administered a peptide challenge, demonstrating that enterorecirculation occurs in primates, is associated with protein intake, and can provide Phe that can be consumed by SYN-PKU-2002.

Figure 22C:
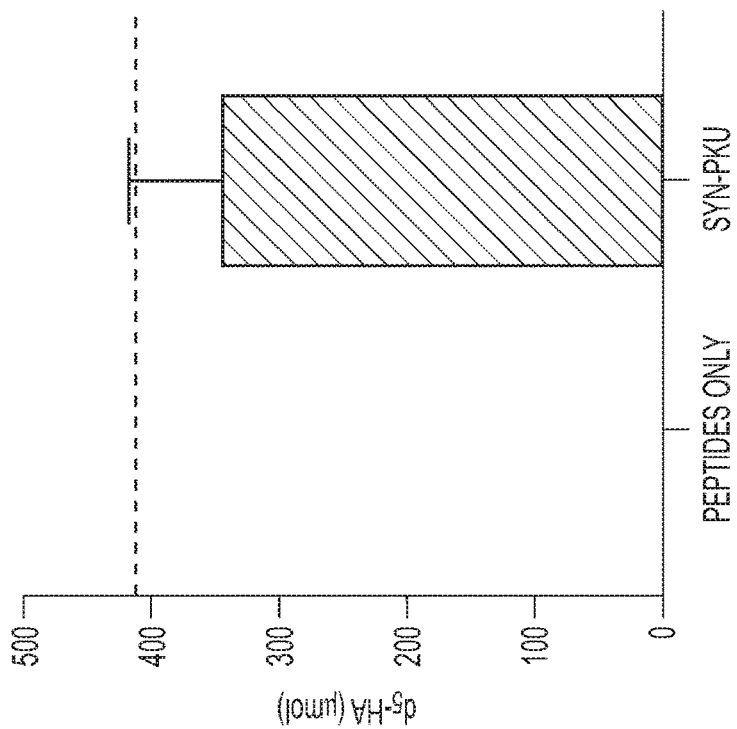
Figure 22E:
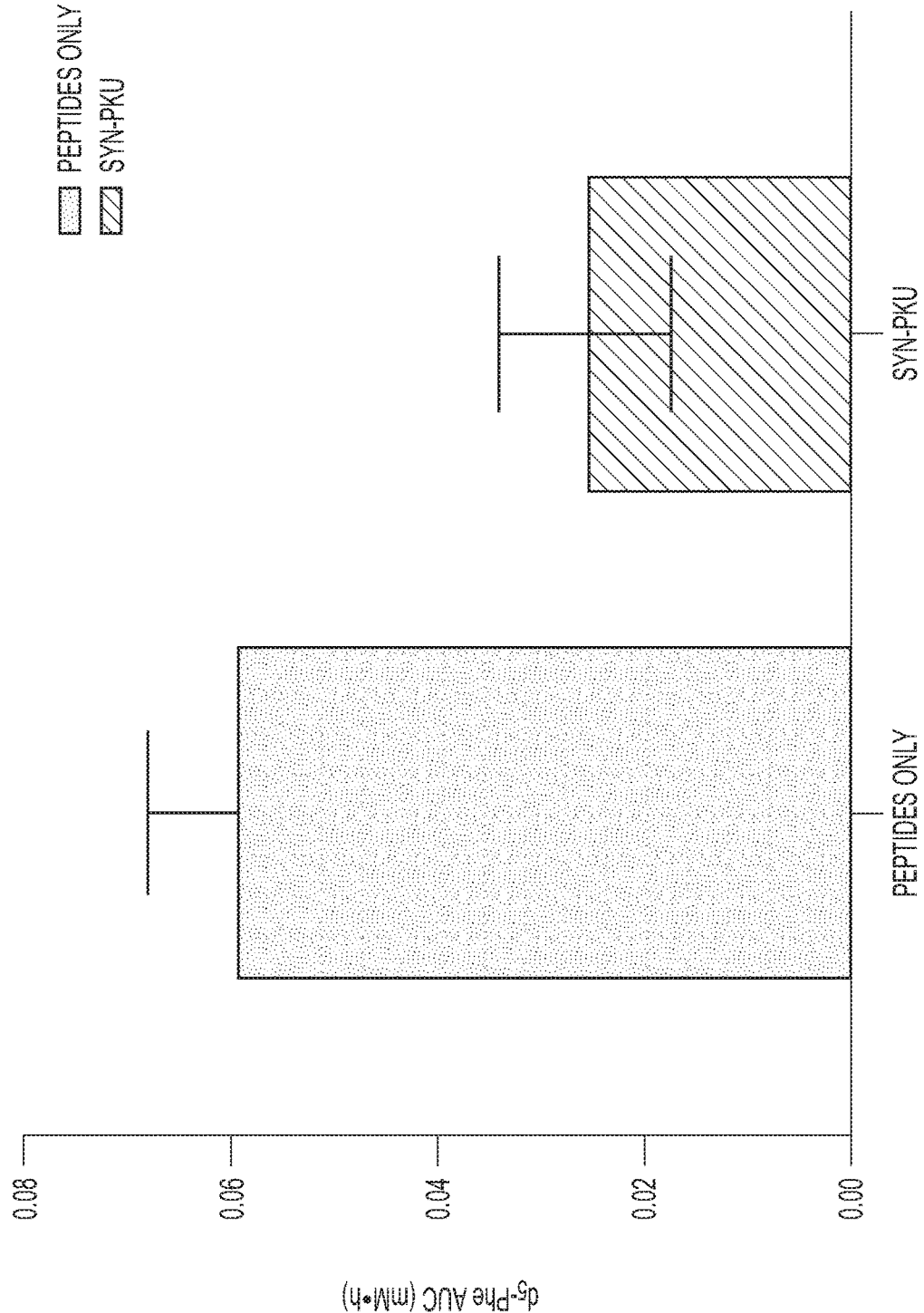
Figure 23A:
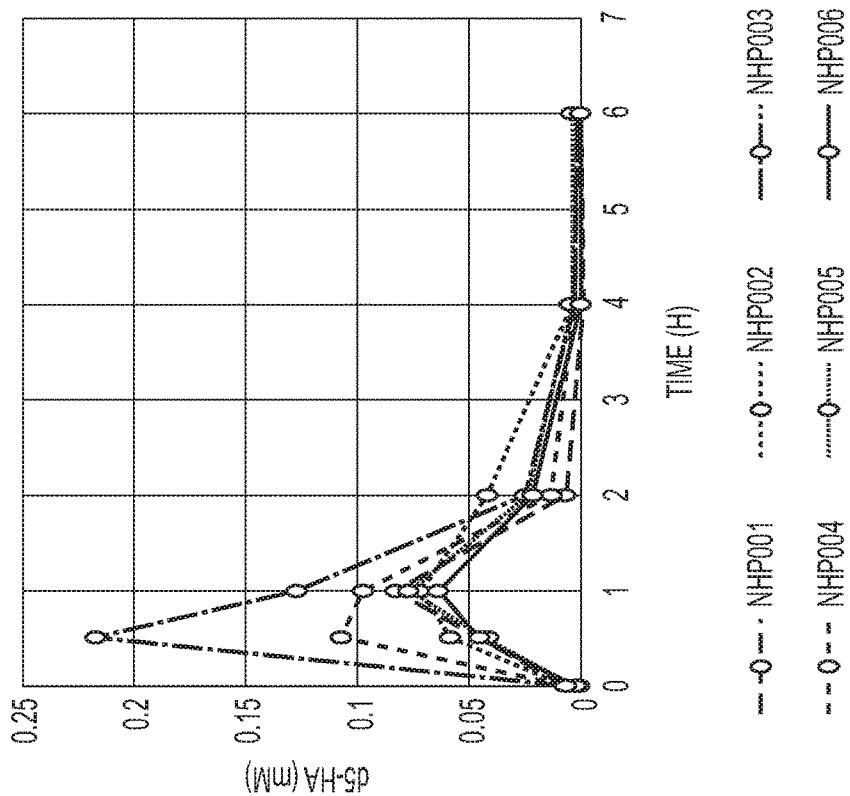
FIG. 23A and FIG. 23B depict graphs showing SYN-PKU-2002 specific metabolite detection in serum of non-human primates. Using LC-MS/MS, serum concentrations of d5-HA (FIG. 23A) and d5-TCA (FIG. 23B) were determined in non-human primates administered d5-Phe and SYN-PKU-2002 orally. No detectable d5-HA or d5-TCA was detected when d5-Phe was administered in the absence of SYN-PKU-2002 (data not shown). The presence of these metabolites demonstrates SYN-PKU-2002-specific activity in these animals.
Figure 23B:
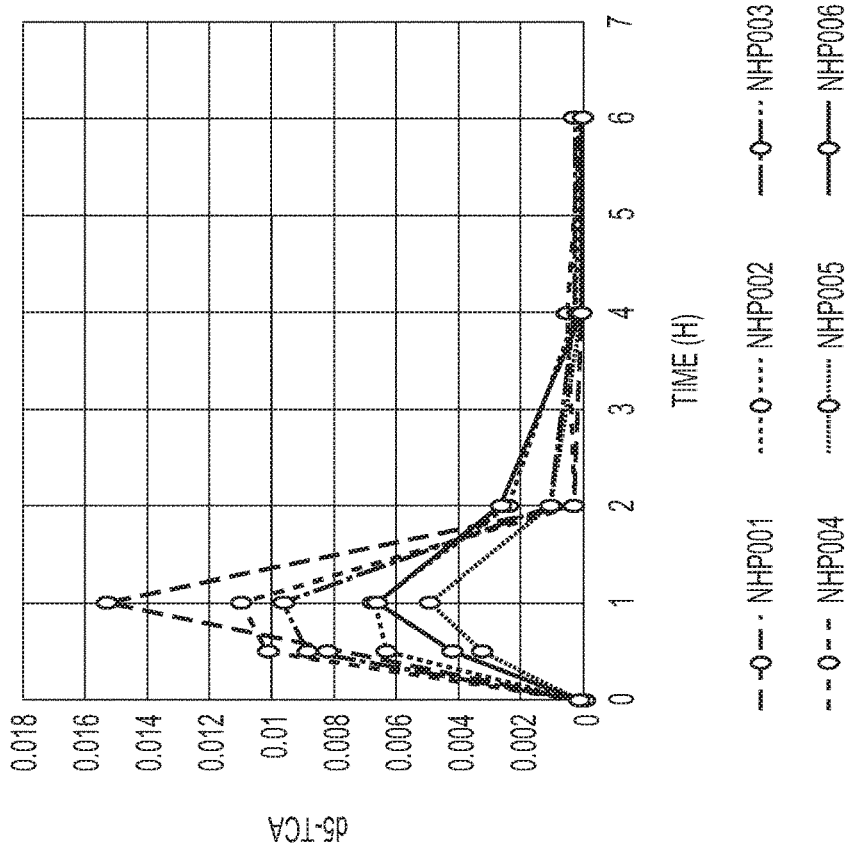

In the definitive study, the ability of SYN-PKU-2002 to lower serum Phe in monkeys was determined. However, this is difficult in healthy subjects (non-PKU), as high concentrations of protein are required to even slightly elevate serum Phe levels (by body mass, the 5 g peptide challenge used in monkeys equates to ~100 g challenge in an average adult male). Baseline Phe levels and its low dynamic response in serum post peptide challenge due to a functional PAH enzyme obfuscates detection of serum Phe lowering by SYN-PKU-2002. For these reasons, an oral deuterated Phe ($d_5$-Phe) challenge was performed. The quantity of $d_5$-Phe administered (70 mg) equated by body mass to the Phe contained in ~30 g protein for an average adult human male, consistent with an amount that may be present in a typical meal (Layman, D. K. Dietary Guidelines should reflect new understandings about adult protein needs. *Nutr Metab* (*Lund*) 6, 12, doi:10.1186/1743-7075-6-12 (2009)). As expected, baseline $d_5$-Phe was undetectable in urine and serum but could be detected in blood following its administration (FIGS. 22C and D). Following SYN-PKU-2002 administration, normalized $d_5$-HA recovery in the urine demonstrate that the majority of the $d_5$-Phe administered was metabolized to $d_5$-HA (FIG. 22C). SYN-PKU-2002-specific metabolites $d_5$-HA and $d_5$-TCA were also detected in serum (FIGS. 23A and B). Most importantly, an increase in serum $d_5$-Phe was remarkably blunted upon SYN-PKU administration (FIG. 22B), concomitant with a highly significant decrease in the AUC of serum $d_5$-Phe (FIG. 22C; 58% decrease with a 90% credible level between 29.4 and 57.8%).

High resting Phe levels in the GI tract of monkeys can also be inferred from the significant HA recovery observed in fasted animals that received SYN-PKU-2002 but no peptide challenge. Enterorecirculation was also shown to exist in monkeys, though difficulty working in a non-PKU background and inability to sample intestinal effluents easily in these animals indicates that more work must be performed to understand the mechanistic basis of this process. Regardless, maintenance of a reservoir of substrate may increase the therapeutic utility of SYN-PKU-2002, and impose less constraints on the timing of therapeutic administration with meals in PKU patients.

Example 74. Assessment of LAAD in Expression of Phe in Non-Human Primates

Efficacy of of LAAD expression and determination of any negative effects on PAL metabolism of Phe was assessed.

Figures 24A, 24B:
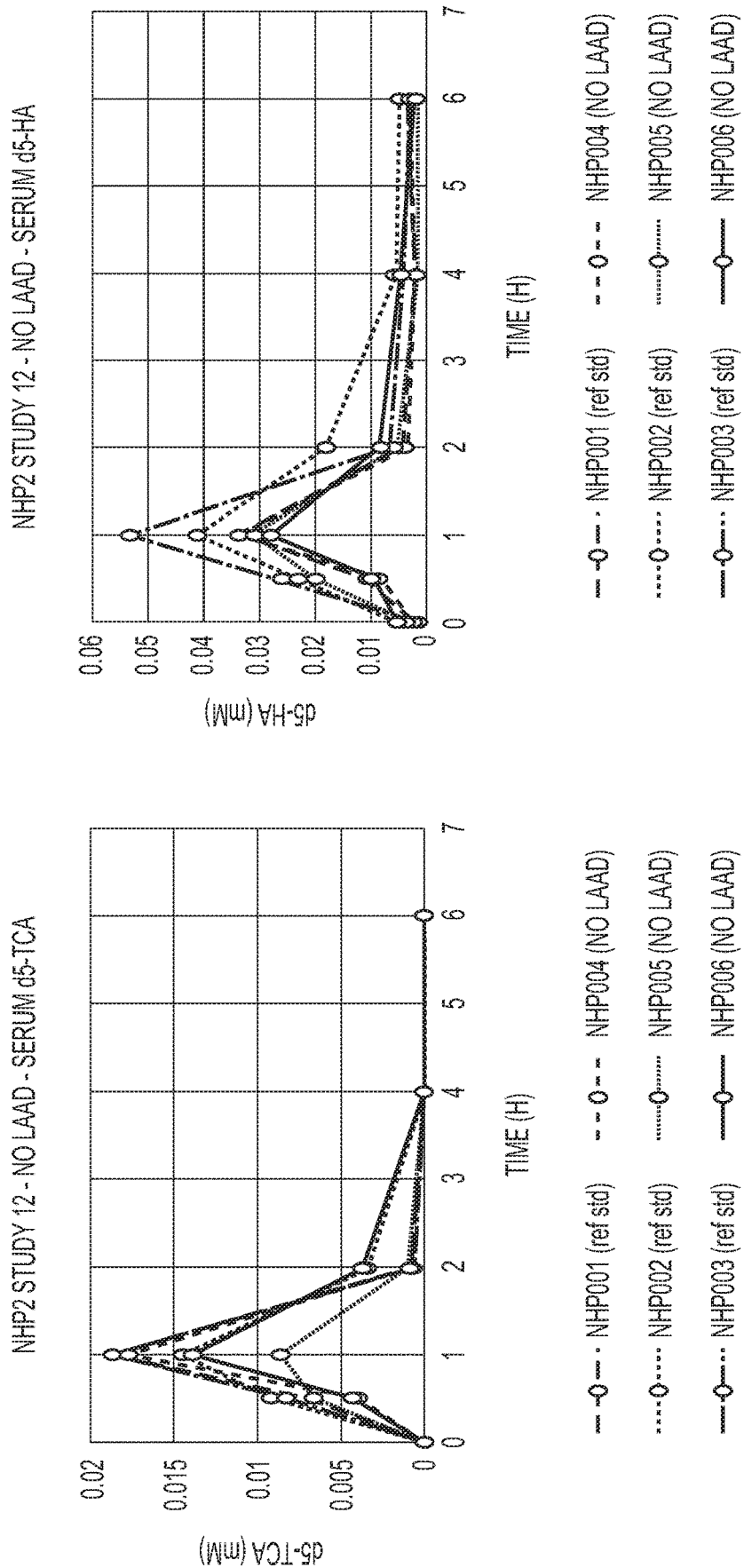
FIG. 24A and FIG. 24B depict the conversion of trans-cinnamate to urinary hippurate in NHPs.

At T=0, the urine pan was emptied, and Non-Human Primates (NHPs) were orally administered 5.5 g of Peptone from meat in 11 mL, and 10 mL of an oral gavage bacteria. A SYN-PKU-2001 ($5 \times 10^{11}$ CFU) oral gavage bacteria strain was administered to NHP's 1-3. A SYN-PKU-2001 ($5 \times 10^{11}$ CFU) without LAAD was administered to NHP's 4-6. Both strains were suspended in formulation buffer (previously grown in activated in a bioreactor and thawed on ice) or formulation buffer alone as a mock. Concurrently, NHP's 1-10 were all administered 5 mL of 0.36M sodium bicarbonate followed by a flush with 5 mL of water Animals were bled at 0, 0.5, 1, 2, 4, and 6 h by venipuncture. At 6 h post dosing, the urine collection pan was removed and the contents poured into a graduated cylinder for volume measurement of 5 mL. Results are shown in FIG. 24A and FIG. 24B confirm that expression of LAAD did not have a negative effect on PAL metabolism of Phe.

Example 75. Oral Tracer Studies with Non-Human Primates (NHPs)

Figure 25:
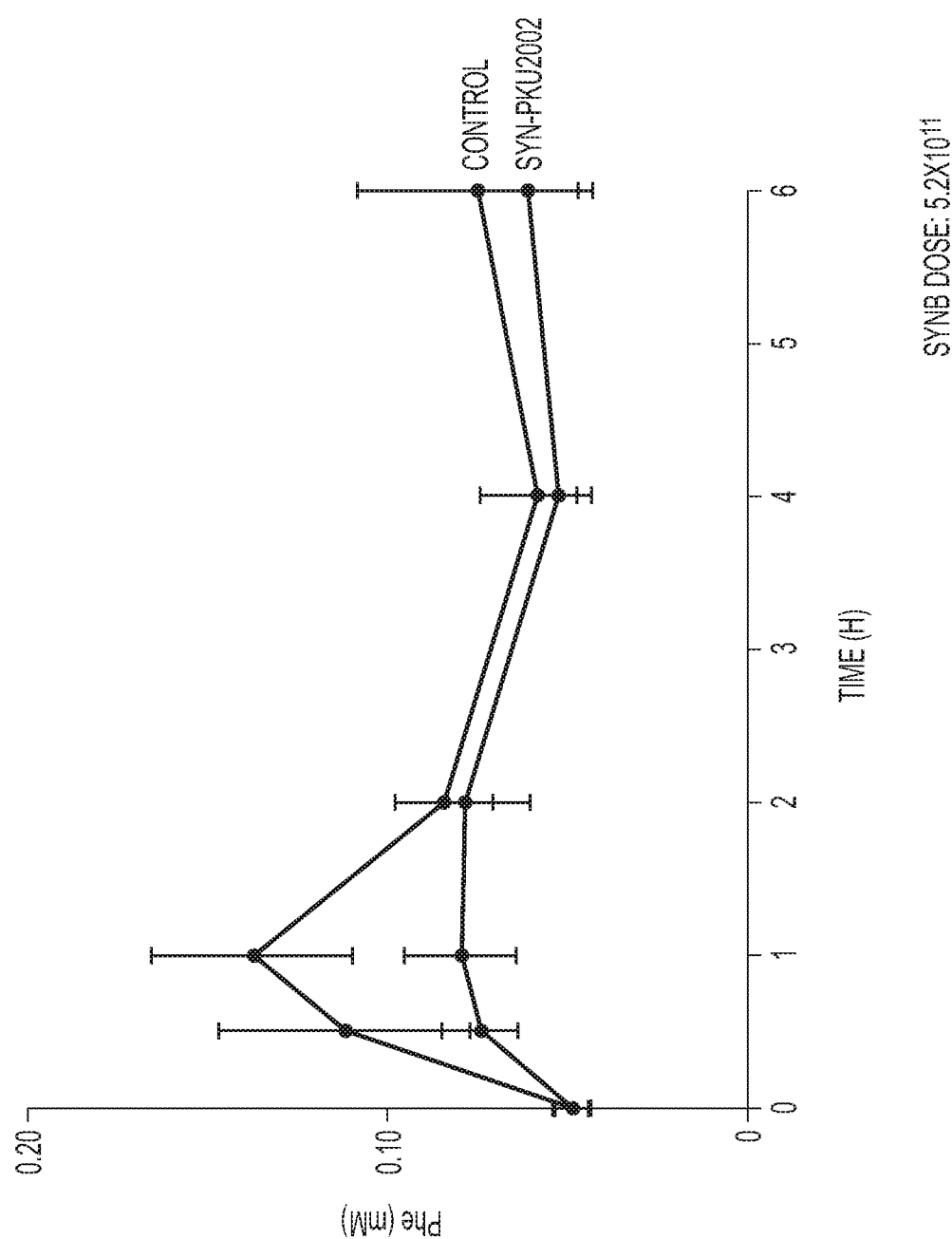
FIG. 25 depicts a graph showing that SYN-PKU-2002 metabolizes Phe when administered orally in healthy non-human primates (NHPs). Gavage with SYN-PKU-2002 reduces the spike in blood phe levels observed upon administration of protein challenge together with radio-labelled Phe.

Oral Tracer studies were conducted to further characterize activity. At T=0, the urine pan was emptied, and NHPs were administered an oral gavage of 5.5 g of Peptone from meat in 11 mL, 4 mL D5-phenylalanine (20 mg/mL), and 10 mL of bacteria ($5.2 \times 10^{11}$ CFU SYN-PKU-2001). Concurrently, NHP's 1-10 were all administered 5 mL of 0.36M sodium bicarbonate followed by a flush with 2 mL of water. Animals were bled at 0, 0.5, 1, 2, 4, and 6 h post dosing, the urine collection pan was removed and the contents poured into a graduated cylinder for volume measurement of 5 mL. FIG. 25 shows the large spike in blood Phe levels upon administration.

For the oral tracer study control, at T=0, the urine pan was emptied, and NHPs were administered an oral gavage of 5.5 g of Peptone from meat in 11 mL, 4 mL D5-phenylalanine (20 mg/mL), and 10 mL formulation buffer. Concurrently, all NHP's were administered 5 mL of 0.36M sodium bicarbonate followed by a flush with 2 mL of water. Animals were bled at 0, 0.5, 1, 2, 4, and 6 h post dosing, the urine collection pan was removed and the contents poured into a graduated cylinder for volume measurement of 5 mL.

Results in FIG. 25 show administration of the oral gavage with the SYN-PKU-2002 effectively metabolizes Phe and reduces the spike in blood Phe levels observed in the control dosage.

Example 76. Dose Dependent Responses of SYN-PKU-2002

Four studies confirmed successful dose dependent conversions of Phe and production of plasma biomarkers t-cinnamic acid (TCA) and hippuric acid (HA) in non-human primates (NHPs) after single dose administration of SYN-PKU-2002 after a protein rich meal.

Study 1: At T=0, the urine pan was emptied, and ten NHPs were orally administered 5.5 g of peptone from meat in 11 mL of water. NHP's 1-5 were administered an oral gavage of 4 ml of SYN-PKU-2002 ($3.6 \times 10^{11}$ CFU). NHPs 6-10 were administered an oral gavage of 4 mL formulation buffer, 2 mL of SYN-PKU-2002 ($1.8 \times 10^{11}$ CFU) followed by an oral gavage of 6 mL of formulation buffer. Concurrently, NHP's 1-10 were all administered 5 mL of 0.36M sodium bicarbonate followed by a flush with 5 mL of water. Animals were bled at 0, 0.5, 1, 2, 4, and 6 h by venipuncture. At 6 h post dosing, the urine collection pan was removed and the contents poured into a graduated cylinder for volume measurement of 5 mL.

Study 2: Ten NHP's were orally administered 5.5 g of Peptone from meat in 11 mL. NHP's 1-5 were gavaged with 8 ml of SYN-PKU-2002 ($7.2 \times 10^{11}$ CFU) bacteria strain. NHP's 6-10 were gavaged with 1 mL of SYN-PKU-2002 ($9.0 \times 10^{10}$ CFU) followed 7 mL of formulation buffer. Concurrently, NHP's 1-10 were all administered 5 mL of 0.36M sodium bicarbonate followed by a flush with water. Animals were bled at 0, 0.5, 1, 2, 4, and 6 h by venipuncture. At 6 h post dosing, the urine collection pan was removed, and the contents poured into a graduated cylinder for volume measurement of 5 mL.

Study 3: Ten NHP's were orally administered 5.5 g of Peptone from meat in 11 mL. NHP's 1-5 were gavaged with 8 ml of SYN-PKU-2002 diluted in formulation buffer ($2.3 \times 10^{10}$ CFU). NHP's 6-10 were gavaged with 8 mL of diluted SYN-PKU-2002 diluted in formulation buffer ($4.5 \times 10^{10}$ CFU). Concurrently, NHP's 1-10 were all administered 5 mL of 0.36M sodium bicarbonate followed by a flush with 5 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. NHP's 1-10 all fasted the previous night.

Study 4: Ten NHP's were orally administered 5.5 g of Peptone from meat in 11 mL. NHP's 1-5 were gavaged with 8 ml of diluted SYN-PKU-2002 ($3.3 \times 10^9$ CFU). NHP's 6-10 were gavaged with 8 mL of diluted SYN-PKU-2002 ($1.1 \times 10^{10}$ CFU). Concurrently, NHP's 1-10 were all administered 5 mL of 0.36M sodium bicarbonate followed by a flush with 5 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. NHP's 1-10 all fasted the previous night.

Results shown in FIGS. 117A, 117B, 117C, and 117D show that Phe metabolism was evident at doses of $9 \times 10^{10}$ CFU and higher. Additionally, dose-dependent conversion of Phe and production of biomarkers TCA and hippuric acid were observed.

Example 77. Casein Study in Non-Human Primates with SYN-PKU-2002

Efficacy of replacing peptones (composed of small peptides) with casein (a whole protein) for expressing Phe, TCA, and HA consumption was evaluated.

At T=0, urine pans were emptied, and NHPs were administered an oral gavage of 28 mL of casein (4.5 g)/biocarbonate/D5-phenylalanine (25 mg; 8 mg/kg). NHPs 1-5 were further administered an oral gavage of 3.5 mL SYN-PKU-2002 ($5 \times 10^{11}$ CFU), and NHPs 6-10 were administered 3.5 mL formulation buffer via oral gavage. Concurrently, the NHPs were administered a flush with 2 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. Results are shown in FIGS. 118A-118C.

The results from this study demonstrate that the genetically engineered bacterial strains of the disclosure can consume Phe that is naturally digested and can prevent a spike in blood Phe observed in the control upon D5-Phe consumption.

Example 78. Phe Metabolism is Clinically Relevant

The disclosed studies in non-human primates demonstrate the relevancy of Phe metabolism and the profound effect it could have on the diet of patients with PKU. The Institute of Medicine has established dietary reference intakes that establish a phenylalanine is assumed to be 80-90 mg/g whole protein. The recommended intake of protein for a human is 50 g (for a 2000 calorie diet). An unrestricted American diet provides approximately 100 g of whole protein (males) and 70 g (female) on average. An unrestricted diet will therefore provide approximately 6-9 g of phenylalanine.

The recommended phenylalanine consumption for patients with PKU >4 years of age is 200-1100 mg (Vockley, et al. 2014, the entire contents of which are incorporated herein by reference), or about <10 g protein/day. Based on the studies above, the highest dosage of SYN-PKU-2002 can be extrapolated (assuming 35% recovery of urinary HA in NHP's) to three $5 \times 10^{11}$ doses per day in patients. Said dosage predicts the daily metabolism of Phe to support a ~25 g of dietary protein intake in humans (25 mg/kg=1.7 g for a 70 kg person). Therefore, the dose of Phe is about 25% of the Phe intake that a PKU patient following an unrestricted diet would receive in 24 hours (FIG. 28). This is ~50% of the daily recommended protein intake (see US RDA; assuming an unrestricted American diet provides on average approximately 100 g (males) and 70 g (females) of whole protein). For PKU patients, this results an a 2.5-fold increase in protein uptake, a result which would liberate the diet and lifestyle of PKU patients.

In some embodiments, upon treatment with the bacteria of the disclosure, PKU patients may increase their dietary protein intake per day to greater than 10 g; from about 10 g to about 30 g, from about 10 g to about 25 g, from about 10 g to about 20 g, from about 10 g to about 15 g. In some embodiments, upon treatment with the bacteria of the disclosure, PKU patients may increase their dietary protein intake per day to about 15 g, about 20 g, or about 25 g.

In some embodiments, upon treatment with the genetically engineered bacteria of the disclosure, PKU patients may increase their daily protein intake by about 2.5 fold. In some embodiments, upon treatment with the genetically engineered bacteria, PKU patients may increase their daily protein intake by about 2.0 fold. In some embodiments, upon treatment with the genetically engineered bacteria, PKU patients may increase their daily protein intake by about 1.5 fold In some embodiments, upon treatment with the genetically engineered bacteria, PKU patients may increase their daily protein intake by about 1.0 fold. In some embodiments, upon treatment with the genetically engineered bacteria, PKU patients may increase their daily protein intake by about 3 fold, 3.5 fold or 4 fold. In some embodiments, upon treatment with the genetically engineered bacteria, PKU patients may increase their daily protein intake by about 50%. In some embodiments, upon treatment with the genetically engineered bacteria, PKU patients may increase their daily protein intake by about 5% to 10%, 10% to 20%, 20% to 30%, 30% to 40%, 40% to 50%, 50% to 60%, 60% to 70%, 70% to 80%, 80% to 90%, 90% to 100%. In some embodiments, upon treatment with the genetically engineered bacteria, PKU patients may increase their daily protein intake by about 5%, 10%, 20%, 30%, 40%, 50%, 60%, 70%, 80%, and 90% to 100%.

Example 79: Characterization of the Growth of SYN766, an *Escherichia coli* Nissle 1917 DAP Auxotroph in Varying Concentrations of Diaminopimelate To determine the minimum amount of DAP required for bacterial growth and division, the growth of SYN766, an EcN DAP auxotroph, was characterized by incubation in a range of DAP concentrations.

All bacterial cultures were started from glycerol stocks stored at −65° C. Bacteria were grown in 14 mL culture tubes overnight with shaking at 250 rpm at 37° C. in LB broth supplemented with DAP at 100 µg/mL. Overnight cultures were then diluted 1:100 in wells of 96-well plates containing 100 µL of LB with various DAP concentrations.

In all experiments, the 96-well plates were sealed with parafilm and analyzed on a Synergy™ Neo Microplate Reader (BioTek Instruments, Inc., Winooski, Vt.). The plate was incubated at 37° C. with shaking for 960 minutes, and the OD600 was measured every 10 minutes.

The data were collected in Gen5™ software version 2.06 (BioTek Instruments, Inc., Winooski, Vt.), exported to Microsoft® Excel to calculate the mean and standard error, and processed in GraphPad Prism version 7.03 (GraphPad Software, Inc., San Diego, Calif.).

Figure 32:
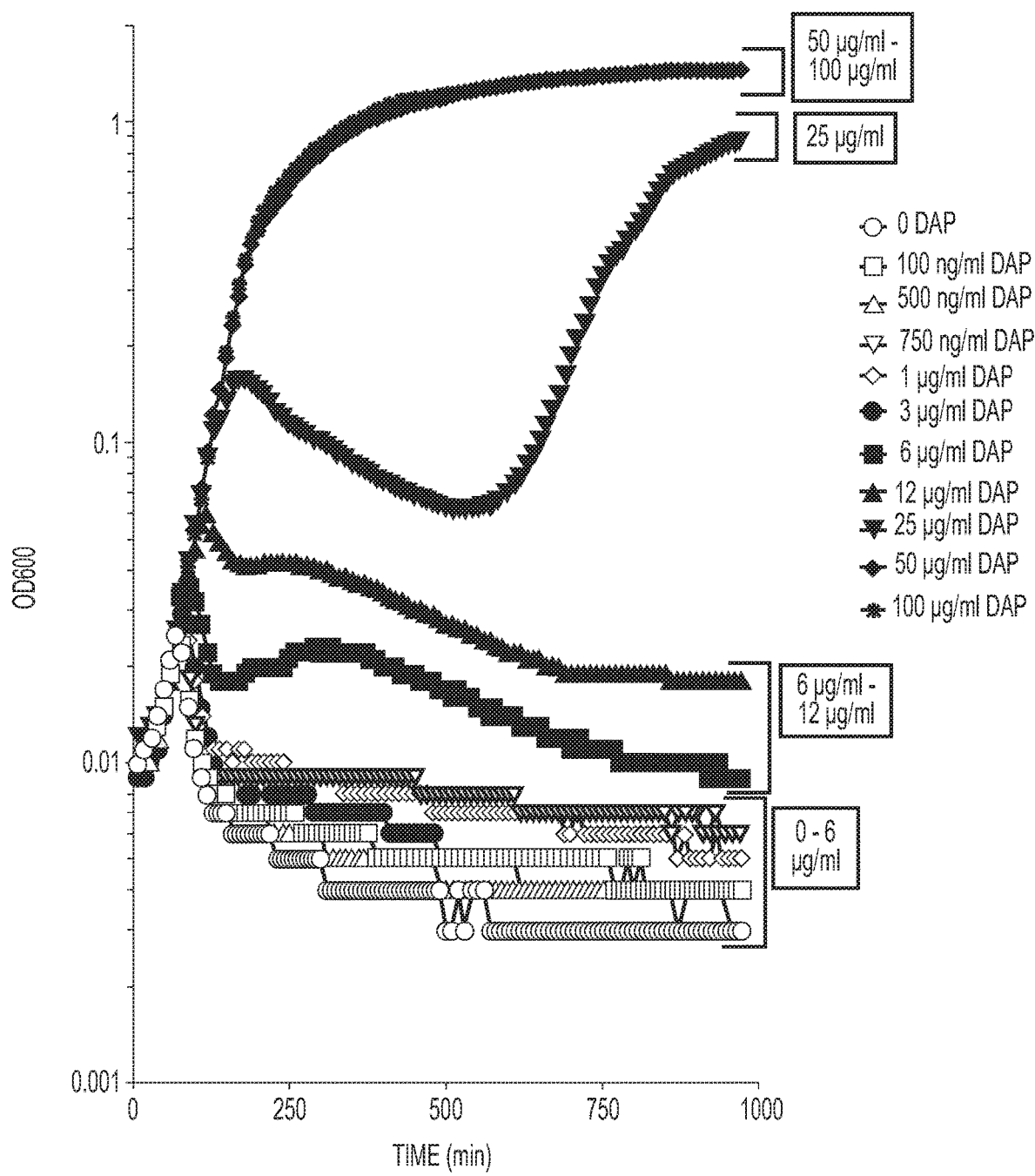
FIG. 32 depicts a graph showing the growth characteristics of SYN766, a diaminopimelate auxotroph in various concentrations of diaminopimelate. SYN766 (E. coli Nissle 1917, ΔdapA) was incubated in growth media which contained decreasing concentrations of DAP at 37° C. for 960 minutes under constant shaking. The OD600 was measured every 10 minutes in order to assess cell growth over time. The average of three biological replicates is plotted for each time point.

SYN766, a DAP auxotroph strain of EcN, was analyzed to determine the concentration of DAP required for growth; the data are displayed in FIG. 32. In liquid media with DAP at concentrations of 50 µg/mL and 100 µg/mL, SYN766 grew exponentially for 350 minutes before entering stationary phase at an OD600 of approximately 1. At a DAP concentration of 25 µg/mL, cells grew for 200 min, reaching an OD600 of 0.15 before declining Growth resumed after 600 min and reached a final OD600 of approximately 0.8, which was significantly less total cell mass than when the DAP concentration was at least 50 µg/mL. At 6 µg/mL and 12 µg/mL DAP, SYN766 grew exponentially for approximately 180 minutes before displaying a declining OD600 for the remainder of the experiment. When DAP concentrations were below 6 µg/mL, SYN766 showed growth for approximately 100 min before displaying a declining $OD_{600}$ for the remainder of the experiment.

Figure 33:
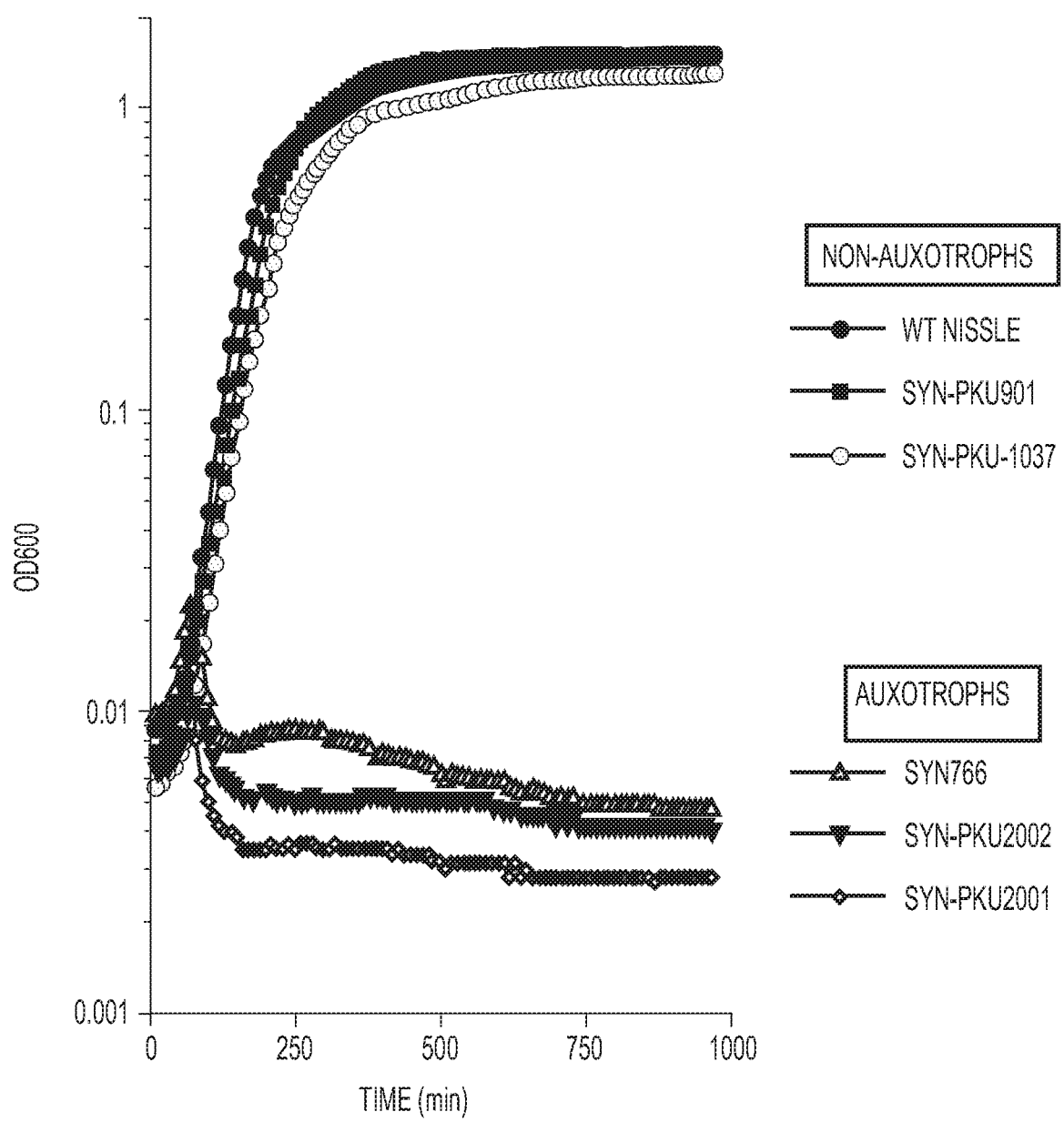
FIG. 33 depicts a graph showing the growth characteristics of various strains of E. coli Nissle in LB growth media without diaminopimelate. To characterize the growth characteristics of various modified strains of EcN in absence of DAP, cultures were incubated in LB that did not contain DAP at 37° C. for 960 minutes under constant shaking. The OD600 was measured every 10 minutes to assess cell growth over time. The average of three biological replicates and two technical replicates is plotted for each time point.

Example 80: Characterization of the Growth of Various Strains of *Escherichia coli* Nissle 1917 in LB Growth Media Without Diaminopimelate Various modified strains of EcN were grown in media without DAP to confirm the growth characteristics of DAP auxotrophs and prototrophs. Similar growth conditions were used to those described in Example 79. Various strains of EcN that have been modified to consume phenylalanine were analyzed for their ability to grow in the absence and presence of DAP. Results are shown in FIG. 33. The non-auxotrophic strains, SYN001, SYN-PKU901 and SYN3282, grew exponentially for approximately 400 minutes before entering stationary phase at an OD600 of approximately 1.2. Under similar conditions, the DAP auxotroph strains, SYN766, SYN-PKU-2001, and SYN-PKU-2002, stayed within the inoculation OD600 of approximately 0.010 for the first 90 min before starting to show a decline, concluding the experiment at an OD600 of approximately 0.005. This shows that the deletion of dapA results in a cessation of growth in the absence of an external source of DAP. The presence of genes involved in Phe degradation in SYN3282 had no effect on growth compared to wild type strains. The combination of DAP auxotrophy with genes involved in Phe degradation in SYN-PKU-2001 and SYN-PKU-2002 had no effect on the growth impairment observed with DAP auxotrophy alone (SYN766). These results show that DAP auxotrophy is the main factor regulating growth and survival of these engineered strains.

Figure 34:
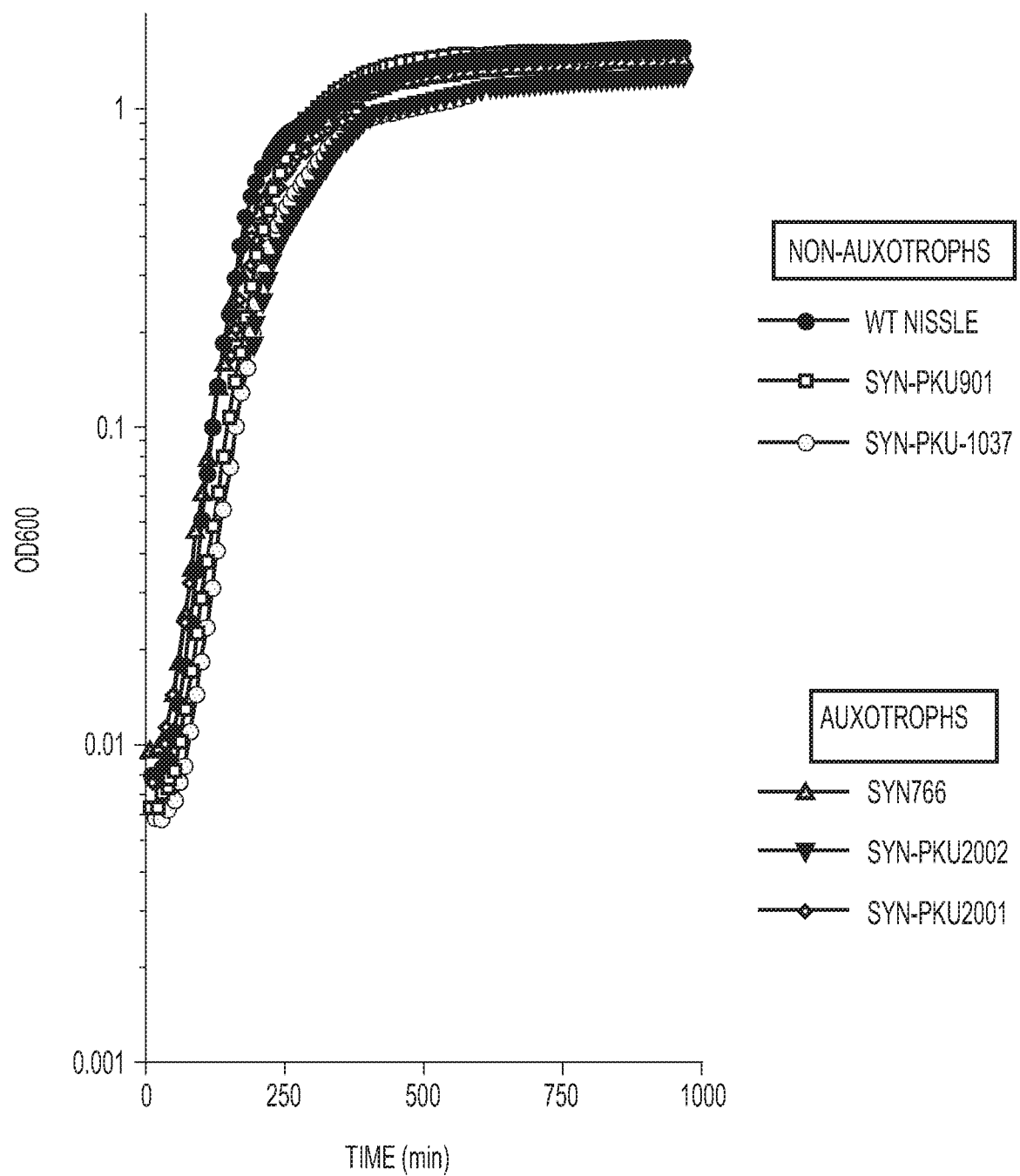
FIG. 34 depicts a graph showing the growth characteristics of various strains of EcN in LB growth media with 100 µg/mL diaminopimelate. To characterize the growth characteristics of various modified strains of EcN in the presence of DAP, they were incubated in growth media with 100 µg/mL DAP, at 37° C. for 960 minutes, constantly shaking. The OD600 was measured every 10 minutes to assess cell growth over time. The average of three biological replicates is plotted for each time point.

Example 81: Characterization of the Growth of Various Strains of *Escherichia coli* Nissle 1917 in LB Growth Media with 100 µg/mL Diaminopimelate Various modified strains of EcN were grown in media with 100 µg/mL DAP, using identical growth conditions to those described in Example 79. In contrast to the results in example 80, when grown in LB supplemented with 100 µg/mL DAP, all of the tested strains of EcN exhibited comparable growth (see FIG. 34). The non-auxotrophic strains SYN001, SYN-PKU901 and SYN3282 and the auxotrophic strains SYN766, SYN-PKU-2001 and SYN-PKU-2002 grew exponentially for approximately 400 minutes before entering stationary phase at an OD600 of approximately 1.4.

Example 82: Fecal Excretion and Clearance of Engineered *Escherichia coli* Nissle 1917 in C57BL/6 Mice Following Oral Administration The major objective of this experiment was to determine the kinetics of fecal excretion of strains containing DAP auxotrophy and/or the Phe-degradation activity compared to wild type EcN. EcN strains utilized for this study included wild type (SYN-PKU901), a DAP auxotroph (SYN766), a strain genetically engineered to encode Phe-degrading activity (SYN3282), and a strain with both DAP auxotropy and Phe-degrading activity (SYN-PKU-2001). SYN-PKU-2001 is a surrogate for the clinical candidate strain SYN-PKU-2002, but contains a chloramphenicol resistance cassette that allows it to be isolated from other microbial flora in intestinal contents and biological tissues by plating on selective media. SYN3282 is identical to SYN-PKU-2001, but does not have DAP auxotrophy. For this purpose, female C57BL/6 mice were weighed and randomized by weight into 3 treatment groups (n=5 each). Each group would receive a single oral dose containing 2 mixed strains of bacteria at approximately $3\times10^9$ CFU/strain (200 µL/dose). Group 1 received SYN-PKU901 and SYN766 to examine the effect of DAP auxotrophy, group 2 received SYN-PKU901 and SYN3282 to examine the effect of Phe-degradation activity, and group 3 received SYN-PKU-2001 and SYN3282 to examine the combined effects of both DAP auxotrophy and Phe-degradation activity.

Before dosing, fecal samples were collected from each individual mouse at T=0 and processed by serial microdilution plating to determine the baseline level of viable CFUs, if any, on LB agar plates selective for the bacterial strains to be dosed within the group. Bacterial doses were then administered immediately after the T=0 h fecal collection. For collection of feces at designated time points, each mouse was isolated in a small empty pipet tip box until a recoverable fecal sample was produced. Samples were moved into 2 mL microcentrifuge tubes. If no sample was produced within 30 minutes of isolation, the time point for that animal was excluded from analysis. Fecal pellets were collected and weighed from each mouse at 4, 6, 8, 24, 30, and 48 h post-dose.

For processing of weighed fecal pellets, 1 mL of PBS was added to each sample and disposable pellet pestles (Kimble, 749521-150) were used for manual homogenization. The samples were then vortexed at maximum speed for 10-20 s. The 10 µL microdilution was used to dilute samples 1:10 across 6 orders of magnitude. Ten (10) µL of these dilutions and the undiluted fecal homogenate were plated on the appropriate selective LB agar plates. Dilutions were plated on LB agar supplemented with antibiotics or DAP where appropriate (SYN-PKU901=streptomycin 300 µg/mL; SYN3282=chloramphenicol 30 µg/mL; SYN766/SYN-PKU-2001=chloramphenicol 30 µg/mL and DAP 100 µg/mL). Plates were incubated overnight at 37° C. and colonies were counted manually the following day. Plates were incubated overnight at 37° C.±2° C. Colonies were counted manually in a dilution that contained at least 10 but no more than 200 individual colonies. The final CFU count was determined by back-calculation using the dilution factor multiplied by the number of colonies counted for calculation of CFU/mL of fecal homogenate. This value was divided by the weight of fecal pellets for calculation of CFU/mg feces.

Next, the effect, if any, of mutation/engineering in modified EcN strains compared to their isogenic parents was examined. The amount of each strain excreted at each time point was divided by the number of CFUs of that strain in the initial dose. Using this normalization, the two strains within a study group could be directly compared for excretion and clearance kinetics.

Figure 35A:
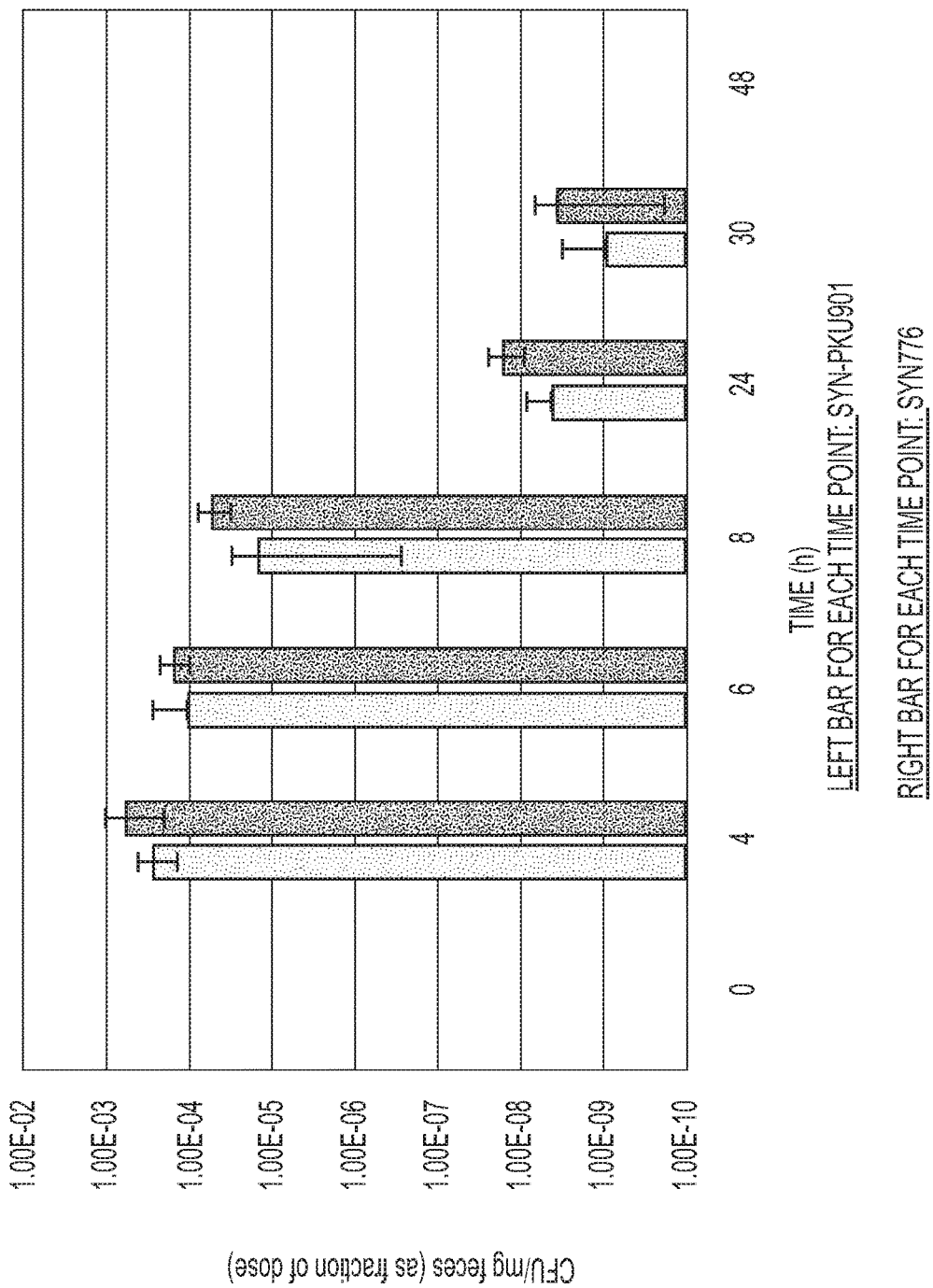
FIGS. 35A, B, and C depict the effect of DAP auxotrophy and Phe degradation activity on EcN survival and transit in C57BL/6 Mice.
Figure 35B:
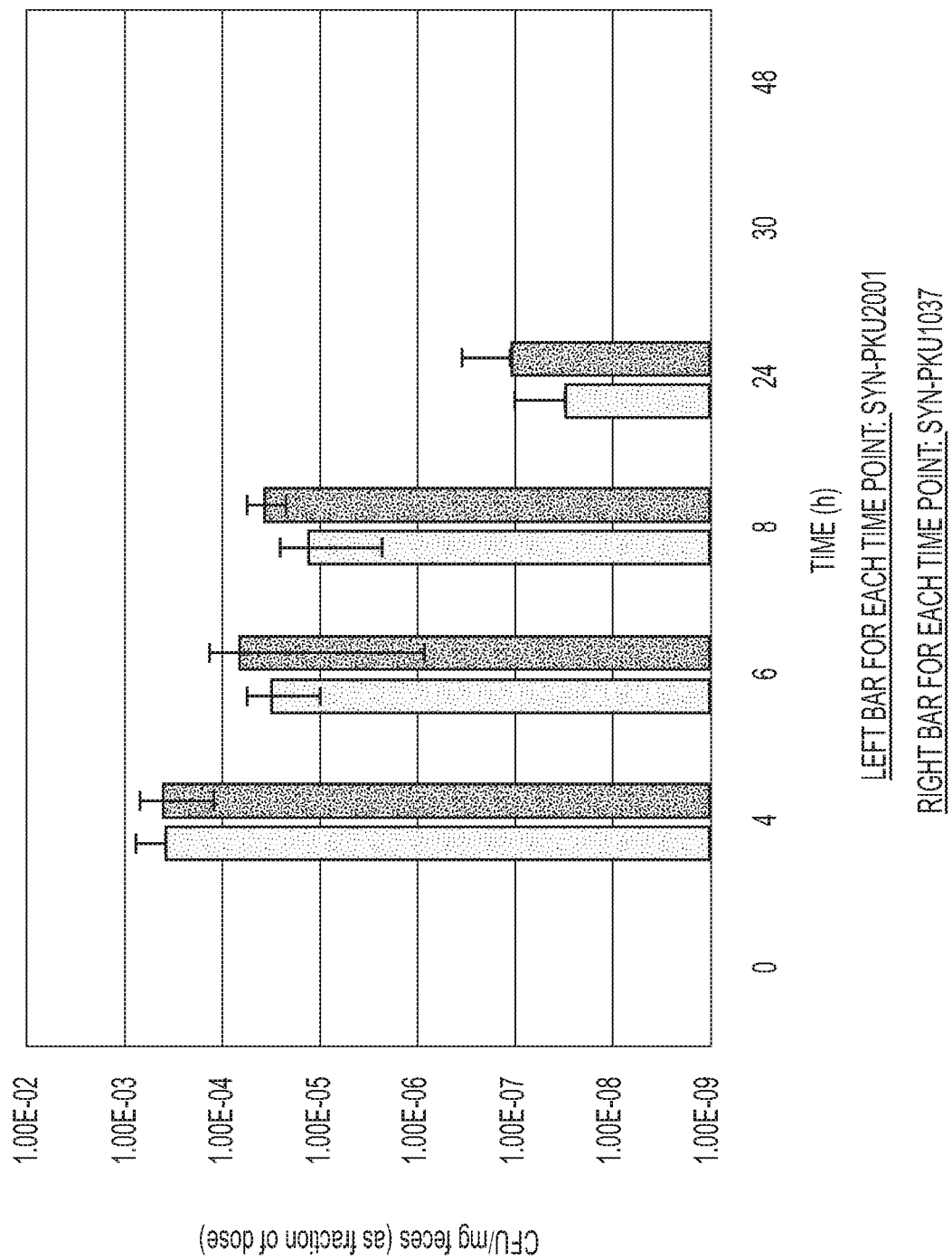
FIG. 35B depicts the effect of genetic engineering for Phe-degradation on fecal clearance in group 2 mice (SYN-PKU901/SYN3282).
Figure 35C:
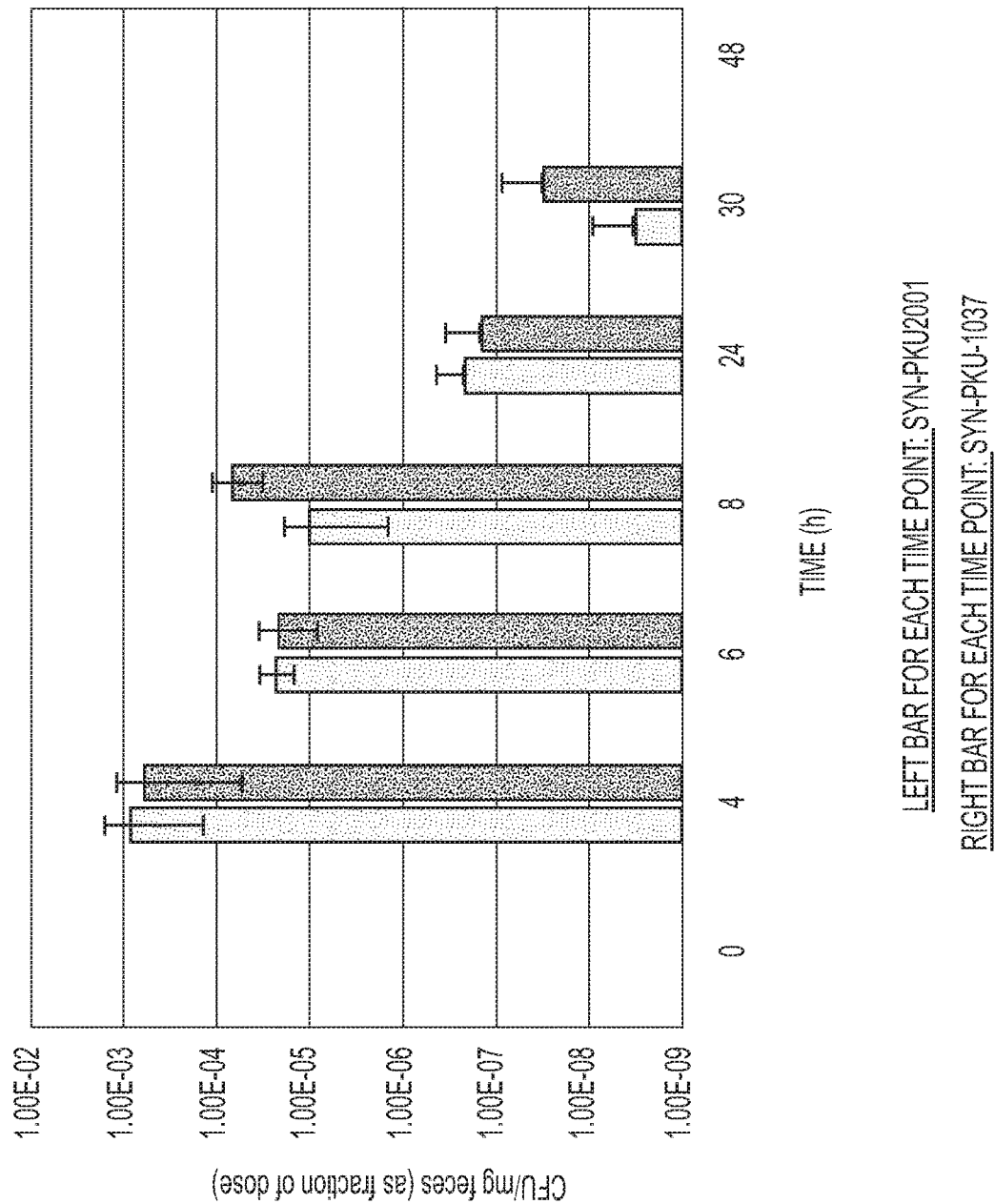
FIG. 35C depicts the effect of genetic engineering for Phe-degradation and DAP auxotrophy on fecal clearance in group 3 mice (SYN-PKU-2001/SYN3282). Mixed doses of bacteria were administered orally to C57BL/6 mice (n=5). Doses were plated for CFU counts in quadruplicate to determine the number of bacteria administered. At each time point, feces were collected, homogenized, and plated for bacterial CFU determination on antibiotic selective media. For each time point, data represent the average CFU/mg counts of 5 fecal samples±standard deviation, normalized for each strain as a fraction of the initial CFU dosed unless otherwise denoted in the appendix. This normalization allows direct comparison of survival/clearance between the 2 strains within a group, even with variation in the actual CFU of each strain administered at T=0.
Figure 36A:
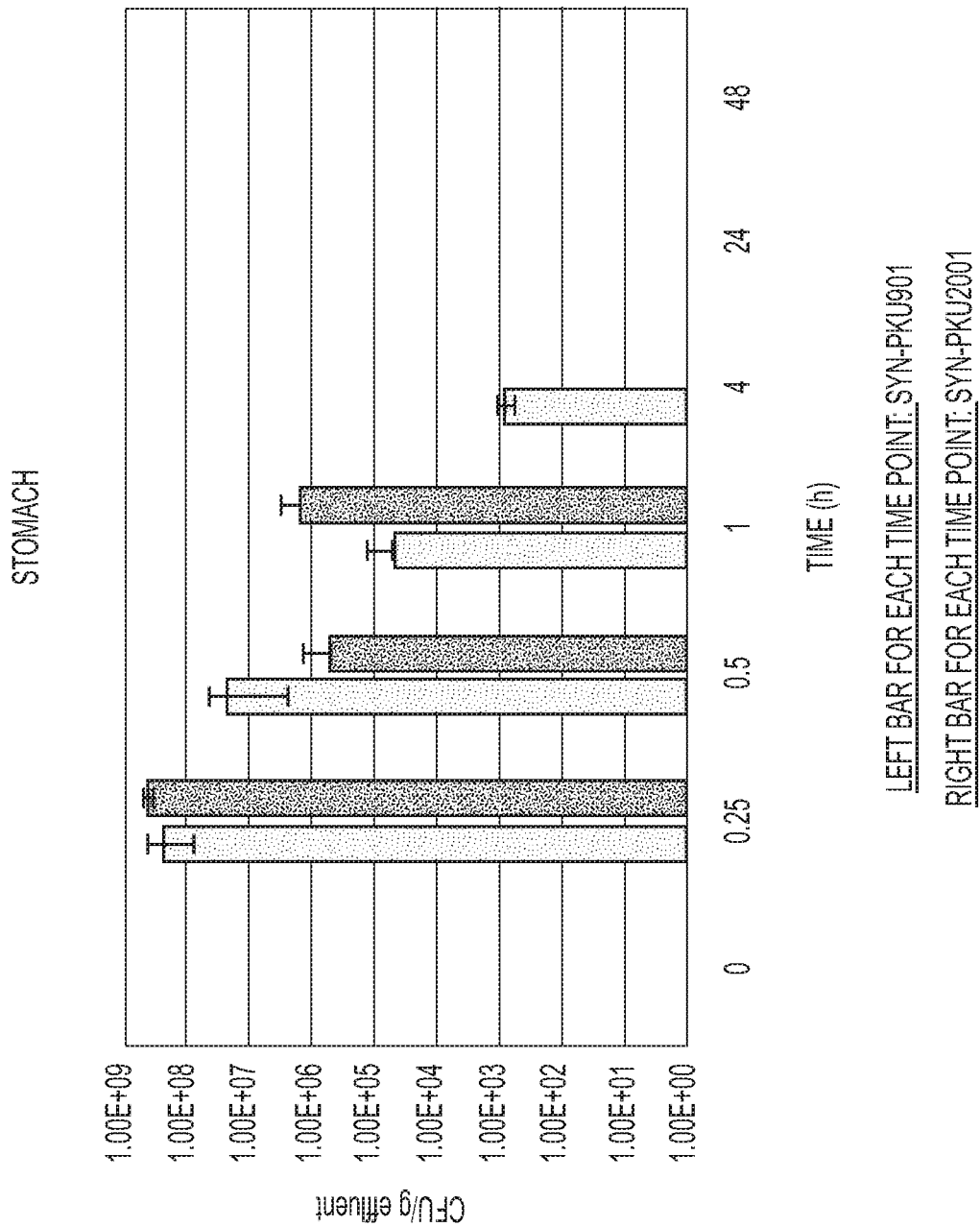
FIGS. 36A-F depicts the effect of DAP auxotrophy and Phe degradation activity on EcN transit and clearance in C57BL/6 mice. SYN-PKU901 or SYN-PKU-2001 were orally administered to C57BL/6 mice (9×109 CFU/dose, n=3/time point). At the indicated times, effluents from the stomach (A), upper small intestine (B), middle small intestine (C), lower small intestine (D), cecum (E) and colon (F) were collected and plated for CFU counts. CFU determination was performed by microdilution on antibiotic selective media. For each time point, data represent the CFUs determined from 3 effluent samples±standard deviation. No CFUs were determined in any sample at 48 h post-dose, indicating complete bacterial clearance.
Figure 36B:
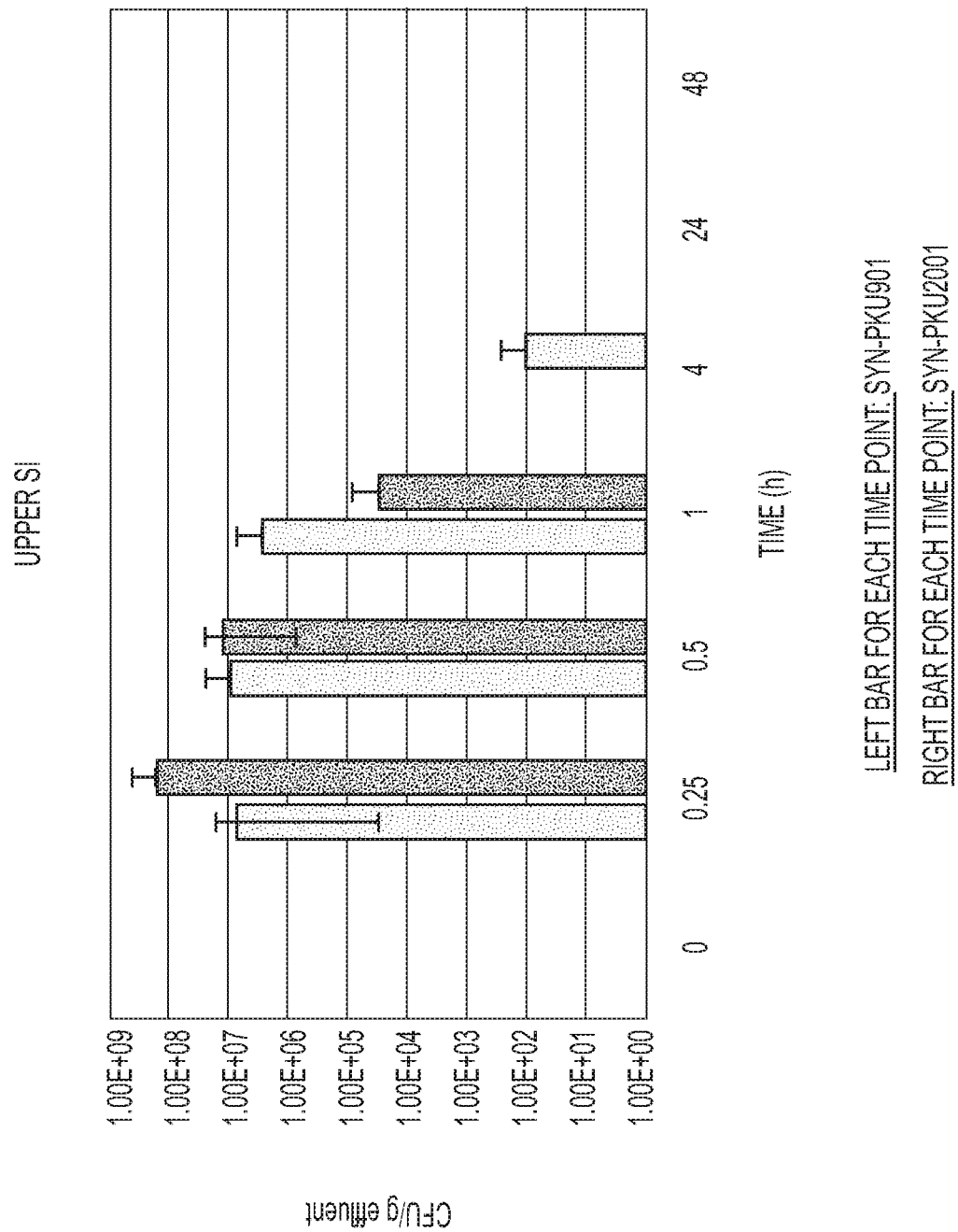
Figure 36C:
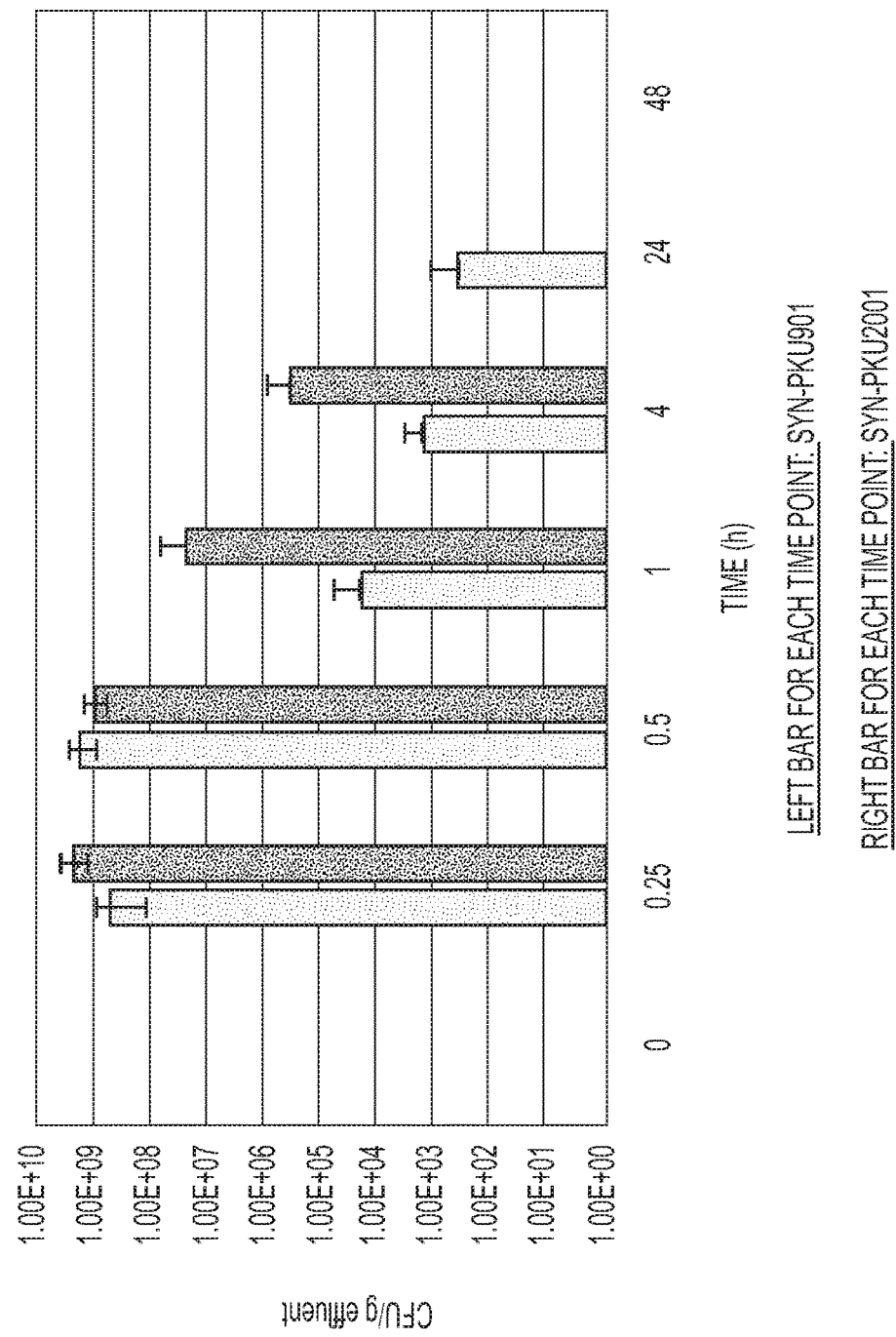
Figure 36D:
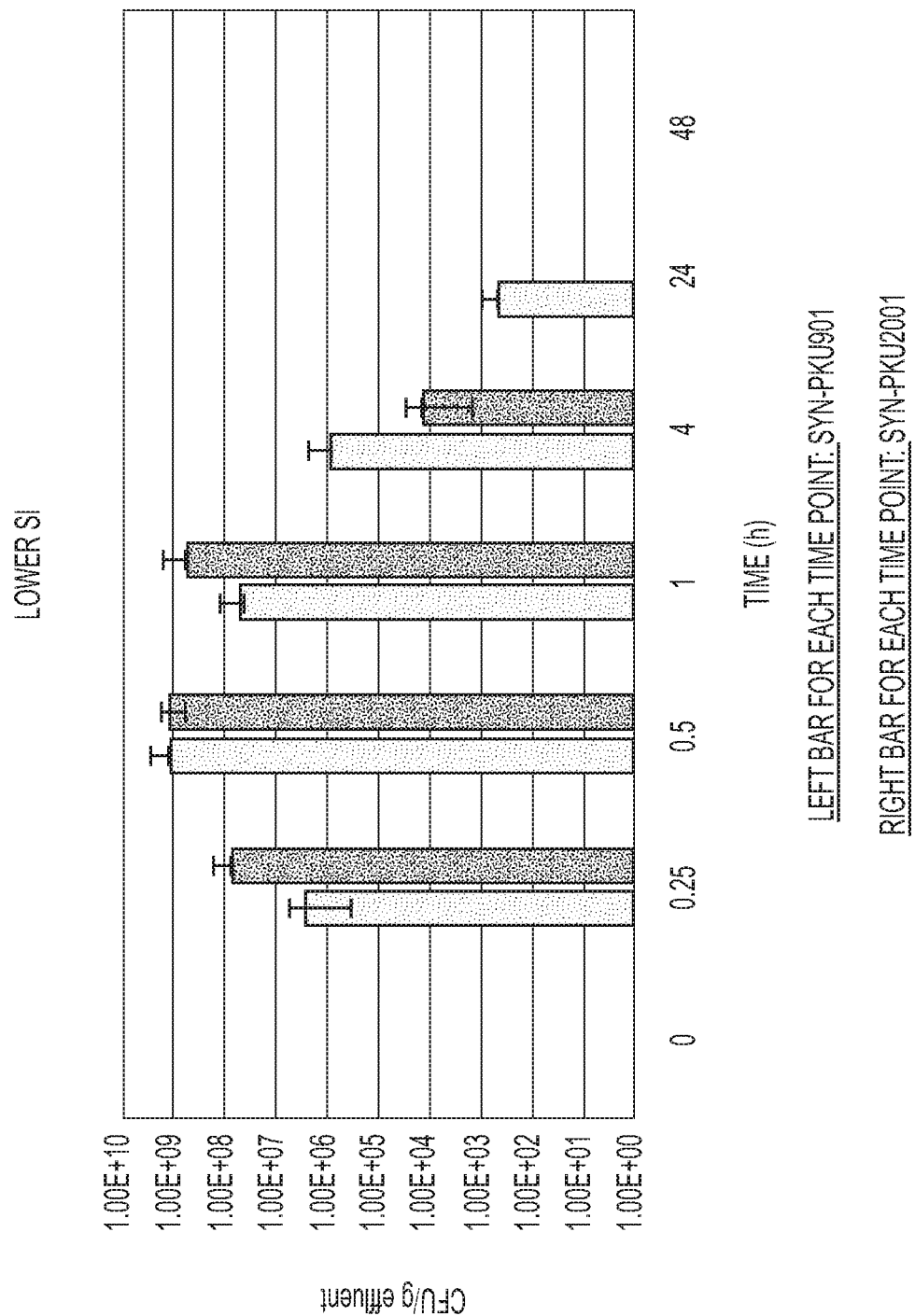
Figure 36E:
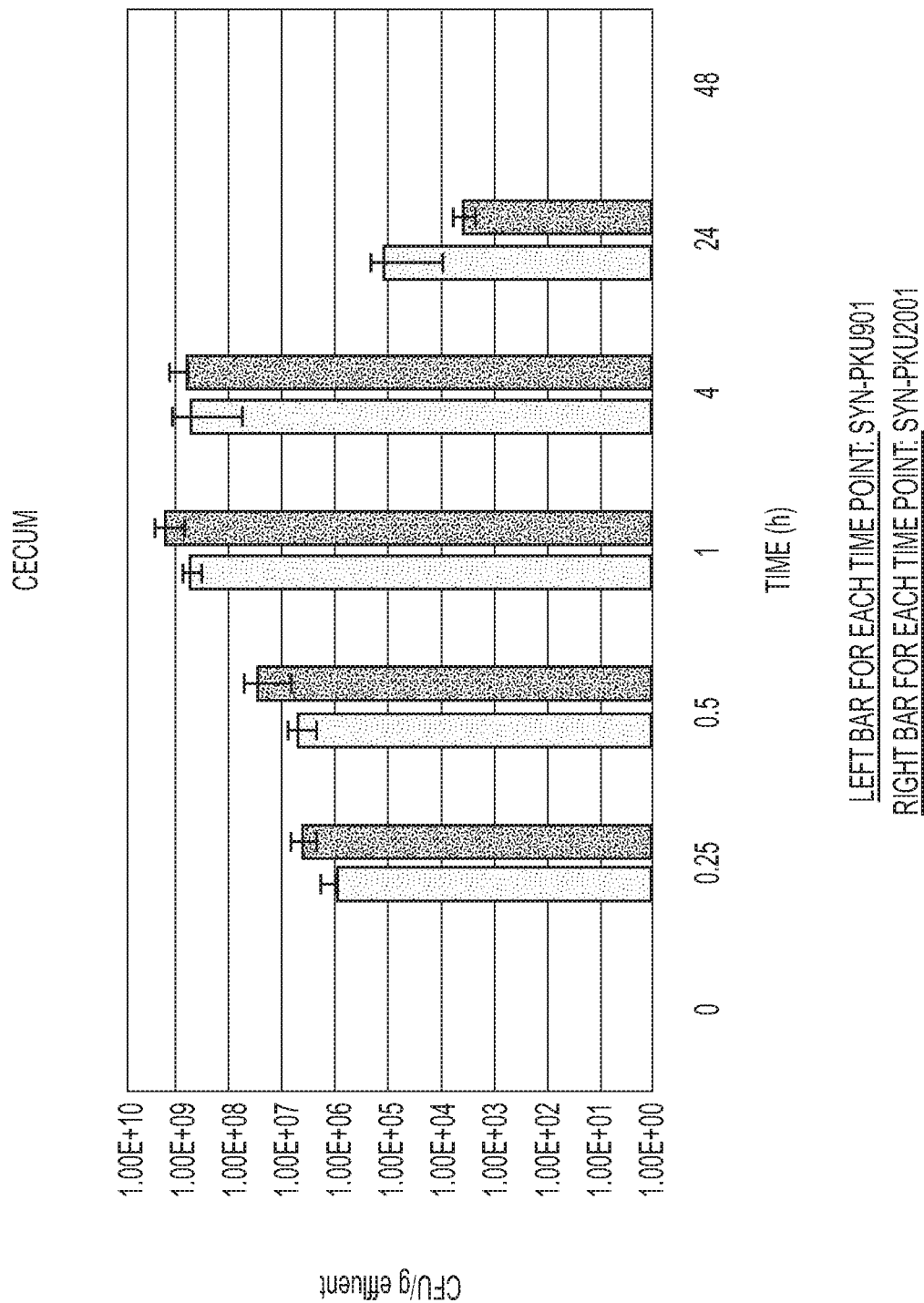
Figure 36F:
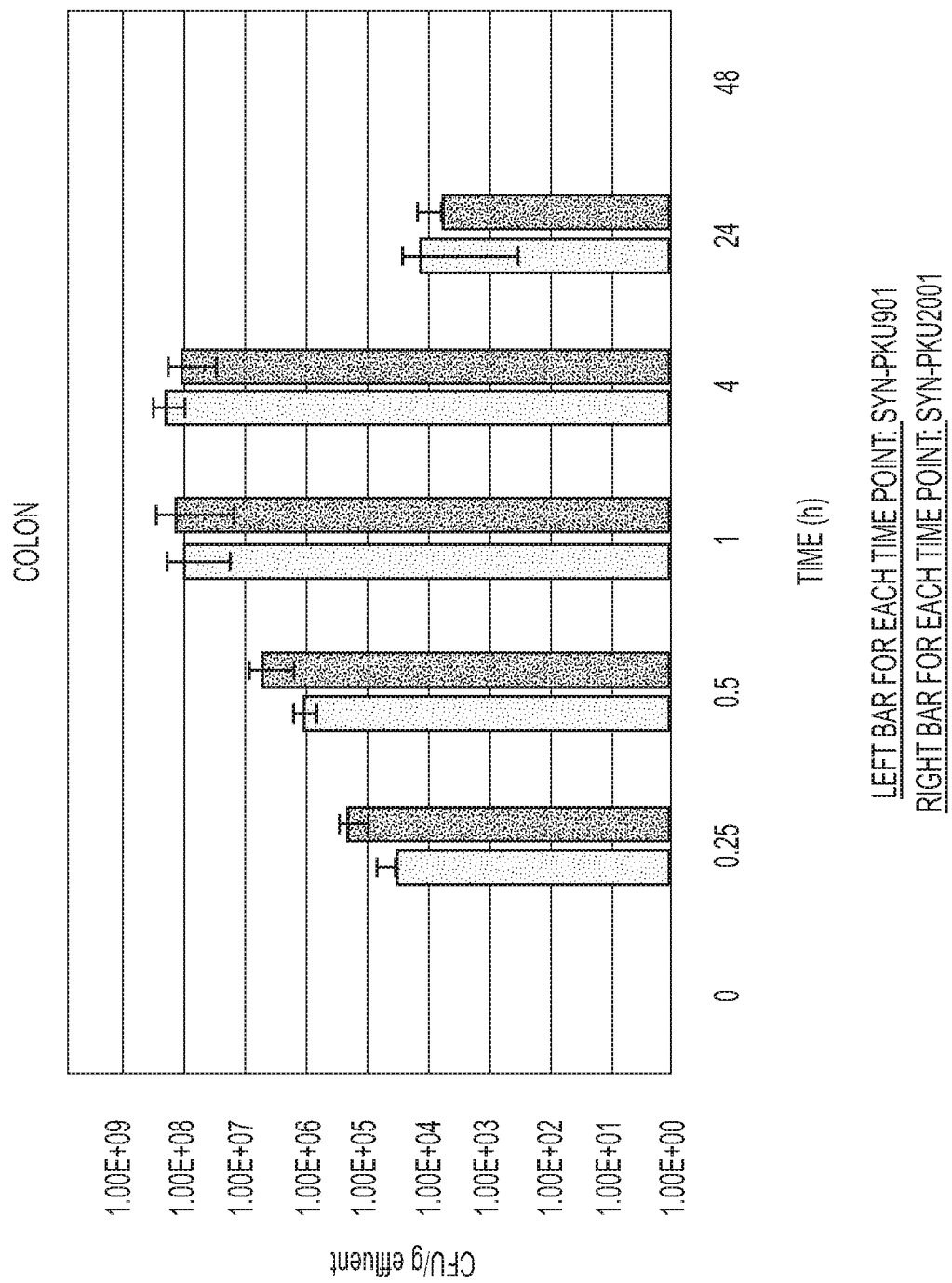
Figure 37:
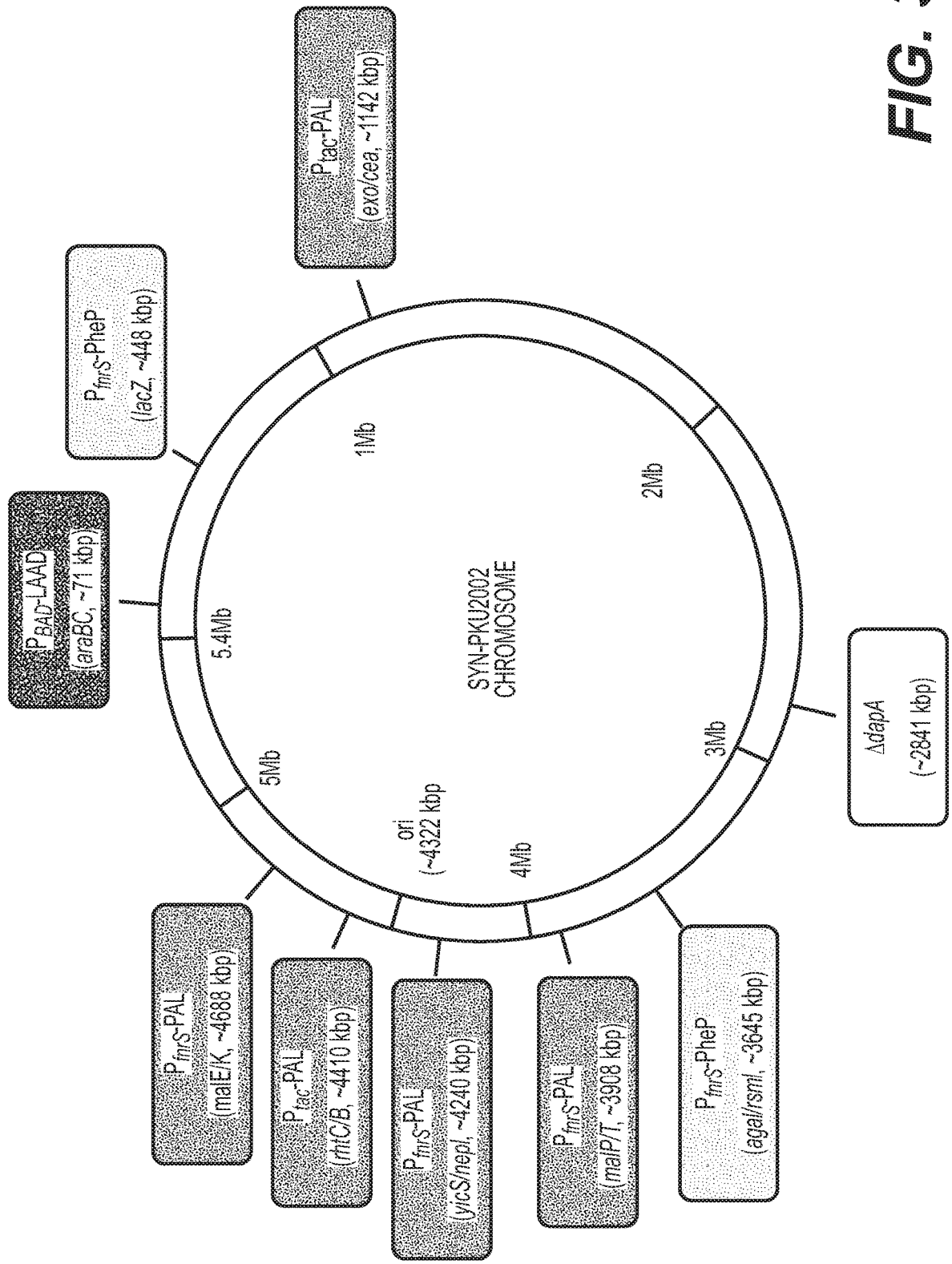
FIG. 37 depicts a schematic of the SYN-PKU-2002 genome. The locations of the genomic modification sites in SYN-PKU-2002 are shown, with kbp designation indicating the chromosomal position relative to the 0/5.4 Mb reference marker. The chromosomal origin of replication is shown as a red line. Green text boxes designate PheP gene insertions, purple text boxes designate PAL gene insertions, orange text box designates LAAD gene insertion, and grey text boxes with A symbol designates the location of the dapA and Φ deletion. Italicized gene names in parenthesis refer to the upstream and downstream genes surrounding the inserted genes.

Results are shown in FIG. 35A-35C. There were no CFUs detected on selective media in the pre-dose (T=0 h) fecal samples for any of the mice, demonstrating that CFUs detected post-dosing were attributable to EcN-derived strains and not due to background growth from the microbiome. In all 3 groups, all strains of bacteria had reached peak amounts in the feces at 4 h post dose and steadily declined over time. By 24 h, bacterial counts in the feces dropped by 3-4 orders of magnitude for all strains. By 30 h, at least 2 mice from groups 1 and 3, and all mice in group 2, contained no detectable EcN-derived bacteria in the feces. By 48 h, all EcN-derived bacteria were cleared from the feces. There were no apparent differences in the kinetics of excretion in the modified EcN strains, as similar rates of elimination were observed for all bacteria, showing that neither DAP auxotropy (SYN766, group 1), Phe-degradation activity (SYN3282, group 2), nor their combination (SYN-PKU-2001, group 3), had any significant effect on intestinal transit time or strain survival in the mouse model compared to the wild type SYN-PKU901 strain.

In conclusion, DAP auxotrophy and/or Phe degradation activity in EcN did not change the survival or disappearance of bacteria from the feces of C57BL/6 mice over time. All orally administered EcN-derived bacterial strains, regardless of genotype, were cleared from the feces of mice within 48 h, suggesting that EcN and its derivatives are not viable long term.

Example 83: In Vivo Survival of *Escherichia coli* Nissle 1917 Derivatives SYN-PKU901 and SYN-PKU-2001 in Healthy Mice The objective of this pharmacology study was to evaluate in female C57BL/6 mice any differences in survival, gastrointestinal (GI) distribution or time to complete clearance of *Escherichia coli* Nissle (EcN) wild type strain SYN-PKU901 compared to the genetically engineered EcN derivative SYN-PKU-2001, a surrogate strain for SYN-PKU-2002, which contained identical diaminopimelate (DAP) auxotrophy and phenylalanine (Phe) degradation elements. GI distribution, transit and clearance kinetics were measured by enumerating colony forming units (CFUs) over a 48-h time period in multiple GI segments of female C57BL/6 mice following a single oral dose of 9×10$^9$ CFUs of SYN-PKU901 or SYN-PKU-2001.

EcN strains utilized for this study included SYN-PKU901, a wild type control, and SYN-PKU-2001, a strain genetically engineered to encode Phe-degrading activity and DAP auxotrophy. SYN-PKU-2001 is a surrogate for the clinical candidate strain SYN-PKU-2002, but contains a chloramphenicol resistance cassette that allows for selection plating from biological tissues.

Female C57BL/6 mice were weighed and randomized by weight into 12 treatment groups (n=3 each) and a control group (n=3). The mice in the control group (T=0) were sacrificed by carbon dioxide asphyxiation followed by cervical dislocation. The stomach, small intestine (SI), cecum, and colon were carefully excised. The SI was further divided into 3 equal length sections (upper, middle, and lower). Each organ section was flushed with 0.5 mL of ice cold phosphate-buffered saline (PBS) and effluents were collected into separate 1.5 mL microcentrifuge tubes. The PBS/effluent samples were weighed and maintained on ice until processing by serial dilution plating on selective media to determine viable CFUs in the effluent of each intestinal segment. In formulations containing 100 mM sodium bicarbonate, animals in the treatment groups received an oral dose of 9×10$^9$ CFUs of SYN-PKU901 (6 groups) or SYN-PKU-2001 (6 groups). At 0.25, 0.5, 1, 4, 24, and 48 h post dose, a SYN-PKU901- and a SYN-PKU-2001-treated group were sacrificed and tissues were processed in a manner identical to the control group.

To calculate CFUs/mL, 10 μL of each weighed effluent sample was used in a 10-fold microdilution series performed in PBS in a sterile 96-well plate. Ten (10) μL of the undiluted effluent and of the dilutions were plated on LB agar supplemented with antibiotics or DAP where appropriate (SYN-PKU901=streptomycin 300 μg/mL; SYN-PKU-2001=chloramphenicol 30 μg/mL and DAP 100 μg/mL). Plates were incubated overnight at 37° C. and colonies were counted manually the following day.

For CFU determination, counts were collected by the manual counting of colonies in a dilution that contained at least 10 but no more than 200 individual colonies. In cases where colonies were only observed at the lowest dilution (the plating of undiluted effluent), all colonies were counted and scored, even when less than 10. The final CFU count was determined by back-calculation using the dilution factor multiplied by both the number of colonies counted and the volume of effluent collected.

See results in FIG. 36A-F. No CFUs were detected on selective media in the effluent samples of mice that did not receive cells, demonstrating that CFUs detected in effluents post-dosing were attributable to EcN-derived strains and not due to background growth from the microbiota. In the effluents obtained from the stomach, upper small intestine, middle small intestine, lower small intestine, cecum and colon of mice dosed with either SYN-PKU-2001 or SYN-PKU901 (control), survival and GI distribution over time were highly similar over the first 24 hours. No CFUs were found for either bacteria at 48 h post-dose, demonstrating complete clearance by this time point.

In conclusion, DAP auxotrophy and/or the phenylalanine-degradation activity of SYN-PKU-2001 did not change the survival, GI distribution or time to complete clearance from the GI tract of C57BL/6 mice compared to the SYN-PKU901 control strain. The complete clearance of all orally administered EcN-derived strains within 48 h suggests that EcN and its derivatives were not viable long term.

Example 84: Phenylalanine Degradation to Trans-Cinnamate and Phenylpyruvate in Bioreactor-Grown *Escherichia coli* Strain SYN-PKU-2002

The conversion of phenylalanine (Phe) into the metabolites trans-cinnamate (TCA) and phenylpyruvate (PP) in modified *Escherichia coli* Nissle 1917 (EcN) strain SYN-PKU-2002 that was grown and activated in a bioreactor was determined as a measure of phenylalanine ammonia lyase (PAL) and L-amino acid deaminase (LAAD) activity. Additional objectives included determining if bioreactor-activated SYN-PKU-2002 could use complex mixtures of Phe-containing peptides or whole protein as substrates for Phe degradation.

EcN-derived strain SYN-PKU-2002, a Phe-degrading strain intended for the therapeutic treatment of phenylketonuria (PKU), was grown and activated in a bioreactor following a process intended to be used for the scale-up of SYN-PKU-2002 for clinical trials. This process, performed on a 5 L scale, included the creation of a low dissolved oxygen (DO) environment that was achieved through control of culture agitation rate. Low DO activated expression of chromosomally integrated copies of genes encoding PAL and high affinity phenylalanine transporter, PheP. Following the drop to low DO, isopropyl β-D-1-thiogalactopyranoside (IPTG; 1 mM) was added to activate expression of additional copies of PAL, and L-arabinose (0.15% final concentration) was added to activate expression of LAAD. Following high density growth, cells were concentrated and frozen at ≤65 C in glycerol-based formulation buffer.

1×10$^8$ activated cells were incubated aerobically at 37 C in assay media containing 50 mM Phe, Phe-Pro, Phe-Gly-Gly, Phe-Val, Phe-Ala, or Gly-Phe peptides, or in 20 g/L of peptone from meat, tryptone, or whole casein powder. Supernatant samples were removed at 30 and 60 min and the concentrations of Phe, TCA, and PP were determined by LC MS/MS.

Figure 31A:
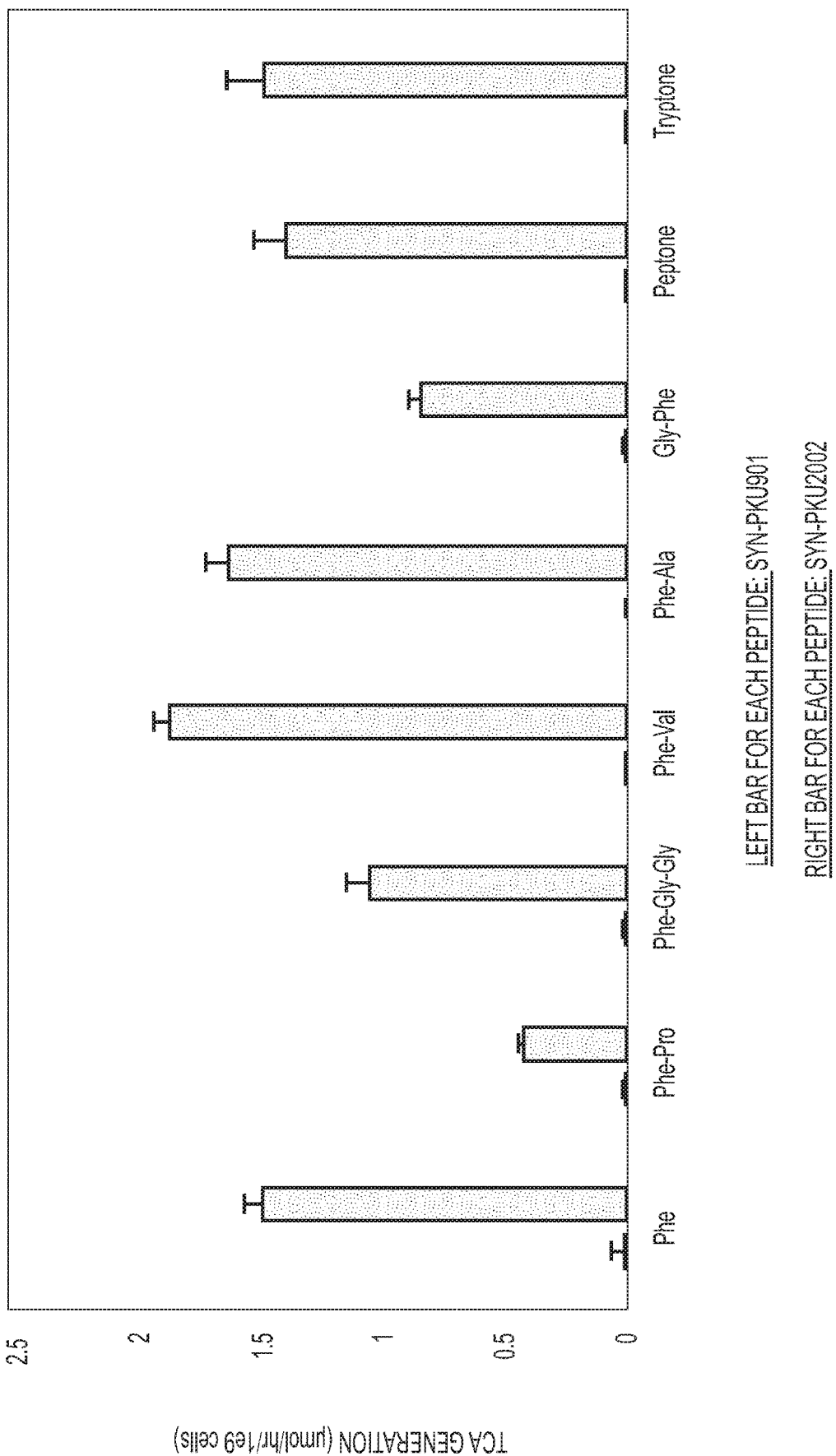
FIG. 31A and FIG. 31B depict graphs showing PAL activity of SYN-PKU-2002 against peptides. SYN-PKU-2002 was grown in a bioreactor and induced for PAL and LAAD activity. Activated cells were incubated for 60 min at 37° C. in Phe assay media containing 50 mM Phe in the form of free Phe, Phe-Pro, Phe-Gly-Gly, Phe-Val, Gly-Phe, or in 5 g/L peptone, or tryptone. The total concentration of trans-cinnamate (FIG. 31A) or phenylpyruvate (FIG. 31B) produced was determined by LC-MS/MS over time, and rates of TCA and PP production were calculated by linear regression. Significant PAL activity was observed with all substrates. LAAD activity was observed only when free Phe was used as a substrate, with a lesser amount of activity when complex substrates peptone or tryptone were used. The graph displays the average and standard deviation of three biological replicates.
Figure 31B:
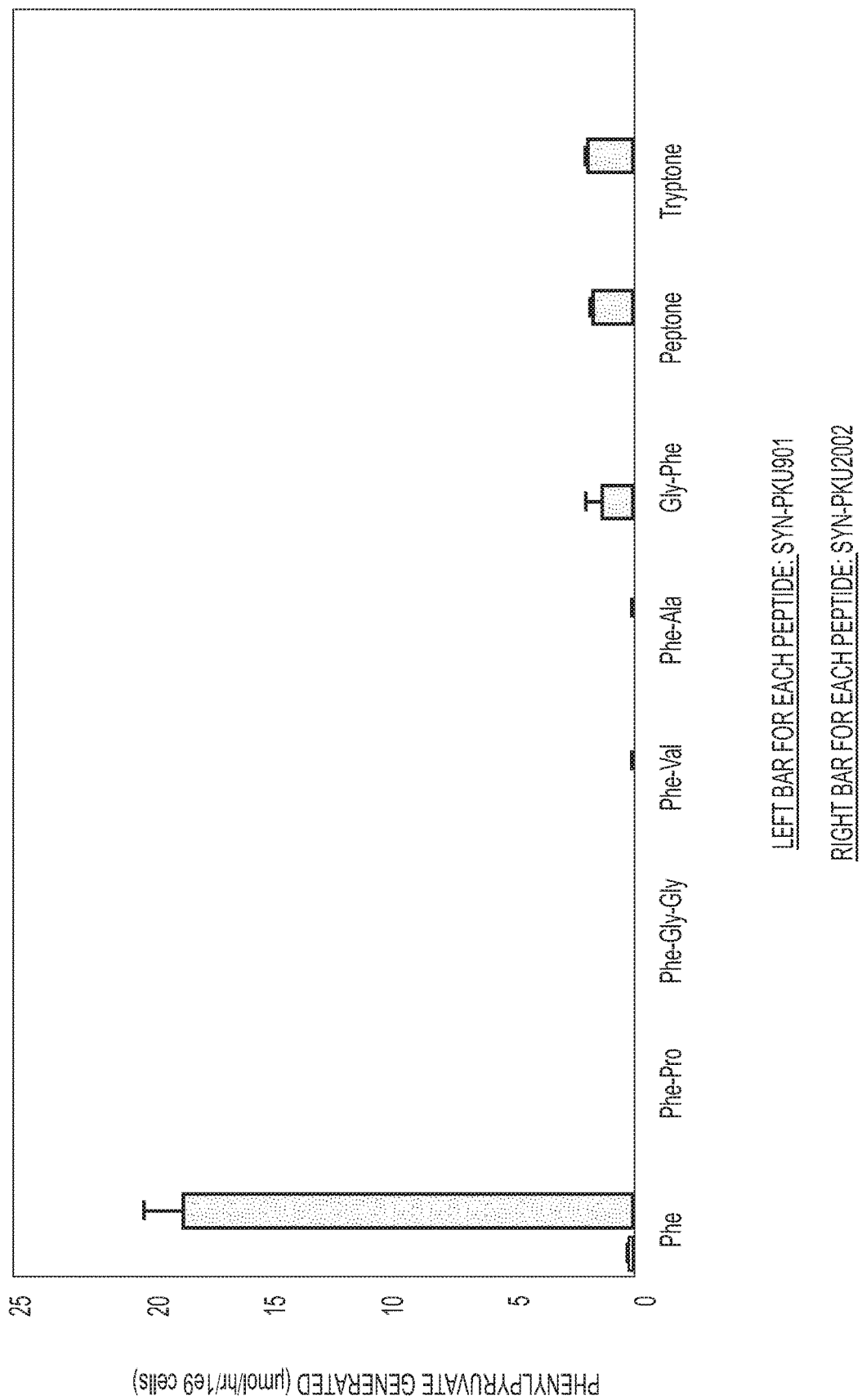

See results in FIGS. 31A and B. Although both PAL and LAAD activities in SYN-PKU-2002 could be detected in vitro when free Phe was used as the substrate, only PAL activity was observed when the provided substrate came in the form of Phe-containing peptides, demonstrating that LAAD may be better at accessing free amino acid than other sources of Phe. No PAL or LAAD activity was observed when undigested casein protein was used as a substrate.

These data demonstrate that SYN-PKU-2002 grown in a bioreactor is capable of growth and activation of both the PAL and LAAD Phe degrading pathways, suggesting that SYN-PKU-2002 is amenable to the production of activated bulk drug at higher volumes. Additionally, it was demonstrated that complex mixtures of Phe-containing peptides, likely to be produced in addition to free Phe during normal digestive processes in the mammalian gastrointestinal tract, are metabolized by the PAL component of SYN-PKU-2002 but not the LAAD component.

Example 85: Dose Response Study of SYN-PKU-2002 in Healthy Non-Human Primates The phenylalanine-metabolizing activity of SYN-PKU-2002 in healthy male cynomolgus monkeys was characterized by measuring the levels of phenylalanine (Phe) and its metabolites in plasma and urine following administration of SYN-PKU-2002 at dose levels ranging from $3.3\times10^9$ to $7.2\times10^{11}$ colony forming units (CFUs).

In this study, healthy male cynomolgus monkeys (2.8-4.5 kg) were fasted overnight. Prior to dosing, plasma samples (heparin) were taken to establish a baseline for unlabeled Phe and downstream metabolites Animals were dosed, by oral gavage, consecutive solutions of 11 mL of peptone (5.5 g), SYN-PKU-2002 (doses ranging from $3.3\times10^9$ to $7.2\times10^{11}$ CFU/dose), and 5 mL of 0.36 M sodium bicarbonate. Plasma was collected 0.5, 1, 2, 4, and 6 hours post dose and frozen until analysis. Plasma samples collected during the study arms were analyzed for the presence of Phe, phenylpyruvate (PP), trans-cinnamate (TCA), and hippurate (HA) using liquid chromatography-tandem mass spectrometry (LC-MS/MS). Urine was collected over the 6-hour post-dose period, the volume measured, and a 5-mL aliquot was frozen and stored until LC-MS/MS analysis.

Figures 26A, 26B:
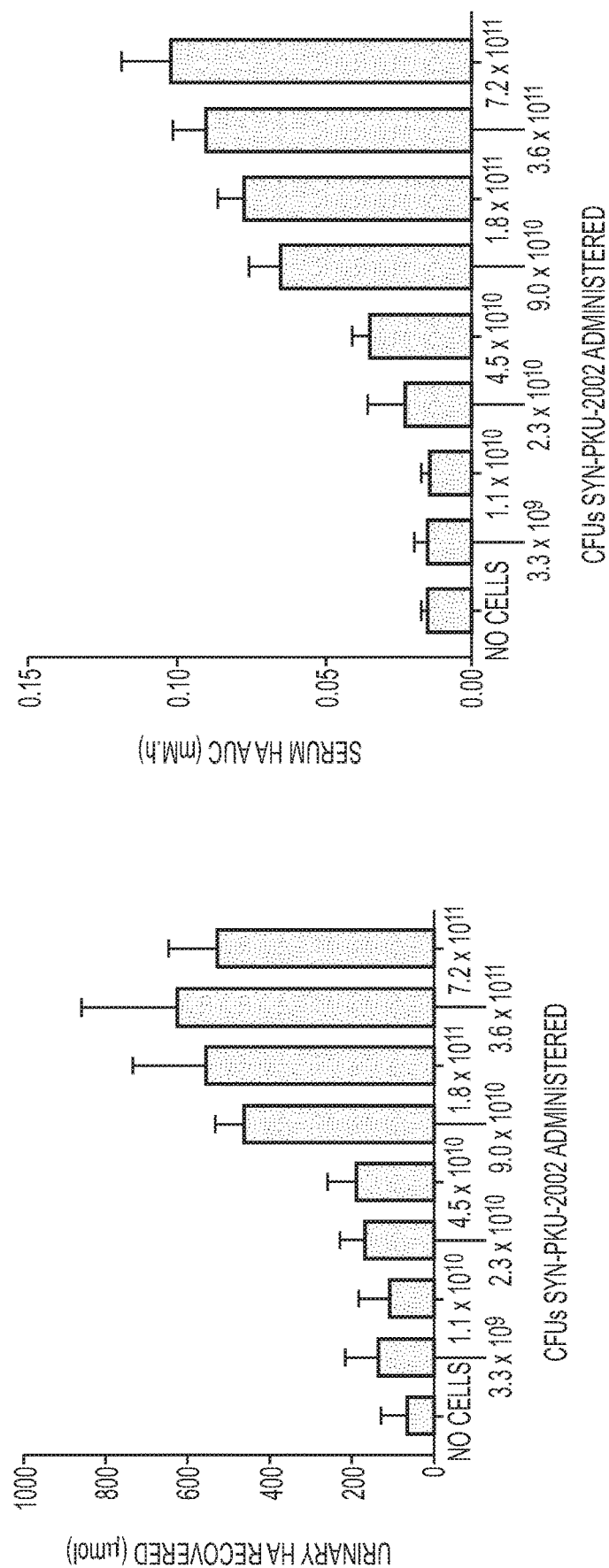
FIG. 26A, FIG. 26B, FIG. 26C, and FIG. 26D depict graphs showing SYN-PKU-2002 dose-dependent conversion of Phe and production of plasma biomarkers in non human primates upon single dose of SYN-PKU-2002 with protein meal, illustrating significant activity and efficacy of of SYN-PKU-2002 in the NHP model. Fasted NHPs (n=5 per dose group) were administered a 5 g peptide bolus with the indicated dose (CFUs) of SYN-PKU-2002. Urine was collected over 6 h and serum at 0, 0.5, 1, 2, 4, and 6 h.
Figure 26C:
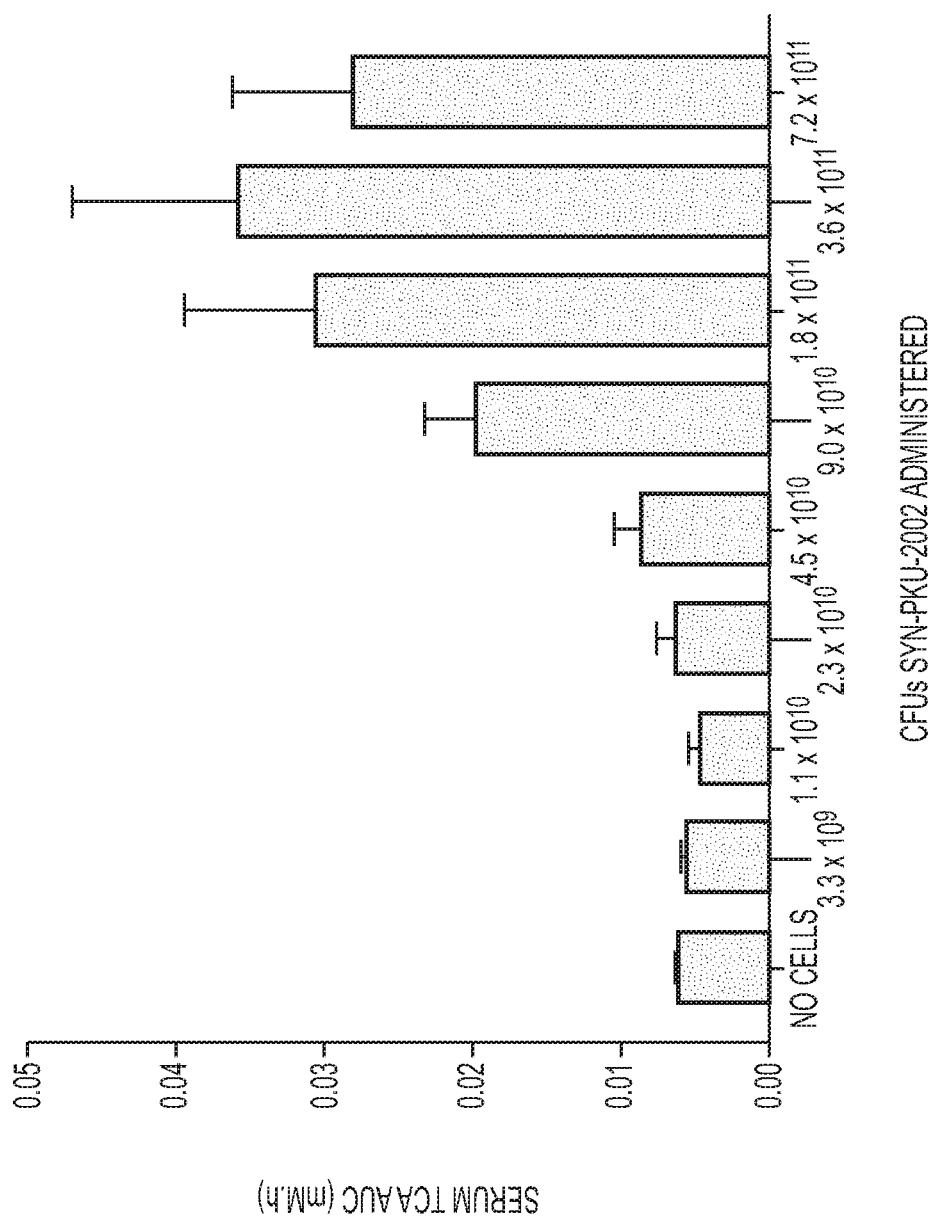
Figure 26D:
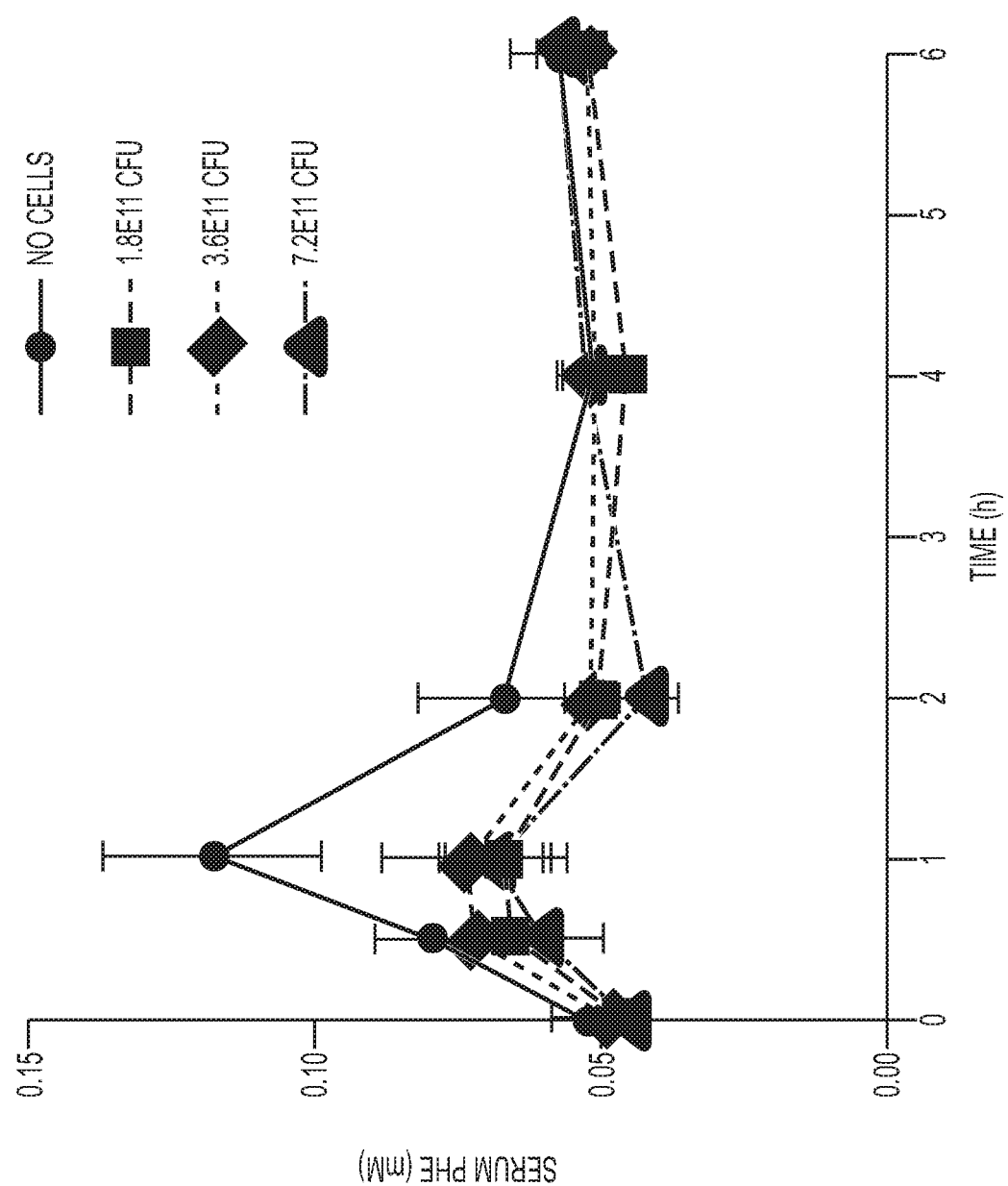
Figure 27A:
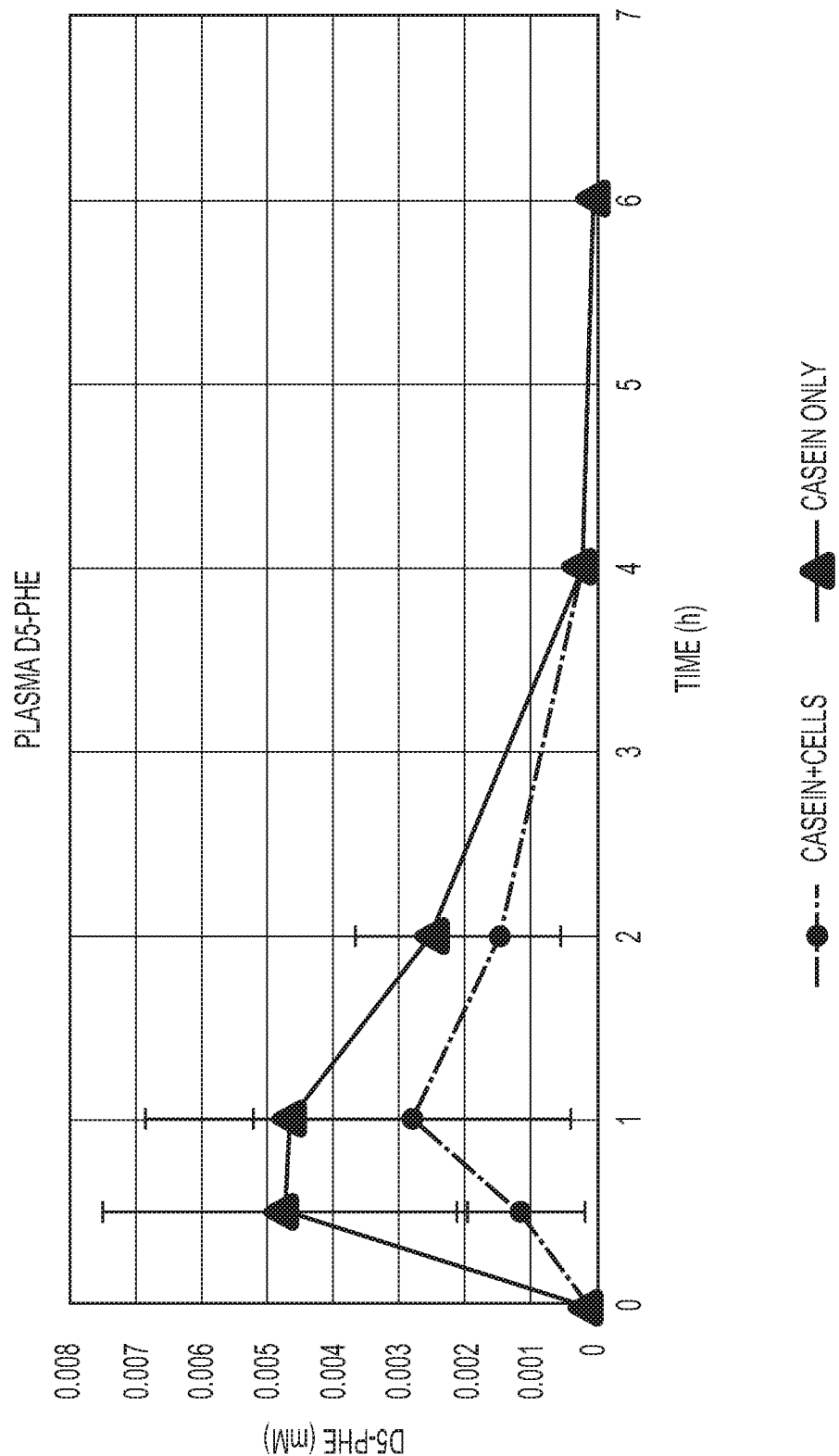
FIG. 27A, FIG. 27B, and FIG. 27C depicts graphs showing SYN-PKU-2002 dose dependent conversion of Phe from casein (FIG. 27A) TCA levels (FIG. 27B), and hippuric acid (FIG. 27C) in NHP's. Blood metabolites were collected for 6 hours.
Figure 27B:
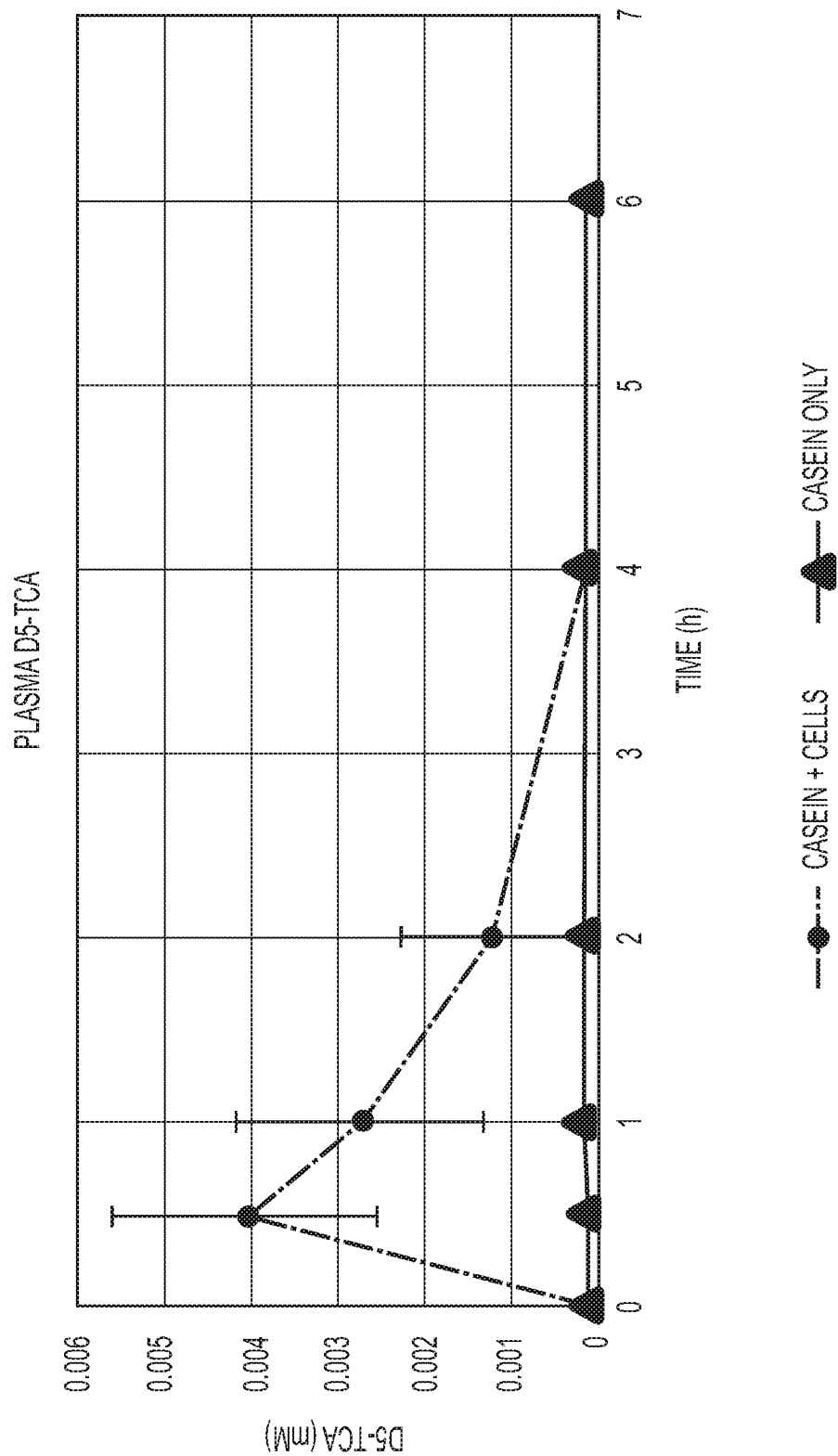
Figure 27C:
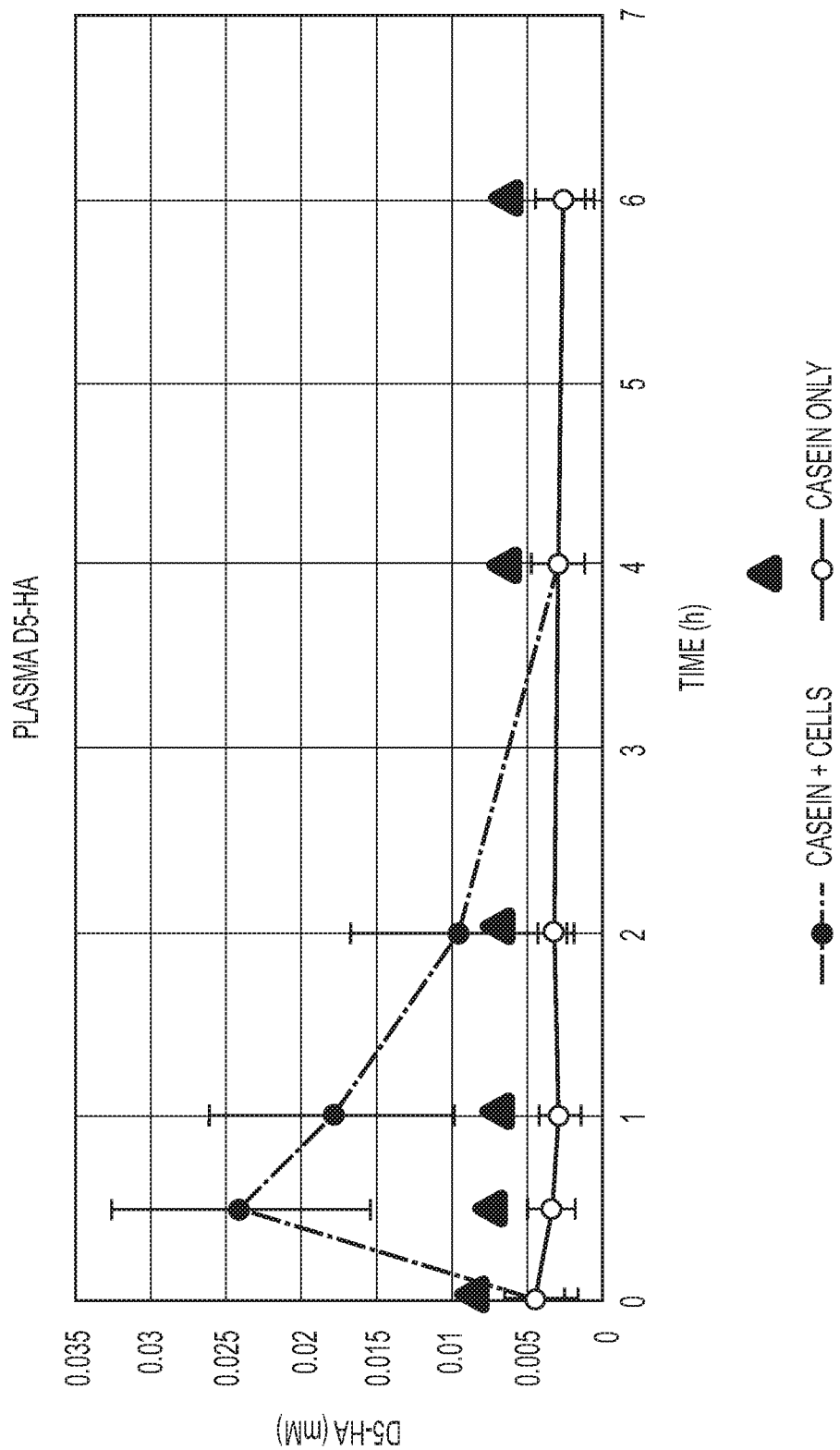

Administration of peptone to healthy monkeys resulted in a spike in plasma Phe concentrations peaking around 1 hour post-administration (see FIG. 26D). Oral dosing of SYN-PKU-2002 to healthy monkeys receiving 5.5 g of peptone resulted in a blunting of this Phe spike. Although not completely dose-proportional over the entire range, plasma concentrations of Phe were generally lower in the SYN-PKU-2002-dosed groups, particularly at or above the dose level of $9\times10^{10}$ CFUs. Concurrent with decreases in Phe following SYN-PKU-2002 dosing, plasma concentrations of TCA (the direct product of phenylalanine ammonia lyase metabolism of Phe, see FIG. 26C) and HA (a metabolite of TCA, see FIG. 26B and FIG. 38) increased in a dose-dependent manner; however, there were no detectable plasma concentrations of PP (the direct product of L-amino acid deaminase metabolism of Phe) in monkeys treated with the highest dose (lower doses not measured). Hippurate is known to be rapidly excreted in urine and consistent with increased plasma TCA and HA concentrations, urinary HA excretion increased in a generally dose dependent manner (see FIG. 26A, no PP was detected in urine of the highest dose monkeys).

These studies demonstrate that SYN-PKU-2002 is able to metabolize Phe in male cynomolgus monkeys. PP was not detected in plasma and urine of monkeys treated with the highest dose. There was a dose-dependent increase in the plasma concentrations of the phenylalanine metabolites TCA and HA as well as dose-dependent increases in urinary HA excretion over 6 hours. This indicates that between the two Phe-degrading enzymes in SYN-PKU-2002, PAL is responsible for most of the Phe metabolism in the monkey, with little or no contribution from LAAD in this model. In addition, this study shows that HA and TCA could potentially serve as biomarkers of SYN-PKU-2002 activity in future clinical studies.

Example 86: Gastrointestinal Tract Characterization of SYN-PKU-2001 in Non-Human Primates Two studies were performed to characterize the phenylalanine-metabolizing activity and colonization of SYN-PKU-2001 within different segments of the gastrointestinal tract of healthy cynomolgus monkeys. In the first study, animals were separated into 2 groups of 3 females each, dosed with 5.5 grams of peptone, 5 mL of 0.36 M Sodium Bicarbonate, 25 mg/kg of D5-Phenylalanine, and either SYN-PKU-2001 or a blank control. Two hours after dosing, animals were euthanized and samples collected. In the second study, one group of 3 male monkeys were dosed with 5.5 grams of peptone, 5 mL of 0.36 M Sodium Bicarbonate, 25 mg/kg of D5-Phenylalanine, and SYN-PKU-2001, and animals were euthanized and samples collected 0.5 hours after doseage.

In both studies, animals were administered test articles (see table below) by a single oral gavage on Day 1. The capped bacteria tube was inverted 3 times before each dose administration. Dose formulations were administered by oral gavage using a disposable catheter attached to a plastic syringe. Following dosing, the gavage tube was rinsed with 5 mL of the animal drinking water, into the animal's stomach. Each animal was dosed with a clean gavage tube. The first day of dosing was designated as Day 1. The animals were temporarily restrained for dose administration and were not sedated.

| | Test and Control Article Identification | | | | |
|---|---|---|---|---|---|
| | Test Article | Test Article | Test Article | Test Article | Test Article |
| Identification | Peptone | Bacteria | D5-Phenylalanine | Formulation buffer | Sodium Bicarbonate |
| Batch ID | | SYN-PKU-2001 2917-C | | | |
| Concentration | 500 g/L | $5.5 \times 10^{10}$ CFU/mL | 20 mg/mL | | 0.36M |
| Physical Description | liquid | liquid | liquid | liquid | liquid |
| Storage Conditions | Controlled Room Temperature | −80° C. | −80° C. | 4° C. | Controlled Room Temperature |

Formulation buffer and D5-Phenylalanine (20 mg/mL) were maintained at 4° C. until use, at which point, aliquots were removed and allowed to warm to room temperature for at least 30 minutes before dosing. Sodium Bicarbonate (0.36M) was stored and administered at ambient temperature.

Shown in the table below are the dose volumes and regimens used for each group of animals.

Experimental Design

| Group (Study No.) | No. Animals | Treatment | Dose Volume (mL) | Dose Regimen |
|---|---|---|---|---|
| Group 1 (Study No. 1) | 3 | Peptone | 11 | PO |
| | | Sodium Bicarbonate | 5 | |
| | | D5-Phe | 1.3 | |
| | | Bacteria | 1.8 | |
| Group 2 (Study No. 1) | 3 | Peptone | 11 | |
| | | Sodium Bicarbonate | 5 | |
| | | D5-Phe | 1.3 | |
| | | Formulation buffer | 1.8 | |
| Group 1 (Study No. 3) | 3 | Peptone | 11 | PO |
| | | Sodium Bicarbonate | 5 | |
| | | D5-Phe | 1.3 | |
| | | Bacteria | 1.8 | |

The dose of 5.5 grams of Peptone is based on a typical 60 kg individual consuming 100 g of protein per day and we wanted to simulate this so that we could measure Phe in the blood after feeding and metabolites of Phe in the urine. The oral dose of 25 mg/kg of D5-Phenylalanine was chosen because it gives measurable levels of D5-Hippurate in the urine of mice when dosed at this level.

In both studies, animals were fasted overnight, and weighed on day 1 before dosing. Blood samples (5 mL) were collected from the femoral vein using Heparin as the anticoagulant, and placed on crushed wet ice before centrifugation. Following centrifugation, the resultant plasma was separated, transferred into two aliquots, immediately frozen over dry ice and transferred to a freezer set to −80° C. Samples were shipped on dry ice to a separate facility for analysis.

Animals were euthanized (without sedation) 2 hours (Study 1) or 0.5 hours (Study 2) post dose via intravenous injection via tail vein, using a percutaneous catheter set-up, of a commercially available veterinary euthanasia solution.

Terminal Procedures for Study

| Study No. | No. of Animals | Scheduled Euthanasia Day[a] | Necropsy Procedures Necropsy | Tissue Collection | Histology Organ Weights | Histopathology |
|---|---|---|---|---|---|---|
| 1 | 6 (F) | 1 | — | X | — | — |
| 2 | 3 (M) | | | | | |

Tissues identified in the Tissue Collection and Preservation table were collected from all animals as indicated.

Tissue Collection and Preservation

| Tissue | Weigh | Collect | Microscopic Evaluation | Comment |
|---|---|---|---|---|
| Large intestine, proximal colon | — | X | — | Contents, whole tissue (Studies 1 and 2) and mucus scrappings (study 2 only). |
| Small intestine, duodenum | — | X | — | Contents and whole tissue in 30 cm segments (see below). |
| Small intestine, ileum | — | X | — | |
| Small intestine, jejunum | — | X | — | |
| Stomach | — | X | — | Contents and whole tissue (see below). |

X = Procedure to be conducted; — = Not applicable.

Following exanguination, the stomach and colon were clamped. Additional clamps were used to section the small intestine at approximately 30 cm segments. 10 mL of cold sterile saline was injected into the stomach and massaged to loosen contents. The stomach was opened and contents drained into a labeled 50 mL conical tube and volume recorded. Approximately 1 mL of contents was transferred to the analysis facility to plate at time of collection. Remaining stomach contents were separated in 3 different aliquots: 1 mL, 1.6 mL (to which sponsor added glycerol before freezing) and remaining. The remaining stomach tissue (whole and collected into a labeled ziplock bag) was frozen on dry ice until shipped, with contents, via same-day courier (frozen on dry ice) to the analysis facility.

Each approximate 30 cm segment of the small intestine was injected with 15 mL of cold sterile saline and contents collected into a labeled 50 mL conical tube and volume recorded. Approximately 1 mL of contents from each segment was transferred to the analysis facility to plate at time of collection. Remaining contents were separated in 3 different aliquots: 1 mL, 1.6 mL (to which sponsor added glycerol before freezing) and remaining Small intestine tissue sections (collected into labeled ziplock bags) were frozen on dry ice until shipped, with contents, via same-day courier (frozen on dry ice) to the analysis facility.

In the first study, no more than 20 mL of proximal colon contents were collected (undiluted) into a clean, pre-weighed glass bottle maintained on wet ice. Approximately 1 mL of contents were transferred to the analysis facility to plate at time of collection. Two different aliquots: 1 mL frozen on dry ice and 1.6 mL (to which sponsor added glycerol before freezing) were transferred to pre-identified tubes. The colon was then opened and the remaining content removed and transferred to the glass bottle (if less than 50 mL was previously collected). Tissue was grasped with forceps and gently rinsed in a basin containing sterile saline. The colon tissue was then scraped using a clean spatula to collect mucus into a labeled and pre-weighed glass bottle. The mucus sample was kept on wet ice until transferred to the analysis facility. The tissue was collected (whole) in a ziplock bag and frozen on dry ice until shipped via same-day courier (frozen on dry ice) to the analysis facility.

In the second study, 15 mL of cold sterile saline was injected into the proximal colon and the content was collected into a labeled 50 mL conical tube and the volume recorded. Approximately 1 mL of contents was transferred to the analysis facility to plate at time of collection. Remaining contents were separated into 3 different aliquots: 1 mL, 1.6 mL (to which sponsor added glycerol before freezing) and remaining Large intestine tissue (collected into labeled ziplock bags) was frozen on dry ice until shipped, with contents, via same-day courier (frozen on dry ice) to the analysis facility at the address below.

Figure 38:
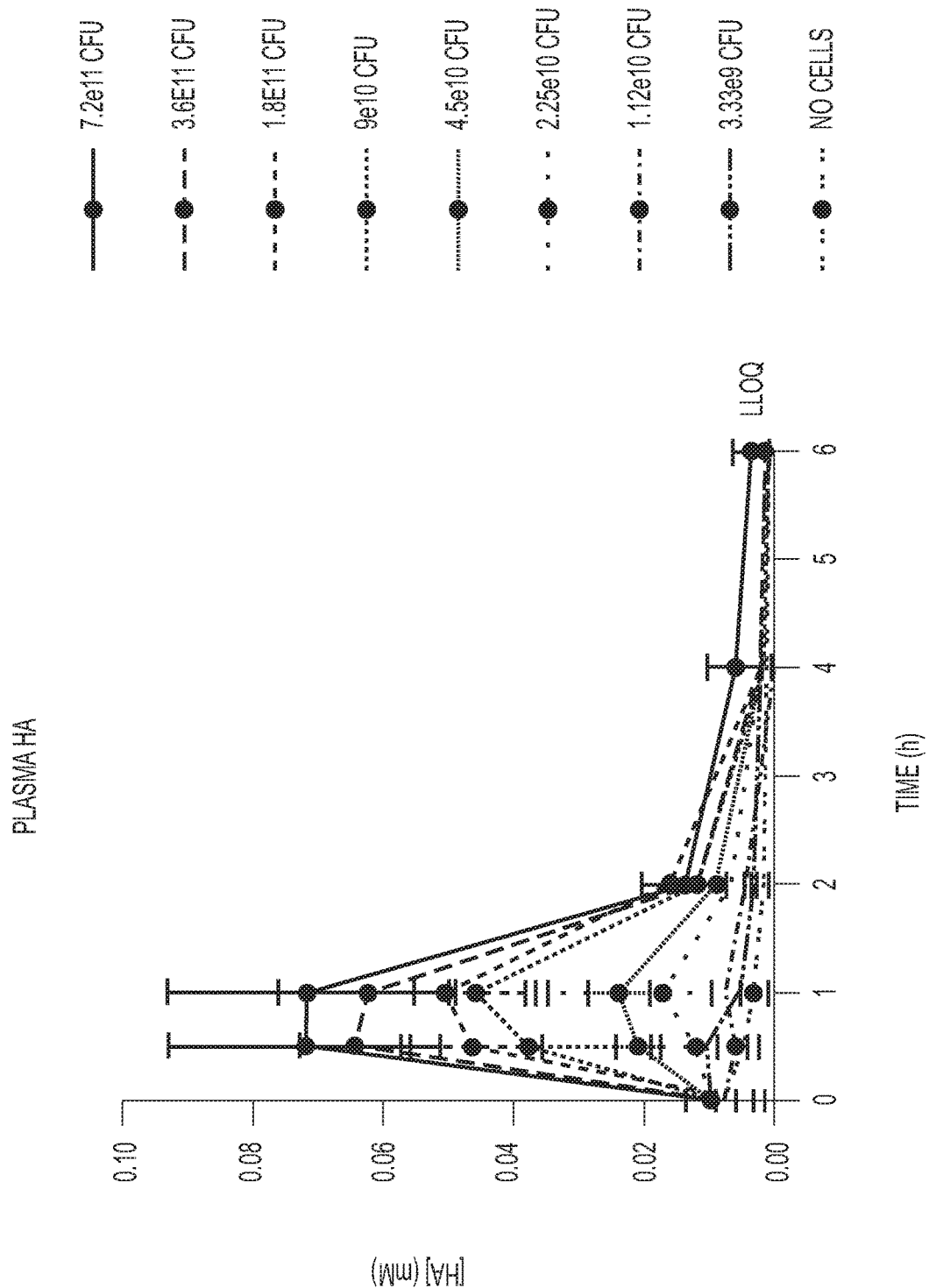
FIG. 38 depicts SYN-PKU-2002 dose-dependent conversion of Phe and production of plasma biomarkers in non-human primates upon single dose of SYN-PKU-2002 with protein meal, illustrating significant activity and efficacy of SYN-PKU-2002 in the NHP model. Fasted NHPs (n=5 per dose group) were administered a 5 g peptide bolus with the indicated dose (CFUs) of SYN-PKU-2002. Plasma was collected at 0, 0.5, 1, 2, 4, and 6 h after dosing at time 0. Each point represents the HA concentration measured in plasma at the time point after dosing. Standard deviations are shown as vertical bars at each point.
Figure 39:
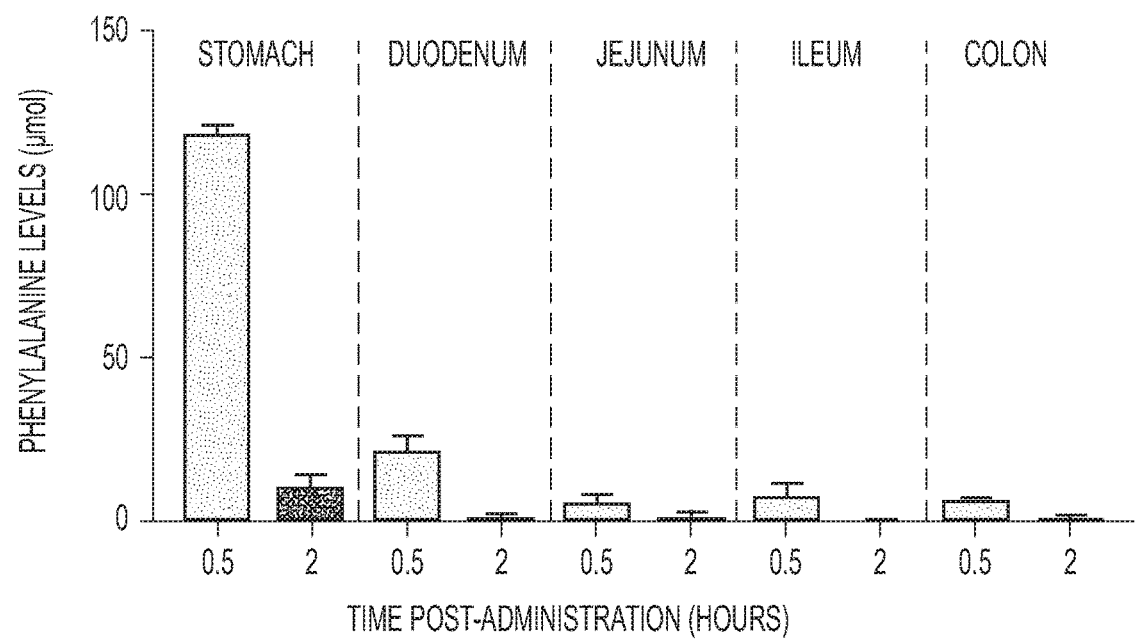
FIG. 39 depicts SYN-PKU-2001 characterization within the gastrointestinal tract of Non-Human Primates. Cynomolgus monkeys were dosed with 5.5 grams of peptone, 5 mL of 0.36 M sodium bicarbonate, 25 mg/kg of D5-Phenylalanine, and SYN-PKU-2001 and euthanized either 0.5 hours or 2 hours after dosing. Following euthanization, tissue samples were collected from various sections of the gastrointestinal tract and analyzed to determine the concentration of Phe and SYN-PKU-2001 in each section.
Figure 39:
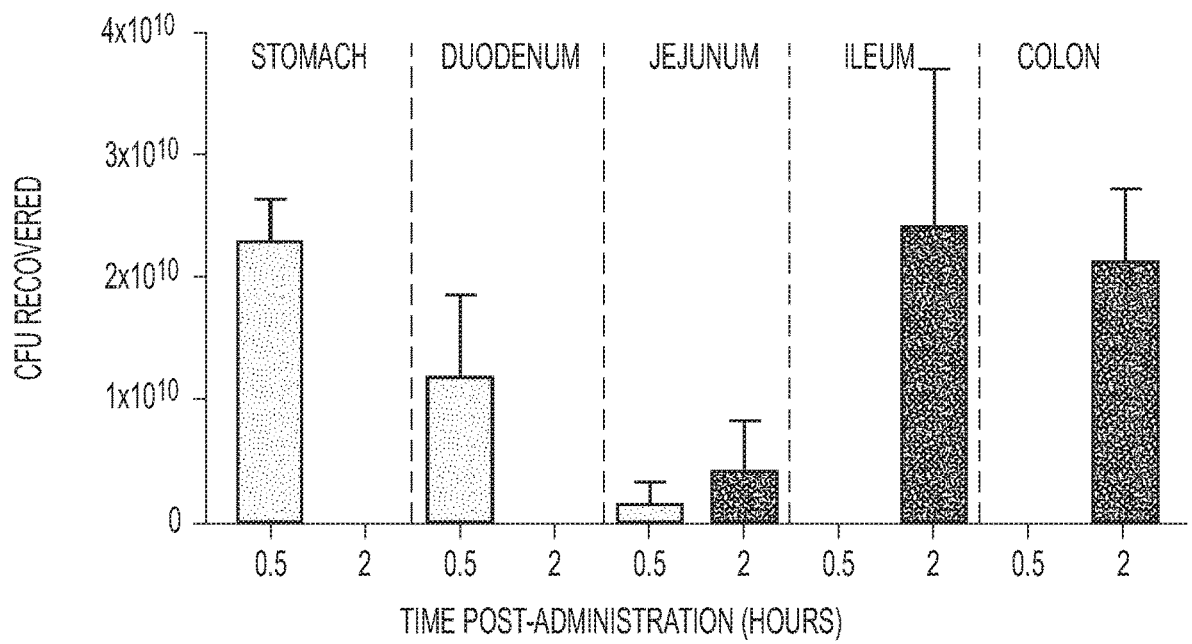

The measured Phe levels and CFU counts for each part of the gastrointestinal tract are displayed in FIG. 38. Both 2 hours, and 0.5 hours after dosage, phenylalanine levels were found to be highest in the stomach and gradually decrease further down the gut. 2 hours after administration, less than 10% of phenylalanine was found in the stomach and duodenum. 2 hours post-dosage, SYN-PKU-2001 was found mainly in the ileum and proximal colon, where very little substrate is available. This suggests that SYN-PKU-2001 activity is limited by substrate availability and should thus be taken with food.

The invention claimed is:

1. An *E. coli* Nissle bacterium, wherein the bacterium comprises
   (i) one or more gene(s) encoding a non-native phenylalanine metabolizing enzyme (PME), and
   (ii) one or more non-native deletions in one or more phage genes in *E. coli* Nissle Phage 3, wherein the one or more phage queens are selected from the group consisting of ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

2. The bacterium of claim 1, wherein the non-native deletions comprise a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175.

3. The bacterium of claim 1, wherein the non-native deletions are: a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and a partial deletion of ECOLIN_10175.

4. The bacterium of claim 3, wherein the deleted phage genes comprise SEQ ID NO:130.

5. The bacterium of claim 4, wherein the deleted phage genes consist of SEQ ID NO:130.

6. The bacterium of claim 1, wherein the bacterium further comprises an antibiotic resistance gene.

7. The bacterium of claim 1, wherein the PME is phenylalanine ammonia lyase (PAL).

8. The bacterium of claim 7, further comprising one or more gene(s) encoding a phenylalanine transporter.

9. The bacterium of claim 8, wherein the phenylalanine transporter is PheP.

10. The bacterium of claim 8, further comprising one or more gene(s) encoding L-amino acid deaminase (LAAD).

11. The bacterium of claim 10, wherein:
    the one or more genes encoding PAL are operably linked to a promoter;
    the one or more genes encoding the phenylalanine transporter are operably linked to a promoter; and
    the one or more genes encoding LAAD are operably linked to a promoter.

12. The bacterium of claim 11, wherein:
    the one or more genes encoding PAL are operably linked to an IPTG-inducible promoter; and
    the one or more genes encoding LAAD are operably linked to an arabinose-inducible promoter.

13. The bacterium of claim 11, wherein:
    the one or more genes encoding PAL are operably linked to an IPTG-inducible promoter;
    the one or more genes encoding the phenylalanine transporter are operably linked to an IPTG-inducible promoter; and
    the one or more genes encoding LAAD are operably linked to an arabinose-inducible promoter.

14. The bacterium of claim 11, wherein:
the one or more genes encoding PAL comprise an amino acid sequence having at least 95% identity to SEQ ID NO: 3 and are operably linked to an IPTG-inducible promoter;
the one or more genes encoding the phenylalanine transporter are operably linked to an IPTG-inducible promoter; and
the one or more genes encoding LAAD are operably linked to an arabinose-inducible promoter.

15. The bacterium of claim 11, wherein:
the one or more genes encoding PAL are operably linked to an FNR-responsive promoter;
the one or more genes encoding the phenylalanine transporter are operably linked to an FNR-responsive promoter; and
the one or more genes encoding LAAD are operably linked to an arabinose-inducible promoter.

16. The bacterium of claim 11, wherein:
one or more of the genes encoding PAL are operably linked to an FNR-responsive promoter;
one or more additional genes encoding PAL are operably linked to an IPTG-inducible promoter;
the one or more genes encoding the phenylalanine transporter are operably linked to an FNR-responsive promoter; and
the one or more genes encoding LAAD are operably linked to an arabinose-inducible promoter.

17. The bacterium of claim 11 wherein:
three copies of the gene encoding PAL are derived from *Photorhabdus luminescens;*
two additional copies of the gene encoding PAL are derived from *Photorhabdus luminescens;*
two copies of the gene encoding the phenylalanine transporter are derived from *Escherichia coli;*
one copy of the gene encoding LAAD is derived from *Proteus mirabilis;* and
the bacterium further comprises a mutation in one or more of ThyA or DapA to generate an auxotrophy.

18. The bacterium of claim 17, wherein:
the promoter operably linked to the three copies of the gene encoding PAL derived from *Photorhabdus luminescens* is inducible under anaerobic or low-oxygen conditions;
the promoter operably linked to the two additional copies of the gene encoding PAL derived from *Photorhabdus luminescens* is an IPTG-inducible promoter;
the promoter operably linked to the two copies of the non-native gene encoding the phenylalanine transporter derived from *Escherichia coli* is inducible under anaerobic or low-oxygen conditions;
the promoter operably linked to the one copy of the gene encoding LAAD derived from *Proteus mirabilis* is an arabinose-inducible promoter; and
the mutation in one or more of ThyA or DapA is a mutation in the DapA gene.

19. The bacterium of claim 18, wherein:
the promoter to which the three copies of the gene encoding PAL derived from *Photorhabdus luminescens* are operably linked to is an FNR-responsive promoter; and
the promoter to which the two copies of the gene encoding the phenylalanine transporter derived from *Escherichia coli* are operably linked to is an FNR-responsive promoter.

20. The bacterium of claim 11, wherein:
four copies of a gene encoding PAL are derived from *Photorhabdus luminescens;*
one copy of a gene encoding PheP phenylalanine transporter is derived from *Escherichia coli;*
one copy of a gene encoding LAAD is derived from *Proteus mirabilis;* and
the bacterium further comprising a mutation in one or more of ThyA or DapA to generate an auxotrophy.

21. The bacterium of claim 20, wherein:
the promoter operably linked to the four copies of the gene encoding PAL derived from *Photorhabdus luminescens* is an IPTG-inducible promoter;
the promoter operably linked to the one copy of the gene encoding the phenylalanine transporter derived from *Escherichia coli* is an IPTG-inducible promoter;
the promoter operably linked to the one copy of the gene encoding LAAD derived from *Proteus mirabilis* is an arabinose-inducible promoter; and
the mutation in one or more of ThyA or DapA is a mutation in the DapA gene.

22. The bacterium of claim 1, wherein the PME is PAL derived from *Anabaena variabilis* (PAL1) or *Photorhabdus luminescens* (PAL3).

23. A pharmaceutically acceptable composition comprising the bacterium of claim 1, and a pharmaceutically acceptable carrier.

24. The composition of claim 23 formulated for oral administration.

* * * * *